US010516117B2

(12) United States Patent
Li et al.

(10) Patent No.: US 10,516,117 B2

(45) Date of Patent: Dec. 24, 2019

(54) METAL-ASSISTED DELAYED FLUORESCENT EMTTTERS EMPLOYING BENZO-IMIDAZO-PHENANTHRIDINE AND ANALOGUES

(71) Applicant: Arizona Board of Regents on behalf of Arizona State University, Scottsdale, AZ (US)

(72) Inventors: Jian Li, Tempe, AZ (US); Yunlong Ji, Mesa, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 15/983,680

(22) Filed: May 18, 2018

(65) Prior Publication Data

US 2018/0337349 A1 Nov. 22, 2018

Related U.S. Application Data

(60) Provisional application No. 62/508,560, filed on May 19, 2017, provisional application No. 62/508,782, filed on May 19, 2017.

(51) Int. Cl.

| | |
|---|---|
| ***H01L 51/00*** | (2006.01) |
| ***C07F 15/00*** | (2006.01) |
| ***C09K 11/06*** | (2006.01) |
| ***H01L 51/50*** | (2006.01) |
| ***H01L 51/52*** | (2006.01) |

(52) U.S. Cl.

CPC ........ *H01L 51/0084* (2013.01); *C07F 15/006* (2013.01); *C07F 15/0033* (2013.01); *C07F 15/0086* (2013.01); *C09K 11/06* (2013.01); *H01L 51/0085* (2013.01); *H01L 51/0087* (2013.01); *C09K 2211/1044* (2013.01); *C09K 2211/1074* (2013.01); *C09K 2211/185* (2013.01); *H01L 51/5016* (2013.01); *H01L 51/5268* (2013.01)

(58) Field of Classification Search

CPC .......................... C07F 15/006; C07F 15/0086

See application file for complete search history.

(56) References Cited

U.S. PATENT DOCUMENTS

| | | | |
|---|---|---|---|
| 5,707,745 | A | 1/1998 | Forrest et al. |
| 6,200,695 | B1 | 3/2001 | Arai |
| 6,780,528 | B2 | 8/2004 | Tsuboyama et al. |
| 7,037,599 | B2 | 5/2006 | Culligan et al. |
| 7,442,797 | B2 | 10/2008 | Itoh et al. |
| 7,501,190 | B2 | 3/2009 | Ise |
| 7,655,322 | B2 | 2/2010 | Forrest et al. |
| 7,947,383 | B2 | 5/2011 | Ise et al. |
| 8,389,725 | B2 | 3/2013 | Li et al. |
| 8,617,723 | B2 | 12/2013 | Stoessel |
| 8,816,080 | B2 | 8/2014 | Li et al. |
| 8,871,361 | B2 | 10/2014 | Xia et al. |
| 8,927,713 | B2 | 1/2015 | Li et al. |
| 8,946,417 | B2 | 2/2015 | Li et al. |
| 9,059,412 | B2 | 6/2015 | Zeng et al. |
| 9,224,963 | B2 | 12/2015 | Li et al. |
| 9,238,668 | B2 | 1/2016 | Li et al. |
| 9,312,505 | B2 | 4/2016 | Brooks et al. |
| 9,318,725 | B2 | 4/2016 | Li |
| 9,324,957 | B2 | 4/2016 | Li et al. |
| 9,382,273 | B2 | 7/2016 | Li |
| 9,385,329 | B2 | 7/2016 | Li et al. |
| 9,425,415 | B2 | 8/2016 | Li et al. |
| 9,461,254 | B2 | 10/2016 | Tsai |
| 9,550,801 | B2 | 1/2017 | Li et al. |
| 9,617,291 | B2 | 4/2017 | Li et al. |
| 9,673,409 | B2 | 6/2017 | Li |
| 9,698,359 | B2 | 7/2017 | Li et al. |
| 9,711,739 | B2 | 7/2017 | Li |
| 9,711,742 | B2 | 7/2017 | Li et al. |
| 9,755,163 | B2 | 9/2017 | Li et al. |
| 9,818,959 | B2 | 11/2017 | Li |
| 9,879,039 | B2 | 1/2018 | Li |
| 9,882,150 | B2 | 1/2018 | Li |
| 9,899,614 | B2 | 2/2018 | Li |
| 9,920,242 | B2 | 3/2018 | Li |
| 9,923,155 | B2 | 3/2018 | Li et al. |
| 9,941,479 | B2 | 4/2018 | Li |
| 9,947,881 | B2 | 4/2018 | Li |
| 10,020,455 | B2 | 7/2018 | Li |
| 10,033,003 | B2 | 7/2018 | Li |
| 10,056,564 | B2 | 8/2018 | Li |
| 10,056,567 | B2 | 8/2018 | Li |
| 2003/0062519 | A1 | 4/2003 | Yamazaki et al. |
| 2003/0186077 | A1 | 10/2003 | Chen |

(Continued)

FOREIGN PATENT DOCUMENTS

| | | |
|---|---|---|
| CN | 1680366 A | 10/2005 |
| CN | 1777663 | 5/2006 |

(Continued)

OTHER PUBLICATIONS

Wong; Challenges in organometallic research—Great opportunity for solar cells and OLEDs, Journal of Organometallic Chemistry, 2009, 694, 2644-2647.

JP2009267244, English Translation from EPO, Nov. 2009, 80 pages.

JP2010135689, English translation from EPO, Jun. 2010, 95 pages.

Chi et al.; Transition-metal phosphors with cyclometalating ligands: fundamentals and applications, Chemical Society Reviews, vol. 39, No. 2, Feb. 2010, pp. 638-655.

(Continued)

*Primary Examiner* — Joseph R Kosack

(74) *Attorney, Agent, or Firm* — Riverside Law LLP

(57) ABSTRACT

Metal-assisted delayed fluorescent emitters employing benzo-imidazo-phenanthridine and analogues for full color displays and lighting applications.

6 Claims, 5 Drawing Sheets

(56) References Cited

U.S. PATENT DOCUMENTS

| | | | |
|---|---|---|---|
| 2005/0170207 | A1 | 8/2005 | Ma et al. |
| 2005/0260446 | A1 | 11/2005 | Mackenzie et al. |
| 2006/0073359 | A1 | 4/2006 | Ise et al. |
| 2006/0094875 | A1 | 5/2006 | Itoh et al. |
| 2006/0182992 | A1 | 8/2006 | Nii et al. |
| 2006/0202197 | A1 | 9/2006 | Nakayama et al. |
| 2006/0210831 | A1 | 9/2006 | Sano et al. |
| 2006/0255721 | A1 | 11/2006 | Igarashi et al. |
| 2006/0263635 | A1 | 11/2006 | Ise |
| 2006/0286406 | A1 | 12/2006 | Igarashi et al. |
| 2007/0057630 | A1 | 3/2007 | Nishita et al. |
| 2007/0059551 | A1 | 3/2007 | Yamazaki |
| 2007/0082284 | A1 | 4/2007 | Stoessel et al. |
| 2007/0103060 | A1 | 5/2007 | Itoh et al. |
| 2008/0001530 | A1 | 1/2008 | Ise et al. |
| 2008/0036373 | A1 | 2/2008 | Itoh et al. |
| 2008/0054799 | A1 | 3/2008 | Satou |
| 2008/0079358 | A1 | 4/2008 | Satou |
| 2008/0111476 | A1 | 5/2008 | Choi et al. |
| 2008/0241518 | A1 | 10/2008 | Satou et al. |
| 2008/0241589 | A1 | 10/2008 | Fukunaga et al. |
| 2009/0026936 | A1 | 1/2009 | Satou et al. |
| 2009/0026939 | A1 | 1/2009 | Kinoshita et al. |
| 2009/0039768 | A1 | 2/2009 | Igarashi et al. |
| 2009/0079340 | A1 | 3/2009 | Kinoshita et al. |
| 2009/0128008 | A1 | 5/2009 | Ise et al. |
| 2009/0136779 | A1 | 5/2009 | Cheng et al. |
| 2009/0153045 | A1 | 6/2009 | Kinoshita et al. |
| 2009/0218561 | A1 | 9/2009 | Kitamura et al. |
| 2009/0261721 | A1 | 10/2009 | Murakami et al. |
| 2009/0267500 | A1 | 10/2009 | Kinoshita et al. |
| 2010/0171111 | A1 | 7/2010 | Takada et al. |
| 2010/0171418 | A1 | 7/2010 | Kinoshita et al. |
| 2010/0204467 | A1 | 8/2010 | Lamarque et al. |
| 2011/0049496 | A1 | 3/2011 | Fukuzaki |
| 2011/0227058 | A1 | 9/2011 | Masui et al. |
| 2012/0095232 | A1 | 4/2012 | Li et al. |
| 2012/0181528 | A1 | 7/2012 | Takada et al. |
| 2012/0202997 | A1 | 8/2012 | Parham et al. |
| 2012/0215001 | A1 | 8/2012 | Li et al. |
| 2012/0223634 | A1 | 9/2012 | Xia et al. |
| 2012/0273736 | A1 | 11/2012 | James et al. |
| 2012/0302753 | A1 | 11/2012 | Li |
| 2013/0048963 | A1 | 2/2013 | Beers et al. |
| 2013/0082245 | A1 | 4/2013 | Kottas et al. |
| 2013/0168656 | A1 | 7/2013 | Tsai et al. |
| 2013/0172561 | A1 | 7/2013 | Tsai et al. |
| 2013/0203996 | A1 | 8/2013 | Li et al. |
| 2013/0237706 | A1 | 9/2013 | Li |
| 2013/0341600 | A1 | 12/2013 | Lin et al. |
| 2014/0014922 | A1 | 1/2014 | Lin et al. |
| 2014/0027733 | A1 | 1/2014 | Zeng et al. |
| 2014/0084261 | A1 | 3/2014 | Brooks et al. |
| 2014/0114072 | A1 | 4/2014 | Li et al. |
| 2014/0191206 | A1 | 7/2014 | Cho |
| 2014/0203248 | A1 | 7/2014 | Zhou et al. |
| 2014/0326960 | A1 | 11/2014 | Kim et al. |
| 2014/0330019 | A1 | 11/2014 | Li et al. |
| 2014/0364605 | A1 | 12/2014 | Li et al. |
| 2015/0008419 | A1 | 1/2015 | Li |
| 2015/0028323 | A1 | 1/2015 | Xia et al. |
| 2015/0069334 | A1 | 3/2015 | Xia et al. |
| 2015/0105556 | A1 | 4/2015 | Li et al. |
| 2015/0162552 | A1 | 6/2015 | Li et al. |
| 2015/0194616 | A1 | 7/2015 | Li et al. |
| 2015/0207086 | A1 | 7/2015 | Li et al. |
| 2015/0228914 | A1 | 8/2015 | Li et al. |
| 2015/0274762 | A1 | 10/2015 | Li et al. |
| 2015/0287938 | A1 | 10/2015 | Li et al. |
| 2015/0318500 | A1 | 11/2015 | Li |
| 2015/0349279 | A1 | 12/2015 | Li et al. |
| 2016/0028028 | A1 | 1/2016 | Li et al. |
| 2016/0072082 | A1 | 3/2016 | Brooks et al. |
| 2016/0133862 | A1 | 5/2016 | Li et al. |
| 2016/0197291 | A1 | 7/2016 | Li et al. |
| 2016/0285015 | A1 | 9/2016 | Li et al. |
| 2016/0359120 | A1 | 12/2016 | Li |
| 2016/0359125 | A1 | 12/2016 | Li |
| 2017/0005278 | A1 | 1/2017 | Li et al. |
| 2017/0012224 | A1 | 1/2017 | Li et al. |
| 2017/0040555 | A1 | 2/2017 | Li et al. |
| 2017/0047533 | A1 | 2/2017 | Li et al. |
| 2017/0066792 | A1 | 3/2017 | Li et al. |
| 2017/0069855 | A1 | 3/2017 | Li et al. |
| 2017/0267923 | A1 | 9/2017 | Li |
| 2017/0271611 | A1 | 9/2017 | Li et al. |
| 2017/0301871 | A1 | 10/2017 | Li |
| 2017/0305881 | A1 | 10/2017 | Li et al. |
| 2017/0309943 | A1 | 10/2017 | Angell |
| 2017/0331056 | A1 | 11/2017 | Li et al. |
| 2017/0373260 | A1 | 12/2017 | Li |
| 2018/0006246 | A1 | 1/2018 | Li |
| 2018/0053904 | A1 | 2/2018 | Li |
| 2018/0130960 | A1 | 5/2018 | Li |
| 2018/0138428 | A1 | 5/2018 | Li |
| 2018/0148464 | A1 | 5/2018 | Li |
| 2018/0166655 | A1 | 6/2018 | Li et al. |
| 2018/0175329 | A1 | 6/2018 | Li |
| 2018/0194790 | A1 | 7/2018 | Li |
| 2018/0219161 | A1 | 8/2018 | Li |
| 2018/0226592 | A1 | 8/2018 | Li |
| 2018/0226593 | A1 | 8/2018 | Li |
| 2018/0337350 | A1 | 11/2018 | Li |

FOREIGN PATENT DOCUMENTS

| | | | |
|---|---|---|---|
| CN | 1894269 | | 1/2007 |
| CN | 101142223 | | 3/2008 |
| CN | 101667626 | | 3/2010 |
| CN | 102449108 | A | 5/2012 |
| CN | 102892860 | | 1/2013 |
| CN | 102971396 | | 3/2013 |
| CN | 104232076 | | 12/2014 |
| CN | 104693243 | | 6/2015 |
| CN | 105367605 | | 3/2016 |
| CN | 105418591 | | 3/2016 |
| EP | 1808052 | | 7/2007 |
| EP | 1874893 | | 1/2008 |
| EP | 1874894 | | 1/2008 |
| EP | 1919928 | | 5/2008 |
| EP | 2036907 | | 3/2009 |
| EP | 2096690 | A2 | 9/2009 |
| EP | 2417217 | | 2/2012 |
| EP | 2112213 | | 7/2012 |
| EP | 2711999 | | 3/2014 |
| JP | 2002105055 | A | 4/2002 |
| JP | 2005267557 | | 9/2005 |
| JP | 2005310733 | | 11/2005 |
| JP | 2006232784 | | 9/2006 |
| JP | 2006242080 | | 9/2006 |
| JP | 2006256999 | | 9/2006 |
| JP | 2006257238 | | 9/2006 |
| JP | 2006261623 | | 9/2006 |
| JP | 2006290988 | | 10/2006 |
| JP | 2006313796 | | 11/2006 |
| JP | 2006332622 | | 12/2006 |
| JP | 2006351638 | | 12/2006 |
| JP | 2007019462 | | 1/2007 |
| JP | 2007031678 | A | 2/2007 |
| JP | 2007042875 | | 2/2007 |
| JP | 2007051243 | | 3/2007 |
| JP | 2007053132 | | 3/2007 |
| JP | 2007066581 | | 3/2007 |
| JP | 2007073620 | | 3/2007 |
| JP | 2007073845 | | 3/2007 |
| JP | 2007073900 | | 3/2007 |
| JP | 2007080593 | | 3/2007 |
| JP | 2007080677 | | 3/2007 |
| JP | 2007088105 | | 4/2007 |
| JP | 2007088164 | | 4/2007 |
| JP | 2007096259 | | 4/2007 |
| JP | 2007099765 | A | 4/2007 |
| JP | 2007110067 | | 4/2007 |
| JP | 2007110102 | | 4/2007 |

(56) References Cited

FOREIGN PATENT DOCUMENTS

| | | | |
|---|---|---|---|
| JP | 2007519614 | | 7/2007 |
| JP | 2007258550 | | 10/2007 |
| JP | 2007324309 | | 12/2007 |
| JP | 2008091860 | | 4/2008 |
| JP | 2008103535 | | 5/2008 |
| JP | 2008108617 | | 5/2008 |
| JP | 2008109085 | | 5/2008 |
| JP | 2008160087 | | 7/2008 |
| JP | 2008198801 | | 8/2008 |
| JP | 2008270729 | | 11/2008 |
| JP | 2008270736 | | 11/2008 |
| JP | 2009016184 | | 1/2009 |
| JP | 2009016579 | | 1/2009 |
| JP | 2009032977 | | 2/2009 |
| JP | 2009032988 | | 2/2009 |
| JP | 2009076509 | A | 4/2009 |
| JP | 2009161524 | | 7/2009 |
| JP | 2009266943 | | 11/2009 |
| JP | 2009267171 | | 11/2009 |
| JP | 2009267244 | | 11/2009 |
| JP | 2009272339 | | 11/2009 |
| JP | 2009283891 | | 12/2009 |
| JP | 2010135689 | | 6/2010 |
| JP | 2010171205 | | 8/2010 |
| JP | 2011071452 | | 4/2011 |
| JP | 2012079895 | | 4/2012 |
| JP | 2012079898 | | 4/2012 |
| JP | 2012522843 | | 9/2012 |
| JP | 2012207231 | | 10/2012 |
| JP | 2012222255 | | 11/2012 |
| JP | 2012231135 | | 11/2012 |
| JP | 2013023500 | | 2/2013 |
| JP | 2013048256 | | 3/2013 |
| JP | 2013053149 | | 3/2013 |
| JP | 2013525436 | | 6/2013 |
| JP | 2014019701 | | 2/2014 |
| JP | 2014058504 | | 4/2014 |
| JP | 5604505 | | 10/2014 |
| JP | 2014221807 | | 11/2014 |
| JP | 2014239225 | | 12/2014 |
| JP | 2015081257 | | 4/2015 |
| KR | 1020060115371 | | 11/2006 |
| KR | 2007061830 | | 6/2007 |
| KR | 2007112465 | | 11/2007 |
| KR | 1020130043460 | | 4/2013 |
| TW | 200701835 | | 1/2007 |
| TW | 201307365 | | 2/2013 |
| TW | 201710277 | | 3/2017 |
| WO | WO2000070655 | | 11/2000 |
| WO | WO2004003108 | | 1/2004 |
| WO | WO2004085450 | | 10/2004 |
| WO | WO2004108857 | | 12/2004 |
| WO | WO2005042444 | | 5/2005 |
| WO | WO2005042550 | | 5/2005 |
| WO | WO2005113704 | | 12/2005 |
| WO | WO2006033440 | | 3/2006 |
| WO | WO2006067074 | | 6/2006 |
| WO | WO2006098505 | | 9/2006 |
| WO | WO2006115299 | | 11/2006 |
| WO | WO2006115301 | | 11/2006 |
| WO | WO2007034985 | | 3/2007 |
| WO | WO2008066192 | | 6/2008 |
| WO | WO2008066195 | | 6/2008 |
| WO | WO2008066196 | | 6/2008 |
| WO | WO2008101842 | | 8/2008 |
| WO | WO2008117889 | | 10/2008 |
| WO | WO2008123540 | | 10/2008 |
| WO | WO2009017211 | | 2/2009 |
| WO | WO2009023667 | | 2/2009 |
| WO | WO2010007098 | | 1/2010 |
| WO | WO2010056669 | | 5/2010 |
| WO | WO2010093176 | | 8/2010 |
| WO | WO2010118026 | | 10/2010 |
| WO | WO2011064335 | | 6/2011 |
| WO | WO2011070989 | | 6/2011 |
| WO | WO2011137429 | | 11/2011 |
| WO | WO2011137431 | | 11/2011 |
| WO | WO2012112853 | | 8/2012 |
| WO | WO2012116231 | | 8/2012 |
| WO | WO2012142387 | | 10/2012 |
| WO | WO2012162488 | | 11/2012 |
| WO | WO2012163471 | | 12/2012 |
| WO | 103102372 | | 5/2013 |
| WO | WO2013130483 | | 9/2013 |
| WO | WO2014016611 | | 1/2014 |
| WO | WO2014031977 | | 2/2014 |
| WO | WO2014047616 | | 3/2014 |
| WO | WO2014109814 | | 7/2014 |
| WO | WO2014208271 | | 12/2014 |
| WO | WO2015027060 | | 2/2015 |
| WO | WO2015131158 | | 9/2015 |
| WO | WO2016025921 | | 2/2016 |
| WO | WO2016029137 | | 2/2016 |
| WO | WO2016029186 | | 2/2016 |
| WO | WO2016197019 | | 12/2016 |
| WO | WO2018071697 | | 4/2018 |
| WO | 2018140765 | A1 | 8/2018 |
| WO | WO2018140765 | | 8/2018 |

OTHER PUBLICATIONS

Baldo et al., "Highly Efficient Phosphorescent Emission from Organic Electroluminescent Devices," Nature, vol. 395, Sep. 10, 1998, pp. 151-154.

Baldo et al., "Very high-efficiency green organic light-emitting devices based on electrophosphorescence," Applied Physics Letters, vol. 75, No. 1, Jul. 5, 1999, pp. 4-6.

Ayan Maity et al., "Room-temperature synthesis of cyclometalated iridium(III) complexes; kinetic isomers and reactive functionalities" Chem. Sci., vol. 4, pp. 1175-1181 (2013).

Shiro Koseki et al., "Spin-orbit coupling analyses of the geometrical effects on phosphorescence in Ir(ppy)3 and its derivatives", J. Phys. Chem. C, vol. 117, pp. 5314-5327 (2013).

Ji Hyun Seo et al., "Efficient blue-green organic light-emitting diodes based on heteroleptic tris-cyclometalated iridium (III) complexes". Thin Solid Films, vol. 517, pp. 1807-1810 (2009).

Barry O'Brien et al.: White organic light emitting diodes using Pt-based red, green and blue phosphorescent dopants. Proc. SPIE, vol. 8829, pp. 1-6, Aug. 25, 2013.

Xiao-Chu Hang et al., "Highly Efficient Blue-Emitting Cyclometalated Platinum(II) Complexes by Judicious Molecular Design," Angewandte Chemie, International Edition, vol. 52, Issue 26, Jun. 24, 2013, pp. 6753-6756.

Shizuo Tokito et al., "Confinement of triplet energy on phosphorescent molecules for highly-efficient organic blue-light-emitting devices," Applied Physics Letters, vol. 83, No. 3, Jul. 21, 2003, pp. 569-571.

Brian W. D'Andrade et al., "Controlling Exciton Diffusion in Multilayer White Phosphorescent Organic Light Emitting Devices," Adv. Mater. , vol. 14, No. 2, Jan. 16, 2002, pp. 147-151.

Dileep A. K. Vezzu et al., "Highly Luminescent Tetradentate Bis-Cyclometalated Platinum Complexes: Design, Synthesis, Structure, Photophysics, and Electroluminescence Application," Inorg. Chem., vol. 49, 2010, pp. 5107-5119.

Evan L. Williams et al., "Excimer-Based White Phosphorescent Organic Light Emitting Diodes with Nearly 100% Internal Quantum Efficiency," Adv. Mater., vol. 19, 2007, pp. 197-202.

Shih-Chun Lo et al., "High-Triplet-Energy Dendrons: Enhancing the Luminescence of Deep Blue Phosphorescent Iridium(III) Complexes," J. Am. Chem. Soc., vol. 131, 2009, pp. 16681-16688.

Jan Kalinowski et al., "Light-emitting devices based on organometallic platinum complexes as emitters," Coordination Chemistry Reviews, vol. 255, 2011, pp. 2401-2425.

Ke Feng et al., "Norbornene-Based Copolymers Containing Platinum Complexes and Bis(carbazolyl)benzene Groups in Their Side-Chains," Macromolecules, vol. 42, 2009, pp. 6855-6864.

Chi-Ming Che et al., "Photophysical Properties and OLED Applications of Phosphorescent Platinum(II) Schiff Base Complexes," Chem. Eur. J., vol. 16, 2010, pp. 233-247.

(56) References Cited

OTHER PUBLICATIONS

Nicholas R. Evans et al., "Triplet Energy Back Transfer in Conjugated Polymers with Pendant Phosphorescent Iridium Complexes," J. Am. Chem. Soc., vol. 128, 2006, pp. 6647-6656.
Hirohiko Fukagawa et al., "Highly Efficient and Stable Red Phosphorescent Organic Light-Emitting Diodes Using Platinum Complexes," Adv. Mater., 2012, vol. 24, pp. 5099-5103.
Eric Turner et al., "Cyclometalated Platinum Complexes with Luminescent Quantum Yields Approaching 100%," Inorg. Chem., 2013, vol. 52, pp. 7344-7351.
Steven C. F. Kui et al., "Robust Phosphorescent Platinum(II) Complexes Containing Tetradentate O^N^C^N Ligands: Excimeric Excited State and Application in Organic White-Light-Emitting Diodes," Chem. Eur. J., 2013, vol. 19, pp. 69-73.
Steven C. F. Kui et al., "Robust phosphorescent platinum(II) complexes with tetradentate O^N^C^N ligands: high efficiency OLEDs with excellent efficiency stability," Chem. Commun., 2013, vol. 49, pp. 1497-1499.
Guijie Li et al., "Efficient and stable red organic light emitting devices from a tetradentate cyclometalated platinum complex," Organic Electronics, 2014, vol. 15 pp. 1862-1867.
Guijie Li et al., Efficient and Stable White Organic Light-Emitting Diodes Employing a Single Emitter, Adv. Mater., 2014, vol. 26, pp. 2931-2936.
Barry O'Brien et al., "High efficiency white organic light emitting diodes employing blue and red platinum emitters," Journal of Photonics for Energy, vol. 4, 2014, pp. 043597-1-8.
Kai Li et al., "Light-emitting platinum(II) complexes supported by tetradentate dianionic bis(N-heterocyclic carbene) ligands: towards robust blue electrophosphors," Chem. Sci., 2013, vol. 4, pp. 2630-2644.
Tyler Fleetham et al., "Efficient "pure" blue OLEDs employing tetradentate Pt complexes with a narrow spectral bandwidth," Advanced Materials (Weinheim, Germany), Vo. 26, No. 41, 2014, pp. 7116-7121.
Murakami; JP 2007258550, English machine translation from EPO, Oct. 4, 2007. 80 pages.
Murakami; JP 2007324309, English machine translation from EPO, Dec. 13, 2007, 89 pages.
Marc Lepeltier et al., "Efficient blue green organic light-emitting devices based on a monofluorinated heteroleptic iridium(III) complex," Synthetic Metals, vol. 199, 2015, pp. 139-146.
Stefan Bernhard, "The First Six Years: A Report," Department of Chemistry, Princeton University, May 2008, 11 pages.
Zhi-Qiang Zhu et.al., "Harvesting All Electrogenerated Excitons through Metal Assisted Delayed Fluorescent Materials," Adv. Mater. 27 (2015) 2533-2537.
Zhi-Qiang Zhu et. al.. "Efficient Cyclometalated Platinum(II) Complex with Superior Operational Stability," Adv. Mater. 29 (2017) 1605002, pp. 1-5.
Chew, S. et al.: Photoluminescence and electroluminescence of a new blue-emitting homoleptic iridium complex. Applied Phys. Letters; 2006, vol. 88, pp. 093510-1-093510-3.
Xin Li et al., "Density functional theory study of photophysical properties of iridium (III) complexes with phenylisoquinoline and phenylpyridine ligands", The Journal of Physical Chemistry C, 2011, vol. 115, No. 42, pp. 20722-20731.
Sylvia Bettington et al. "Tris-Cyclometalated Iridium(III) Complexes of Carbazole(fluorenyl)pyridine Ligands: Synthesis, Redox and Photophysical Properties, and Electrophosphorescent Light-Emitting Diodes" Chemistry: A European Journal, 2007, vol. 13, pp. 1423-1431.
Christoph Ulbricht et al., "Synthesis and Characterization of Oxetane-Functionalized Phosphorescent Ir(III)-Complexes", Macromol. Chem. Phys. 2009, 210, pp. 531-541.
Dan Wang et al., "Carbazole and arylamine functionalized iridium complexes for efficient electro-phosphorescent light-emitting diodes", Inorganica Chimica Acta 370 (2011) pp. 340-345.
Huaijun Tang et al., "Novel yellow phosphorescent iridium complexes containing a carbazoleeoxadiazole unit used in polymeric light-emitting diodes", Dyes and Pigments 91 (2011) pp. 413-421.
Hoe-Joo Seo et al., "Blue phosphorescent iridium(III) complexes containing carbazole-functionalized phenyl pyridine for organic light-emitting diodes: energy transfer from carbazolyl moieties to iridium(III) cores", RSC Advances, 2011, vol. 1, pp. 755-757.
Jack W. Levell et al., "Carbazole/iridium dendrimer side-chain phosphorescent copolymers for efficient light emitting devices", New J. Chem., 2012, vol. 36, pp. 407-413.
Z Liu et al., "Green and blue-green phosphorescent heteroleptic iridium complexes containing carbazole-functionalized beta-diketonate for non-doped organic light-emitting diodes", Organic Electronics 9 (2008) pp. 171-182.
Zhaowu Xu et al., "Synthesis and properties of iridium complexes based 1,3,4-oxadiazoles derivatives", Tetrahedron 64 (2008) pp. 1860-1867.
D.F. O'Brien et al., "Improved energy transfer in electrophosphorescent devices," Appl. Phys. Lett., vol. 74, No. 3, Jan. 18, 1999, pp. 442-444.
Vadim Adamovich et al., "High efficiency single dopant white electrophosphorescent light emitting diodes," New J. Chem., 2002, 26, pp. 1171-1178.
Kwon-Hyeon Kim et al., "Controlling Emitting Dipole Orientation with Methyl Substituents on Main Ligand of Iridium Complexes for Highly Efficient Phosphorescent Organic Light-Emitting Diodes", Adv. Optical Mater. 2015, 3, pp. 1191-1196.
Matthew J. Jurow et al., "Understanding and predicting the orientation of heteroleptic phosphors in organic light-emitting materials", Nature Materials, vol. 15, Jan. 2016, pp. 85-93.
Kwon-Hyeon Kim et al., "Crystal Organic Light-Emitting Diodes with Perfectly Oriented Non-Doped Pt-Based Emitting Layer", Adv. Mater. 2016, 28, pp. 2526-2532.
Maestri et al., "Absorption Spectra and Luminescence Properties of Isomeric Platinum (II) and Palladium (II) Complexes Containing 1,1'-Biphenyldiyl, 2-Phenylpyridine, and 2,2'- Bipyridine as Ligands," Helvetica Chimica Acta, vol. 71, Issue 5, Aug. 10, 1988, pp. 1053-1059.
Guijie Li et al., "Modifying Emission Spectral Bandwidth of Phosphorescent Platinum(II) Complexes Through Synthetic Control," Inorg. Chem. 2017, 56, 8244-8256.
Tyler Fleetham et al., "Efficient Red-Emitting Platinum Complex with Long Operational Stability," ACS Appl. Mater. Interfaces 2015, 7, 16240-16246.
Supporting Information: Xiao-Chun Hang et al., "Highly Efficient Blue-Emitting Cyclometalated Platinum(II) Complexes by Judicious Molecular Design," Wiley-VCH 2013, 7 pages.
Russell J. Holmes et al., "Blue and Near-UV Phosphorescence from Iridium Complexes with Cyclometalated Pyrazolyl or N-Heterocyclic Carbene Ligands," Inorganic Chemistry, 2005, vol. 44, No. 22, pp. 7995-8003.
Pui Keong Chow et al., "Strongly Phosphorescent Palladium(II) Complexes of Tetradentate Ligands with Mixed Oxygen, Carbon, and Nitrogen Donor Atoms: Photophysics, Photochemistry, and Applications," Angew. Chem. Int. Ed. 2013, 52, 11775-11779.
Pui-Keong Chow et al., "Highly luminescent palladium(II) complexes with sub-millisecond blue to green phosphorescent excited states. Photocatalysis and highly efficient PSF-OLEDs," Chem. Sci., 2016, 7, 6083-6098.

MC46

METAL-ASSISTED DELAYED FLUORESCENT EMTTTERS EMPLOYING BENZO-IMIDAZO-PHENANTHRIDINE AND ANALOGUES

CROSS-REFERENCE TO RELATED APPLICATIONS

This application claims the benefit of U.S. Application No. 62/508,560 entitled "METAL-ASSISTED DELAYED FLUORESCENT EMITTERS EMPLOYING BENZO-IMIDAZO-PHENANTHRIDINE AND ANALOGUES" and U.S. Application No. 62/508,782 entitled "OCTAHEDRAL IRIDIUM (III) METAL-ASSISTED DELAYED FLUORESCENT EMITTERS EMPLOYING BENZO-IMIDAZO-PHENANTHRIDINE AND ANALOGUES," both of which were filed on May 19, 2017, and both of which are incorporated herein by reference in their entirety.

STATEMENT OF GOVERNMENT INTEREST

This invention was made with government support under DE-EE0007090 awarded by the Department of Energy. The government has certain rights in the invention.

TECHNICAL FIELD

This invention relates to metal-assisted delayed fluorescent (MADF) emitters employing benzo-imidazo-phenanthridine and analogues for full color displays and lighting applications.

BACKGROUND

Compounds capable of absorbing or emitting light can be used in a variety of optical and electro-optical devices, including photo-absorbing devices (e.g., solar- and photo-sensitive devices), photo-emitting devices, organic light-emitting diodes (OLEDs), and devices capable of photo-absorption and photo-emission. Much research has been devoted to the discovery and optimization of organic and organometallic materials for use in optical and electro-optical devices. Metal complexes can be used for many applications, such as emitters for OLEDs. Despite advances in research devoted to optical and electro-optical materials, many currently available materials exhibit a number of disadvantages, including poor processing ability, inefficient emission or absorption, and insufficient stability.

SUMMARY

General Formulas I-III represent MAIN emitters based on cyclic platinum (II) and palladium (II) complexes employing benzo-imidazo-phenanthridine and analogues.

General Formula I

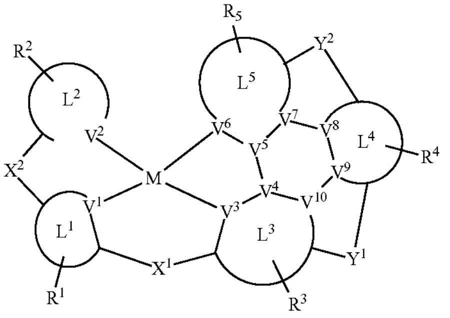

-continued

General Formula II

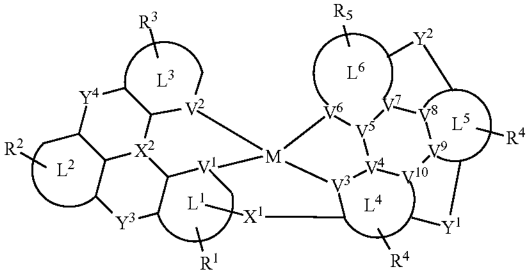

General Formula III

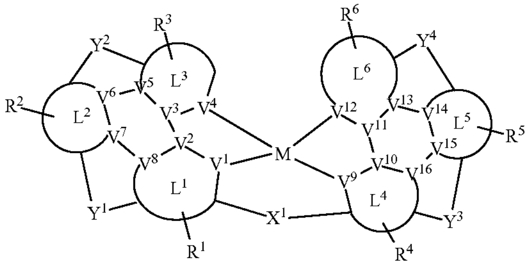

In General Formulas I-III:

M is Pt (II) or Pd (II), each of $V^1$-$V^{16}$, if present, is independently C, N, Si, O, S, Ge, P, As, Se, B, Al, or Bi, each of $X^1$, $X^2$, $Y^1$, $Y^2$, $Y^3$, and $Y^4$ is independently present or absent, and each $X^1$, $X^2$, $Y^1$, $Y^2$, $Y^3$, and $Y^4$ present independently represents C, N, Si, O, S, Ge, P, As, Se, B, Al, or Bi, or if valency permits, each independently represents $CR^7$, $SiR^7$, $GeR^7$, $NR^7$, P=O, As=O, B, $BR^7$, $AlR^7$, Bi=O, $CR^7R^8$, C=O, $SiR^7R^8$, $GeR^7R^8$, $NR^7$, $PR^7$, $PR^7R^8$, $R^7P$=O, $AsR^7$, $R^7As$=O, S=O, $SO_2$, Se=O, $SeO_2$, $BR^7$, $BR^7R^8$, $AlR^7$, $AlR^7R^8$, $R^7Bi$=O, or $BiR^7$, each of $L^1$, $L^2$, $L^3$, and $L^4$ is independently present or absent, and each $L^1$, $L^2$, $L^3$, and $L^4$ present independently represents a substituted or unsubstituted aryl, heteroaryl, or N-heterocyclic carbene, and each of R, $R^1$, $R^2$, $R^3$, $R^4$, $R^5$, $R^6$, $R^7$, and $R^8$ is independently absent or present as a single substituent or multiple substituents, valency permitting, and each R, $R^1$, $R^2$, $R^3$, $R^4$, $R^5$, $R^6$, $R^7$, and $R^8$ present independently represents deuterium, halogen, hydroxyl, thiol, nitro, cyanide, isocyanide, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

General Formula IV represents MADF emitters based on cyclic platinum (II) and palladium (II) complexes employing benzo-imidazo-phenanthridine and analogues.

General Formula IV
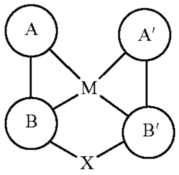
In General Formula IV:
M is Pt (II) or Pd (II)
X represents a single bond or $CR^7R^8$, C═O, $SiR^7R^8$, $GeR^7R^8$, $NR^7$, $PR^7$, $PR^7R^8$, $R^7R$═O, $AsR^7$, $R^7As$═O, O, S, S═O, $SO_2$, Se, Se═O, $SeO_2$, $BR^7$, $BR^7R^8$, $AlR^7$, $AlR^7R^8$, $R^7Bi$═O, or $BiR^7$,
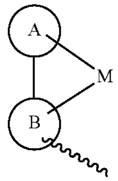
and
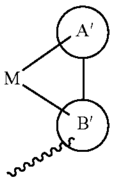
each independently represents one of the following chemical moieties:
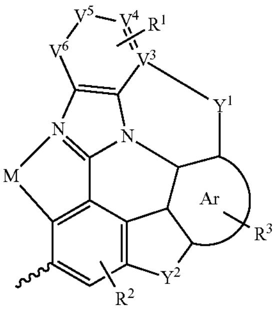
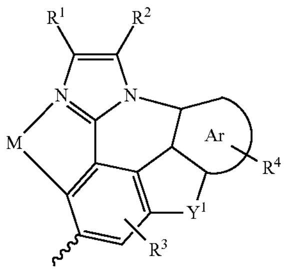
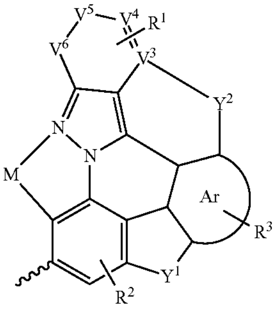
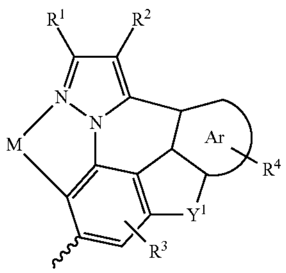
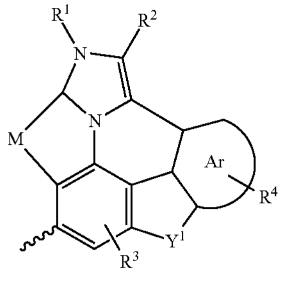
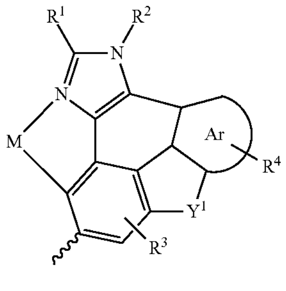
-continued
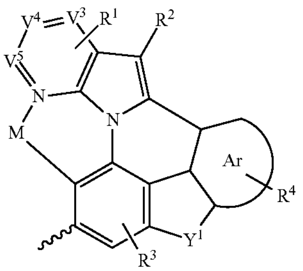
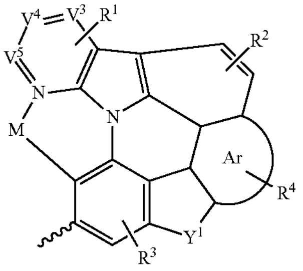
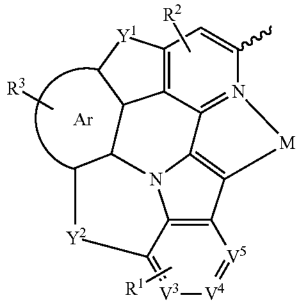
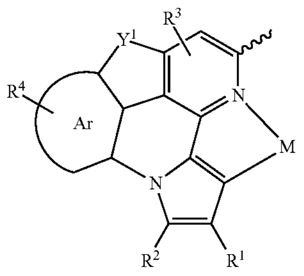
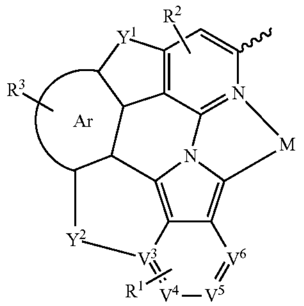
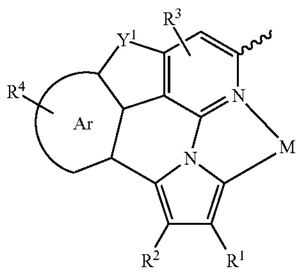

-continued
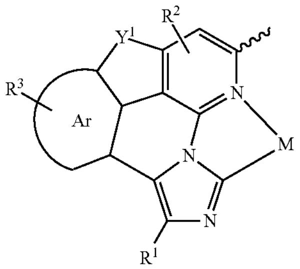
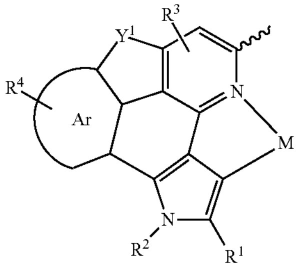
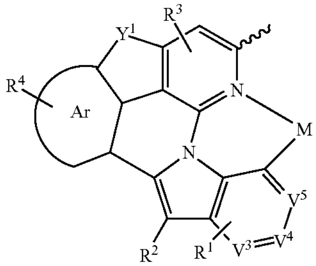
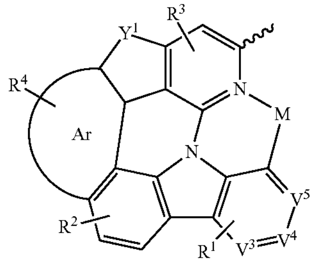
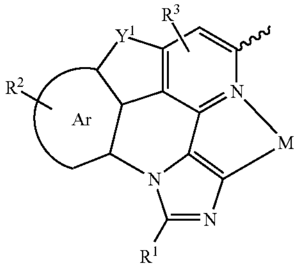
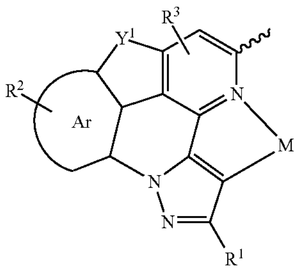
-continued
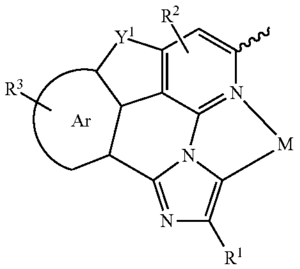
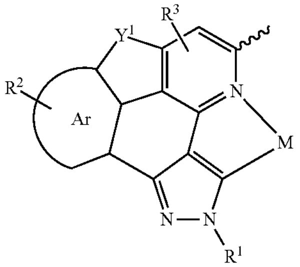
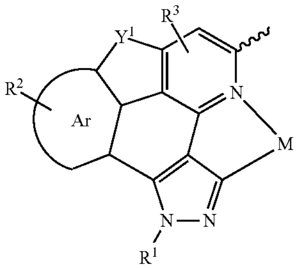
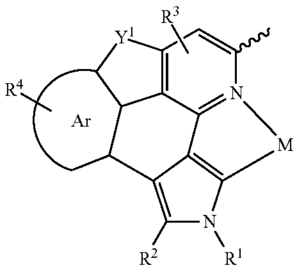
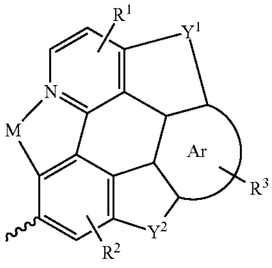
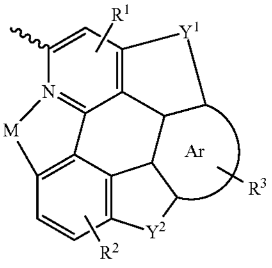
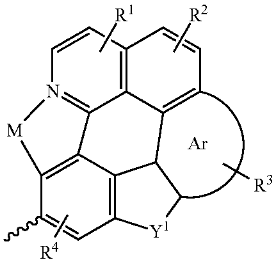
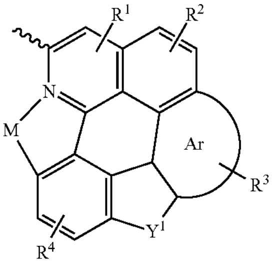

-continued
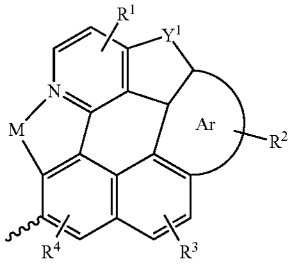
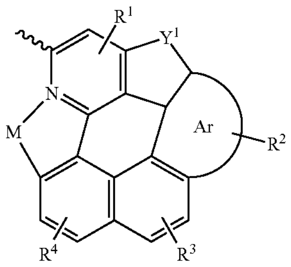
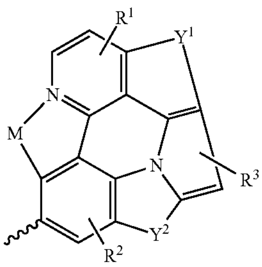
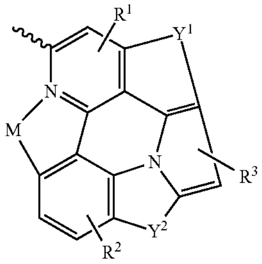
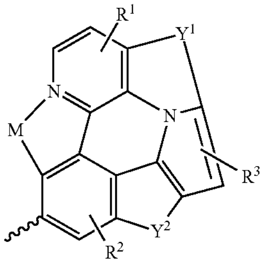
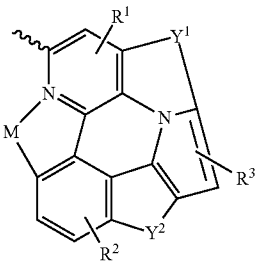
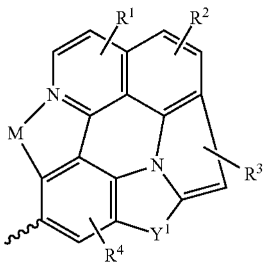
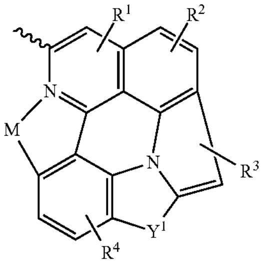
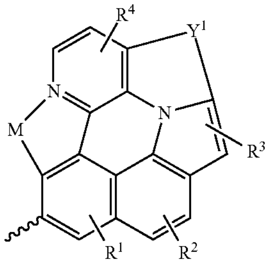
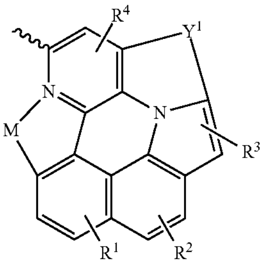
-continued
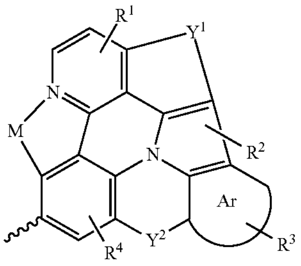
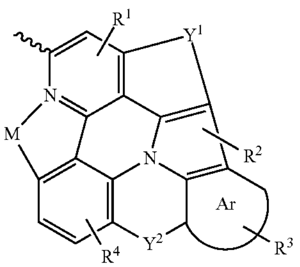
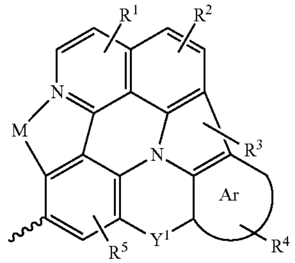
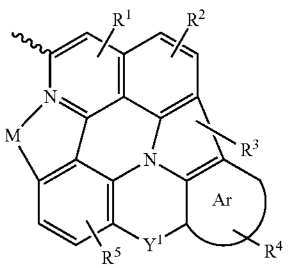
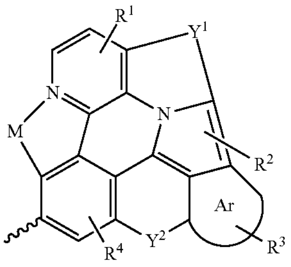
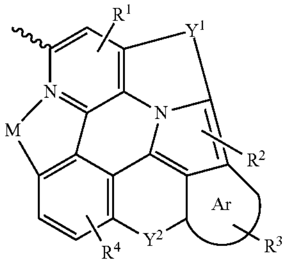

-continued
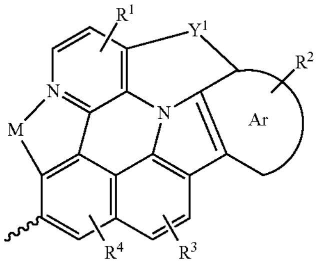
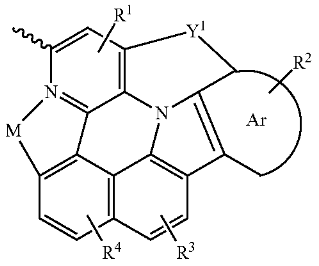
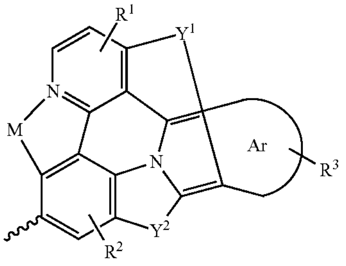
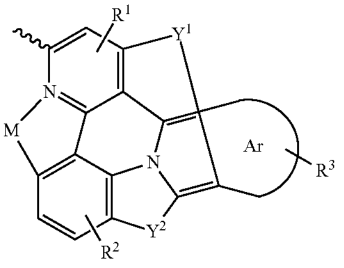
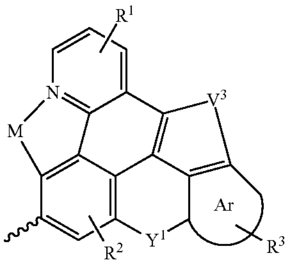
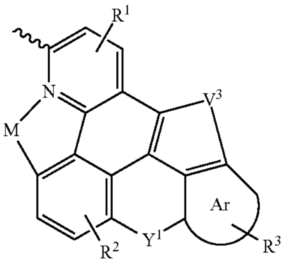
-continued
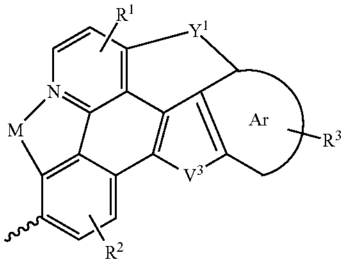
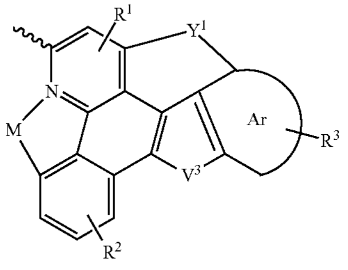
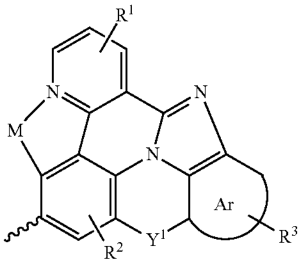
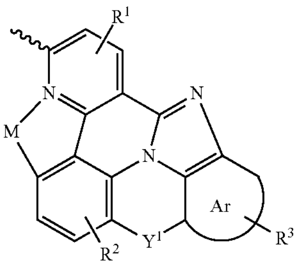
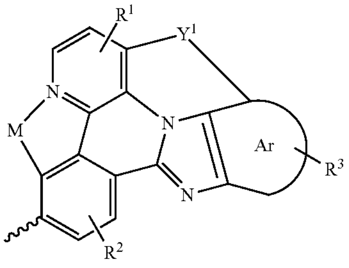
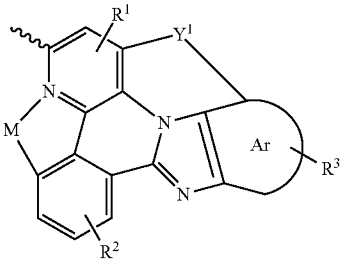

-continued

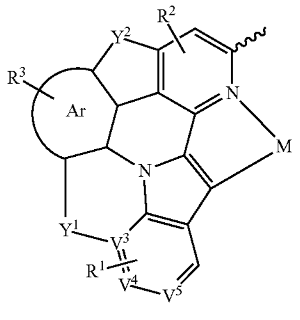

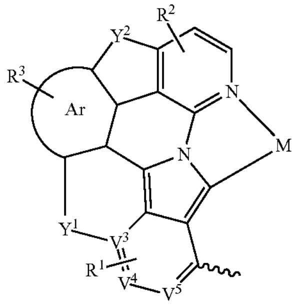

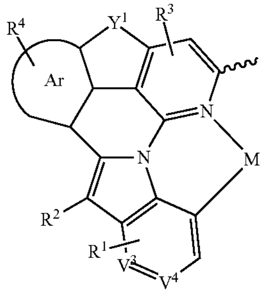

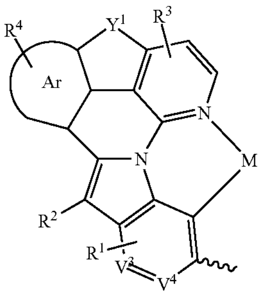

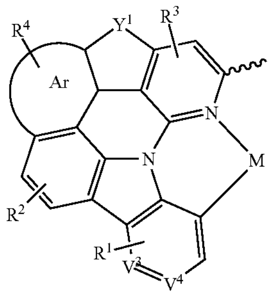

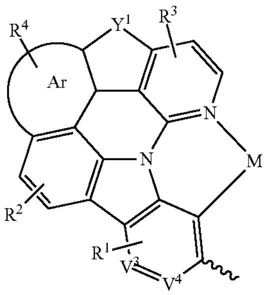

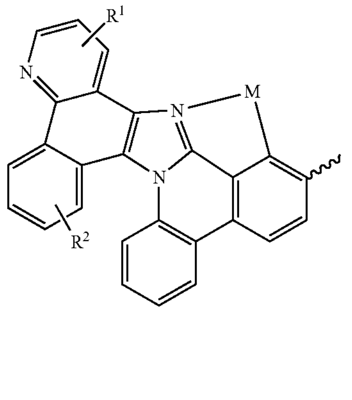

-continued

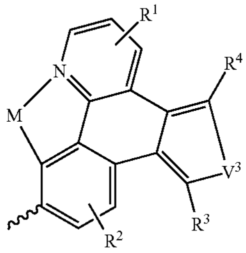

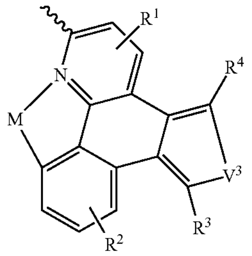

where:

N is nitrogen, each of $V^1$, $V^2$, $V^3$, $V^4$, $V^5$, and $V^6$, if present, is independently C, N, Si, O, S, Ge, P, As, Se, B, Al, or Bi, each of $X^1$, $X^2$, $Y^2$, $Y^3$, and $Y^4$ is independently present or absent, and each $X^1$, $X^2$, $Y^1$, $Y^2$, $Y^3$, and $Y^4$ present independently represents C, N, Si, O, S, Ge, P, As, Se, B, Al, or Bi, or valency permitting, $CR^7$, $SiR^7$, $GeR^7$, $NR^7$, P═O, As═O, B, $BR^7$, $AlR^7$, Bi═O, $CR^7R^8$, C═O, $SiR^7R^8$, $GeR^7R^8$, $NR^7$, $PR^7$, $PR^7R^8$, $R^7P$═O, $AsR^7$, $R^7As$═O, S═O, $SO_2$, Se═O, $SeO_2$, $BR^7$, $BR^7R^8$, $AlR^7$, $AlR^7R^8$, $R^7Bi$═O, or $BiR^7$, each of $L^1$, $L^2$, $L^3$, and $L^4$ is independently present or absent, and each $L^1$, $L^2$, $L^3$, and $L^4$ present independently represents a substituted or unsubstituted aryl, heteroaryl, or N-heterocyclic carbene, each of R, $R^1R^2$, $R^3$, $R^4$, $R^5$, $R^6$, $R^7$, and $R^8$ is independently absent or present as a single substituent or multiple substituents, valency permitting, and each R, $R^1$, $R^2$, $R^3$, $R^4$, $R^5$, $R^6$, $R^7$, and $R^8$ present independently represents deuterium, halogen, hydroxyl, thiol, nitro, cyanide, isocyanide, sulfinyl, mercapto, sulfo, carboxyl, hydrazino; substituted or unsubstituted: aryl, cycloalkyl, cycloalkenyl, heterocyclyl, heteroaryl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and each of

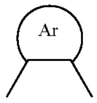

is independently present or absent, and each Ar present independently represents a substituted or unsubstituted aryl, heteroaryl, or N-heterocyclic carbene.

General Formulas V-XIII represent MADF emitters based on cyclic platinum (II) and palladium (II) complexes employing benzo-imidazo-phenanthridine and analogues.

General Formula V
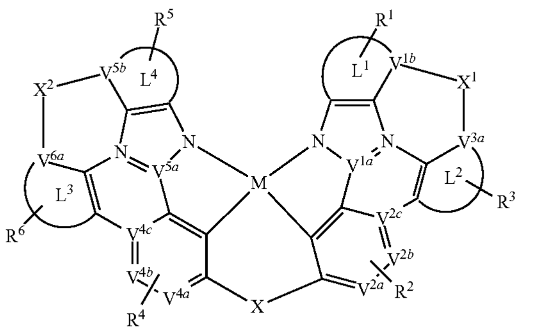
General Formula VI
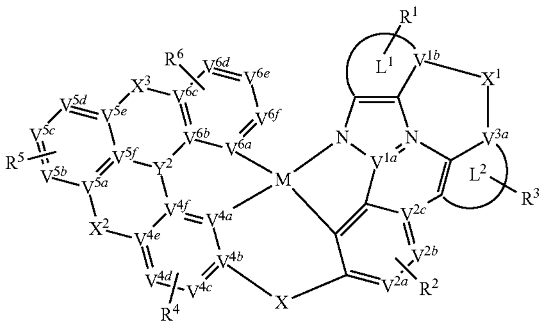
General Formula VII
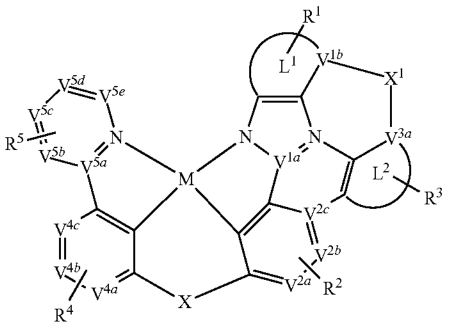
General Formula VIII
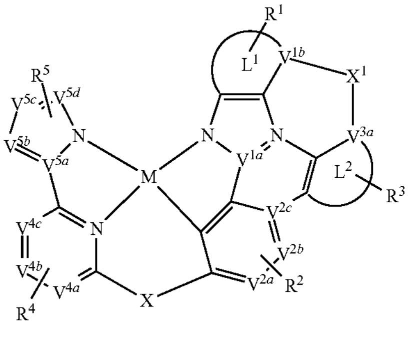
-continued
General Formula IX
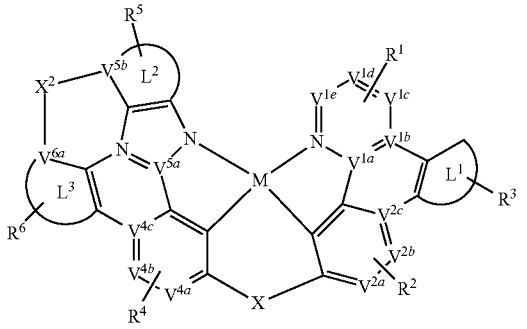
General Formula X
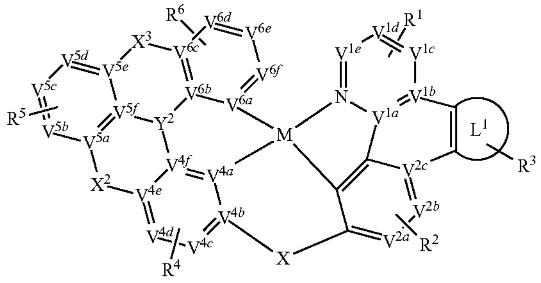
General Formula XI
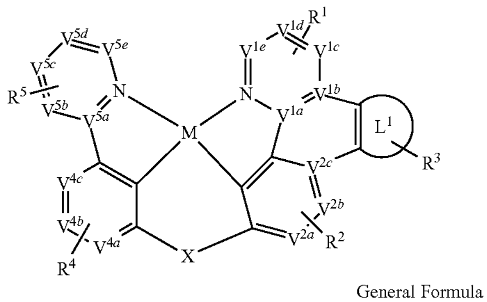
General Formula XII
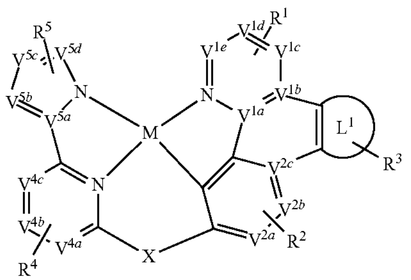
General Formula XIII
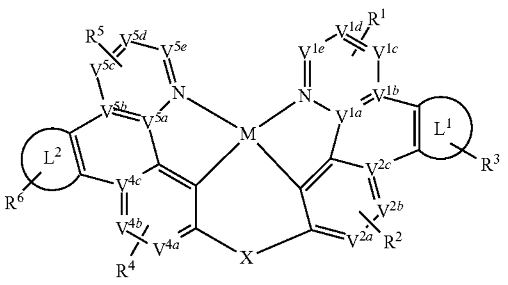
In General Formulas V-XIII,
M is Pt (II) or Pd (II),
N is nitrogen, each of $V^{1a}$-$V^{1f}$, $V^{2a}$-$V^{2f}$, $V^{3a}$-$V^{3f}$, $V^{4a}$-$V^{4f}$, $V^{5a}$-$V^{5f}$, and $V^{6a}$-$V^{6f}$, if present, is independently N, C, P, O, S, or Si, each of X, $X^1$, $X^2$, $X^3$, and $X^4$ is independently present or absent, and each X, $X^1$, $X^2$, $X^3$, and $X^4$ present independently represents a single bond, $CR^7R^8$, C═O, $SiR^7R^8$, $GeR^7R^8$, $NR^7$, $PR^7$, $PR^7R^8$, $R^7P$═O, $AsR^7$, $R^7As$═O, O, S, S═O, $SO_2$, Se, Se═O, $SeO_2$, $BR^7$, $BR^7R^8$, $AlR^7$, $AlR^7R^8$, $R^7Bi$═O, or $BiR^7$, each of $Y^1$ and $Y^2$ is independently CR, SiR, GeR, N, NR, P, P═O, As, As═O, B, BR, Al, AlR, Bi═O, or Bi, each of $L^1$, $L^2$, $L^3$, and $L^4$ is independently present or absent, and each $L^1$, $L^2$, $L^3$, and $L^4$ present independently represents a substituted or unsubstituted aryl, heteroaryl, or N-heterocyclic carbene, each of R, $R^1$, $R^2$, $R^3$, $R^4$, $R^5$, $R^6$, $R^7$, and $R^8$ is independently absent or present as a single substituent or multiple substituents, valency permitting, and each R, $R^1$, $R^2$, $R^3$, $R^4$, $R^5$, $R^6$, $R^7$, and $R^8$ present independently represents deuterium, halogen, hydroxyl, thiol, nitro, cyanide, isocyanide, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

Octahedral iridium (III) metal-assisted delayed fluorescent (MADF) emitters employing benzo-imidazo-phenanthridine are represented by General Formulas XIV-XVII.

General Formula XIV

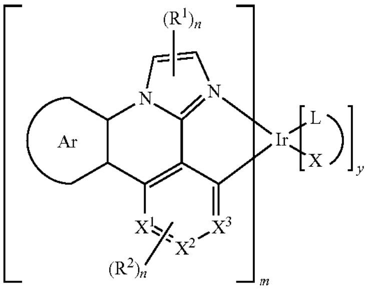

General Formula XV

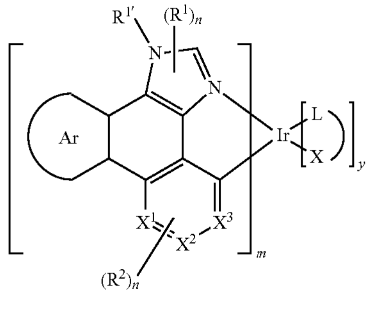

-continued

General Formula XVI

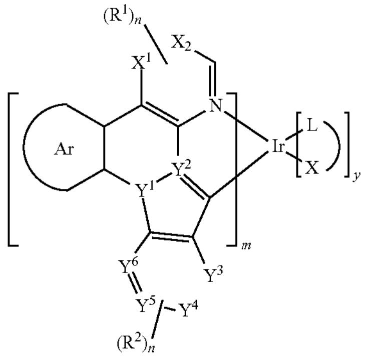

General Formula XVII

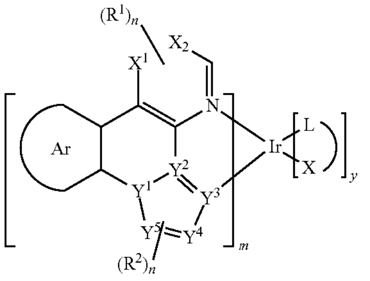

In General Formulas XIV-XVII, y=0, 1, or 2, and m+y=3. For m=3, the moieties can be the same or different. That is, when m=3, the three moieties can be the same, two of the moieties can be the same, or all three of the moieties can be different.

Implementations include a light emitting diode including a complex of General Formulas I-XVII, and a lighting device including such light emitting diode.

These general and specific aspects may be implemented using a device, system or method, or any combination of devices, systems, or methods. The details of one or more embodiments are set forth in the accompanying drawings and the description below. Other features, objects, and advantages will be apparent from the description and drawings, and from the claims.

DETAILED DESCRIPTION

Figure 1:
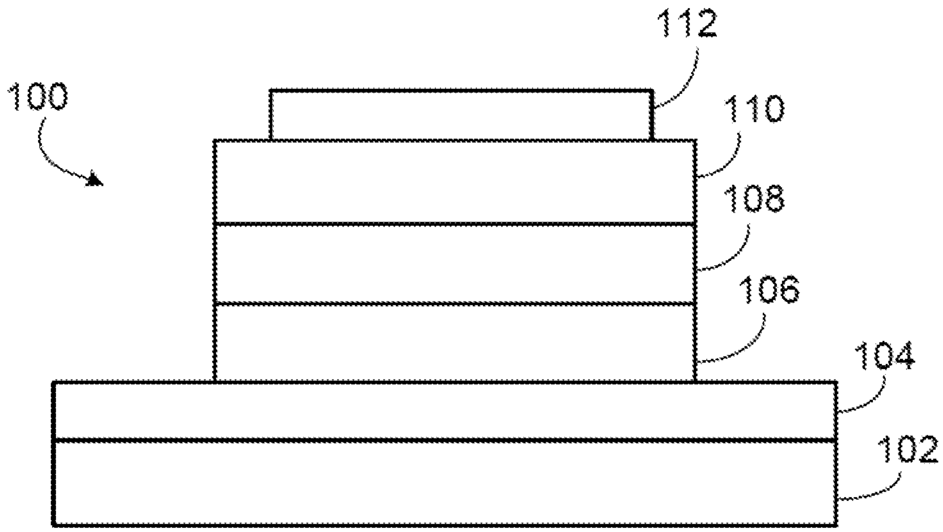
FIG. 1 depicts a cross-sectional view of an organic light-emitting device.

Cyclometalated Pt (II) and Pd (II) complexes have found wide applications as emitters for OLEDs in recent decades. Metal-assisted delayed fluorescent (MADF) emitters based on Pt (II) and Pd (II) complexes can exhibit both singlet and triplet excitons, resulting in a unity internal quantum efficiency and short lifetimes. Through the judicious design of cyclometalating ligands, MADF emitters can display singlet-triplet energy splitting.

MADF emitters based on cyclic platinum (II) and palladium (II) complexes employing benzo-imidazo-phenanthridine and analogues are disclosed. The triplet state consists mostly of the lower energy C^N portion of the molecules which is localized on the benzo-imidazo-phenanthridine (or analogues). The singlet energy can be reduced by extending the conjugation of benzo-imidazo-phenanthridine (or analogues) with no or little energy change of triplet energy. The small enemy gap between singlet and triplet allows excitons to be thermally promoted to the singlet state and efficiently emitted via thermally assisted delayed fluorescence (TADF) while the remaining triplet excitons can emit via the available efficient phosphorescent pathway. This class of emitters is suitable for full color displays and lighting applications.

MADF emitters employing benzo-imidazo-phenanthridine and analogues include compounds of General Formulas I-III shown below.

General Formula I

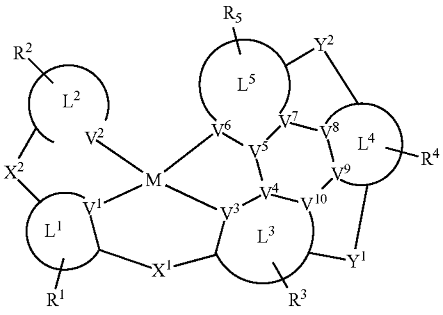

General Formula II

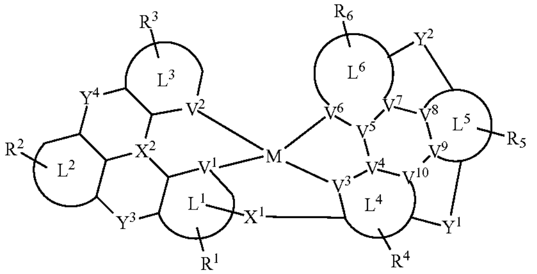

General Formula III

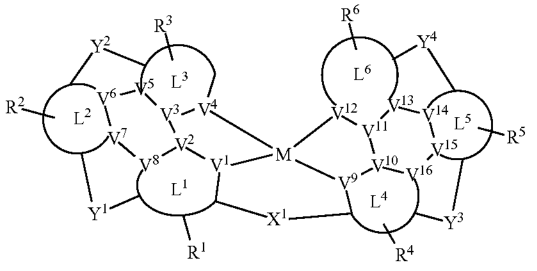

In General Formulas I-III:

M is Pt (II) or Pd (II), each of $V^1$-$V^{16}$, if present, is independently C, N, Si, O, S, Ge, P, As, Se, B, Al, or Bi, each of $X^1$, $X^2$, $Y^1$, $Y^2$, $Y^3$, and $Y^4$ is independently present or absent, and each $X^1$, $X^2$, $Y^1$, $Y^2$, $Y^3$, and $Y^4$ present independently represents C, N, Si, O, S, Ge, P, As, Se, B, Al, or Bi, or if valency permits, each independently represents $CR^7$, $SiR^7$, $GeR^7$, $NR^7$, P═O, As═O, B, $BR^7$, $AlR^7$, Bi═O, $CR^7R^8$, C═O, $SiR^7R^8$, $GeR^7R^8$, $NR^7$, $PR^7$, $PR^7R^8$, $R^7P$═O, $AsR^7$, $R^7As$═O, S═O, $SO_2$, Se═O, $SeO_2$, $BR^7$, $BR^7R^8$, $AlR^7$, $AlR^7R^8$, $R^7Bi$═O, or $BiR^7$, each of $L^1$, $L^2$, $L^3$, $L^4$, $L^5$, and $L^6$ is independently present or absent, and each $L^1$, $L^2$, $L^3$, $L^4$, $L^5$, and $L^6$ present independently represents a substituted or unsubstituted aryl, heteroaryl, or N-heterocyclic carbene, and each of R, $R^1$, $R^2$, $R^3$, $R^4$, $R^6$, $R^7$, and $R^8$ is independently absent or present as a single substituent or multiple substituents, valency permitting, and each R, $R^1$, $R^2$, $R^3$, $R^4$, $R^5$, $R^6$, $R^7$, and $R^8$ present independently represents deuterium, halogen, hydroxyl, thiol, nitro, cyanide, isocyanide, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

Examples of suitable substituents $R^1$-$R^8$ include:

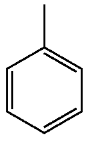
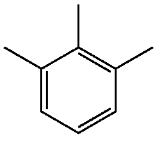
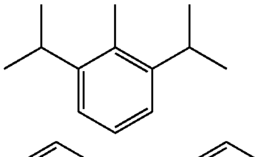
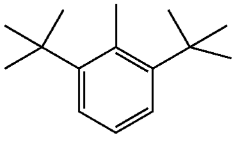
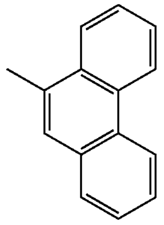
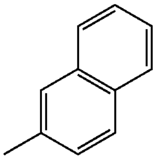
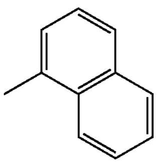
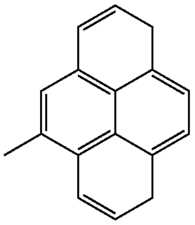
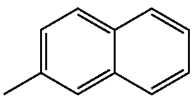
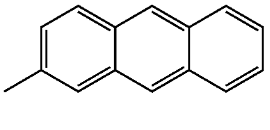
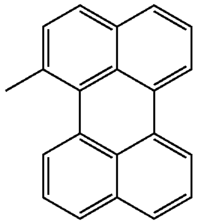

-continued
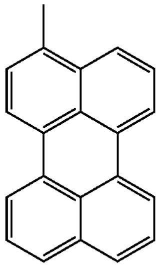
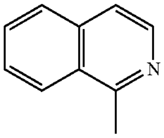
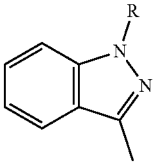
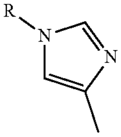
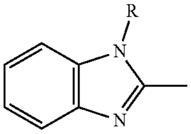
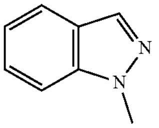
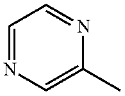
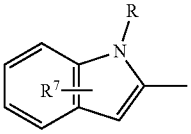
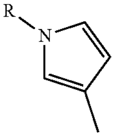
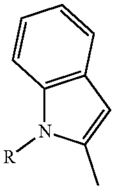
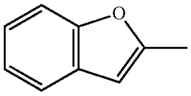
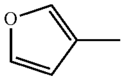
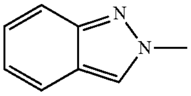
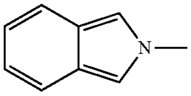
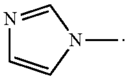
Examples of General Formulas I-III are shown below.
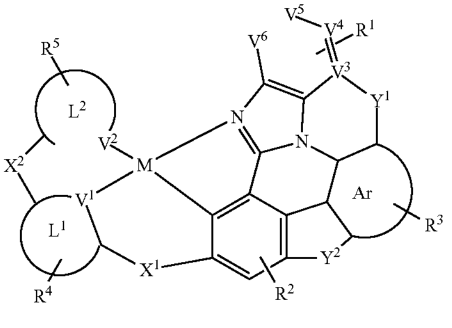
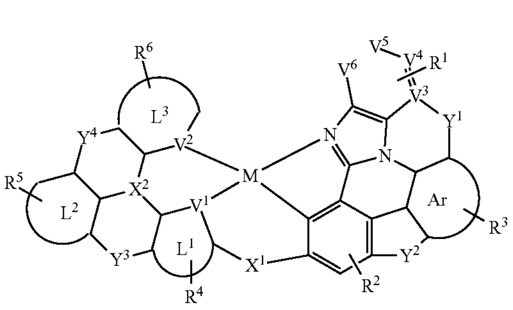
-continued
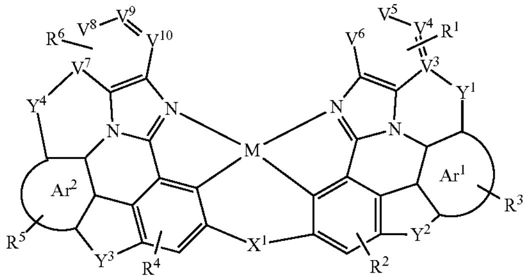
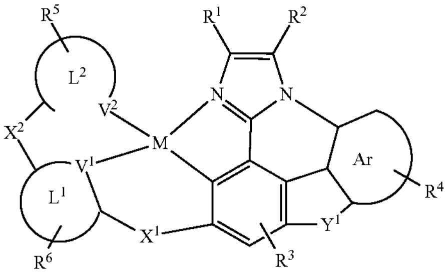
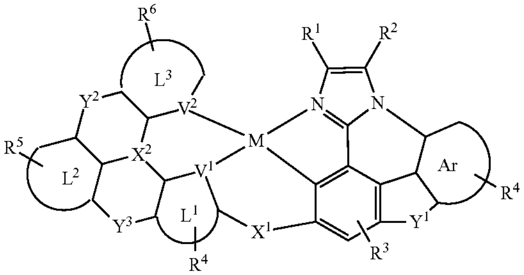
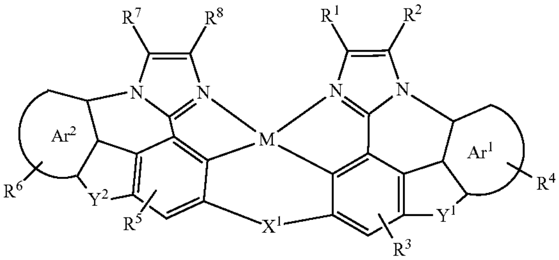
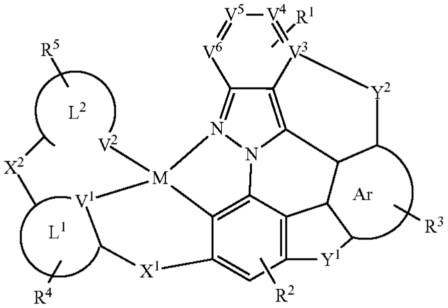
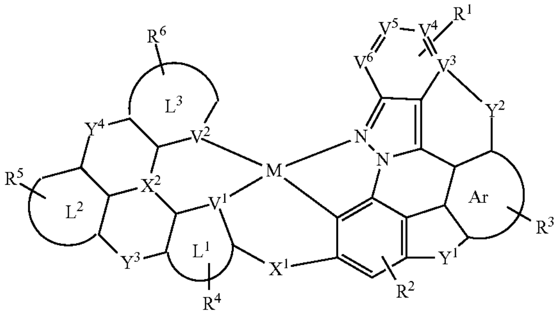

-continued
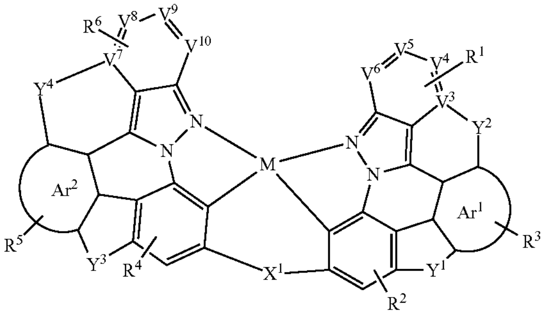
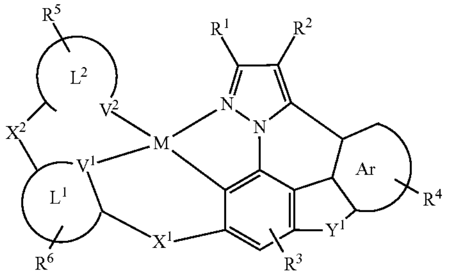
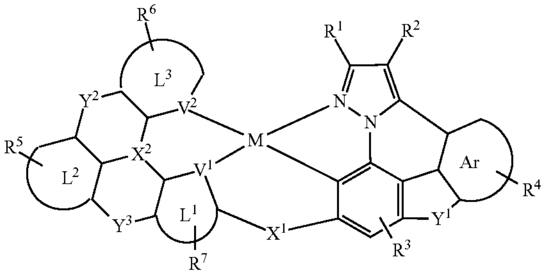
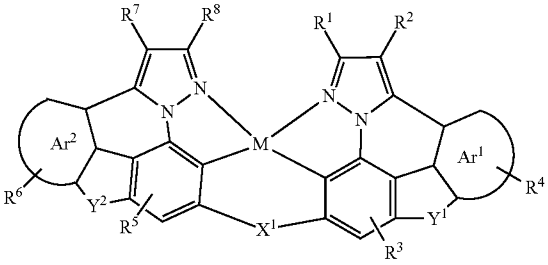
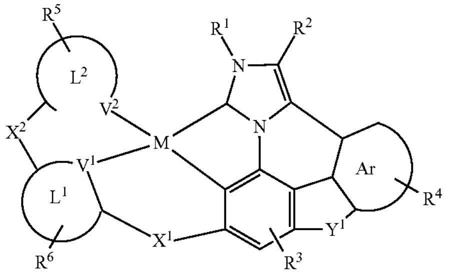
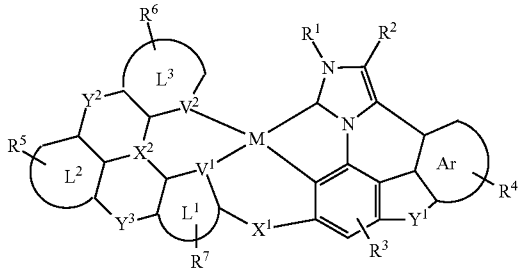
-continued
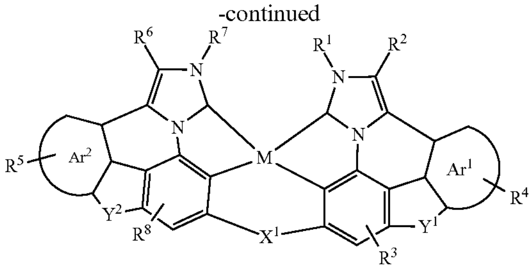
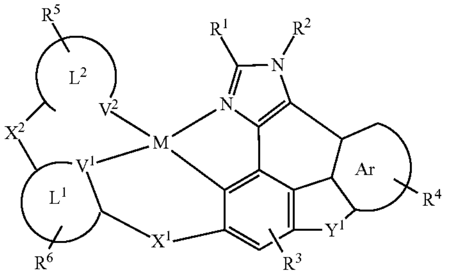
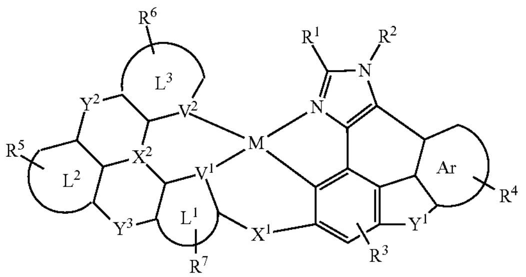
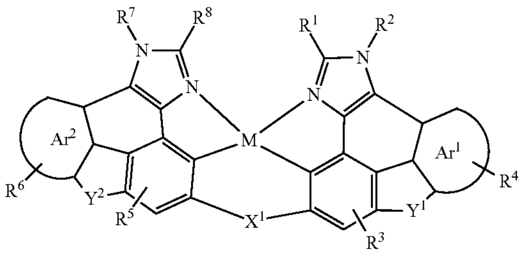
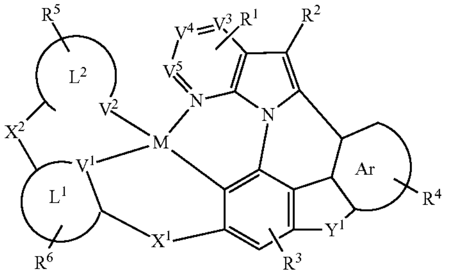
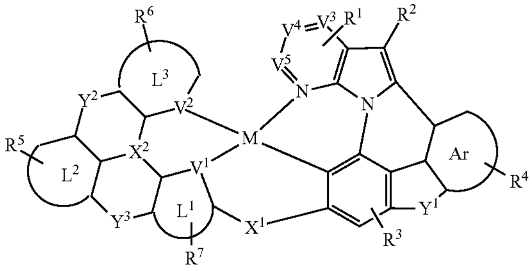

-continued
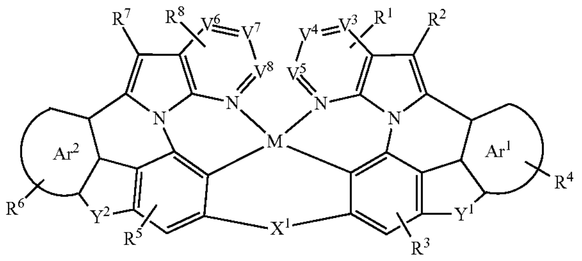
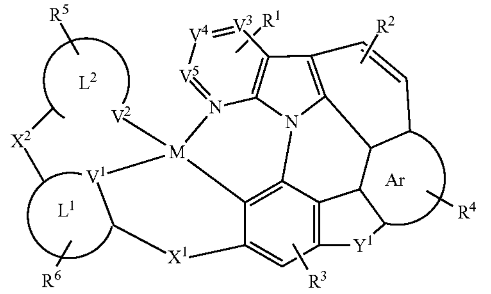
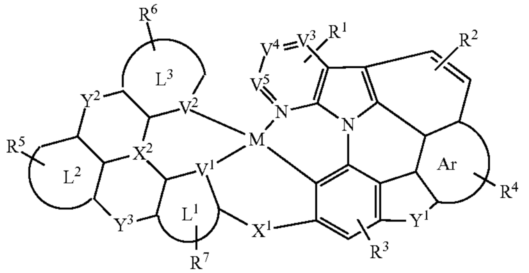
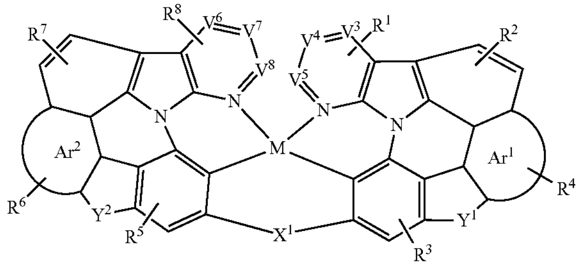
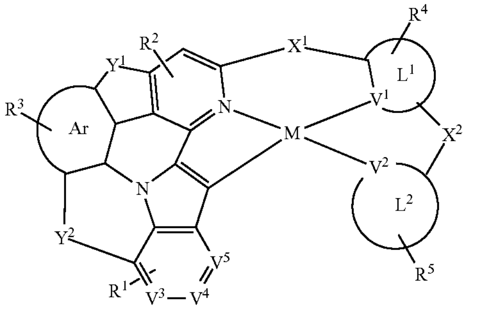
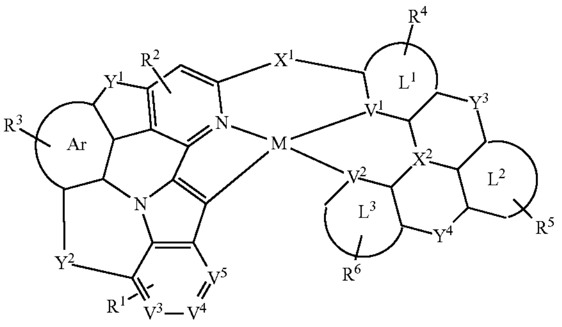
-continued
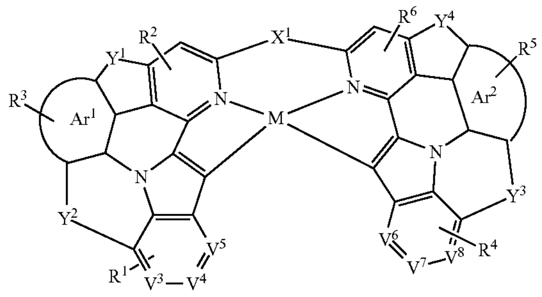
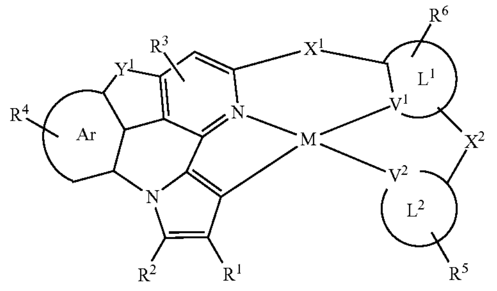
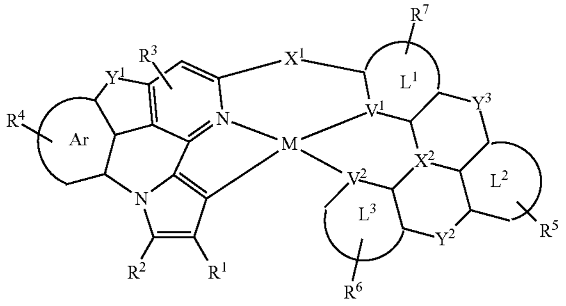
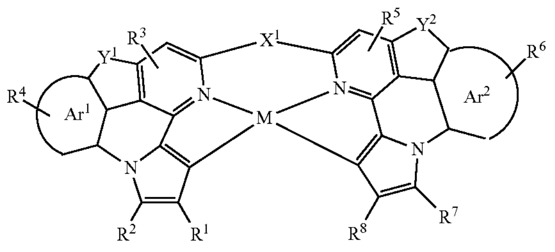
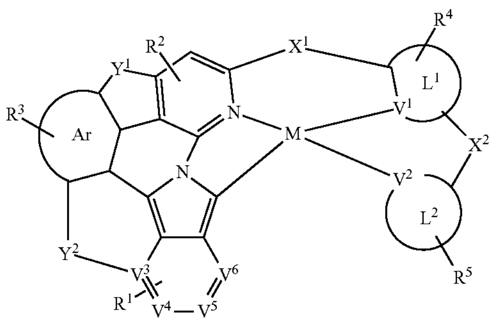

-continued
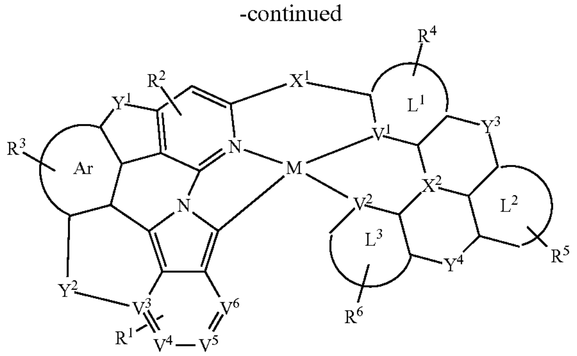
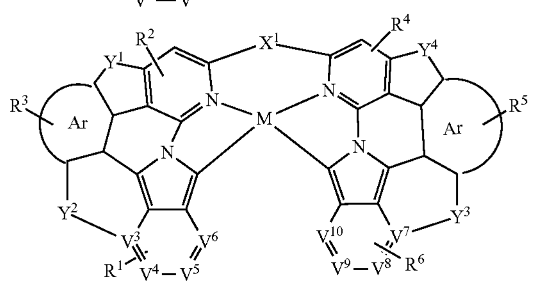
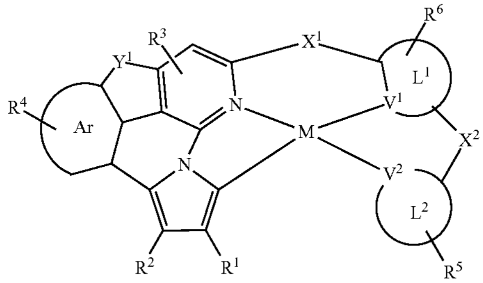
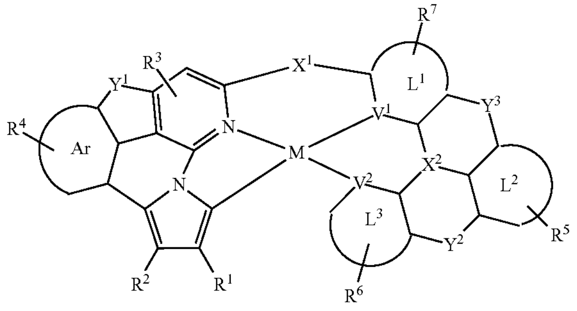
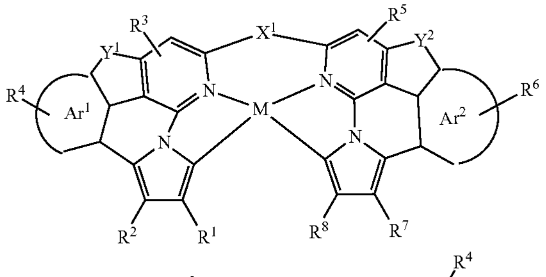
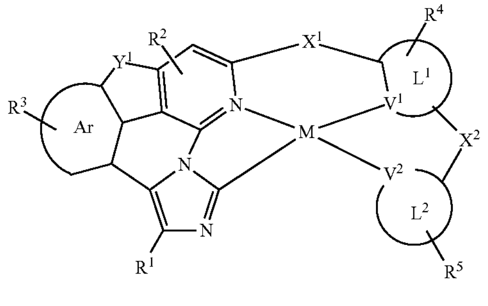
-continued
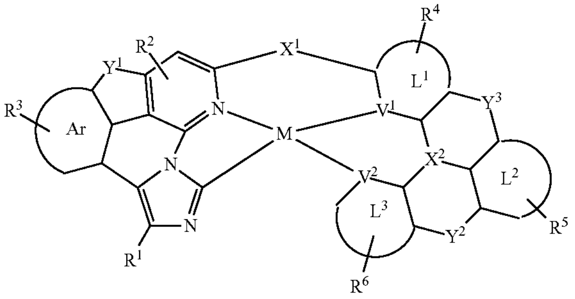
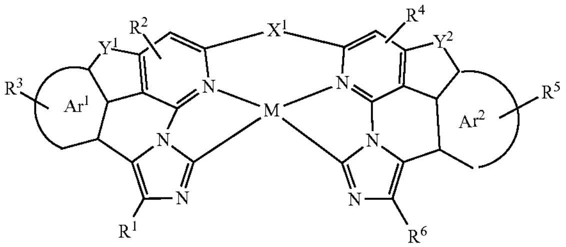
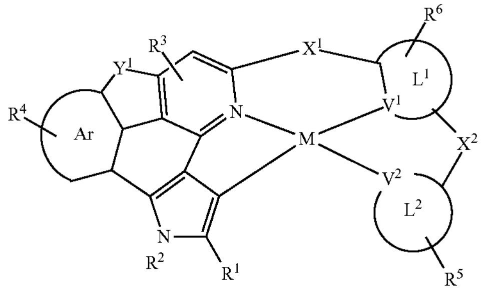
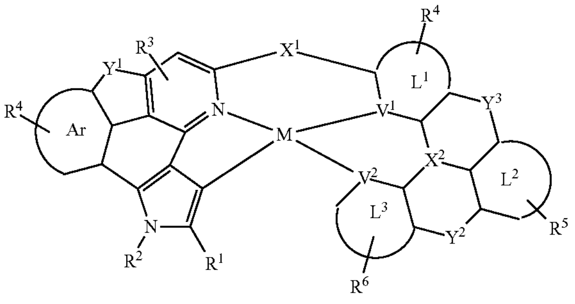
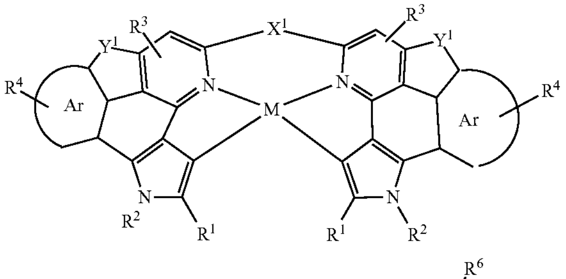
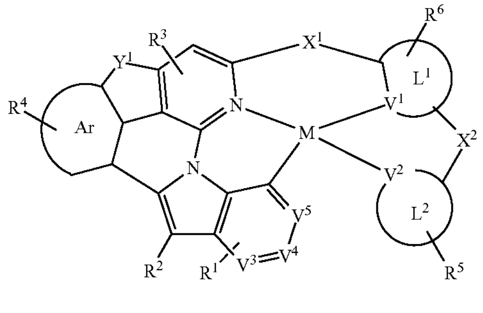

-continued
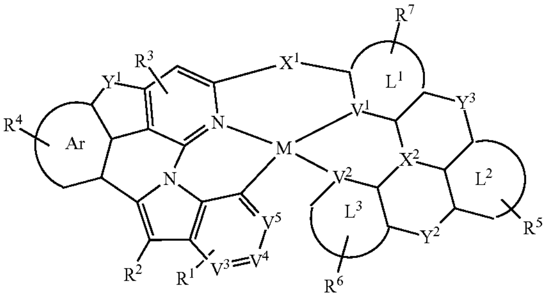
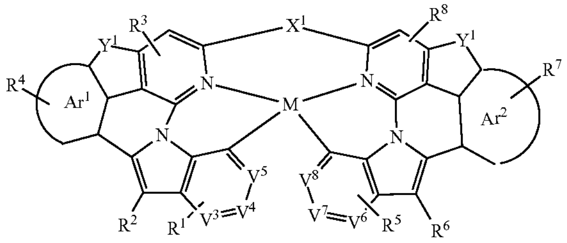
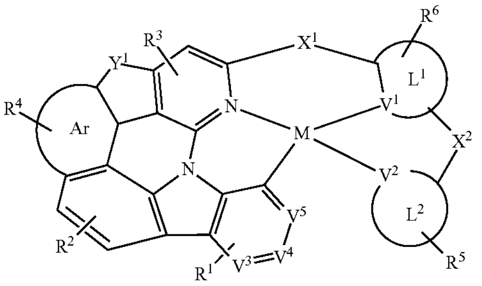
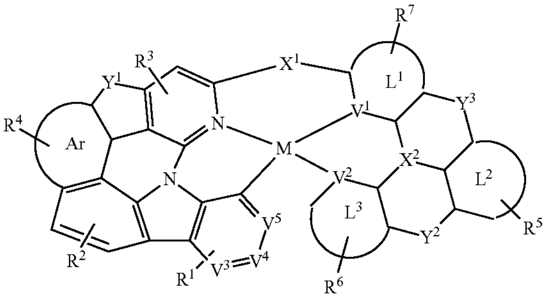
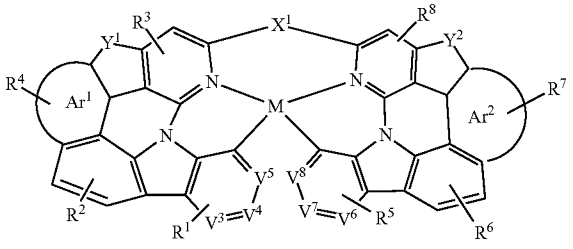
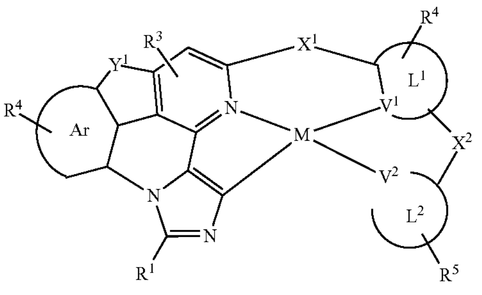
-continued
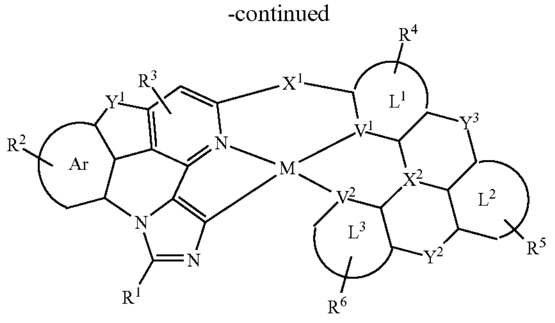
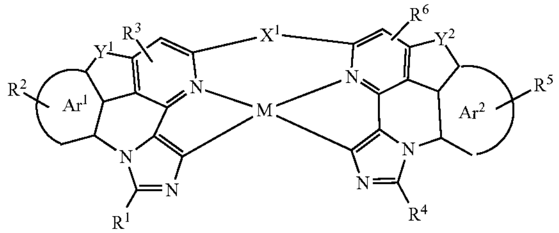
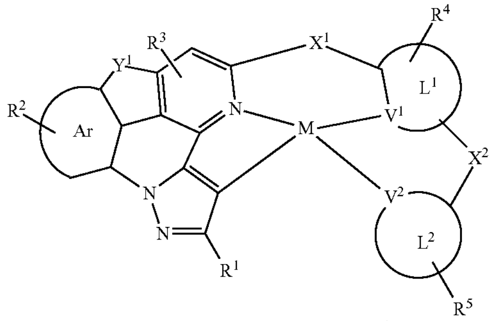
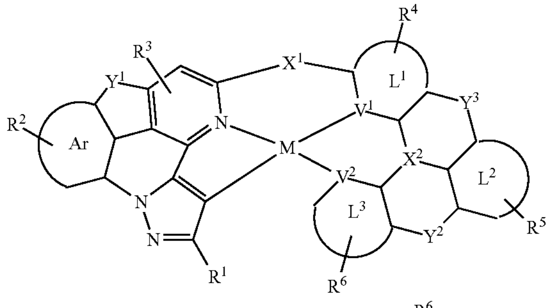
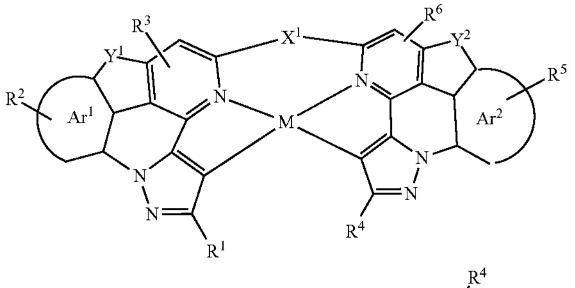
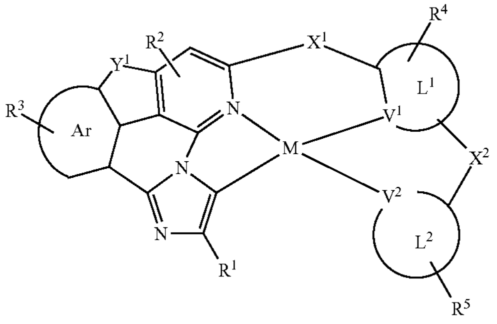

-continued
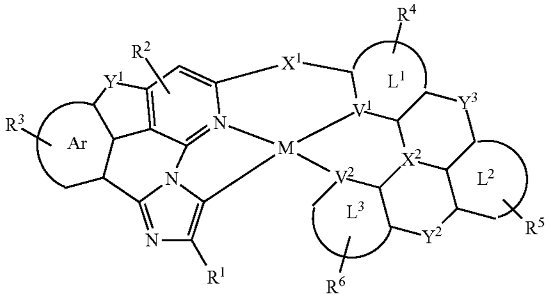
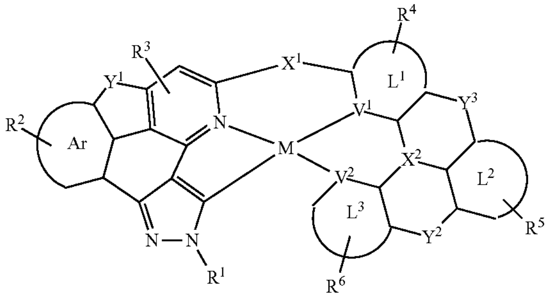
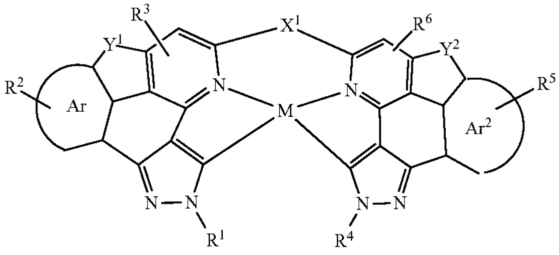
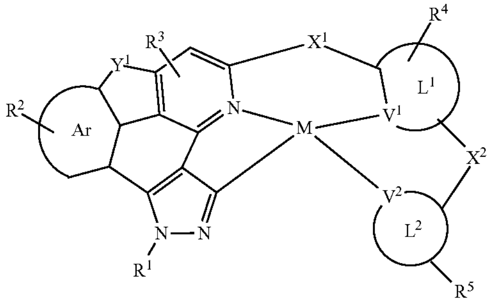
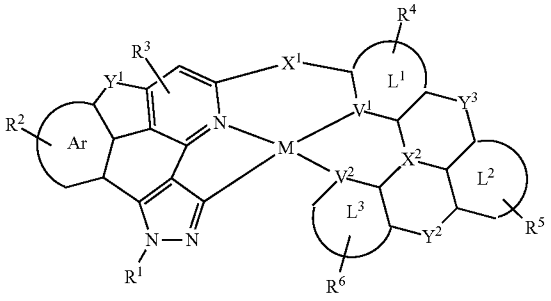
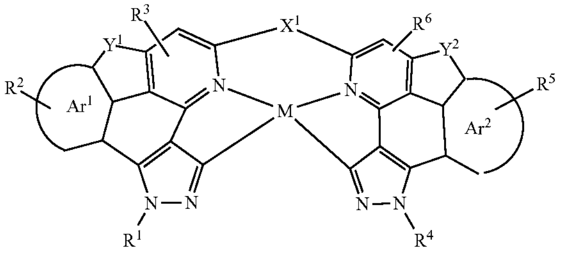
-continued
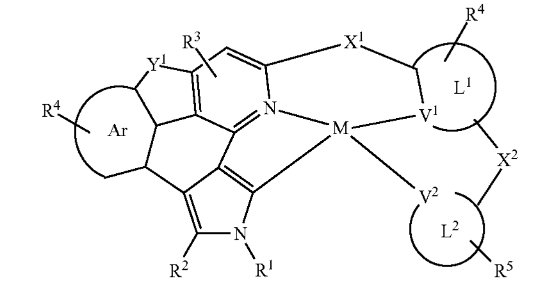
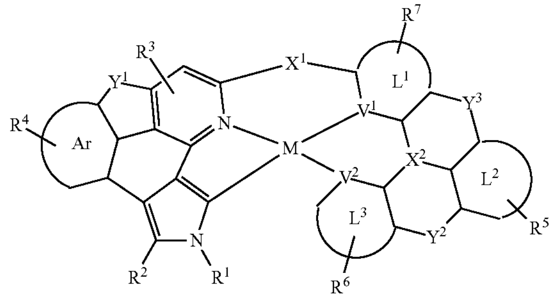
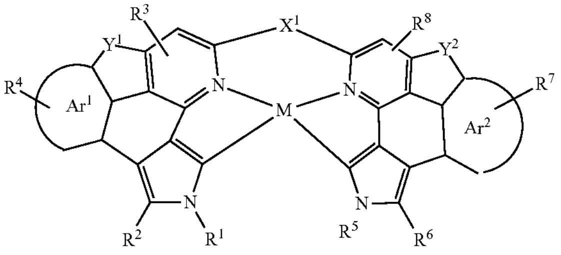
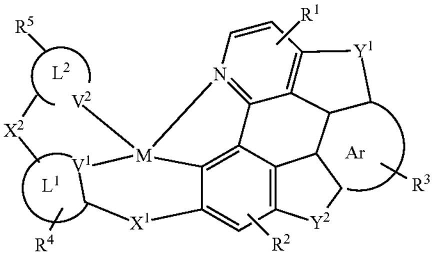
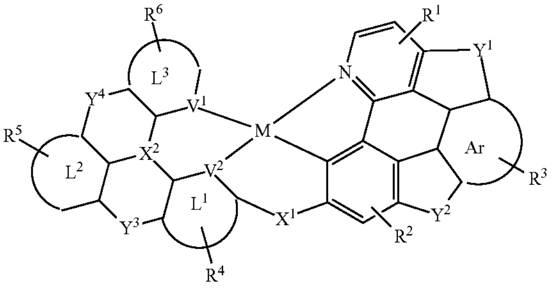
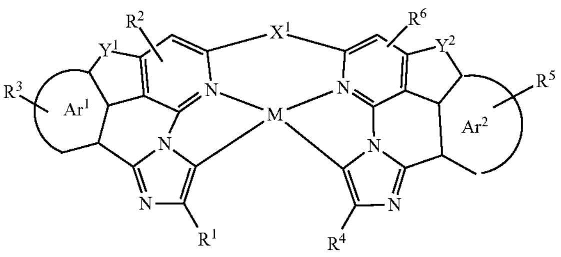

-continued
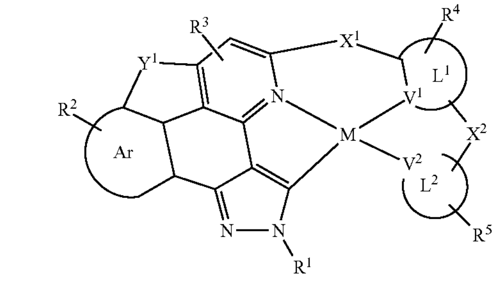
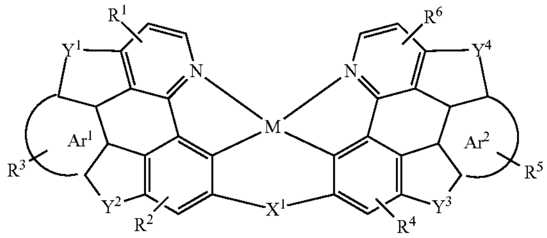
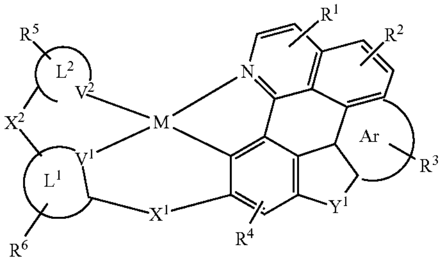
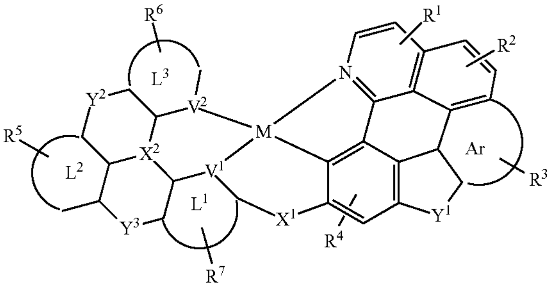
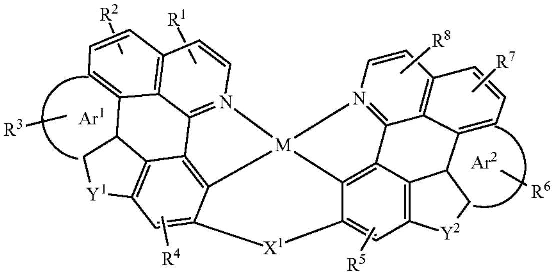
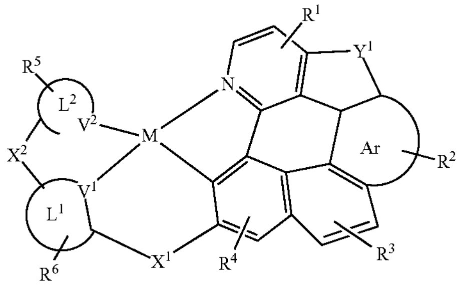
-continued
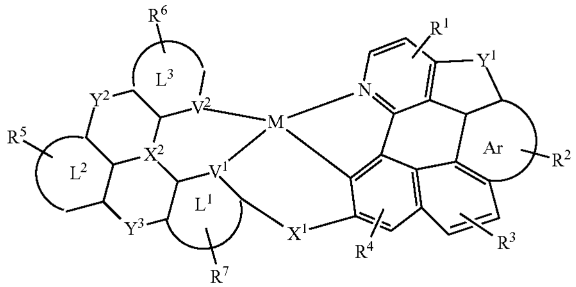
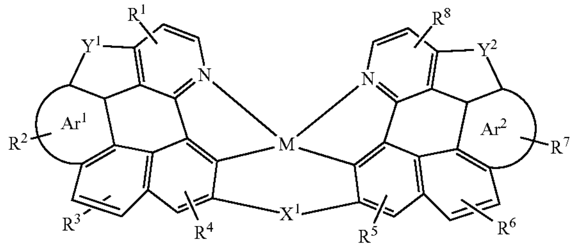
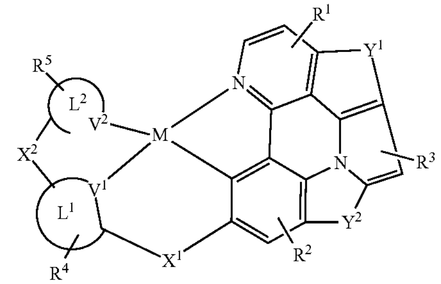
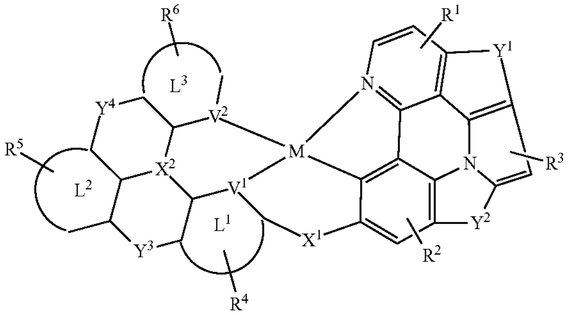
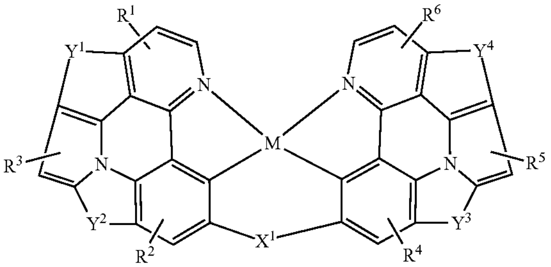
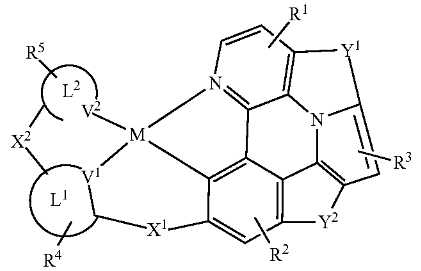

-continued
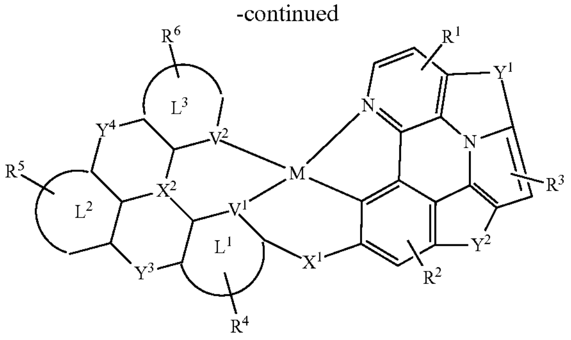
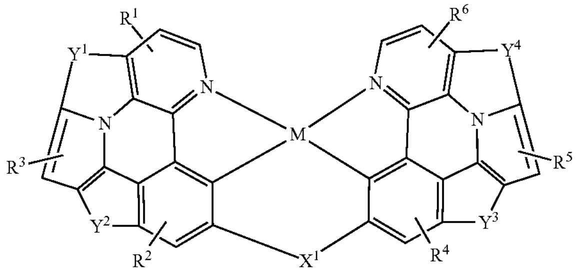
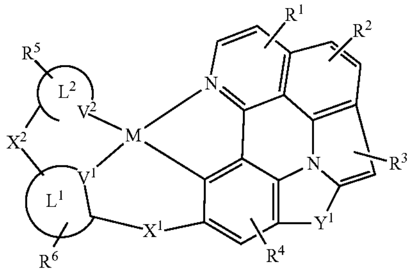
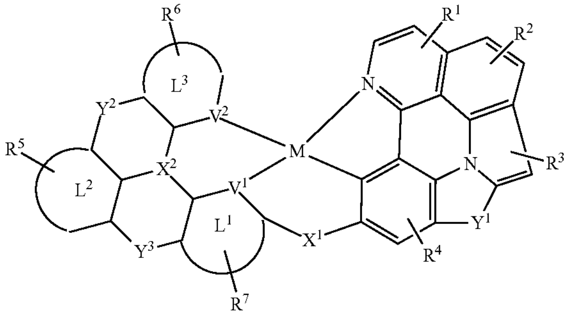
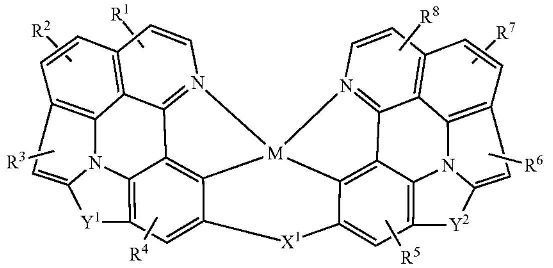
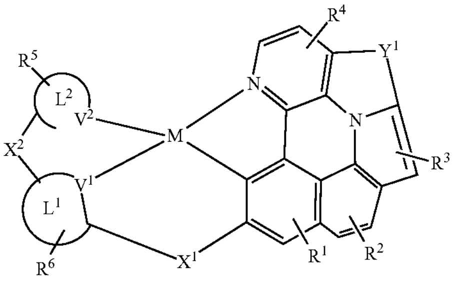
-continued
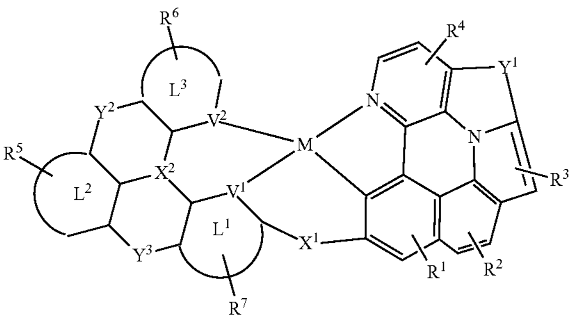
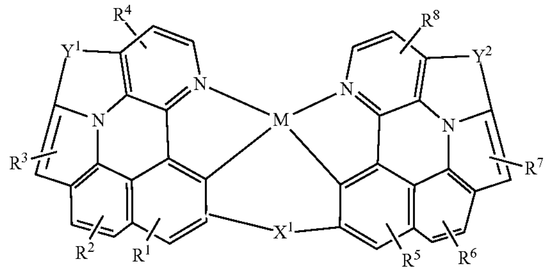
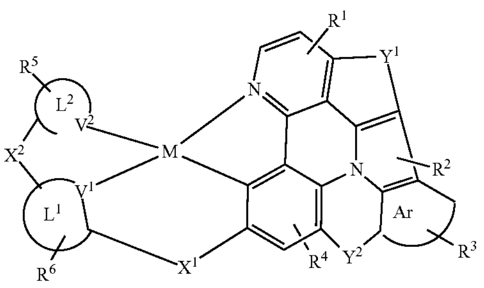
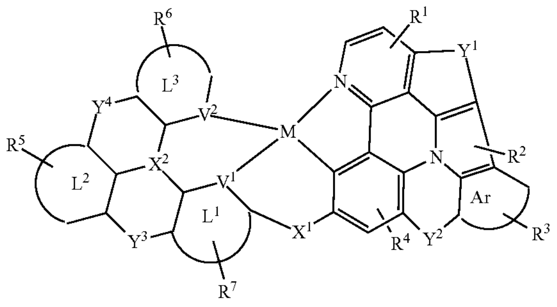
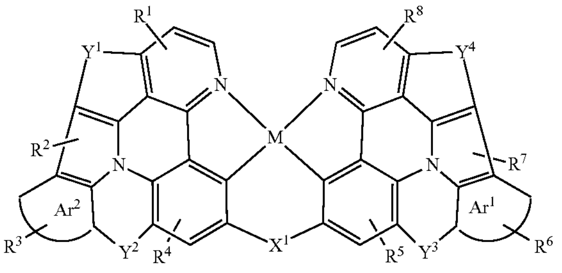
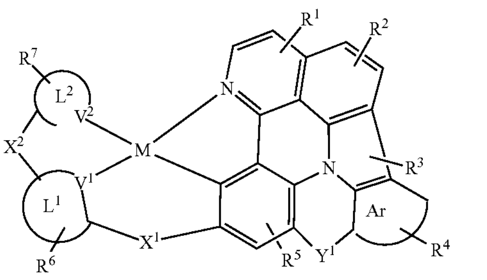

-continued
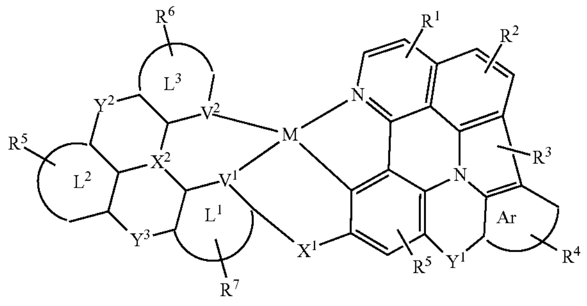
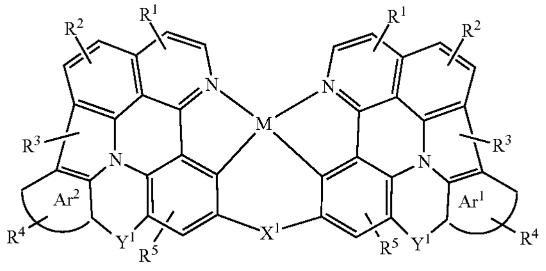
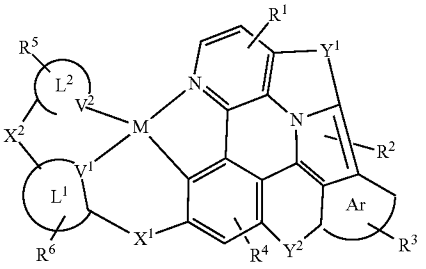
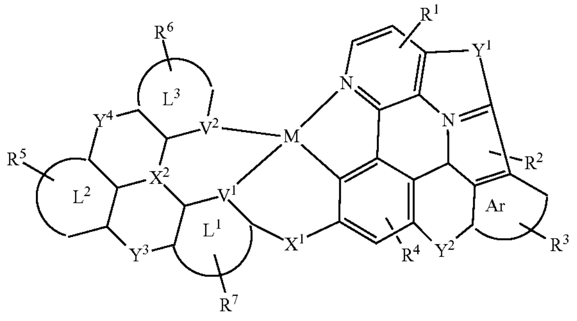
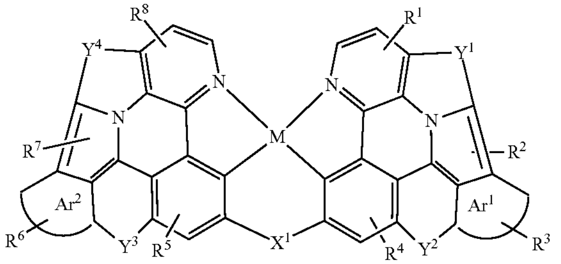
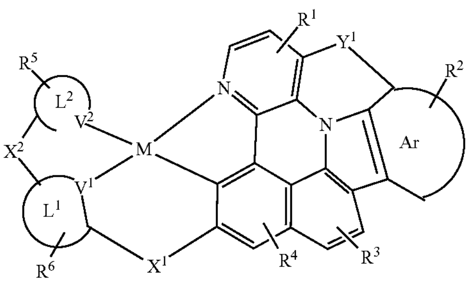
-continued
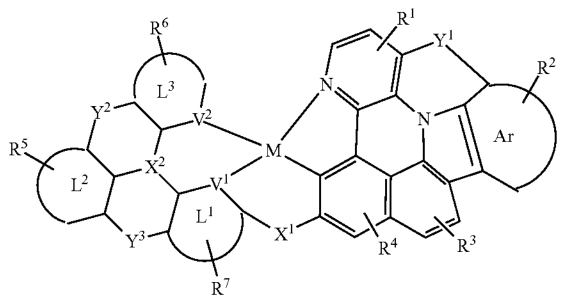
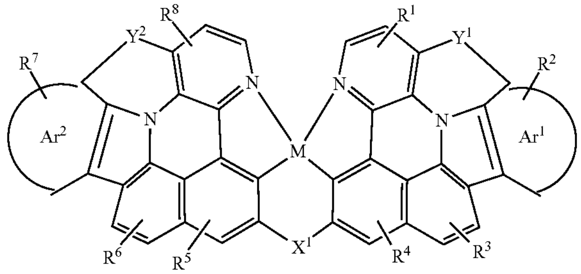
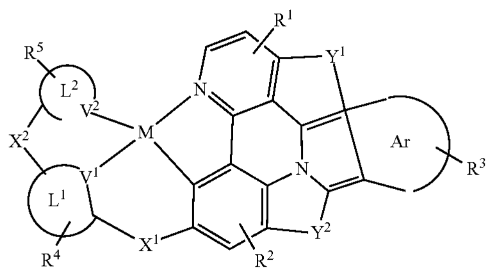
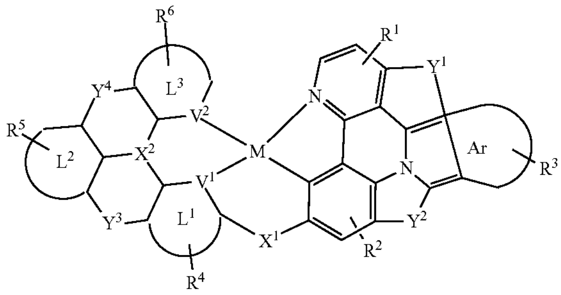
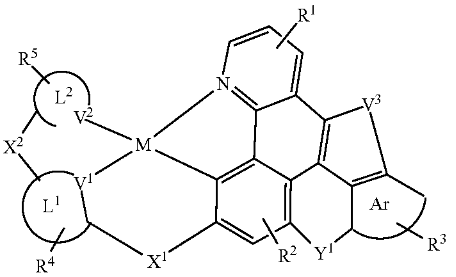
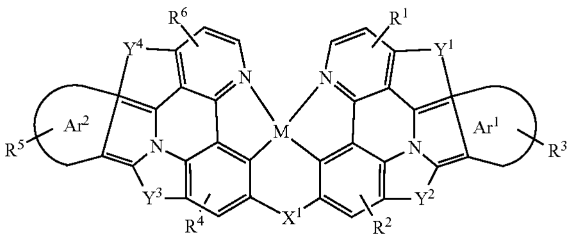

-continued
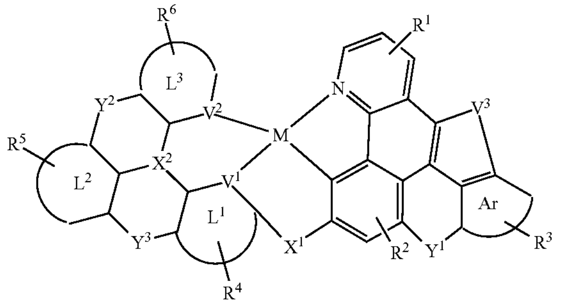
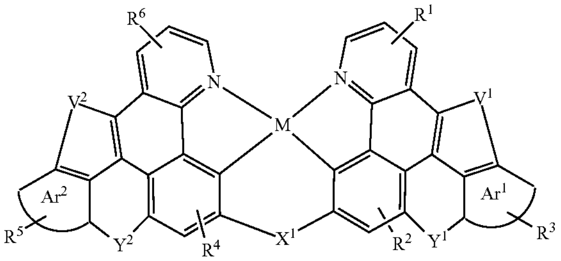
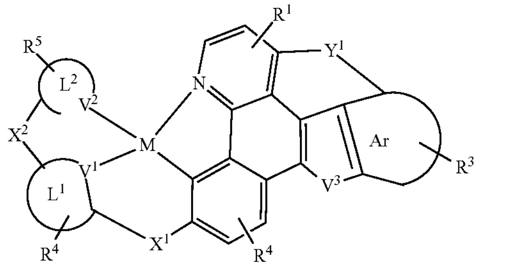
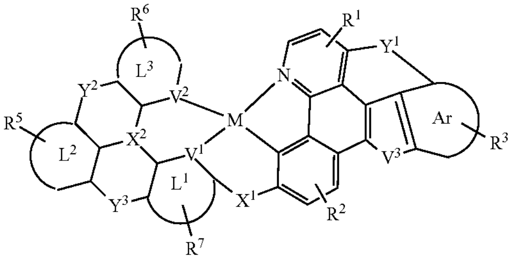
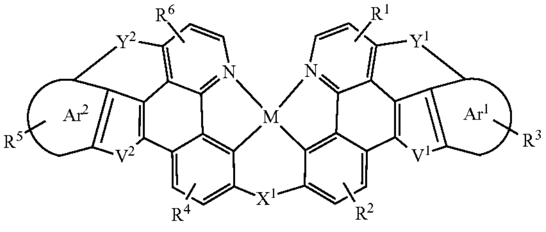
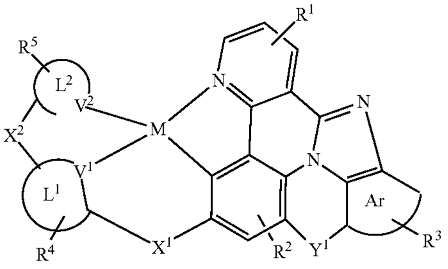
-continued
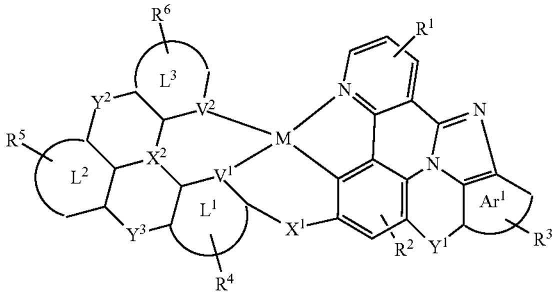
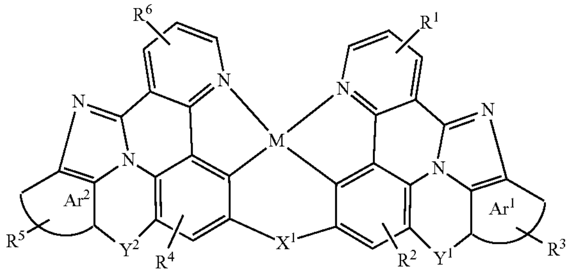
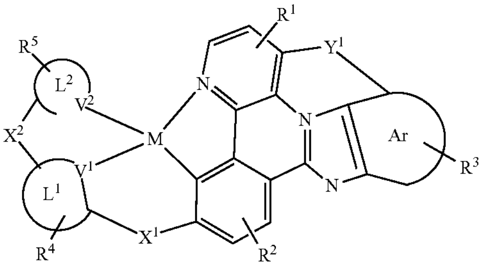
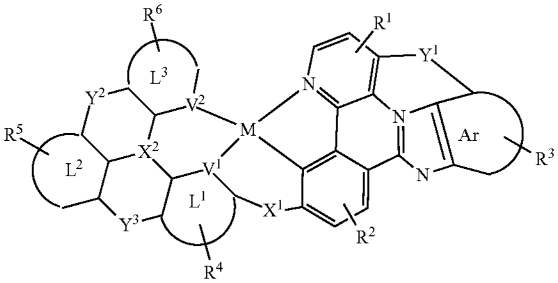
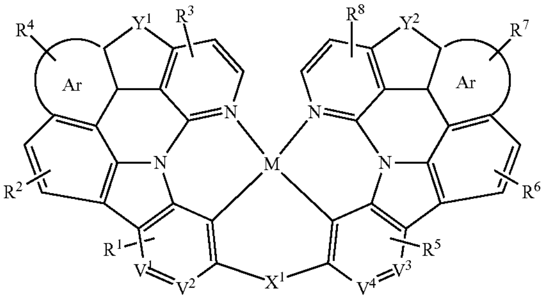
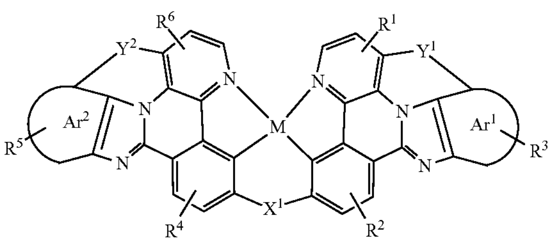

-continued
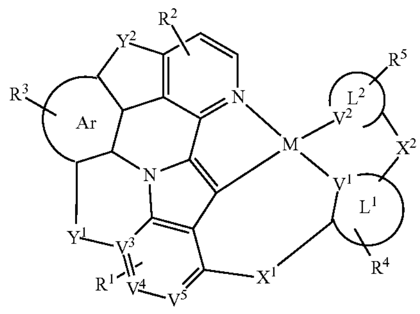
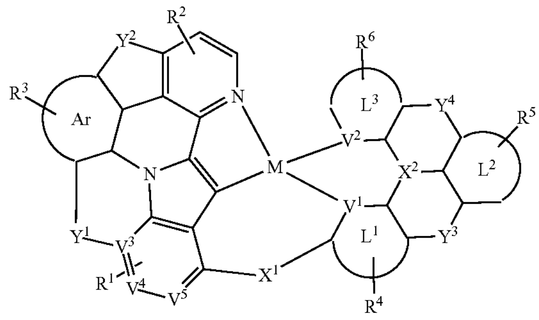
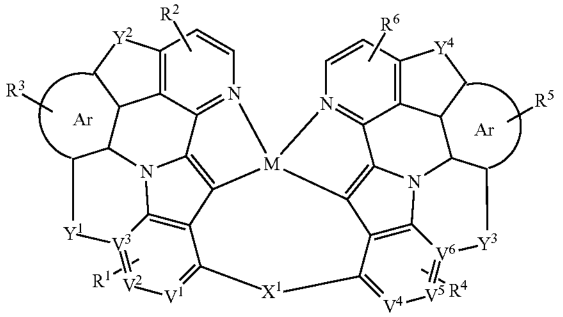
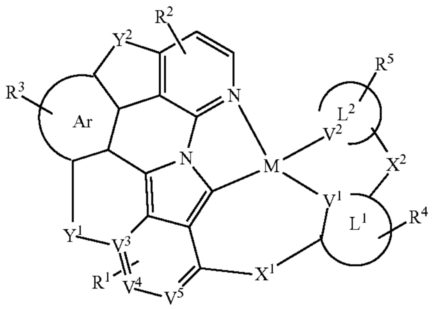
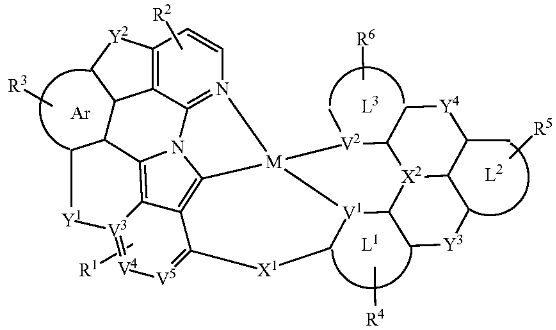
-continued
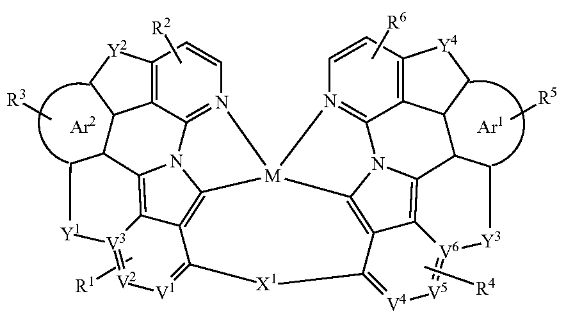
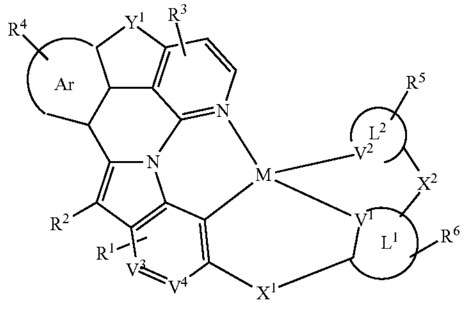
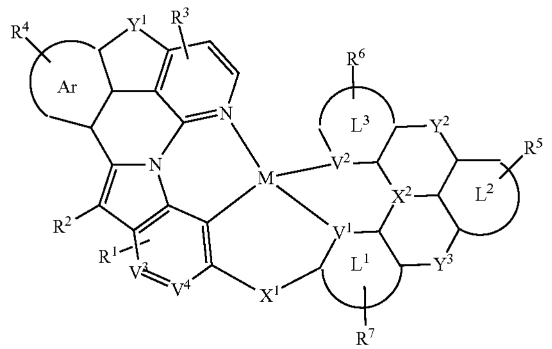
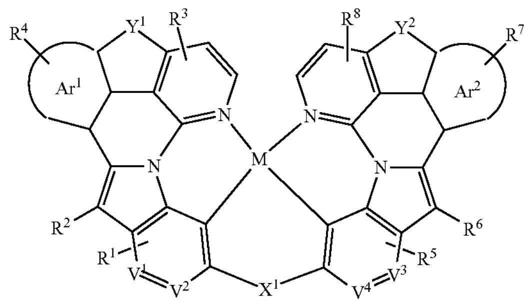
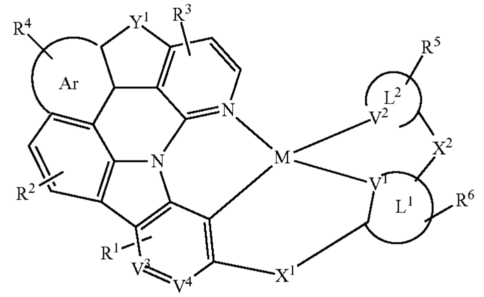

-continued

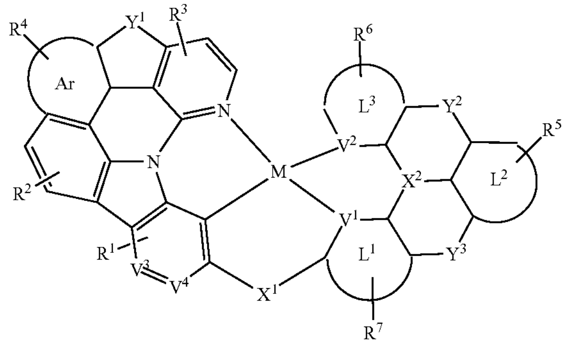

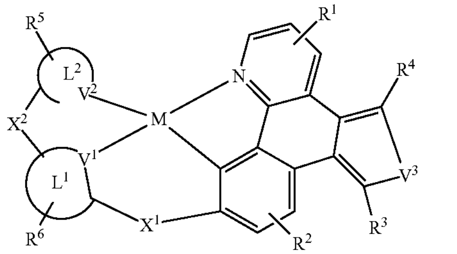

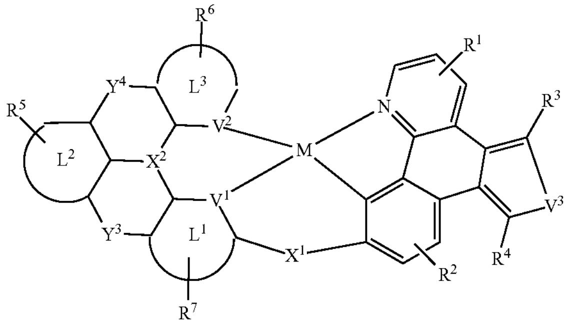

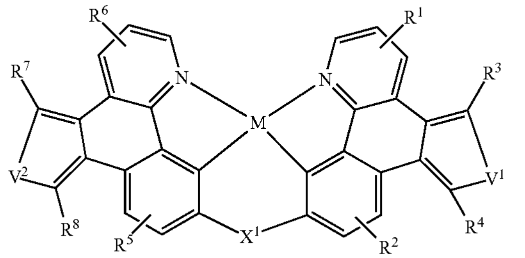

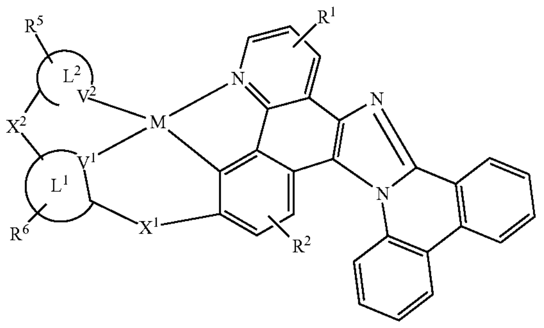

-continued

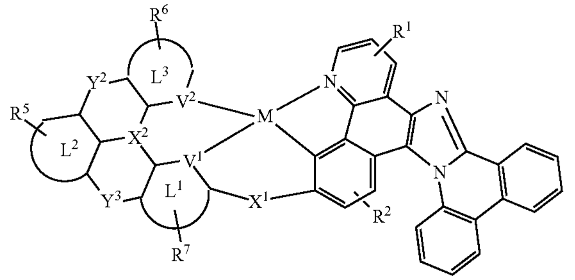

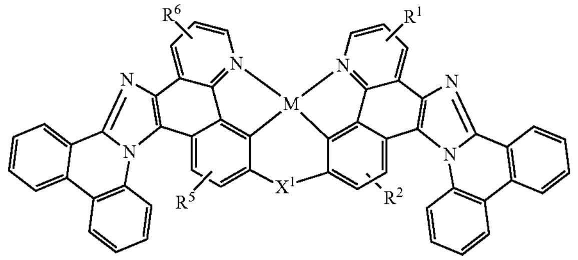

In these implementations of General Formulas I-III:

M is Pt (II) or Pd (II),

N is nitrogen, each of $V^1$-$V^6$, if present, is independently C, N, Si, O, S, Ge, P, As, Se, B, Al, or Bi, each of $X^1$, $X^2$, $Y^1$, $Y^2$, $Y^3$, and $Y^4$ is independently present or absent, and if present, each $X^1$, $X^2$, $Y^1$, $Y^2$, $Y^3$, and $Y^4$ independently represents C, N, Si, O, S, Ge, P, As, Se, B, Al, or Bi, or valency permitting, each independently represents $CR^7$, $SiR^7$, $GeR^7$, $NR^7$, P═O, As═O, B, $BR^7$, $AlR^7$, Bi═O, $CR^7R^8$, C═O, $SiR^7R^8$, $GeR^7R^8$, $NR^7$, $PR^7$, $PR^7R^8$, $R^7P$═O, $AsR^7$, $R^7As$═O, S═O, $SO_2$, Se═O, $SeO_2$, $BR^7$, $BR^7$, $R^8$, $AlR^7$, $AlR^7R^8$, $R^7Bi$═O, or $BiR^7$, each of $L^1$, $L^2$, $L^3$, and $L^4$ is independently present or absent, and each $L^1$, $L^2$, $L^3$, and $L^4$ present independently represents a substituted or unsubstituted aryl, heteroaryl, or N-heterocyclic carbene, each of R, $R^1$, $R^2$, $R^3$, $R^4$, $R^5$, $R^6$, $R^7$, and $R^8$ is independently absent or present as a single substituent or multiple substituents, valency permitting, and each R, $R^1$, $R^2$, $R^3$, $R^4$, $R^5$, $R^6$, $R^7$, and $R^8$ present independently represents deuterium, halogen, hydroxyl, thiol, nitro, cyanide, isocyanide, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

Examples of suitable substituents $R^1$-$R^8$ include:

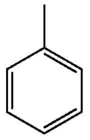 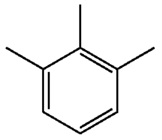 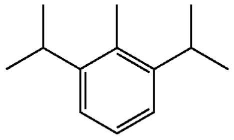

-continued
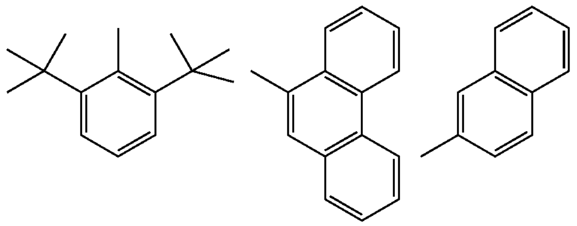
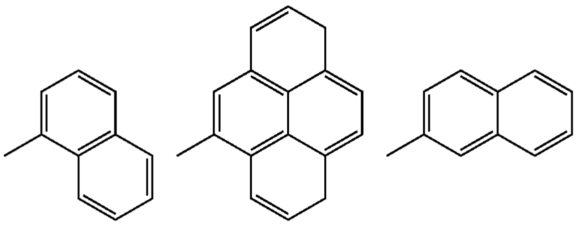
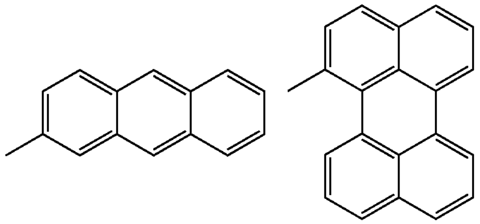
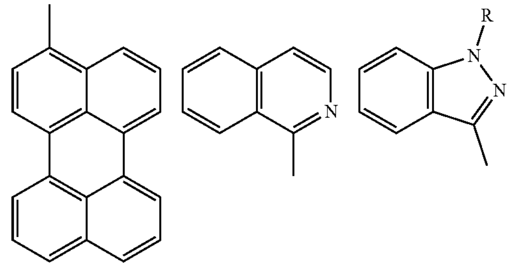
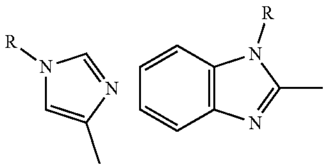
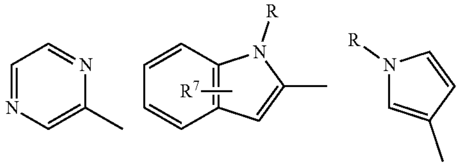
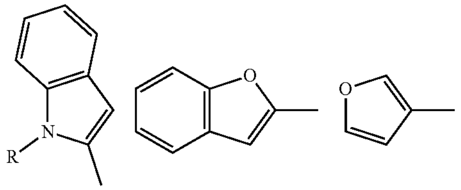
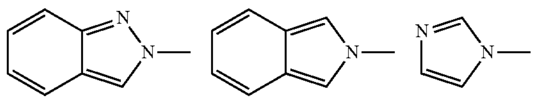
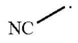
In the implementations of General Formulas I-III, each of
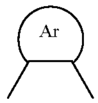
is independently present or absent, and each Ar present independently represents a substituted or unsubstituted aryl, heteroaryl, or N-heterocyclic carbene, including the following moieties:
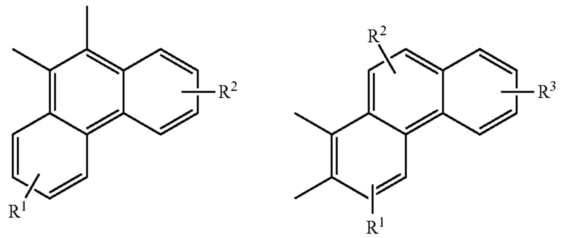
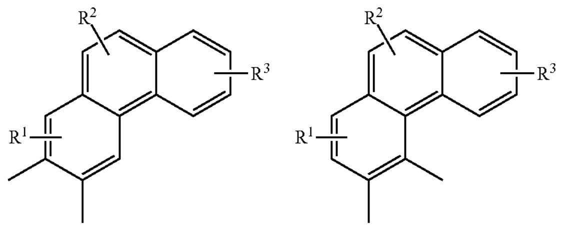
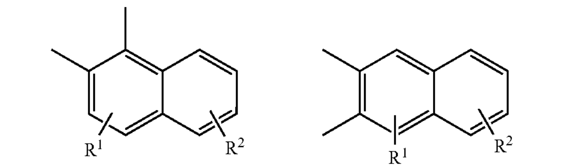
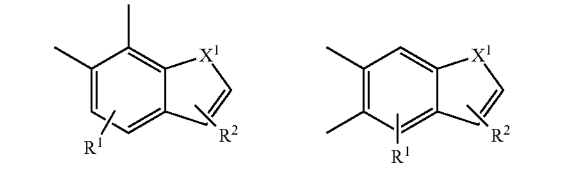
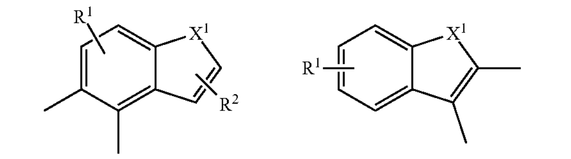
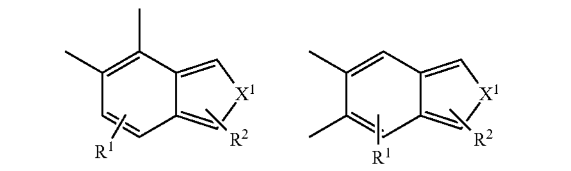
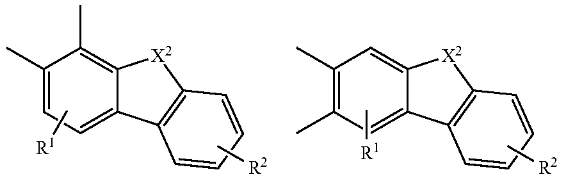

-continued
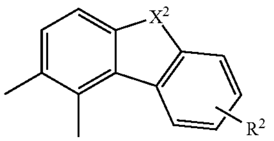
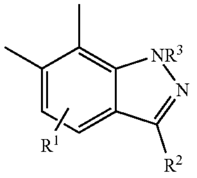
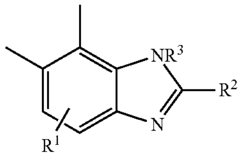
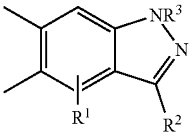
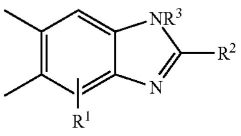
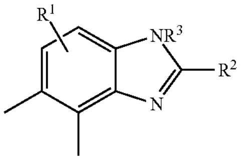
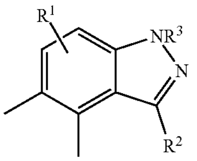
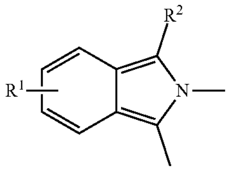
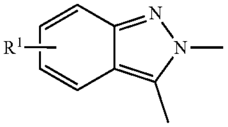
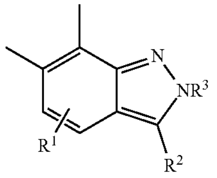
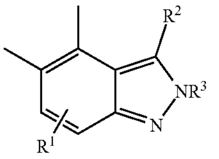
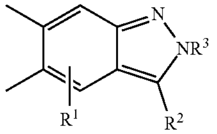
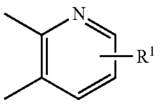
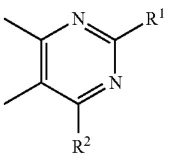
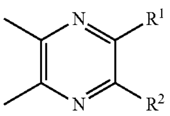
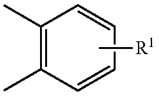
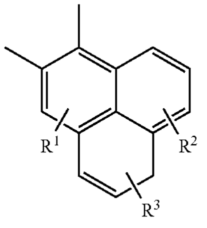
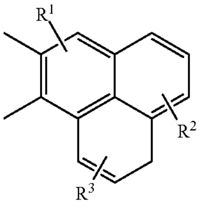
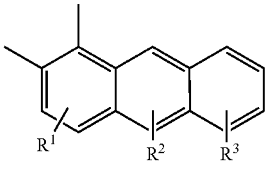
-continued
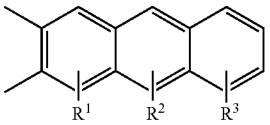
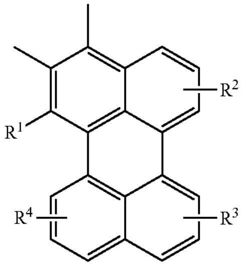
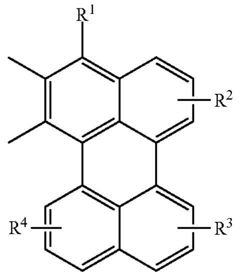
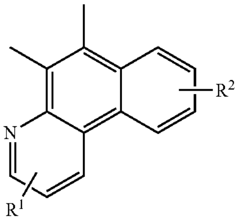
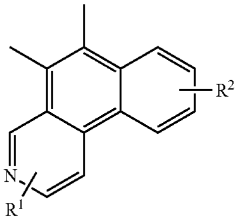
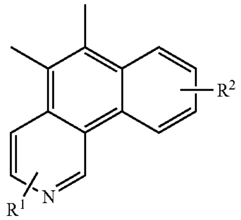
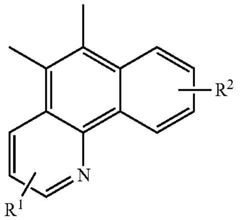
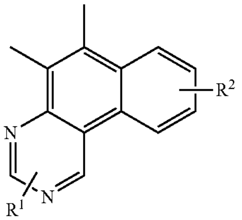
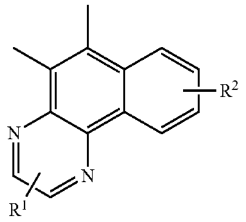
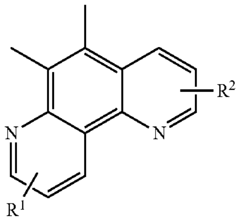
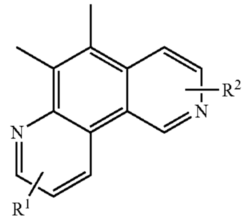
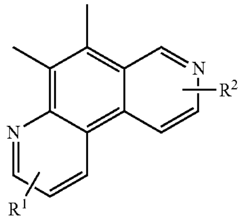
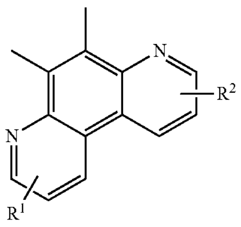
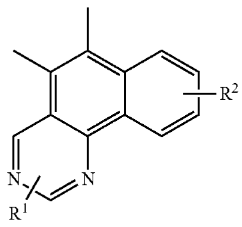

-continued
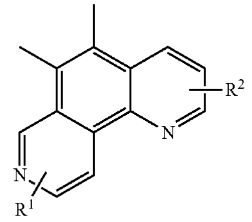
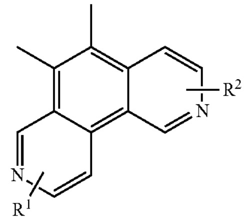
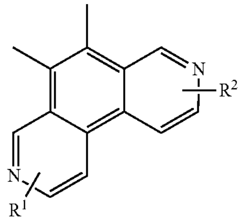
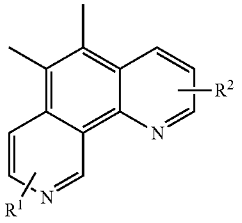
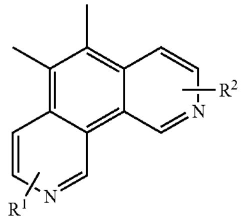
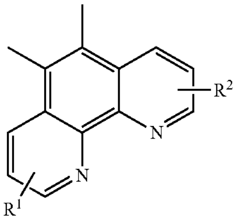
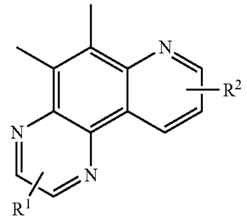
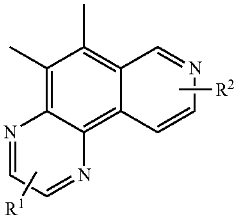
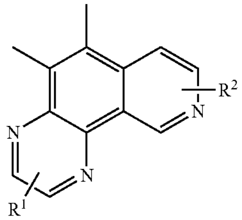
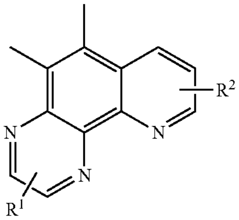
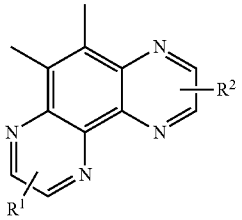
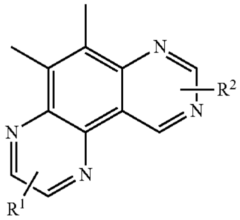
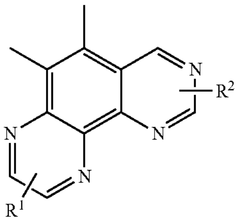
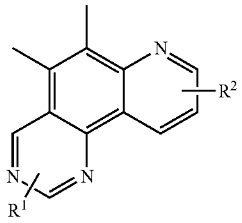
-continued
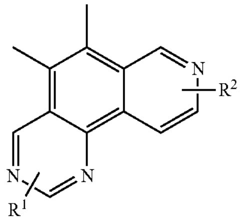
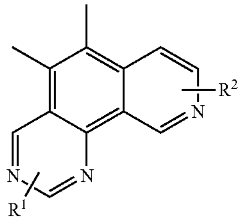
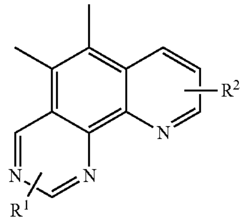
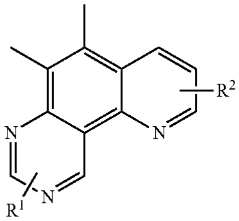
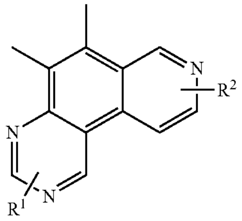
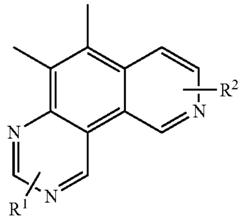
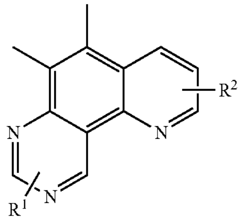
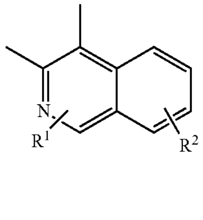
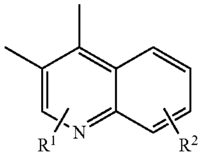
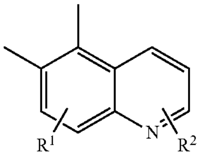
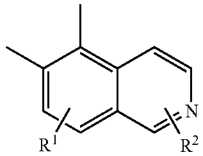
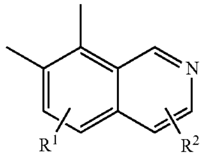
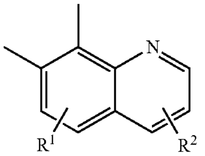
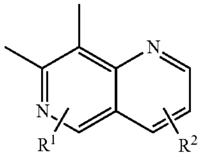
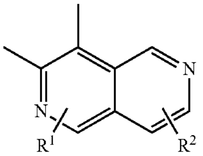
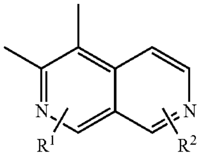
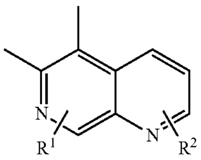
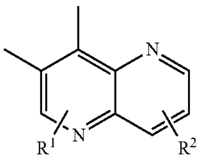

-continued
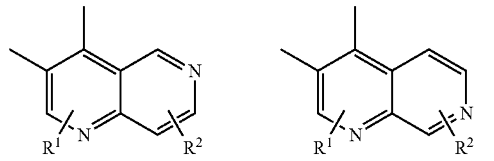
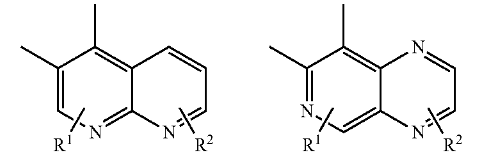
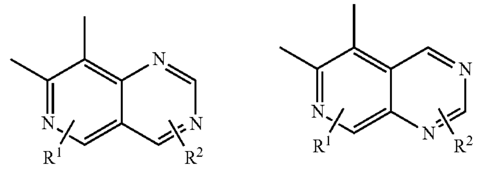
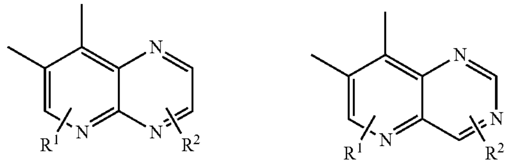
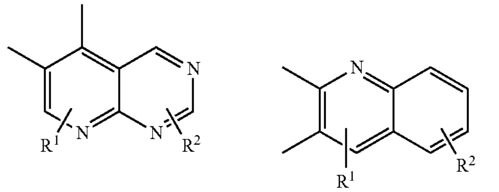
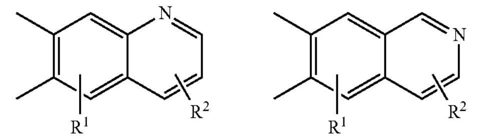
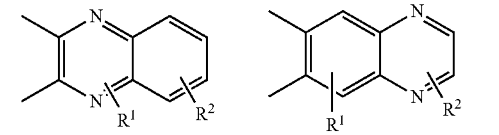
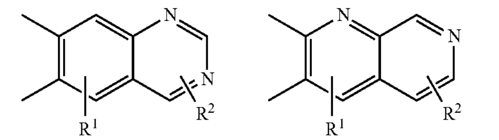
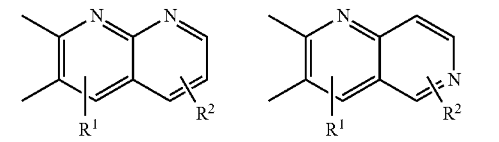
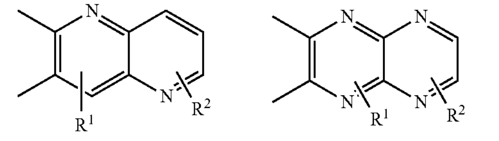
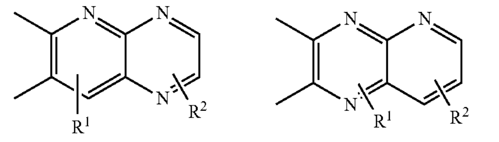
-continued
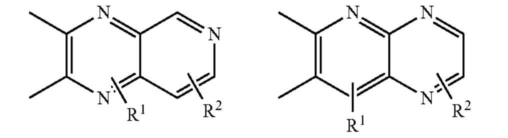
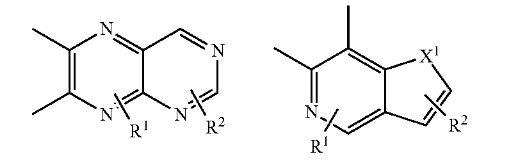
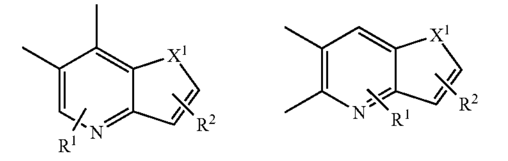
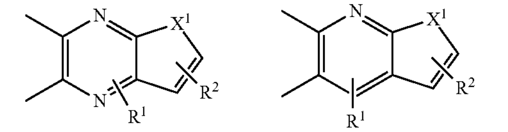
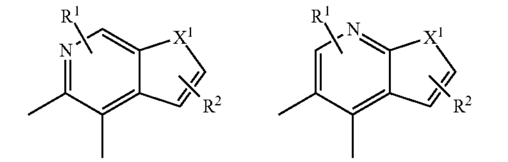
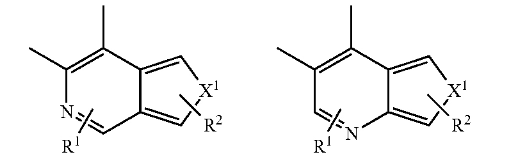
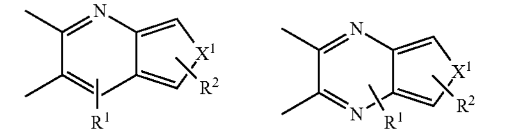
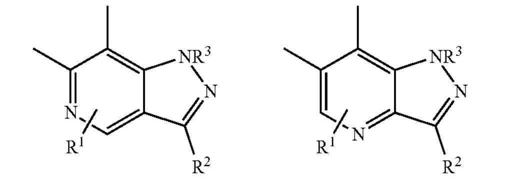
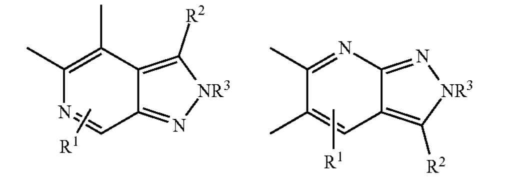
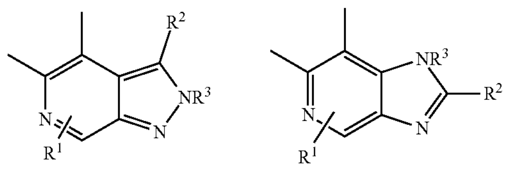
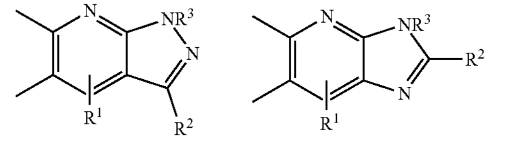

-continued
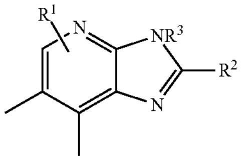
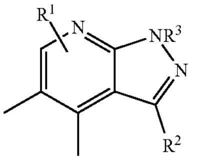
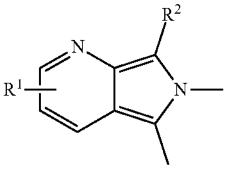
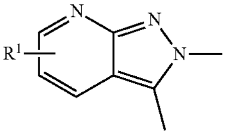
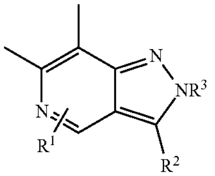
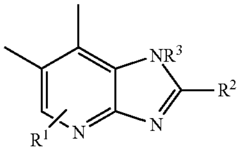
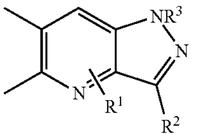
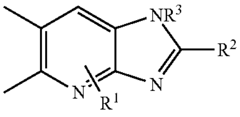
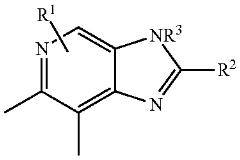
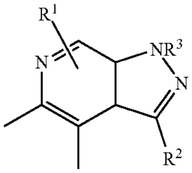
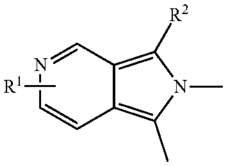
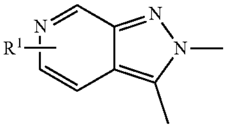
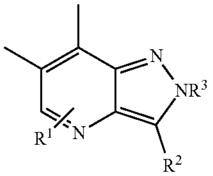
in which $R^1$, $R^2$, $R^3$, $R^4$, $X^1$, and $X^2$ are as defined herein.
Compounds of General Formulas I-III are shown below.
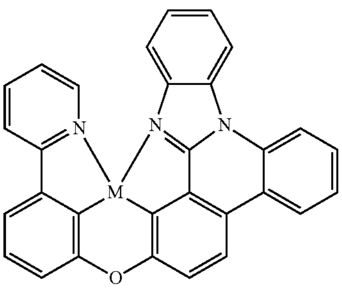
-continued
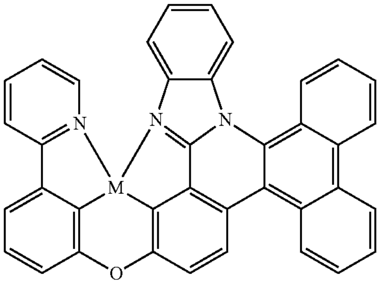
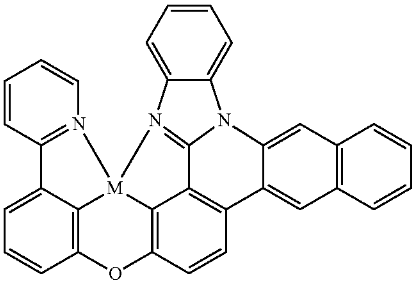
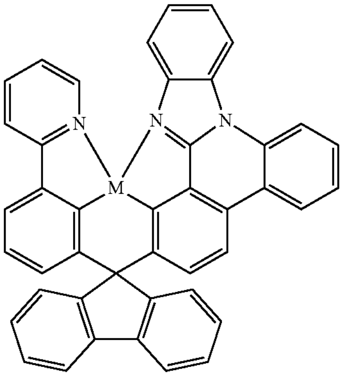
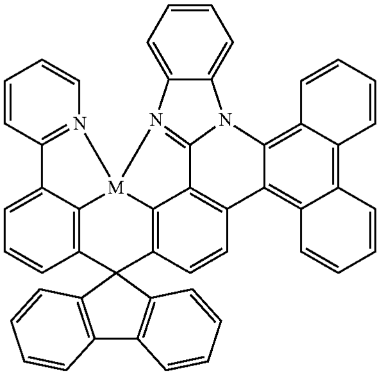
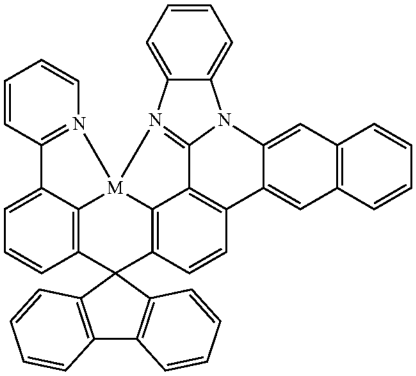

-continued
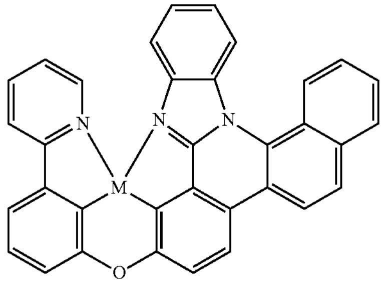
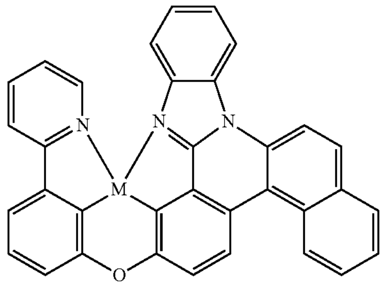
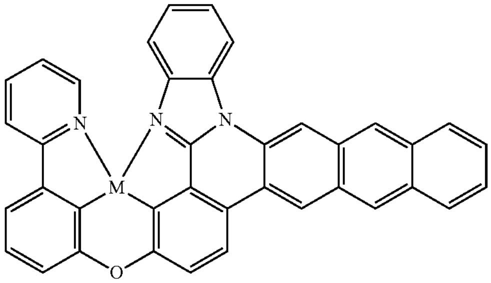
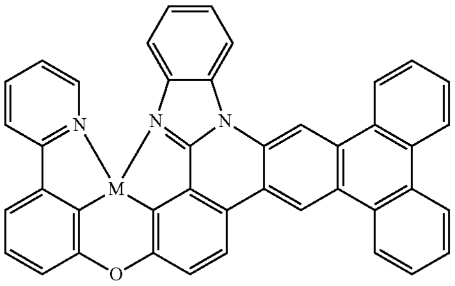
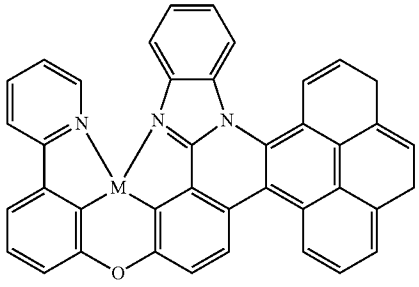
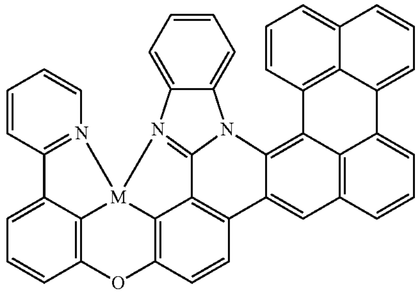
-continued
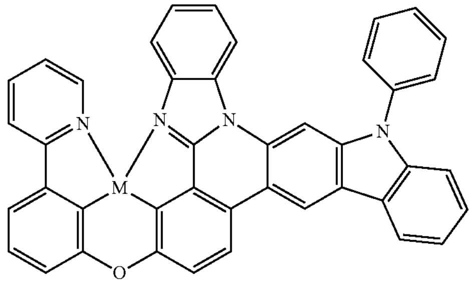
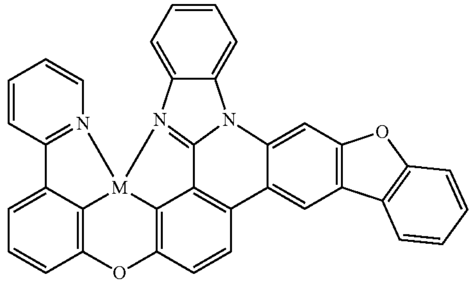
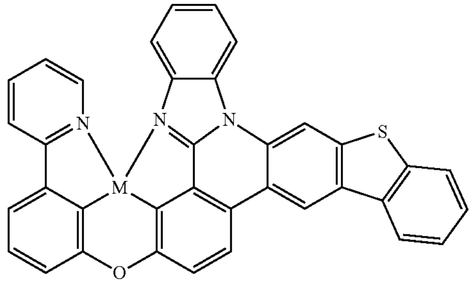
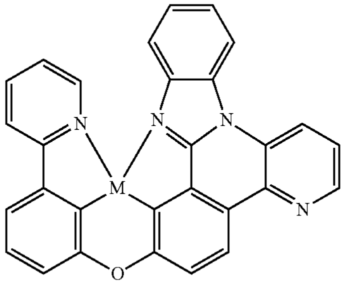
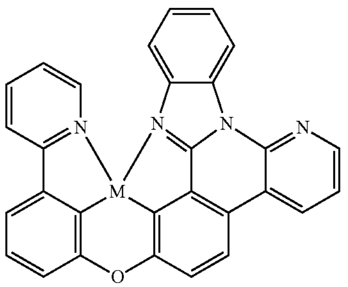
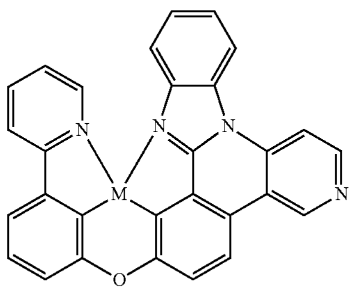

-continued
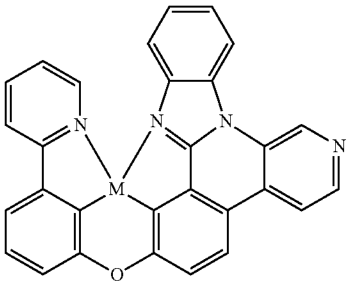
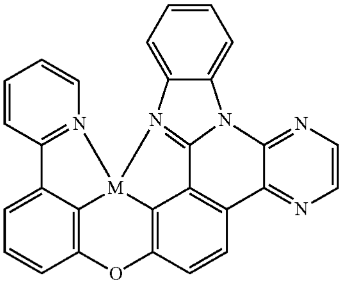
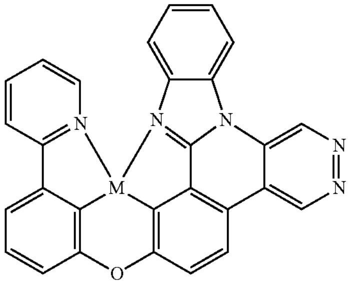
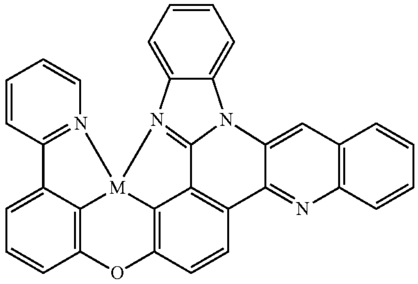
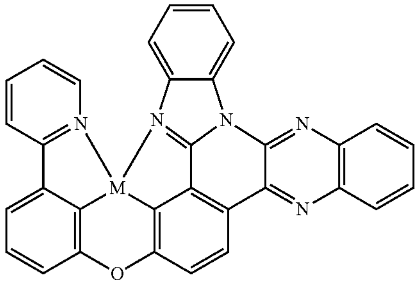
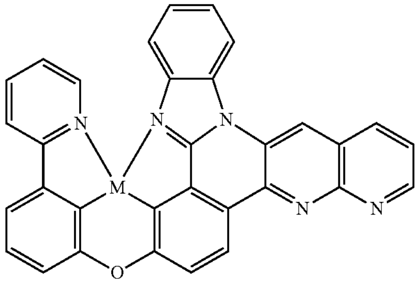
-continued
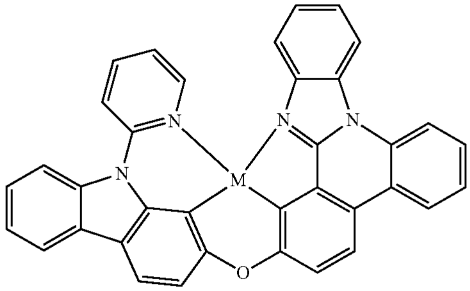
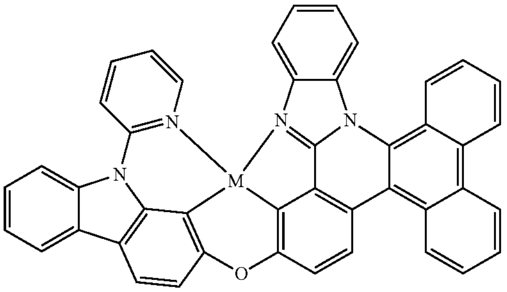
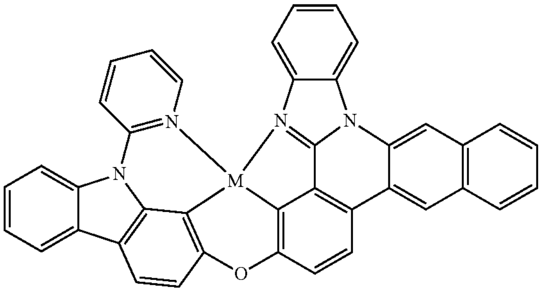
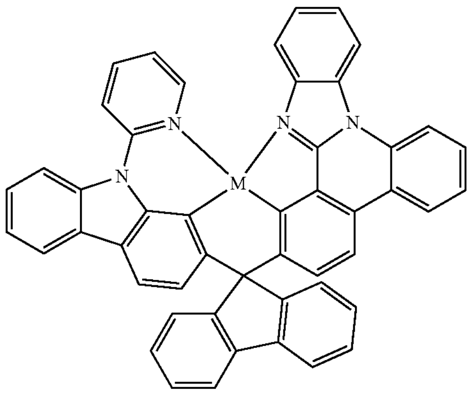
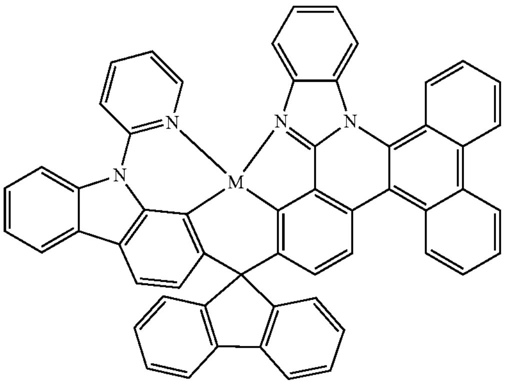

-continued
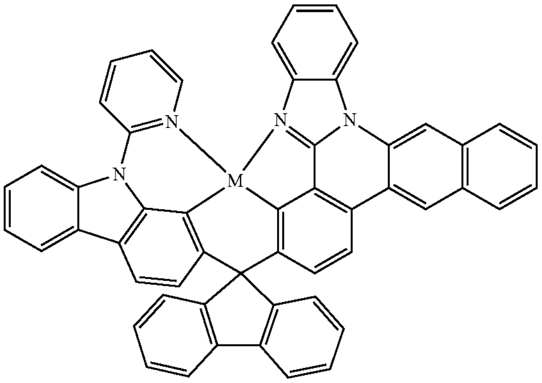
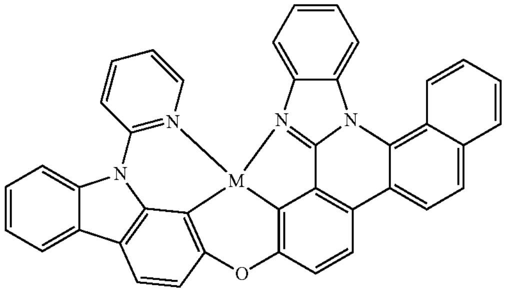
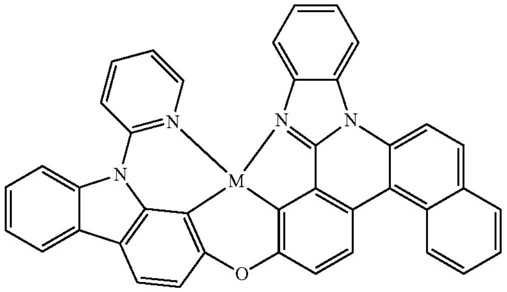
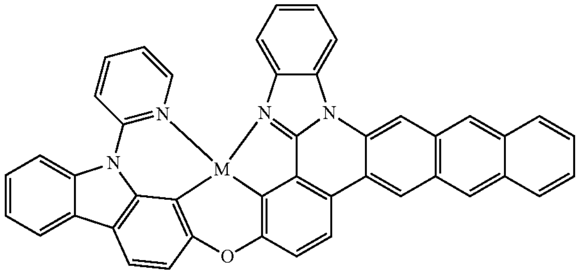
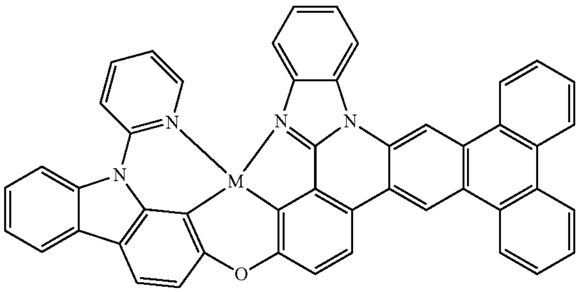
-continued
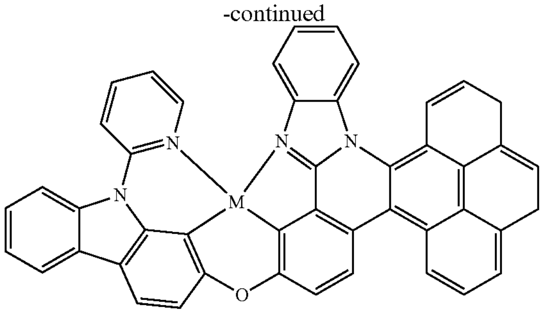
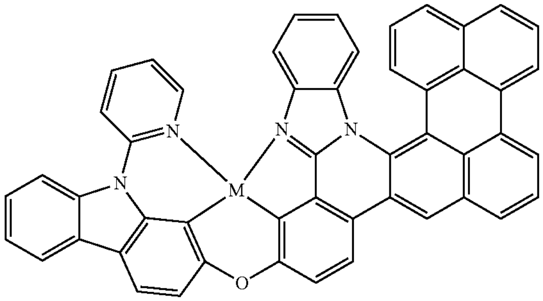
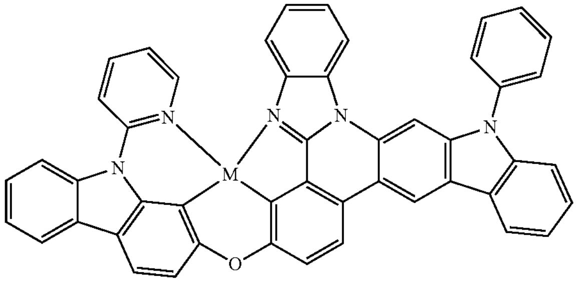
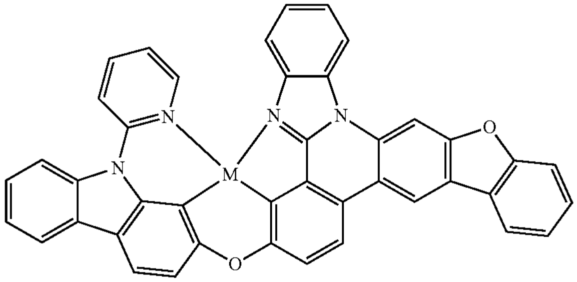
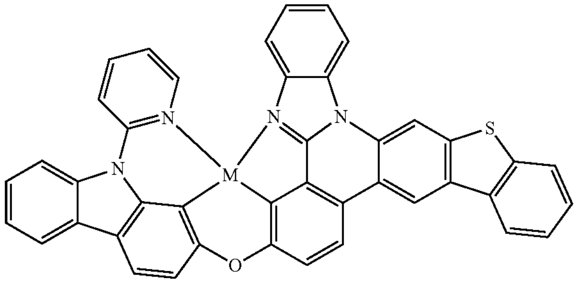
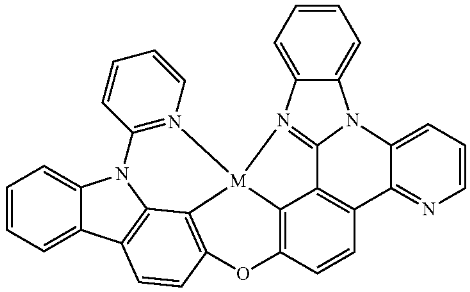

-continued
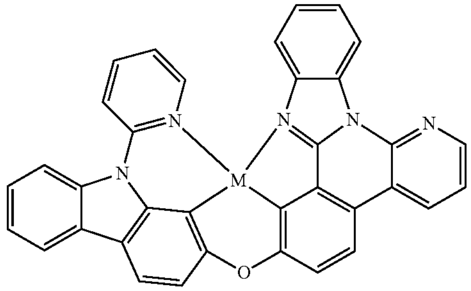
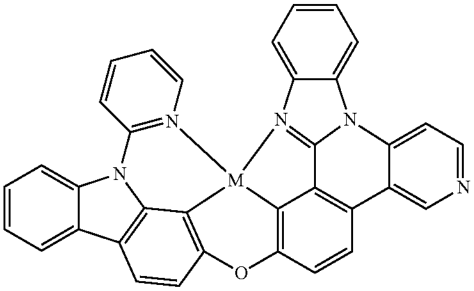
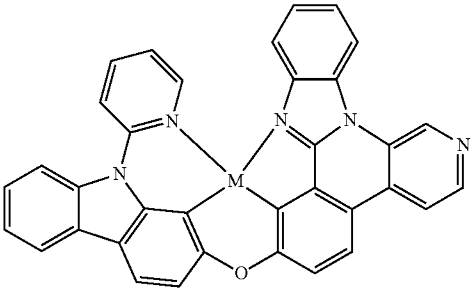
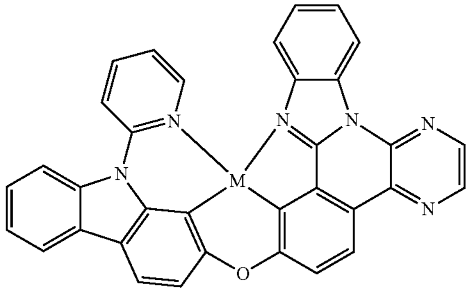
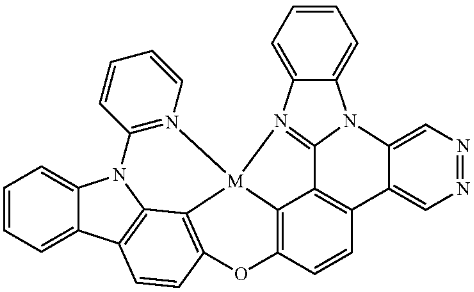
-continued
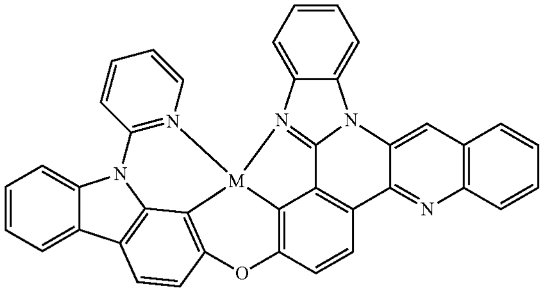
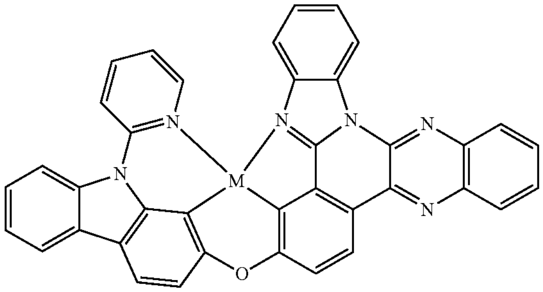
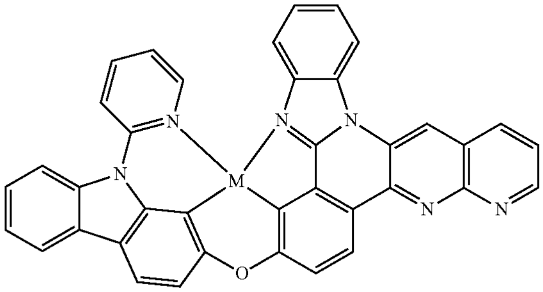
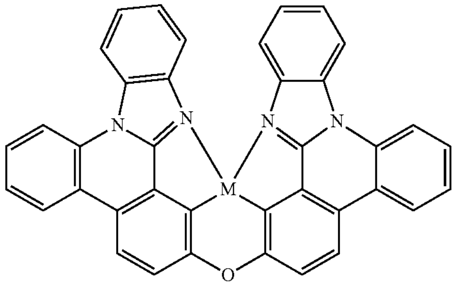
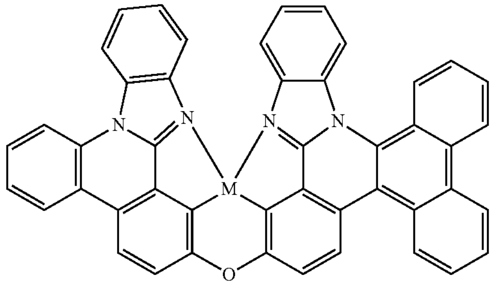
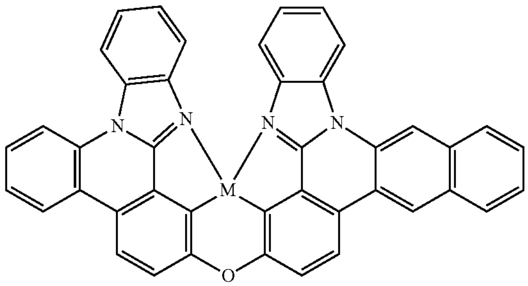

-continued
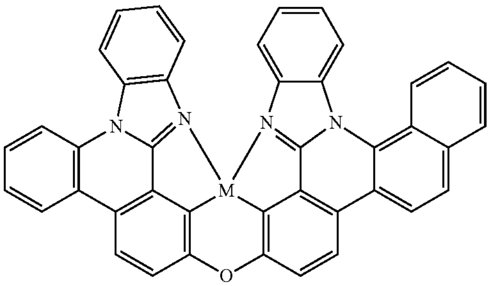
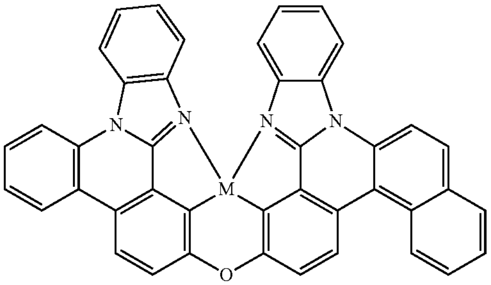
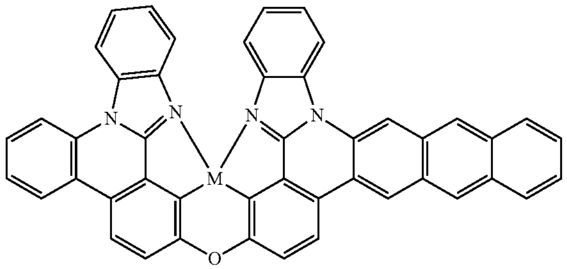
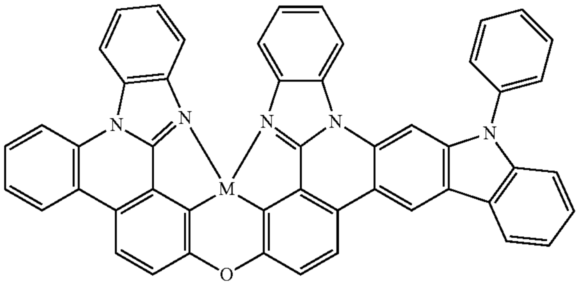
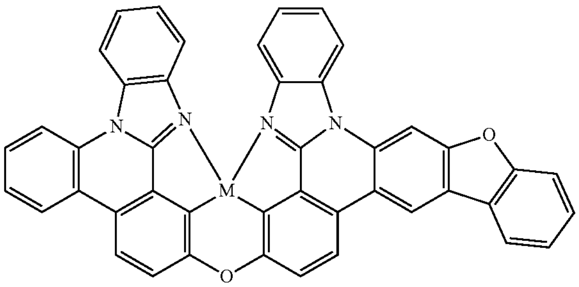
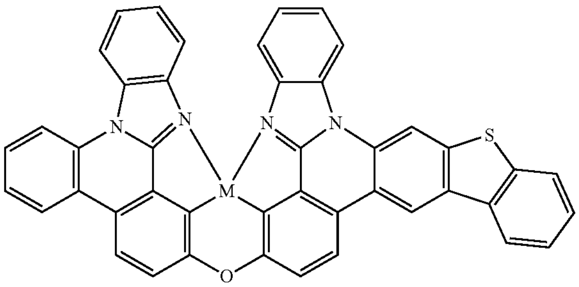
-continued
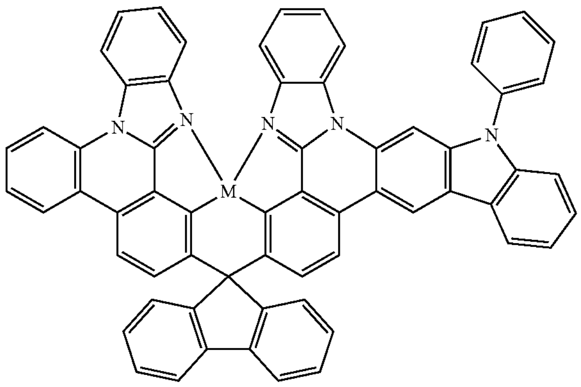
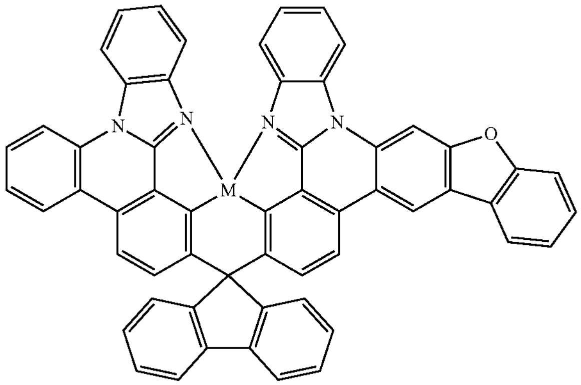
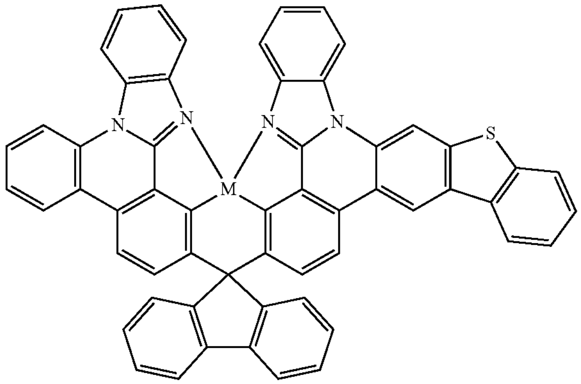
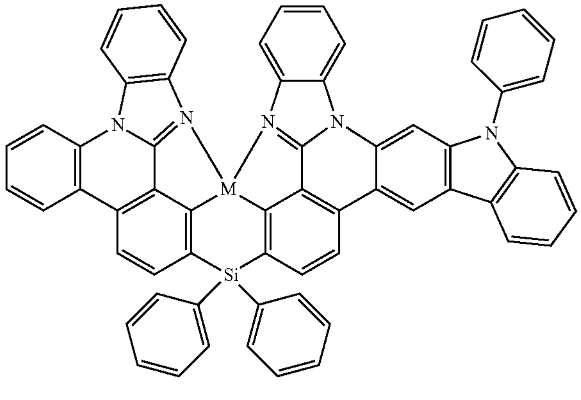

-continued
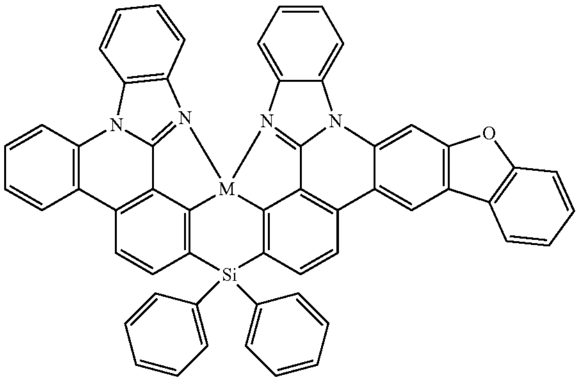
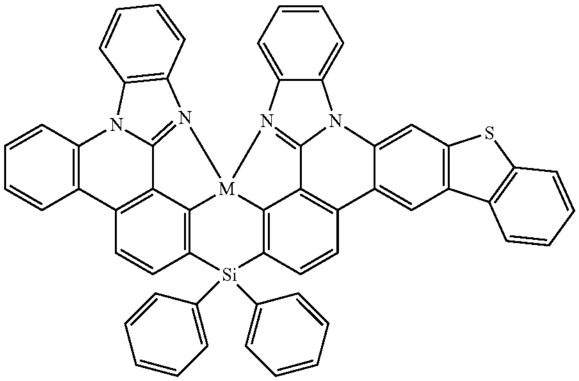
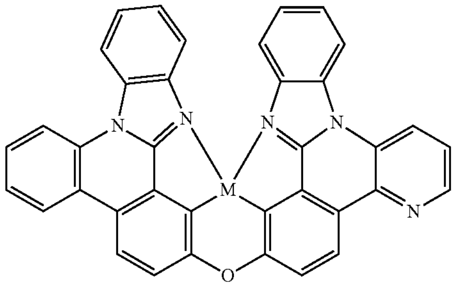
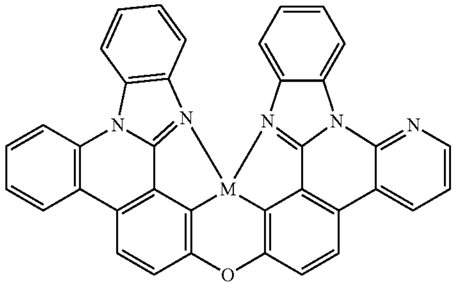
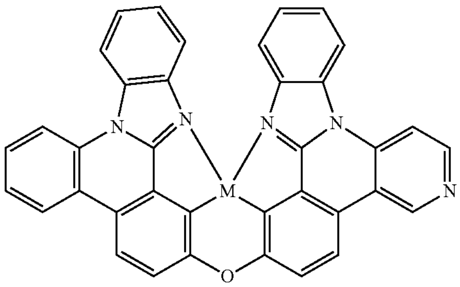
-continued
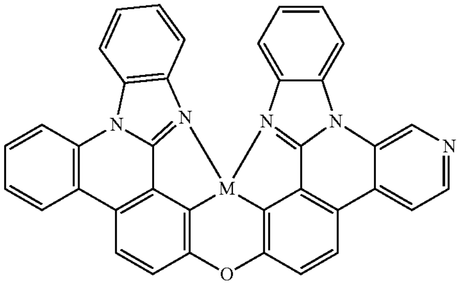
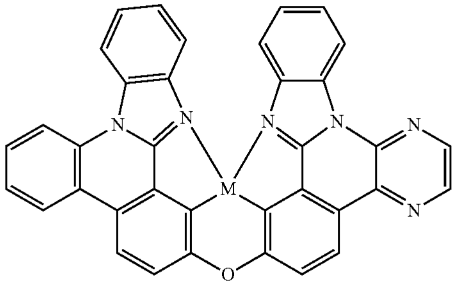
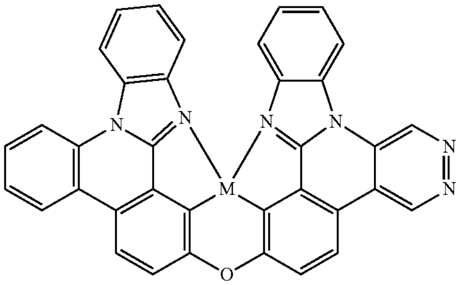
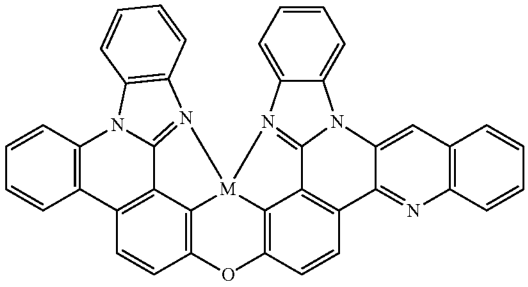
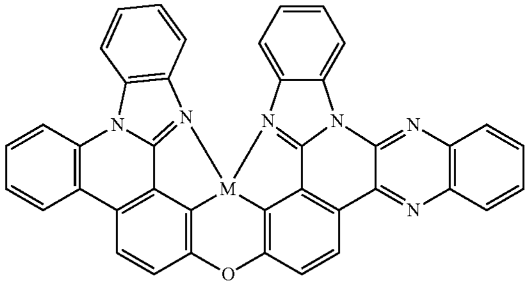
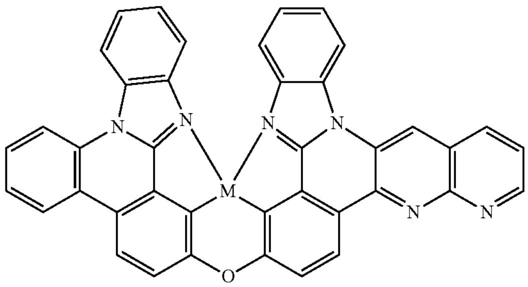

-continued
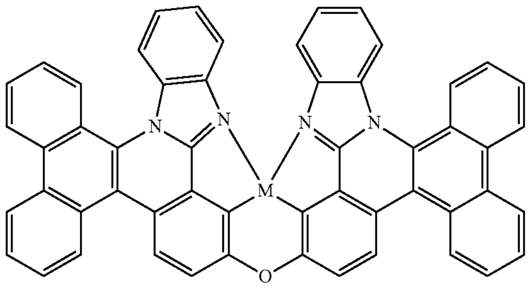
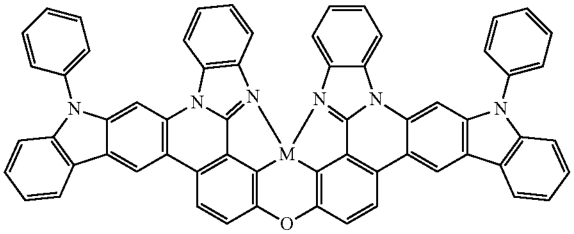
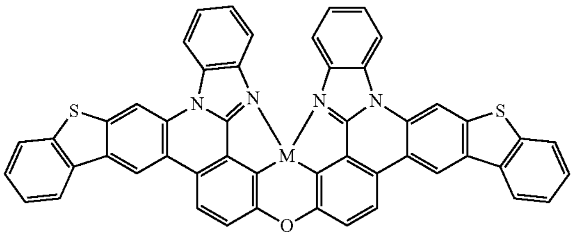
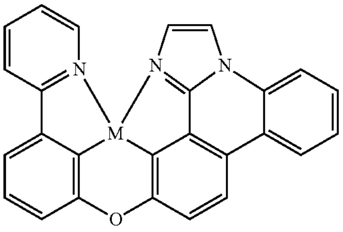
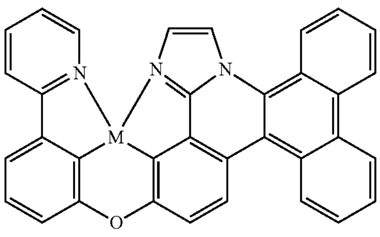
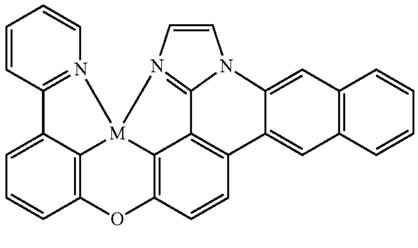
-continued
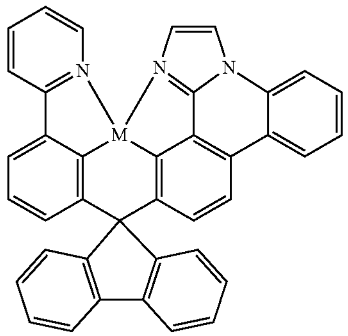
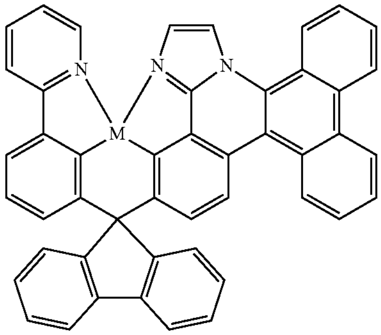
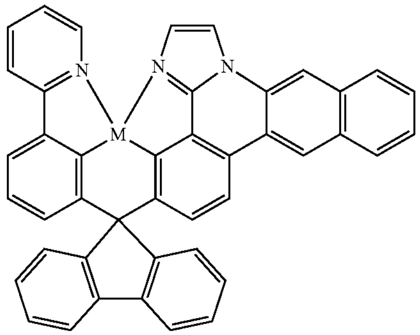
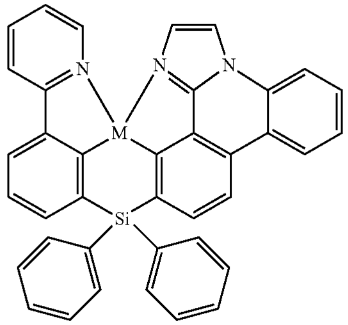
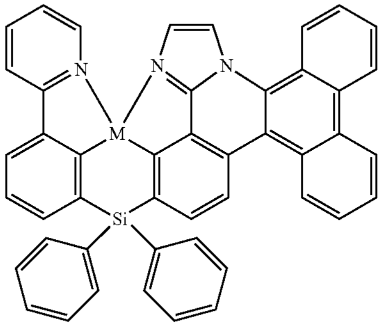

-continued
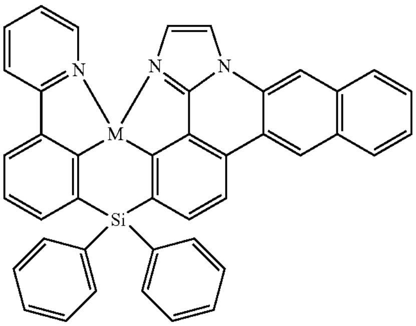
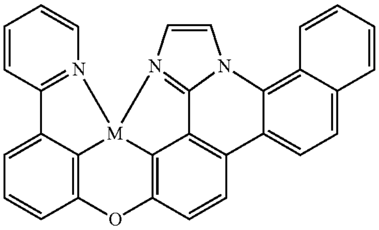
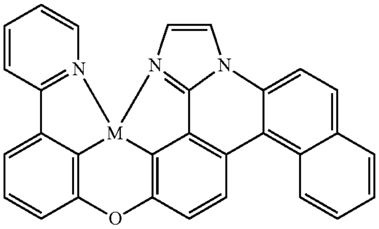
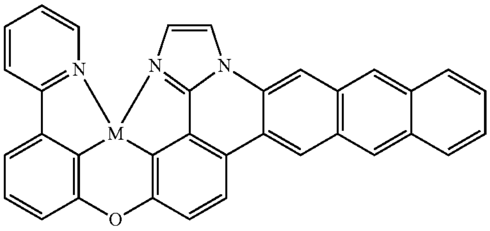
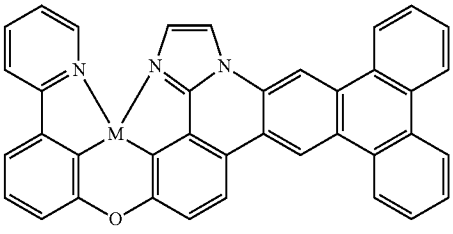
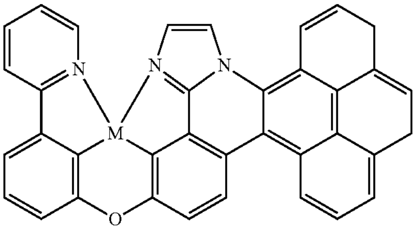
-continued
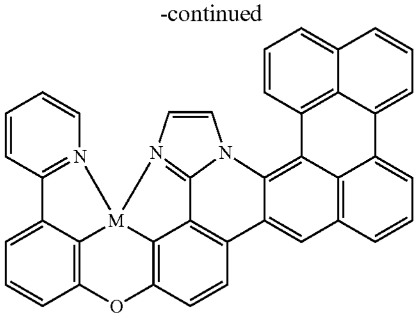
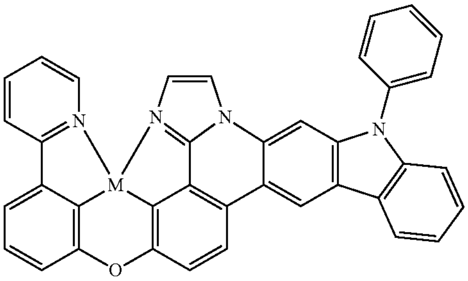
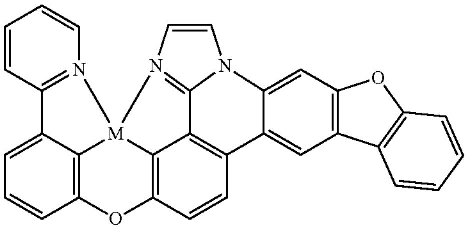
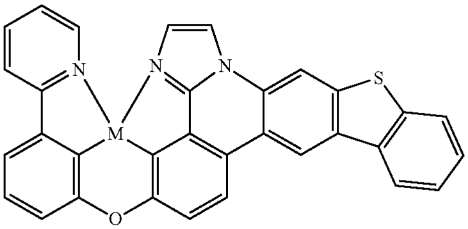
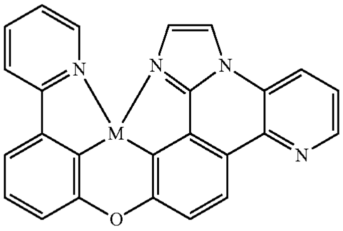
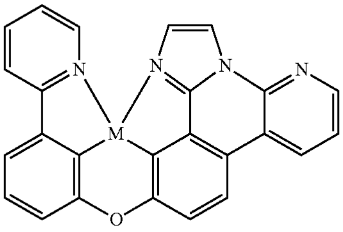
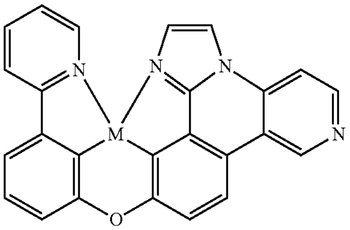

-continued
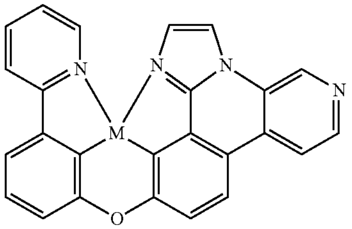
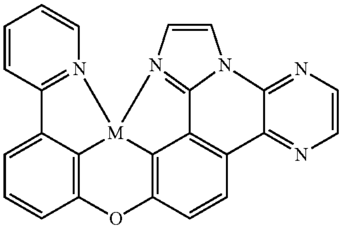
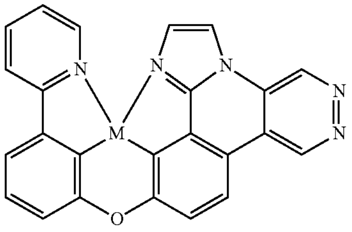
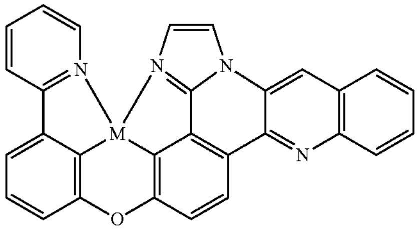
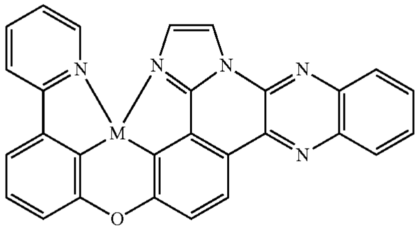
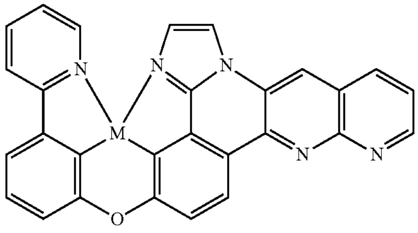
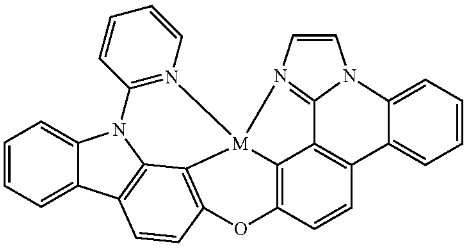
-continued
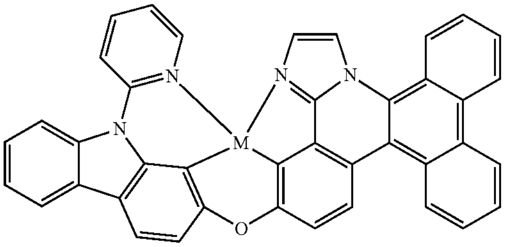
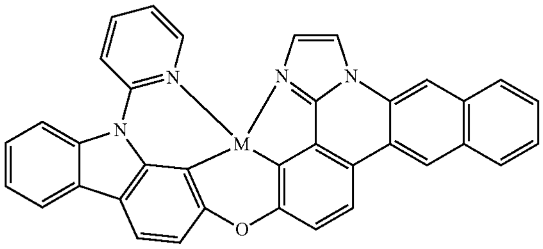
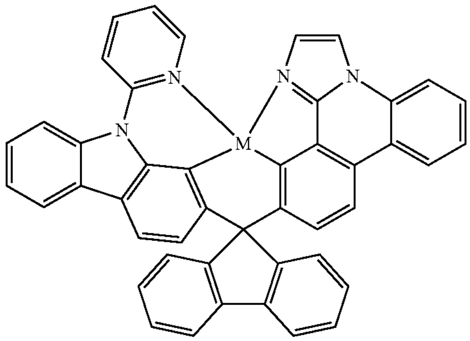
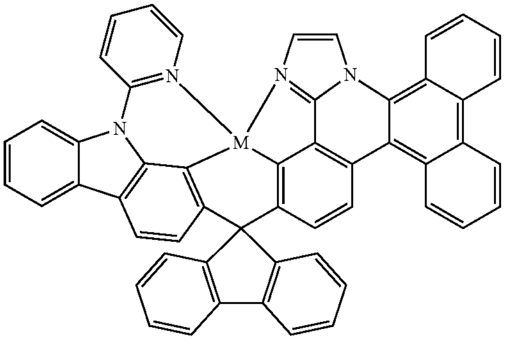
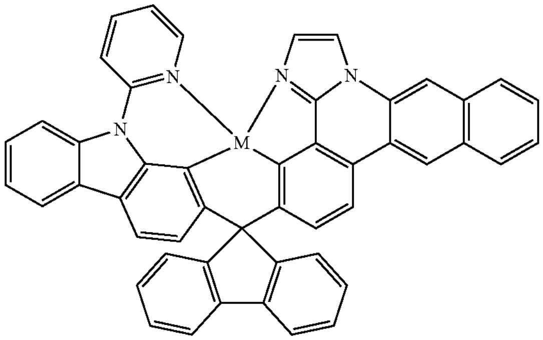

-continued
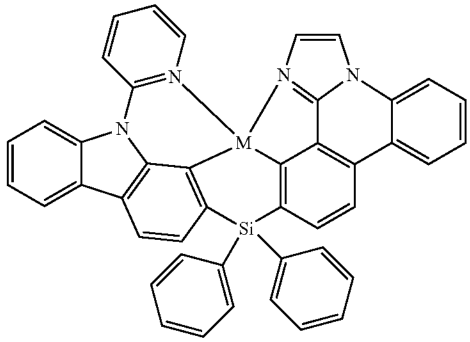
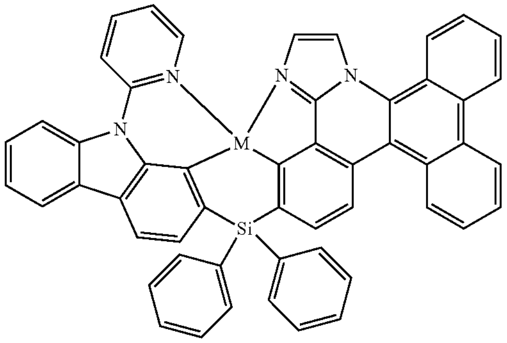
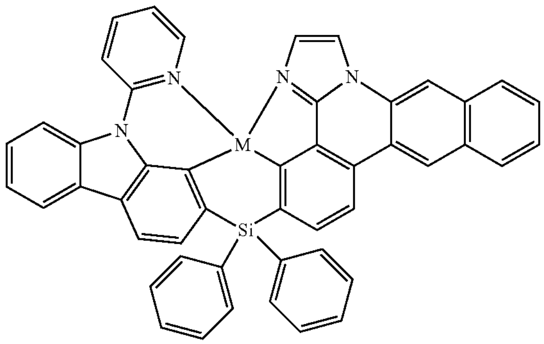
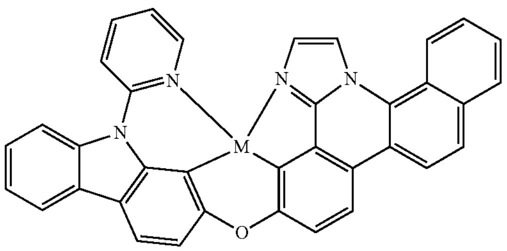
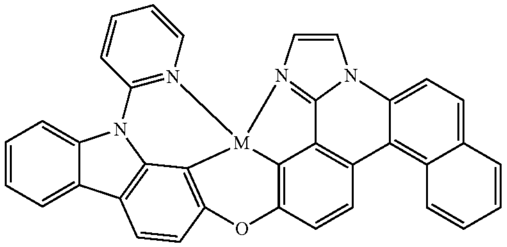
-continued
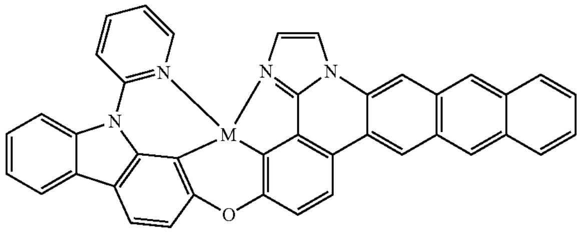
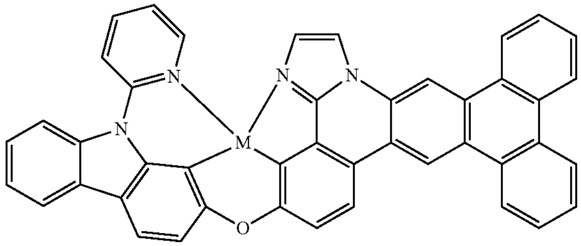
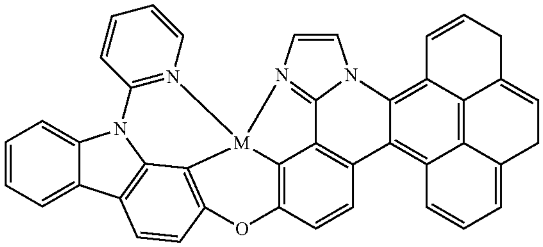
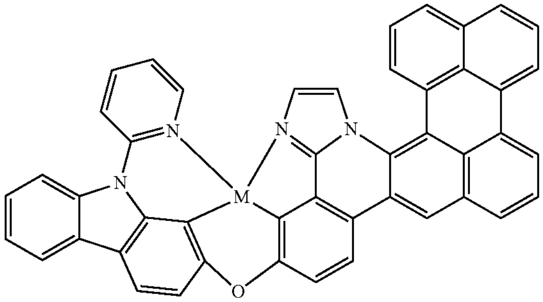
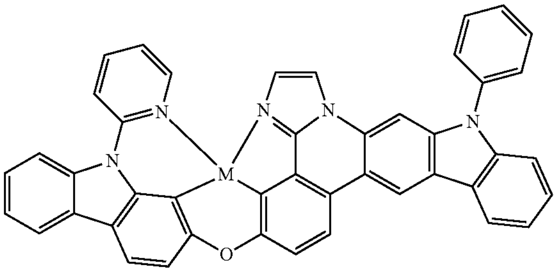
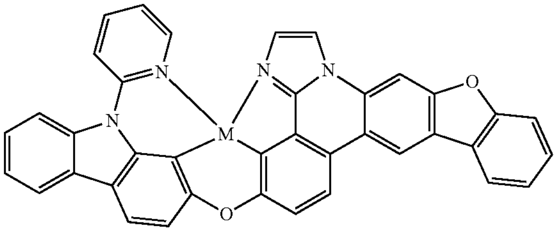

-continued
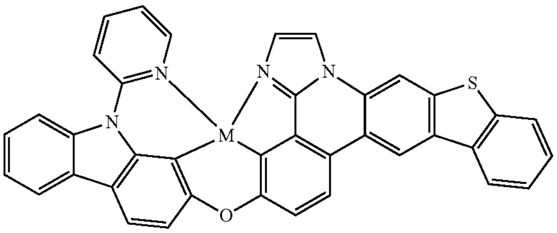
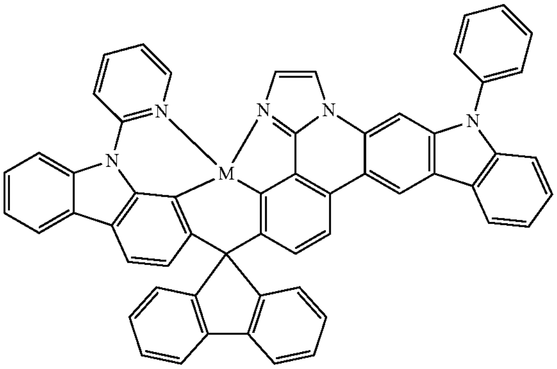
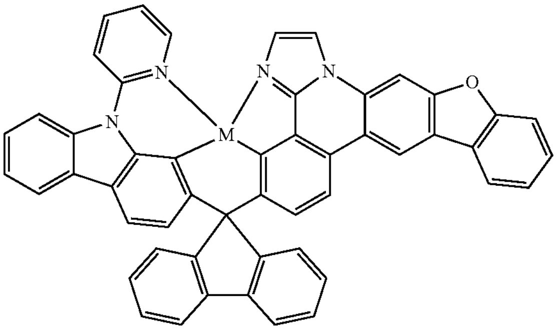
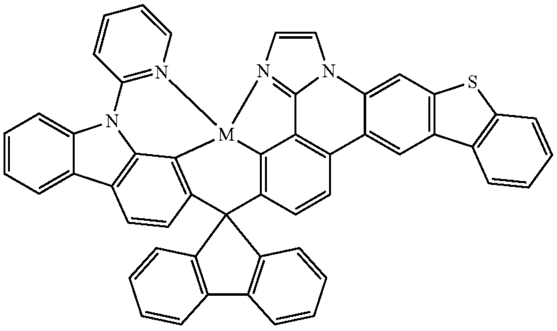
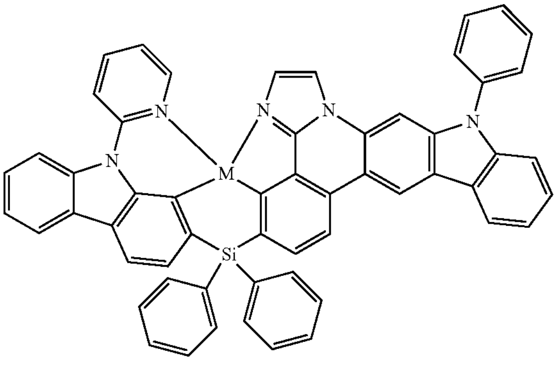
-continued
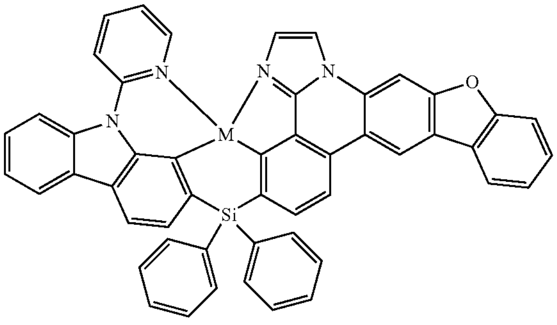
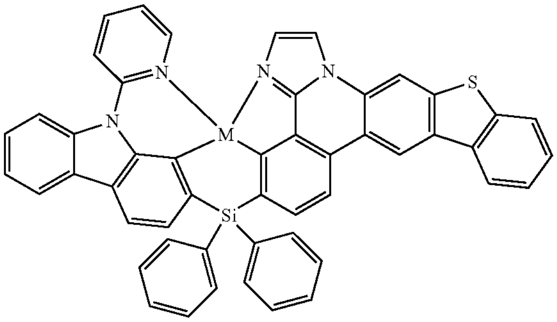
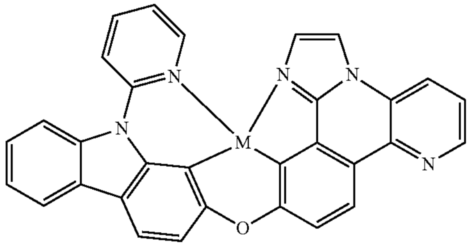
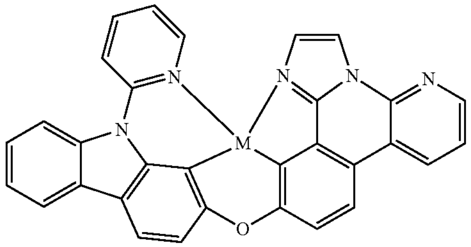
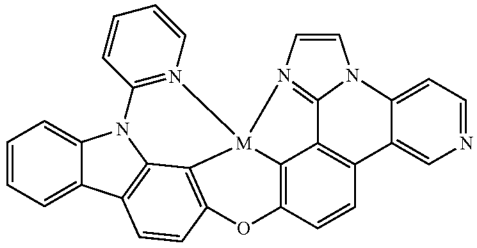
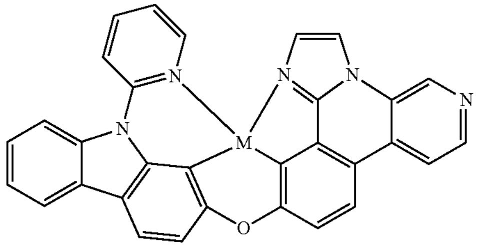

-continued
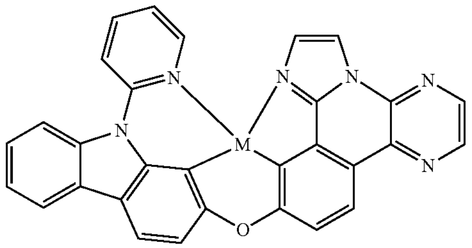
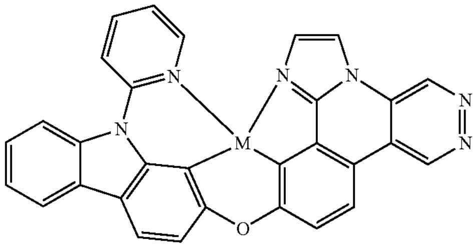
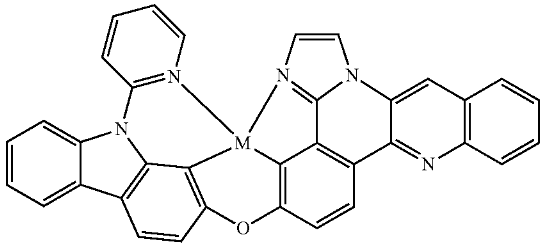
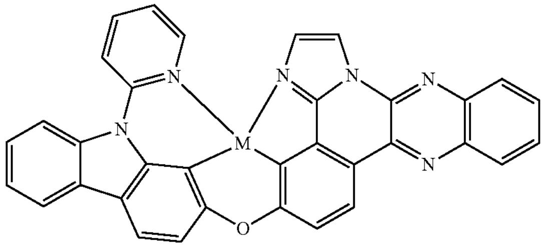
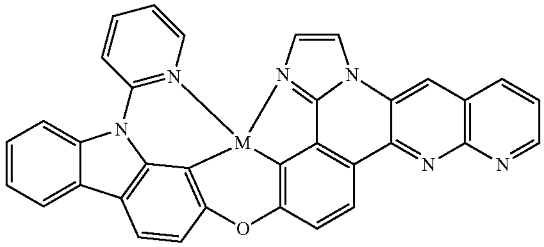
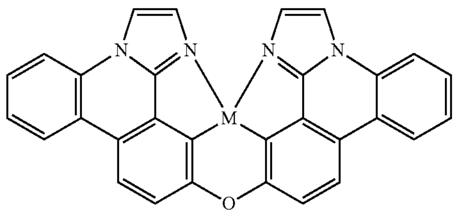
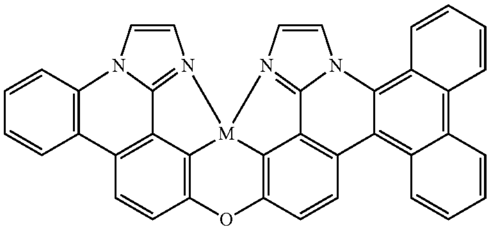
-continued
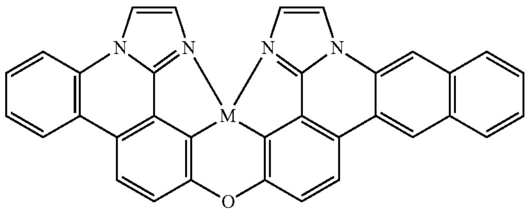
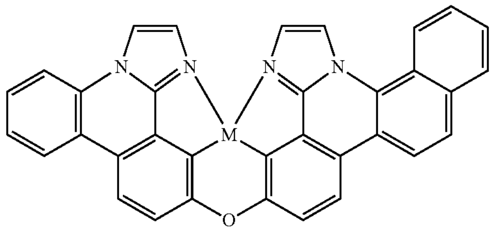
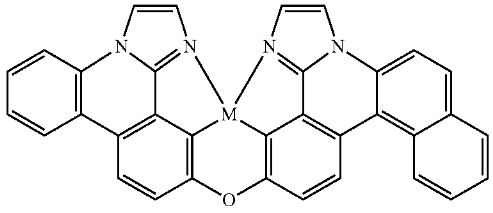
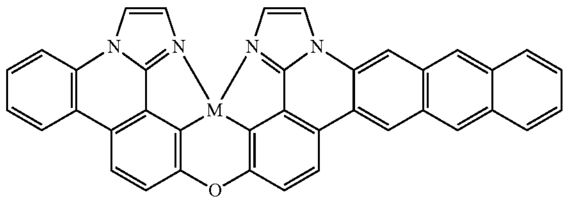
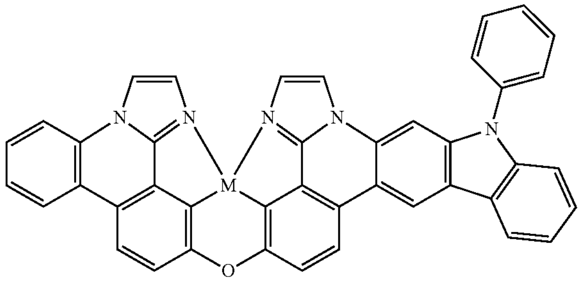
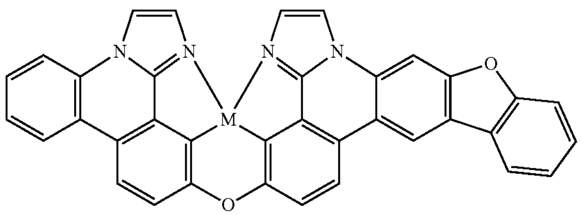
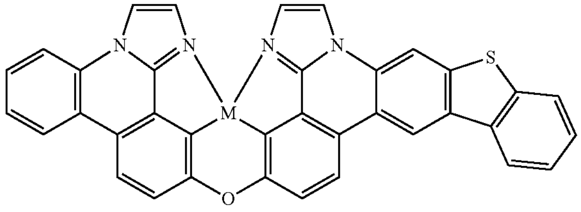

-continued
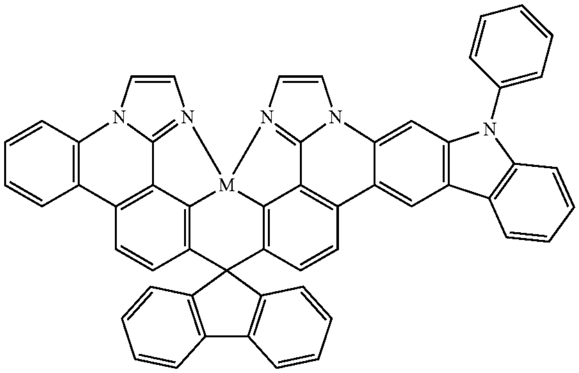
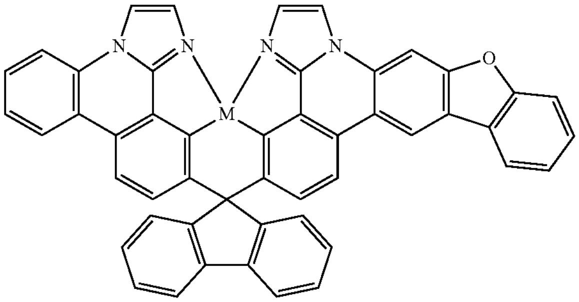
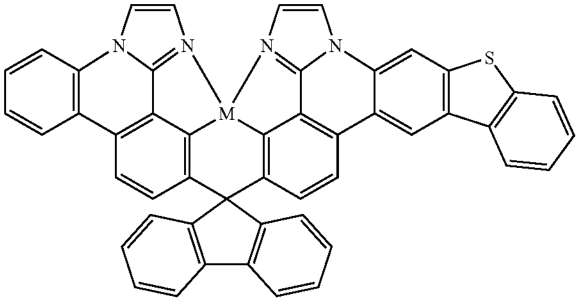
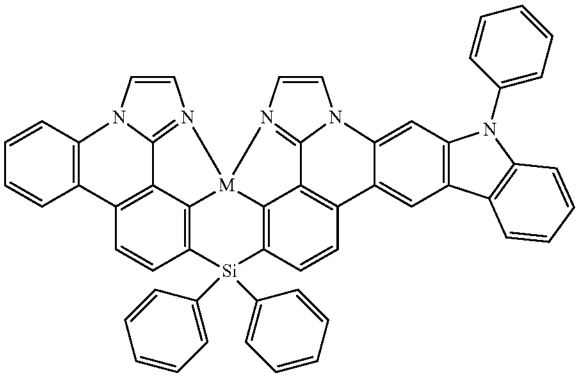
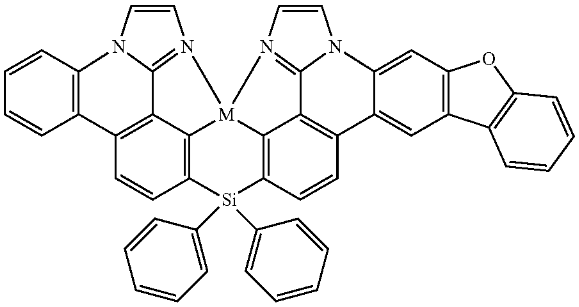
-continued
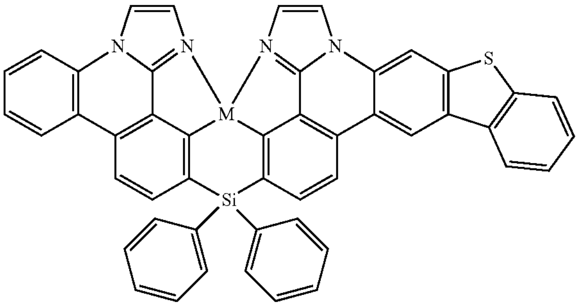
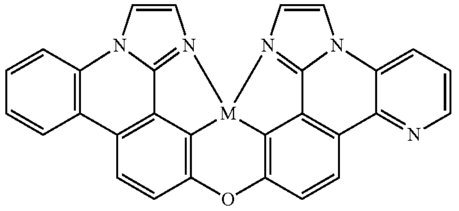
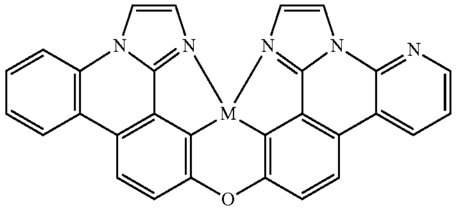
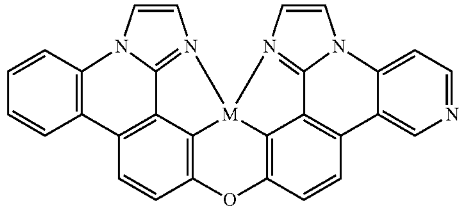
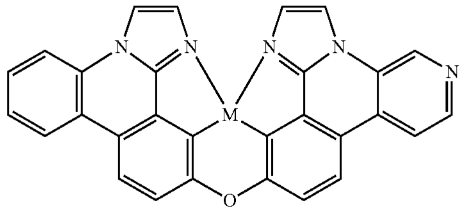
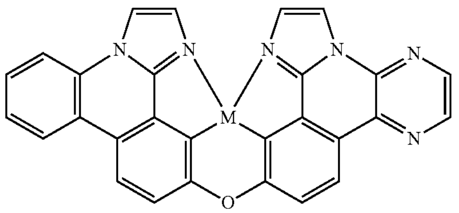
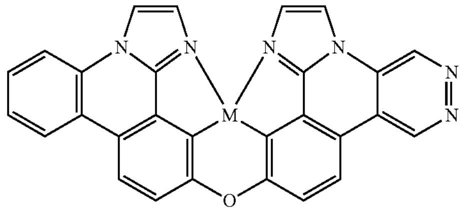

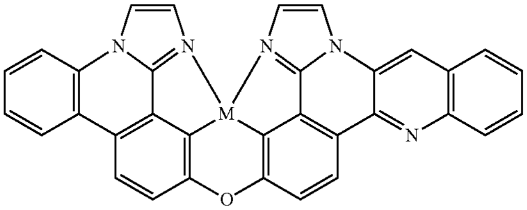
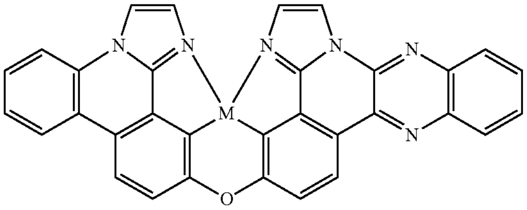
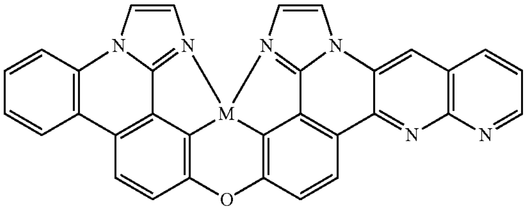
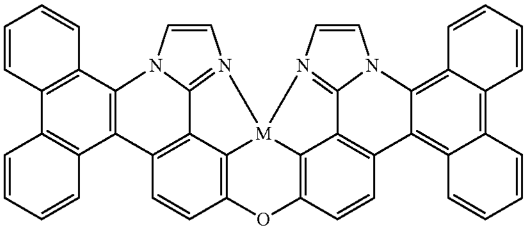
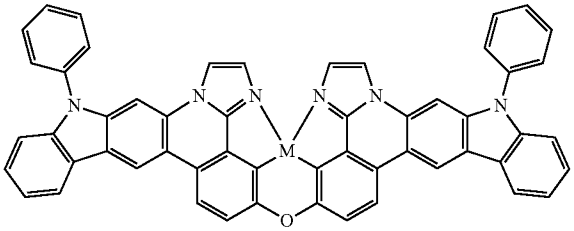
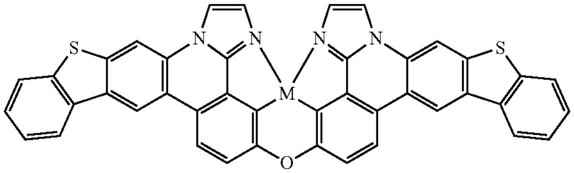
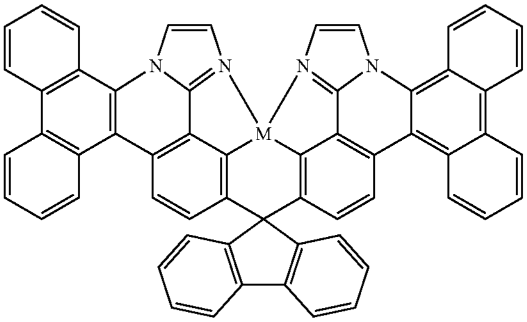
-continued
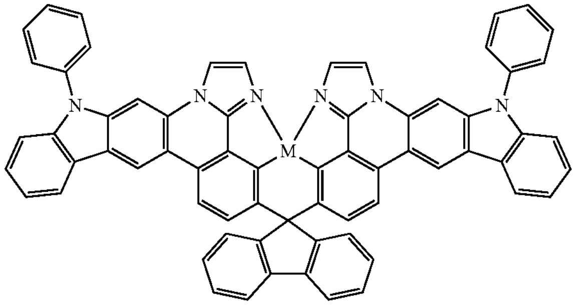
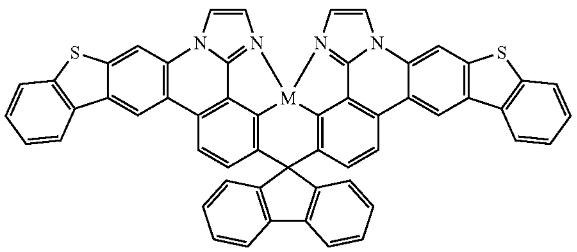
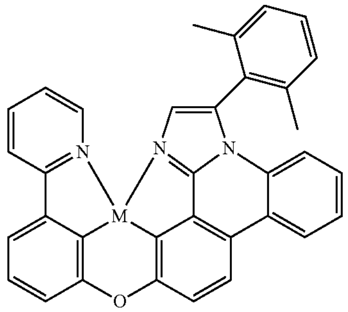
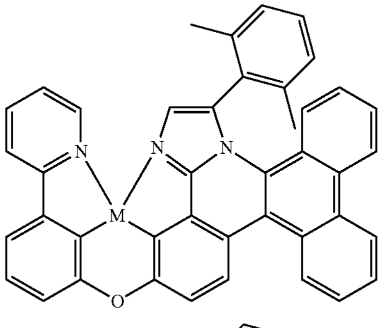
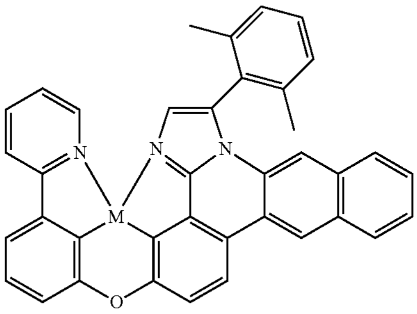

-continued
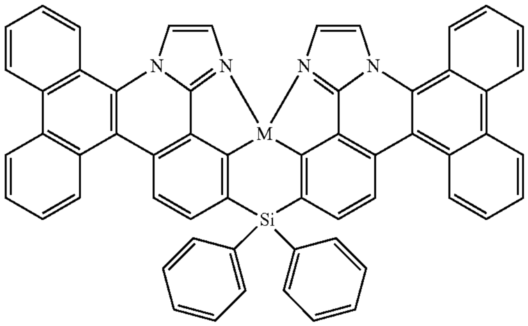
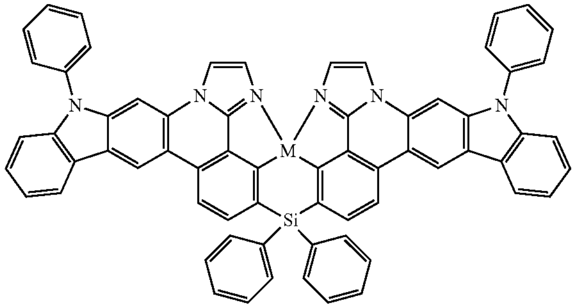
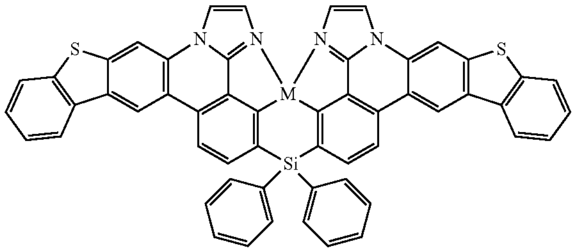
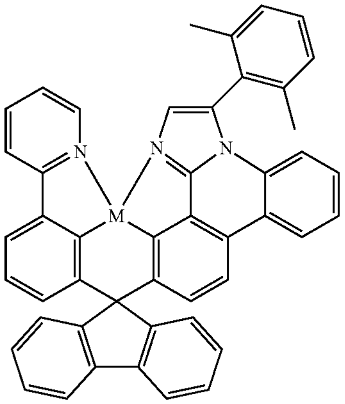
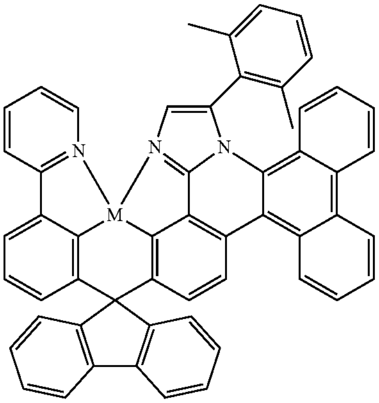
-continued
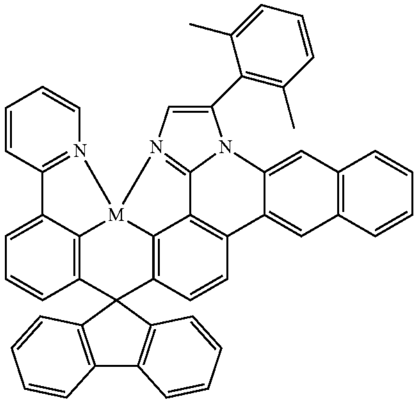
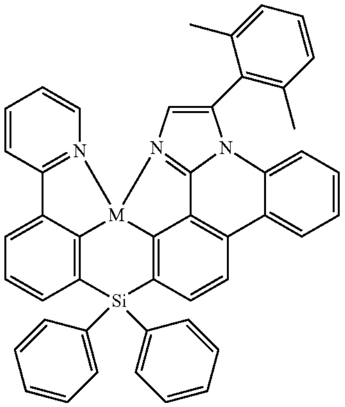
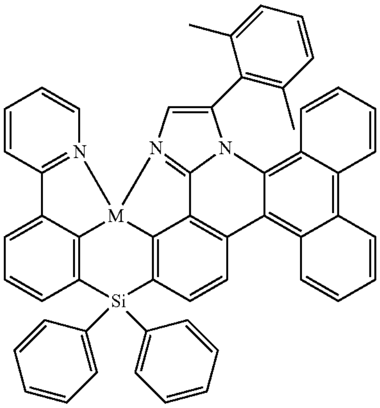
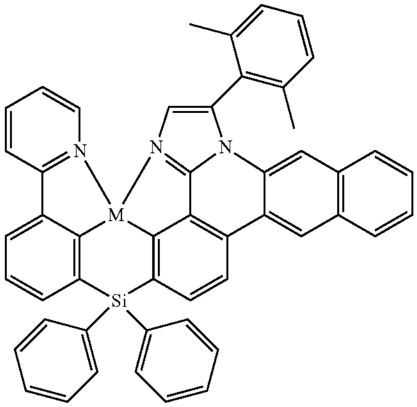

-continued
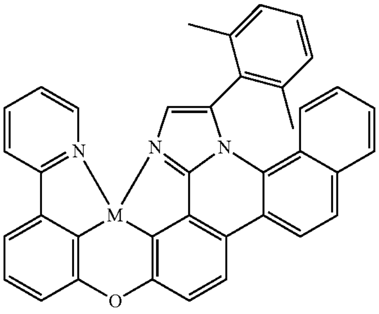
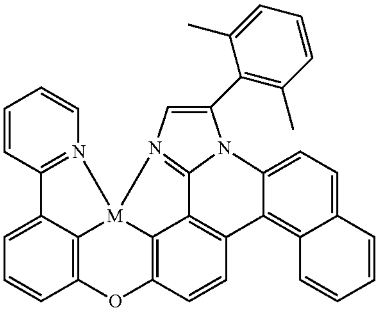
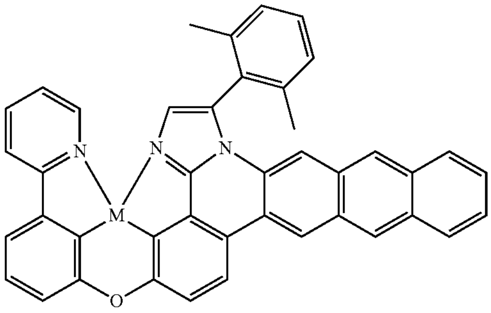
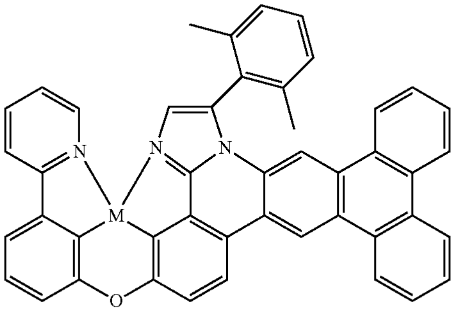
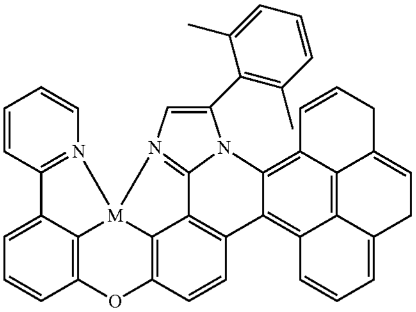
-continued
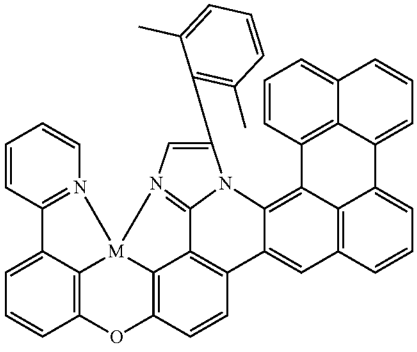
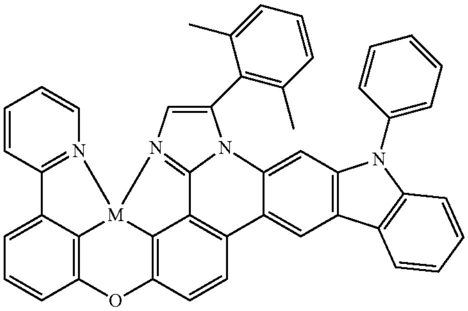
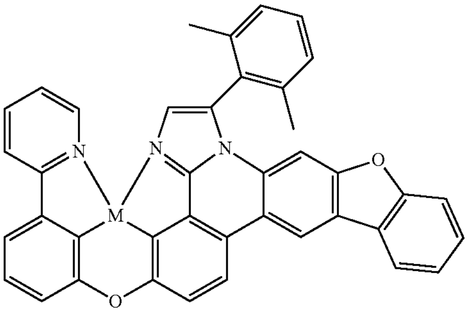
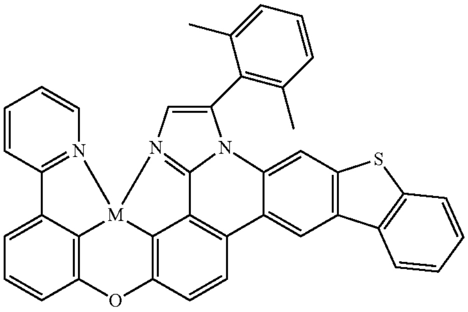
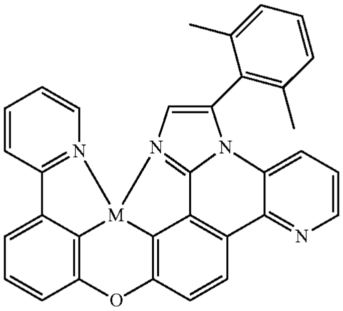

-continued
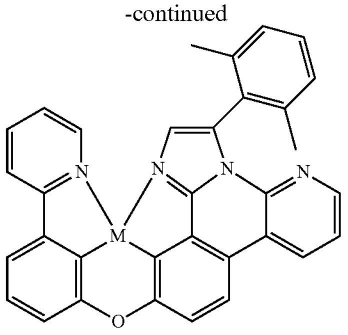
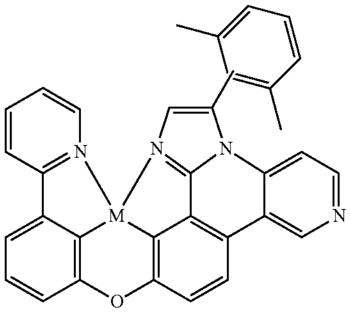
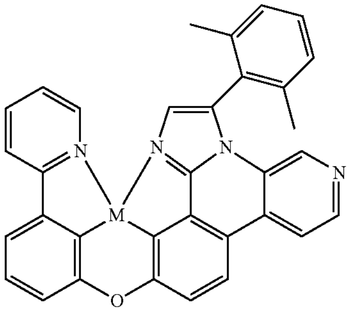
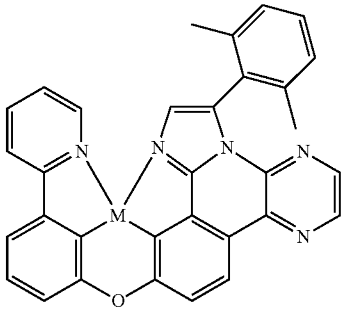
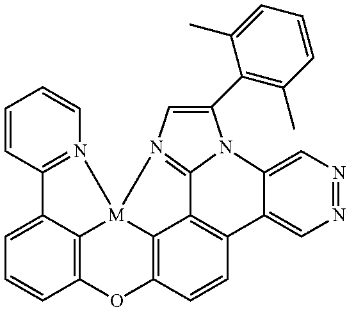
-continued
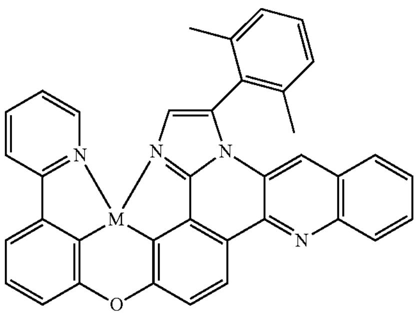
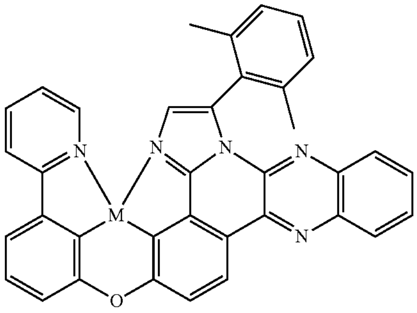
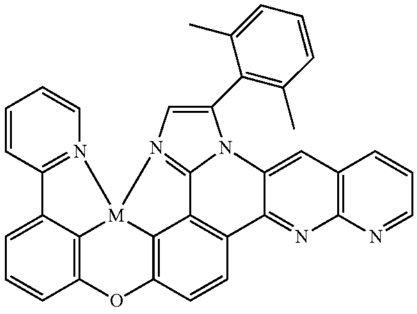
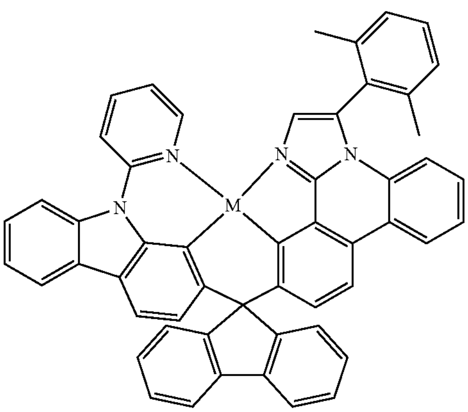

-continued
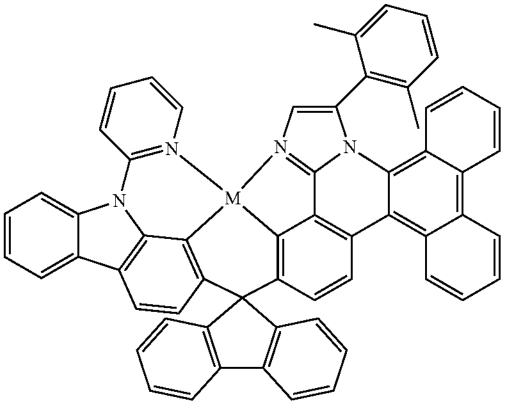
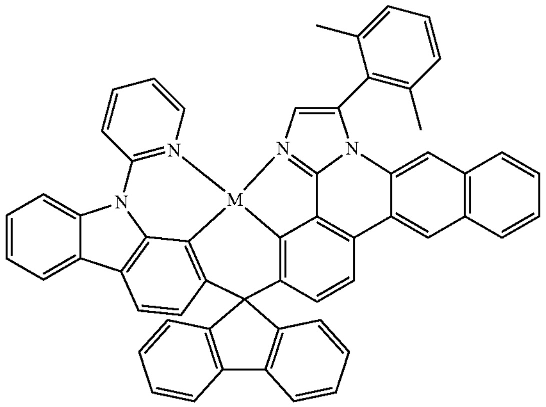
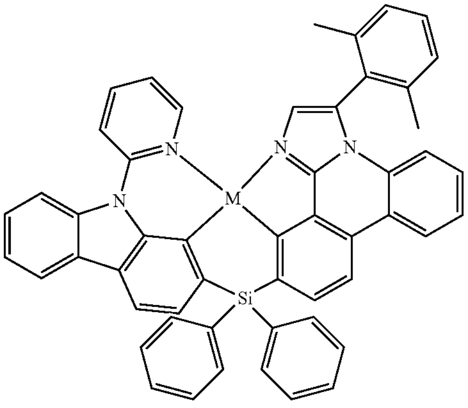
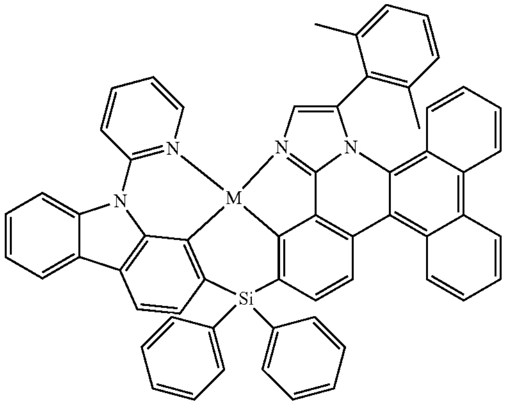
-continued
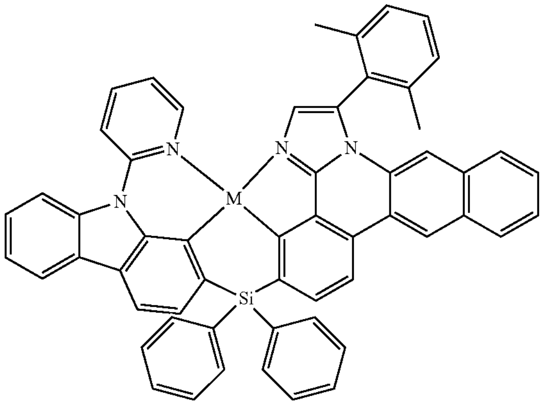
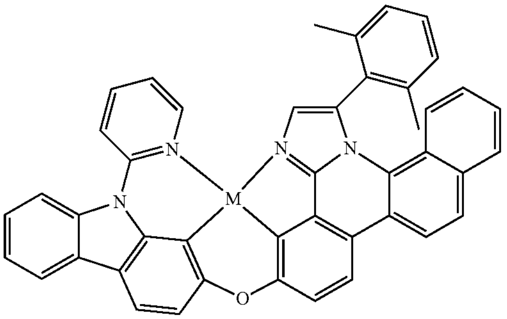
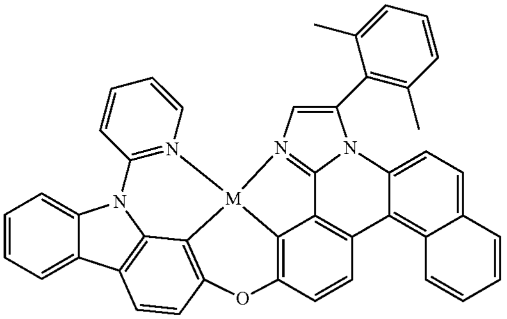
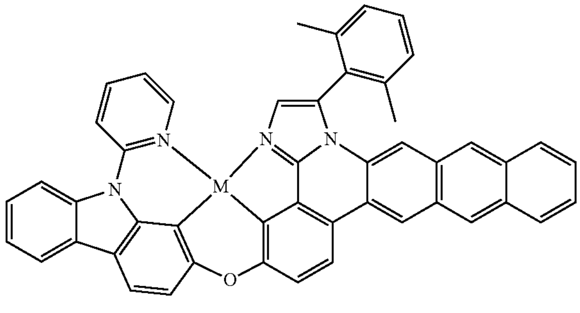
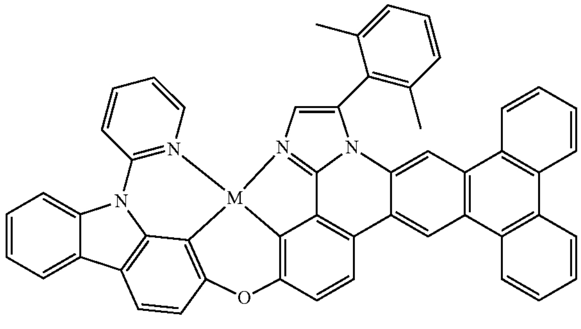

-continued
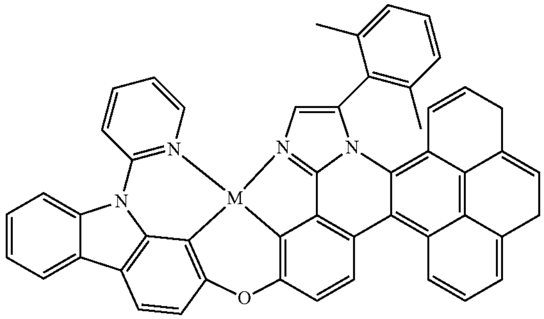
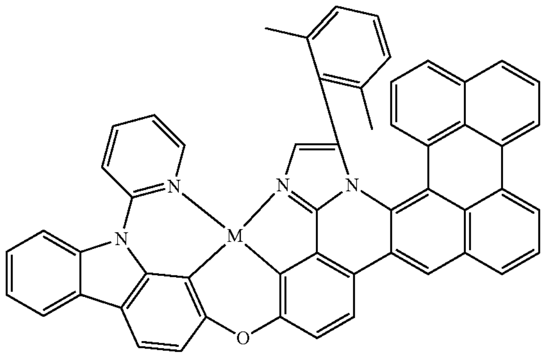
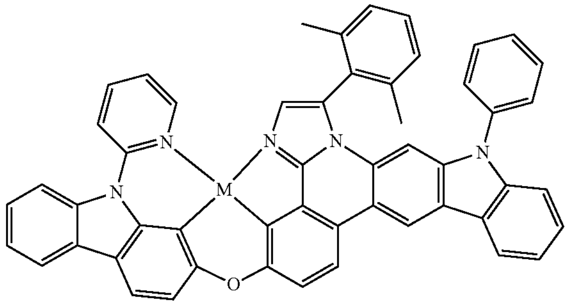
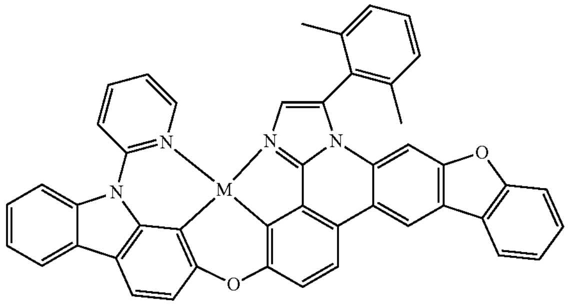
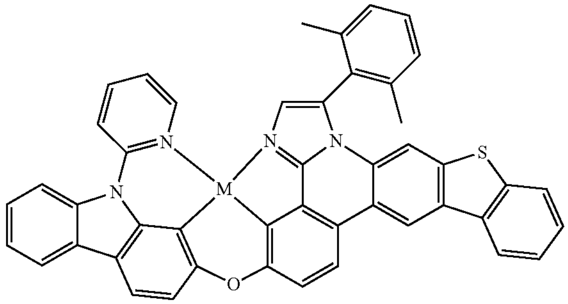
-continued
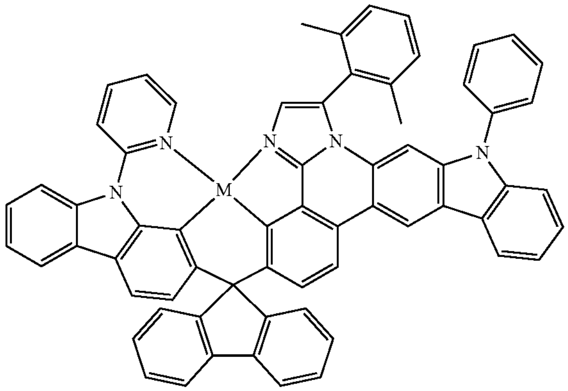
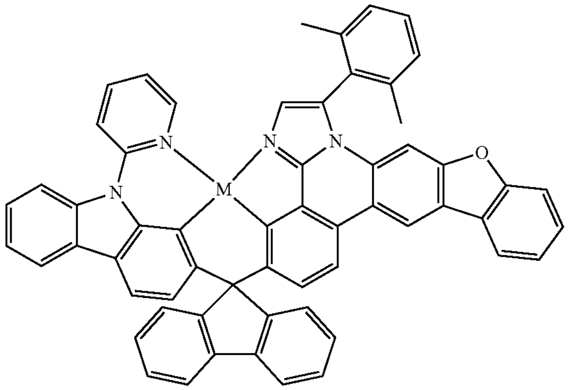
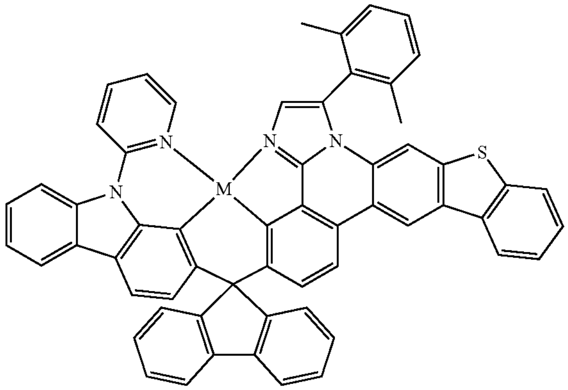
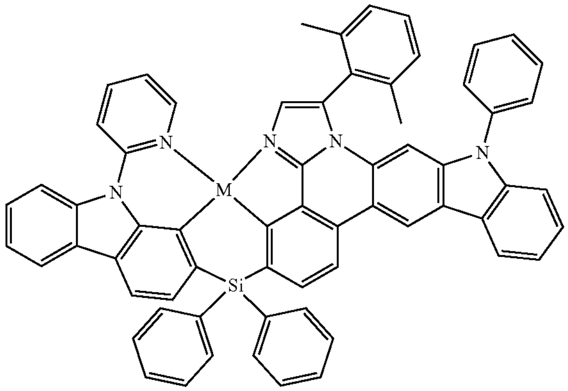

-continued
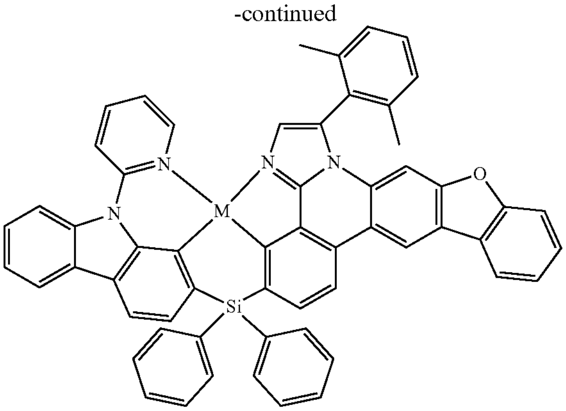
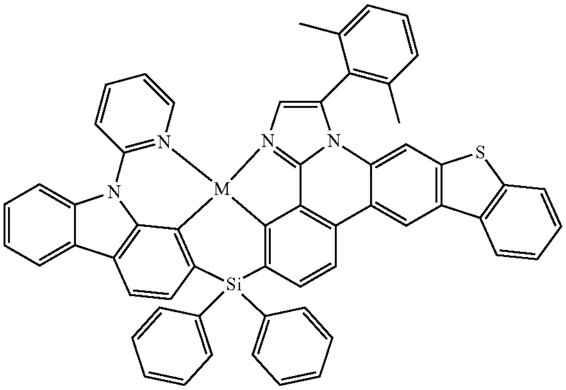
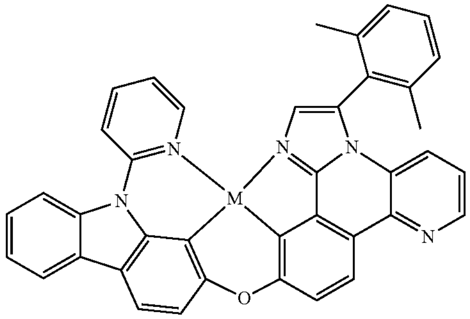
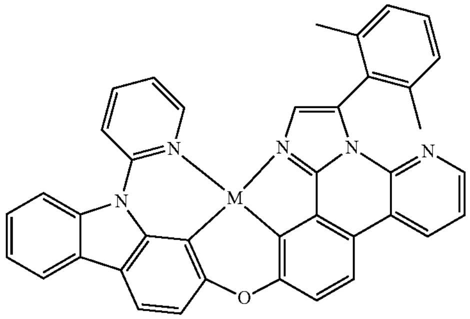
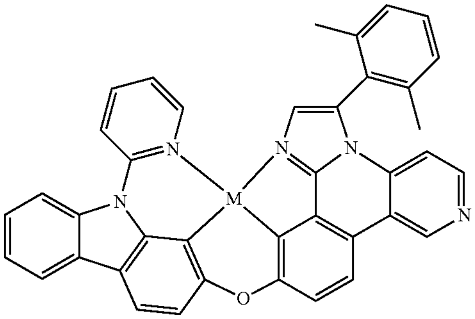
-continued
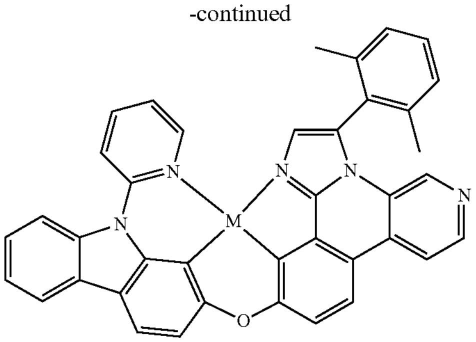
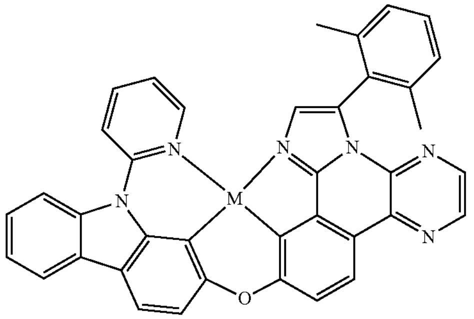
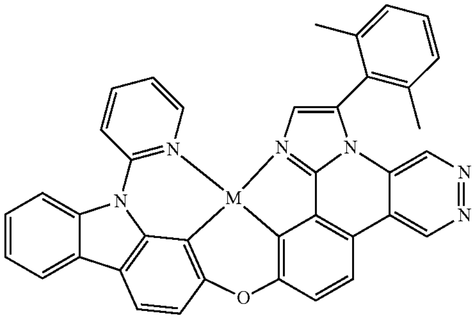
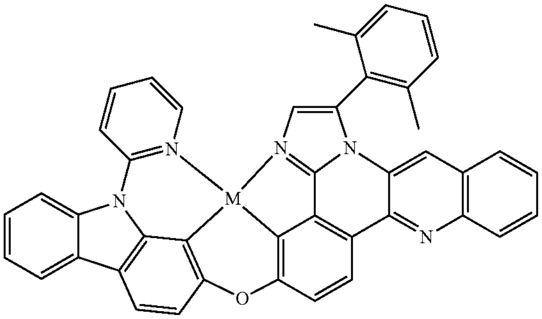
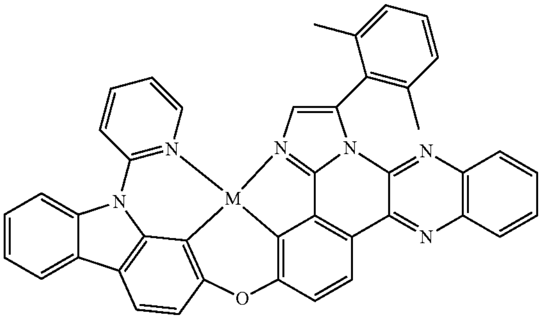

-continued
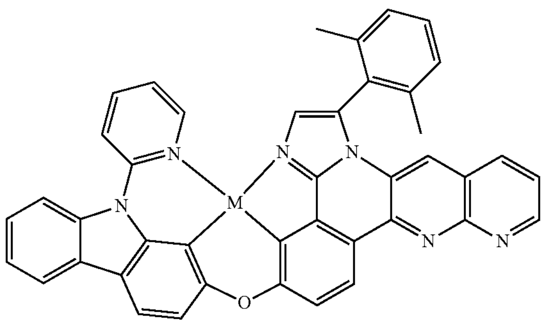
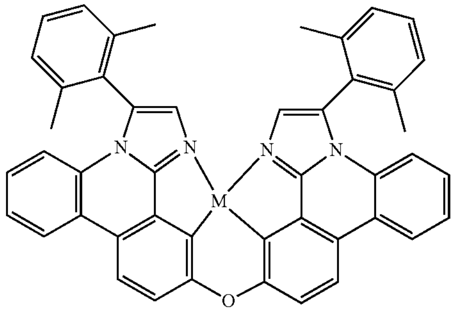
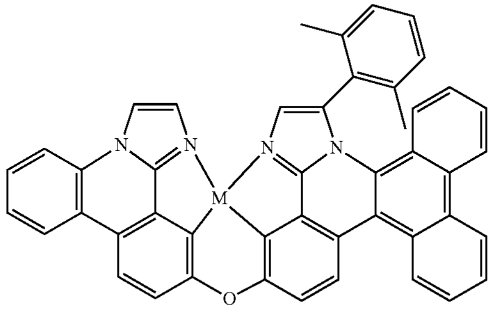
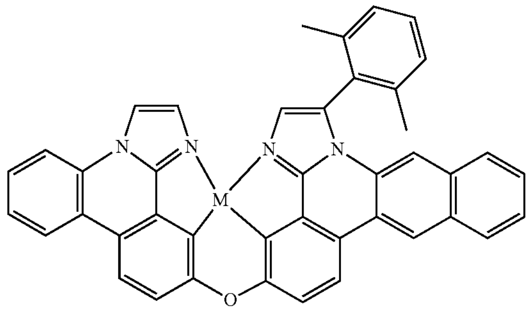
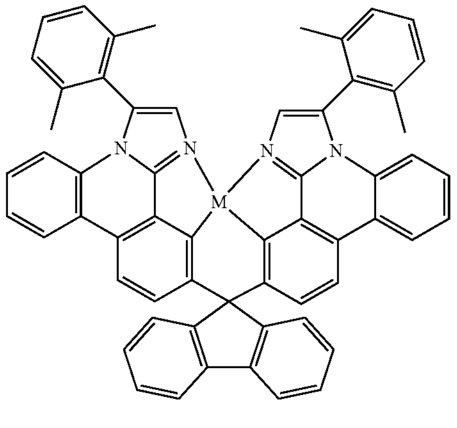
-continued
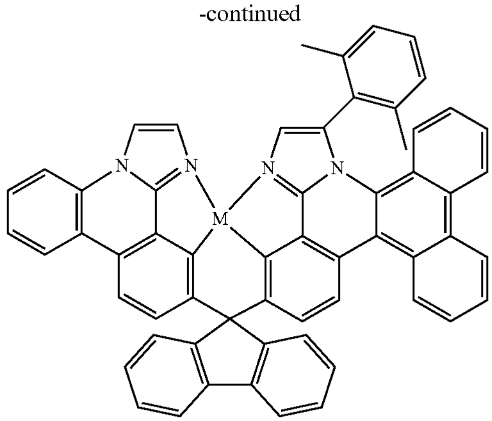
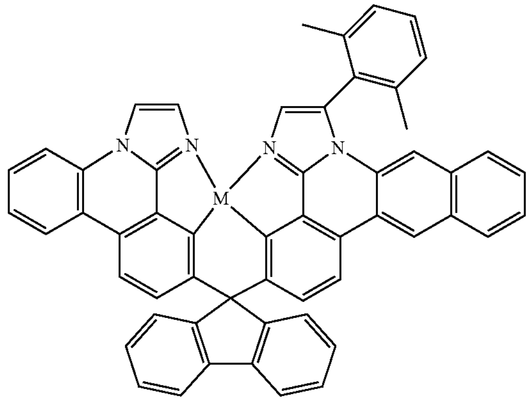
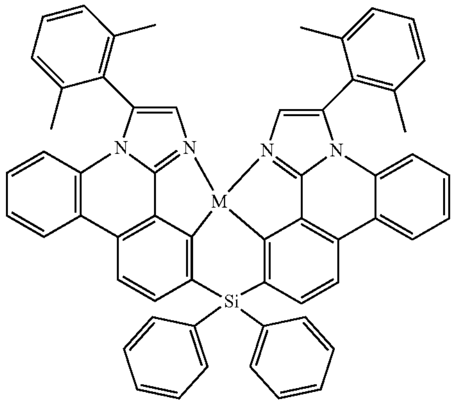
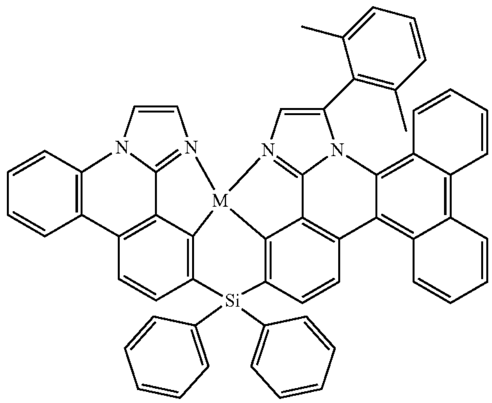

-continued
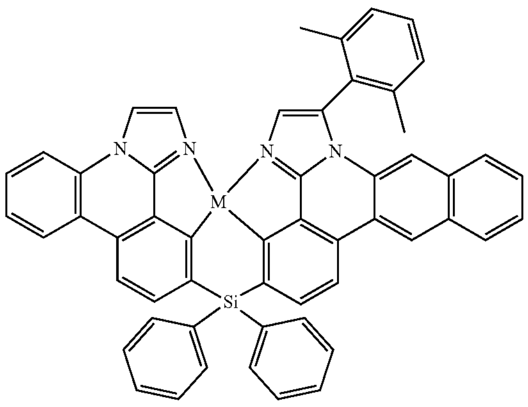
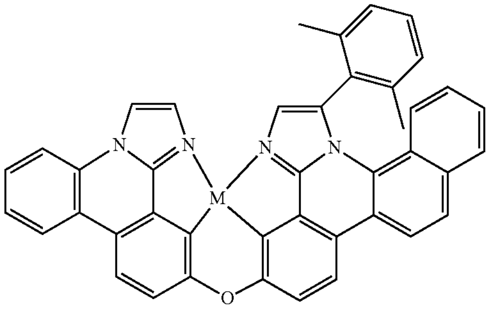
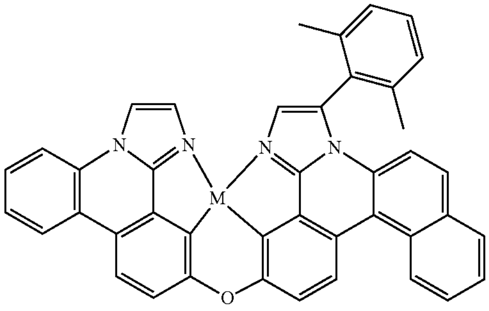
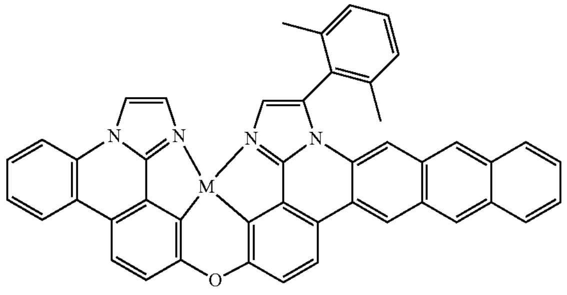
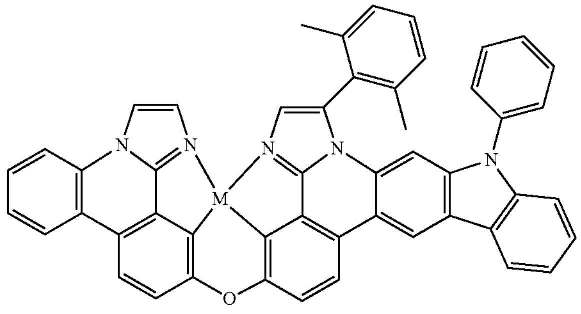
-continued
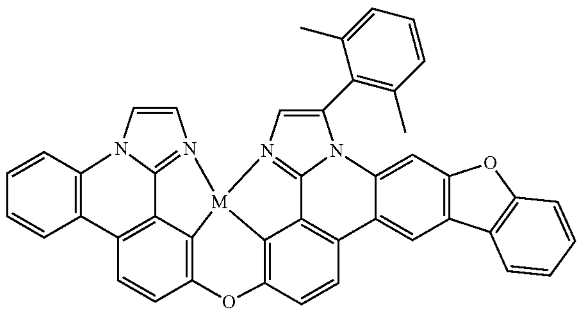
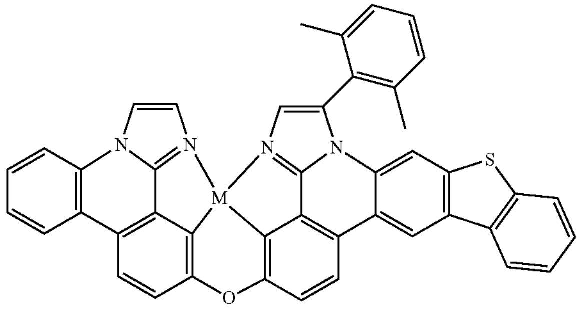
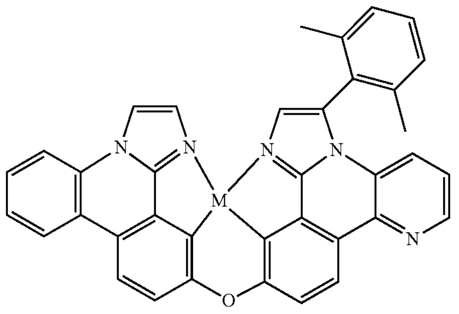
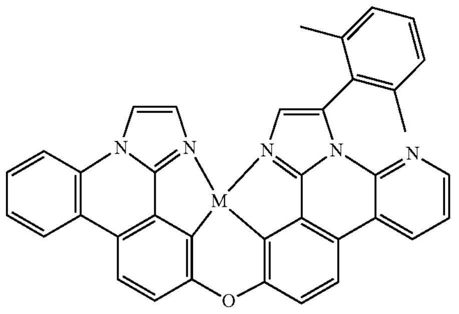
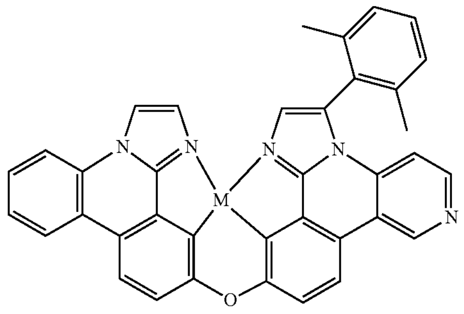

-continued
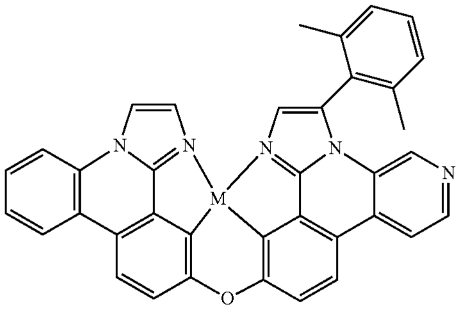
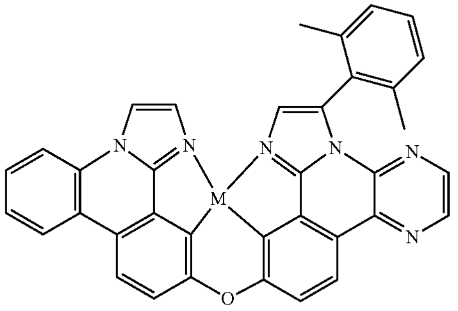
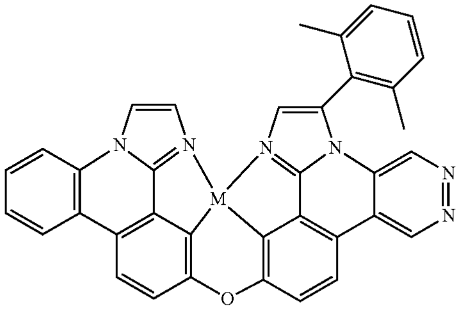
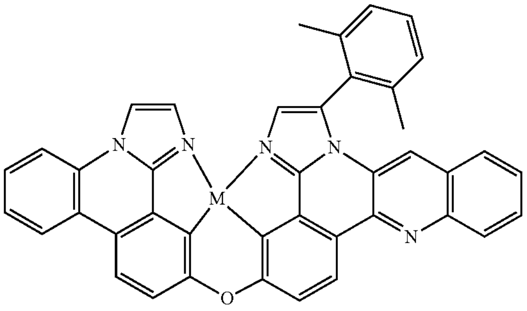
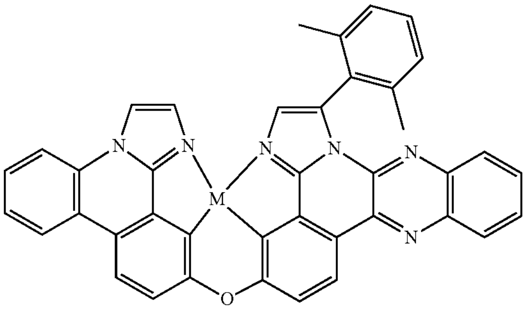
-continued
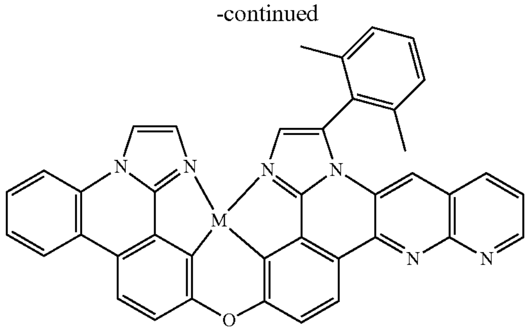
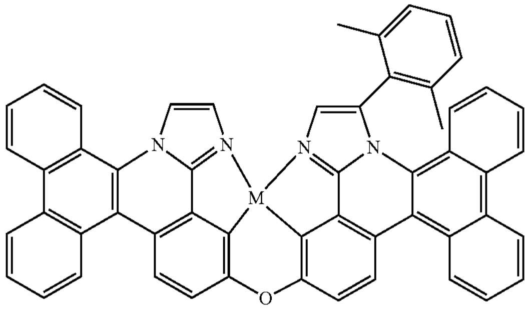
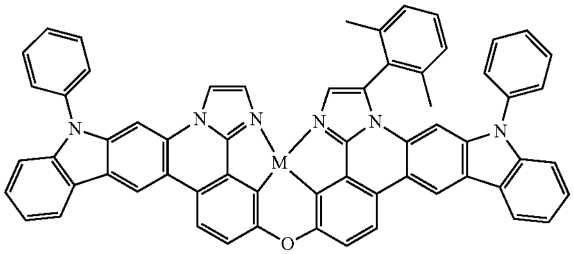
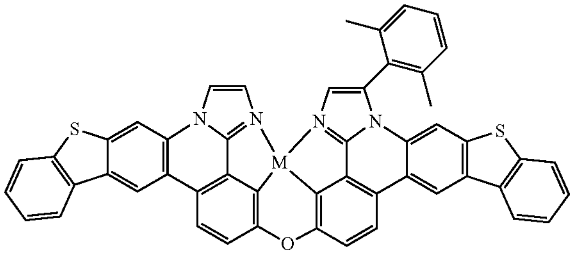
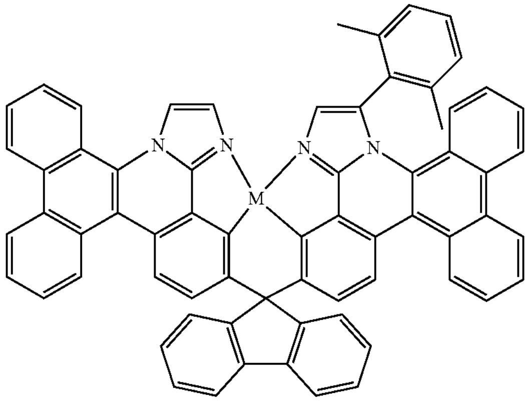

-continued
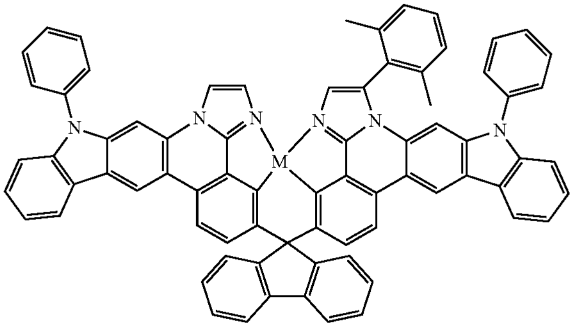
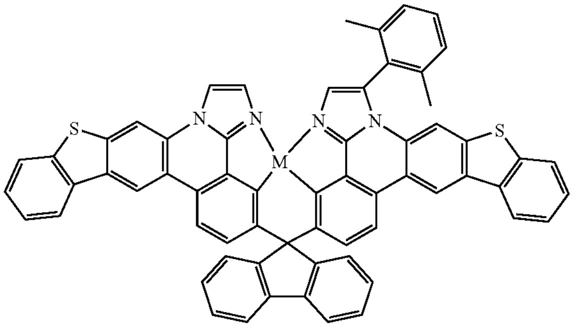
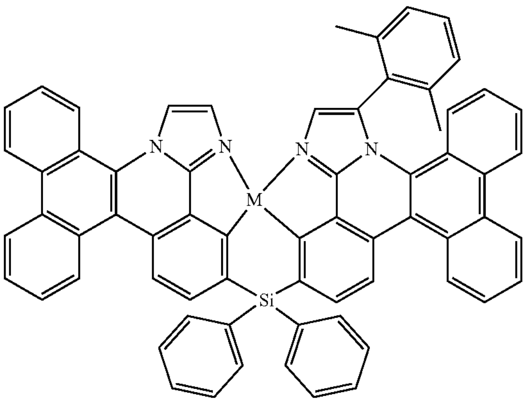
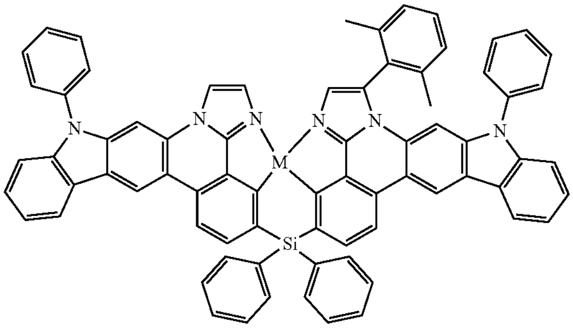
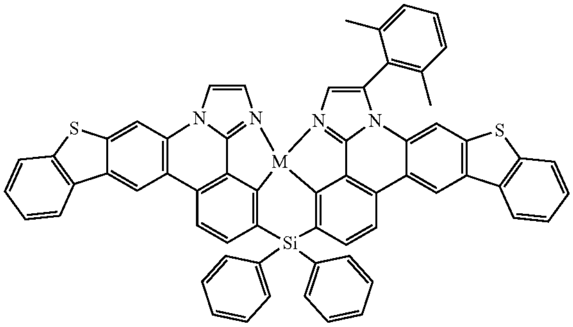
-continued
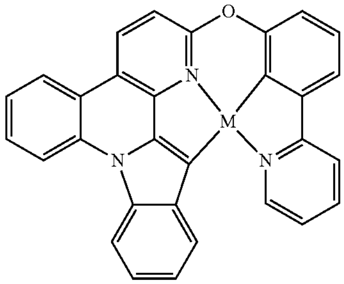
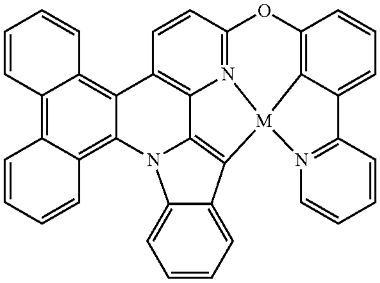
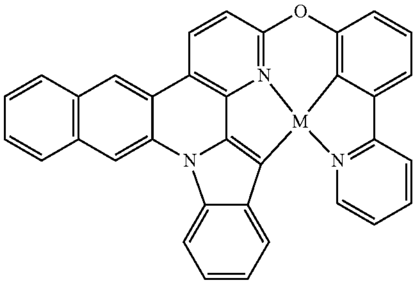
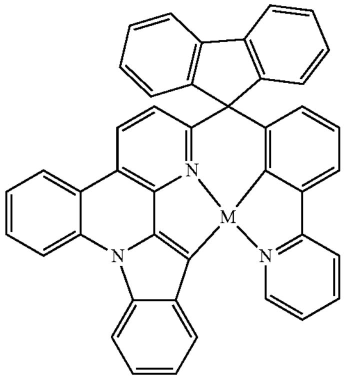
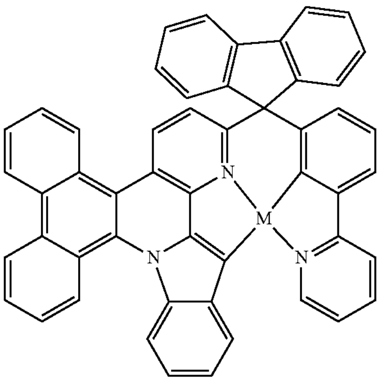

-continued
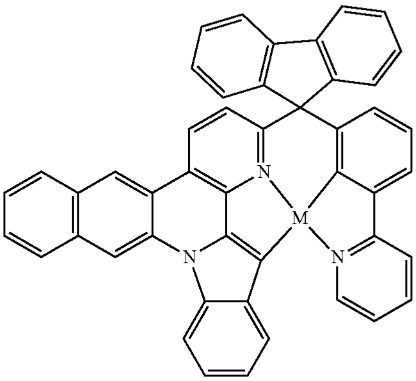
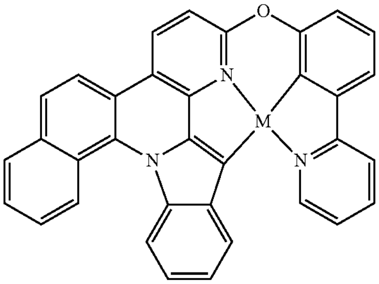
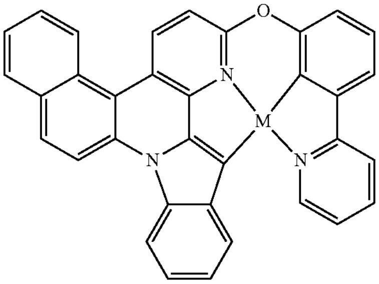
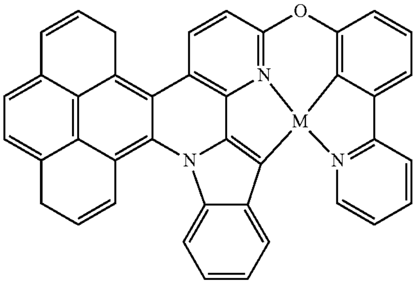
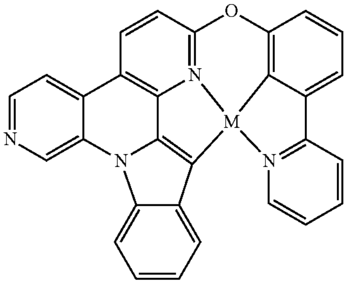
-continued
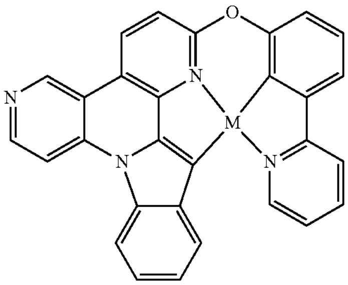
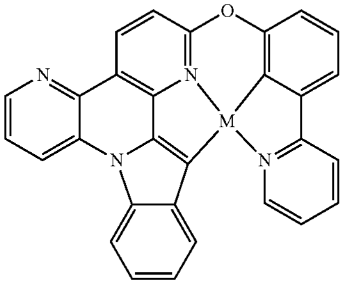
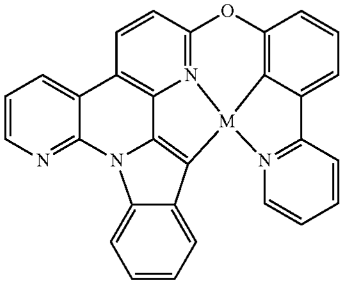
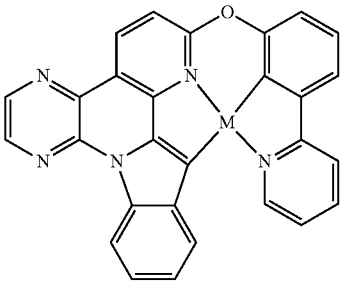
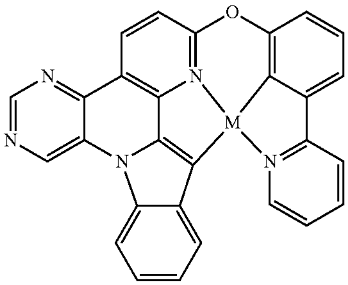
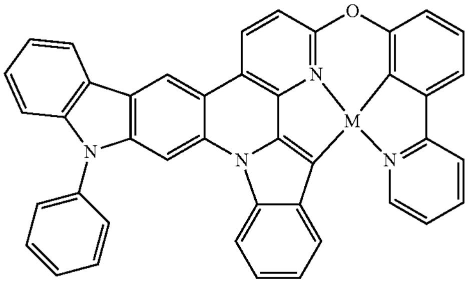

-continued
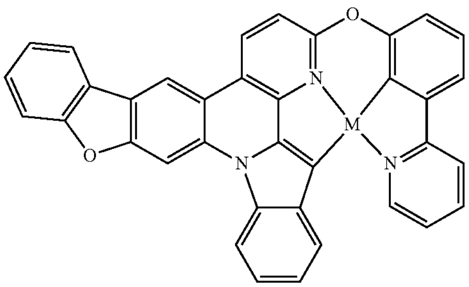
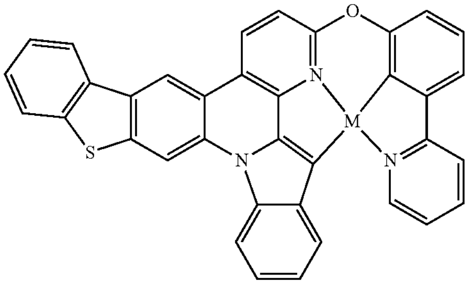
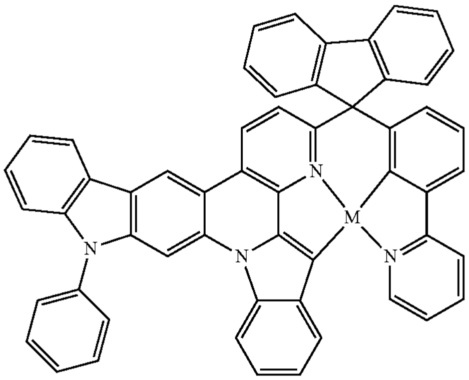
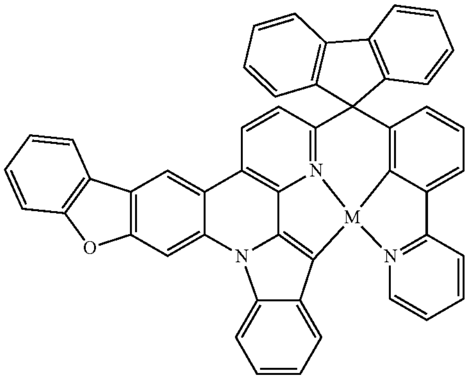
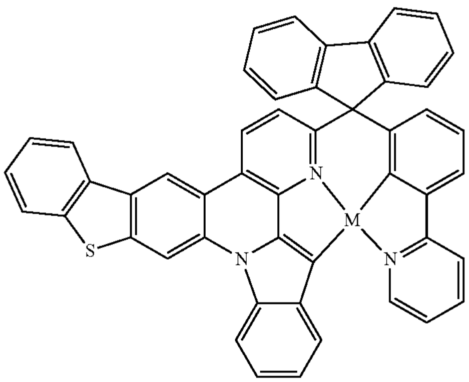
-continued
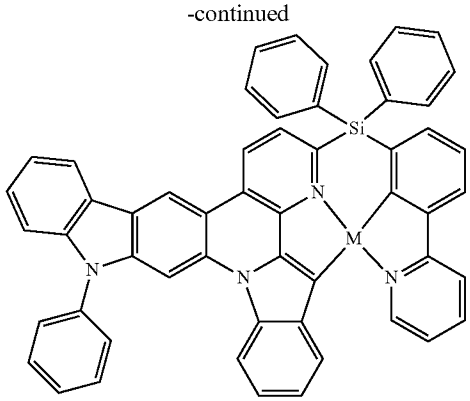
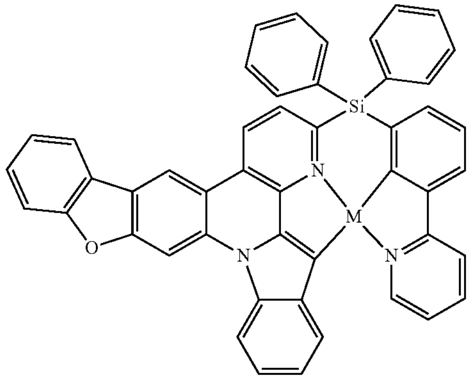
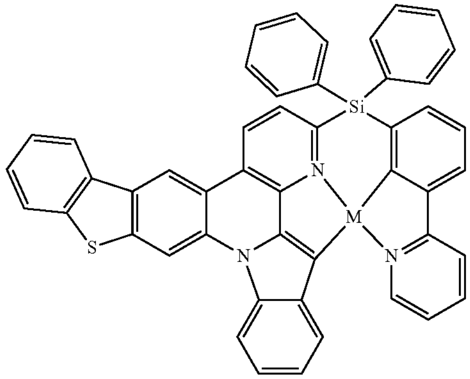
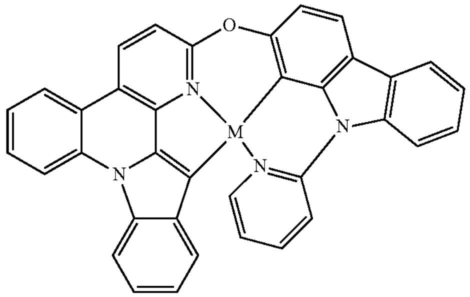
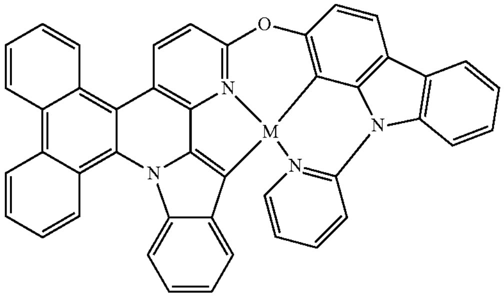

-continued
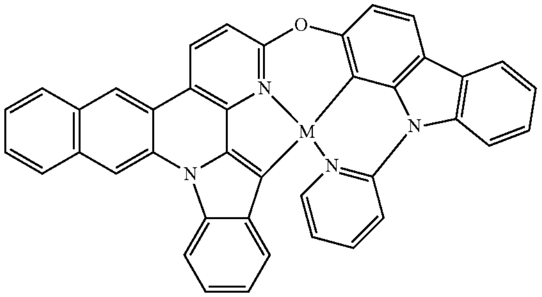
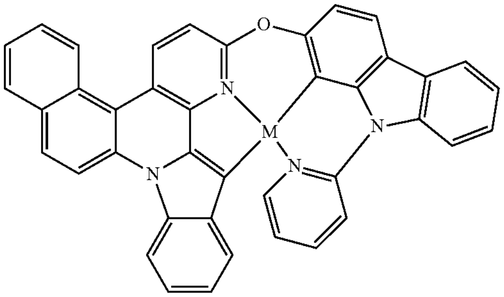
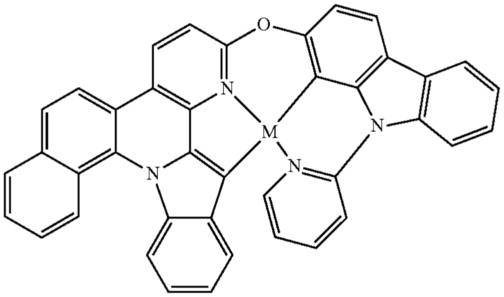
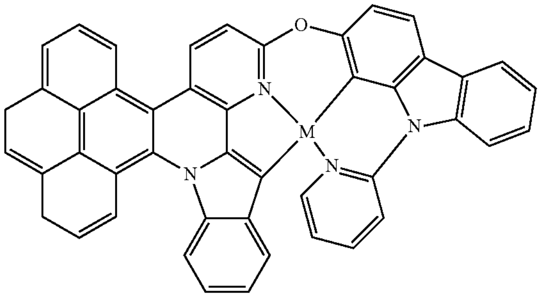
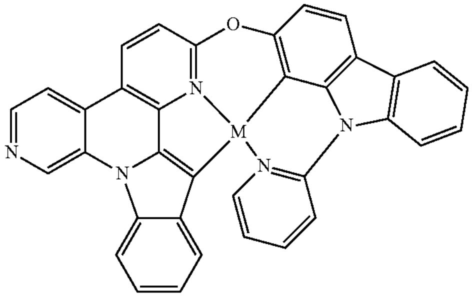
-continued
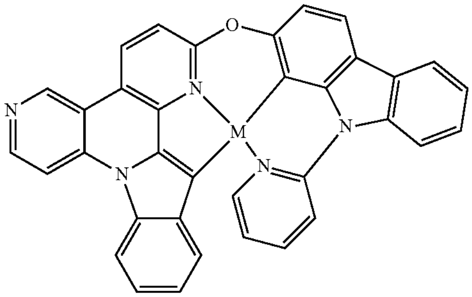
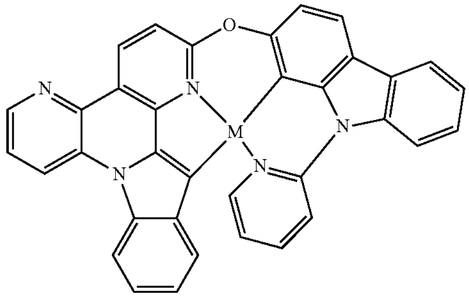
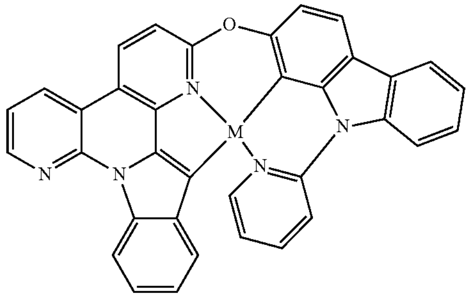
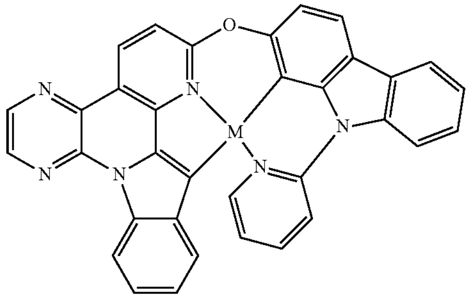
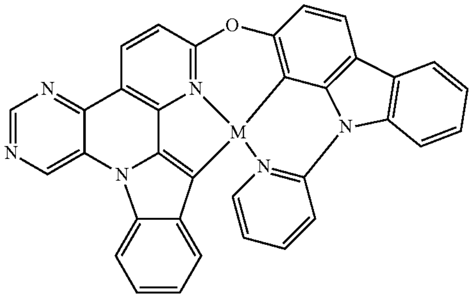

-continued
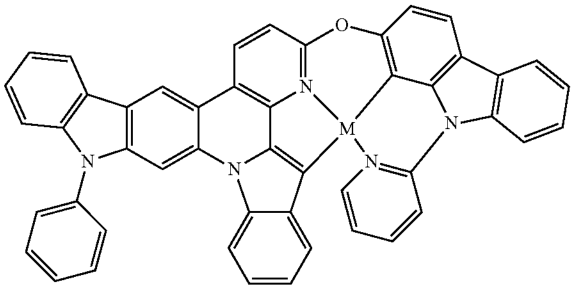
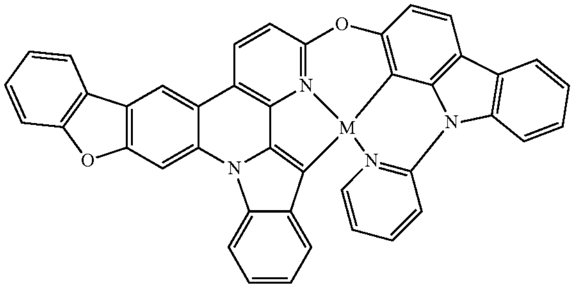
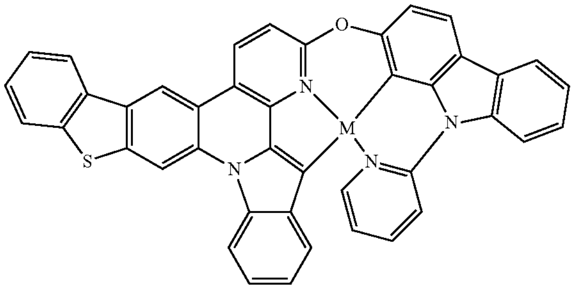
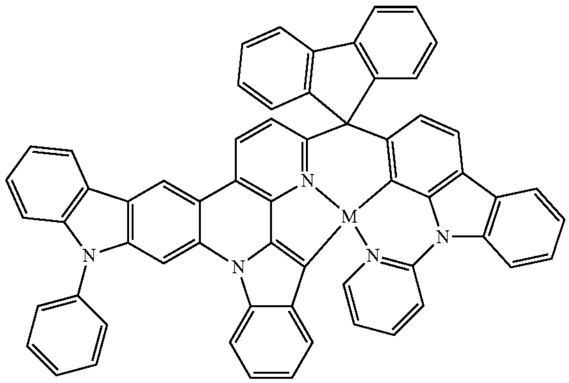
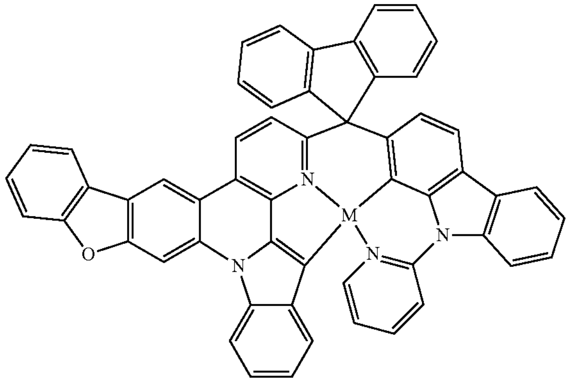
-continued
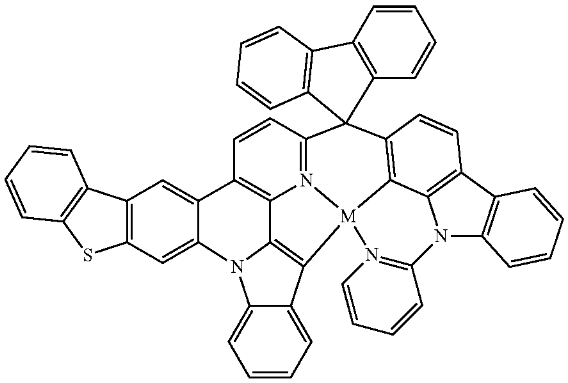
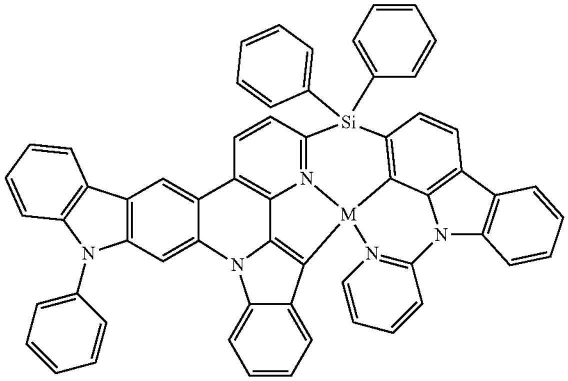
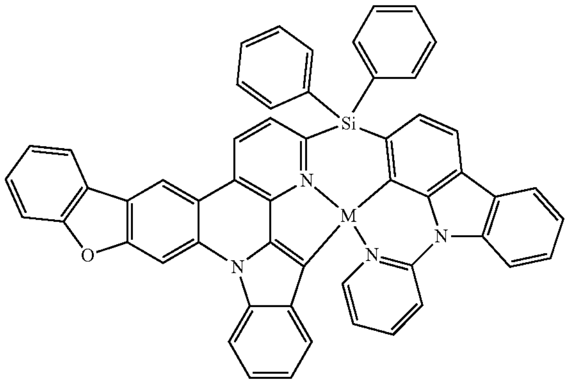
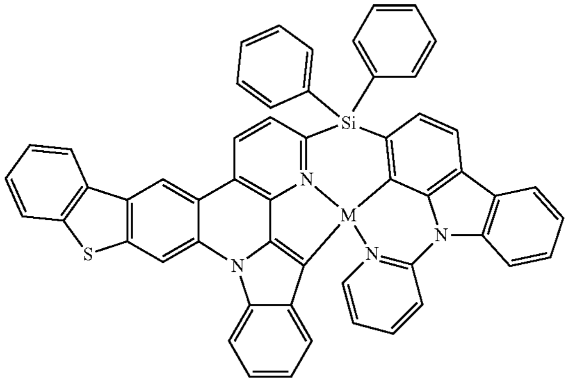

-continued
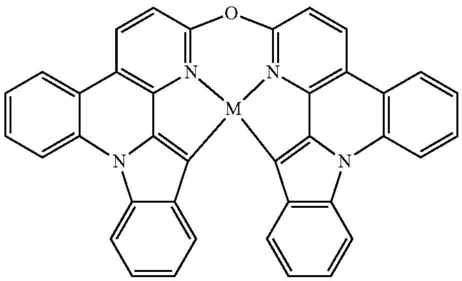
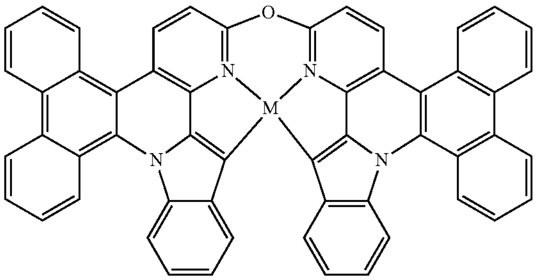
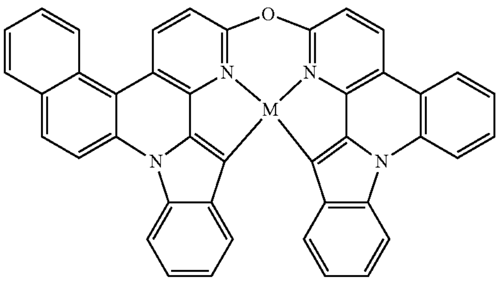
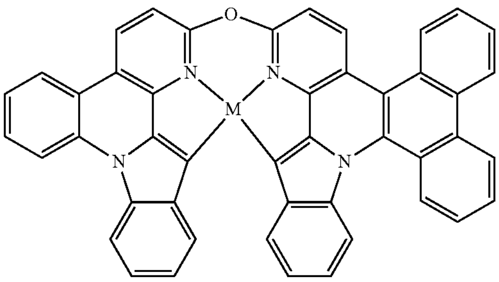
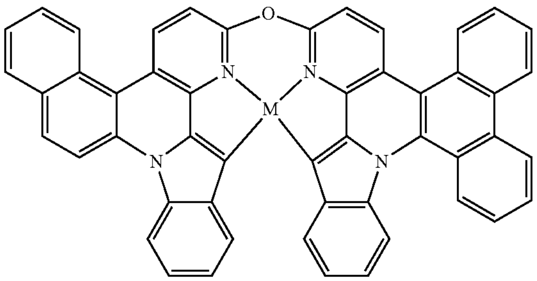
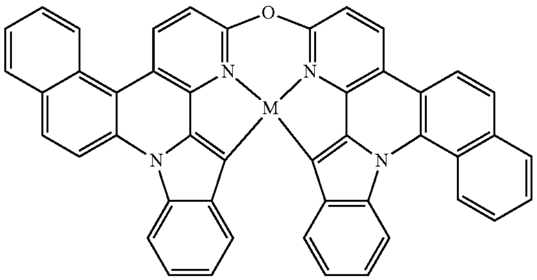
-continued
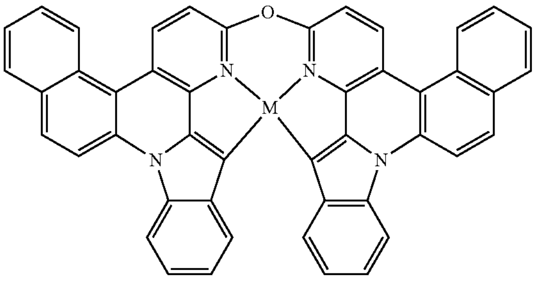
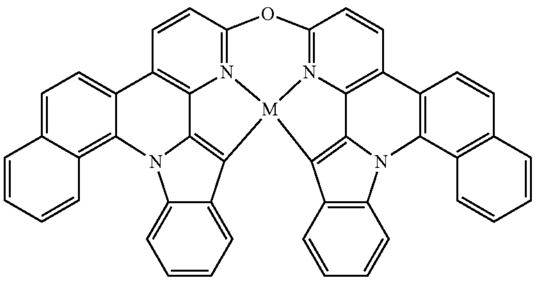
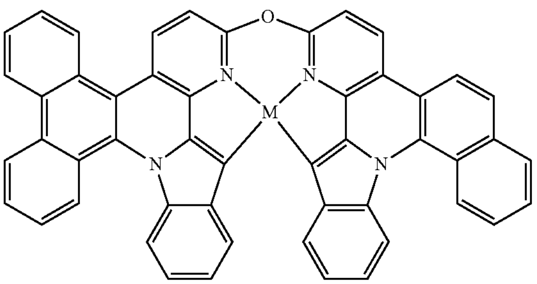
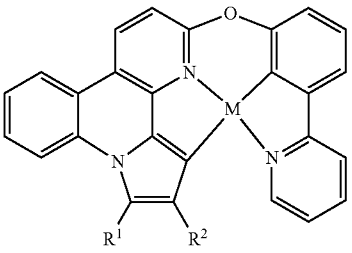
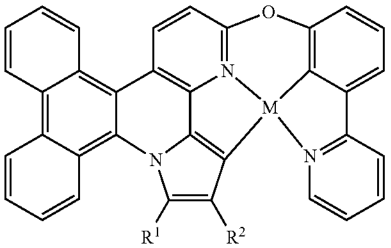
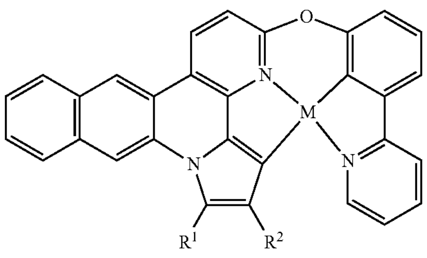

-continued
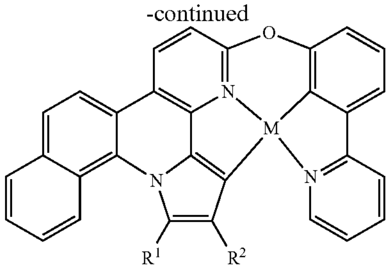
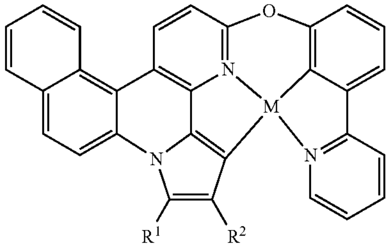
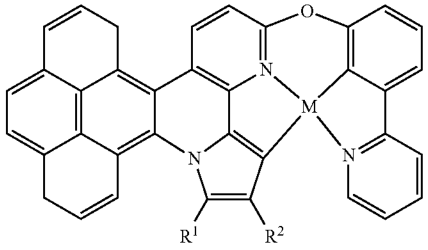
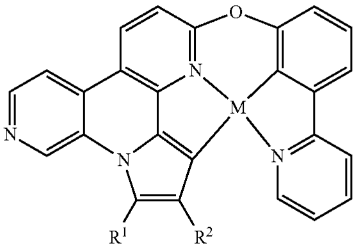
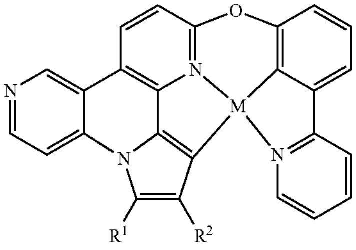
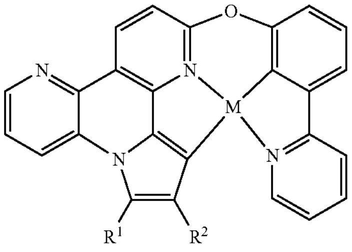
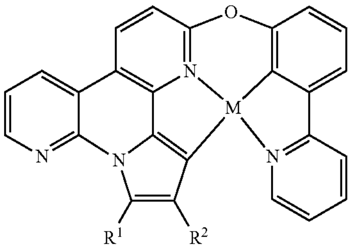
-continued
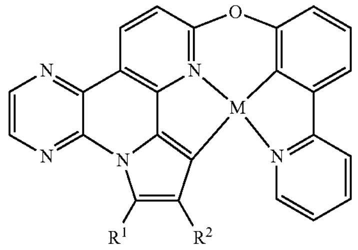
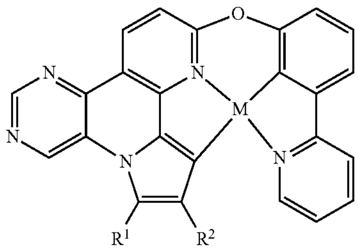
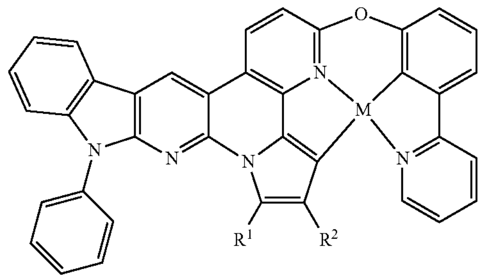
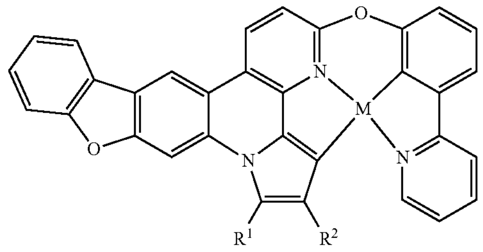
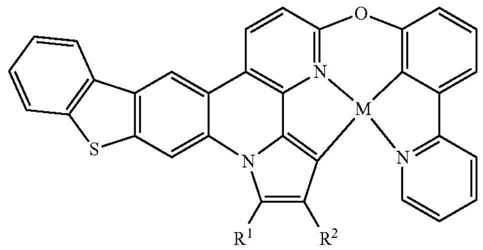
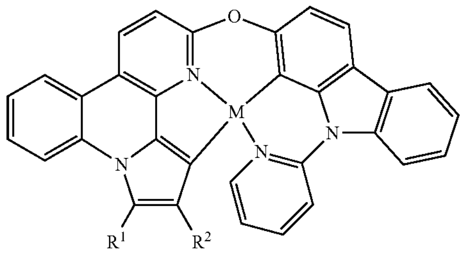

-continued
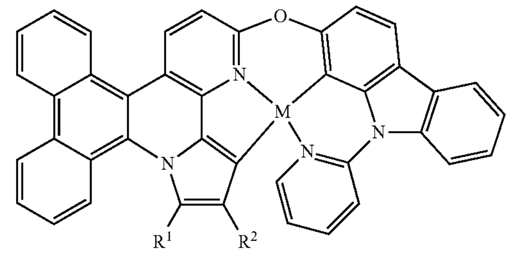
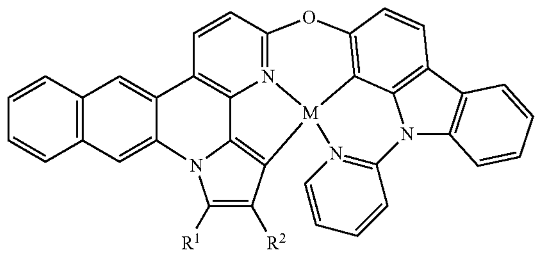
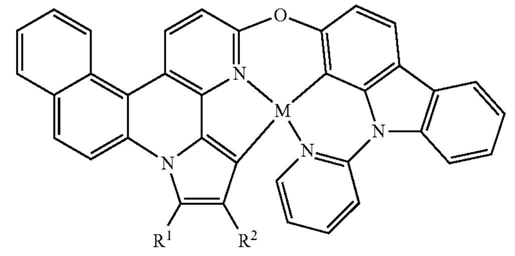
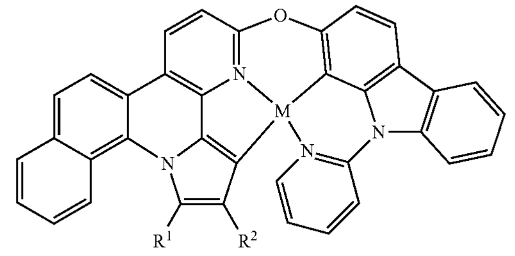
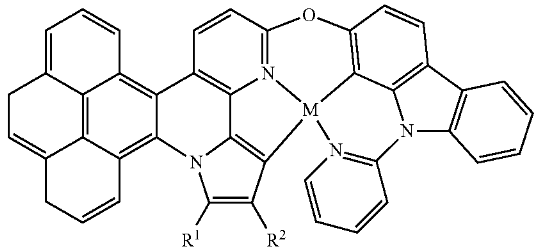
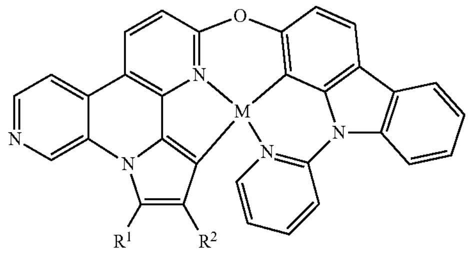
-continued
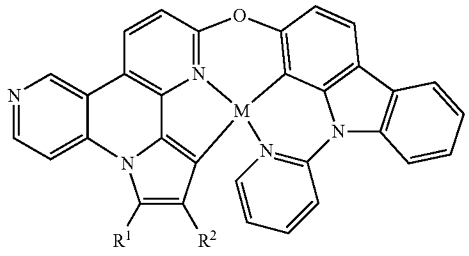
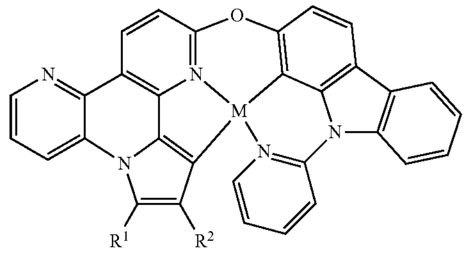
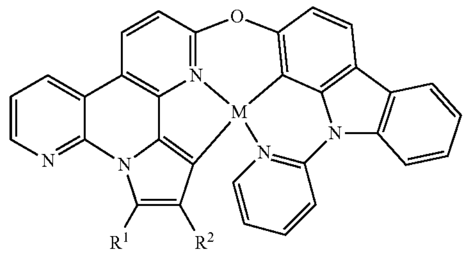
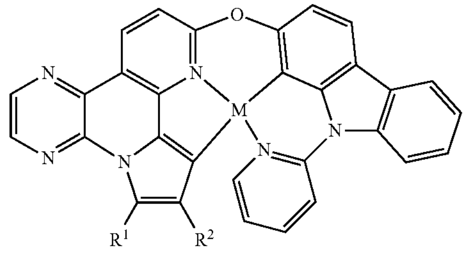
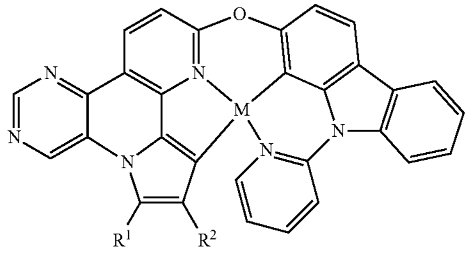
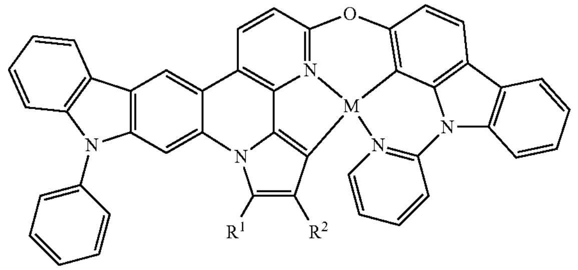

-continued
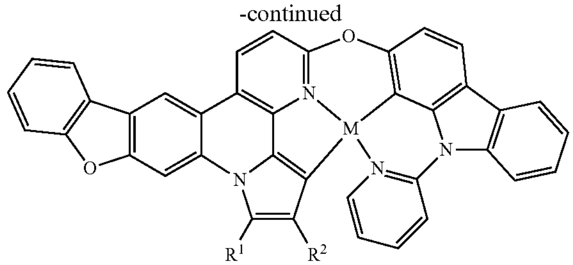
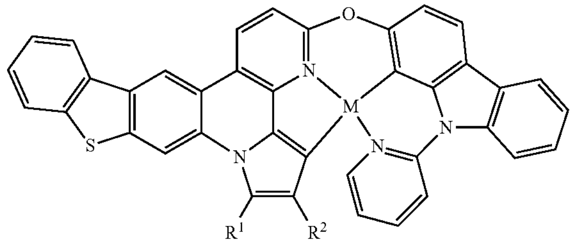
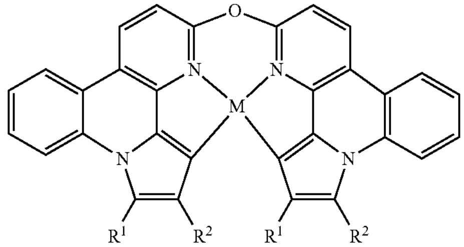
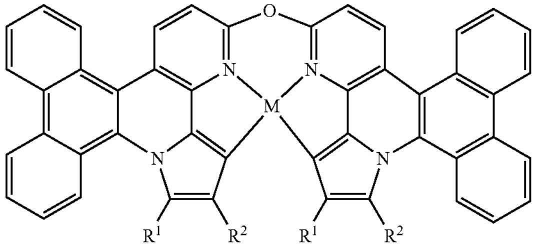
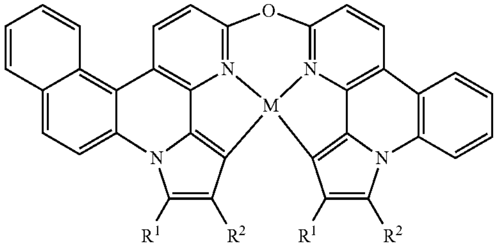
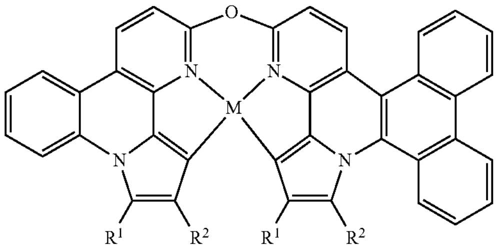
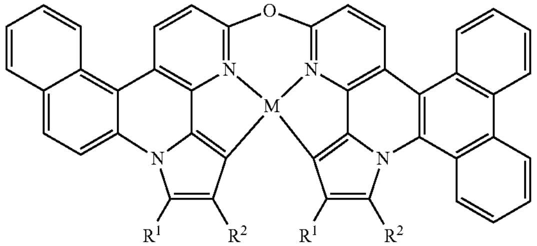
-continued
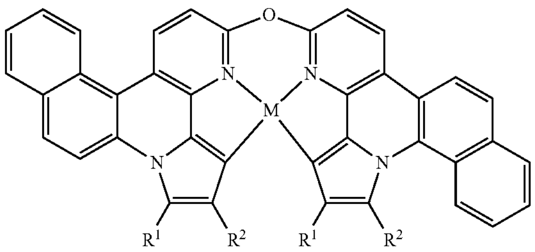
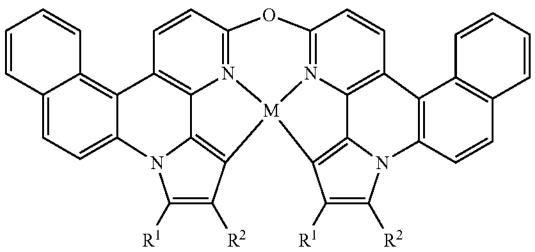
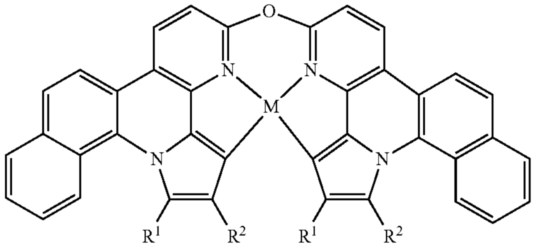
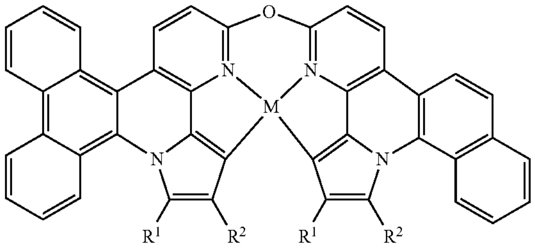
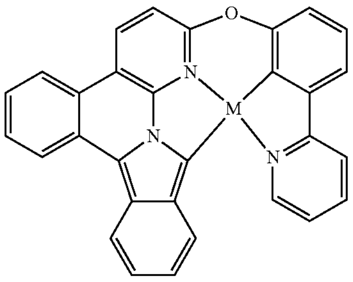
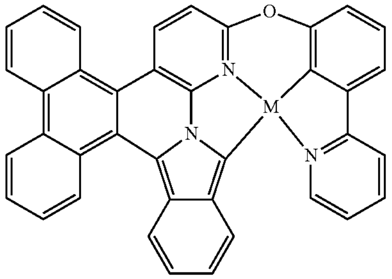

-continued
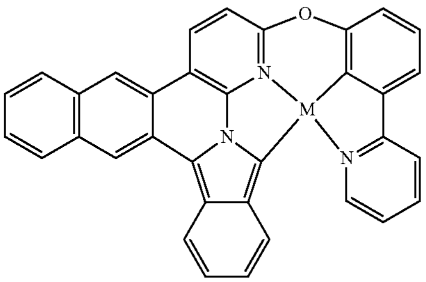
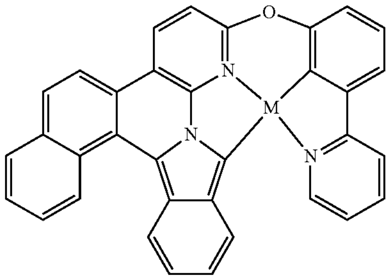
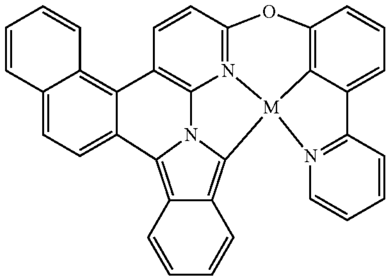
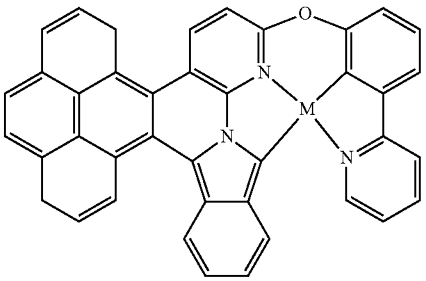
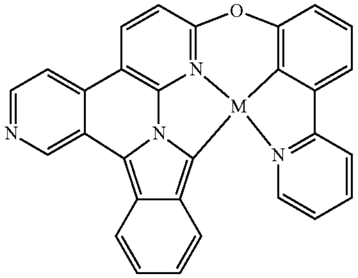
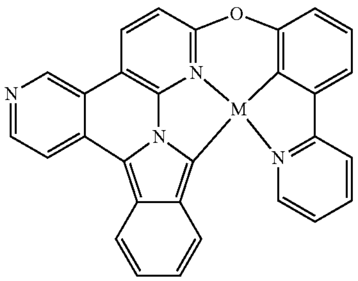
-continued
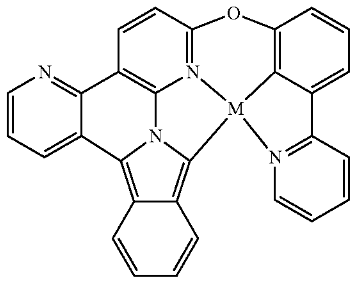
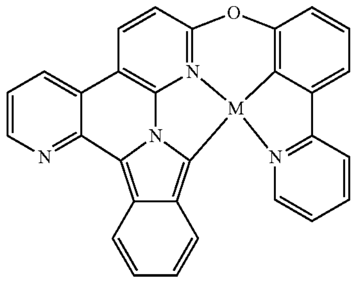
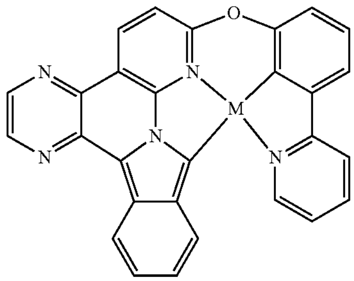
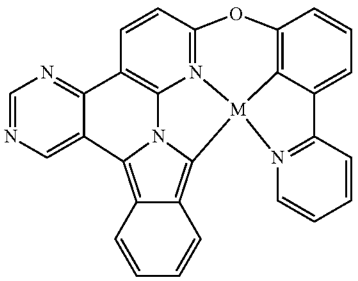
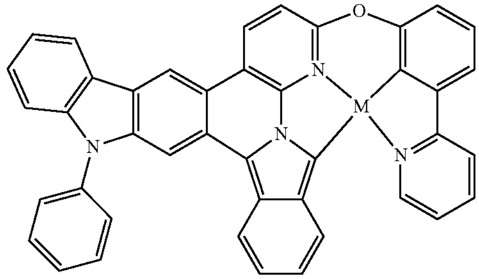
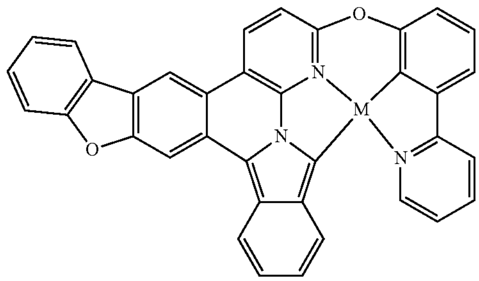

-continued
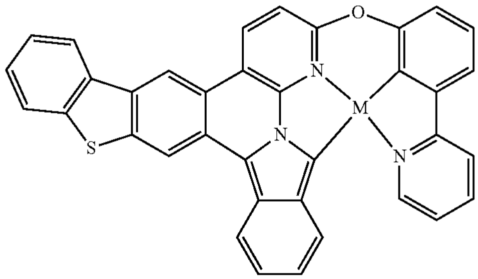
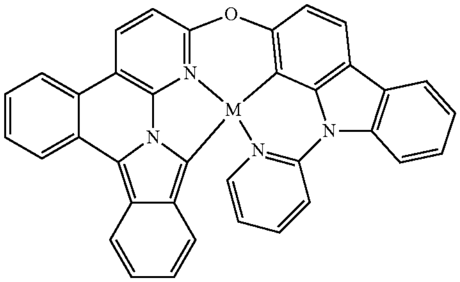
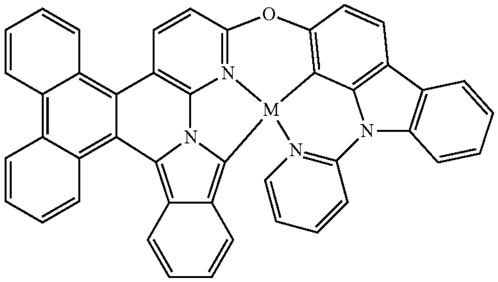
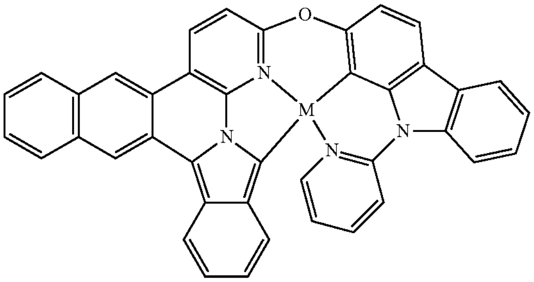
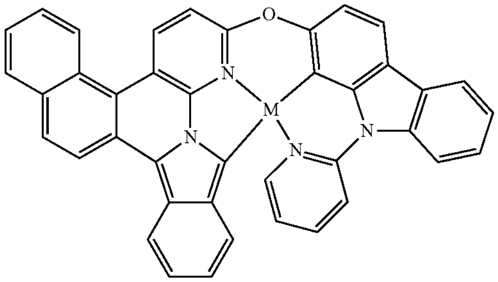
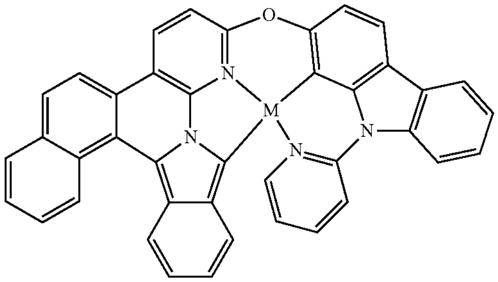
-continued
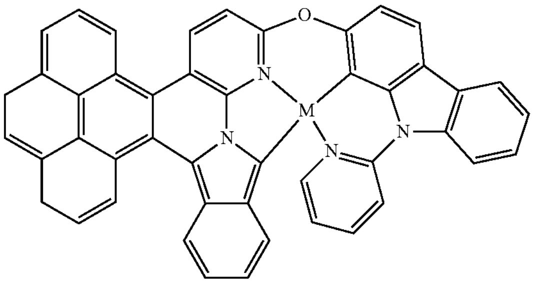
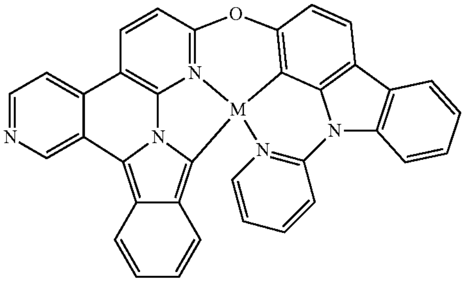
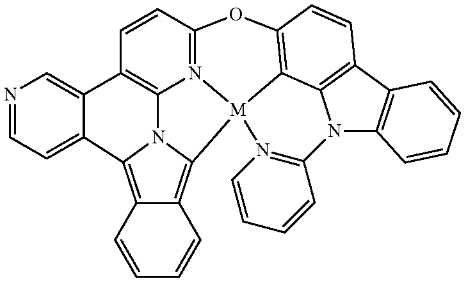
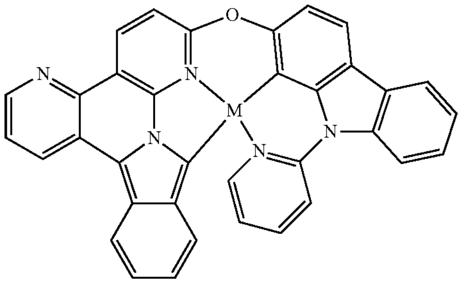
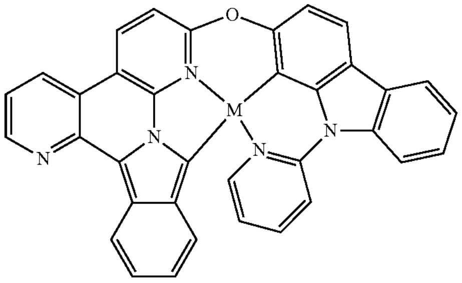
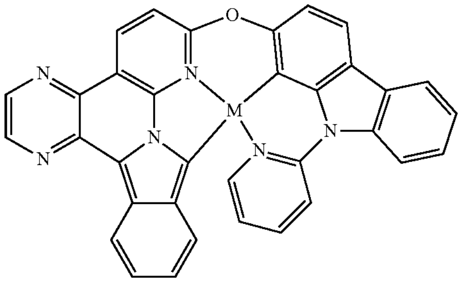

-continued
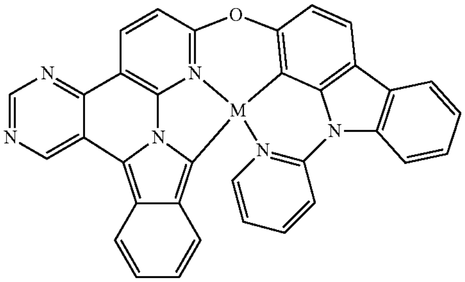
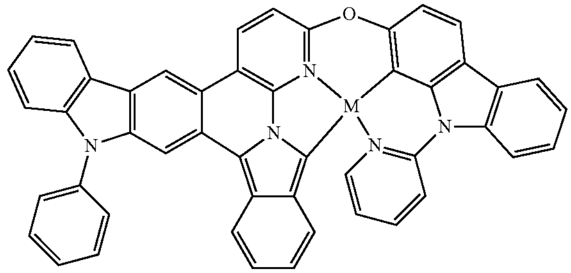
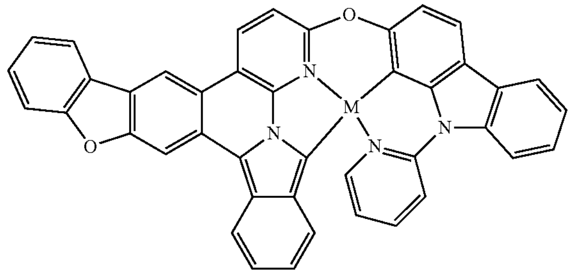
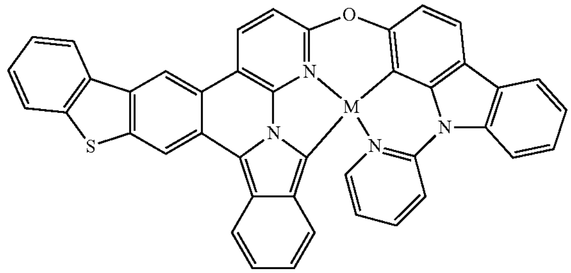
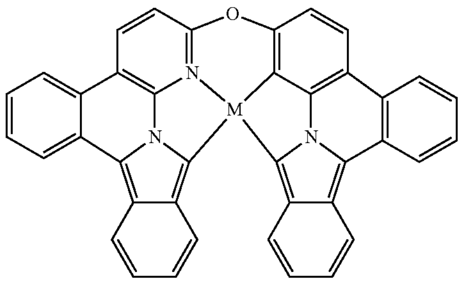
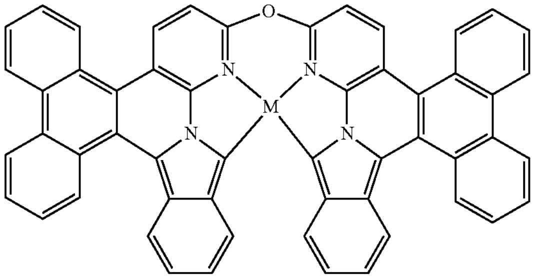
-continued
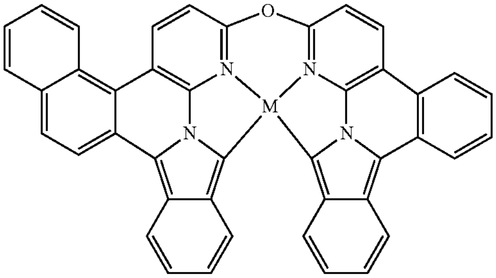
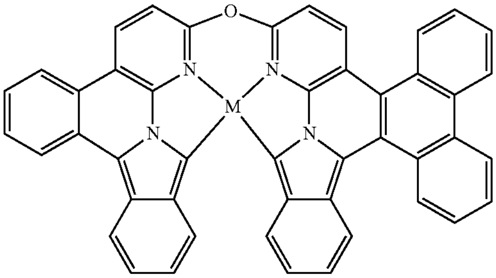
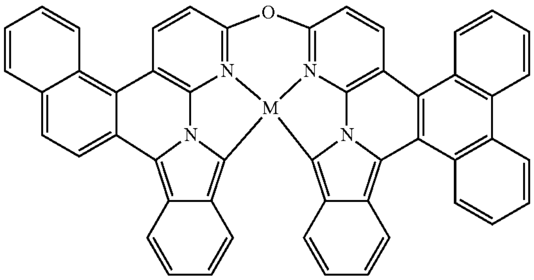
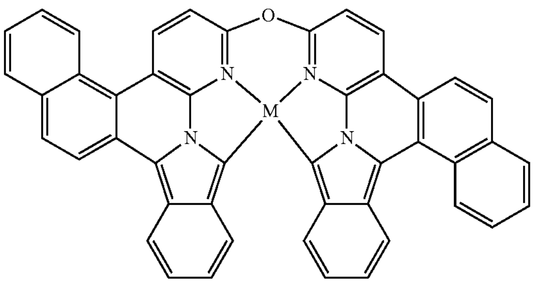
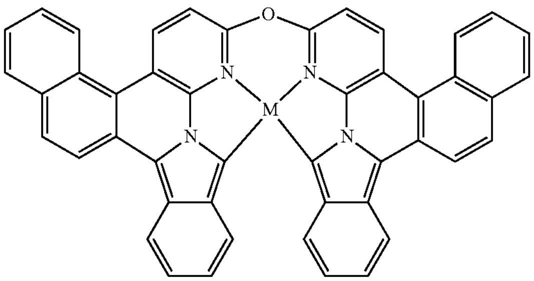
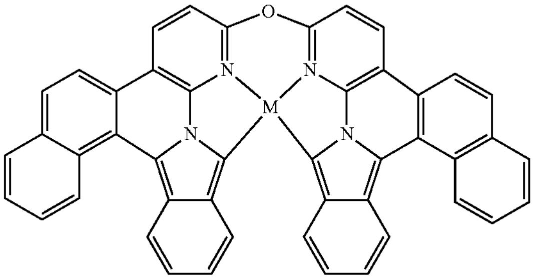

-continued
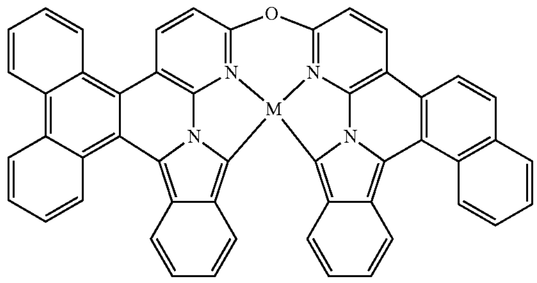
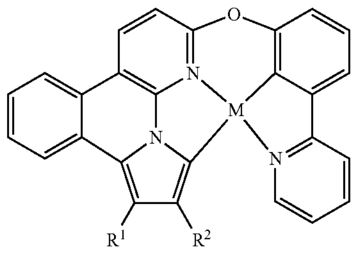
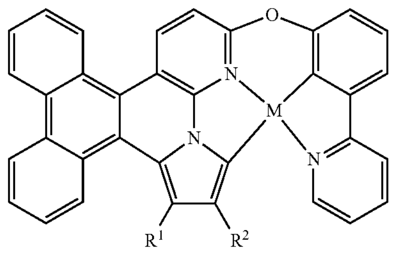
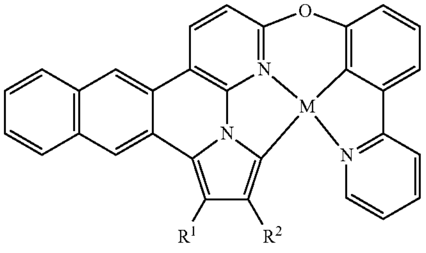
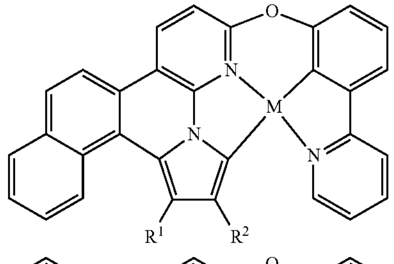
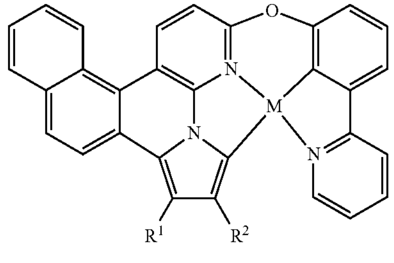
-continued
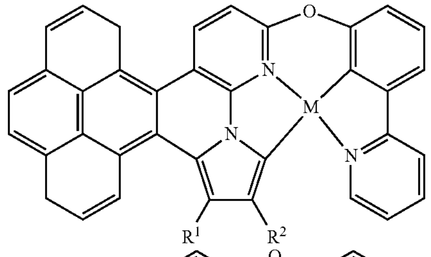
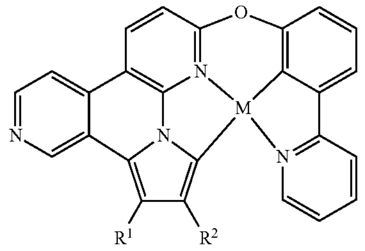
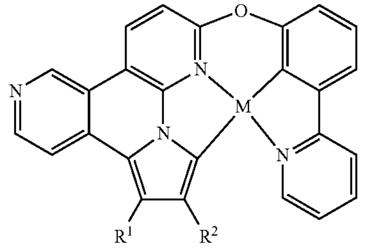
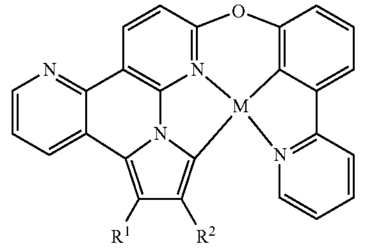
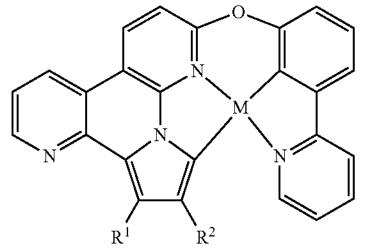
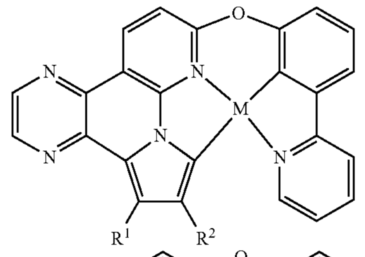
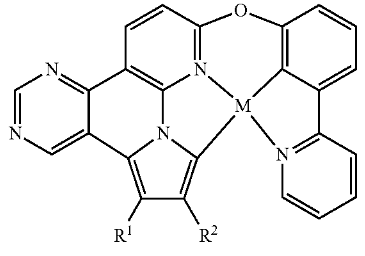

-continued
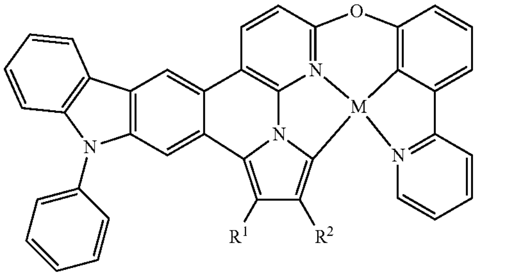
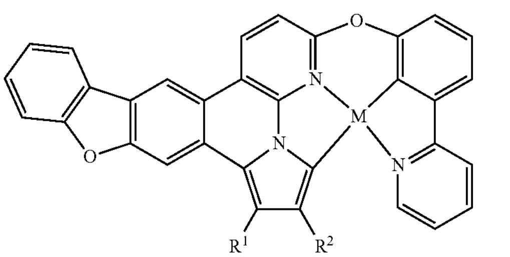
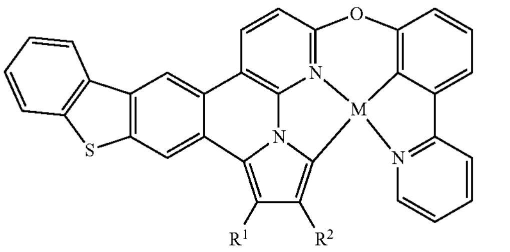
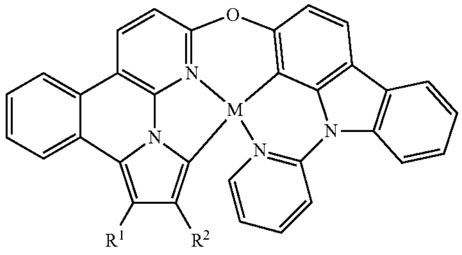
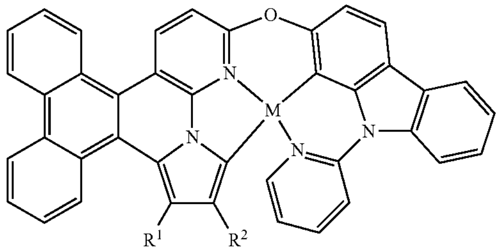
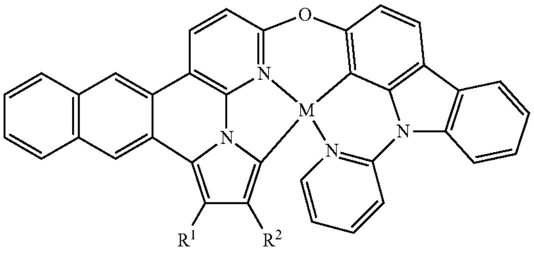
-continued
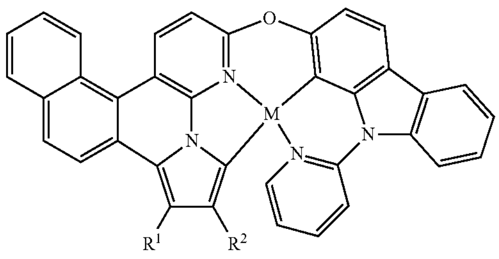
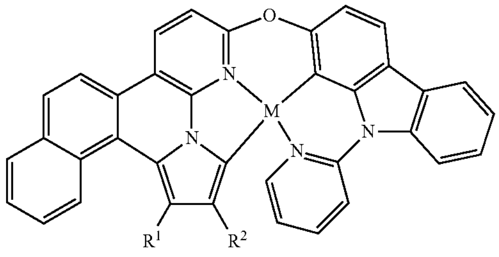
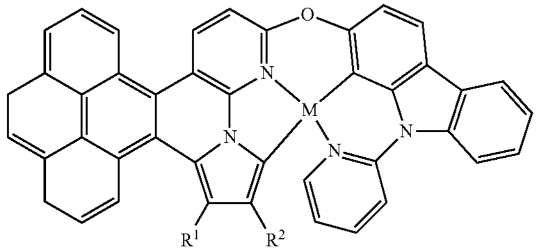
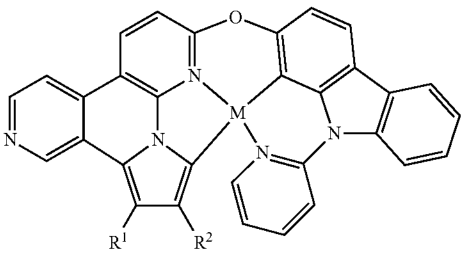
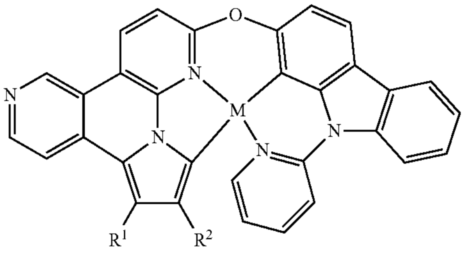
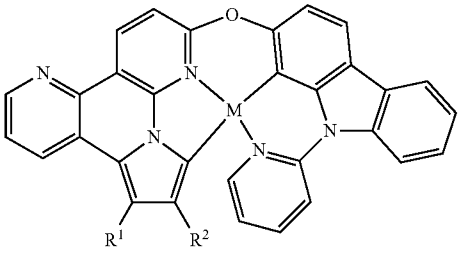

-continued
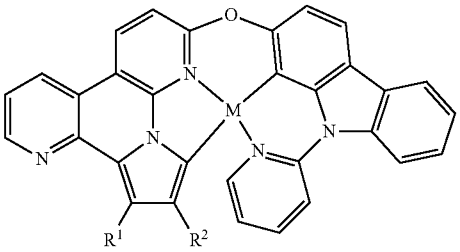
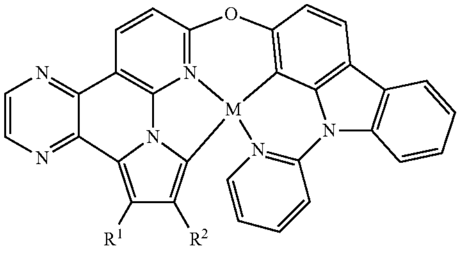
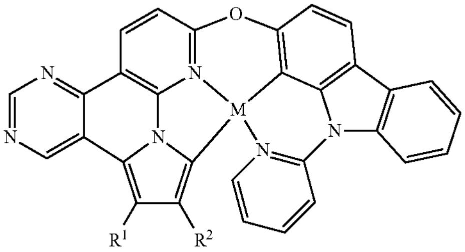
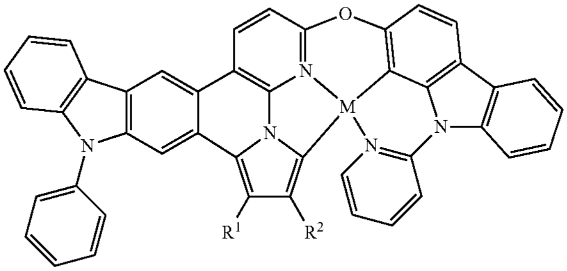
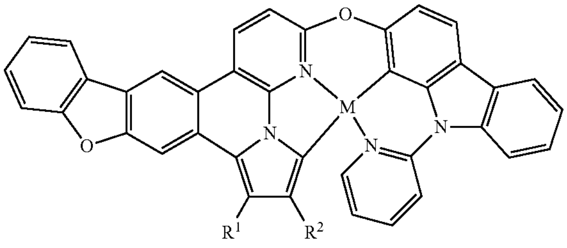
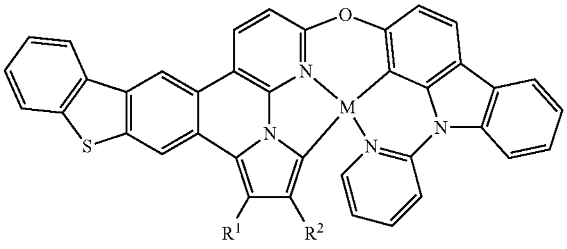
-continued
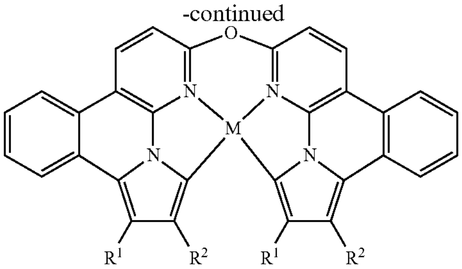
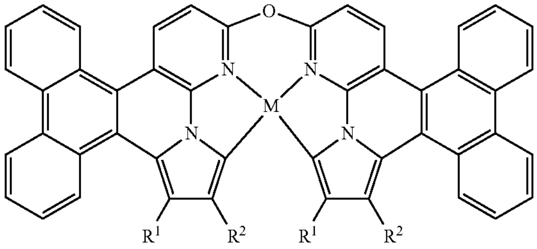
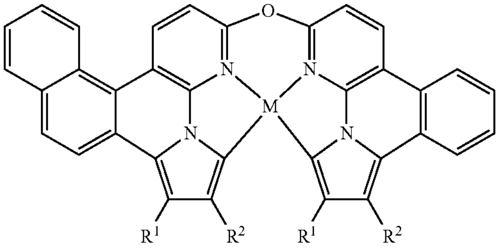
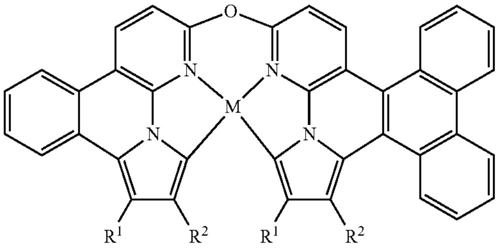
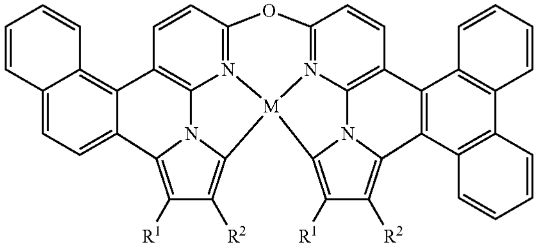
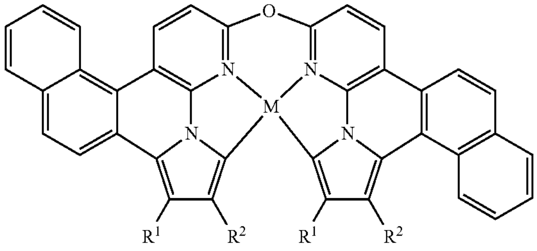
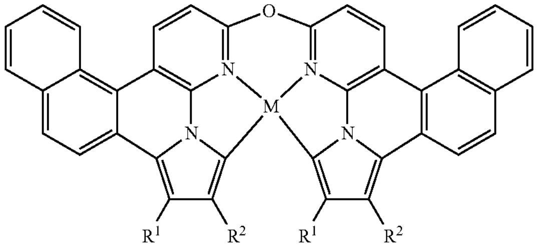

-continued
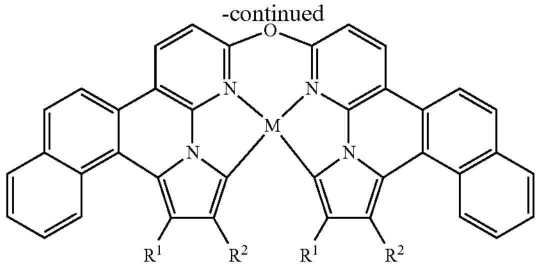
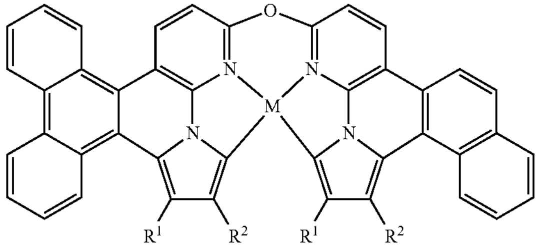
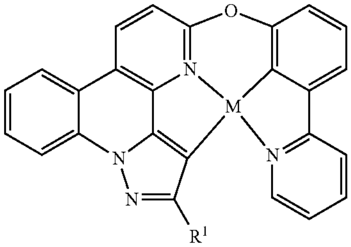
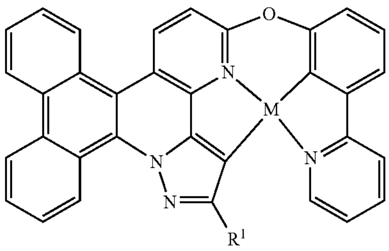
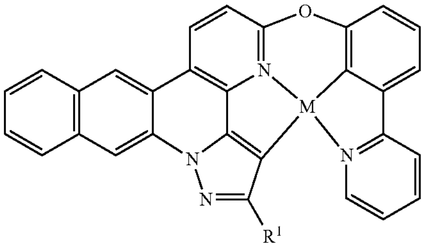
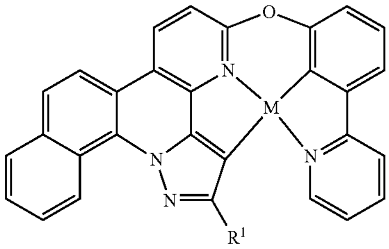
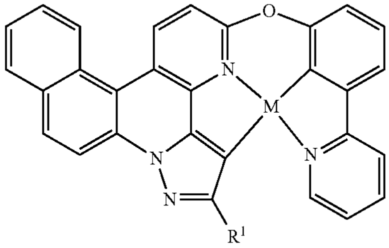
-continued
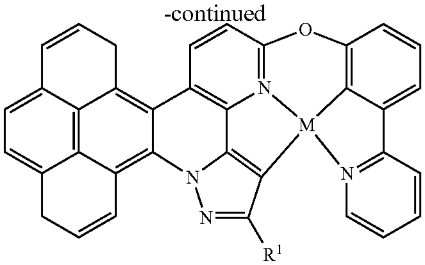
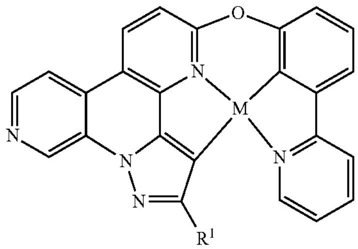
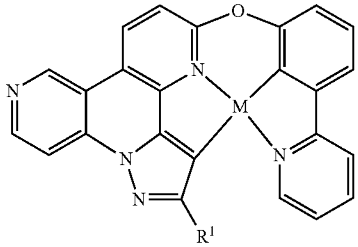
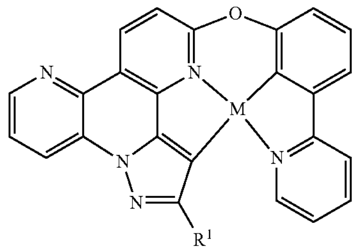
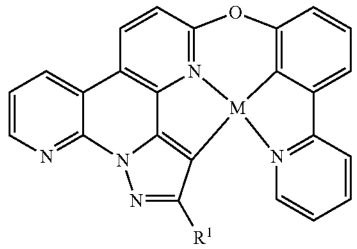
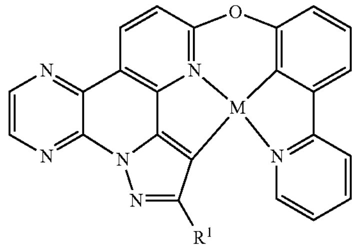
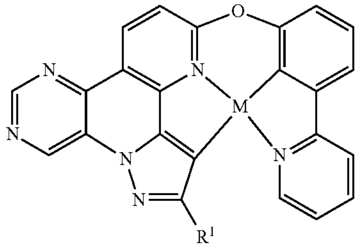

-continued
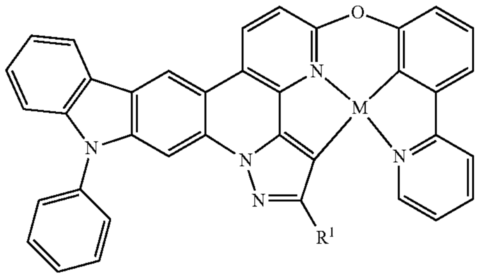
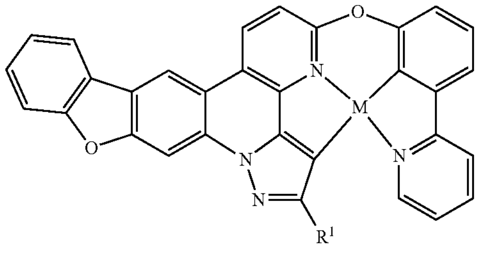
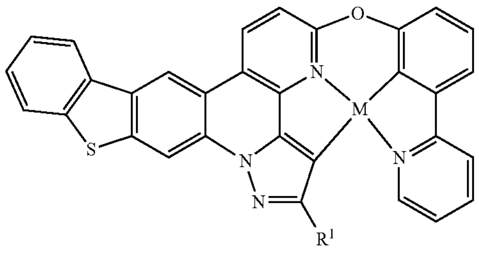
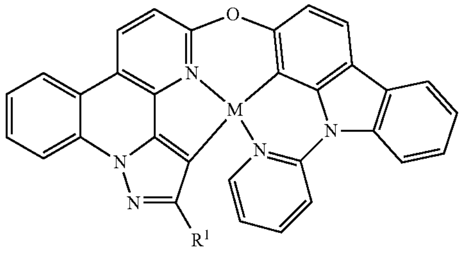
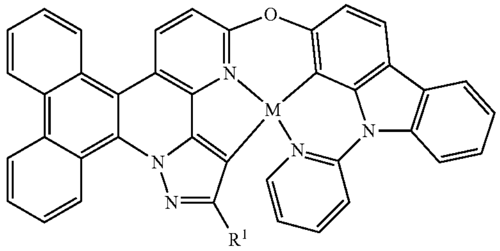
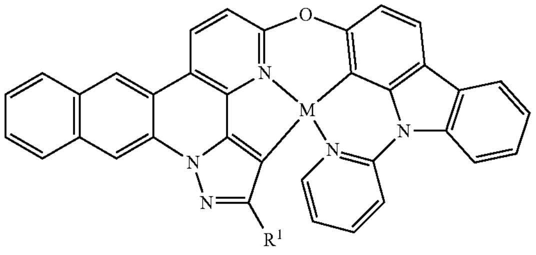
-continued
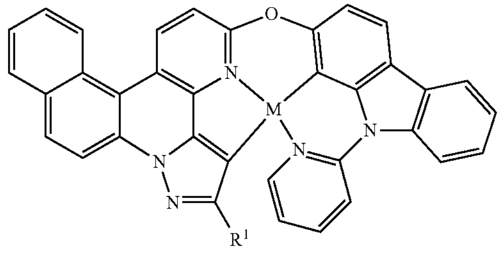
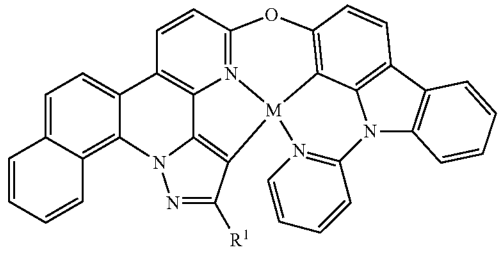
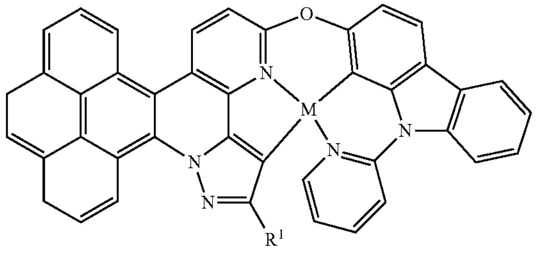
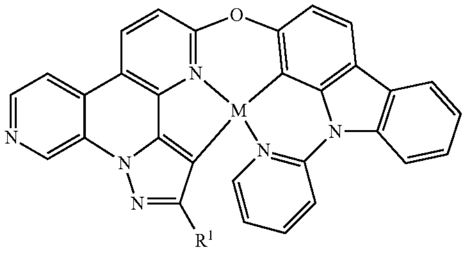
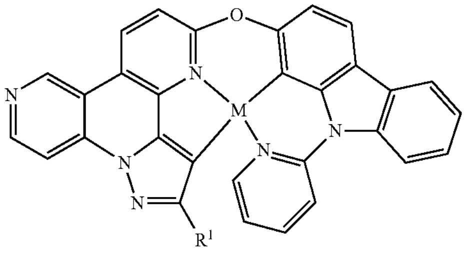
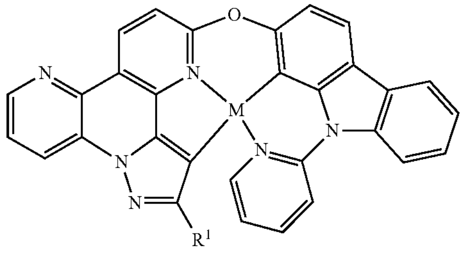

-continued
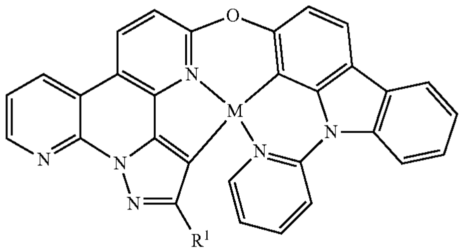
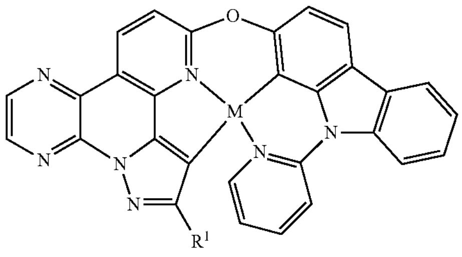
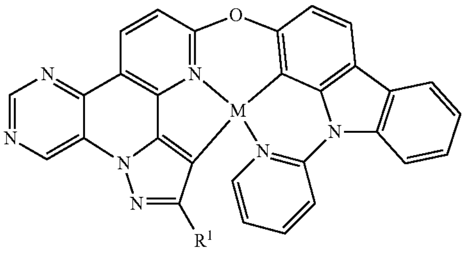
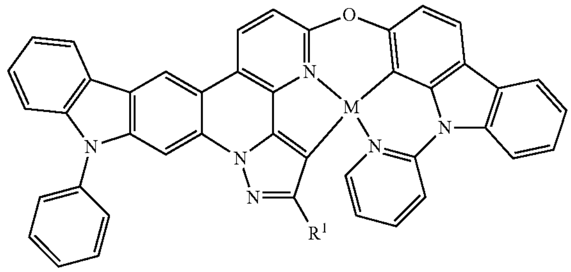
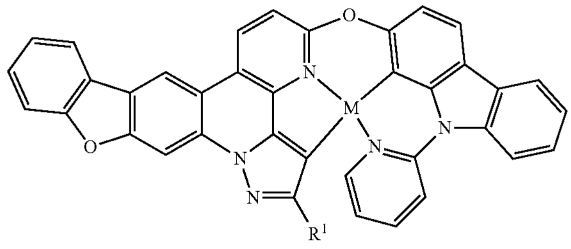
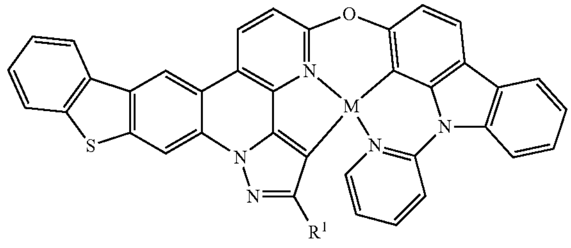
-continued
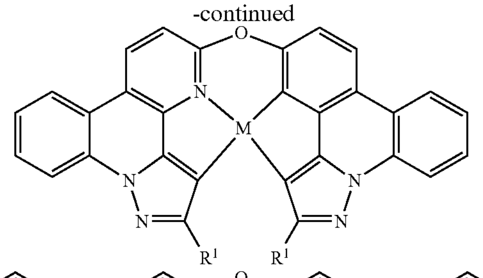
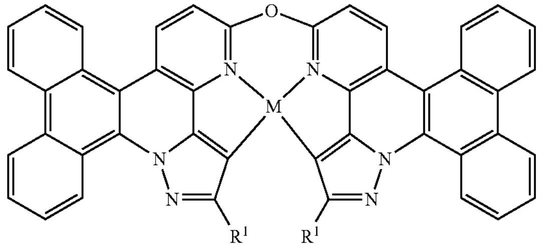
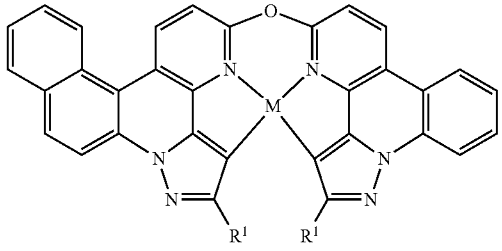
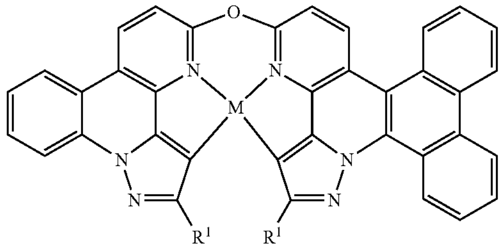
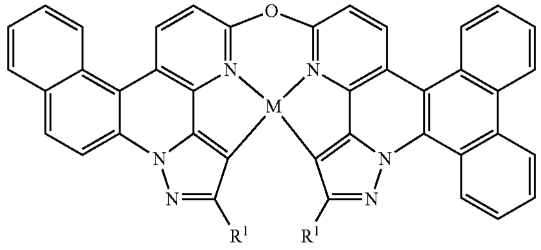
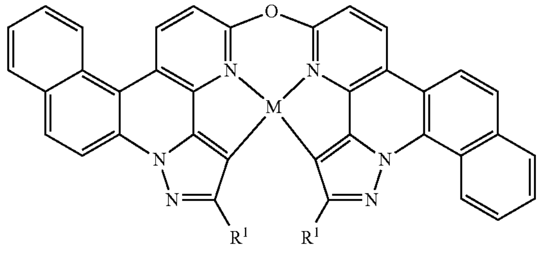
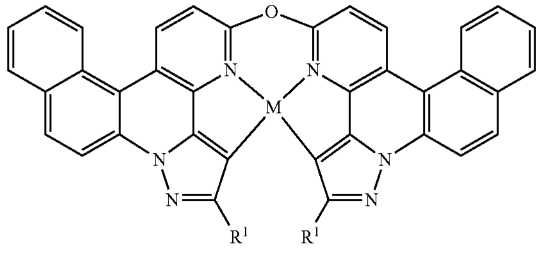

-continued
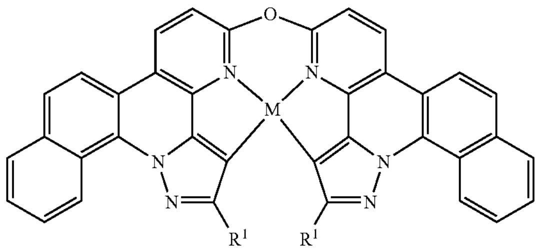
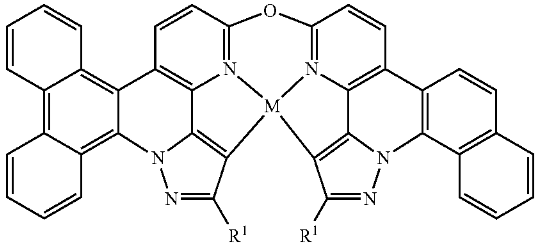
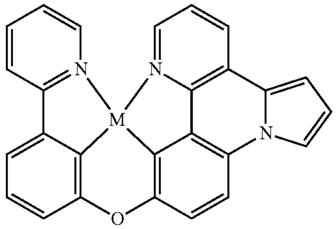
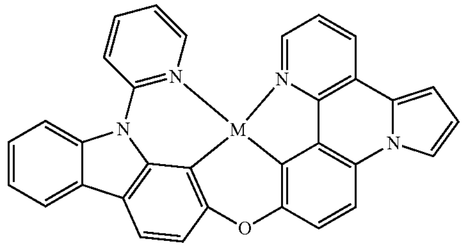
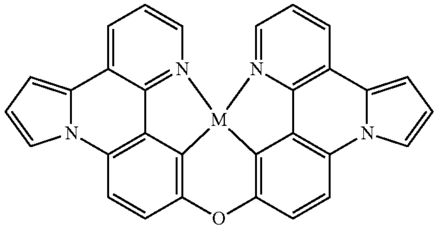
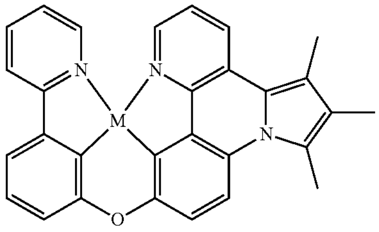
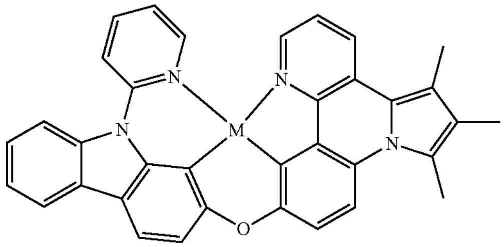
-continued
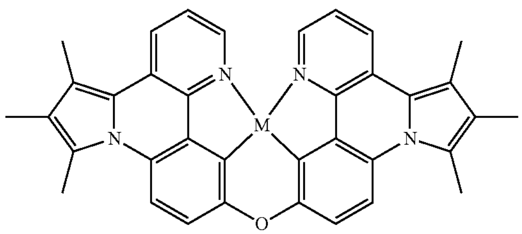
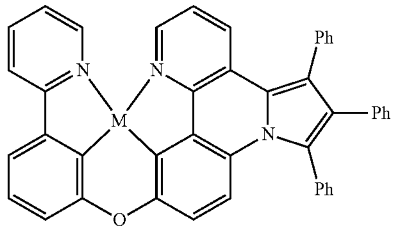
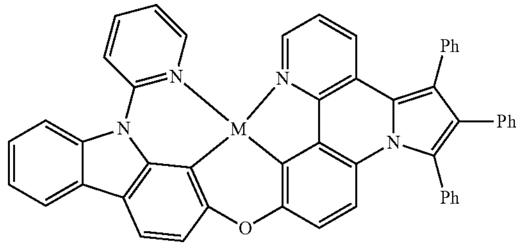
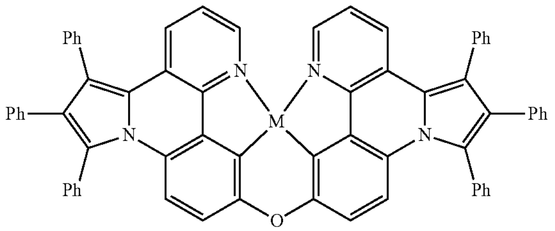
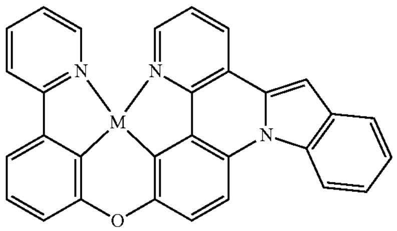
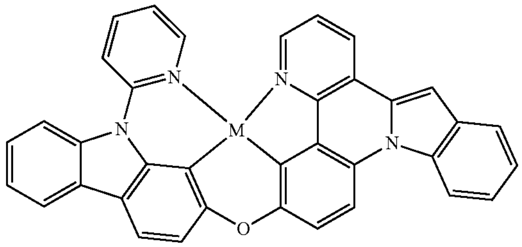
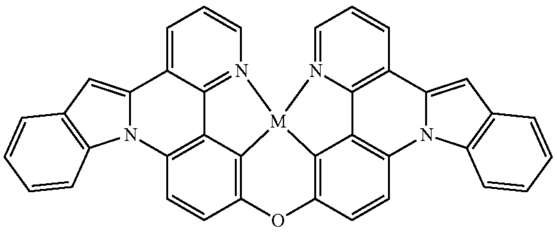

-continued
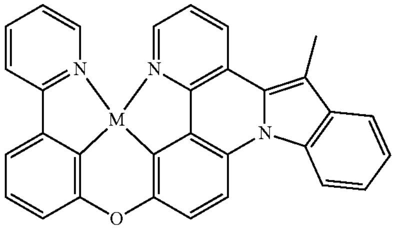
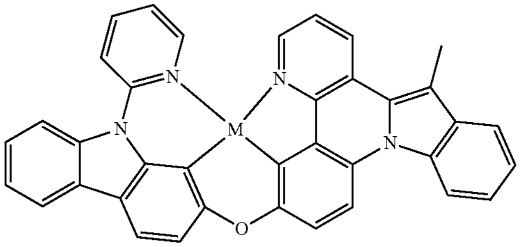
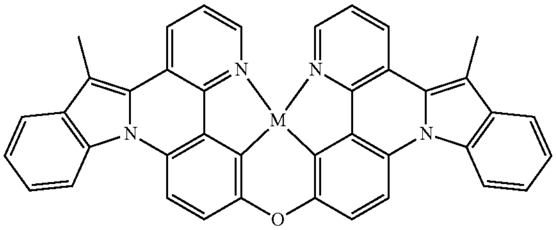
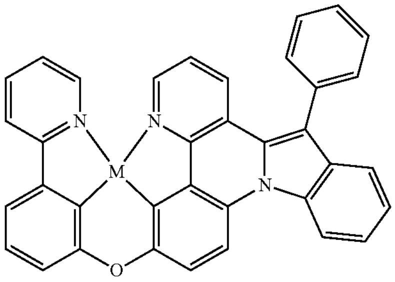
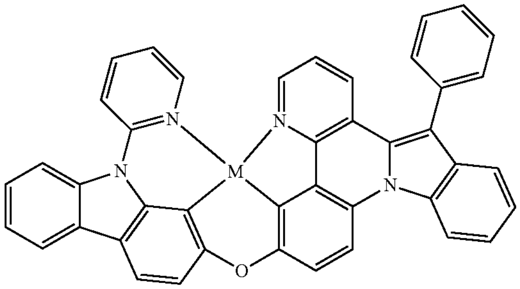
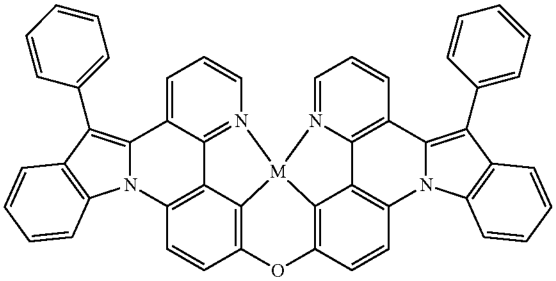
-continued
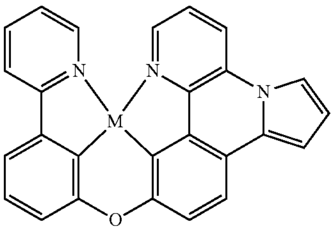
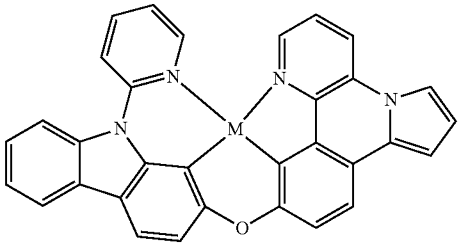
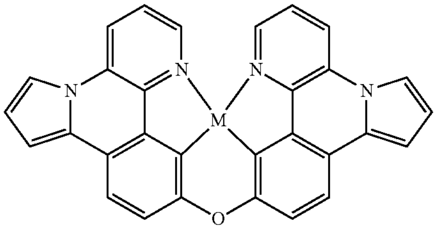
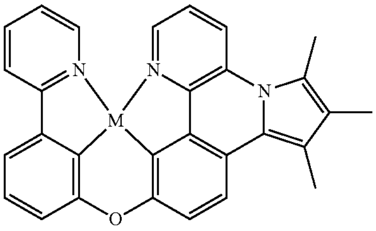
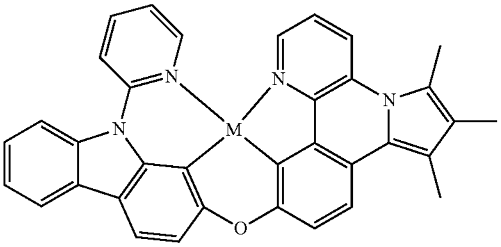
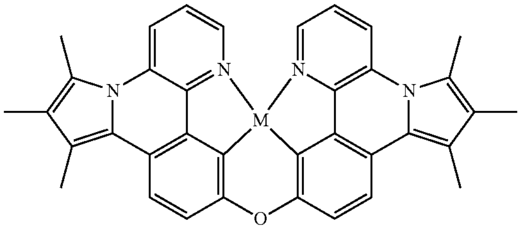
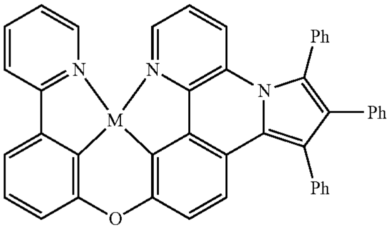

-continued
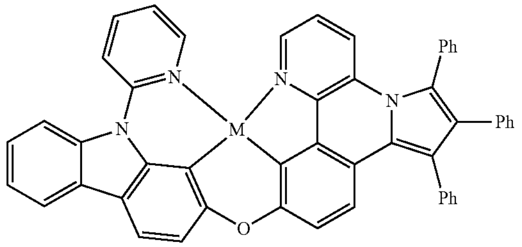
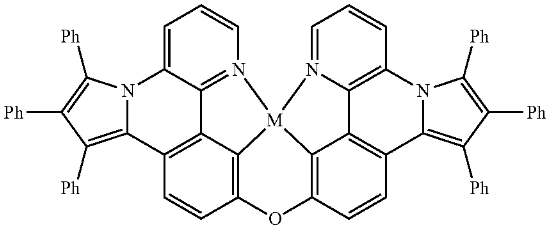
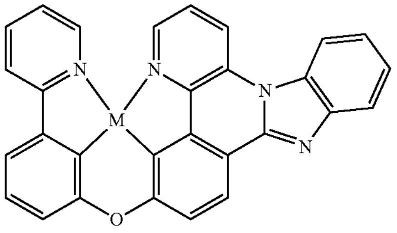
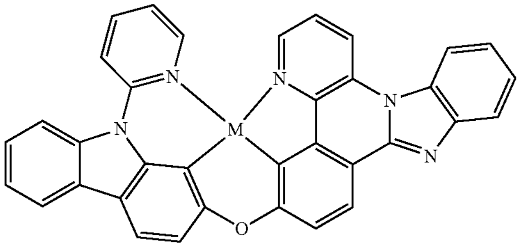
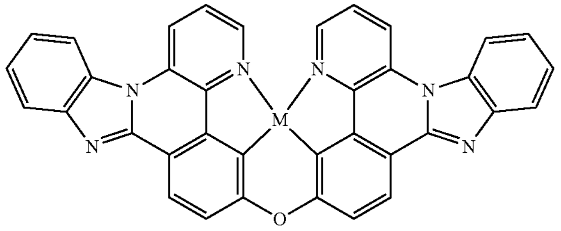
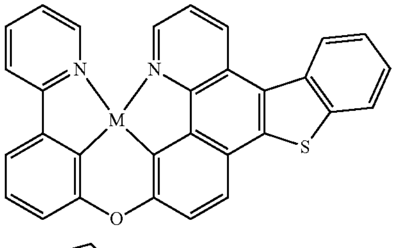
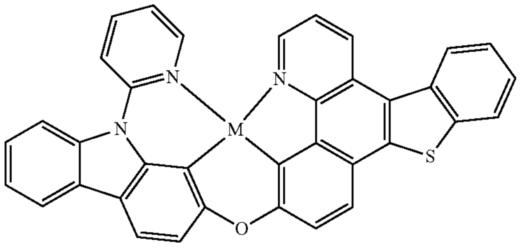
-continued
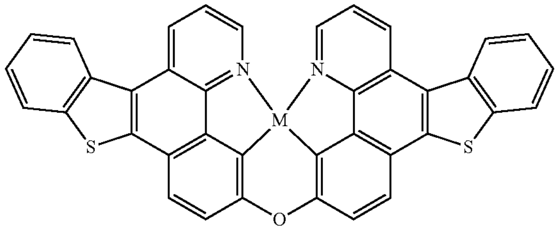
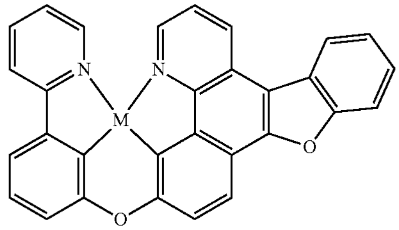
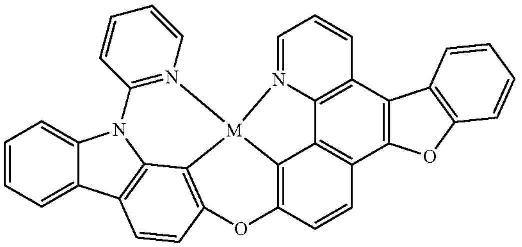
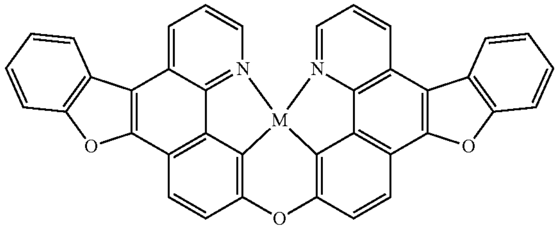
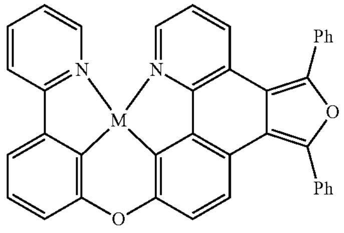
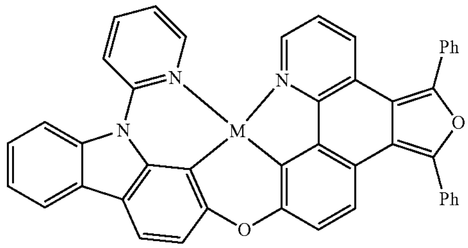
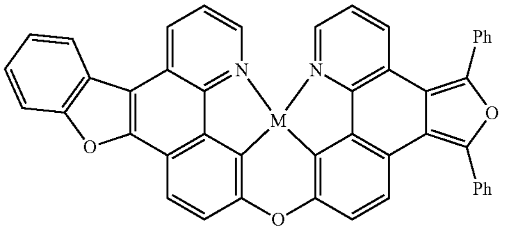

-continued
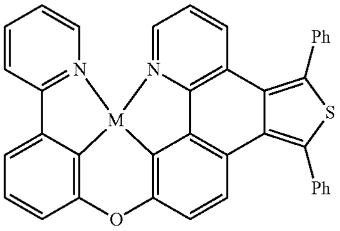
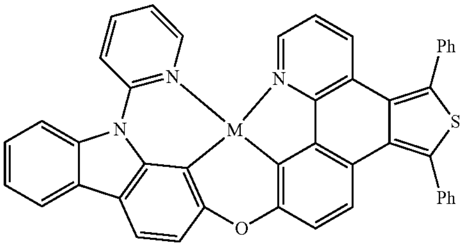
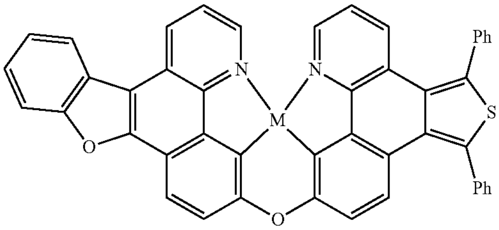
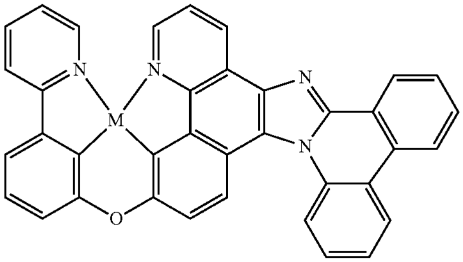
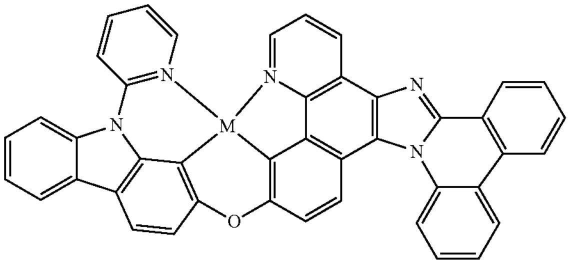
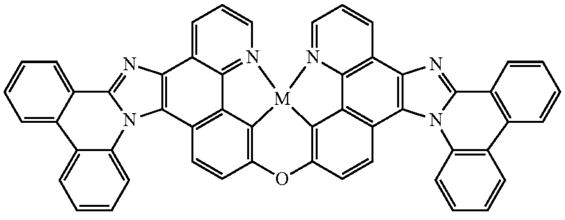
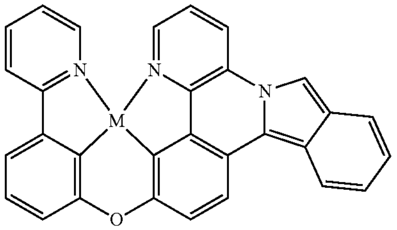
-continued
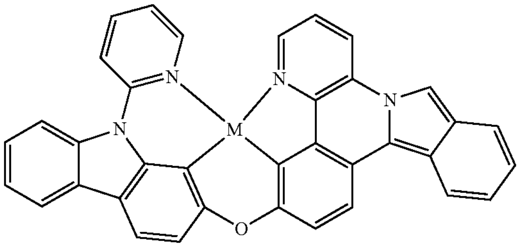
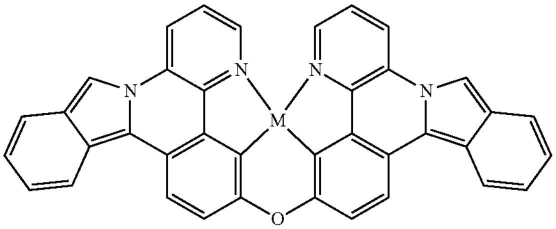
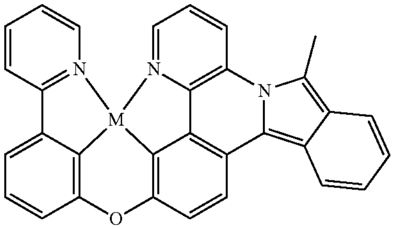
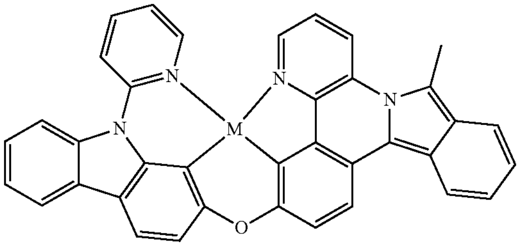
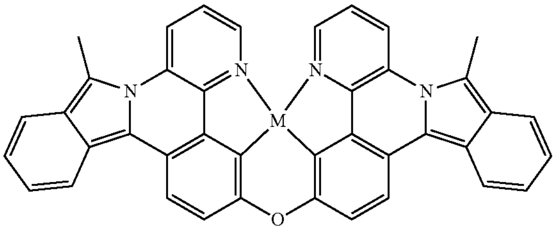
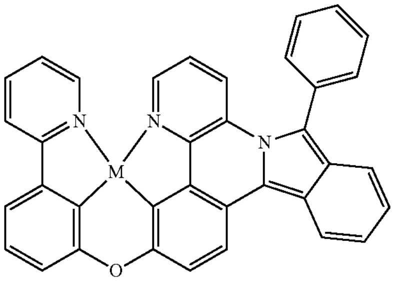

-continued
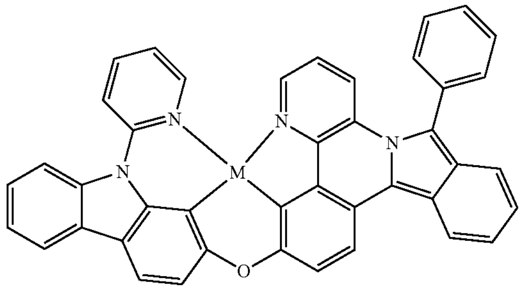
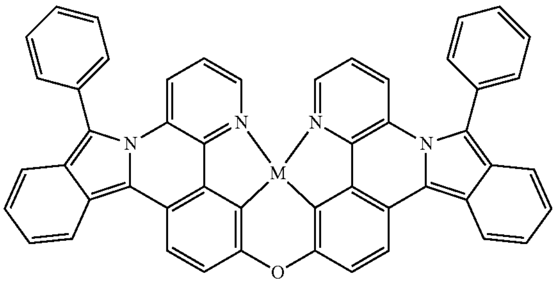
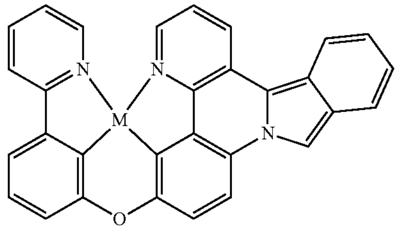
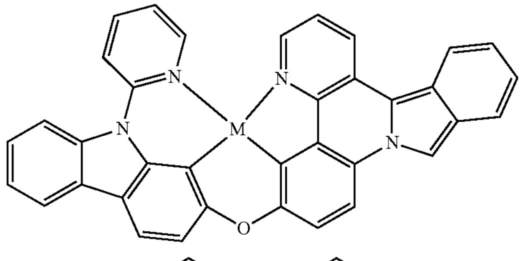
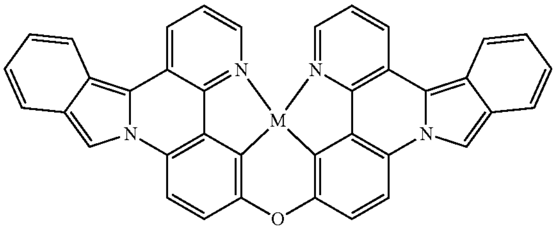
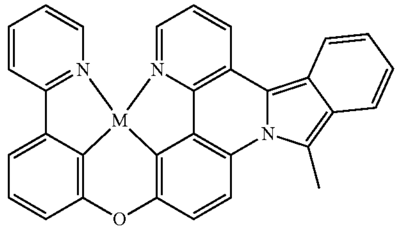
-continued
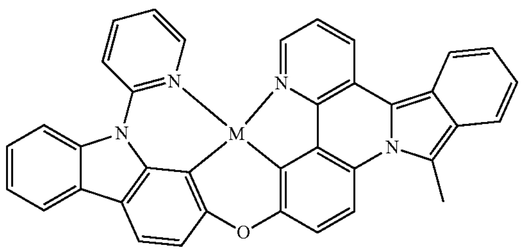
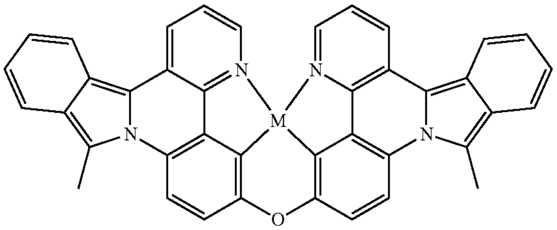
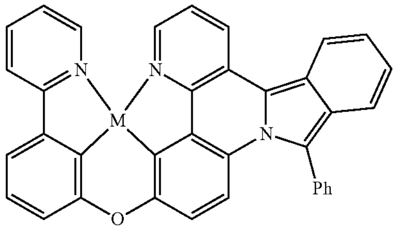
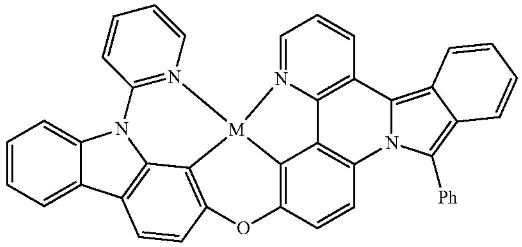
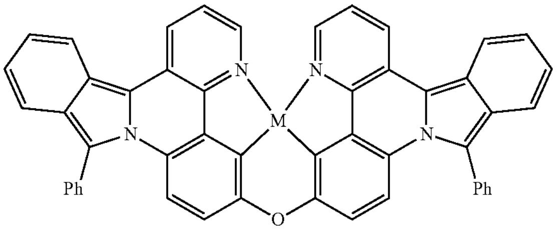
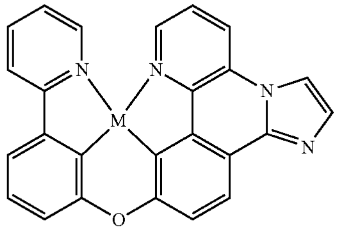
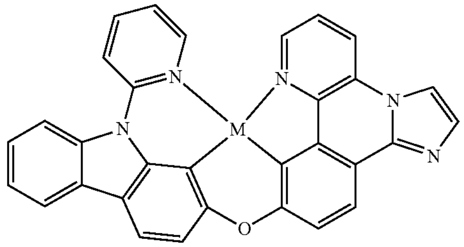

-continued
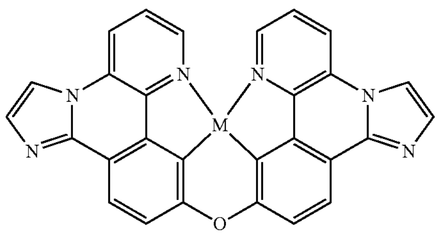
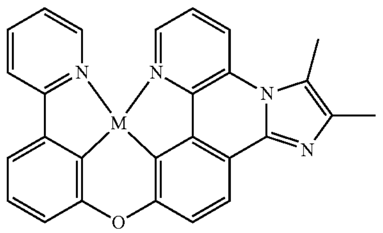
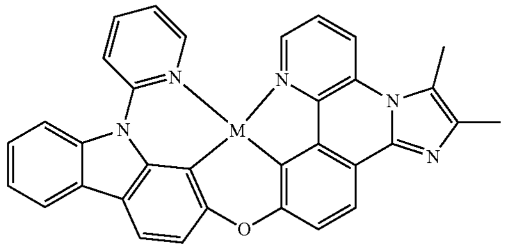
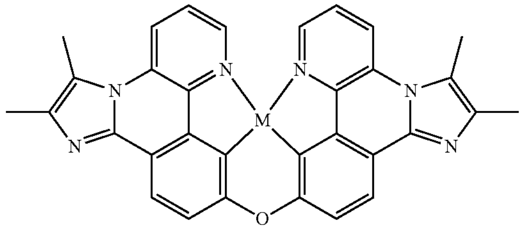
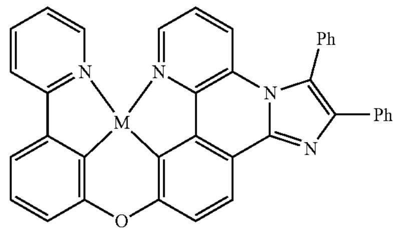
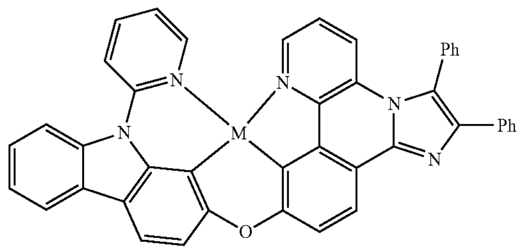
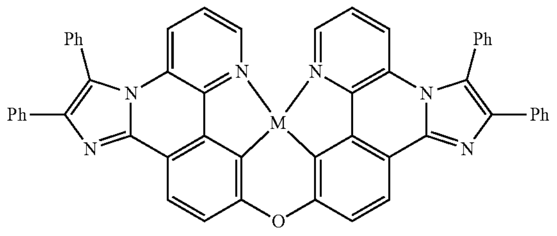
-continued
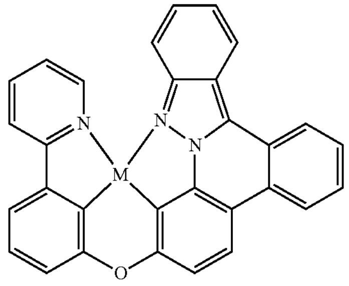
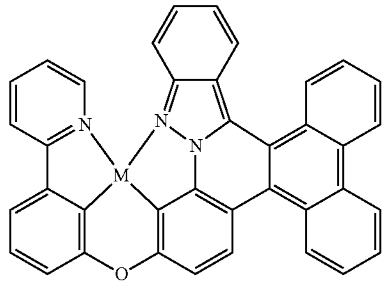
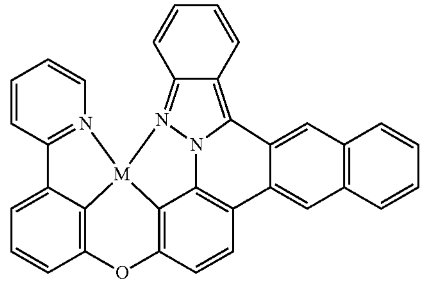
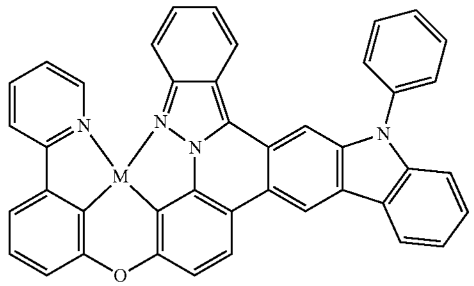
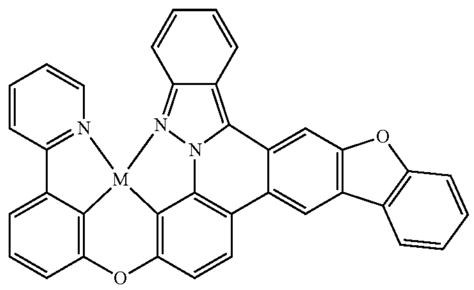
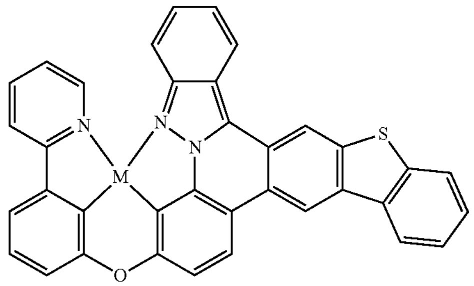

-continued
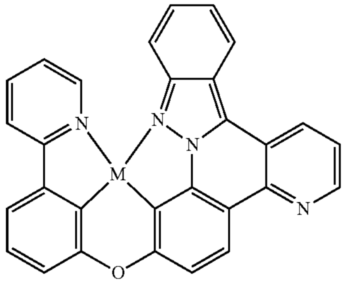
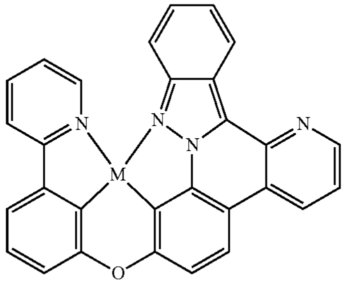
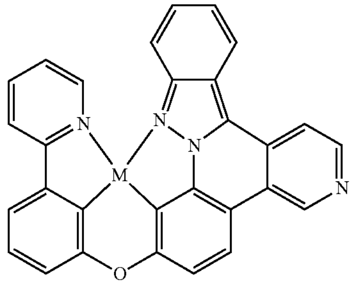
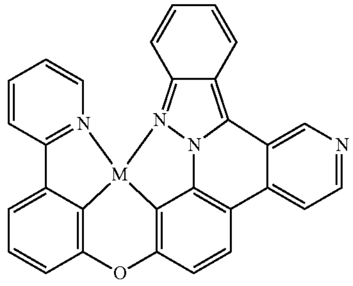
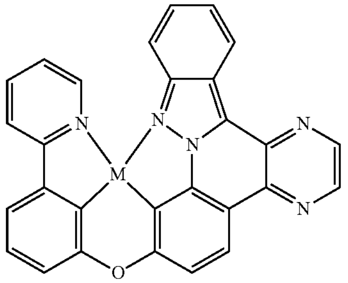
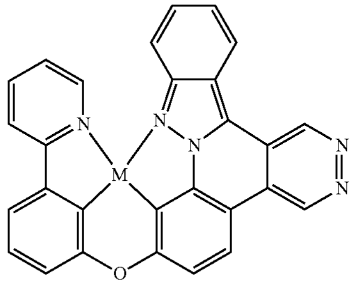
-continued
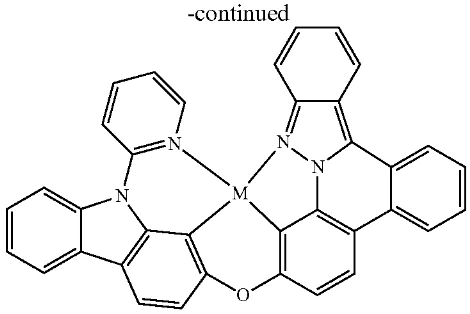
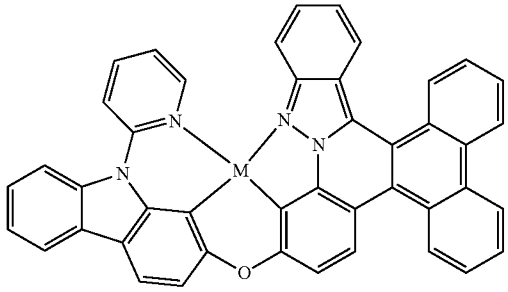
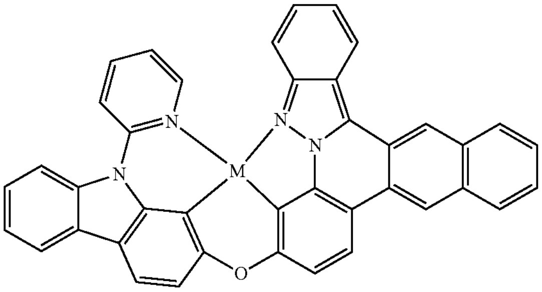
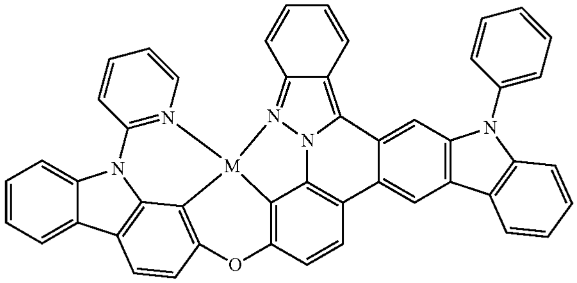
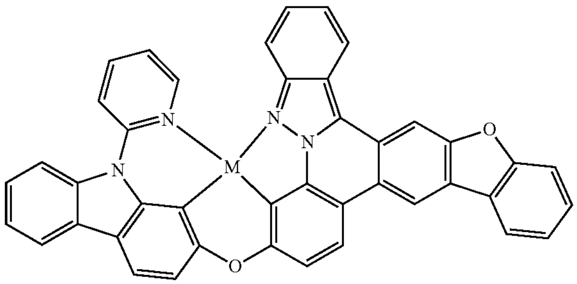
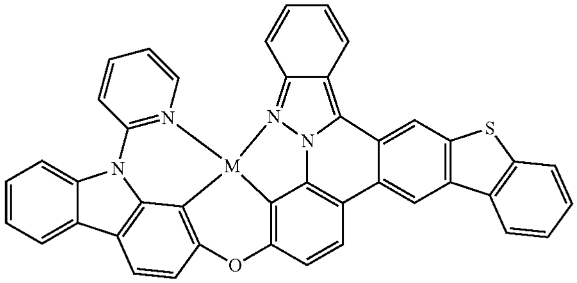

-continued
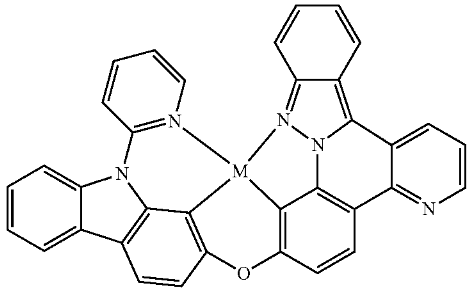
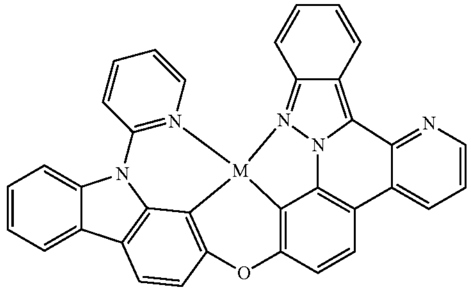
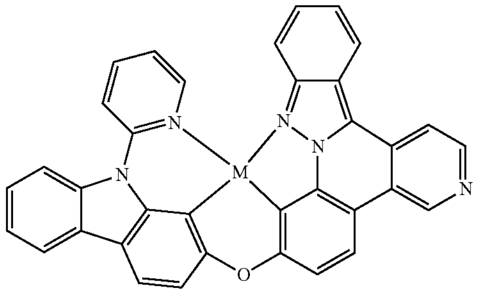
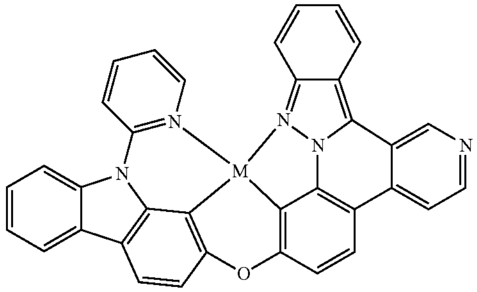
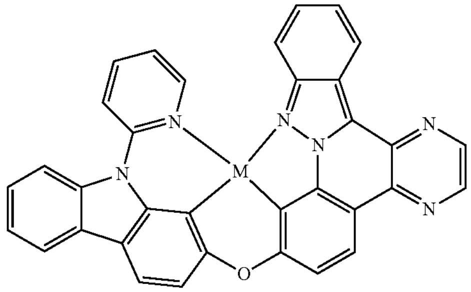
-continued
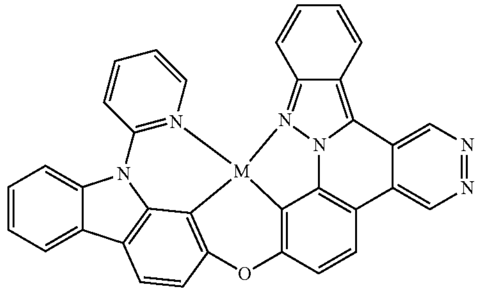
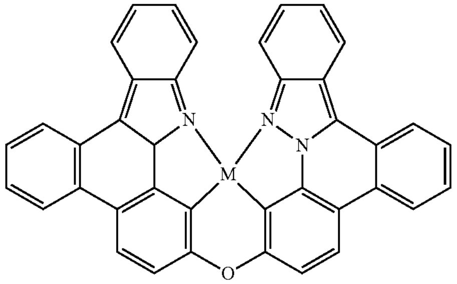
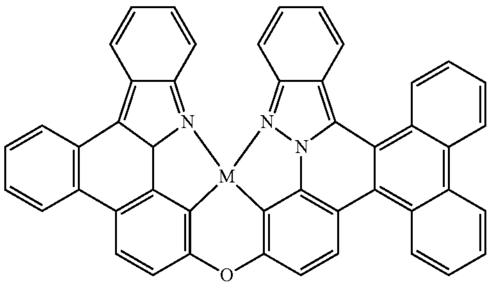
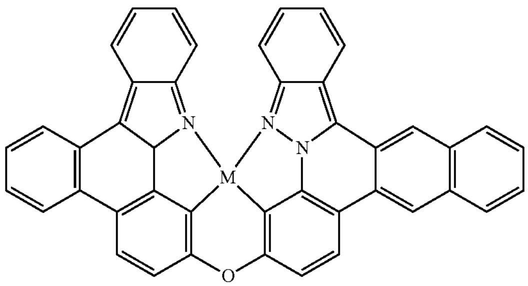
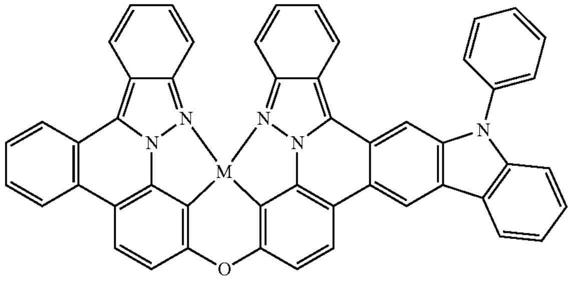
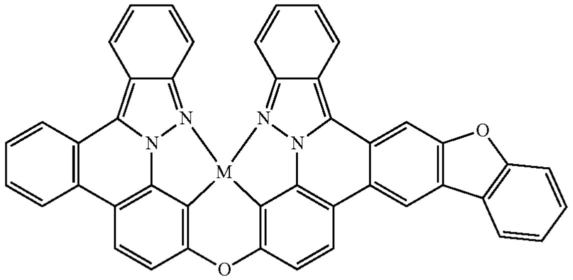

-continued
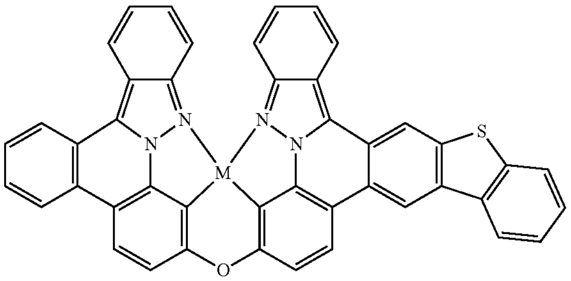
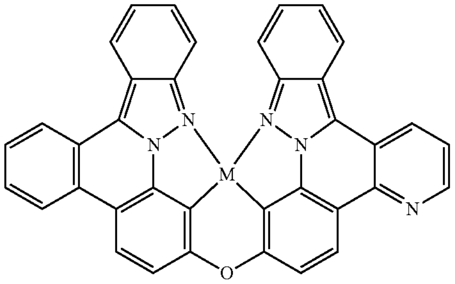
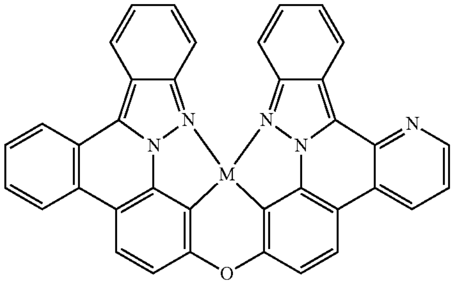
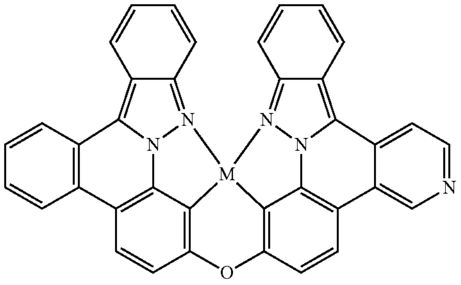
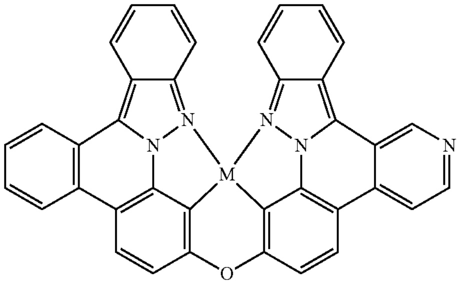
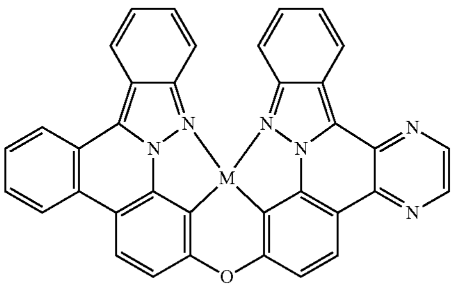
-continued
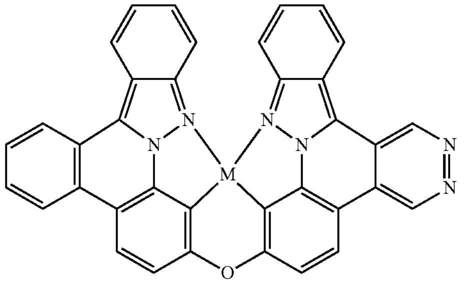
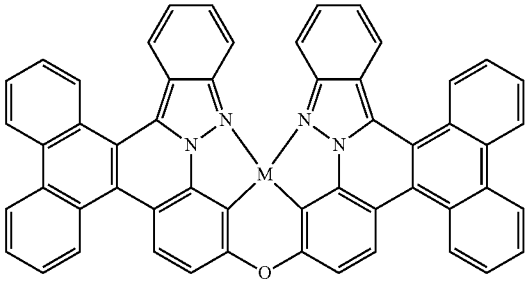
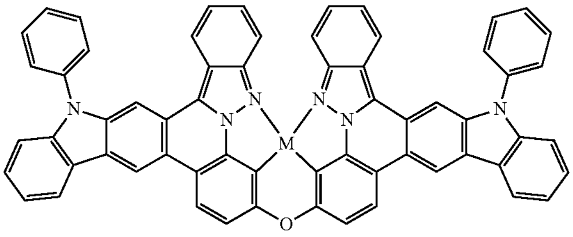
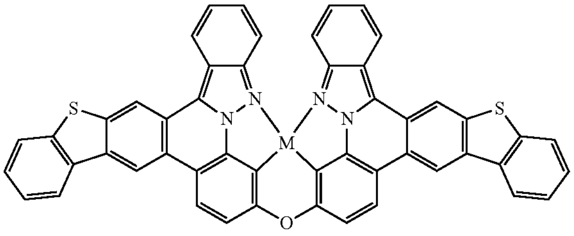
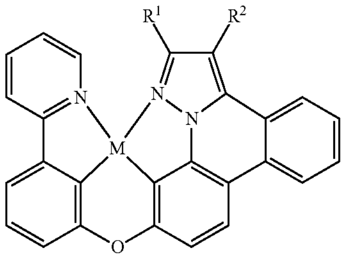
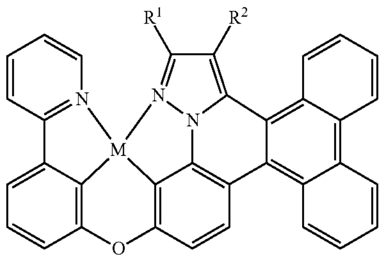

-continued
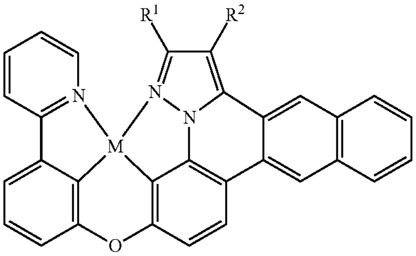
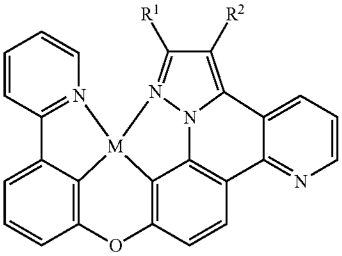
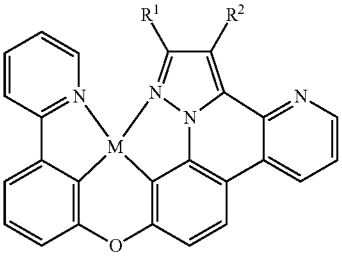
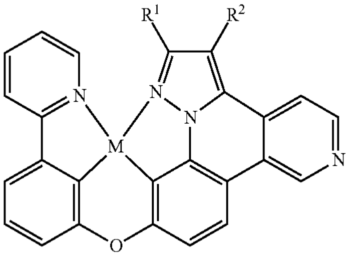
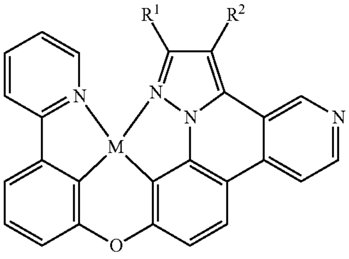
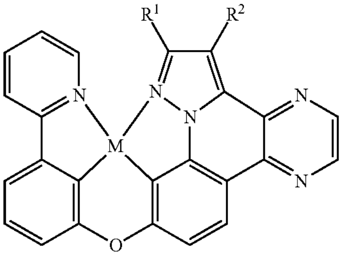
-continued
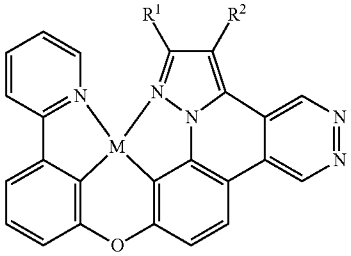
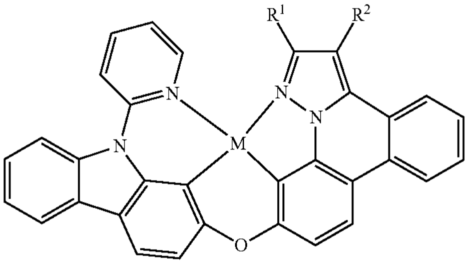
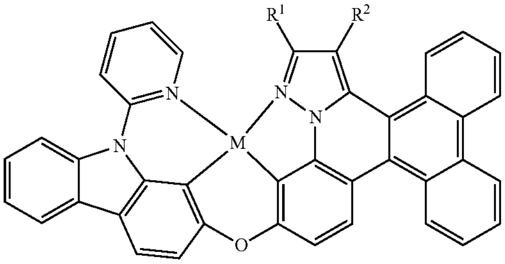
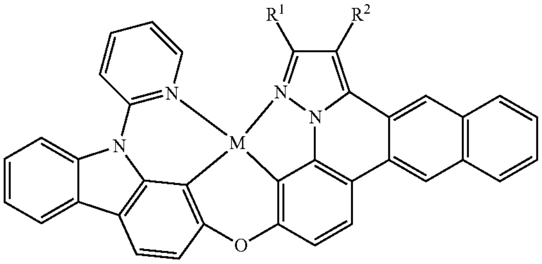
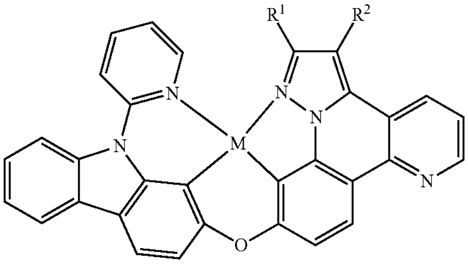
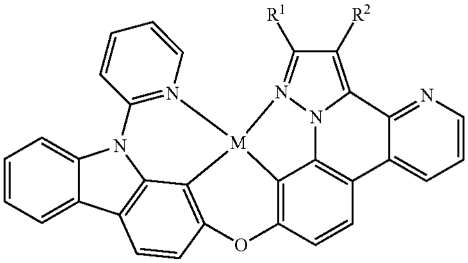

-continued
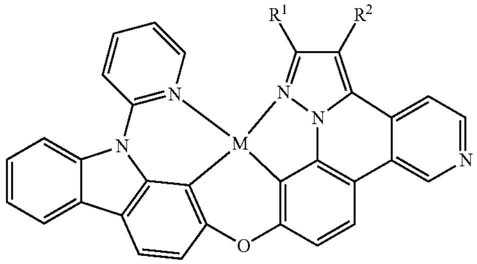
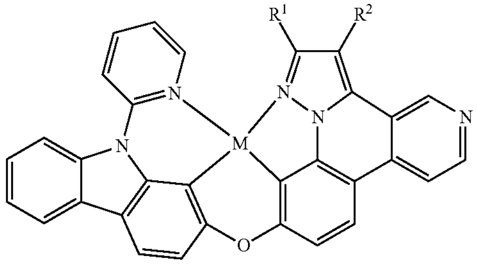
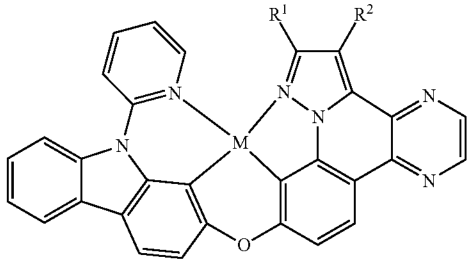
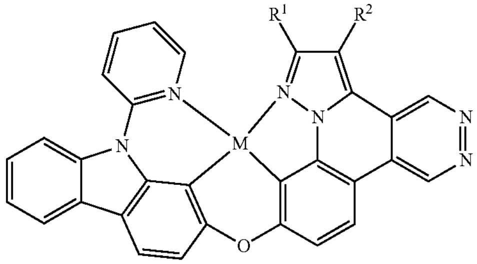
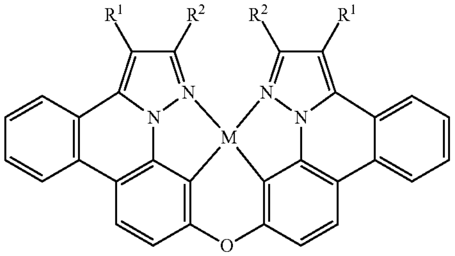
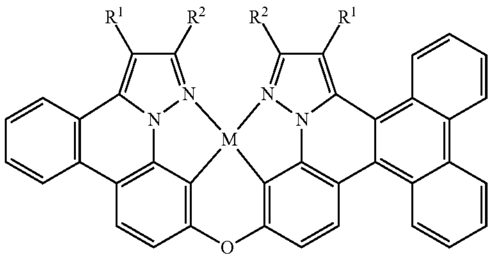
-continued
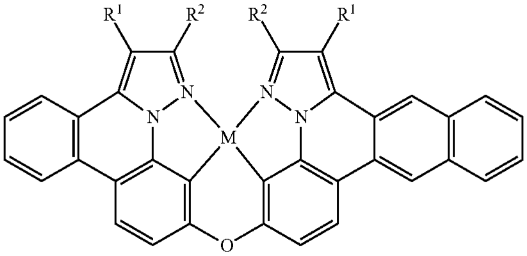
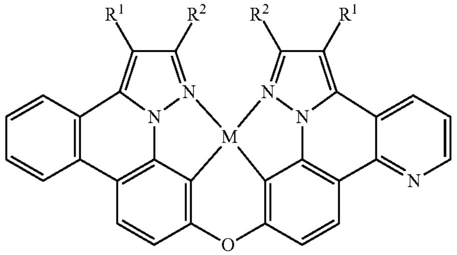
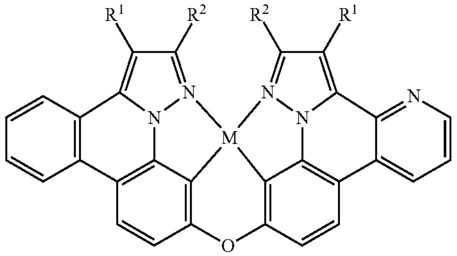
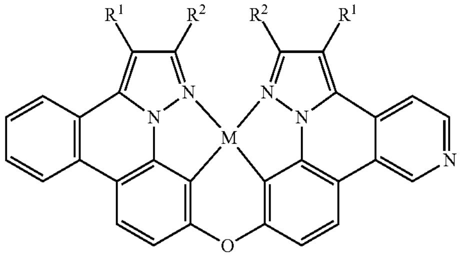
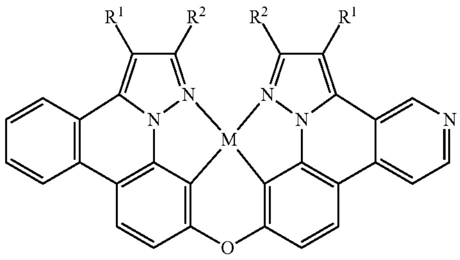
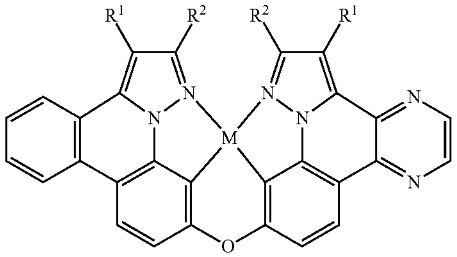

-continued
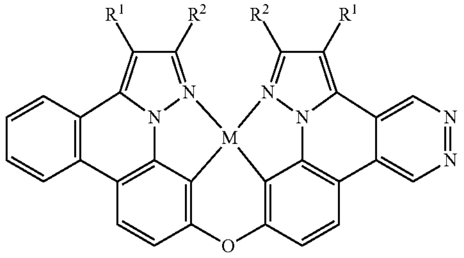
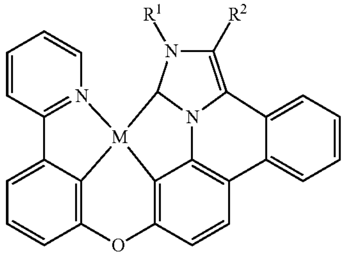
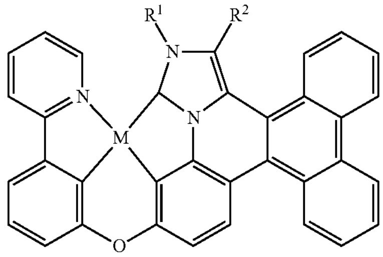
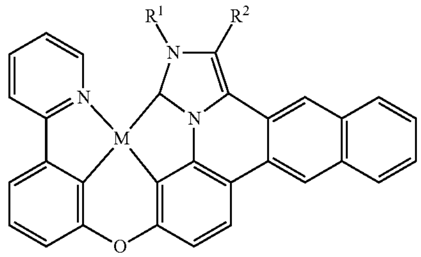
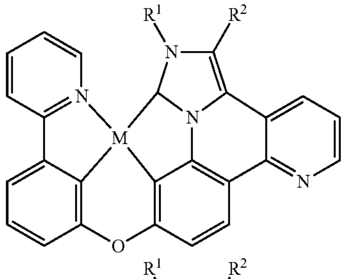
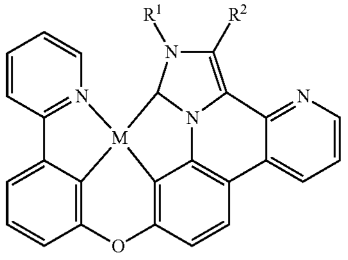
-continued
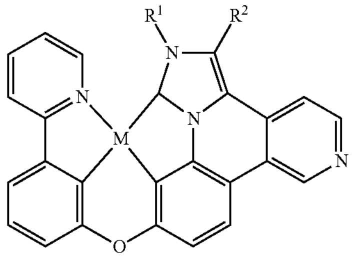
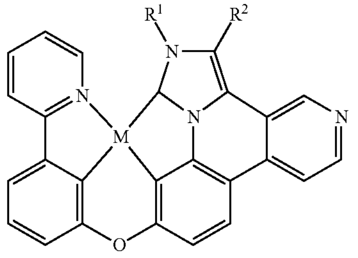
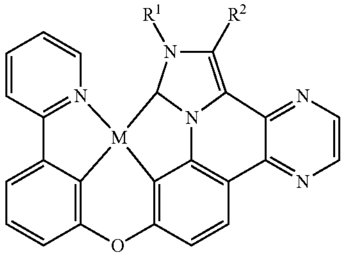
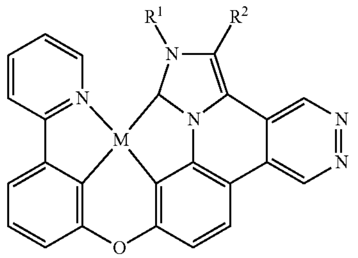
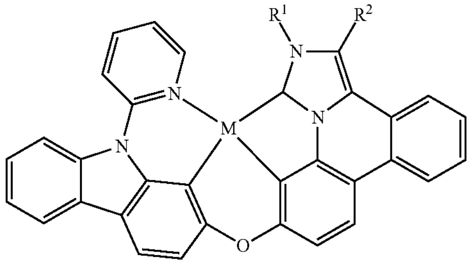
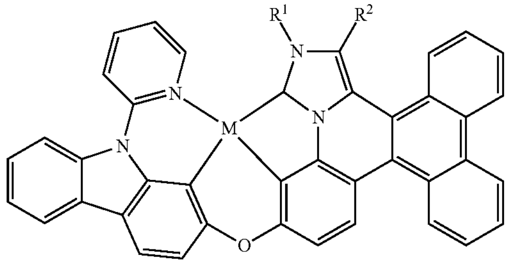

-continued
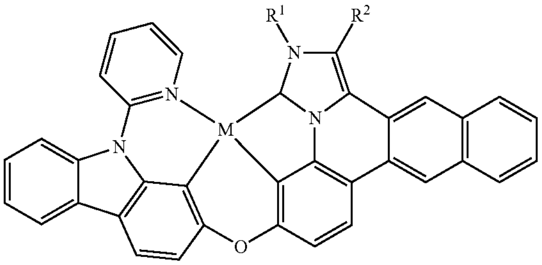
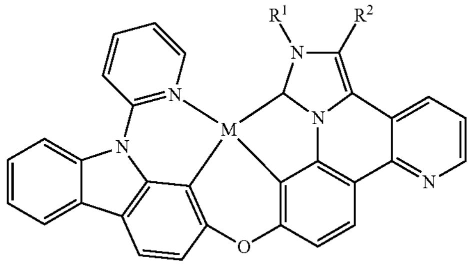
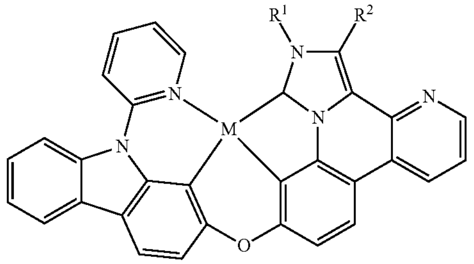
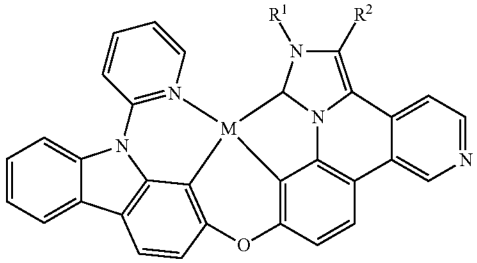
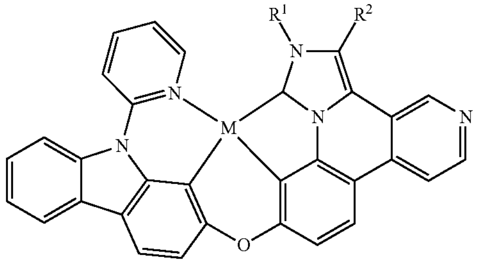
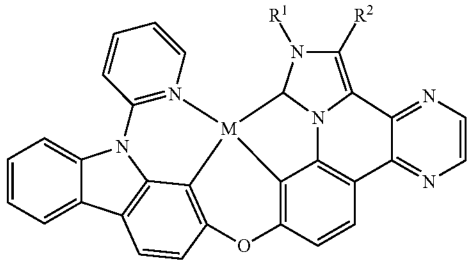
-continued
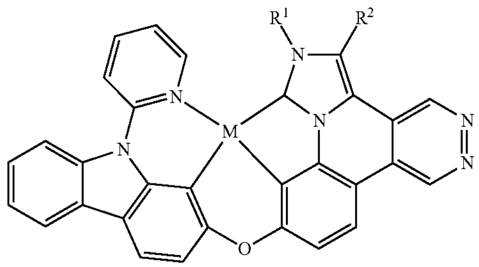
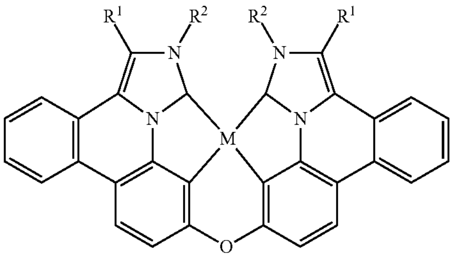
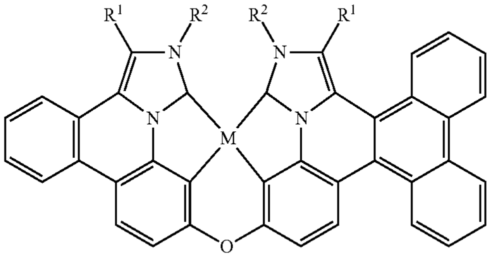
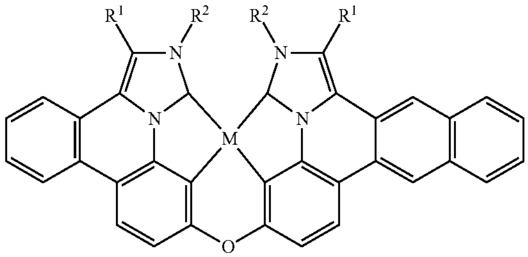
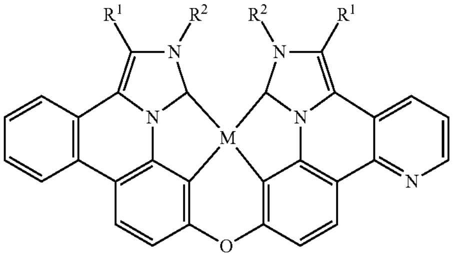
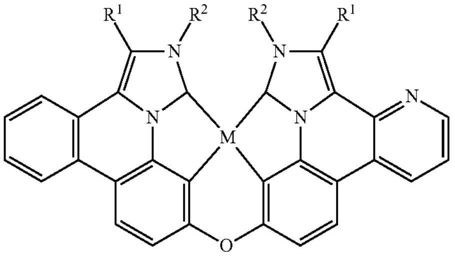

-continued
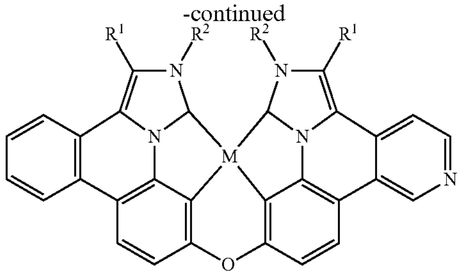
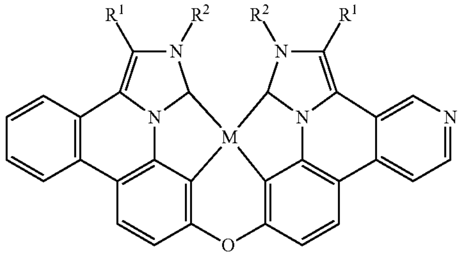
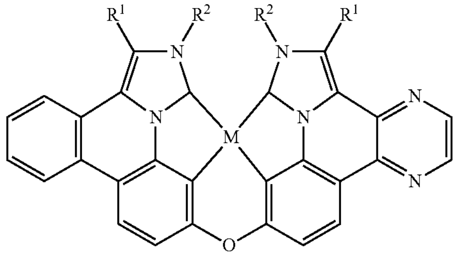
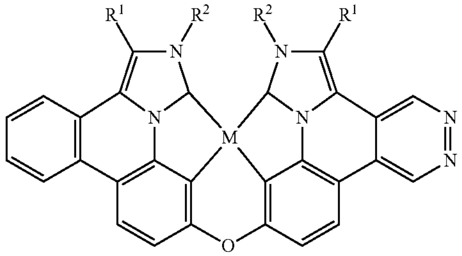
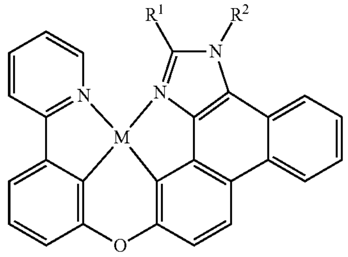
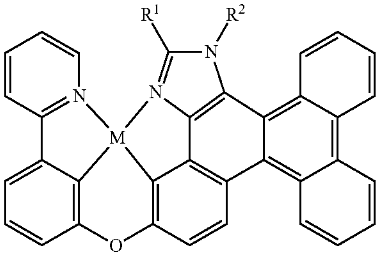
-continued
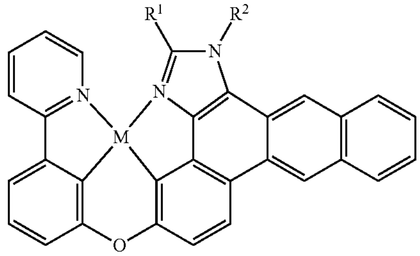
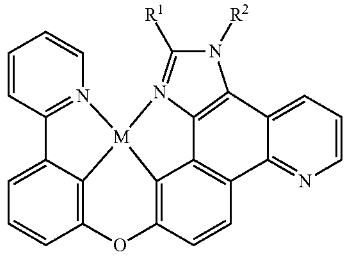
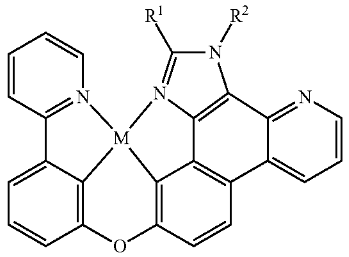
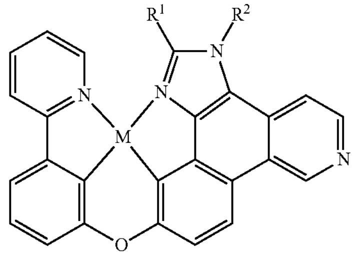
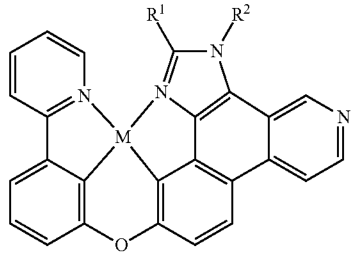
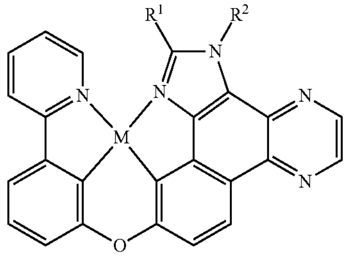

-continued
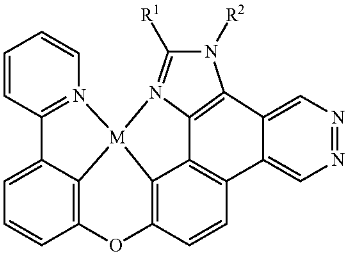
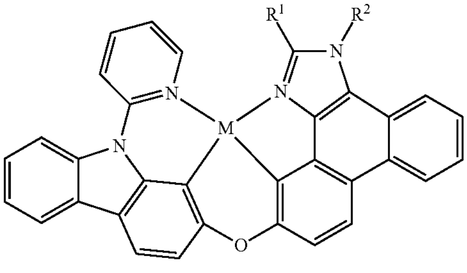
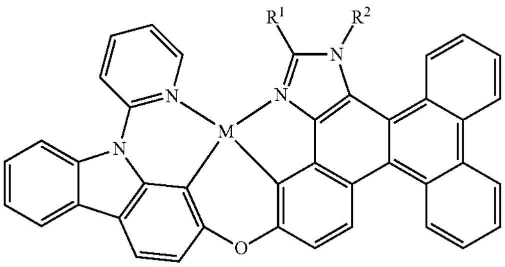
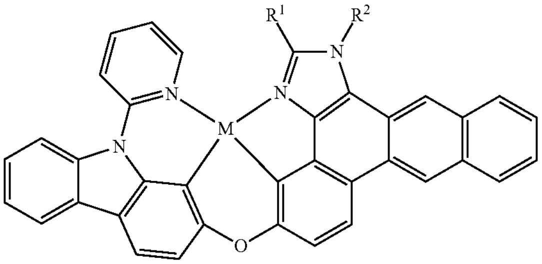
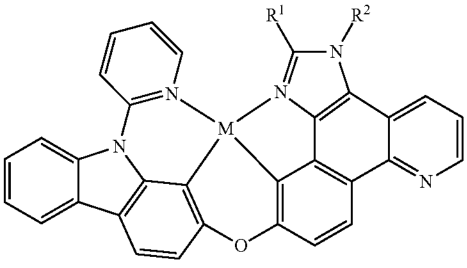
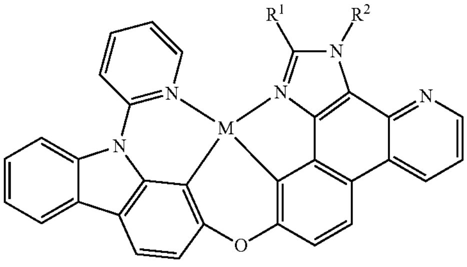
-continued
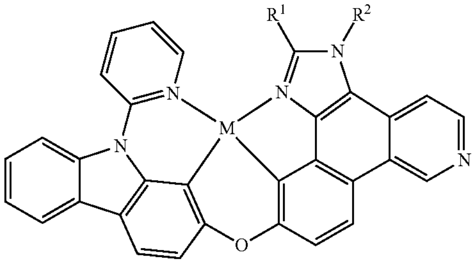
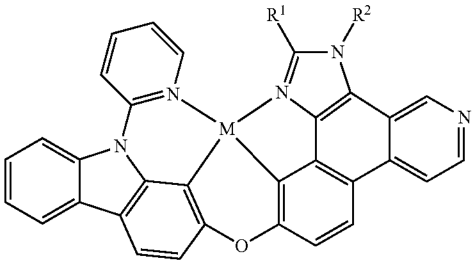
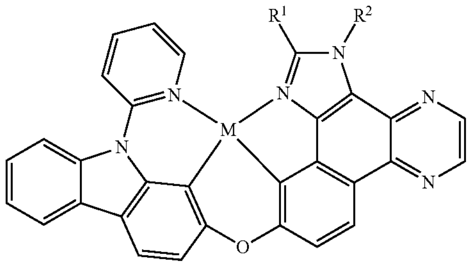
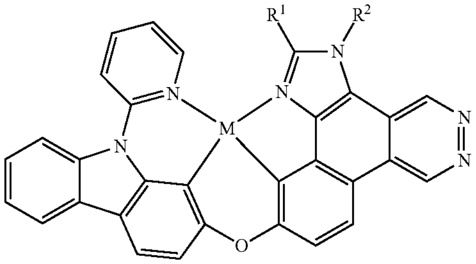
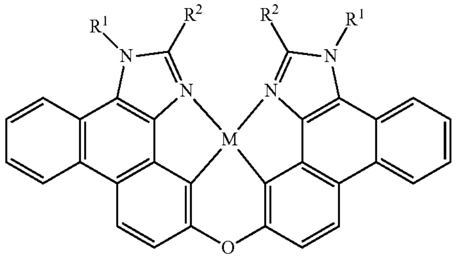
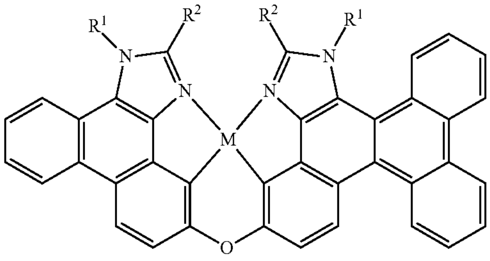

-continued
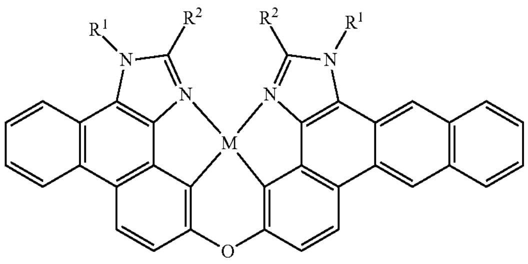
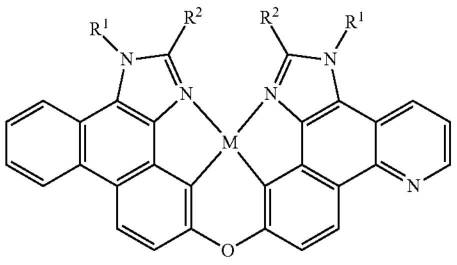
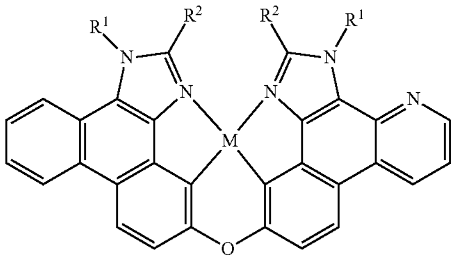
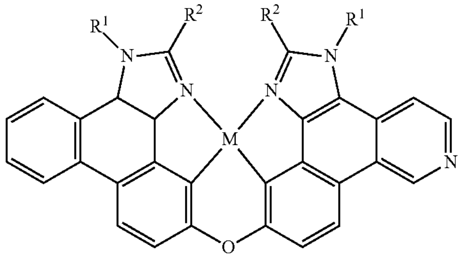
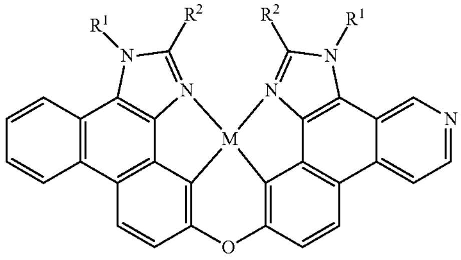
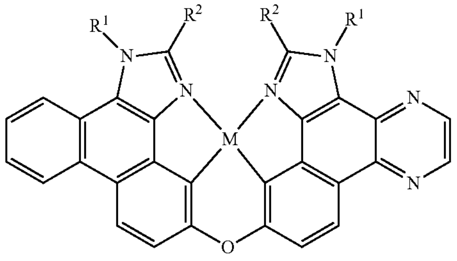
-continued
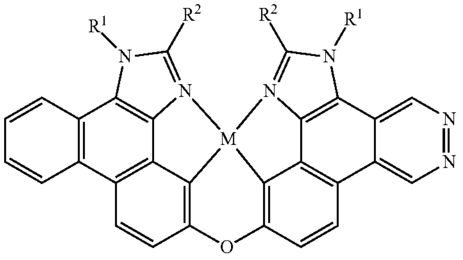
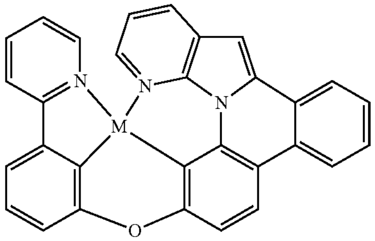
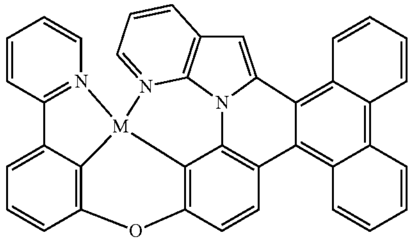
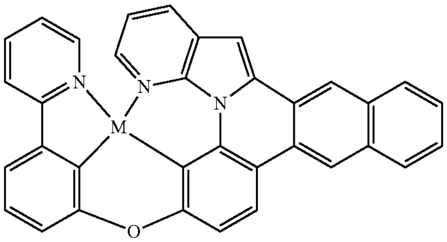
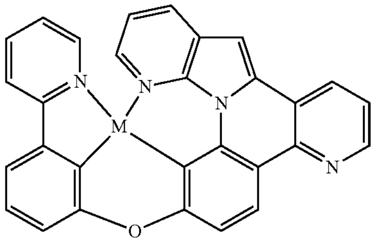
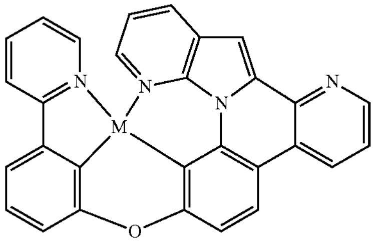
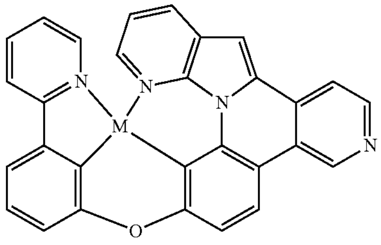

-continued
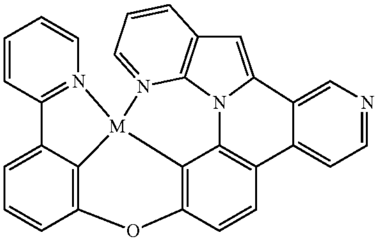
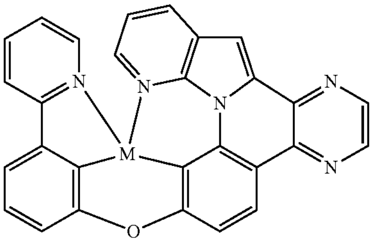
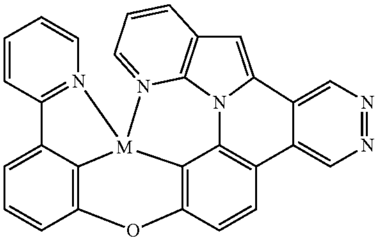
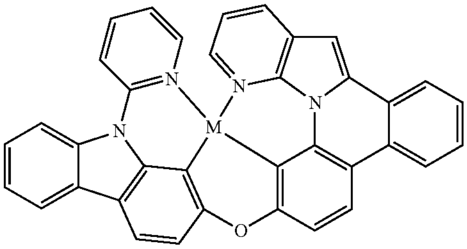
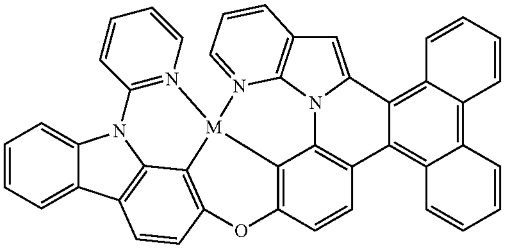
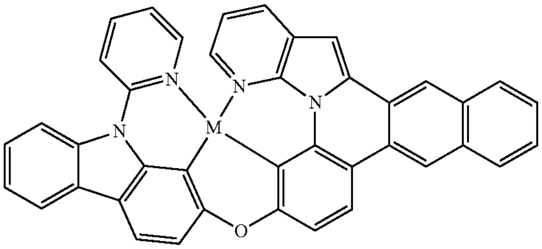
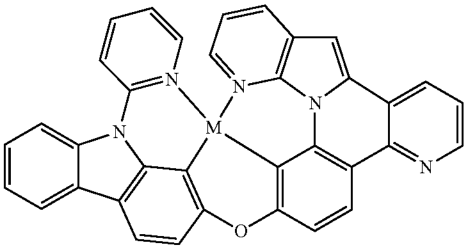
-continued
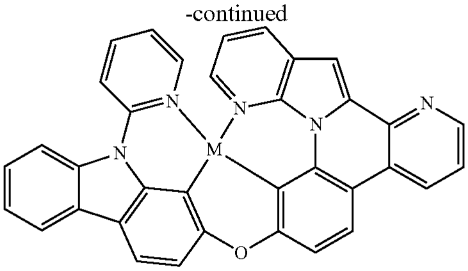
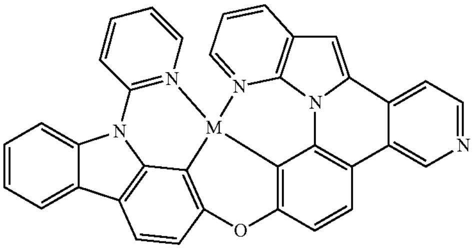
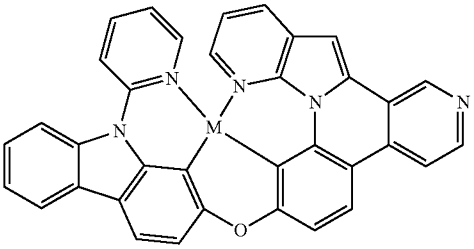
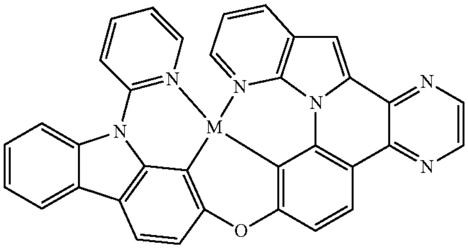
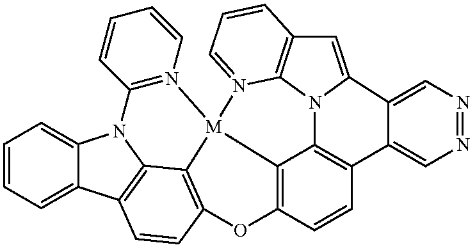
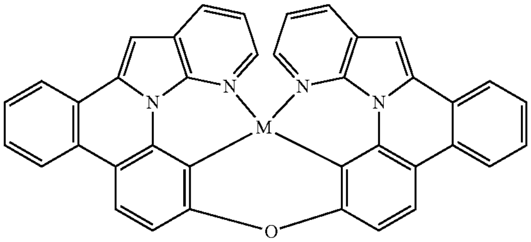
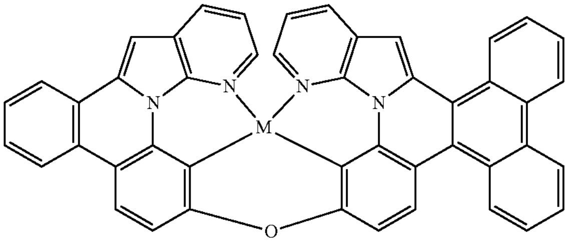

-continued
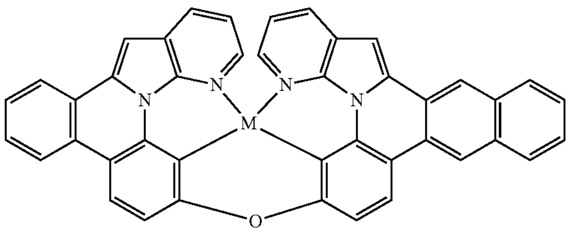
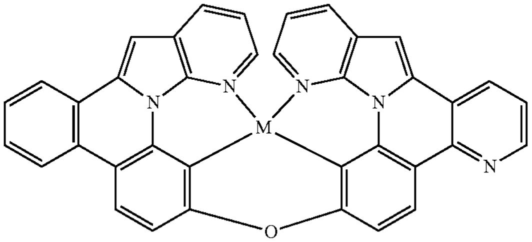
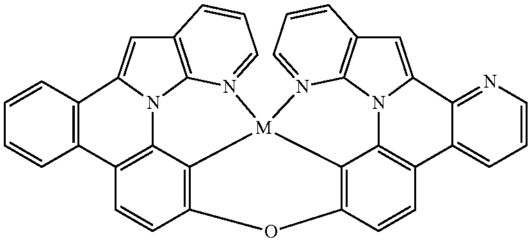
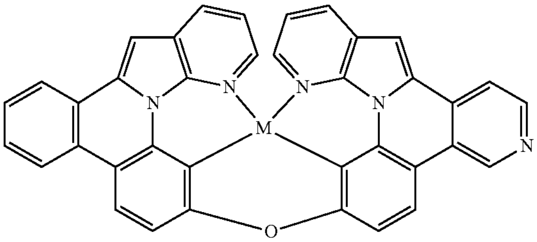
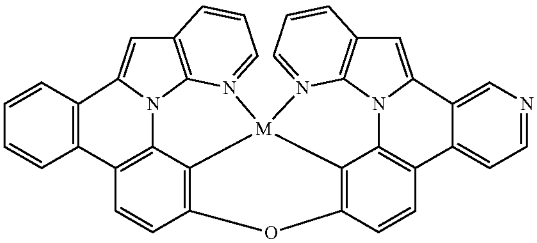
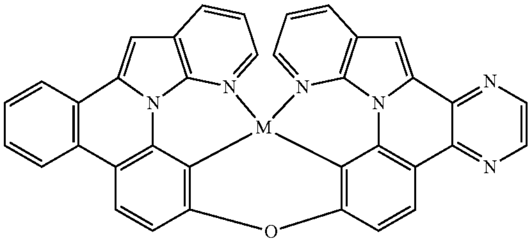
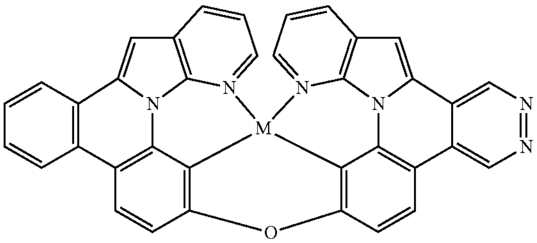
-continued
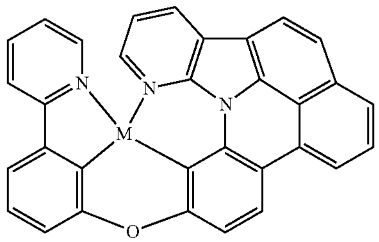
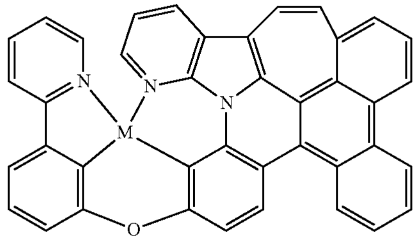
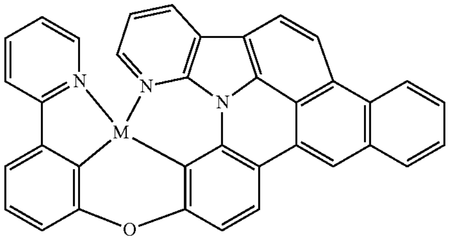
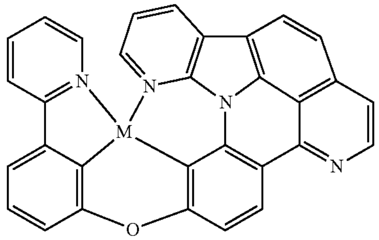
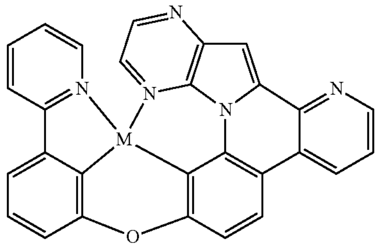
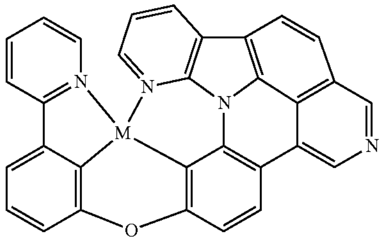
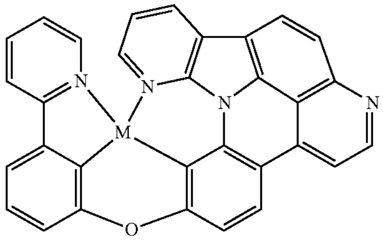

-continued
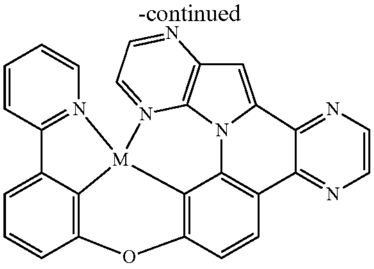
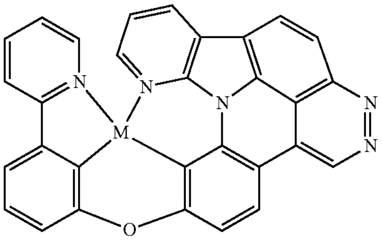
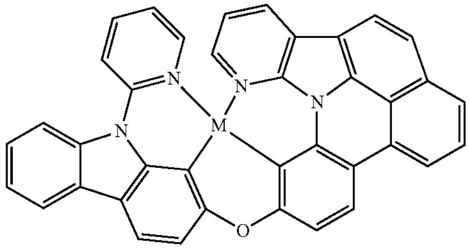
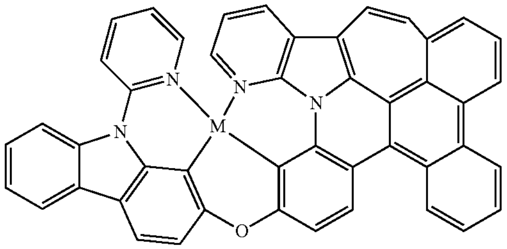
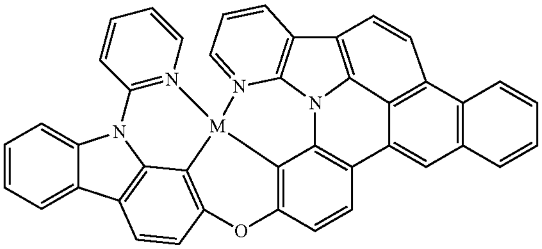
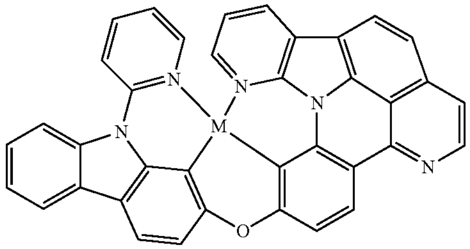
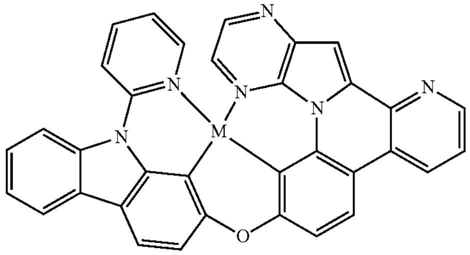
-continued
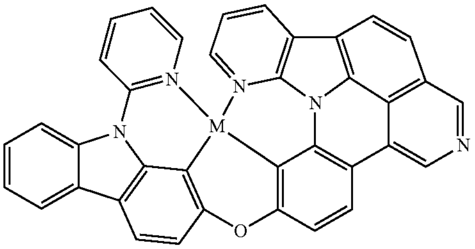
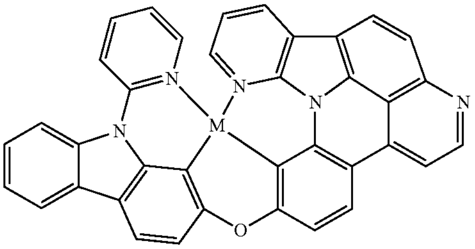
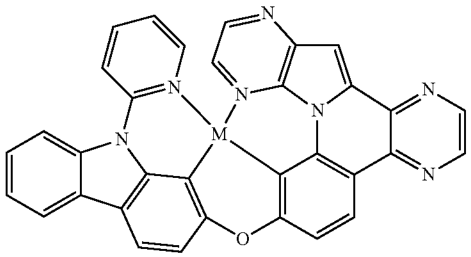
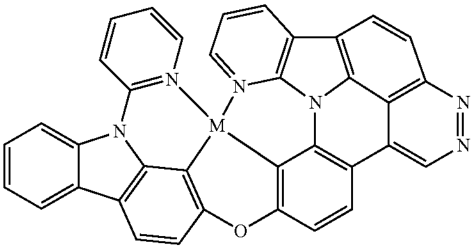
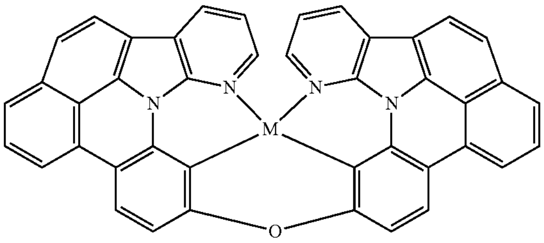
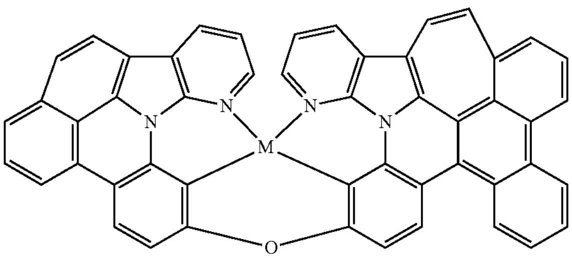
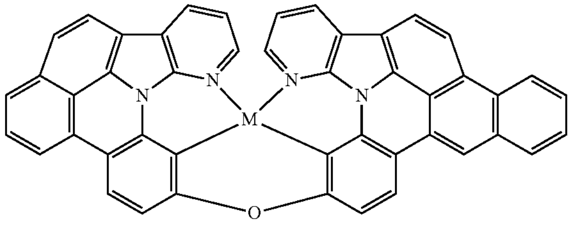

-continued
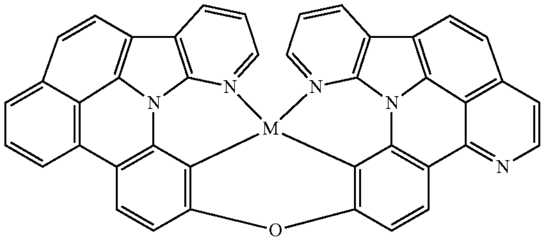
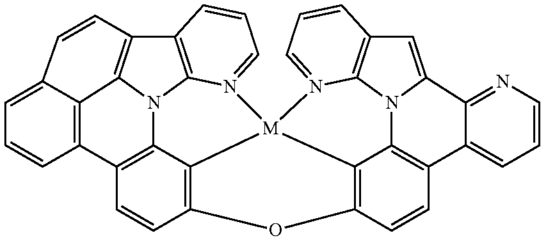
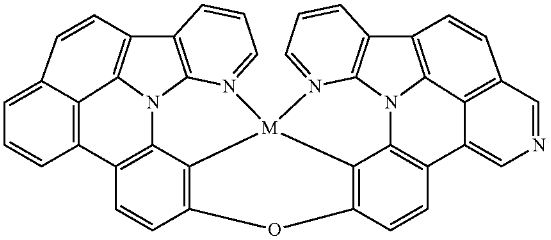
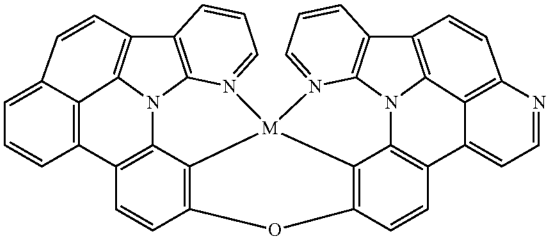
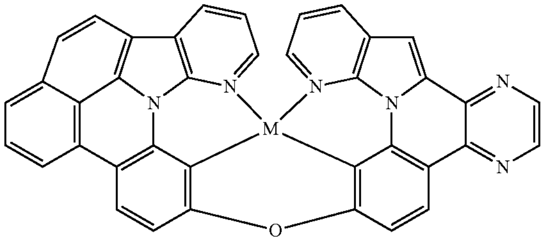
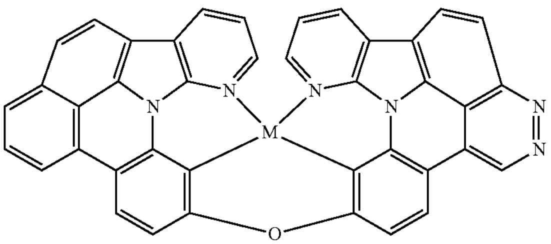
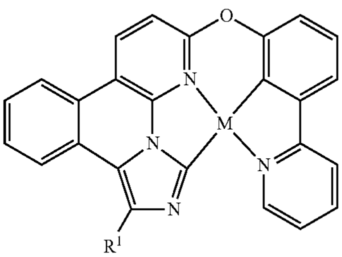
-continued
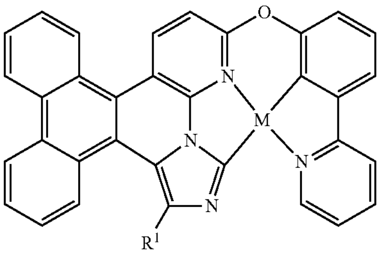
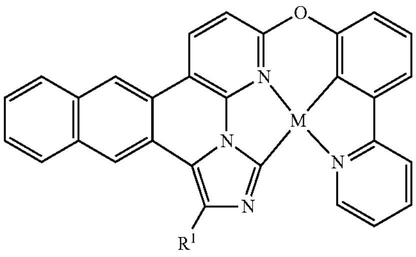
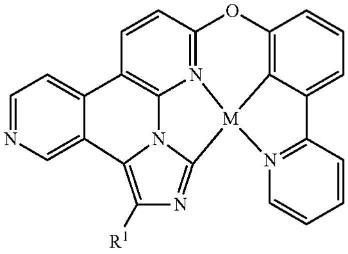
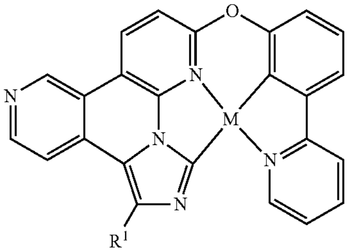
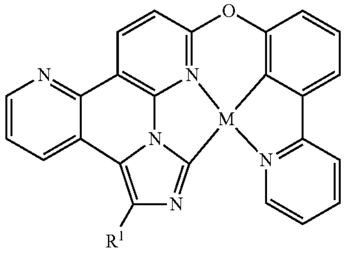
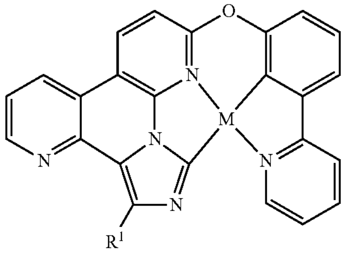

-continued
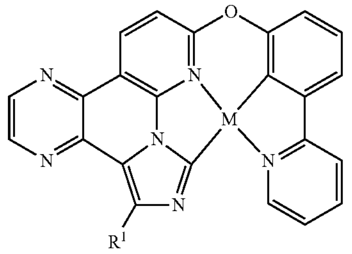
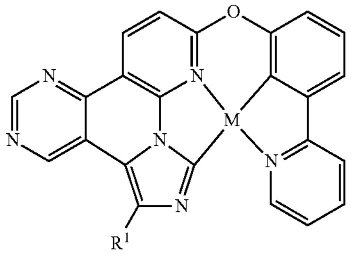
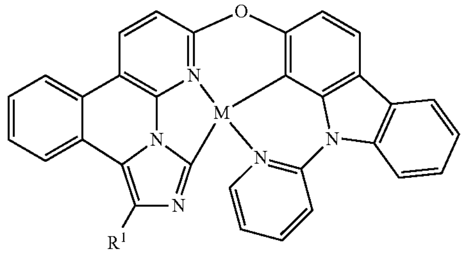
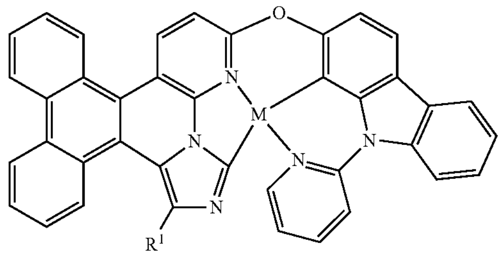
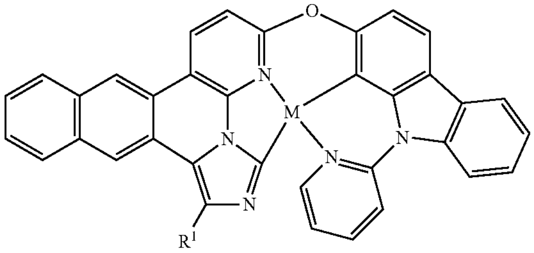
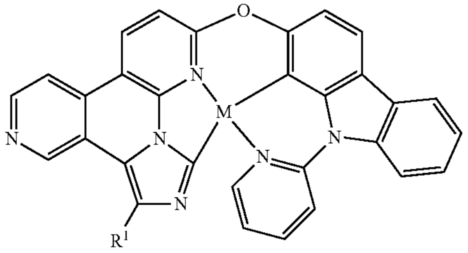
-continued
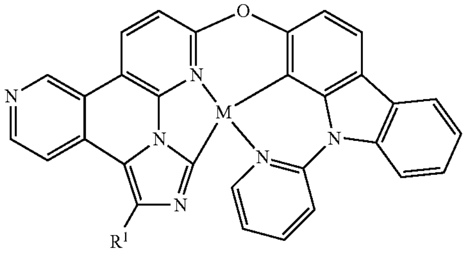
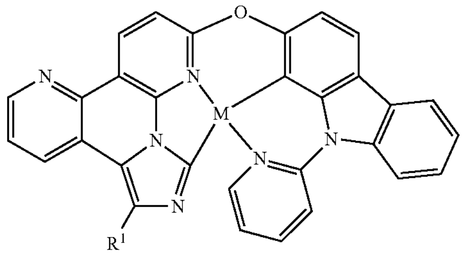
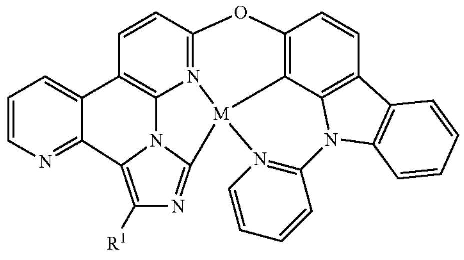
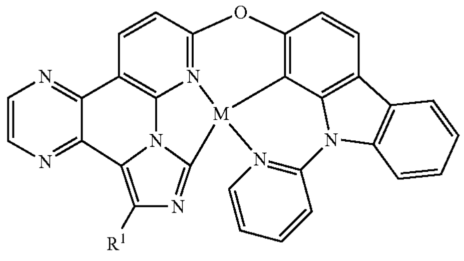
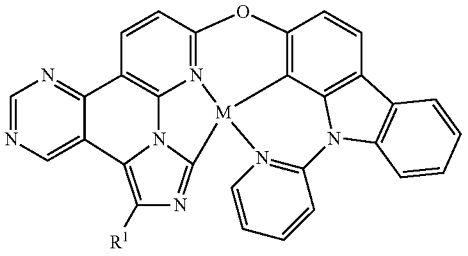
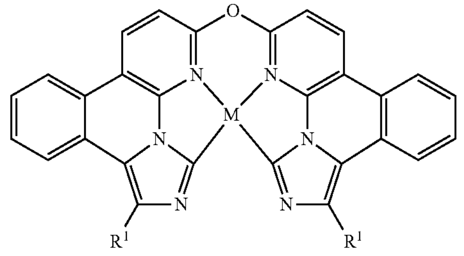

-continued
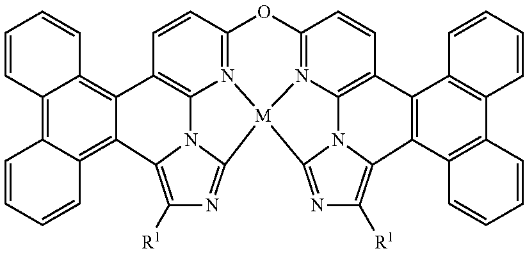
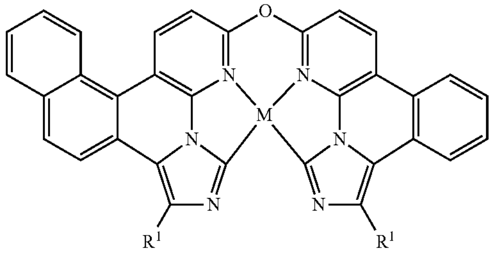
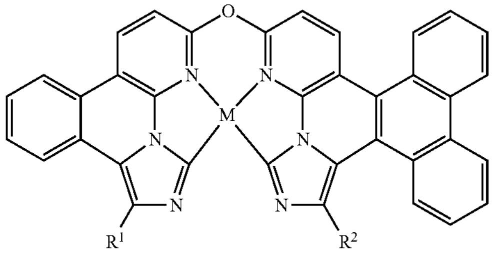
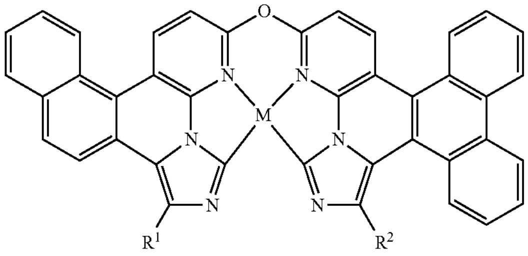
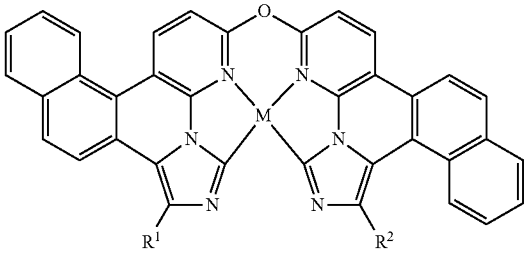
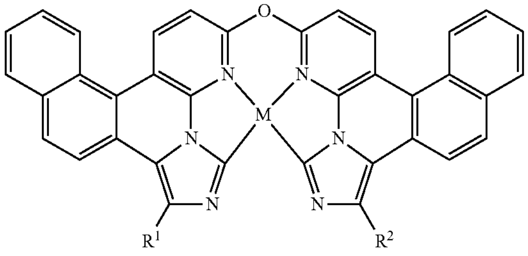
-continued
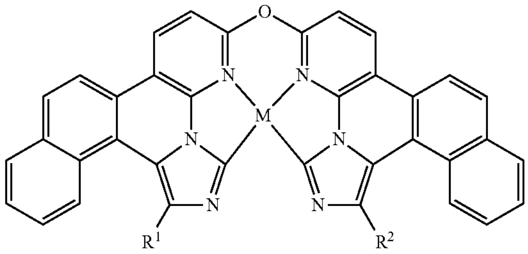
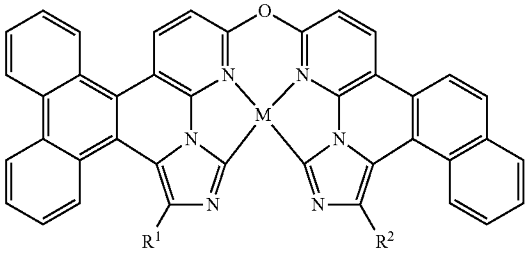
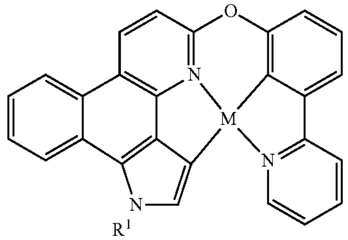
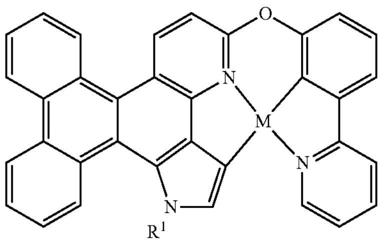
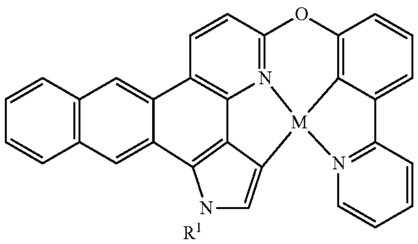
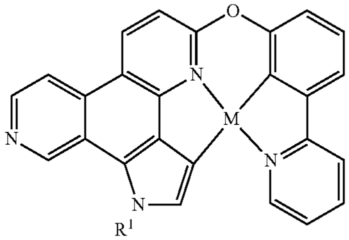
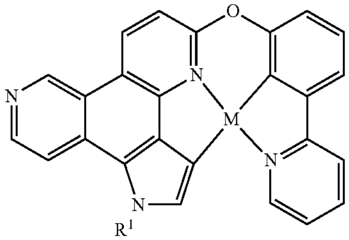

-continued
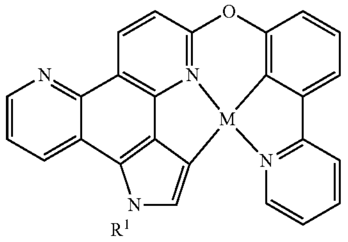
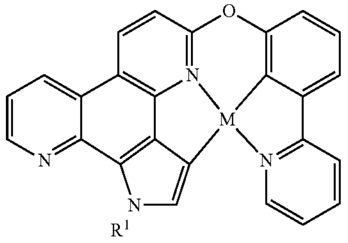
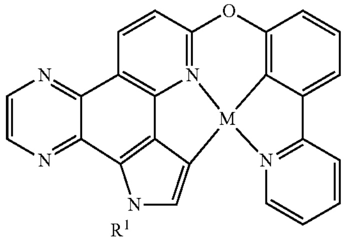
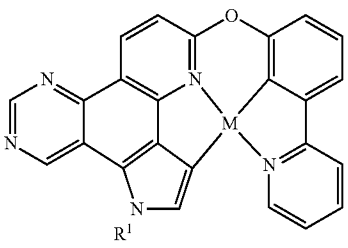
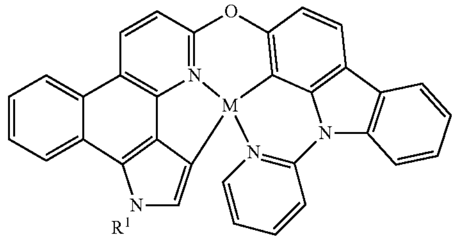
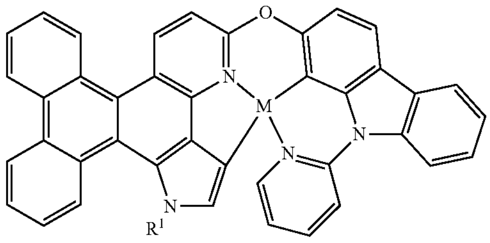
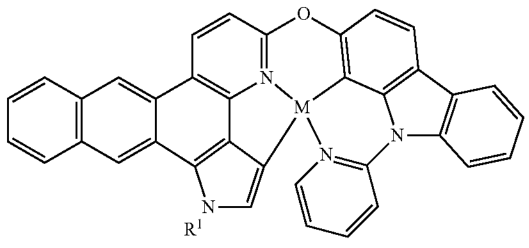
-continued
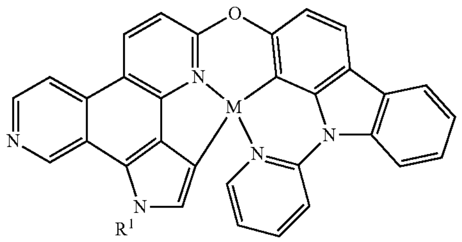
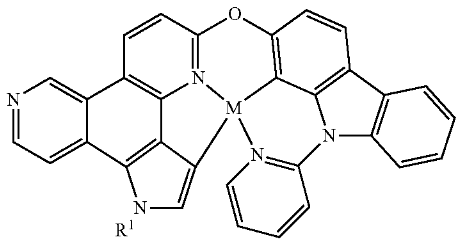
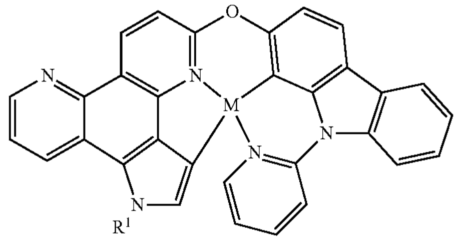
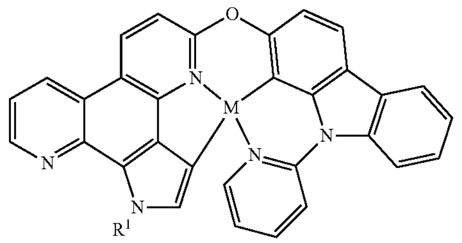
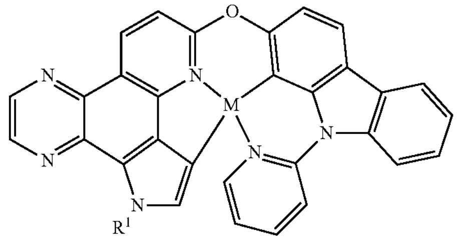
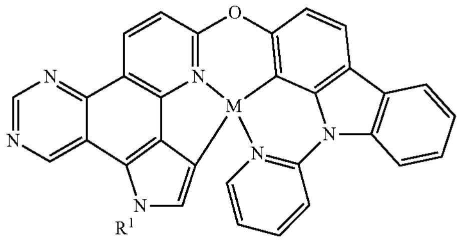
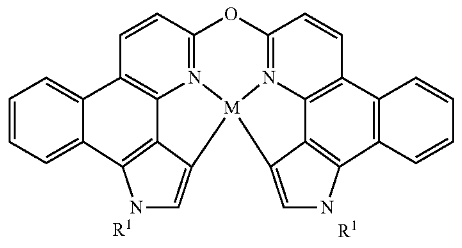

-continued
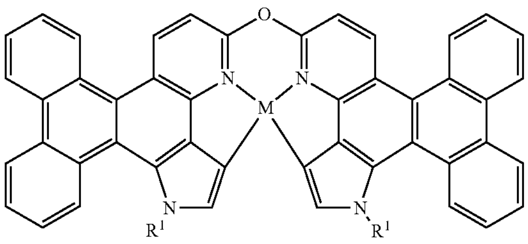
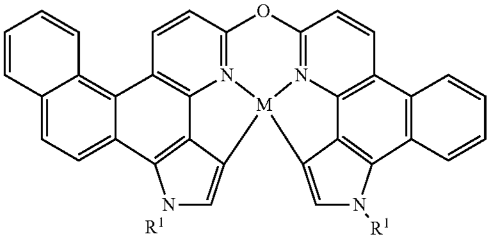
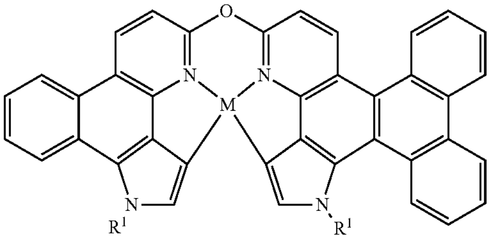
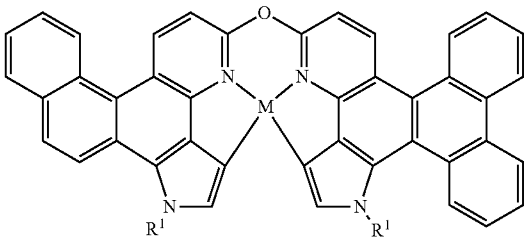
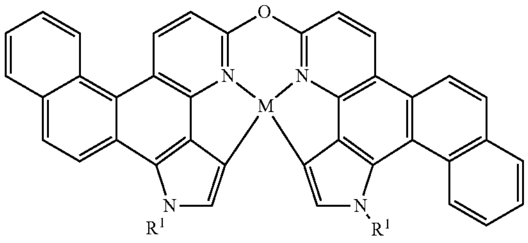
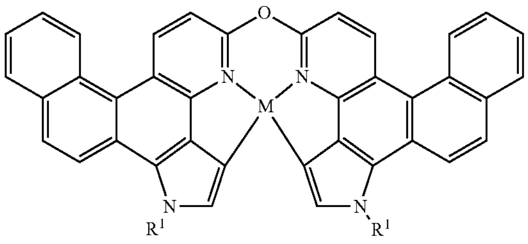
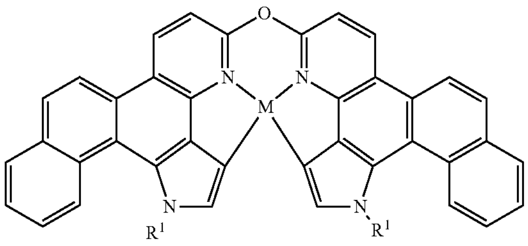
-continued
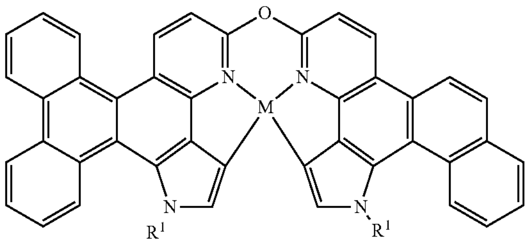
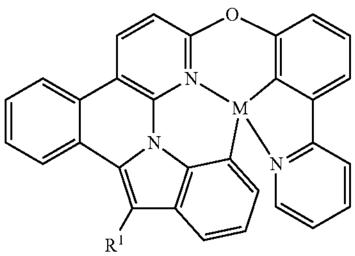
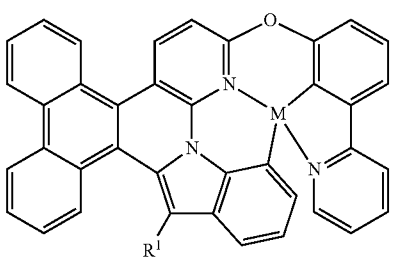
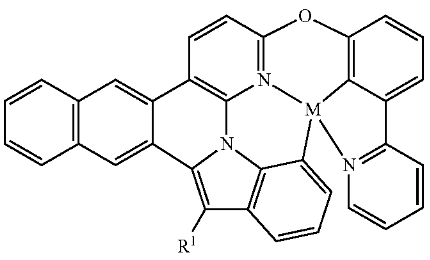
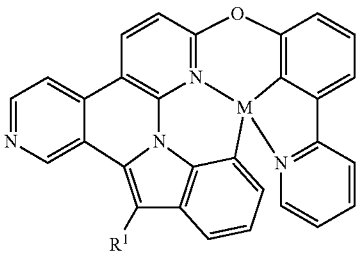
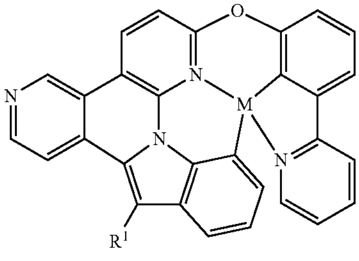

-continued
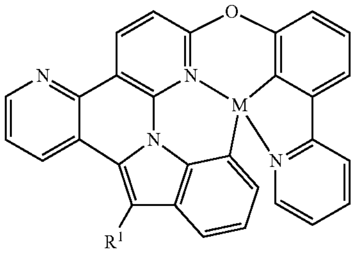
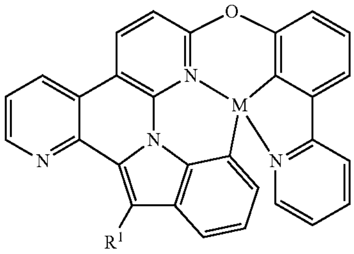
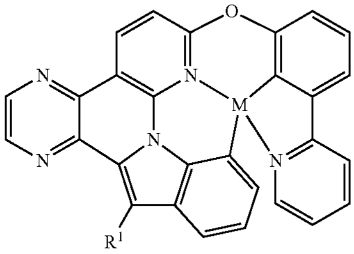
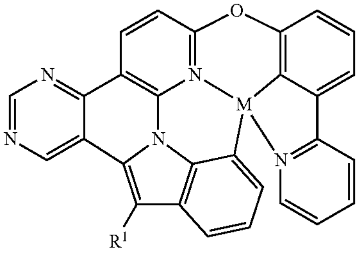
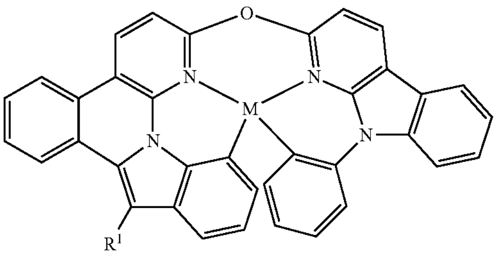
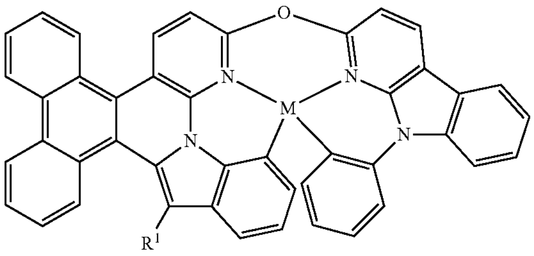
-continued
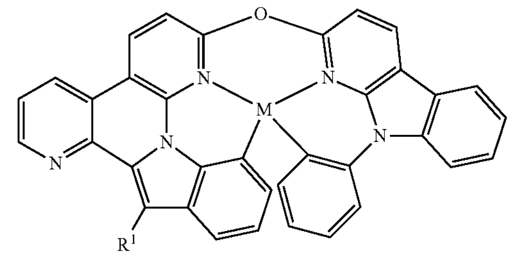
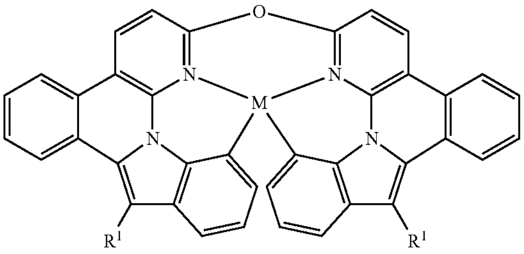
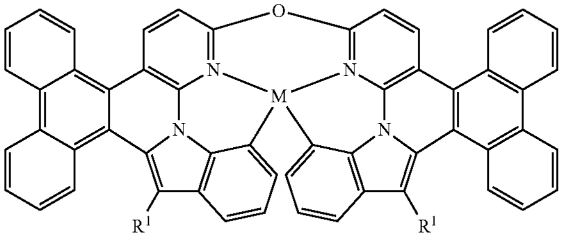
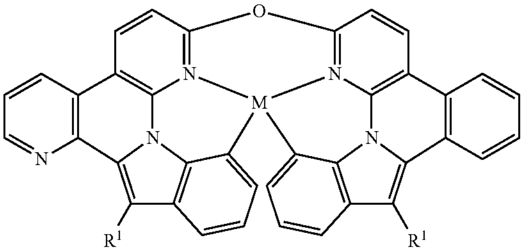
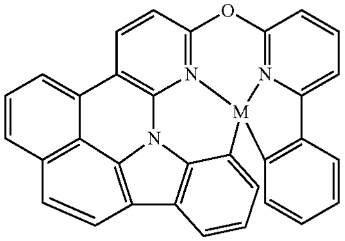
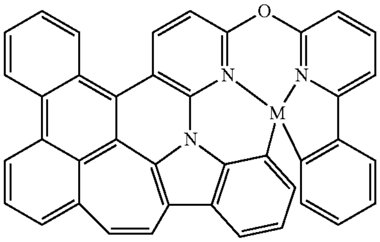
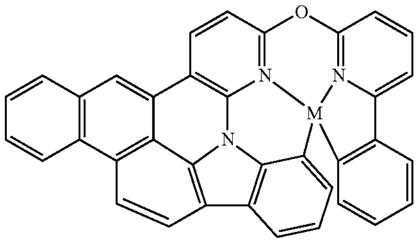

-continued
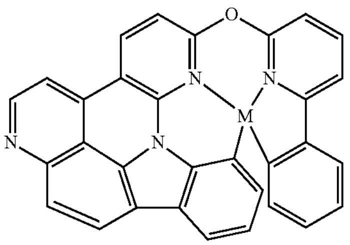
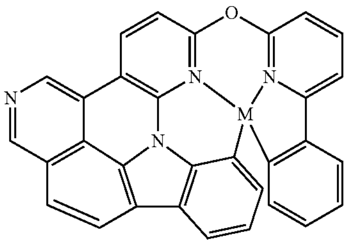
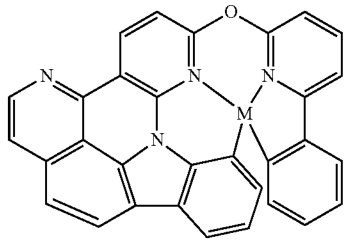
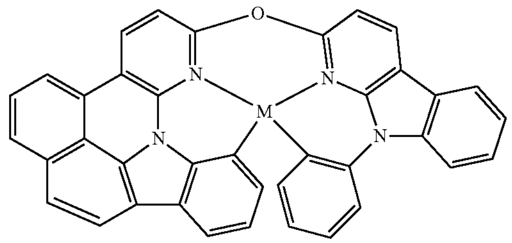
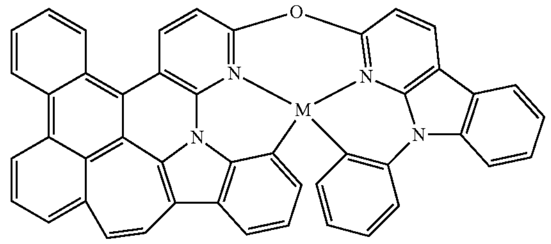
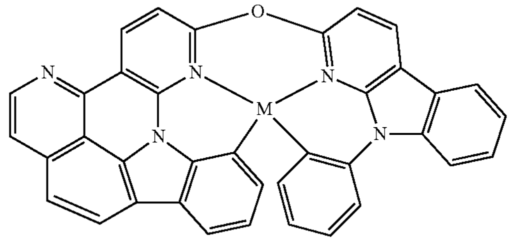
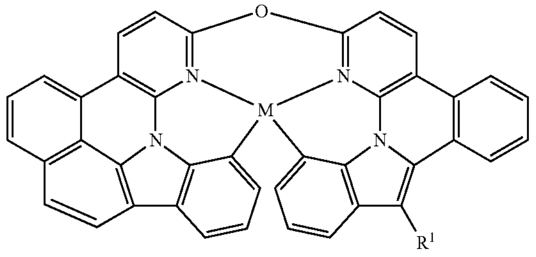
-continued
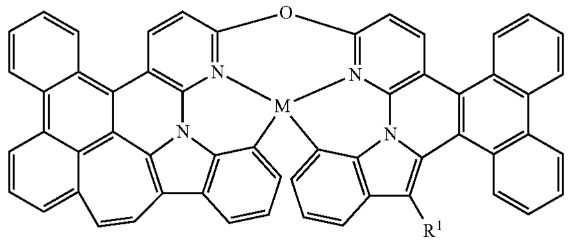
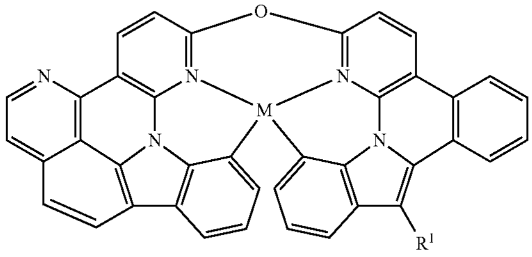
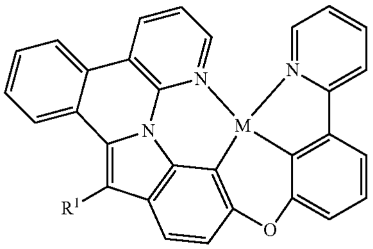
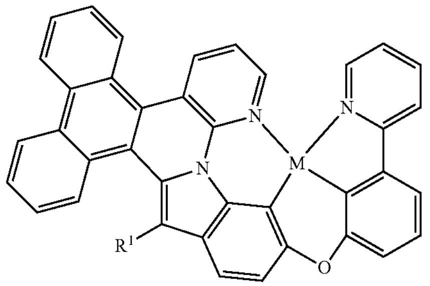
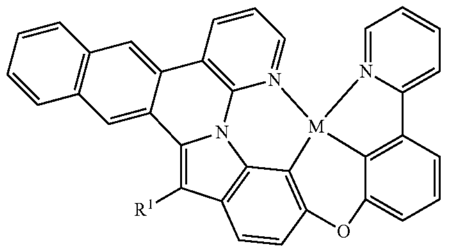
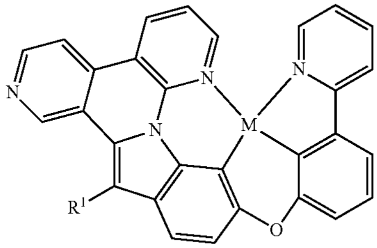

-continued
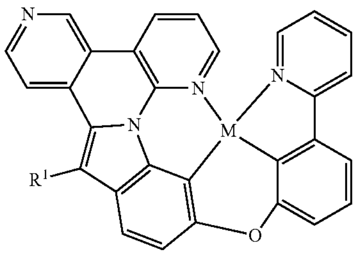
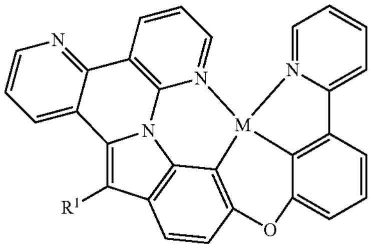
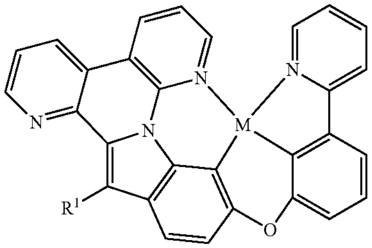
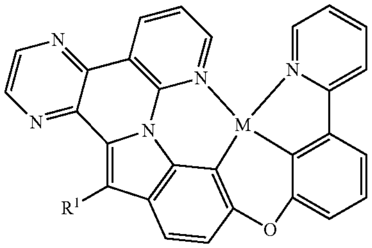
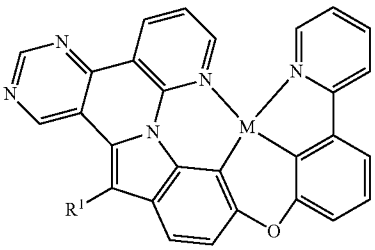
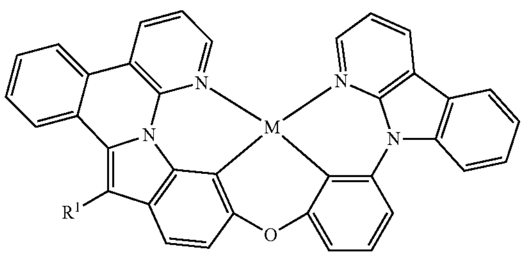
-continued
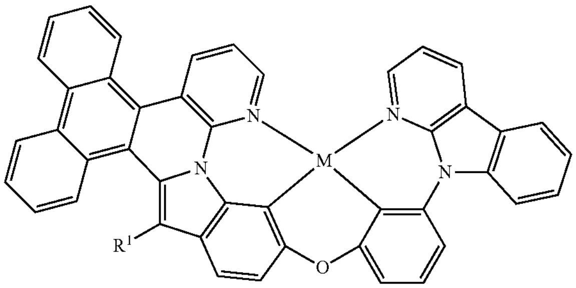
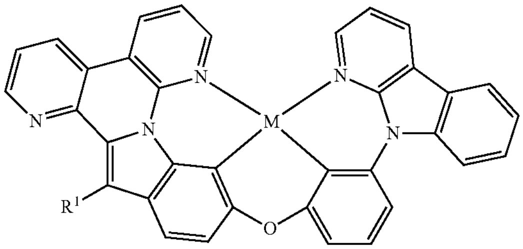
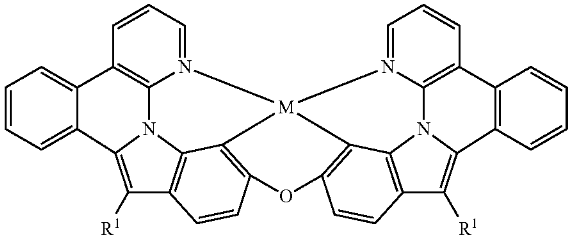
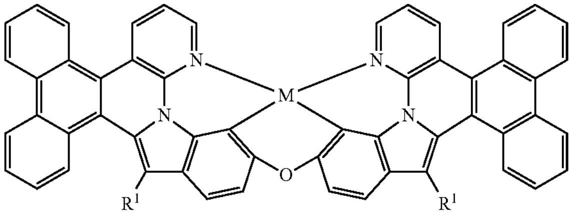
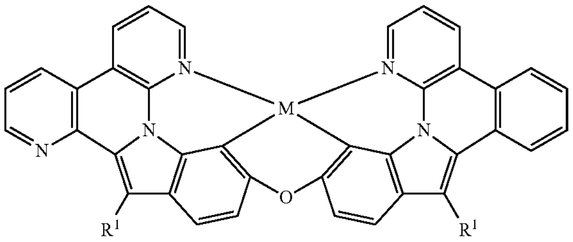
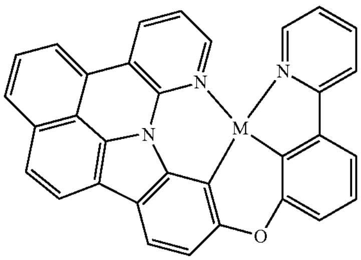

-continued
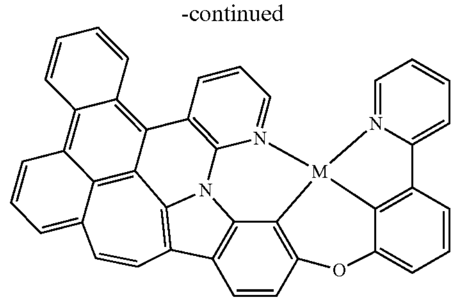
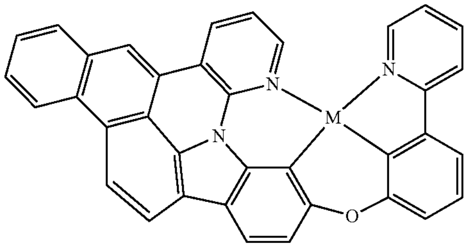
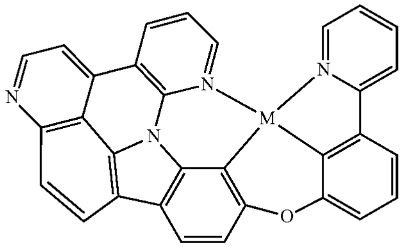
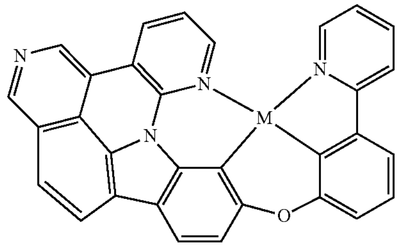
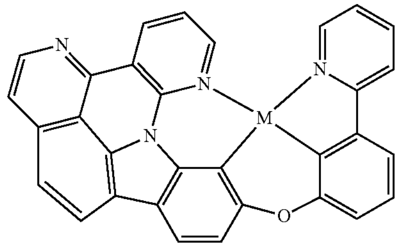
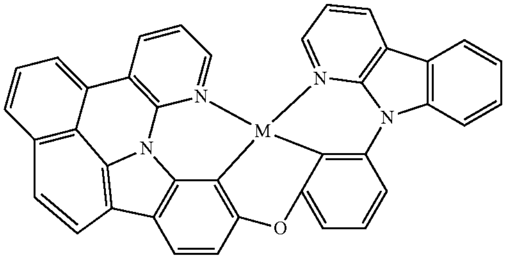
-continued
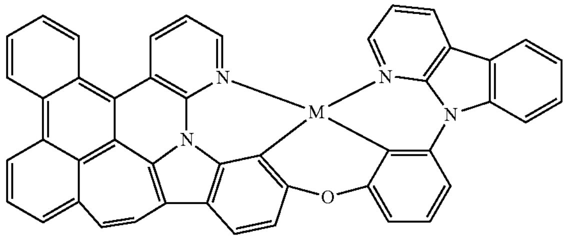
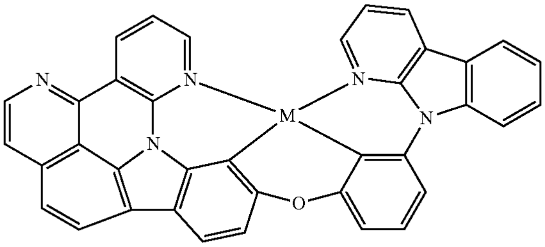
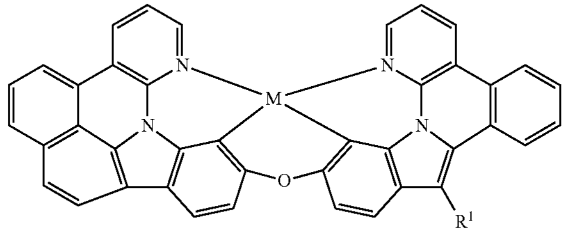
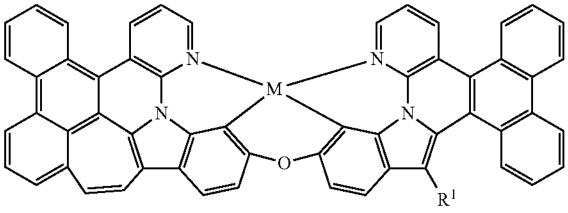
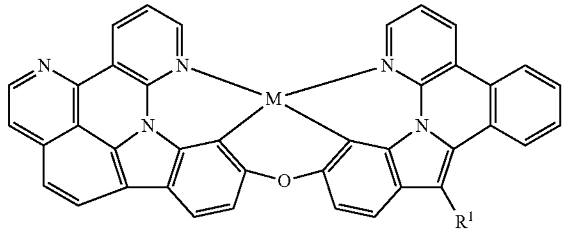
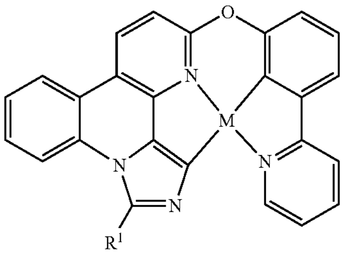
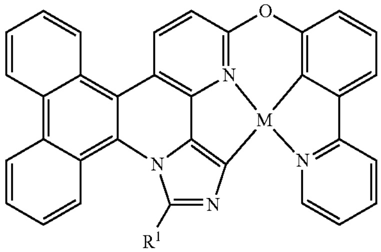

-continued
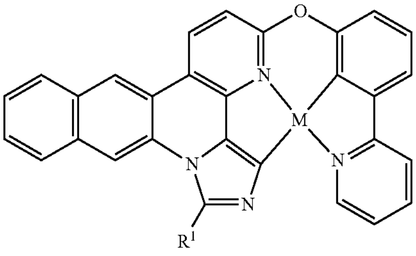
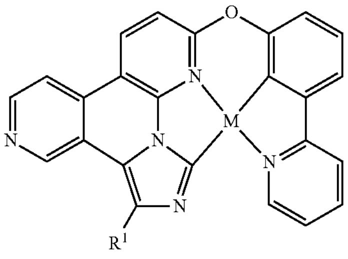
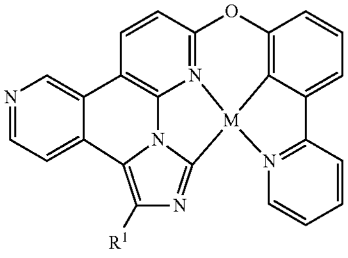
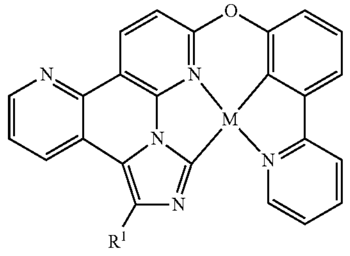
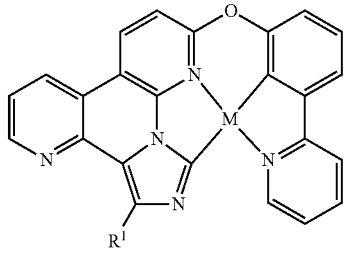
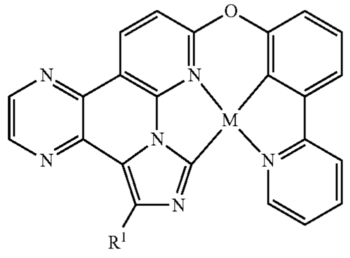
-continued
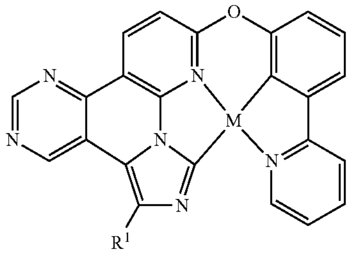
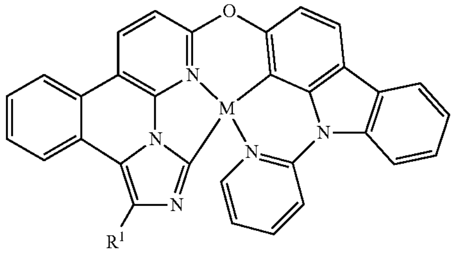
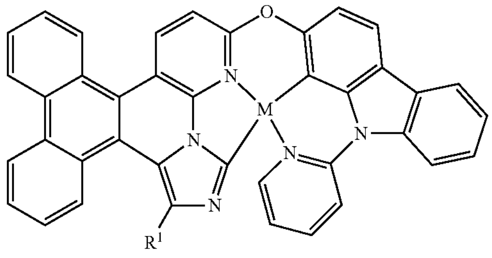
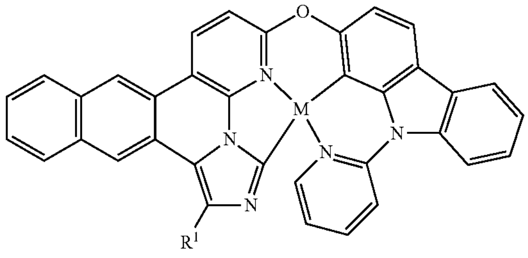
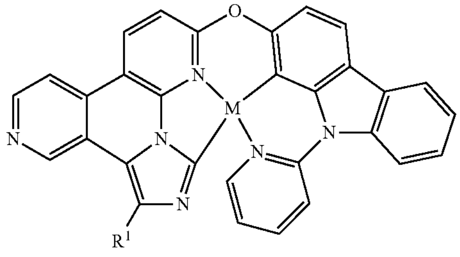
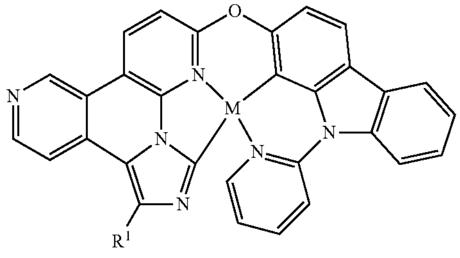

-continued
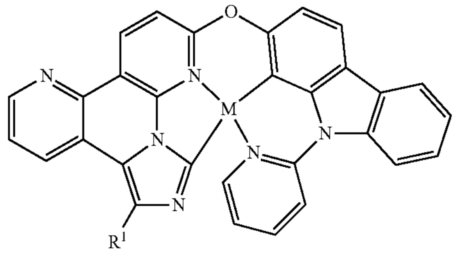
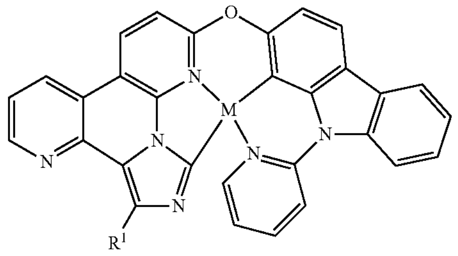
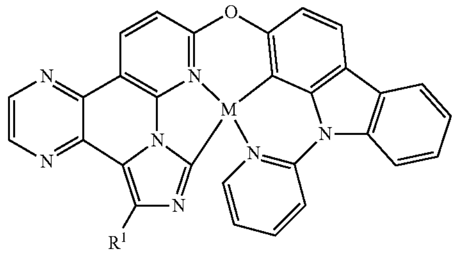
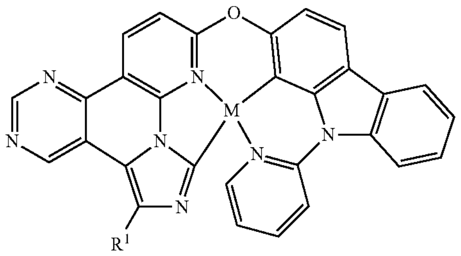
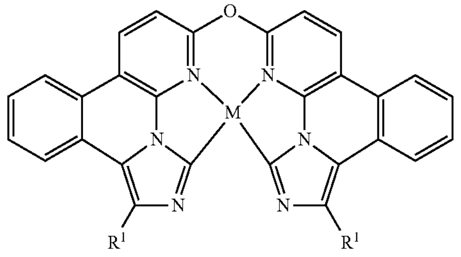
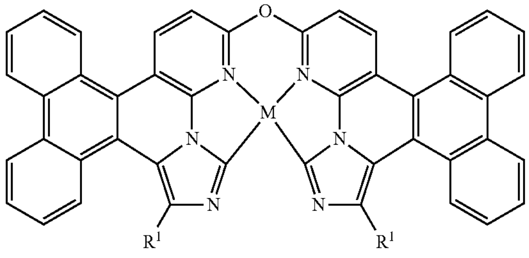
-continued
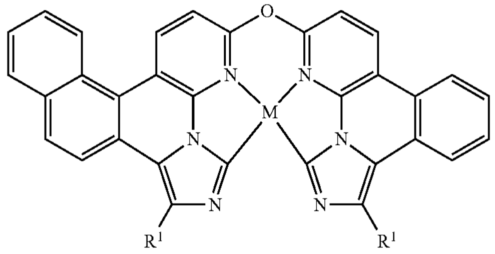
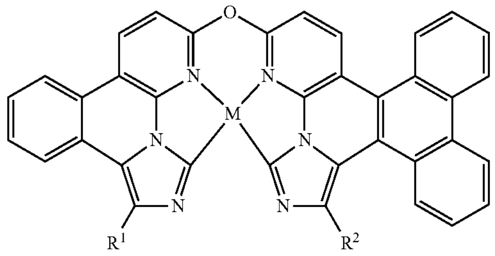
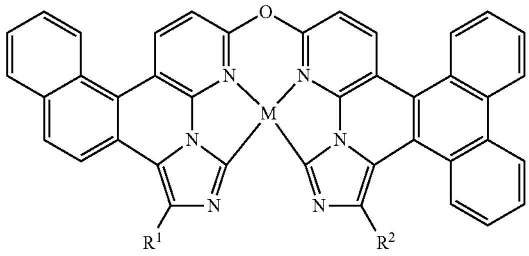
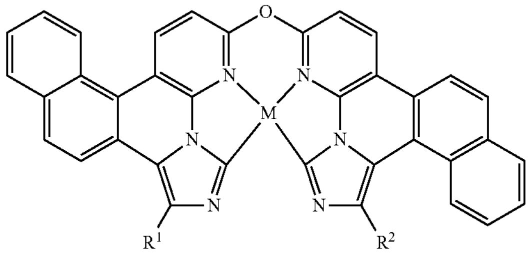
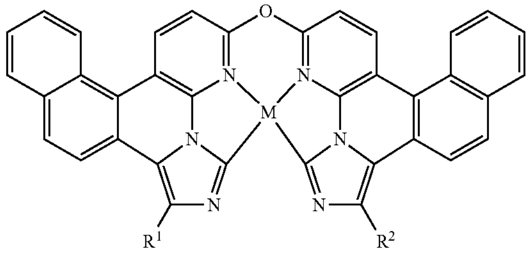
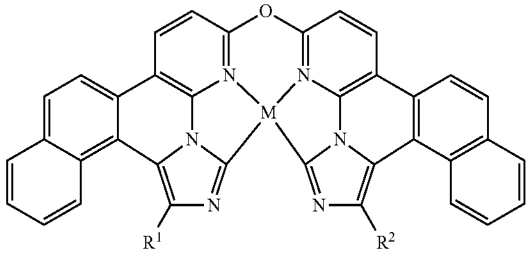

-continued
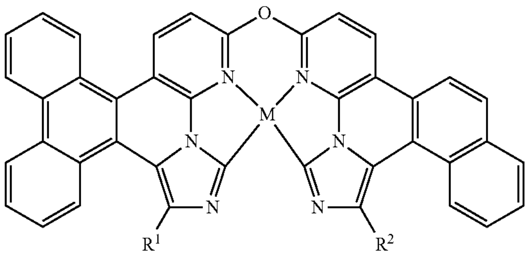
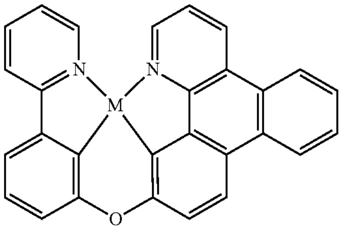
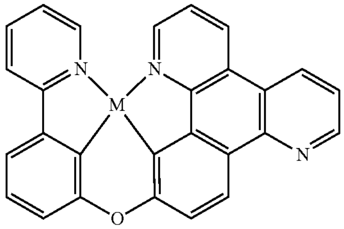
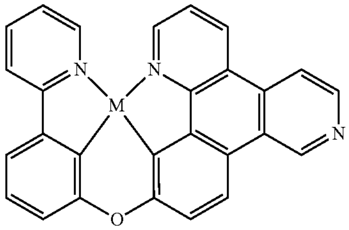
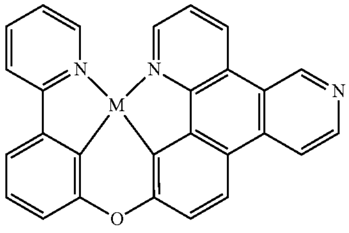
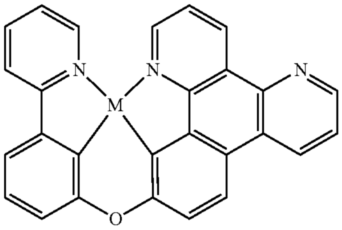
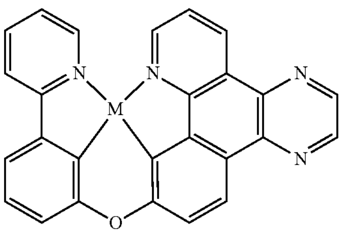
-continued
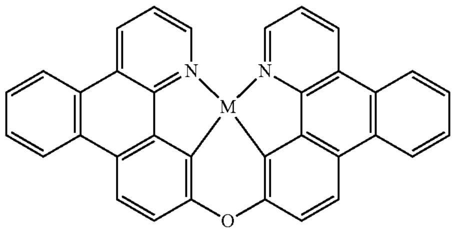
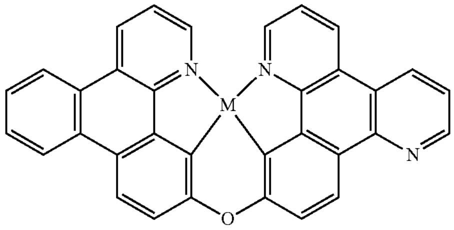
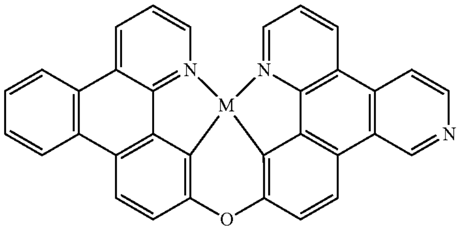
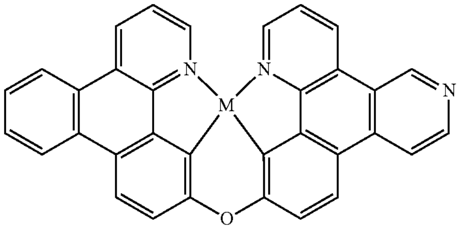
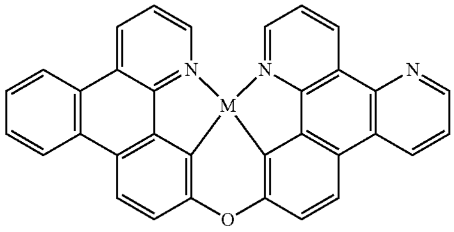
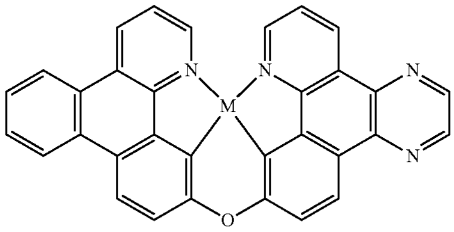
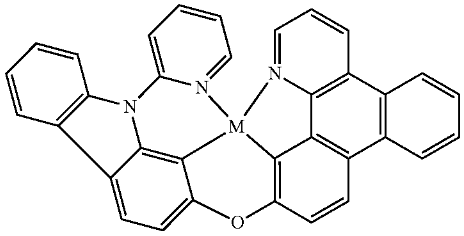

-continued
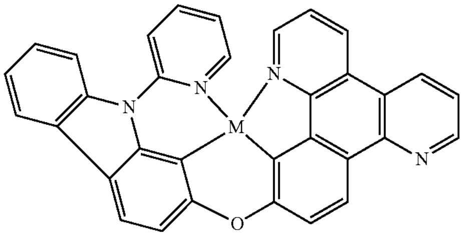
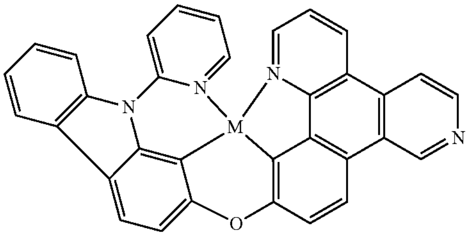
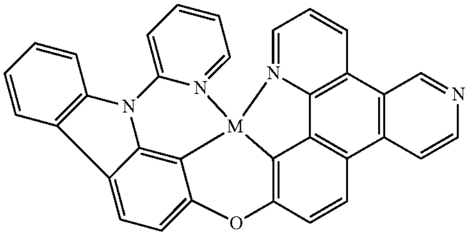
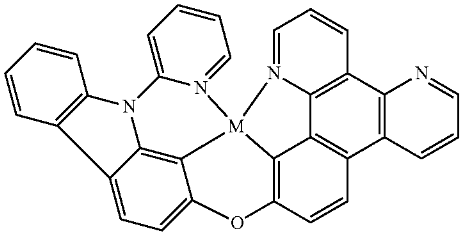
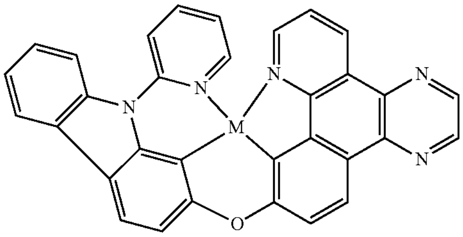
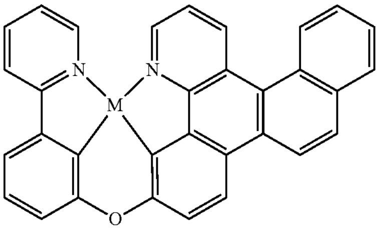
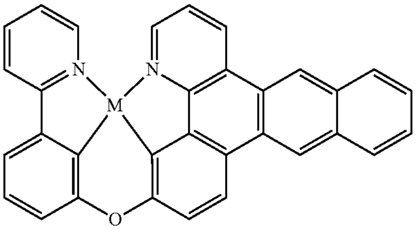
-continued
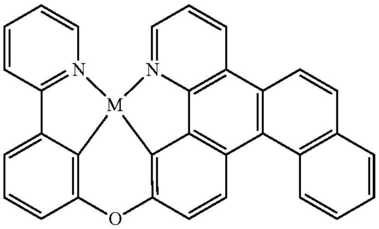
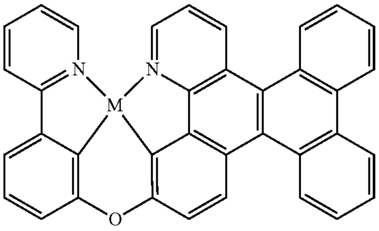
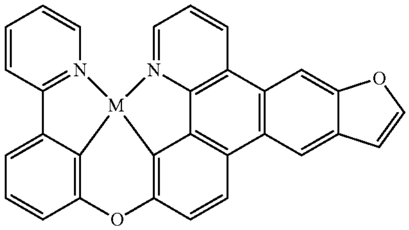
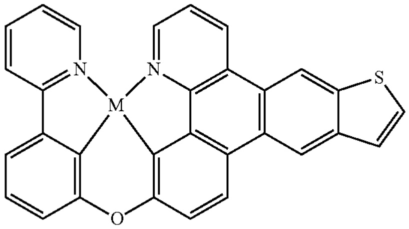
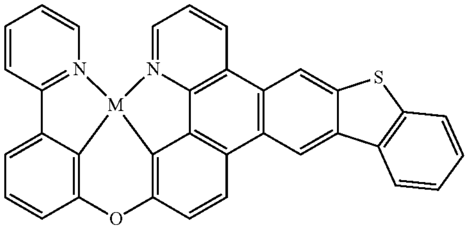
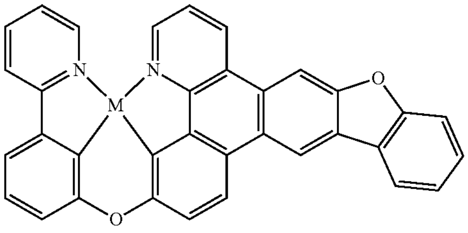
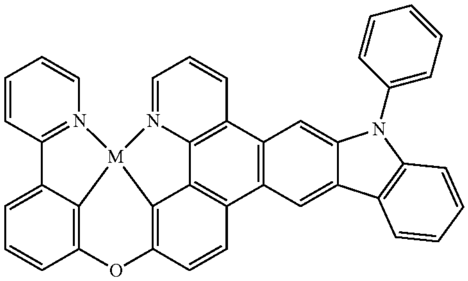

-continued

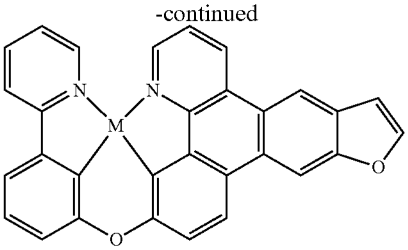

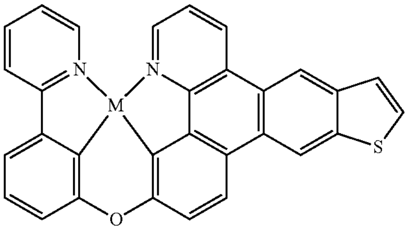

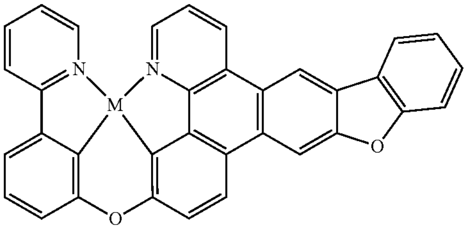

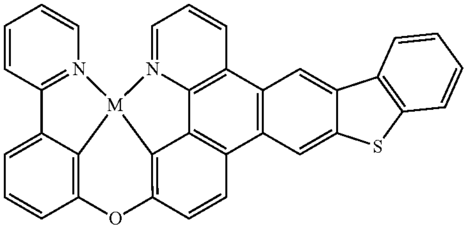

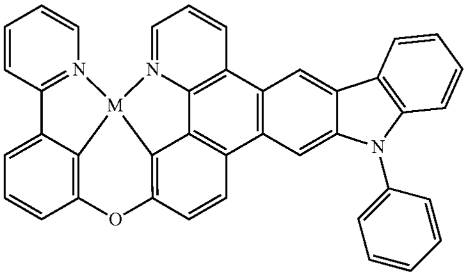

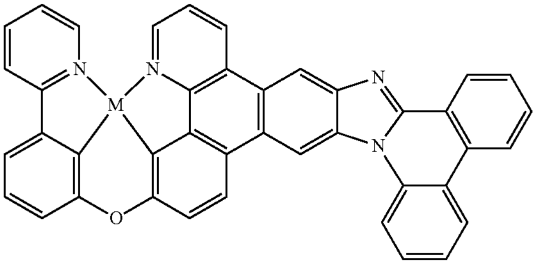

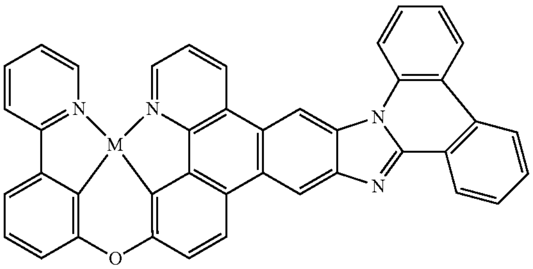

-continued

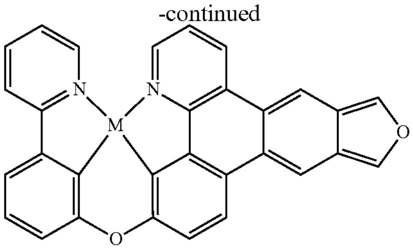

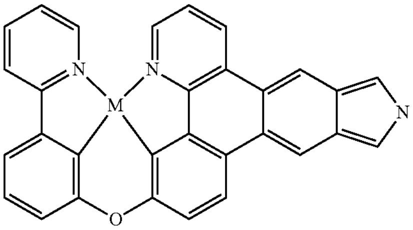

MADF emitters based on cyclic platinum (II) and palladium (II) complexes employing benzo-imidazo-phenanthridine and analogues include compounds of General Formula IV shown below.

General Formula IV

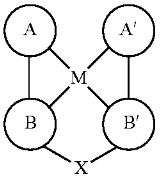

In General Formula IV:

M is Pt (II) or Pd (II)

X represents a single bond or $CR^7R^8$, C═O, $SiR^7R^8$, $GeR^7R^8$, $NR^7$, $PR^7$, $PR^7R^8$, $R^7R$═O, $AsR^7$, $R^7As$═O, O, S, S═O, $SO_2$, Se, Se═O, $SeO_2$, $BR^7$, $BR^7R^8$, $AlR^7$, $AlR^7R^8$, $R^7Bi$═O, or $BiR^7$,

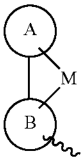 and 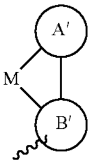

each independently represents one of the following chemical moieties:

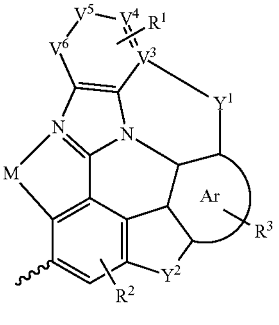

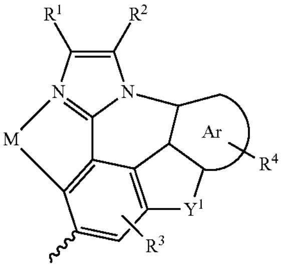

-continued
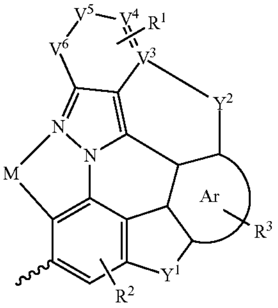
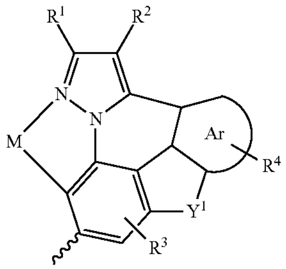
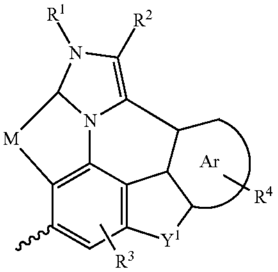
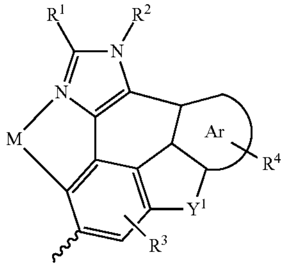
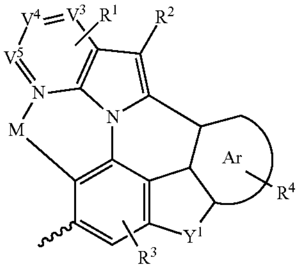
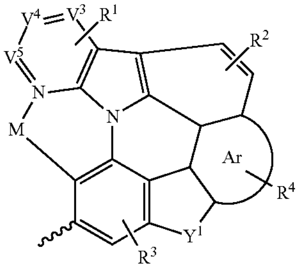
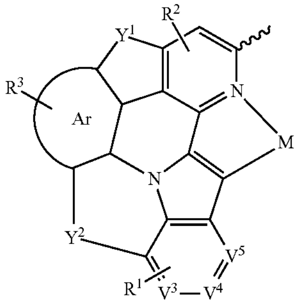
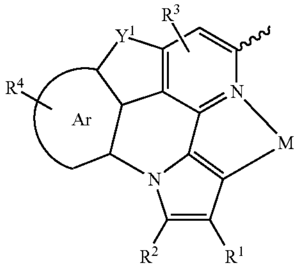
-continued
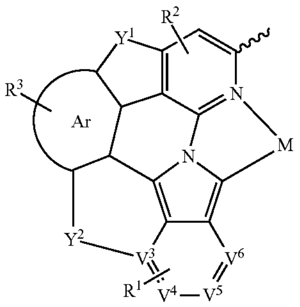
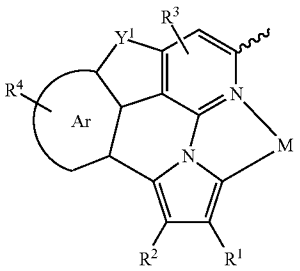
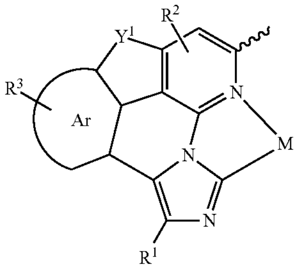
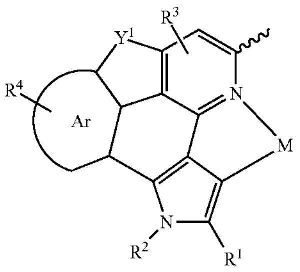
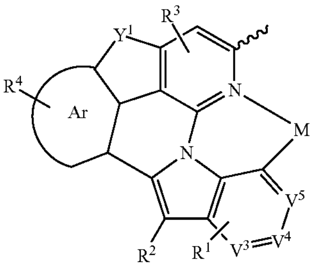
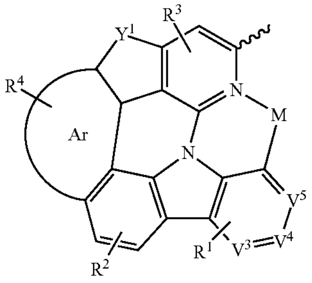

-continued
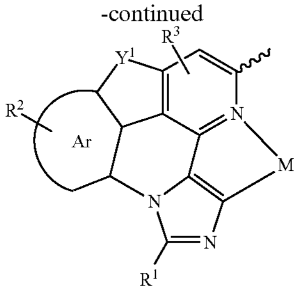
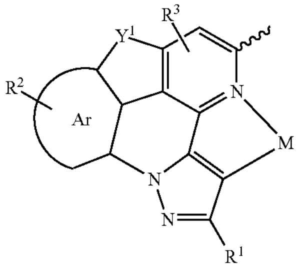
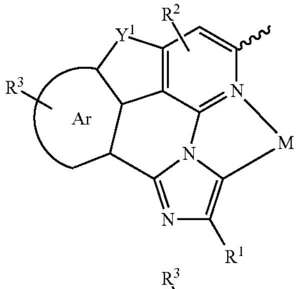
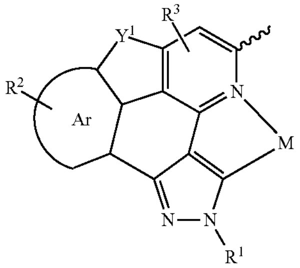
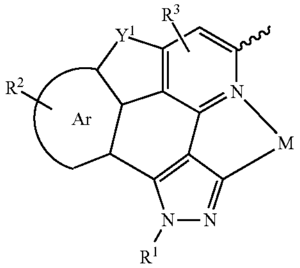
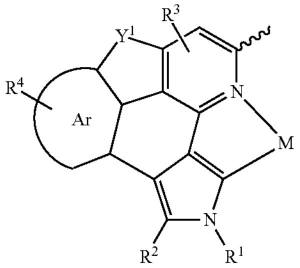
-continued
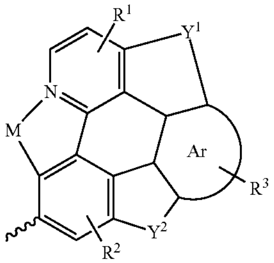
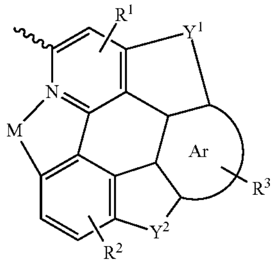
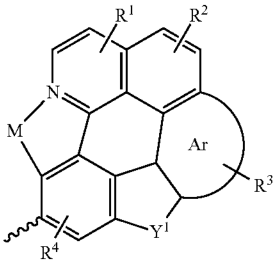
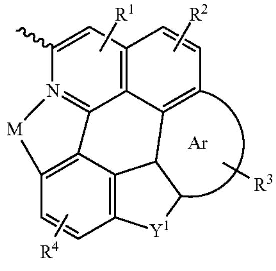
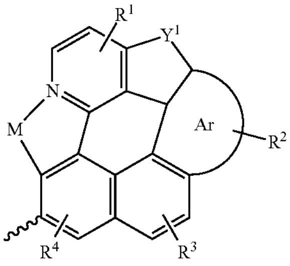
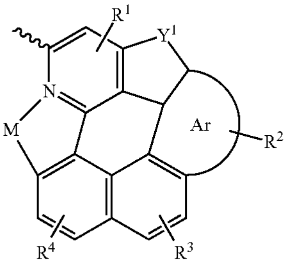
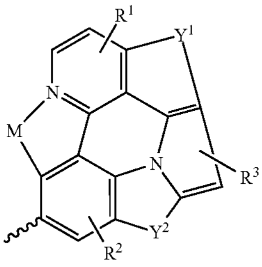
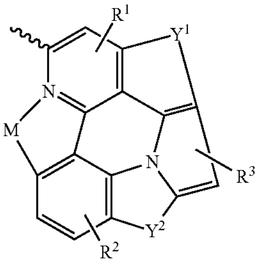
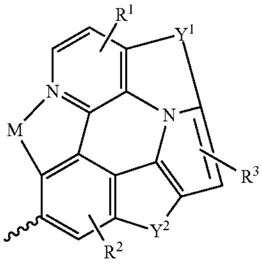
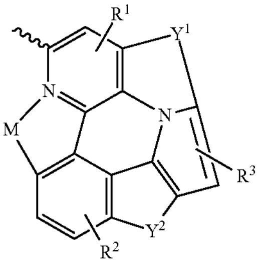
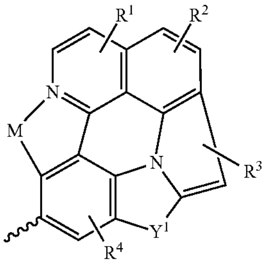

-continued
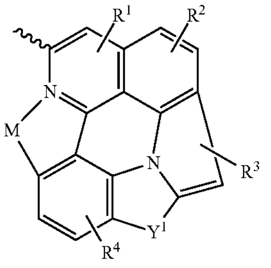
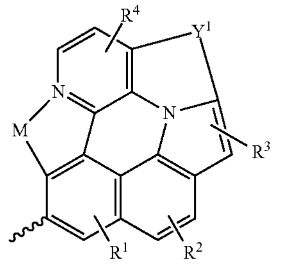
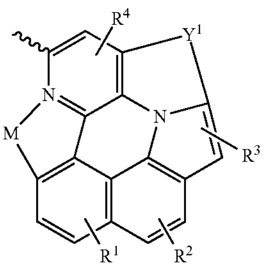
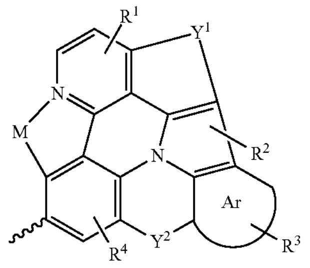
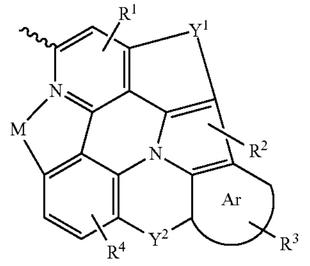
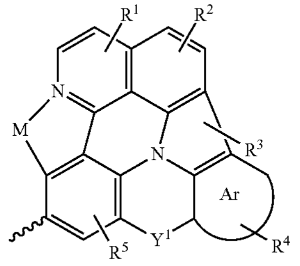
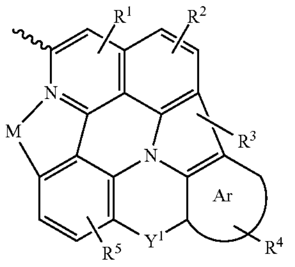
-continued
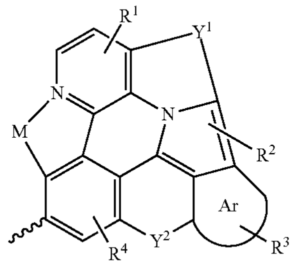
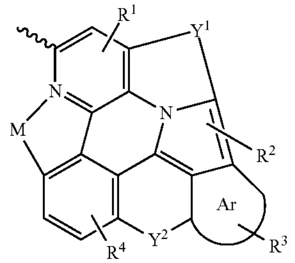
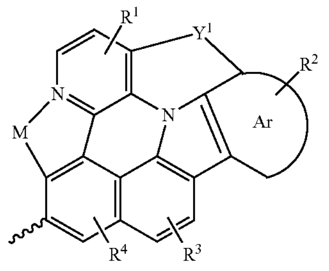
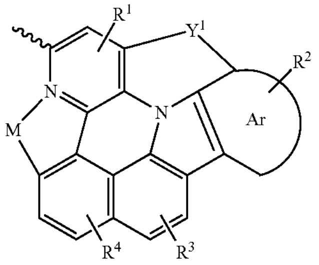
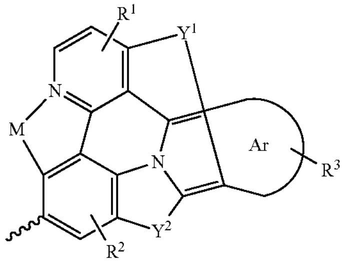
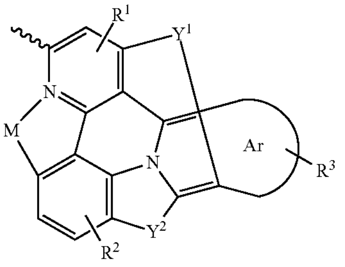

-continued
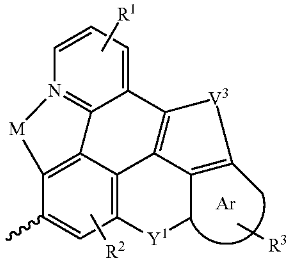
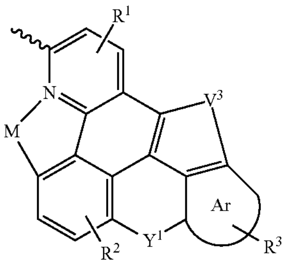
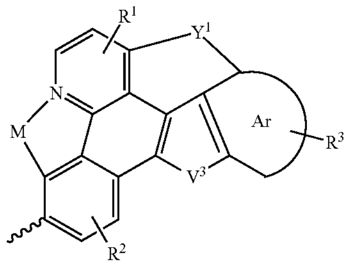
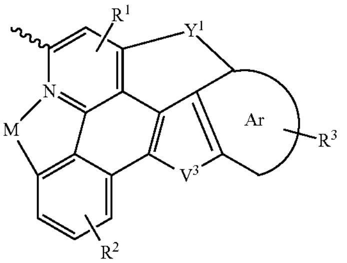
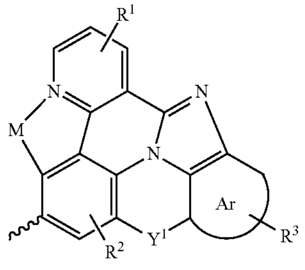
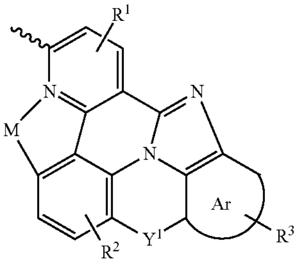
-continued
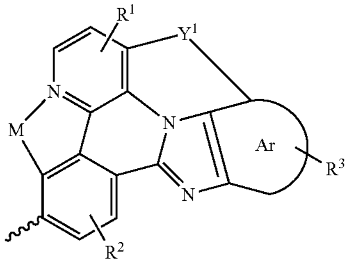
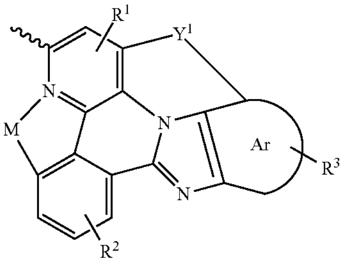
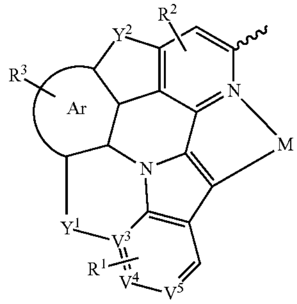
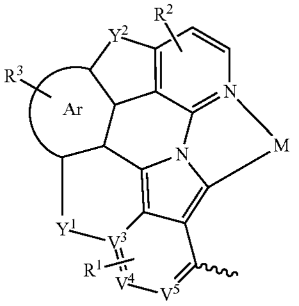
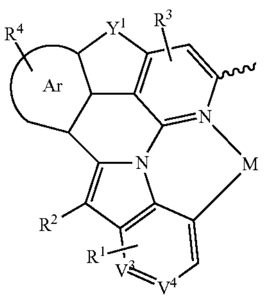
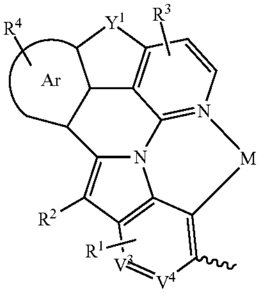
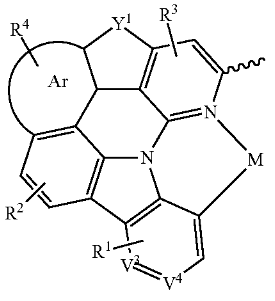
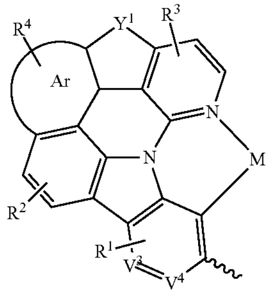

-continued

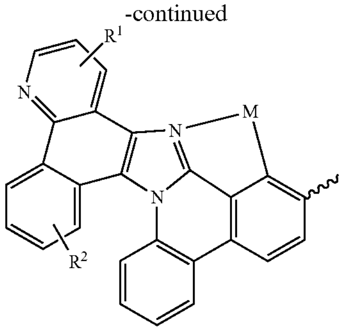

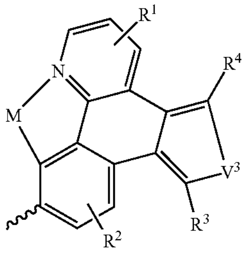

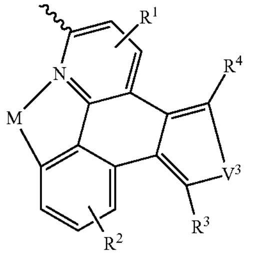

where:

N is nitrogen, each of $V^1$, $V^2$, $V^3$, $V^4$, $V^5$, and $V^6$, if present, is independently C, N, Si, O, S, Ge, P, As, Se, B, Al, or Bi, each of $X^1$, $X^2$, $Y^1$, $Y^2$, $Y^3$, and $Y^4$ is independently present or absent, and each $X^1$, $X^2$, $Y^1$, $Y^2$, $Y^3$, and $Y^4$ present independently represents C, N, Si, O, S, Ge, P, As, Se, B, Al, or Bi, or valency permitting, $CR^7$, $SiR^7$, $GeR^7$, $NR^7$, P=O, As=O, B, $BR^7$, $AlR^7$, Bi=O, $CR^7R^8$, C=O, $SiR^7R^8$, $GeR^7R^8$, $NR^7$, $PR^7$, $PR^7R^8$, $R^7P$=O, $AsR^7$, $R^7As$=O, S=O, $SO_2$, Se=O, $SeO_2$, $BR^7$, $BR^7R^8$, $AlR^7$, $AlR^7R^8$, $R^7Bi$=O, or $BiR^7$, each of $L^1$, $L^2$, $L^3$, and $L^4$ is independently present or absent, and each $L^1$, $L^2$, $L^3$, and $L^4$ present independently represents a substituted or unsubstituted aryl, heteroaryl, or N-heterocyclic carbene, each of R, $R^1$, $R^2$, $R^3$, $R^4$, $R^5$, $R^6$, $R^7$, and $R^8$ is independently absent or present as a single substituent or multiple substituents, valency permitting, and each R, $R^1$, $R^2$, $R^3$, $R^4$, $R^5$, $R^6$, $R^7$, and $R^8$ present independently represents deuterium, halogen, hydroxyl, thiol, nitro, cyanide, isocyanide, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, and each of

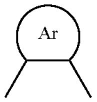

is independently present or absent, and each Ar present independently represents a substituted or unsubstituted aryl, heteroaryl, or N-heterocyclic carbene, where suitable examples of substituents include the following:

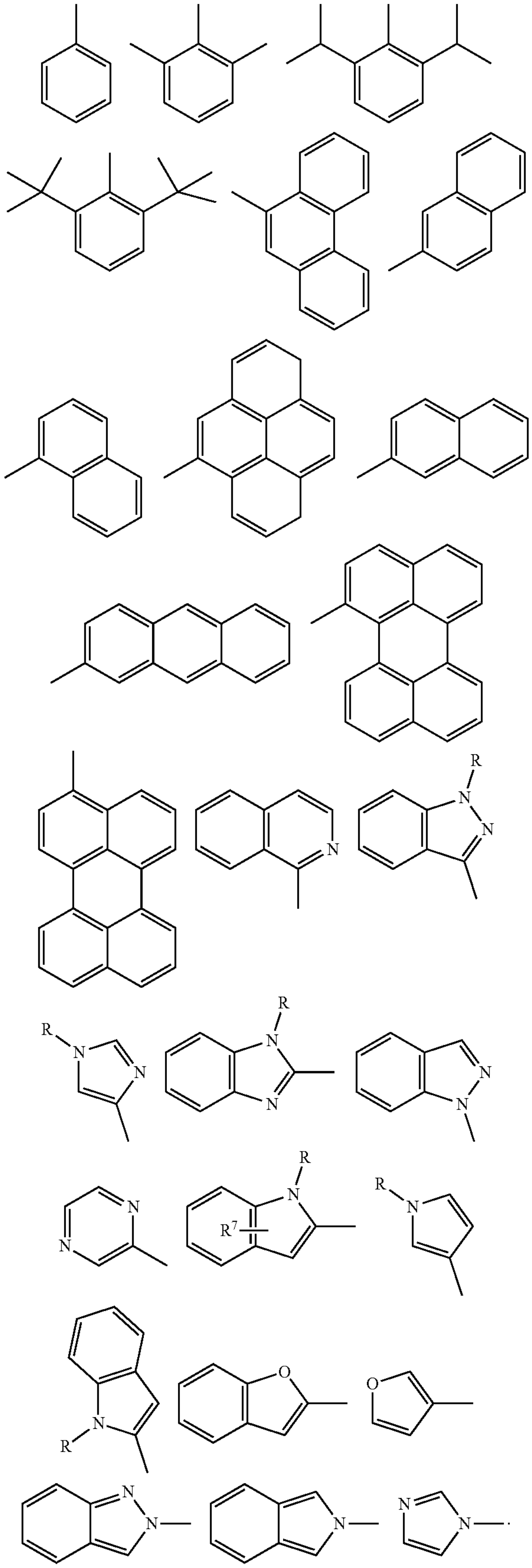

In A-B and A'-B' is independently present or absent, and each Ar present independently represents a substituted or unsubstituted aryl, heteroaryl, or N-heterocyclic carbene. Suitable examples of Ar include the following:
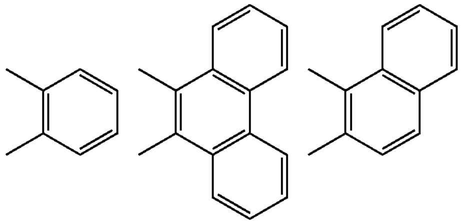
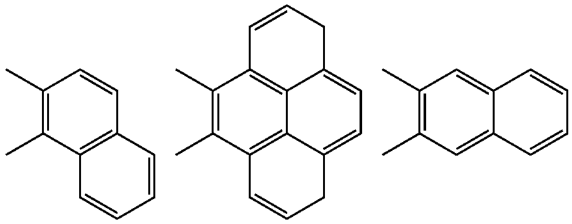
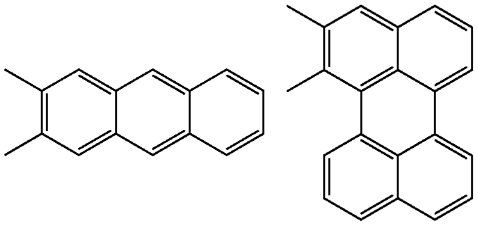
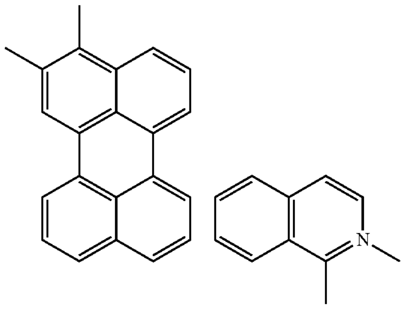
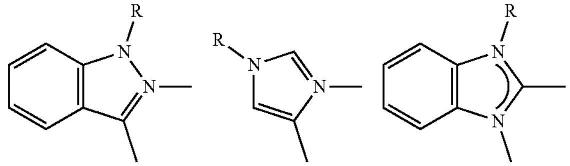
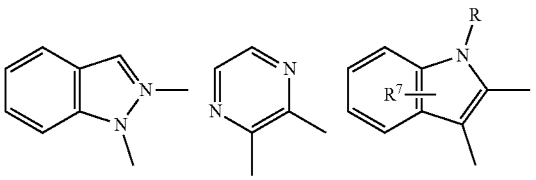
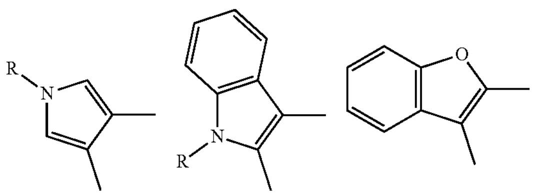
-continued
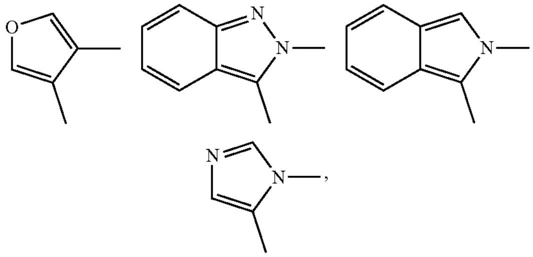
in which R and $R^7$ are as defined herein.
Compounds of General Formula IV are shown below.
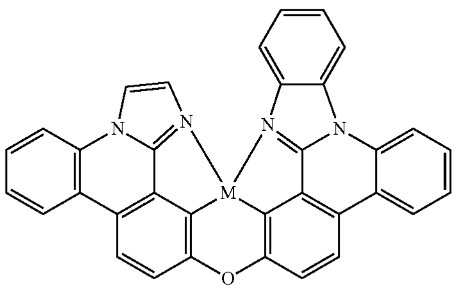
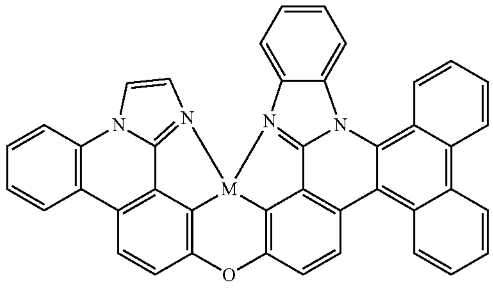
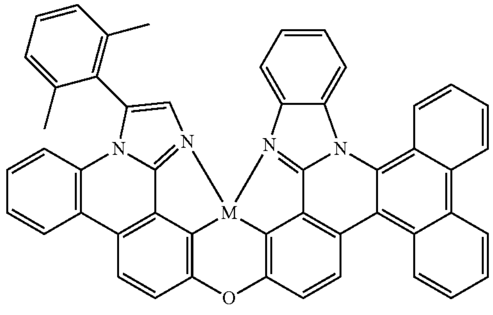
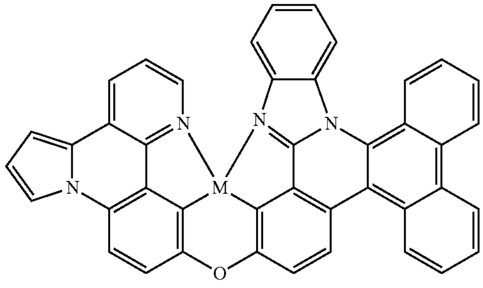

-continued
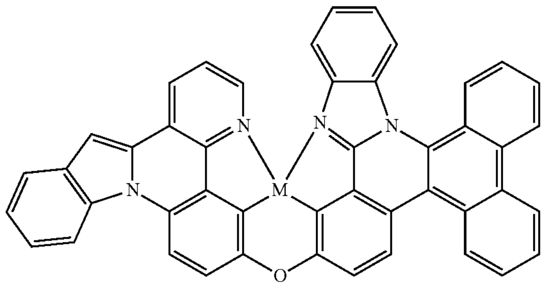
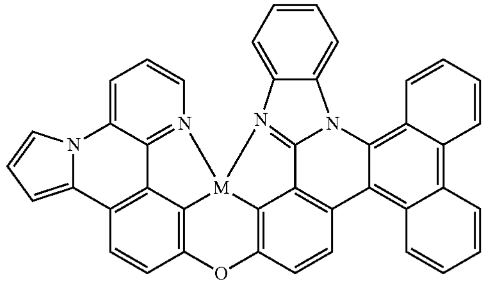
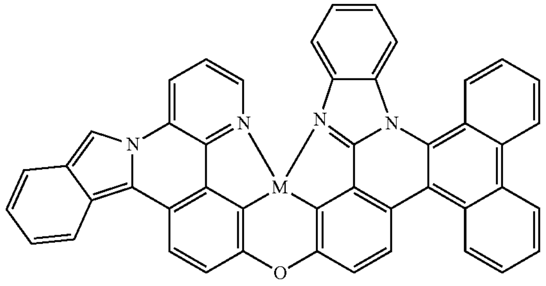
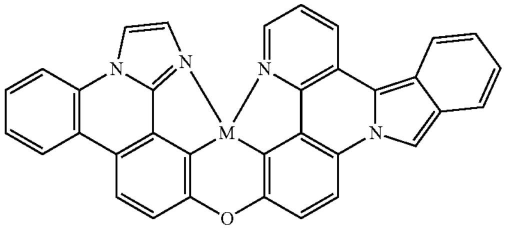
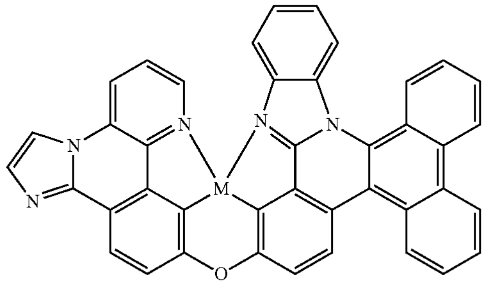
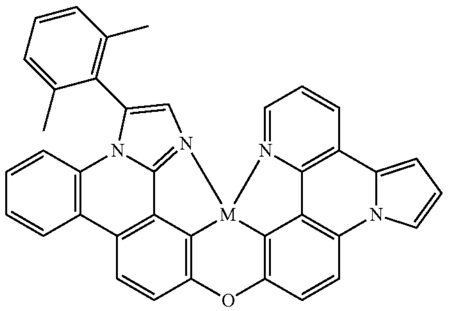
-continued
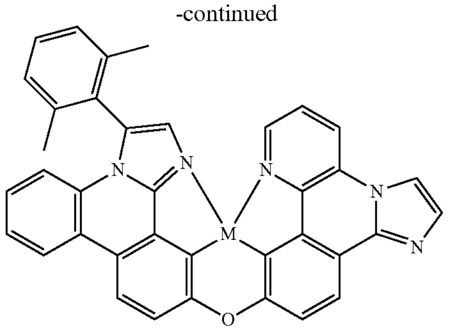
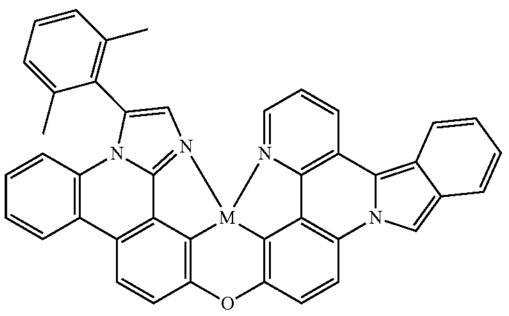
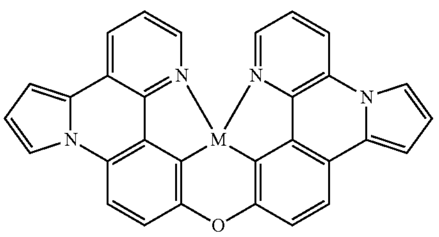
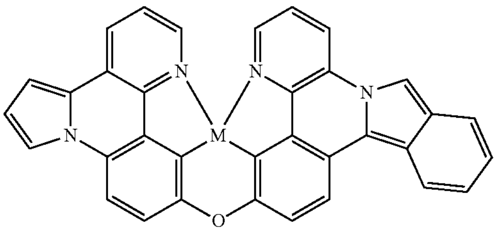
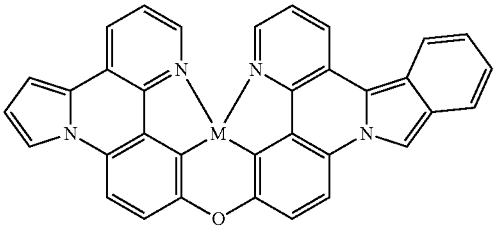
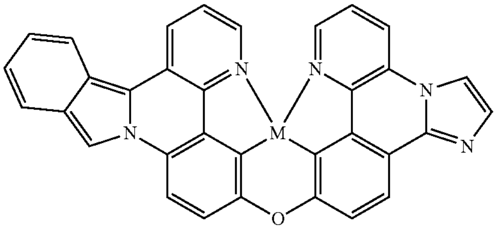

-continued
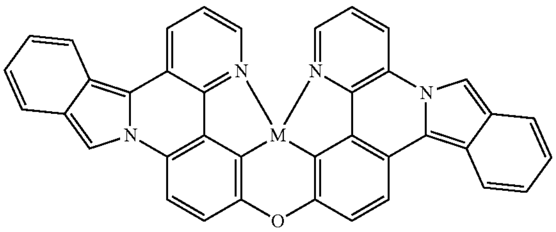
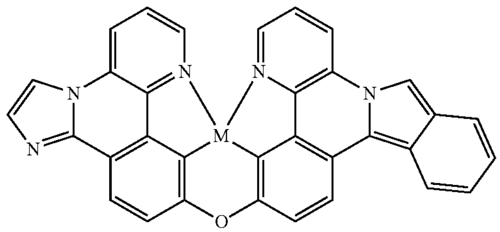
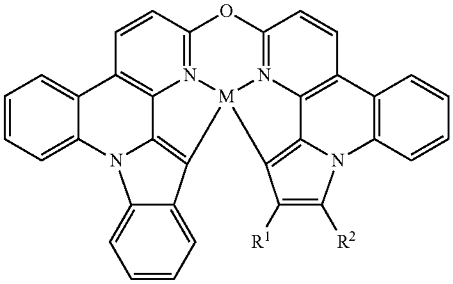
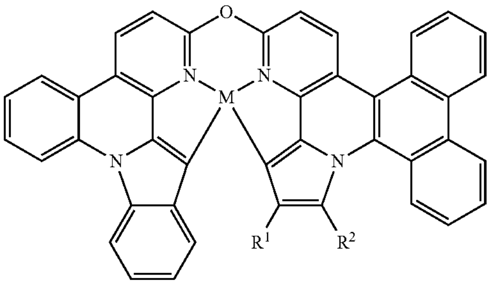
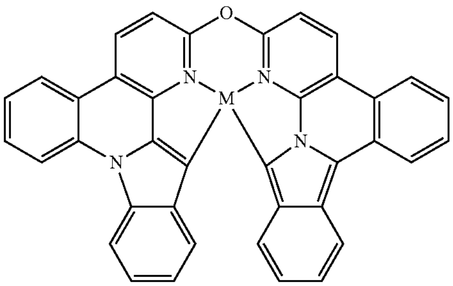
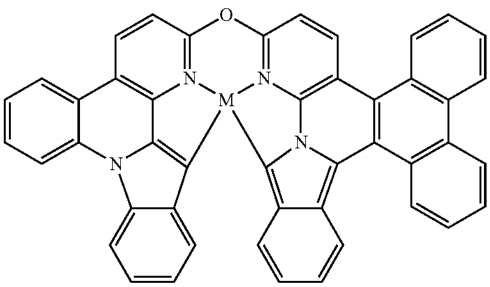
-continued
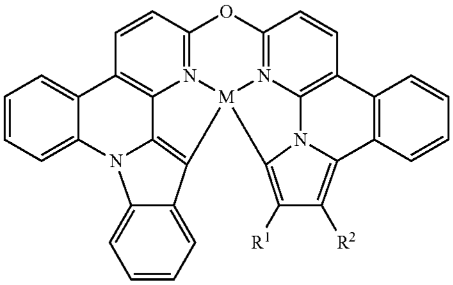
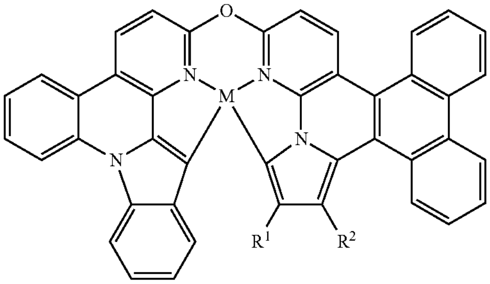
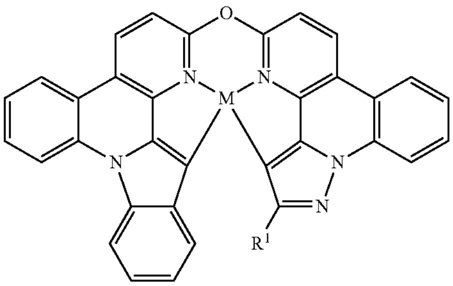
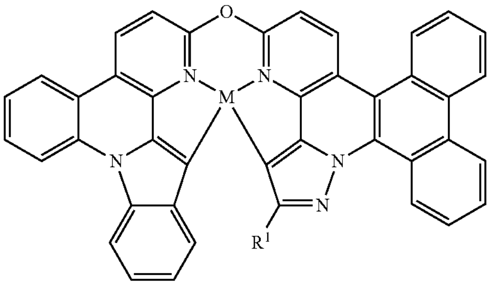
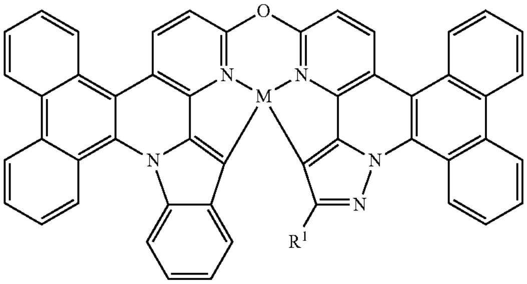
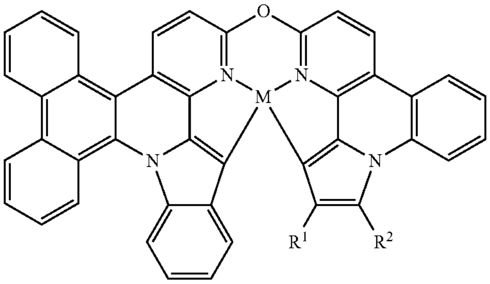

-continued
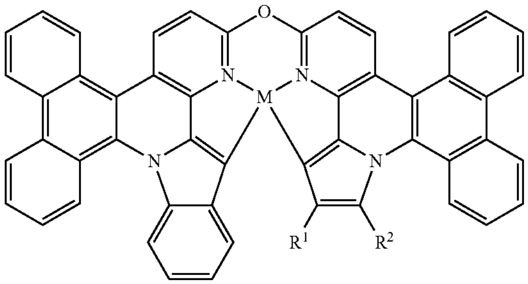
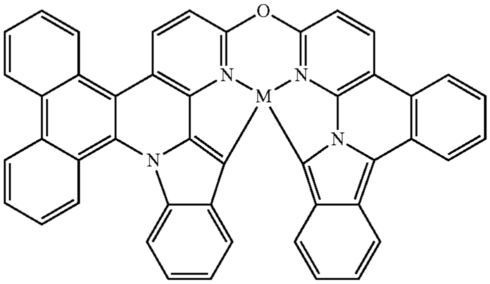
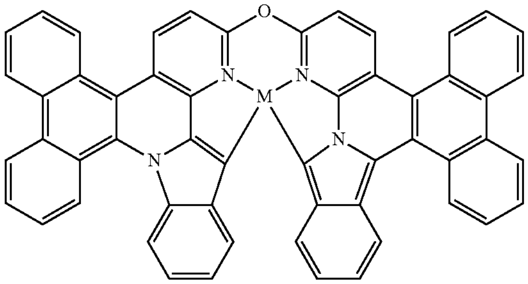
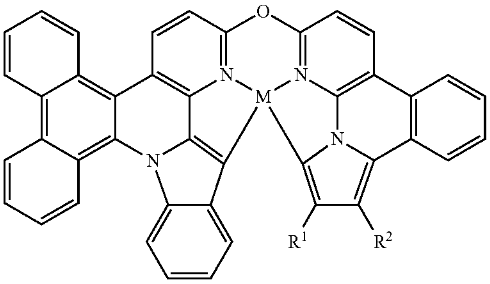
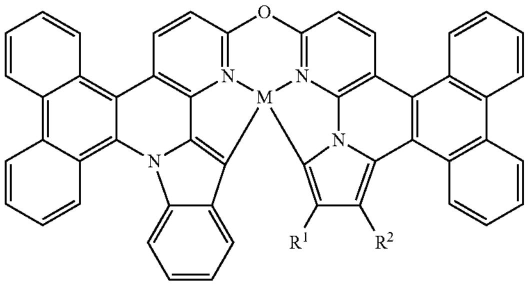
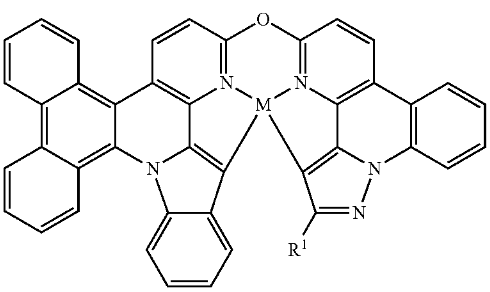
-continued
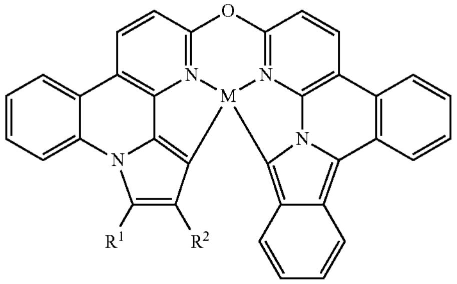
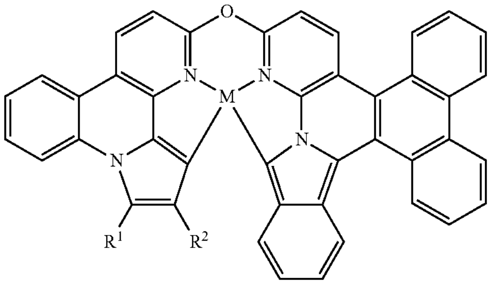
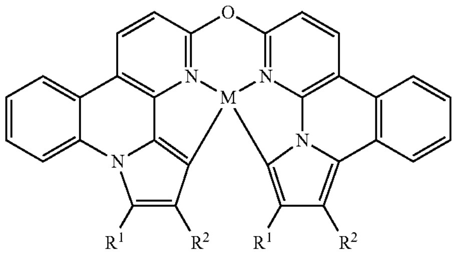
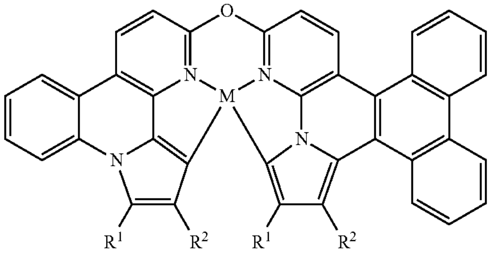
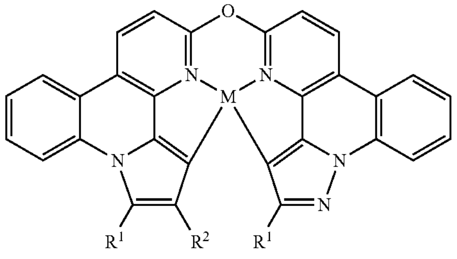
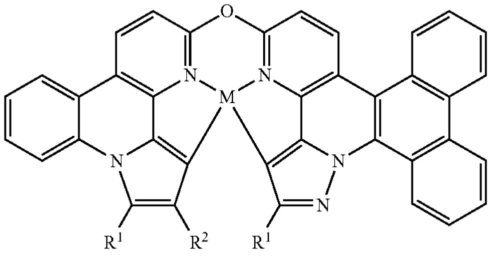

-continued
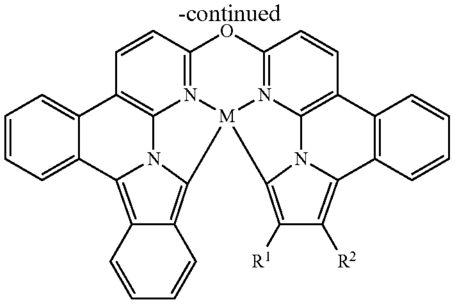
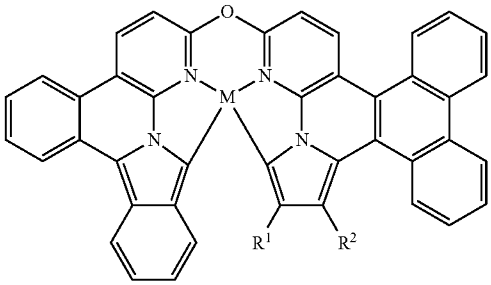
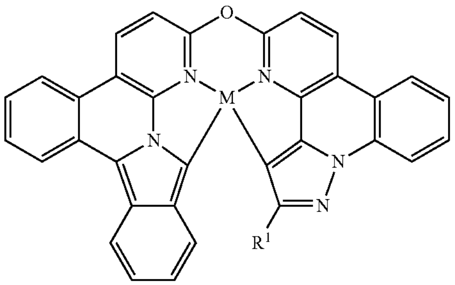
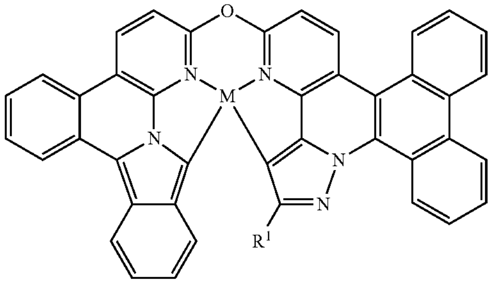
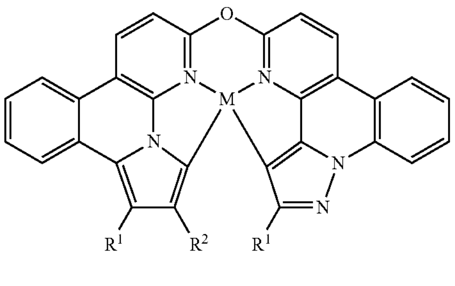
MADF emitters based on cyclic platinum (II) and palladium (II) complexes employing benzo-imidazo-phenanthridine and analogues include General Formulas V-XIII,
General Formula V
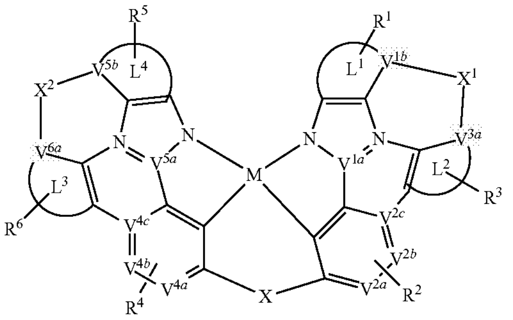
General Formula VI
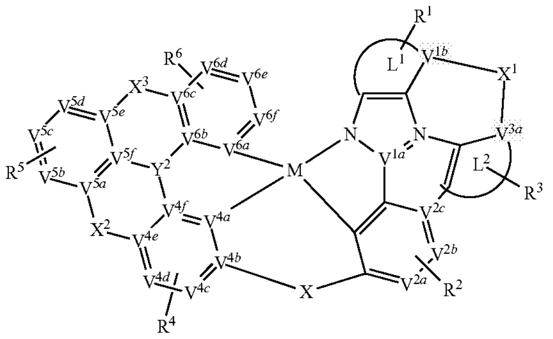
General Formula VII
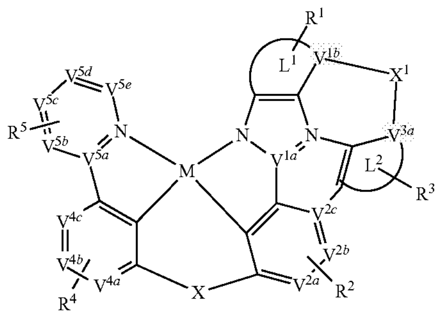
General Formula VIII
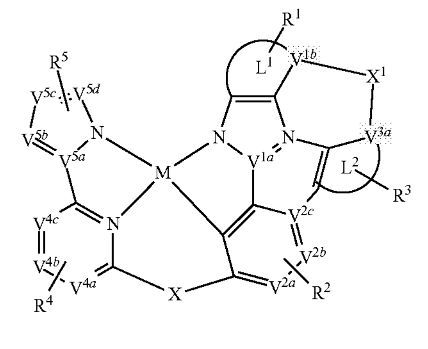

-continued

General Formula IX

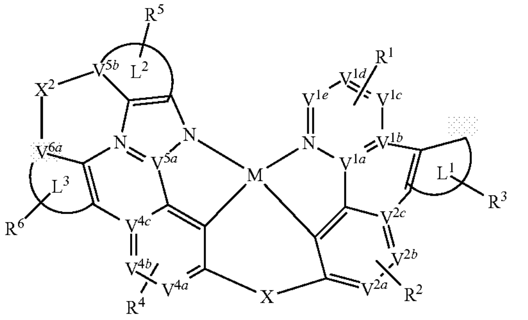

General Formula X

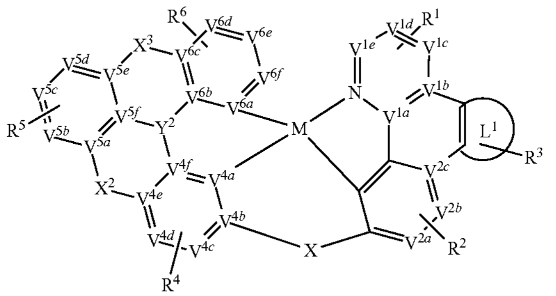

General Formula XI

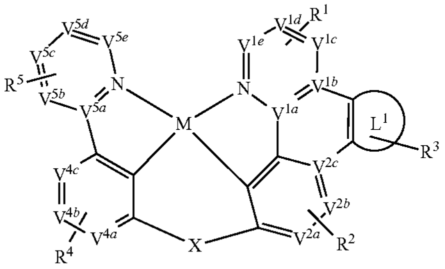

General Formula XII

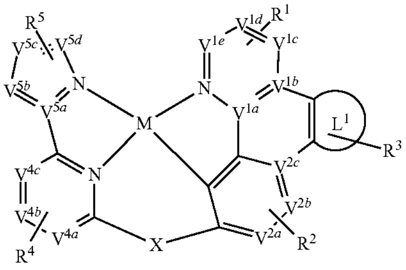

General Formula XIII

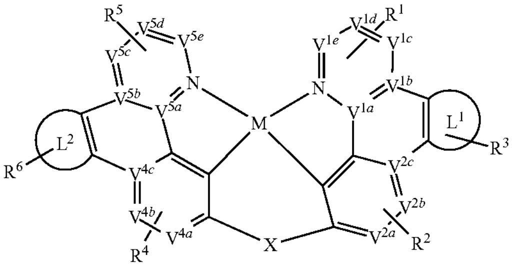

In General Formulas V-XIII:

M is Pt (II) or Pd (II),

N is nitrogen, each of $V^{1a}$-$V^{1f}$, $V^{2a}$-$V^{2f}$, $V^{3a}$-$V^{3f}$, $V^{4a}$-$V^{4f}$, $V^{5a}$-$V^{5f}$, and $V^{6a}$-$V^{6f}$, if present, is independently N, C, P, O, S, or Si, each of X, $X^1$, $X^2$, $X^3$, and $X^4$ is independently present or absent, and each X, $X^1$, $X^2$, $X^3$, and $X^4$ present independently represents a single bond. $CR^7R^8$, C═O, $SiR^7R^8$, $GeR^7R^8$, $NR^7$, $PR^7$, $PR^7R^8$, $R^7R$═O, $AsR^7$, $R^7As$═O, O, S, S═O, $SO_2$, Se, Se═O, $SeO_2$, $BR^7$, $BR^7R^8$, $AlR^7$, $AlR^7R^8$, $R^7Bi$═O, or $BiR^7$, each of $Y^1$ and $Y^2$ is independently CR, SiR, GeR, N, NR, P, P═O, As, As═O, B, BR, Al, AlR, Bi═O, or Bi, each of $L^1$, $L^2$, $L^3$, and $L^4$ is independently present or absent, and each $L^1$, $L^2$, $L^3$, and $L^4$ present independently represents a substituted or unsubstituted aryl, heteroaryl, or N-heterocyclic carbene, each of R, $R^1$, $R^2$, $R^3$, $R^4$, $R^5$, $R^6$, $R^7$, and $R^8$ is independently absent or present as a single substituent or multiple substituents, valency permitting, and each R, $R^1$, $R^2$, $R^3$, $R^4$, $R^5$, $R^6$, $R^7$, and $R^8$ present independently represents deuterium, halogen, hydroxyl, thiol, nitro, cyanide, isocyanide, sulfinyl, mercapto, sulfa, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

Compounds of General Formulas V-XIII include the following.

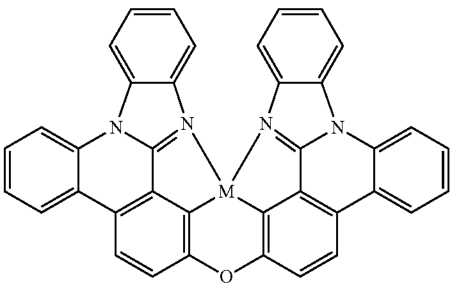

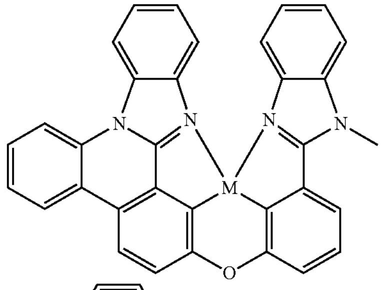

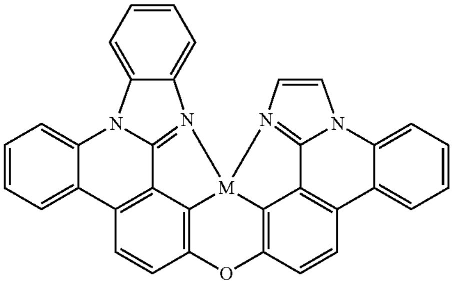

-continued
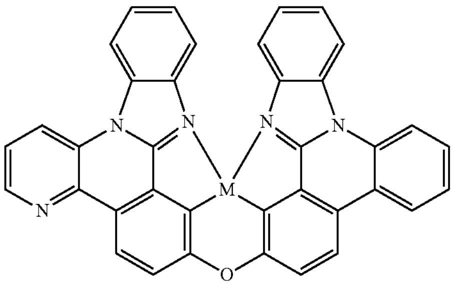
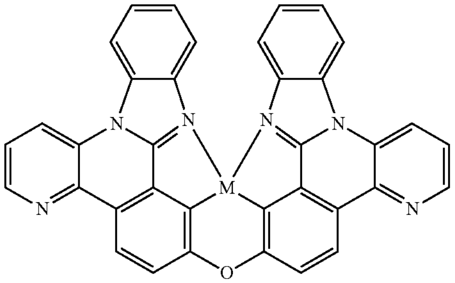
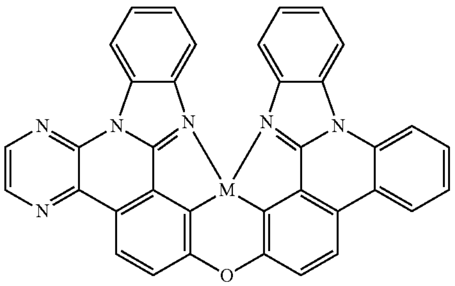
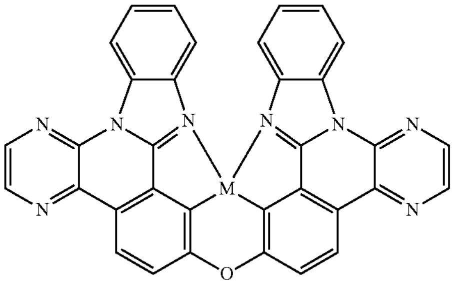
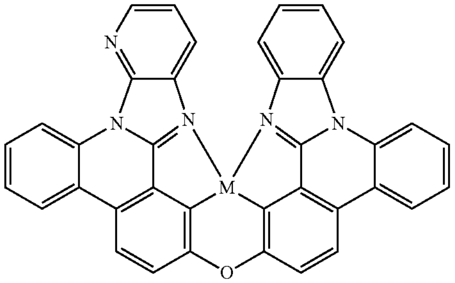
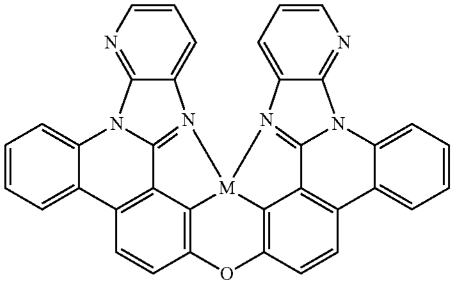
-continued
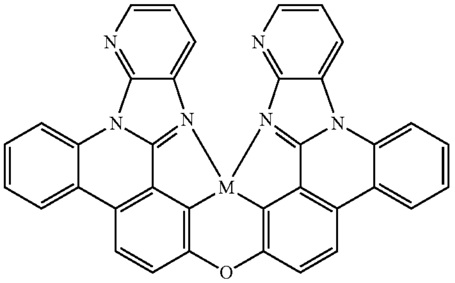
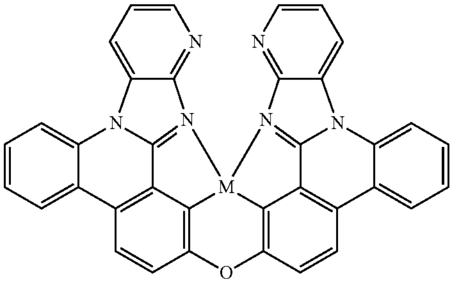
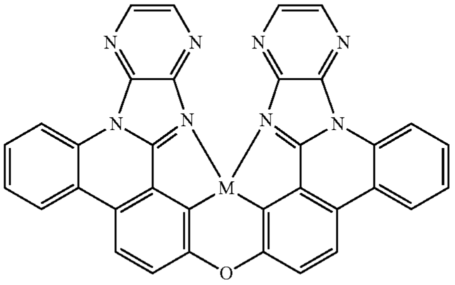
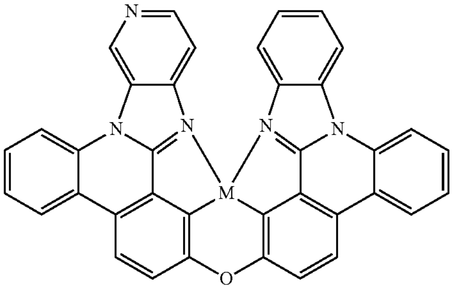
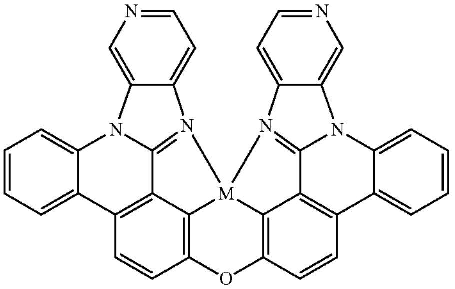
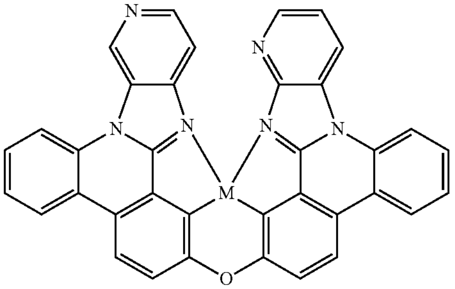

-continued
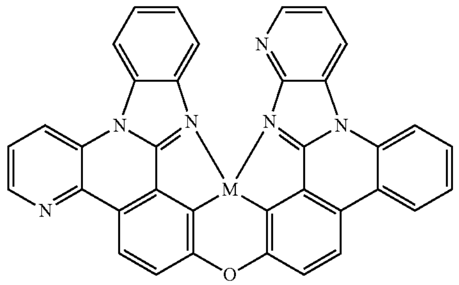
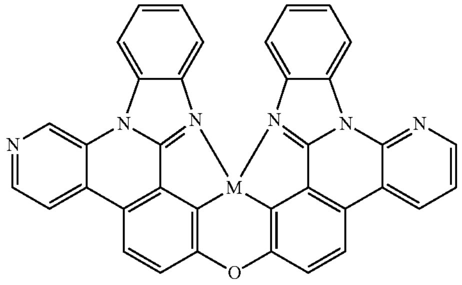
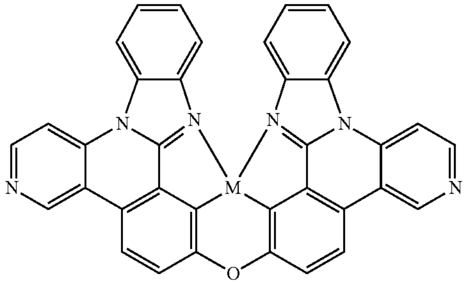
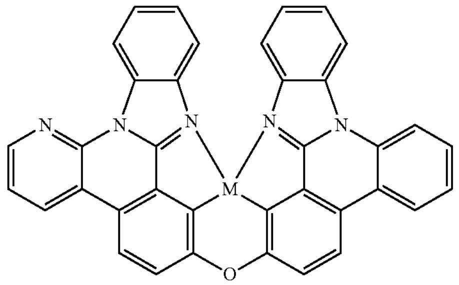
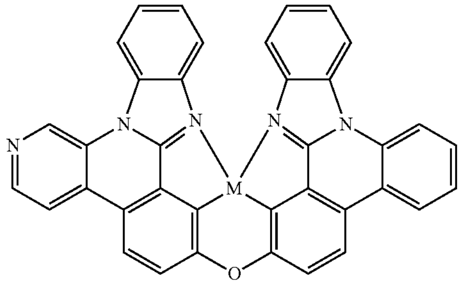
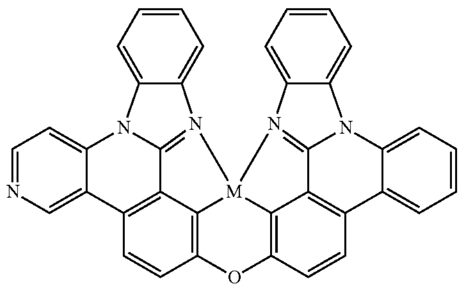
-continued
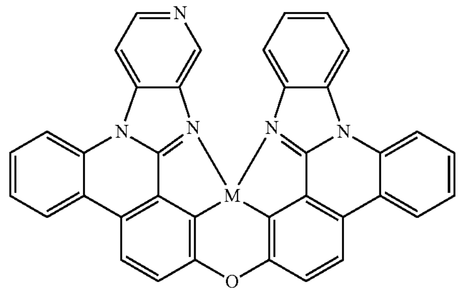
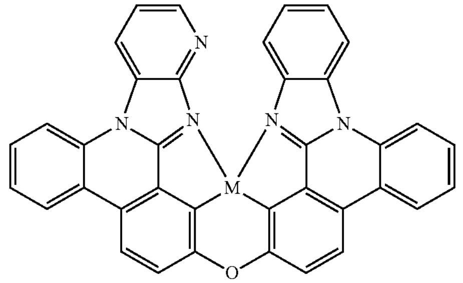
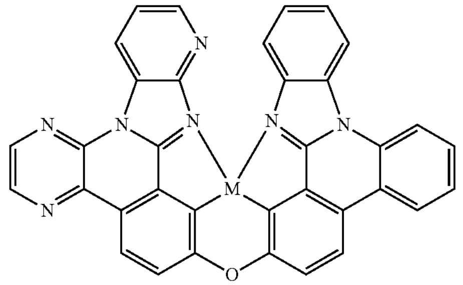
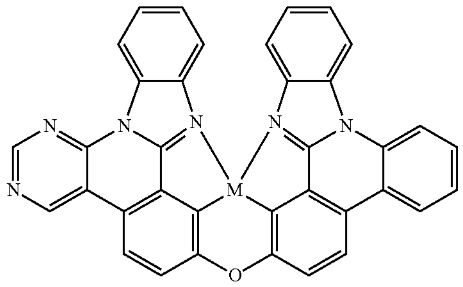
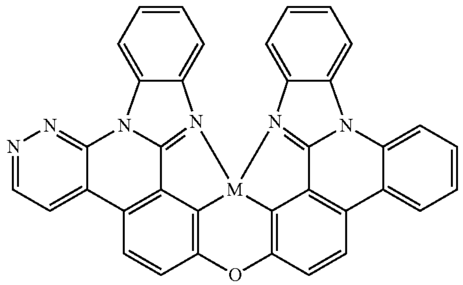
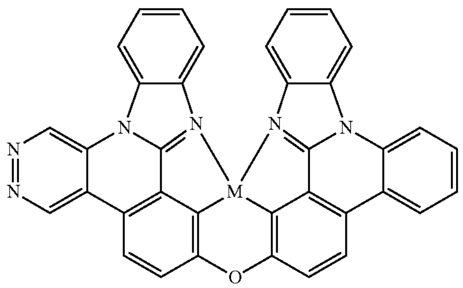

-continued
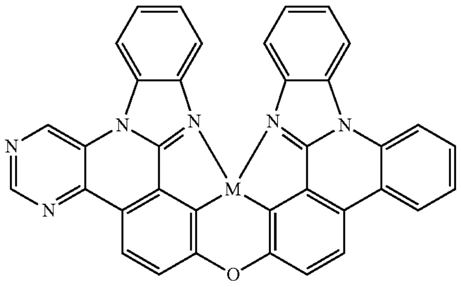
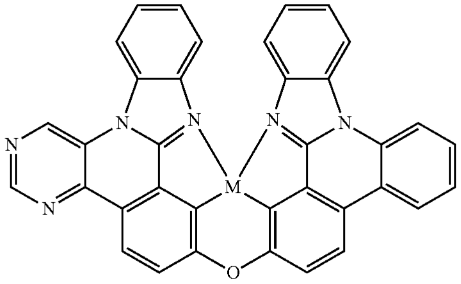
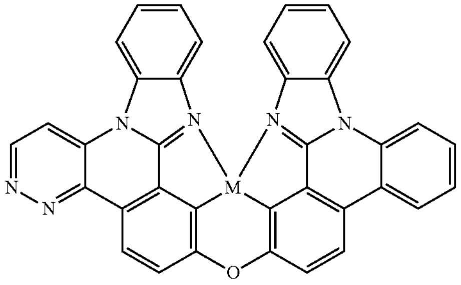
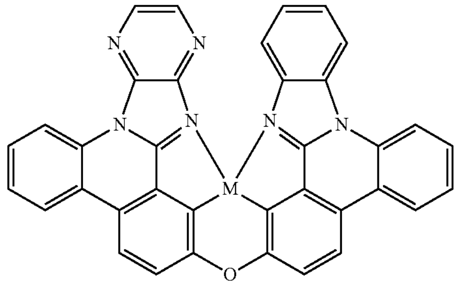
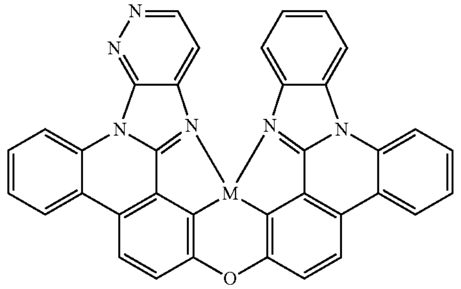
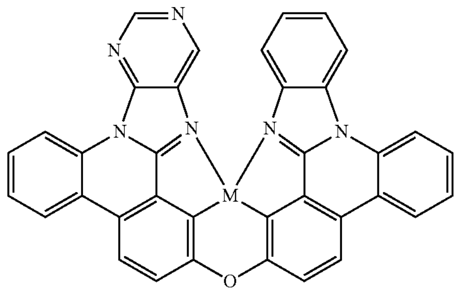
-continued
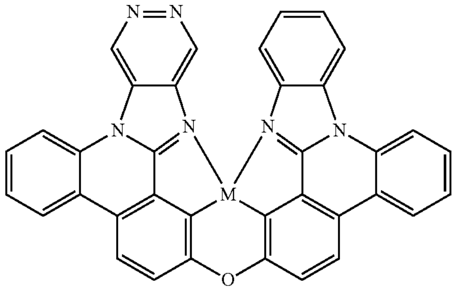
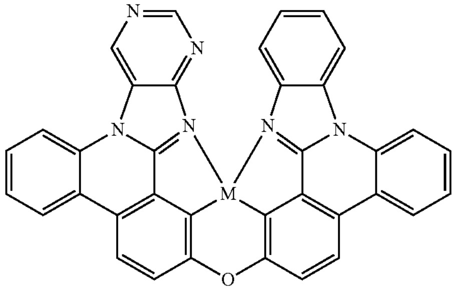
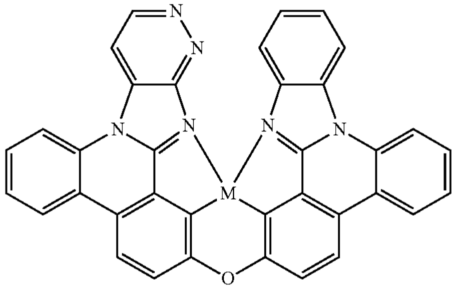
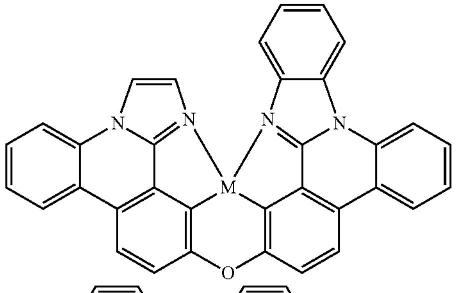
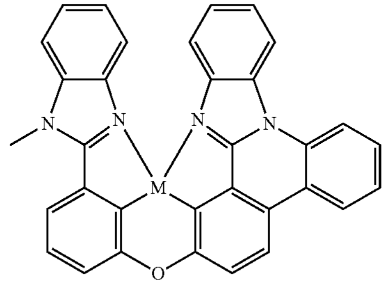
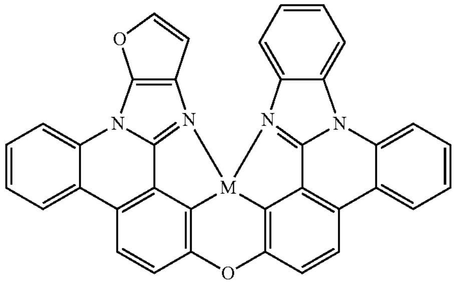

-continued
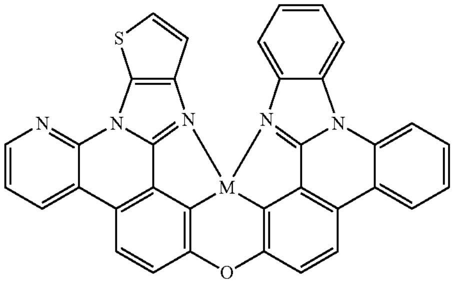
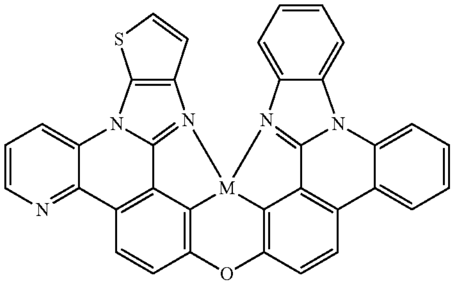
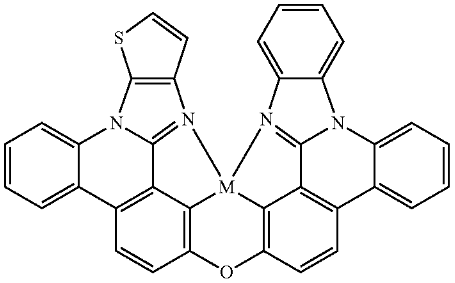
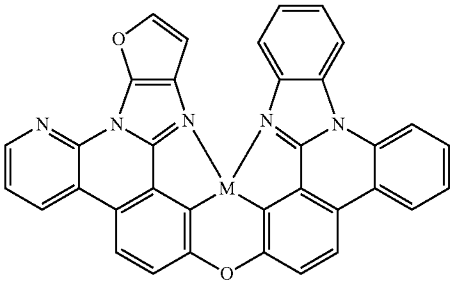
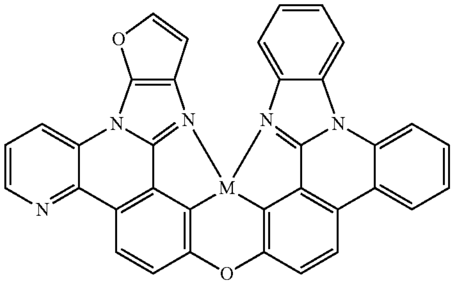
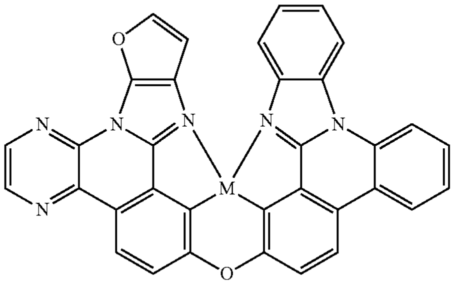
-continued
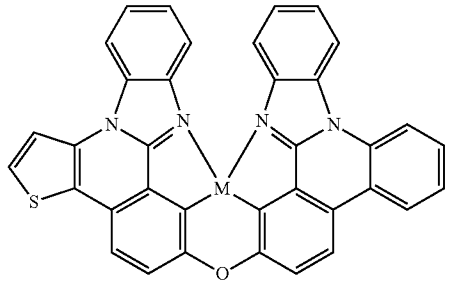
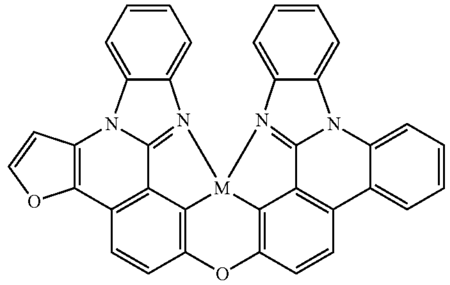
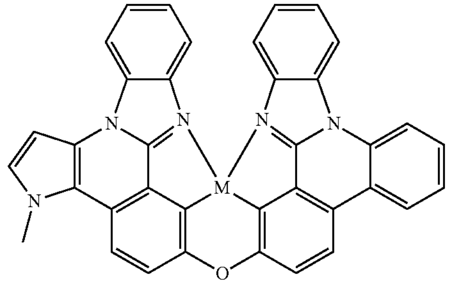
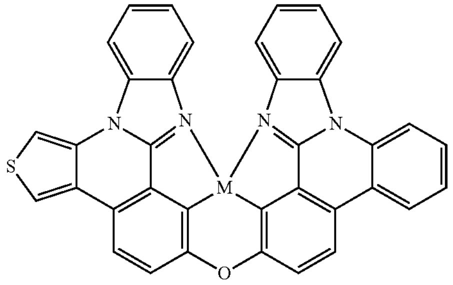
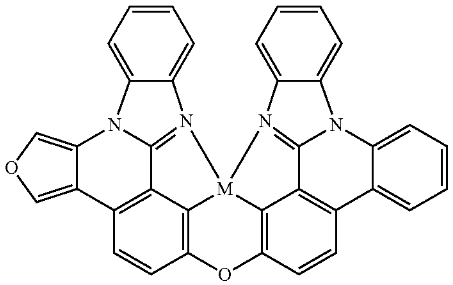
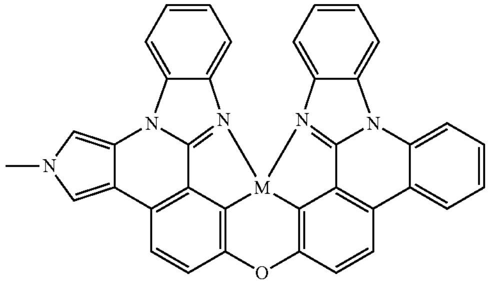

-continued
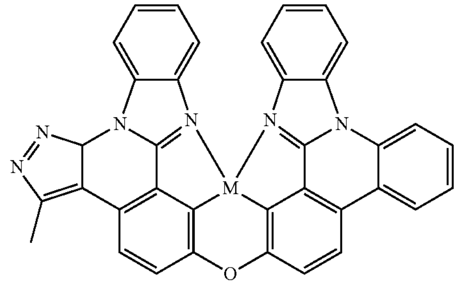
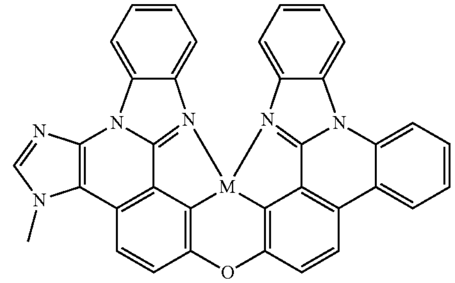
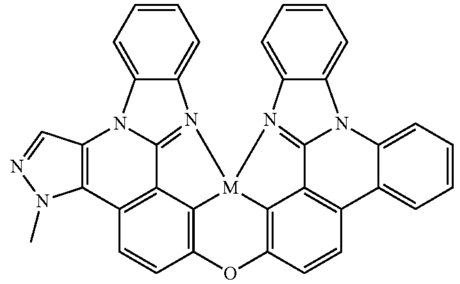
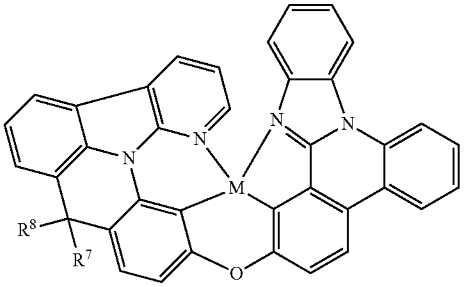
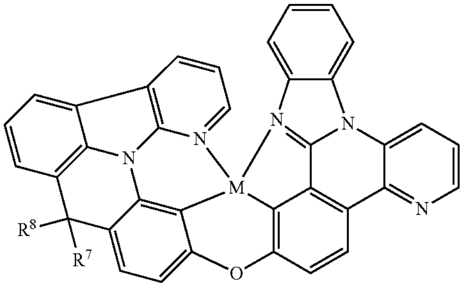
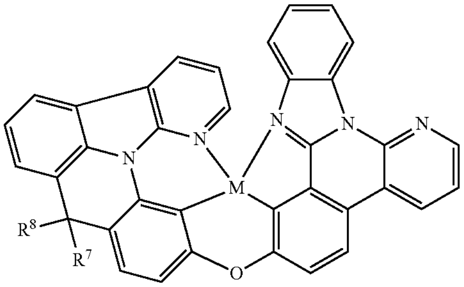
-continued
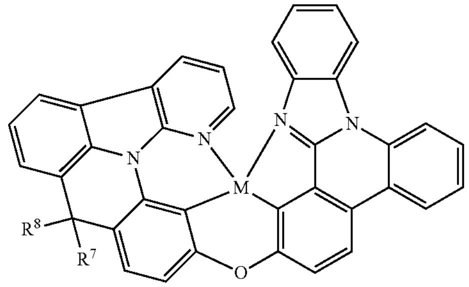
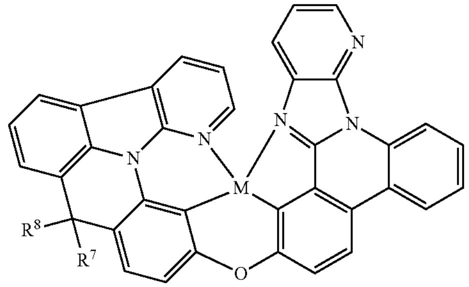
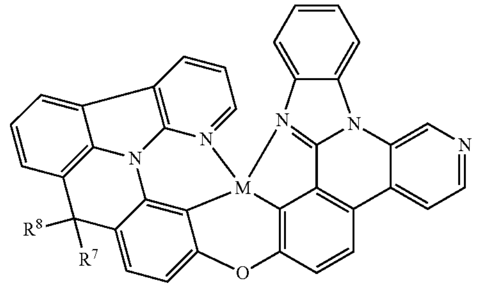
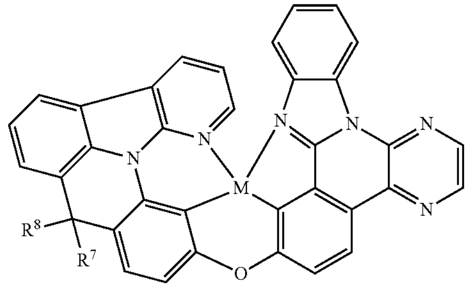
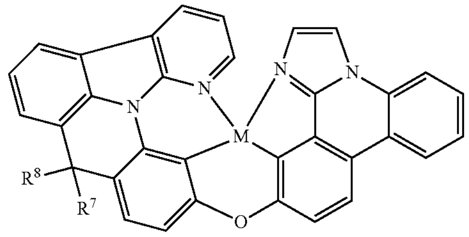
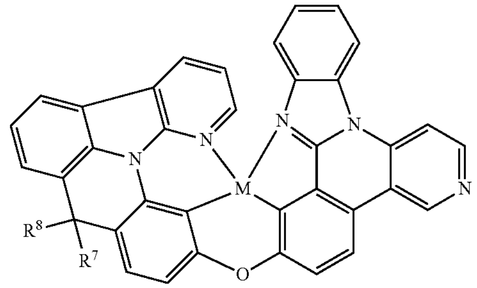

-continued
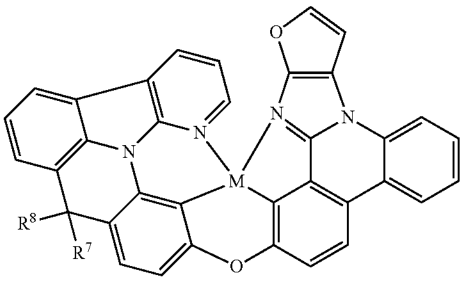
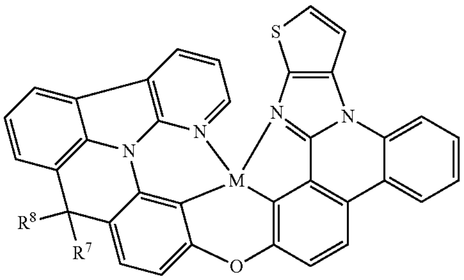
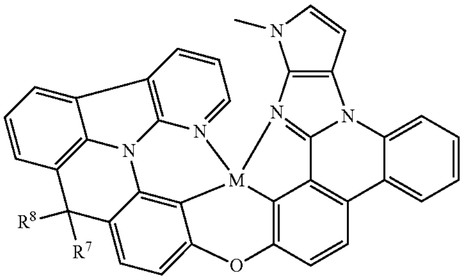
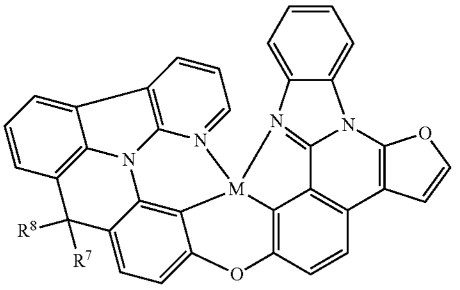
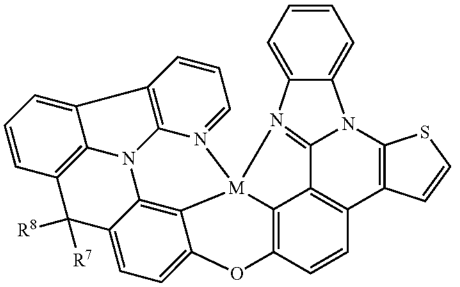
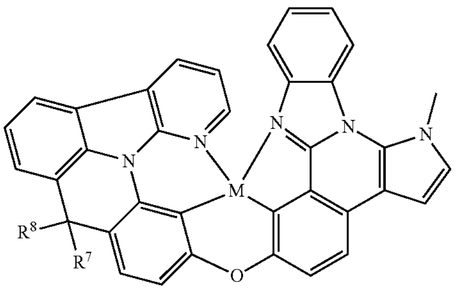
-continued
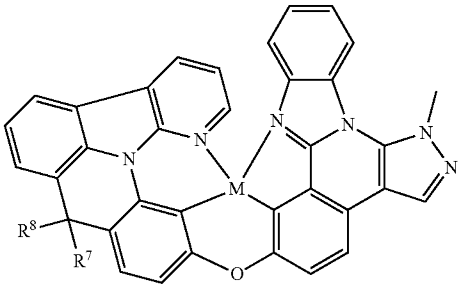
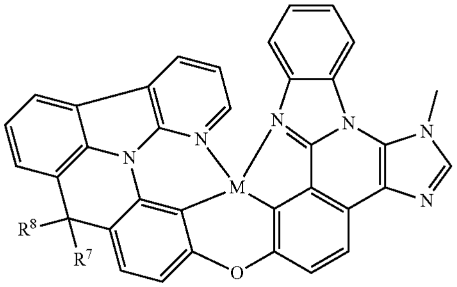
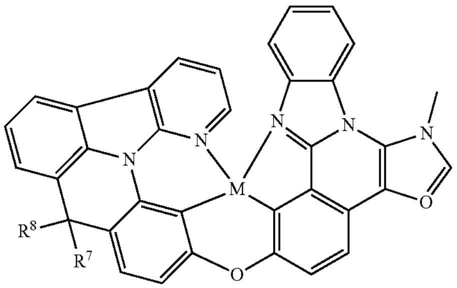
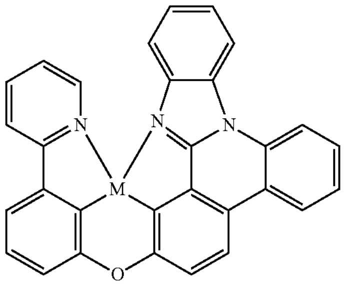
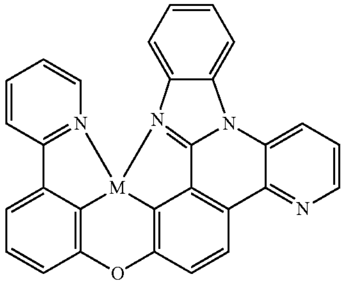
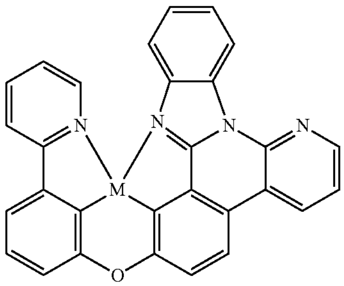

-continued
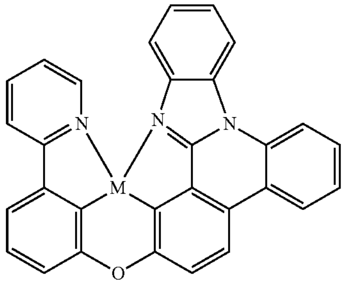
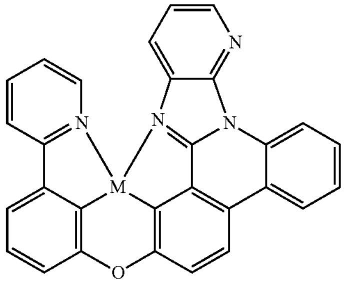
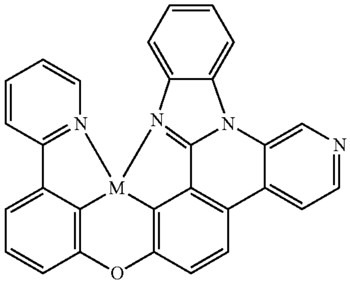
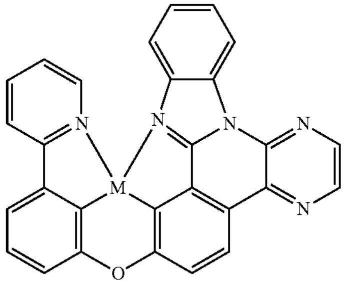
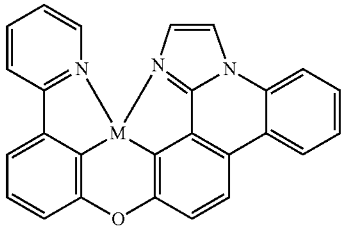
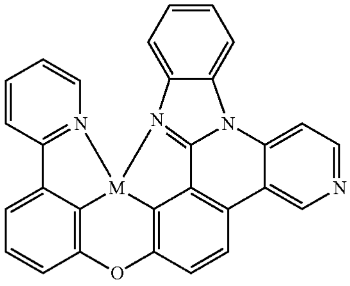
-continued
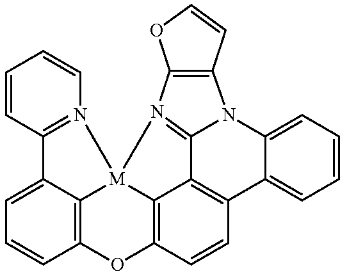
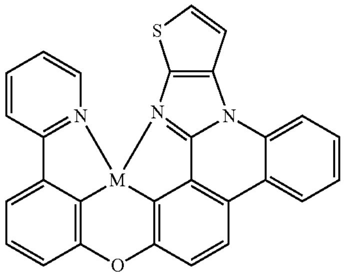
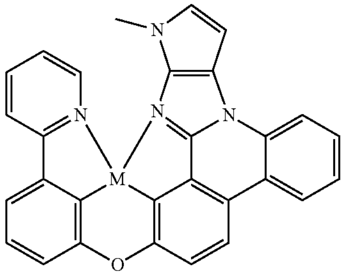
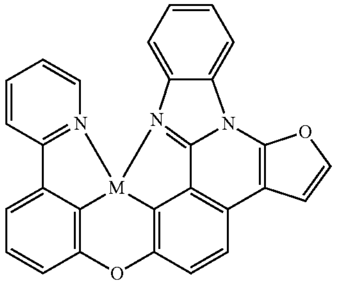
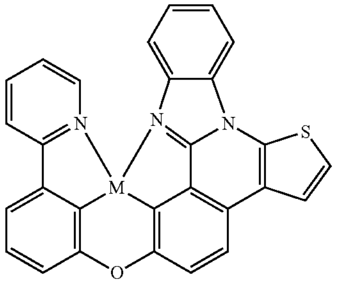
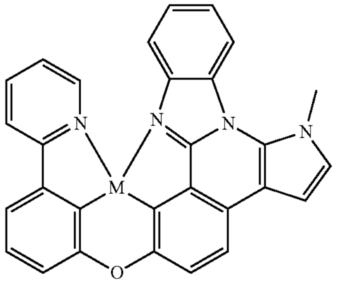

-continued
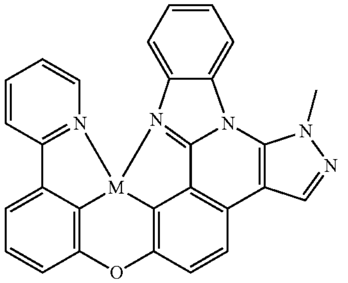
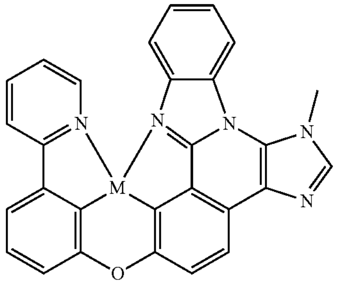
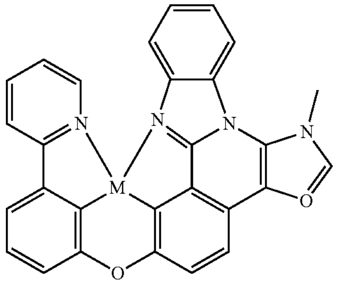
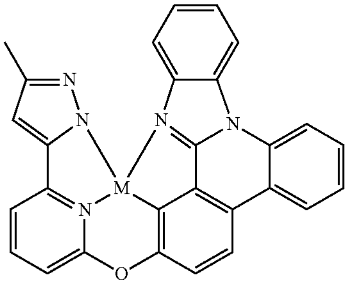
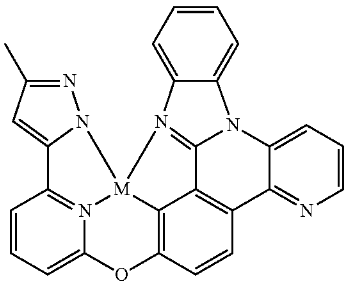
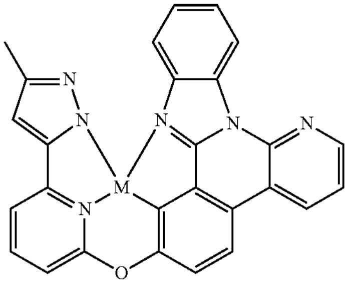
-continued
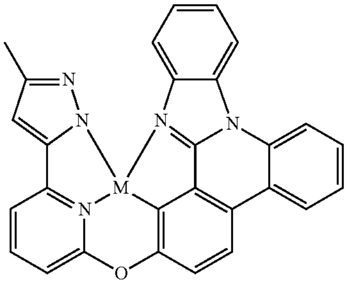
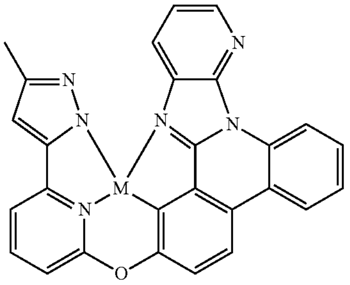
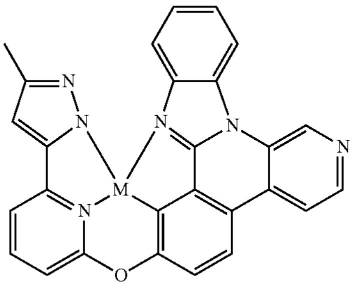
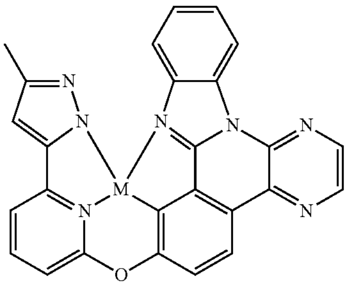
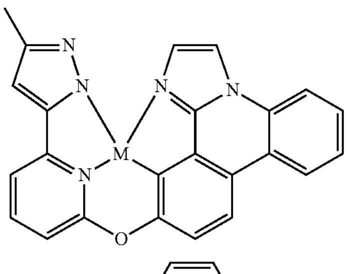
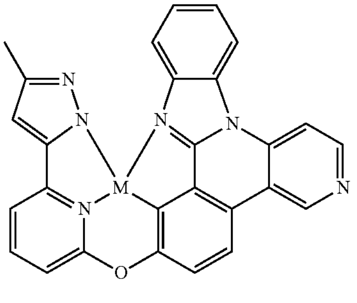

-continued
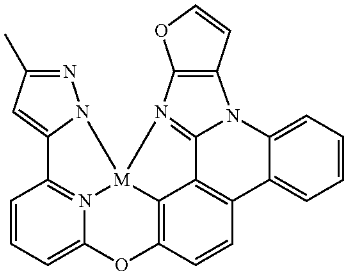
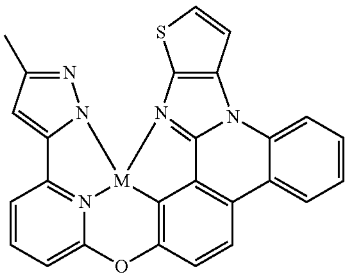
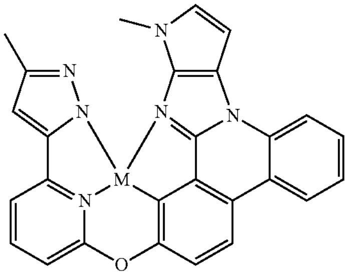
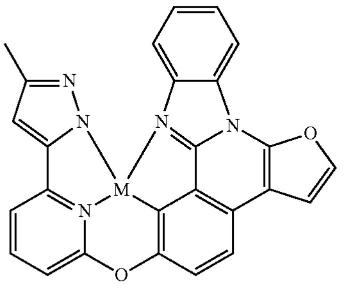
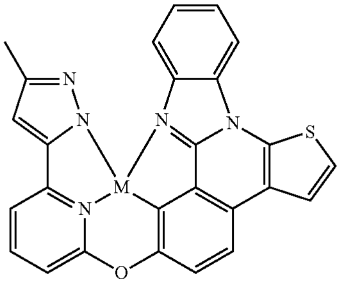
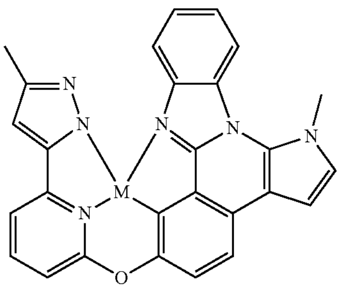
-continued
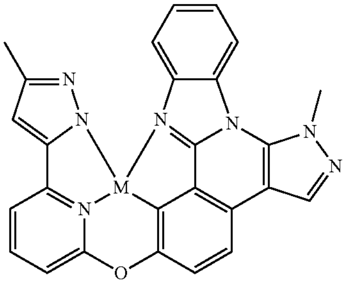
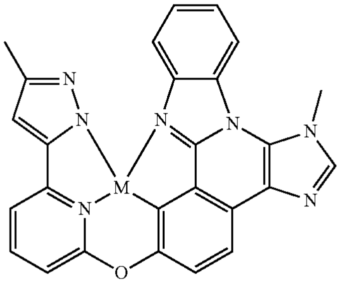
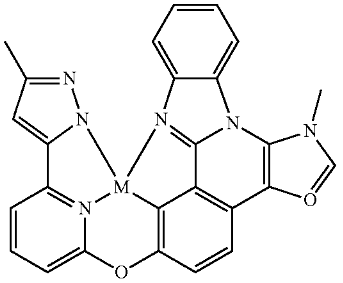
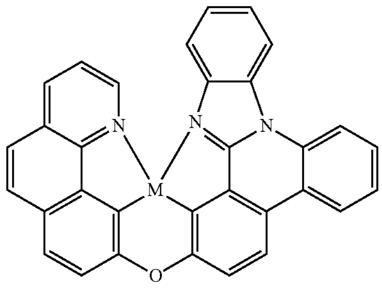
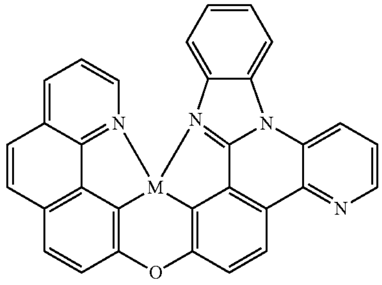
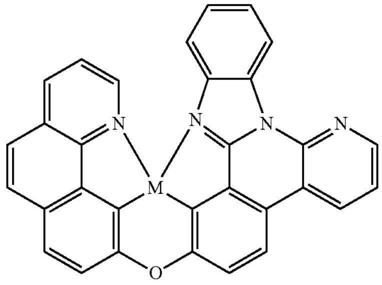

-continued
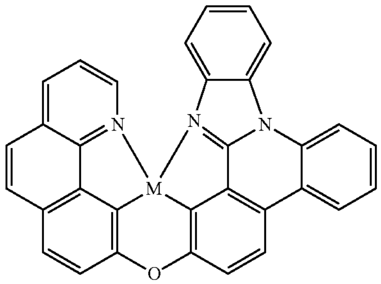
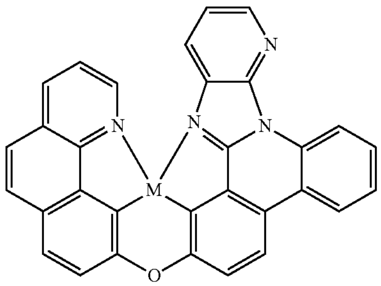
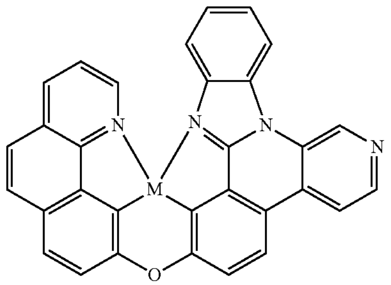
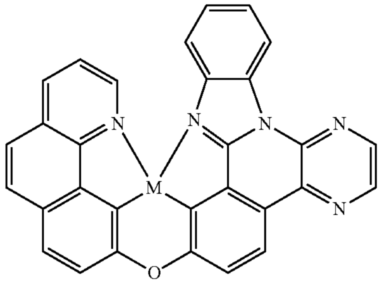
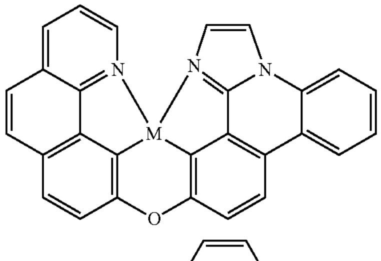
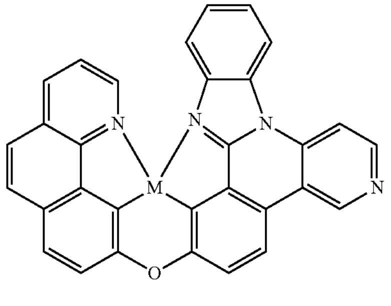
-continued
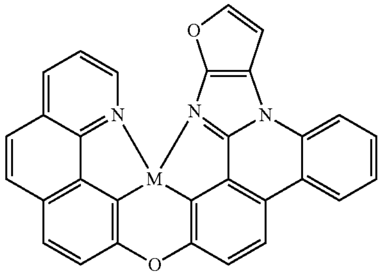
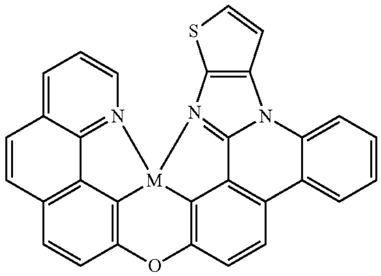
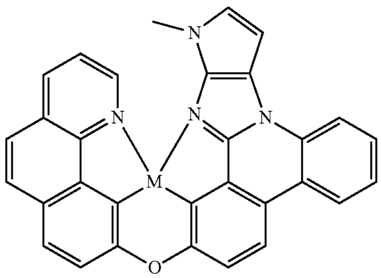
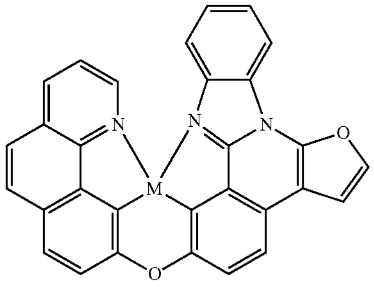
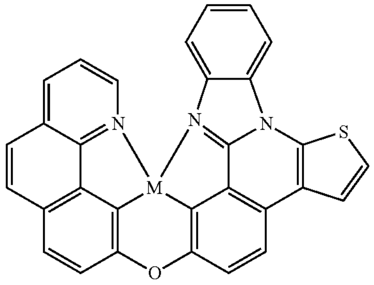
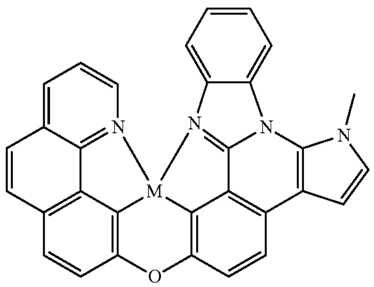

-continued
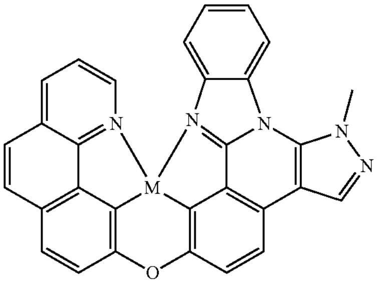
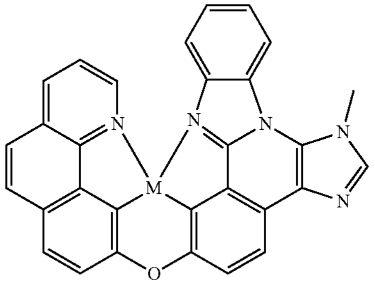
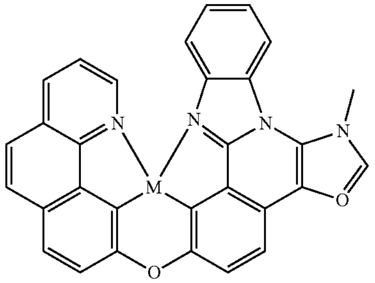
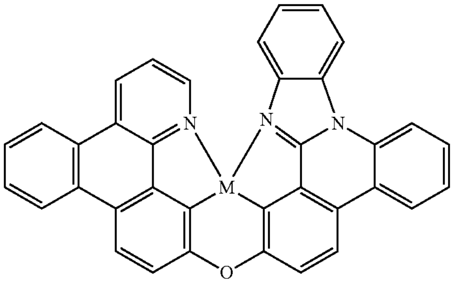
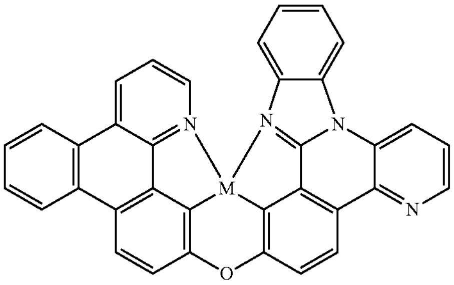
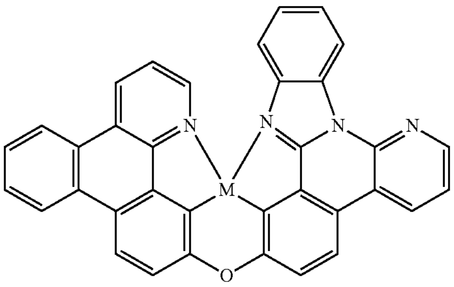
-continued
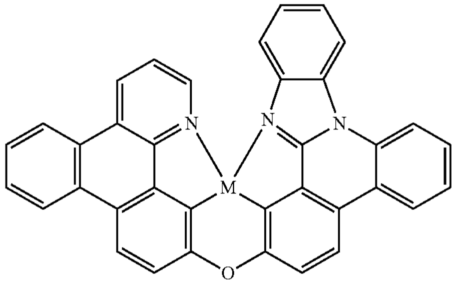
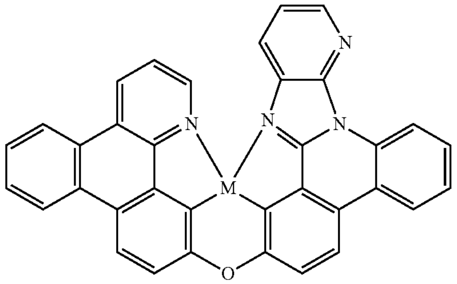
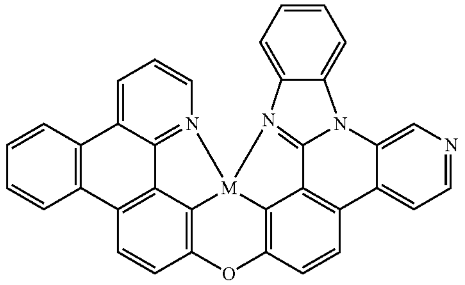
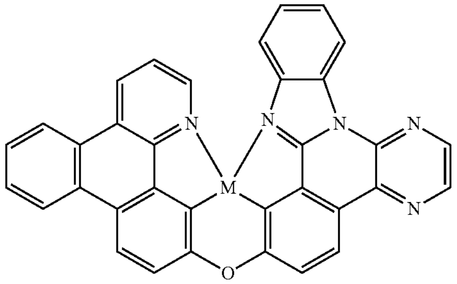
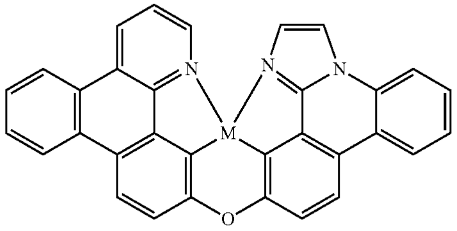
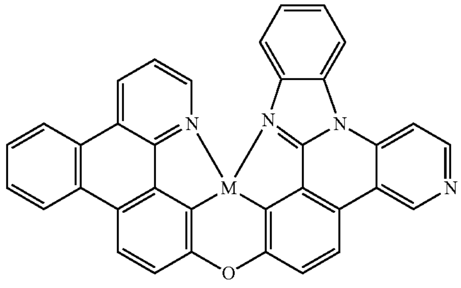

-continued
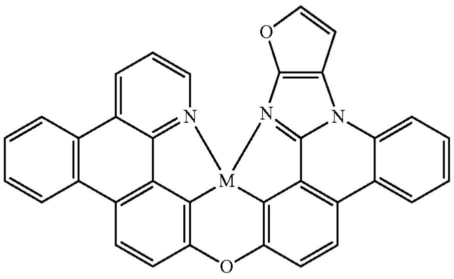
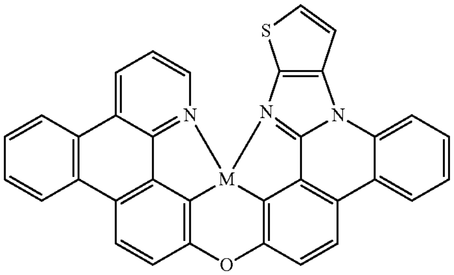
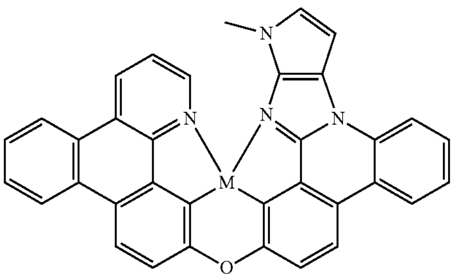
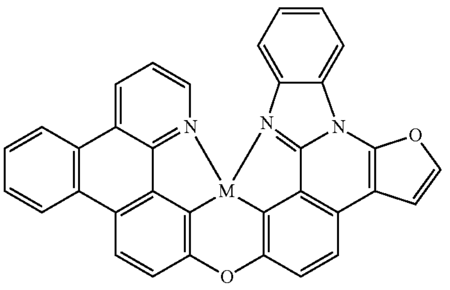
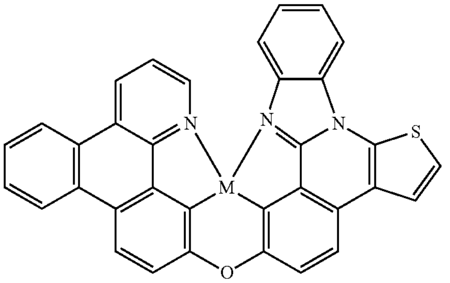
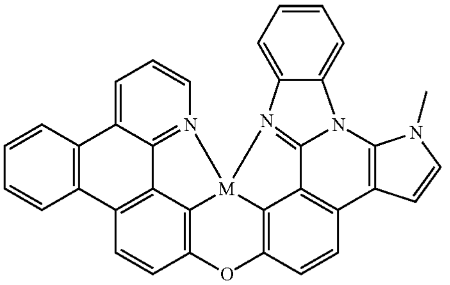
-continued
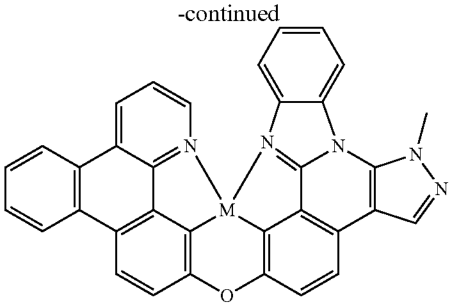
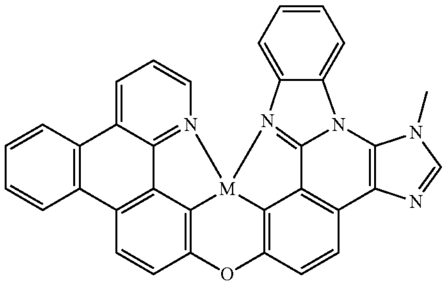
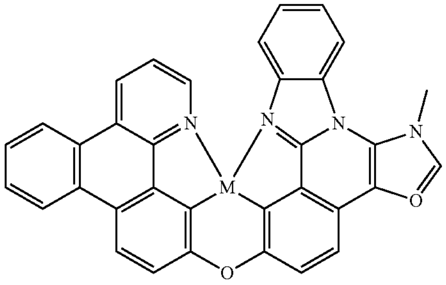
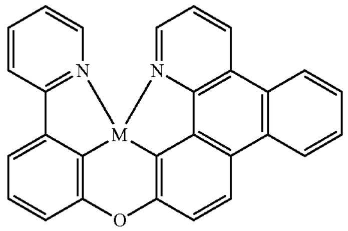
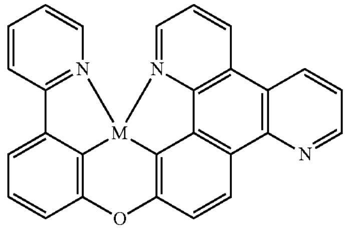
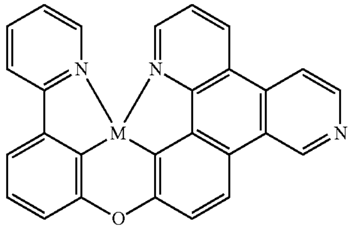

-continued
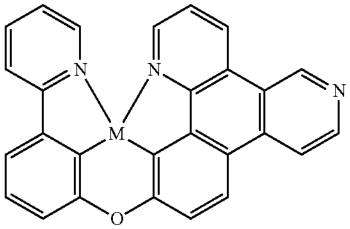
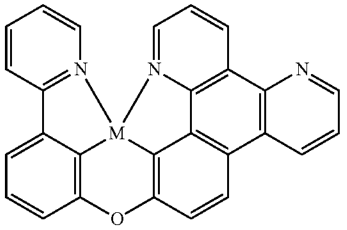
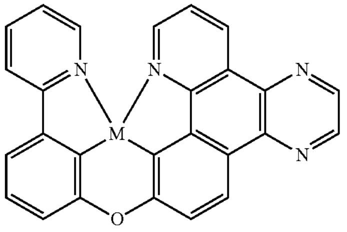
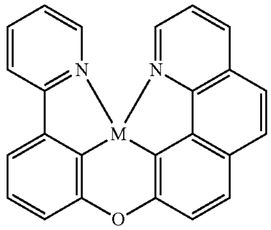
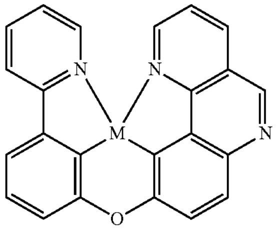
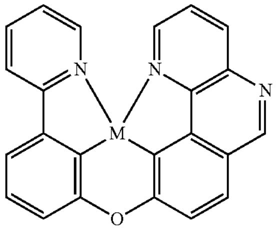
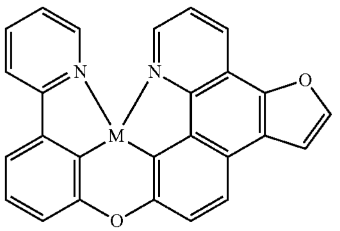
-continued
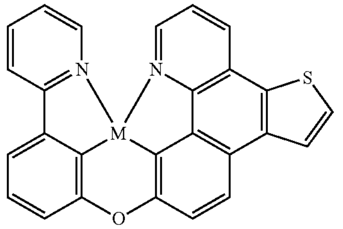
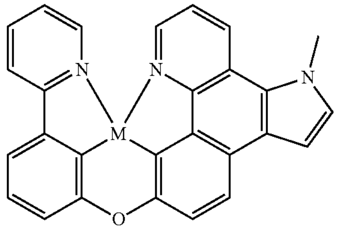
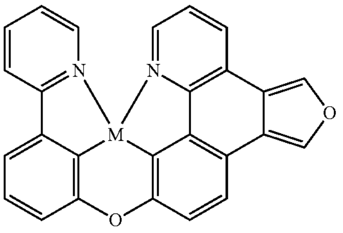
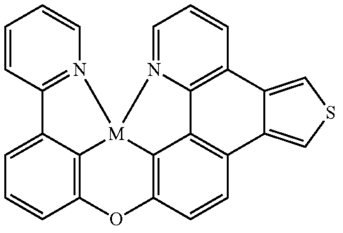
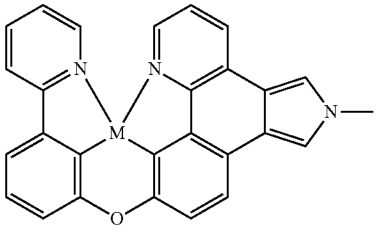
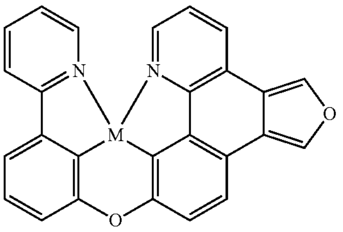
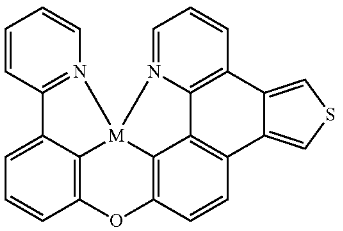

-continued
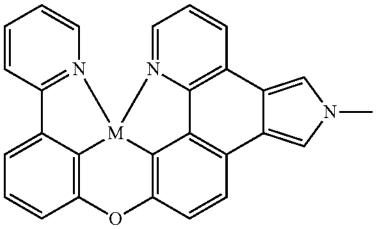
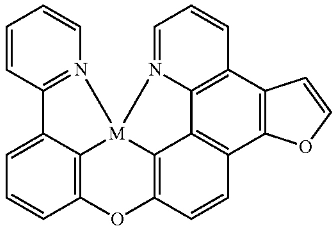
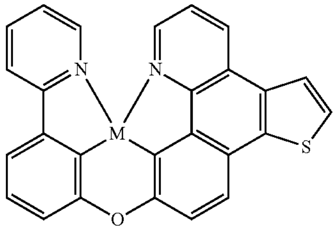
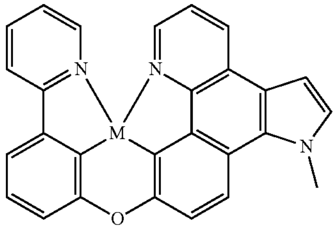
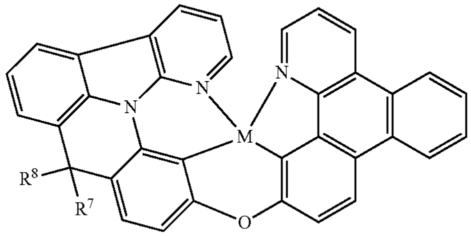
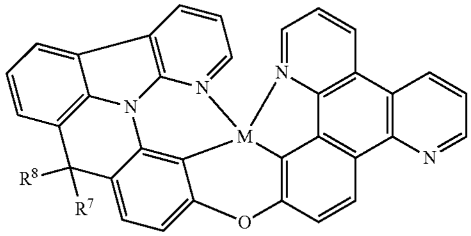
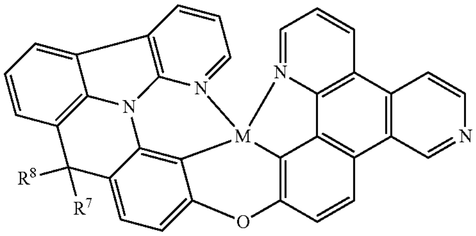
-continued
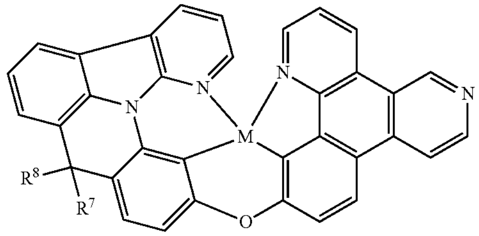
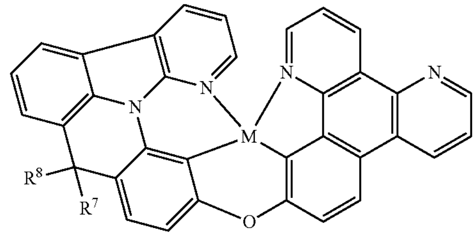
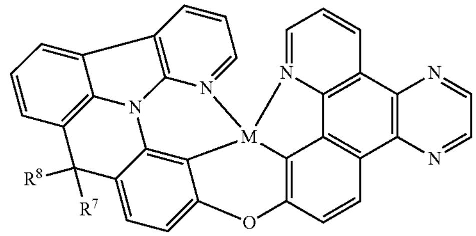
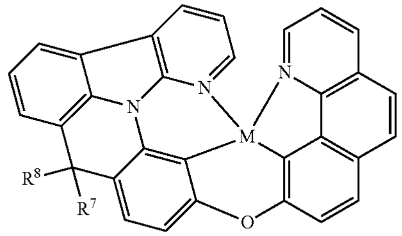
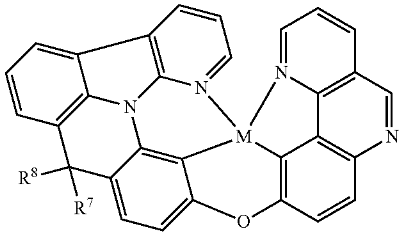
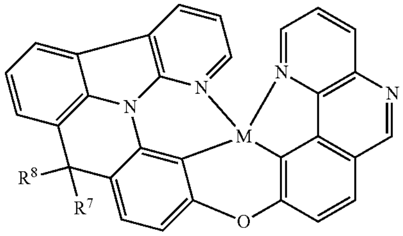
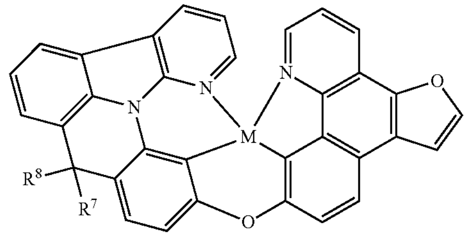

-continued
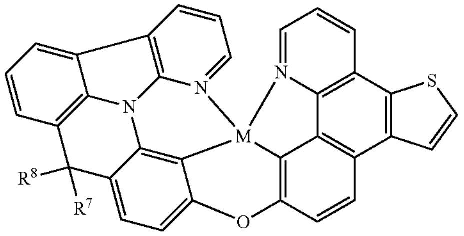
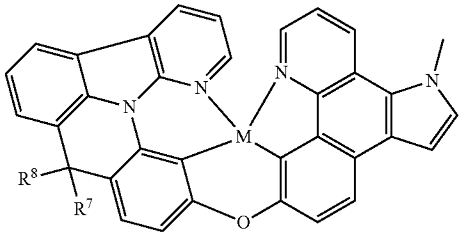
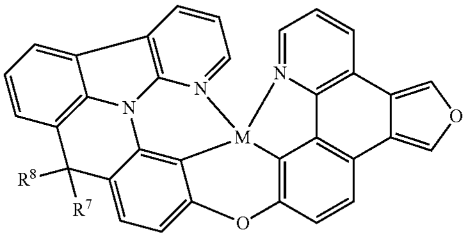
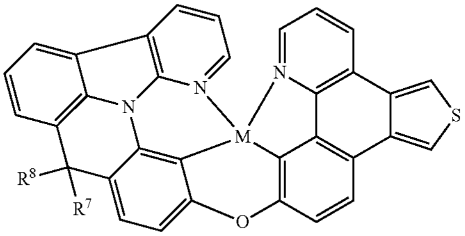
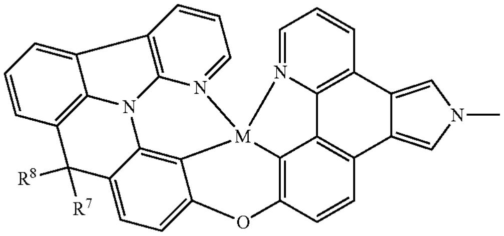
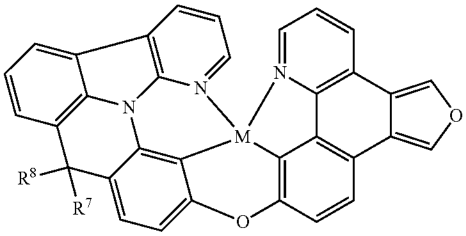
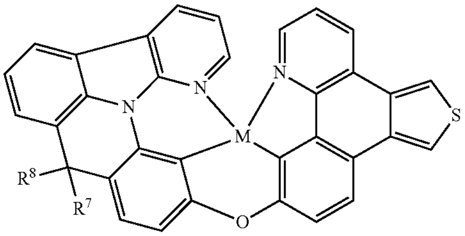
-continued
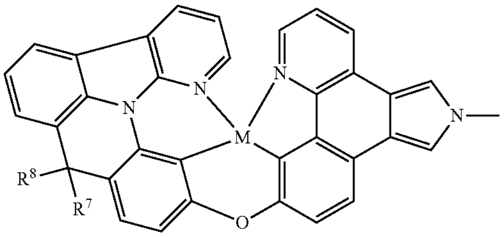
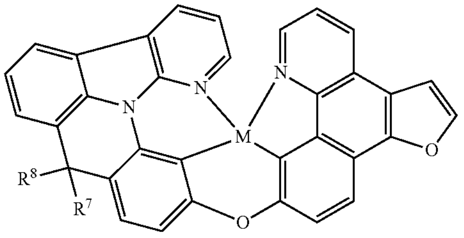
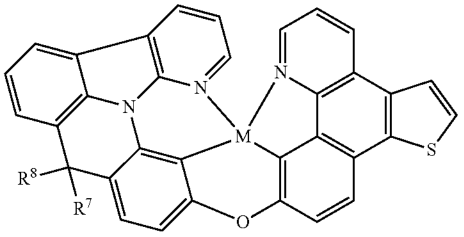
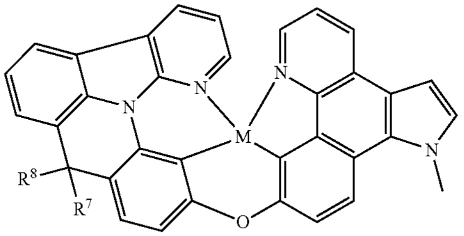
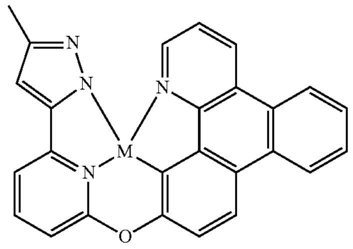
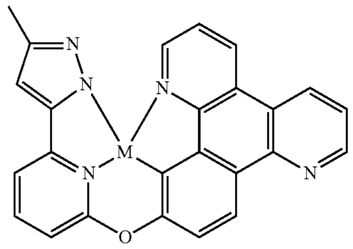
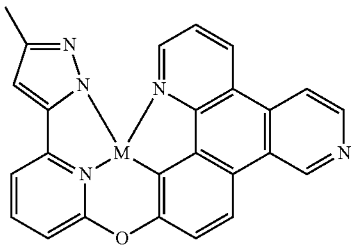

-continued
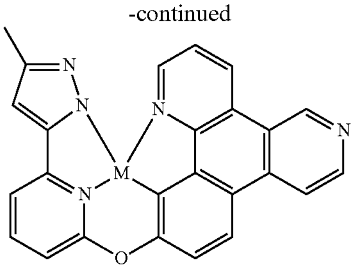
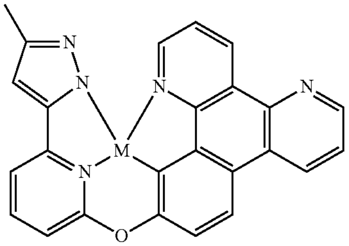
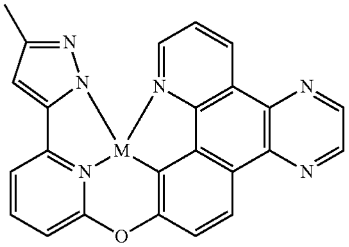
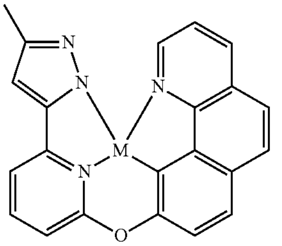
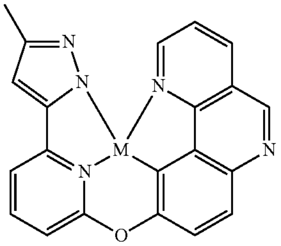
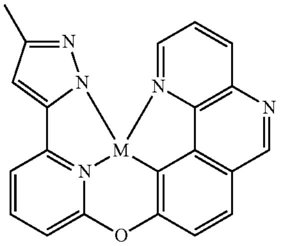
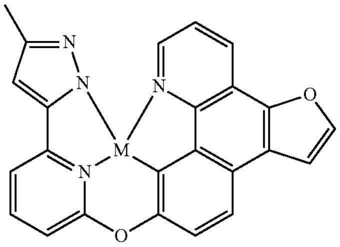
-continued
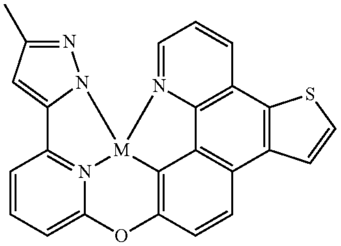
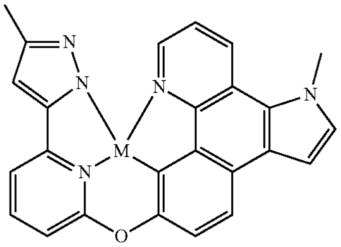
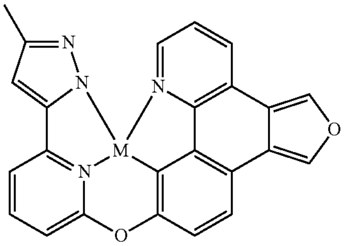
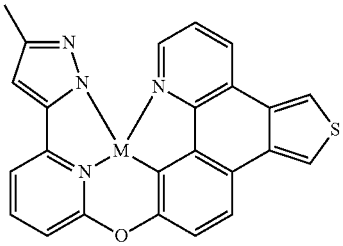
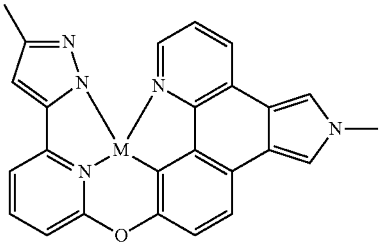
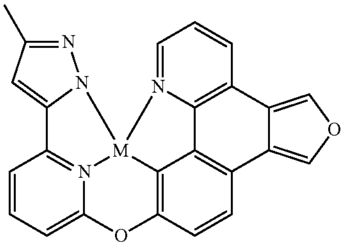
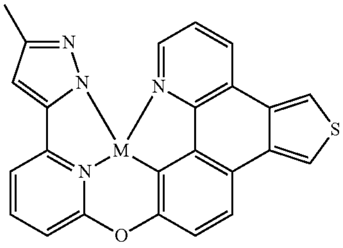

-continued
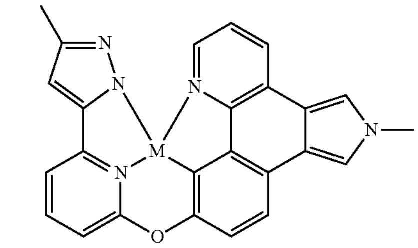
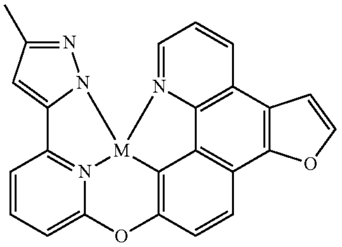
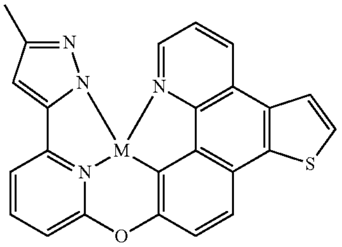
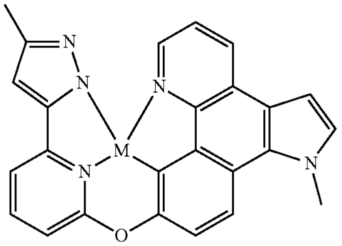
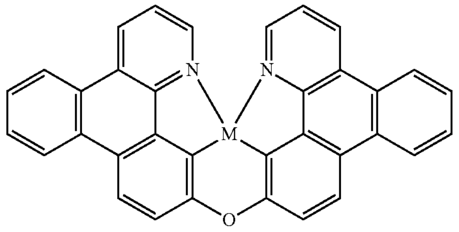
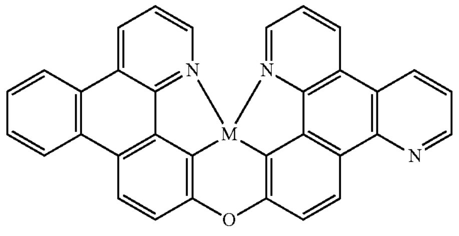
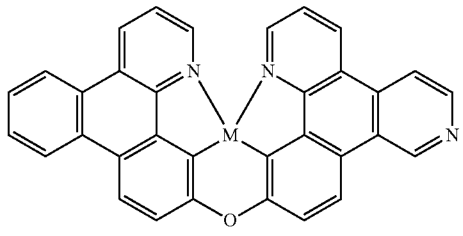
-continued
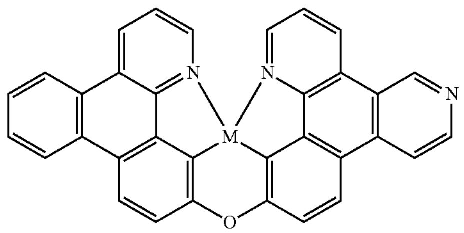
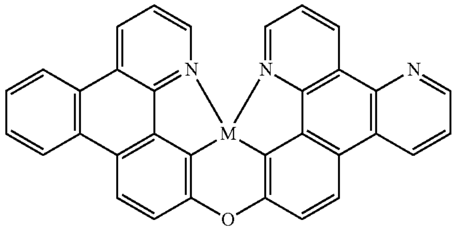
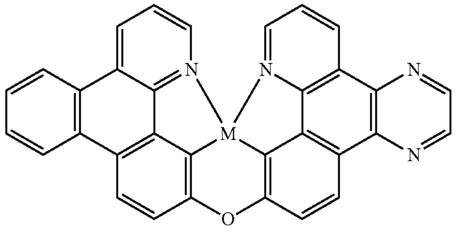
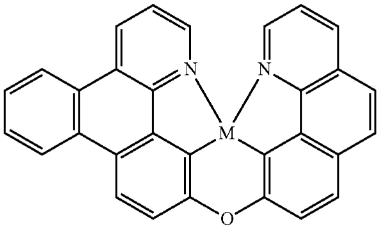
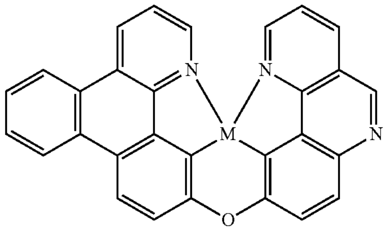
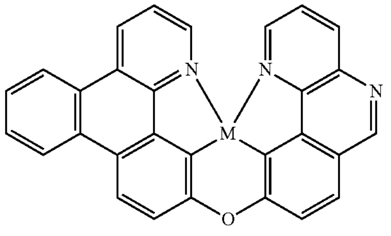
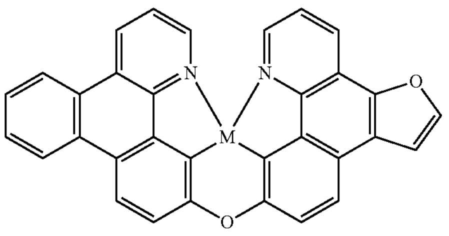

-continued
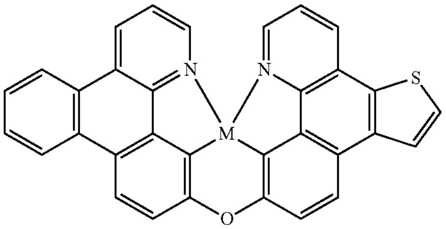
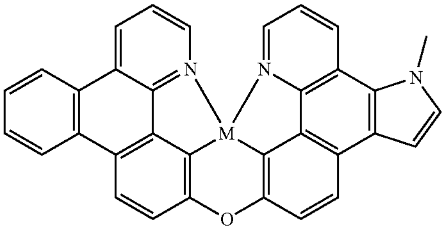
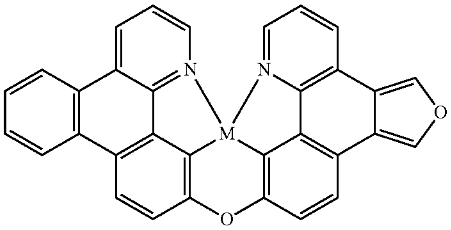
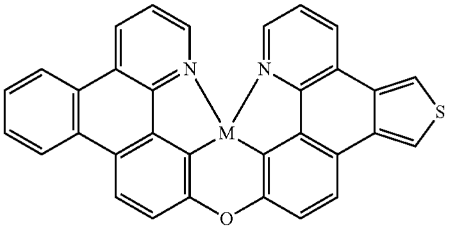
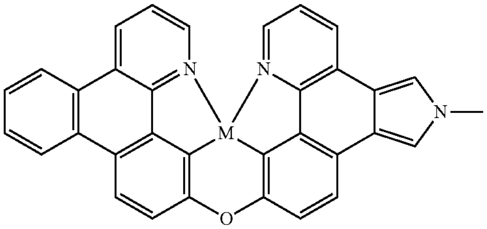
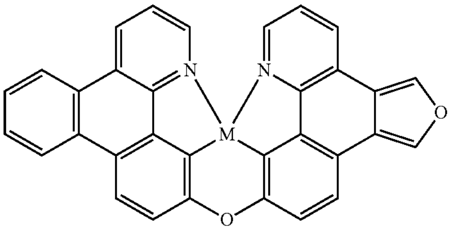
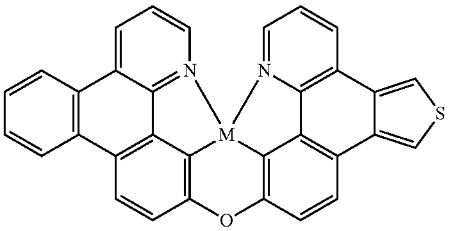
-continued
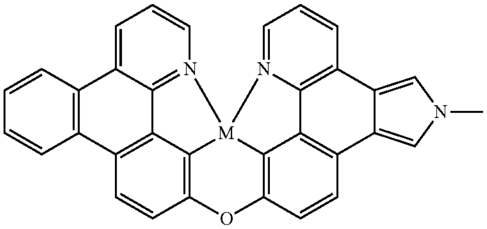
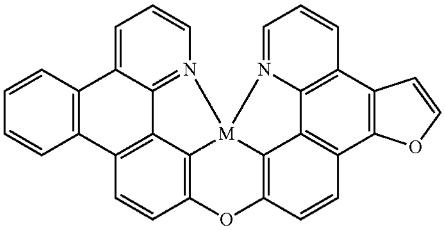
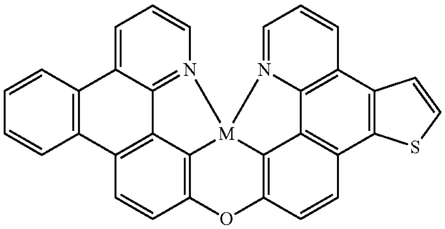
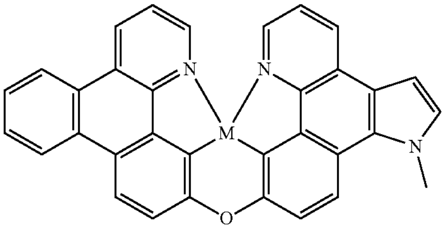
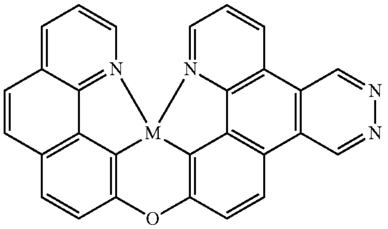
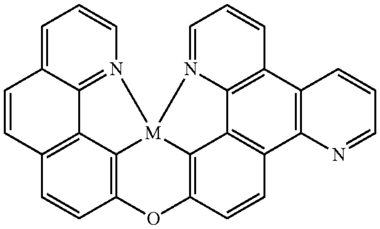
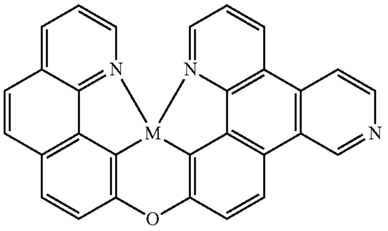

-continued
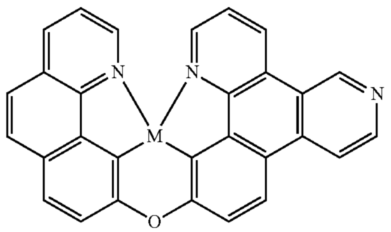
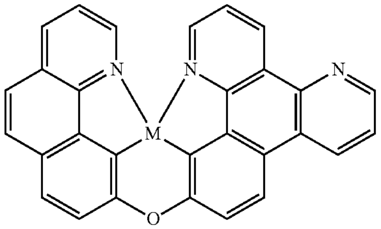
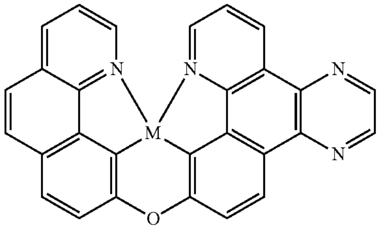
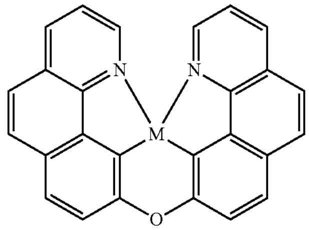
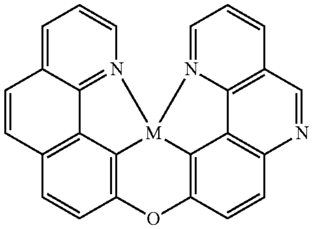
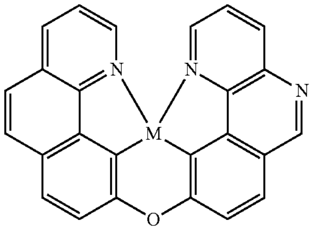
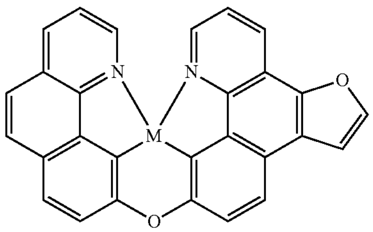
-continued
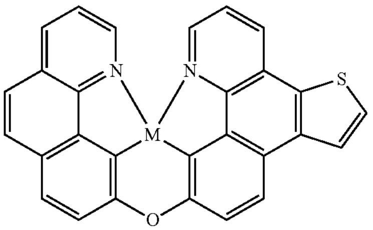
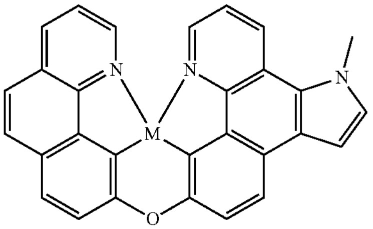
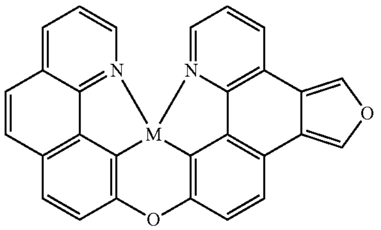
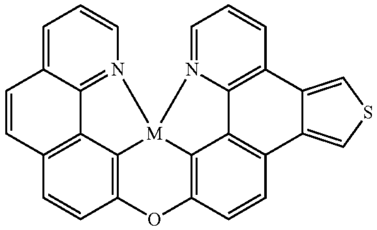
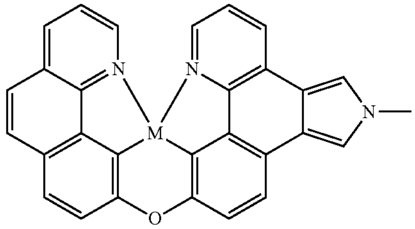
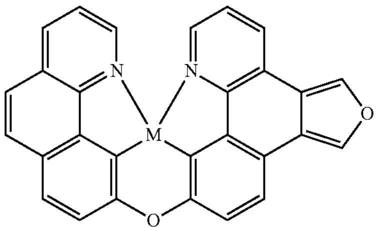
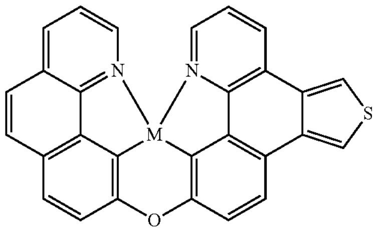

-continued

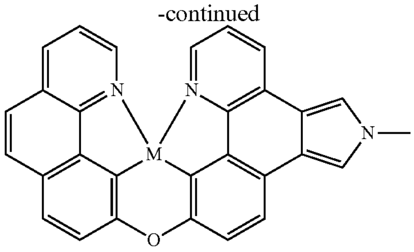

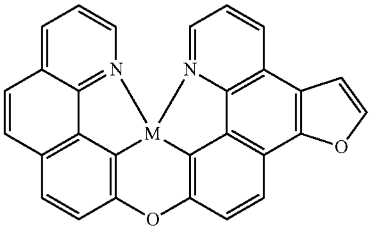

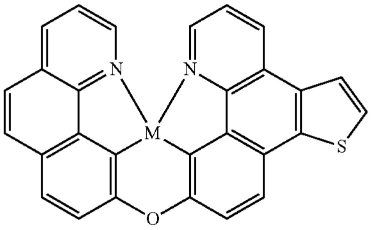

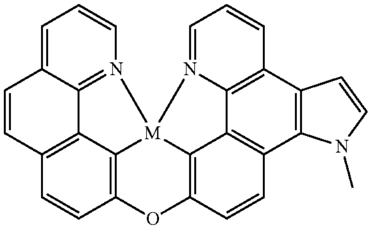

The substituents in these compounds are as defined herein.

Octahedral iridium (III) metal-assisted delayed fluorescent (MADF) emitters employing benzo-imidazo-phenanthridine are represented by General Formulas XIV-XVII:

General Formula XIV

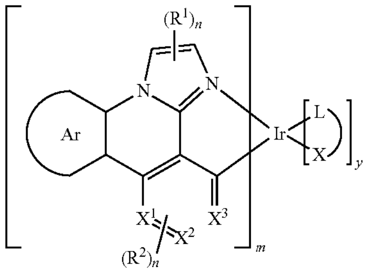

General Formula XV

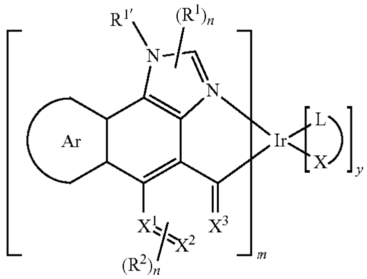

-continued

General Formula XVI

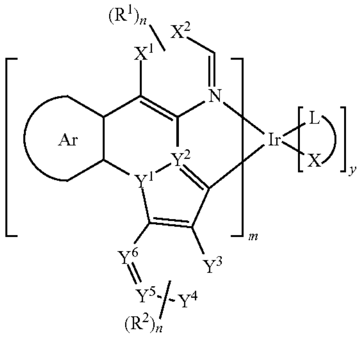

General Formula XVII

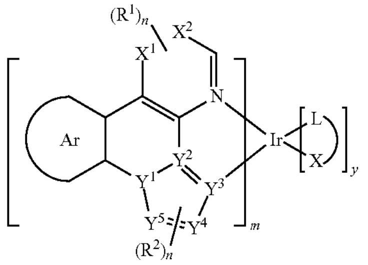

In General Formulas XIV-XVII,

N is nitrogen,

Ir is iridium, m+y=3, and when m=3, y=0, when m=2, y=1, when m=1, y=2, each n is independently an integer, valency permitting, each

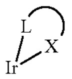

represents one of the following chemical moieties:

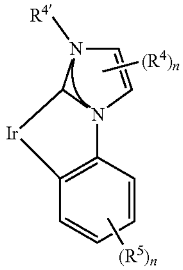

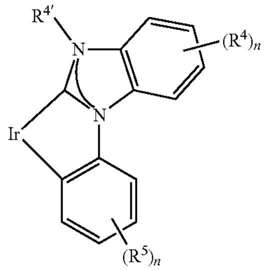

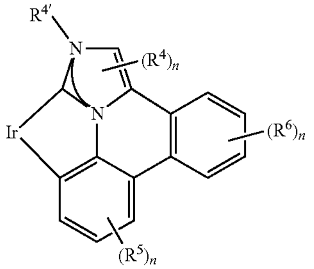

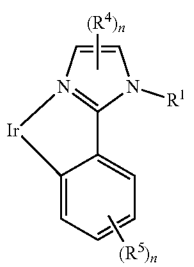

-continued

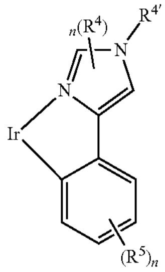 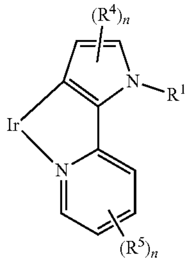 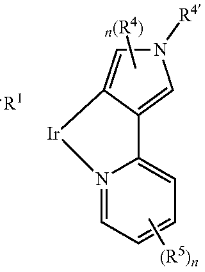

-continued

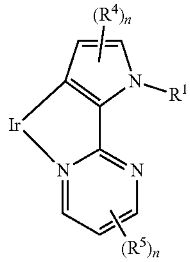 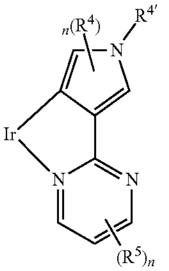 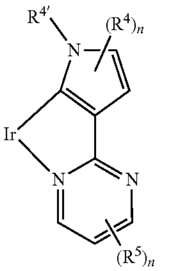

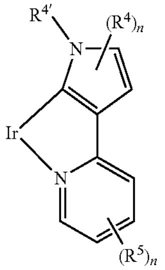 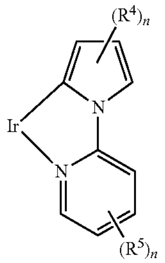 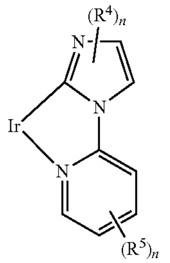

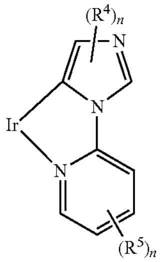 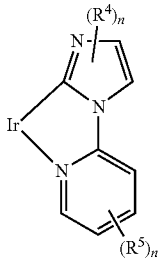 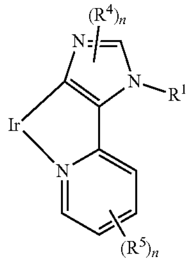

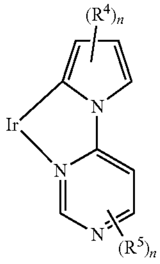 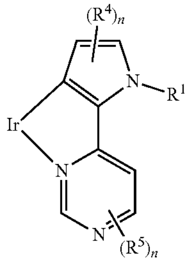 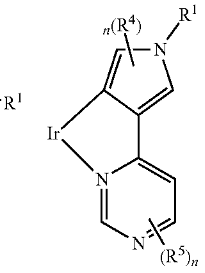

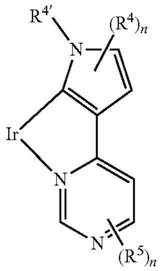 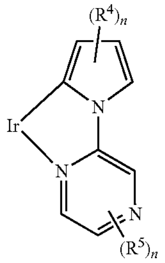 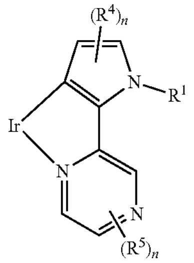

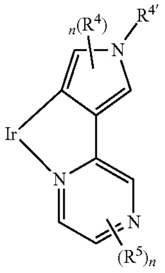 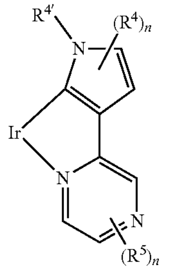 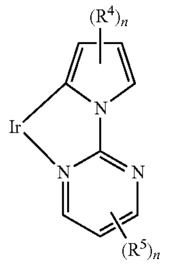

each of R, $R^1$, $R^2$, $R^3$, $R^4$, $R^5$, $R^6$, $R^{1'}$, and $R^{4'}$ is independently absent or present as a single substituent or multiple substituents, valency permitting, and each R, $R^1$, $R^2$, $R^2$, $R^3$, $R^4$, $R^5$, $R^6$, $R^{1'}$, and $R^{4'}$ present independently represents deuterium, halogen, hydroxyl, thiol, nitro, cyanide, isocyanide, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof, where the following are examples:

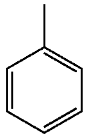 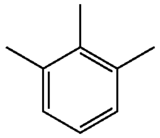 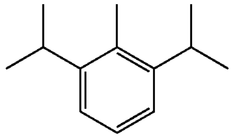

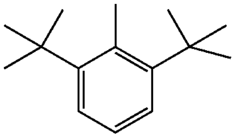 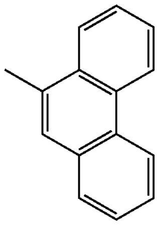 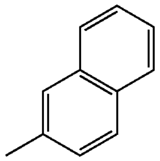

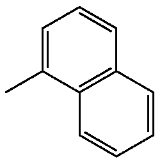 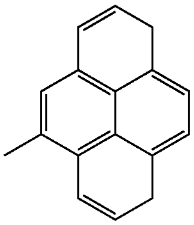 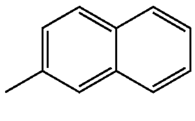

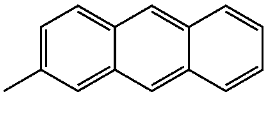 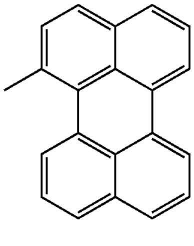

-continued

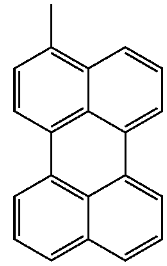
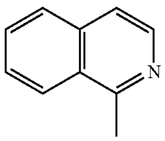
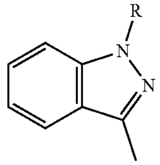
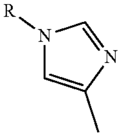
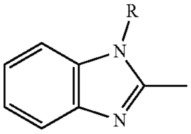
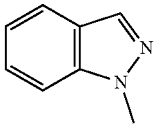
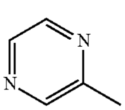
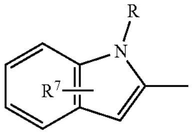
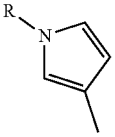
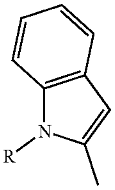
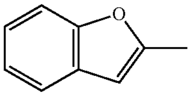
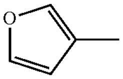
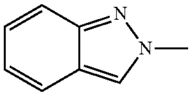
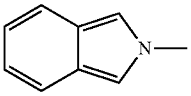
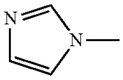

each of $X^1$, $X^2$, $X^3$, $X^4$, $Y^1$, $Y^2$, $Y^3$, $Y^4$, $Y^5$, $Y^6$, and $Y^7$ is independently present or absent, and each $X^1$, $X^2$, $X^3$, $X^4$, $Y^1$, $Y^2$, $Y^3$, $Y^4$, $Y^5$, $Y^6$, and $Y^7$ present independently represents C, N, Si, O, S, Ge, P, As, Se, B, Al, or Bi, or, valency permitting, $CR^7$, $SiR^7$, $GeR^7$, $NR^7$, P═O, As═O, B, $BR^7$, $AlR^7$, Bi═O, $CR^7R^8$, C═O, $SiR^7R^8$, $GeR^7R^8$, $NR^7$, $PR^7$, $PR^7R^8$, $R^7$P═O, $AsR^7$, $R^7$, As═O, S═O, $SO_2$, Se═O, $SeO_2$, $BR^7$, $BR^7R^8$, $AlR^7$, $AlR^7R^8$, $R^7$Bi═O, or $BiR^7$, each

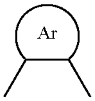

is independently present or absent, and each Ar present independently represents a substituted or unsubstituted aryl, heteroaryl, or N-heterocyclic carbene, and the following chemical moieties:

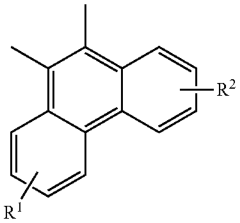
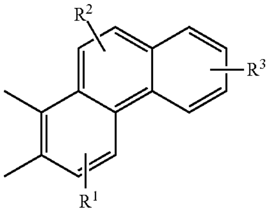
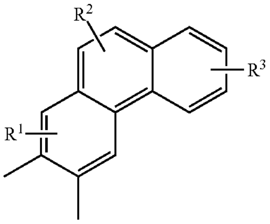
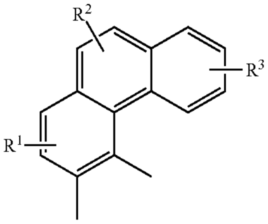
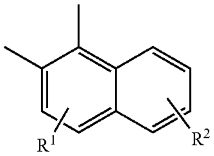
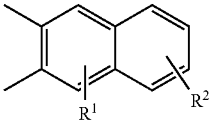
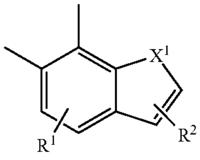
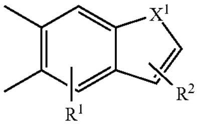
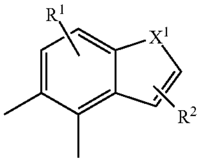
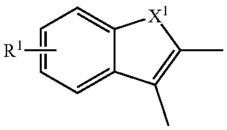
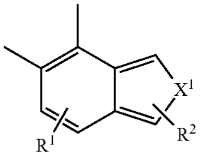
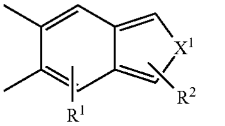
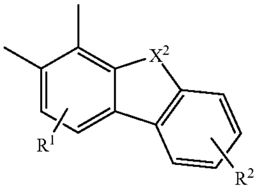
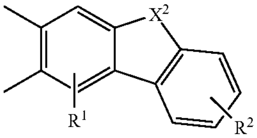
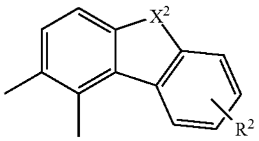
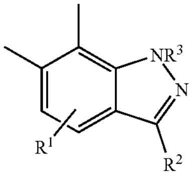
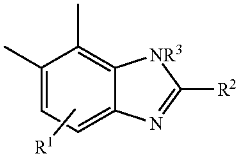
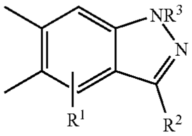

-continued
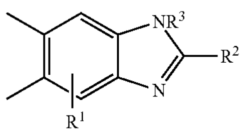
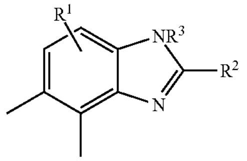
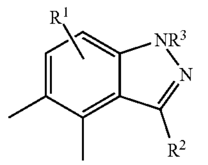
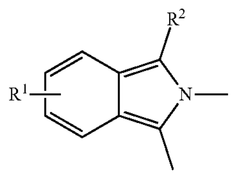
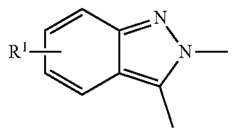
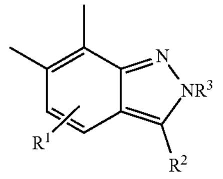
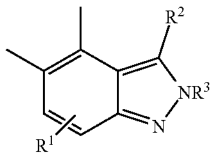
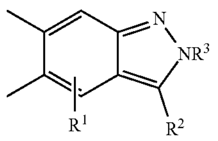
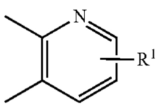
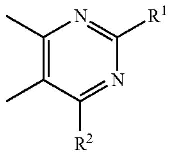
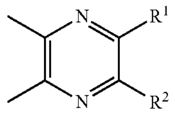
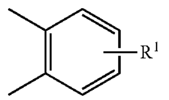
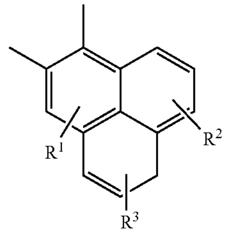
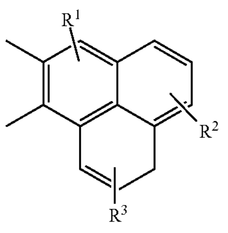
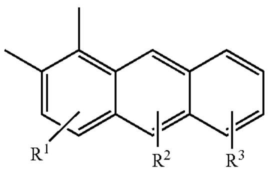
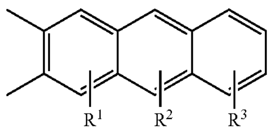
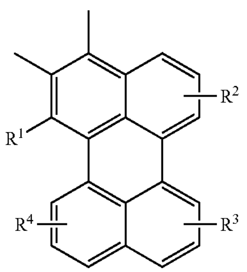
-continued
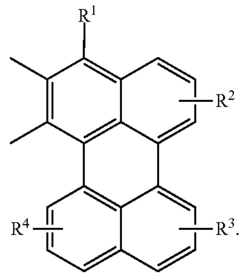
In General Formulas XIV-XVII, for m=3, the moieties can be the same or different. That is, when m=3, the three moieties can be the same, two of the moieties can be the same, or all three of the moieties can be different.
Implementations of General Formulas XIV-XVII include the following:
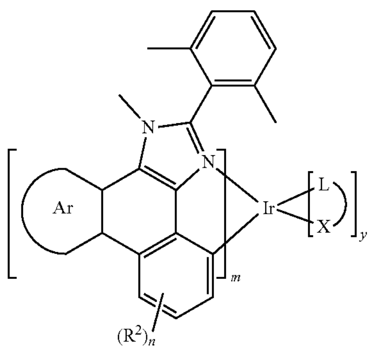
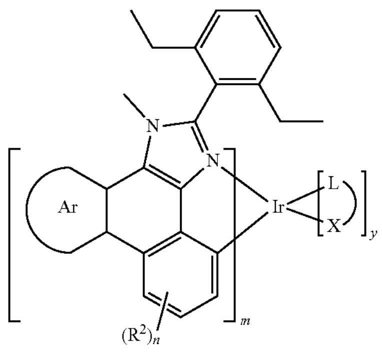
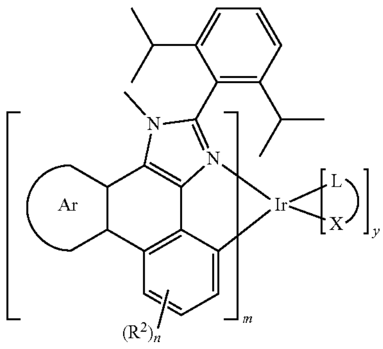

-continued
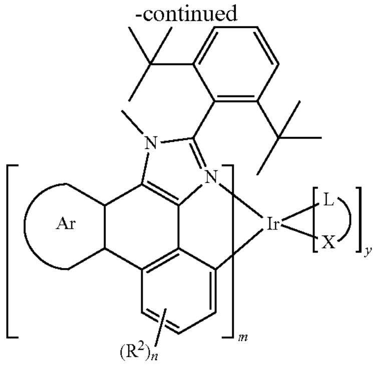
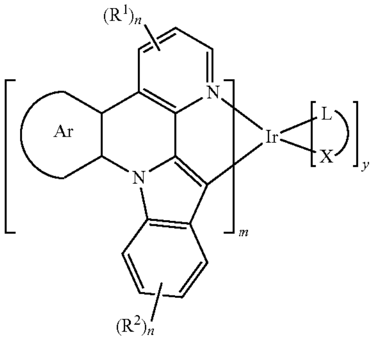
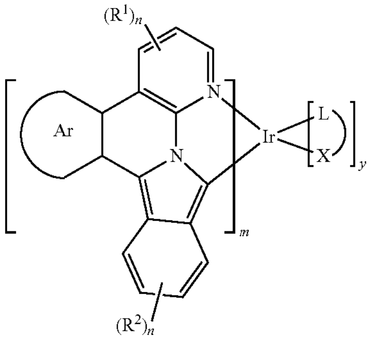
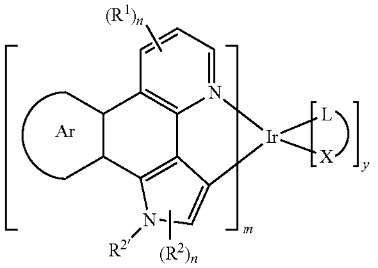
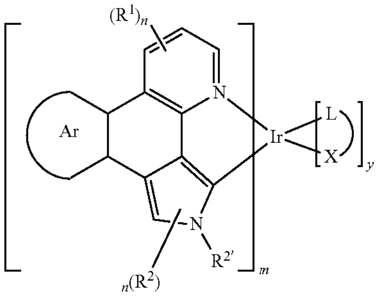
-continued
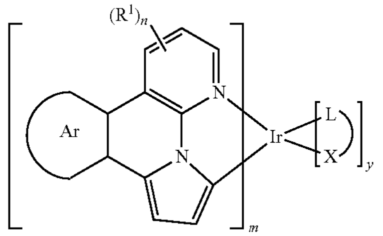
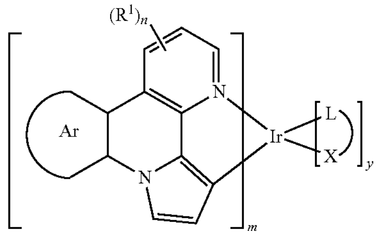
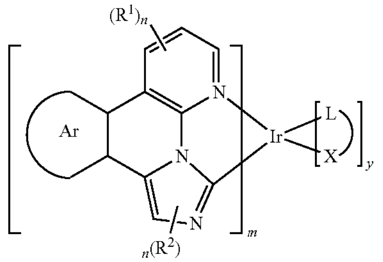
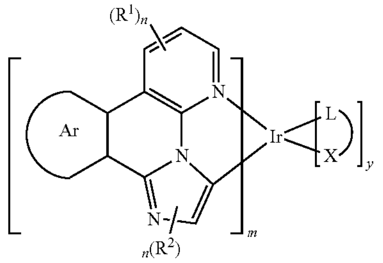
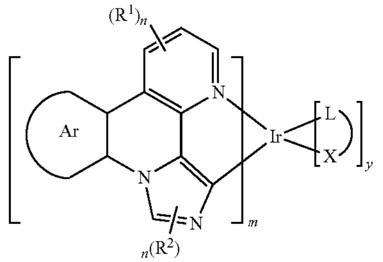
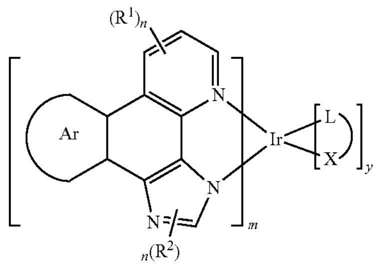

-continued
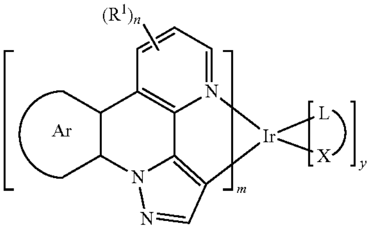
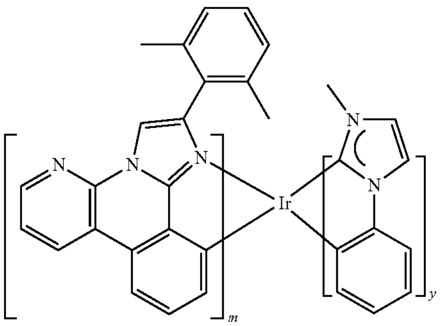
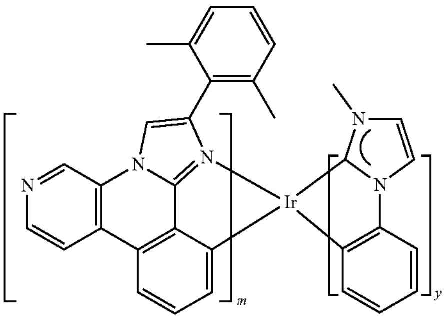
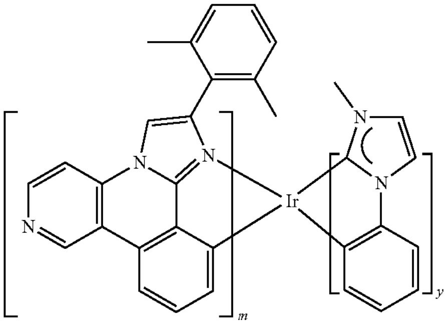
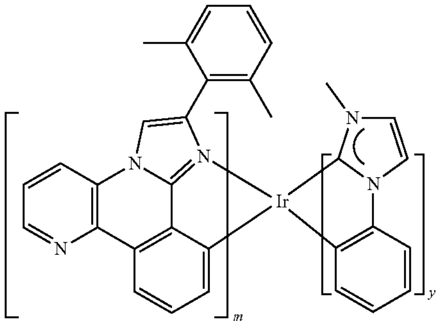
-continued
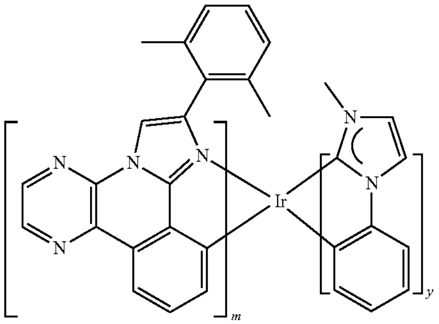
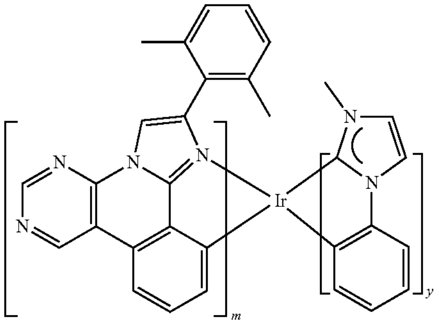
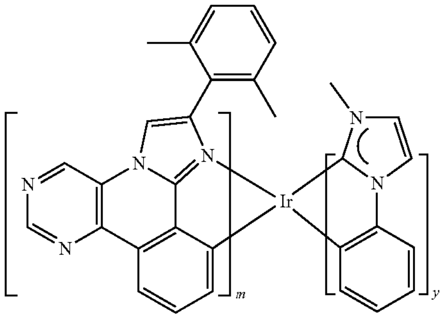
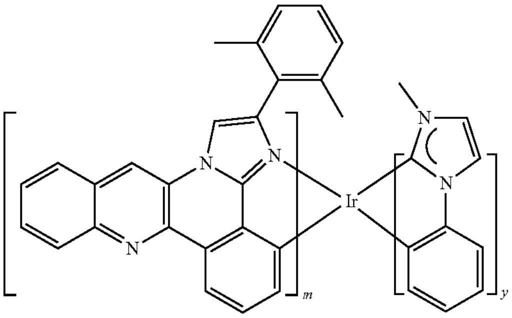
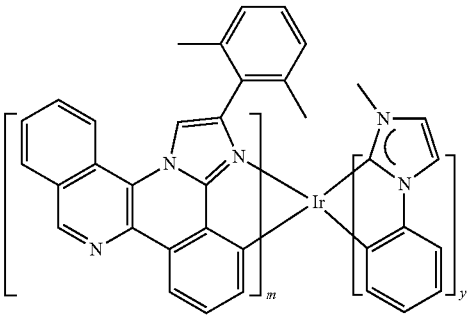

-continued
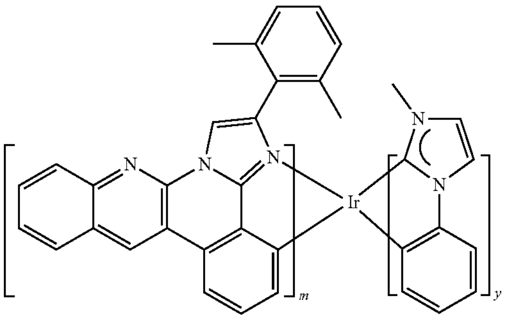
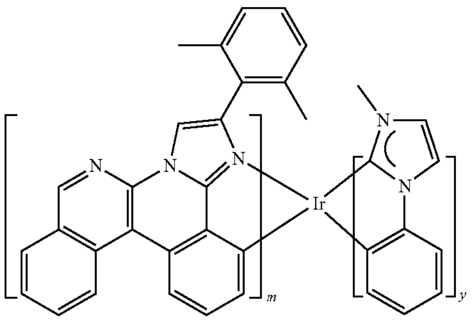
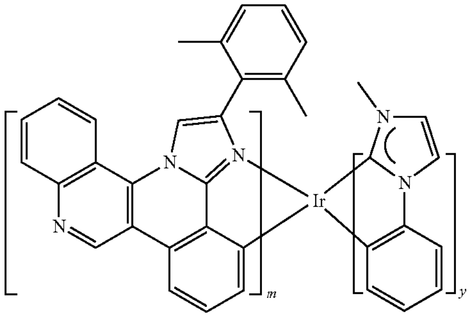
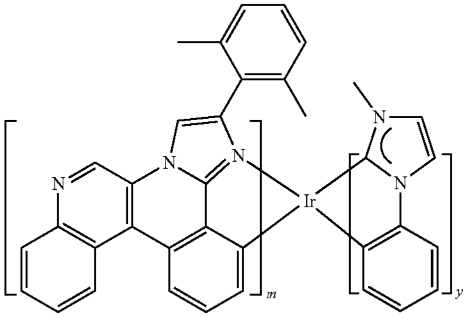
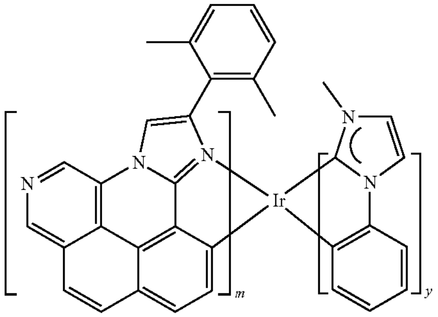
-continued
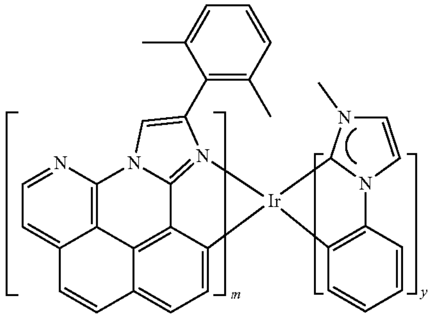
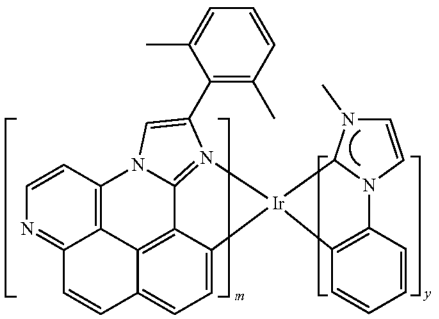
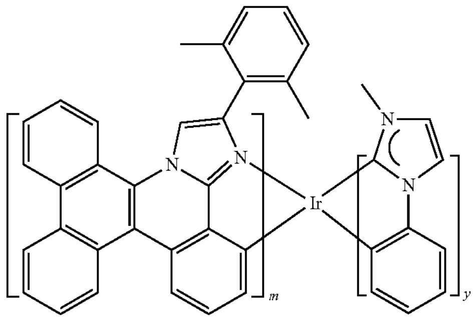
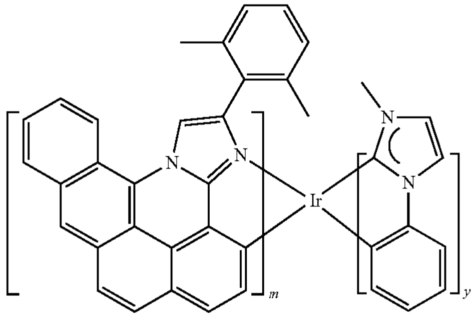
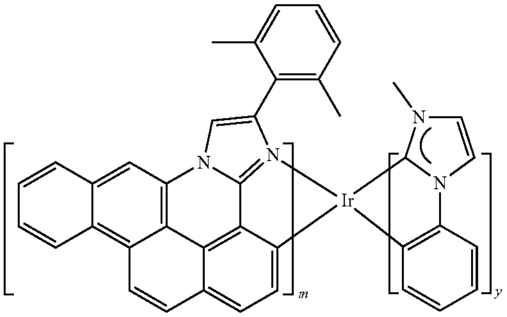

-continued
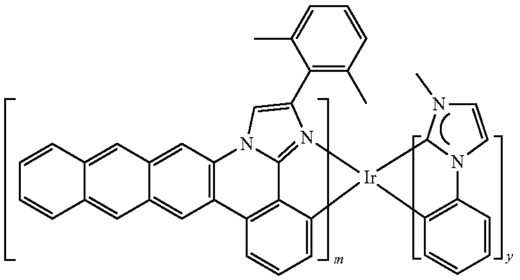
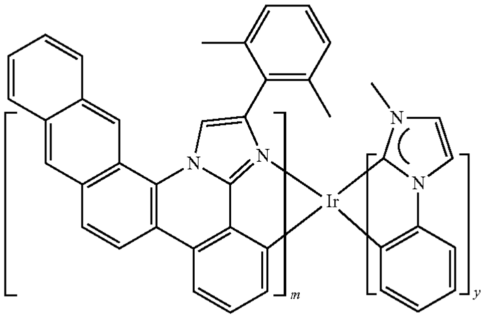
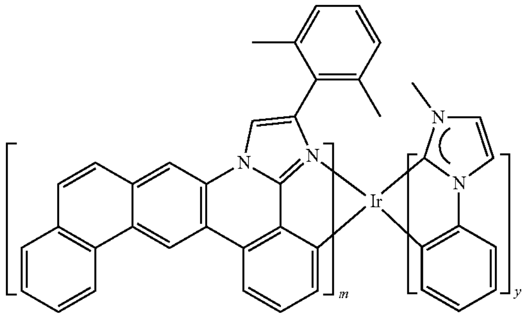
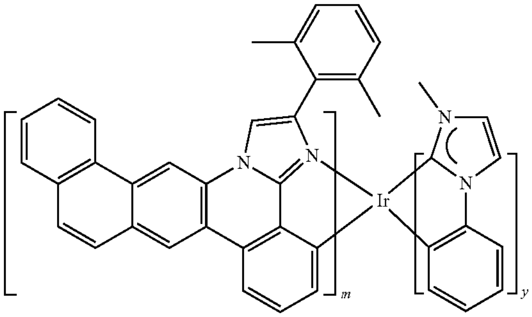
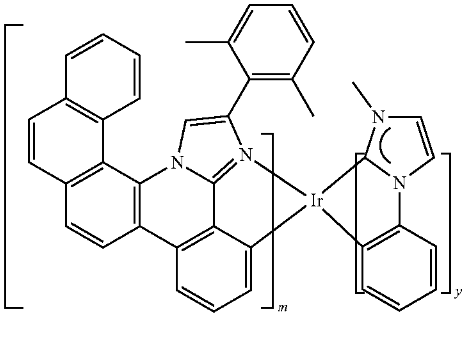
-continued
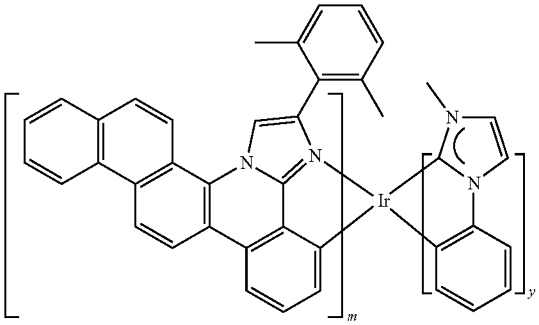
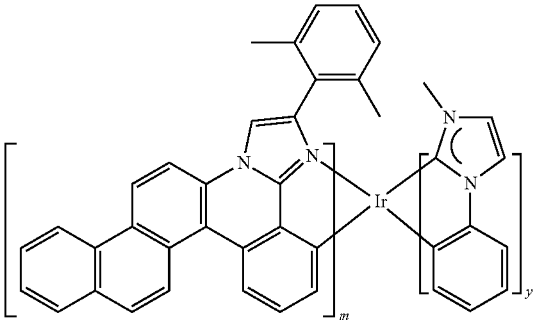
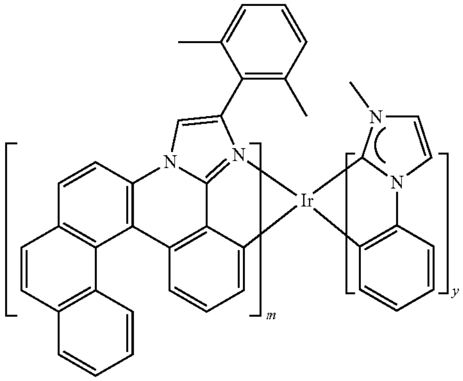
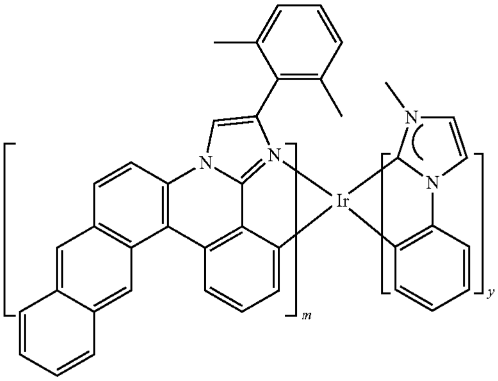
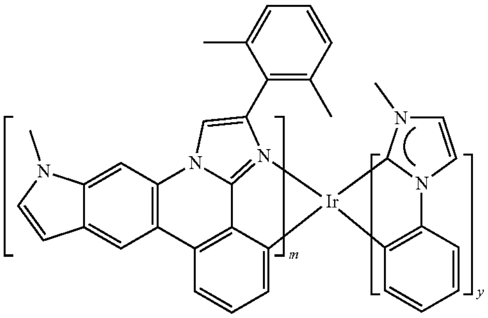

-continued
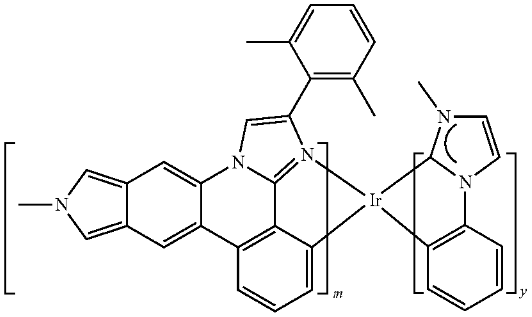
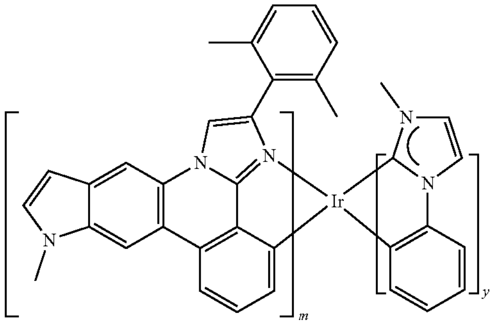
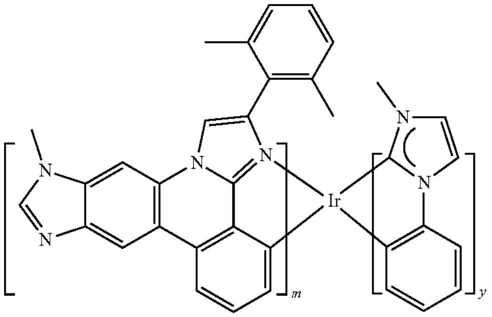
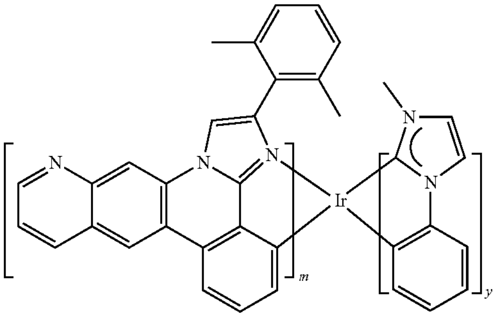
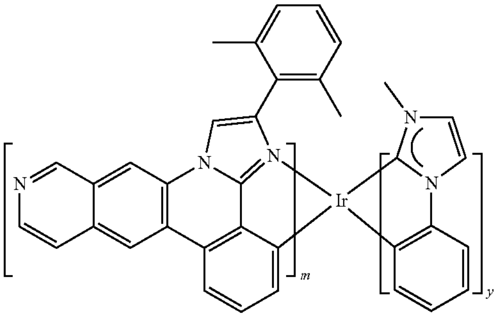
-continued
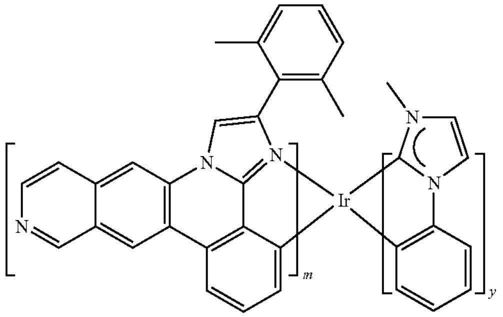
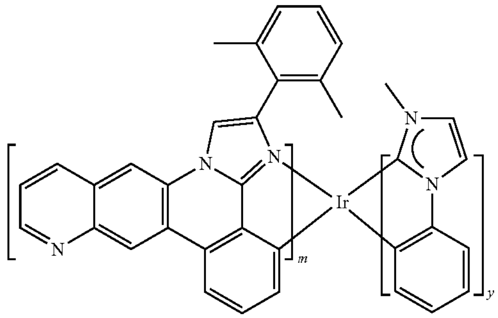
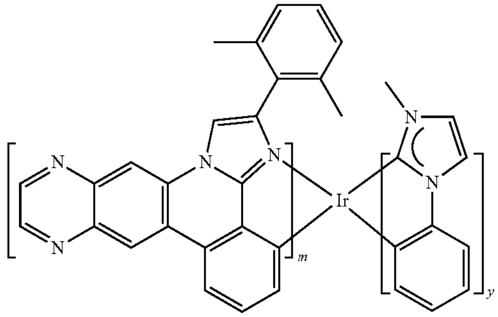
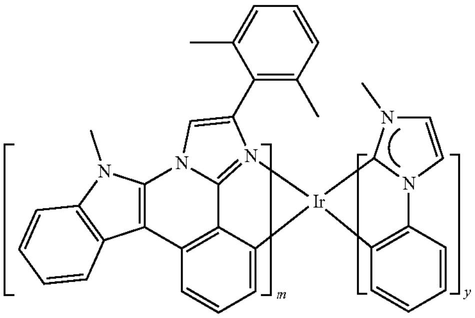
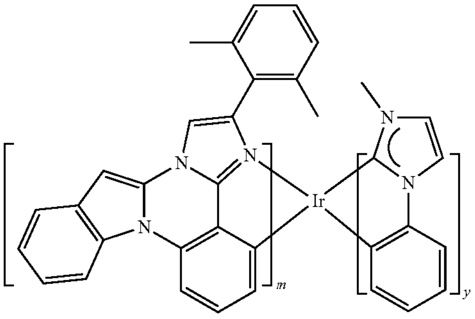

-continued
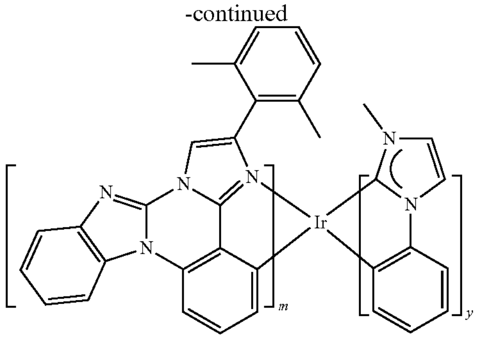
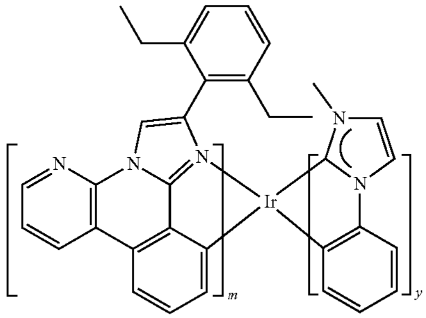
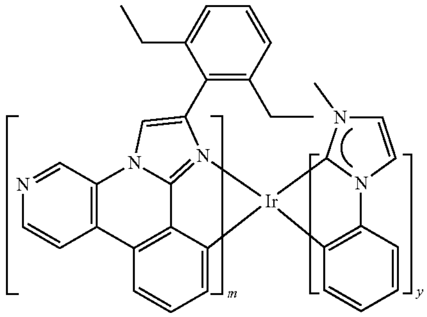
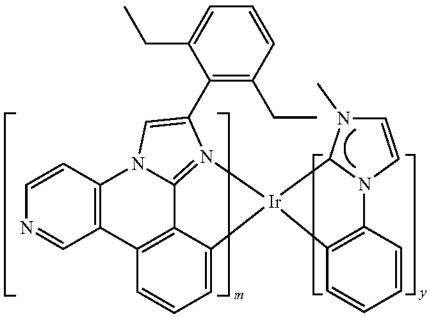
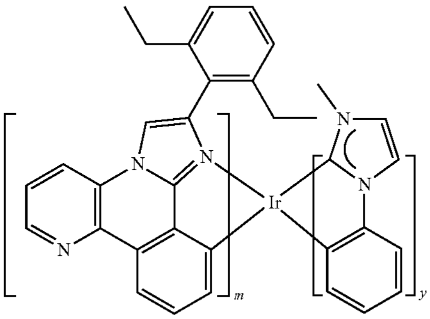
-continued
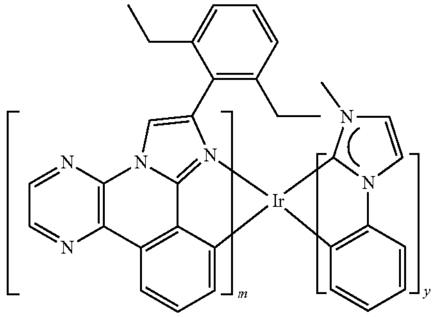
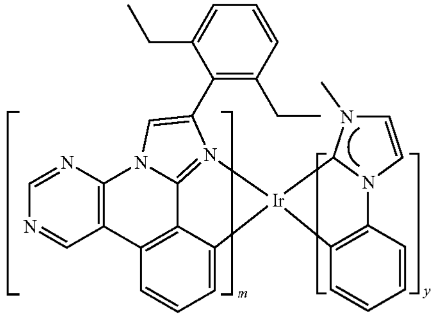
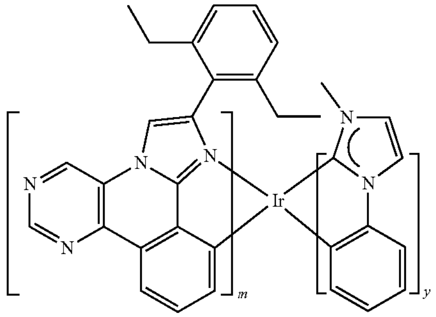
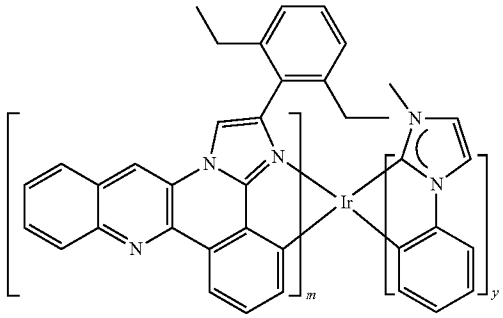
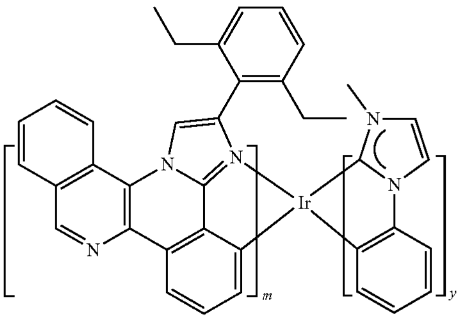

-continued
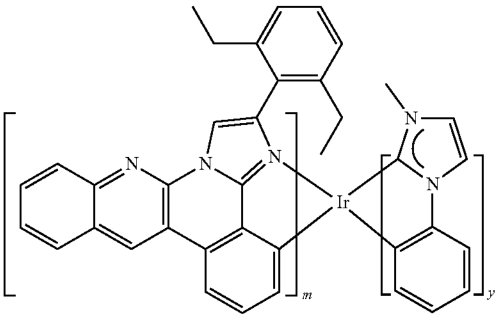
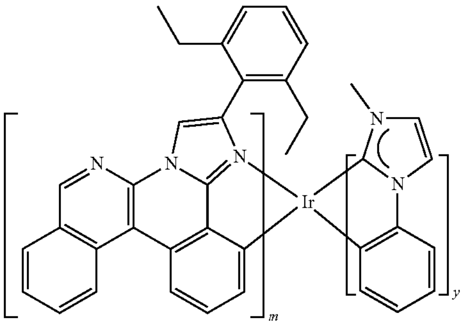
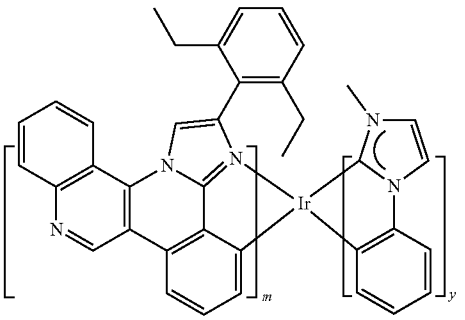
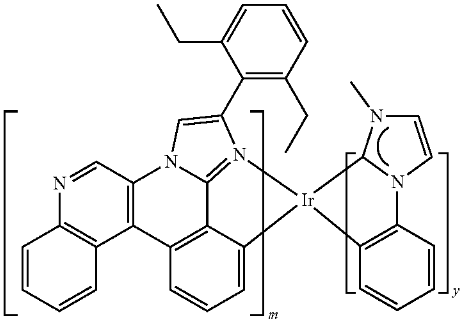
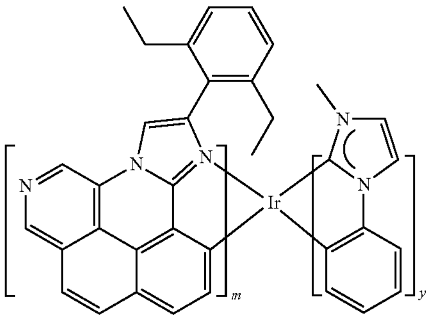
-continued
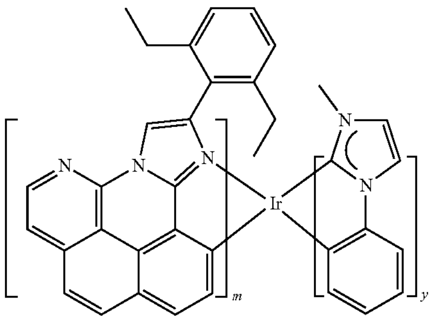
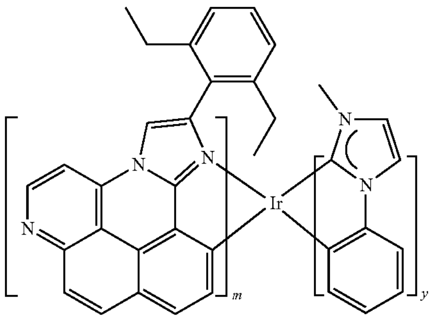
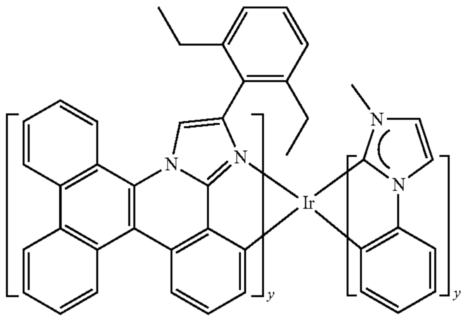
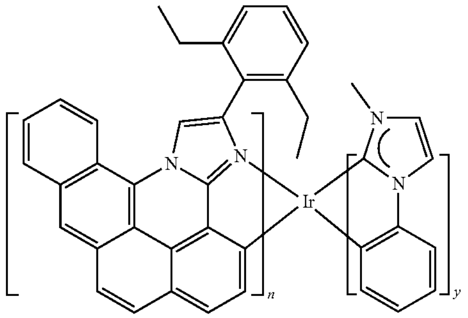
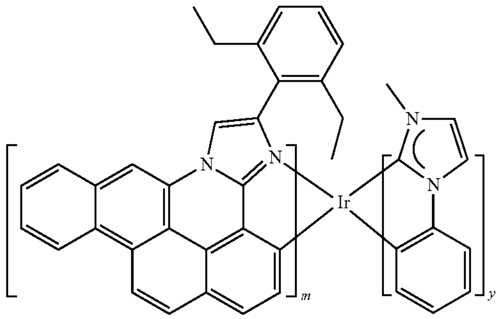

-continued
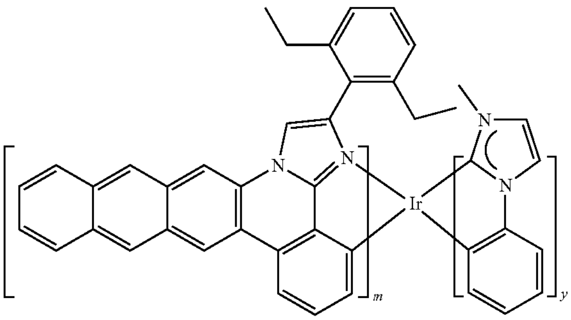
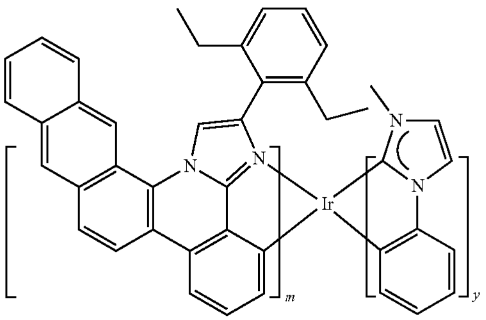
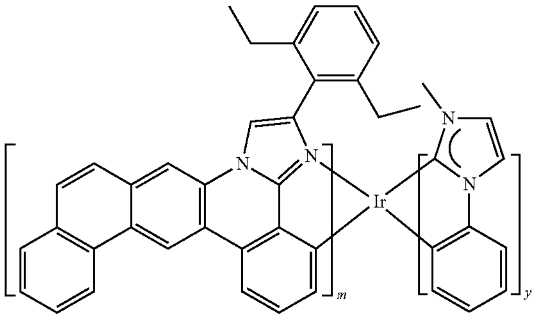
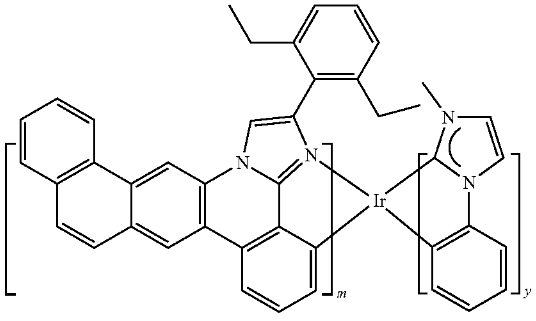
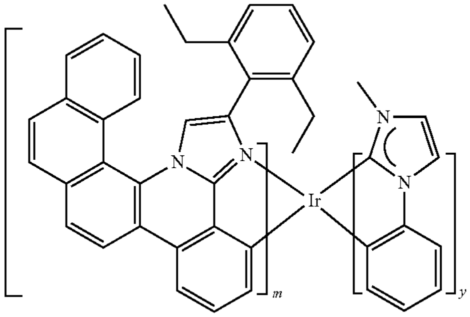
-continued
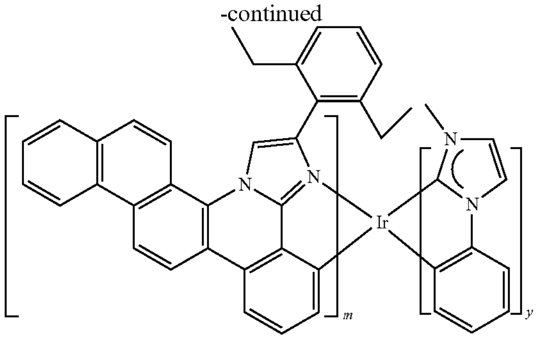
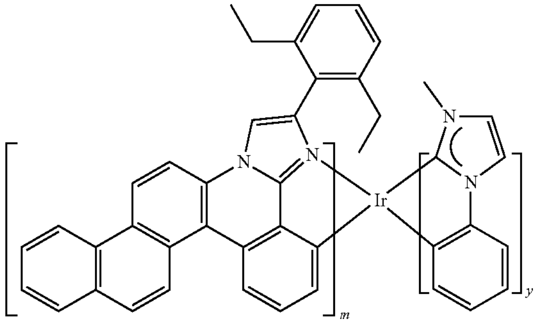
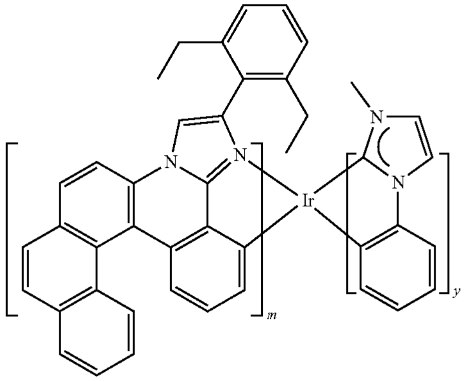
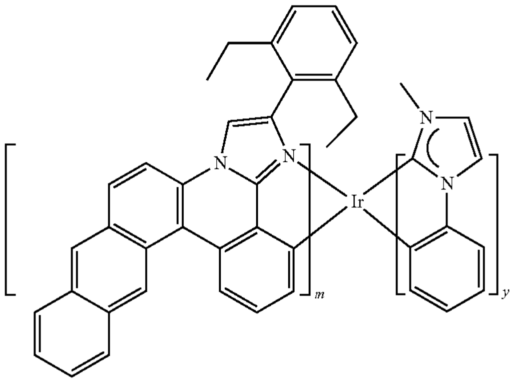
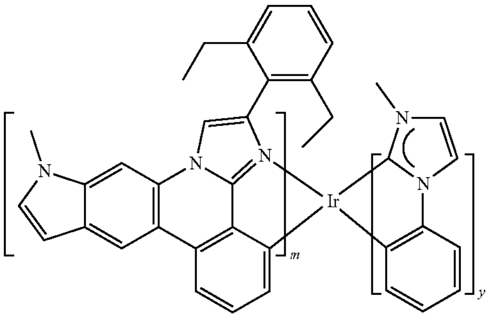

-continued
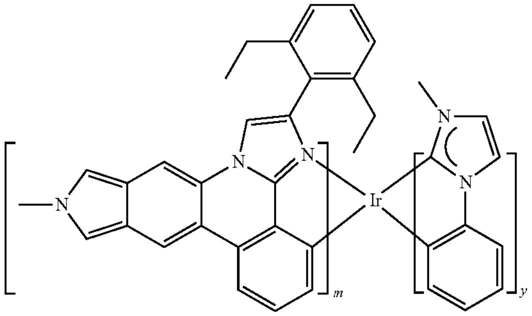
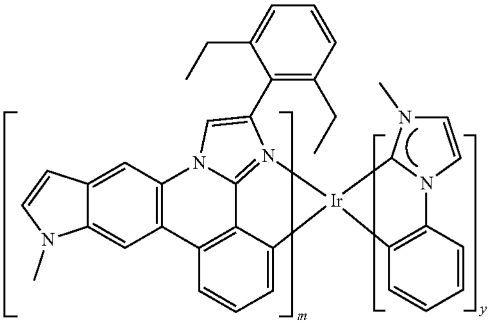
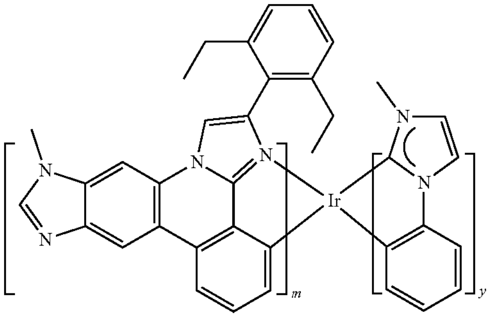
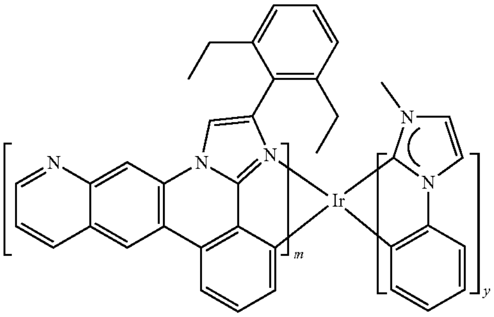
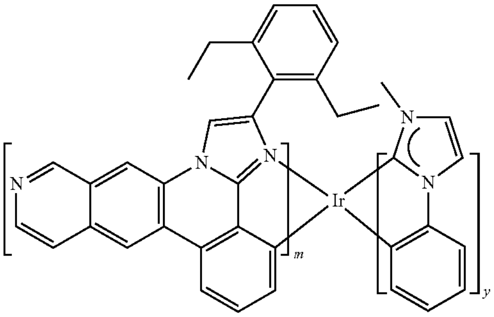
-continued
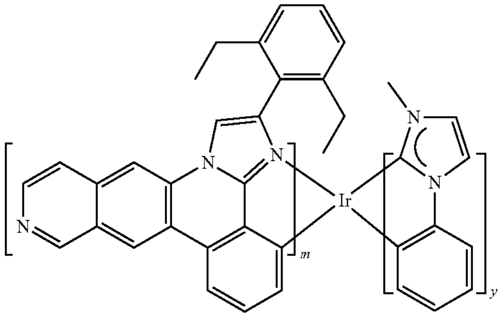
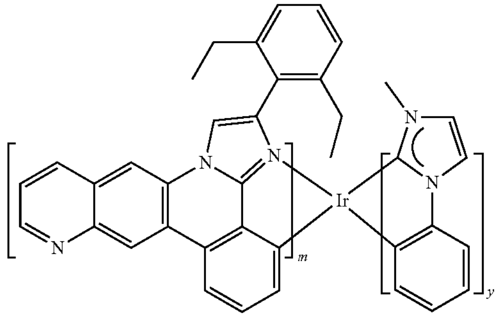
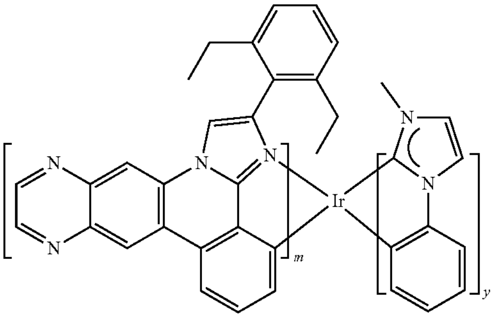
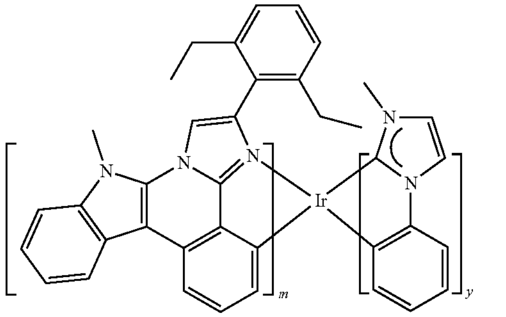
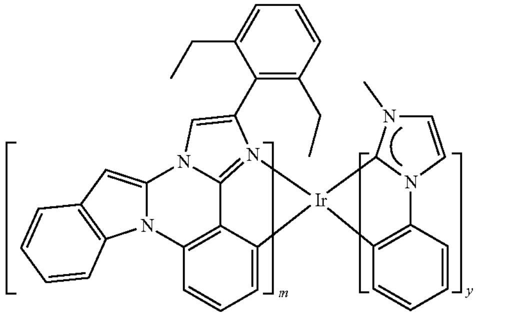

-continued
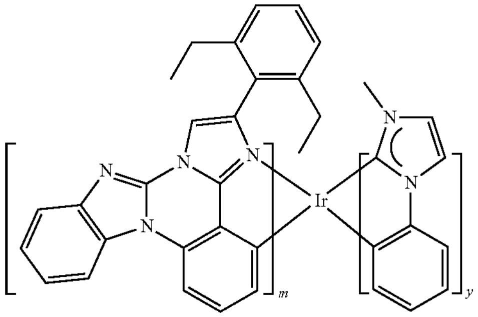
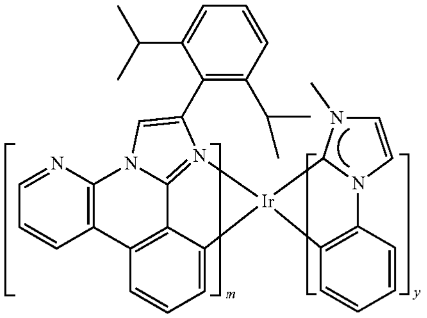
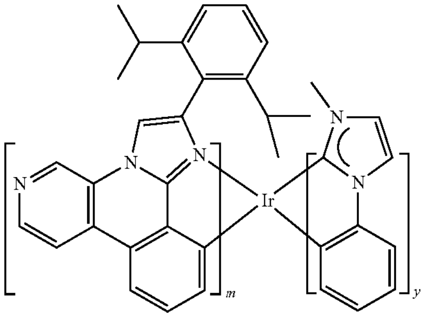
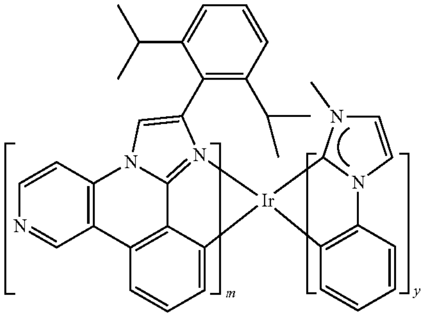
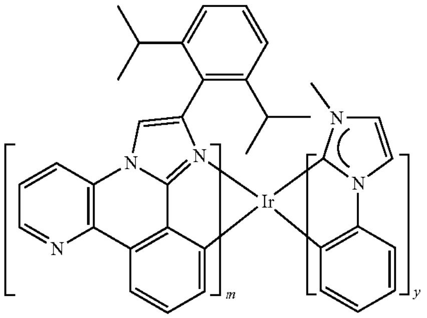
-continued
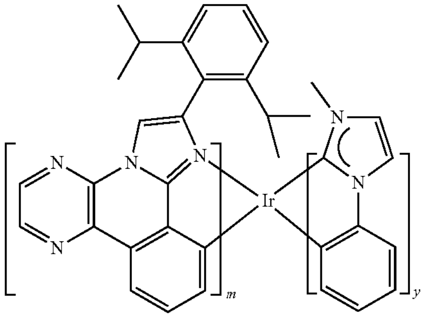
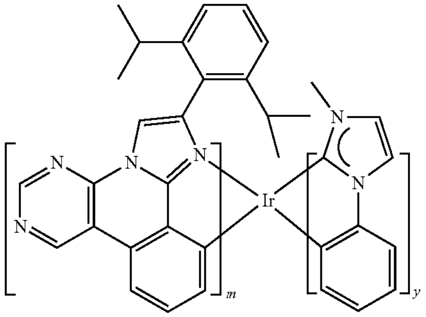
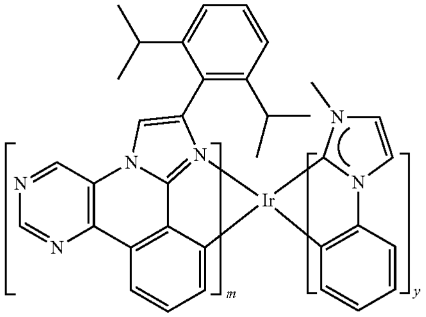
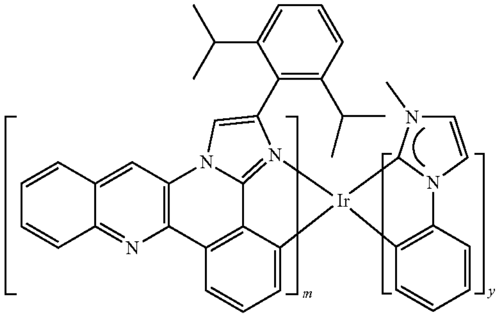
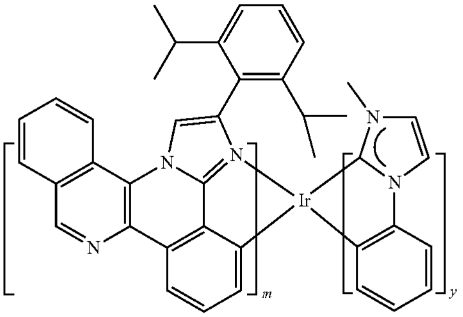

-continued
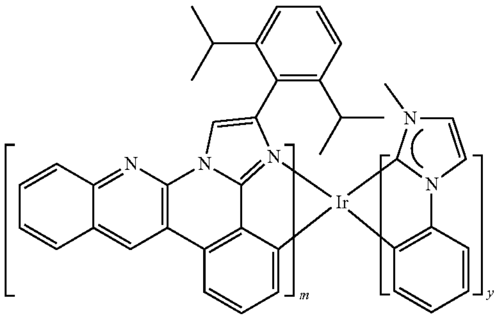
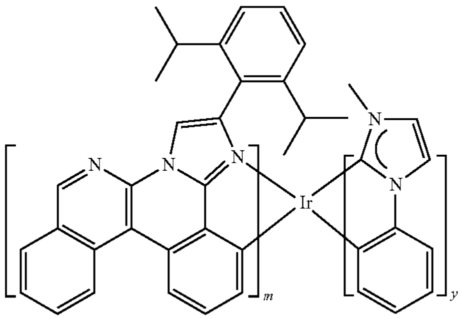
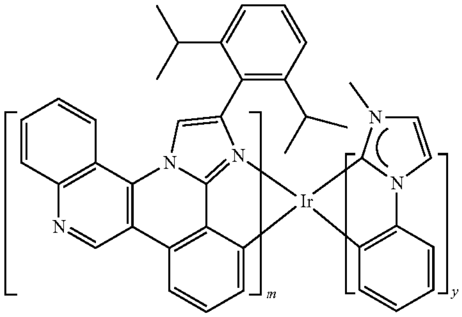
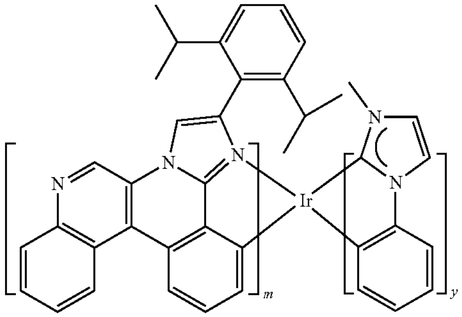
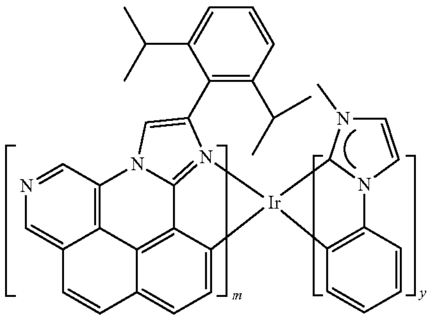
-continued
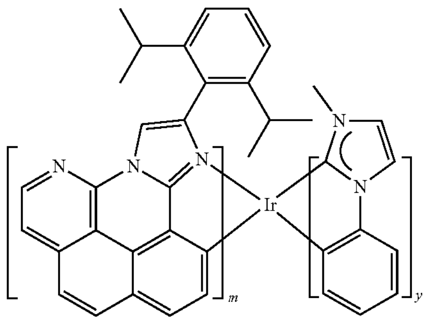
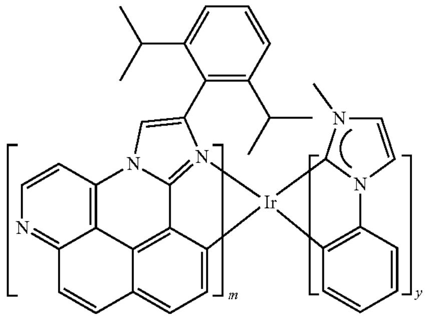
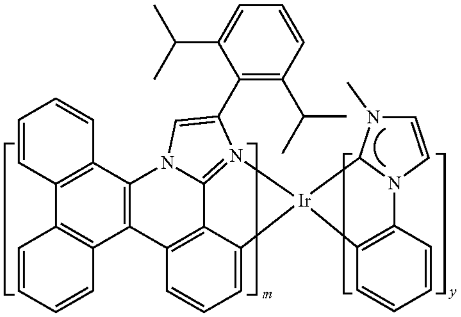
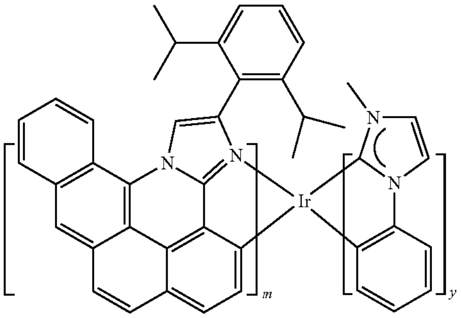
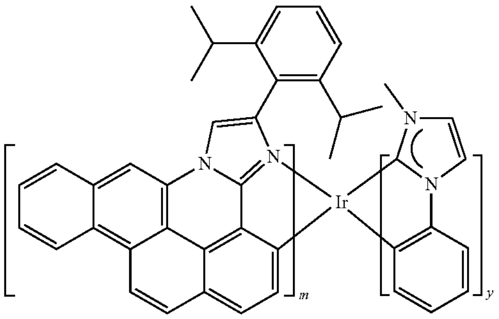

-continued
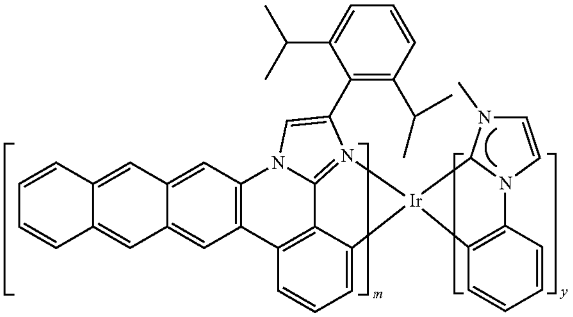
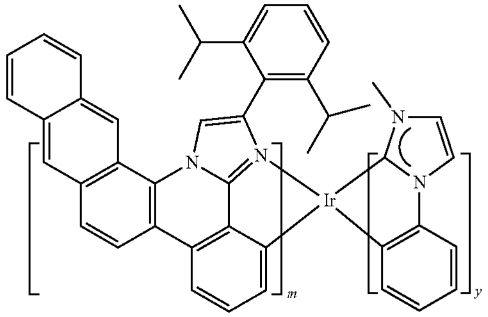
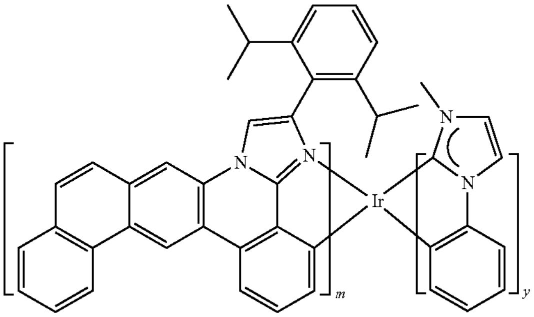
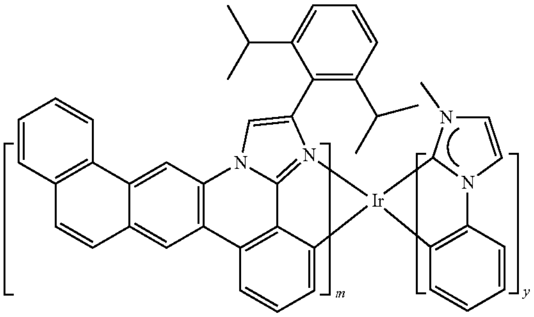
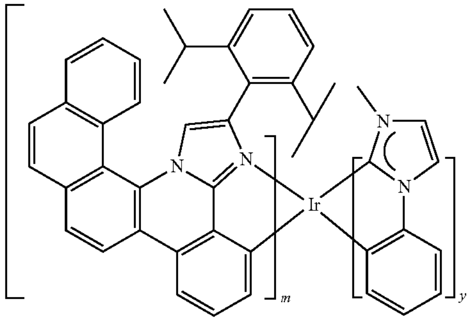
-continued
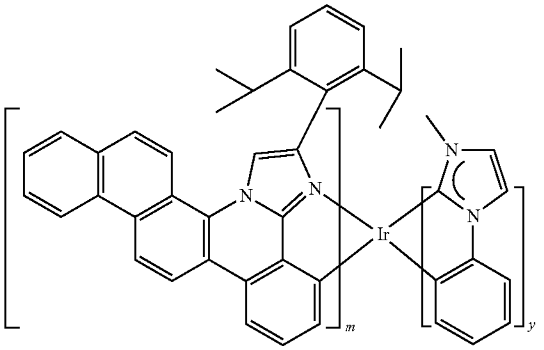
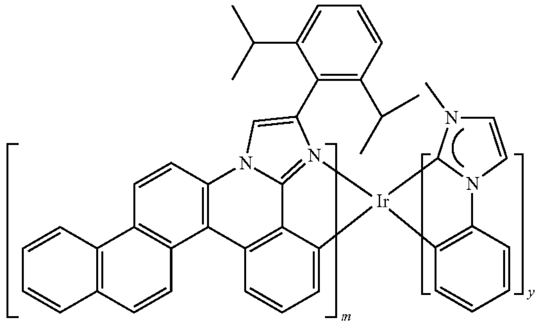
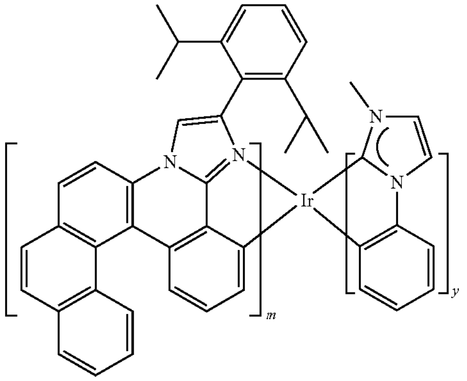
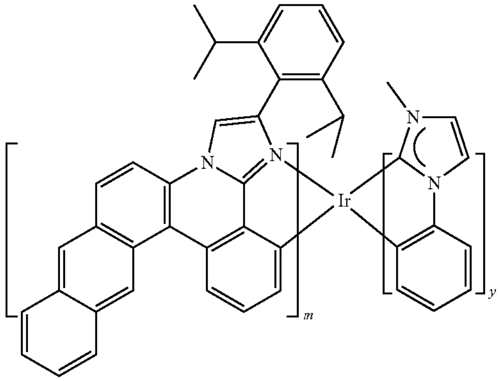

-continued
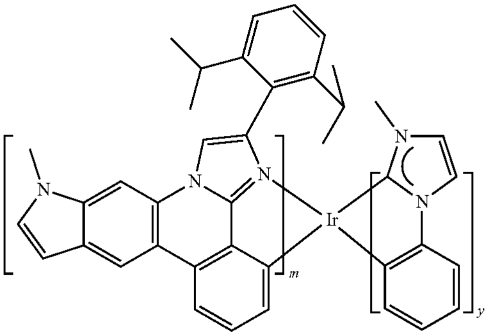
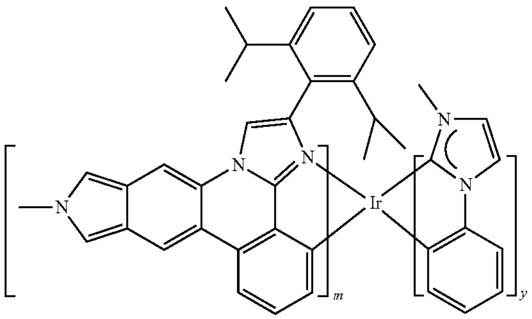
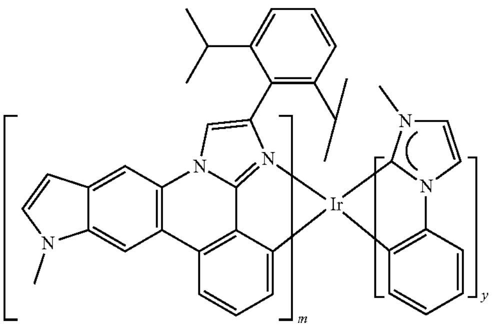
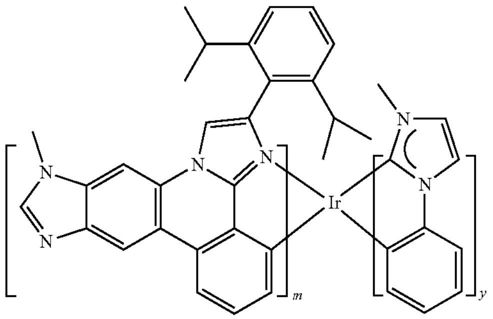
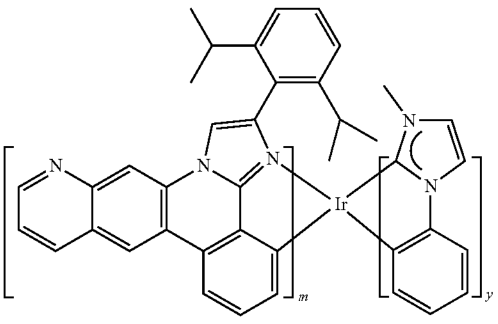
-continued
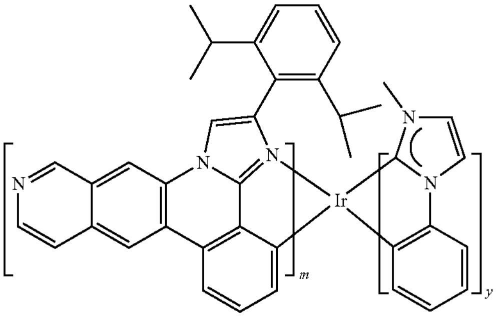
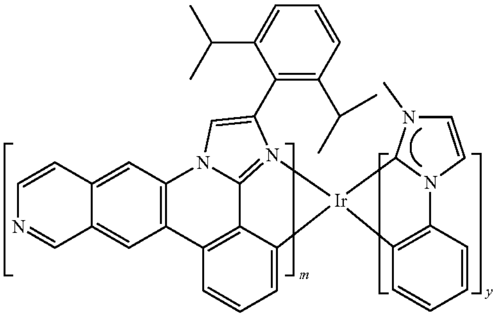
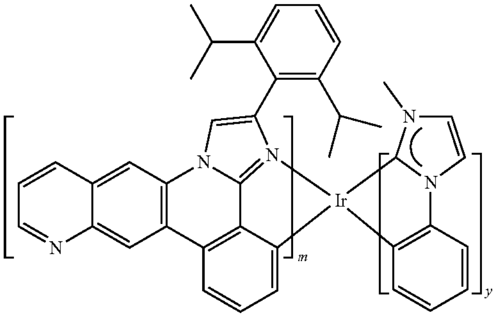
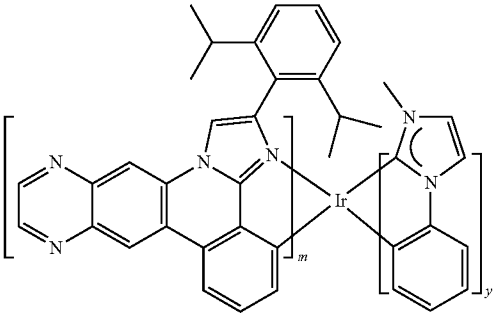
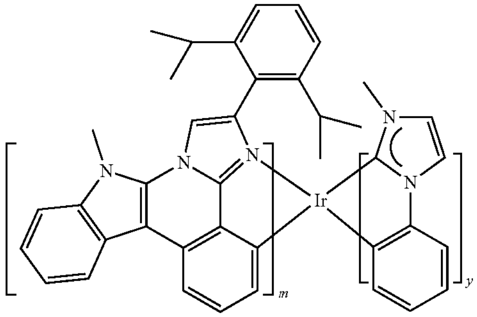

-continued
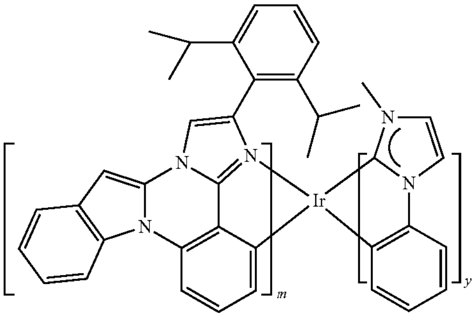
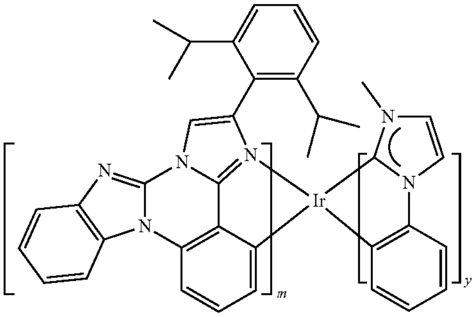
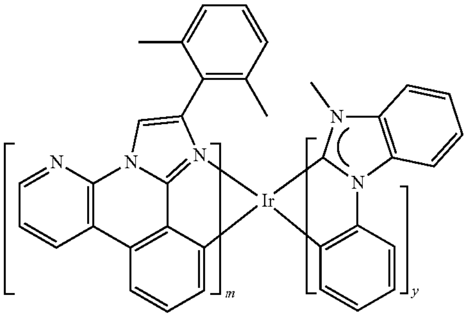
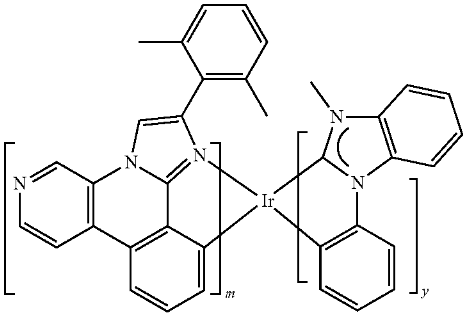
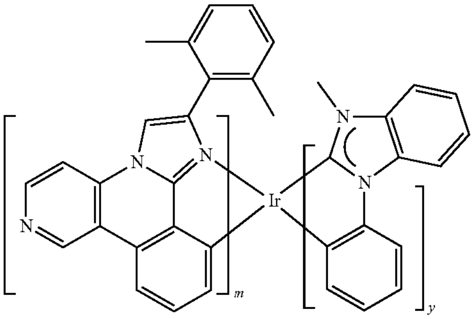
-continued
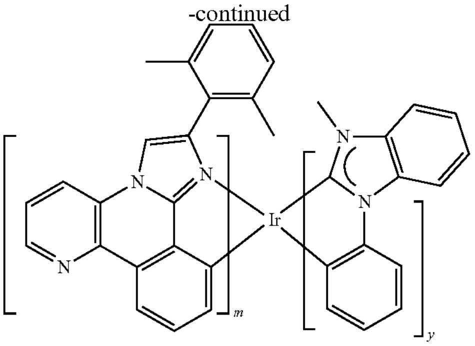
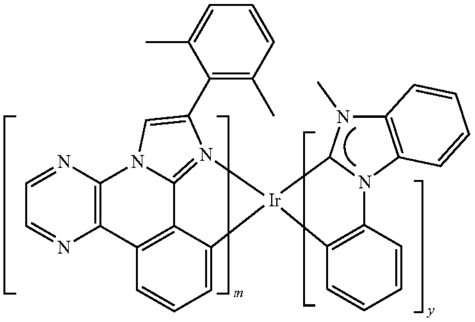
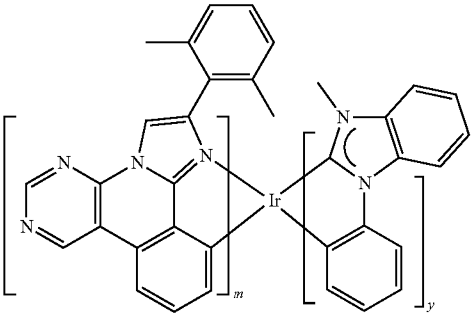
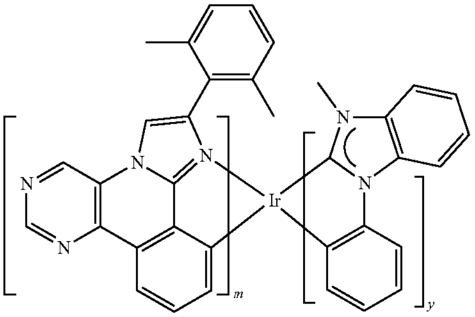
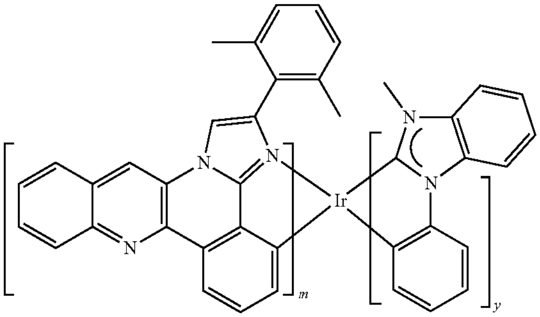

-continued
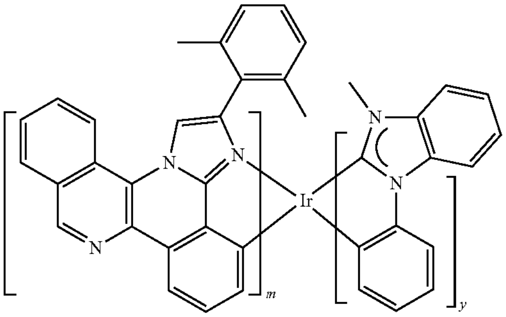
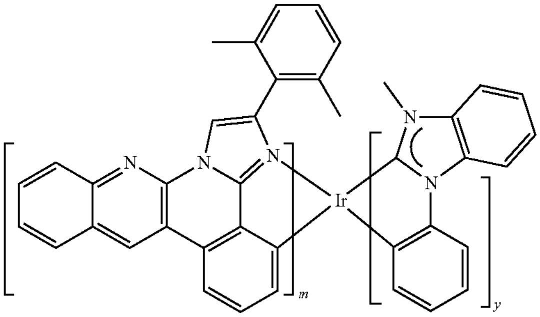
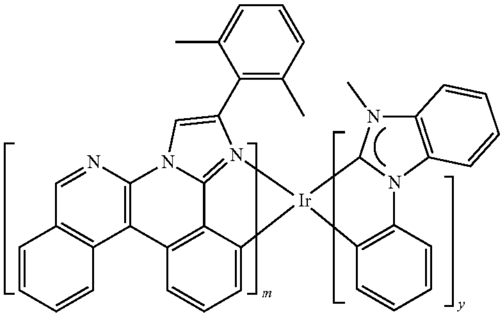
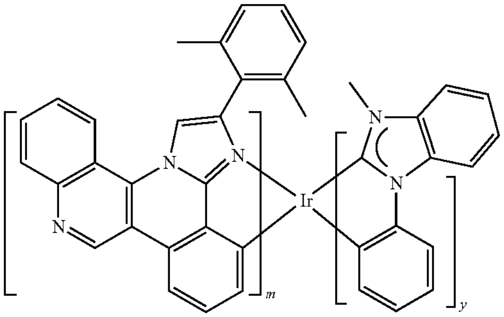
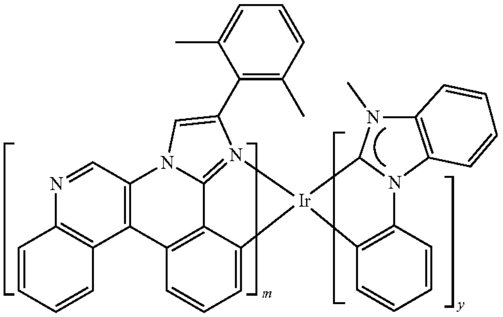
-continued
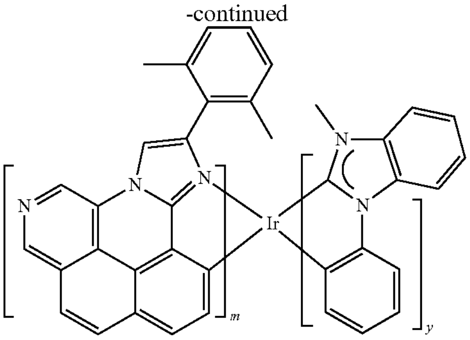
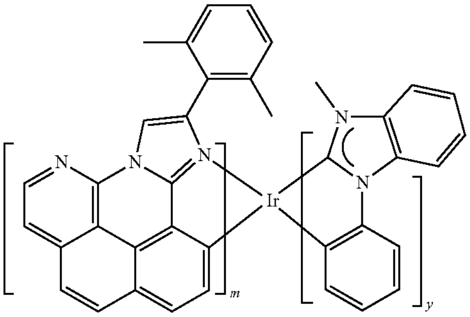
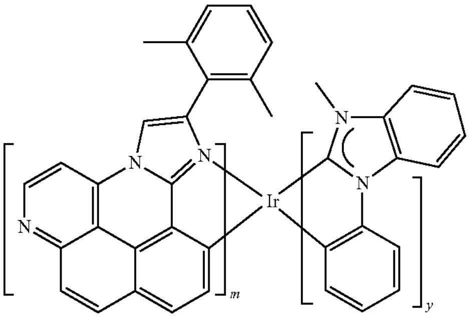
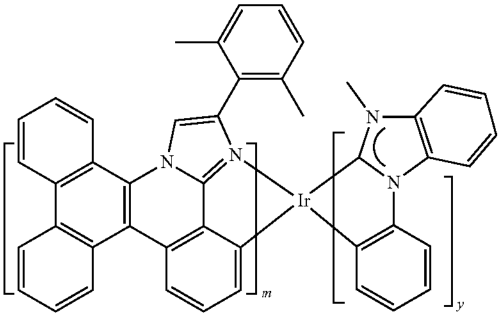
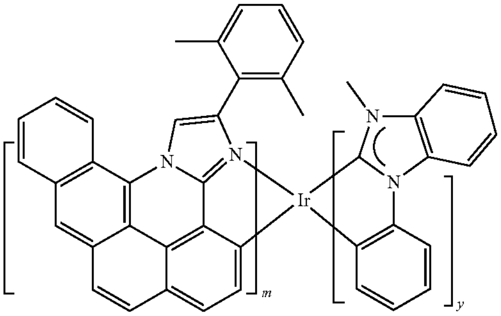

-continued
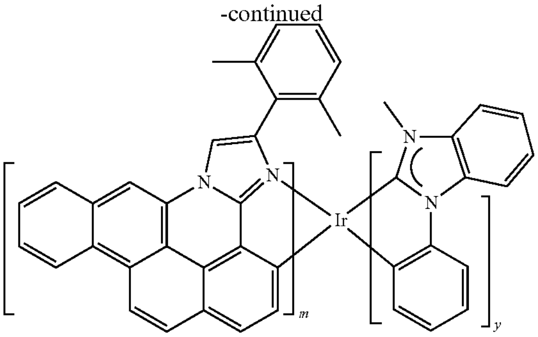
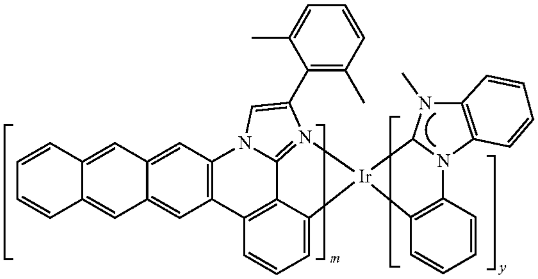
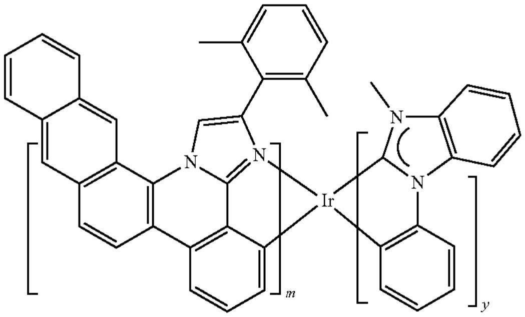
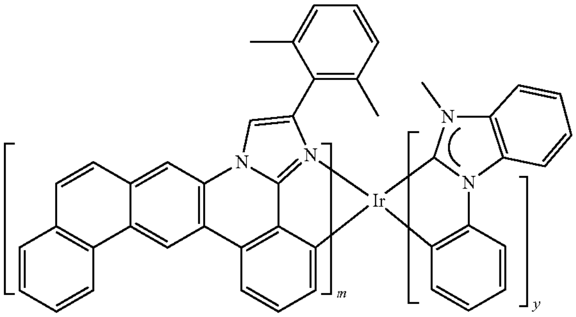
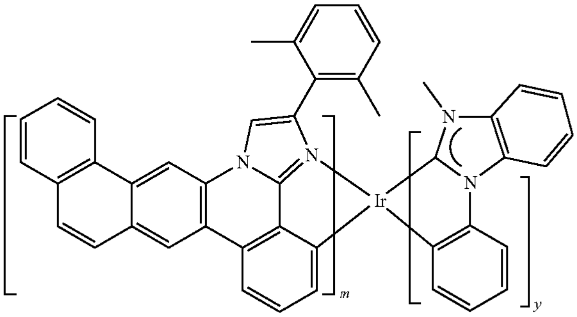
-continued
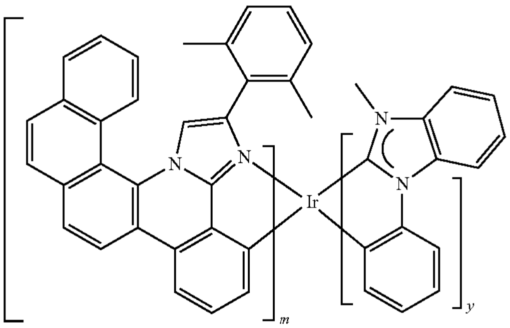
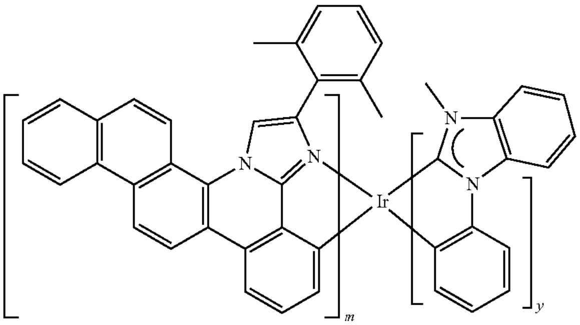
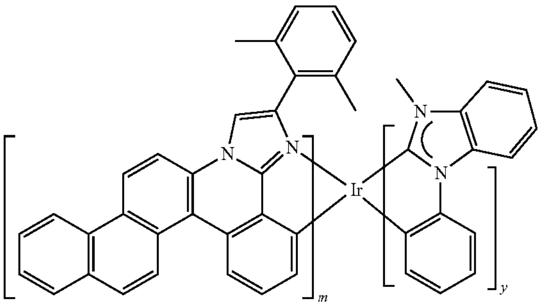
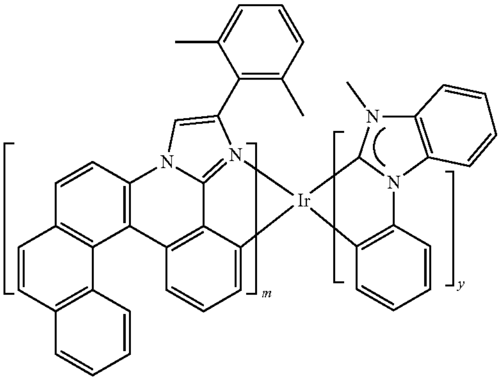
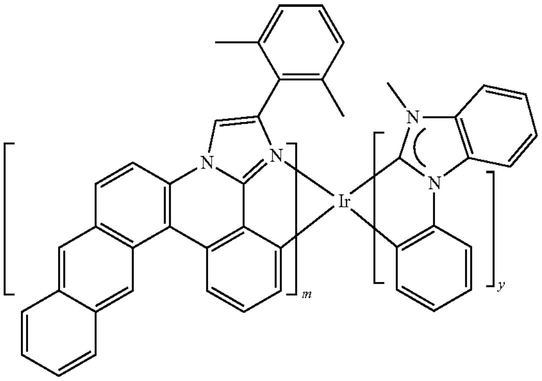

-continued
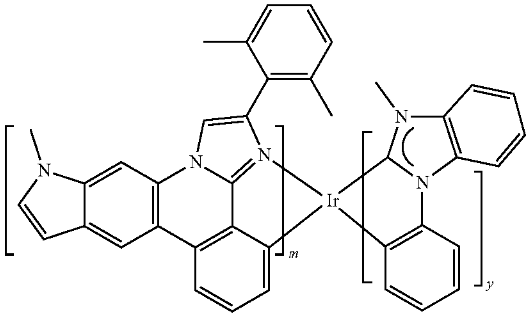
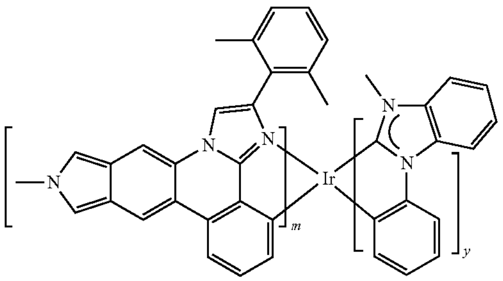
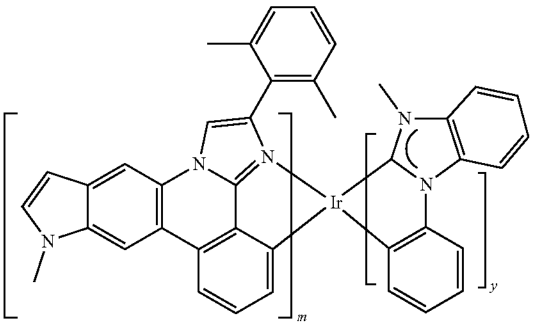
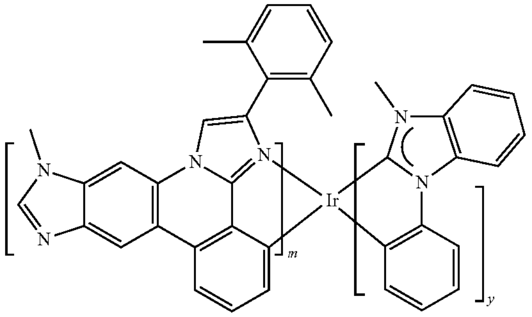
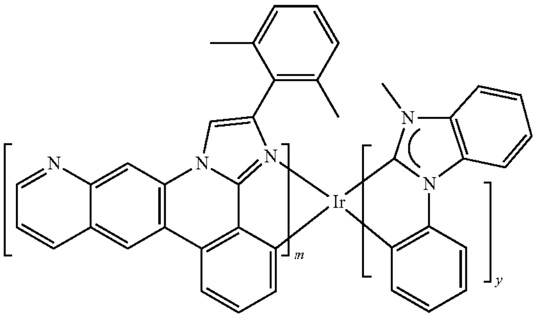
-continued
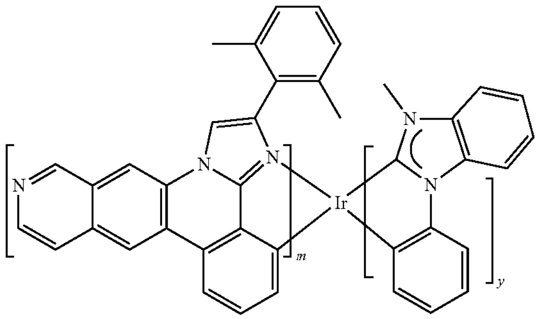
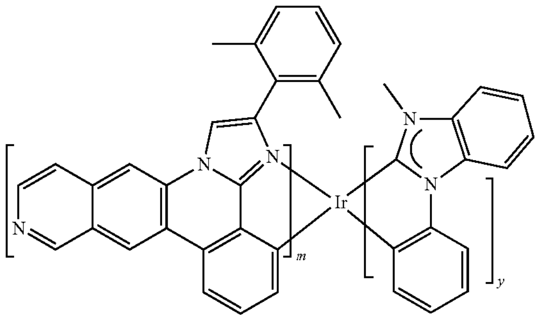
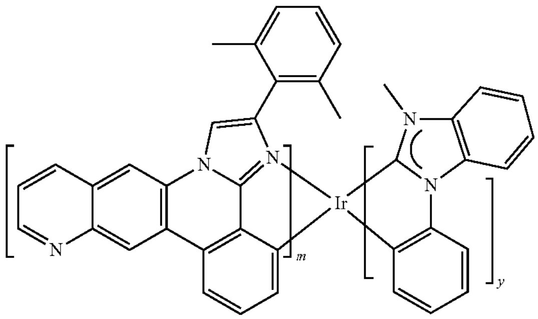
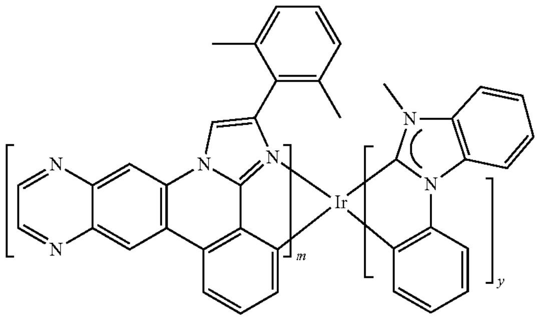
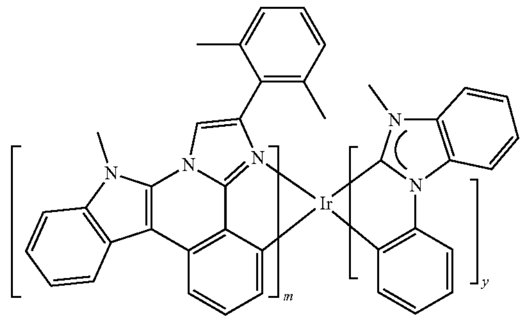

-continued
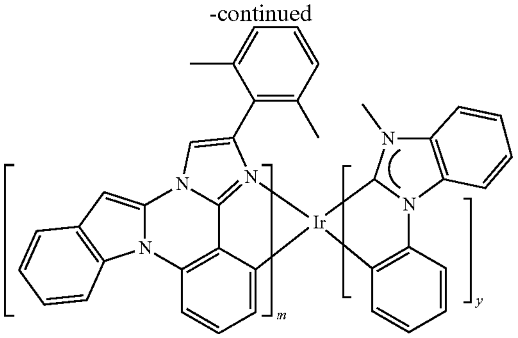
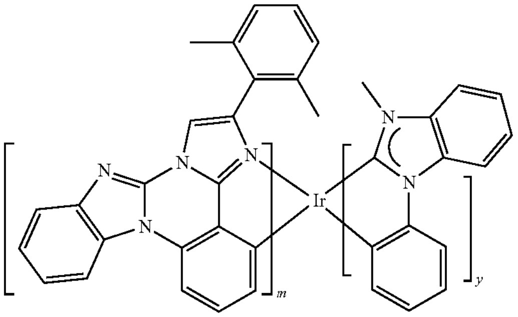
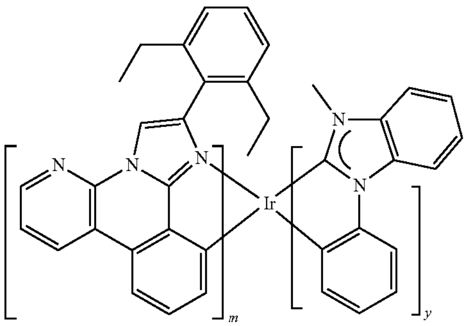
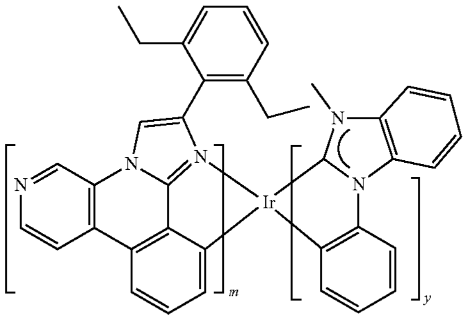
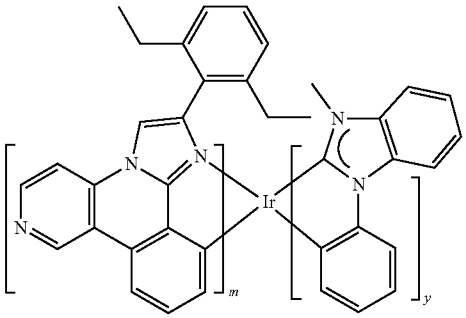
-continued
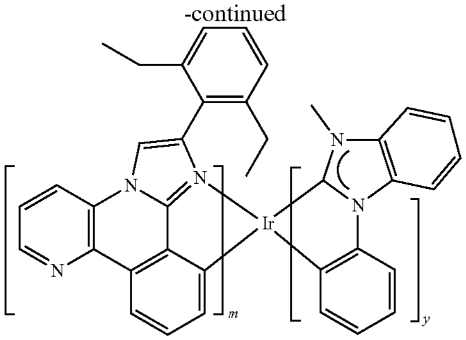
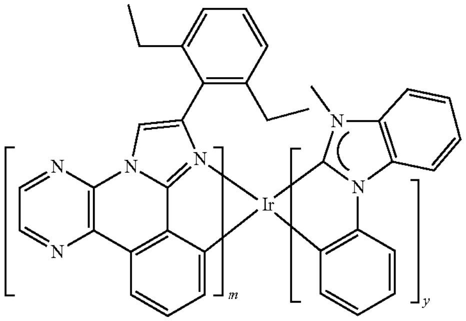
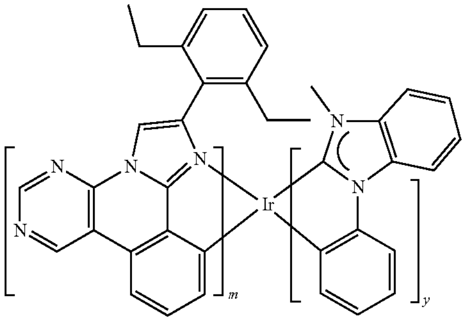
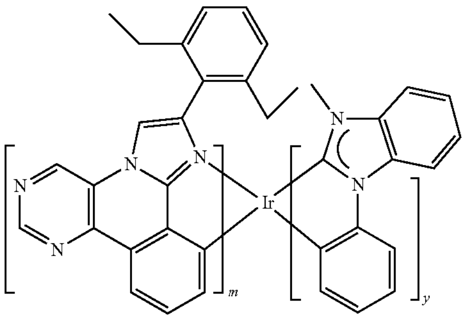
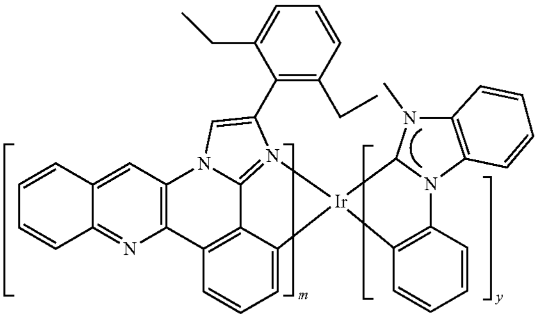

-continued
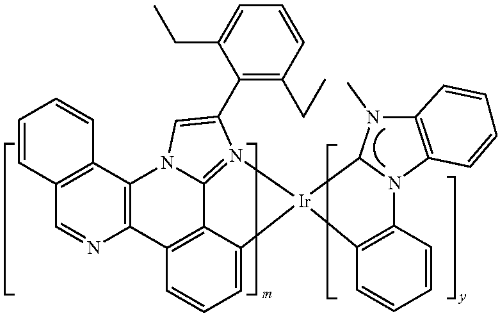
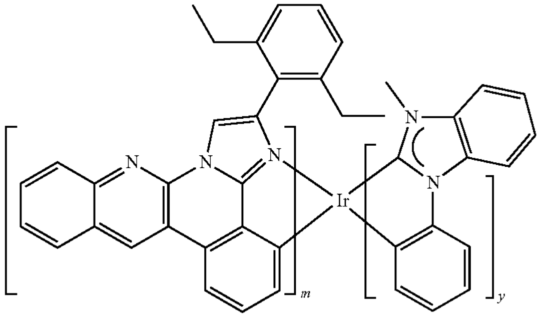
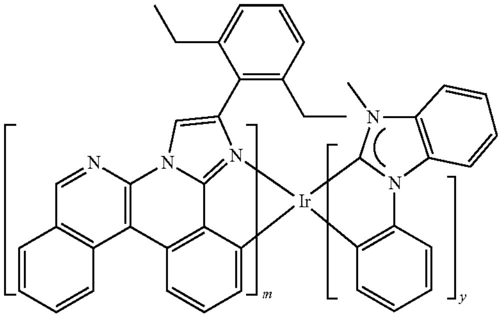
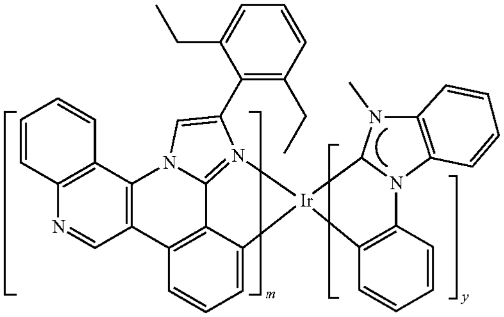
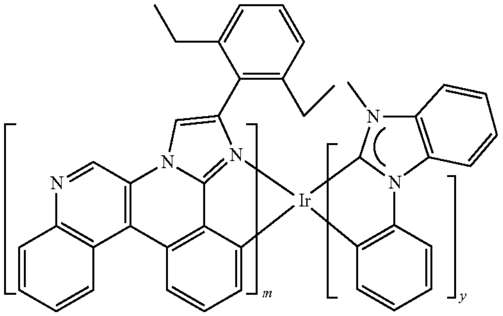
-continued
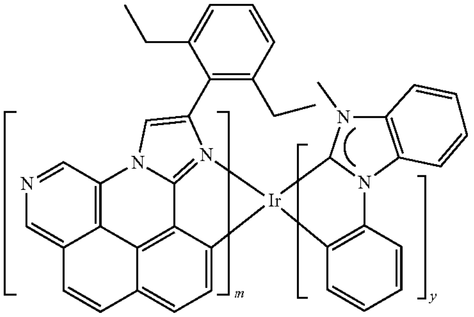
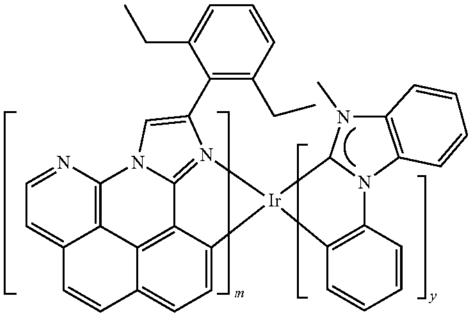
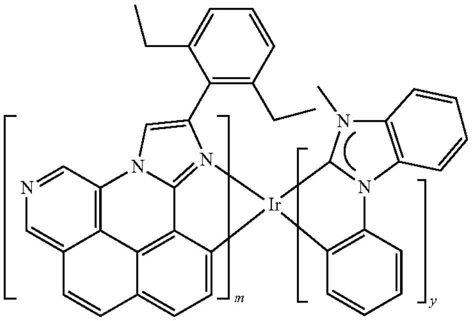
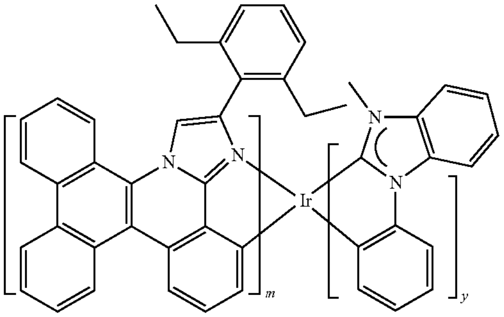
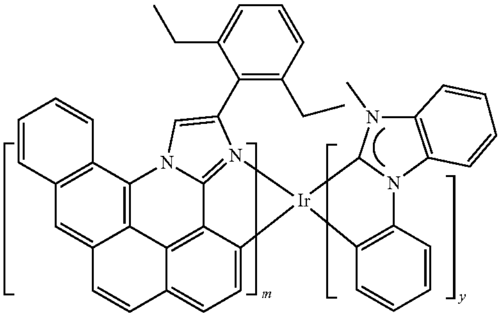

-continued
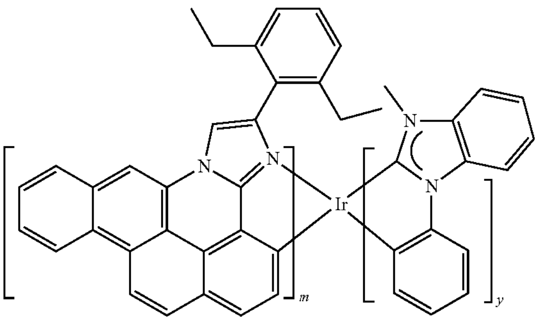
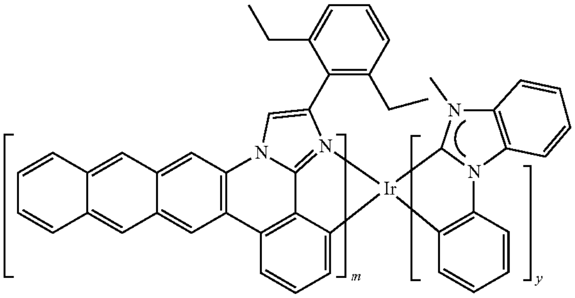
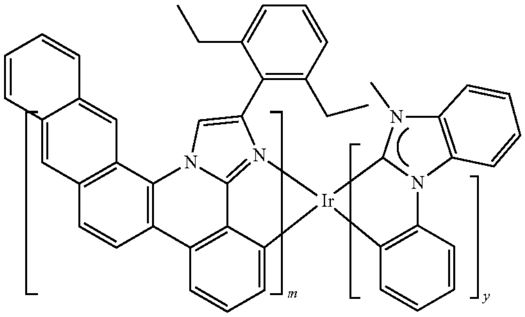
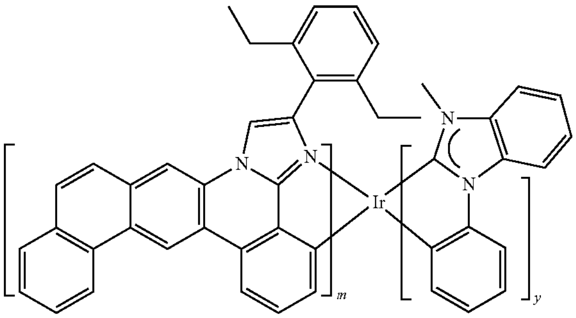
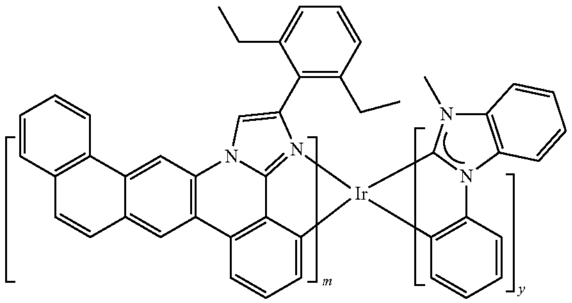
-continued
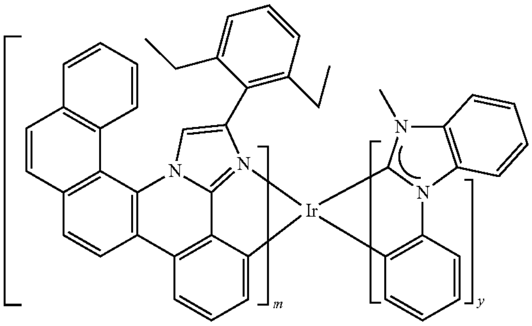
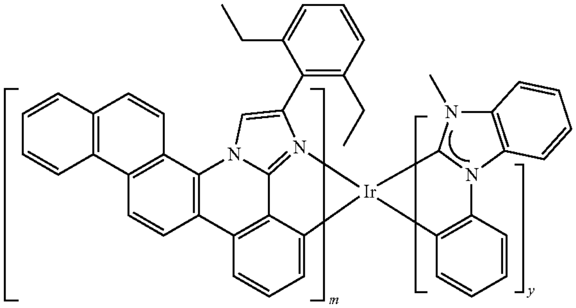
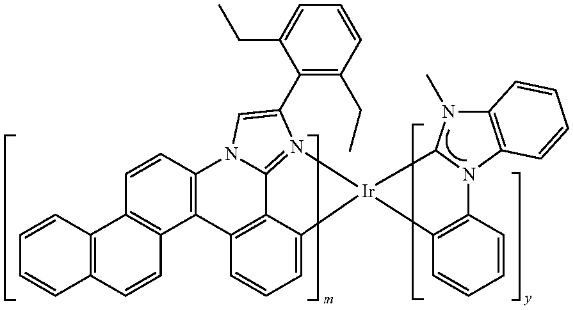
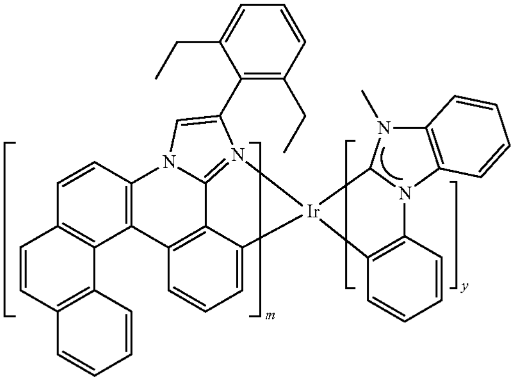
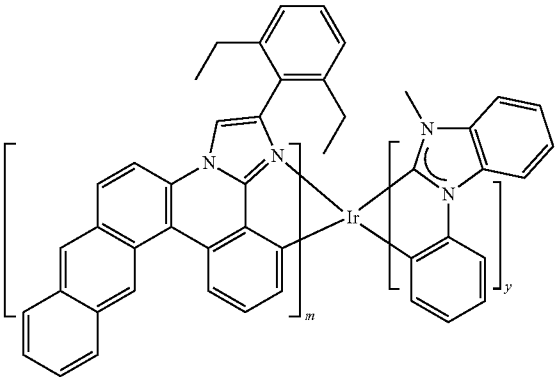

-continued
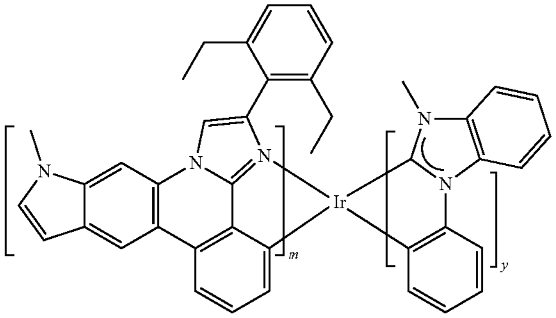
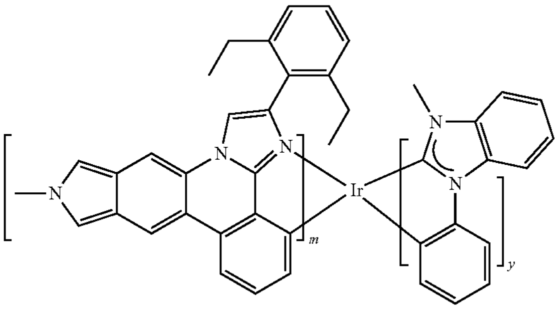
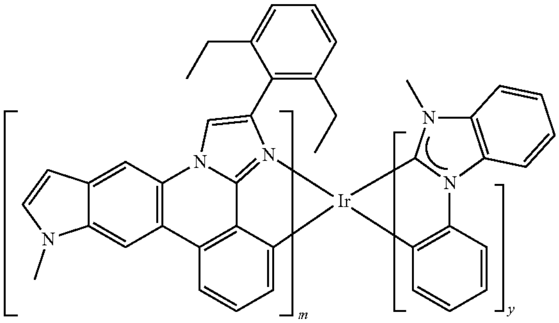
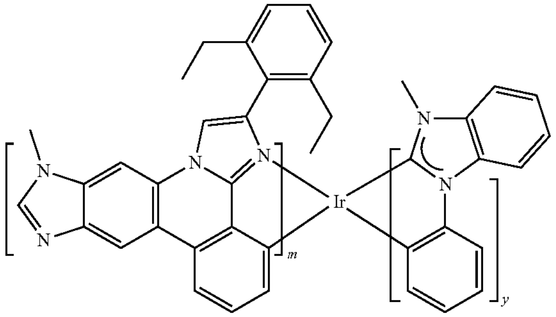
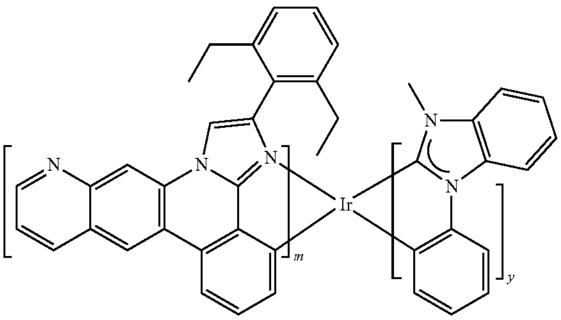
-continued
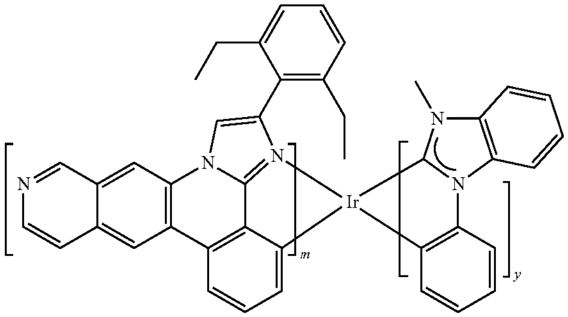
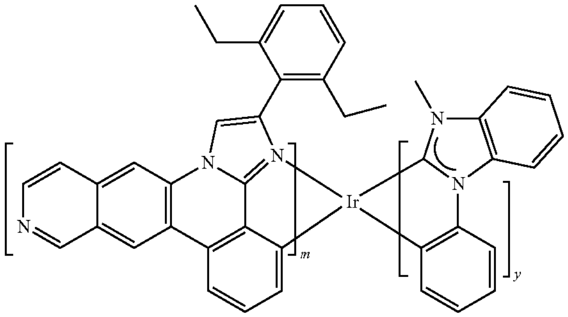
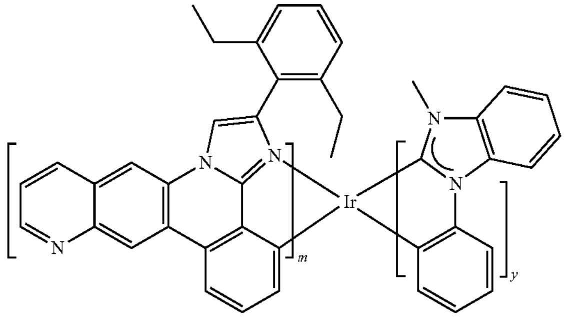
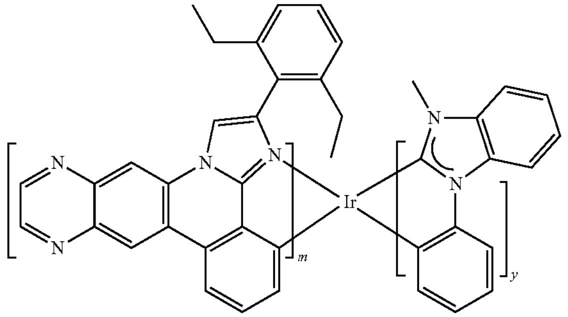
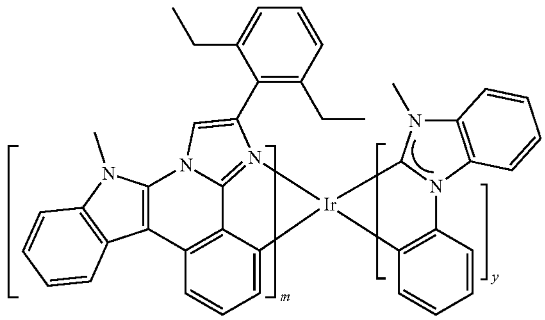

-continued
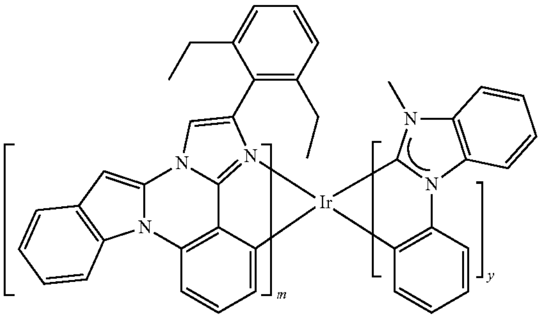
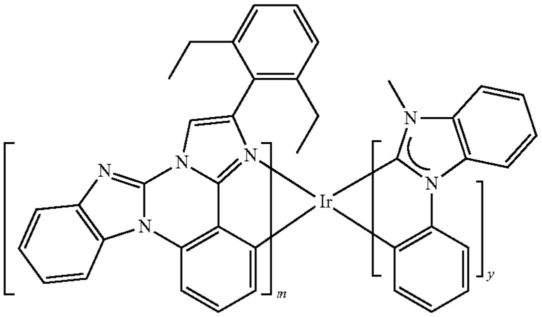
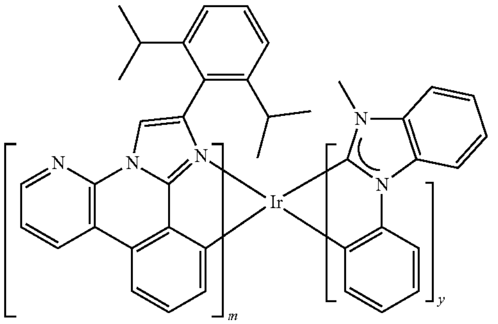
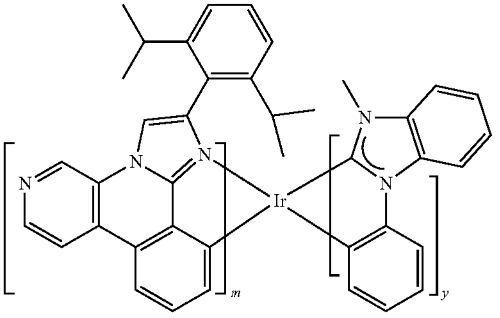
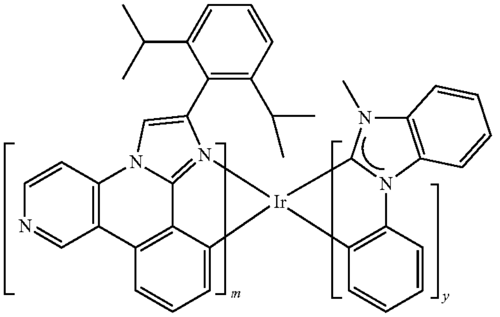
-continued
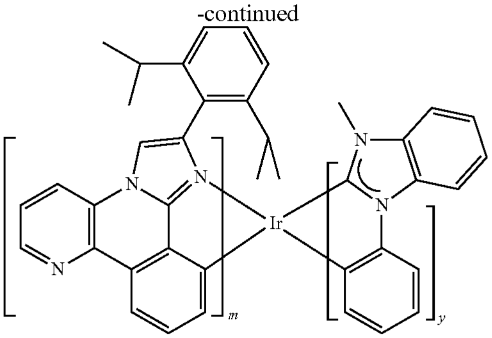
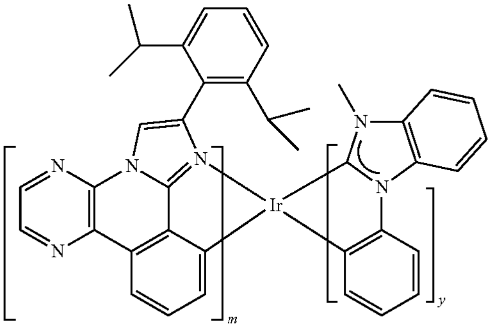
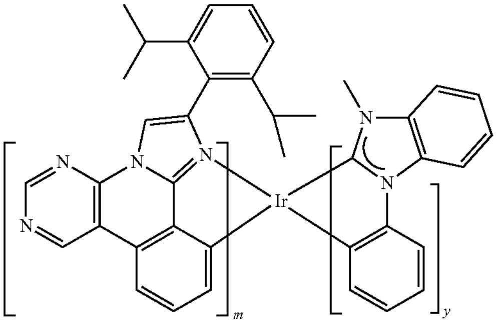
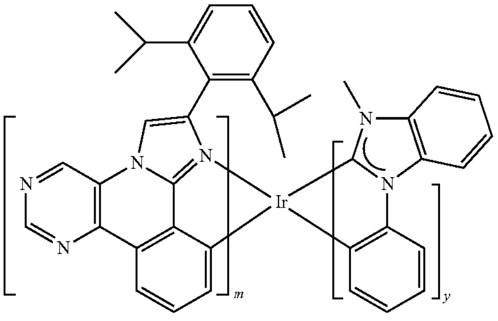
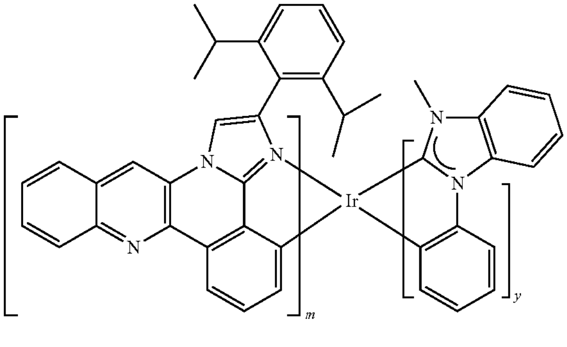

-continued
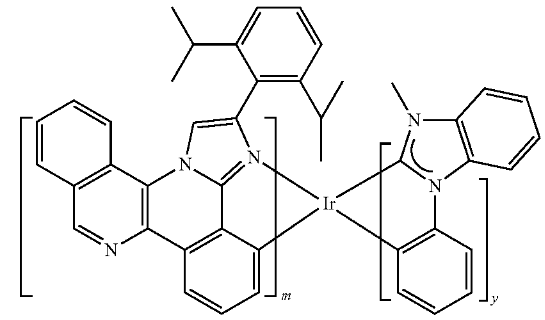
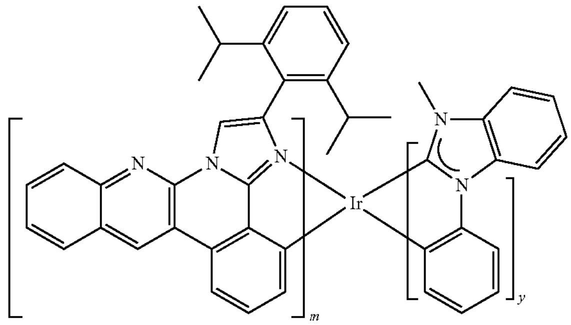
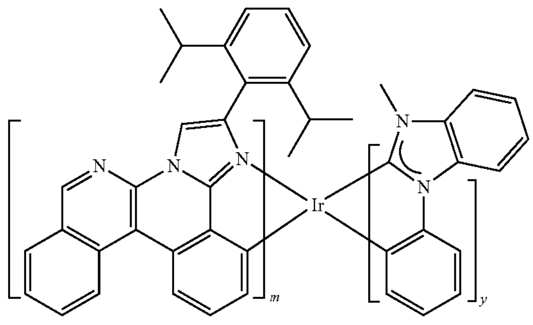
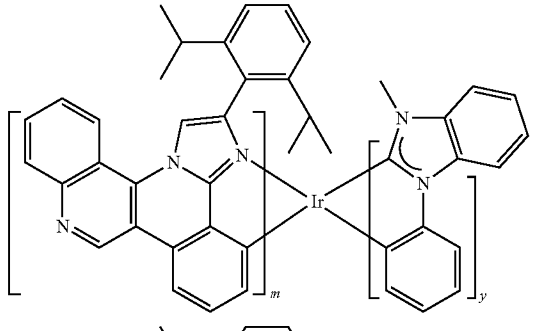
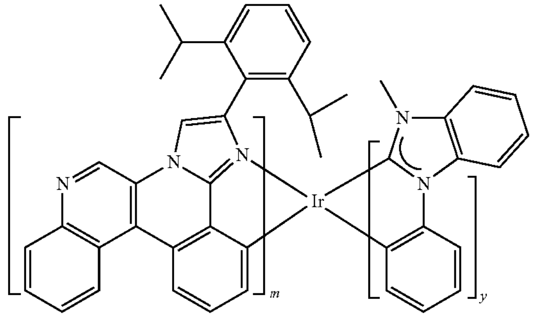
-continued
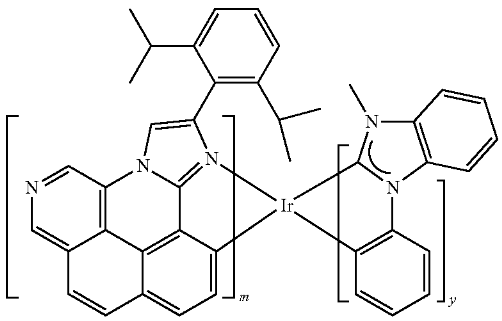
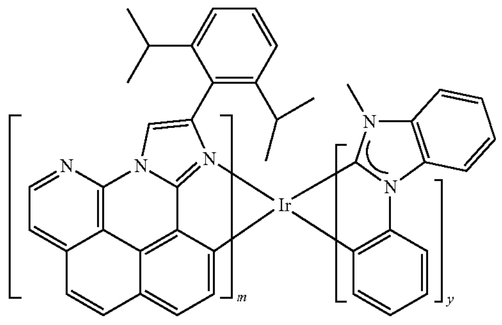
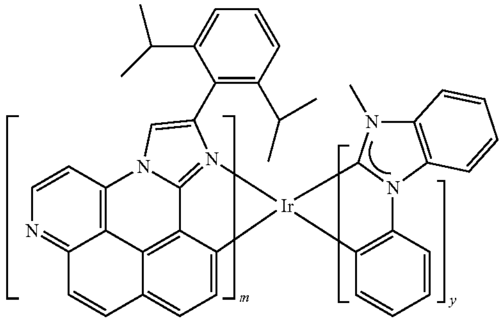
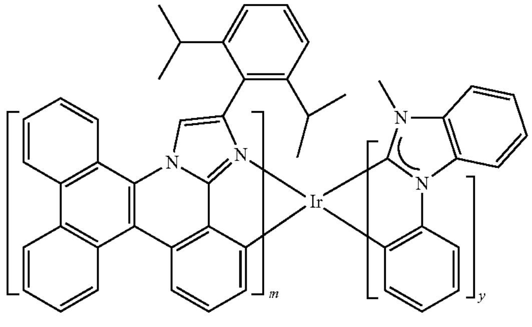
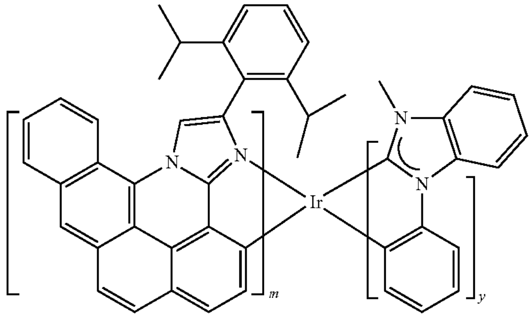

-continued
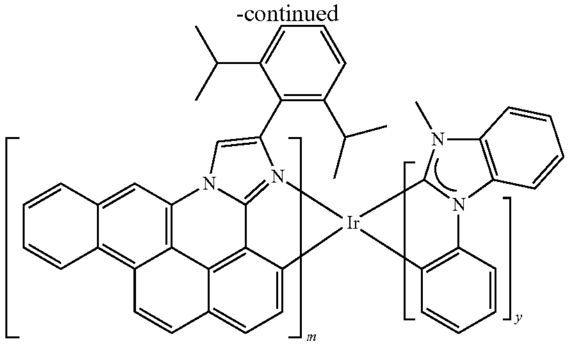
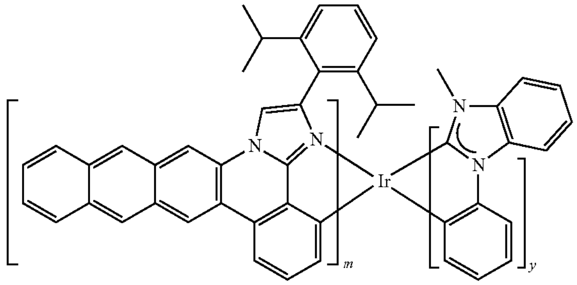
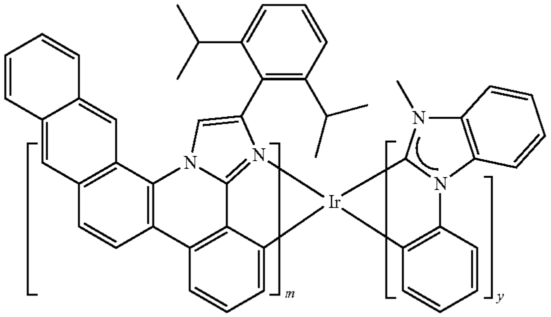
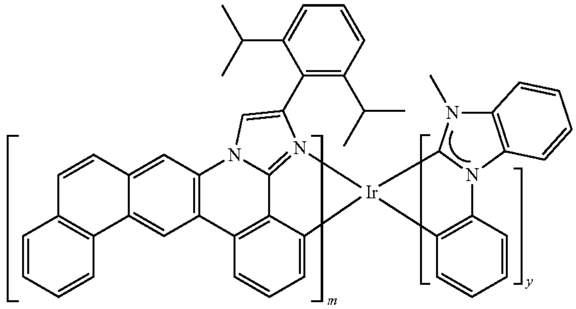
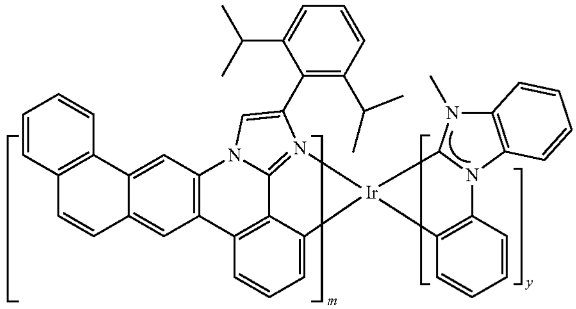
-continued
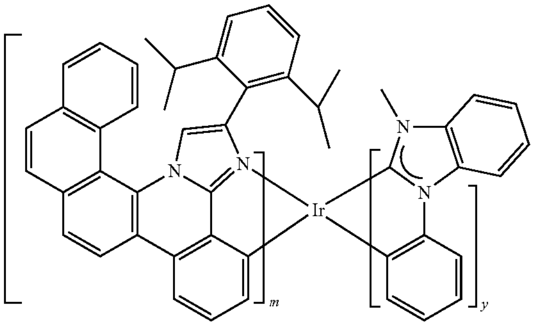
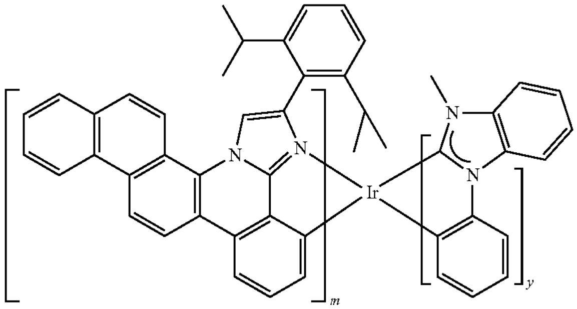
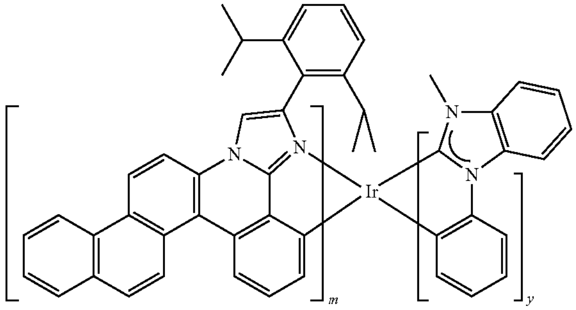
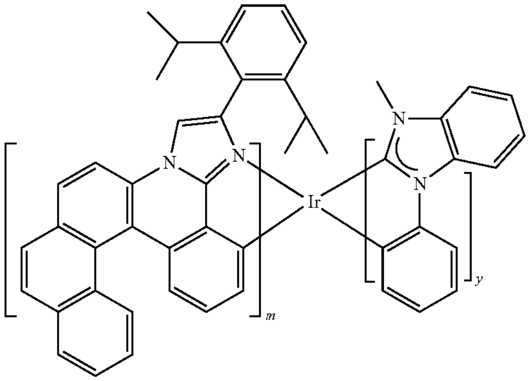
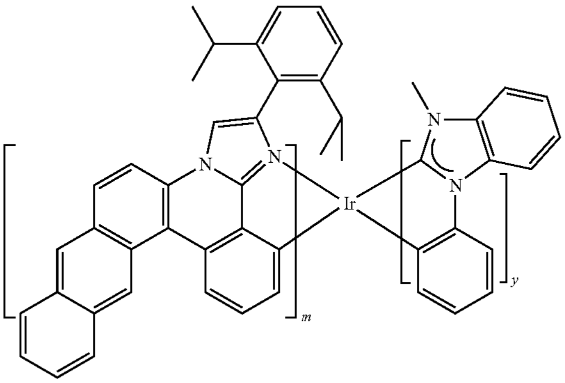

-continued
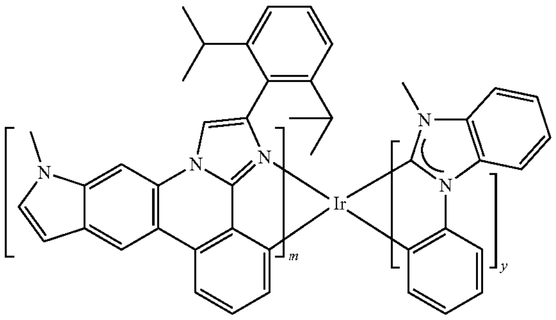
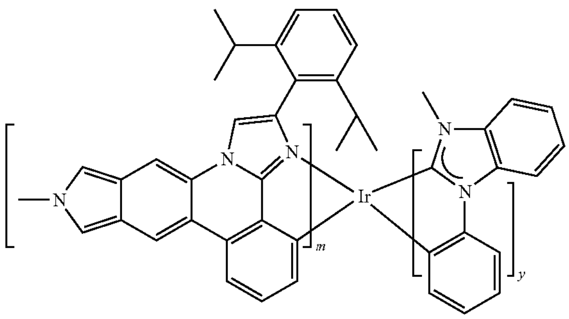
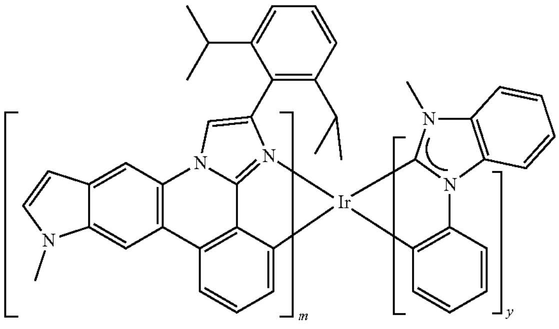
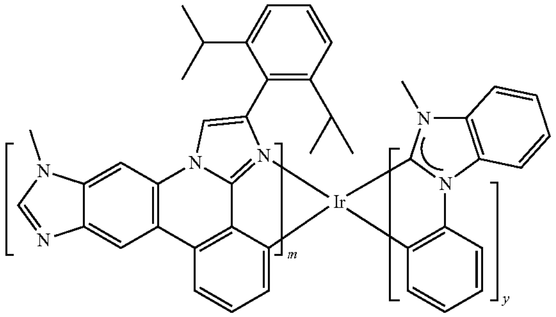
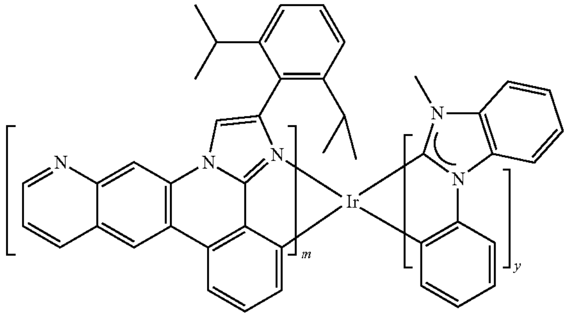
-continued
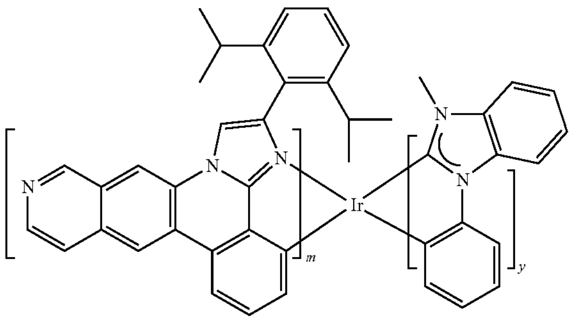
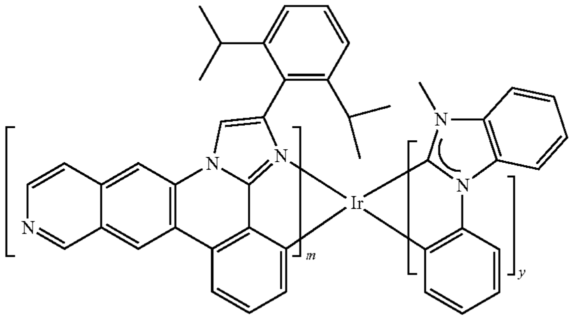
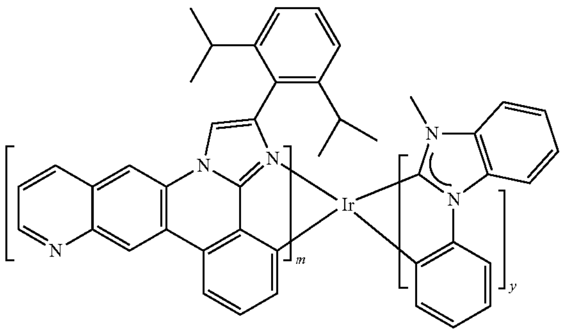
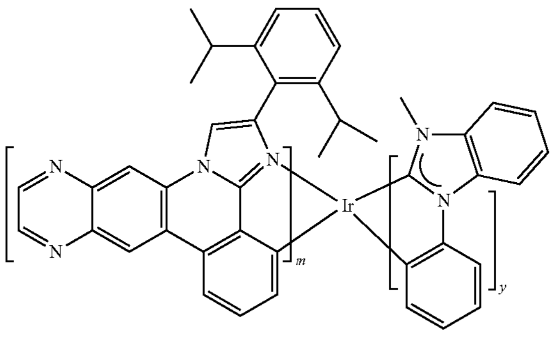
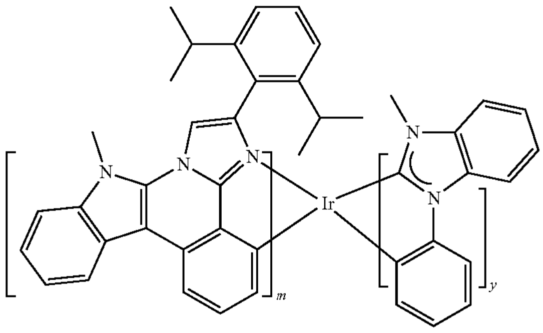

-continued
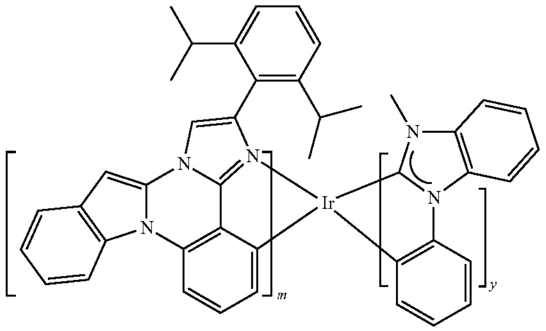
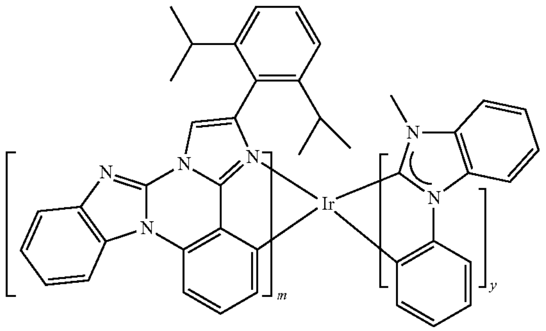
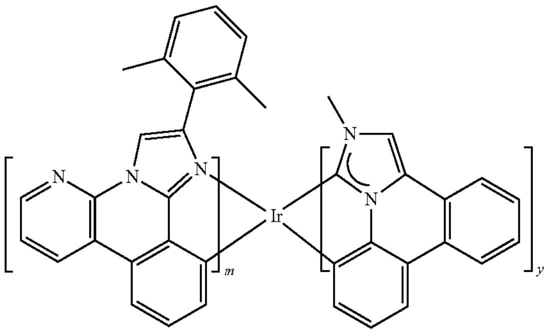
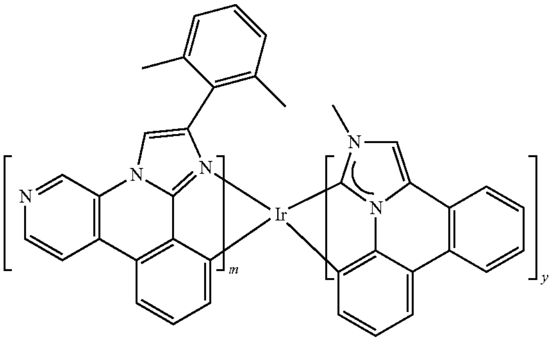
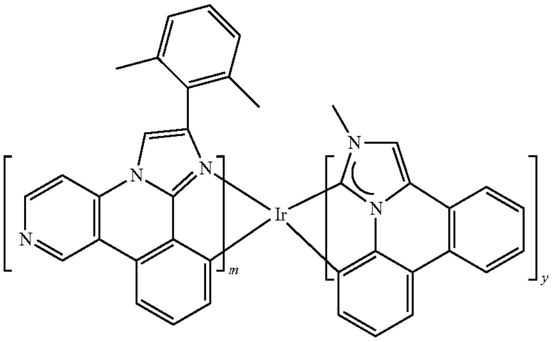
-continued
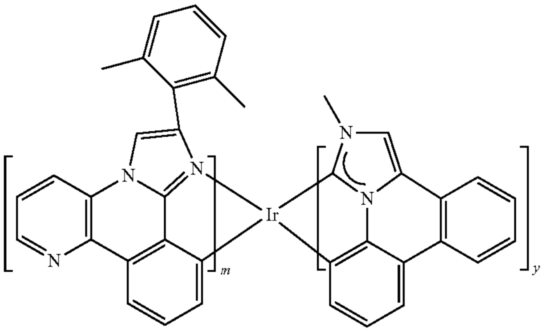
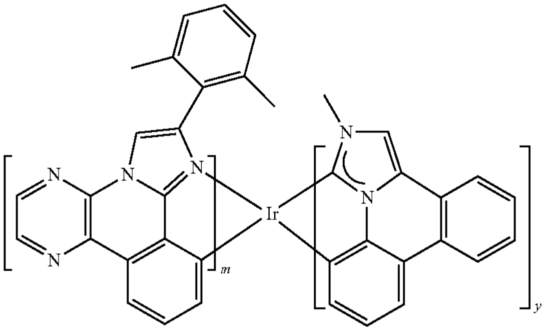
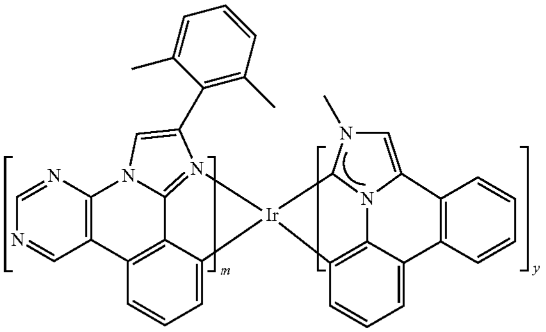
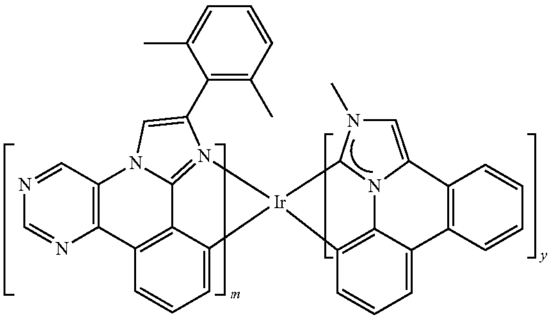
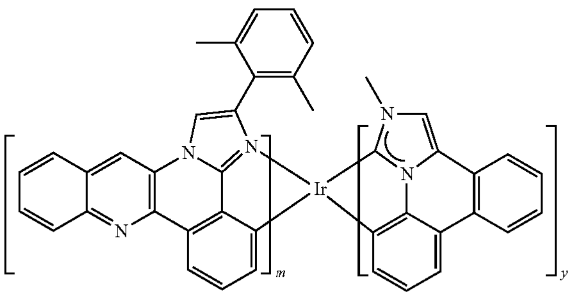

-continued
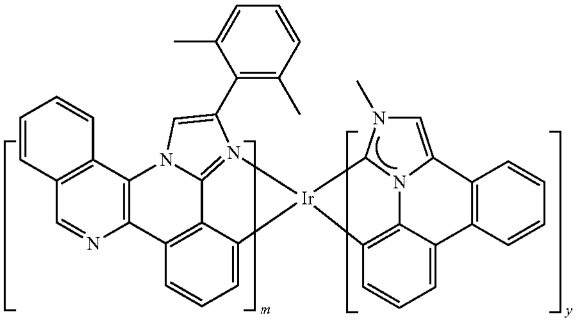
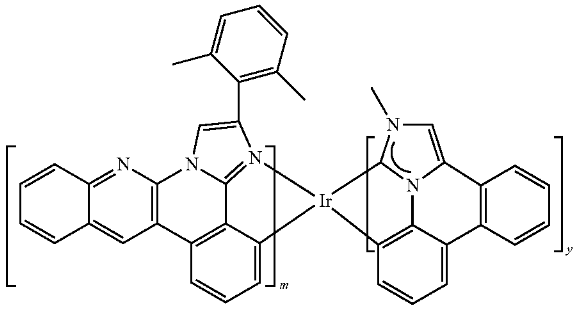
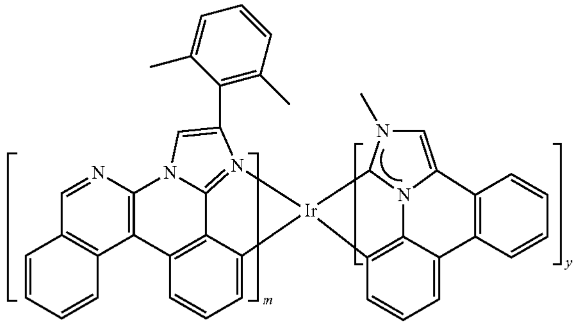
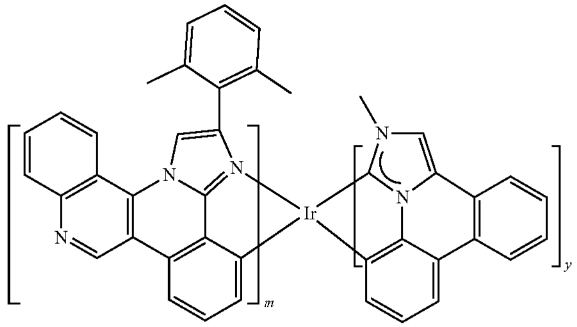
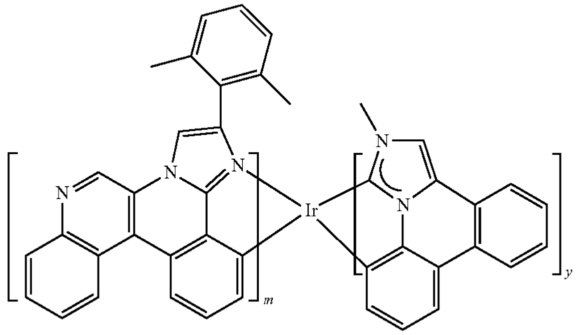
-continued
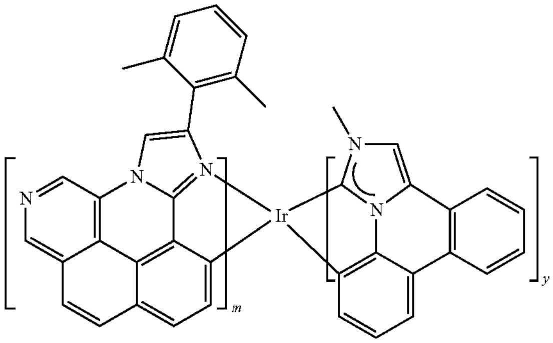
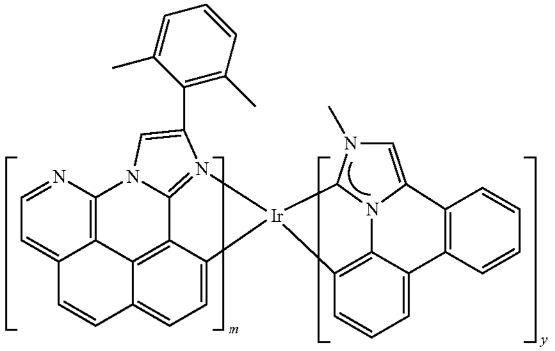
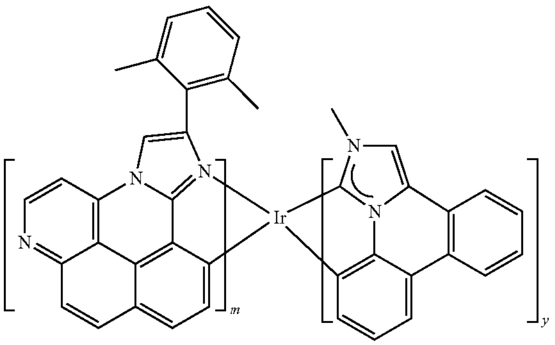
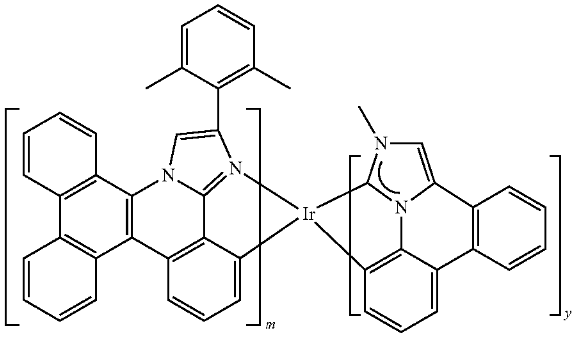
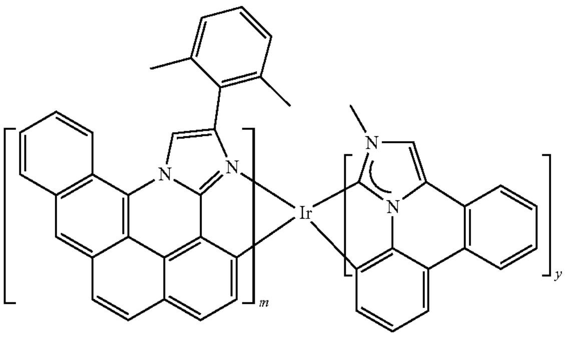

-continued
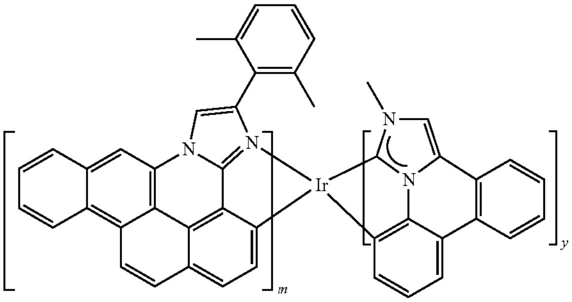
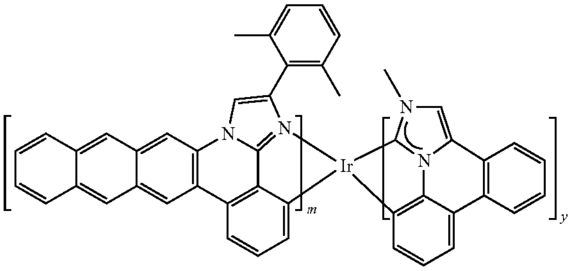
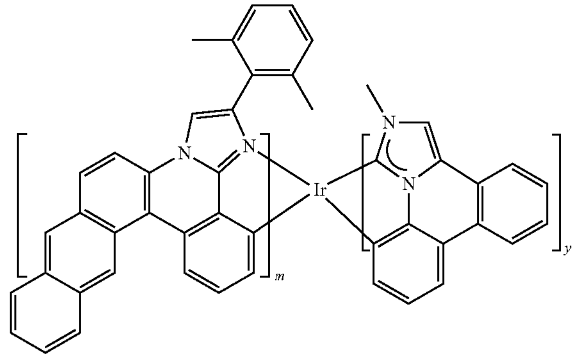
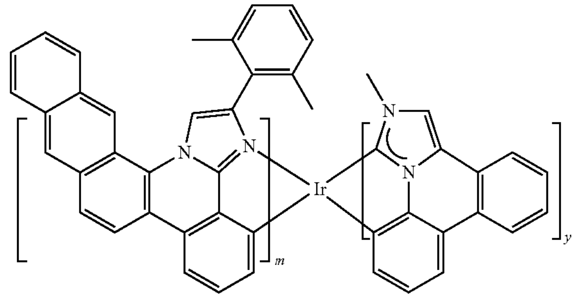
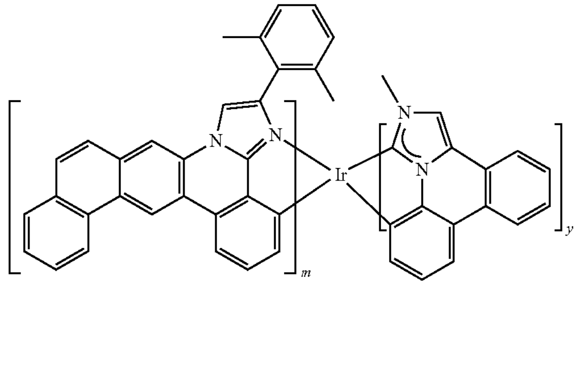
-continued
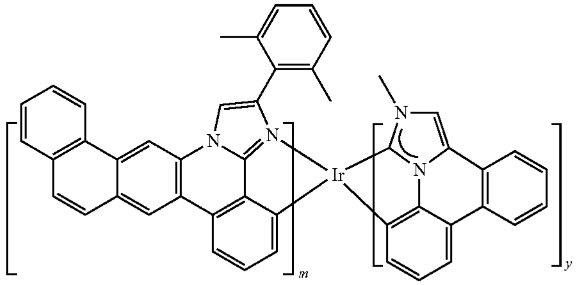
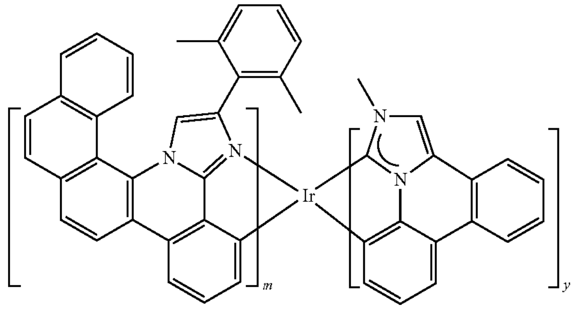
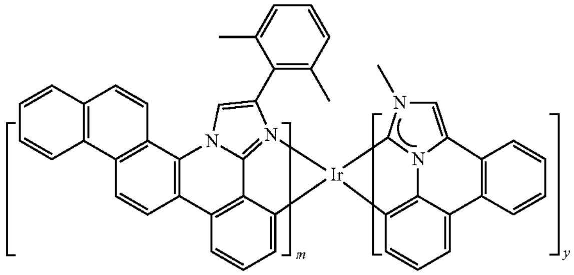
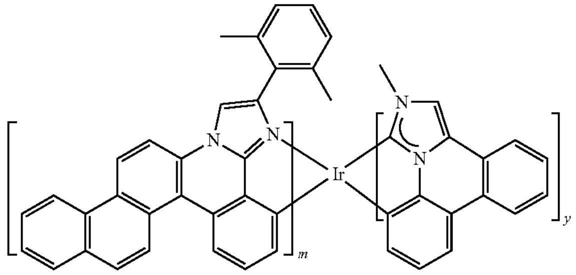
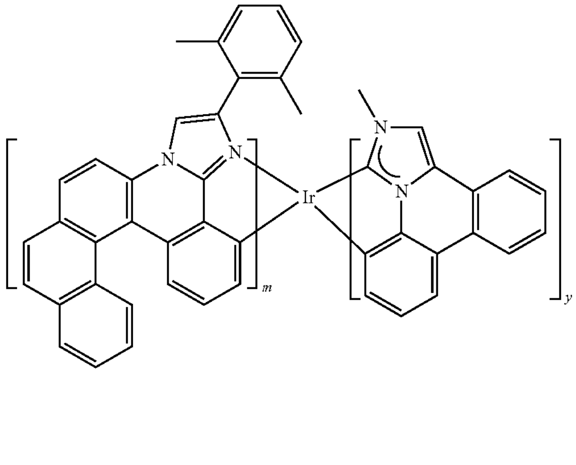

-continued
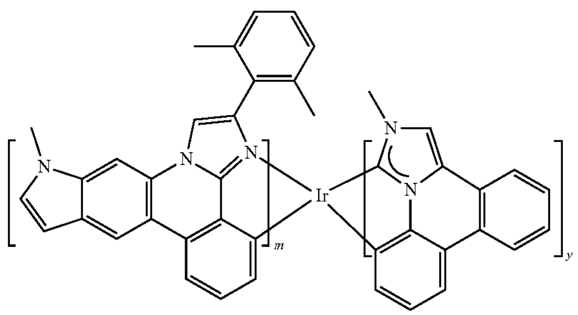
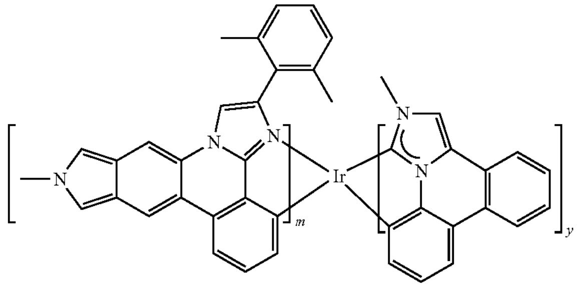
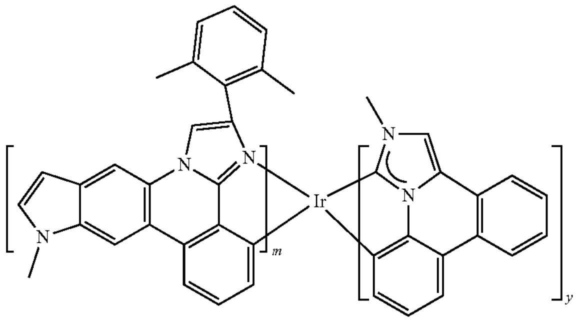
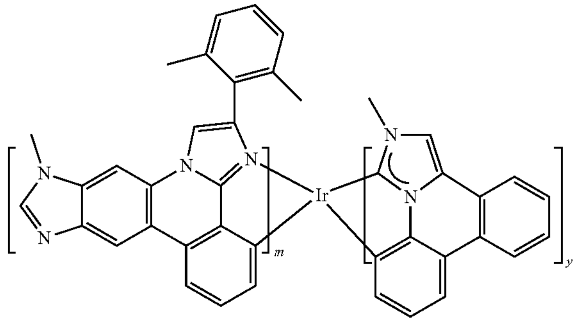
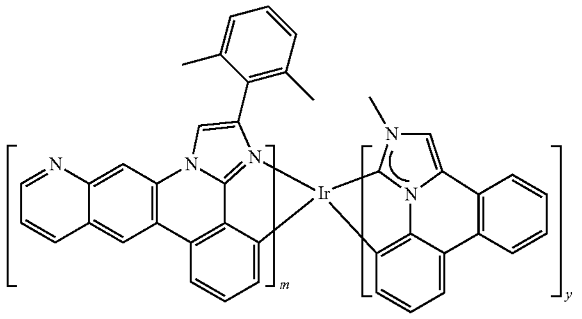
-continued
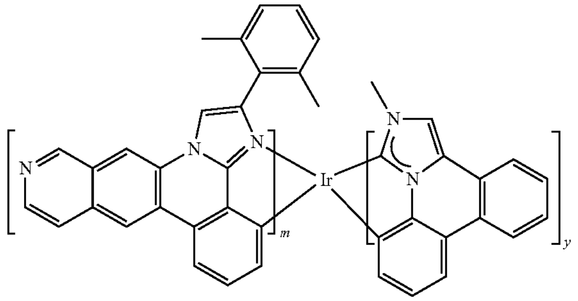
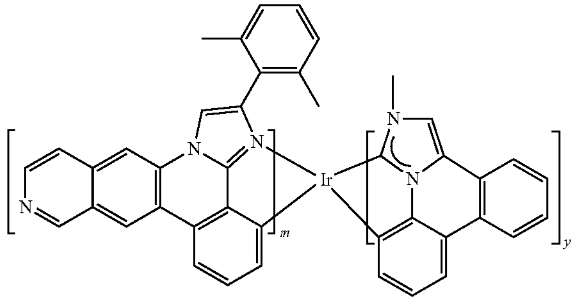
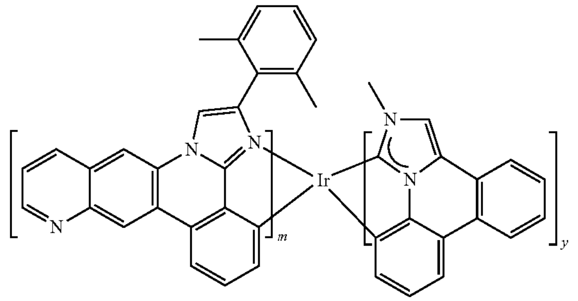
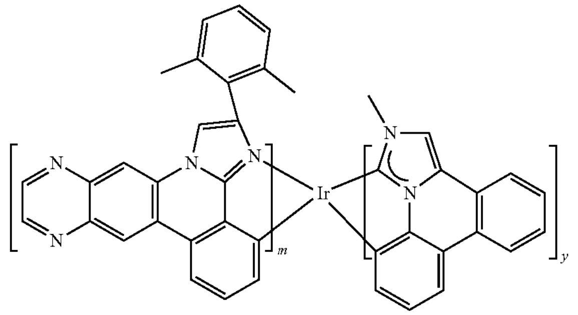
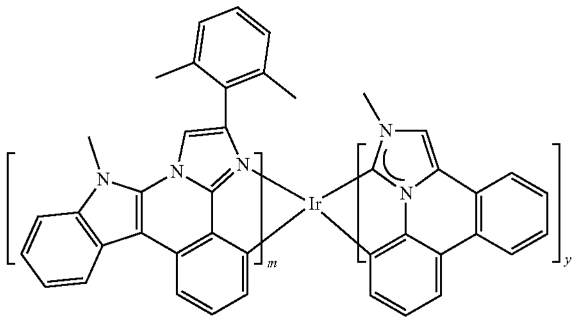

-continued
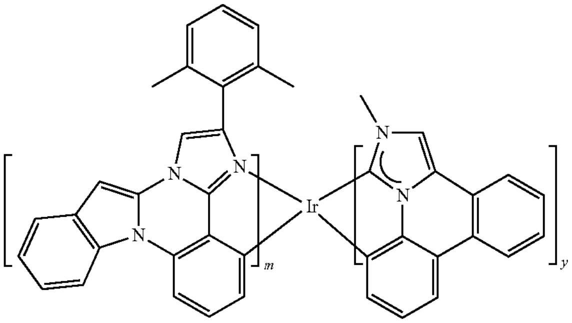
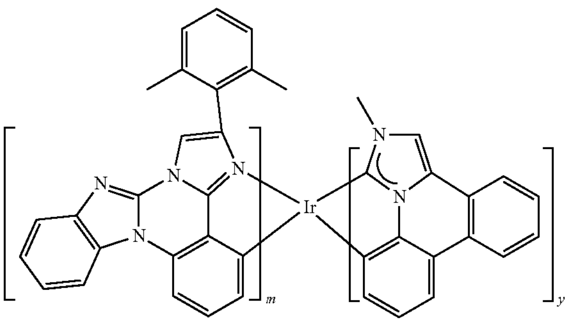
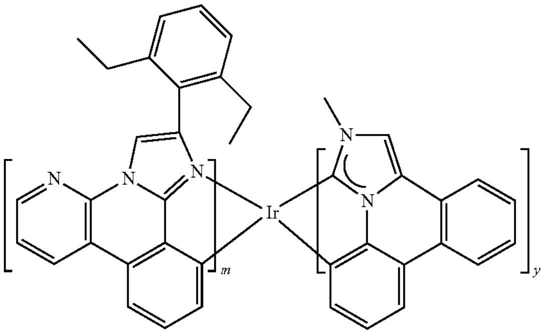
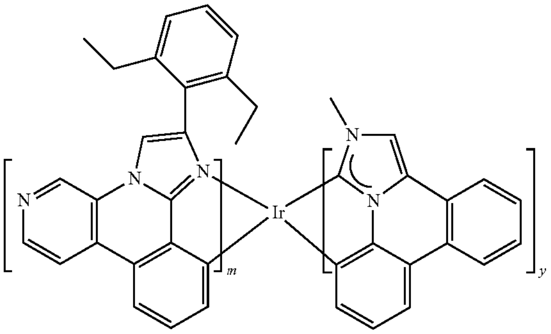
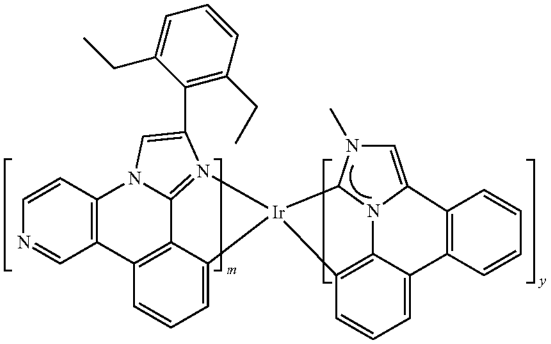
-continued
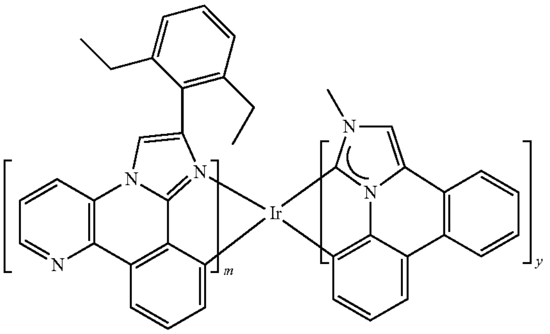
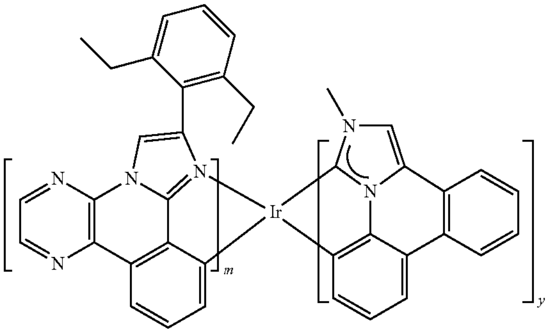
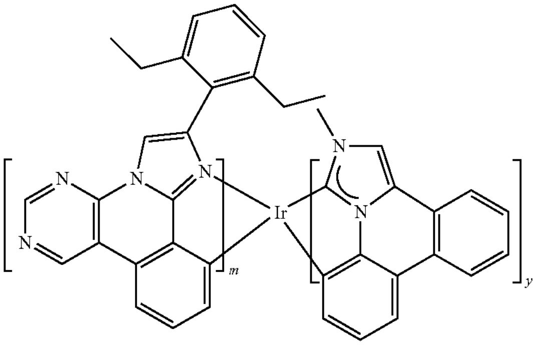
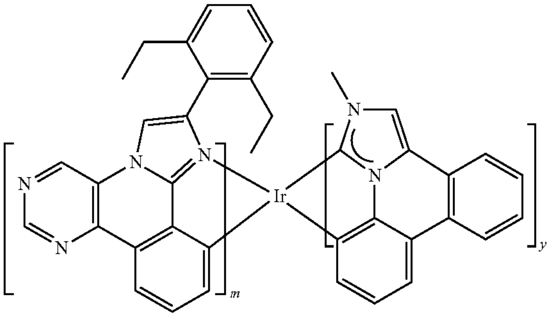
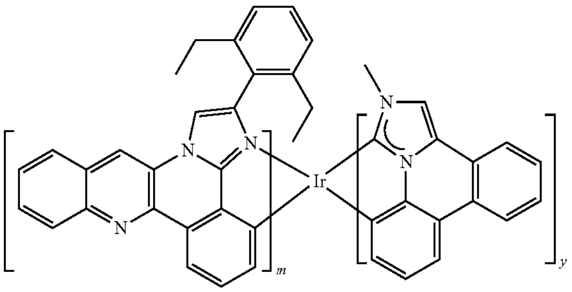

-continued
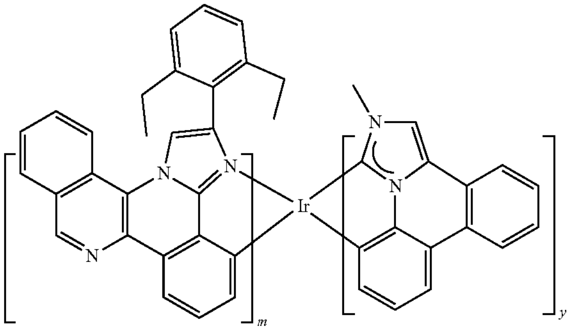
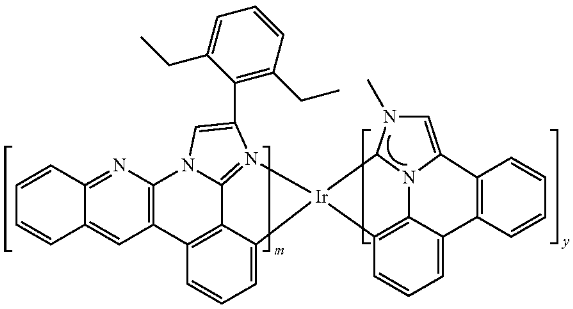
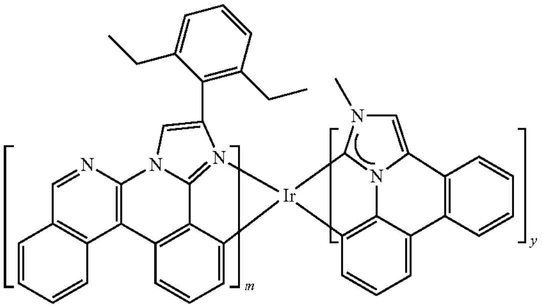
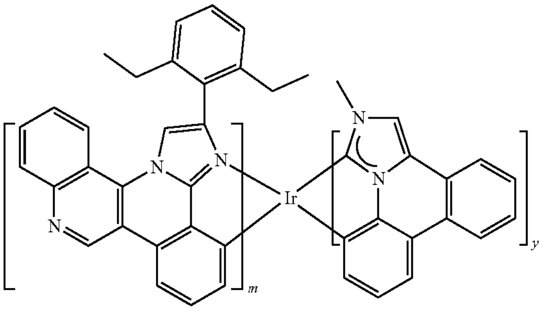
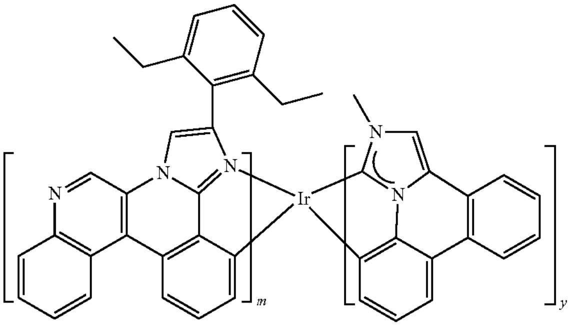
-continued
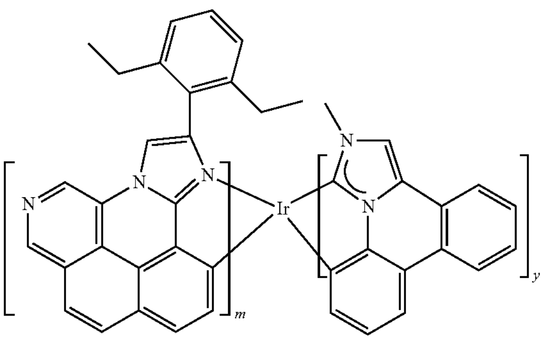
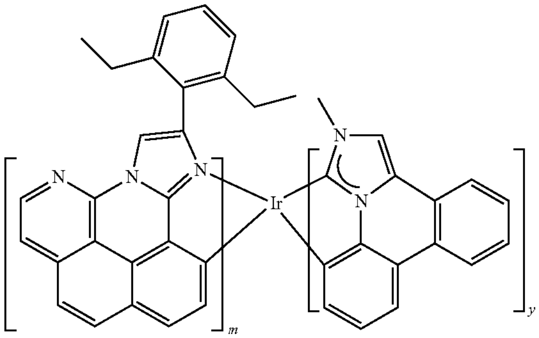
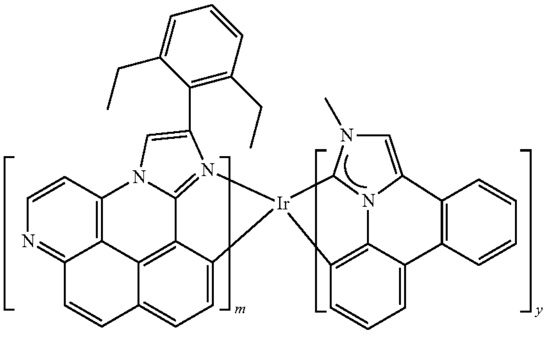
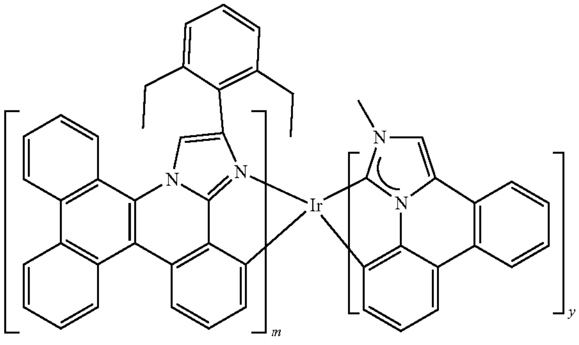
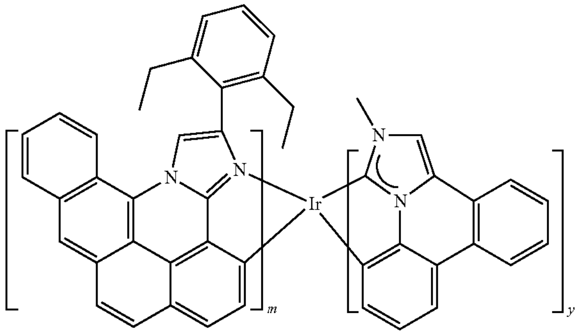

-continued
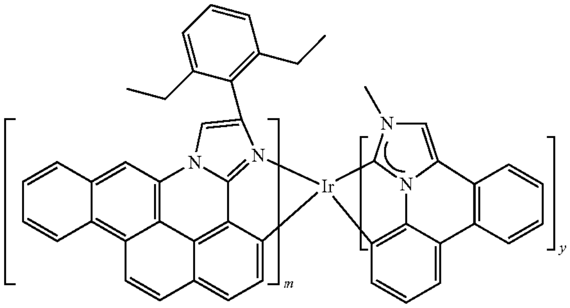
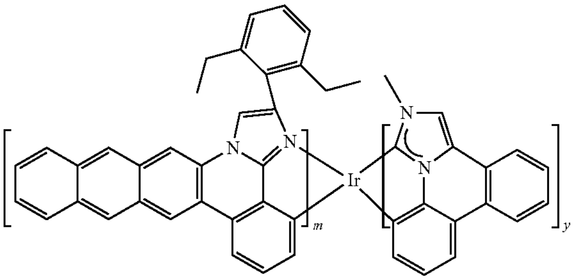
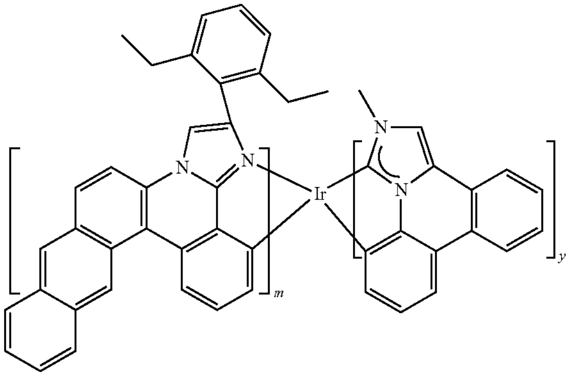
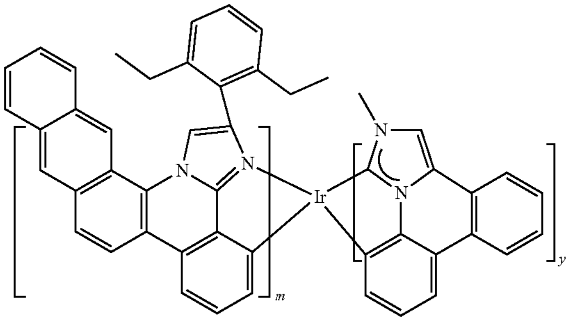
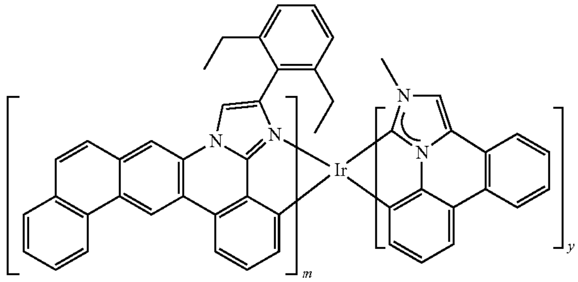
-continued
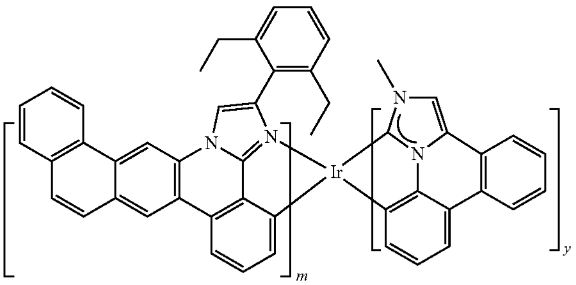
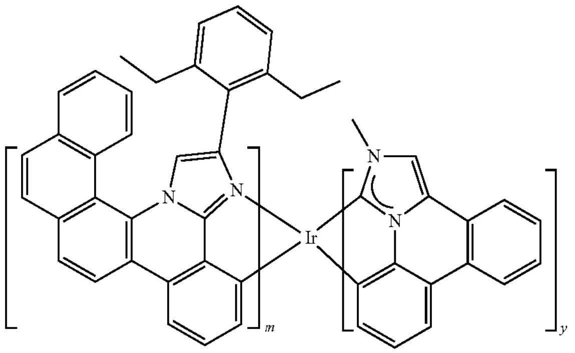
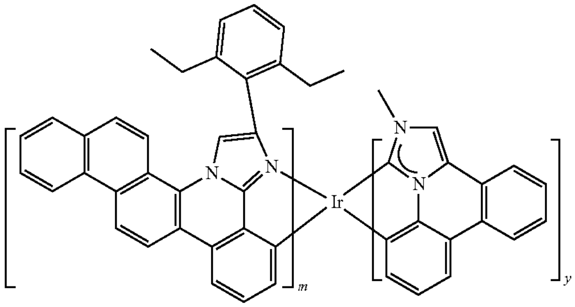
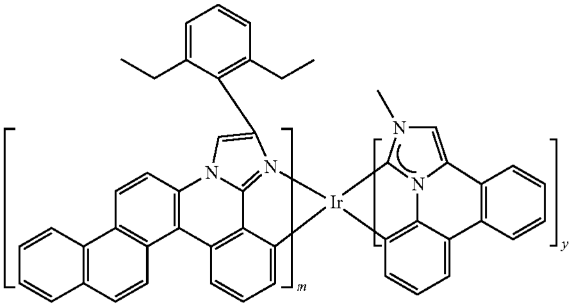
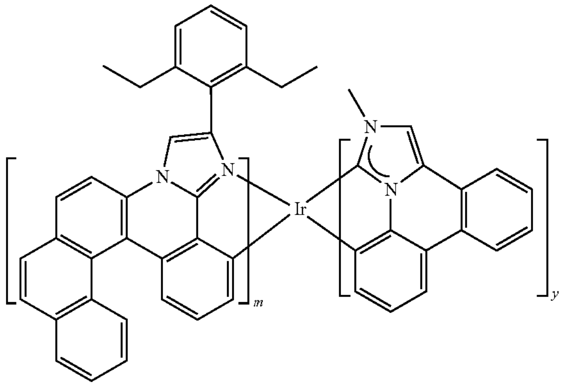

-continued
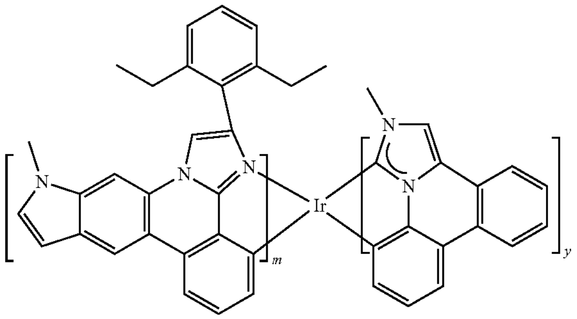
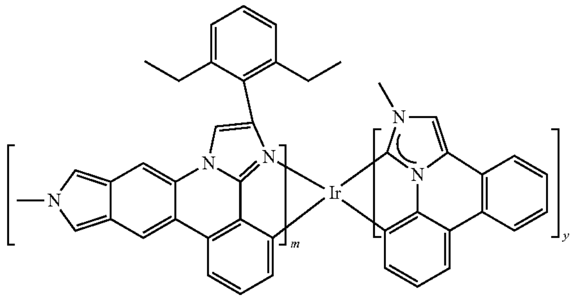
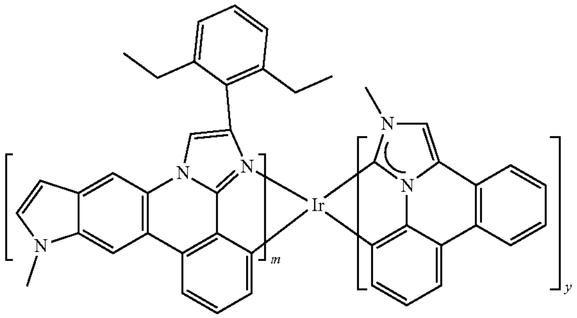
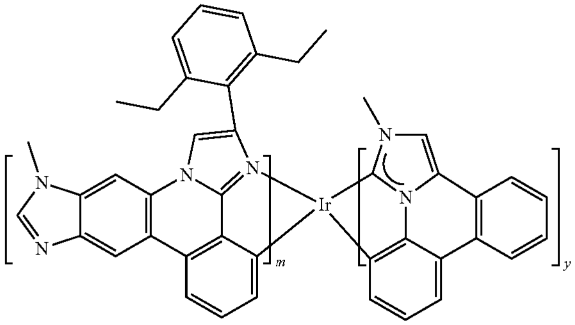
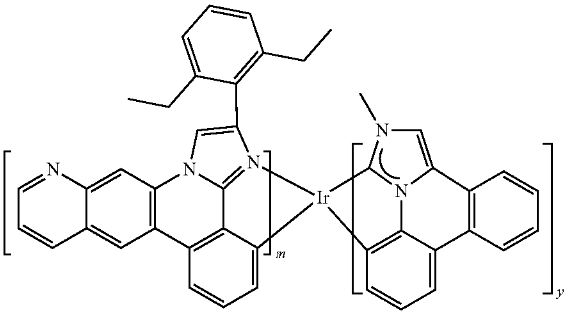
-continued
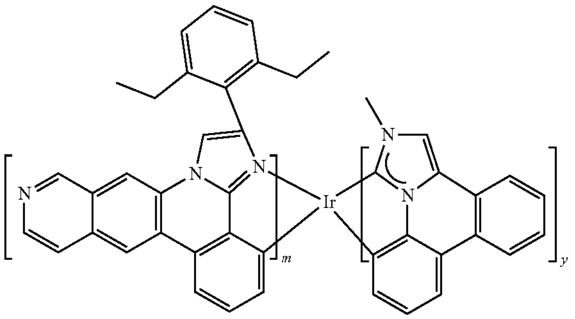
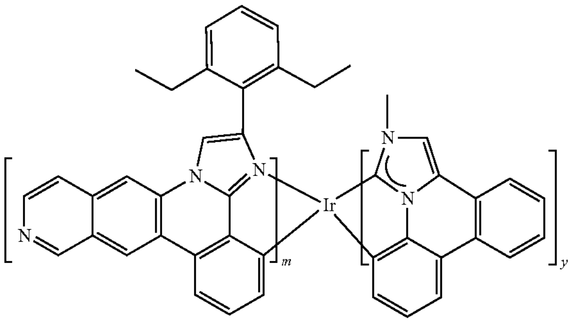
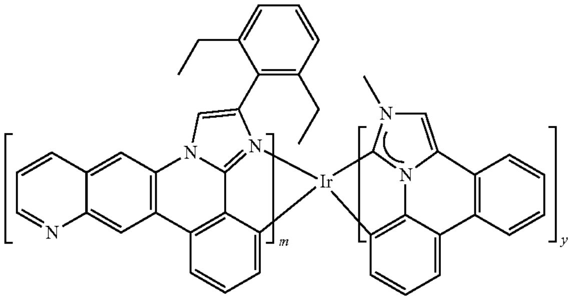
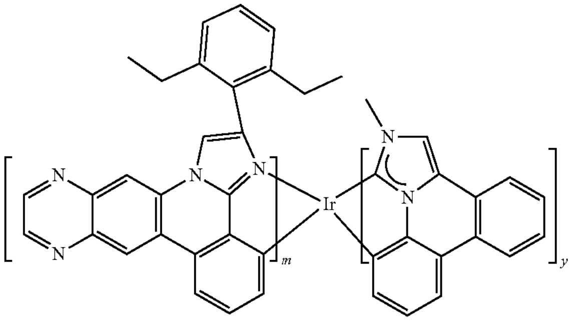
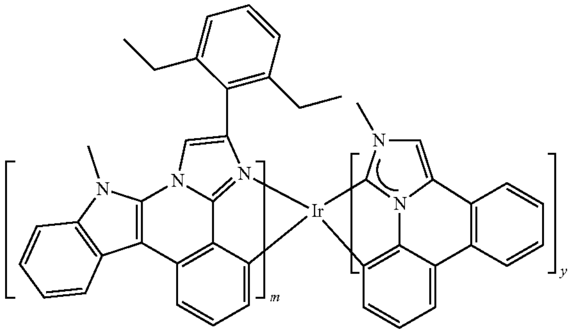

-continued
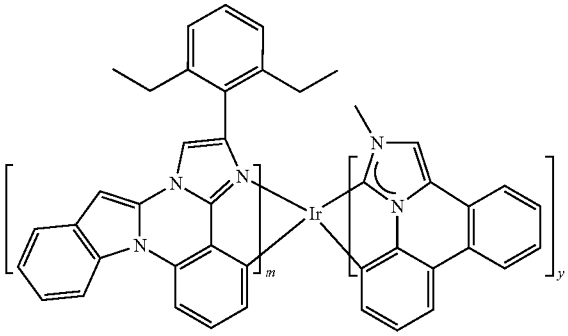
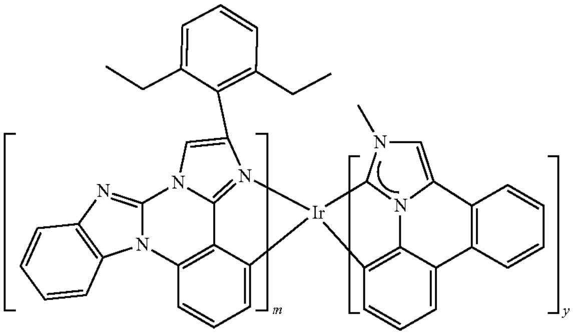
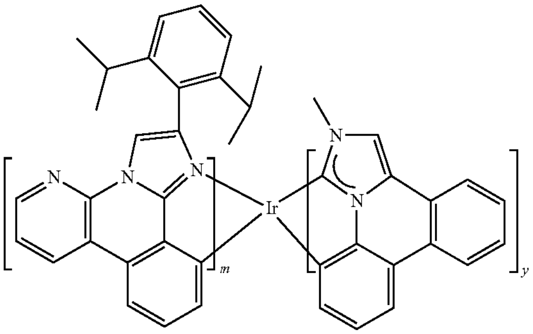
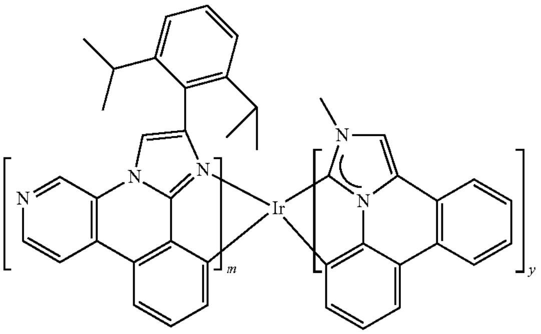
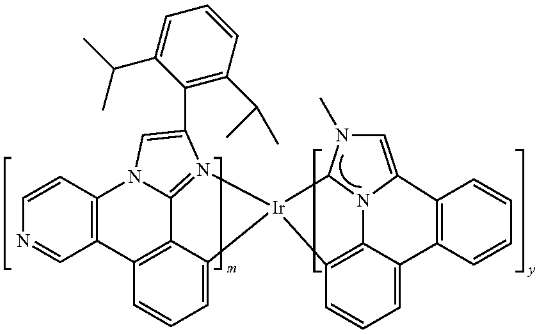
-continued
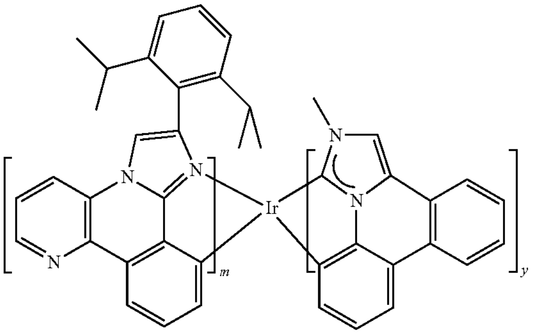
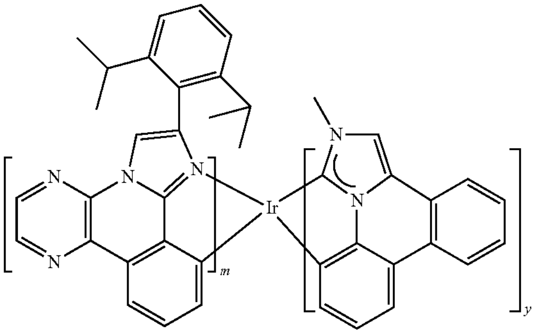
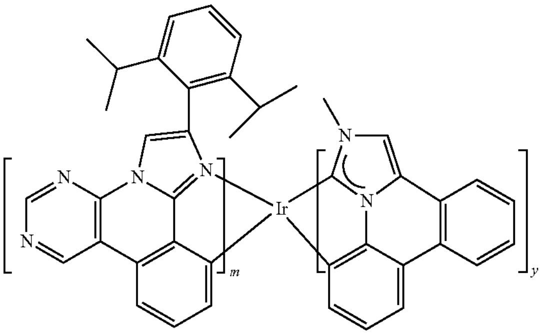
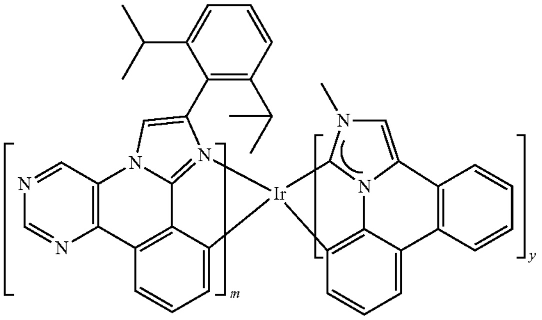
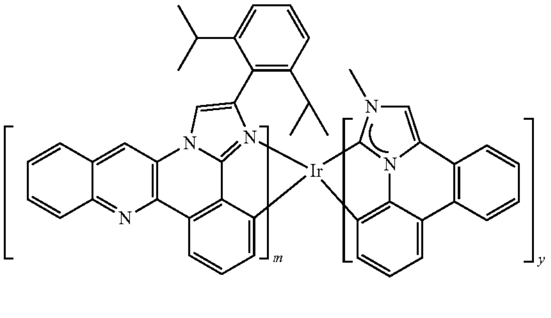

-continued
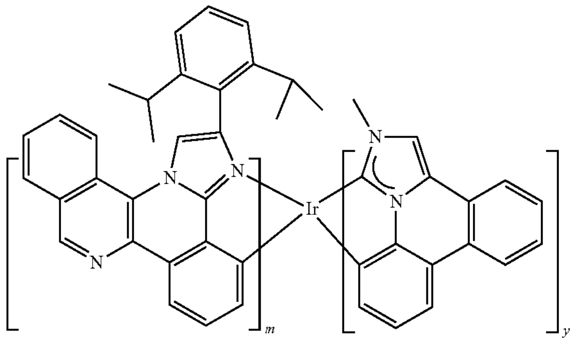
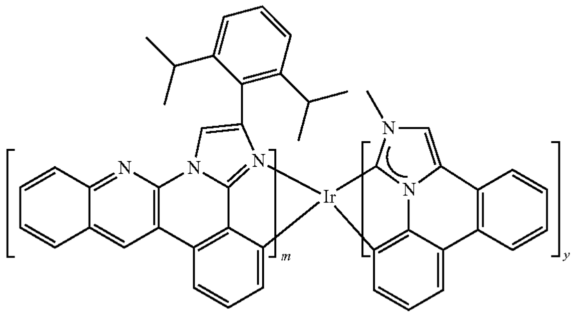
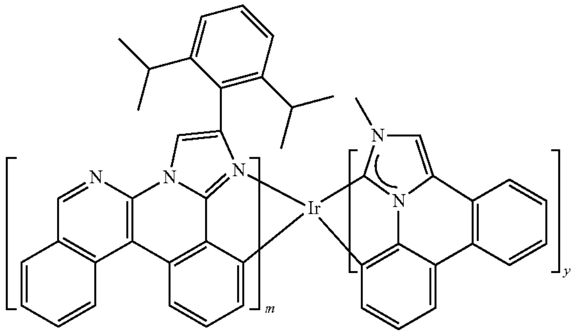
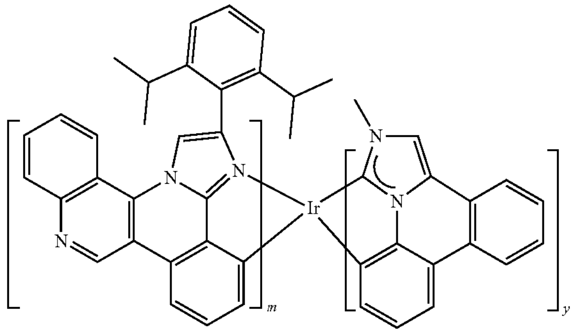
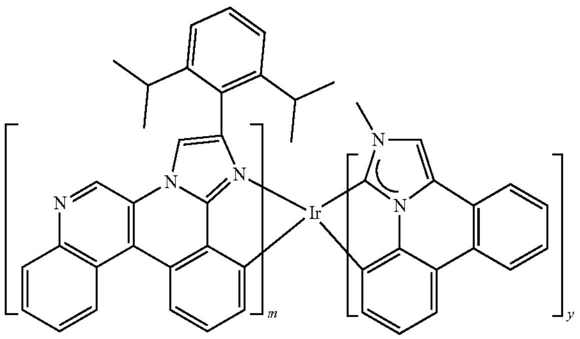
-continued
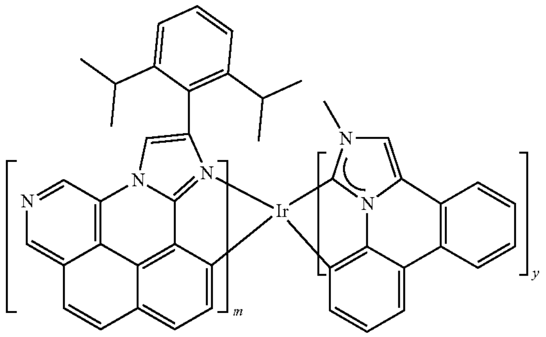
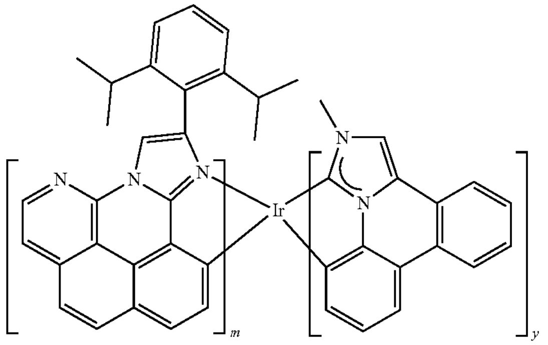
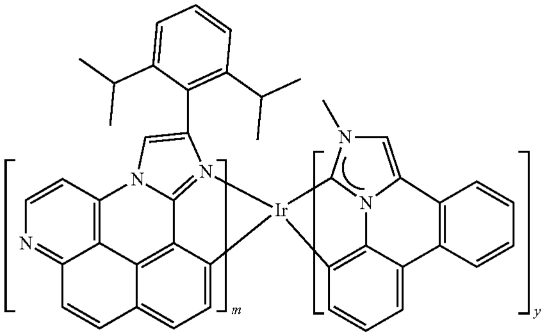
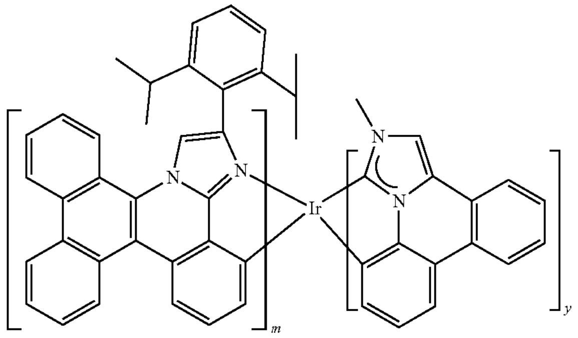
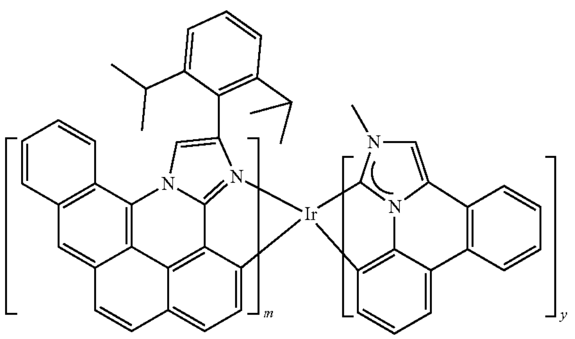

-continued
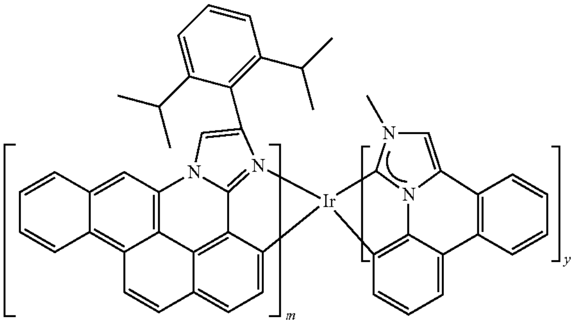
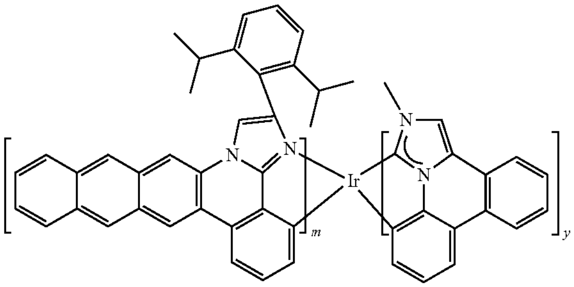
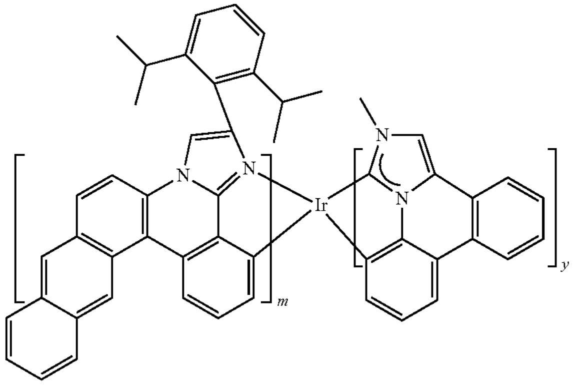
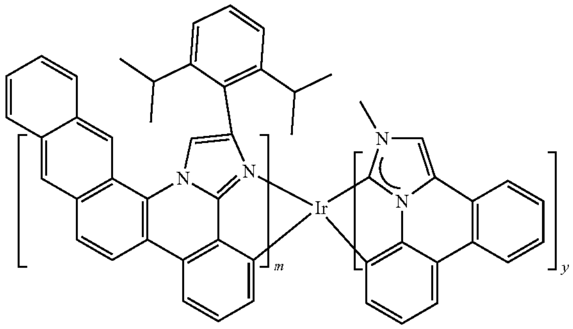
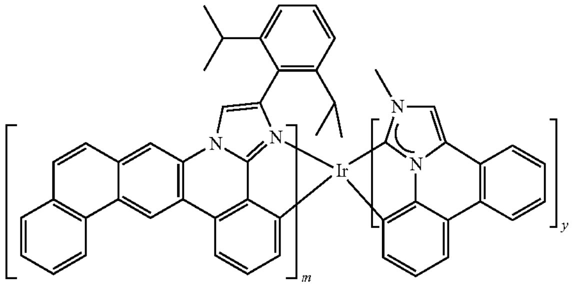
-continued
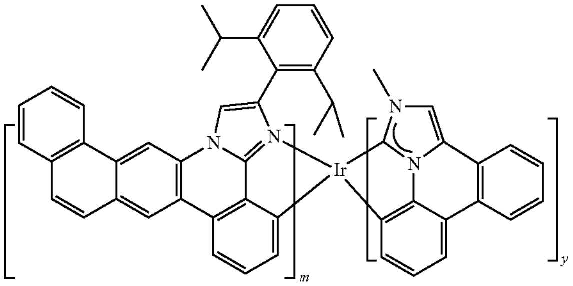
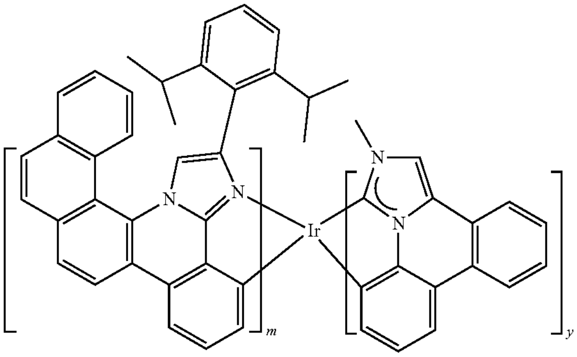
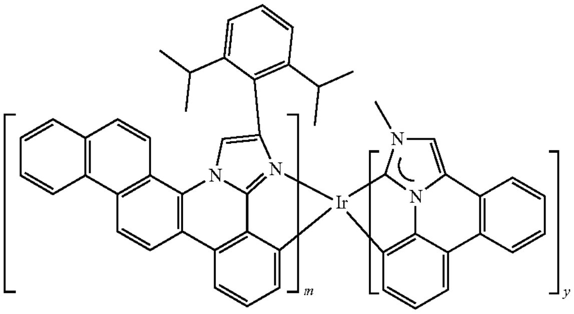
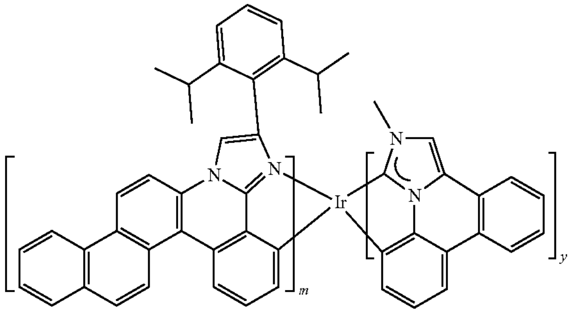
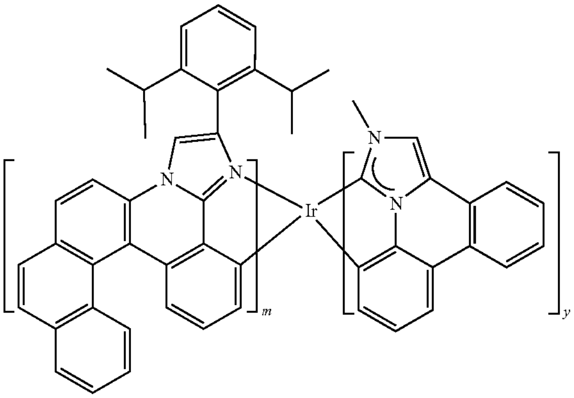

-continued
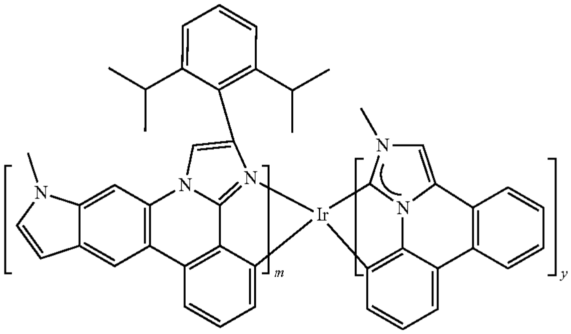
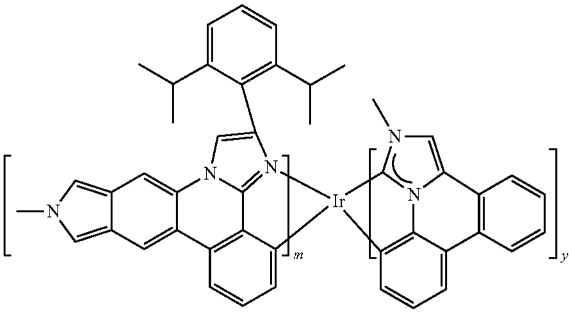
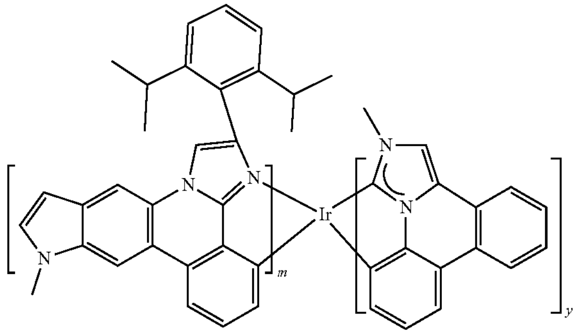
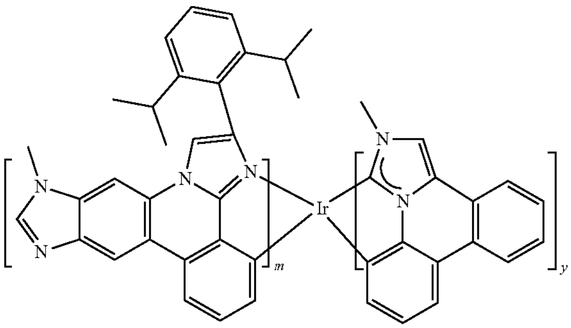
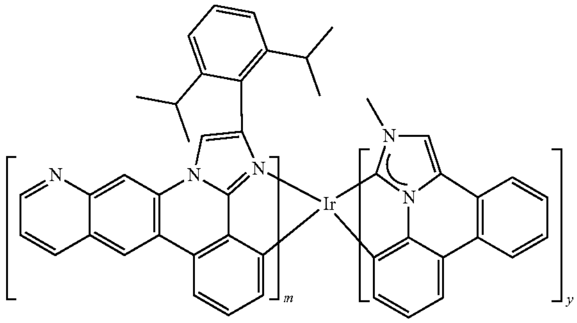
-continued
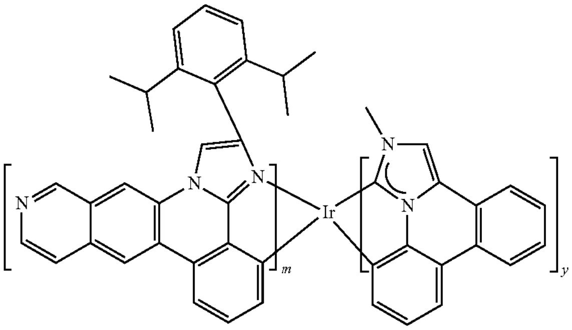
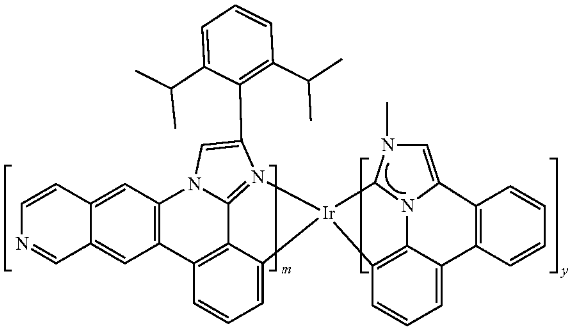
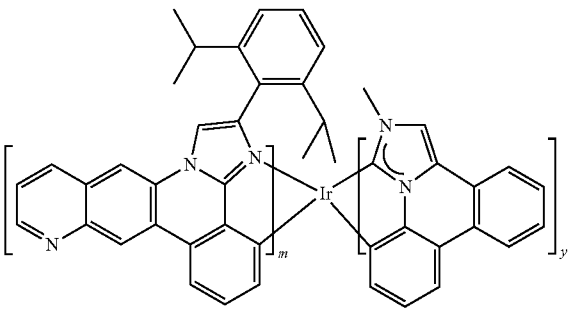
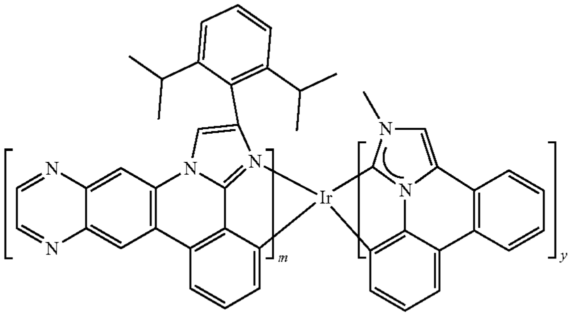
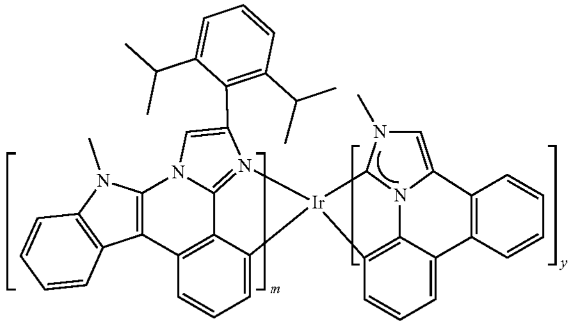

-continued
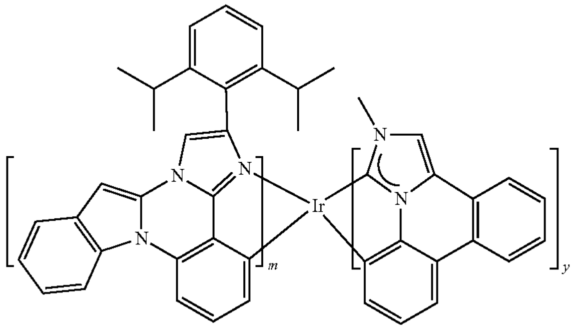
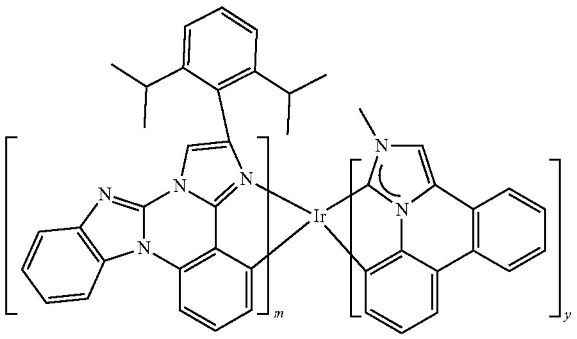
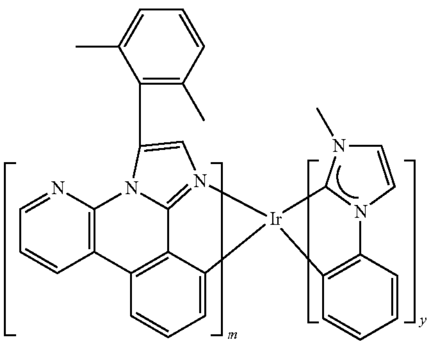
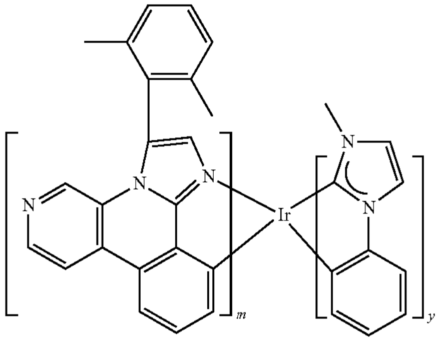
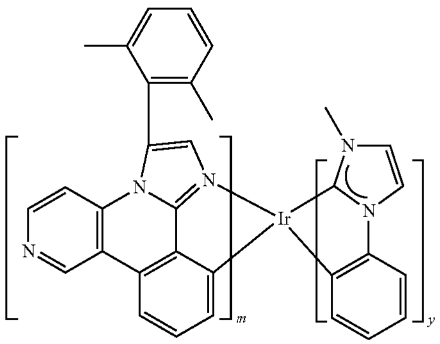
-continued
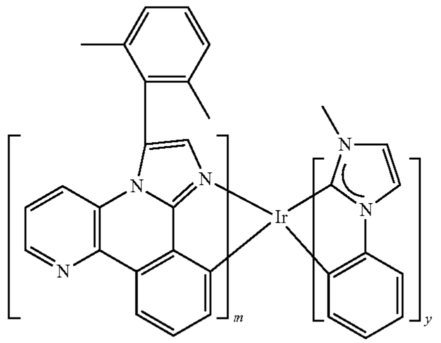
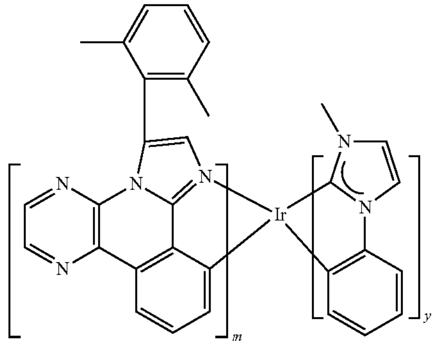
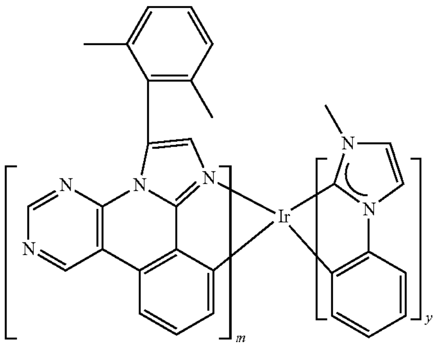
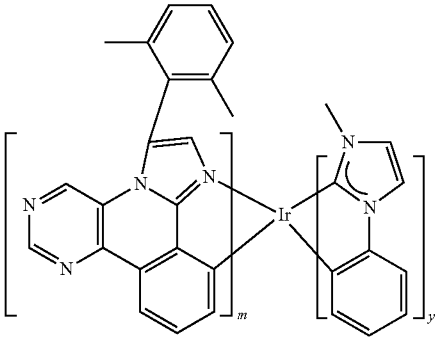
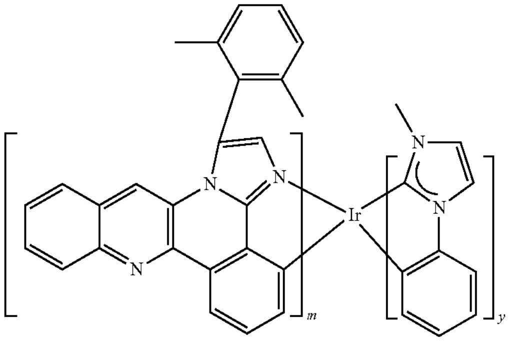

-continued
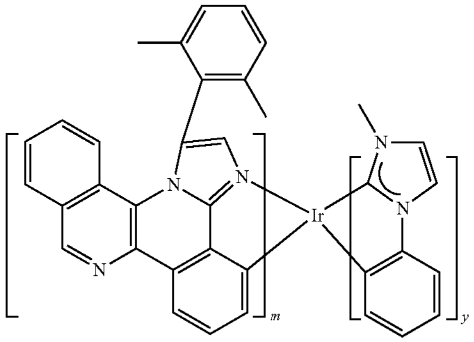
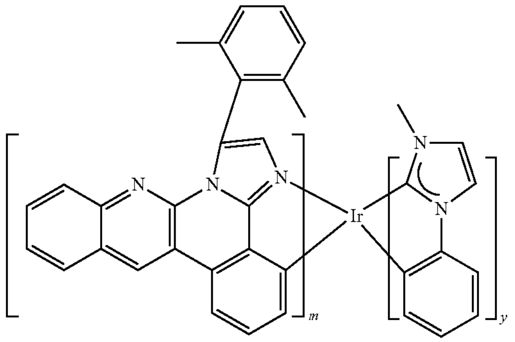
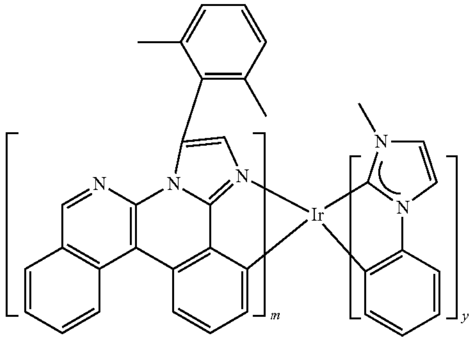
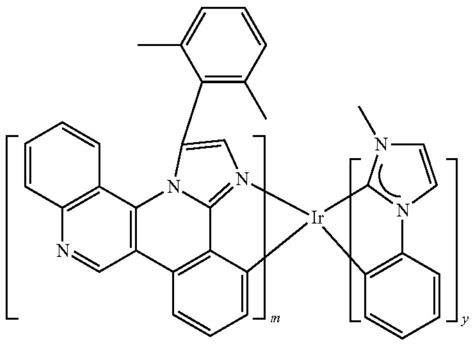
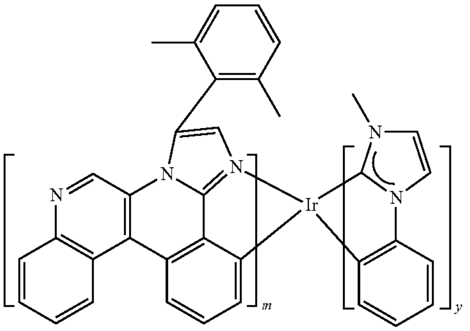
-continued
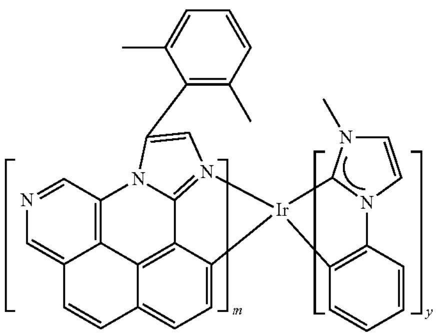
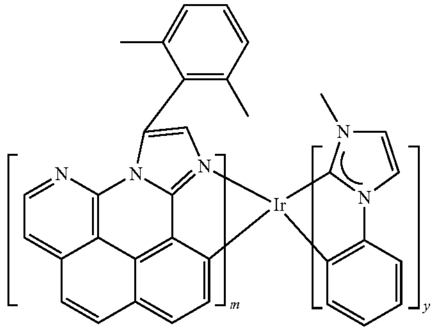
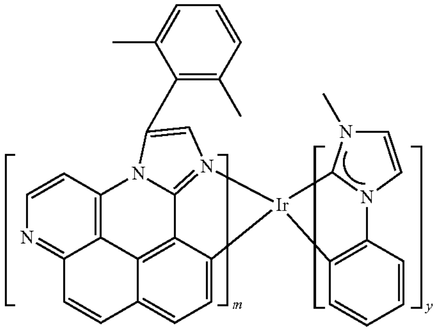
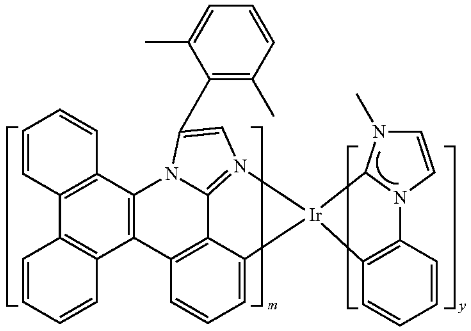
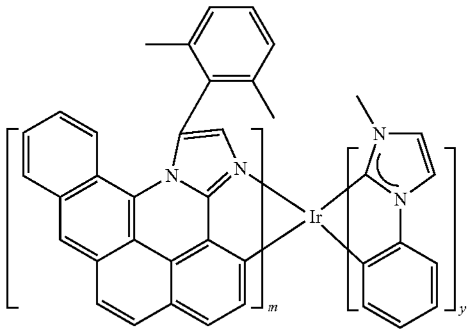

-continued
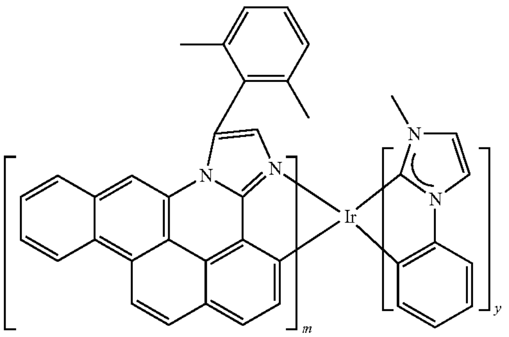
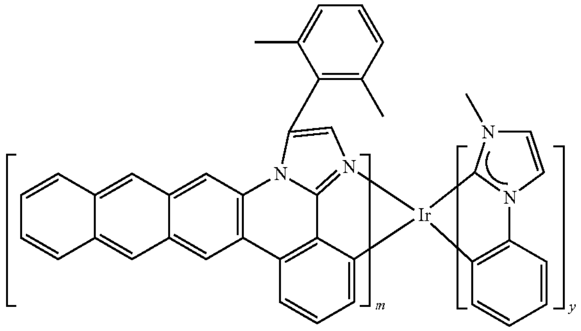
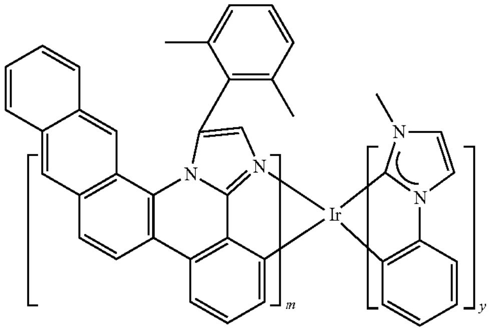
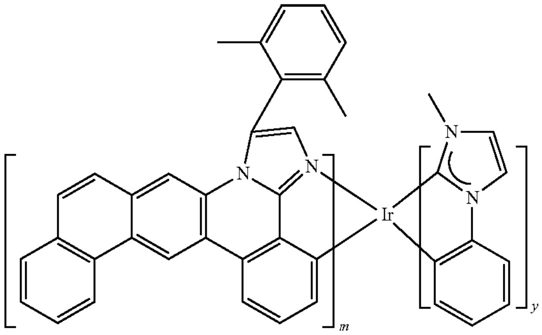
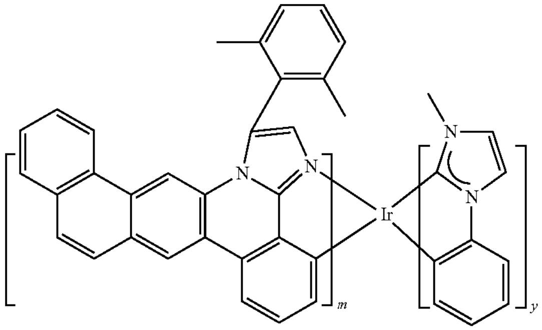
-continued
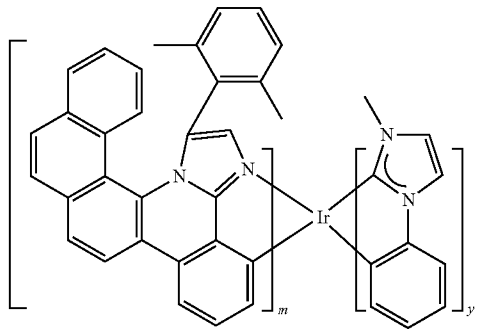
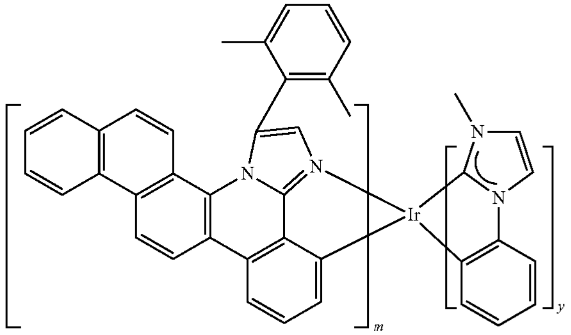
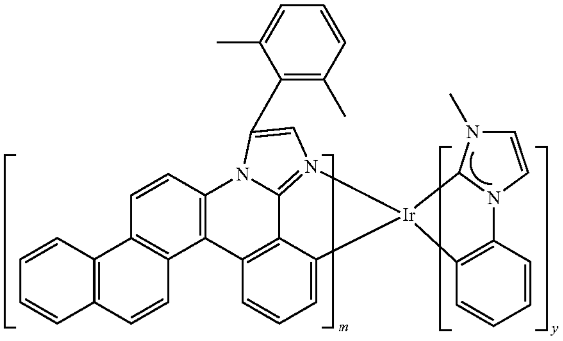
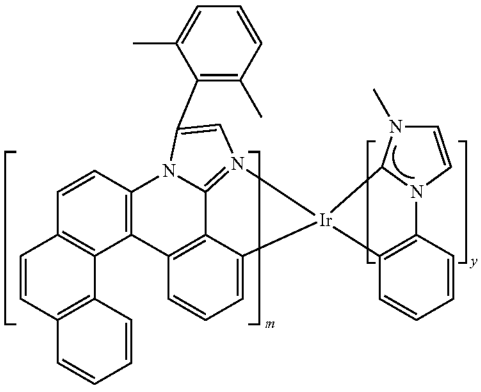

-continued
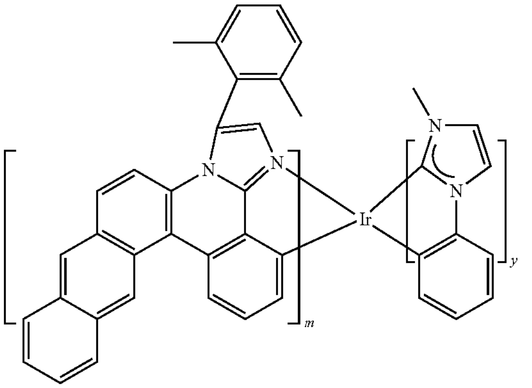
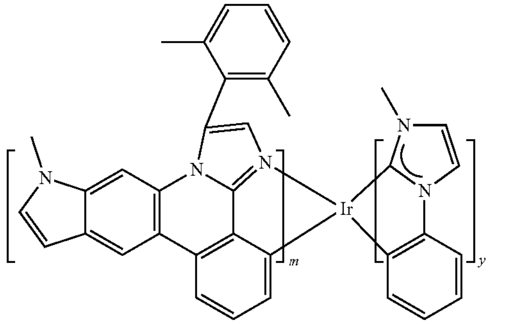
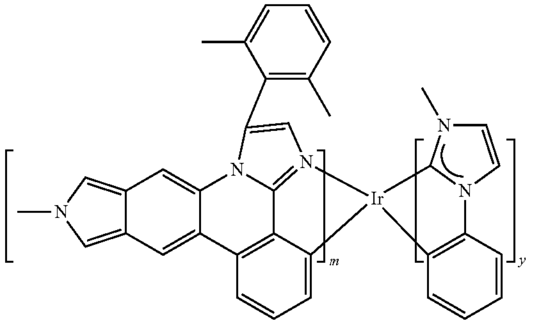
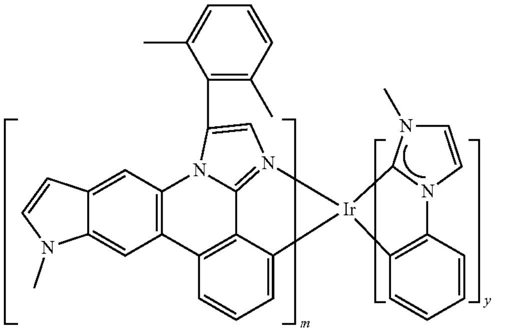
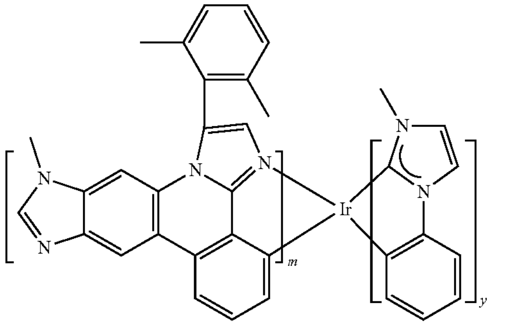
-continued
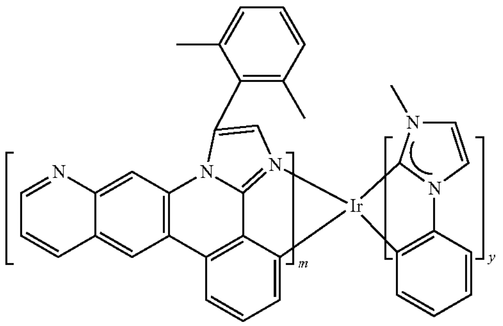
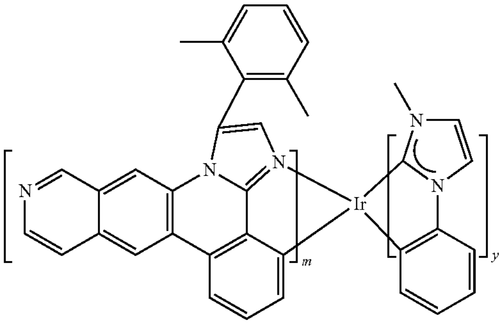
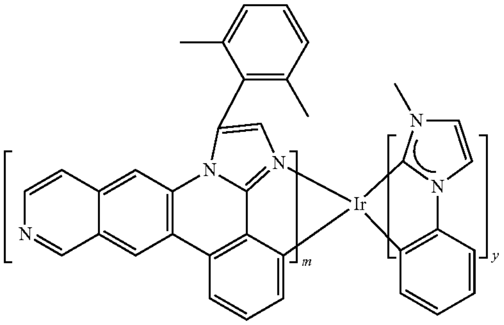
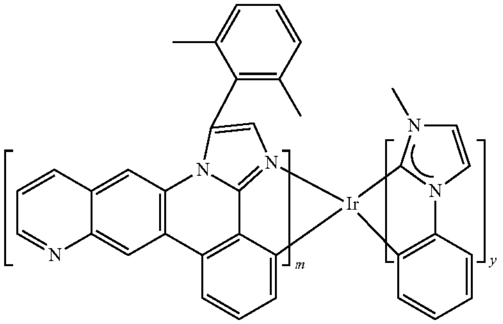
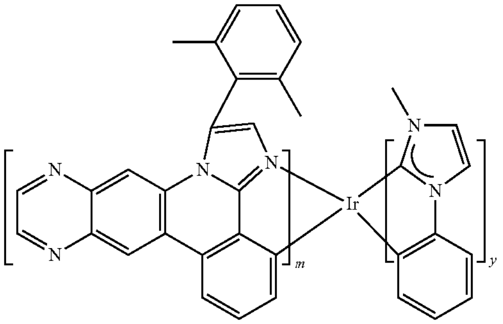

-continued
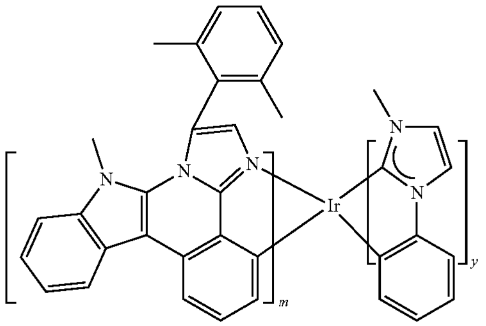
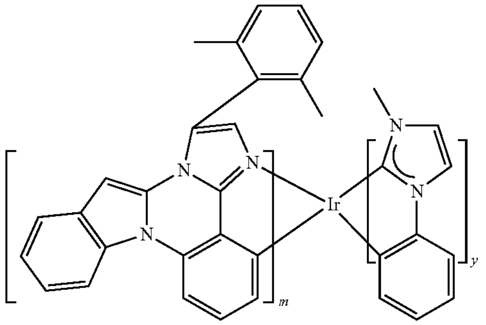
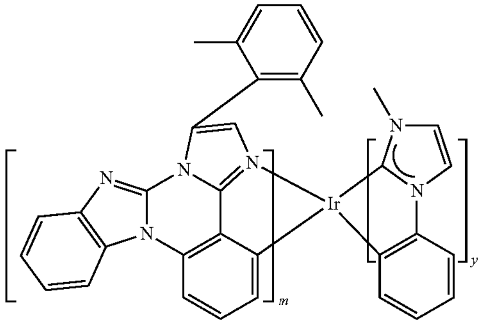
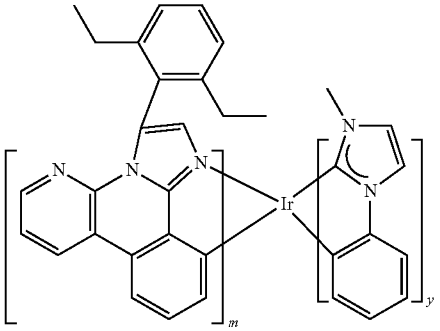
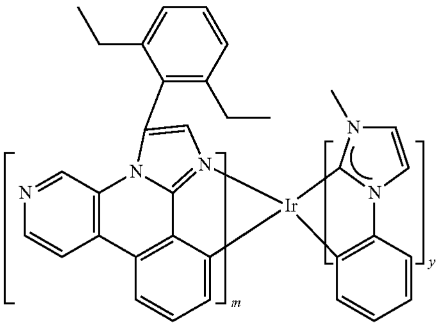
-continued
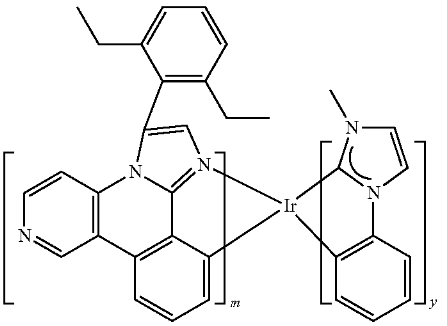
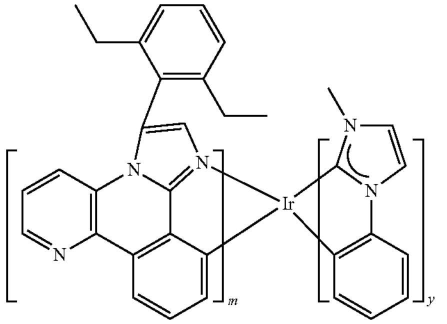
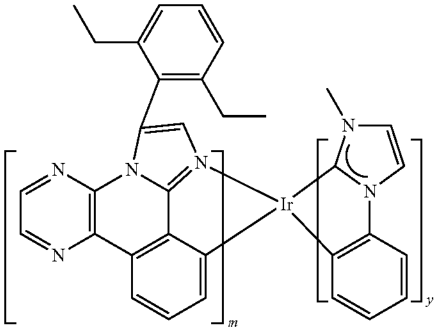
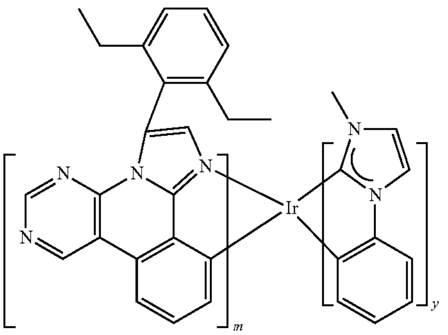
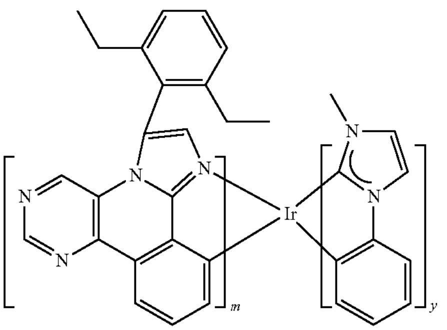

-continued
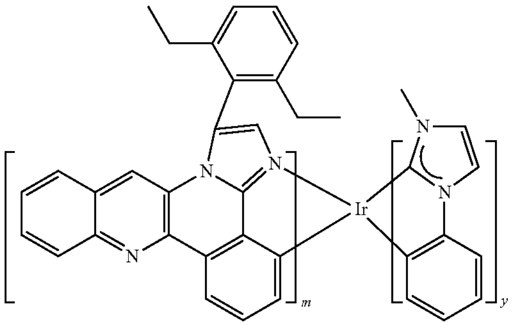
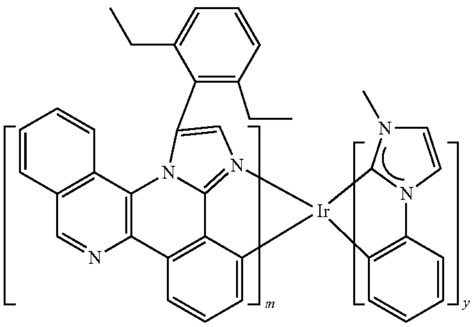
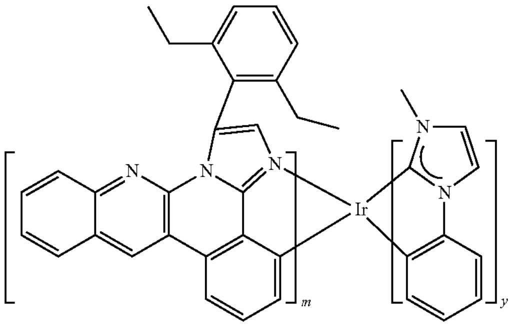
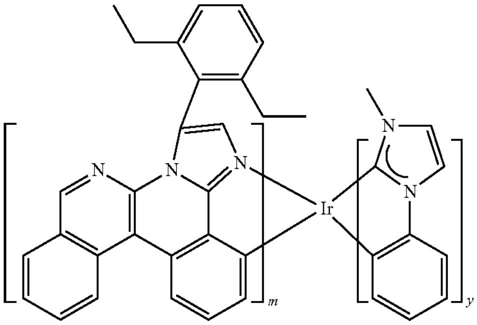
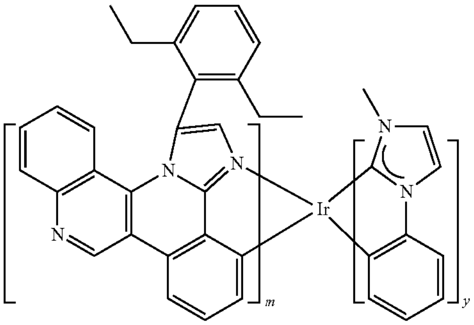
-continued
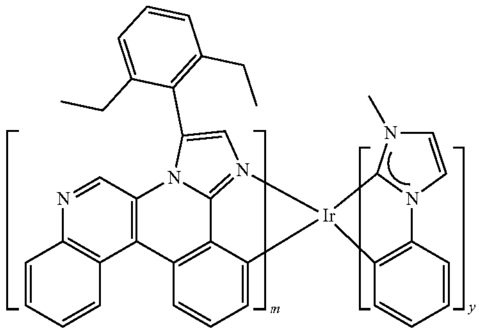
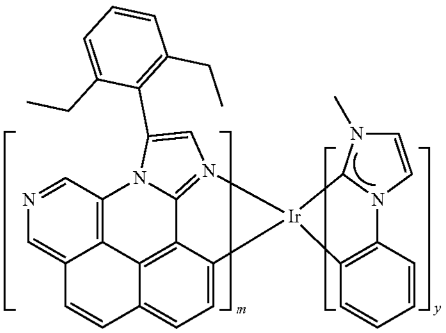
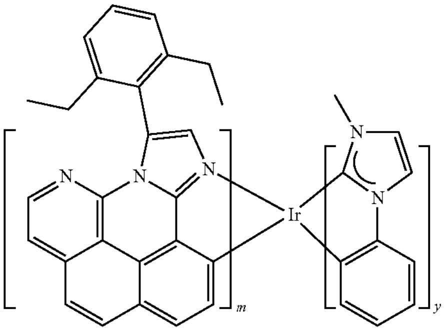
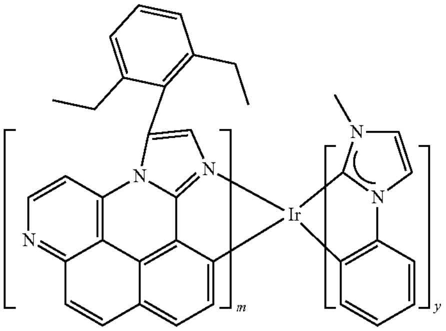
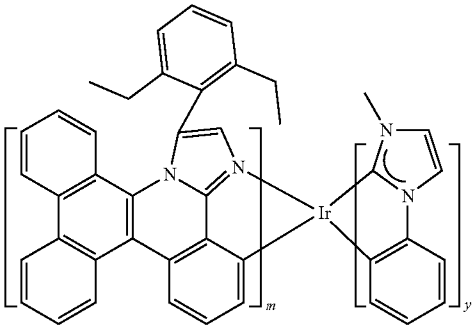

-continued
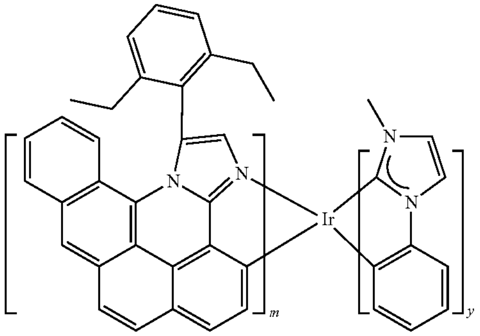
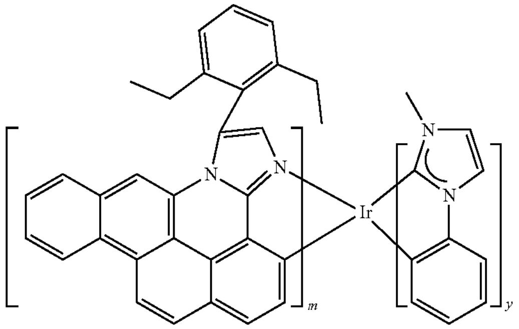
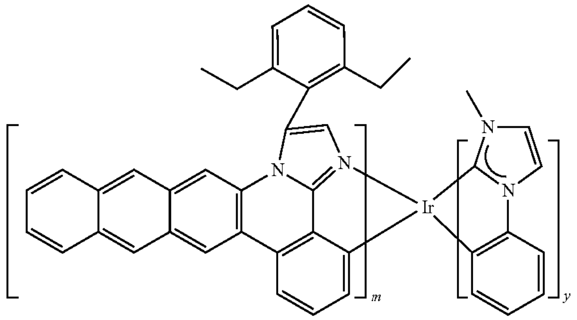
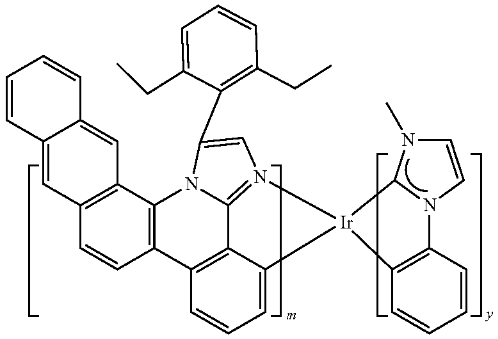
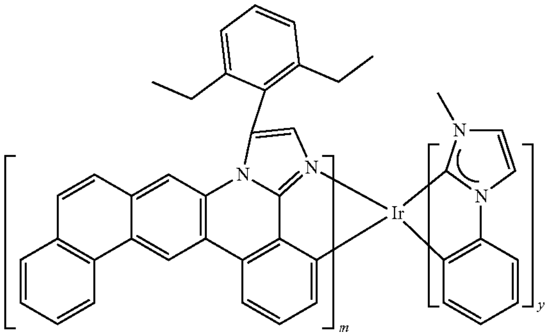
-continued
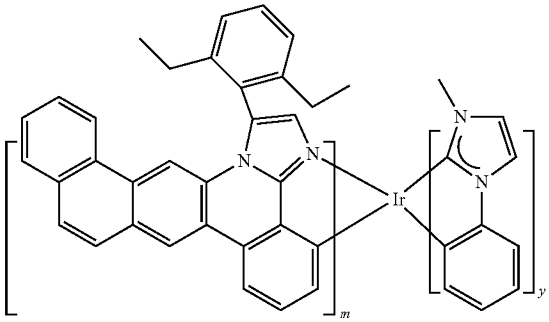
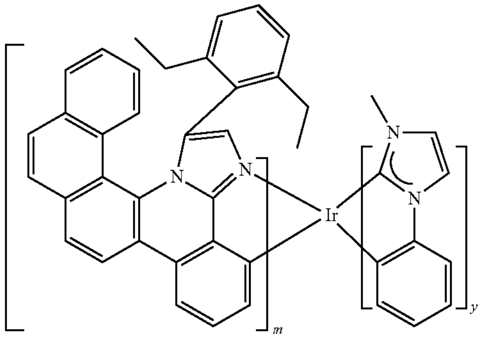
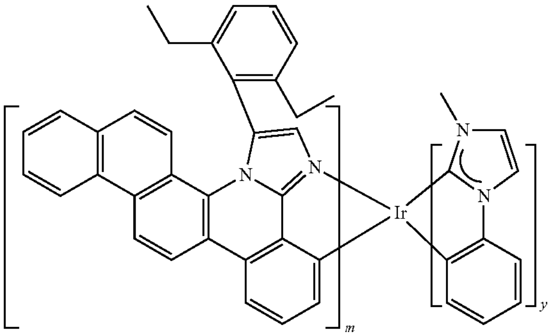
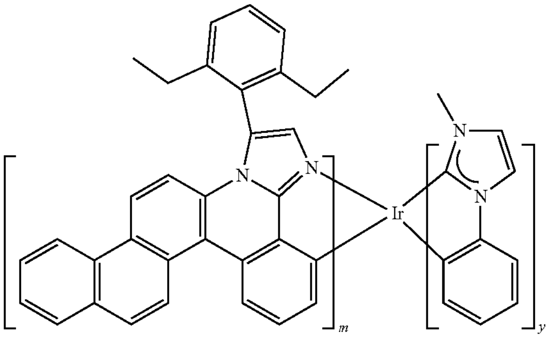
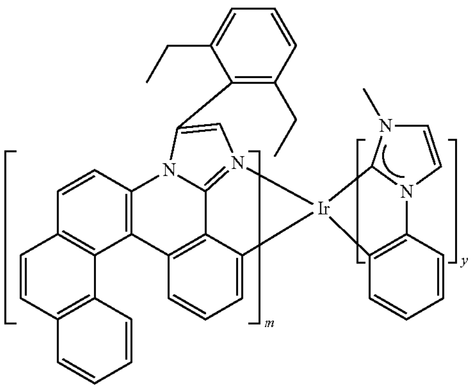

-continued
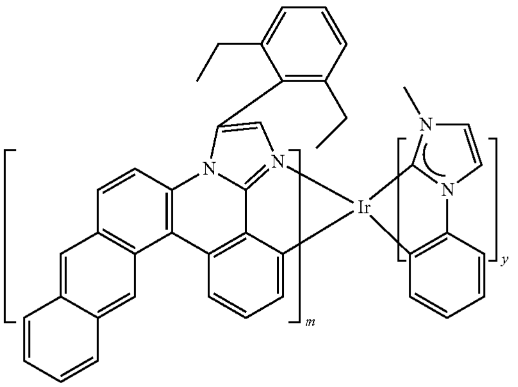
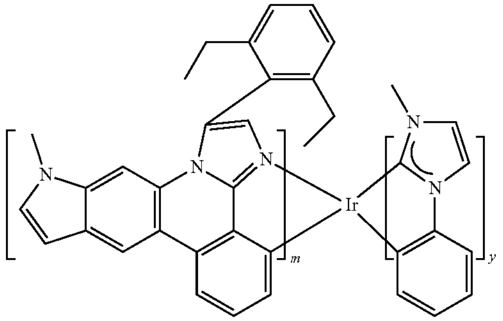
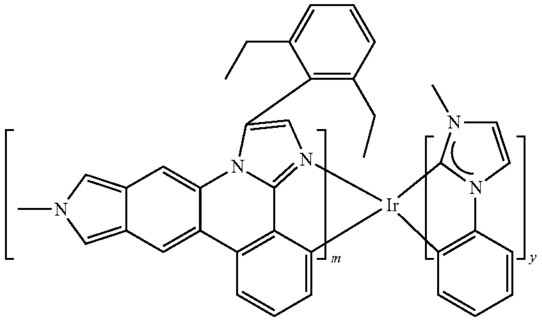
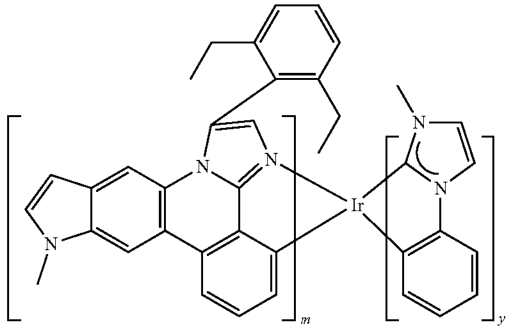
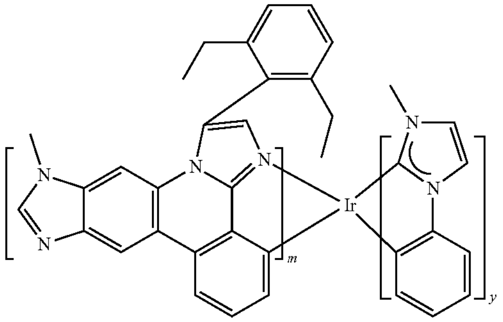
-continued
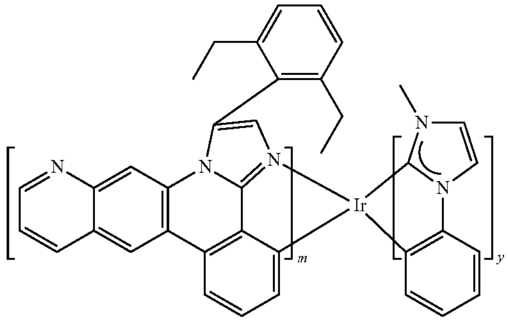
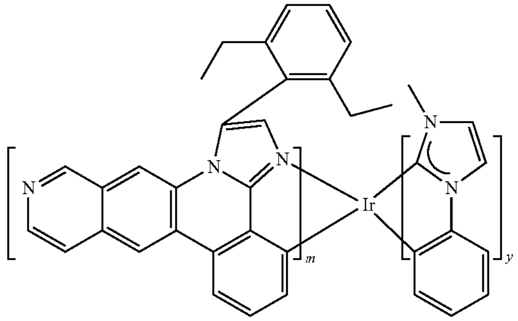
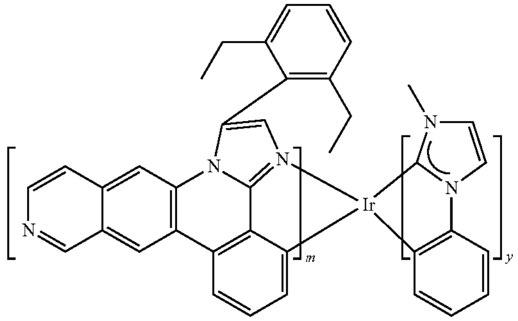
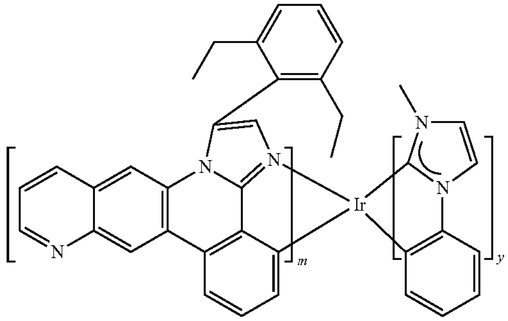
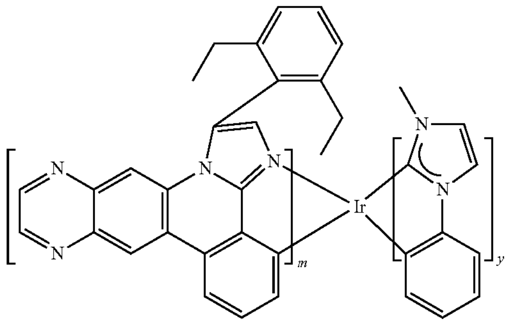

-continued
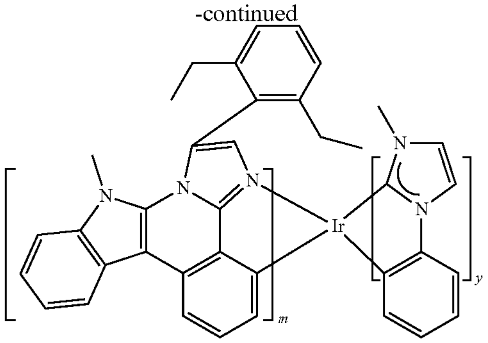
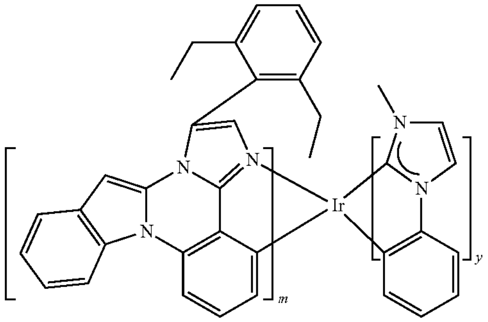
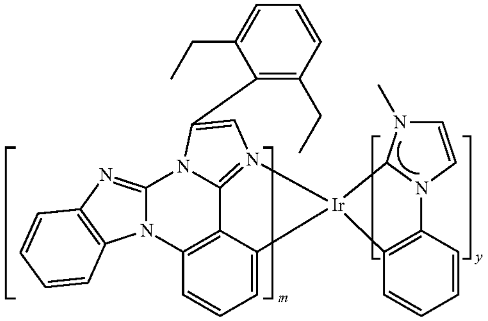
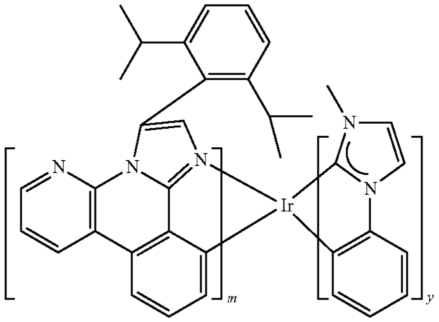
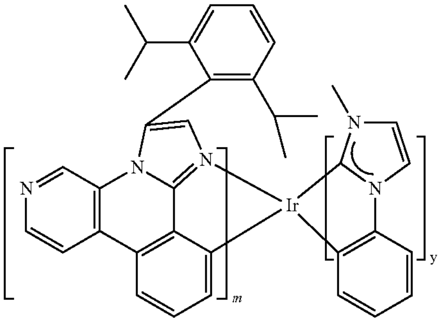
-continued
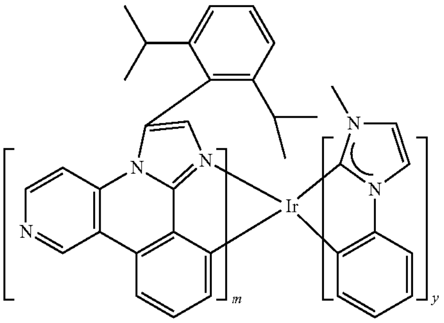
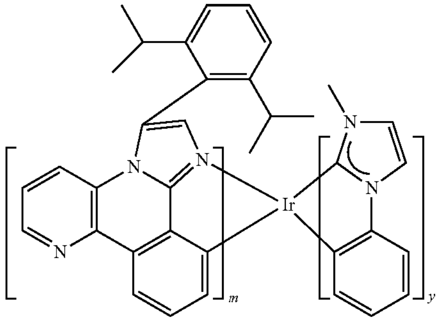
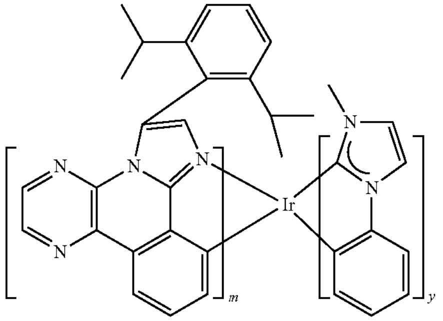
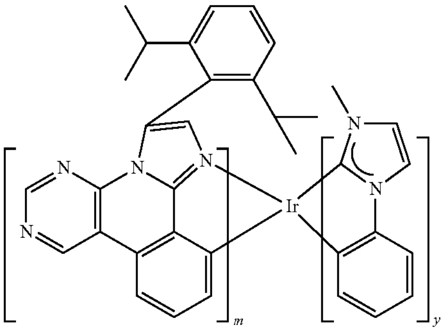
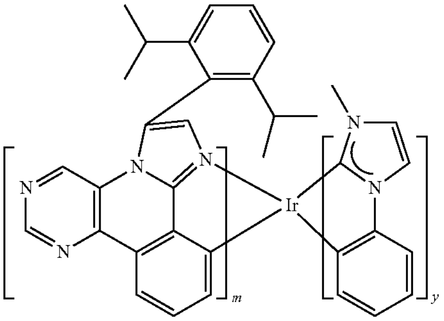

-continued
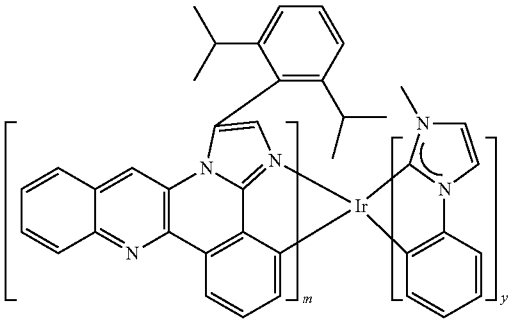
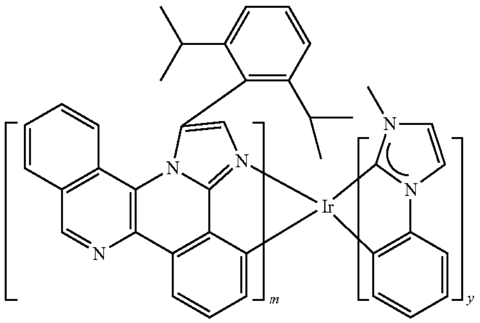
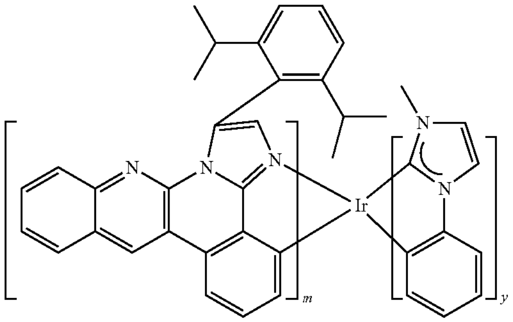
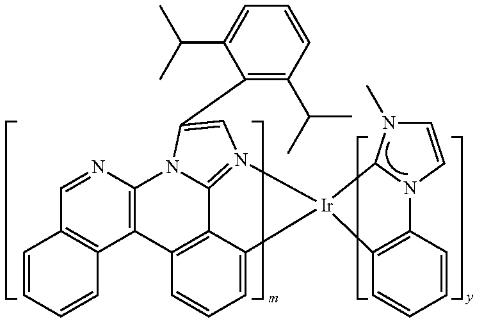
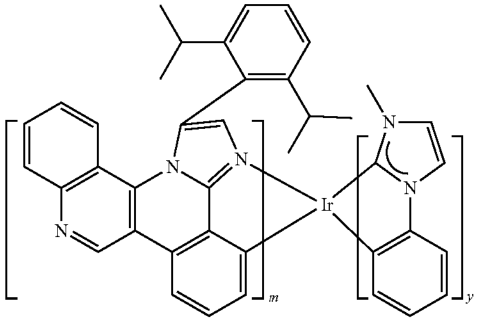
-continued
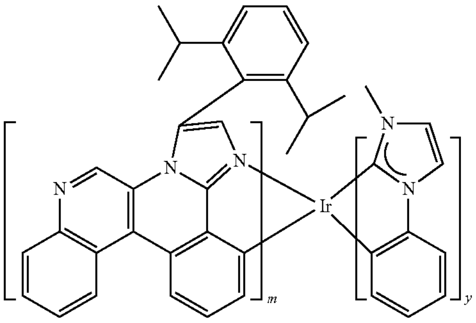
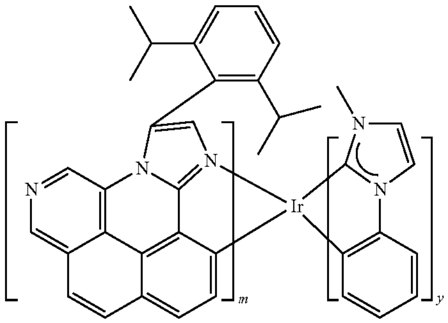
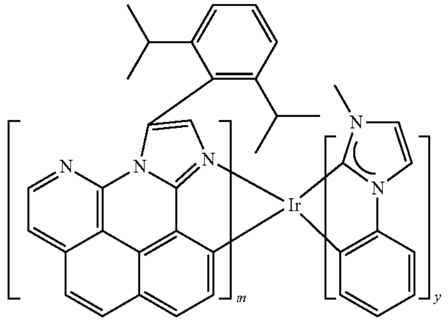
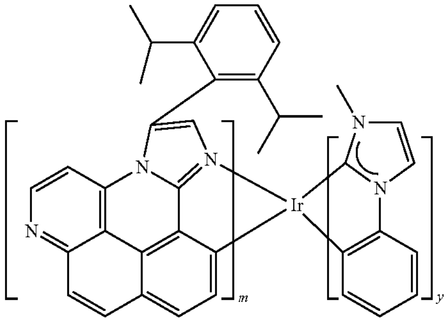
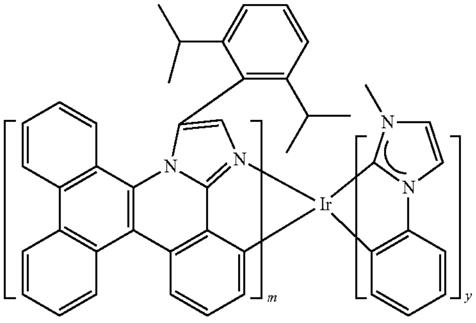

-continued
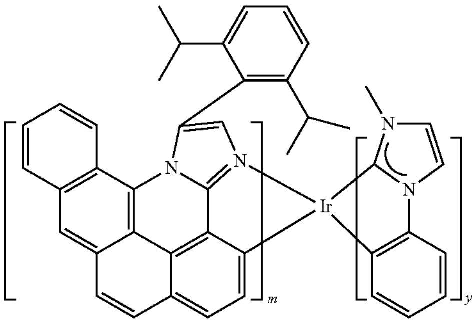
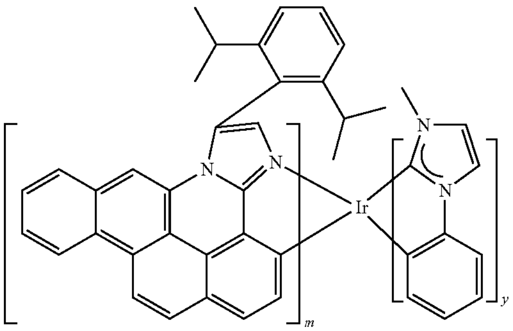
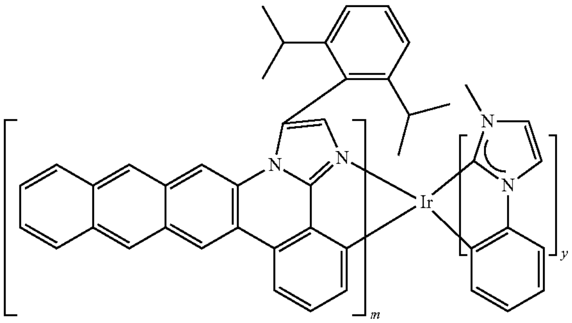
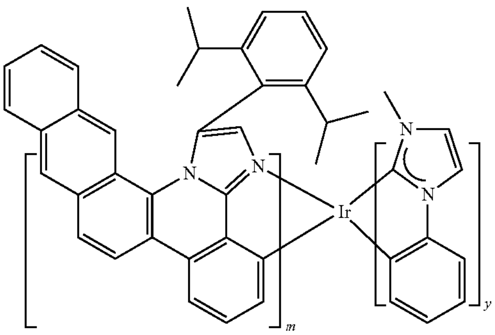
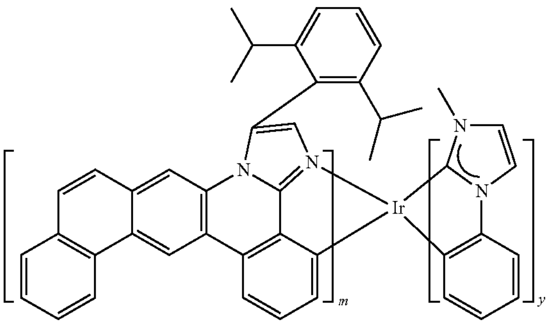
-continued
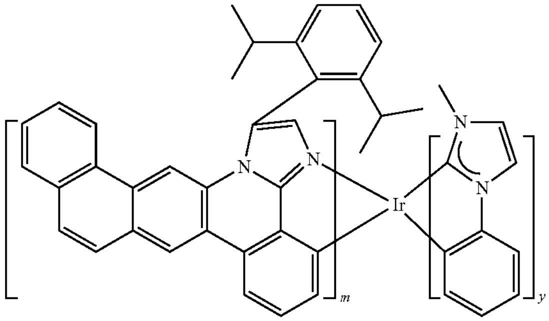
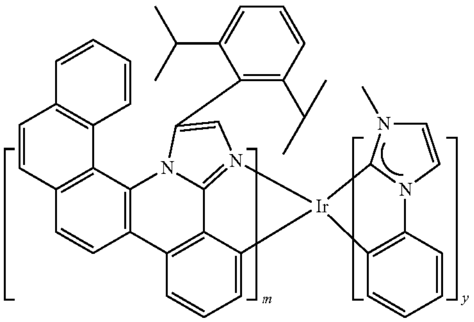
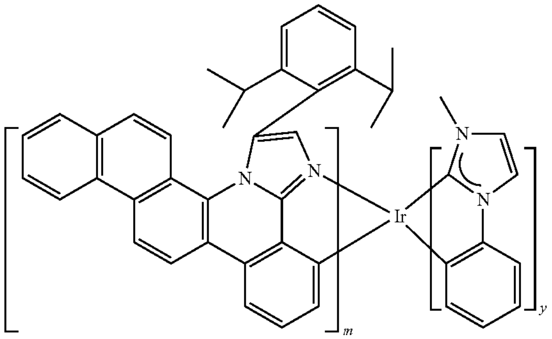
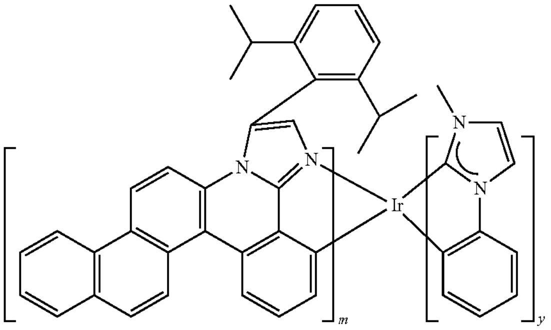
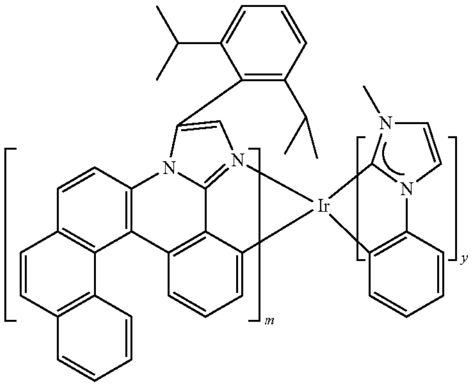

-continued
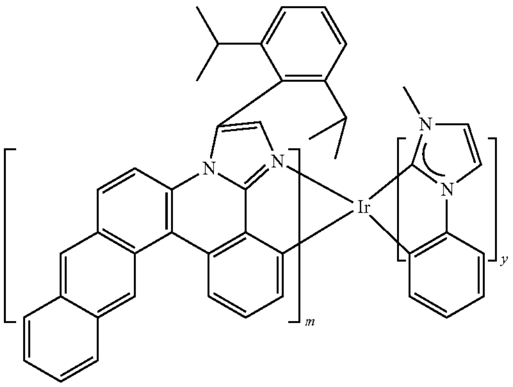
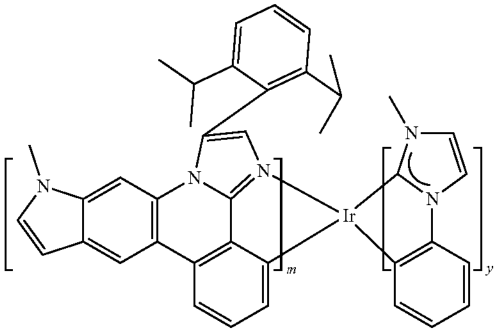
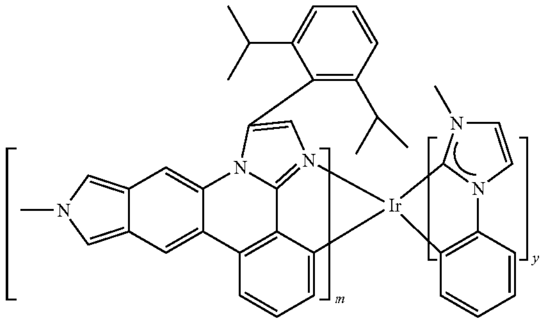
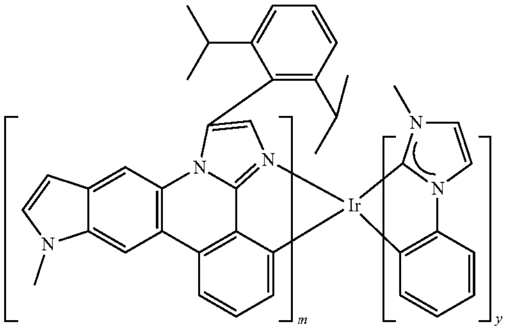
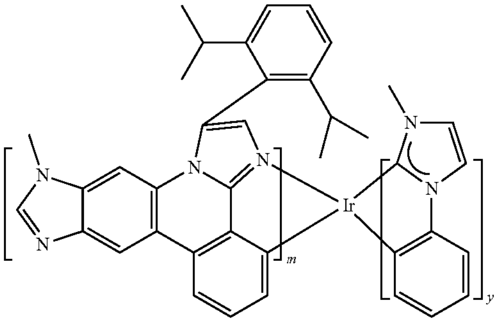
-continued
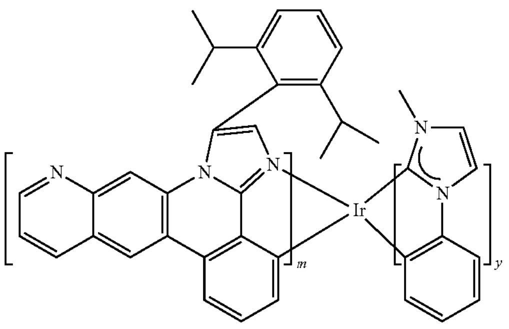
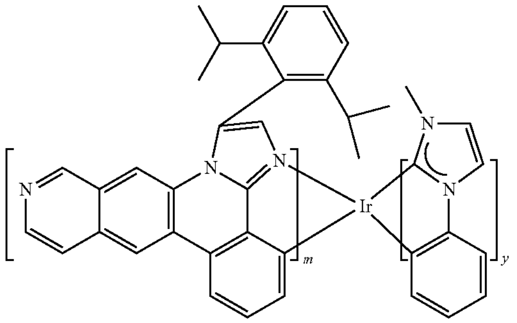
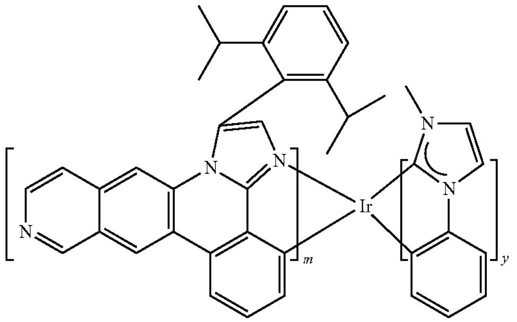
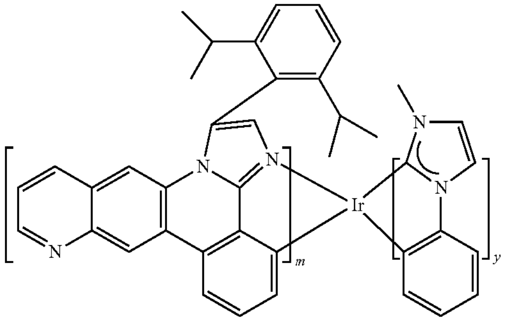
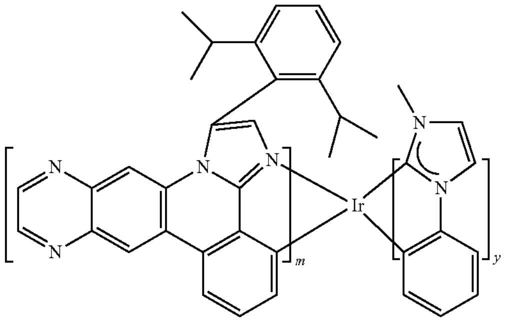

-continued
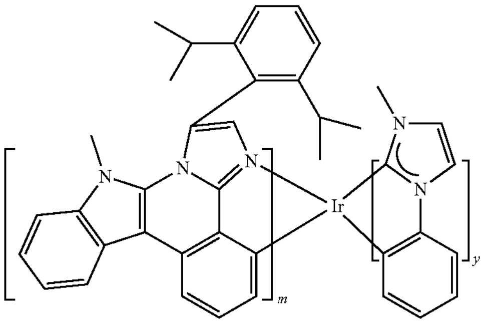
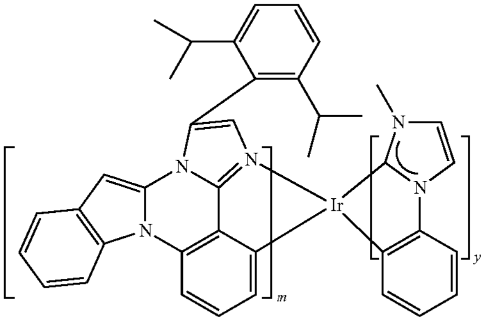
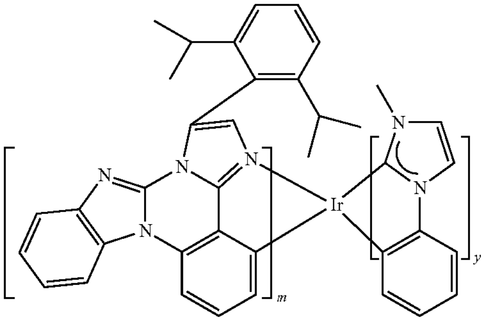
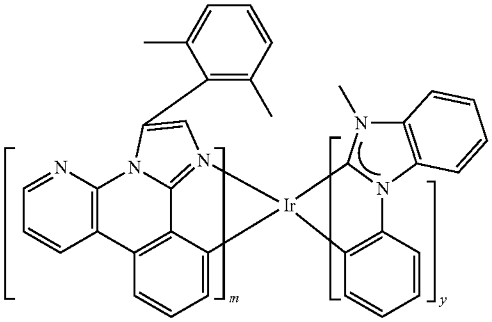
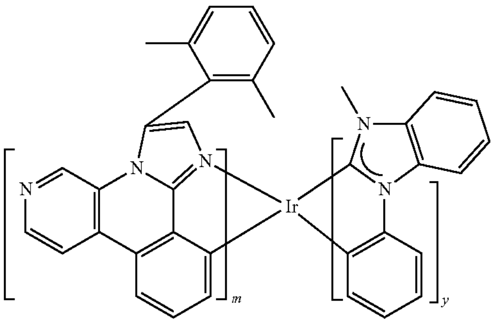
-continued
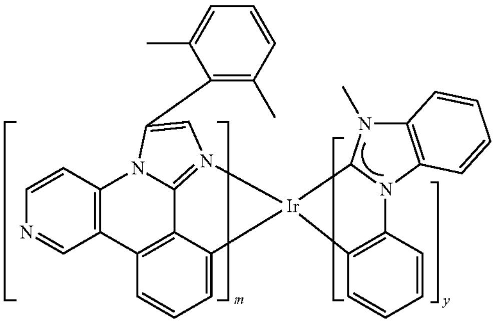
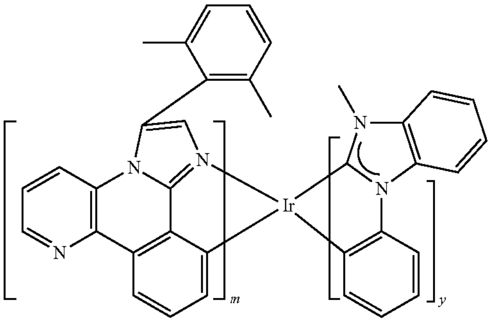
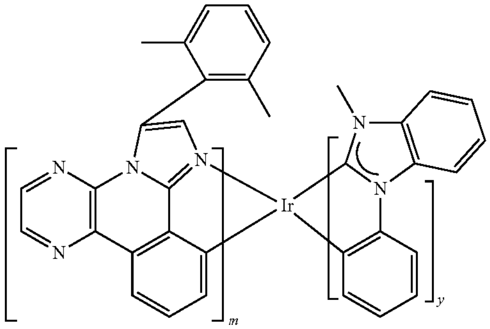
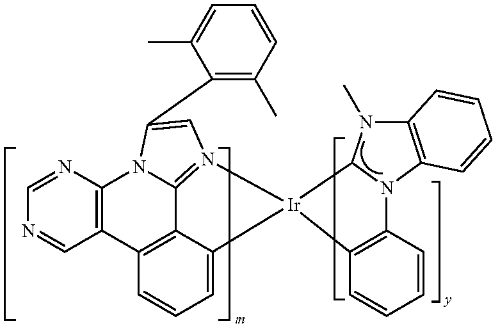
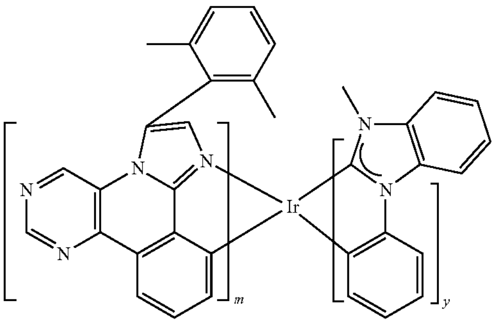

-continued
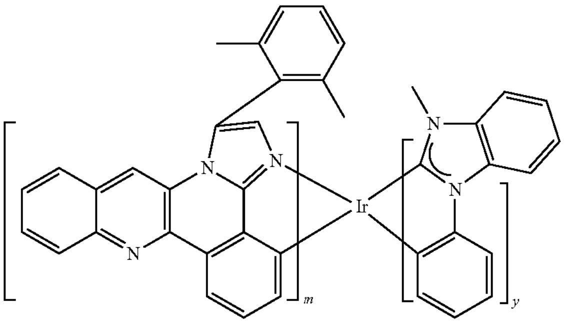
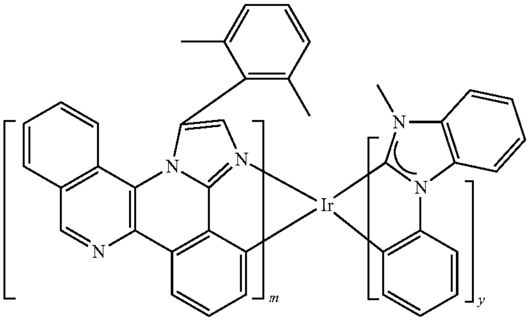
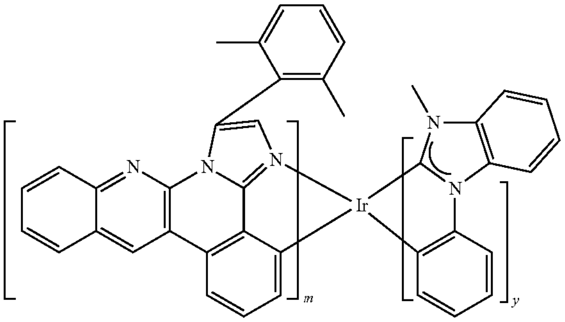
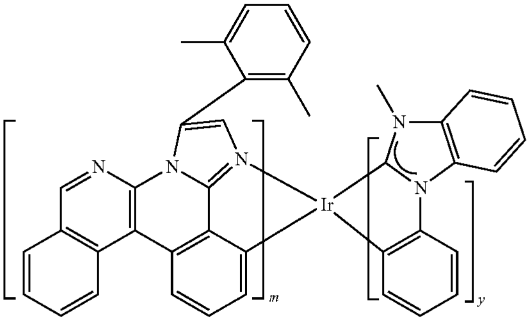
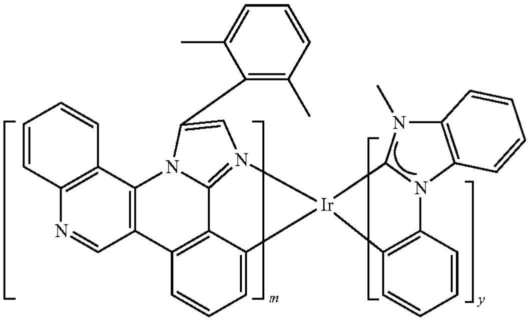
-continued
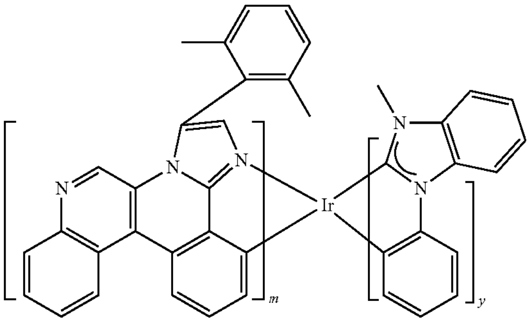
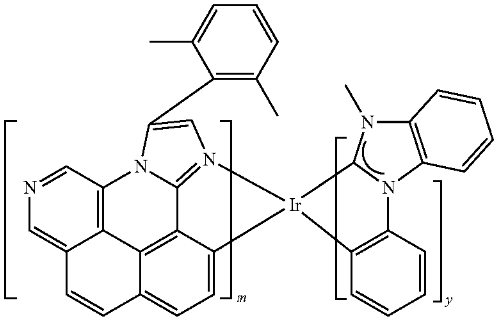
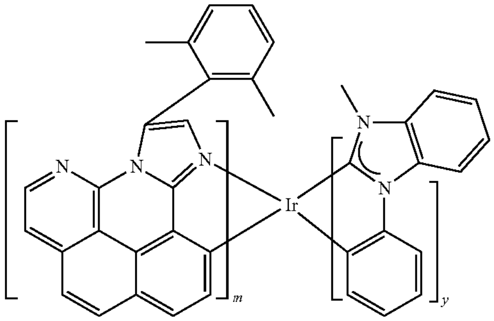
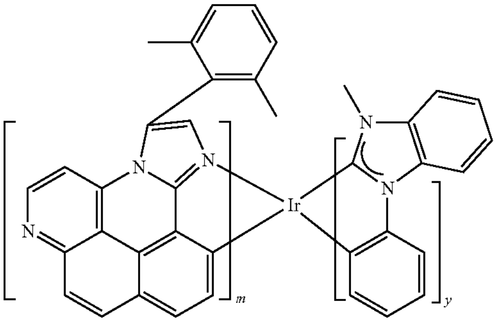
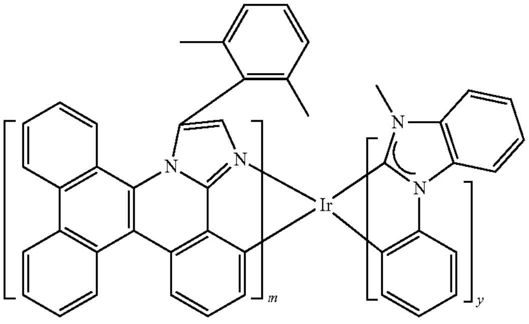

-continued
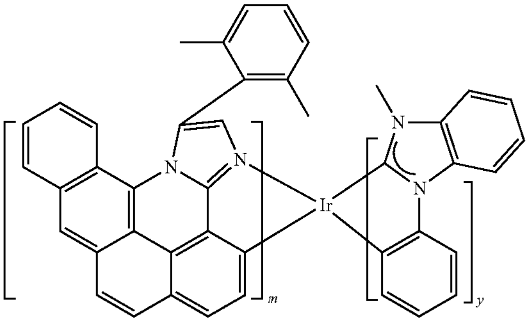
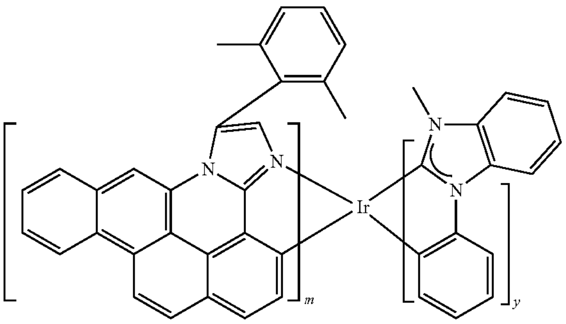
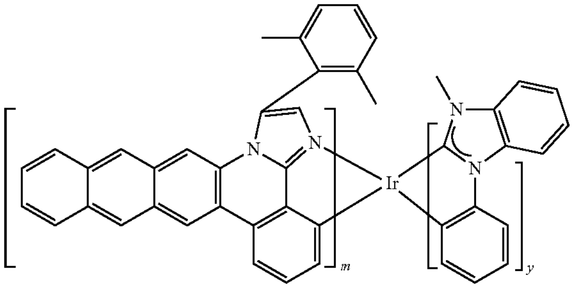
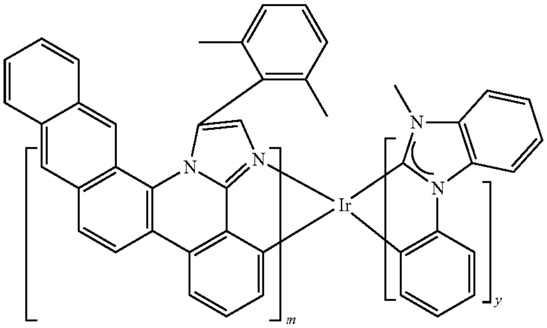
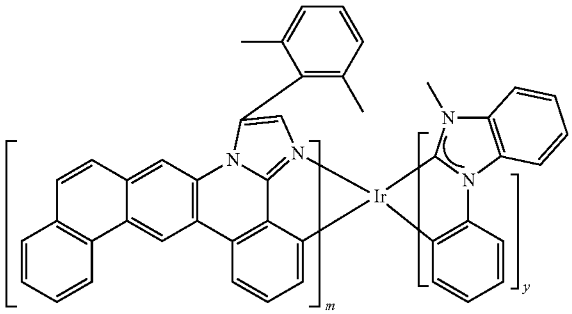
-continued
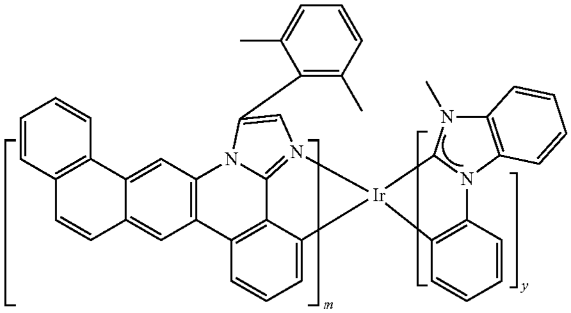
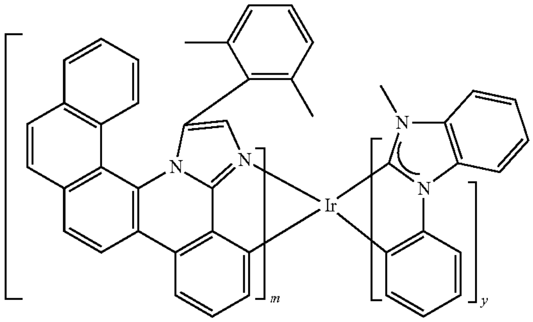
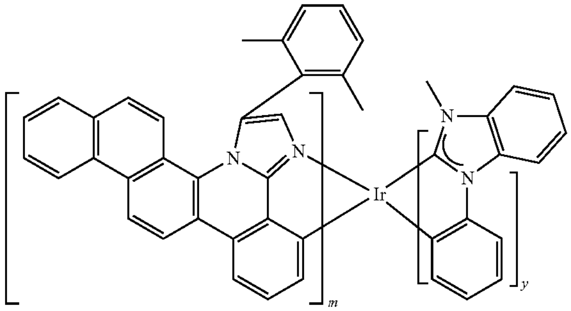
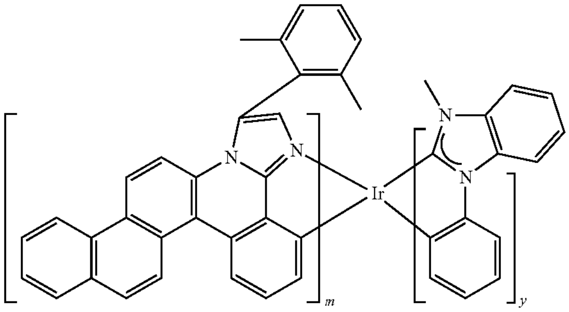
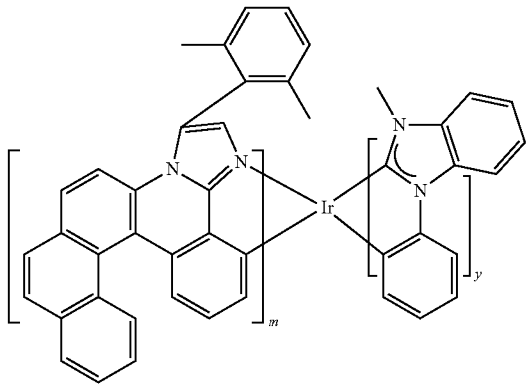

-continued
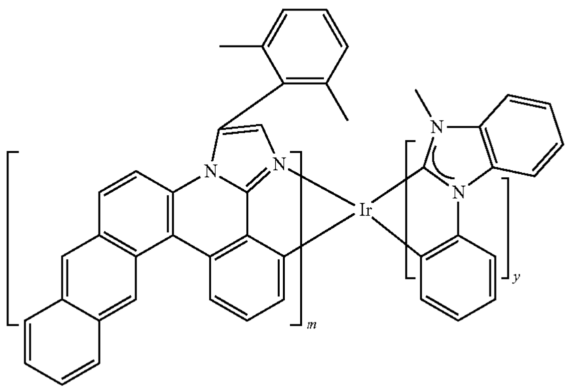
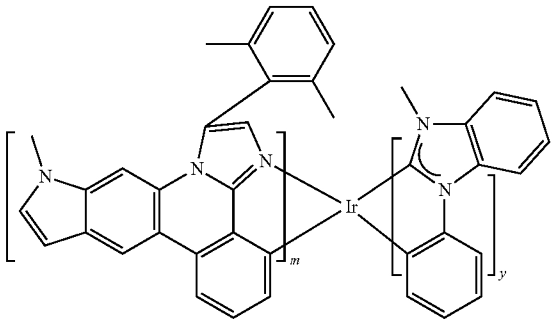
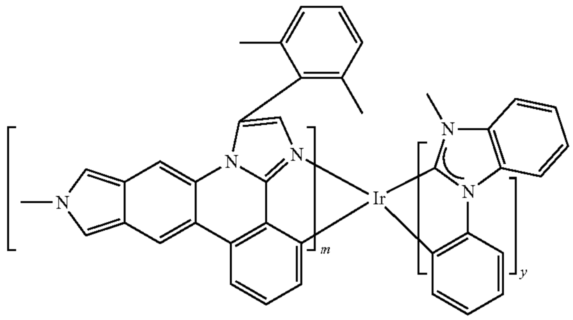
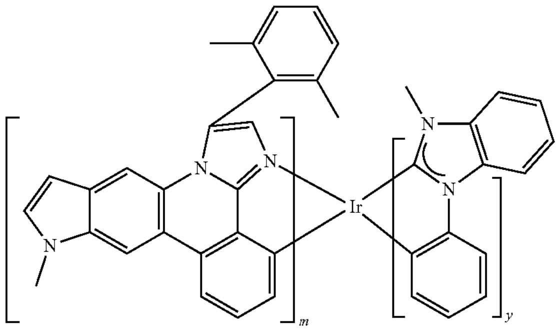
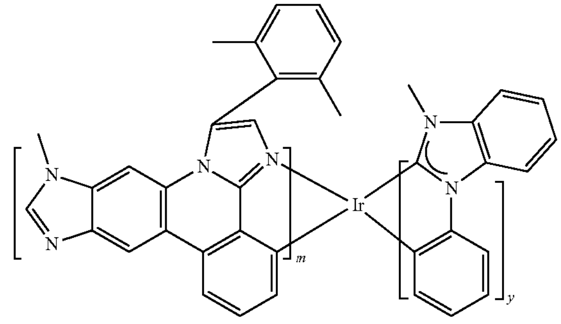
-continued
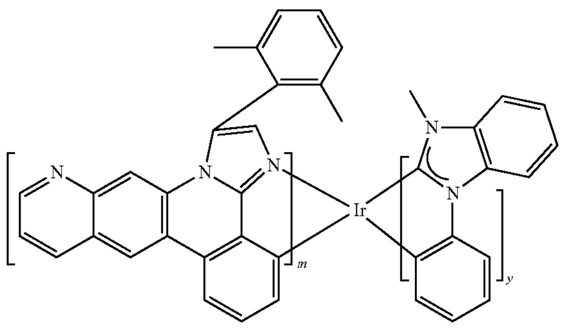
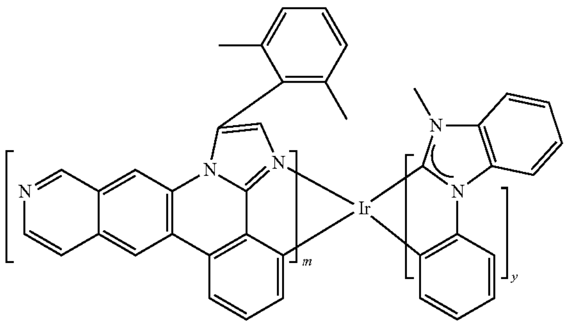
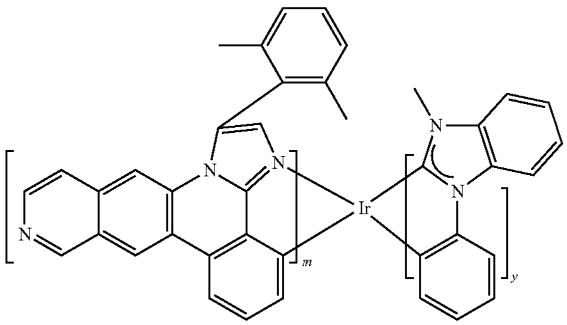
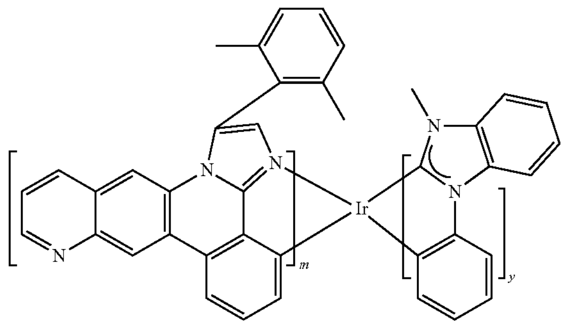
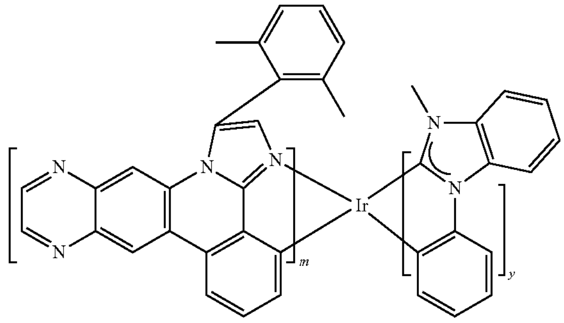

-continued
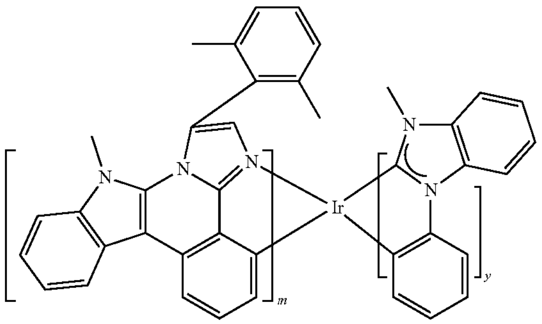
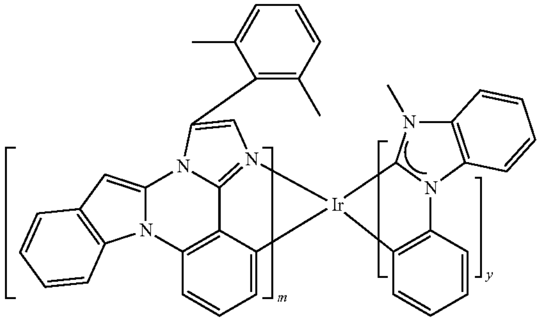
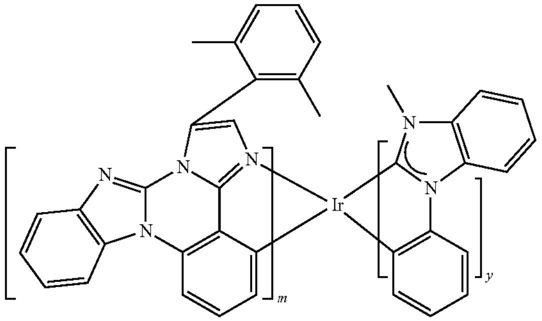
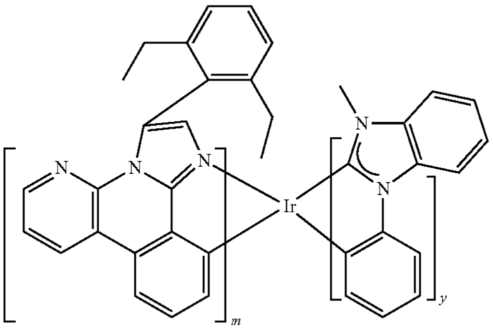
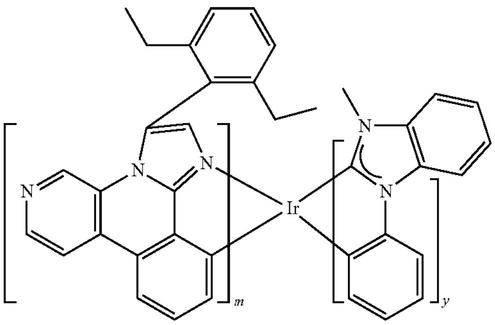
-continued
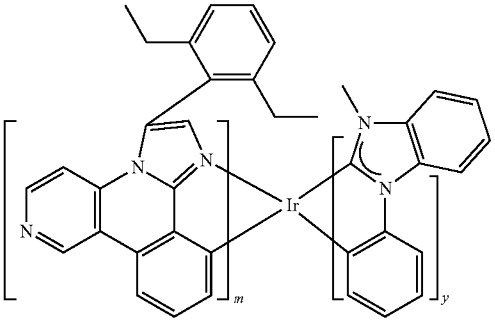
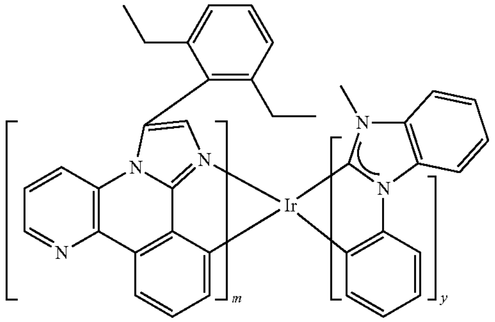
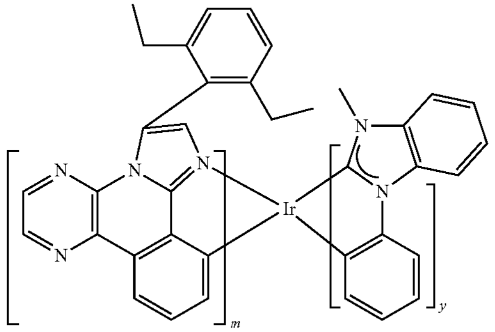
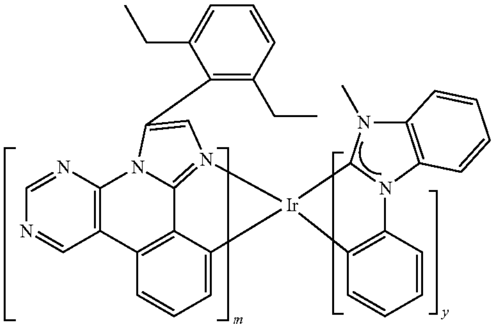
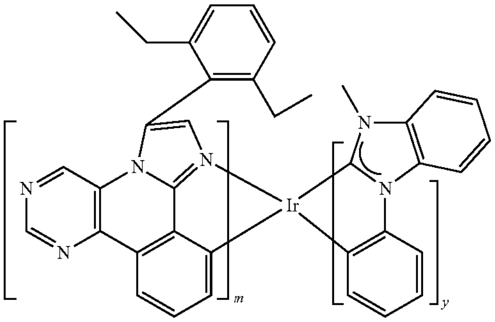

-continued
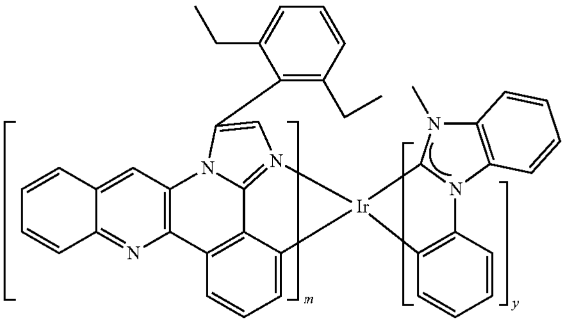
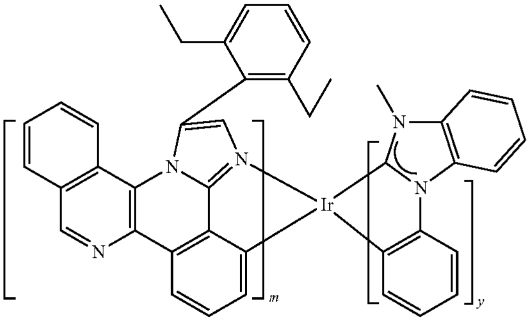
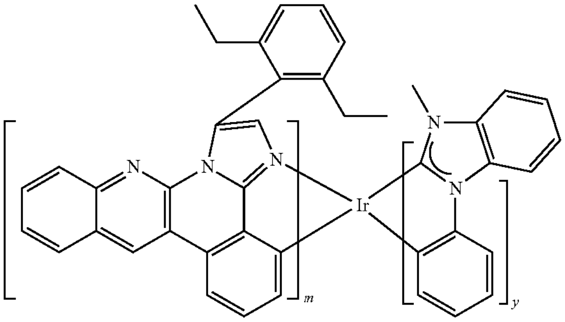
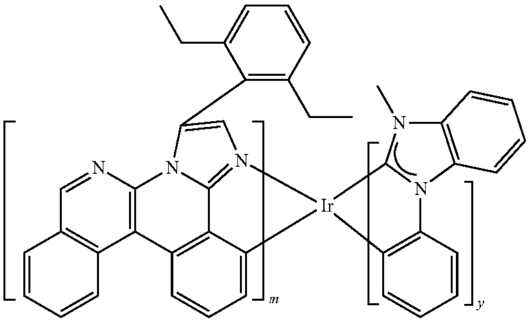
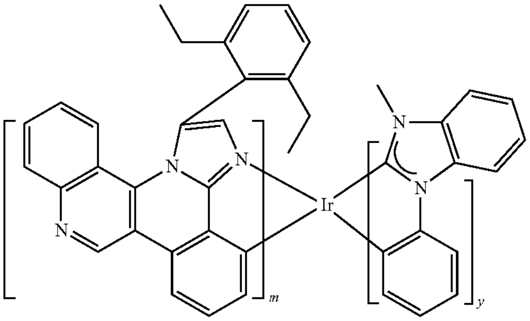
-continued
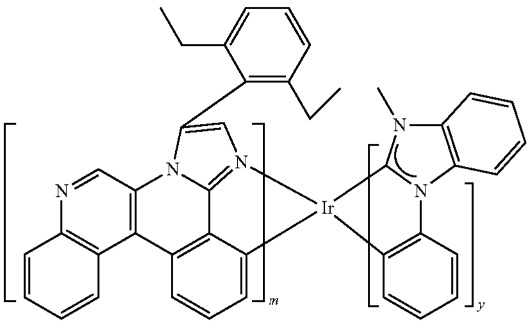
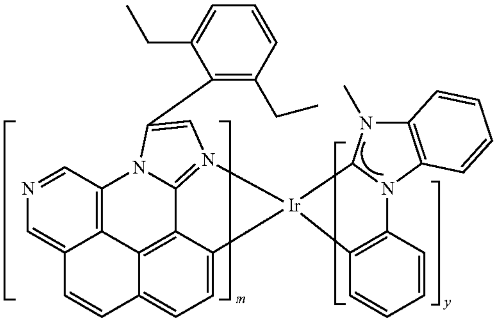
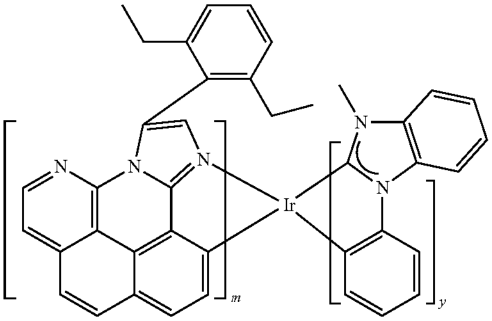
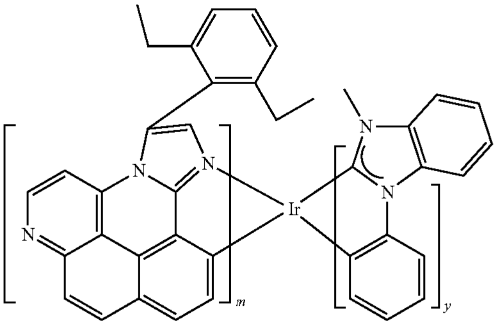
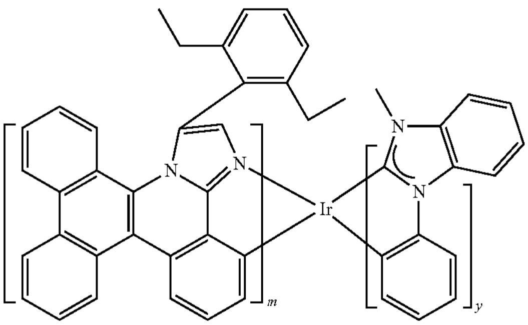

-continued
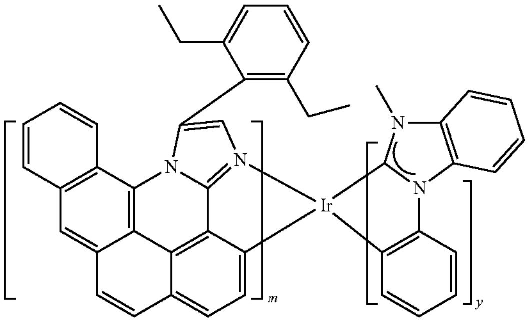
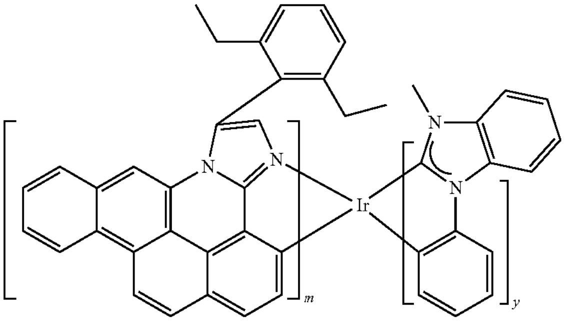
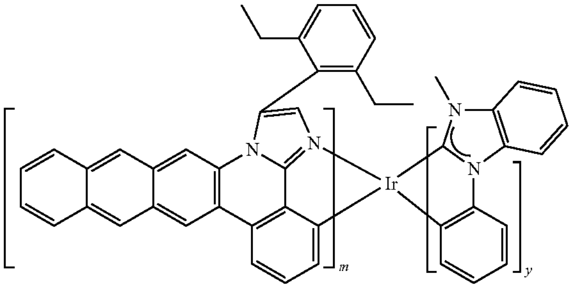
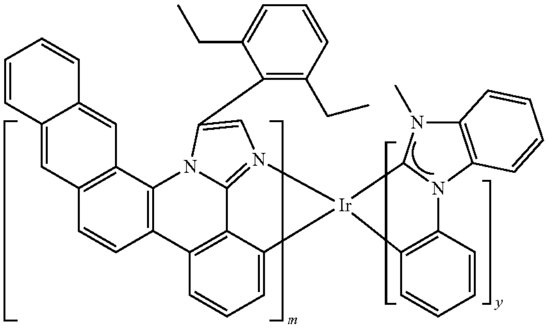
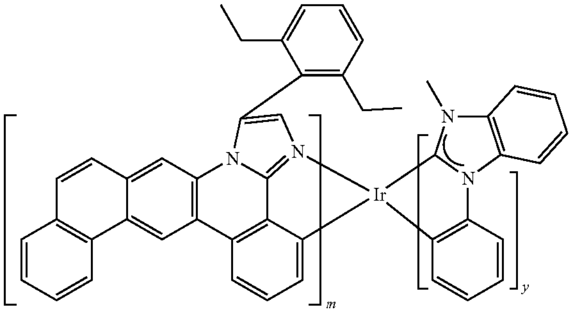
-continued
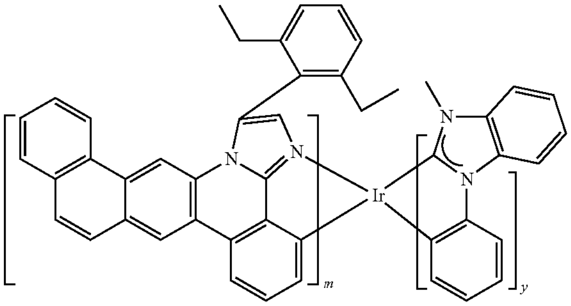
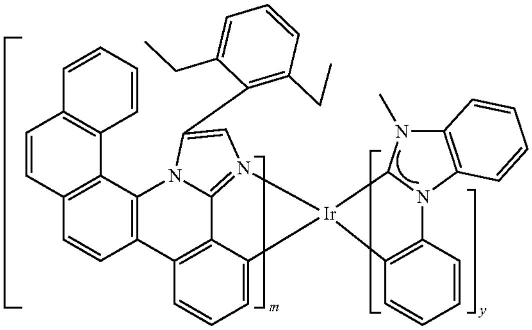
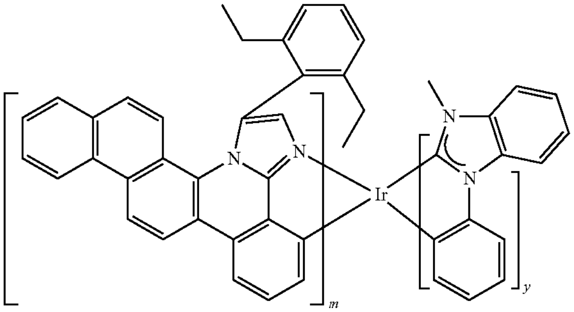
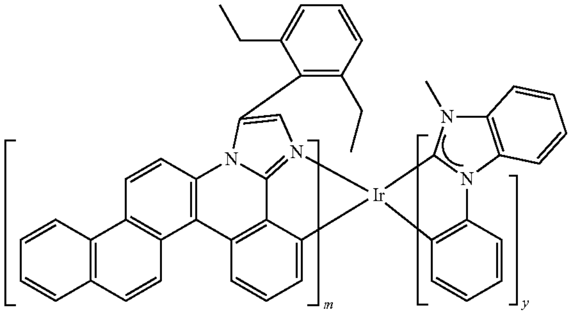
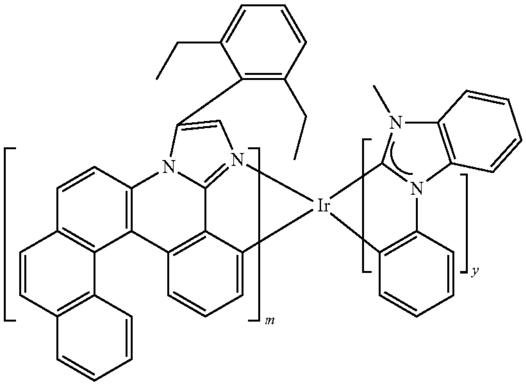

-continued
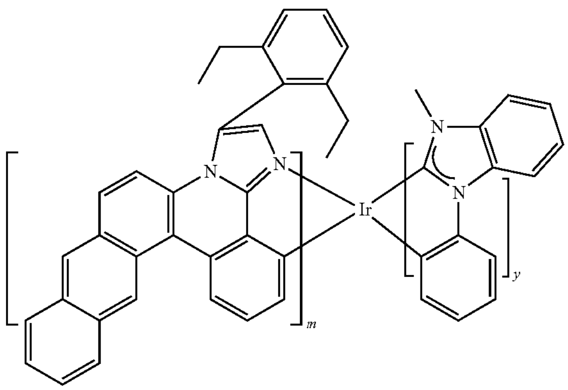
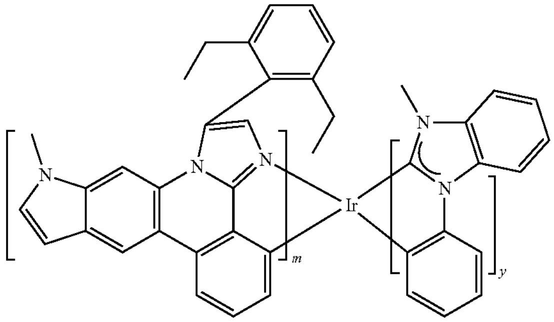
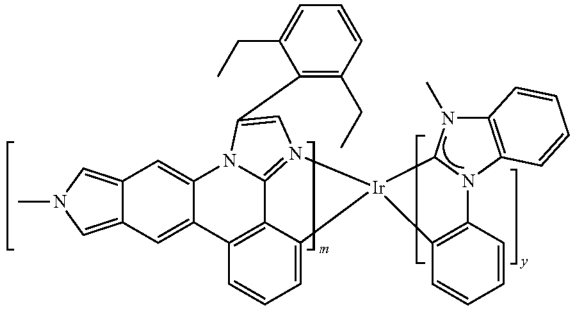
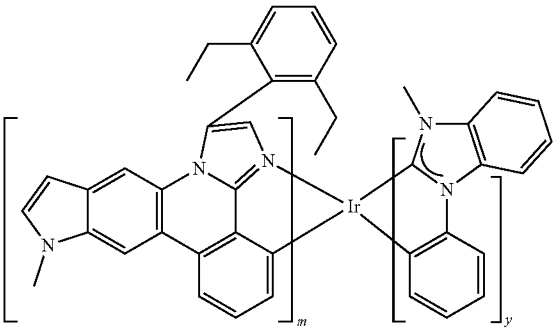
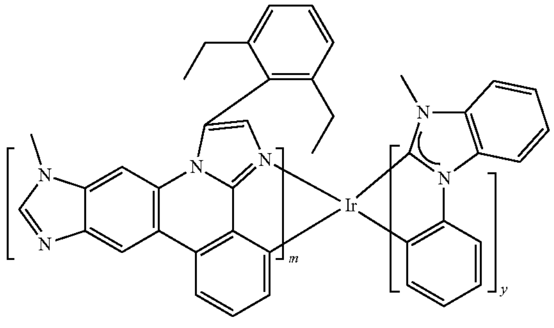
-continued
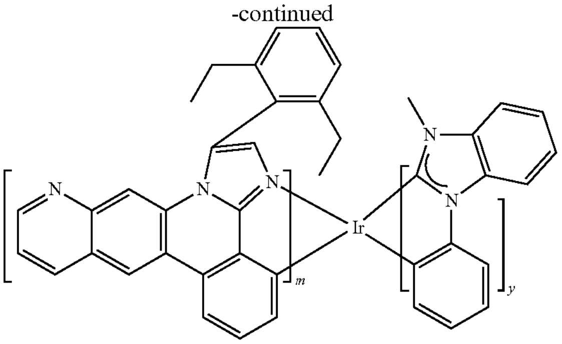
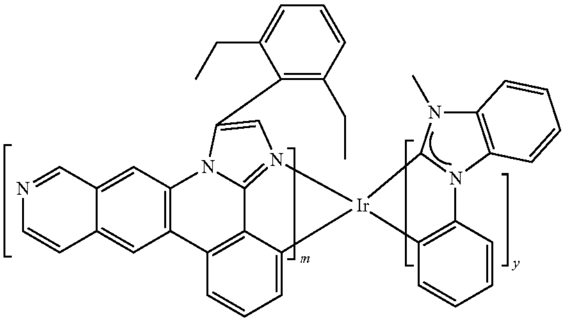
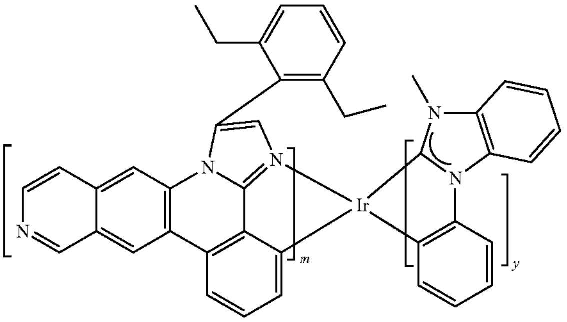
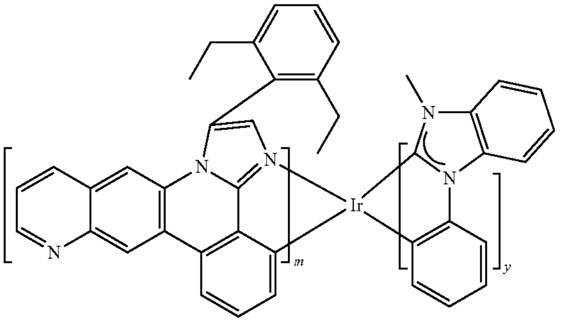
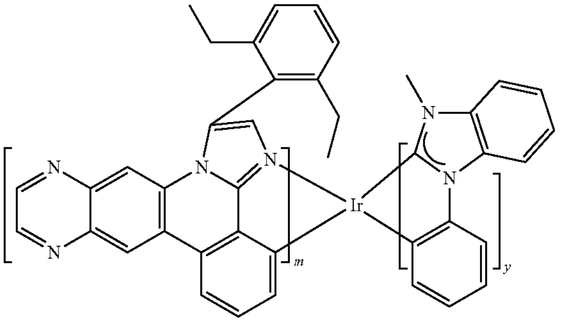

-continued
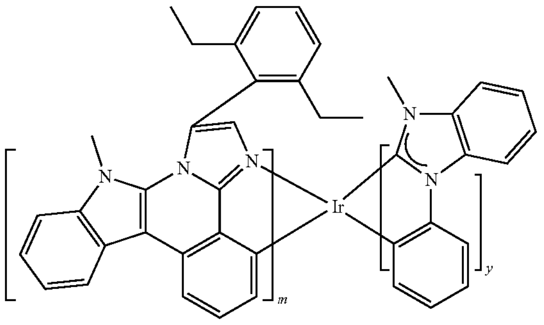
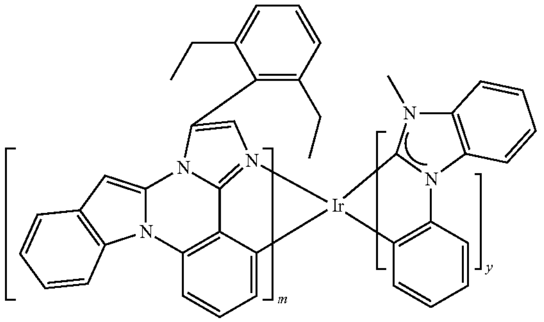
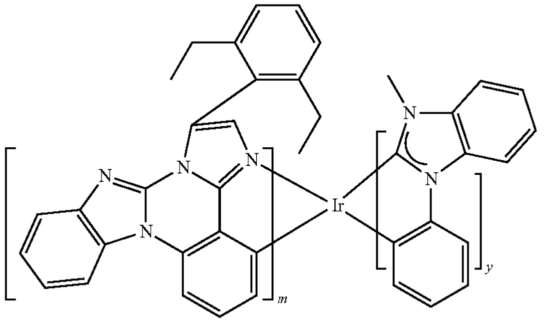
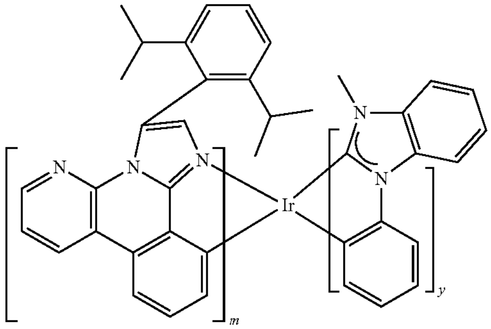
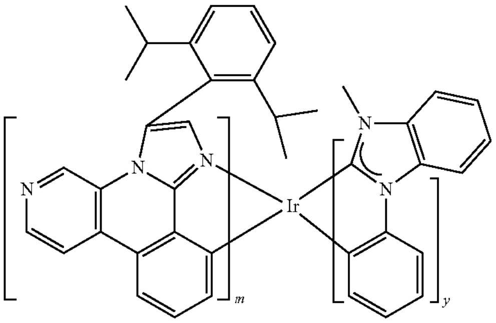
-continued
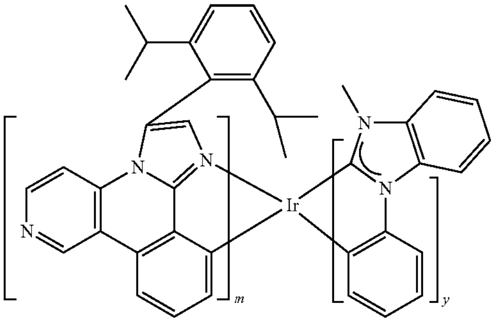
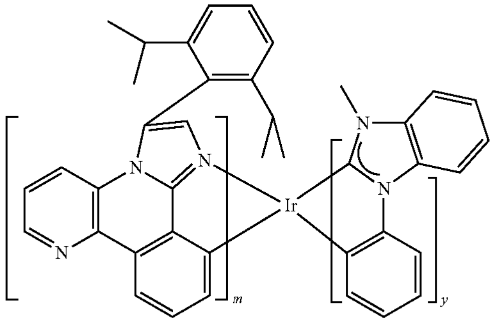
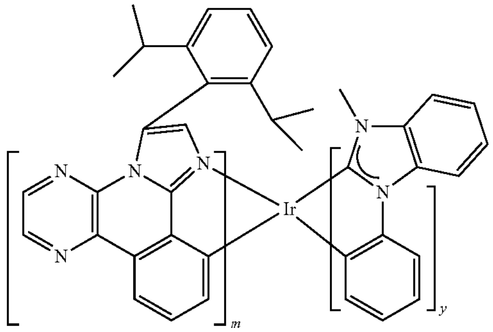
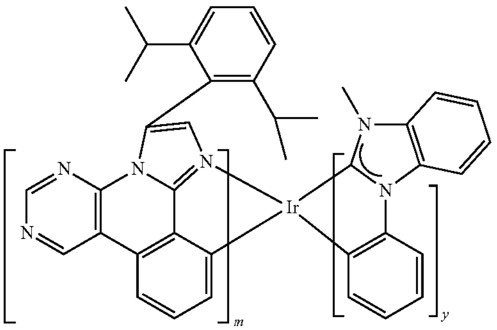
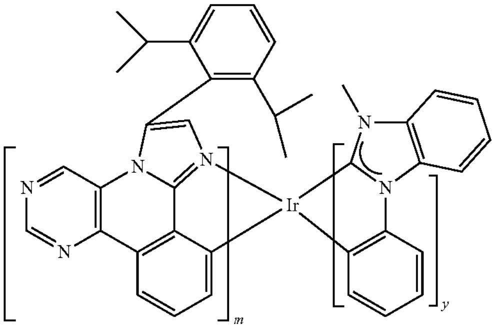

-continued
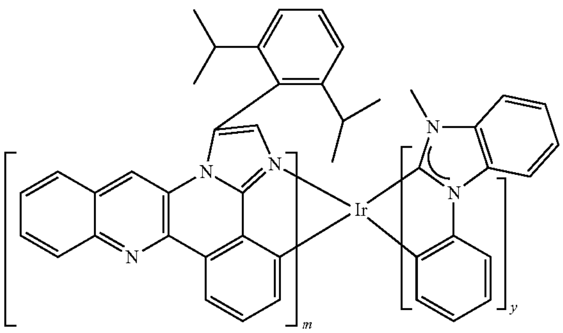
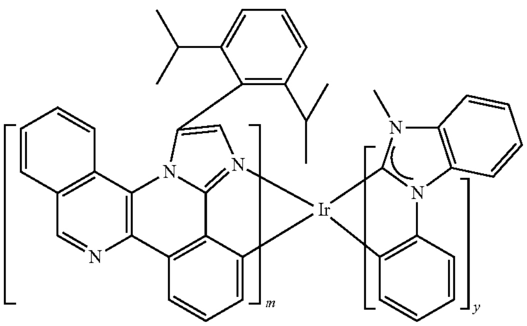
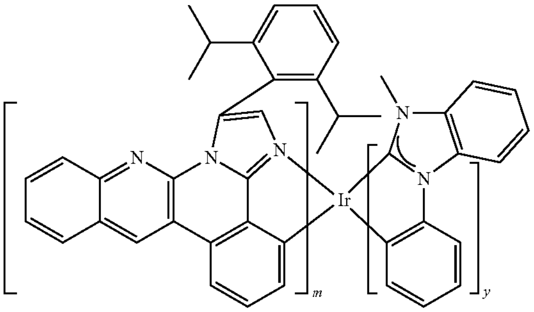
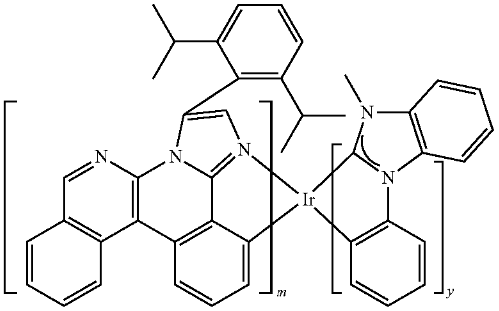
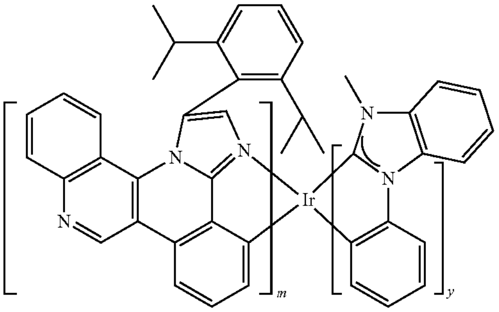
-continued
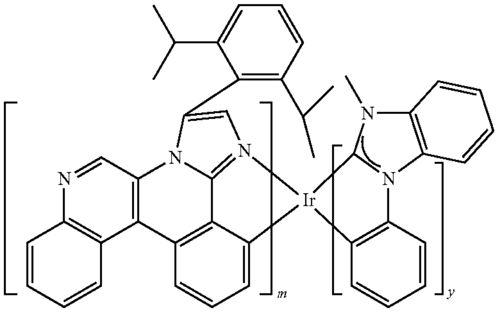
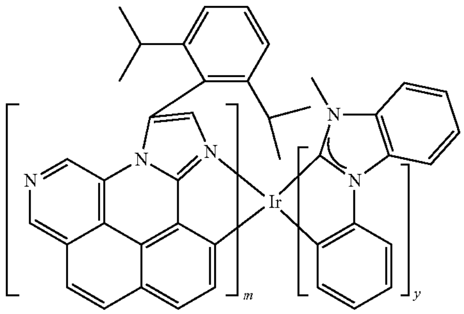
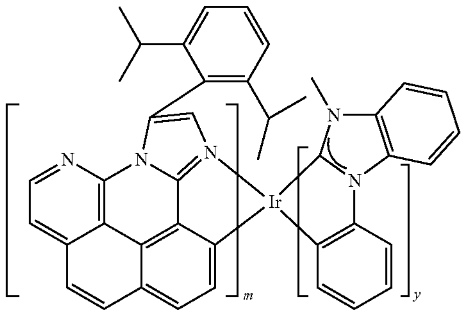
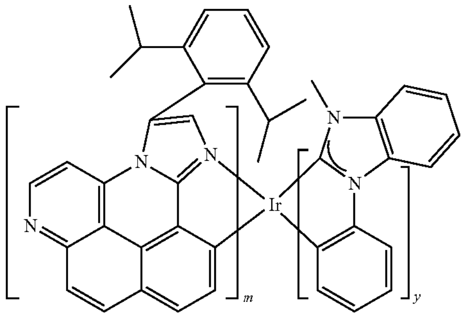
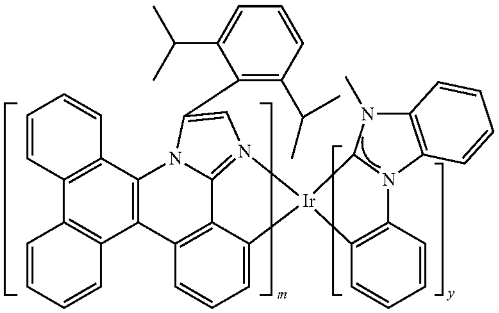

-continued
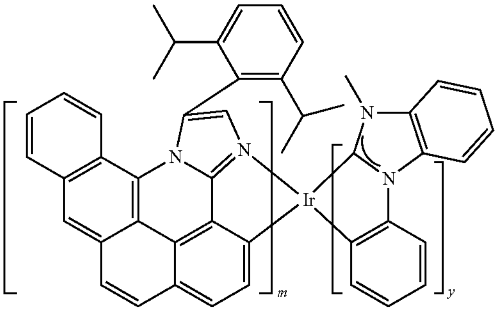
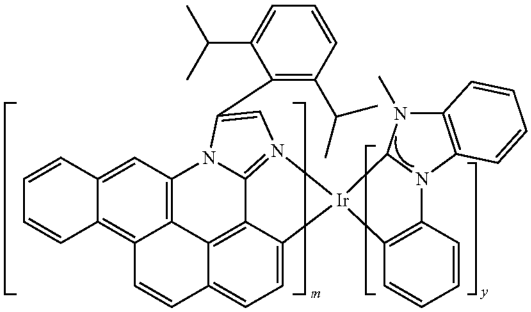
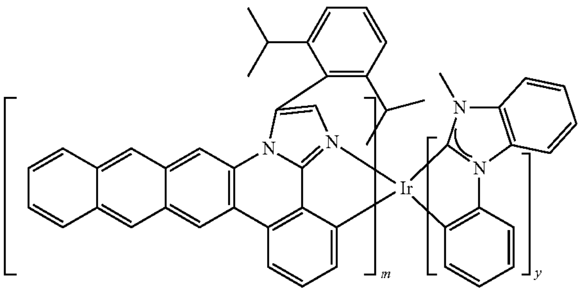
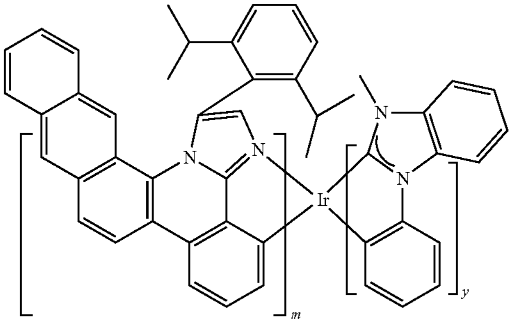
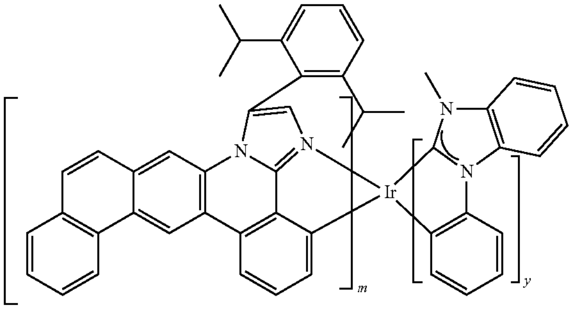
-continued
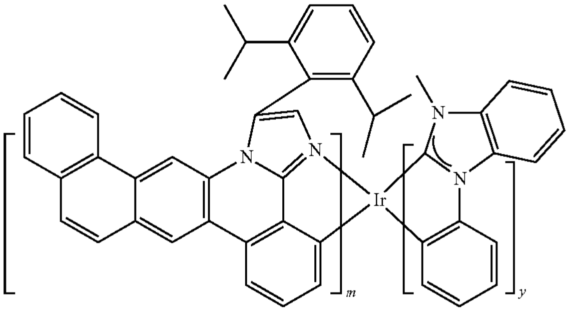
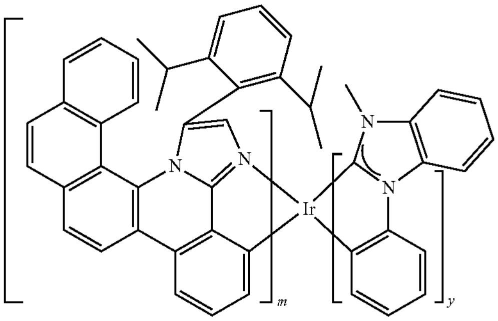
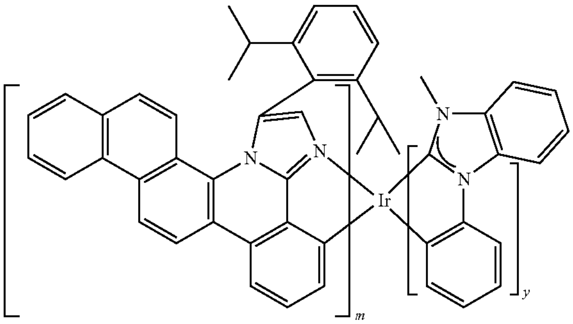
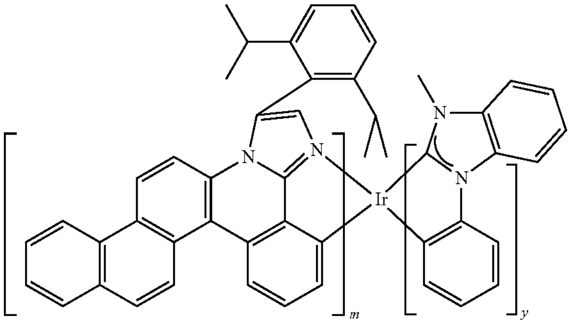
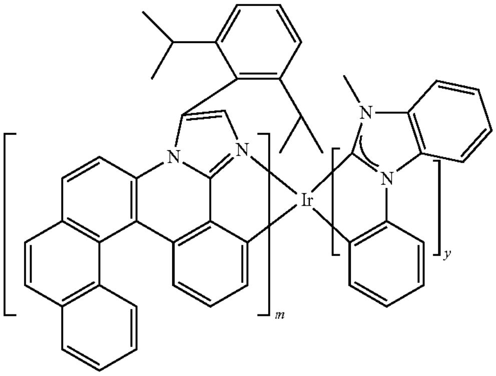

-continued
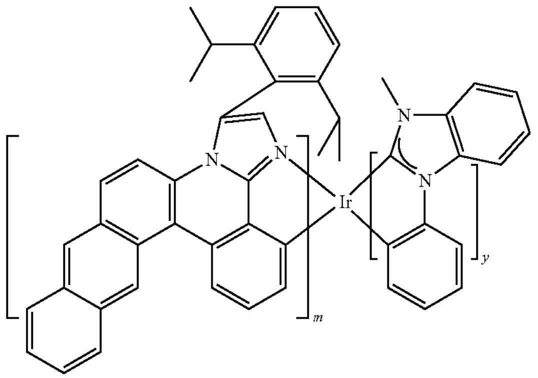
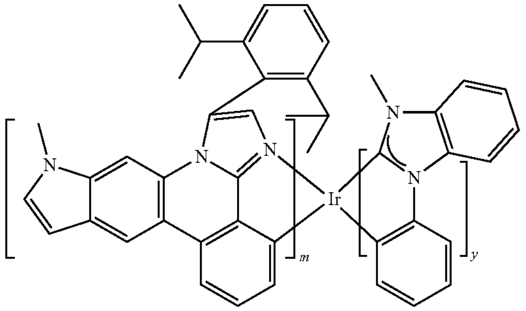
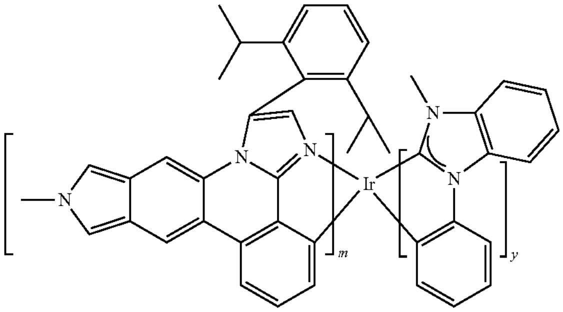
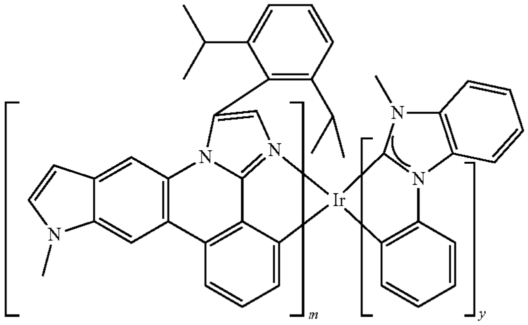
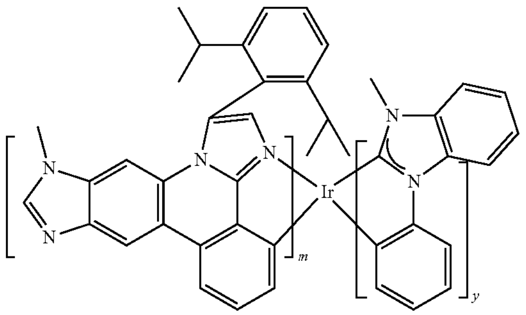
-continued
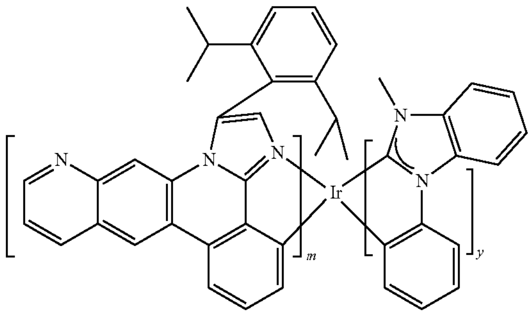
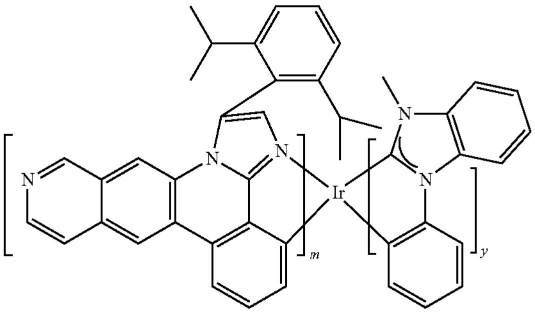
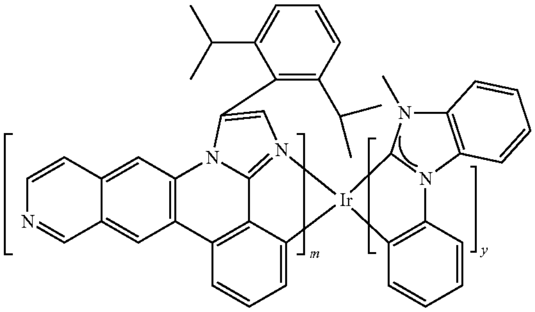
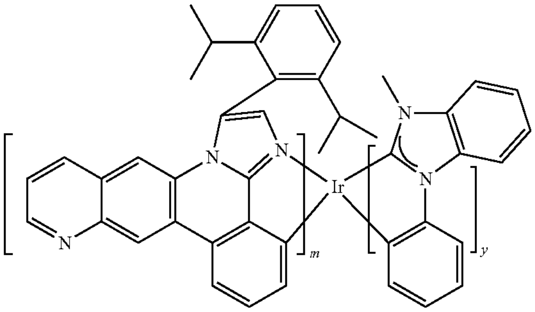
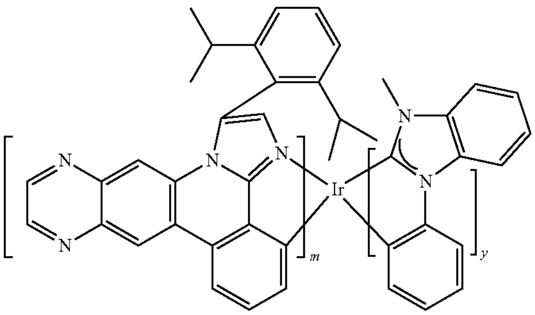

-continued
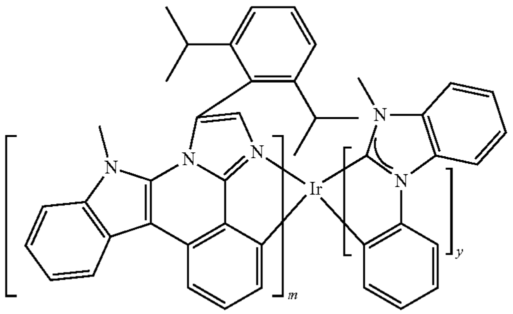
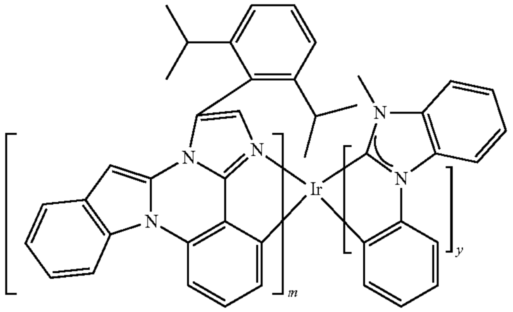
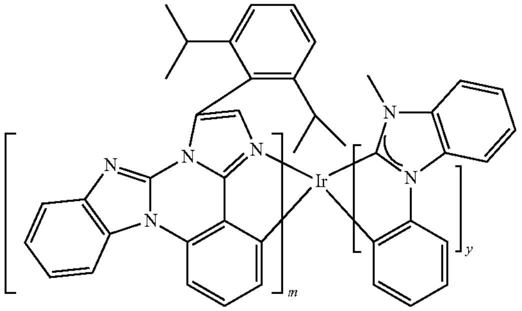
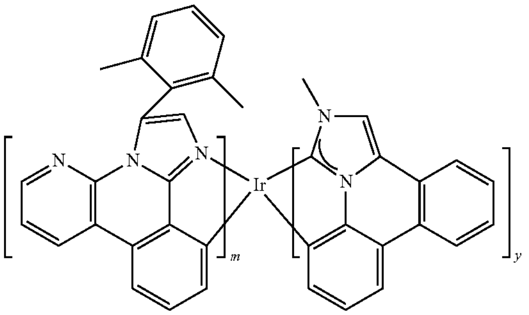
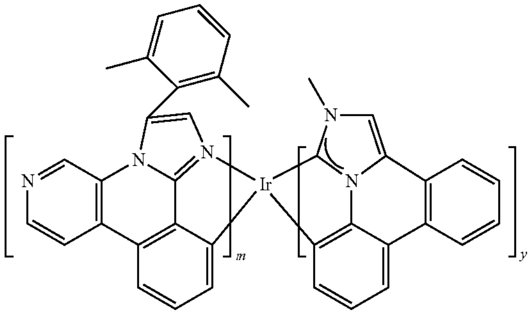
-continued
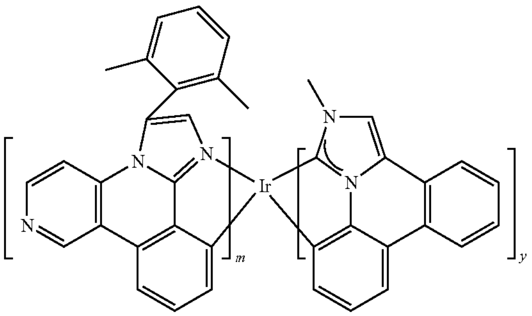
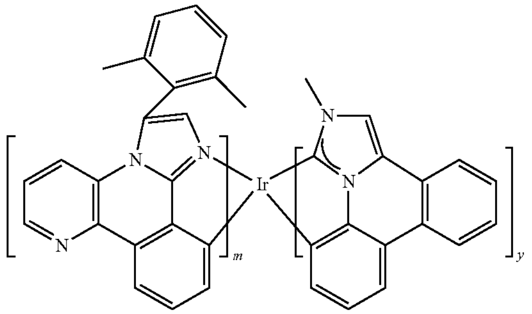
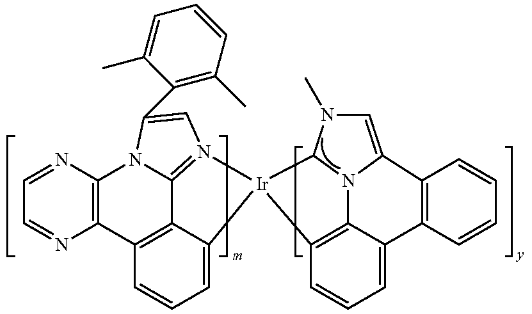
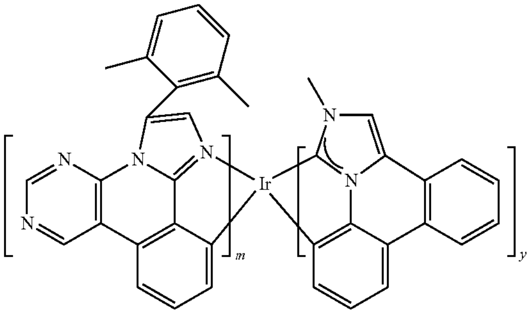
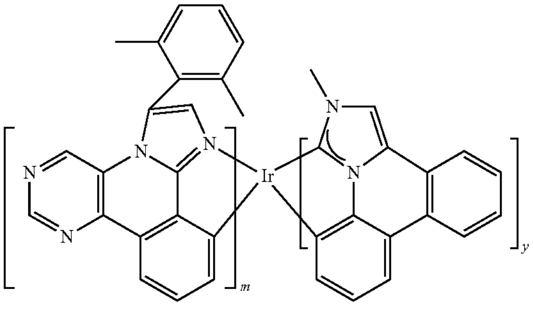

-continued
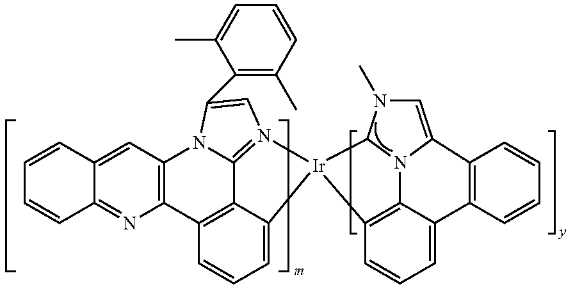
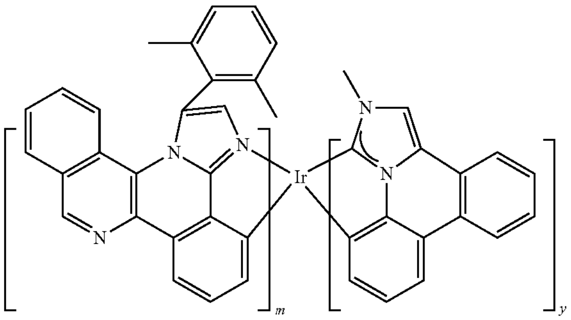
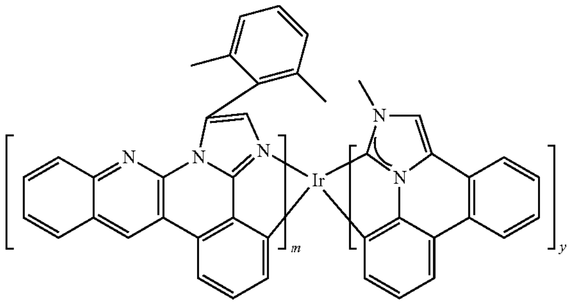
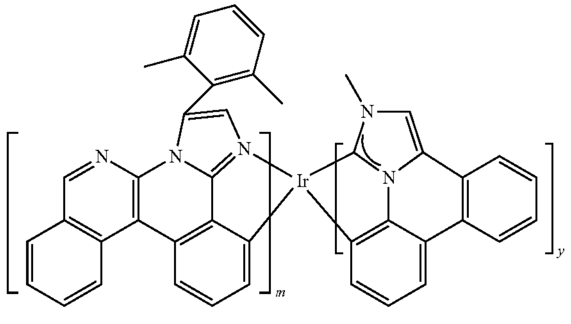
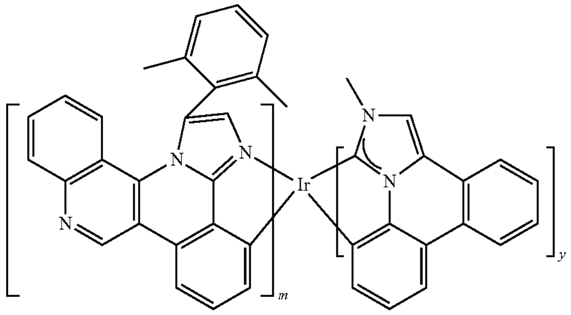
-continued
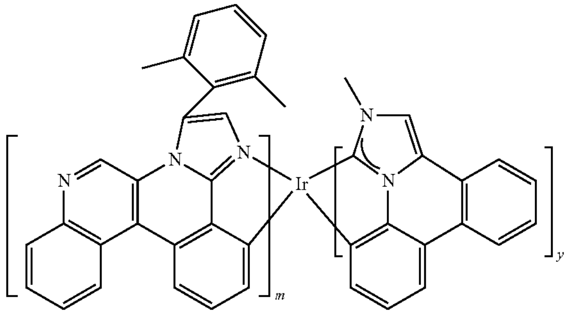
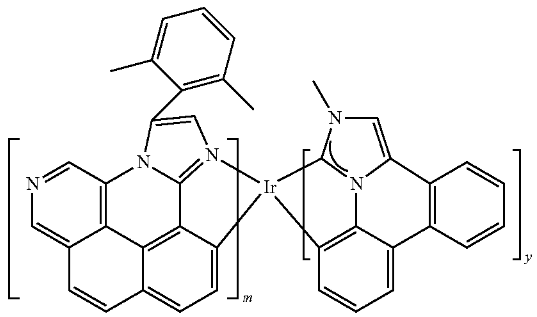
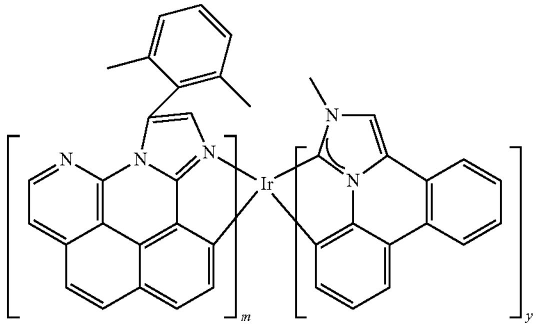
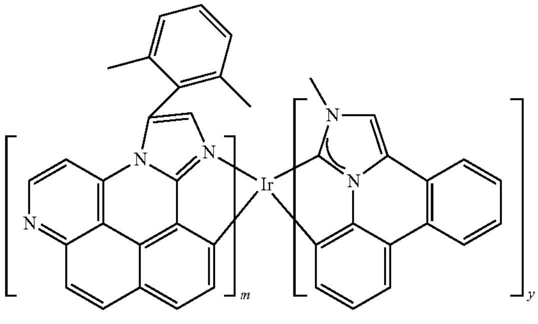
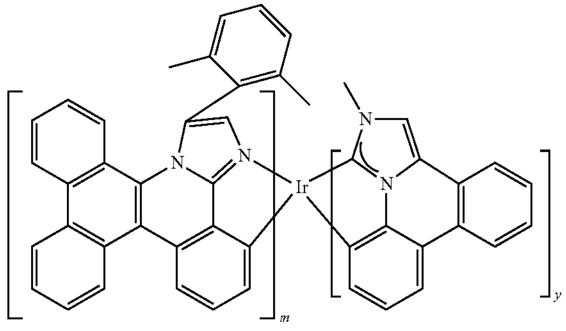

-continued
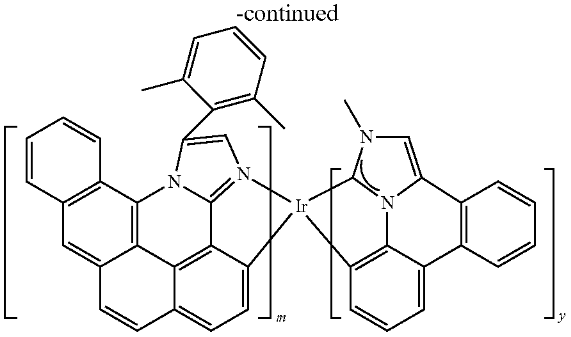
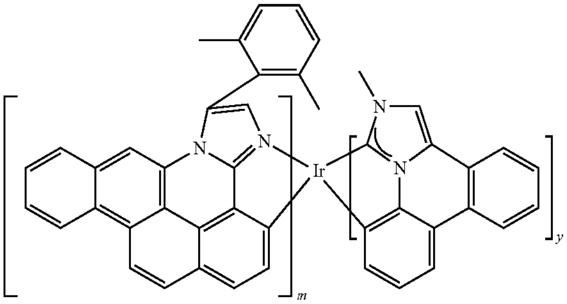
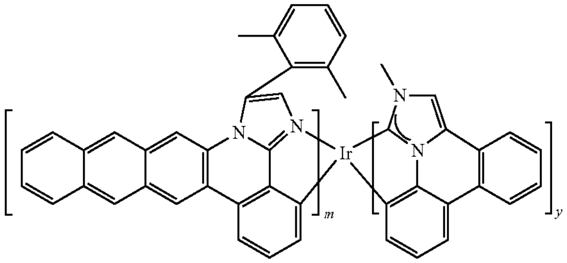
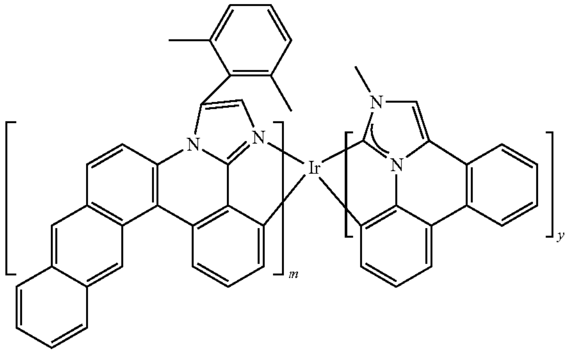
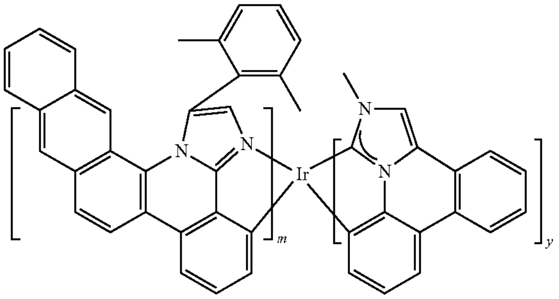
-continued
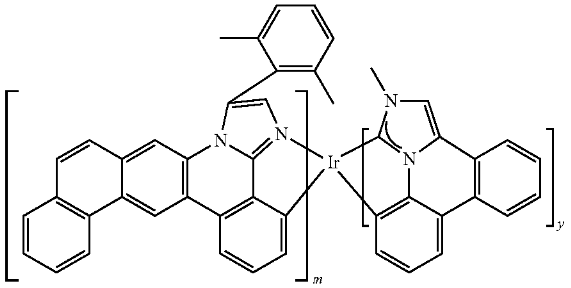
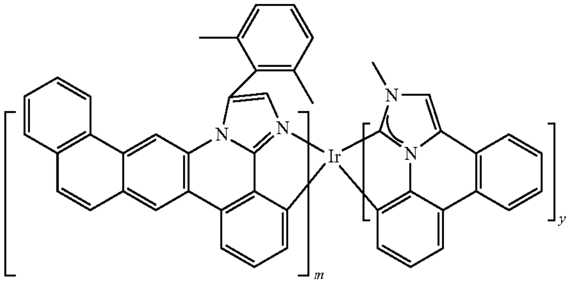
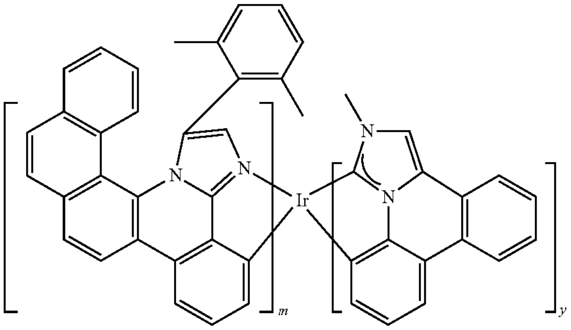
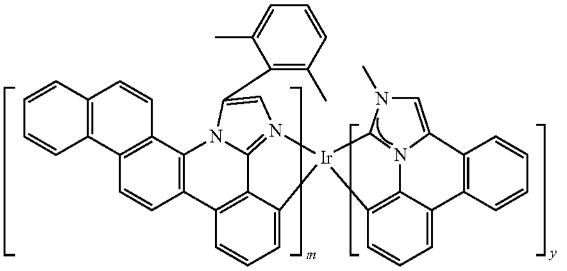
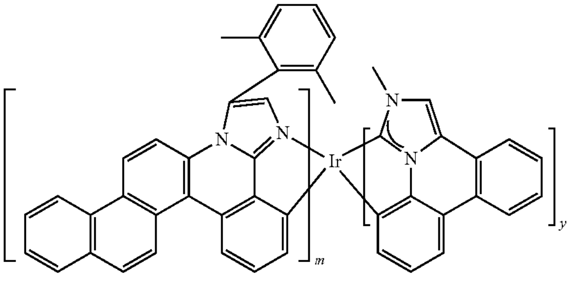

-continued
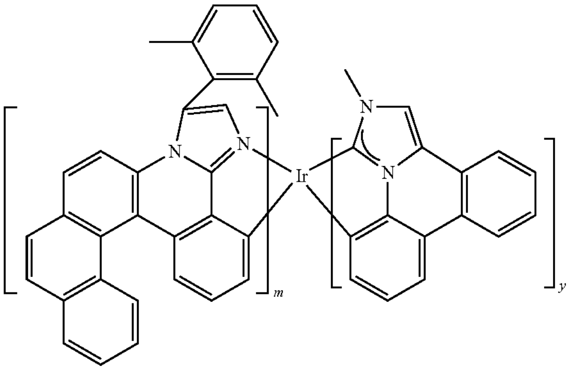
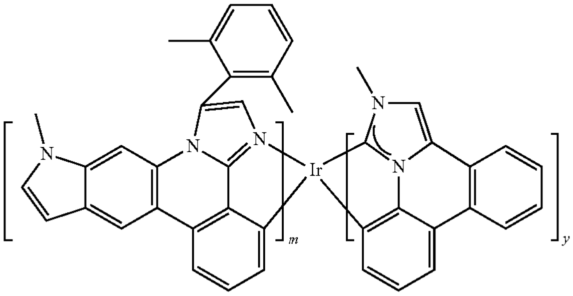
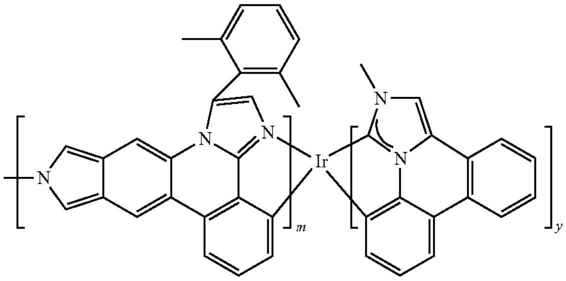
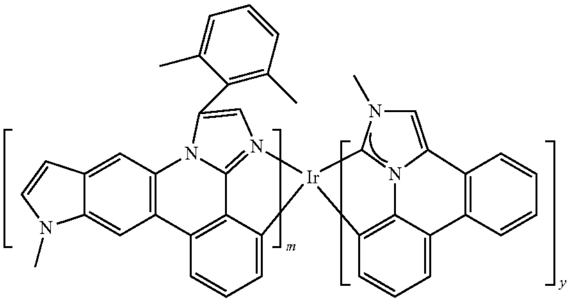
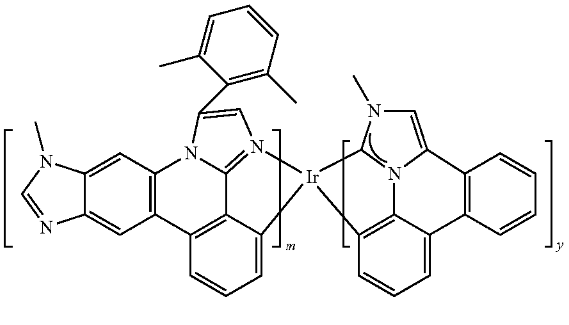
-continued
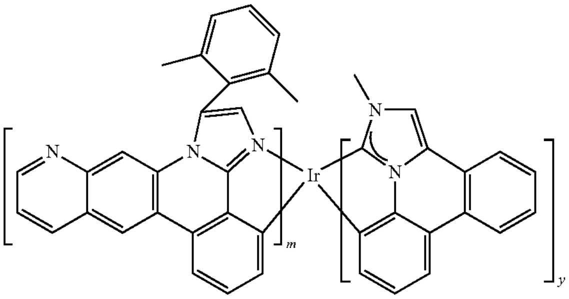
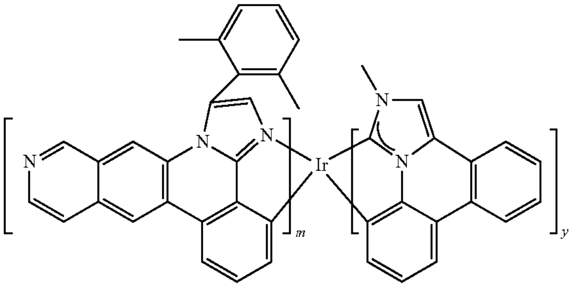
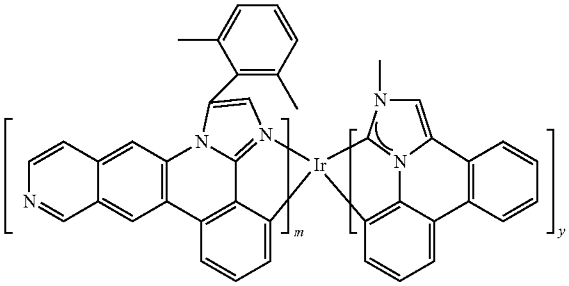
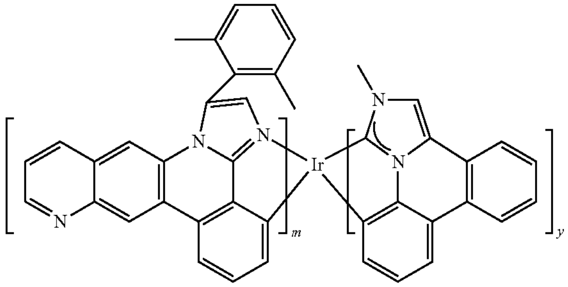
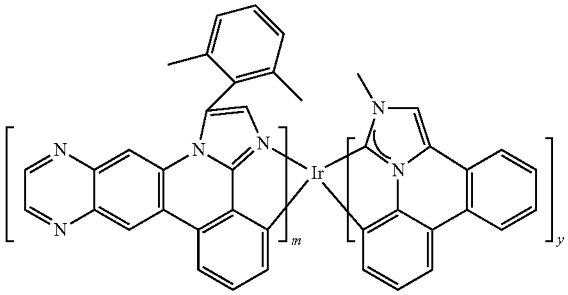

-continued
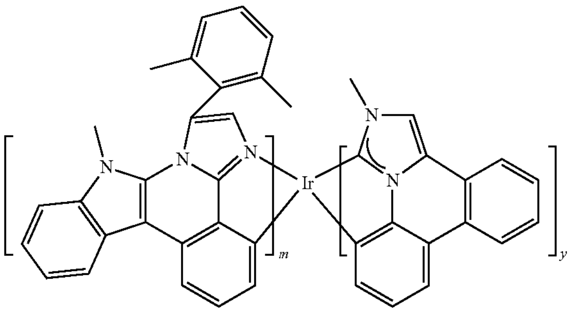
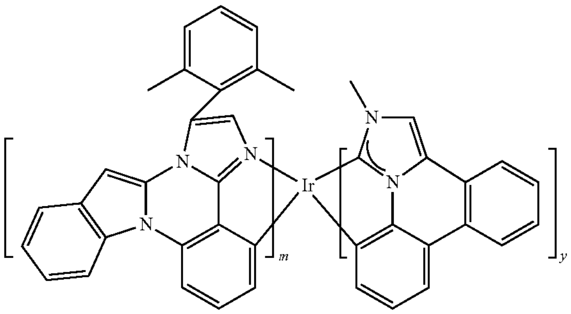
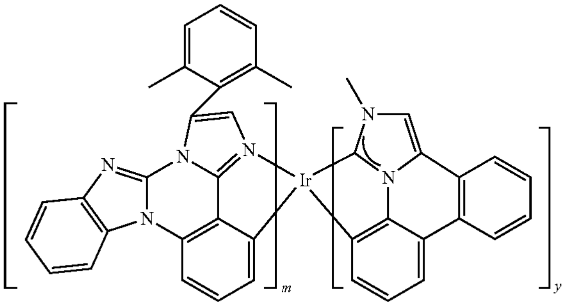
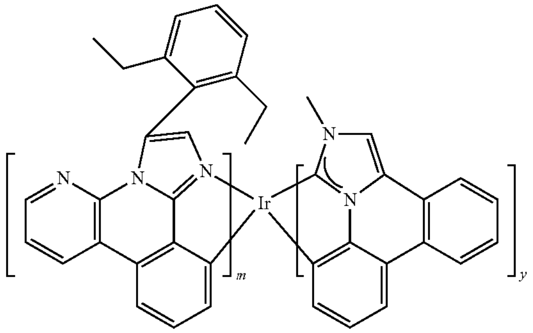
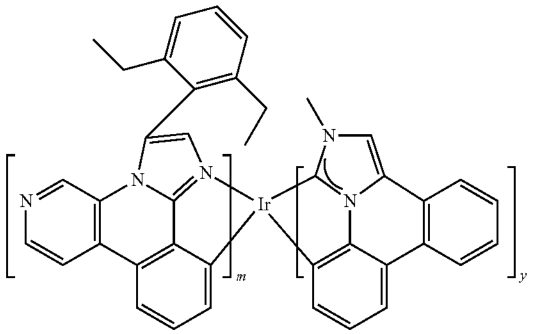
-continued
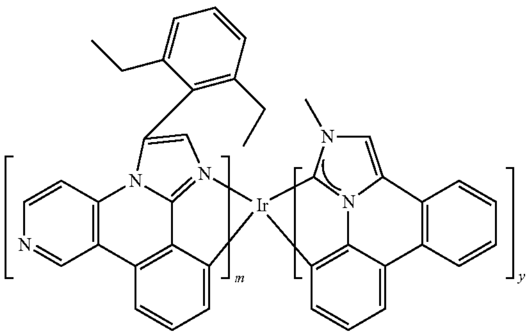
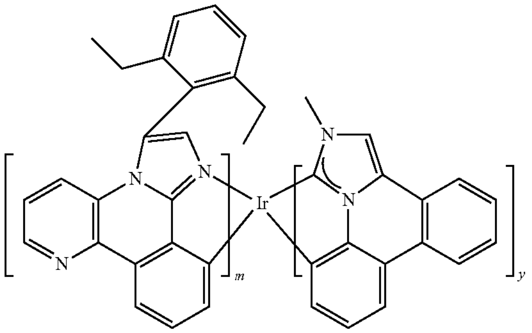
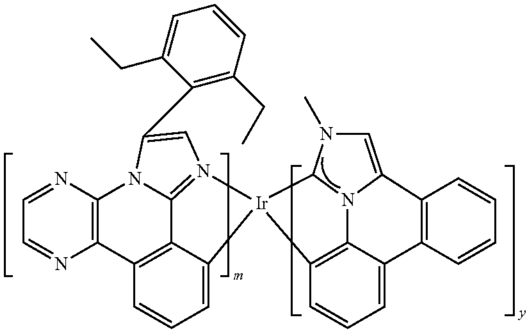
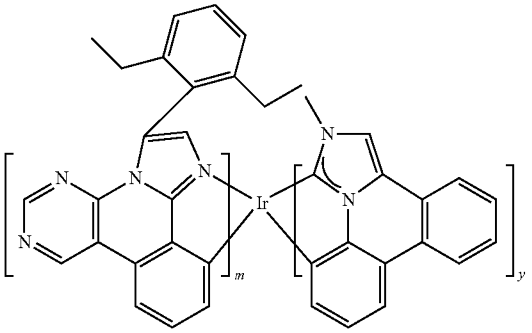
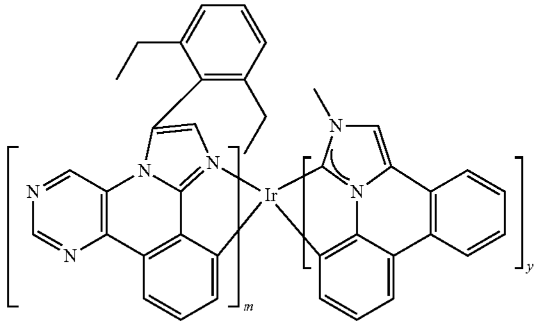

-continued
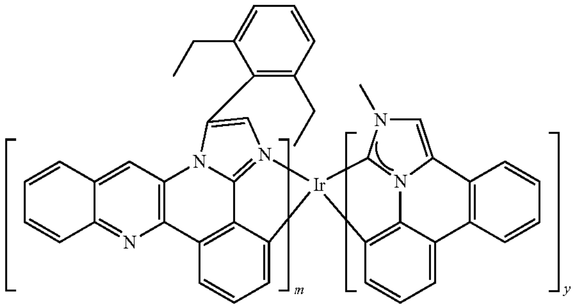
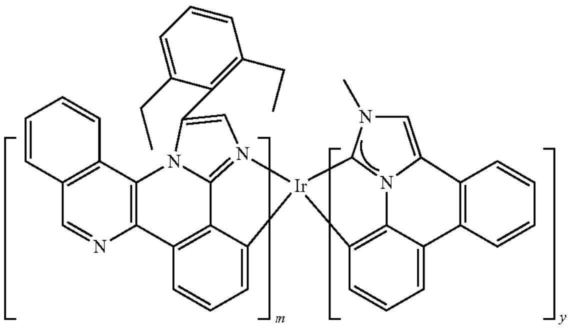
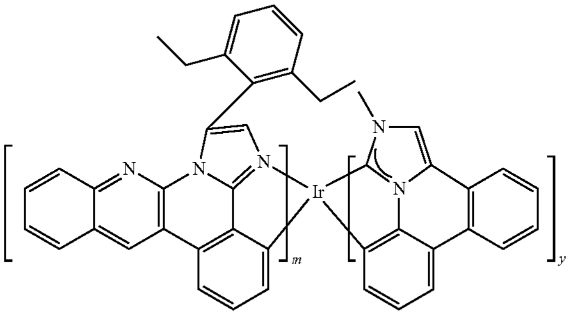
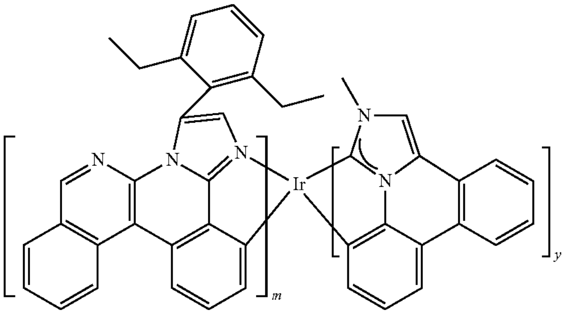
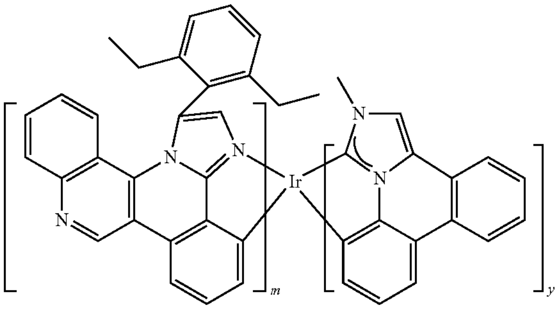
-continued
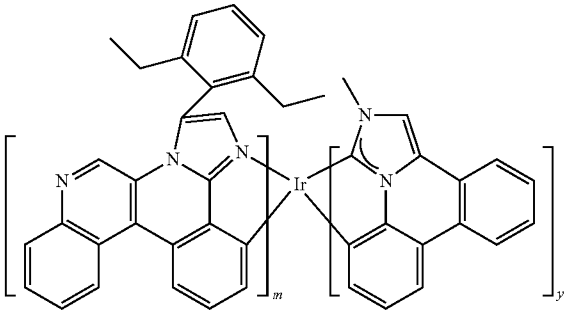
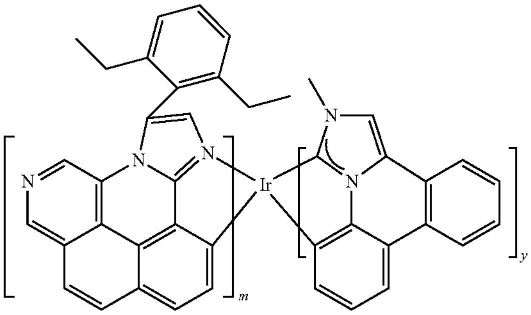
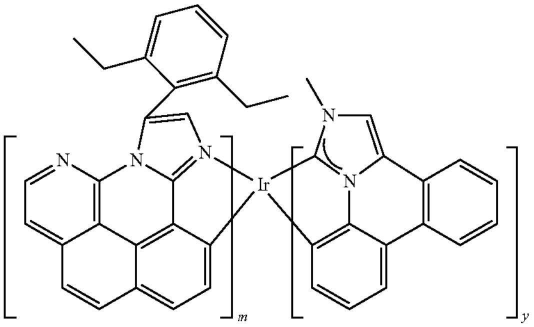
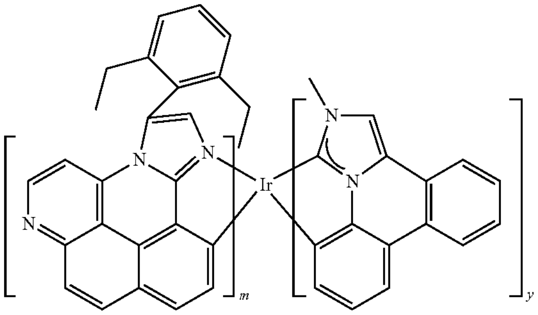
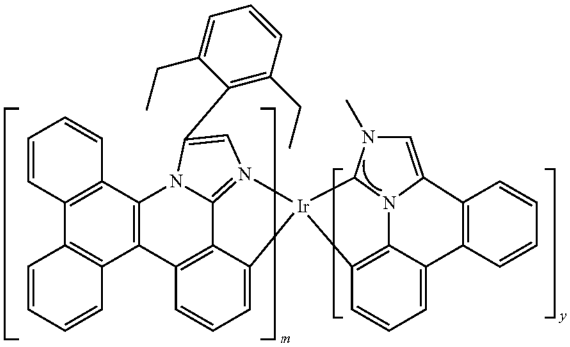

-continued
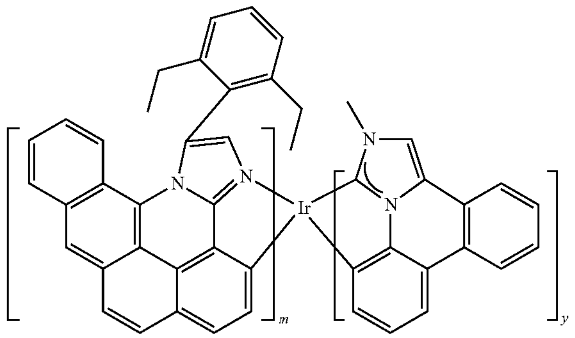
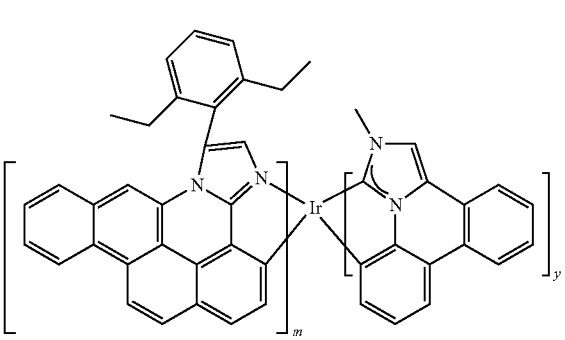
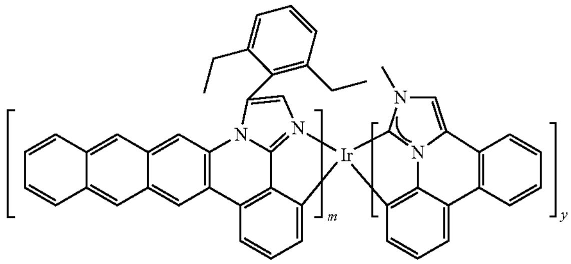
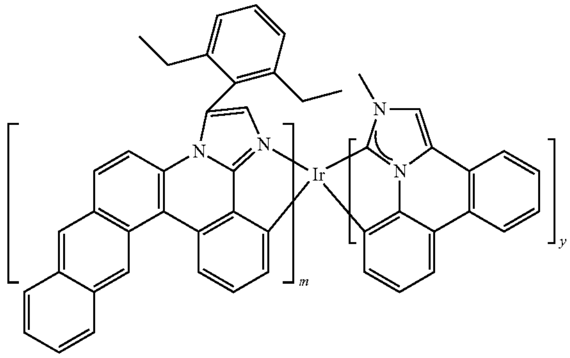
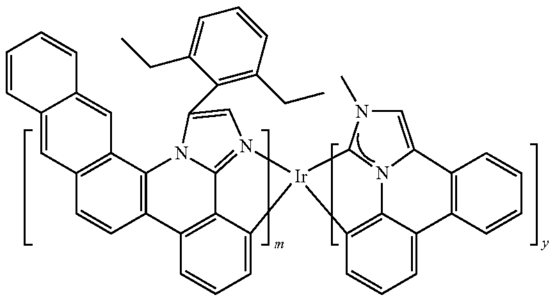
-continued
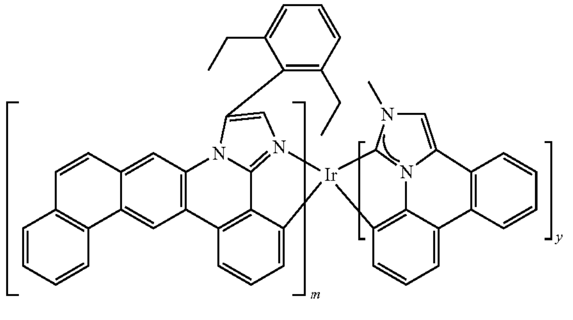
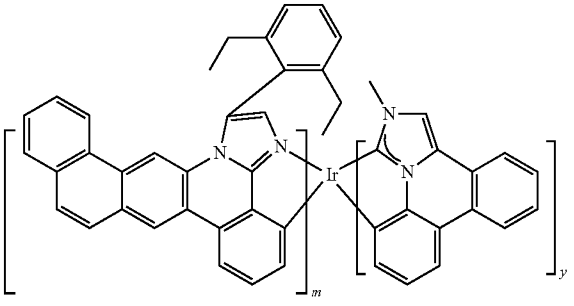
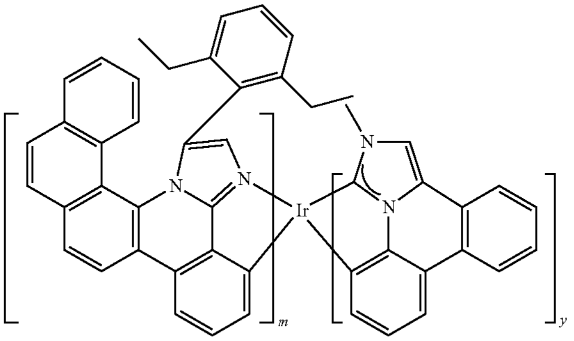
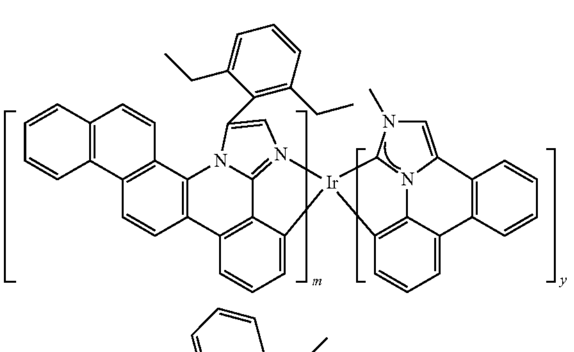
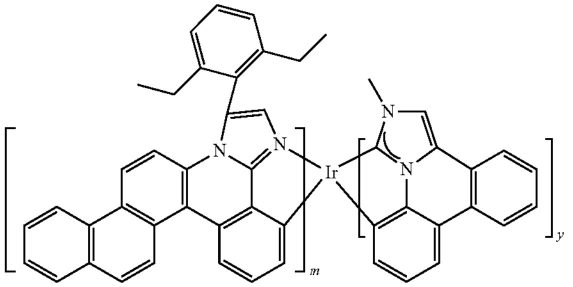

-continued
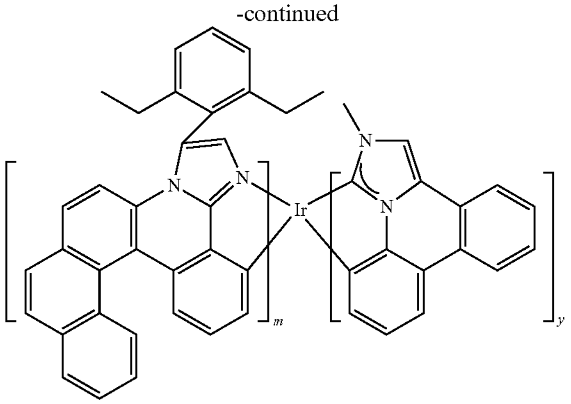
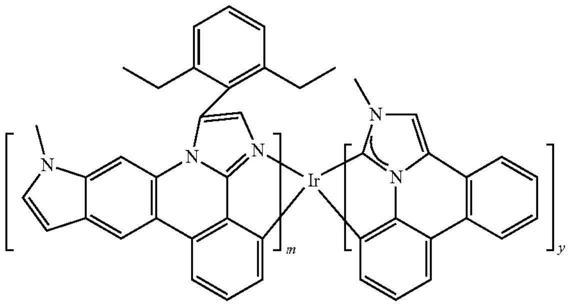
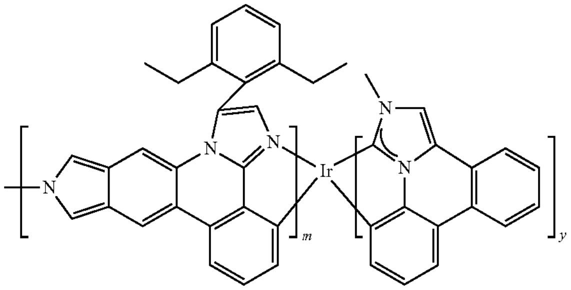
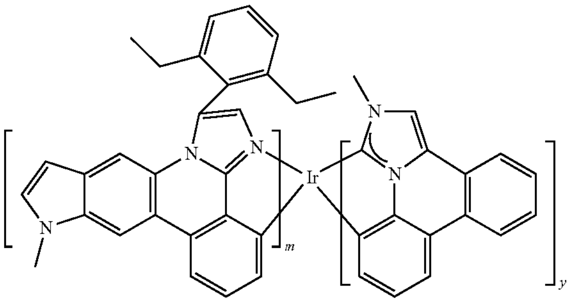
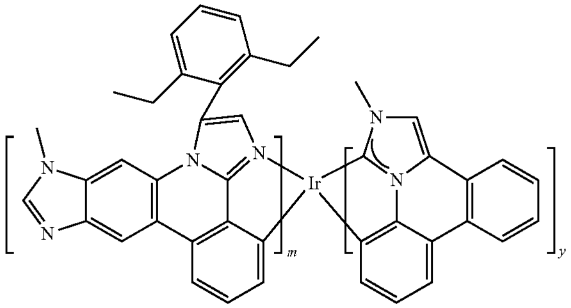
-continued
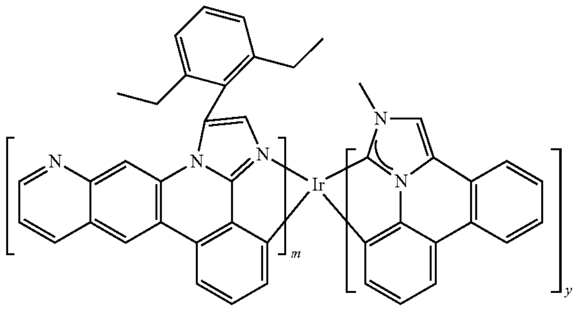
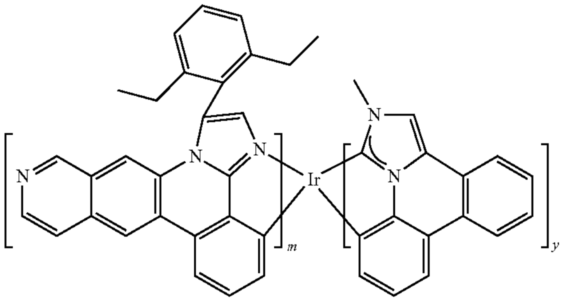
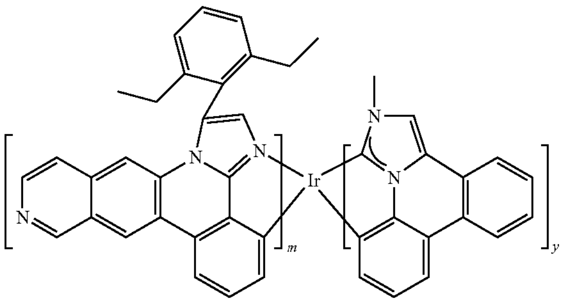
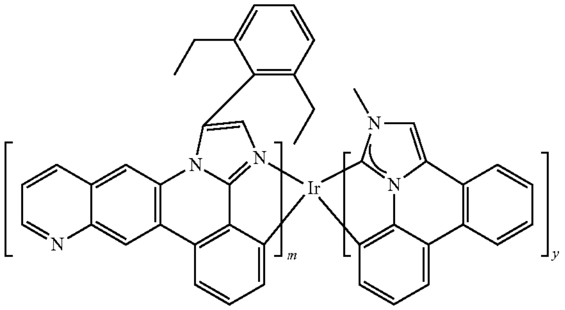
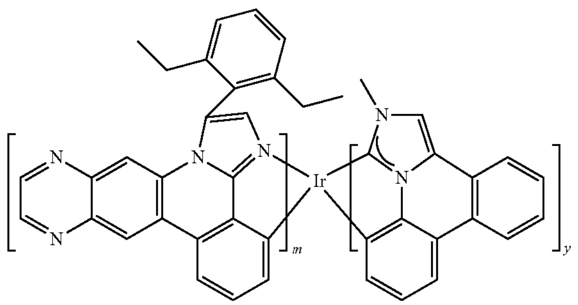

-continued
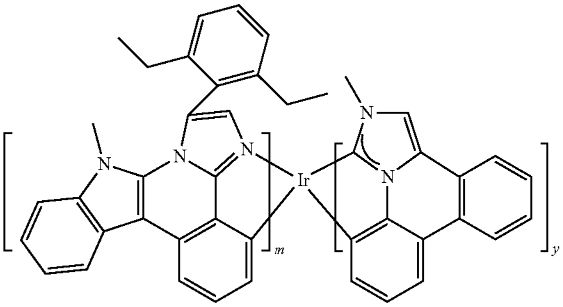
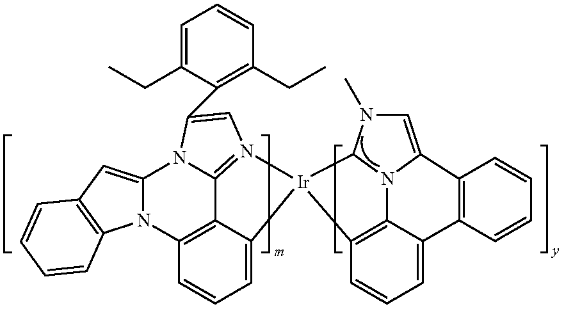
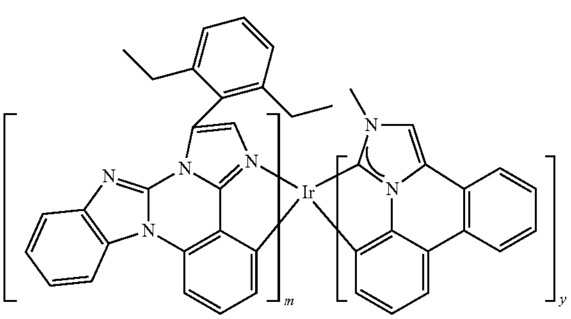
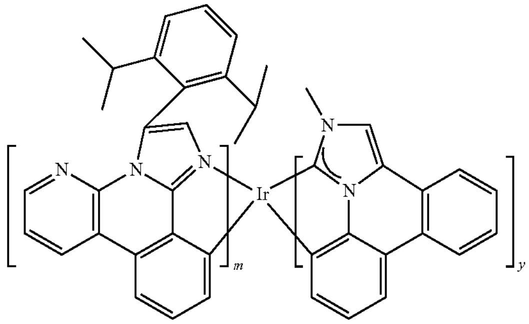
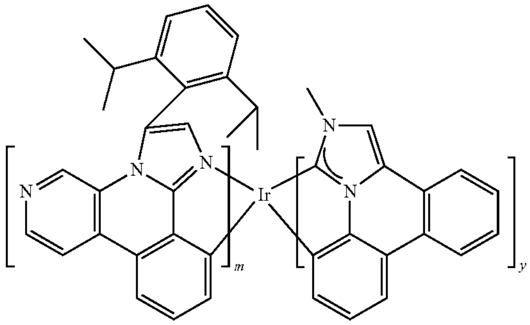
-continued
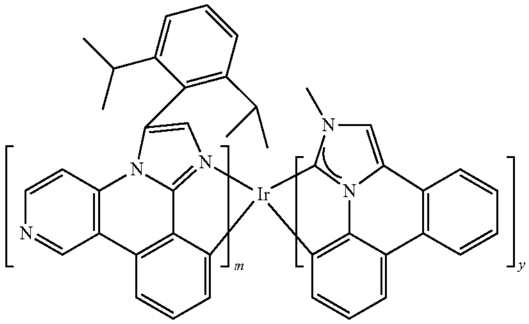
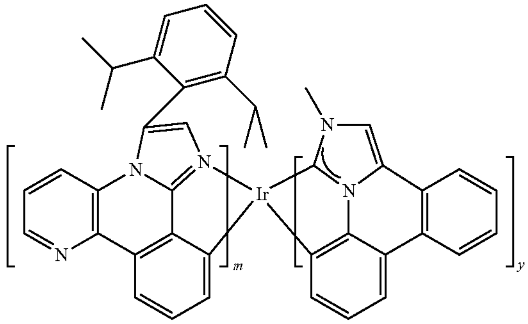
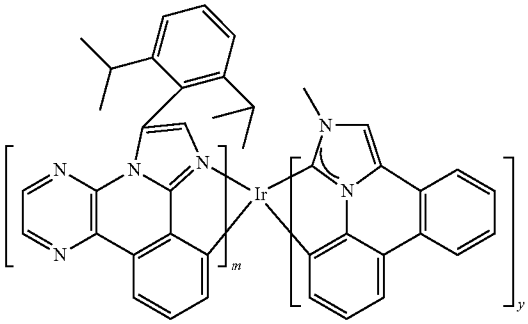
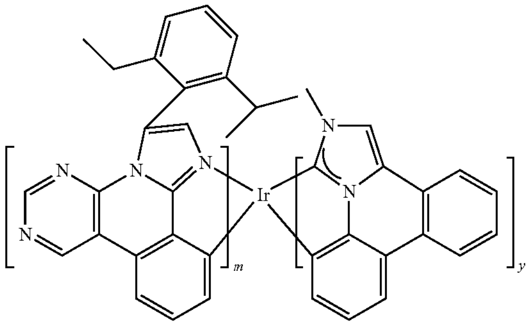
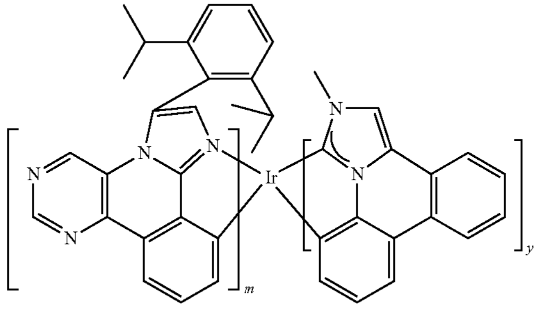

-continued
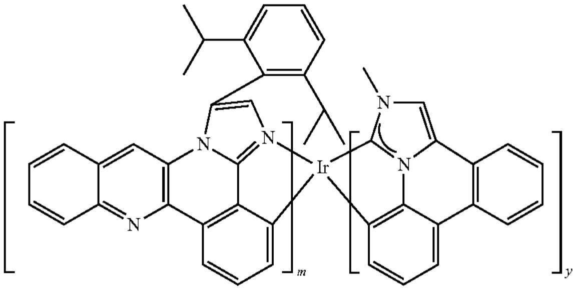
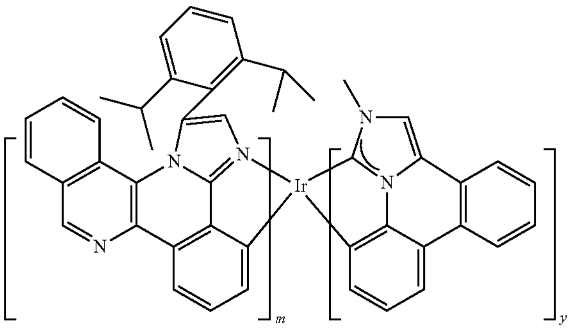
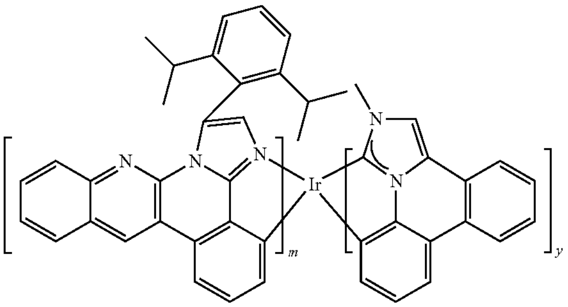
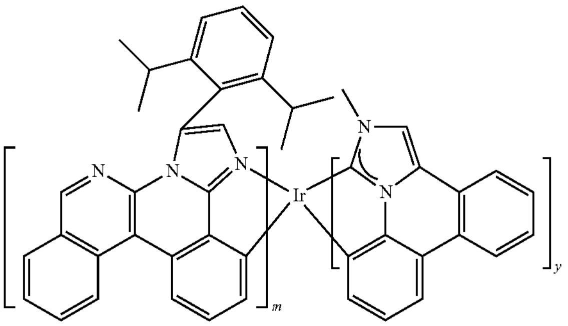
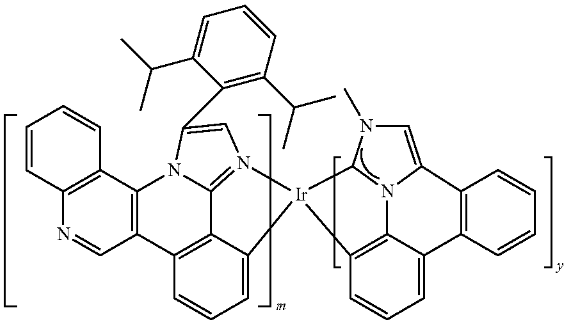
-continued
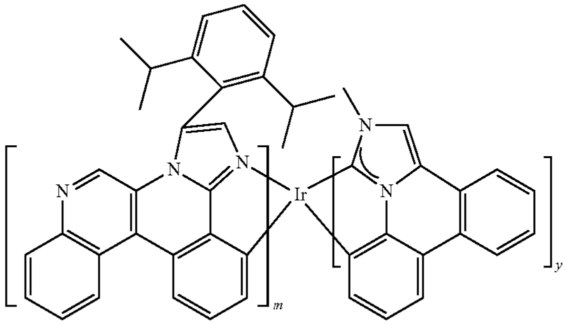
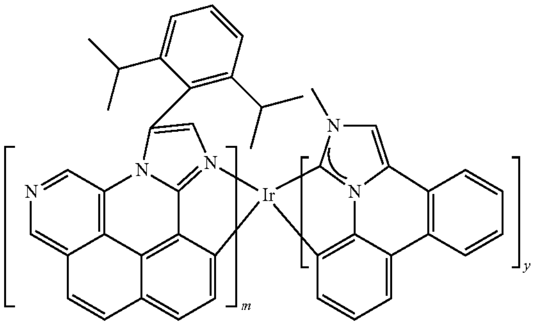
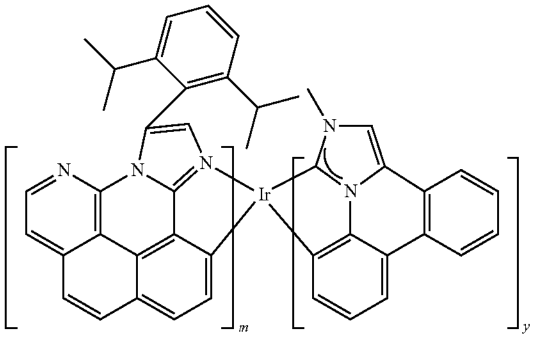
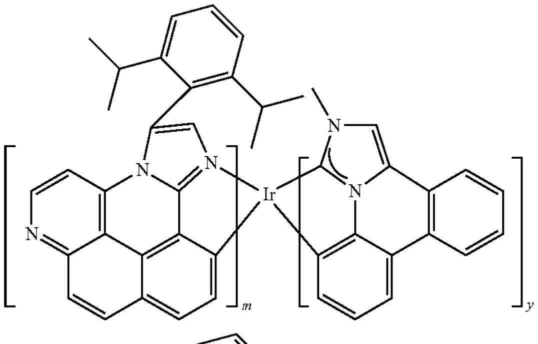
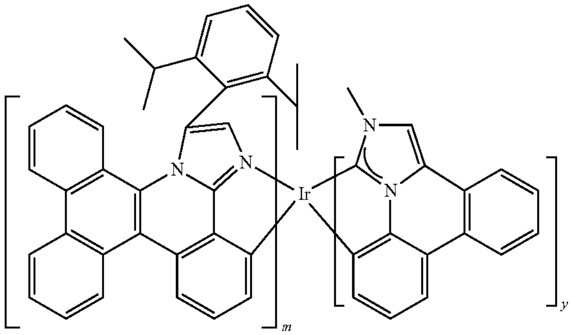

-continued
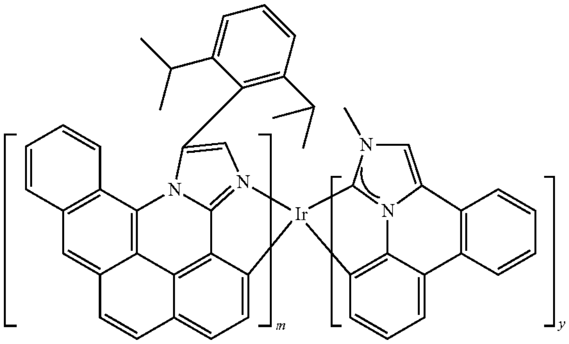
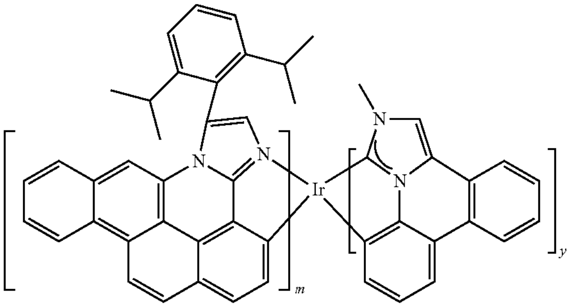
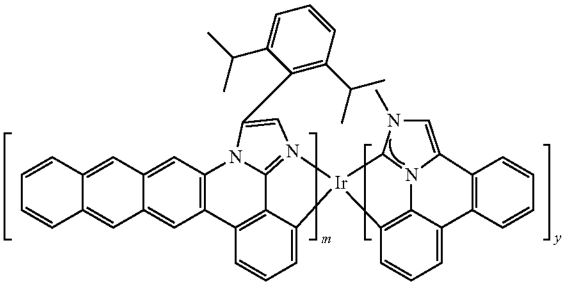
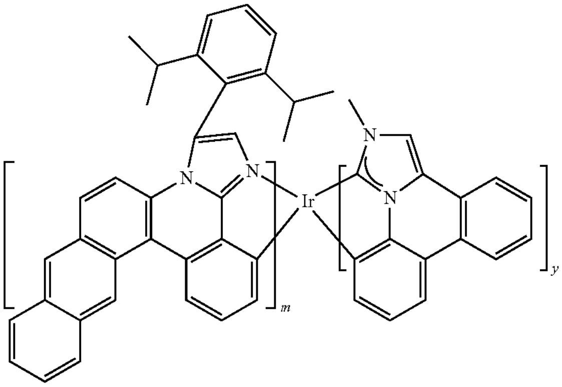
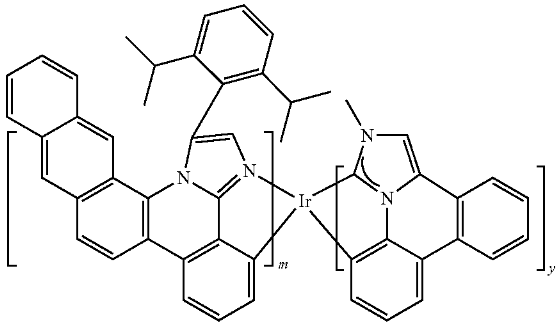
-continued
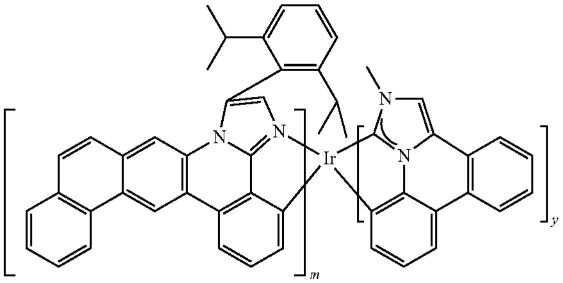
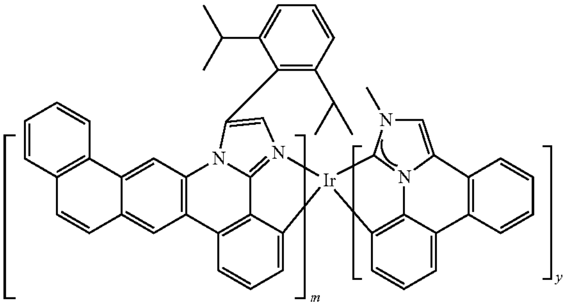
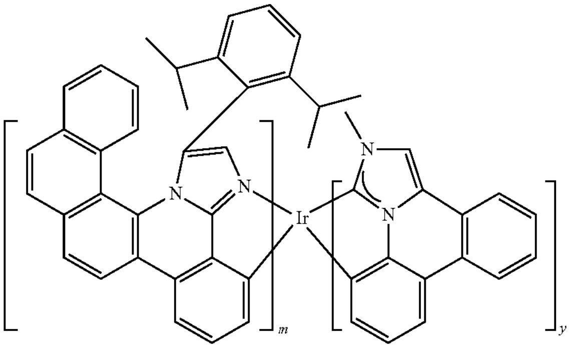
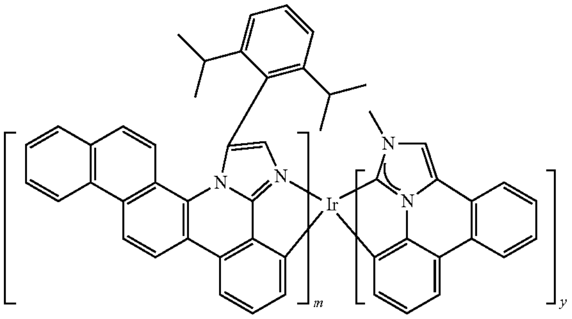
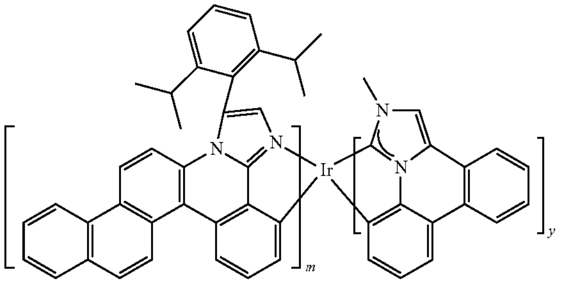

-continued
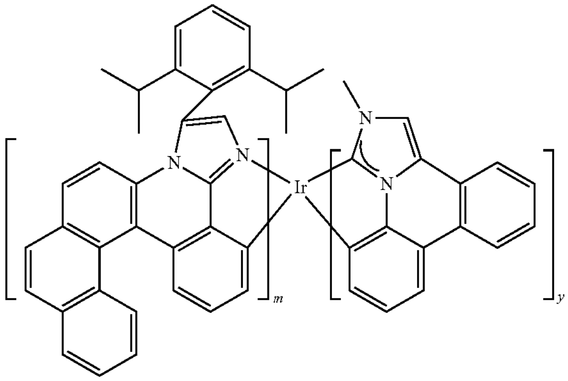
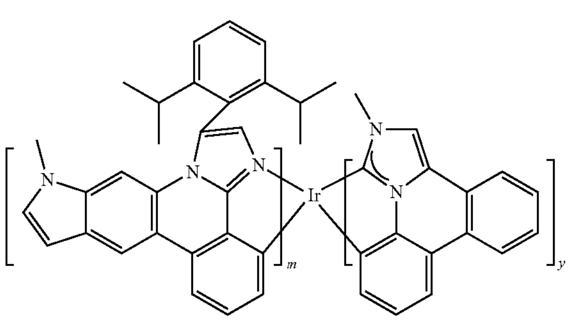
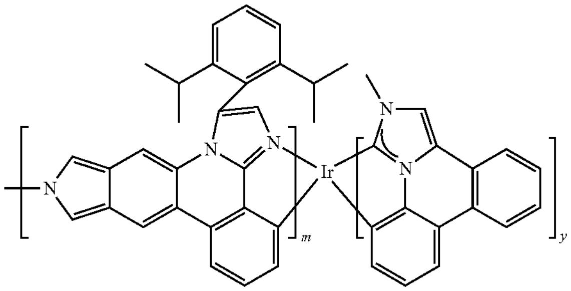
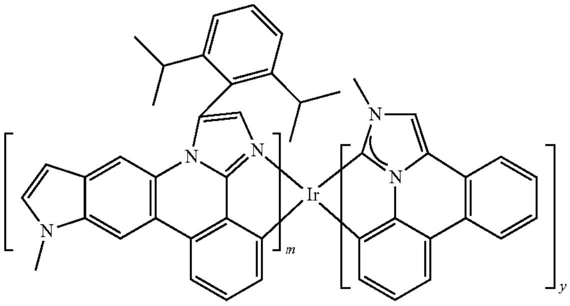
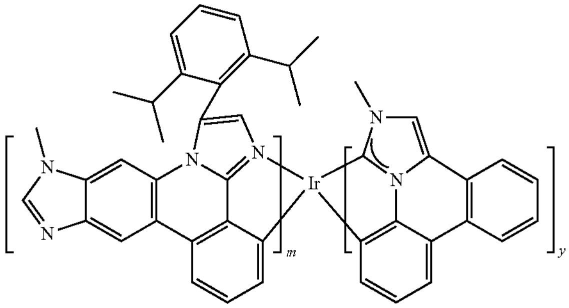
-continued
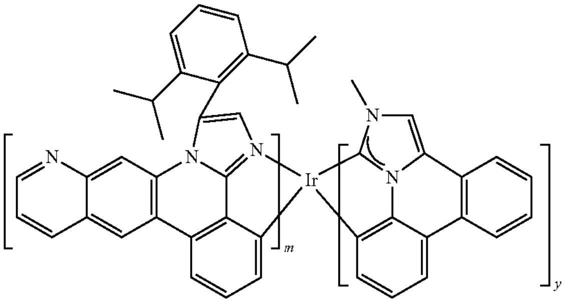
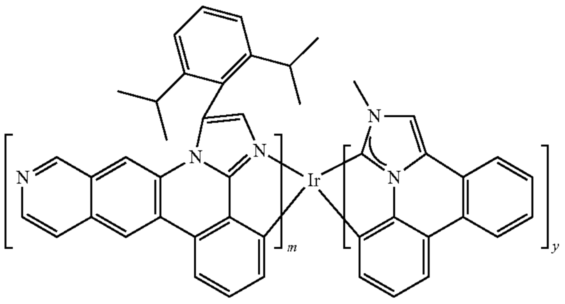
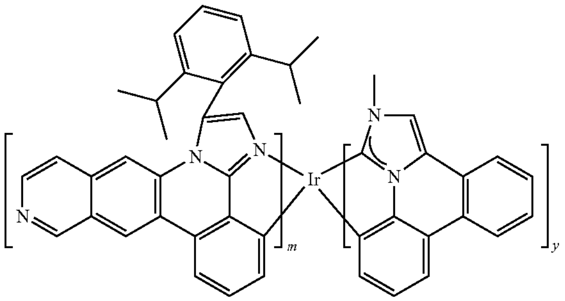
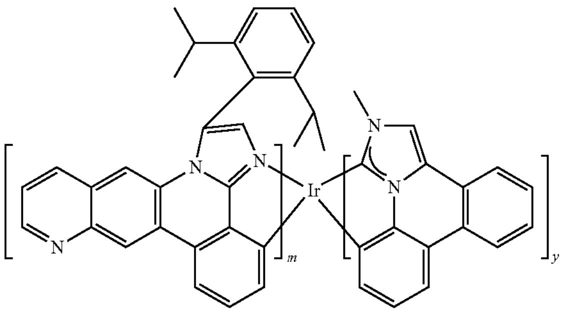
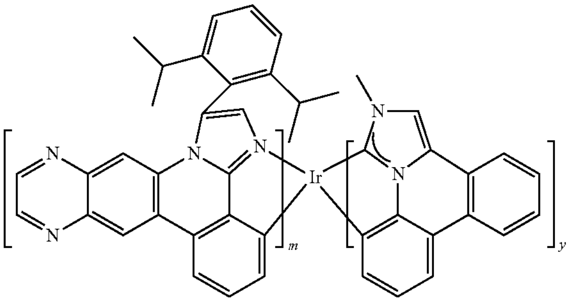

-continued
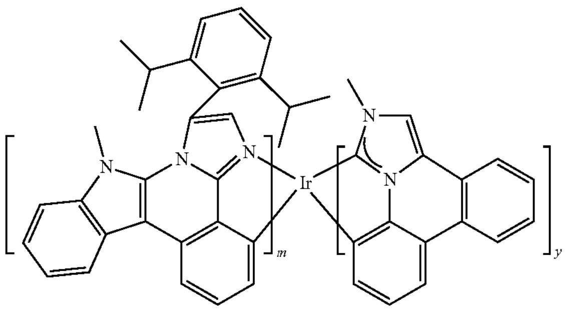
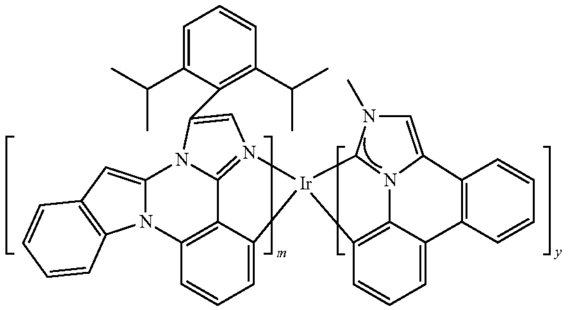
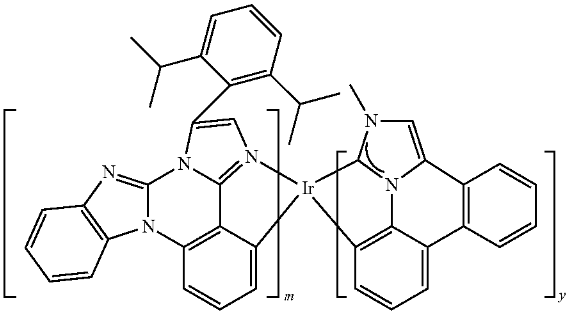
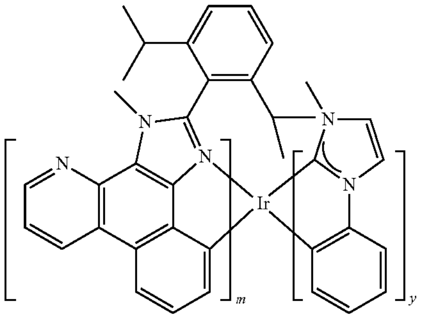
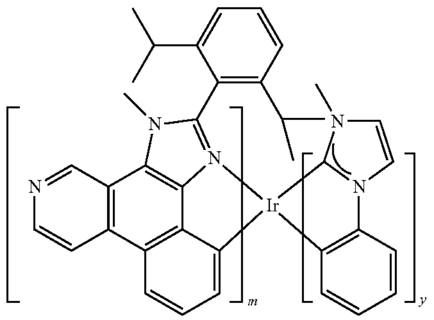
-continued
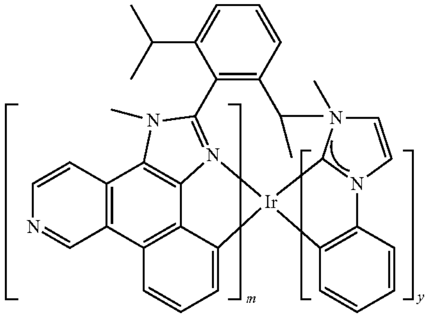
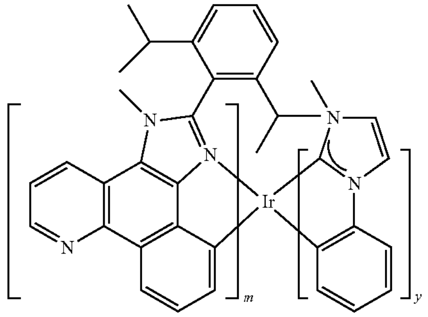
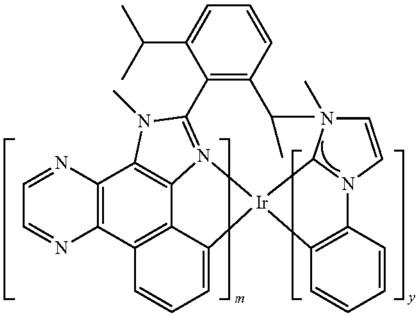
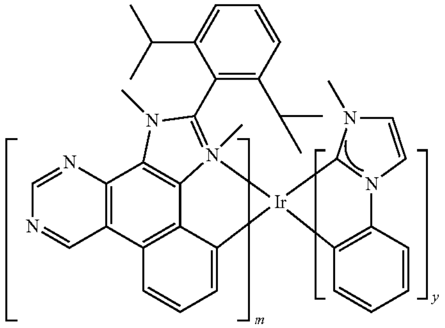
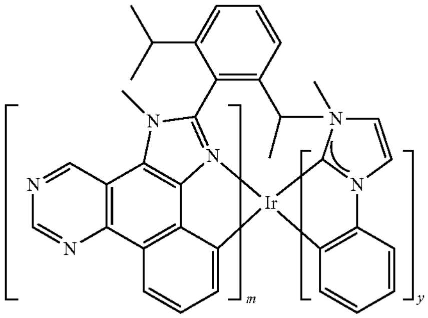

-continued
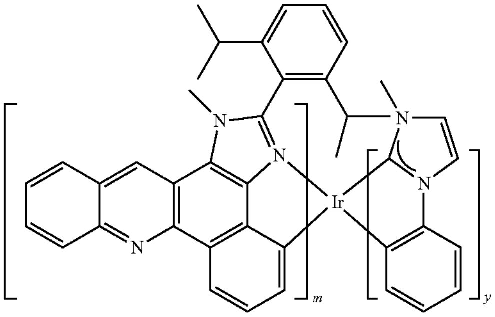
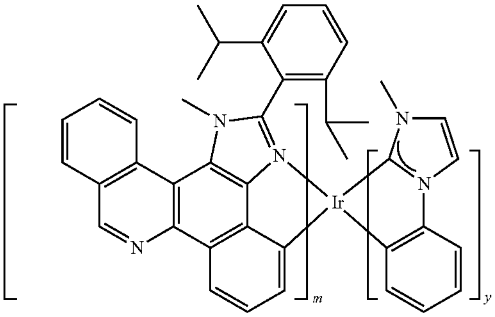
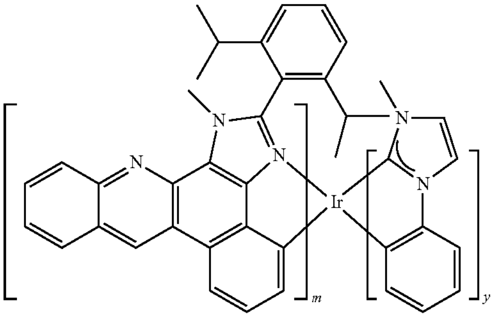
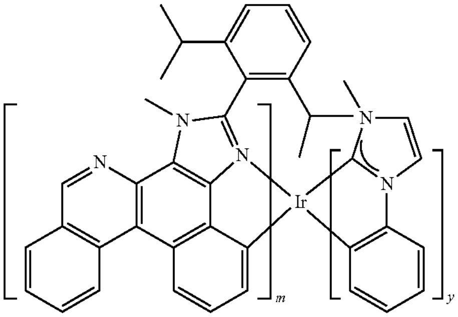
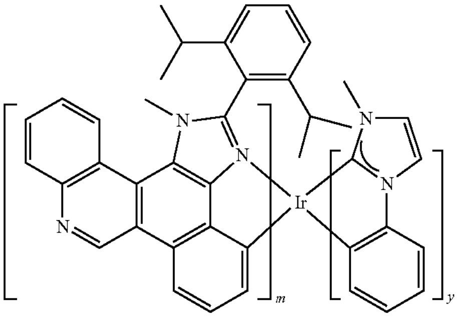
-continued
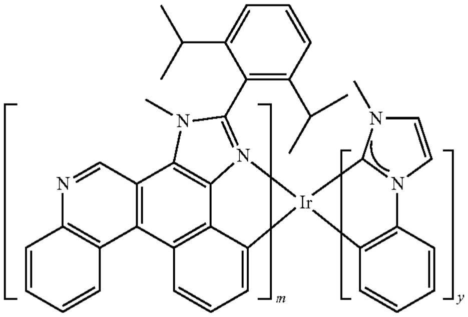
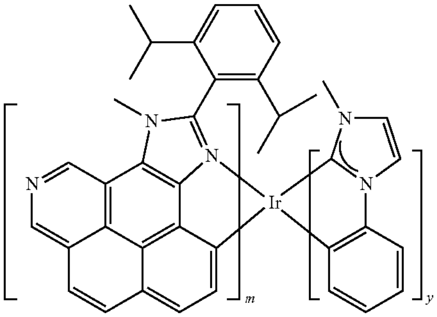
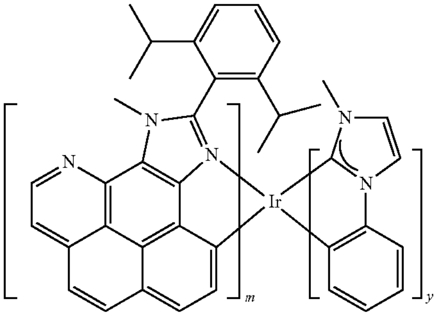
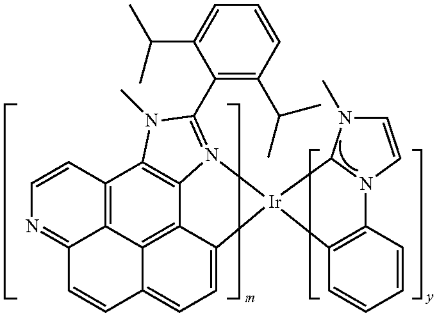
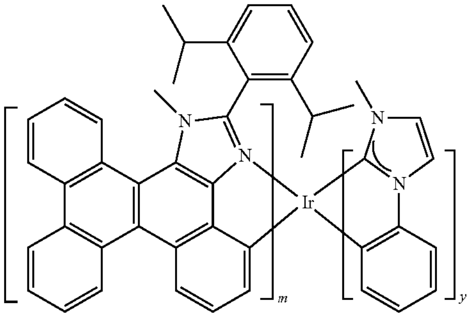

-continued
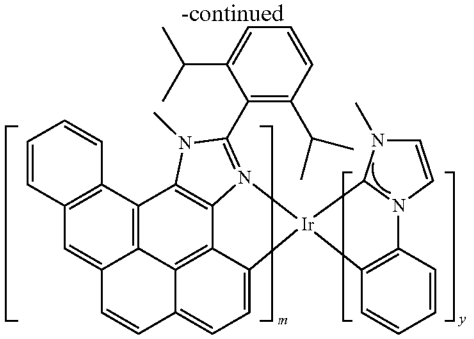
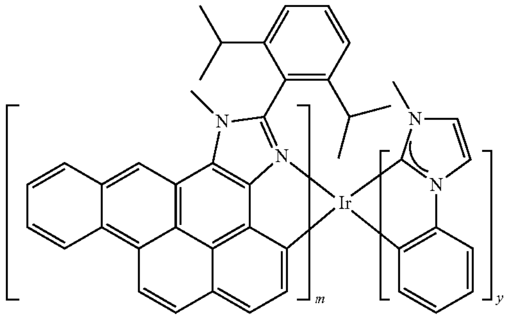
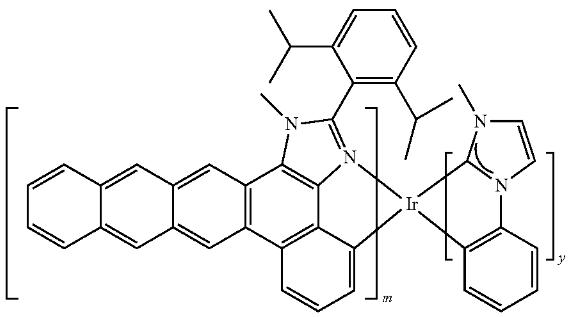
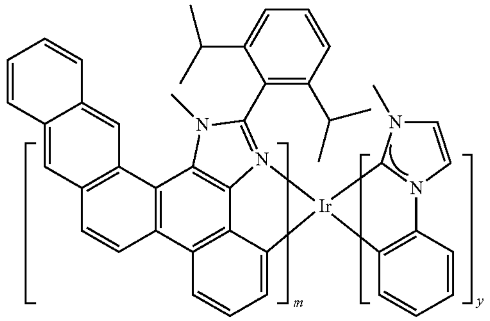
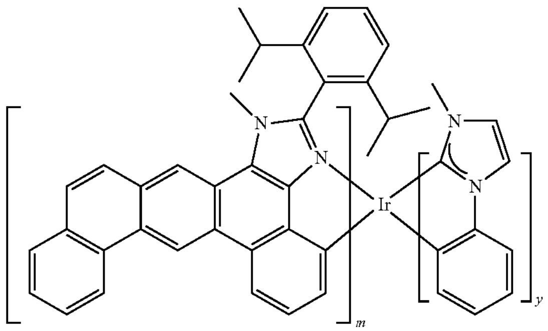
-continued
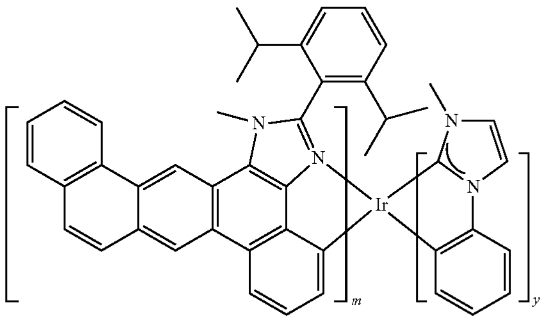
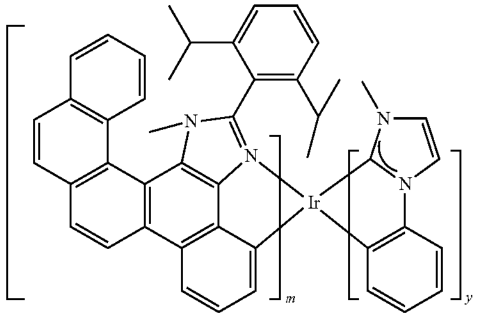
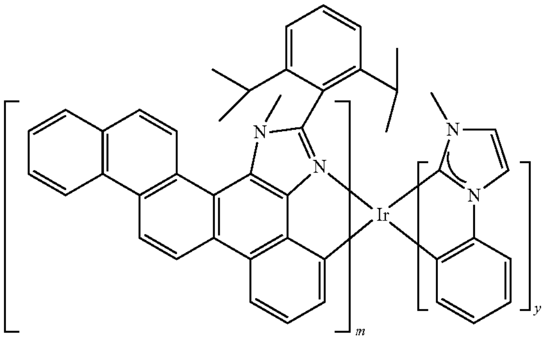
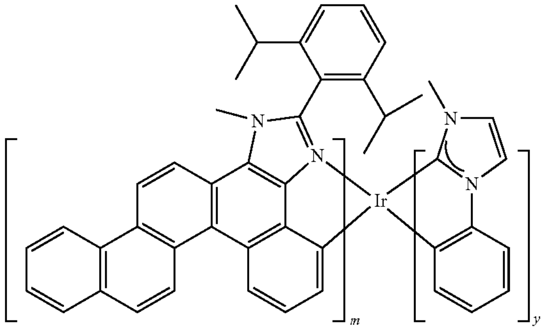
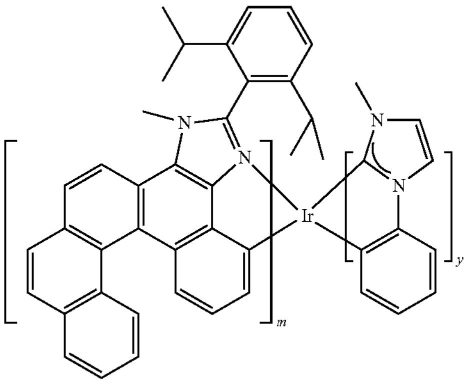

-continued
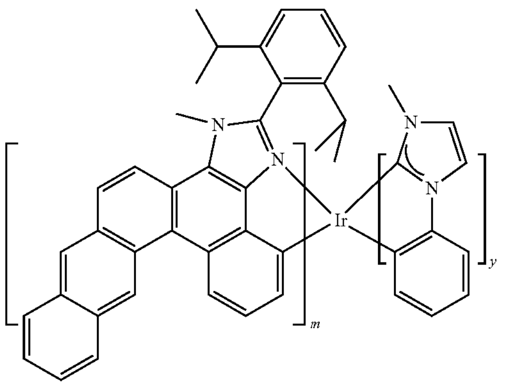
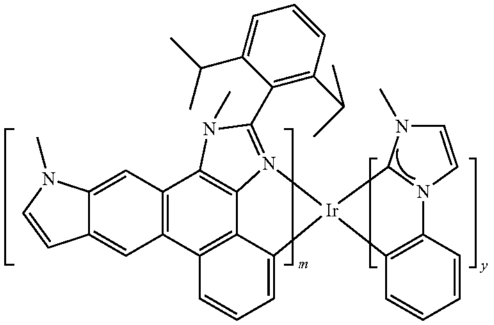
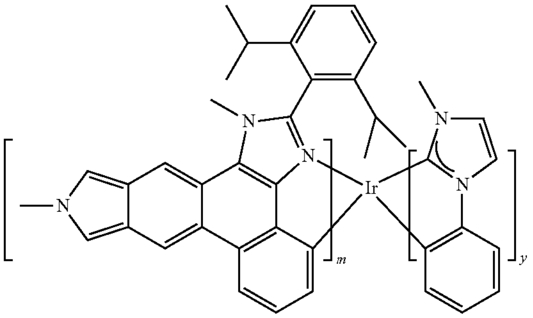
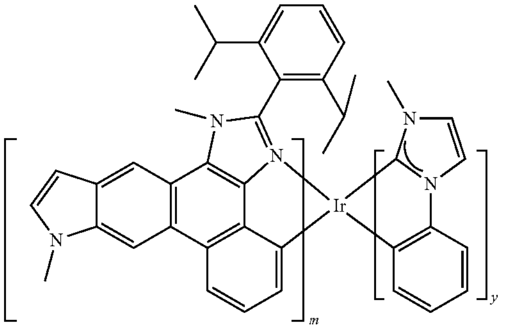
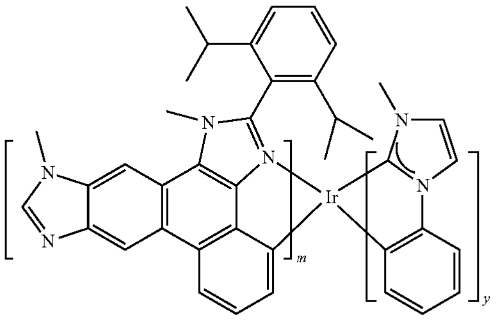
-continued
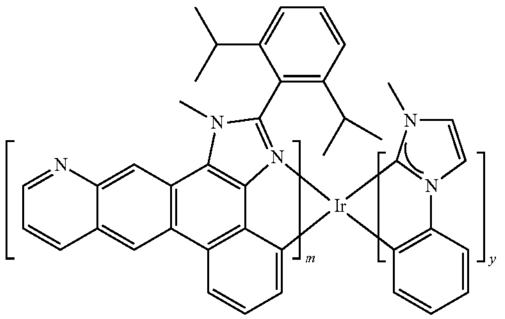
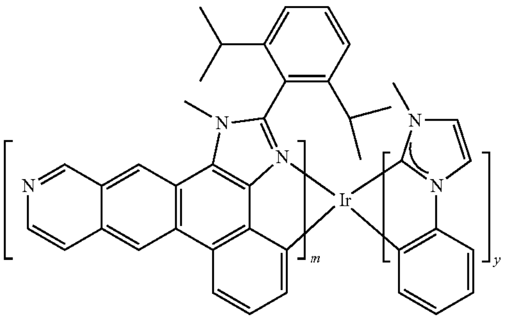
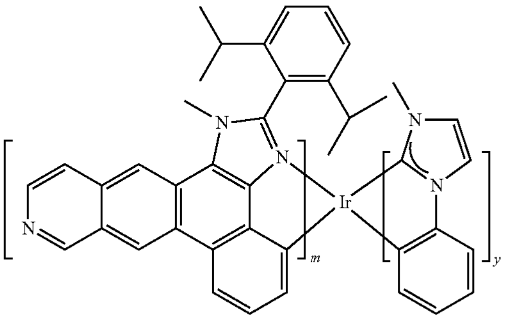
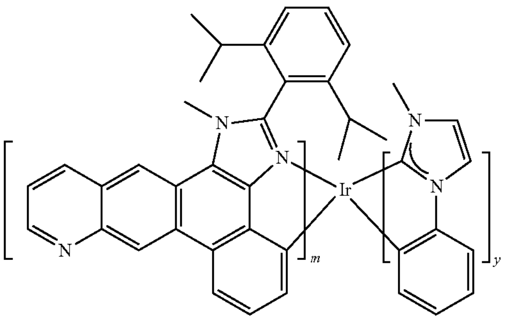
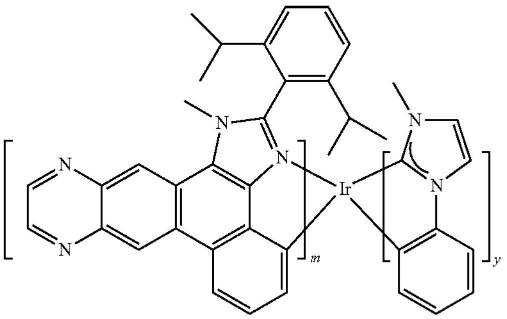

-continued
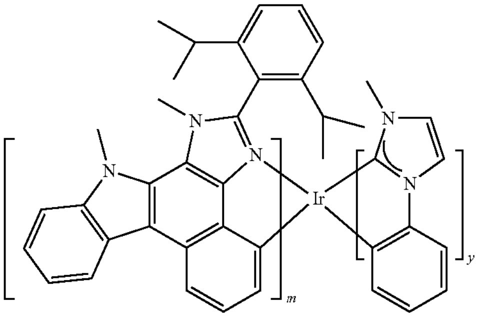
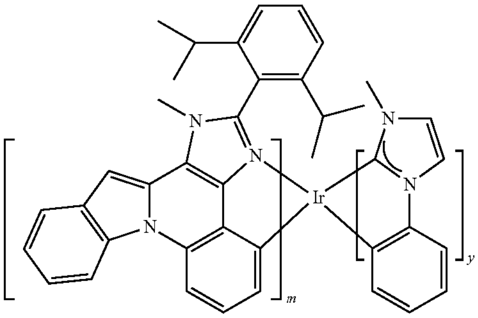
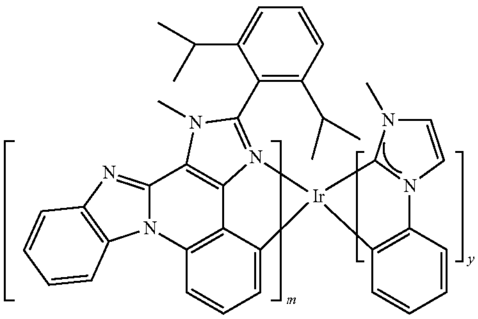
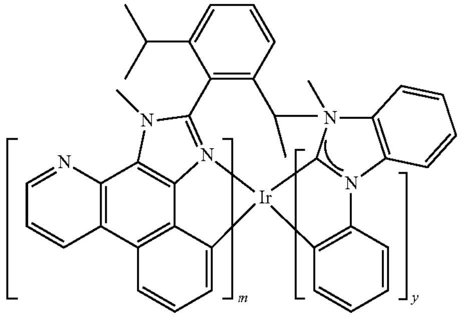
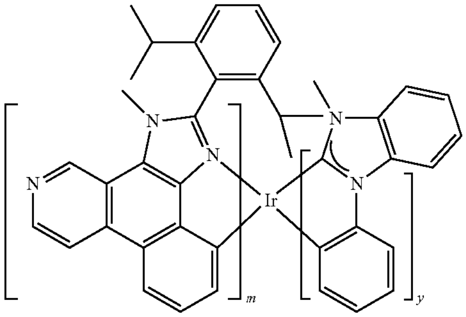
-continued
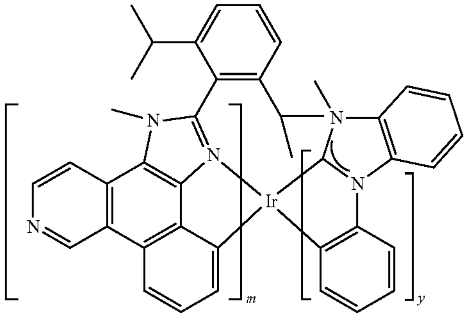
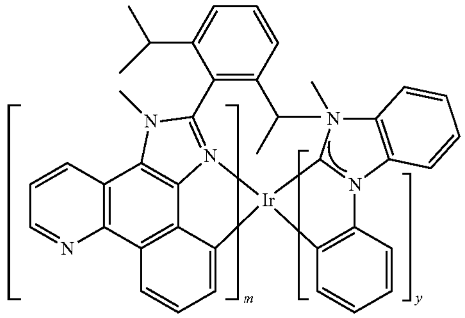
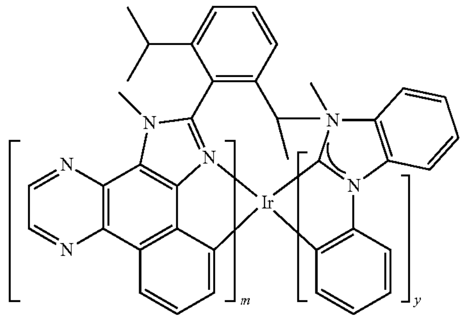
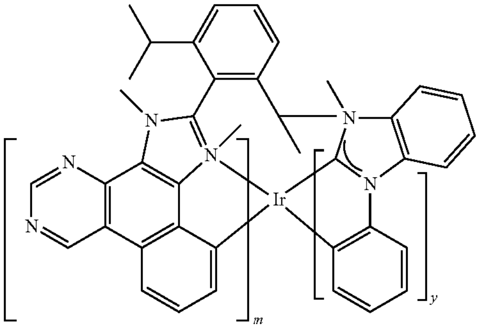
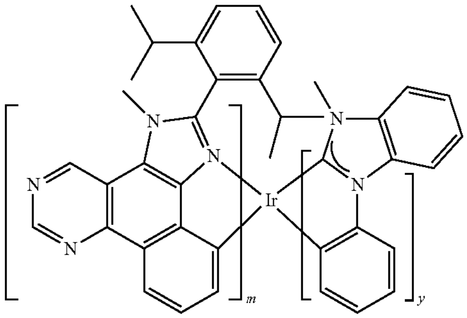

-continued
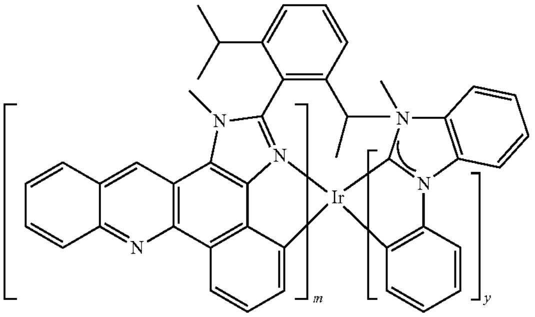
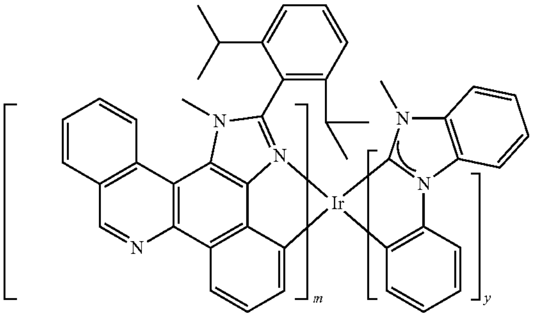
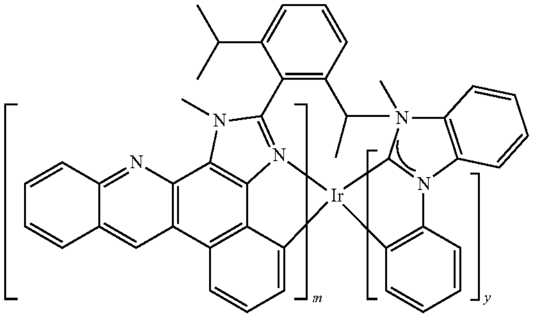
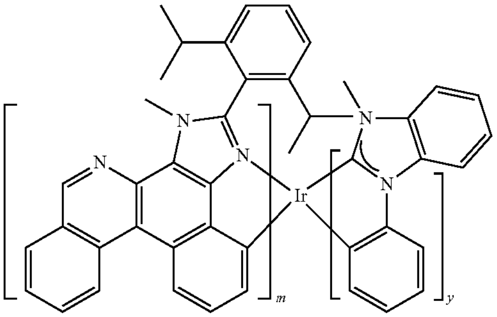
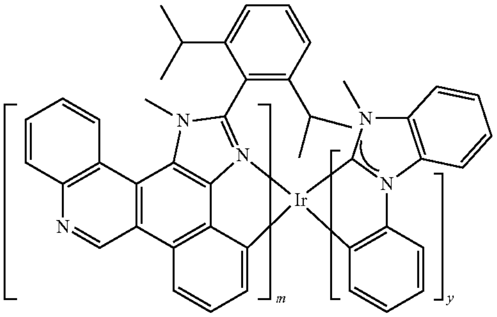
-continued
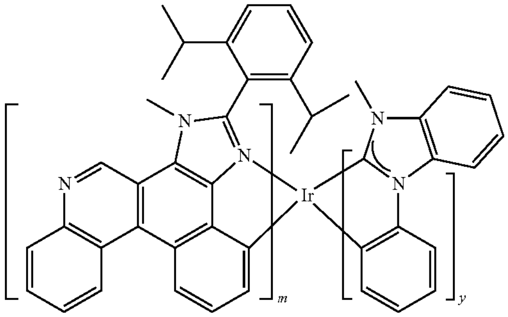
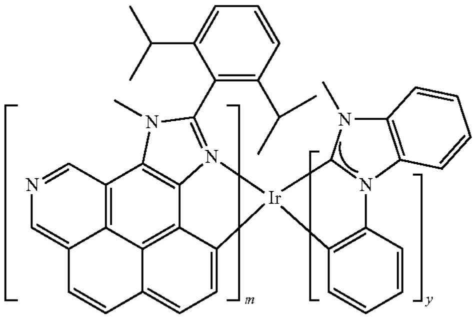
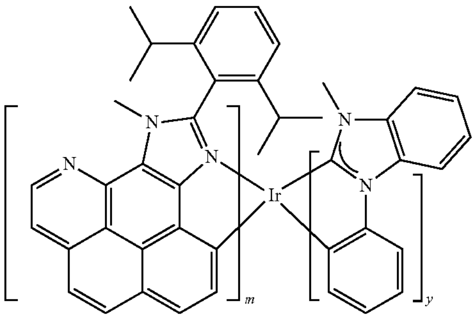
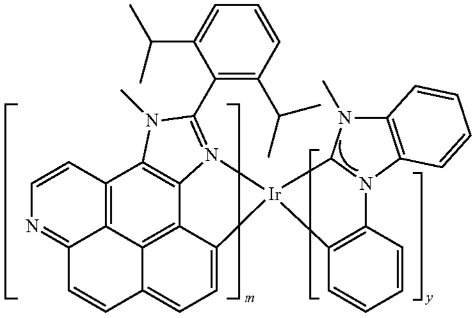
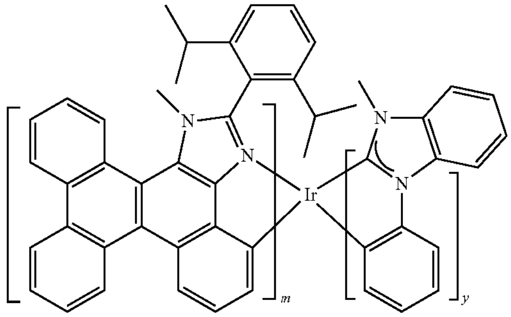

-continued
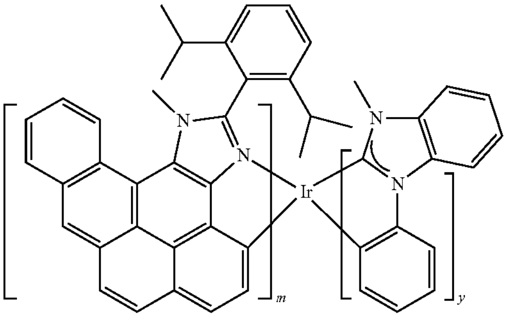
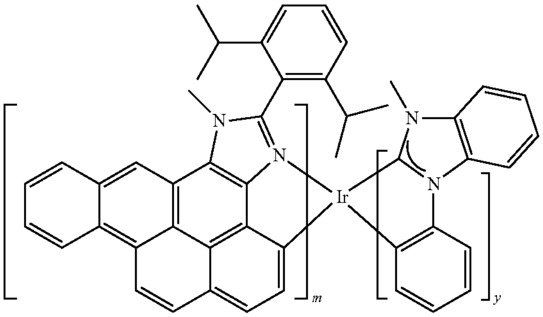
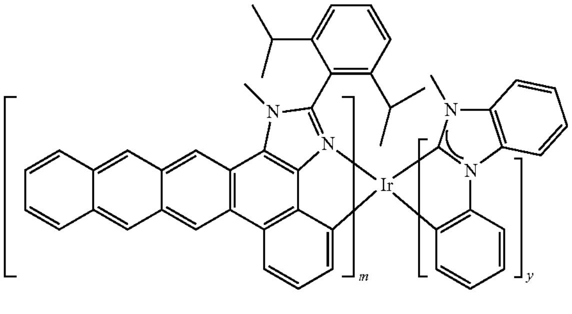
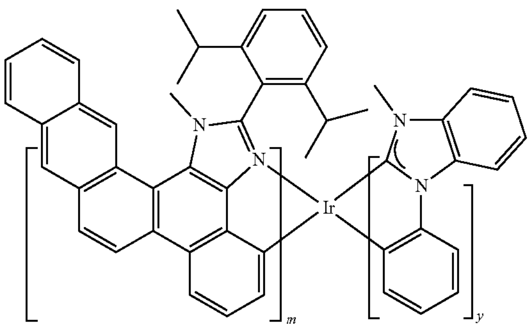
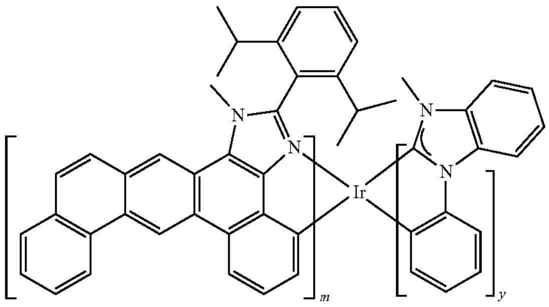
-continued
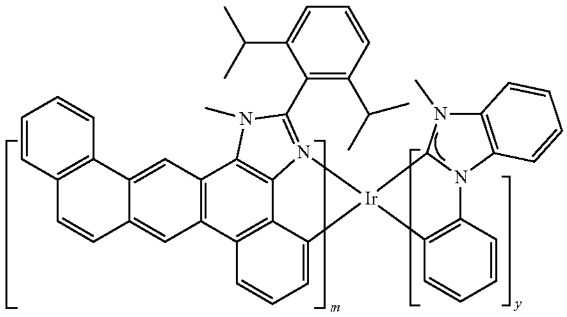
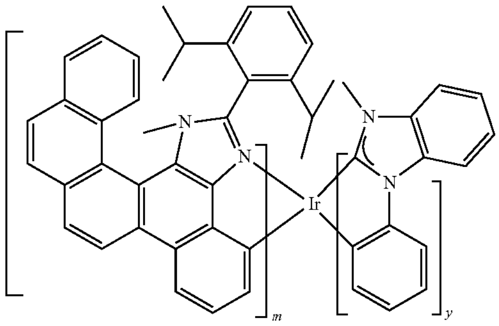
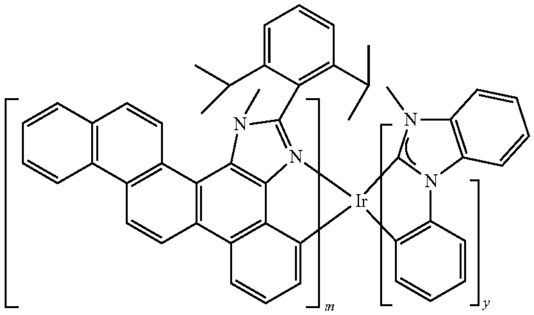
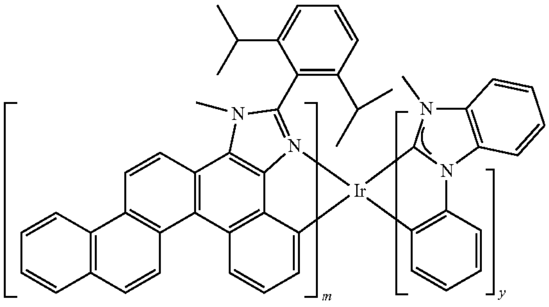
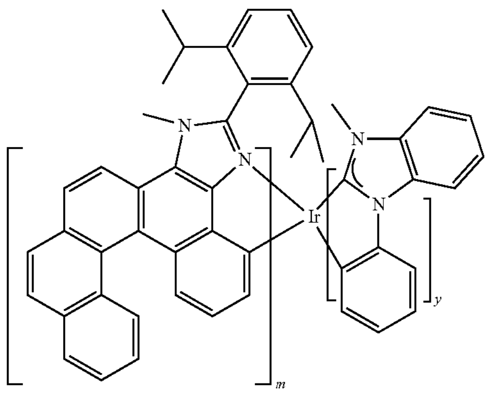

-continued
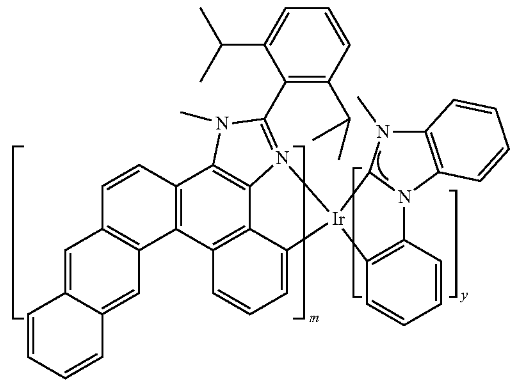
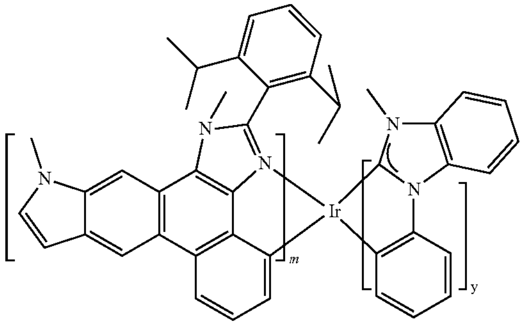
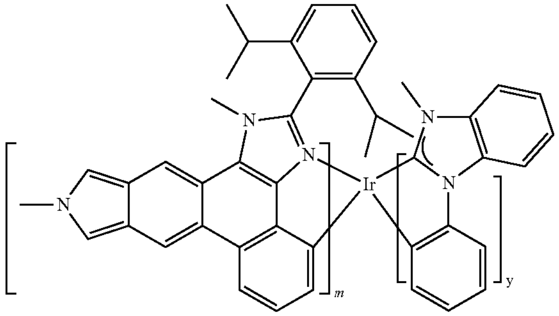
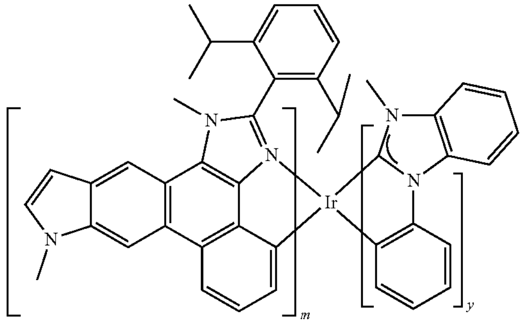
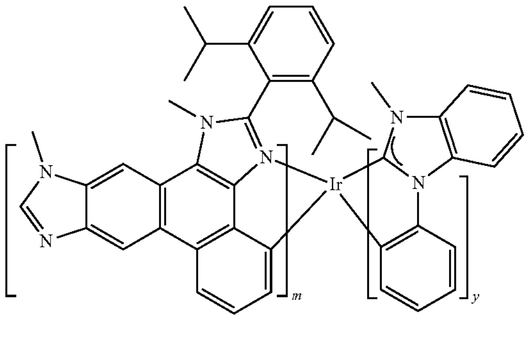
-continued
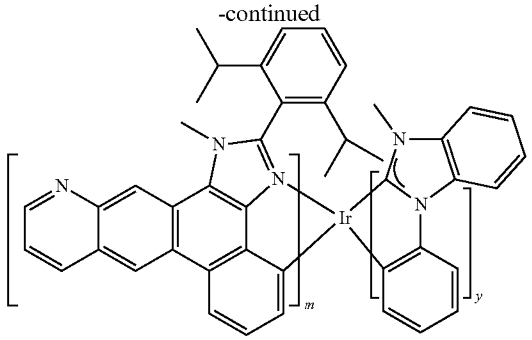
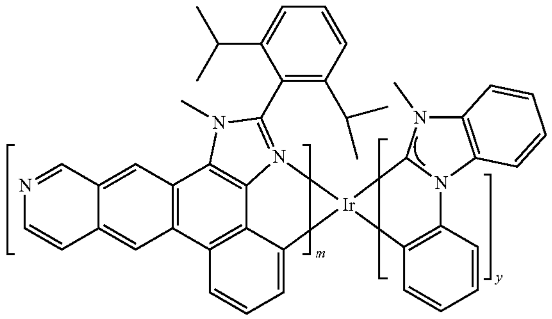
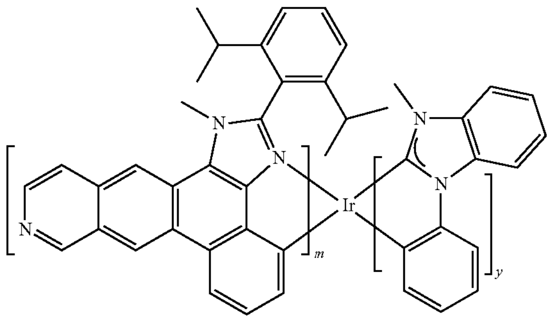
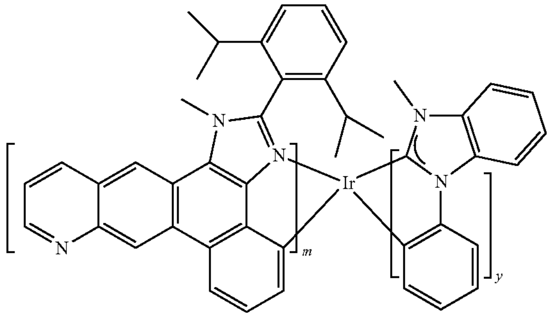
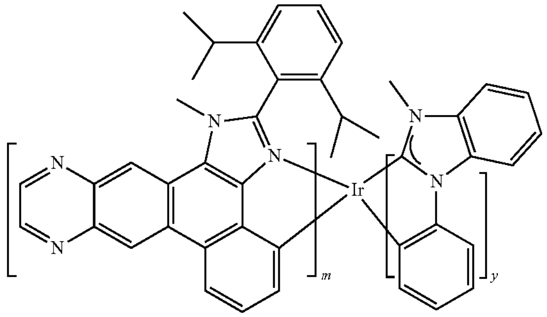

-continued
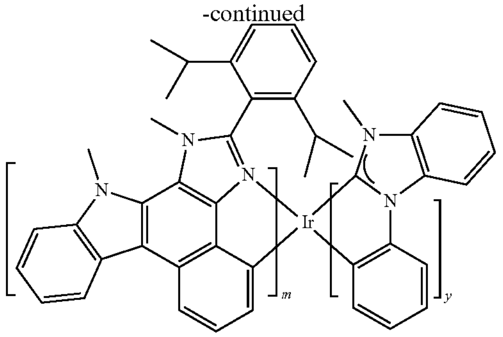
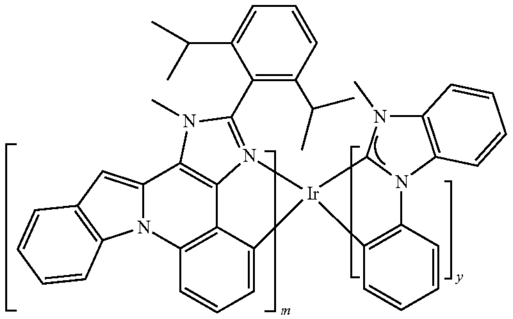
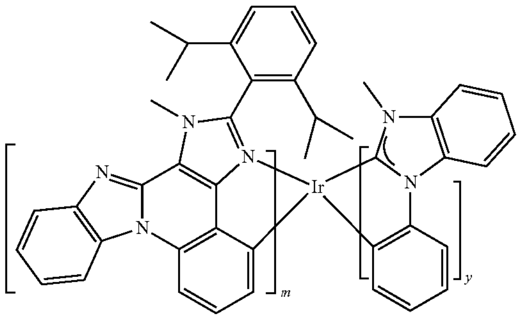
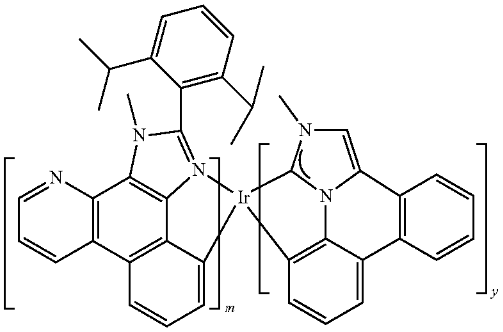
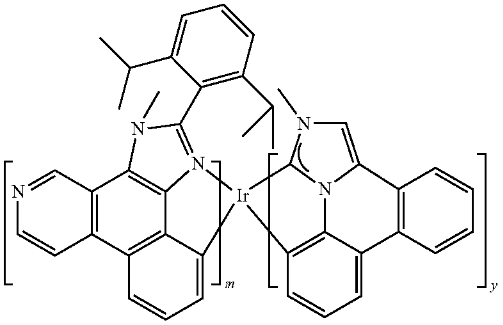
-continued
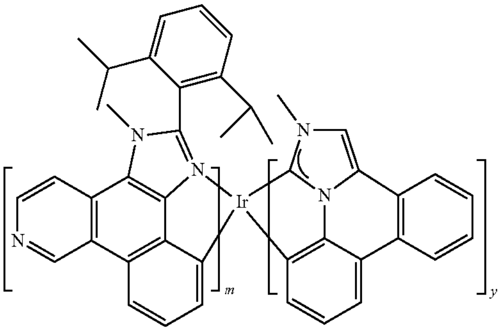
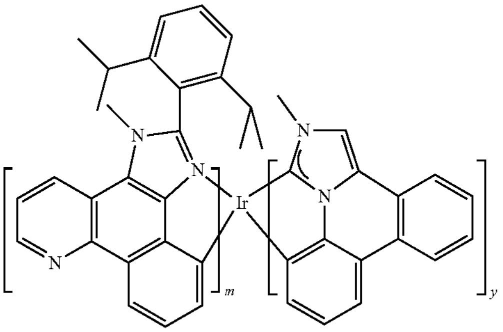
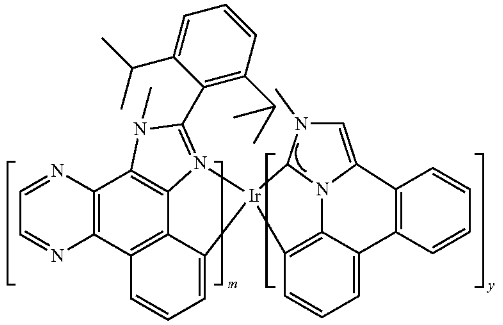
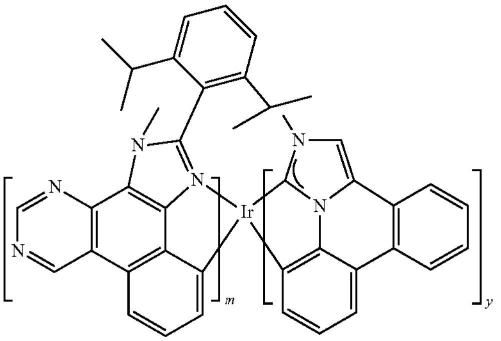
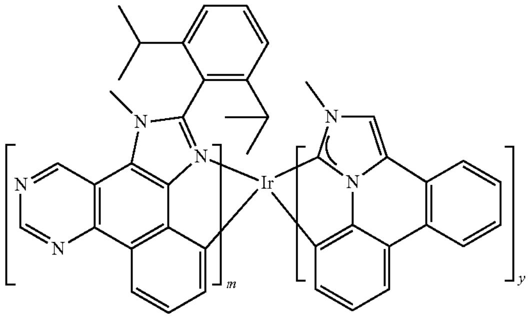

-continued
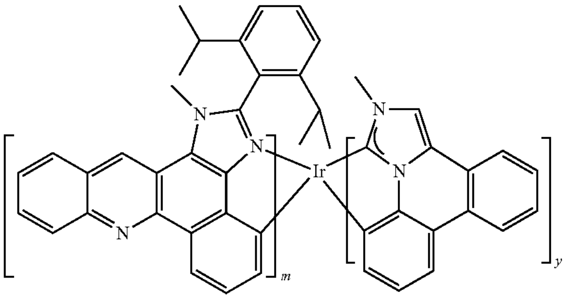
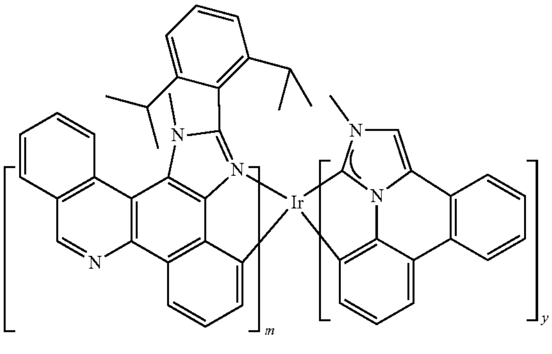
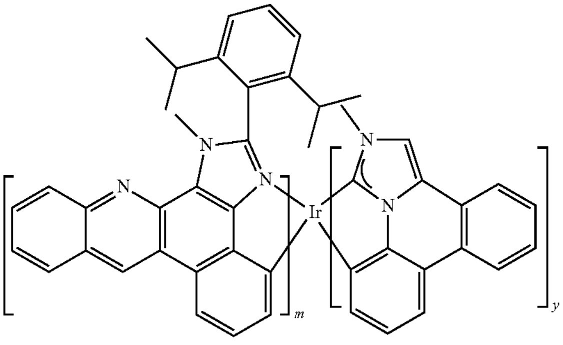
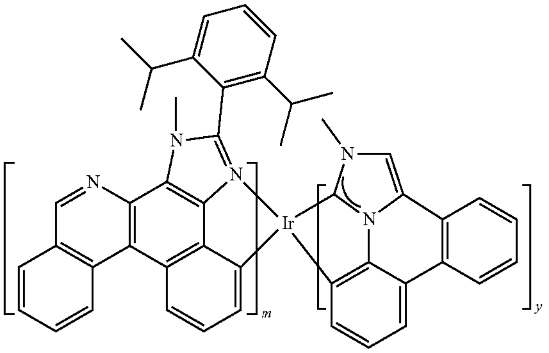
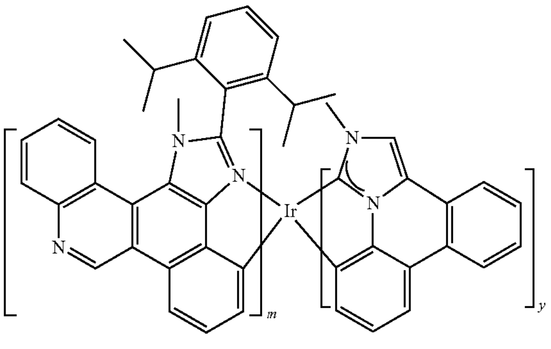
-continued
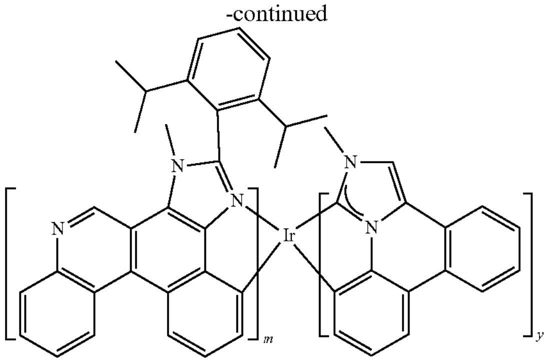
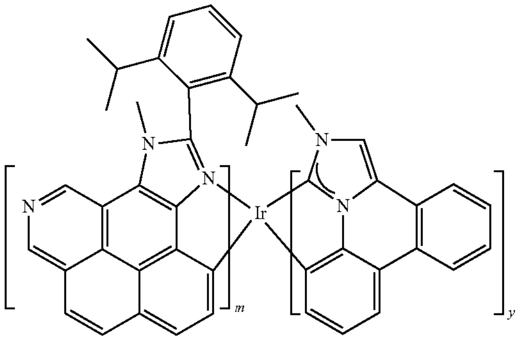
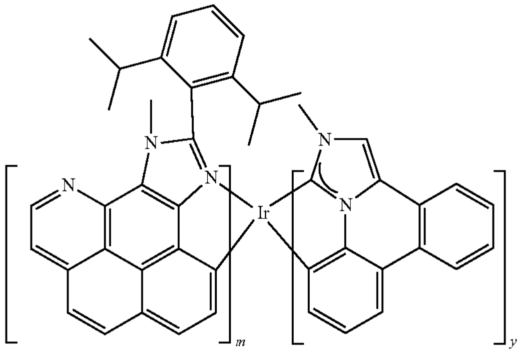
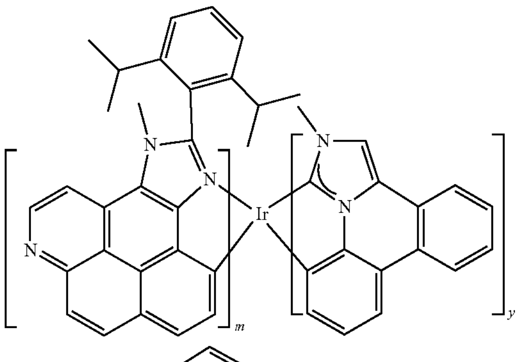
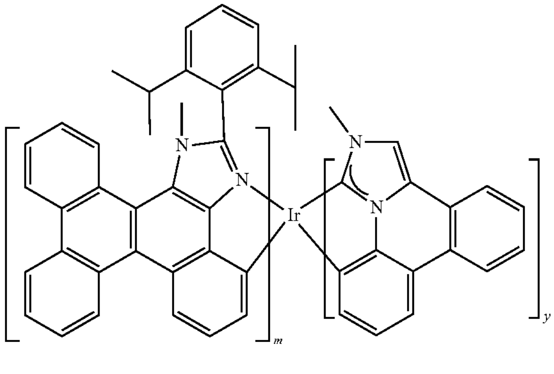

-continued
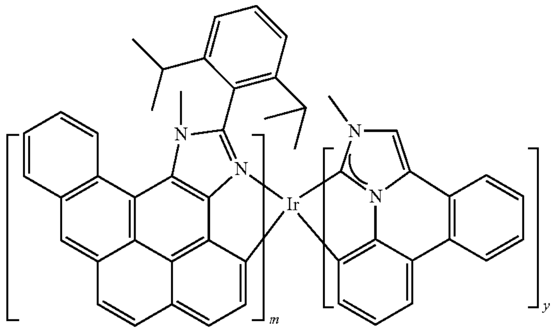
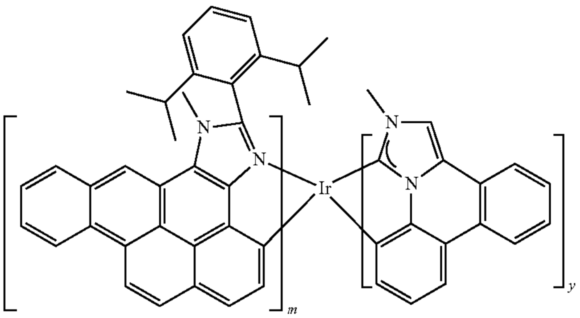
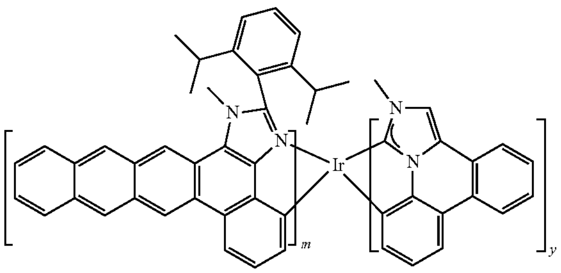
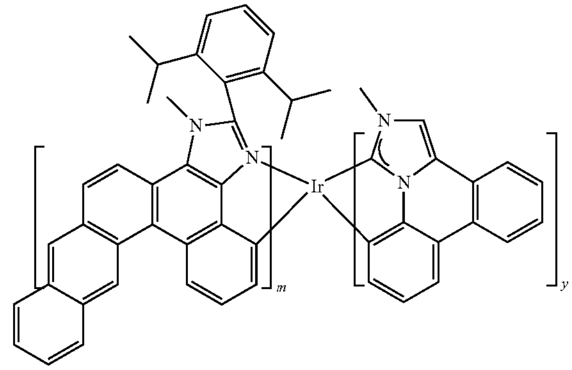
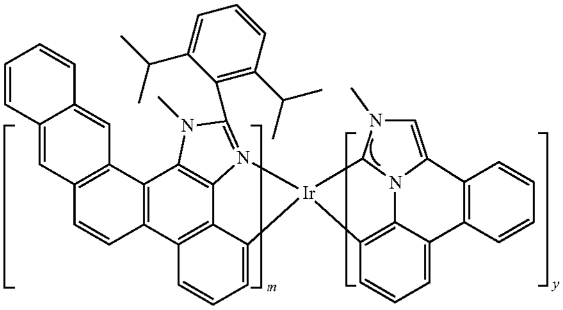
-continued
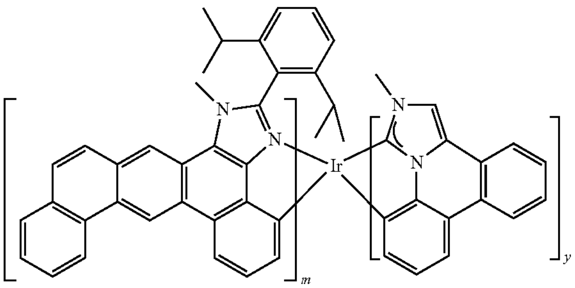
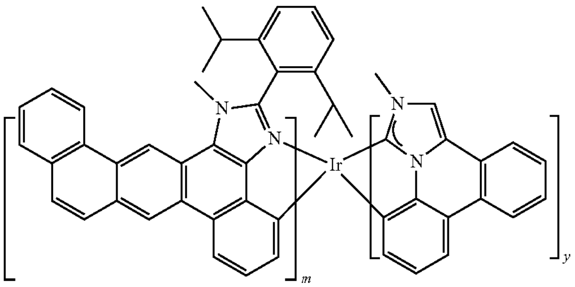
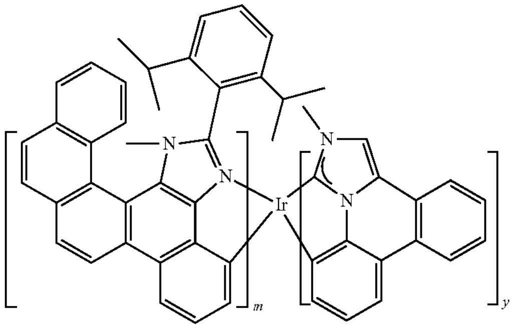
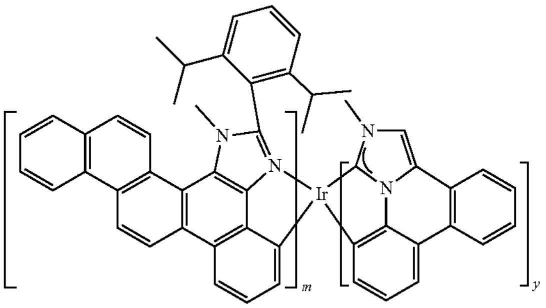
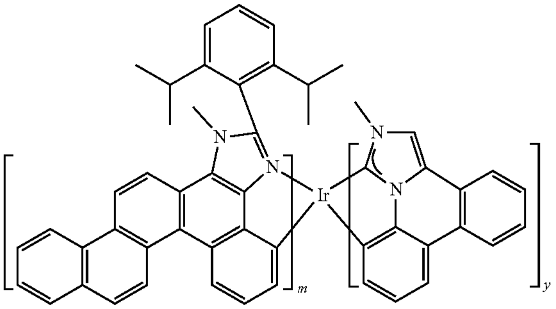

-continued
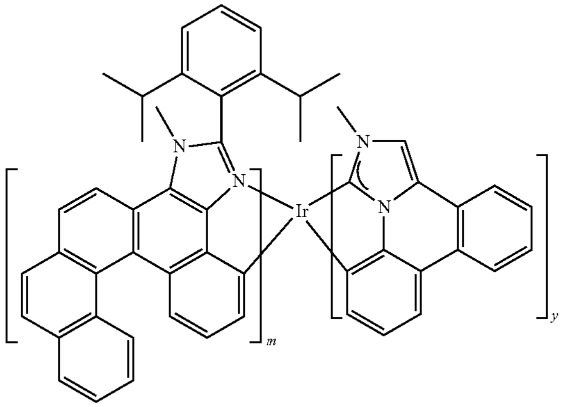
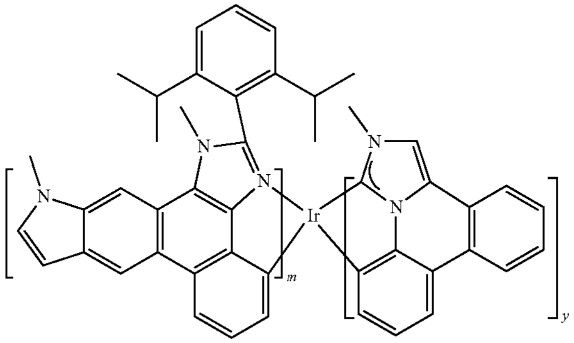
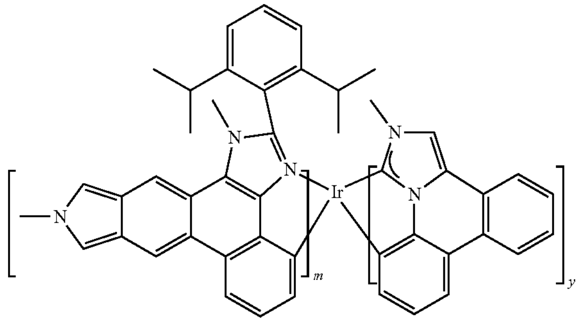
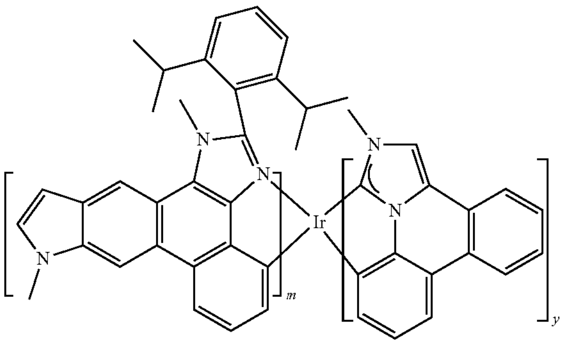
-continued
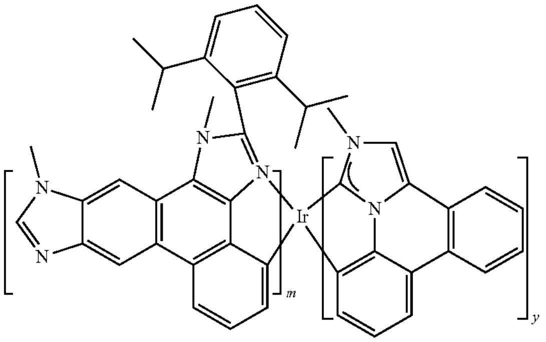
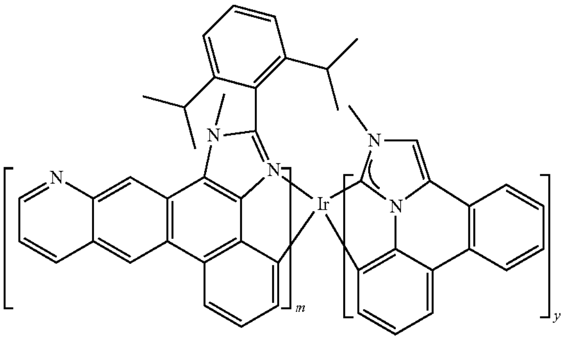
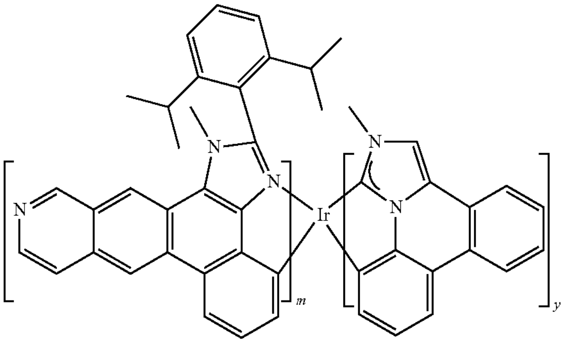
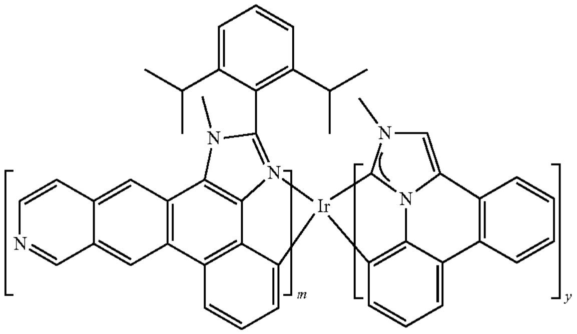
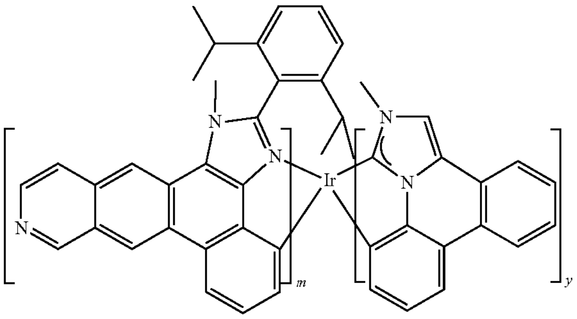

-continued
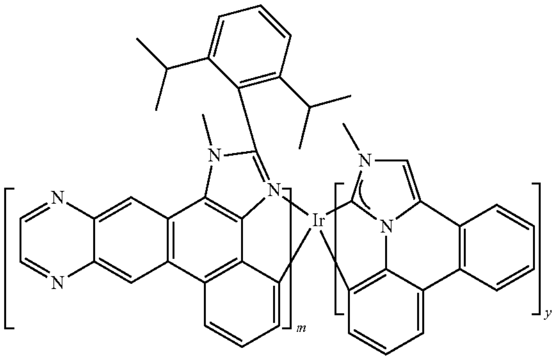
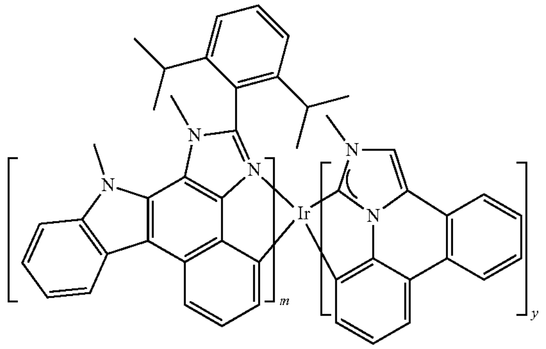
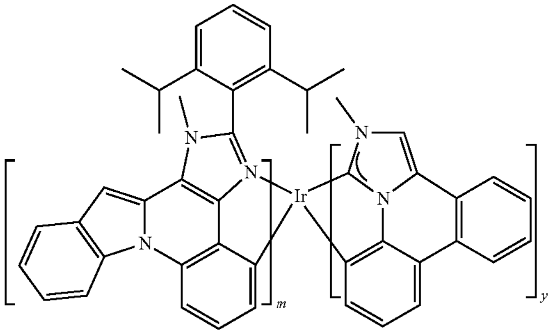
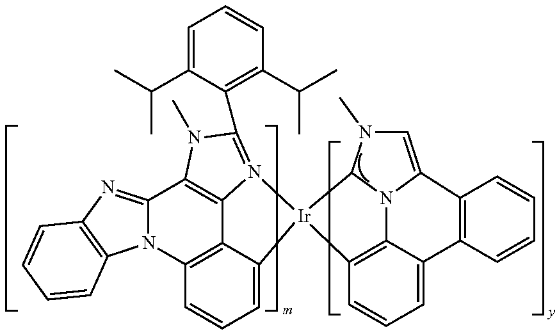
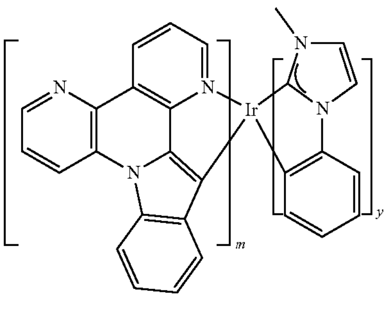
-continued
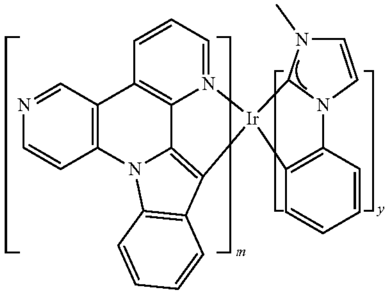
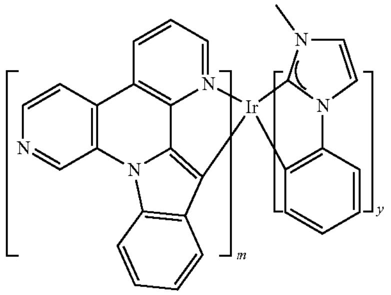
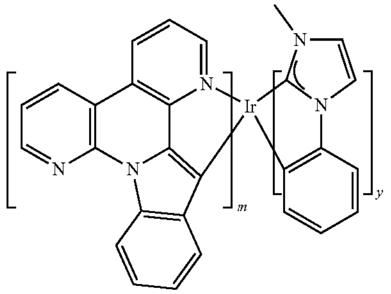
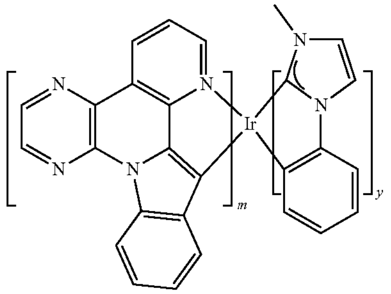
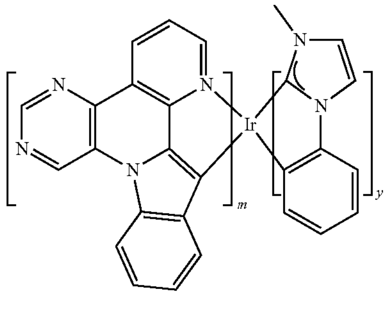

-continued
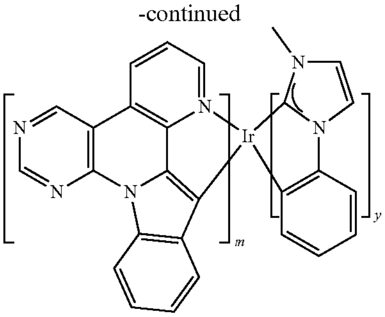
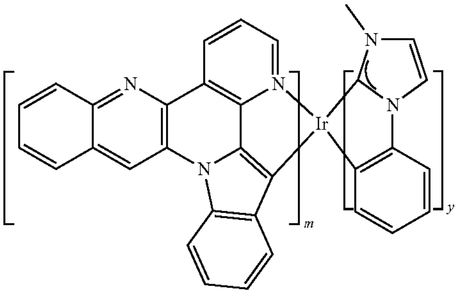
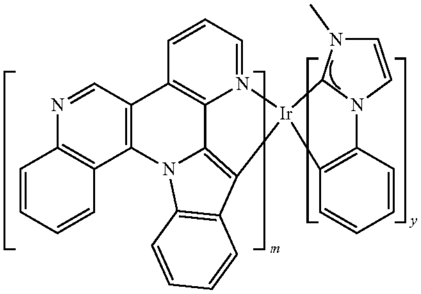
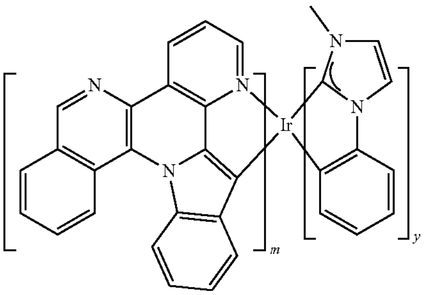
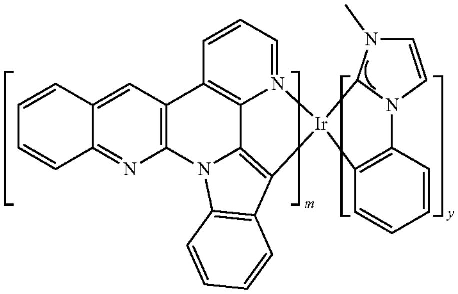
-continued
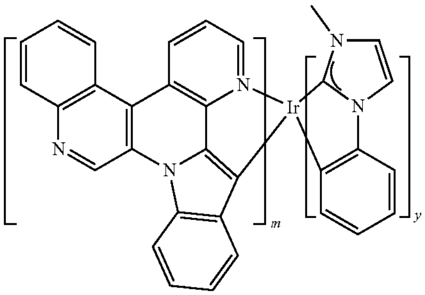
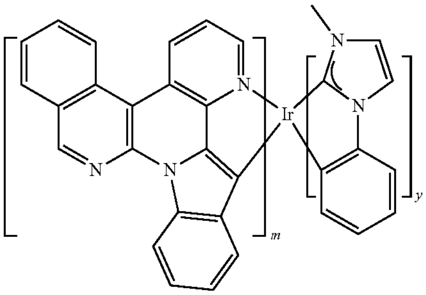
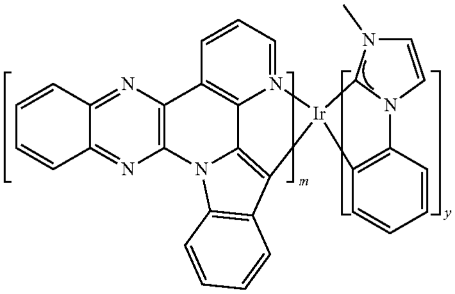
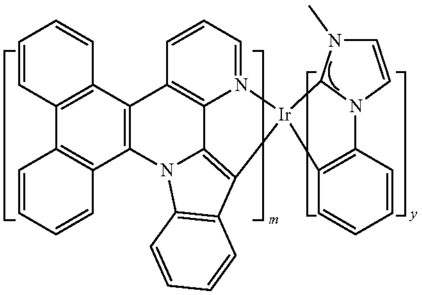
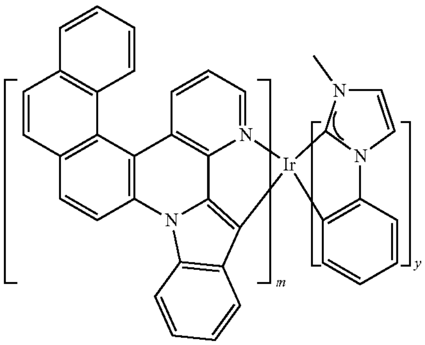

-continued
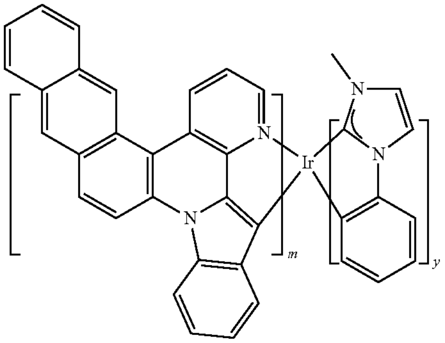
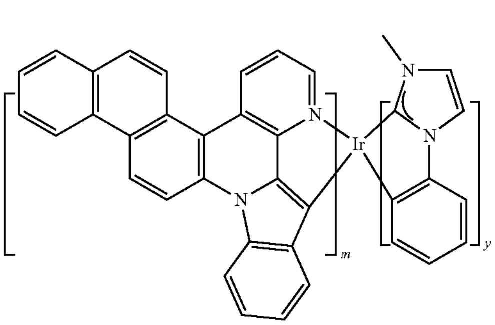
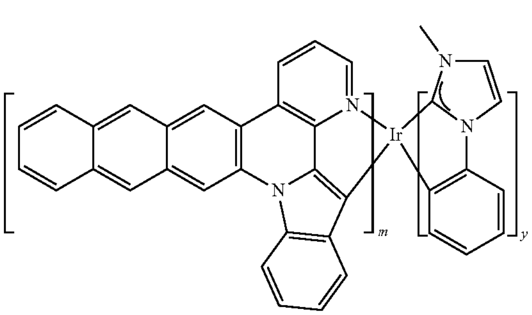
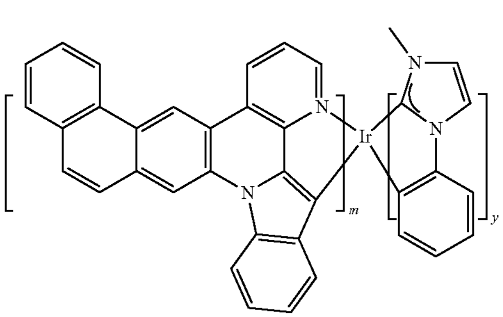
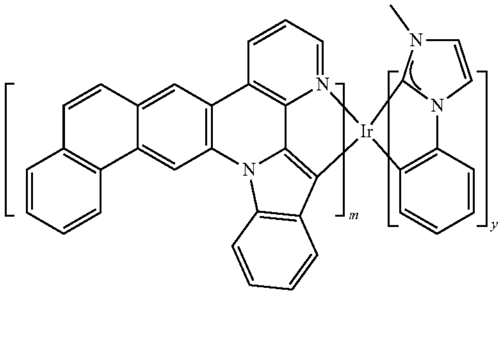
-continued
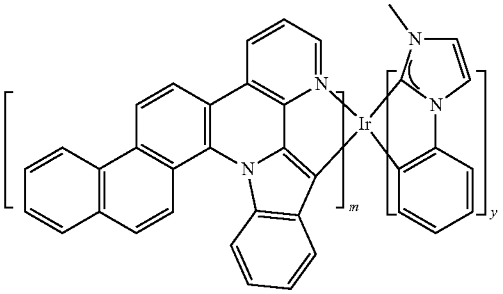
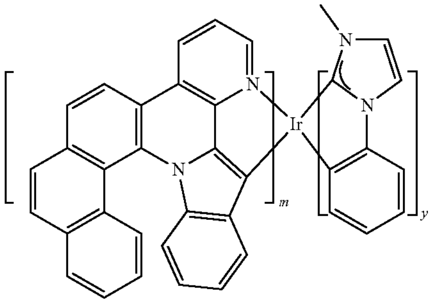
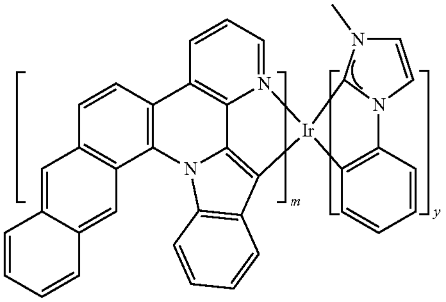
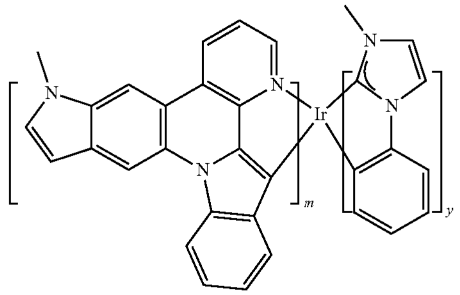
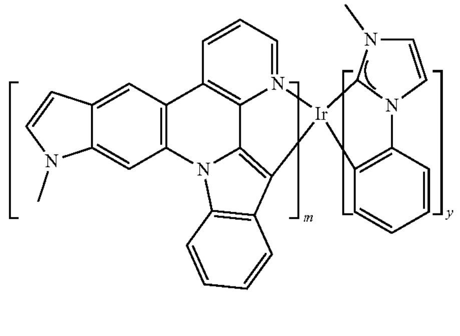

-continued
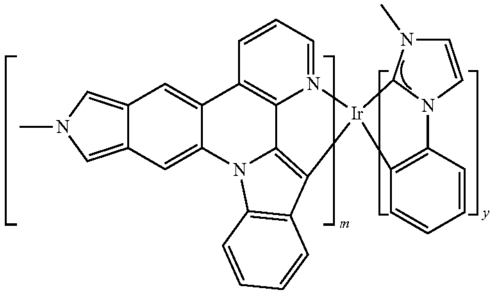
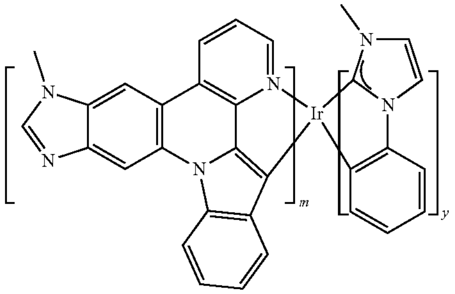
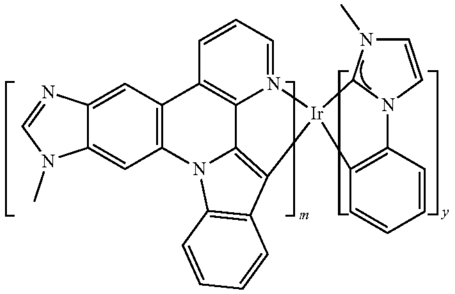
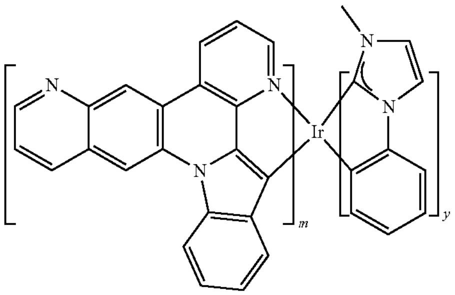
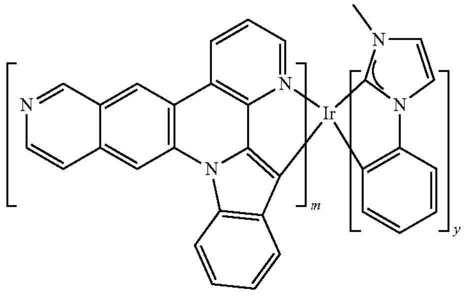
-continued
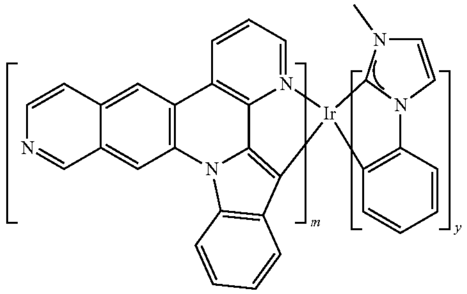
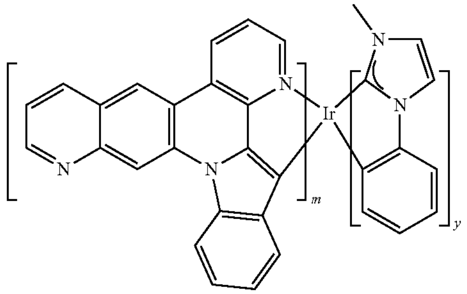
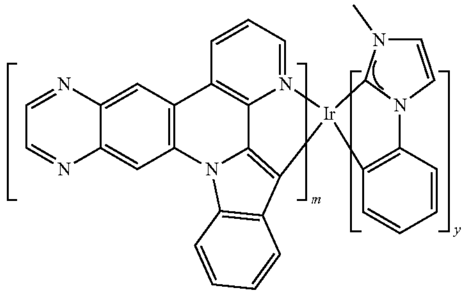
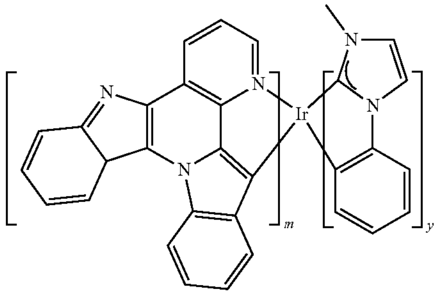
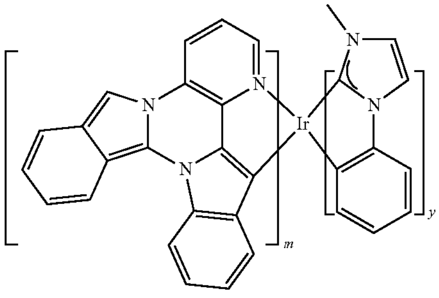

-continued
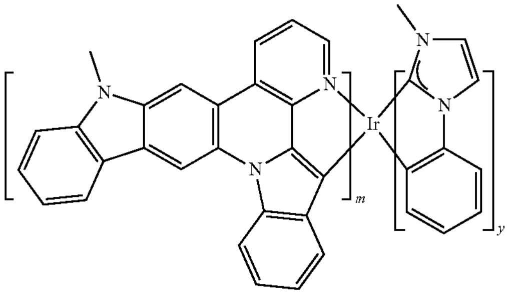
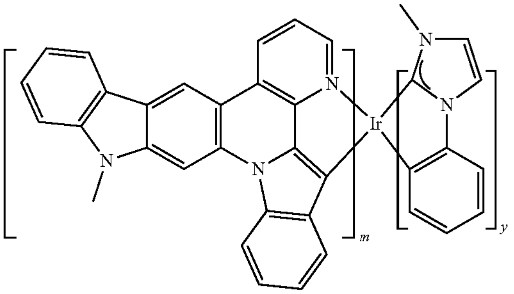
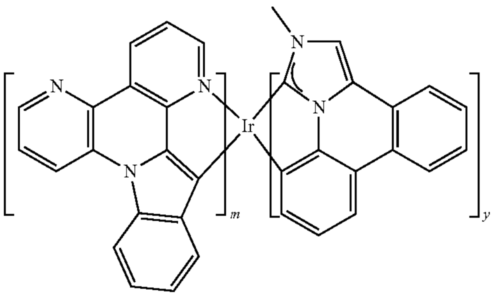
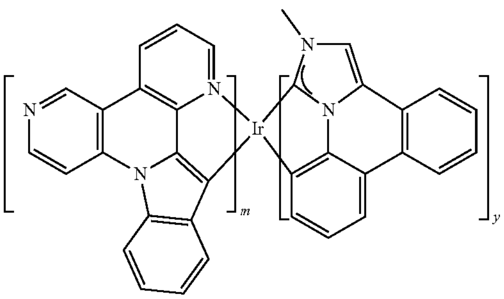
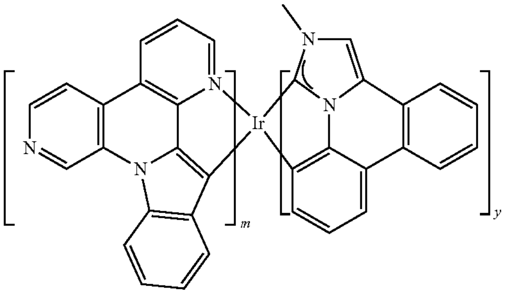
-continued
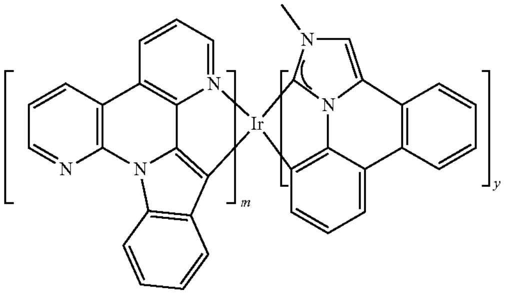
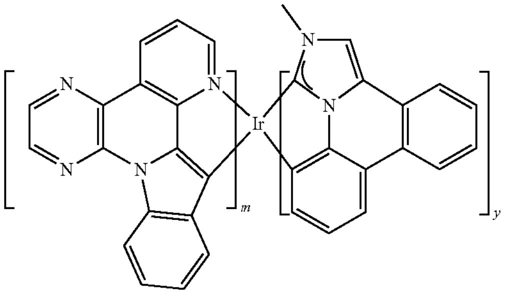
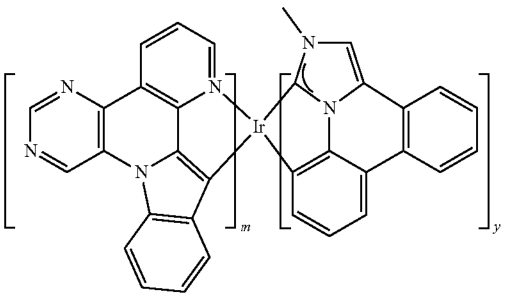
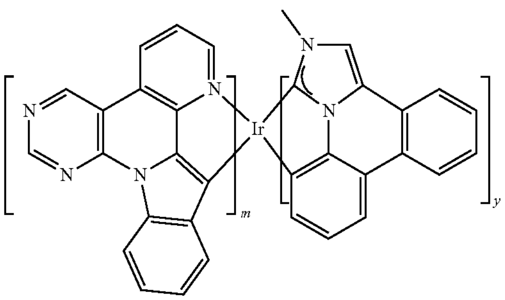
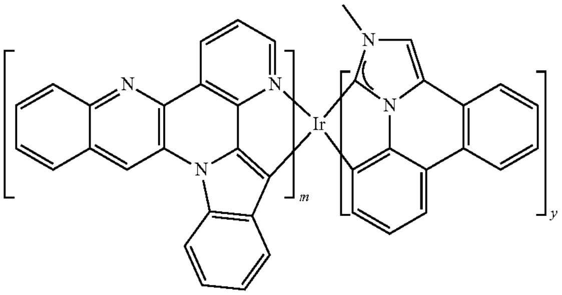

-continued
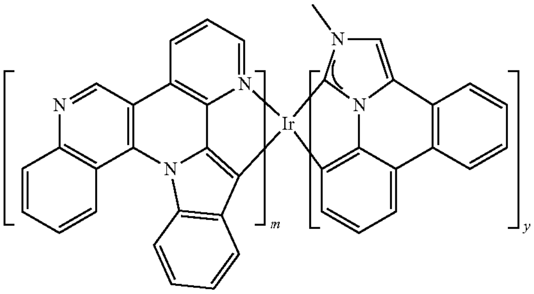
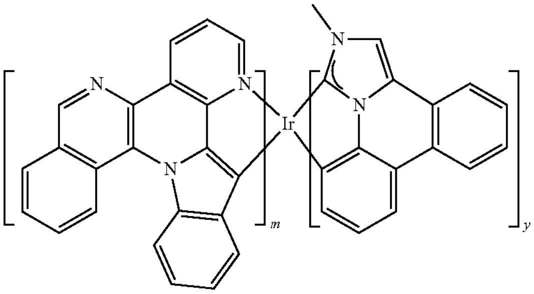
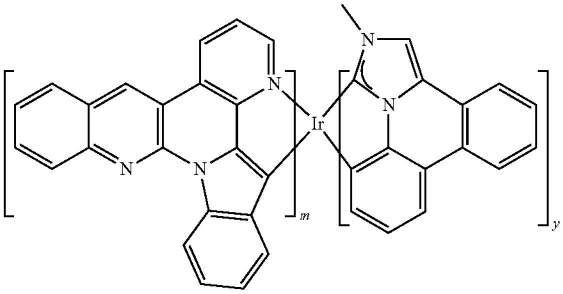
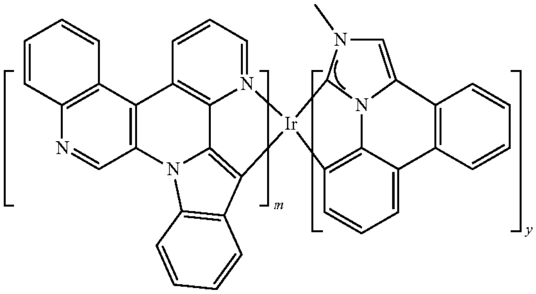
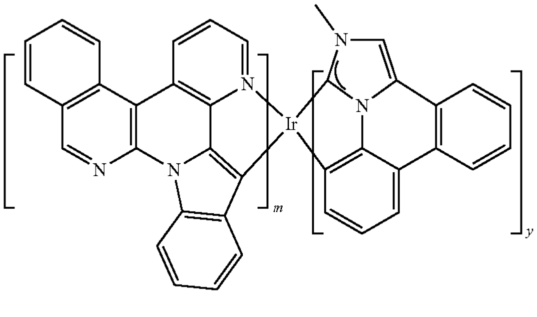
-continued
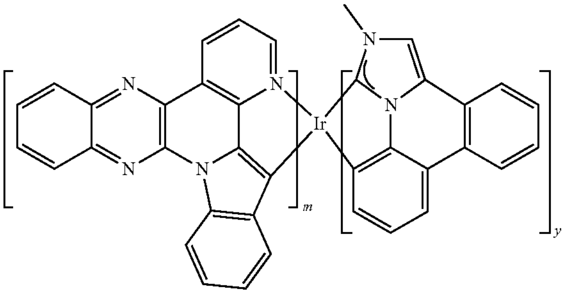
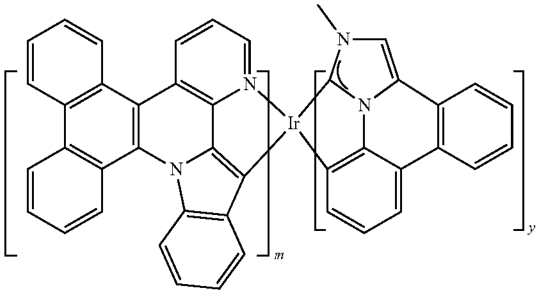
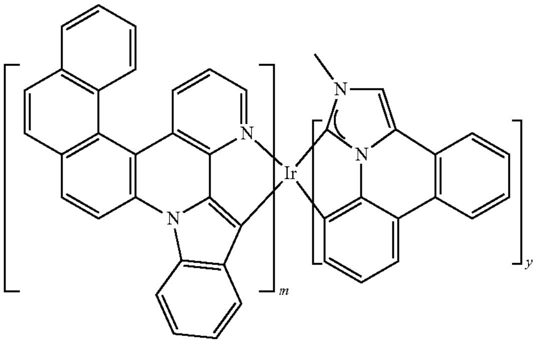
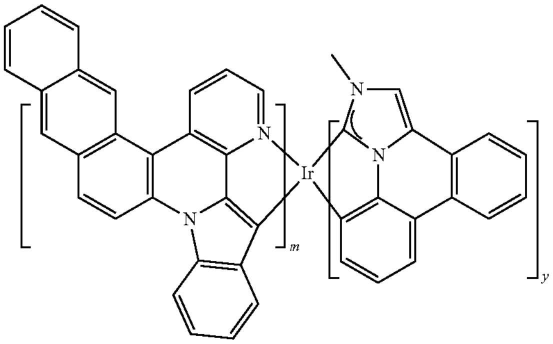
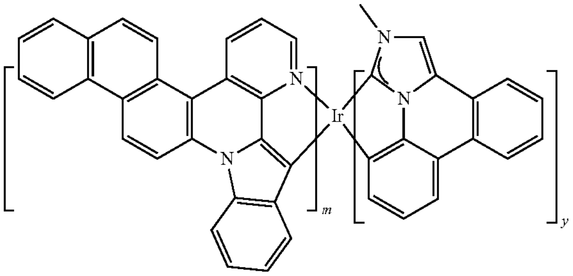

-continued
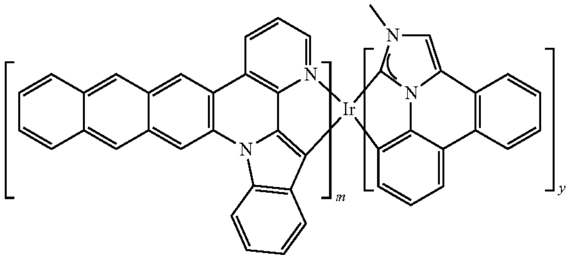
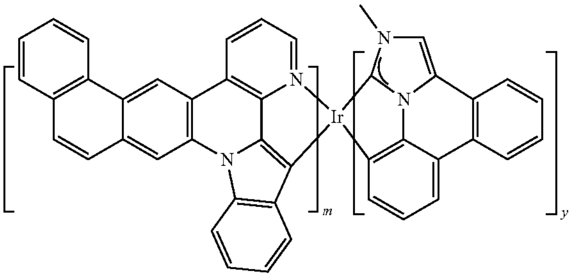
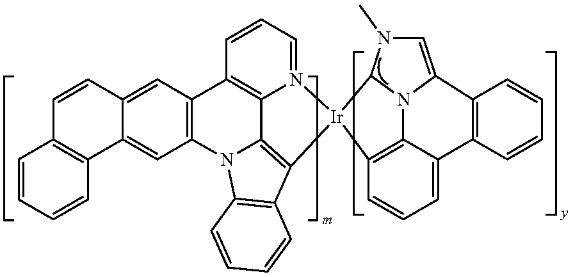
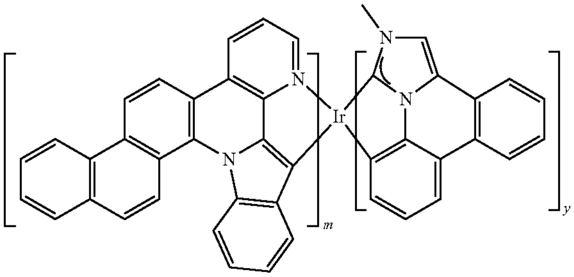
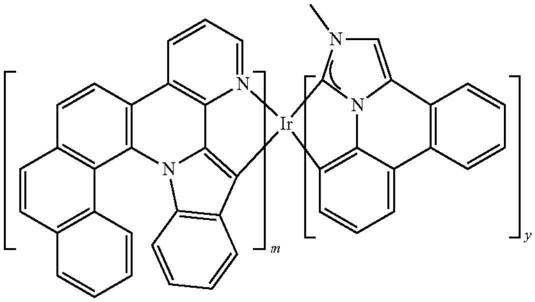
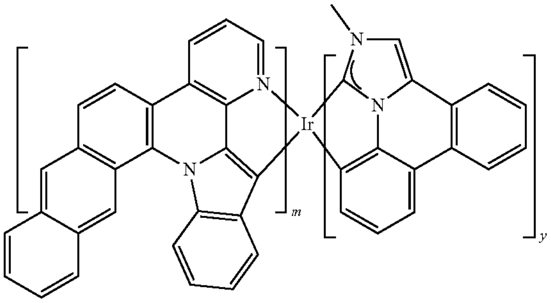
-continued
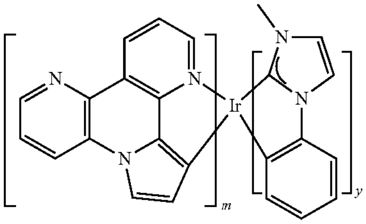
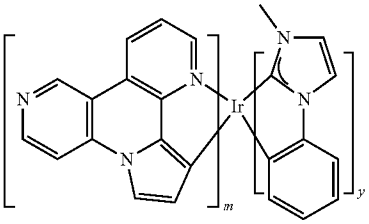
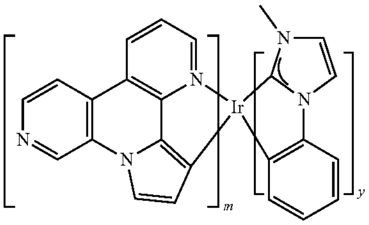
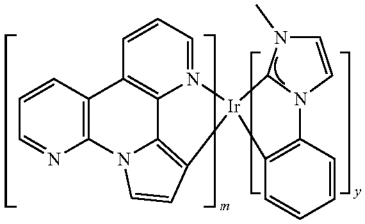
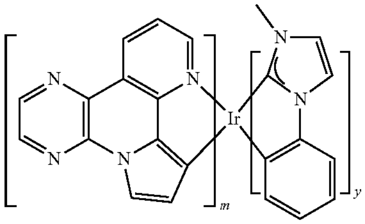
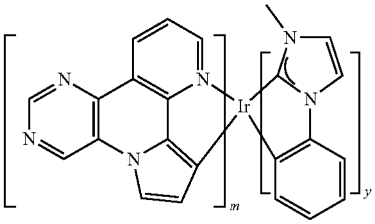
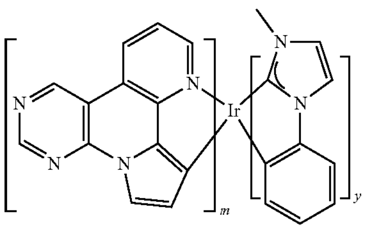

-continued
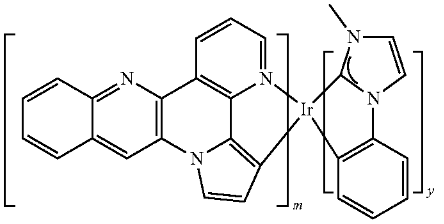
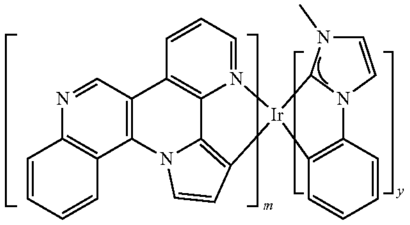
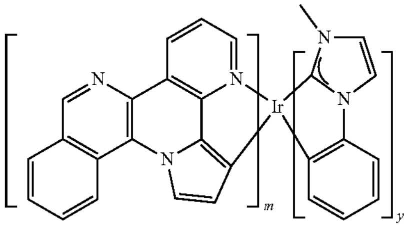
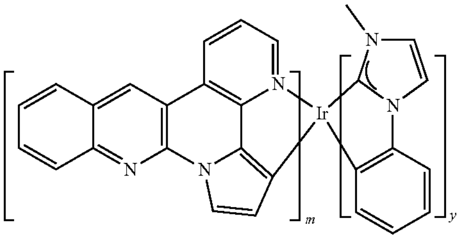
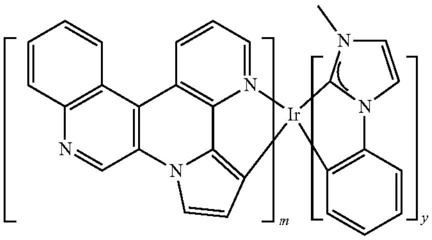
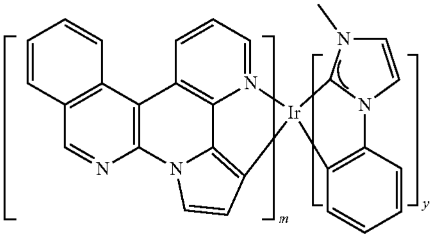
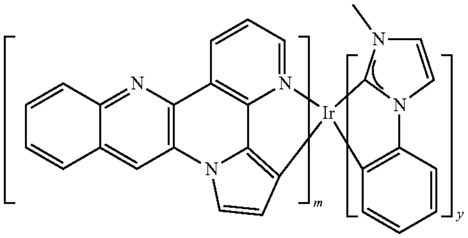
-continued
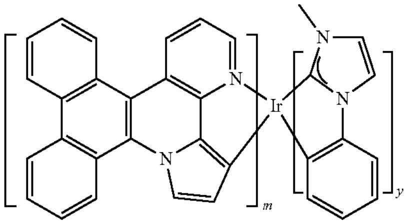
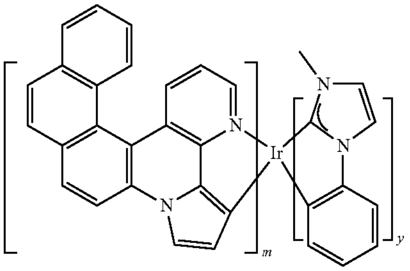
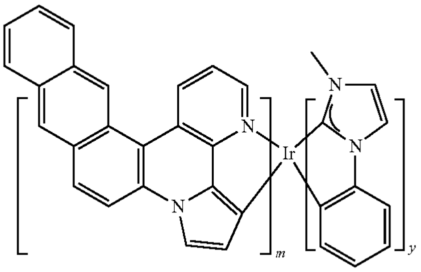
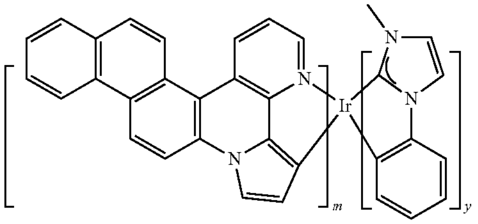
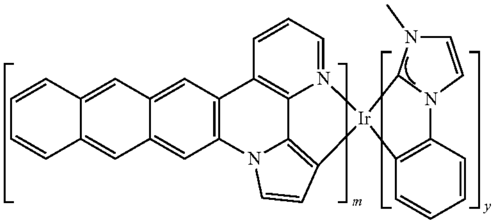
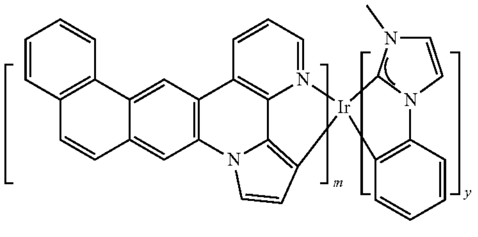
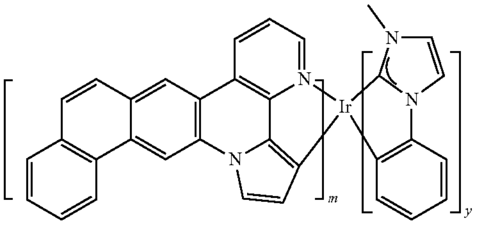

-continued
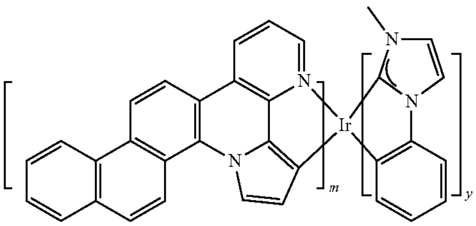
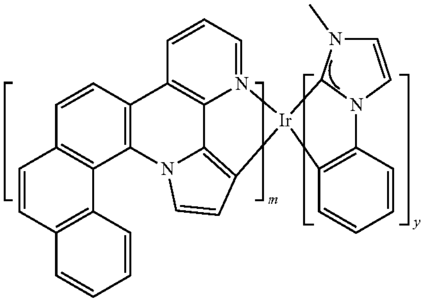
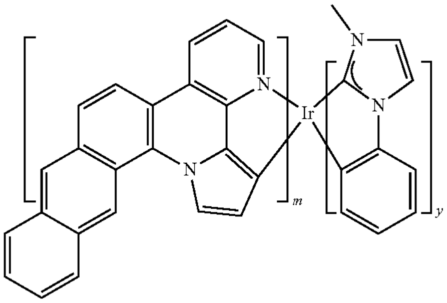
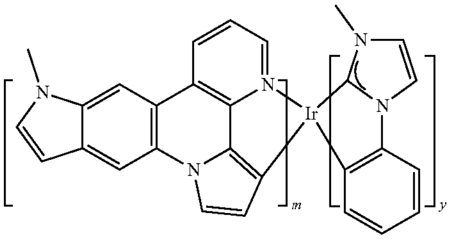
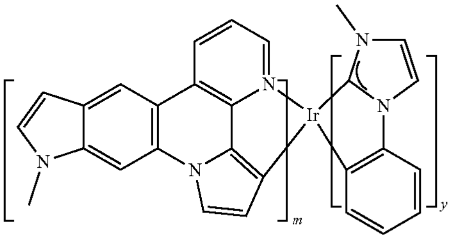
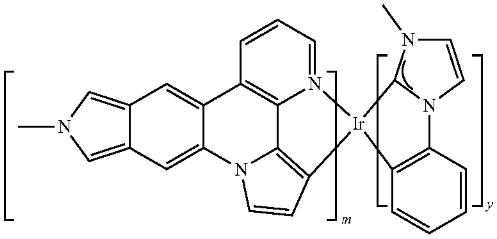
-continued
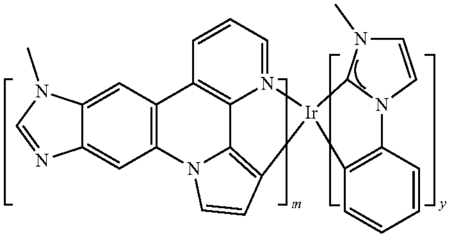
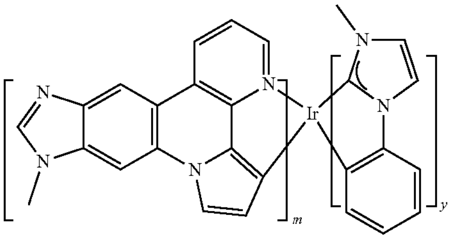
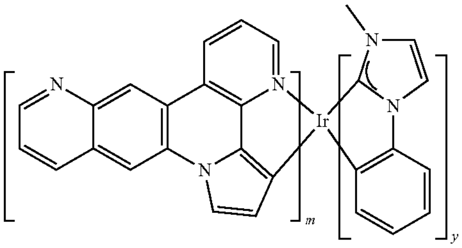
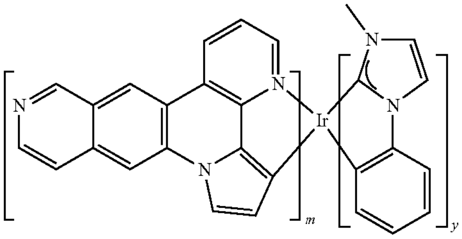
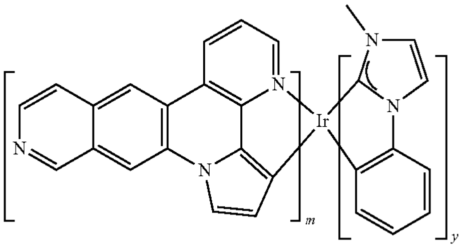
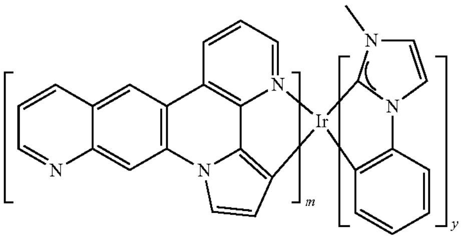
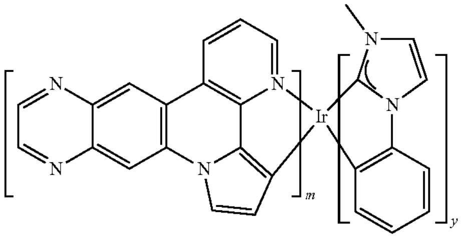

-continued
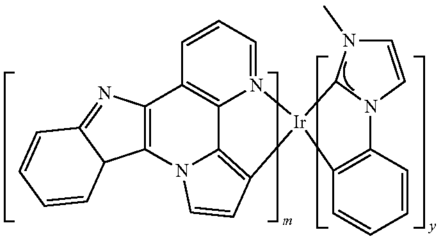
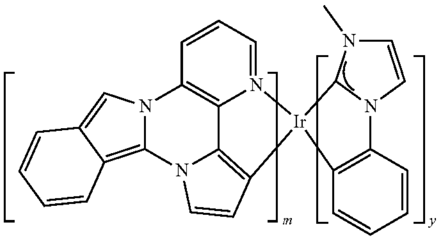
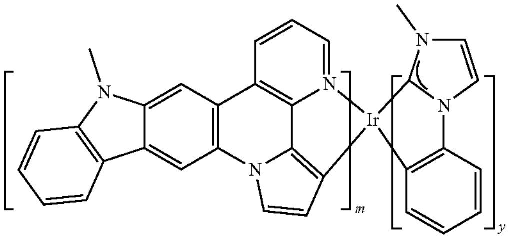
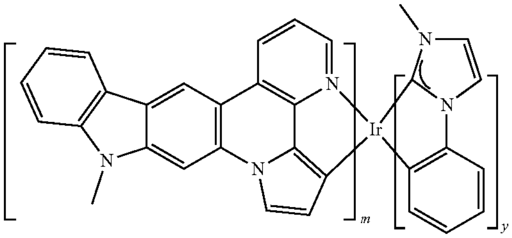
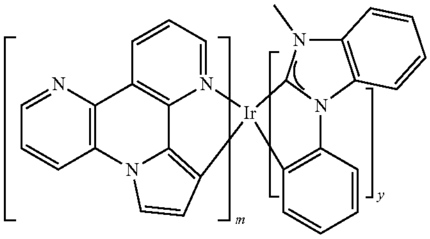
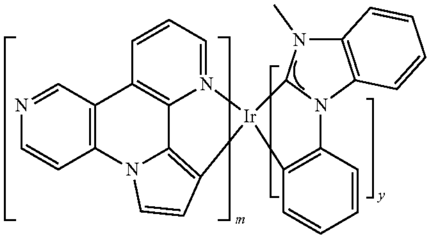
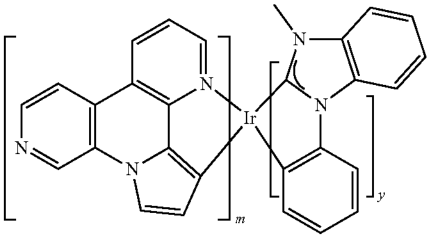
-continued
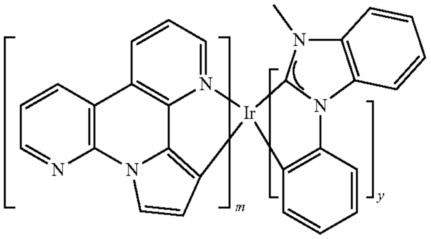
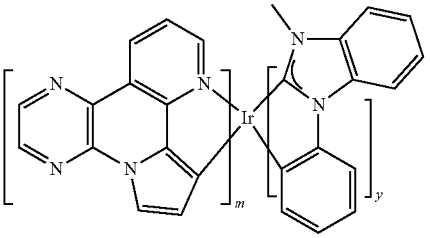
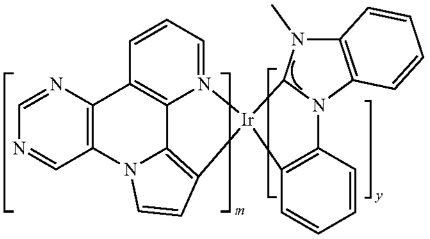
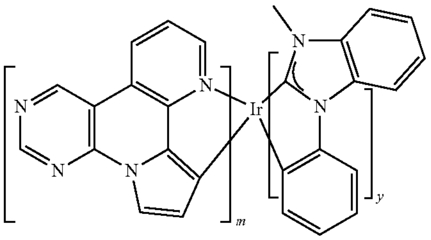
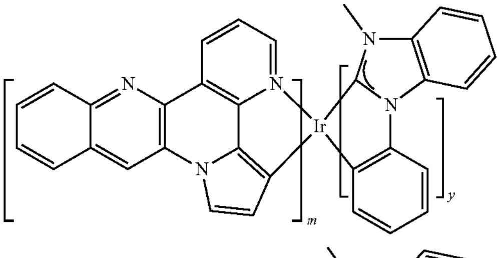
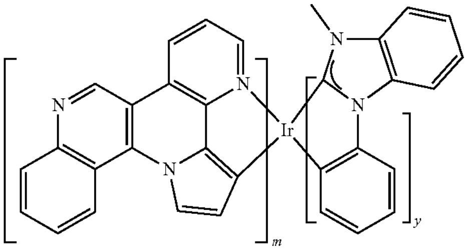
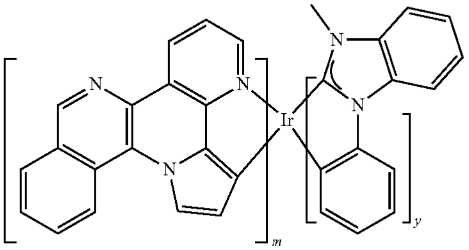

-continued
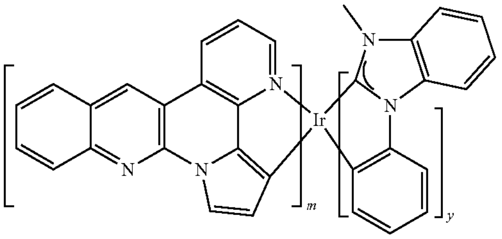
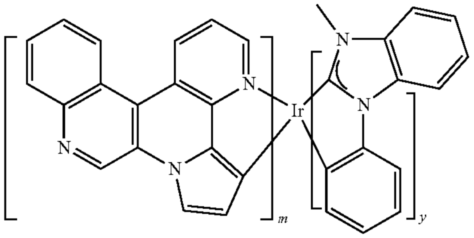
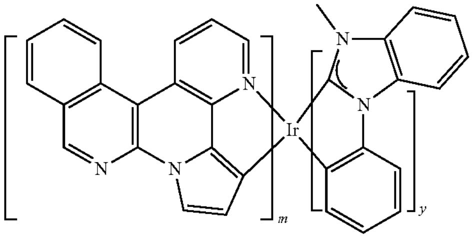
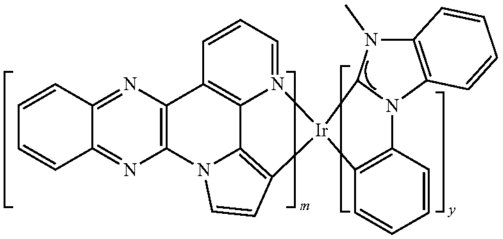
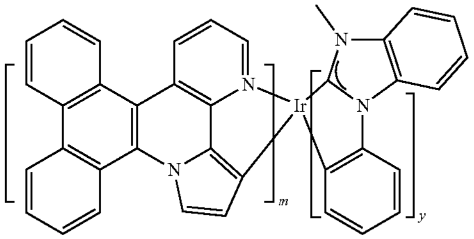
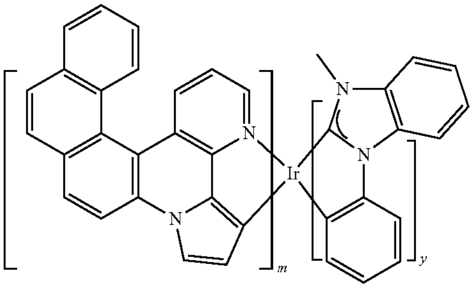
-continued
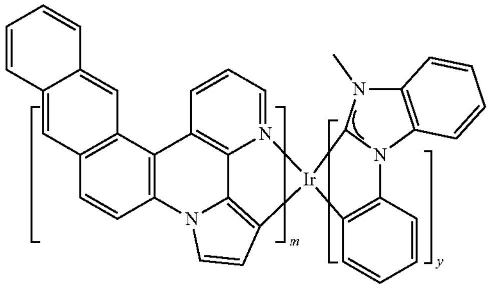
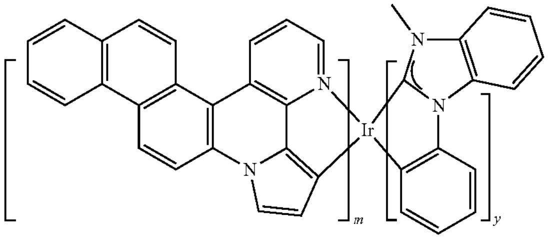
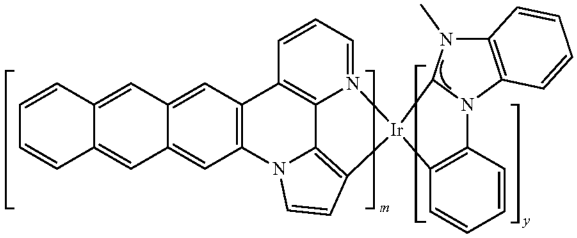
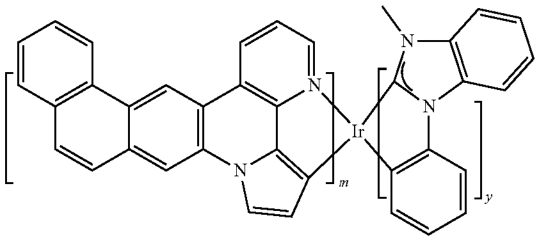
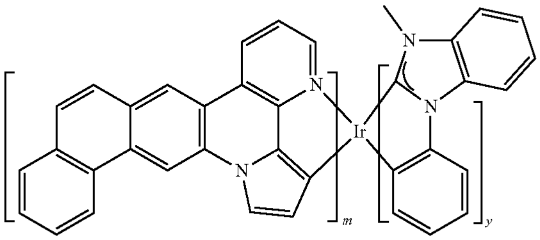
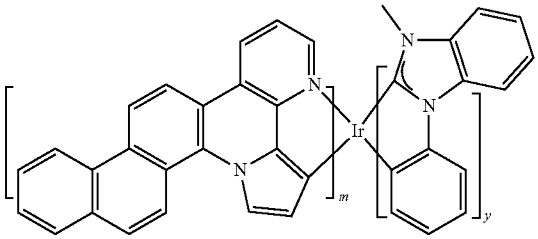

-continued
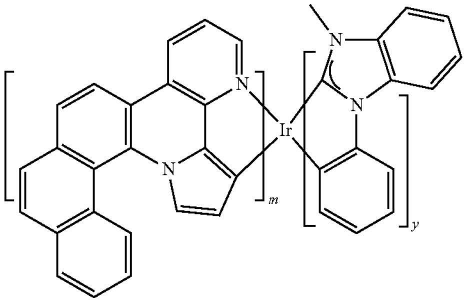
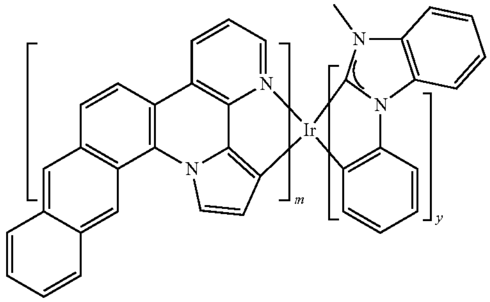
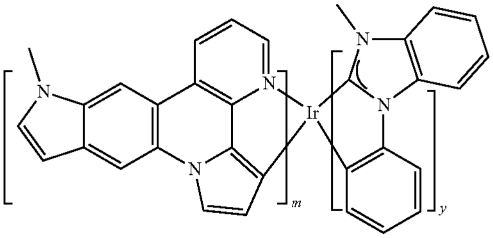
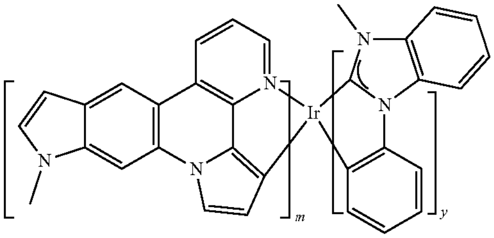
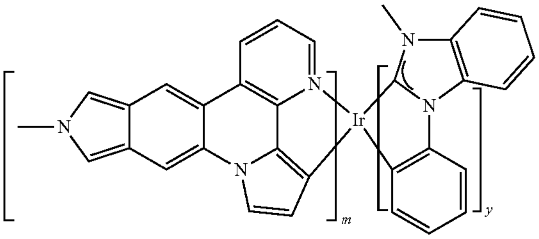
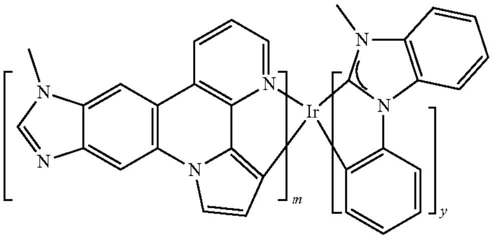
-continued
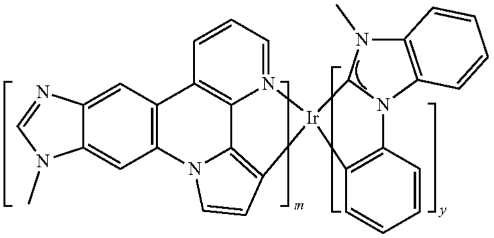
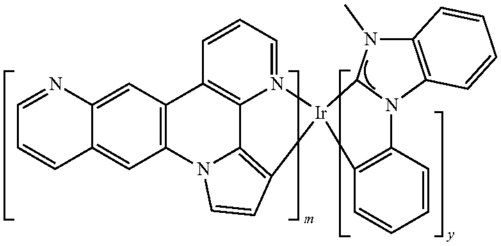
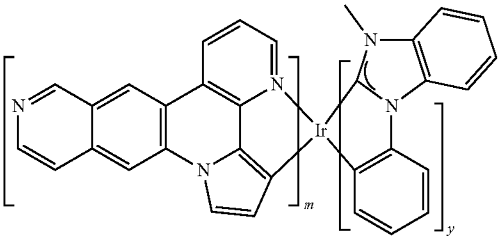
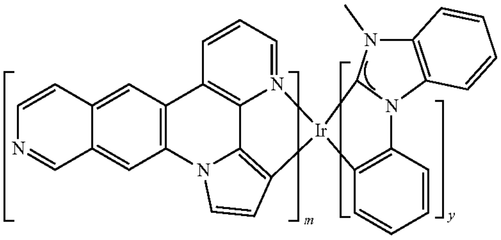
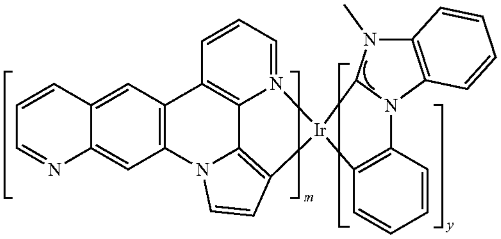
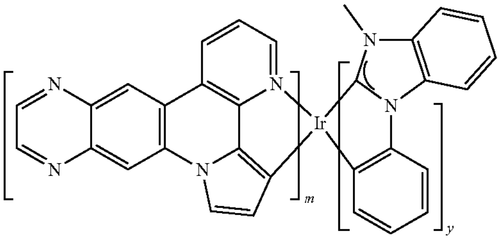
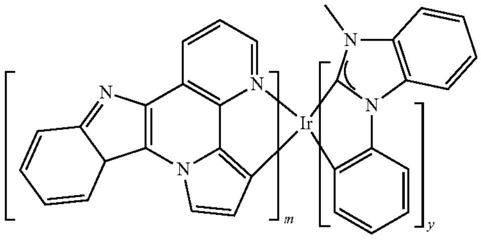

-continued
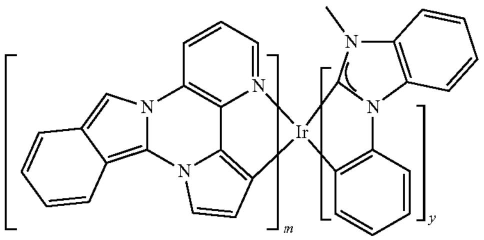
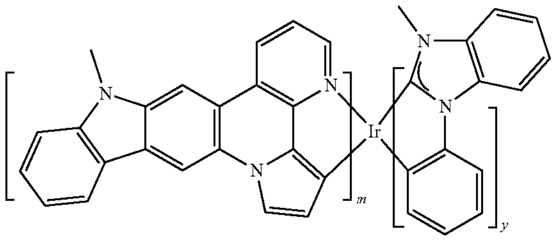
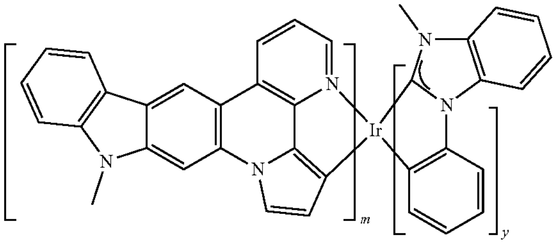
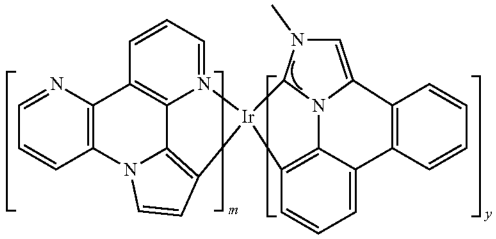
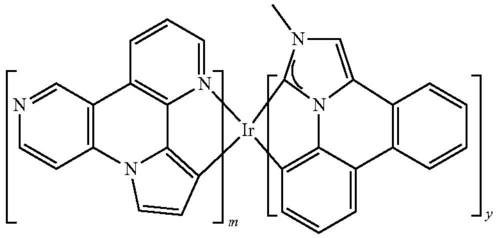
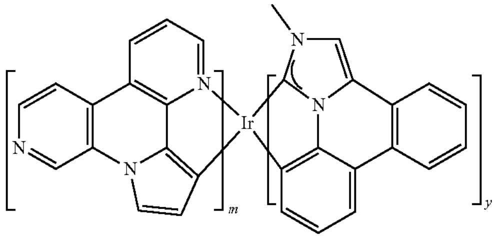
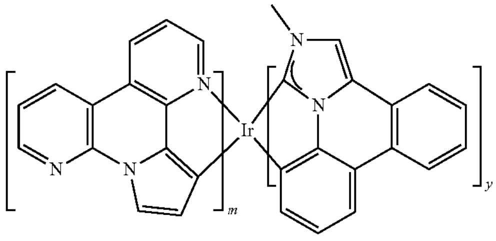
-continued
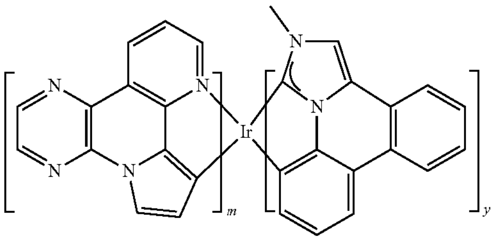
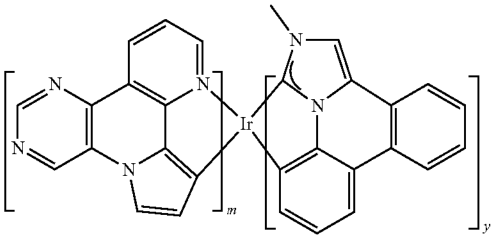
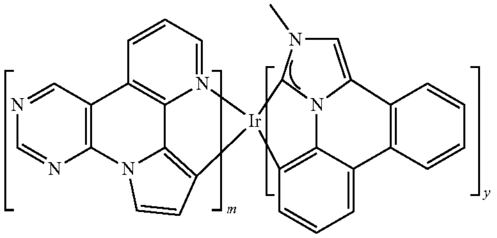
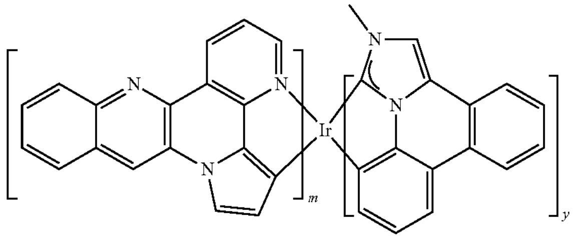
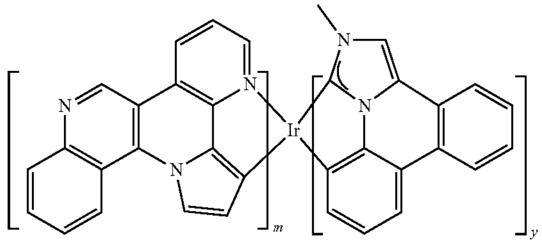
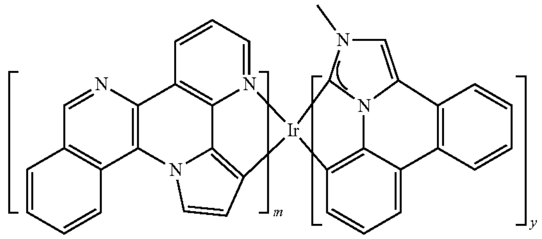
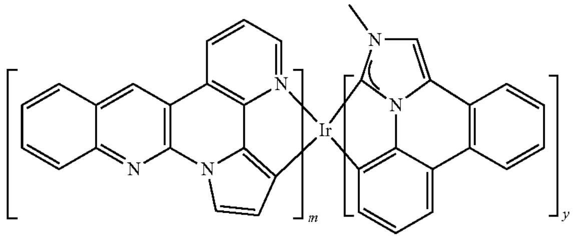

-continued
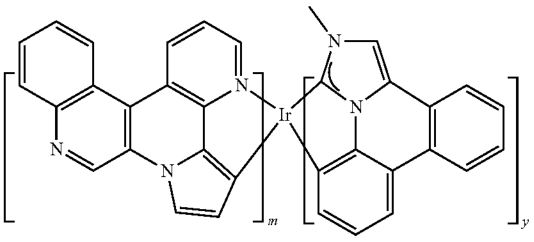
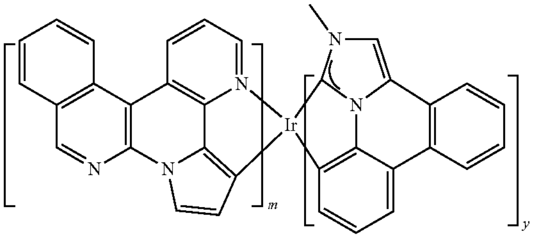
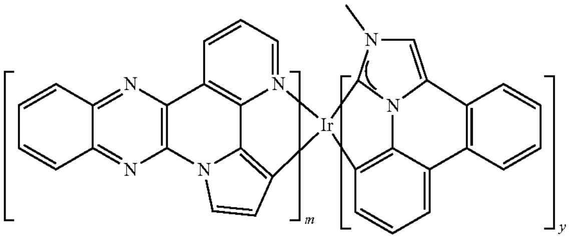
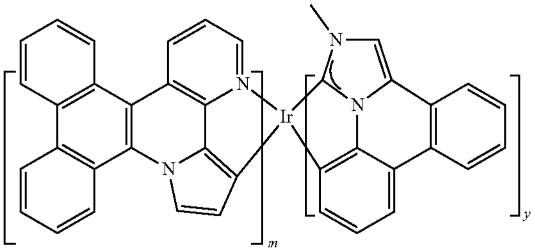
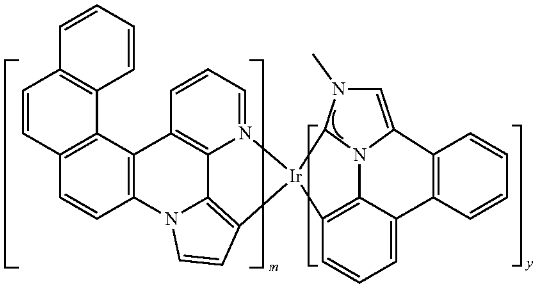
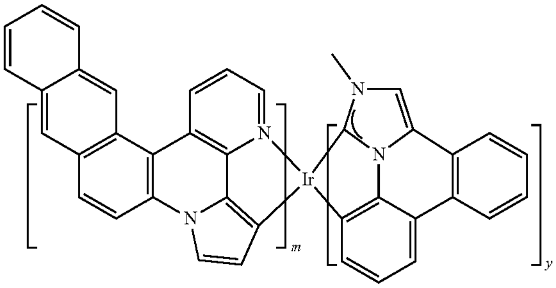
-continued
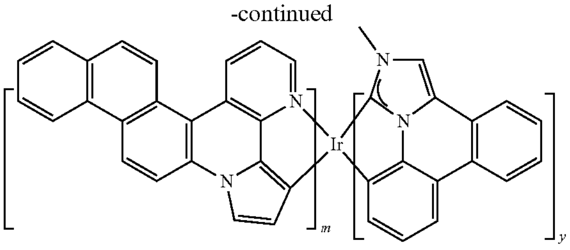
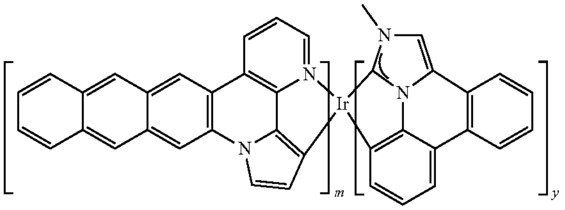
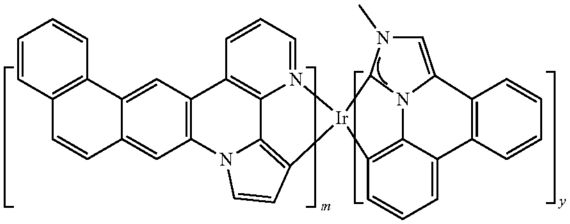
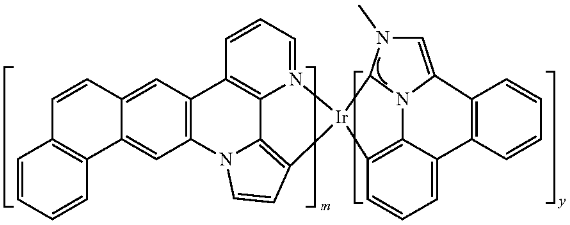
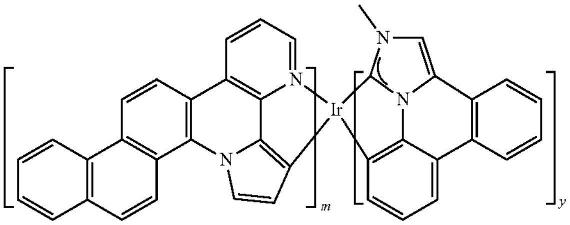
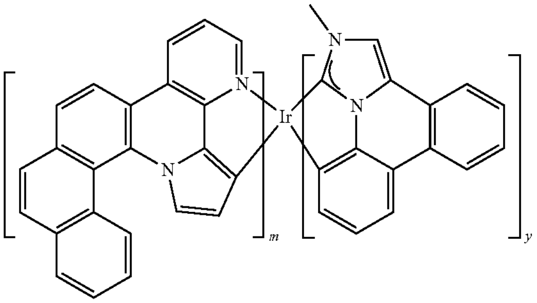
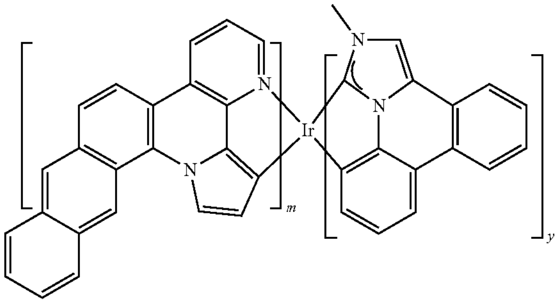

-continued
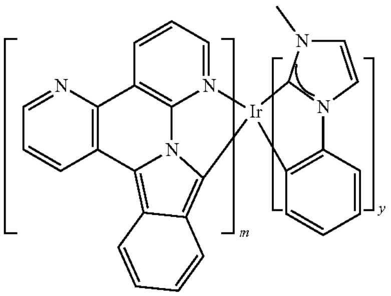
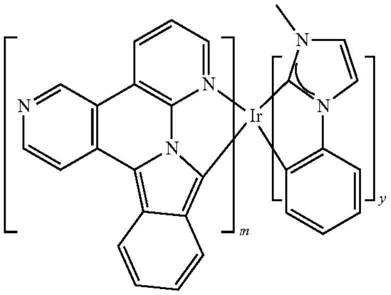
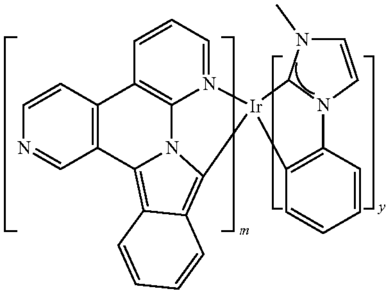
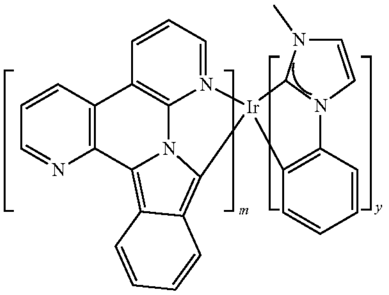
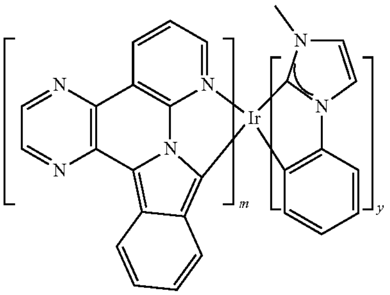
-continued
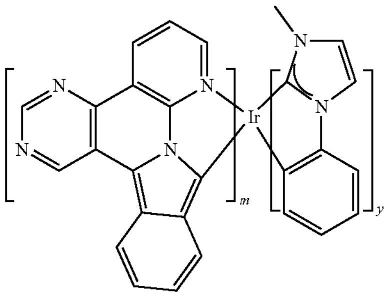
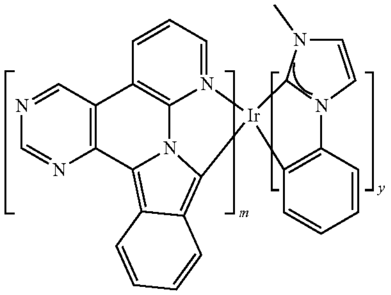
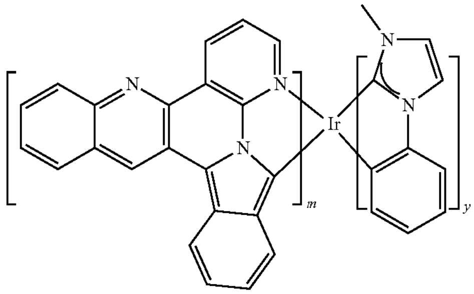
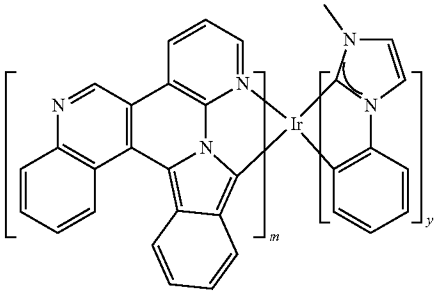
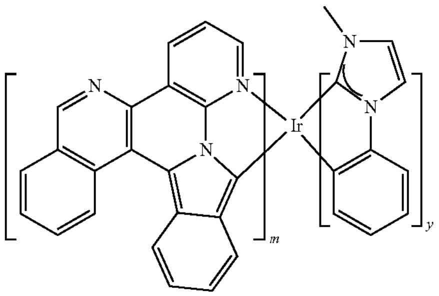

-continued
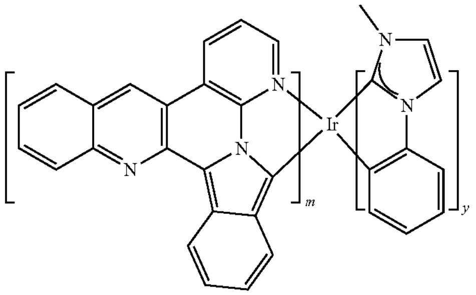
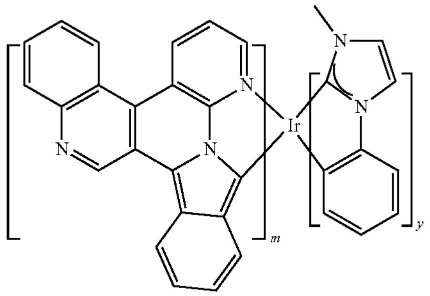
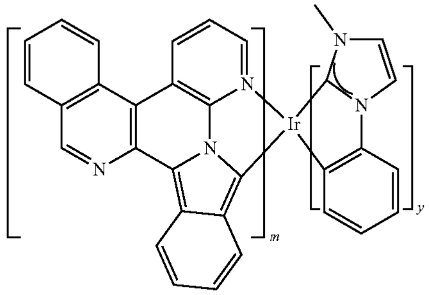
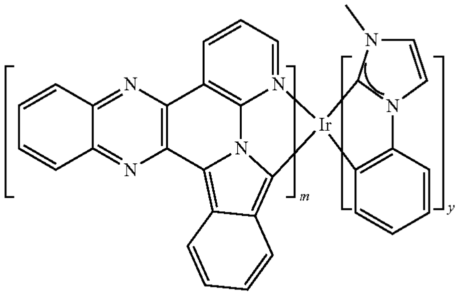
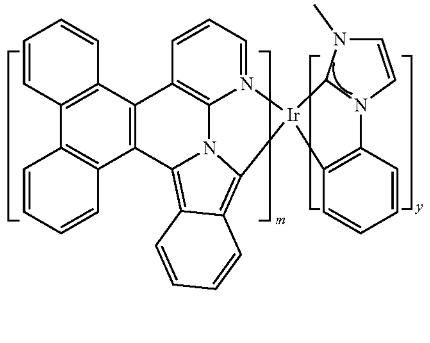
-continued
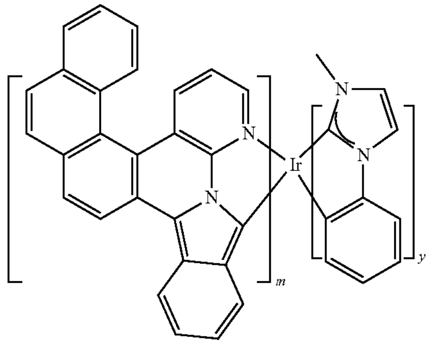
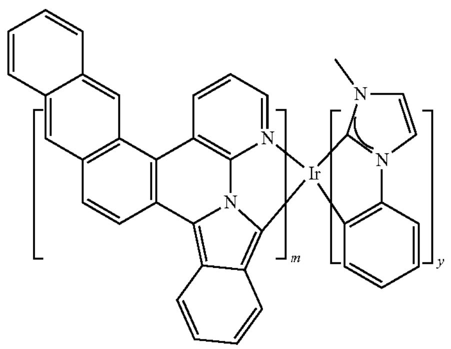
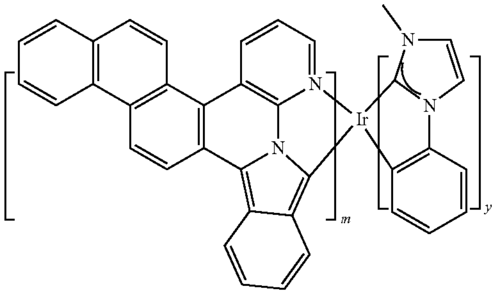
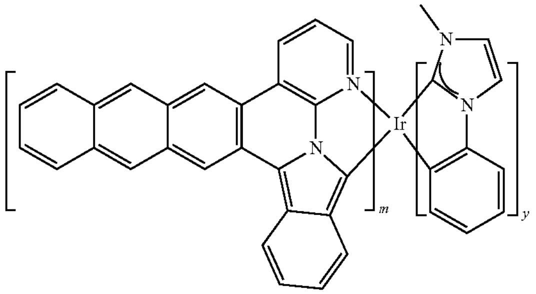
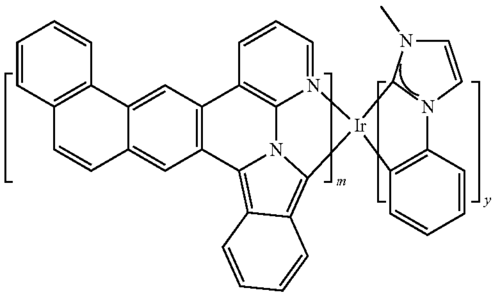

-continued
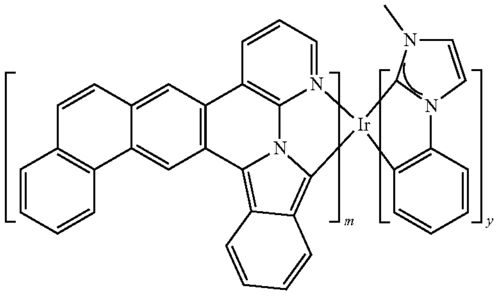
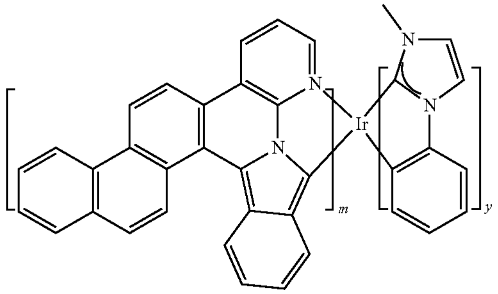
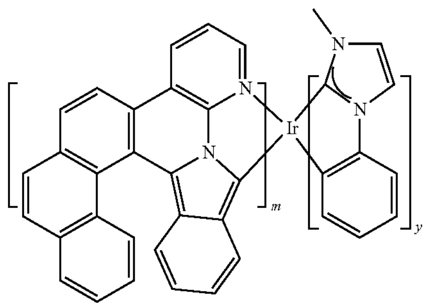
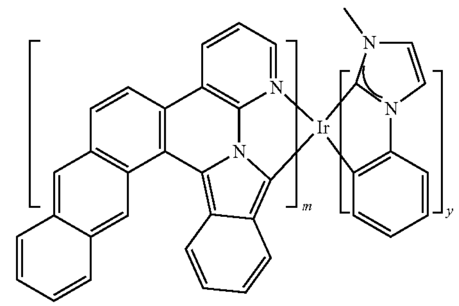
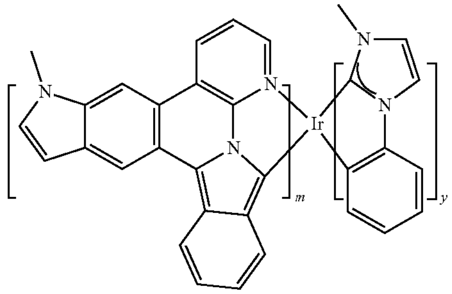
-continued
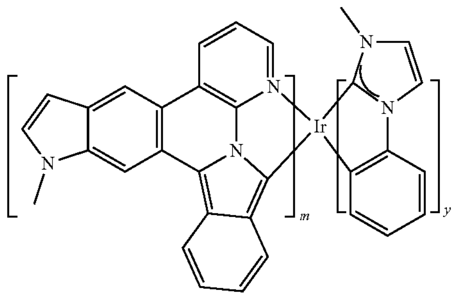
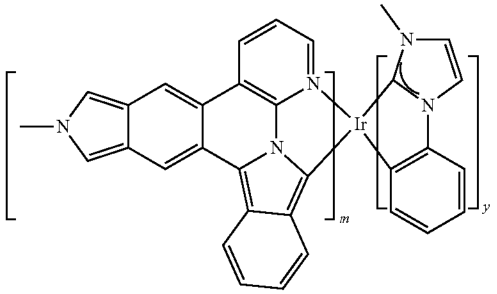
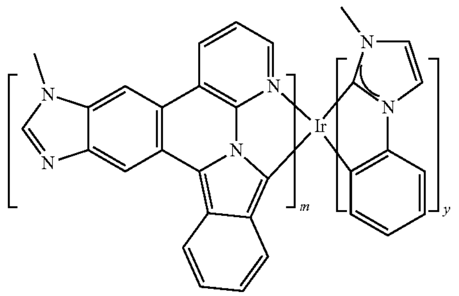
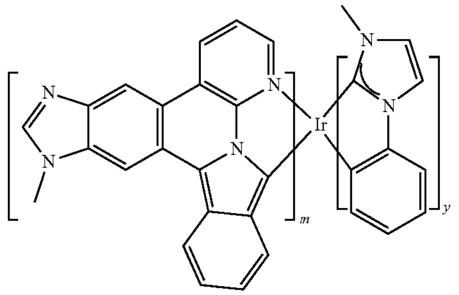
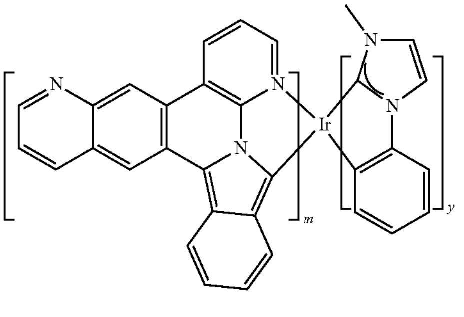

-continued
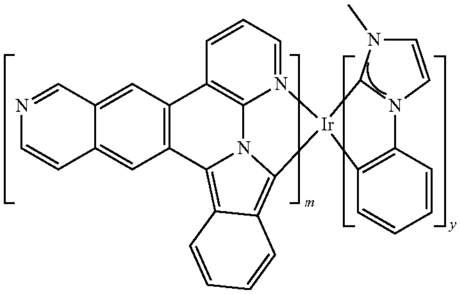
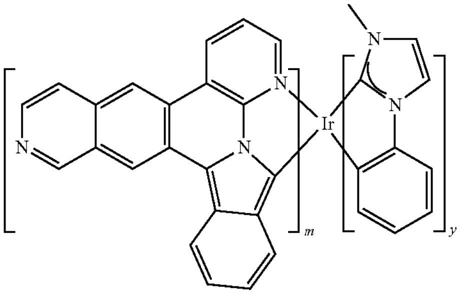
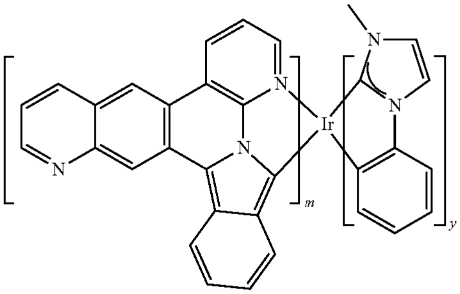
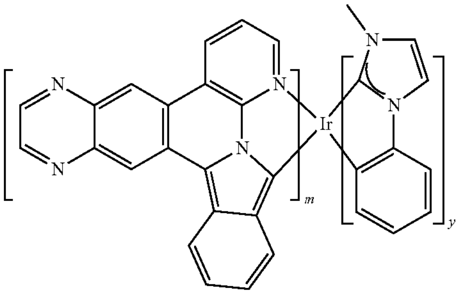
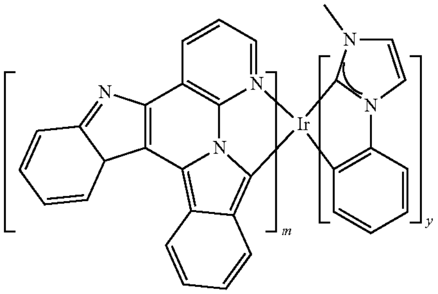
-continued
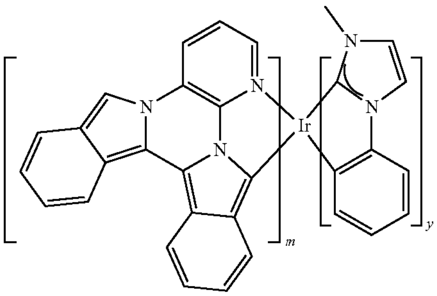
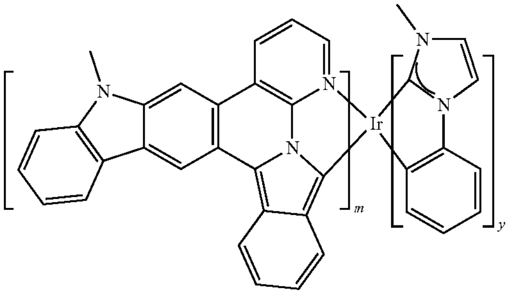
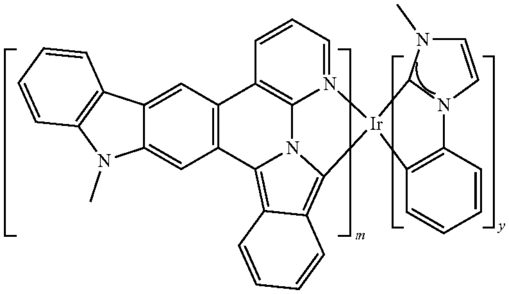
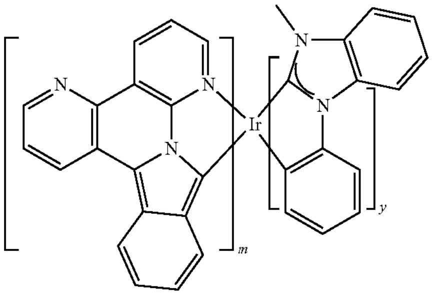
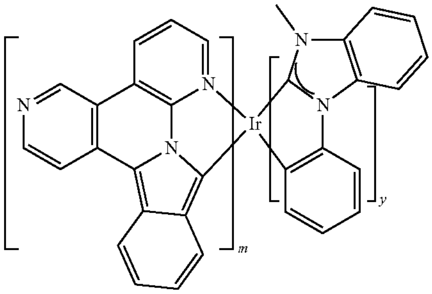

-continued
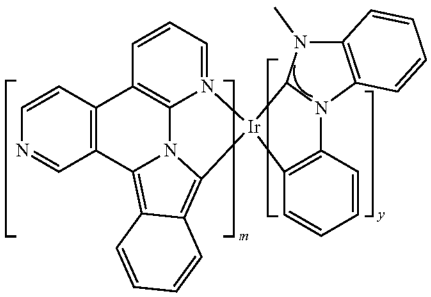
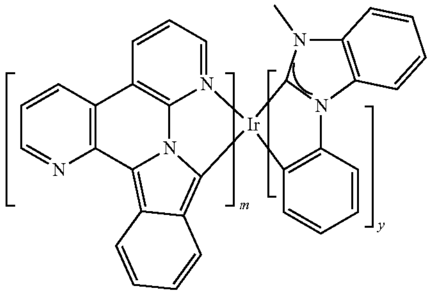
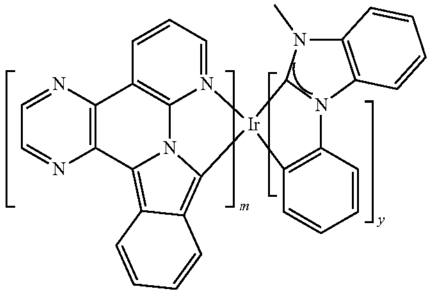
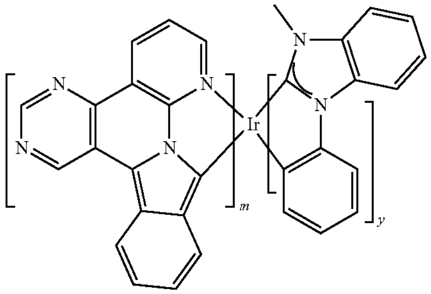
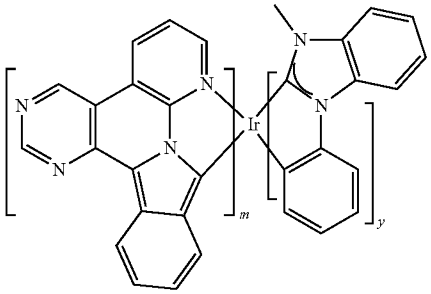
-continued
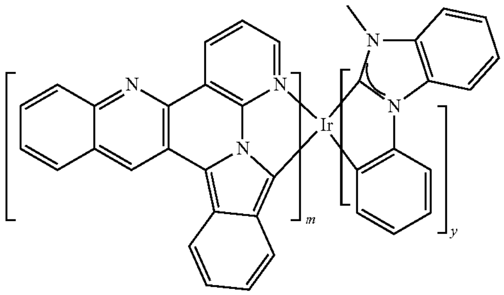
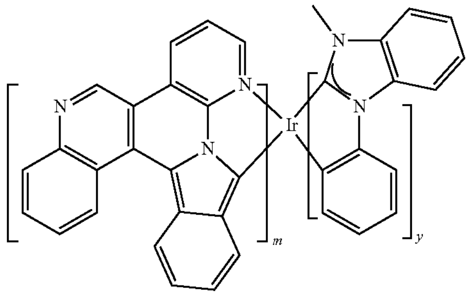
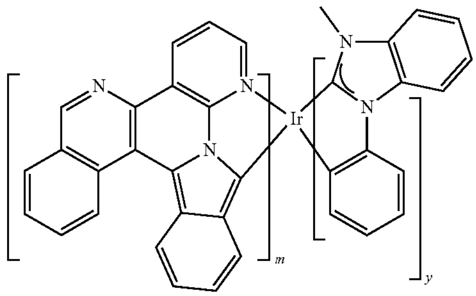
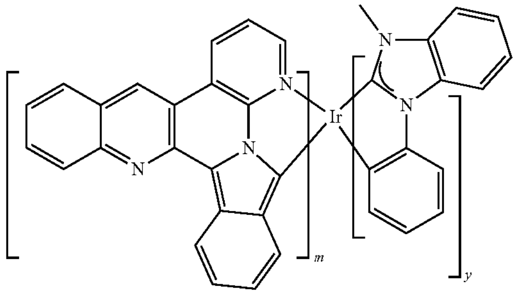
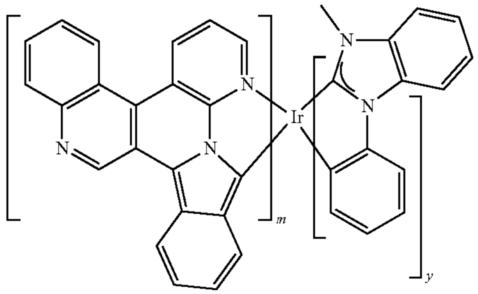

-continued
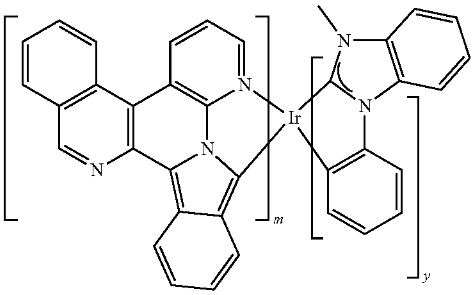
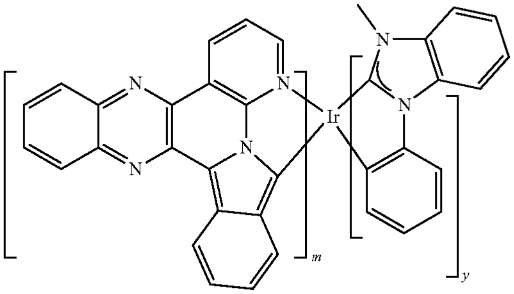
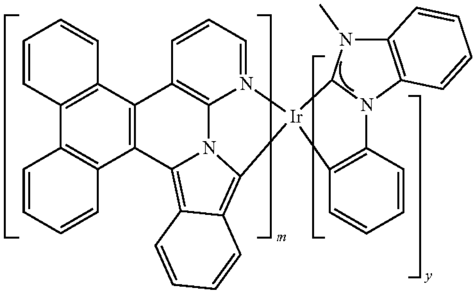
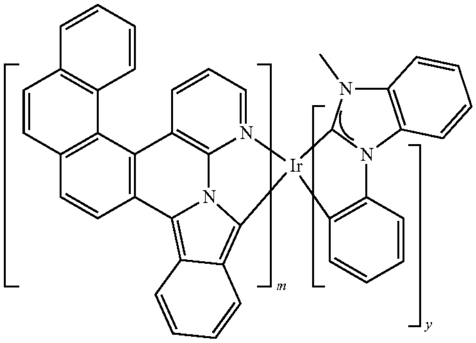
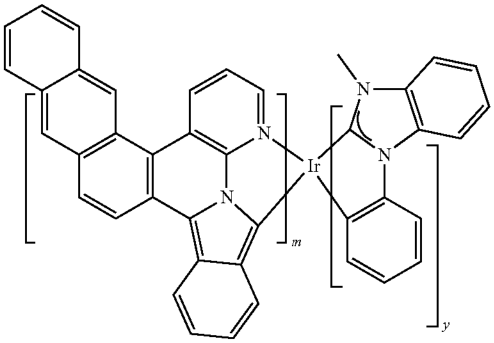
-continued
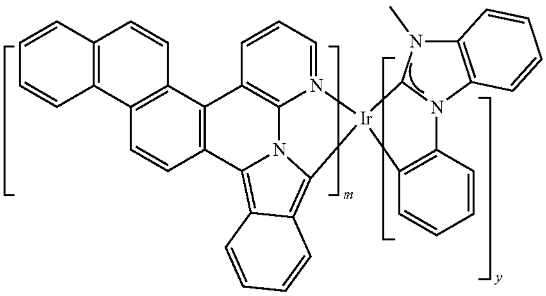
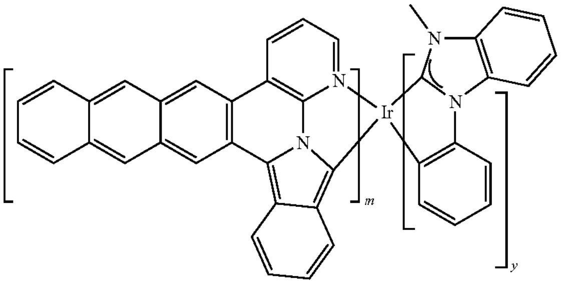
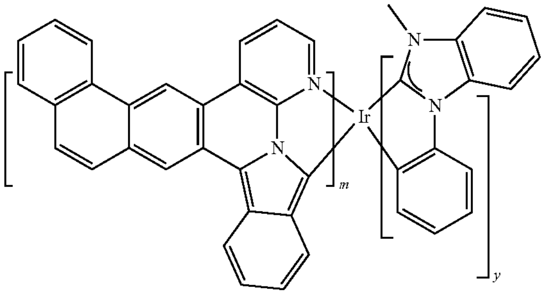
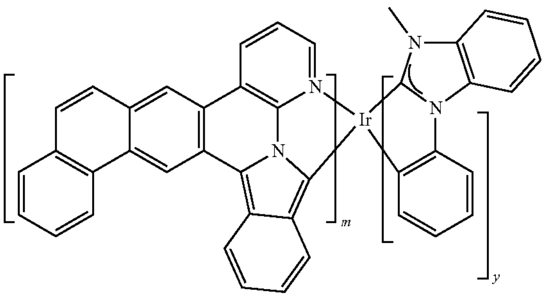
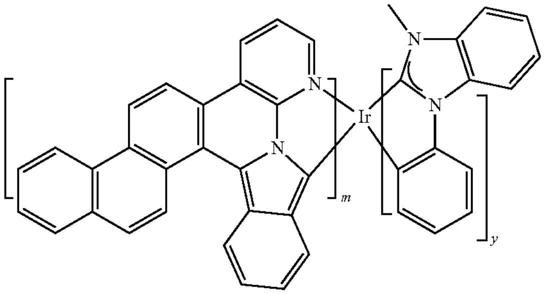

-continued
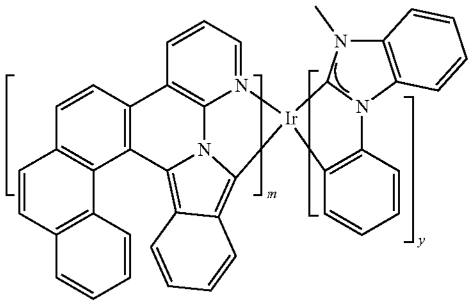
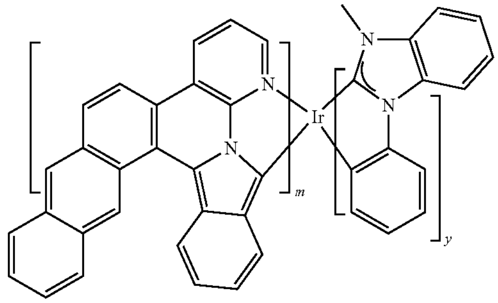
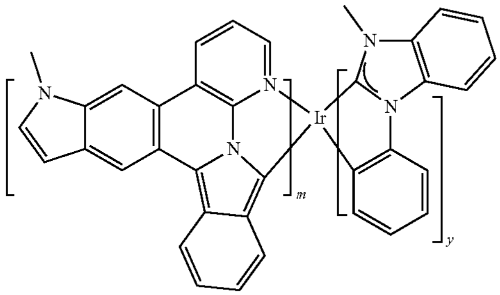
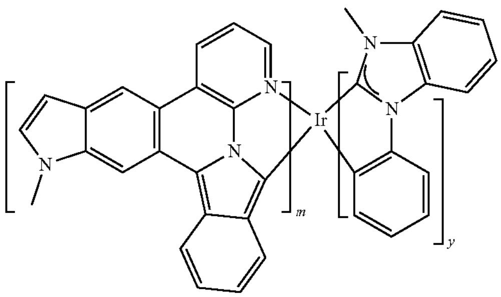
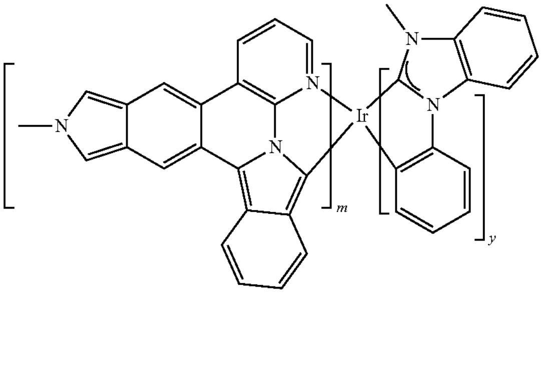
-continued
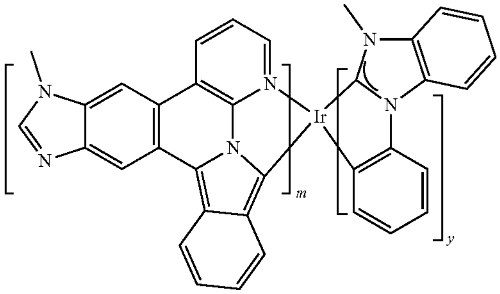
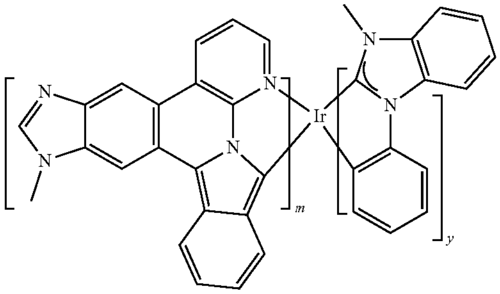
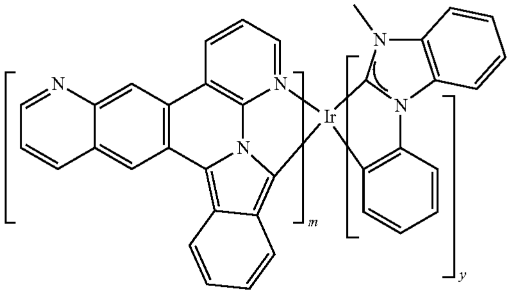
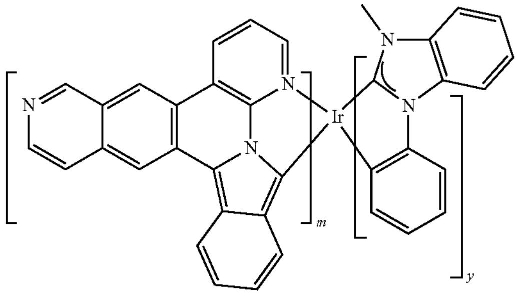
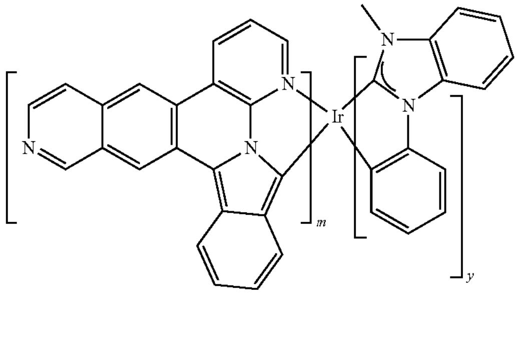

-continued
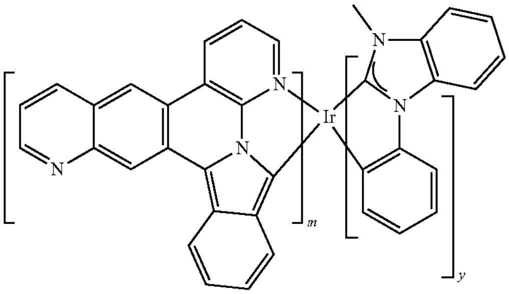
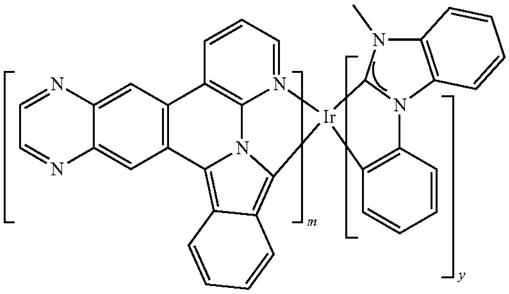
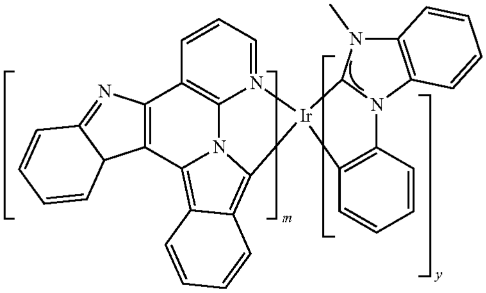
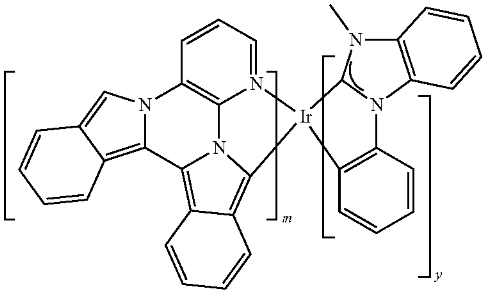
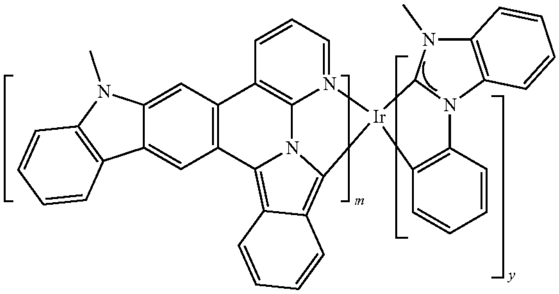
-continued
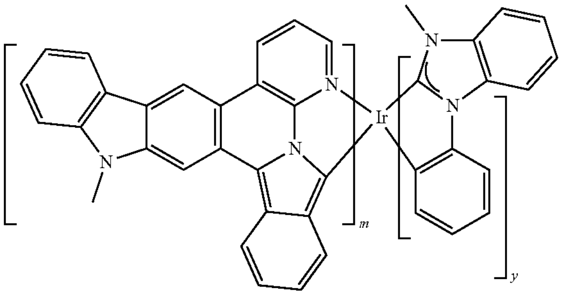
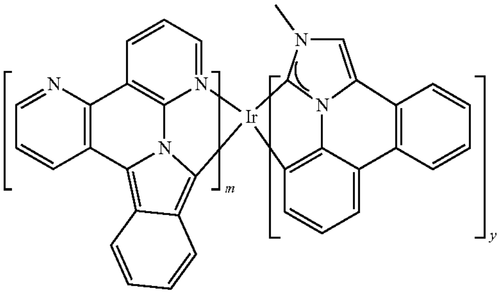
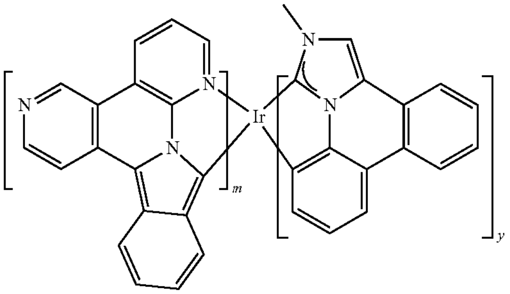
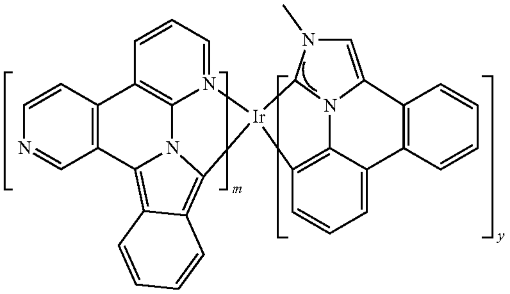
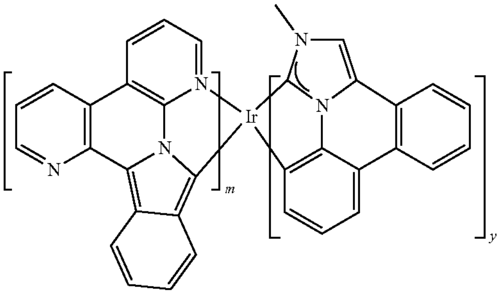

-continued
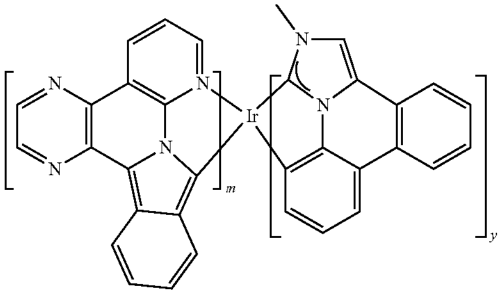
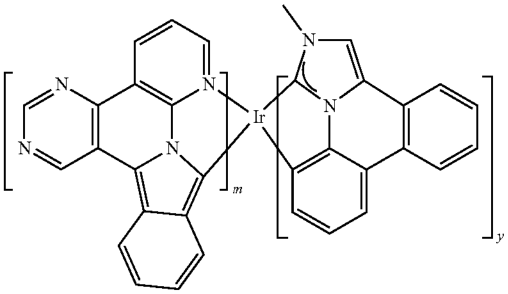
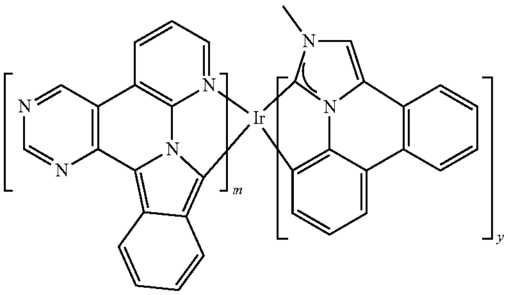
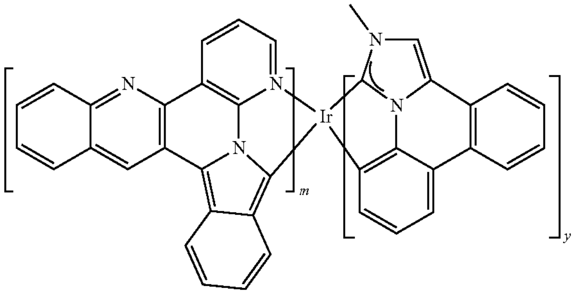
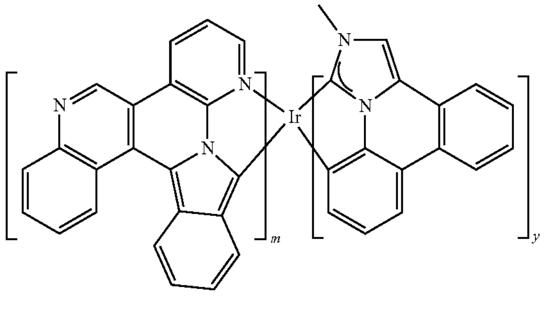
-continued
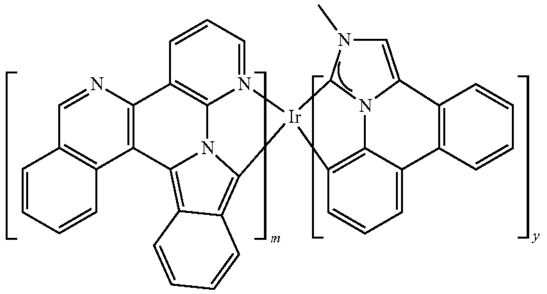
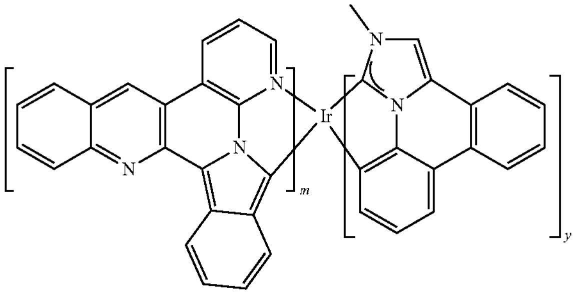
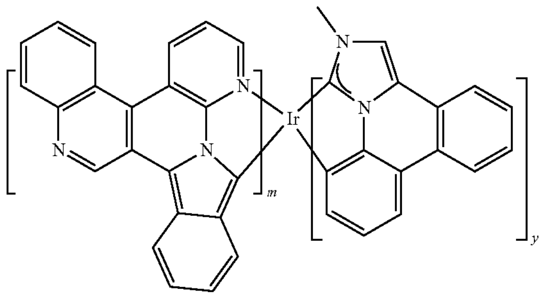
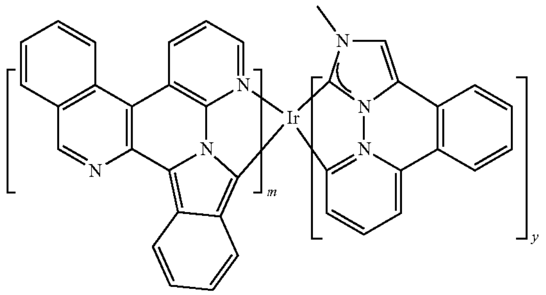
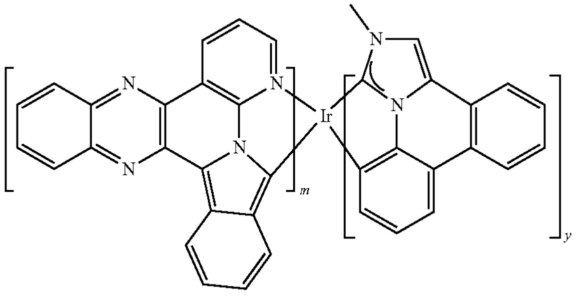

-continued
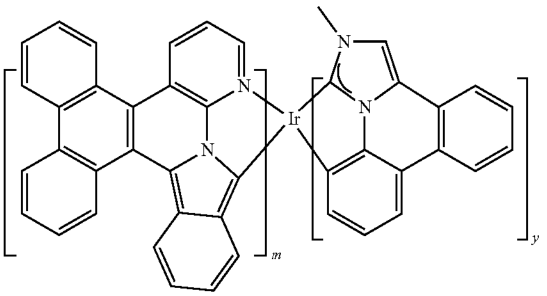
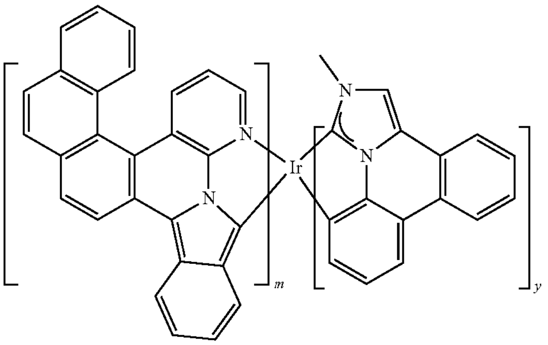
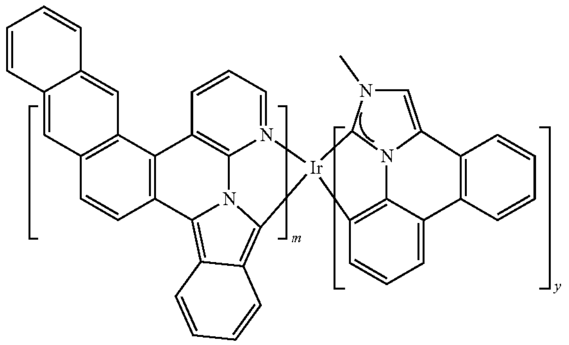
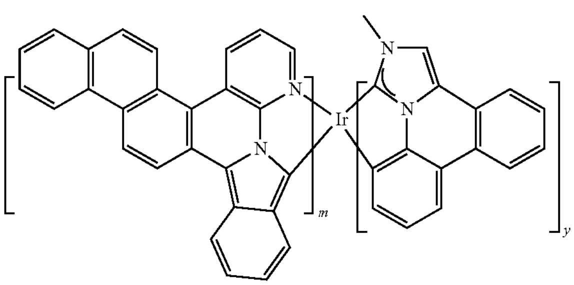
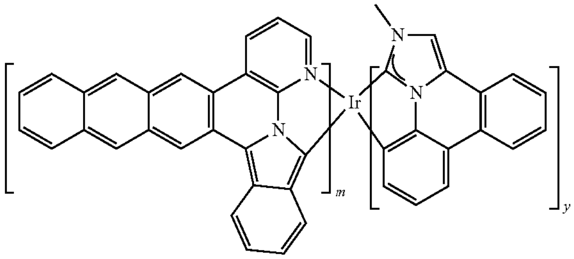
-continued
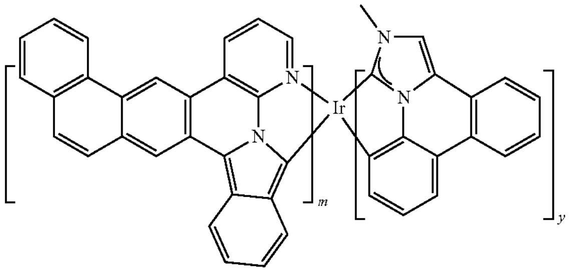
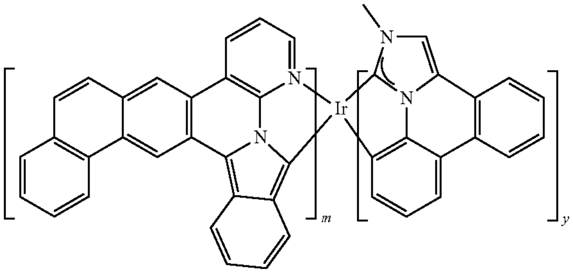
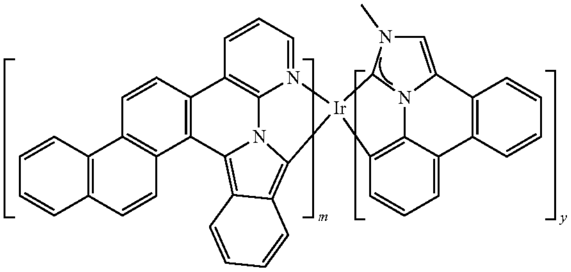
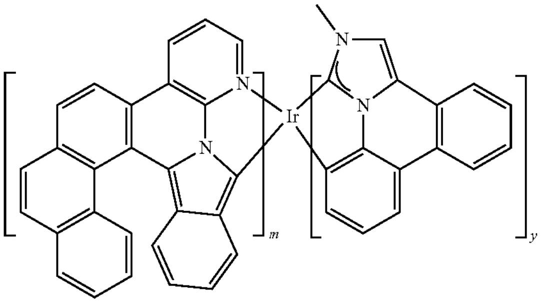
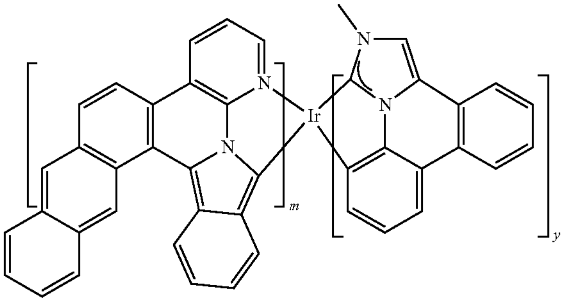
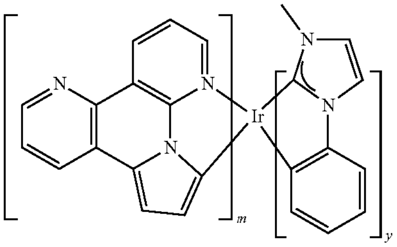

-continued
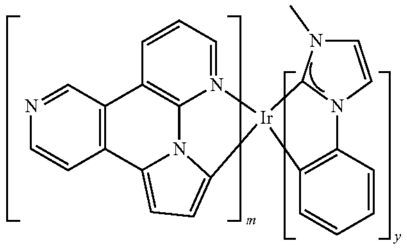
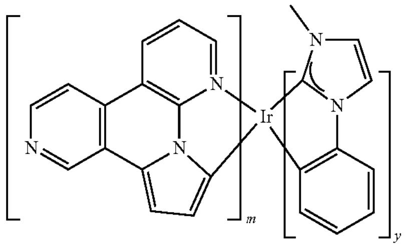
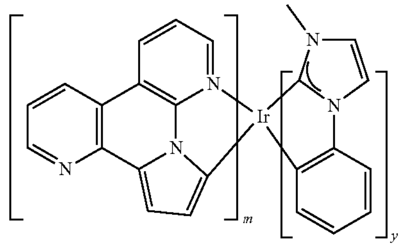
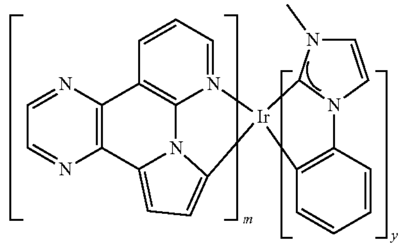
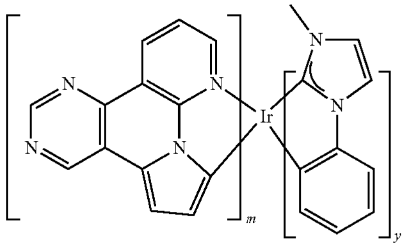
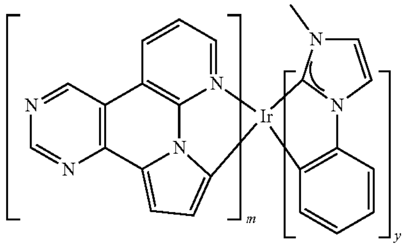
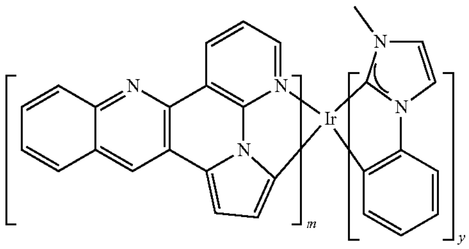
-continued
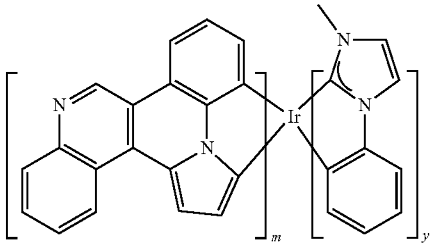
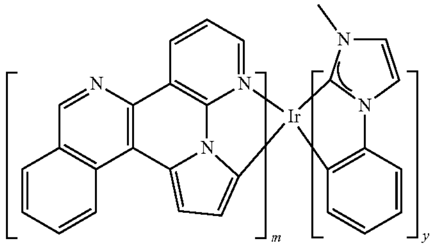
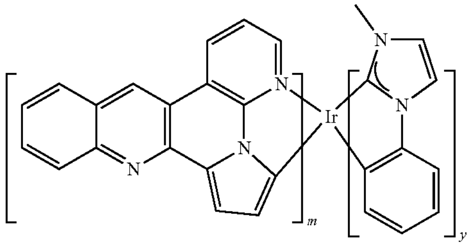
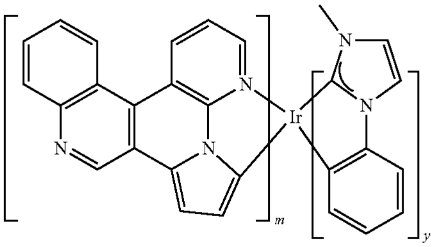
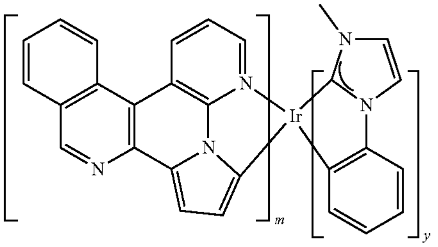
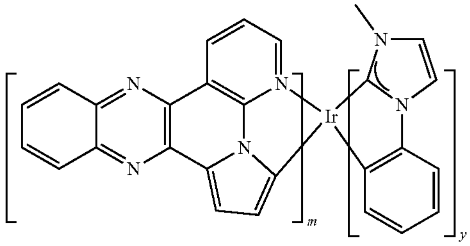
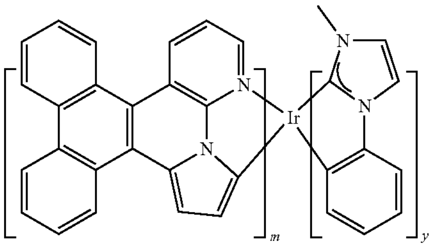

-continued
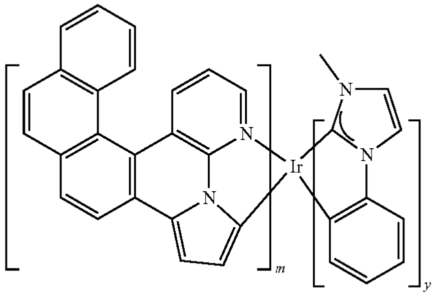
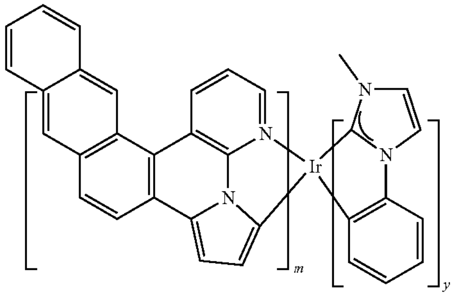
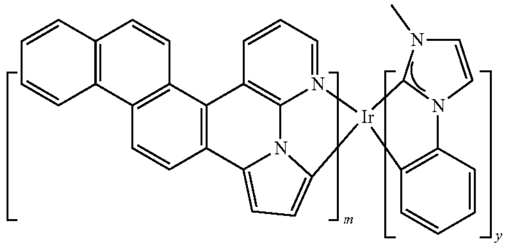
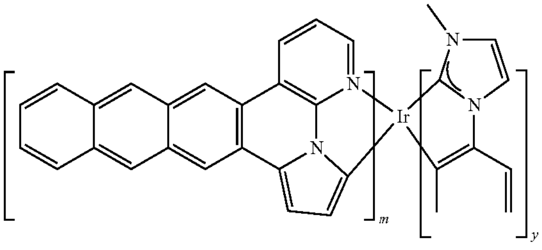
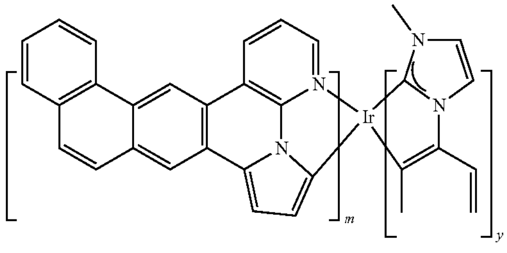
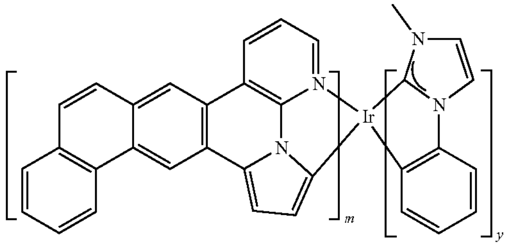
-continued
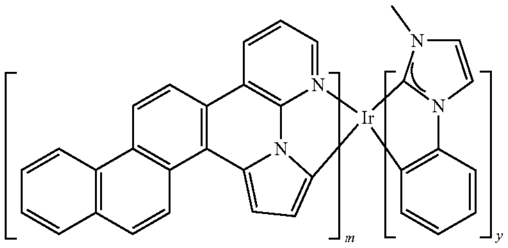
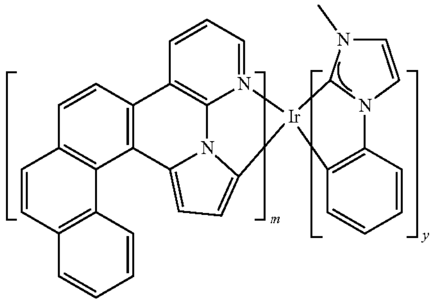
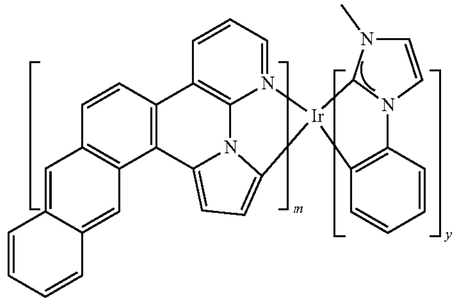
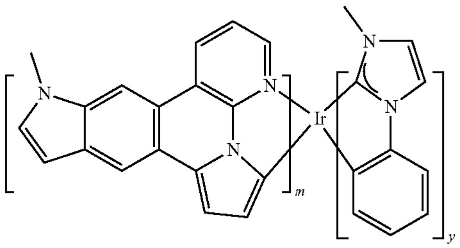
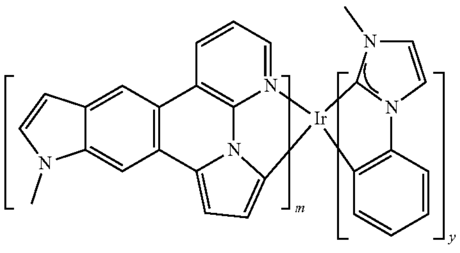
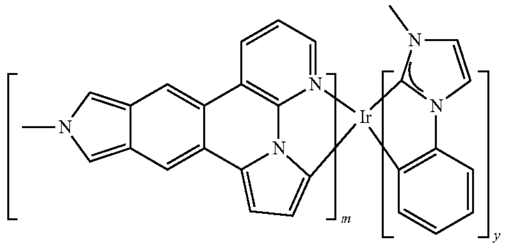

-continued
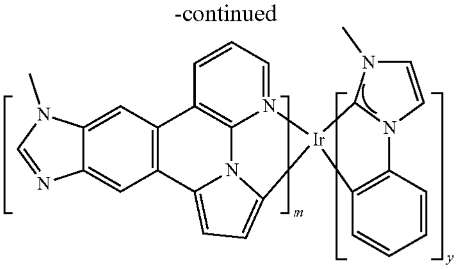
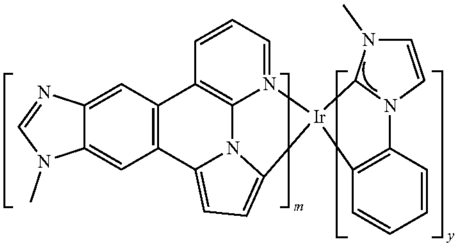
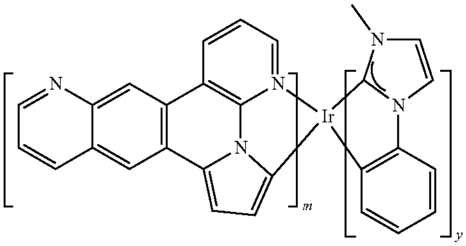
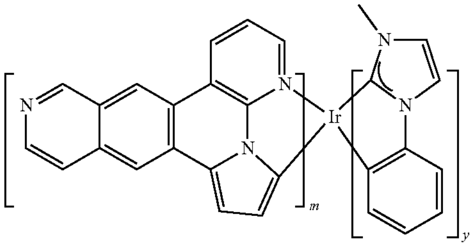
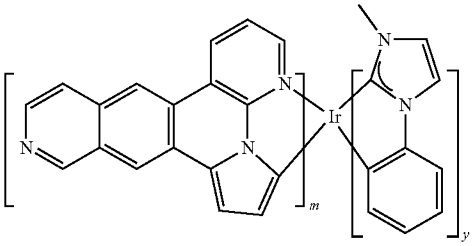
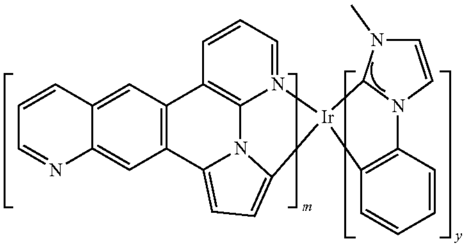
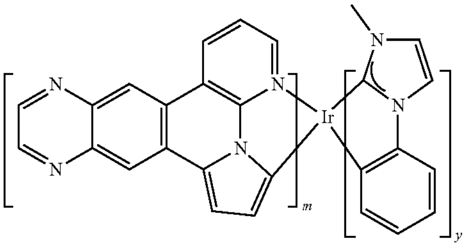
-continued
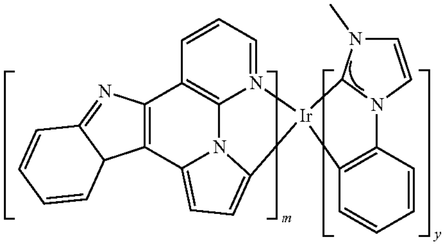
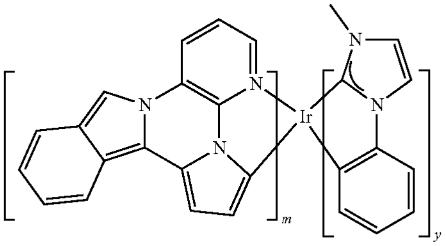
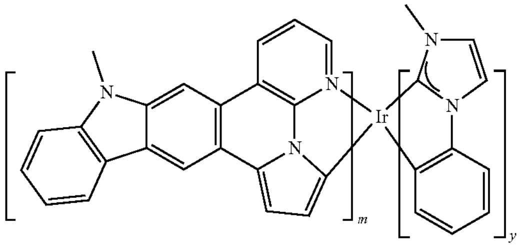
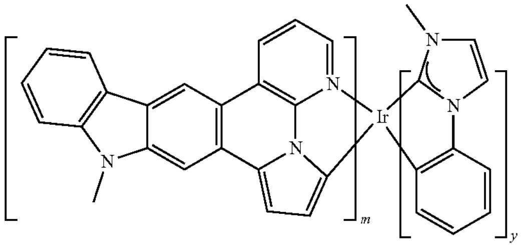
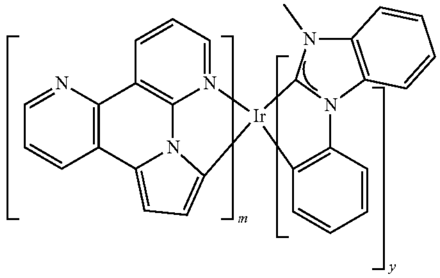
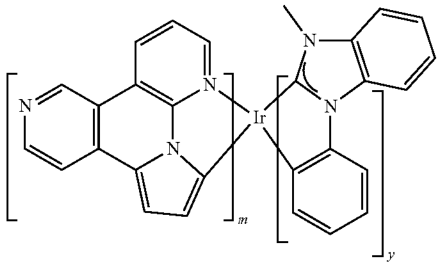

-continued
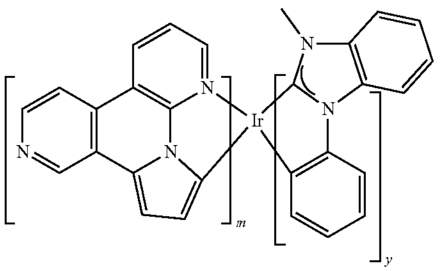
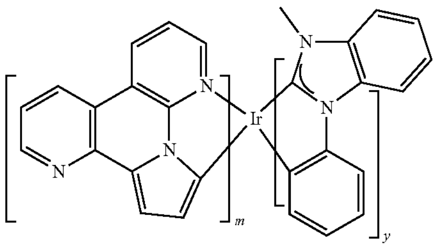
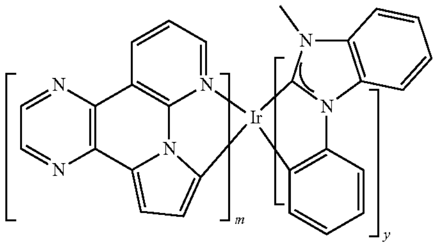
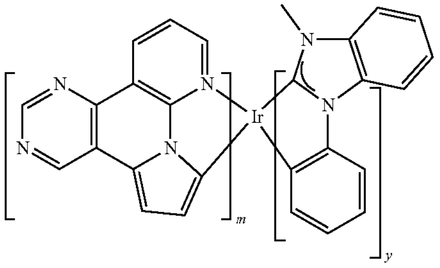
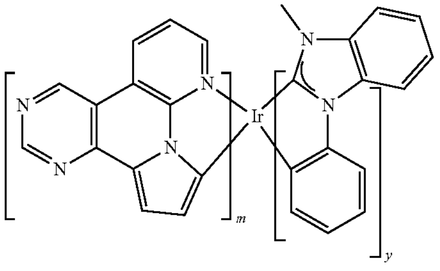
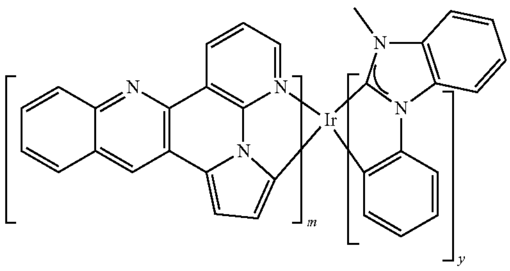
-continued
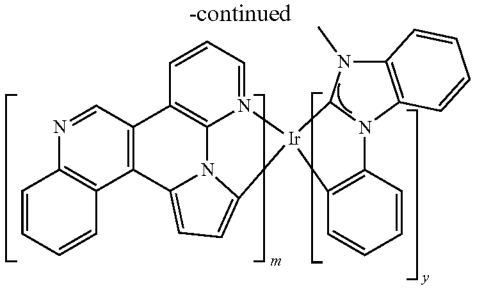
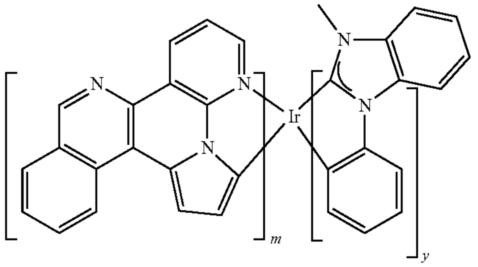
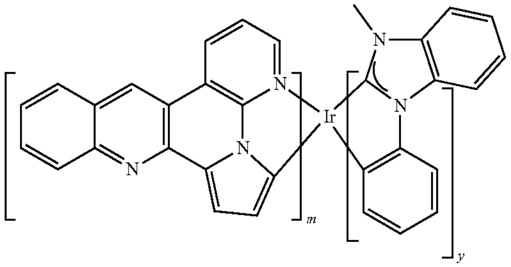
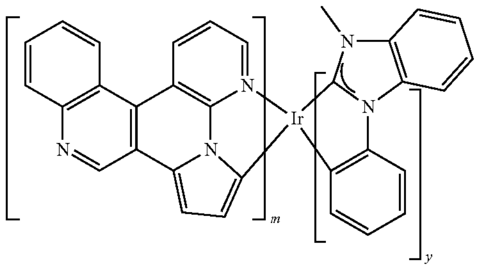
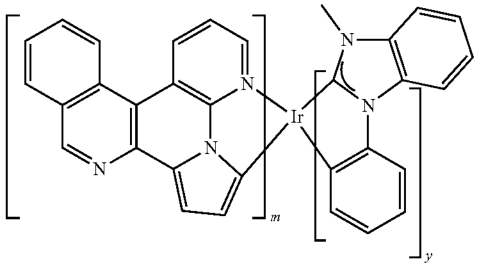
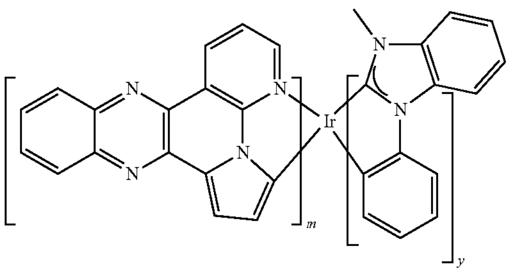

-continued
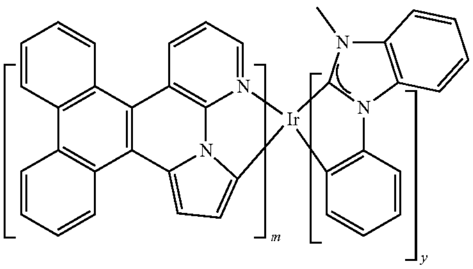
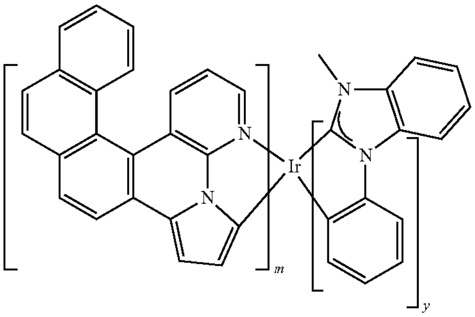
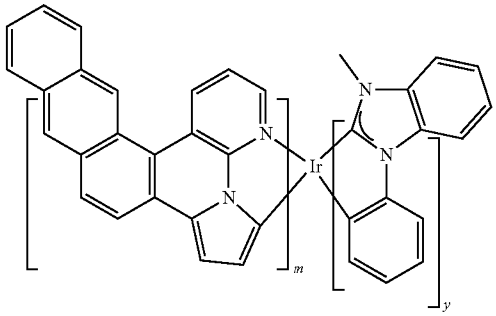
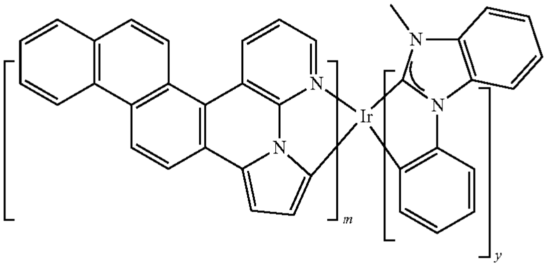
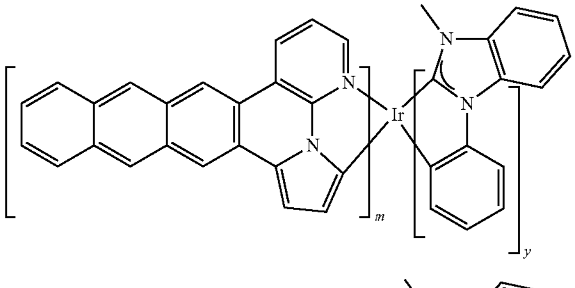
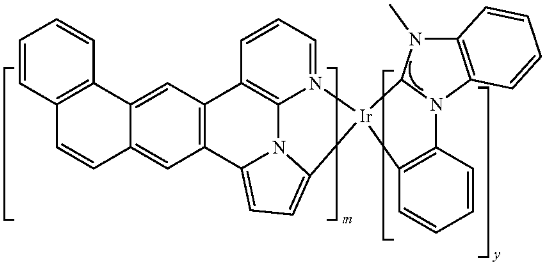
-continued
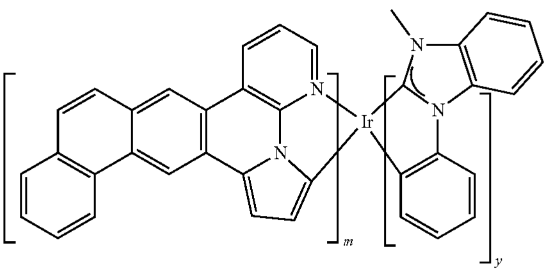
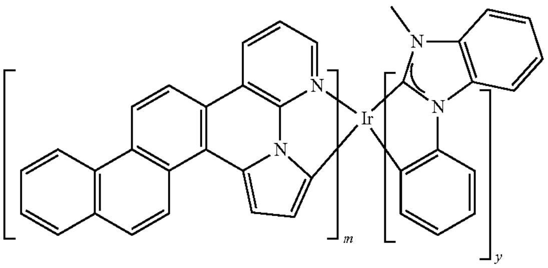
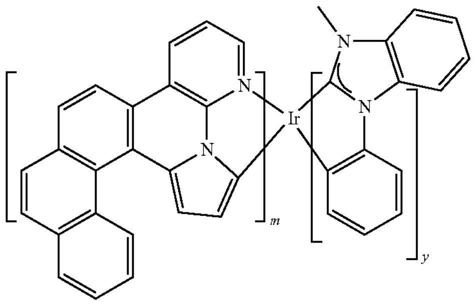
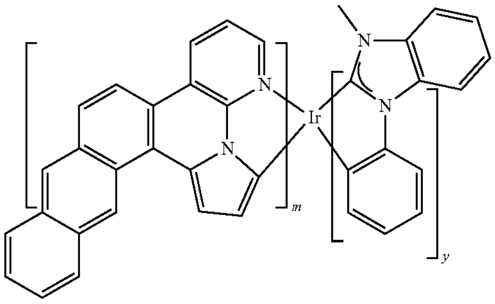
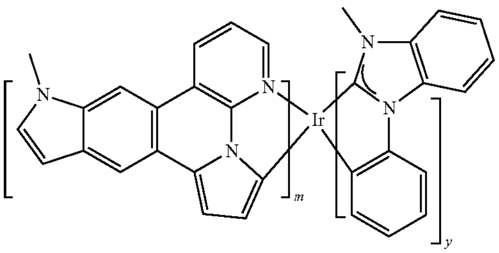
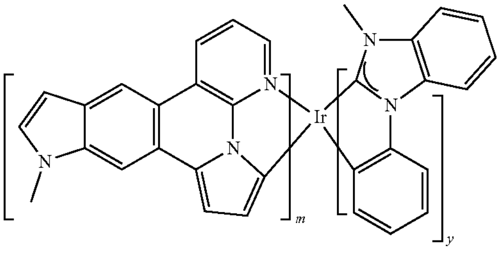

-continued
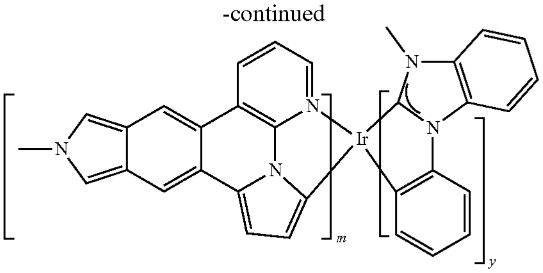
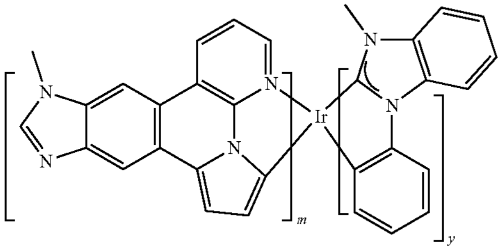
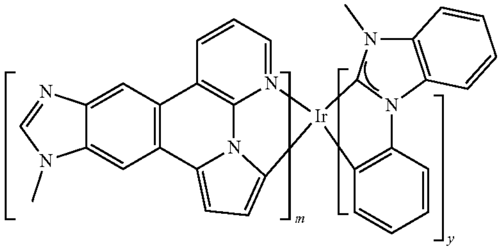
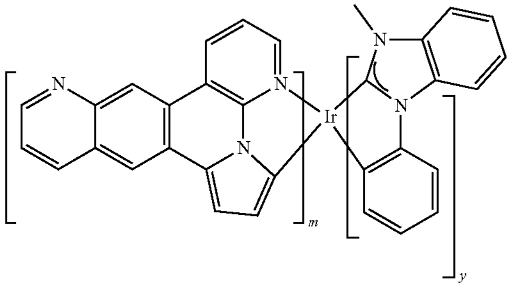
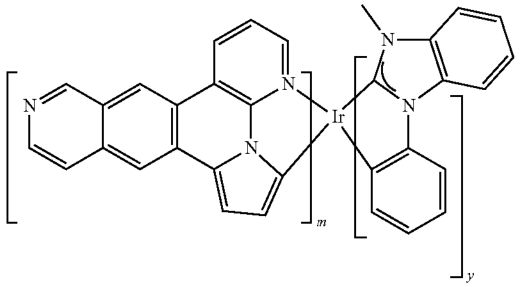
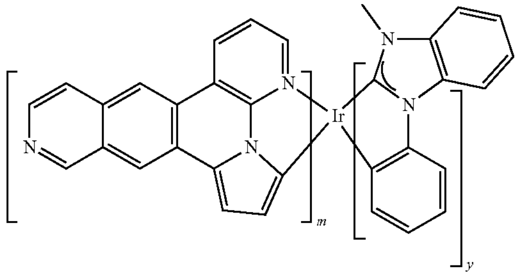
-continued
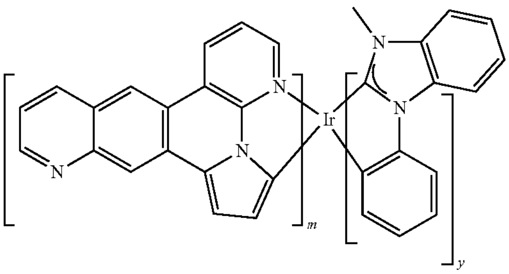
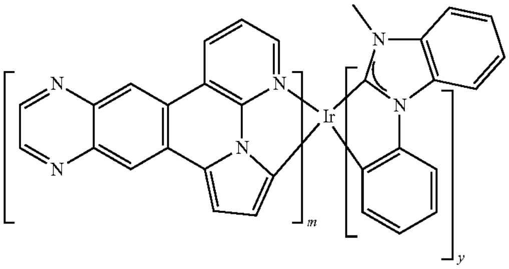
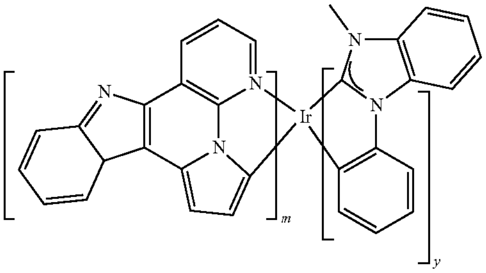
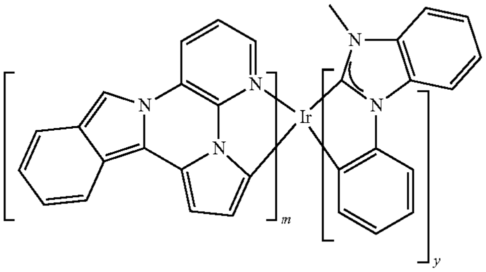
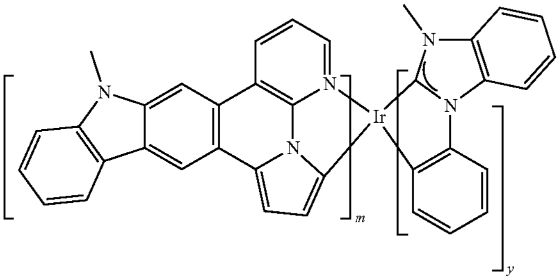
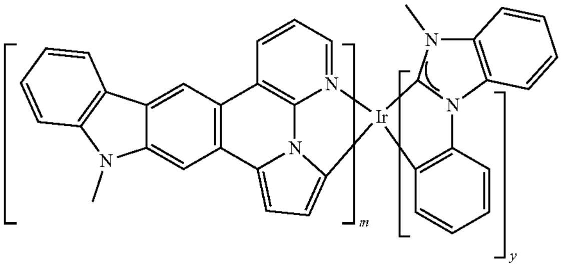

-continued
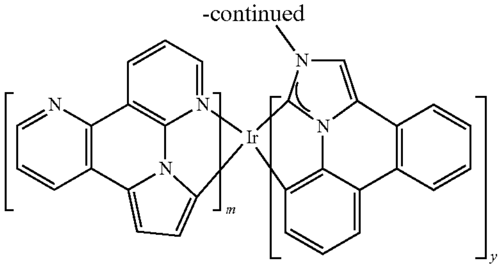
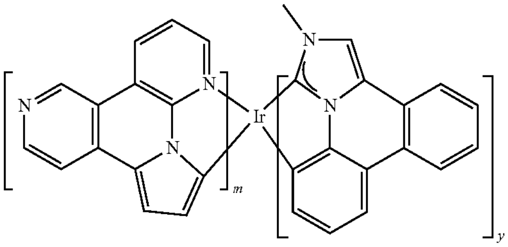
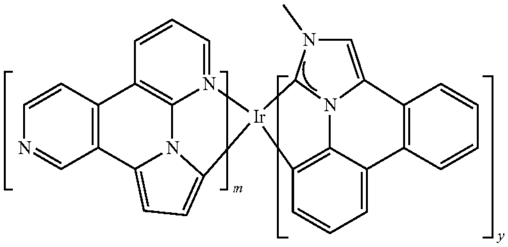
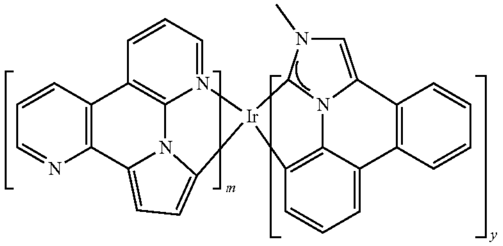
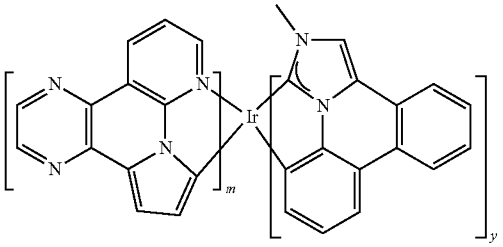
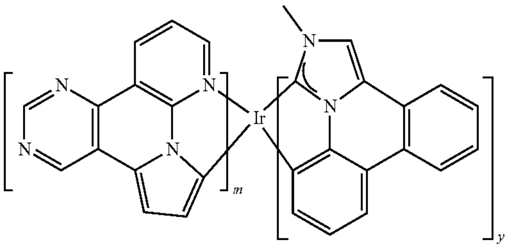
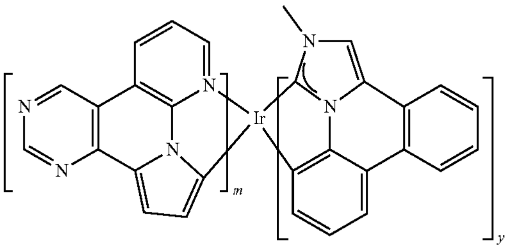
-continued
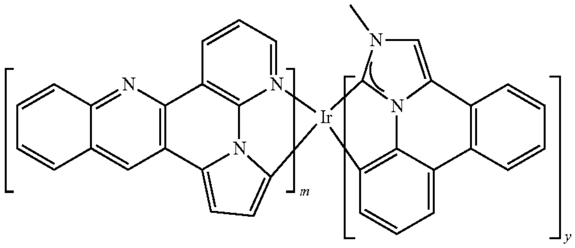
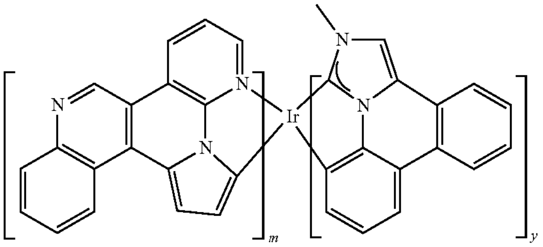
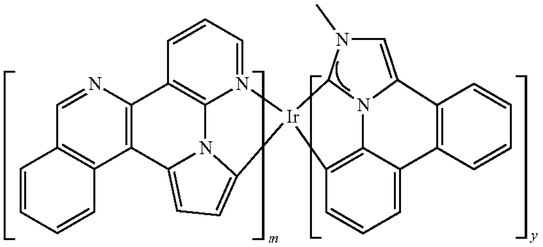
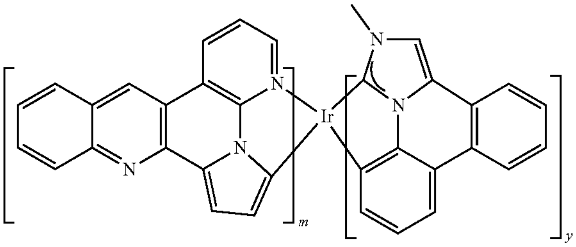
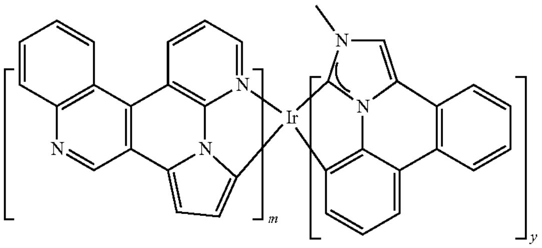
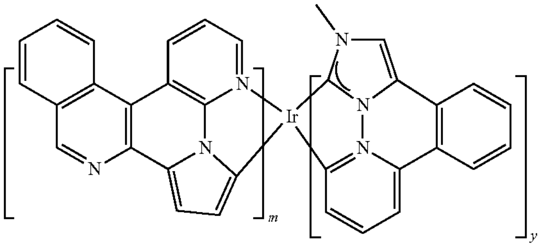
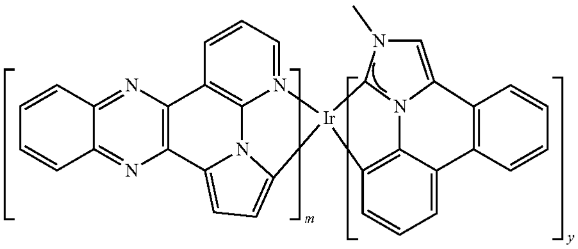

-continued
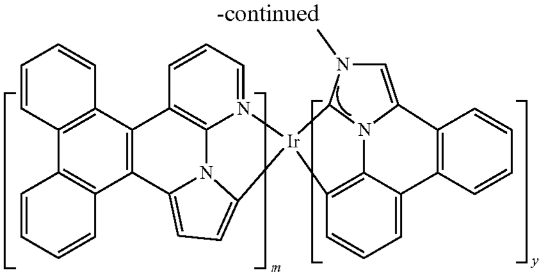
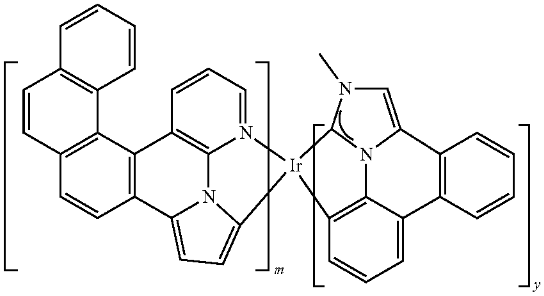
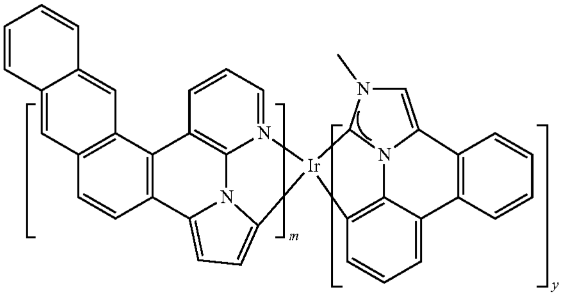
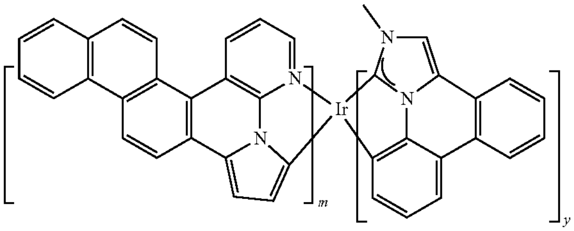
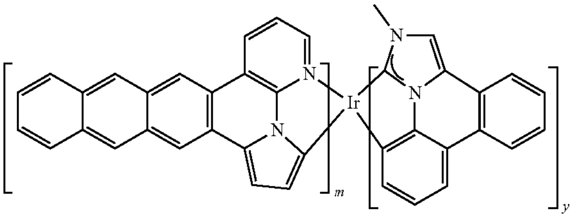
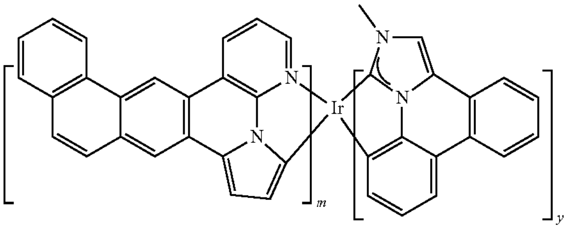
-continued
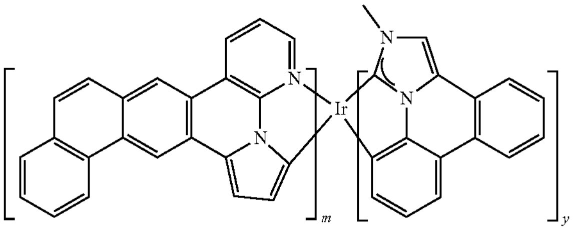
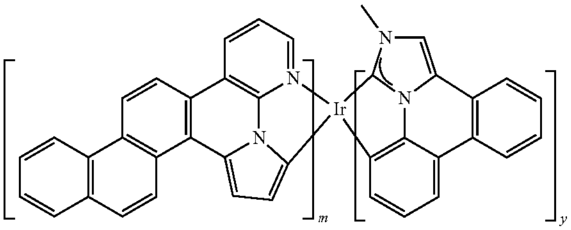
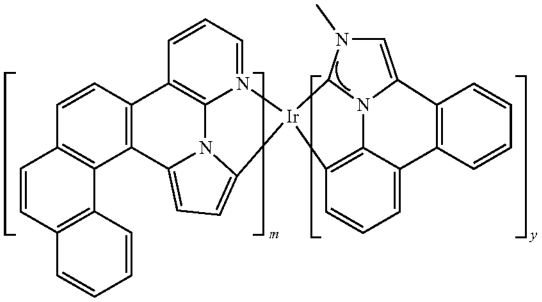
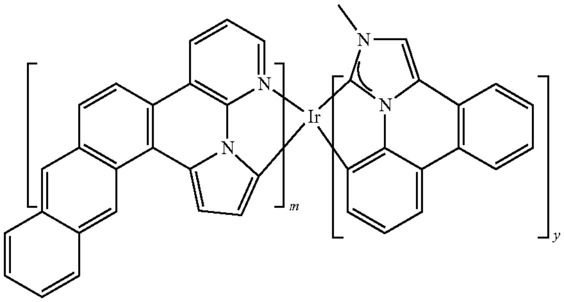
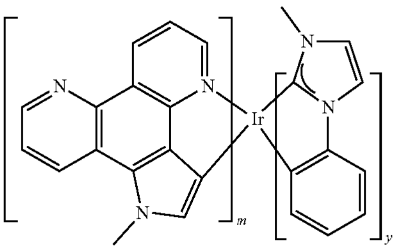
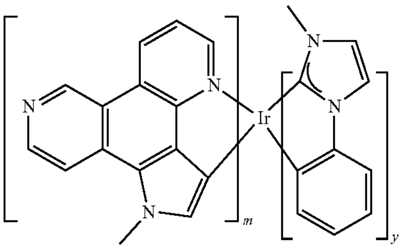

-continued
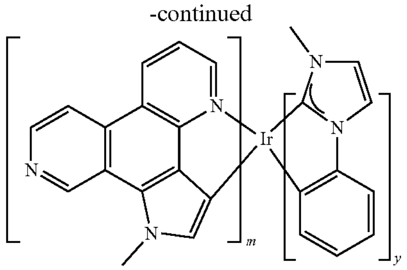
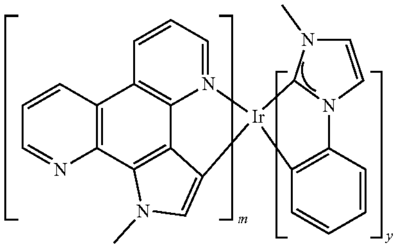
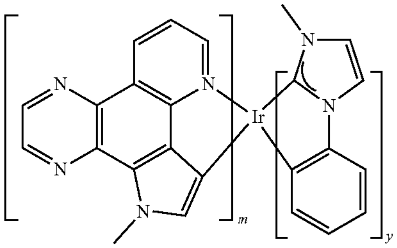
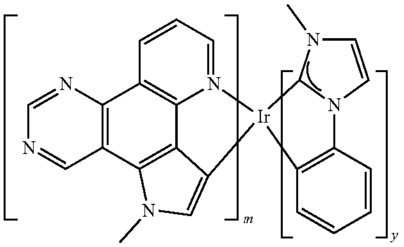
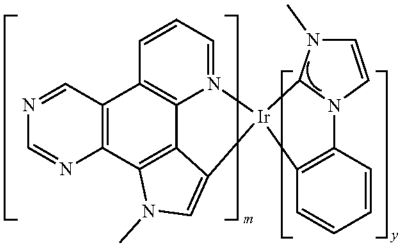
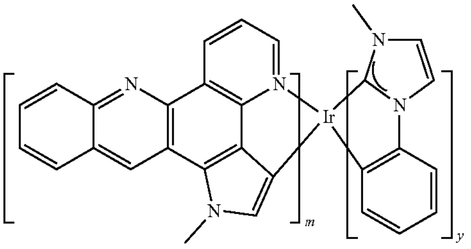
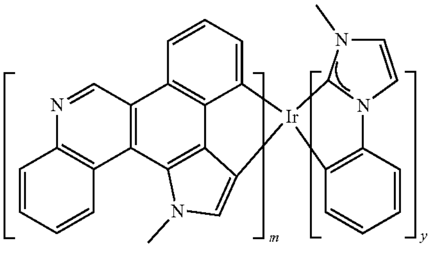
-continued
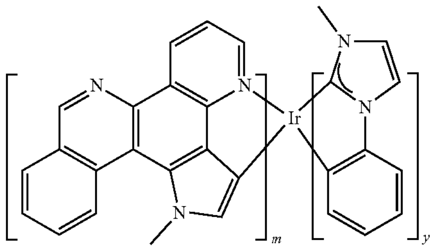
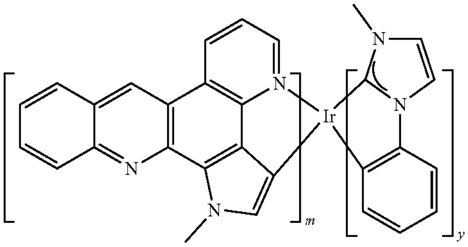
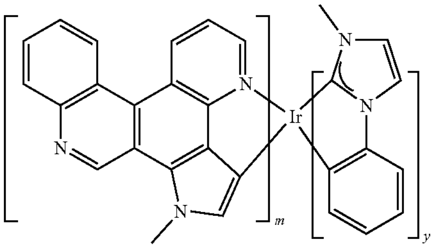
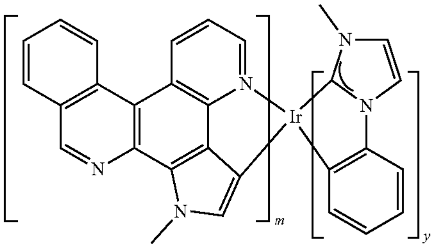
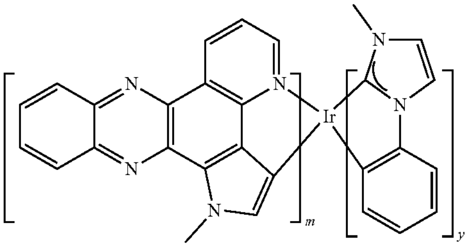
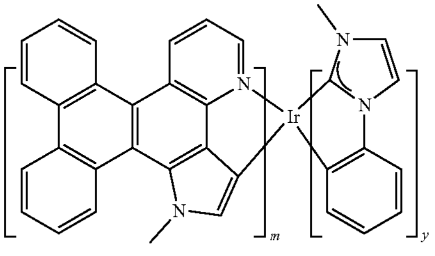

-continued
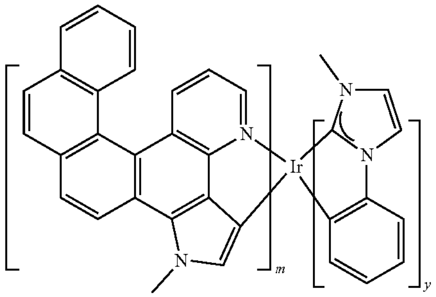
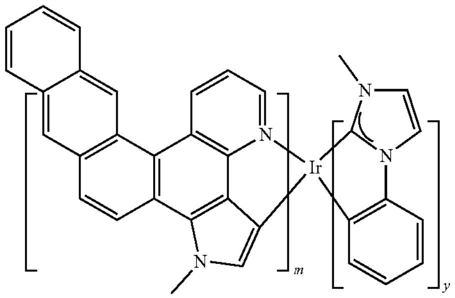
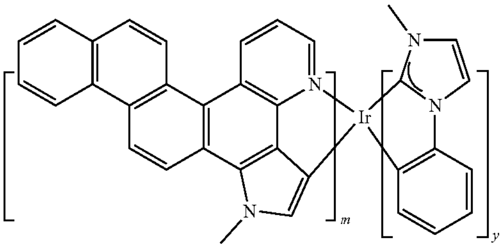
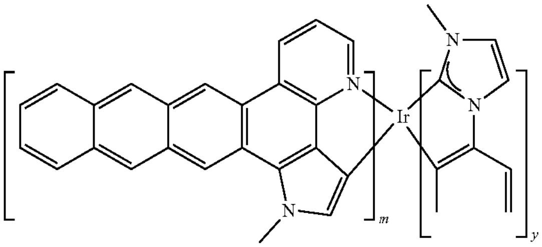
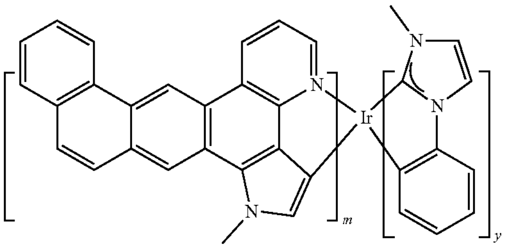
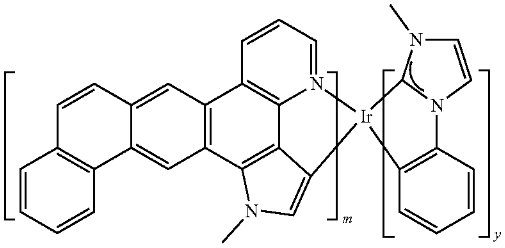
-continued
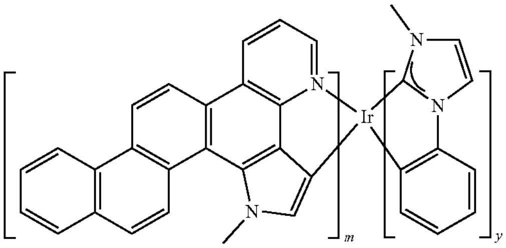
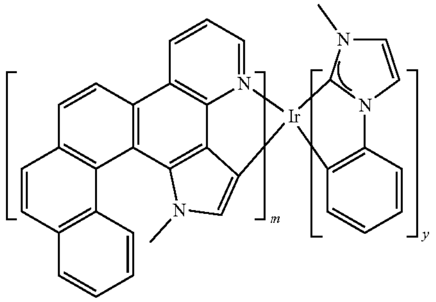
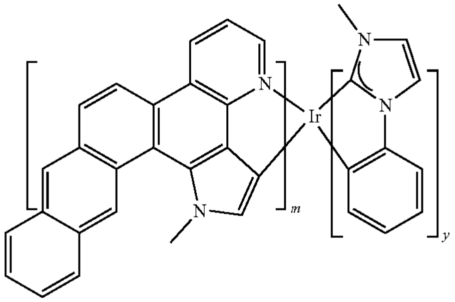
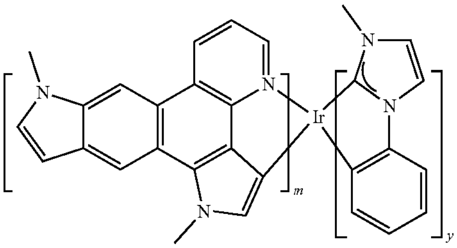
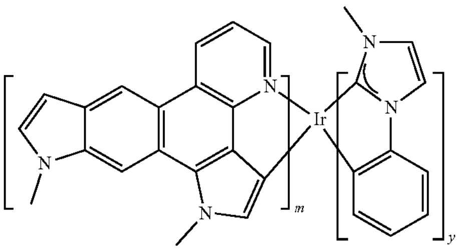
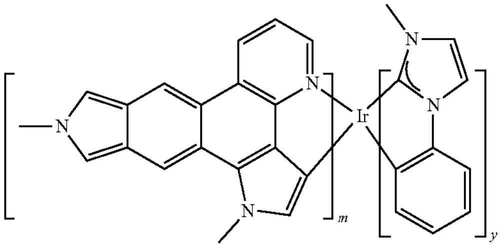

-continued
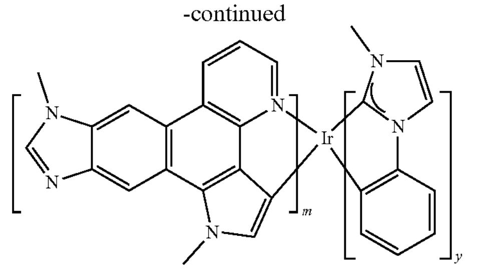
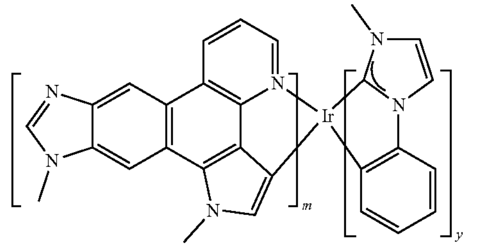
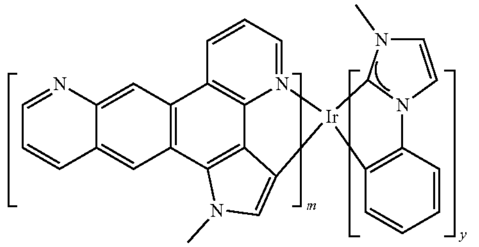
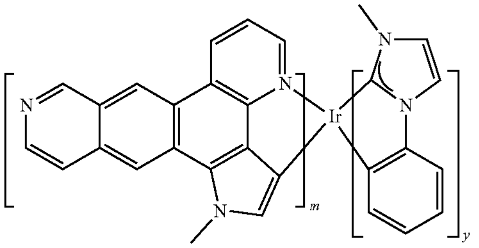
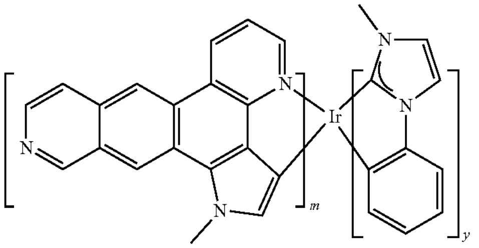
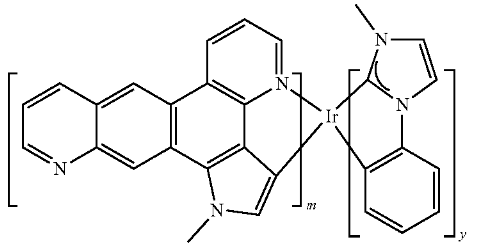
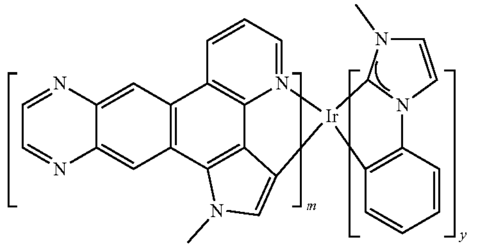
-continued
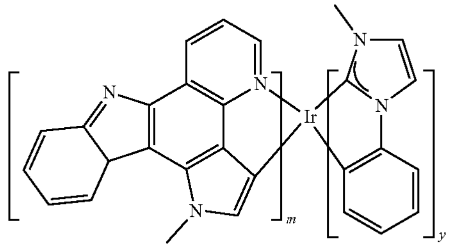
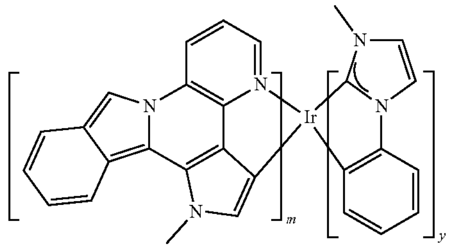
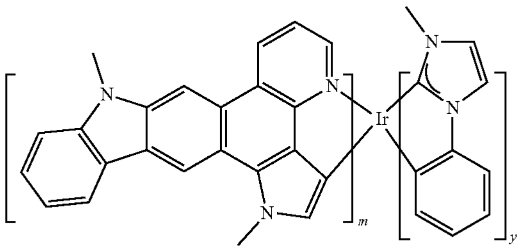
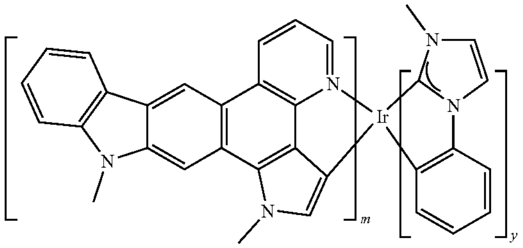
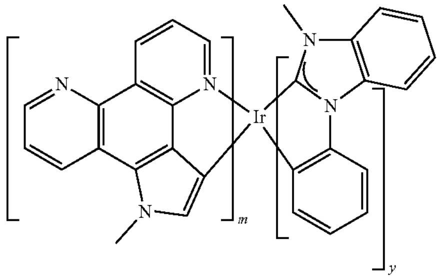
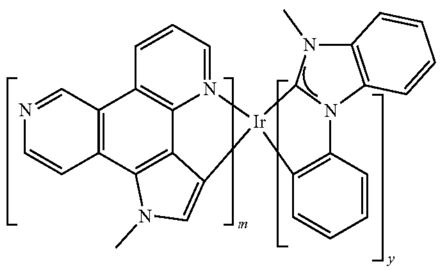

-continued
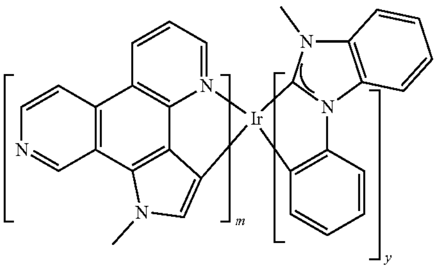
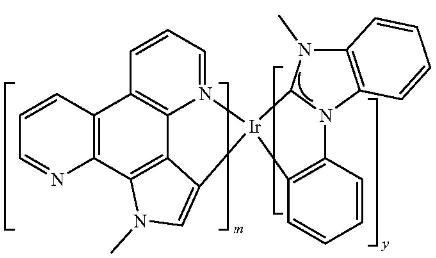
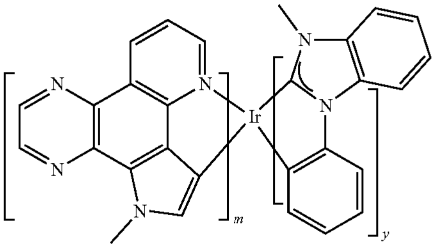
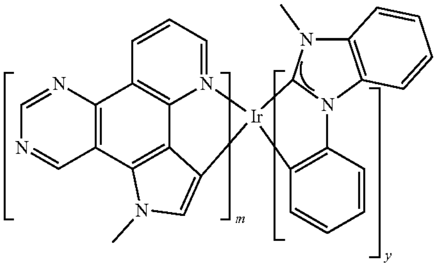
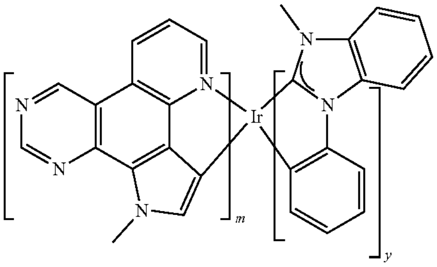
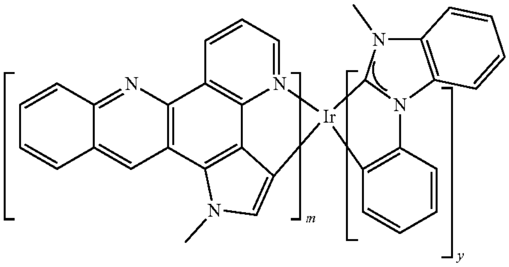
-continued
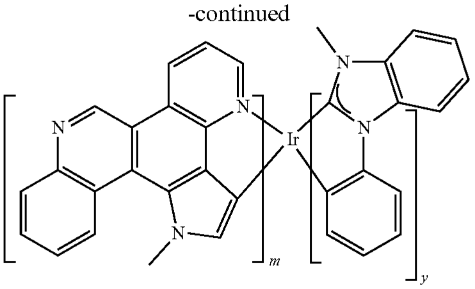
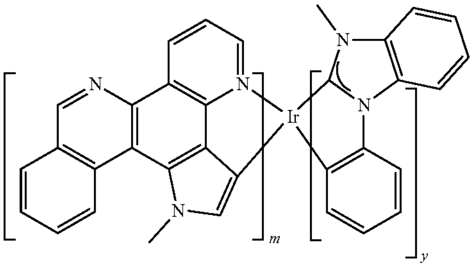
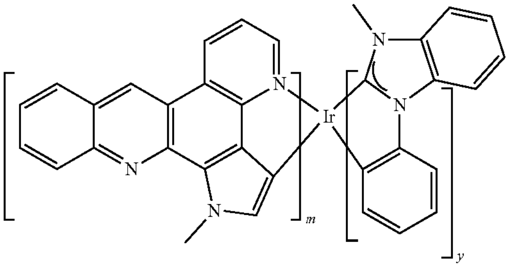
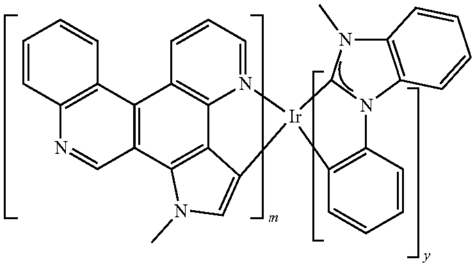
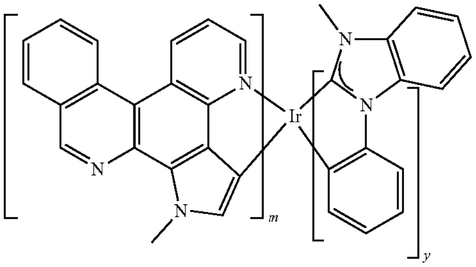
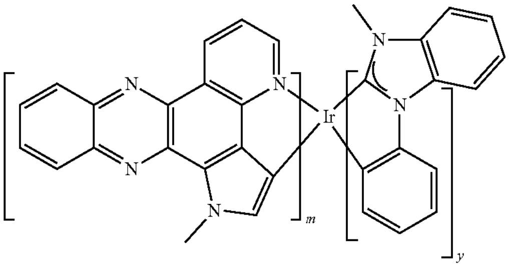

-continued
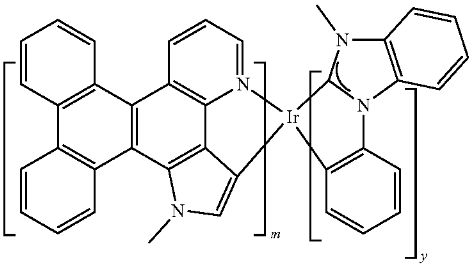
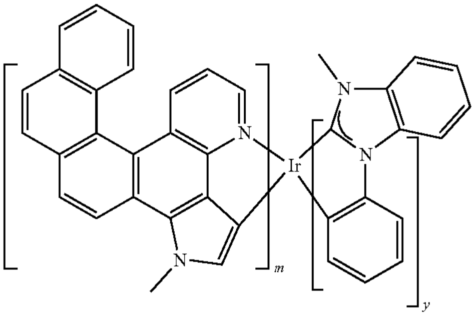
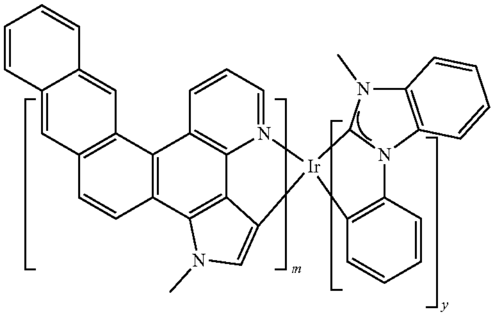
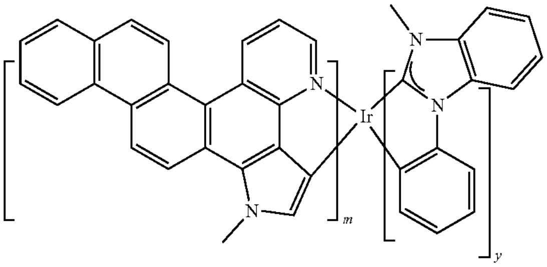
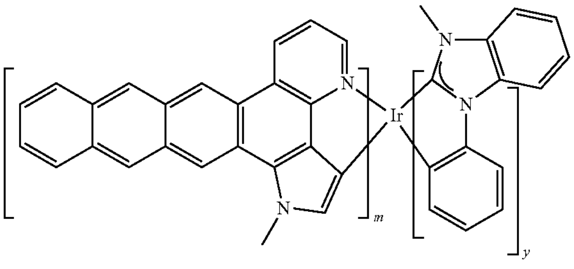
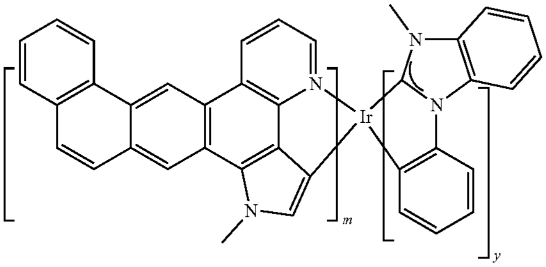
-continued
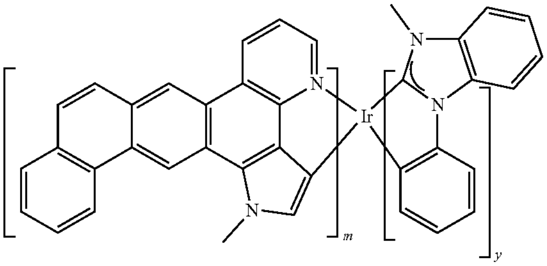
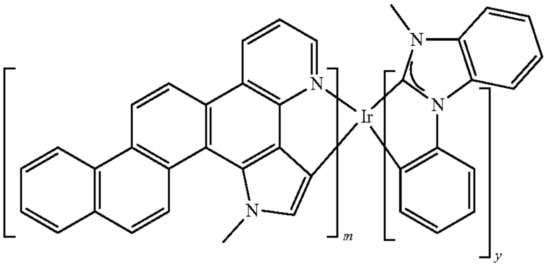
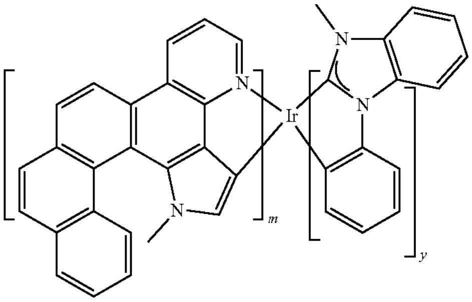
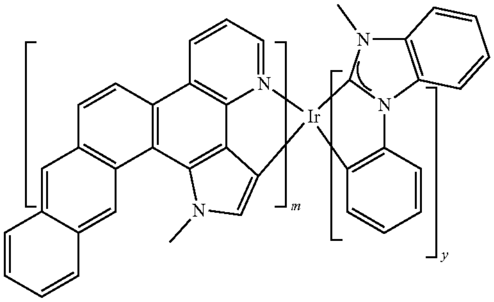
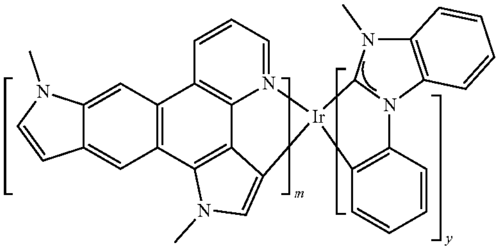
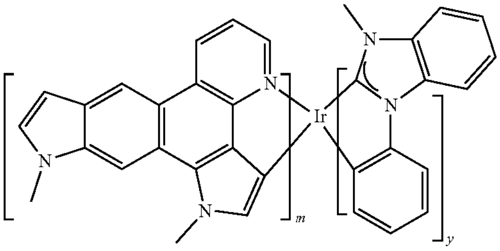

-continued
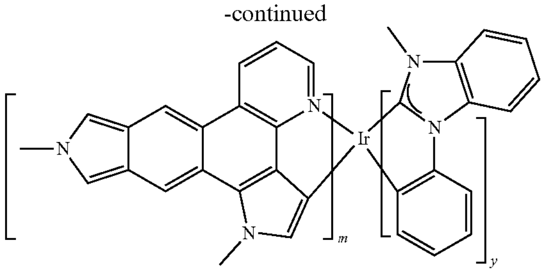
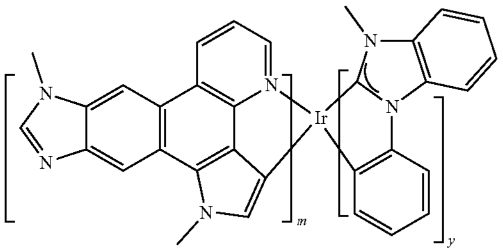
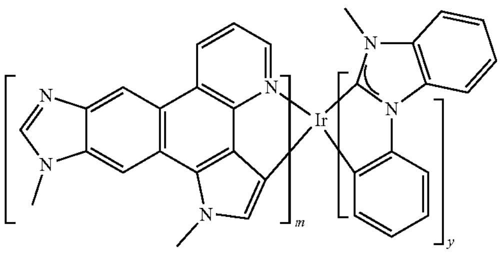
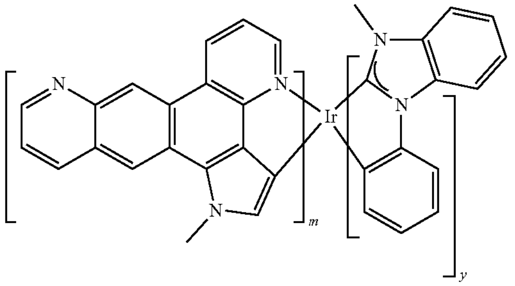
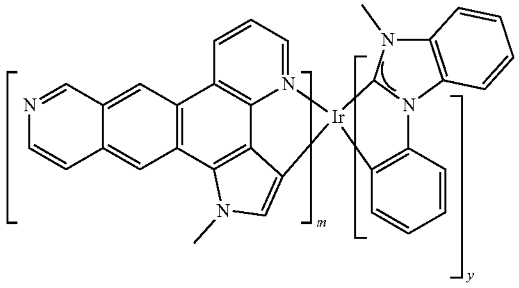
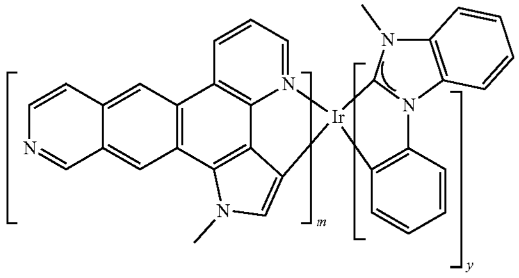
-continued
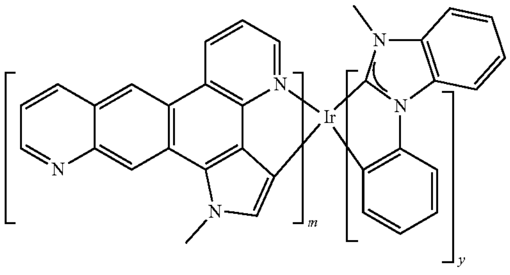
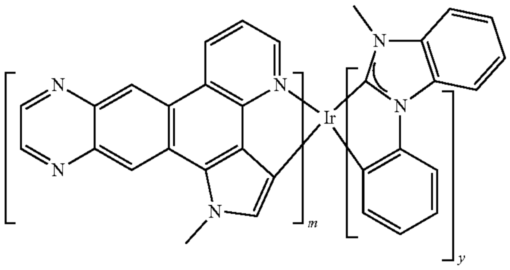
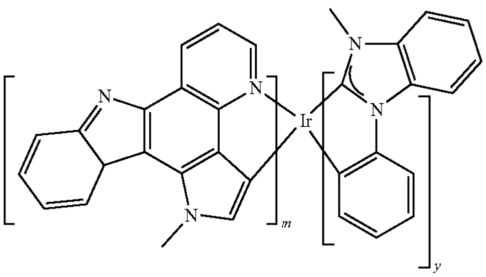
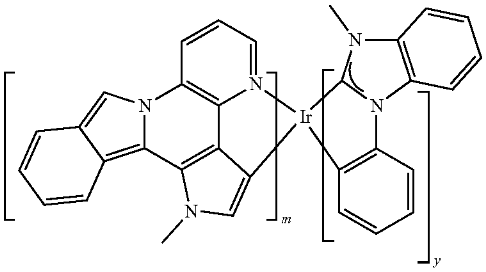
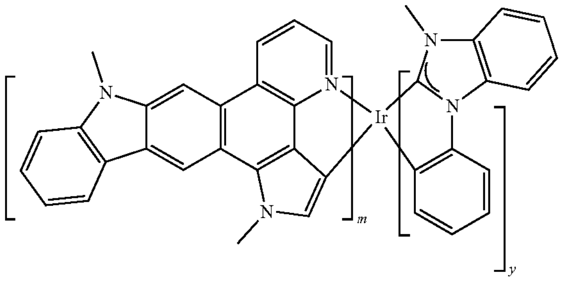
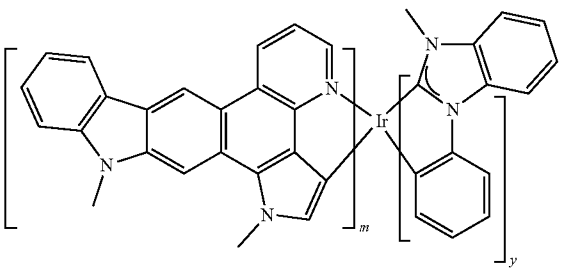

-continued
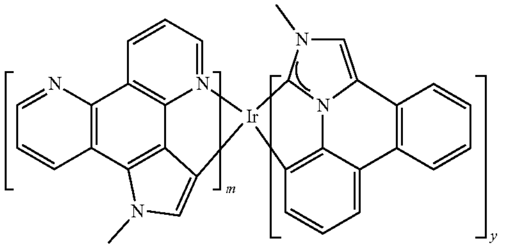
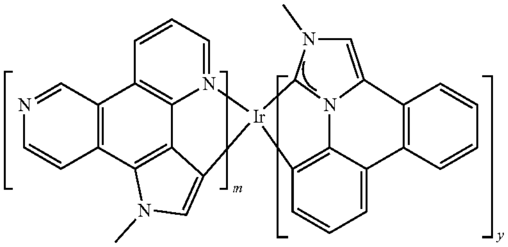
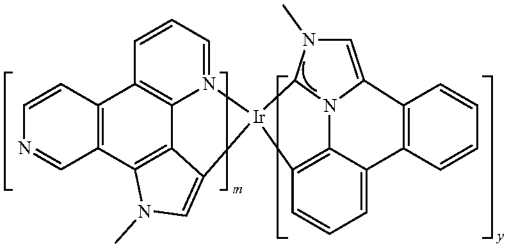
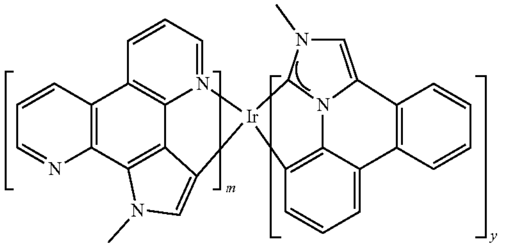
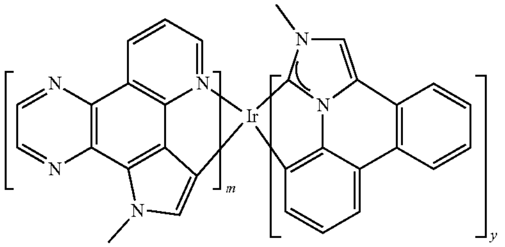
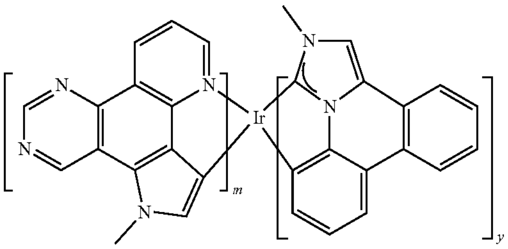
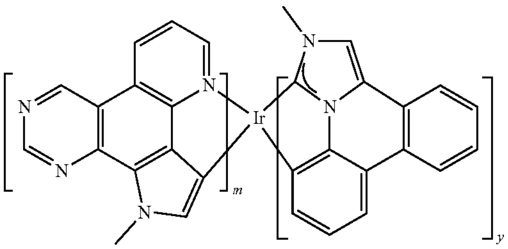
-continued
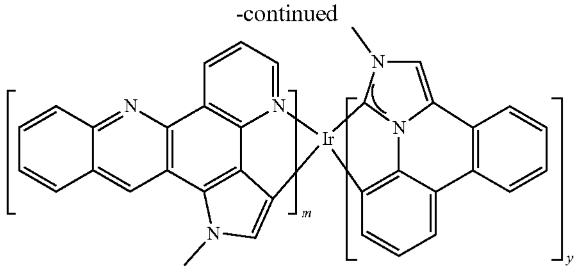
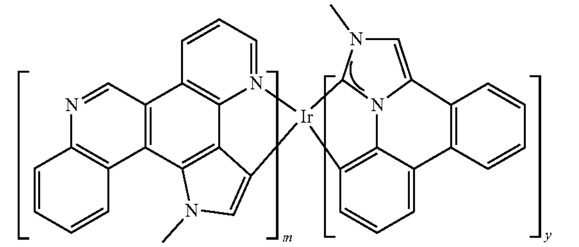
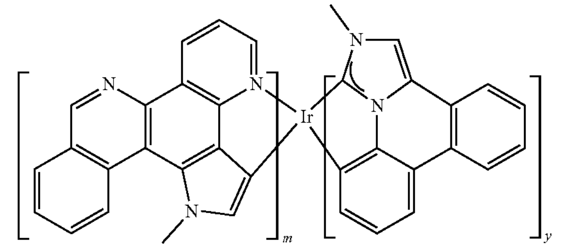
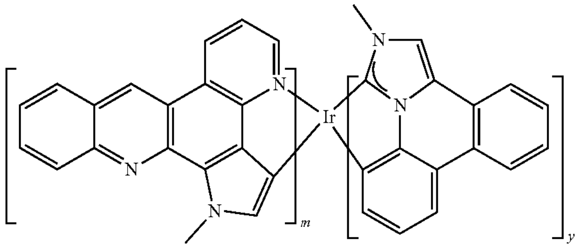
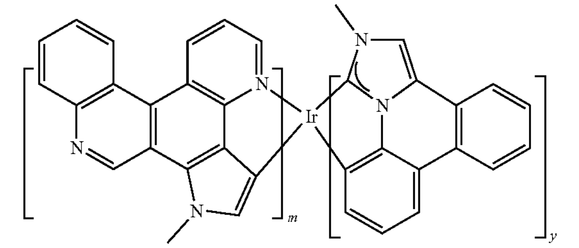
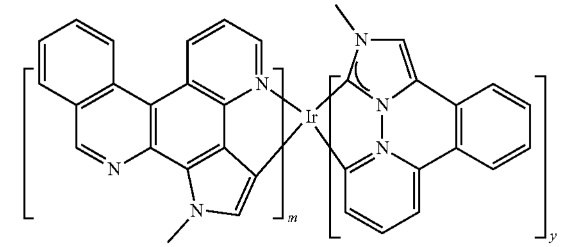
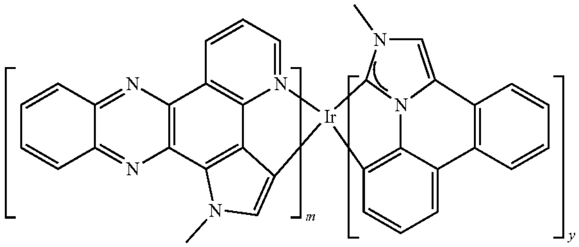

-continued
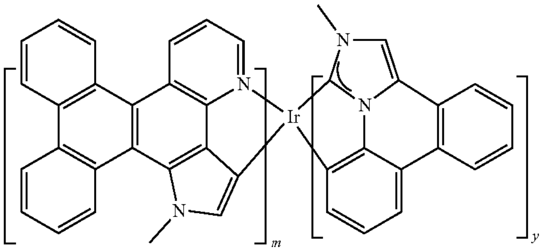
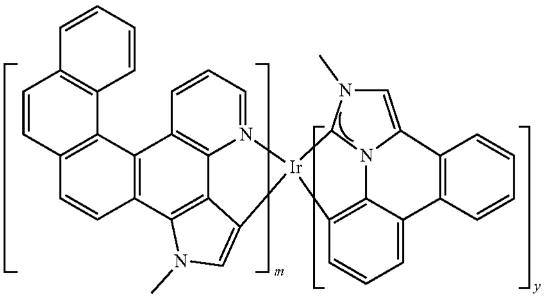
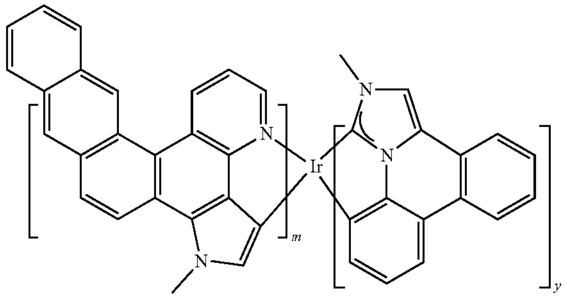
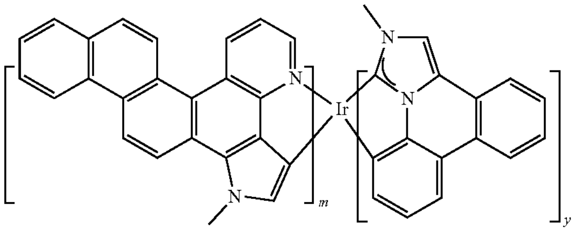
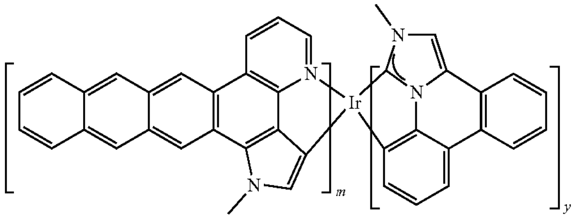
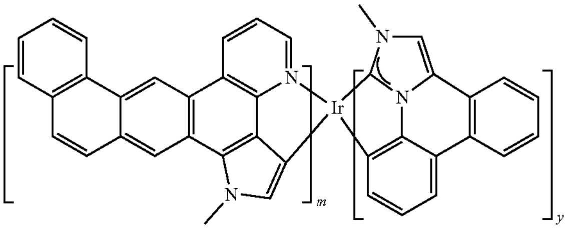
-continued
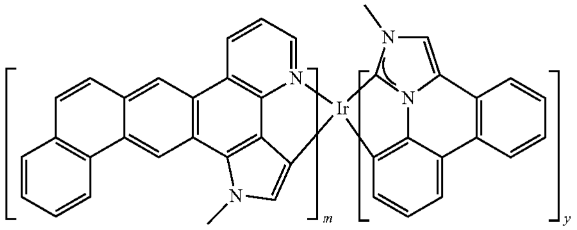
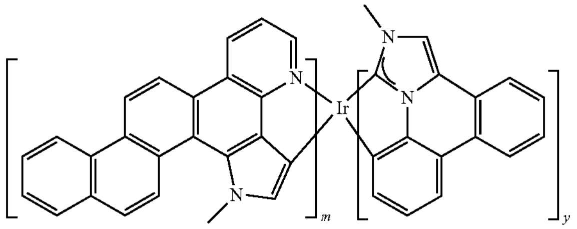
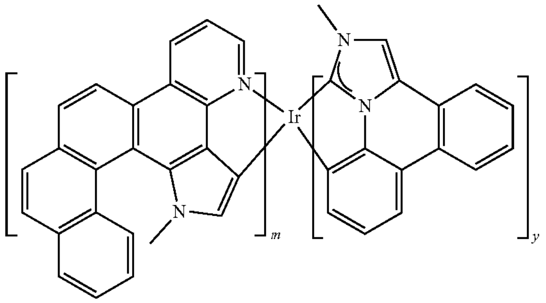
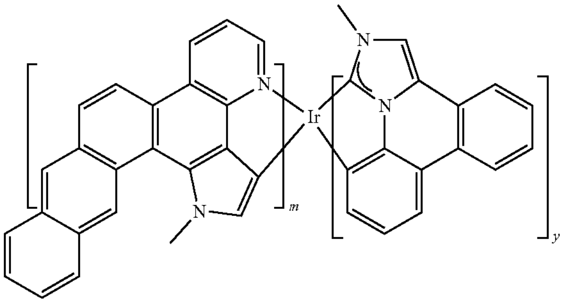
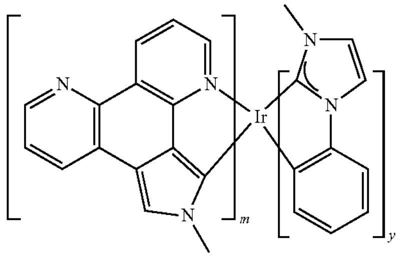
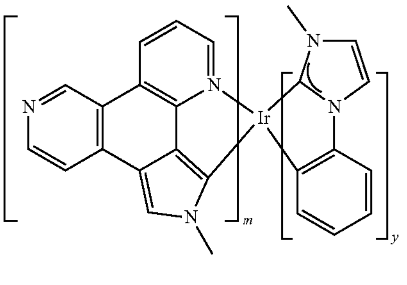

-continued
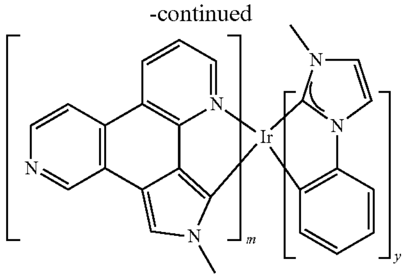
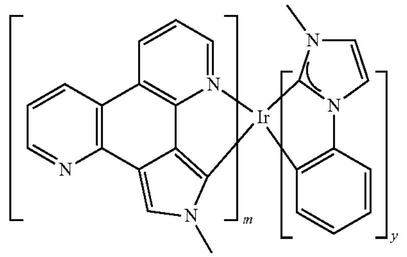
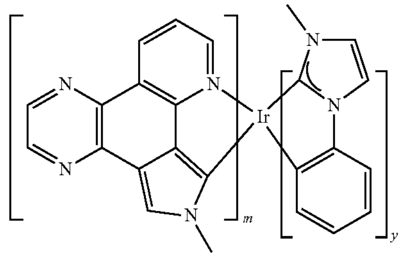
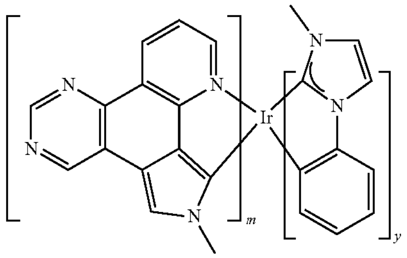
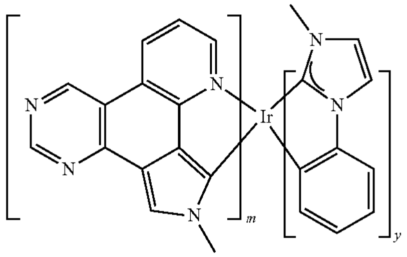
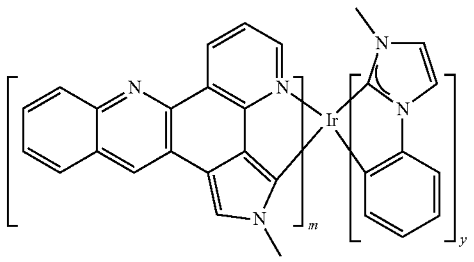
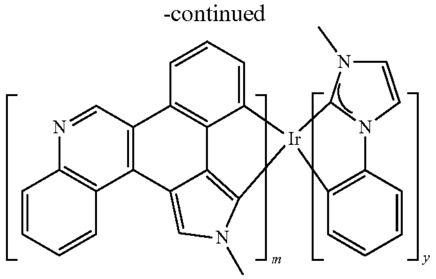
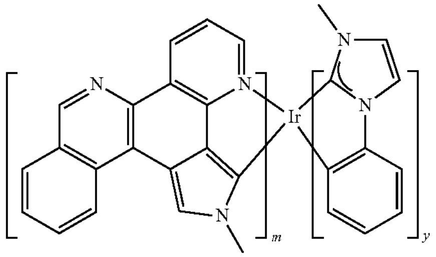
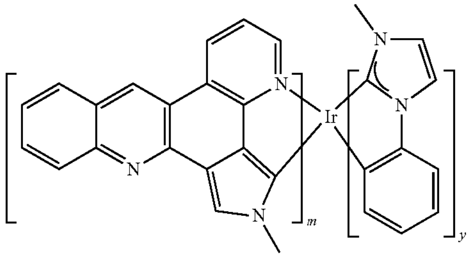
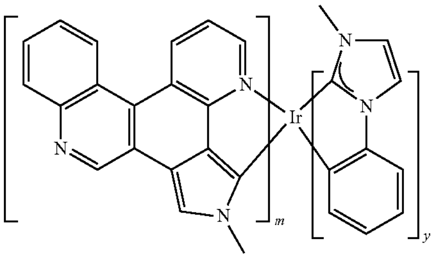
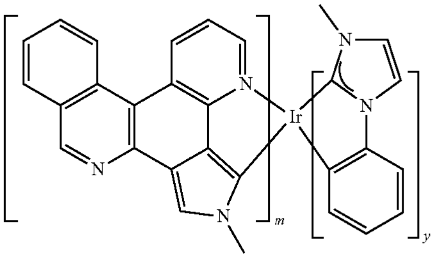
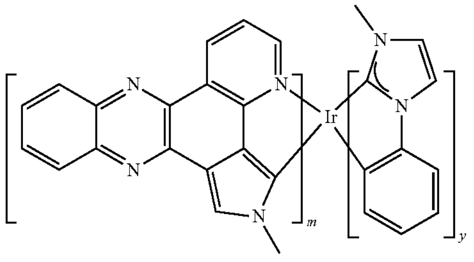
-continued -continued
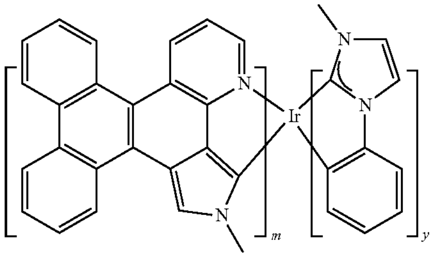
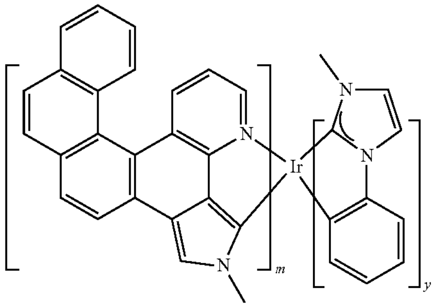
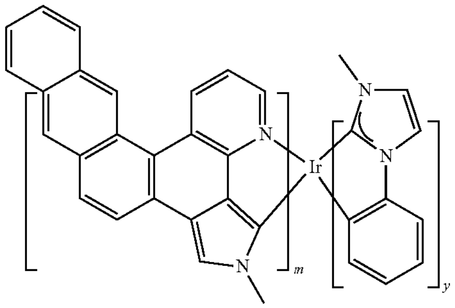
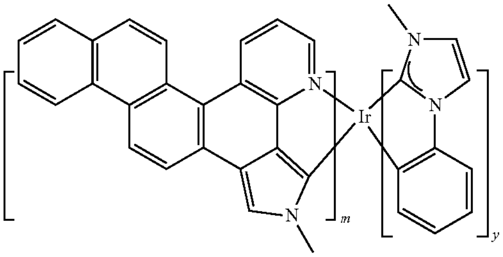
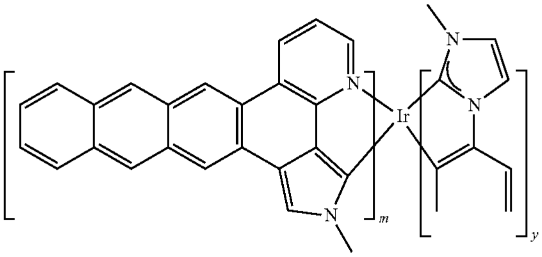
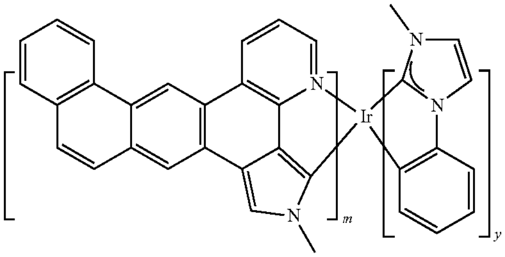
-continued
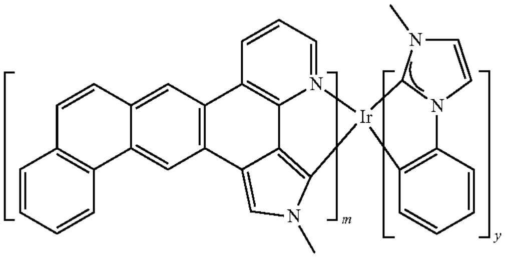
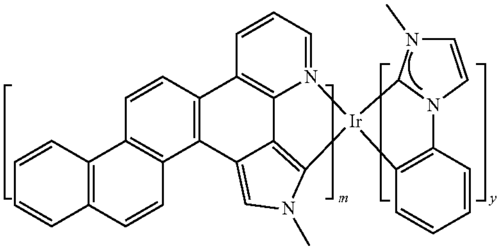
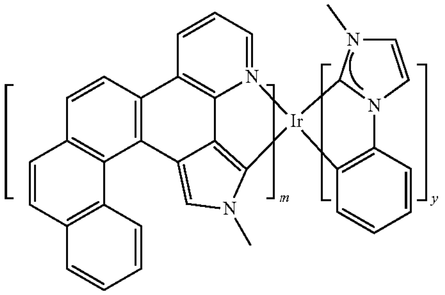
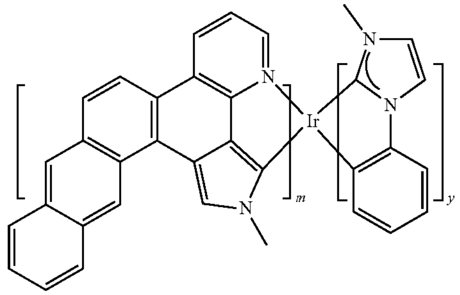
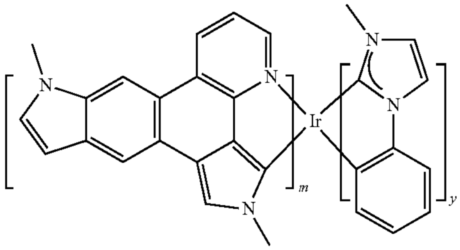
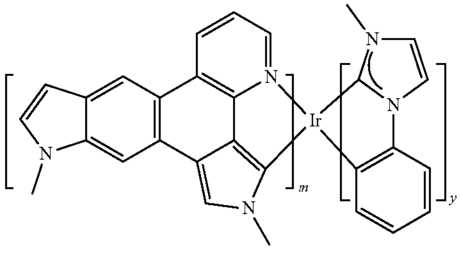

-continued
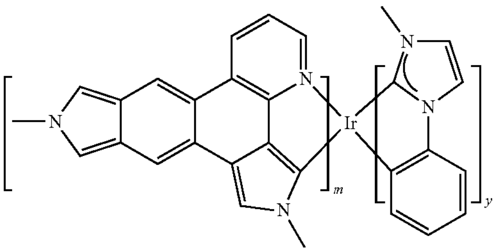
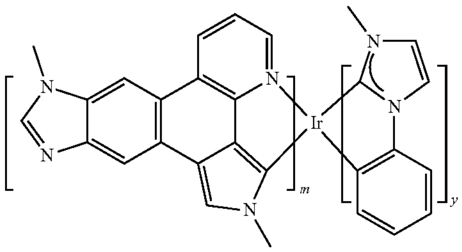
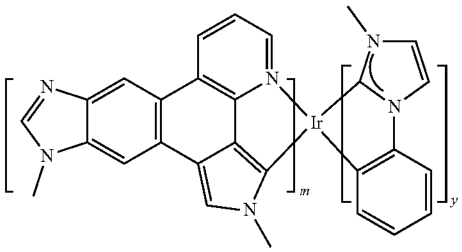
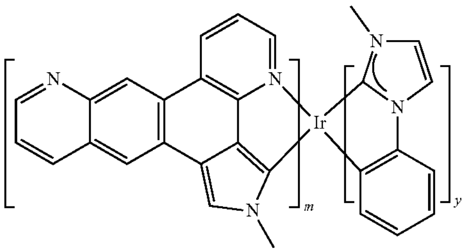
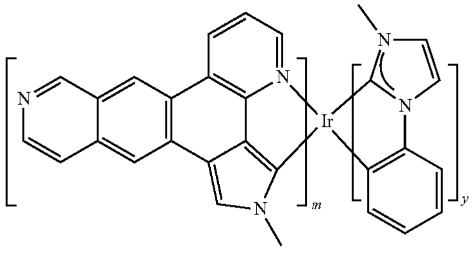
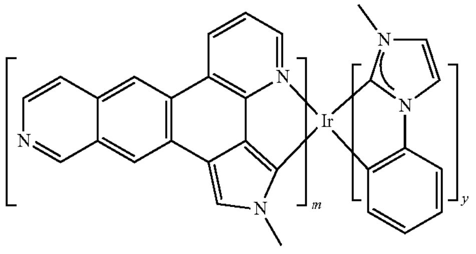
-continued
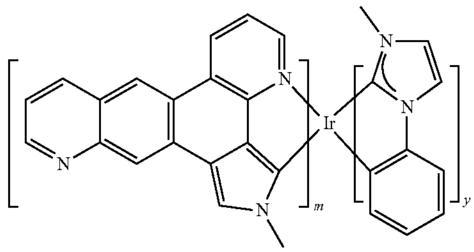
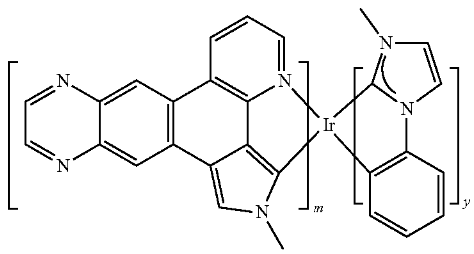
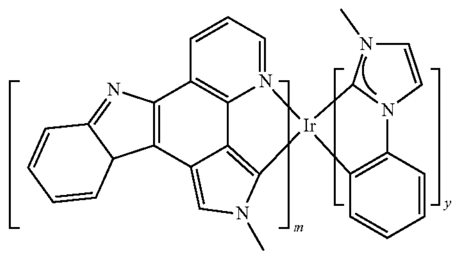
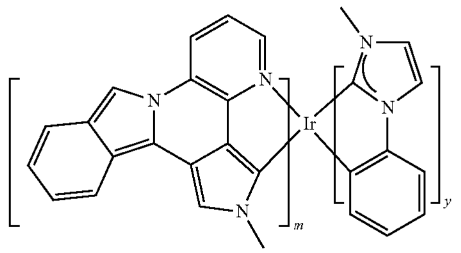
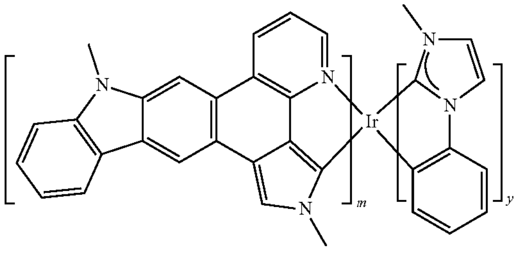
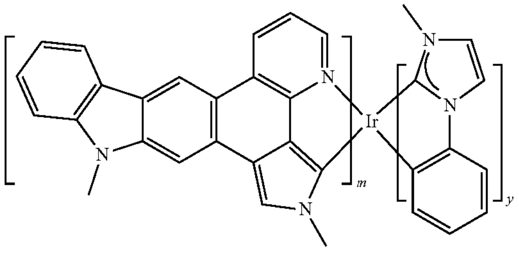

-continued
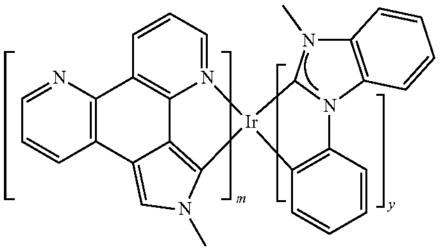
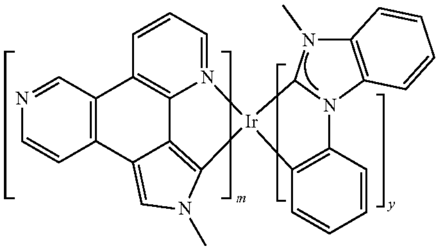
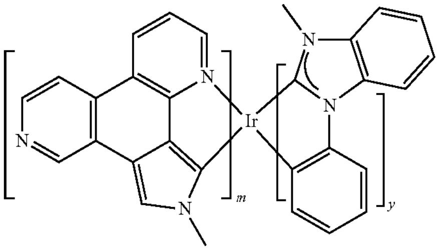
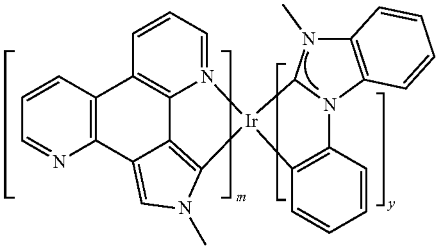
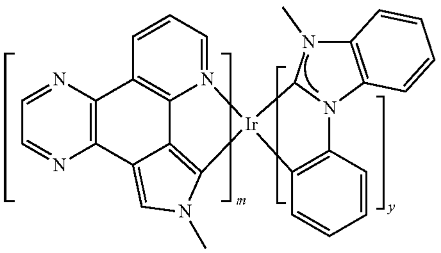
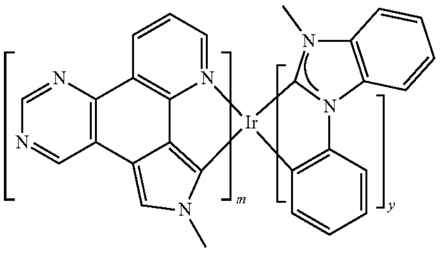
-continued
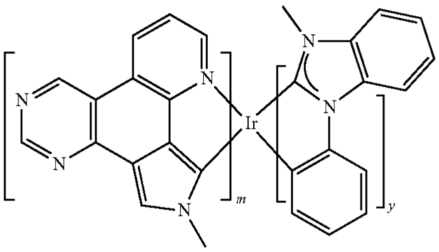
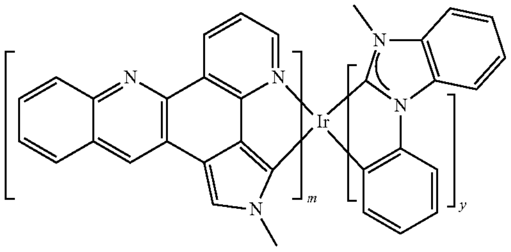
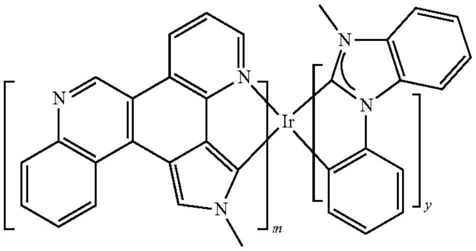
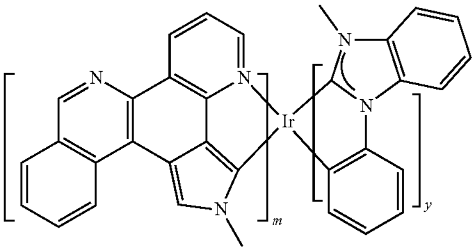
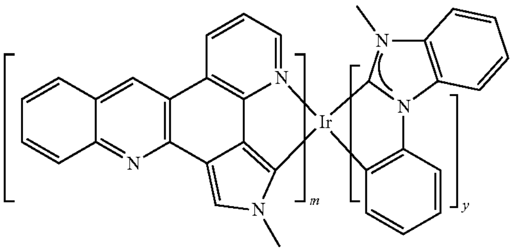
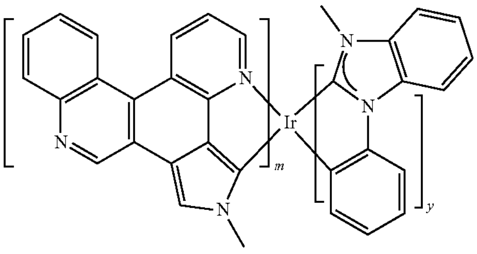

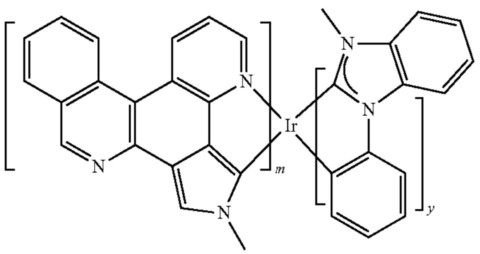
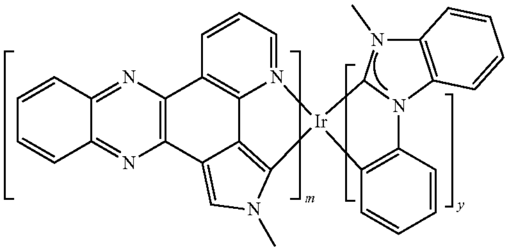
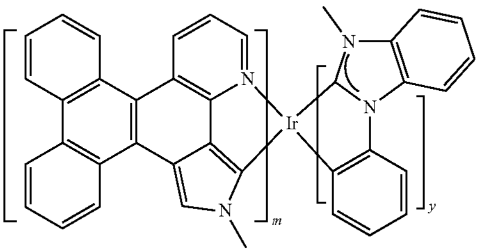
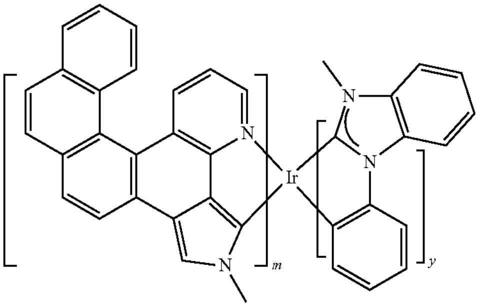
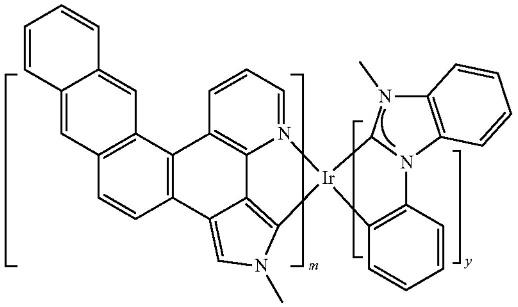
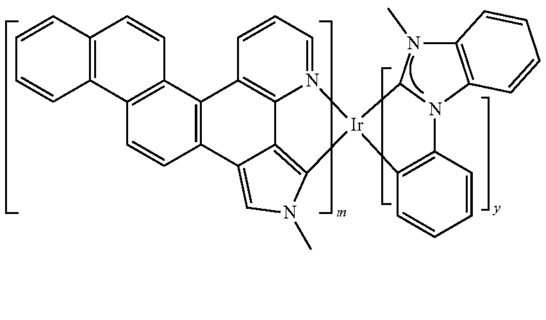
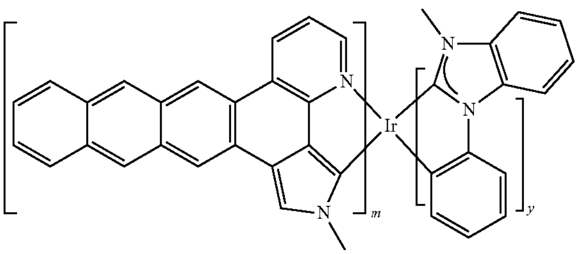
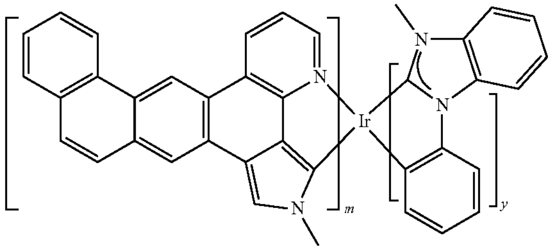
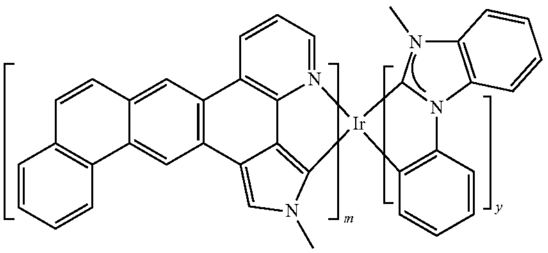
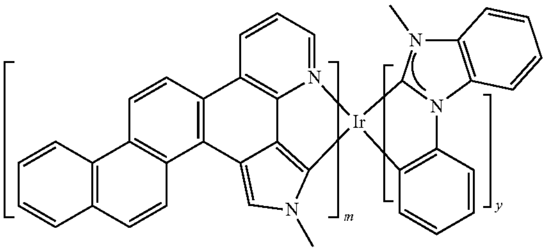
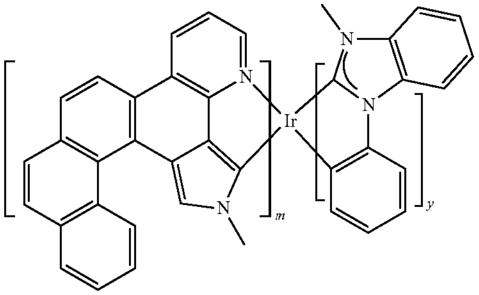
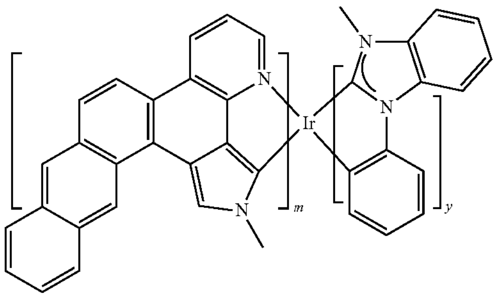

-continued
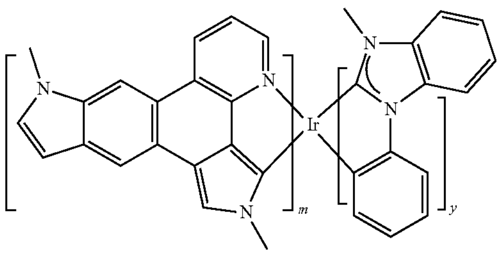
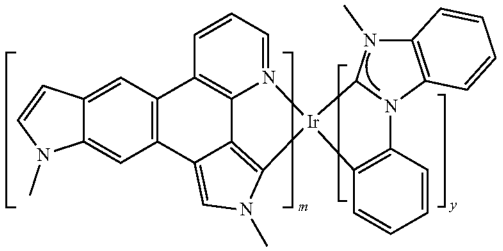
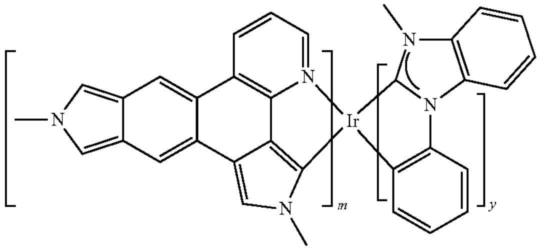
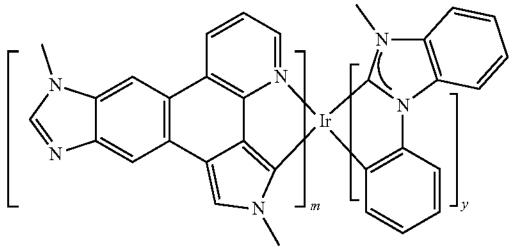
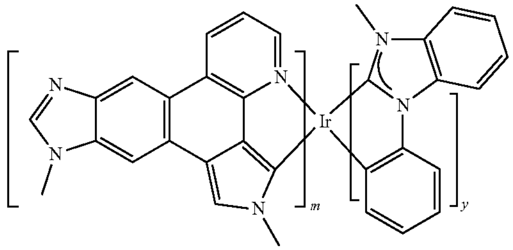
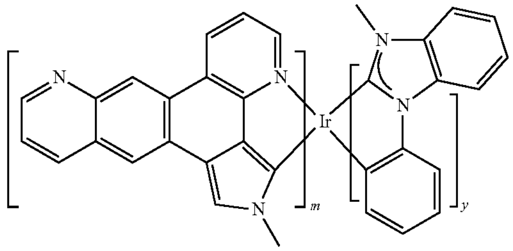
-continued
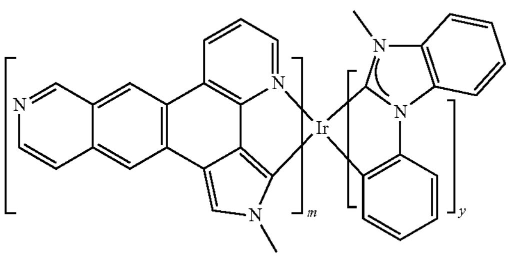
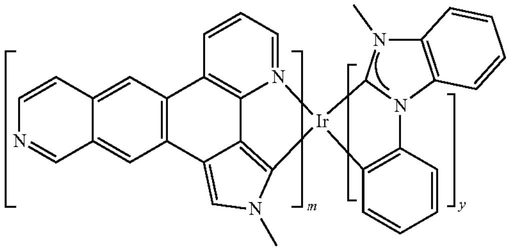
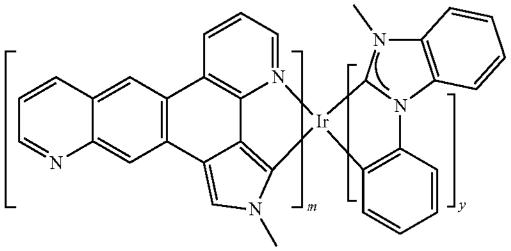
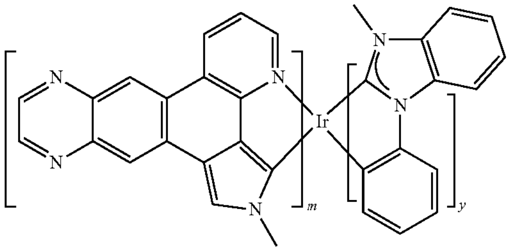
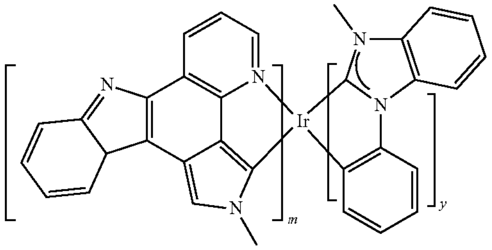
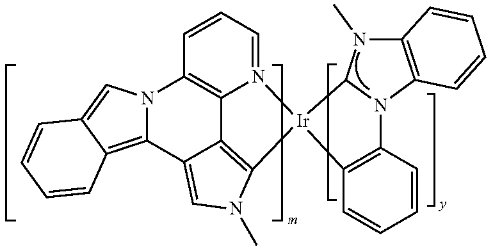

-continued
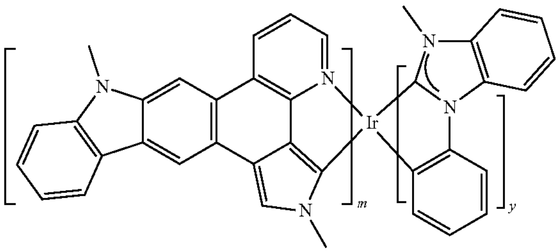
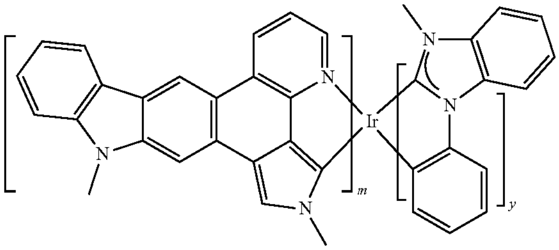
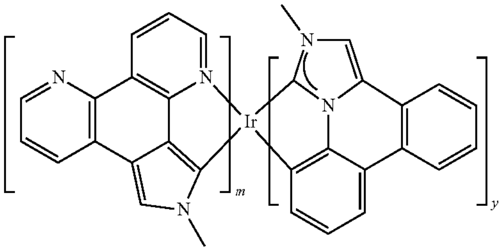
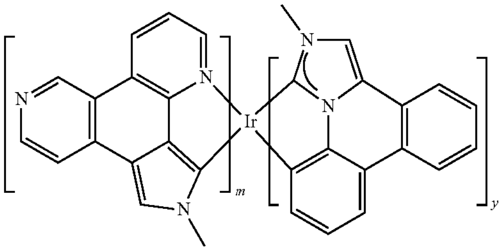
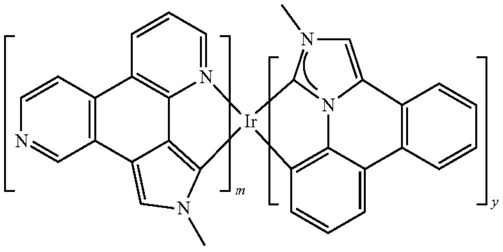
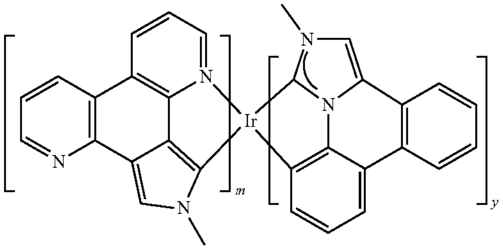
-continued
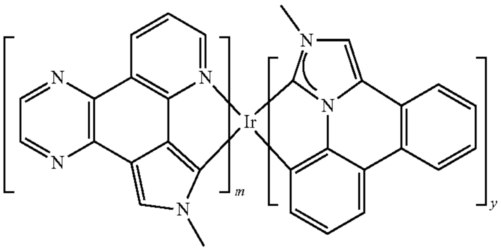
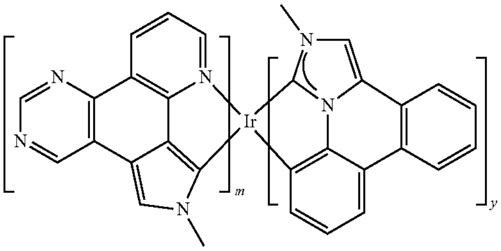
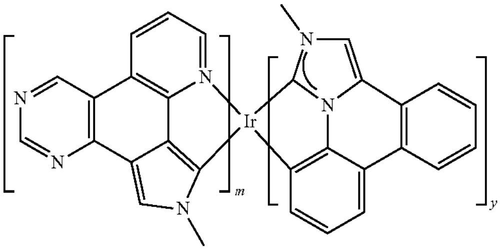
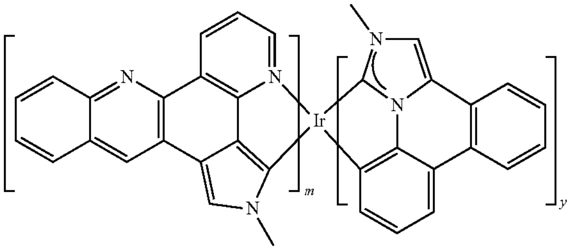
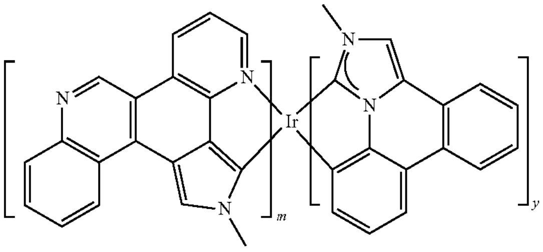
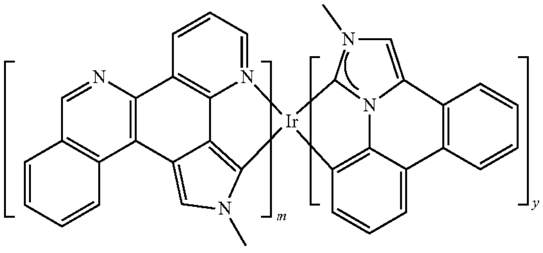

-continued
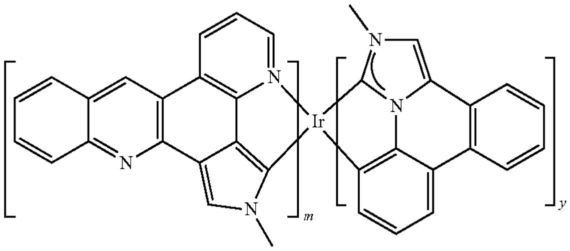
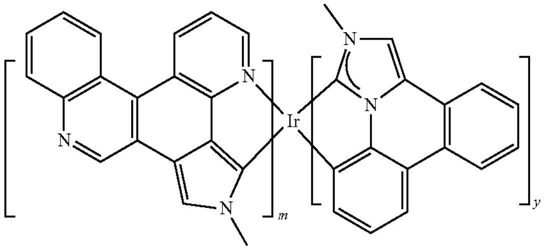
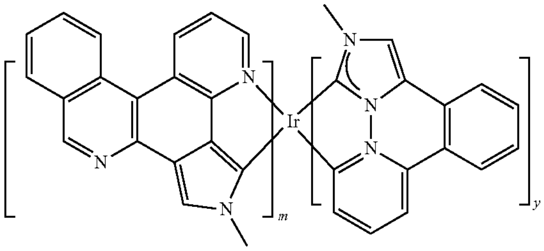
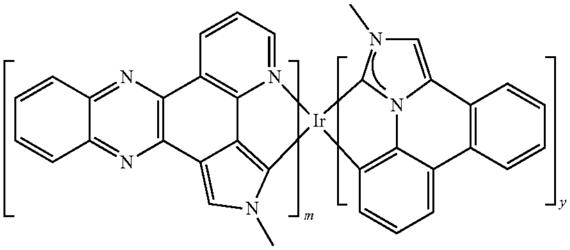
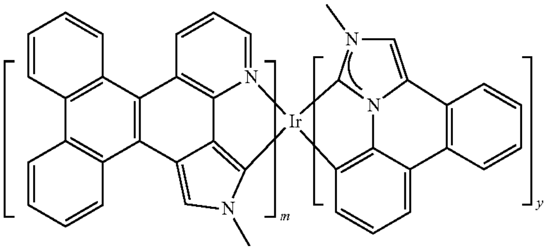
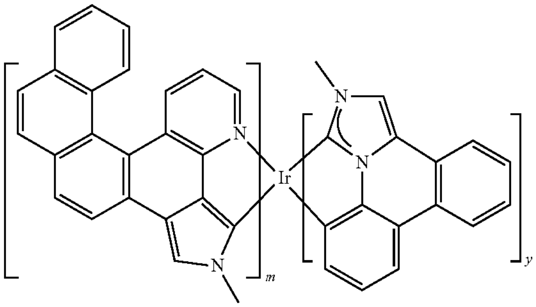
-continued
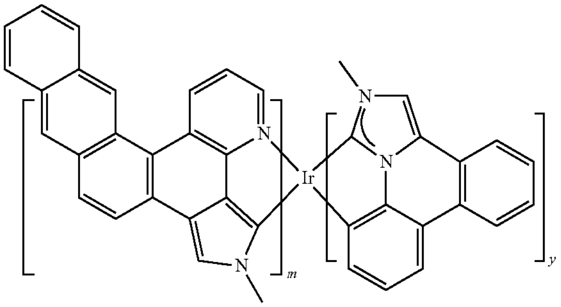
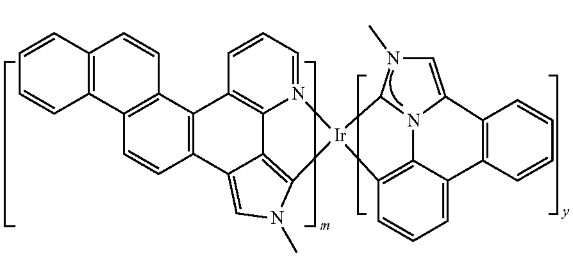
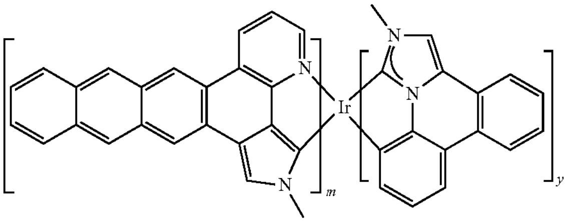
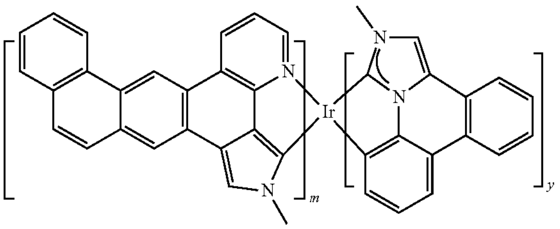
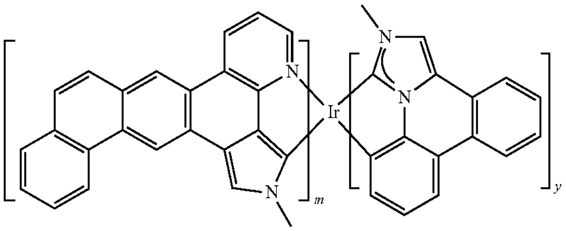
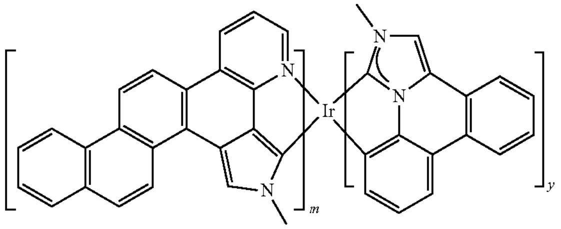

-continued
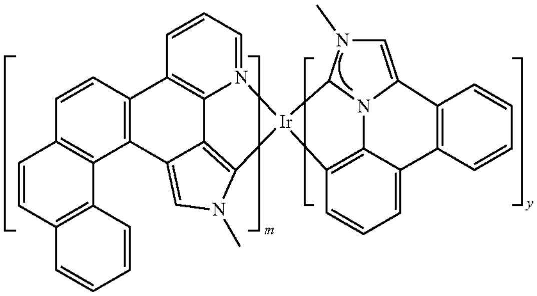
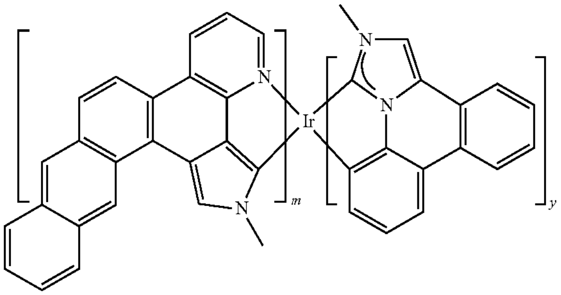
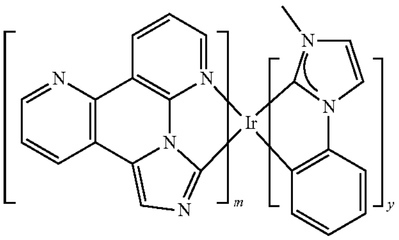
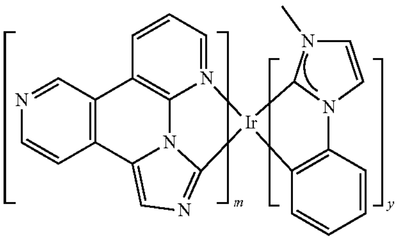
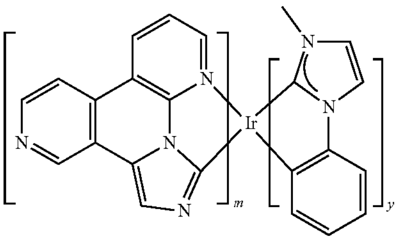
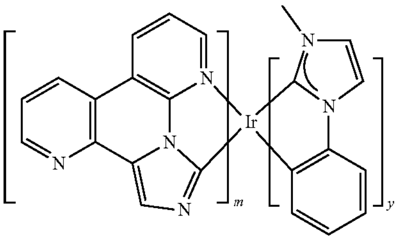
-continued
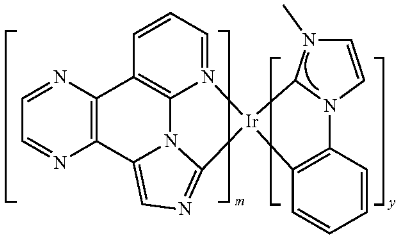
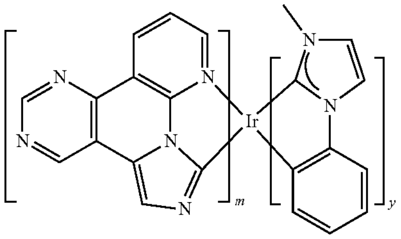
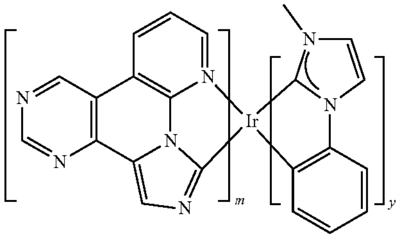
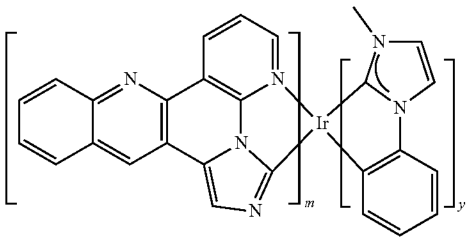
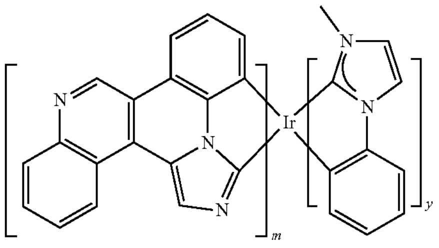
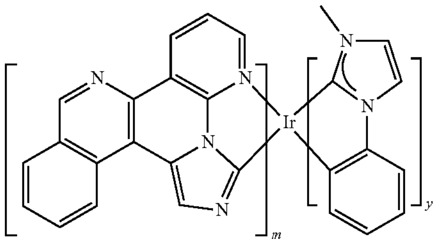
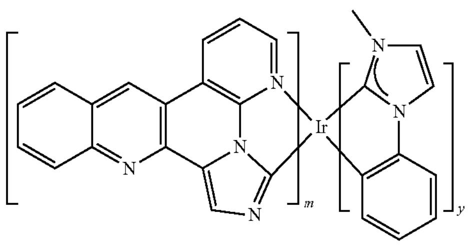

-continued
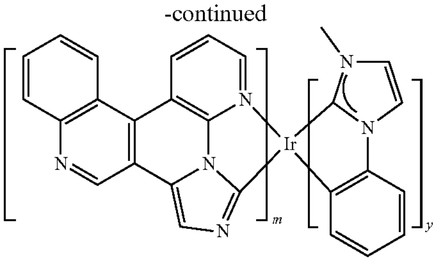
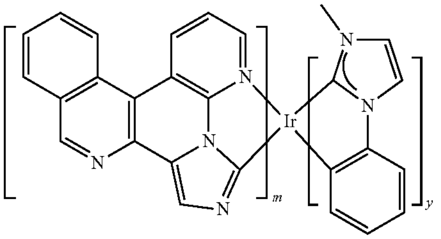
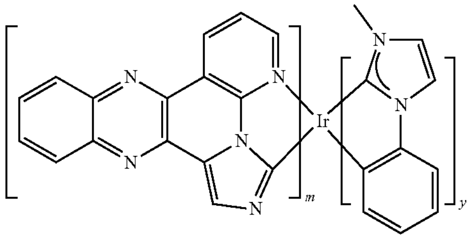
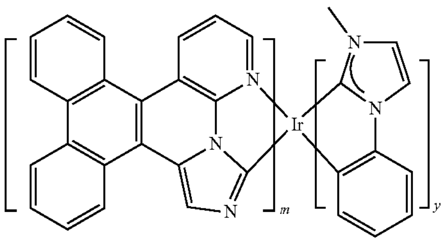
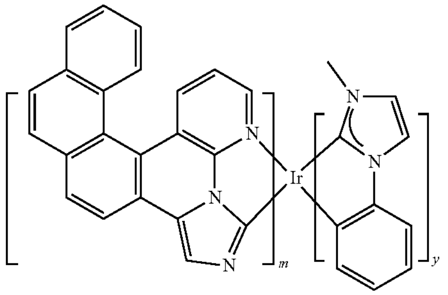
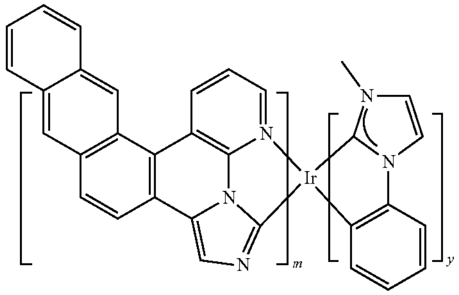
-continued
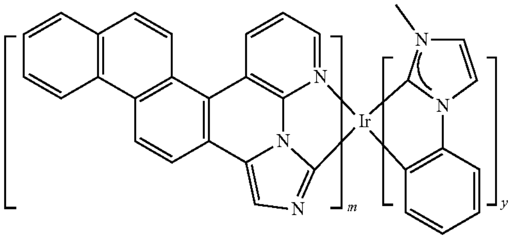
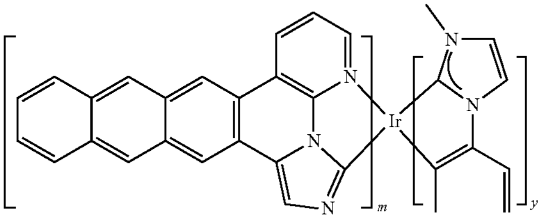
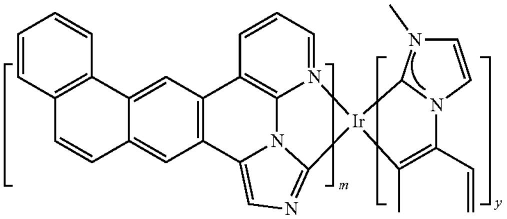
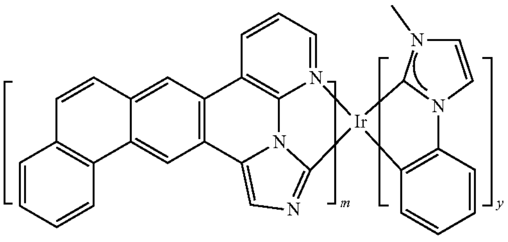
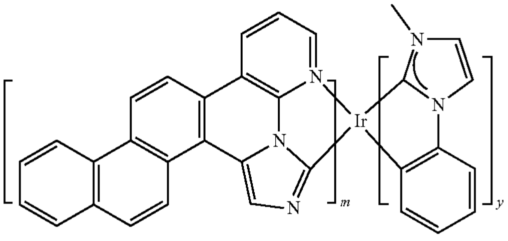
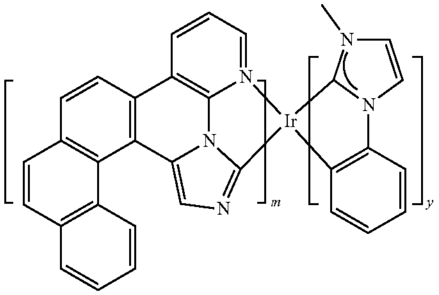

-continued
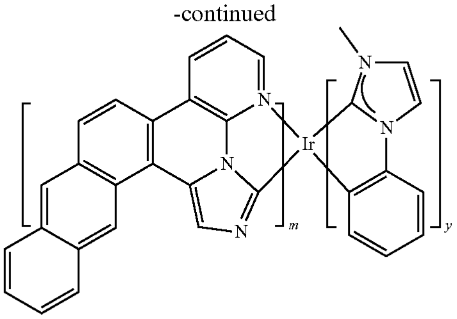
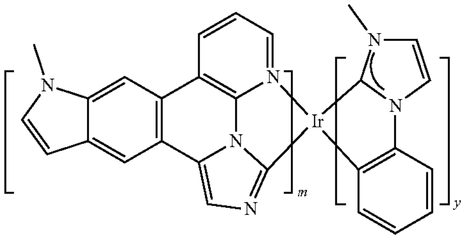
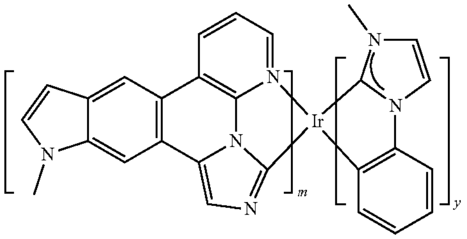
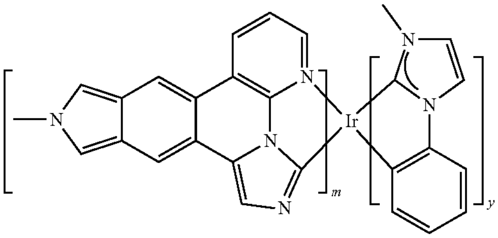
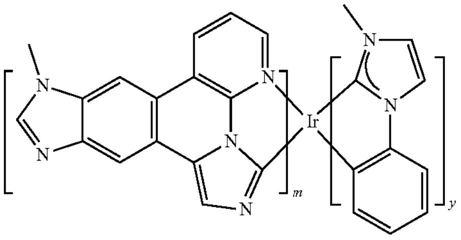
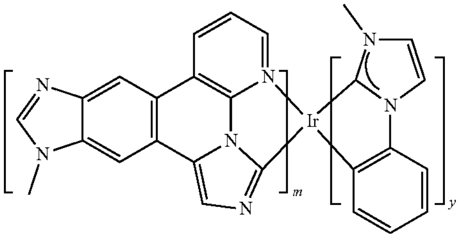
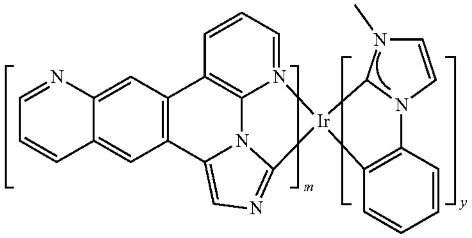
-continued
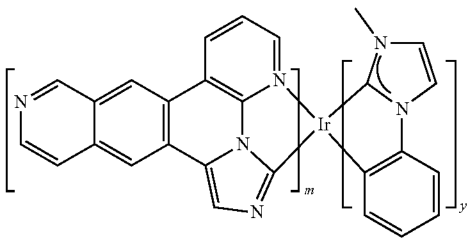
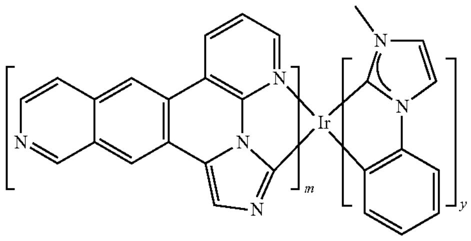
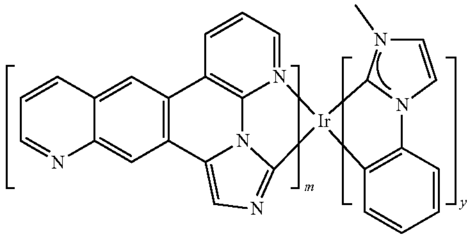
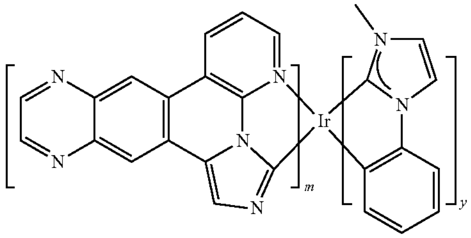
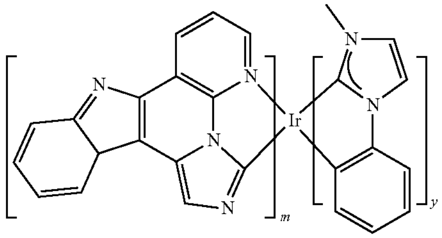
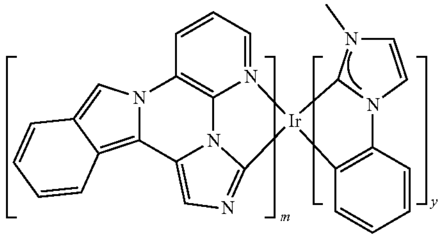
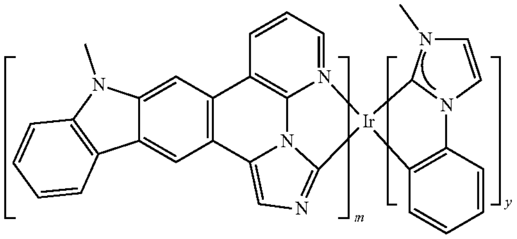

-continued
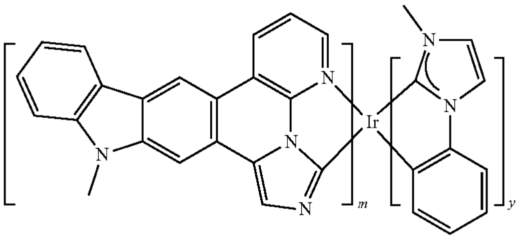
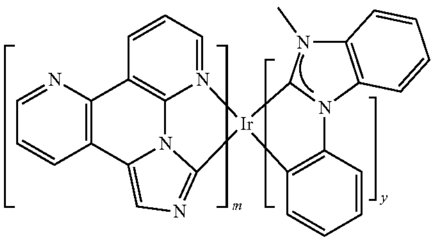
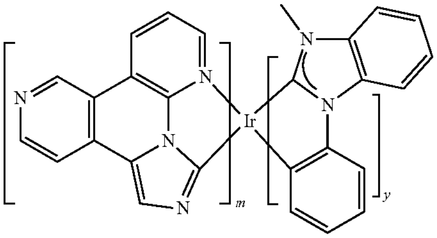
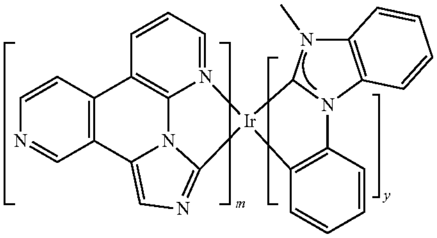
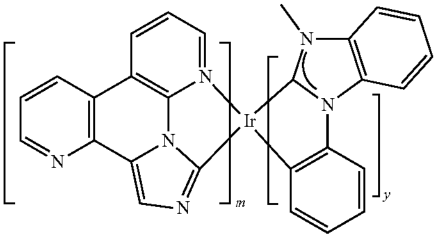
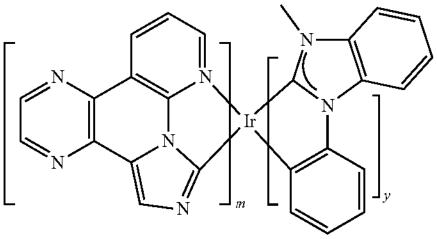
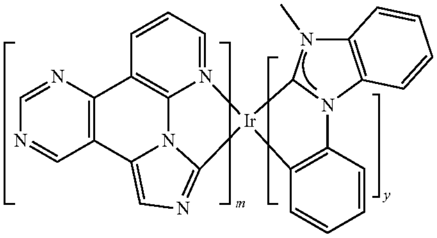
-continued
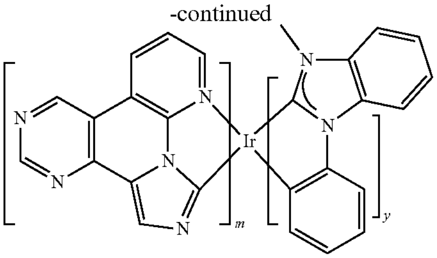
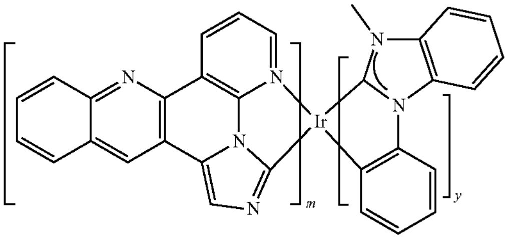
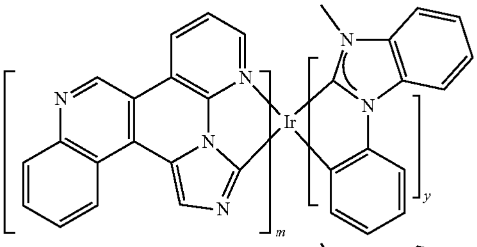
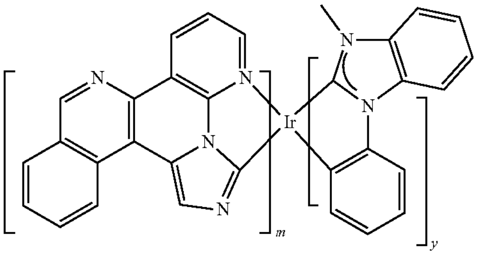
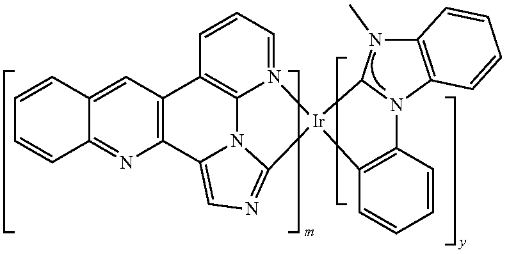
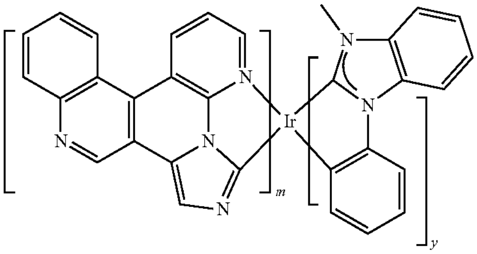
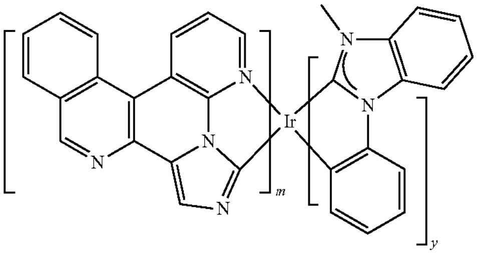

-continued
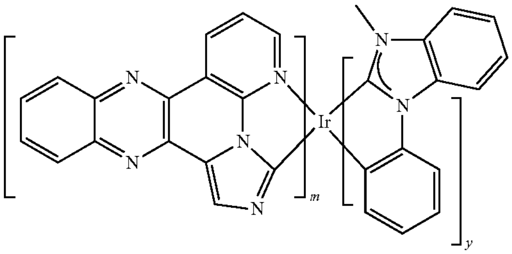
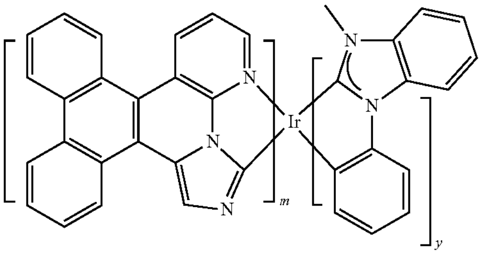
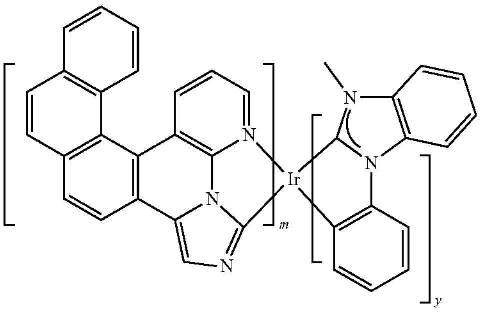
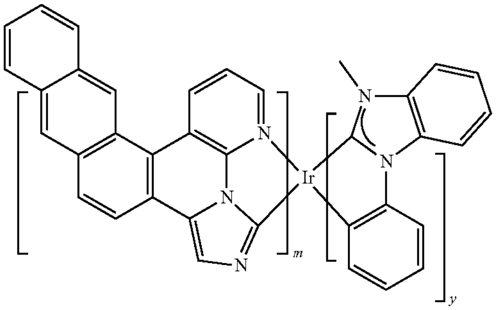
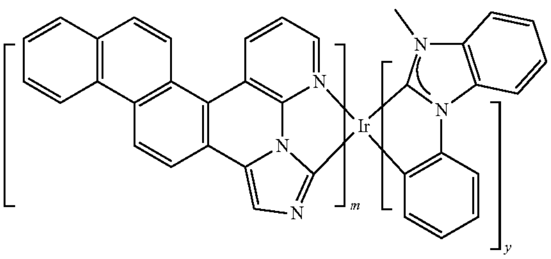
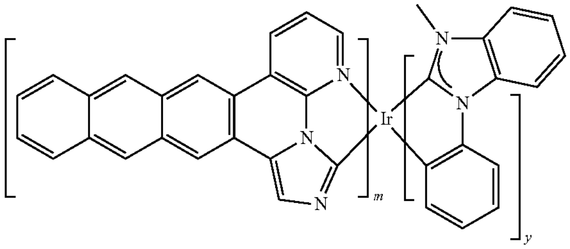
-continued
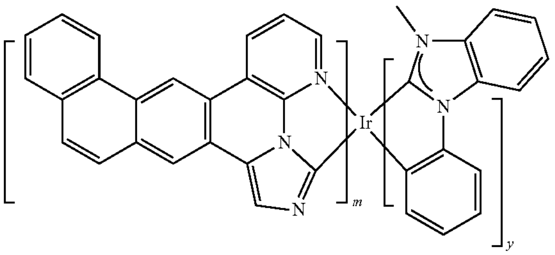
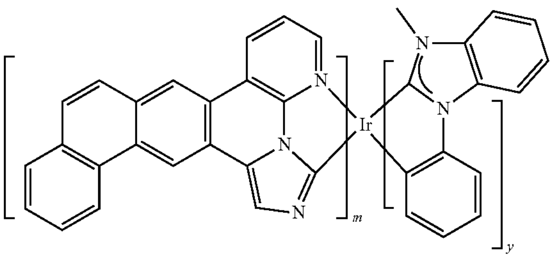
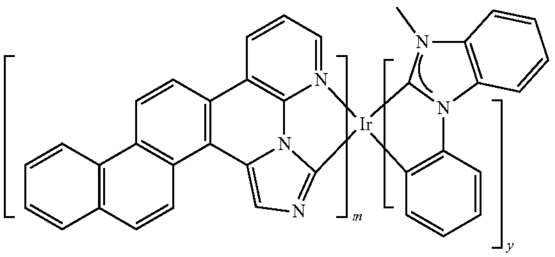
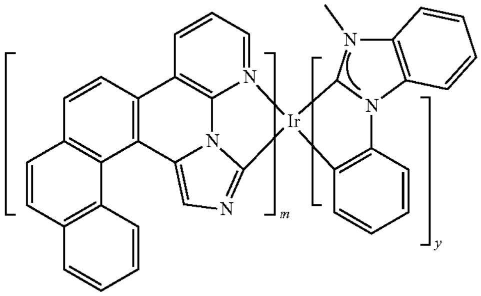
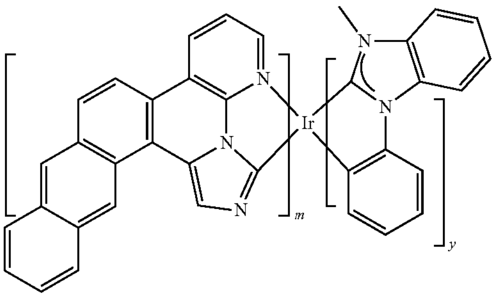
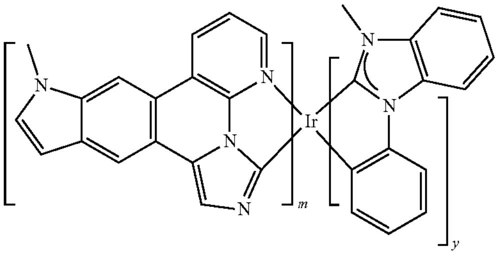

-continued
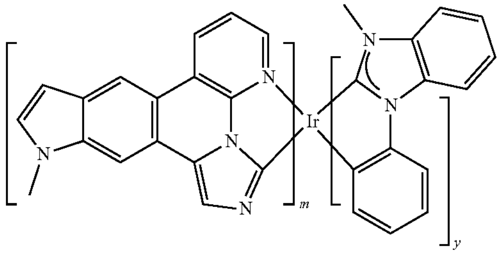
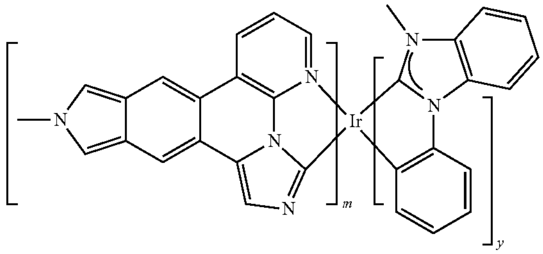
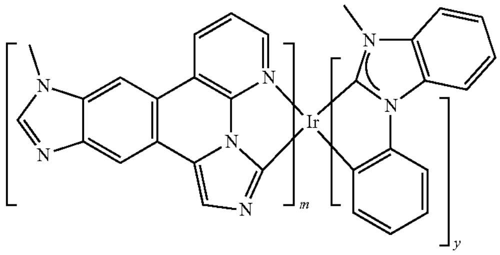
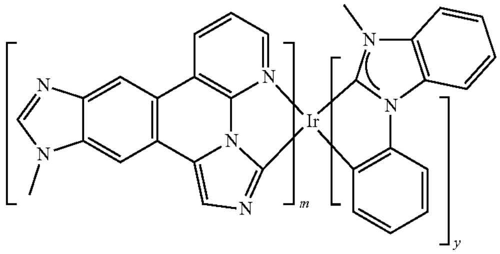
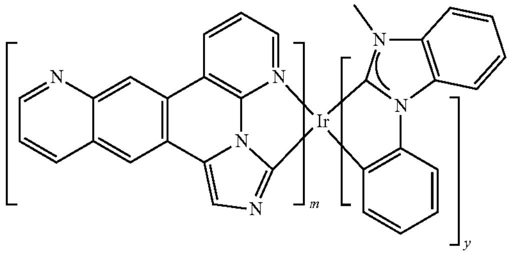
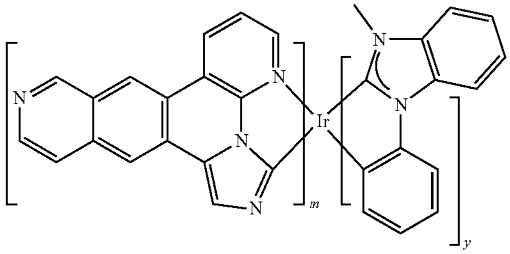
-continued
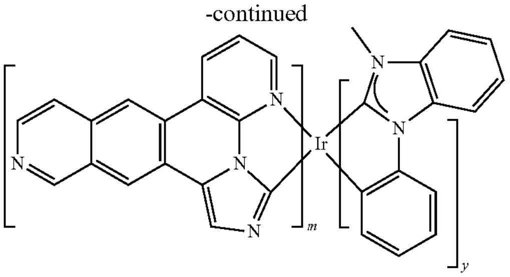
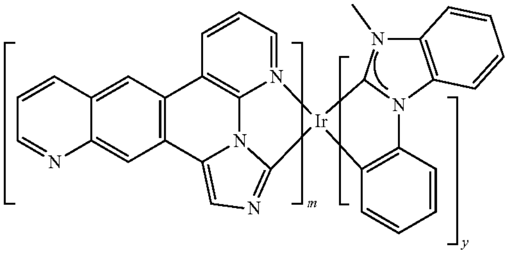
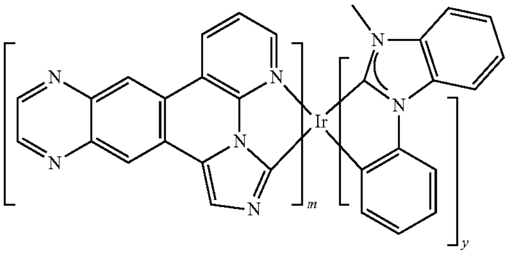
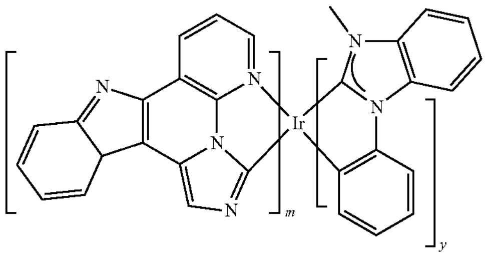
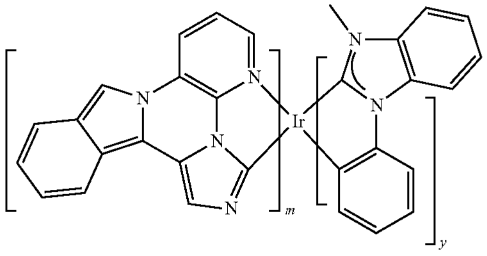
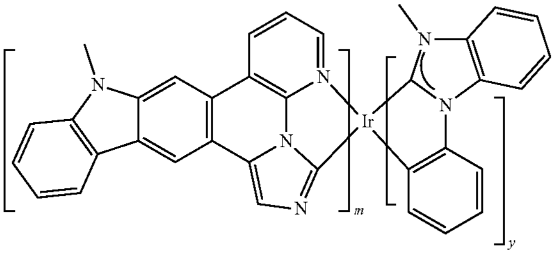

-continued
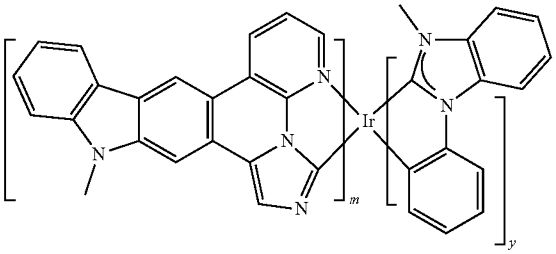
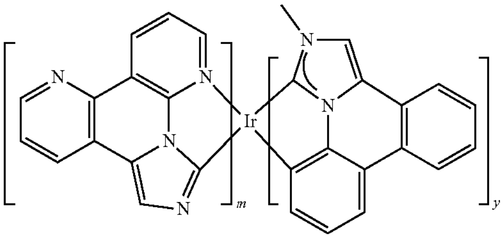
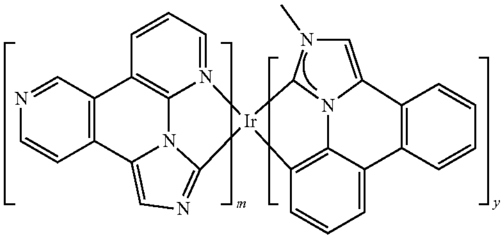
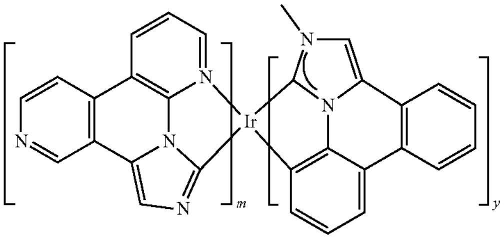
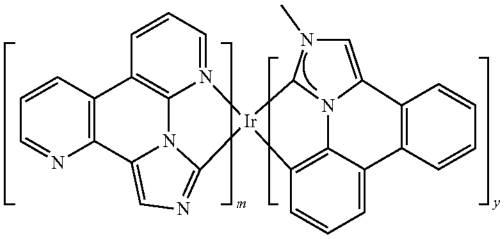
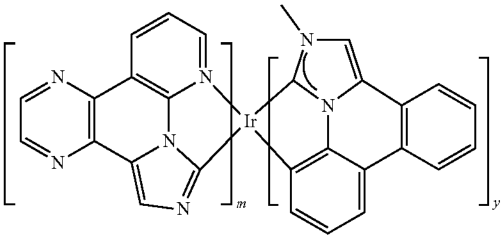
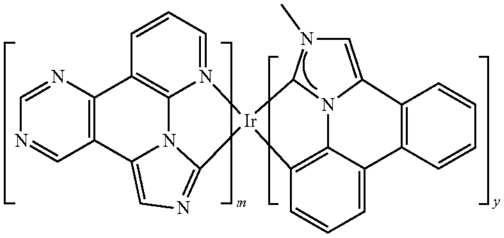
-continued
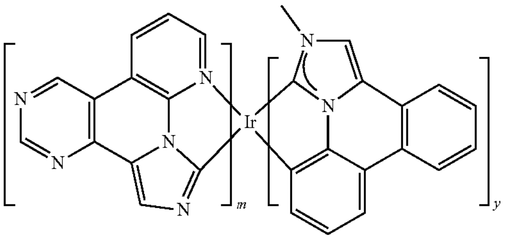
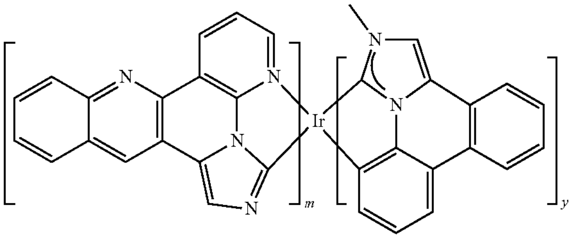
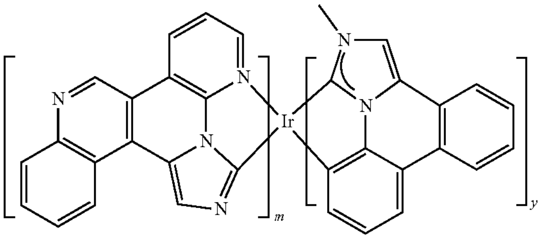
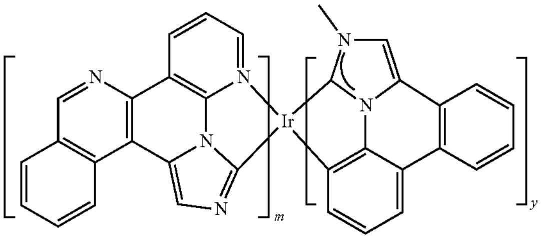
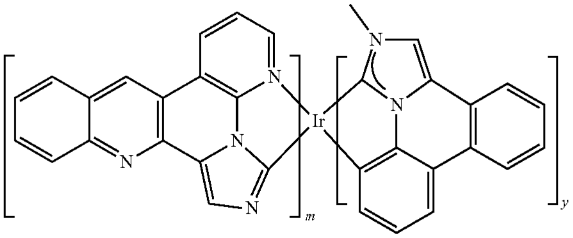
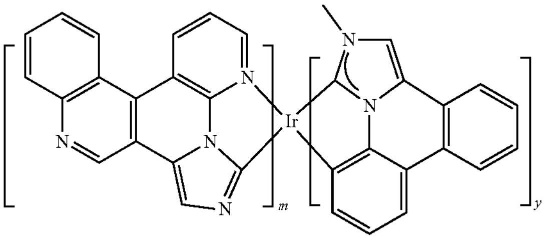
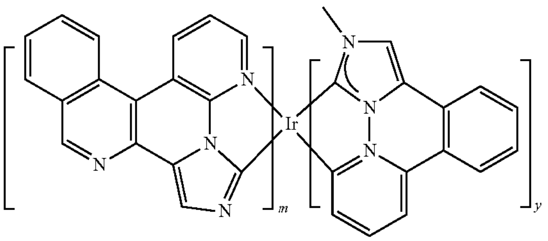

-continued
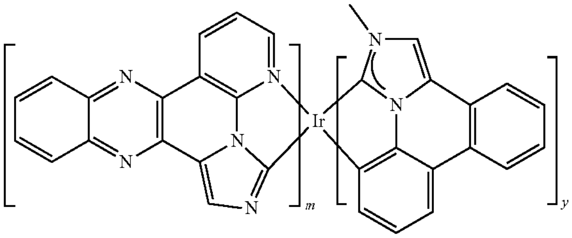
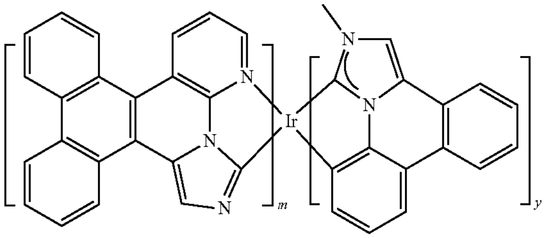
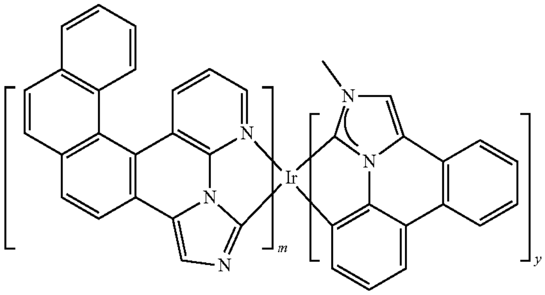
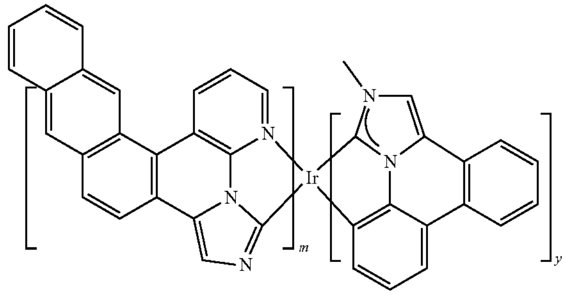
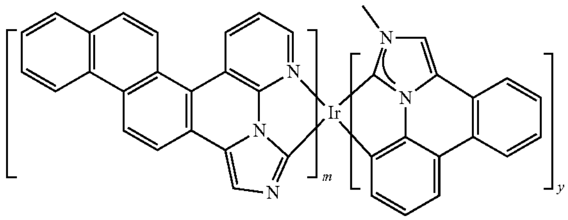
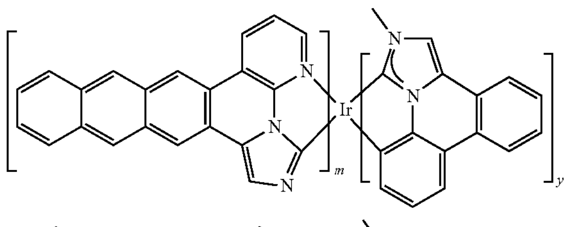
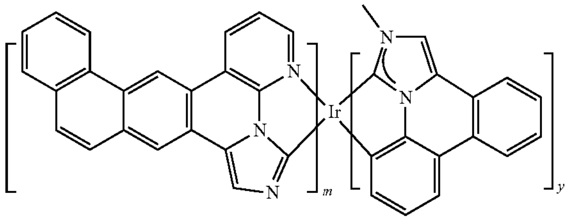
-continued
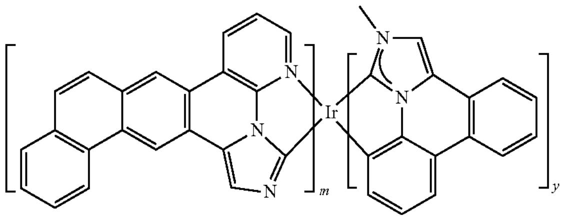
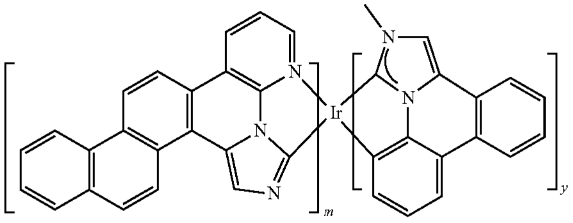
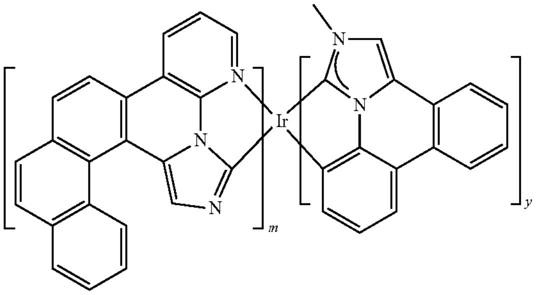
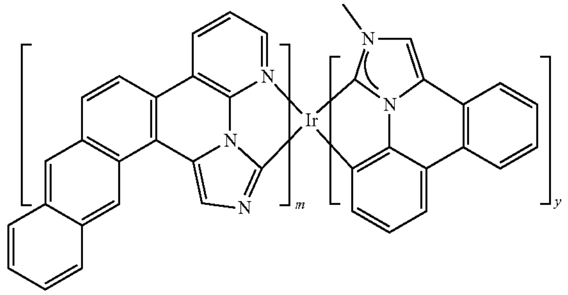
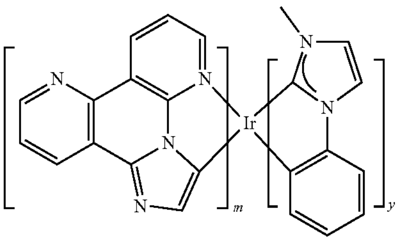
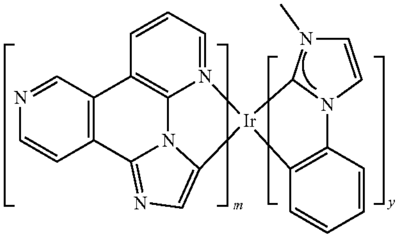

-continued
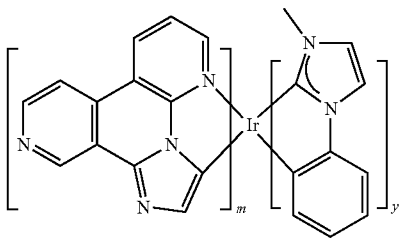
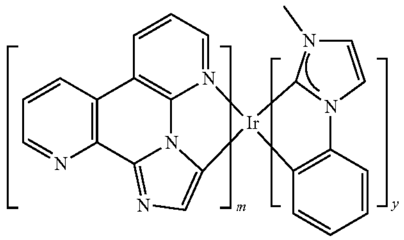
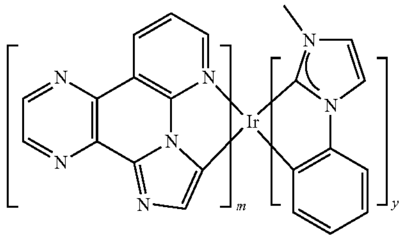
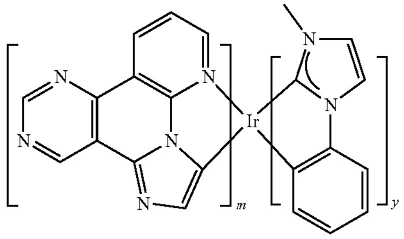
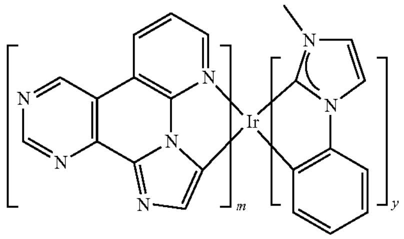
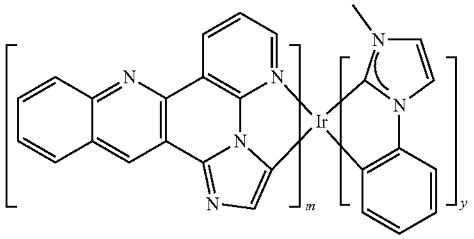
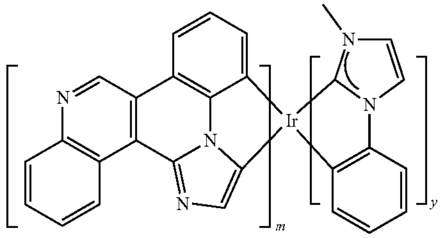
-continued
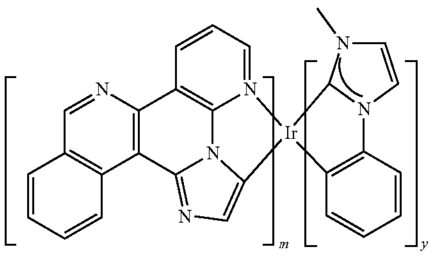
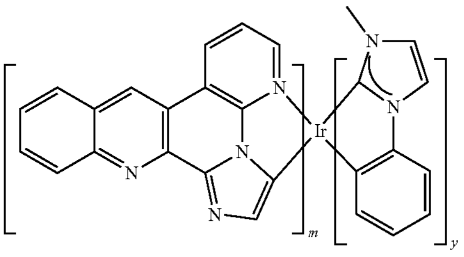
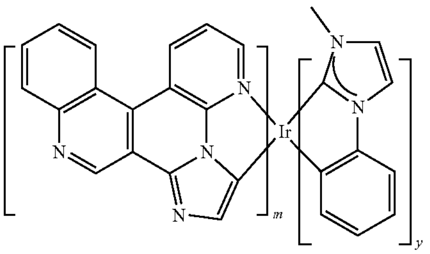
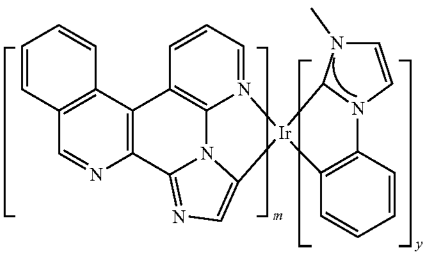
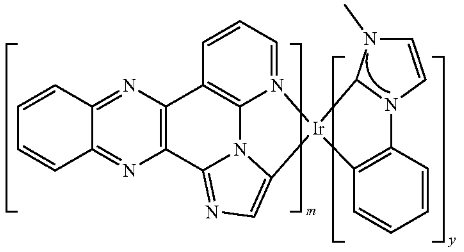
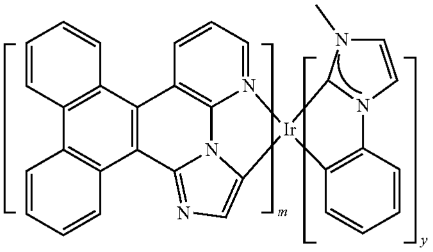

-continued
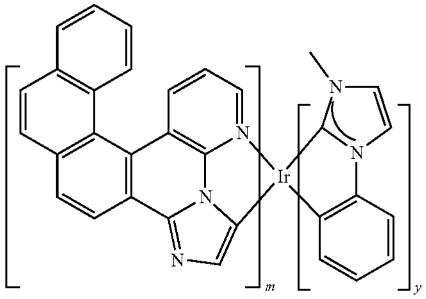
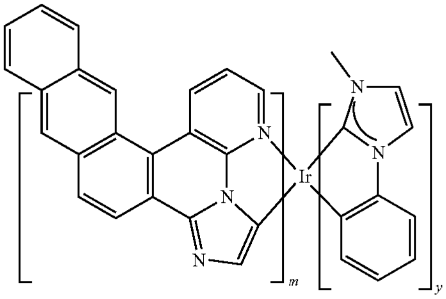
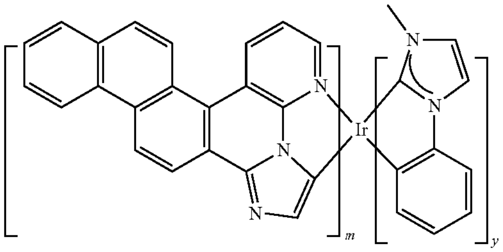
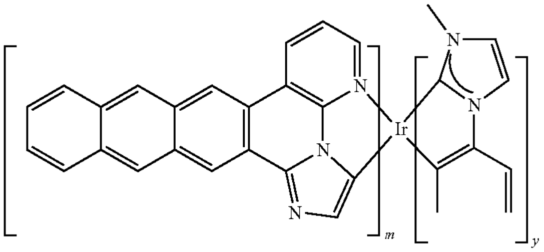
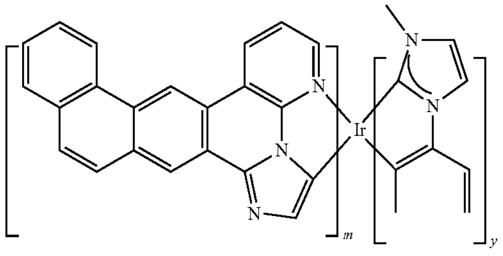
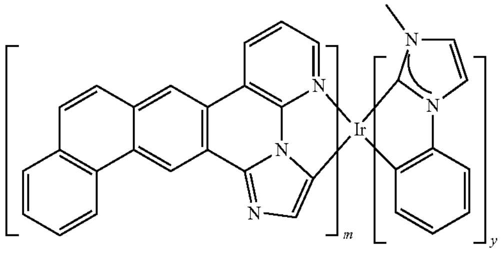
-continued
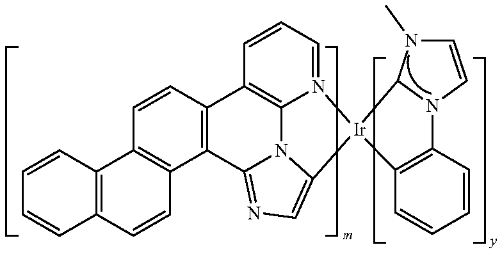
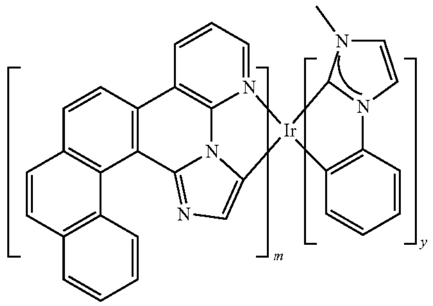
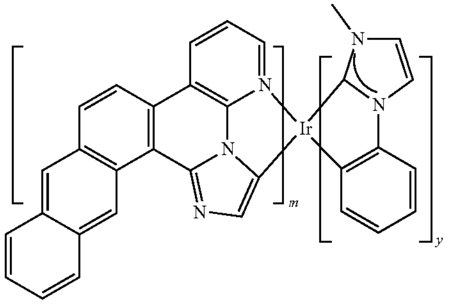
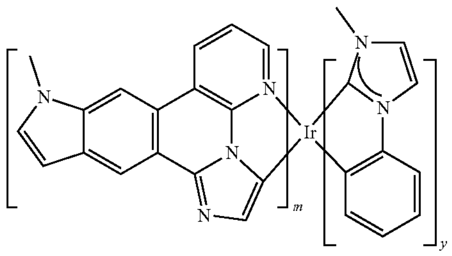
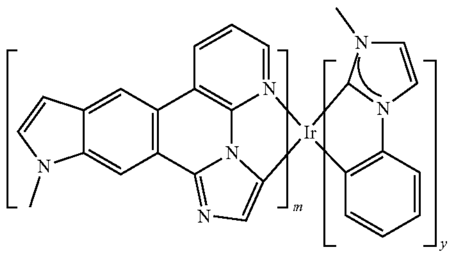
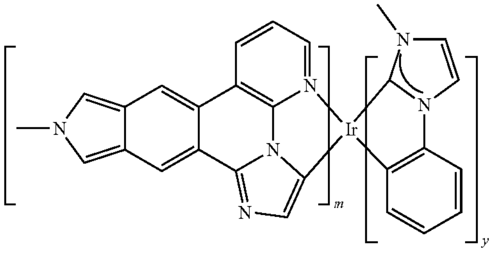

-continued
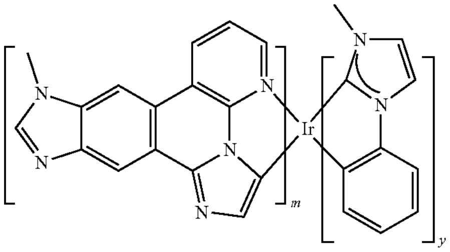
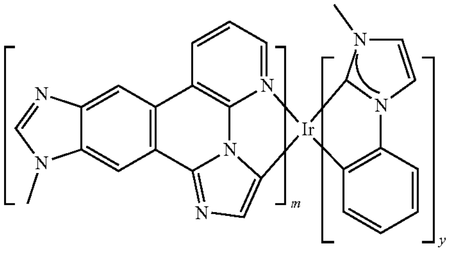
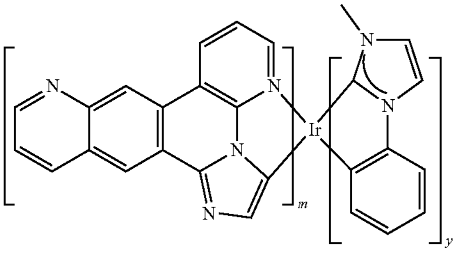
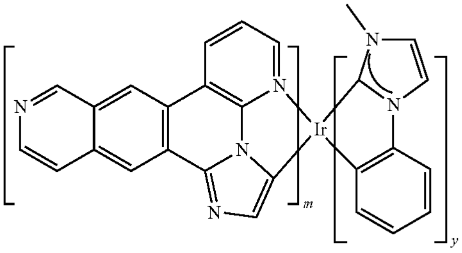
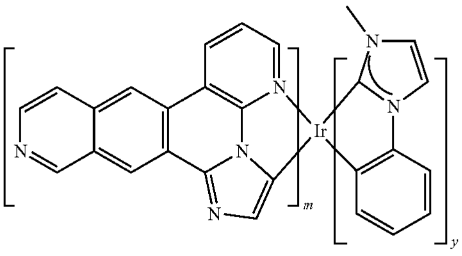
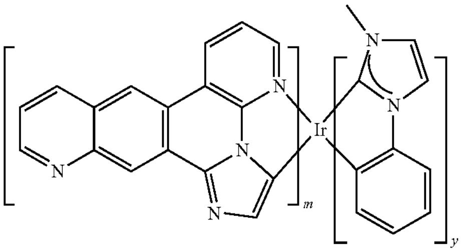
-continued
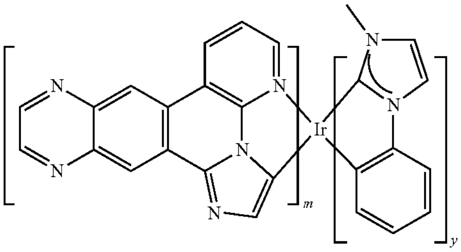
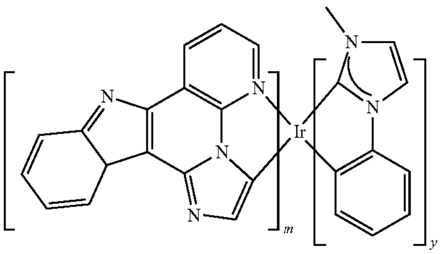
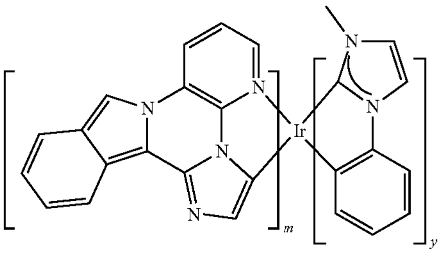
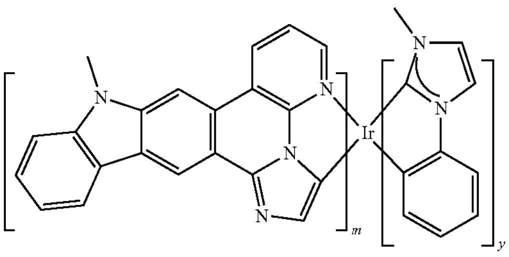
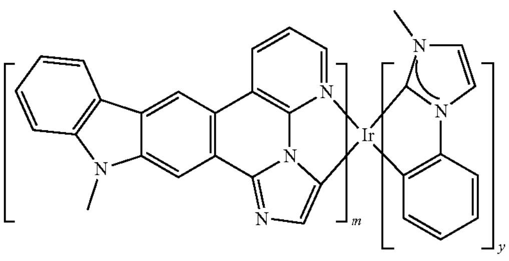
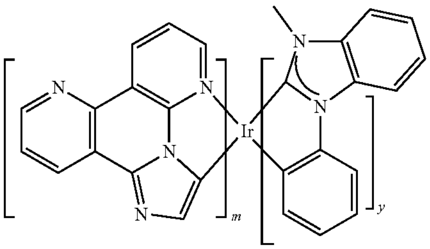

-continued
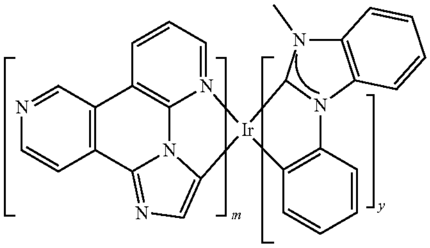
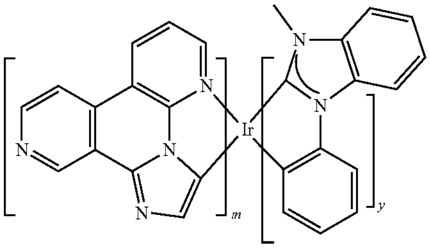
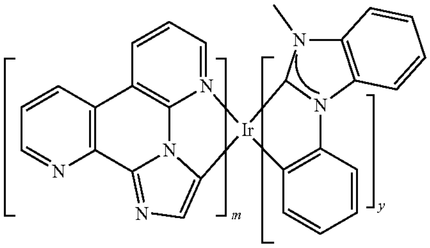
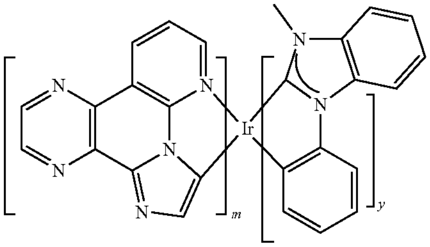
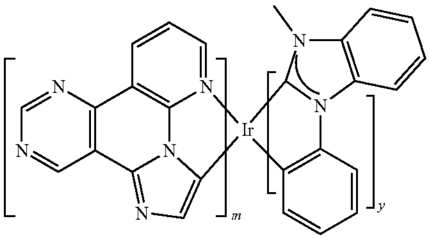
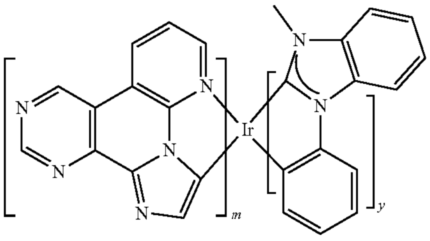
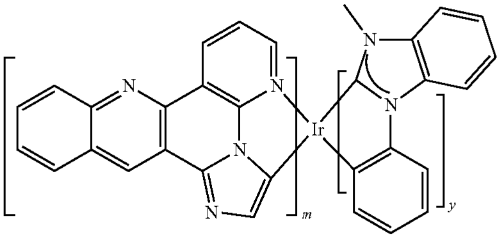
-continued
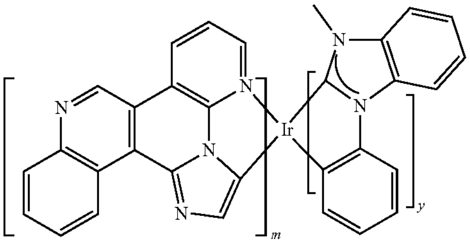
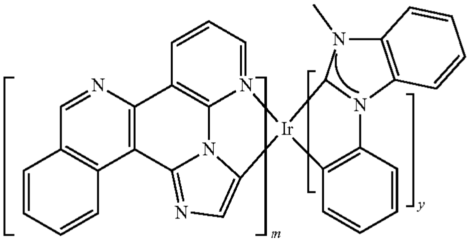
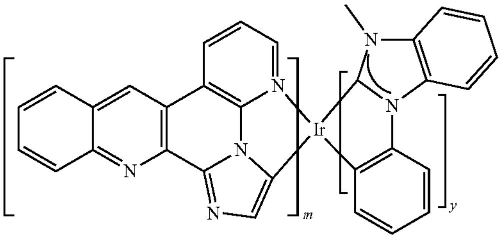
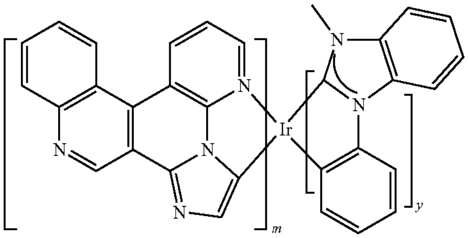
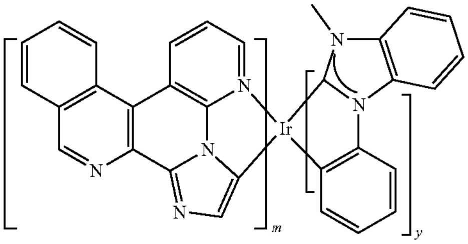
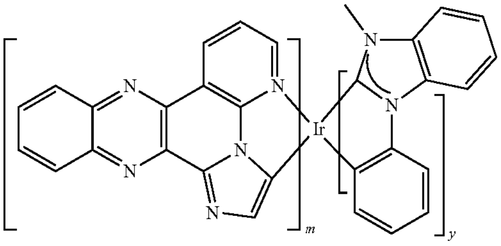
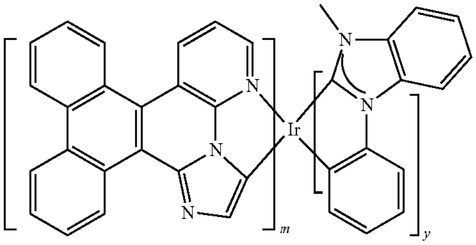

-continued
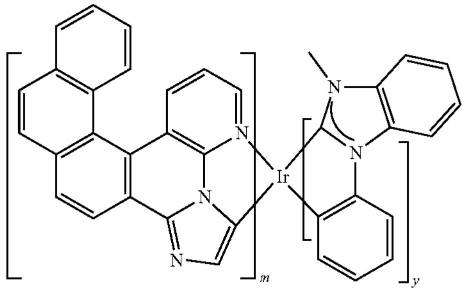
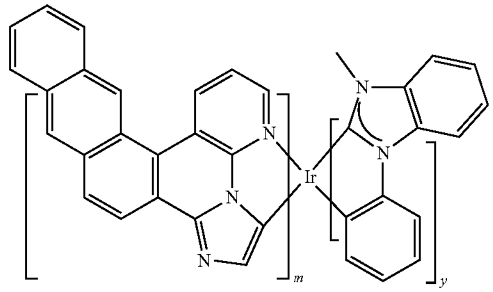
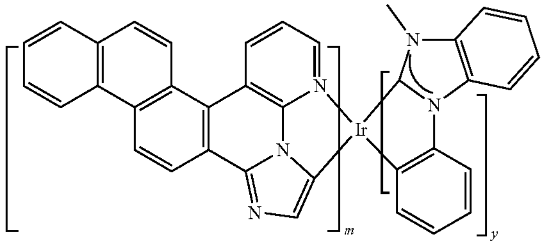
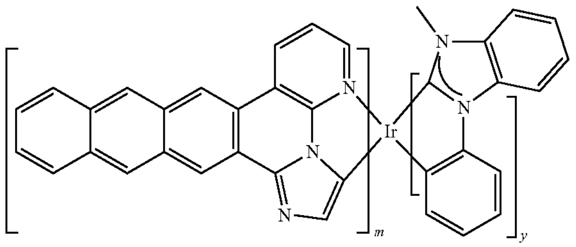
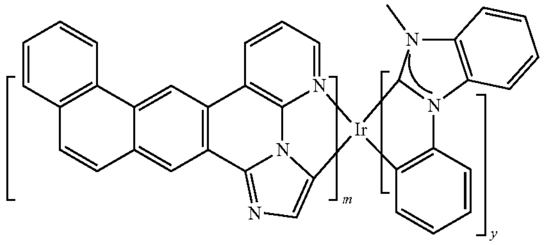
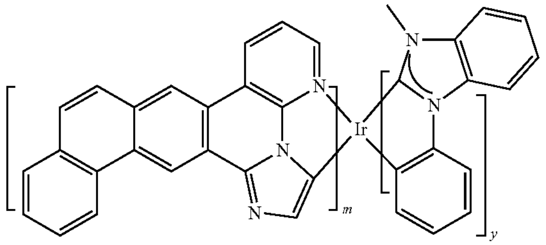
-continued
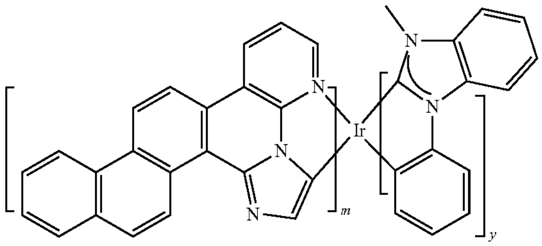
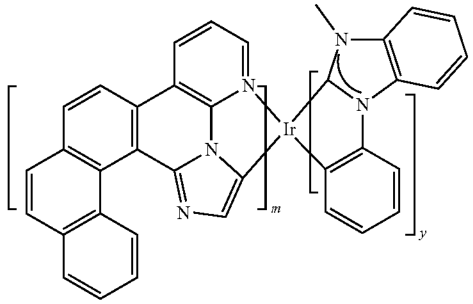
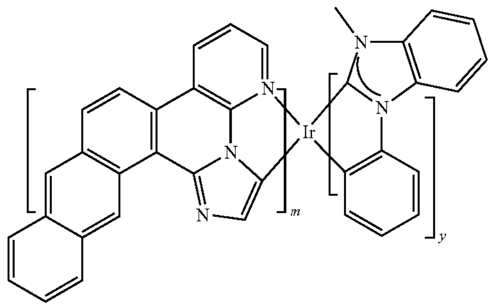
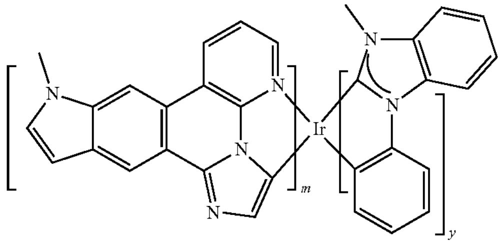
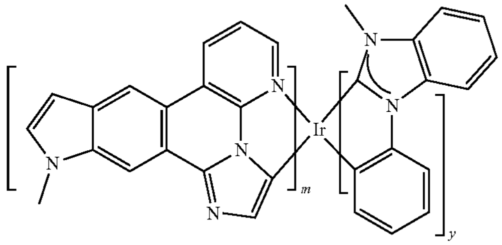
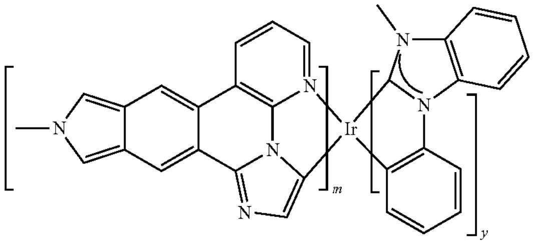

-continued
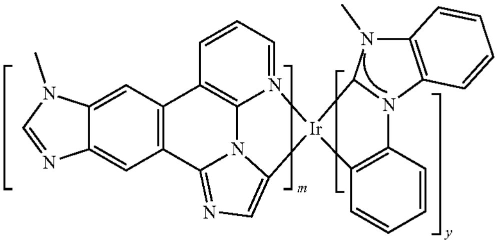
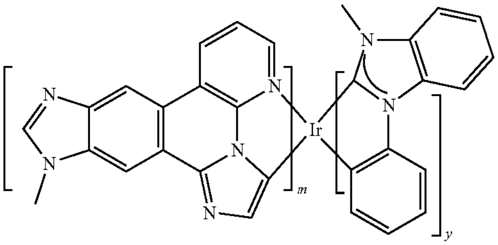
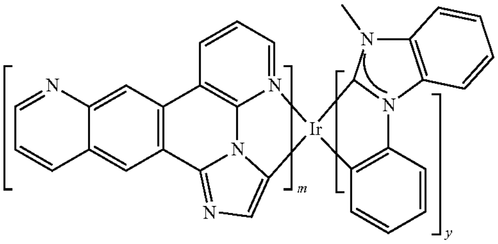
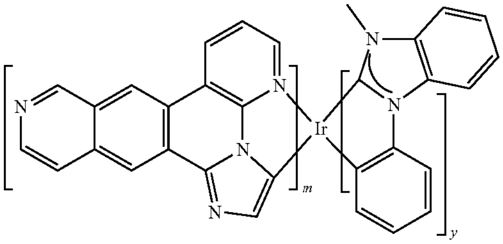
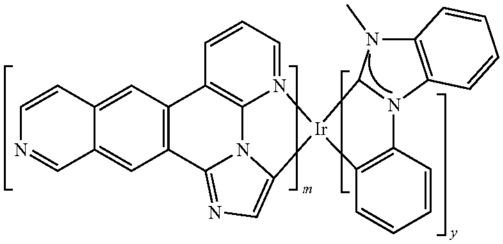
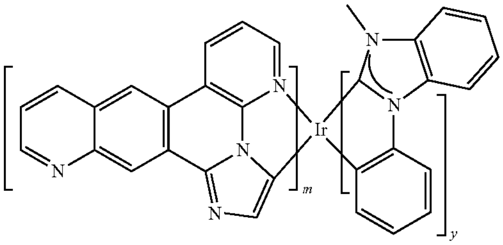
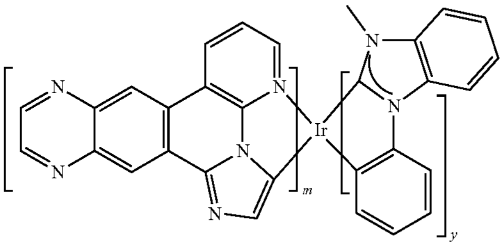
-continued
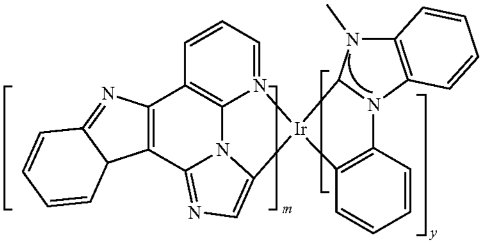
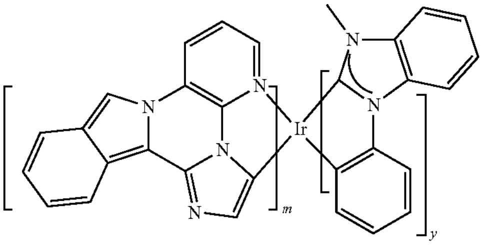
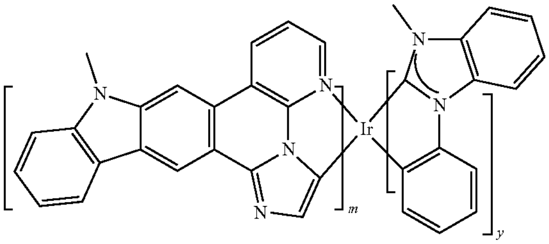
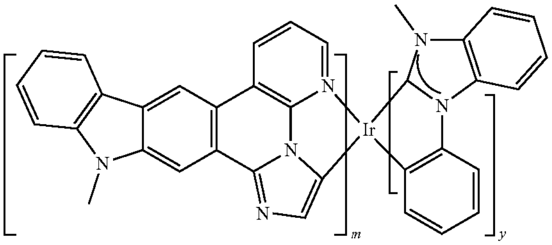
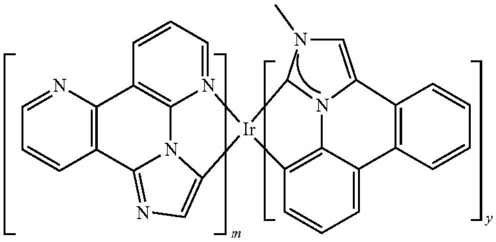
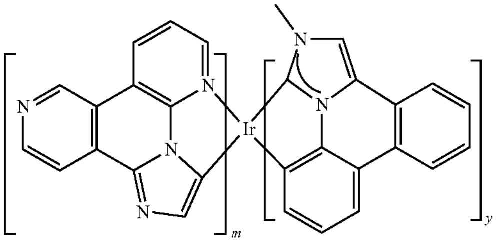
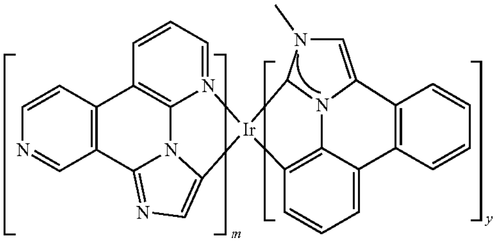

-continued
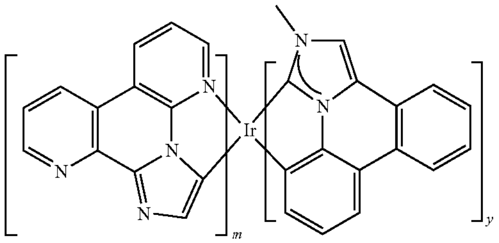
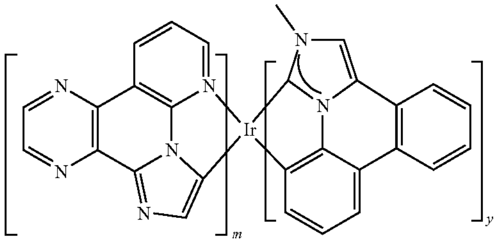
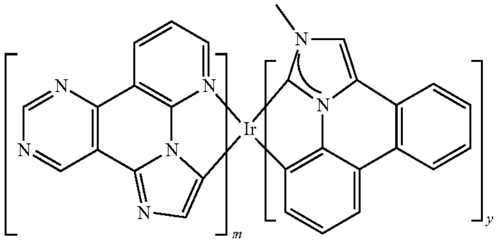
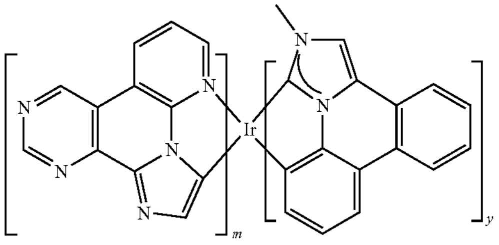
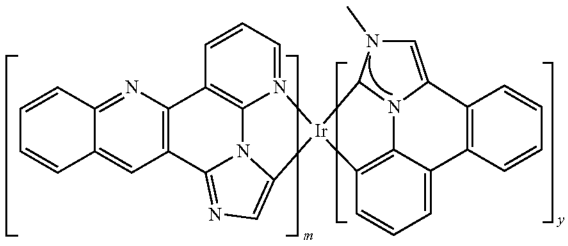
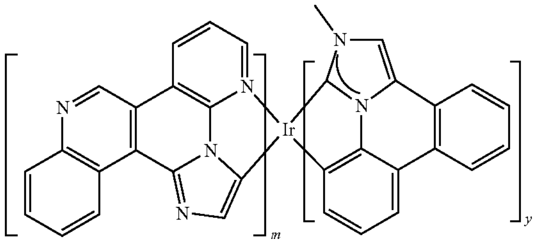
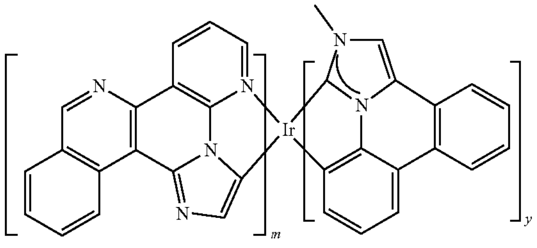
-continued
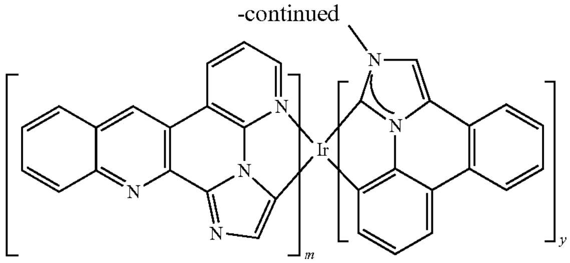
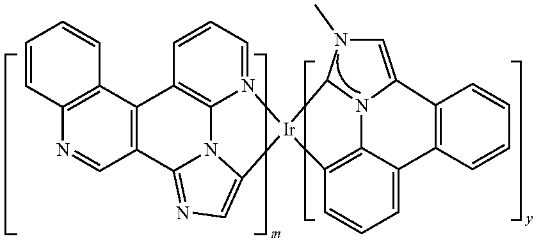
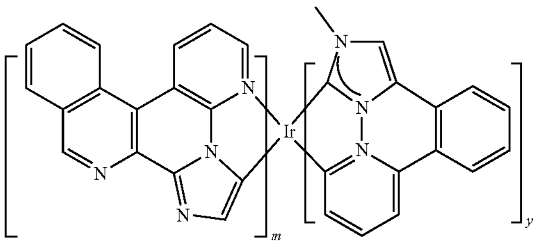
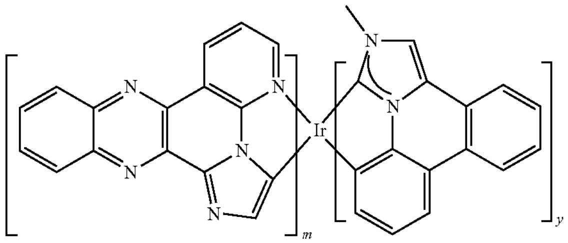
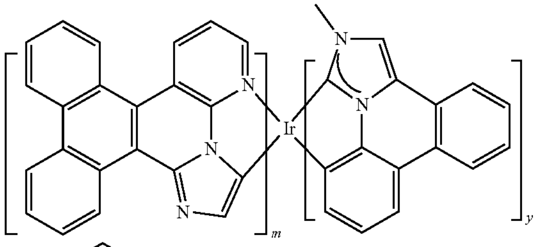
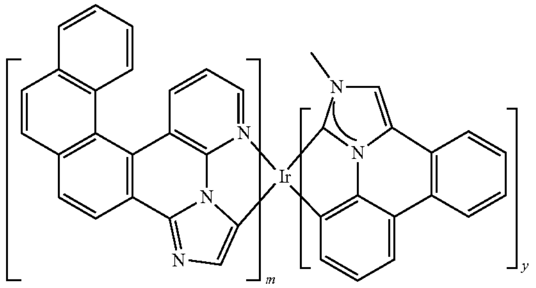

-continued
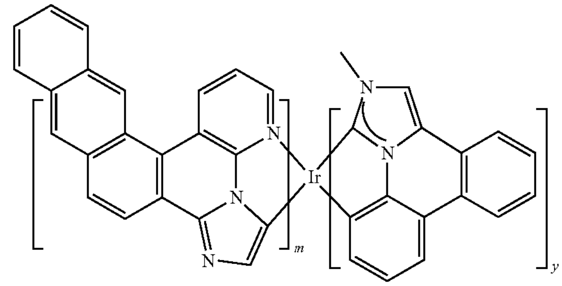
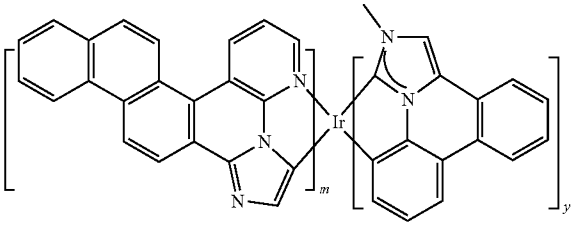
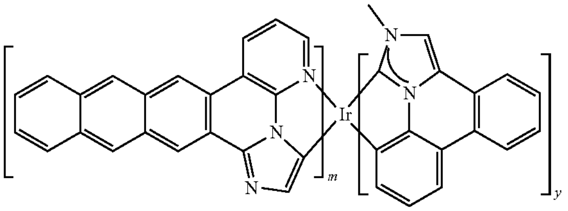
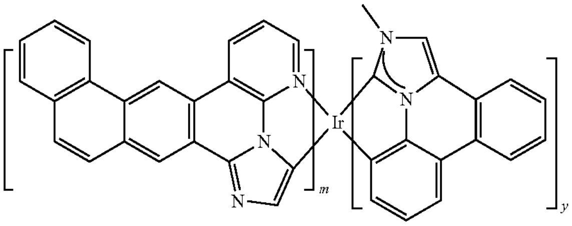
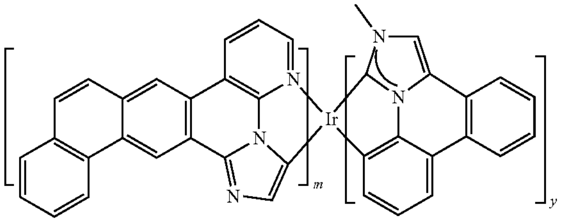
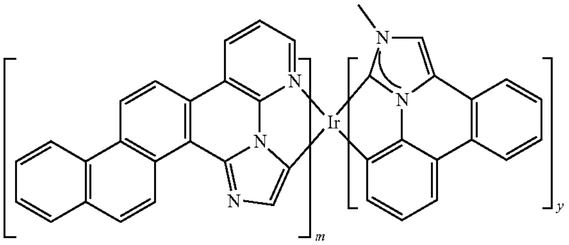
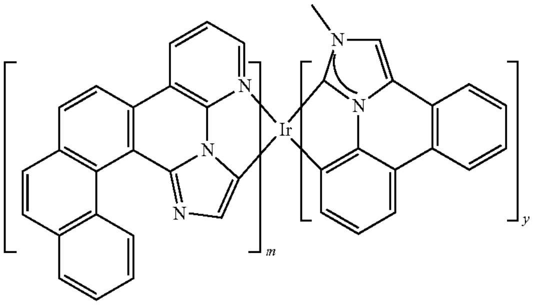
-continued
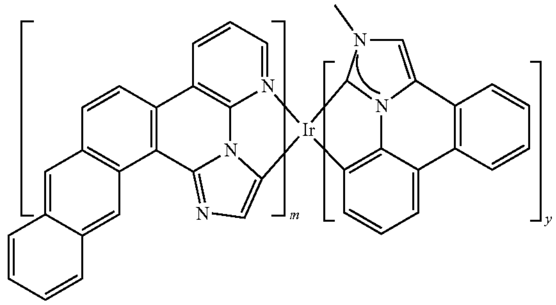
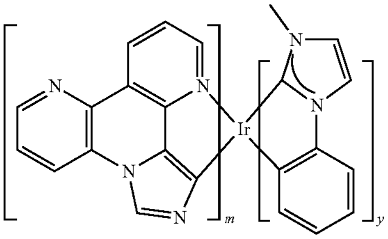
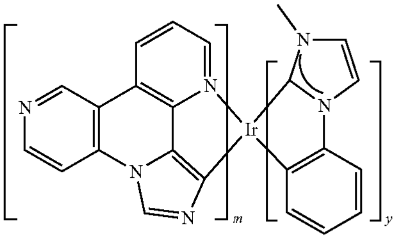
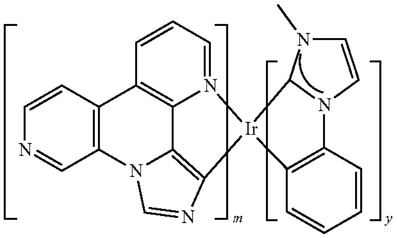
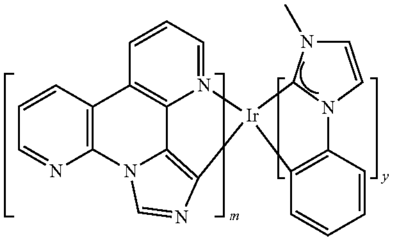
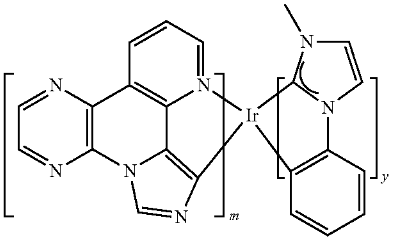

-continued
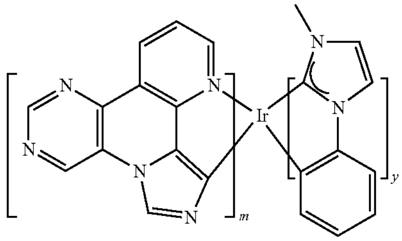
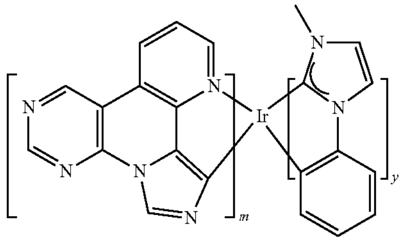
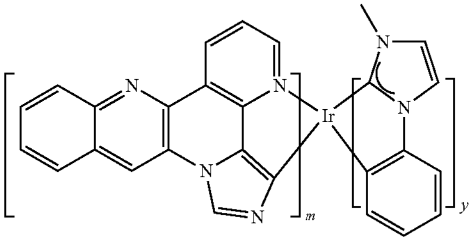
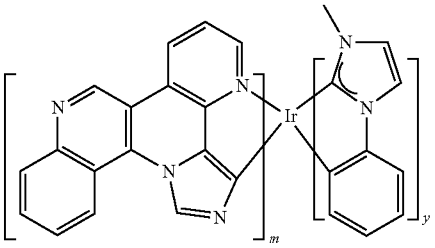
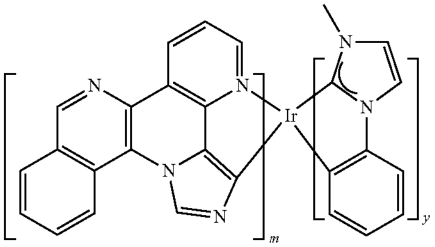
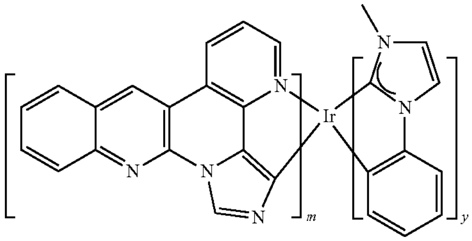
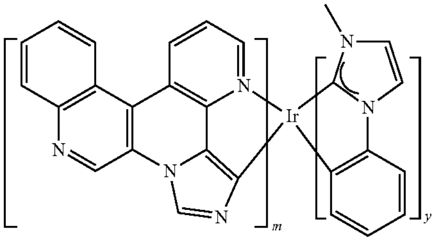
-continued
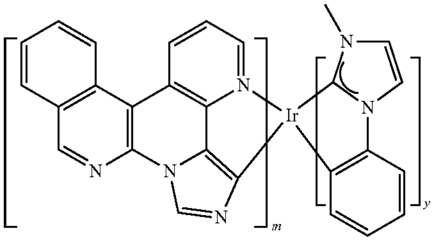
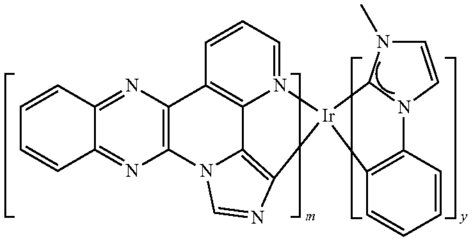
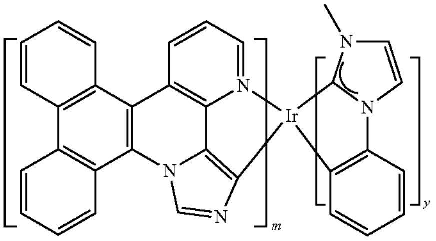
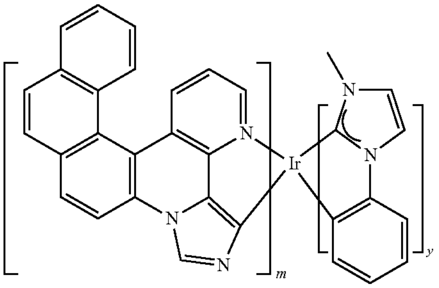
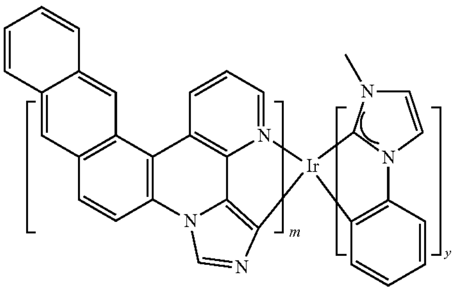
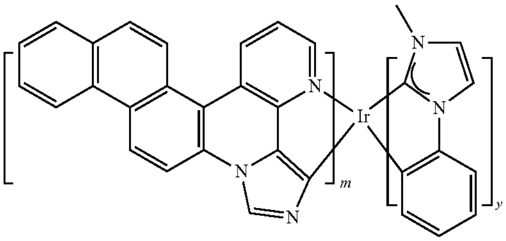

-continued
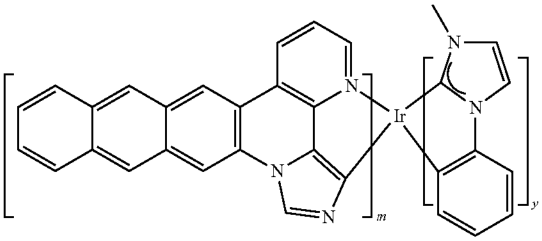
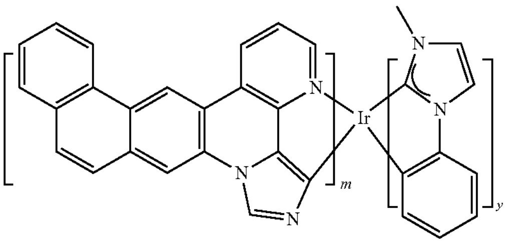
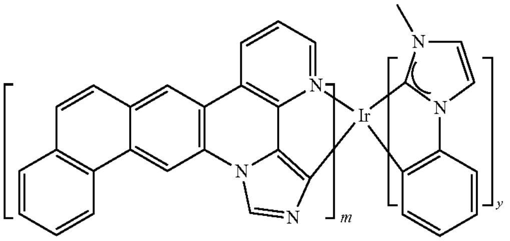
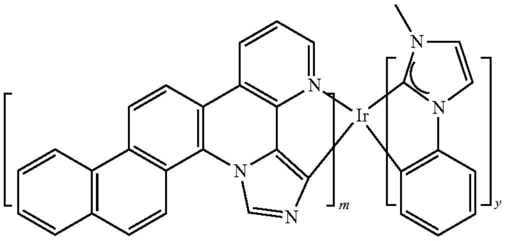
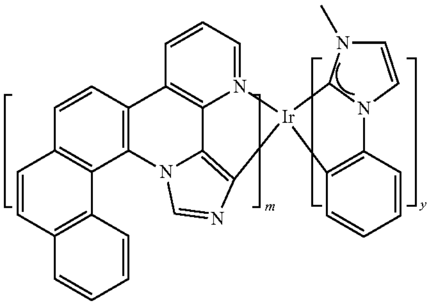
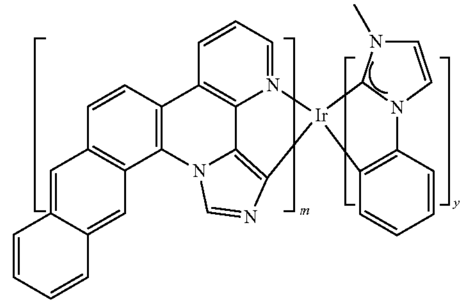
-continued
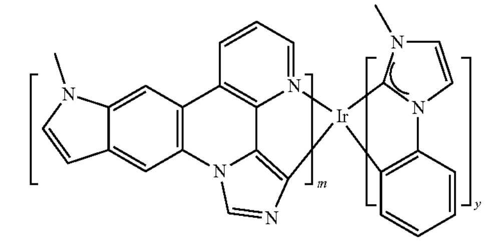
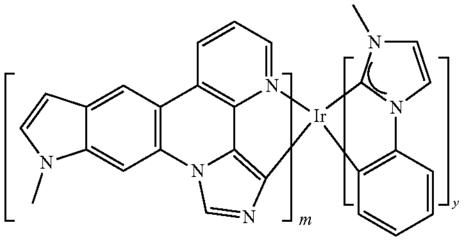
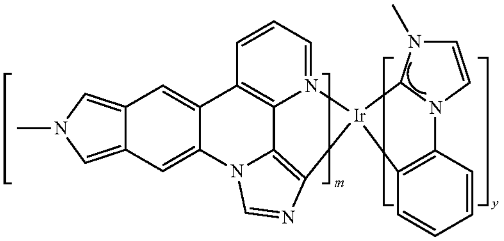
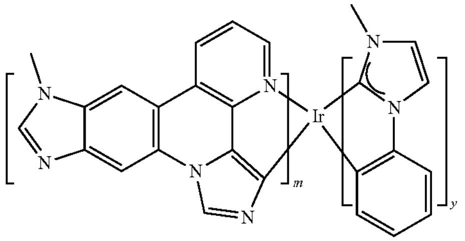
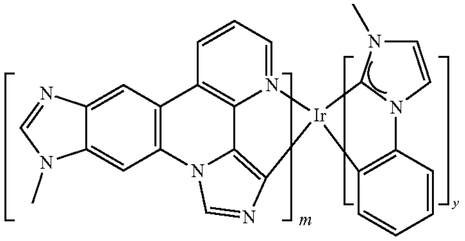
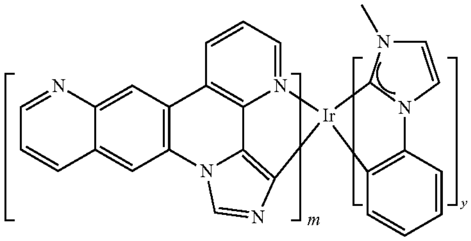
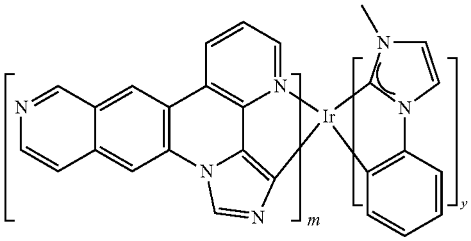

-continued
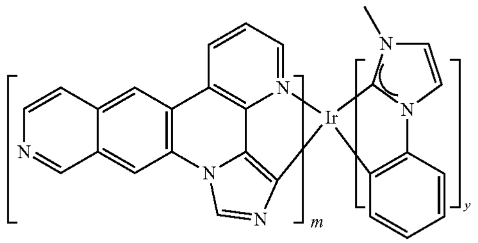
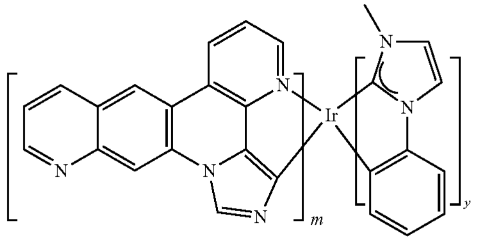
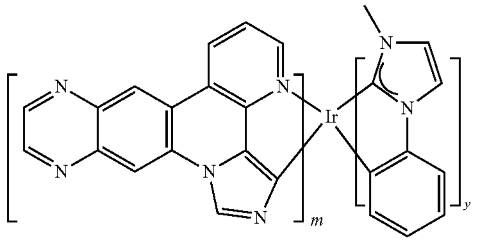
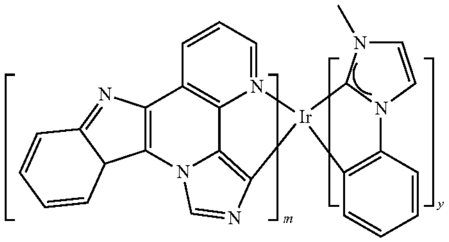
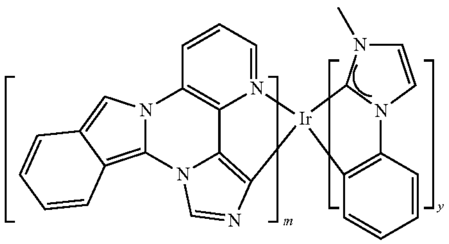
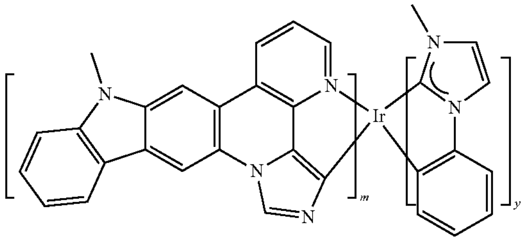
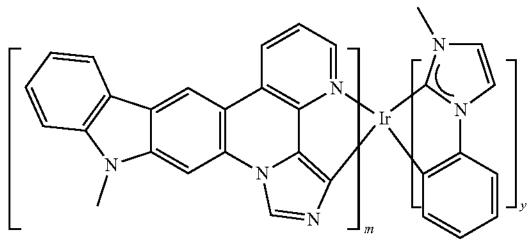
-continued
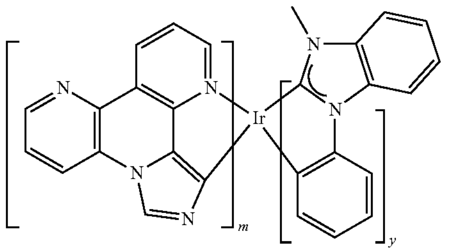
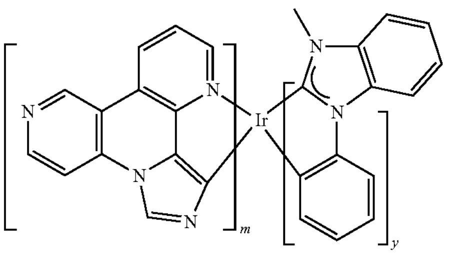
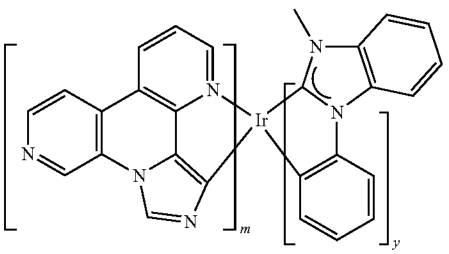
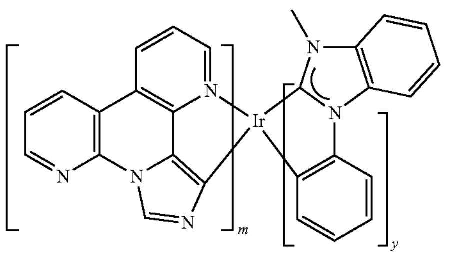
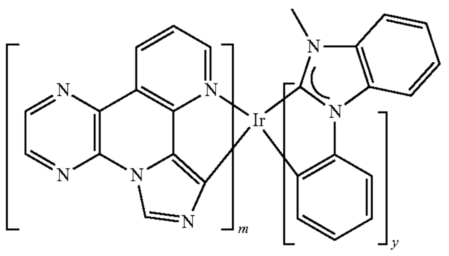
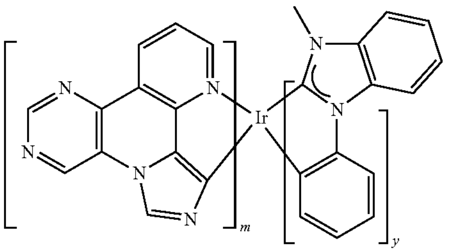

-continued
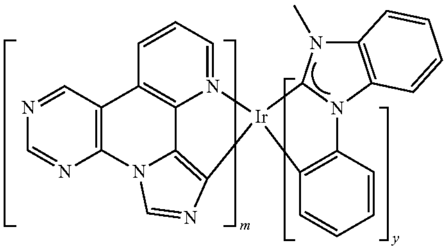
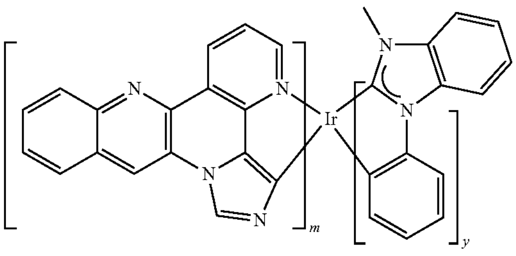
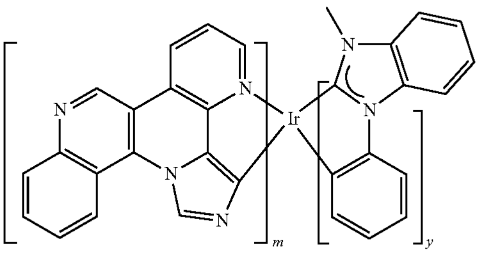
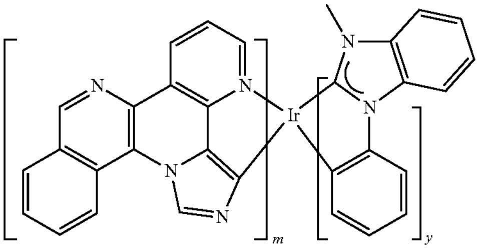
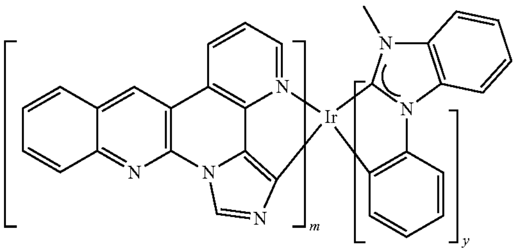
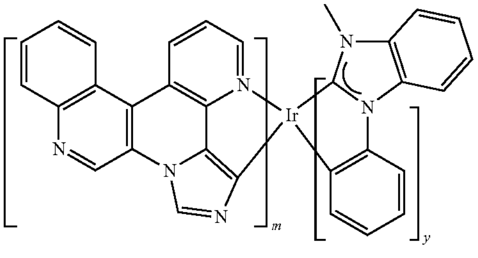
-continued
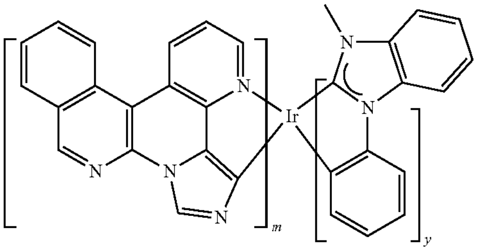
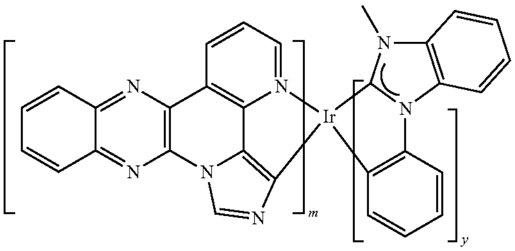
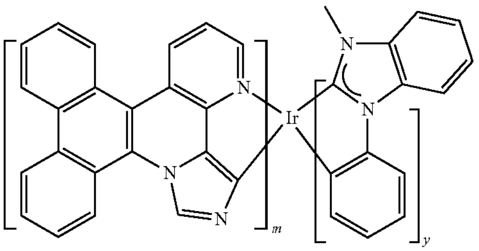
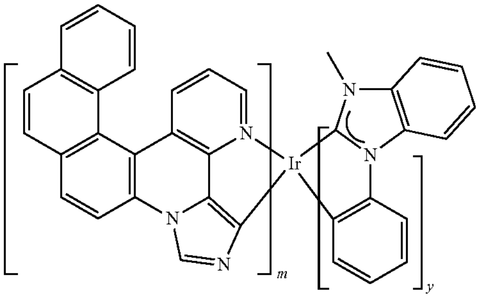
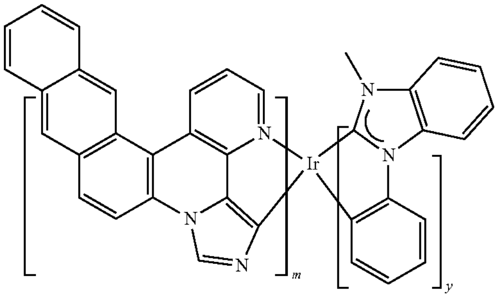
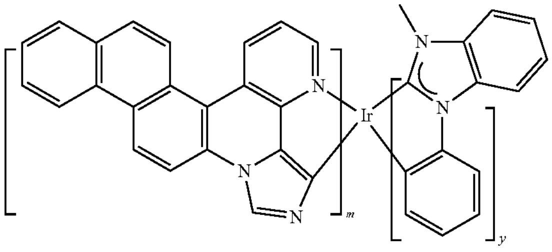

-continued
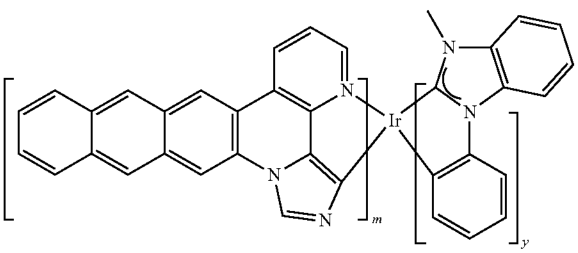
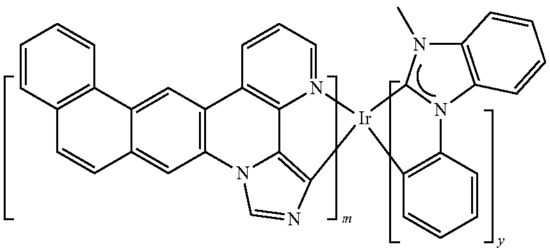
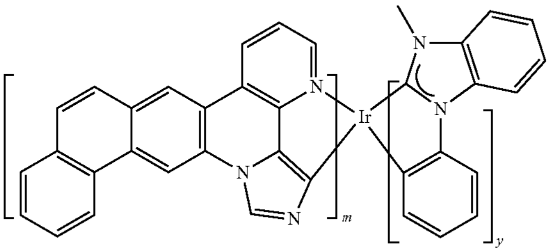
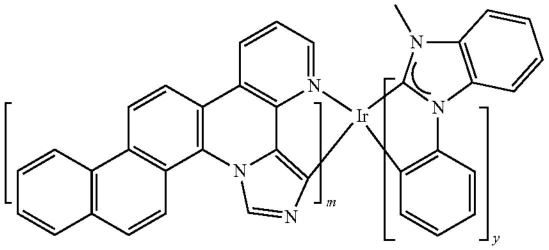
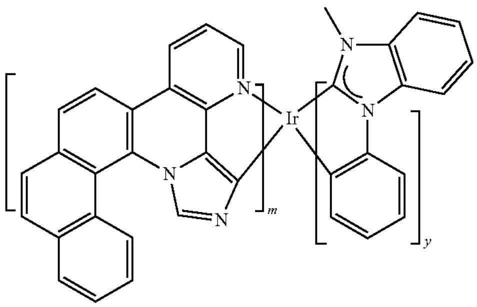
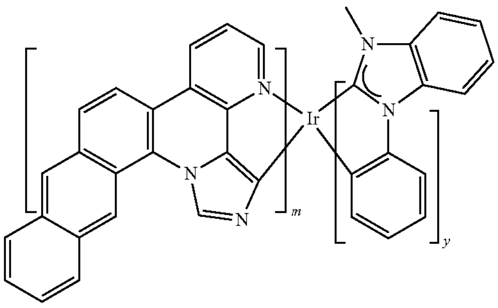
-continued
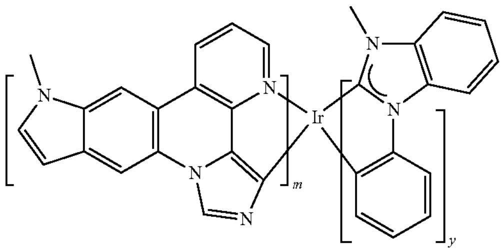
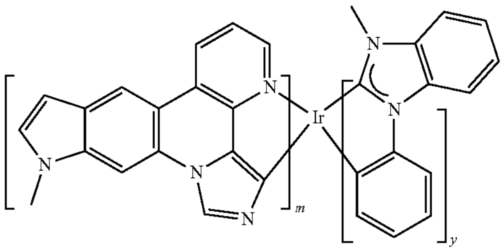
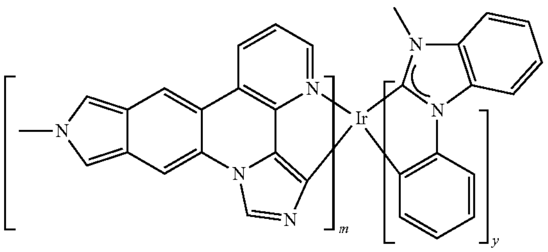
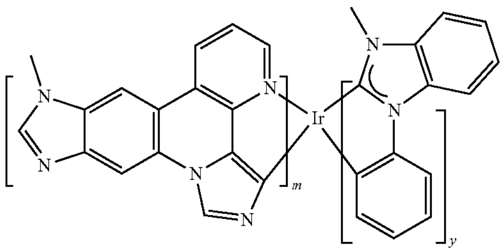
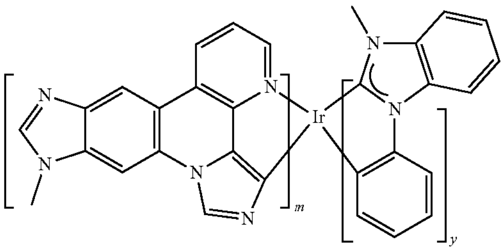
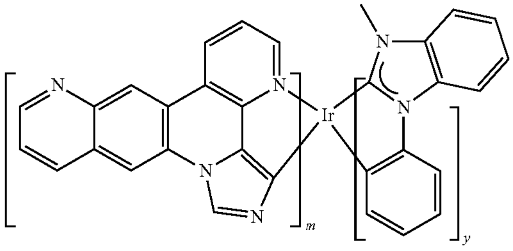

-continued
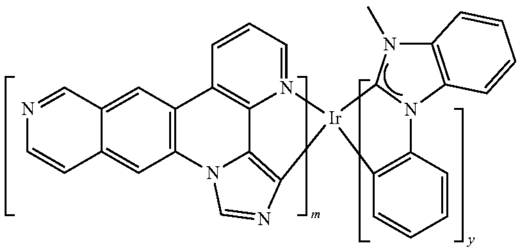
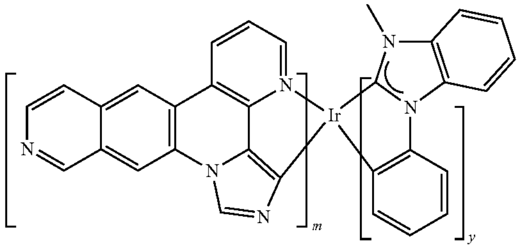
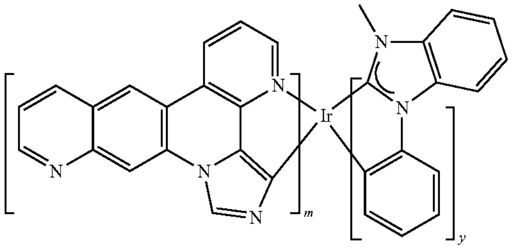
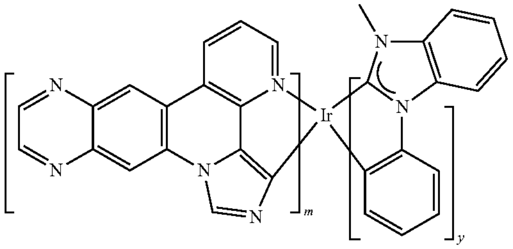
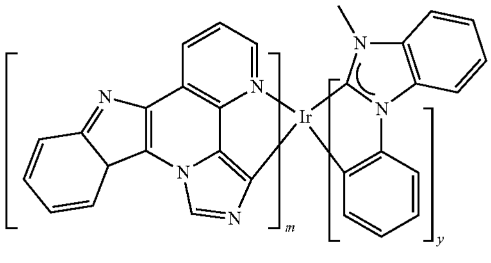
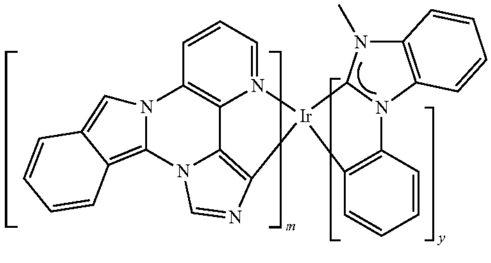
-continued
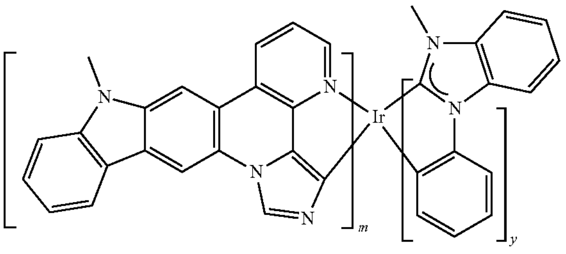
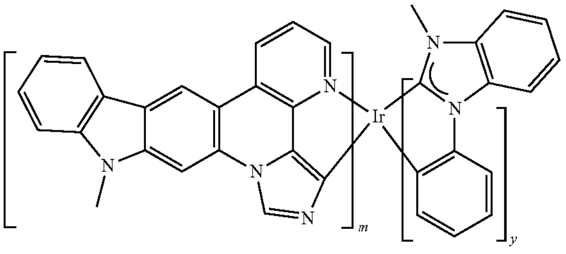
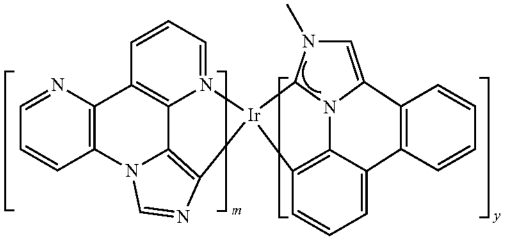
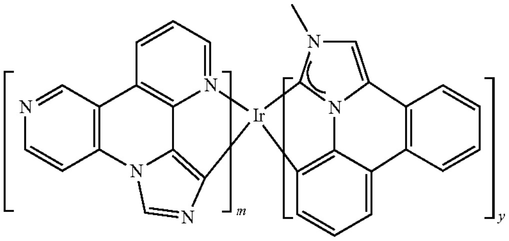
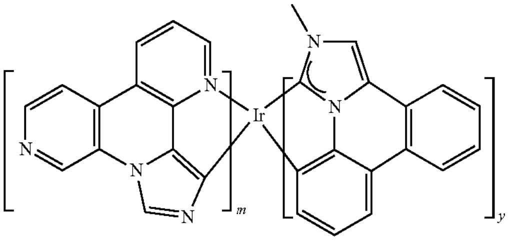
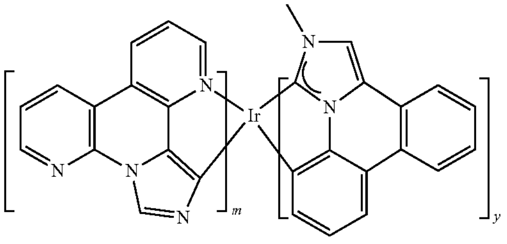
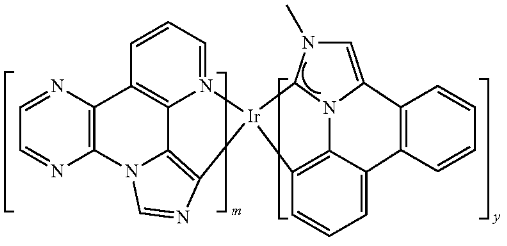

-continued
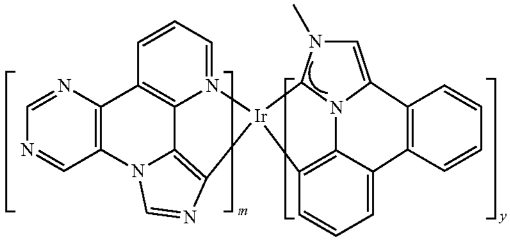
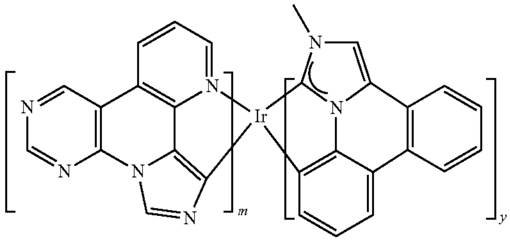
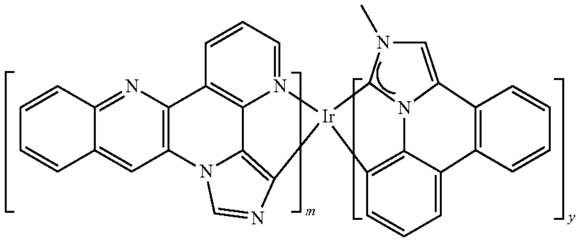
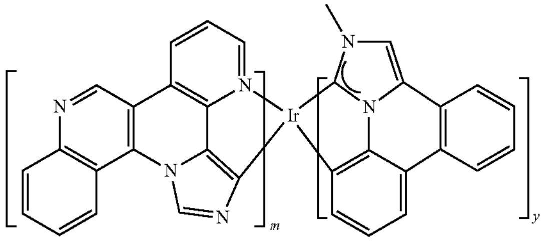
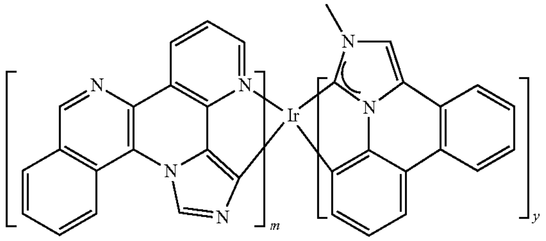
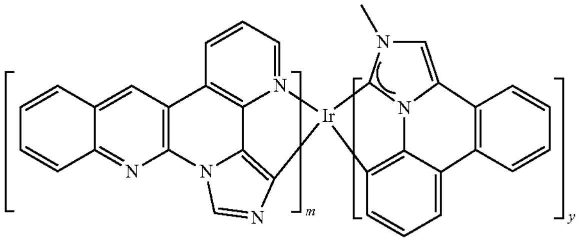
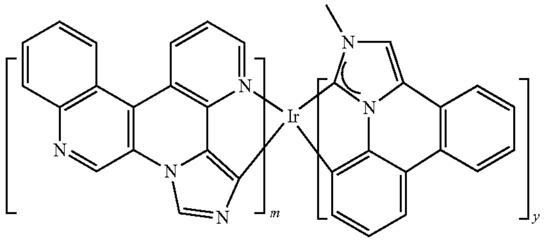
-continued
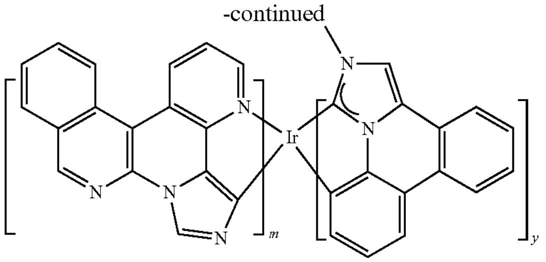
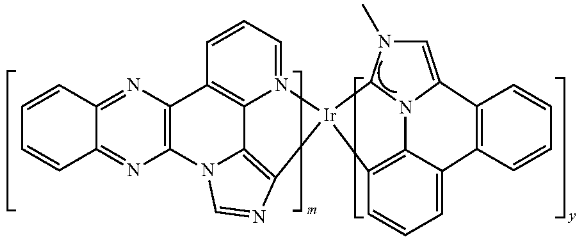
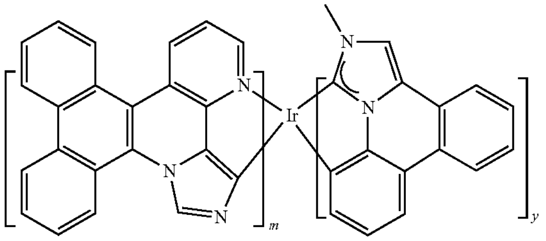
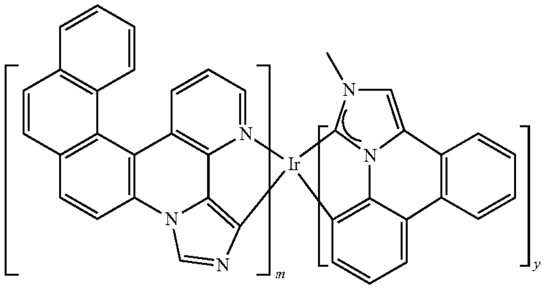
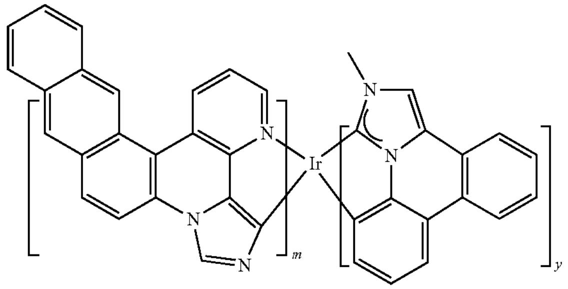
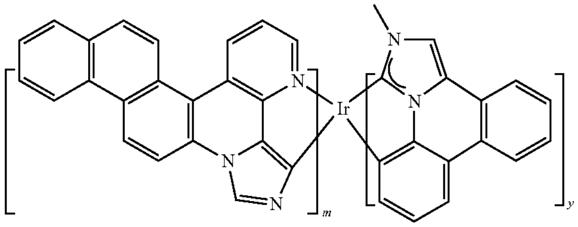

-continued
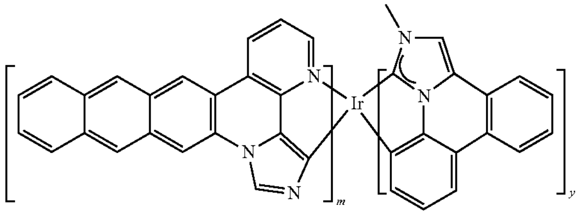
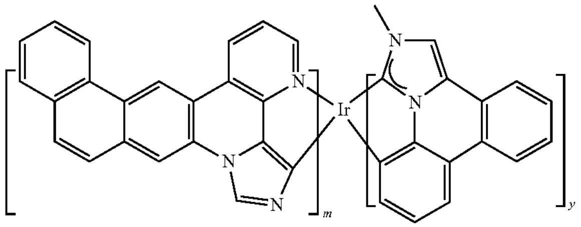
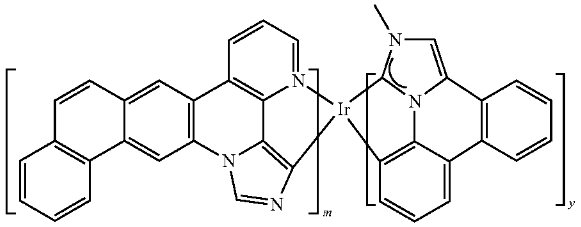
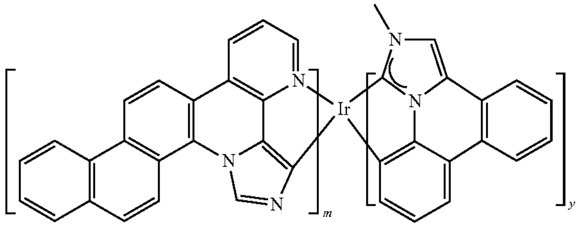
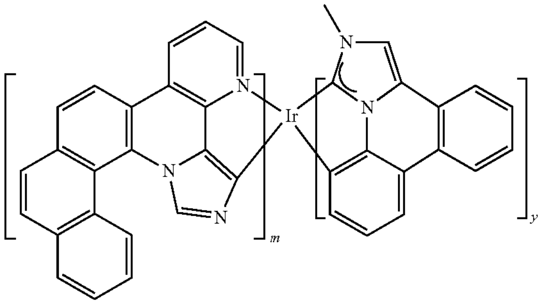
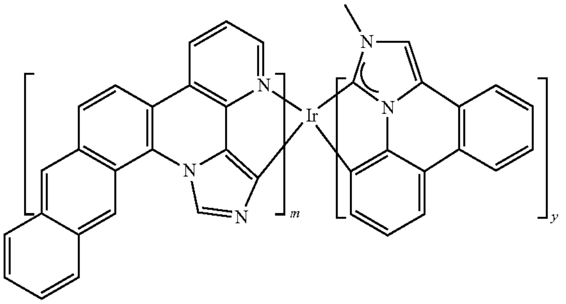
-continued
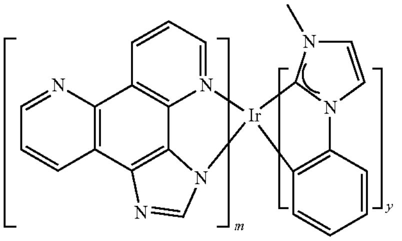
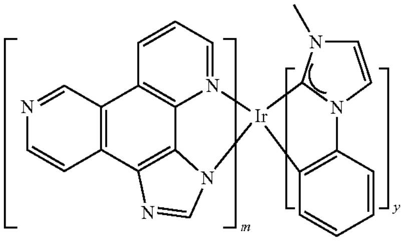
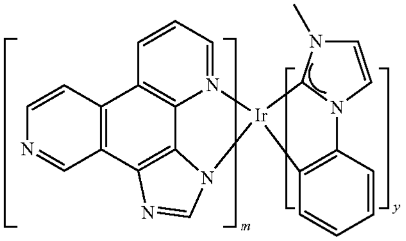
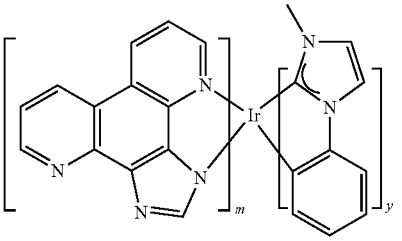
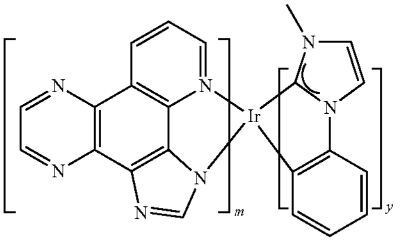
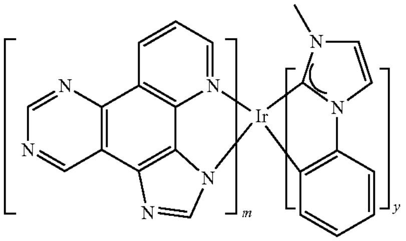
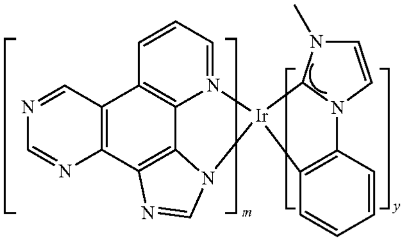

-continued
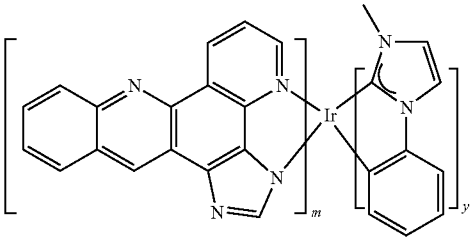
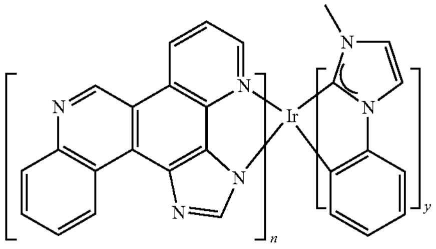
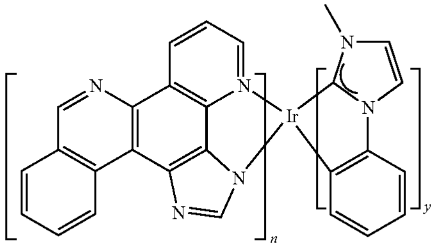
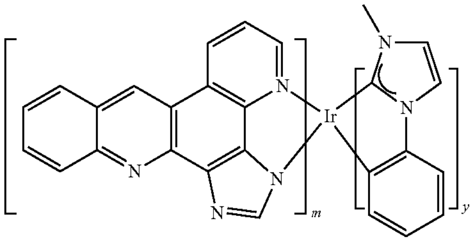
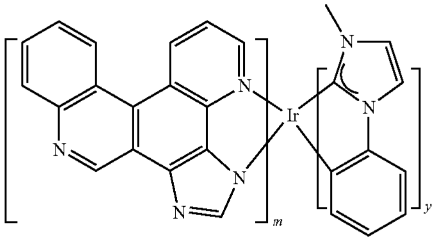
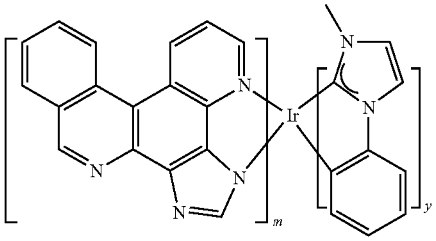
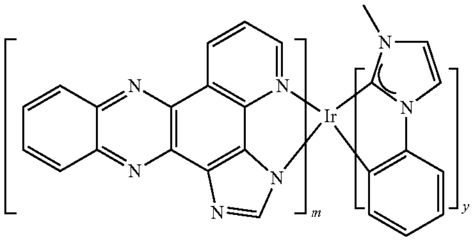
-continued
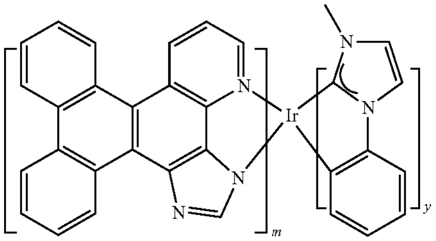
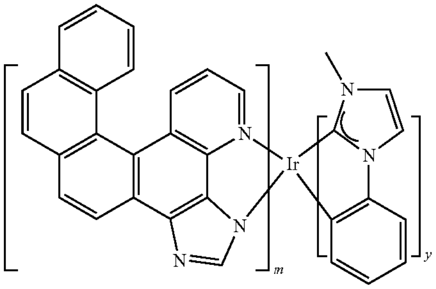
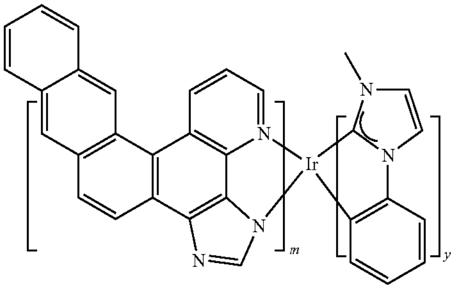
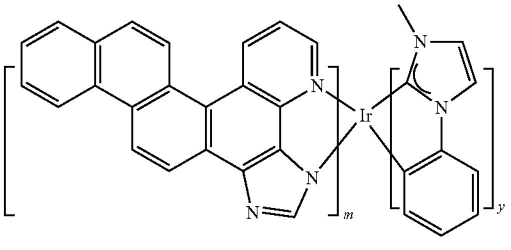
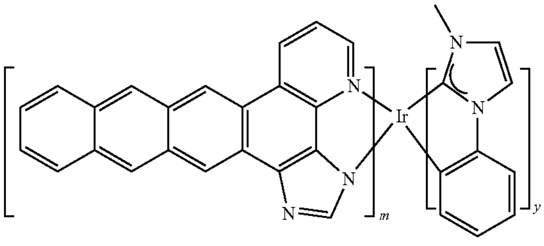
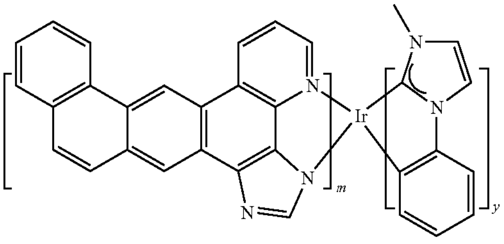

-continued
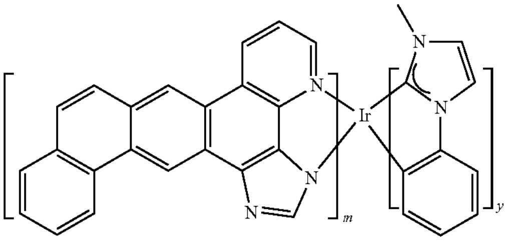
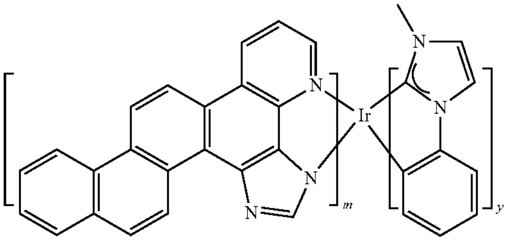
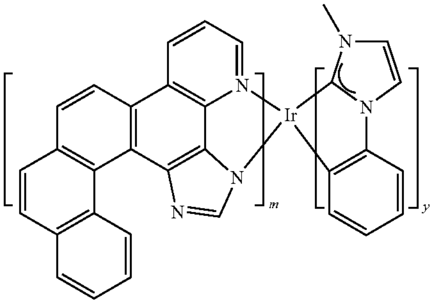
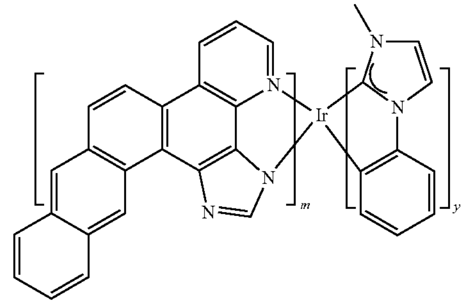
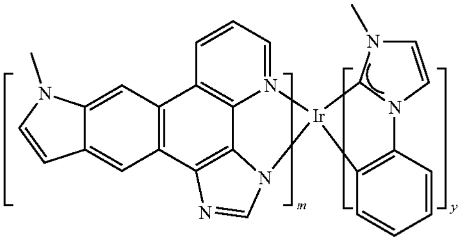
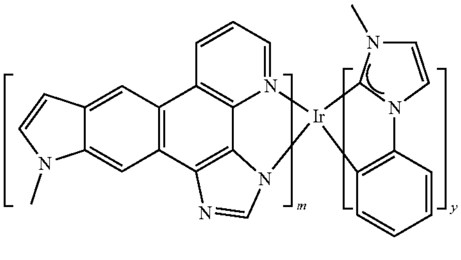
-continued
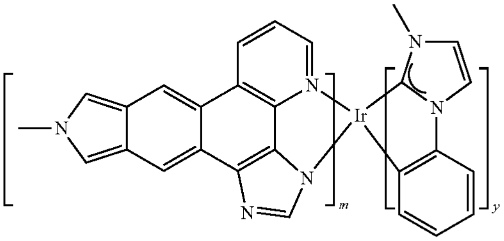
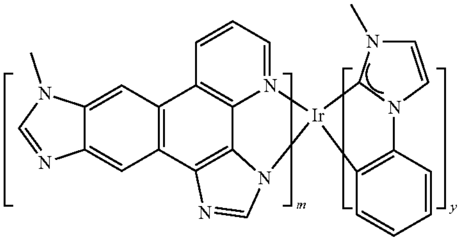
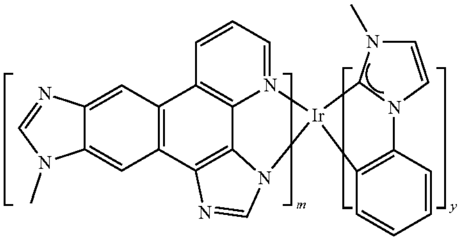
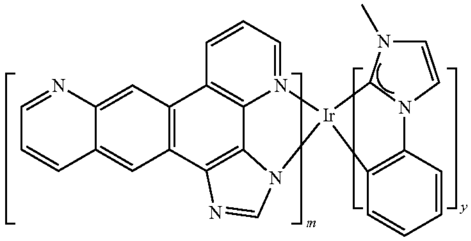
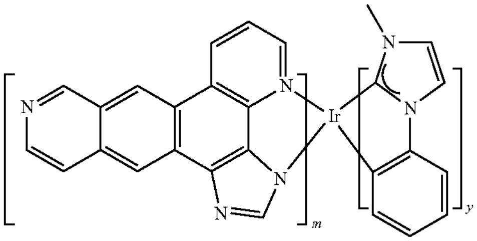
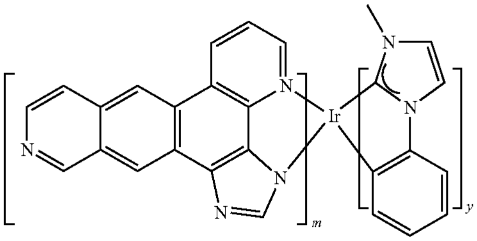
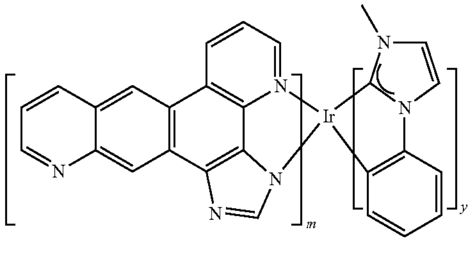

-continued
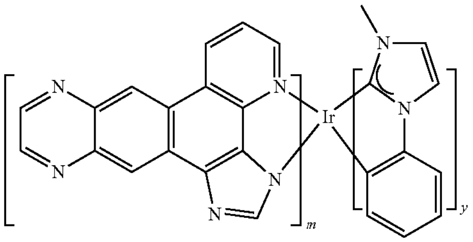
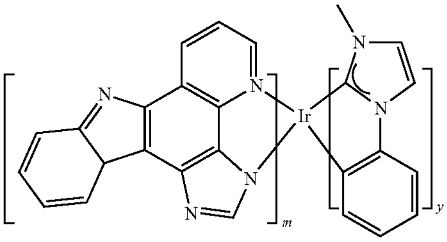
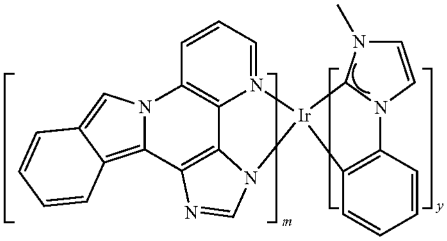
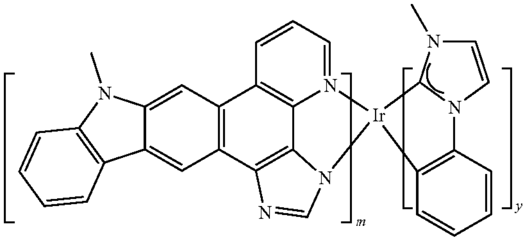
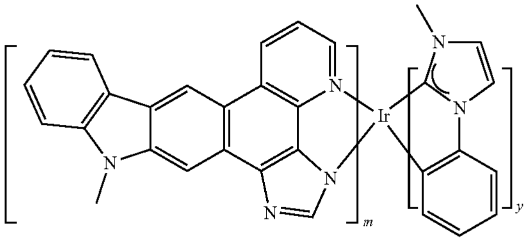
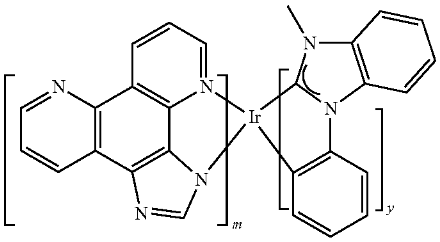
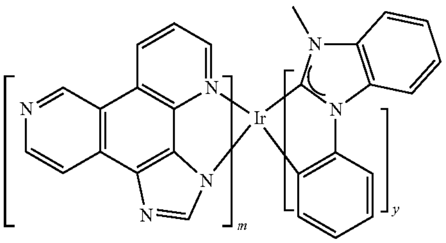
-continued
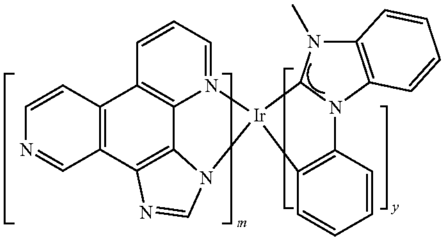
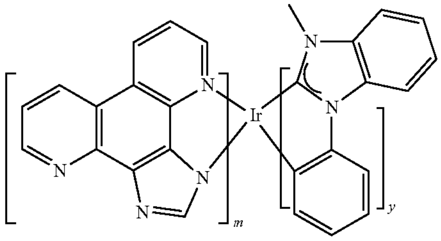
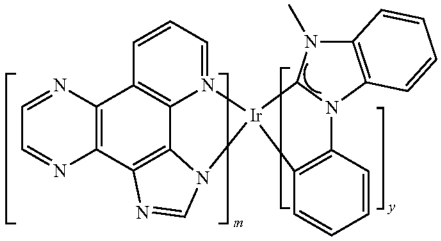
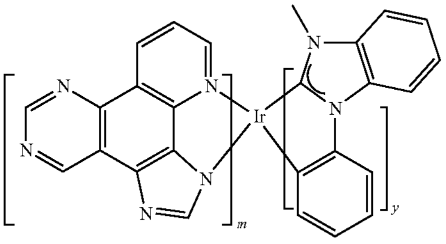
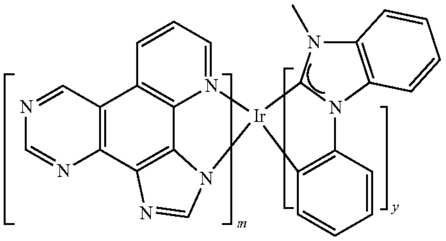
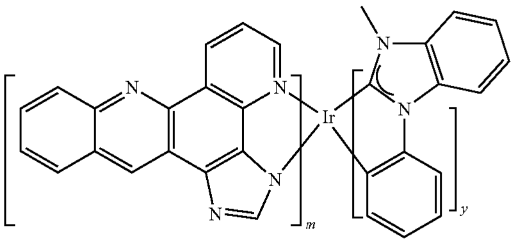
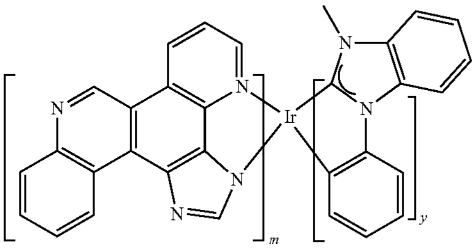

-continued
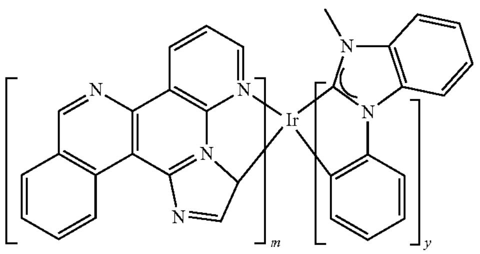
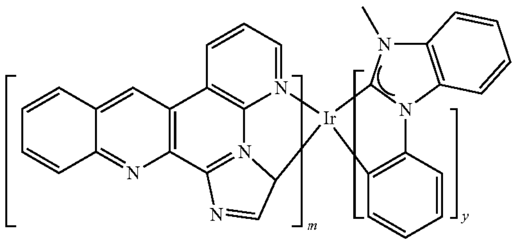
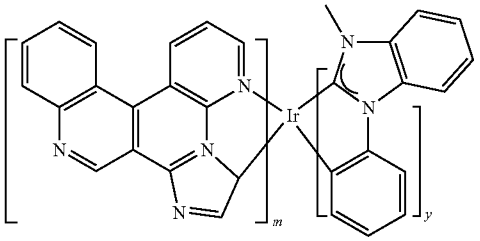
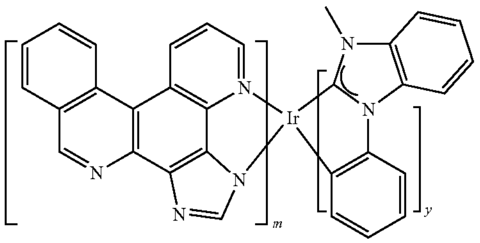
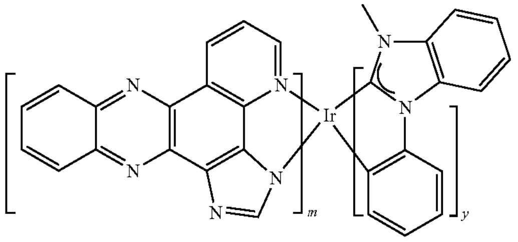
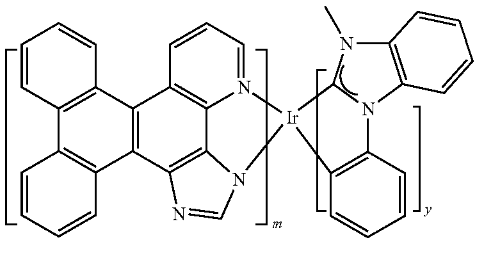
-continued
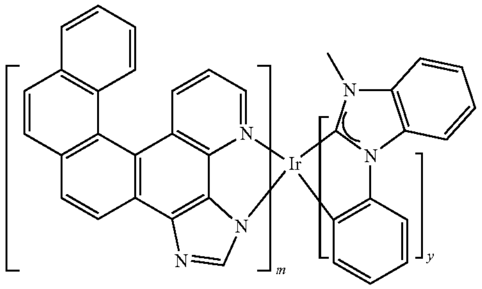
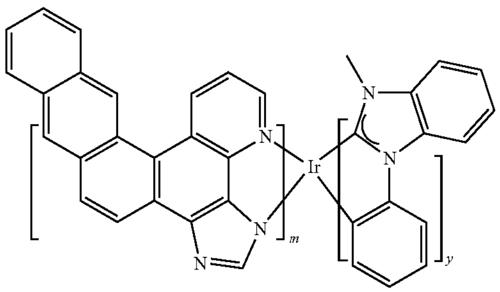
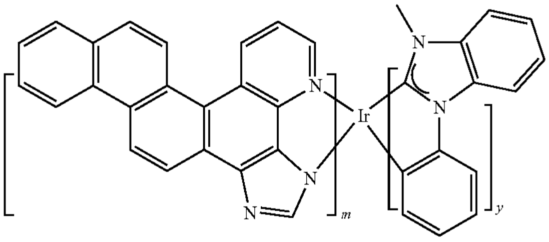
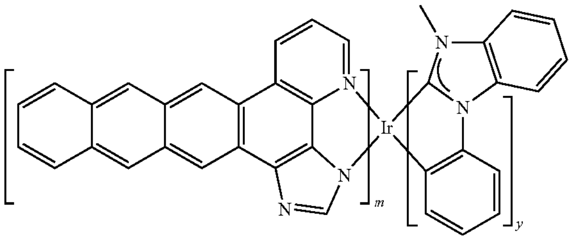
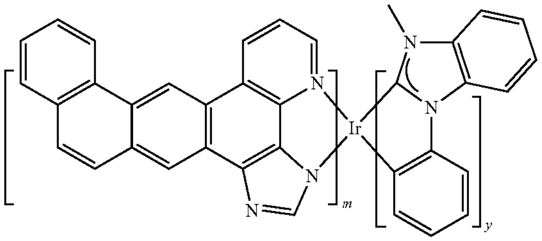
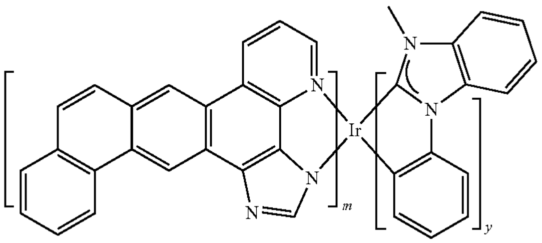

-continued
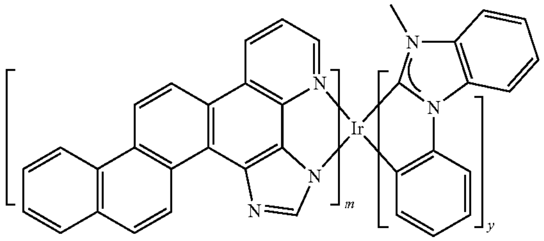
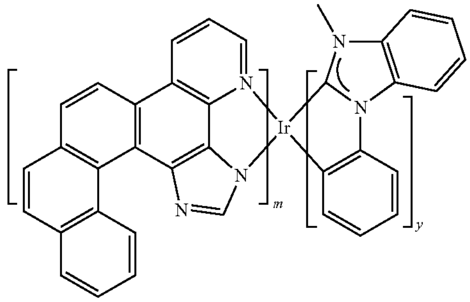
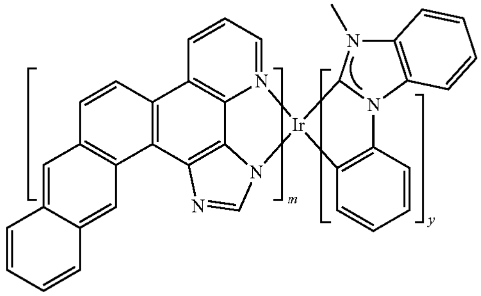
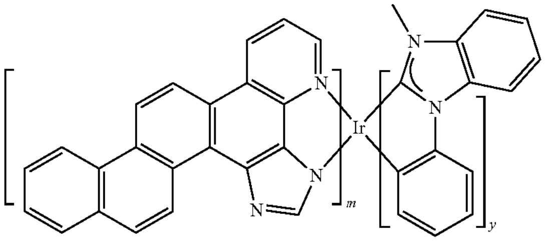
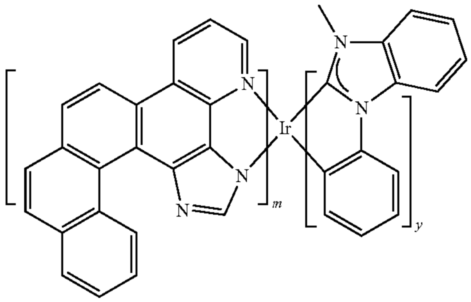
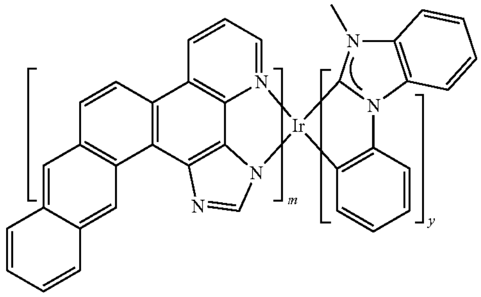
-continued
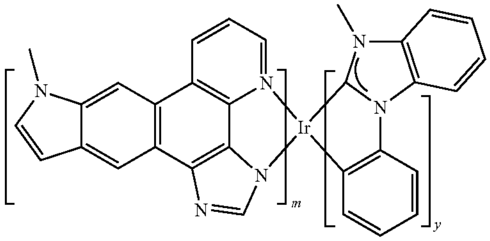
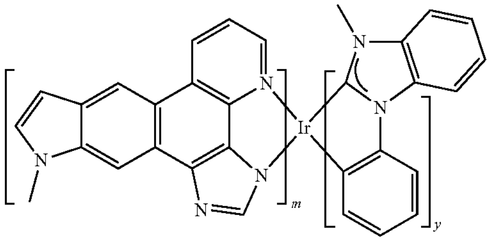
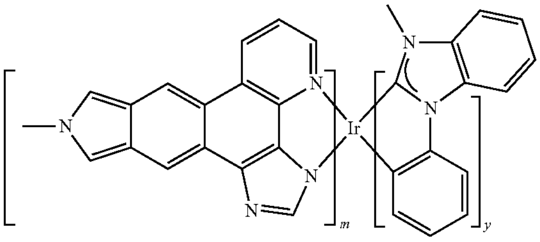
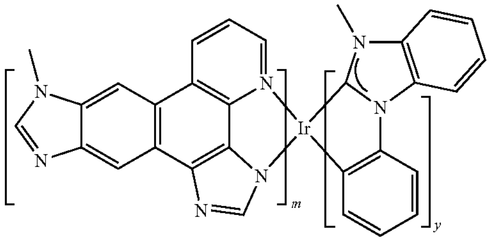
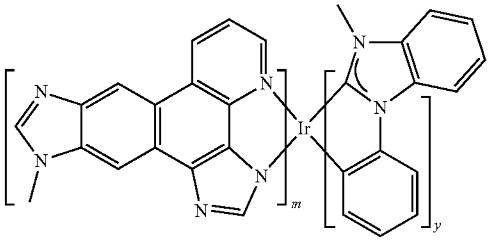
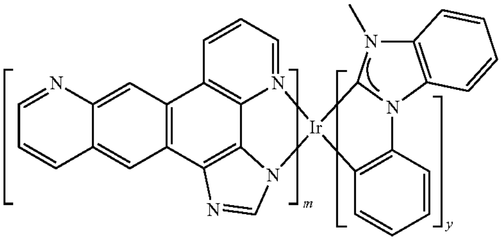
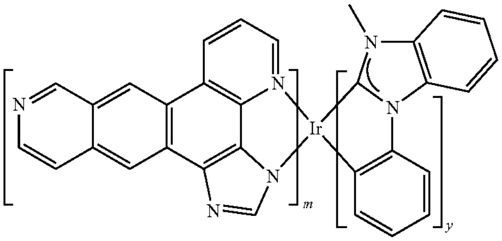

-continued
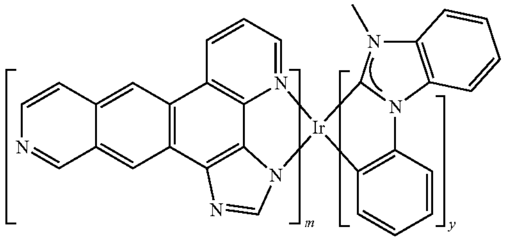
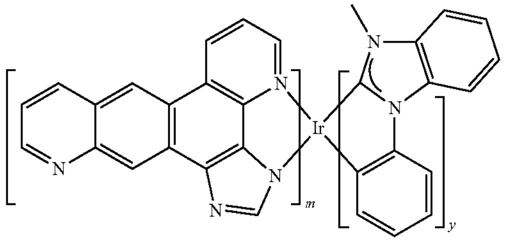
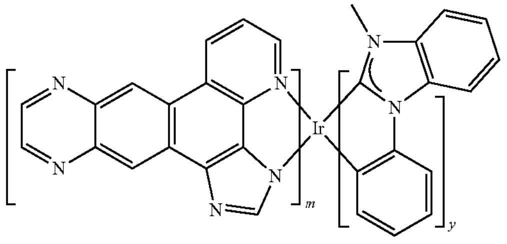
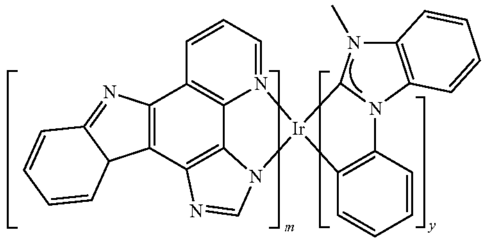
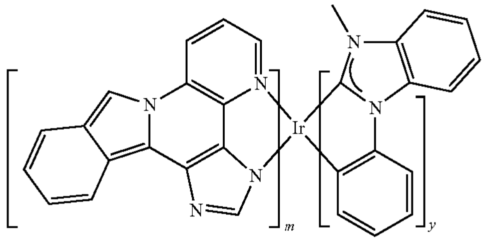
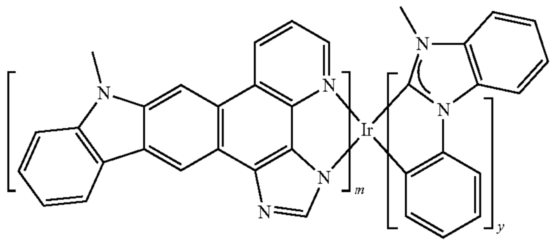
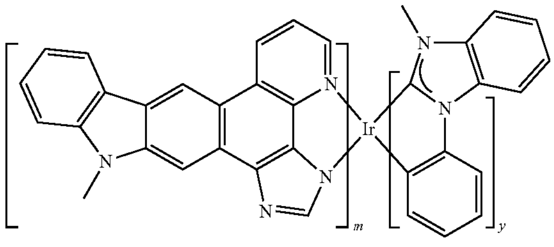
-continued
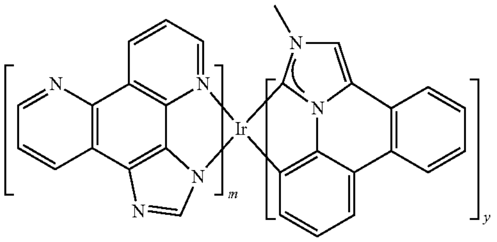
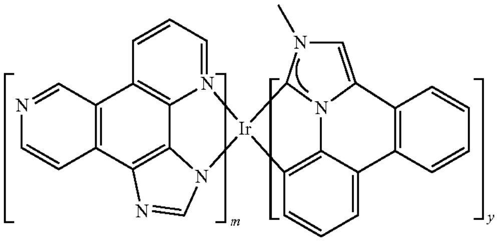
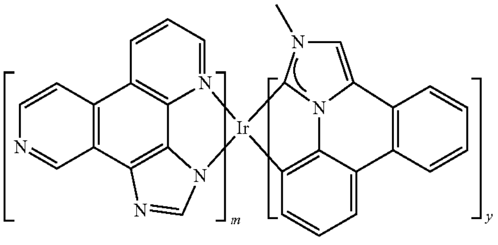
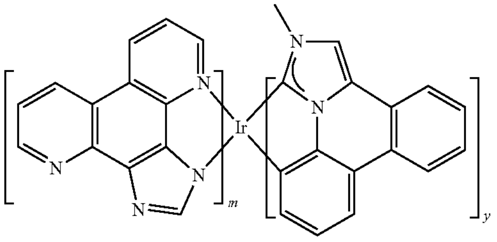
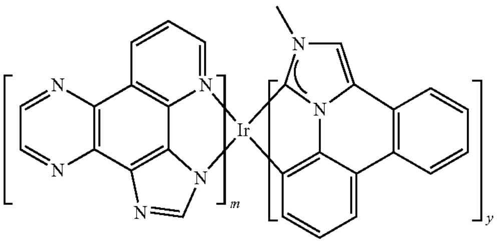
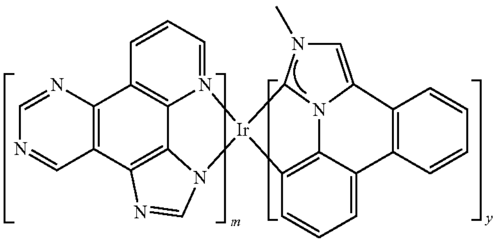
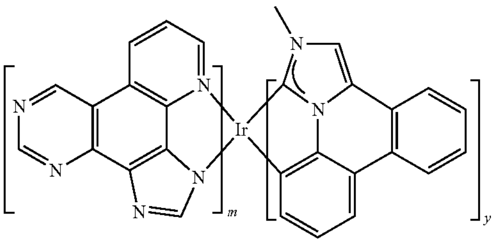

-continued
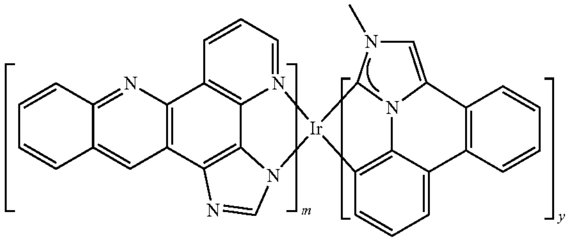
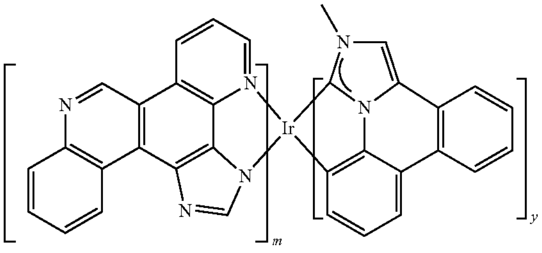
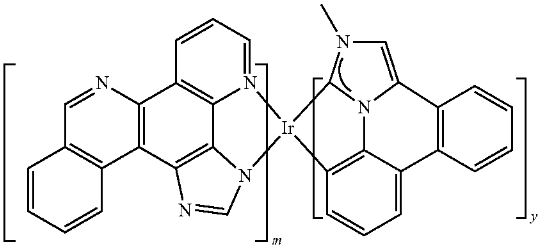
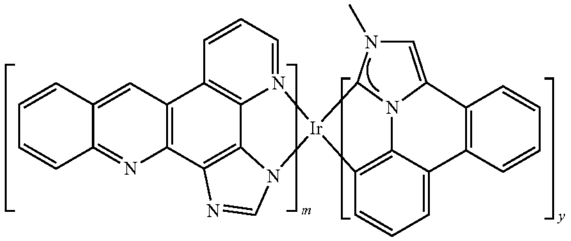
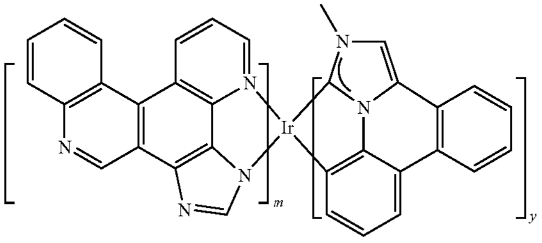
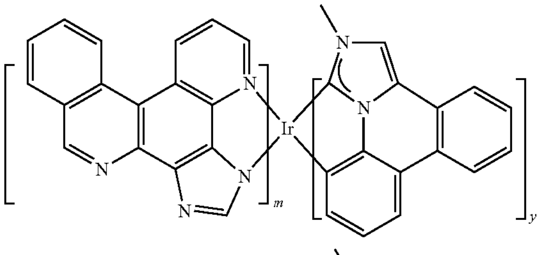
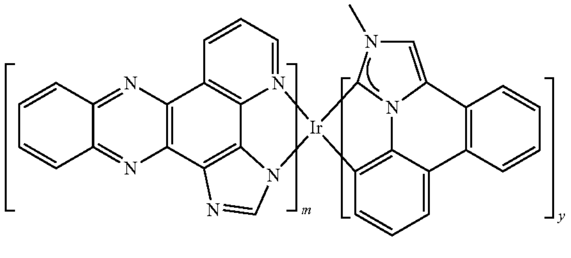
-continued
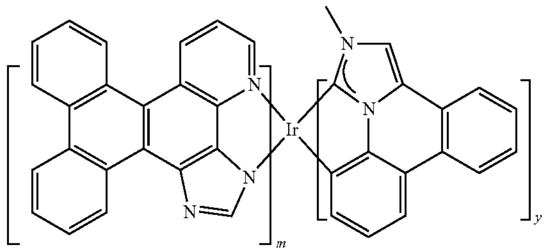
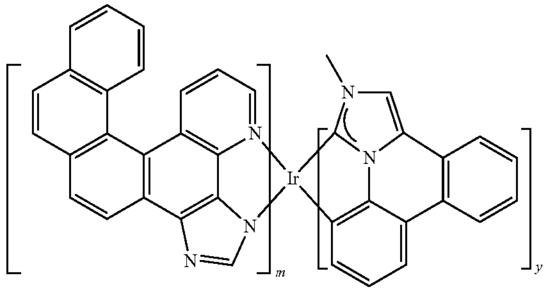
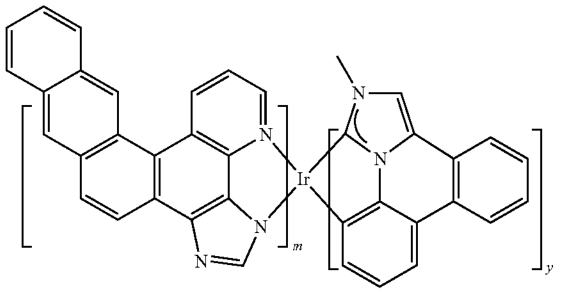
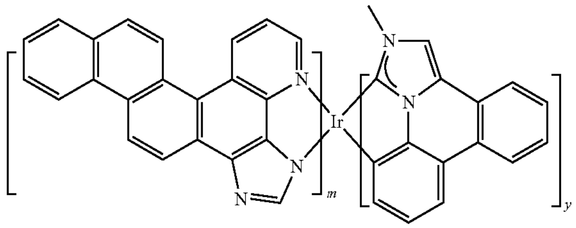
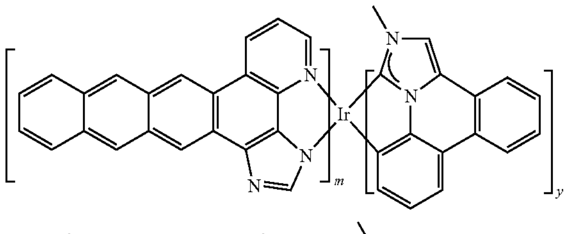
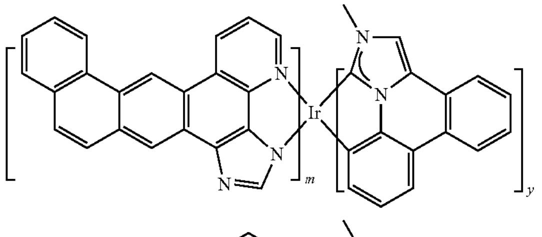
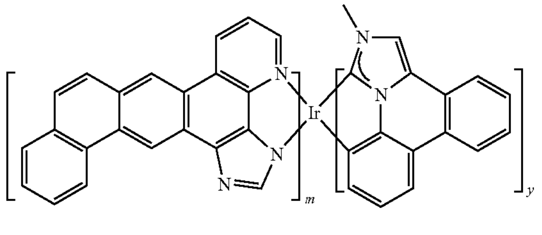

-continued
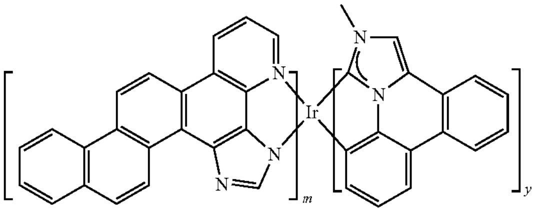
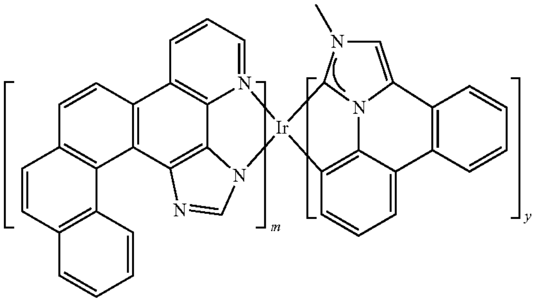
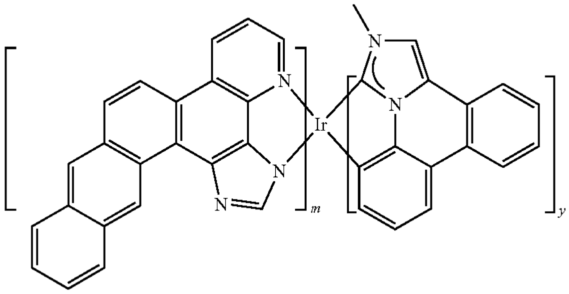
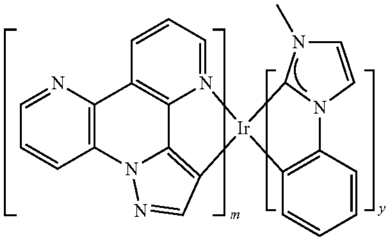
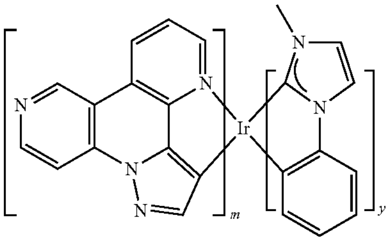
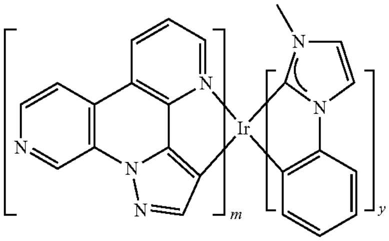
-continued
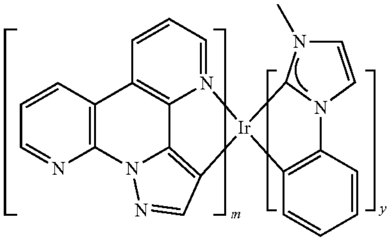
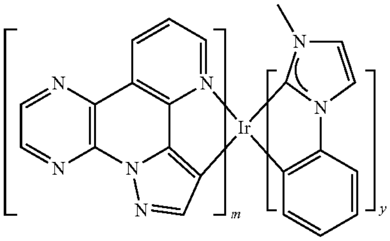
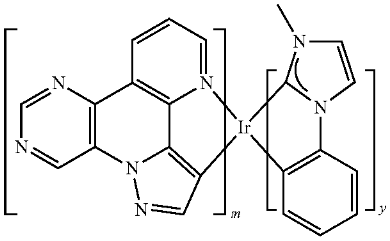
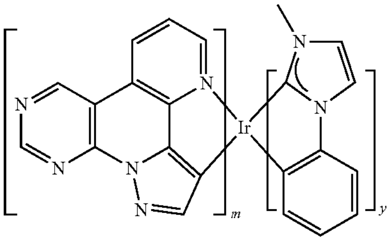
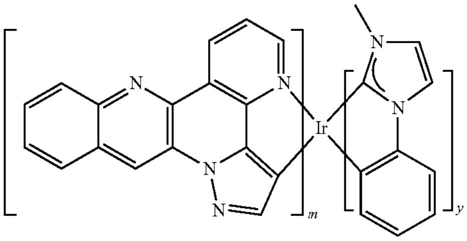
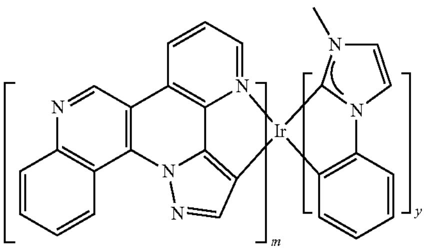
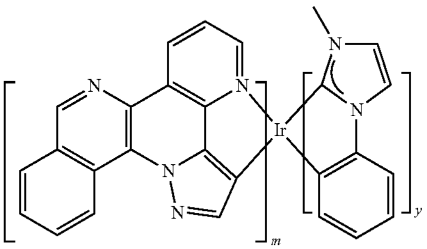

-continued
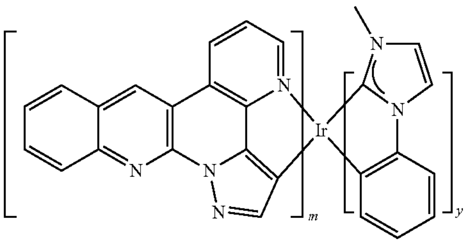
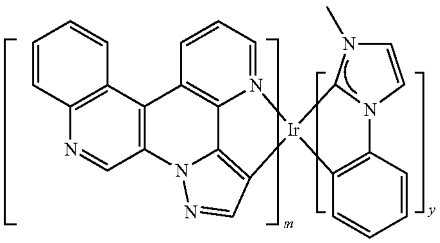
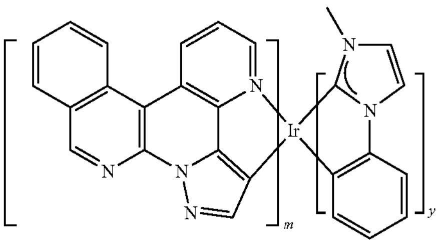
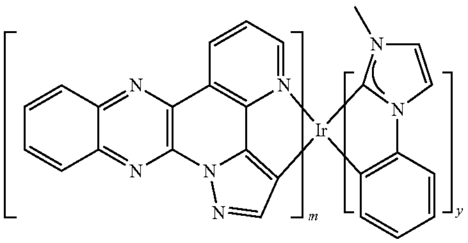
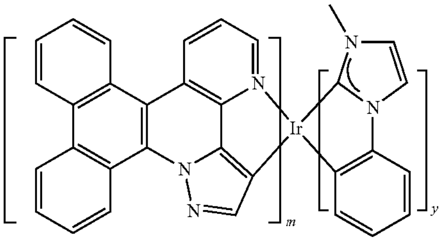
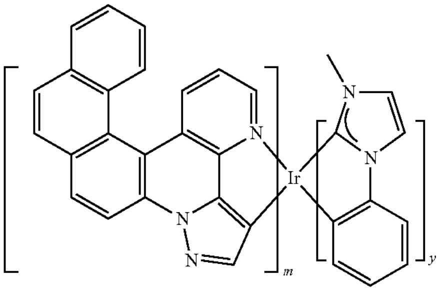
-continued
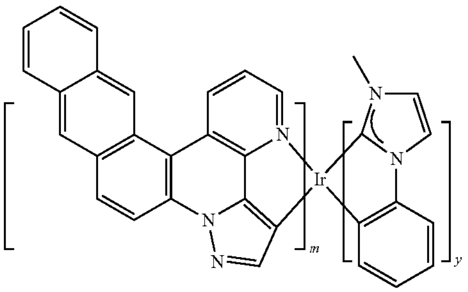
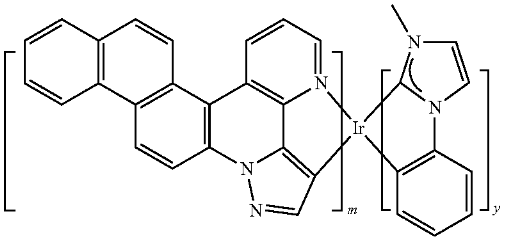
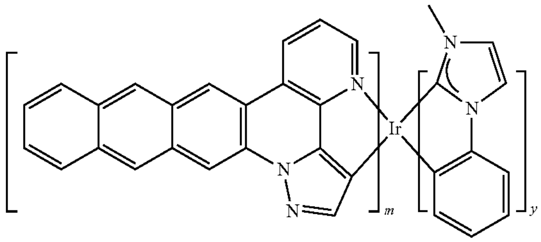
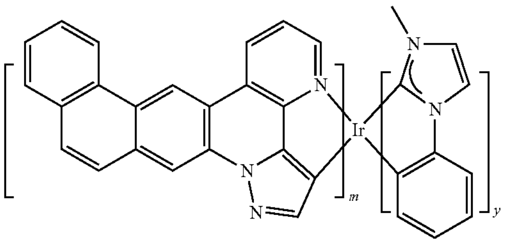
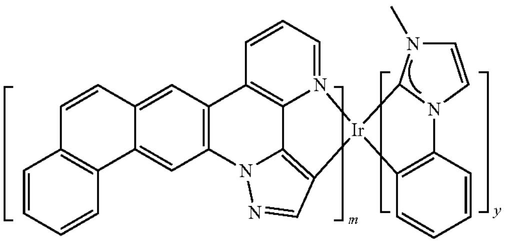
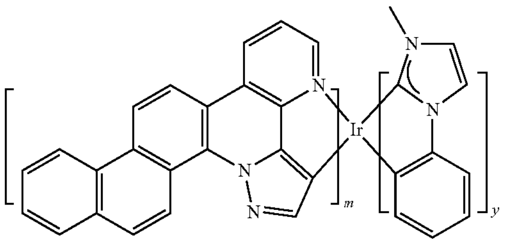

-continued
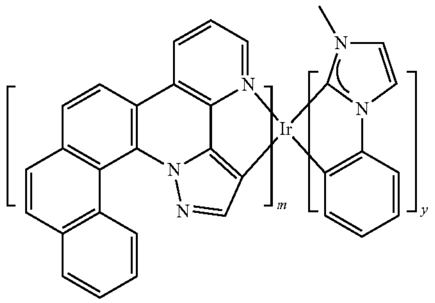
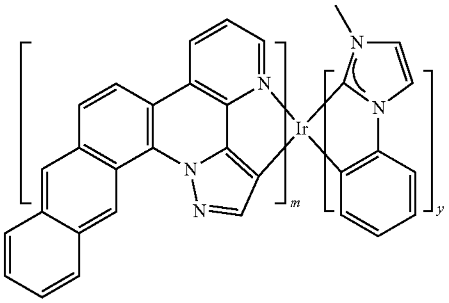
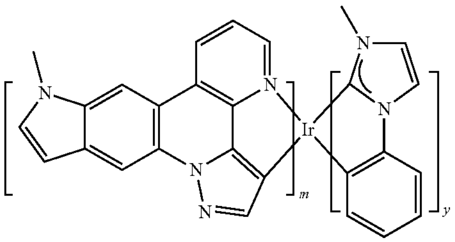
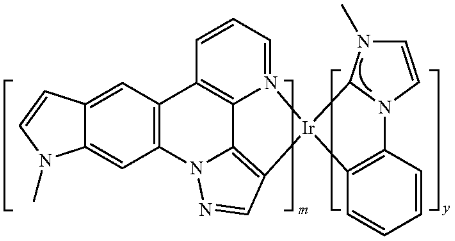
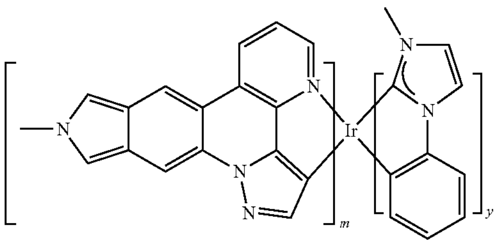
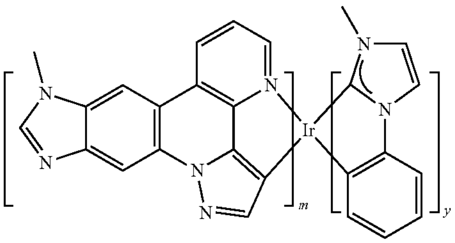
-continued
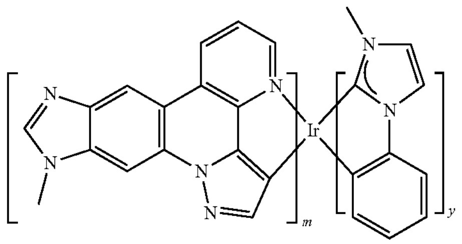
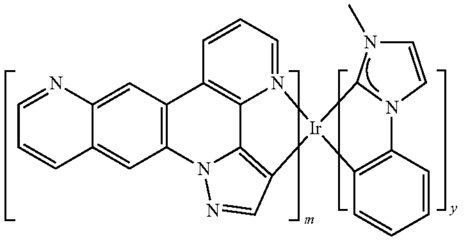
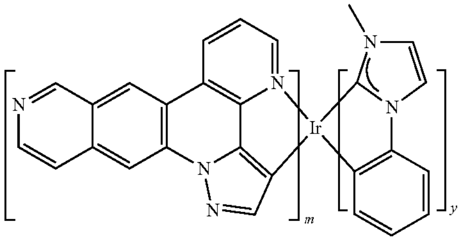
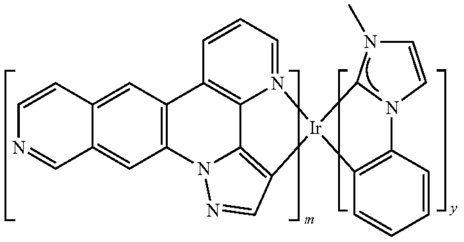
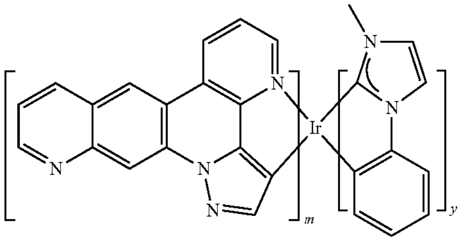
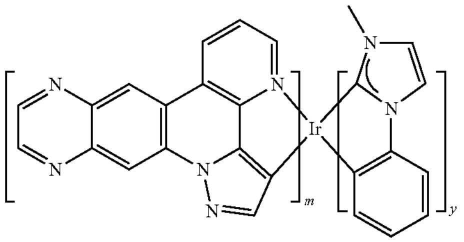
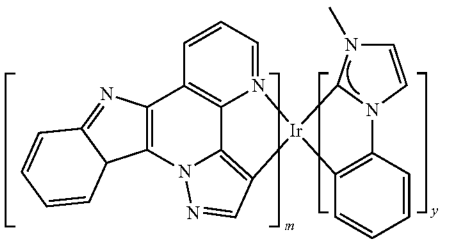

-continued
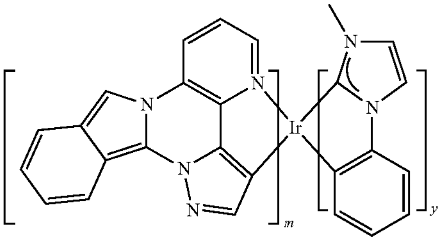
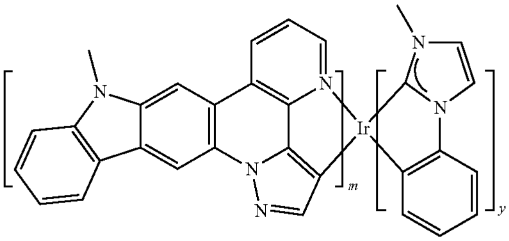
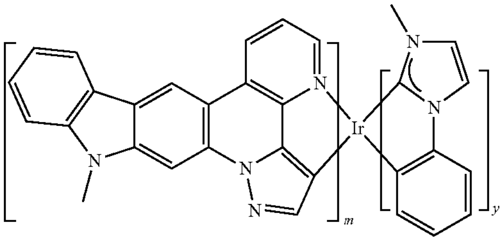
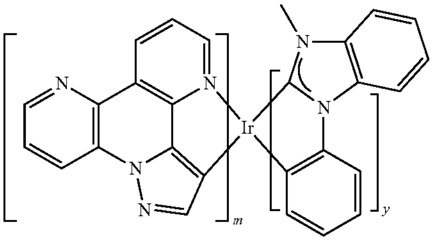
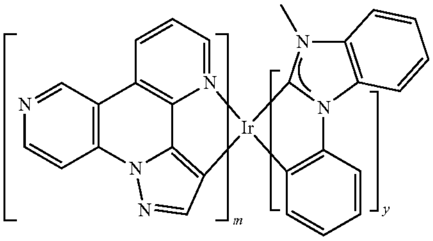
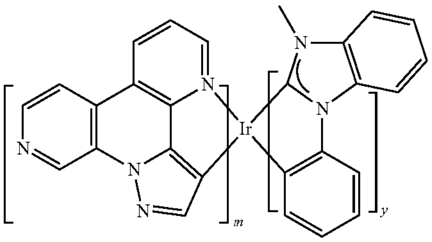
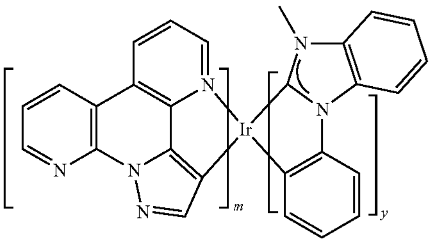
-continued
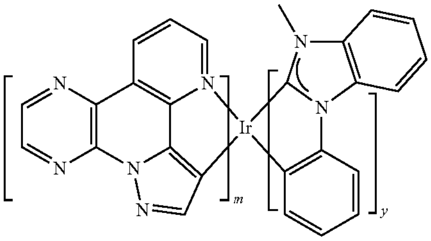
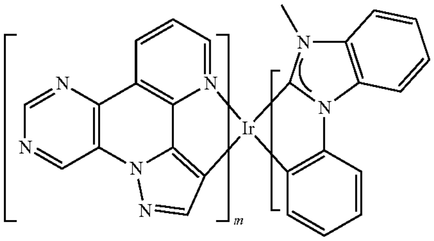
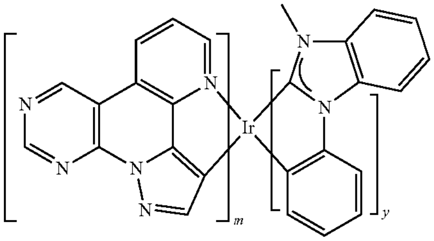
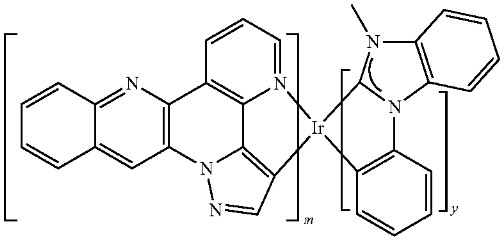
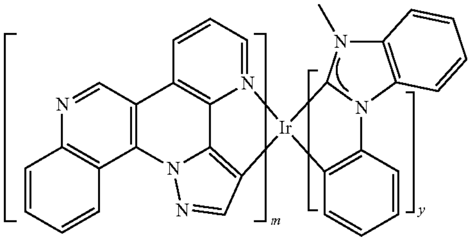
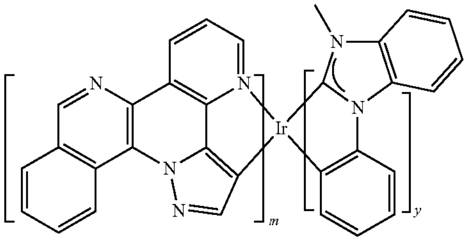
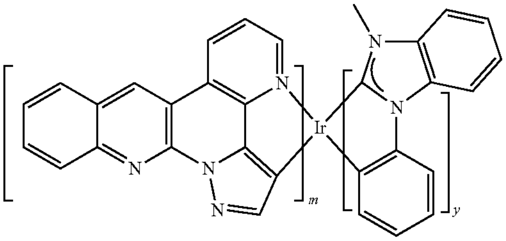

-continued
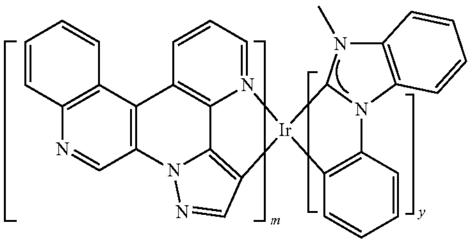
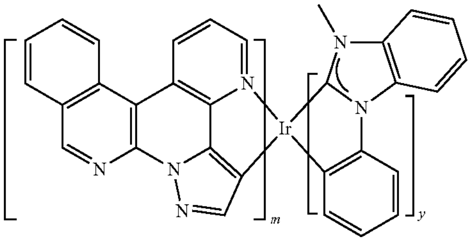
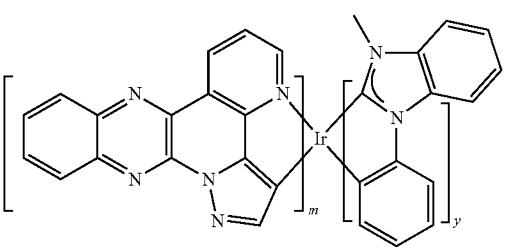
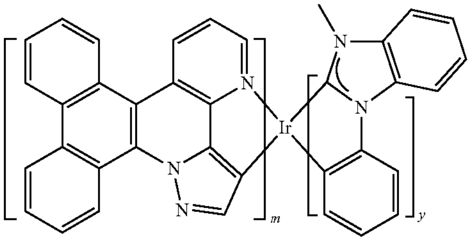
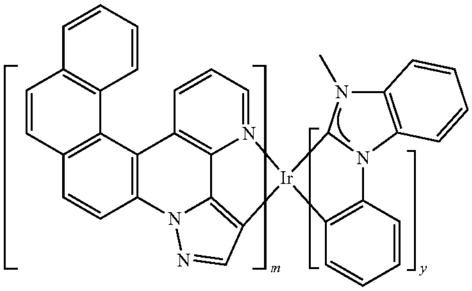
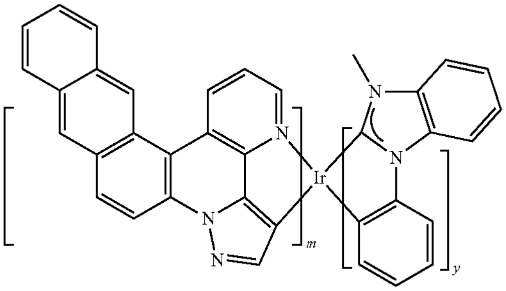
-continued
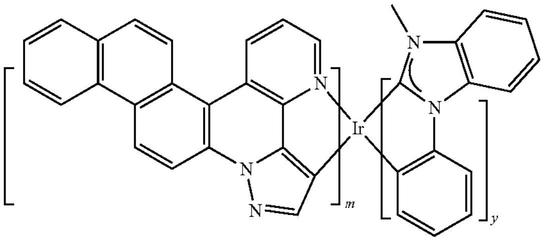
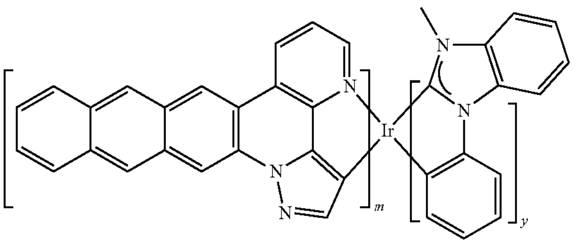
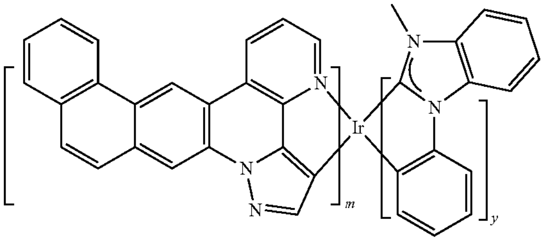
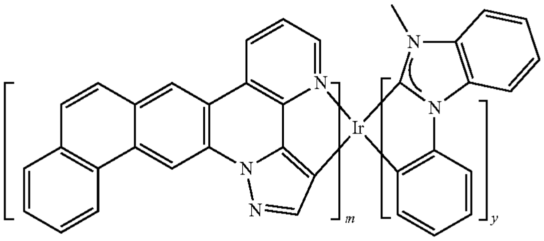
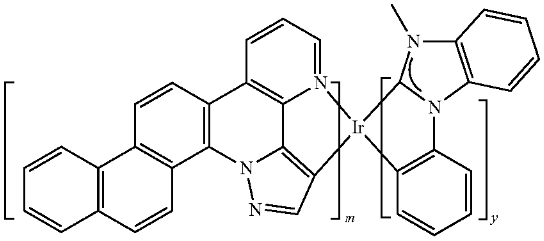
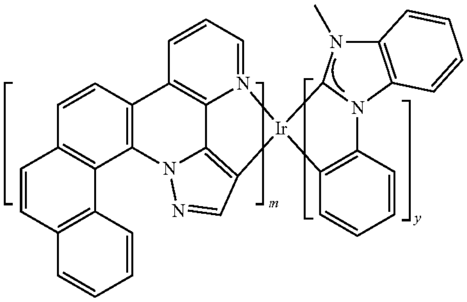

-continued
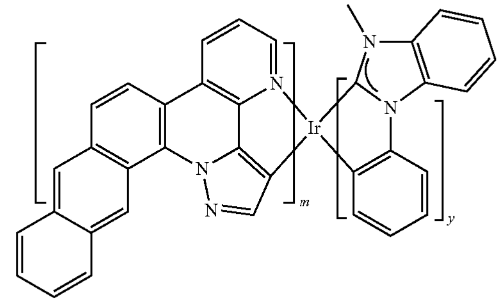
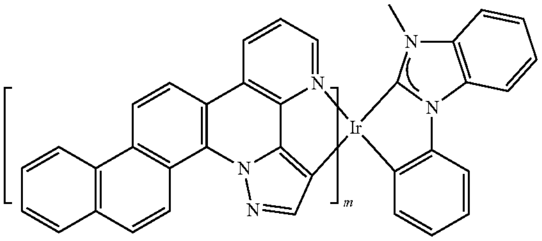
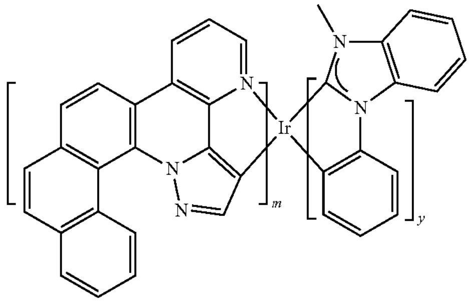
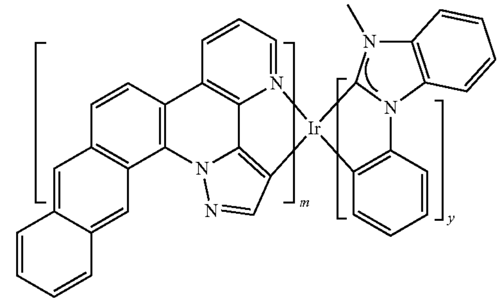
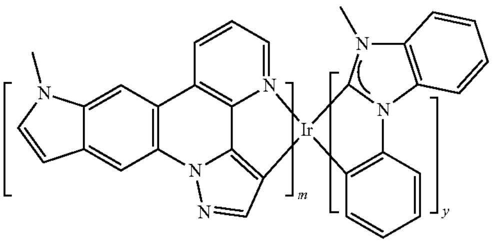
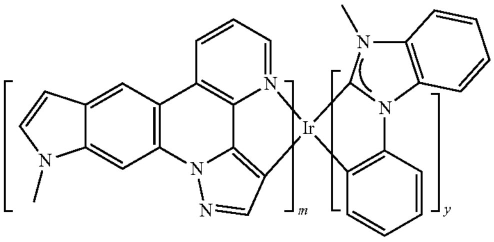
-continued
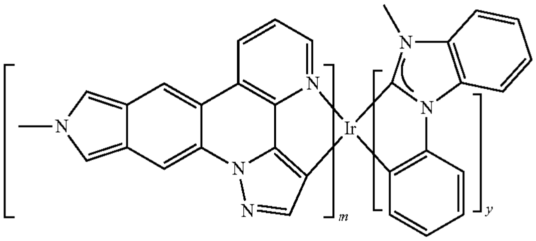
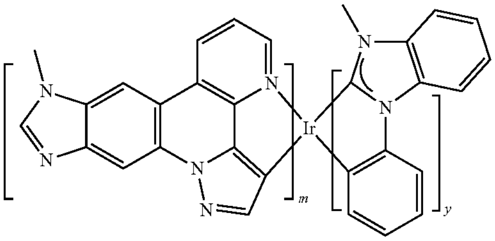
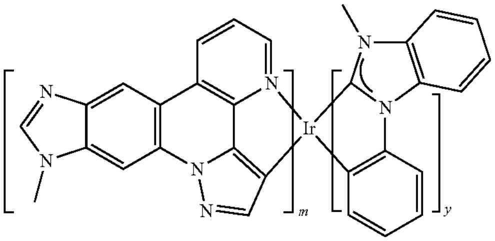
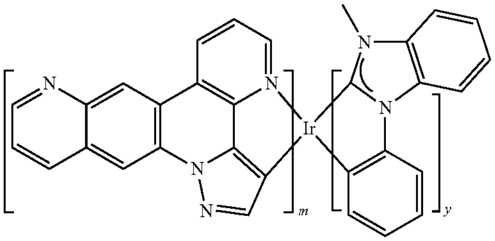
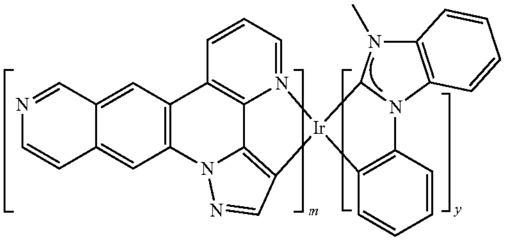
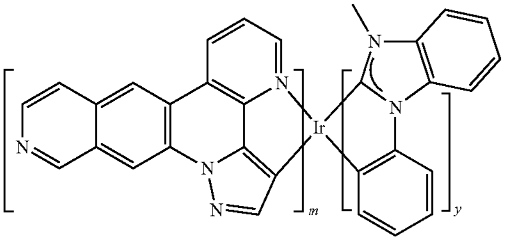
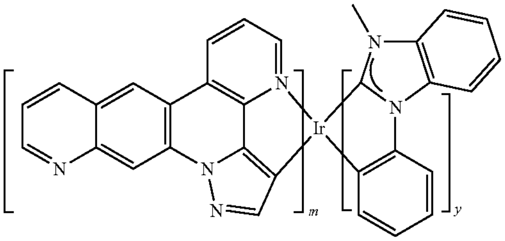

-continued
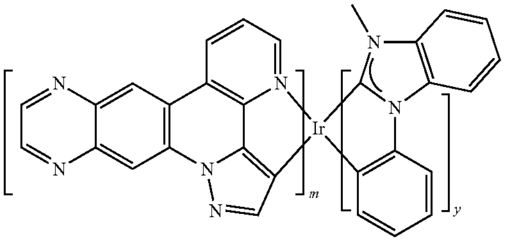
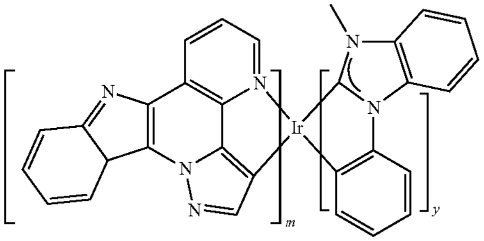
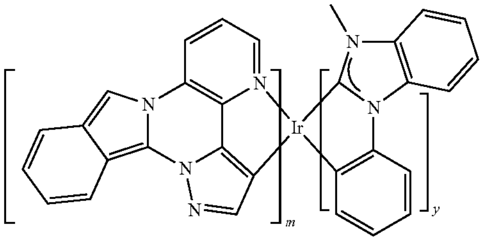
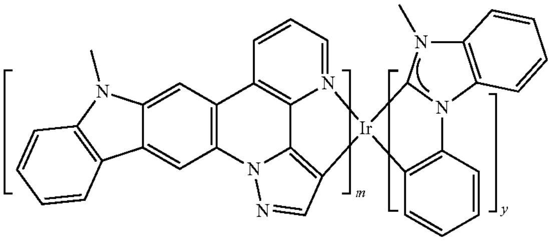
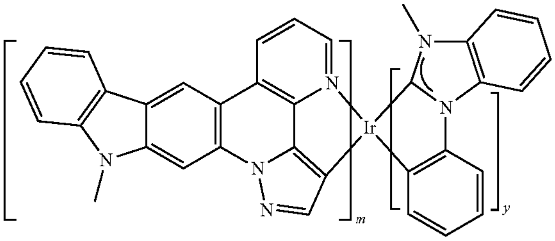
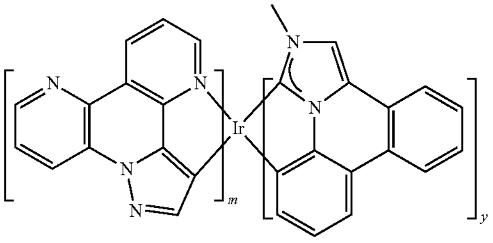
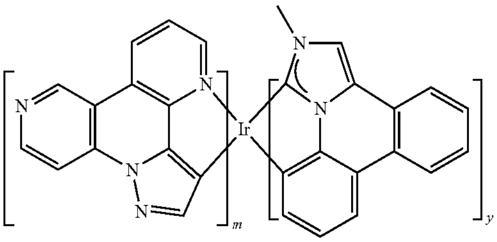
-continued
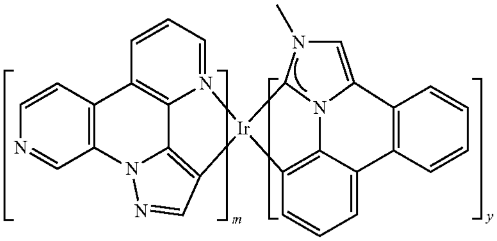
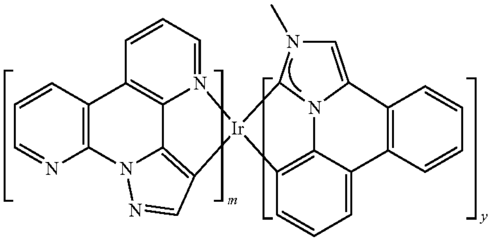
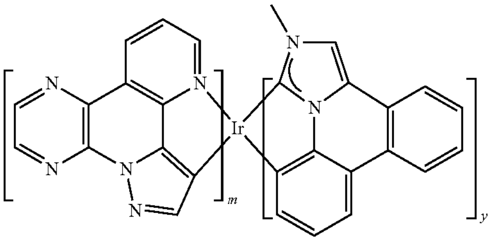
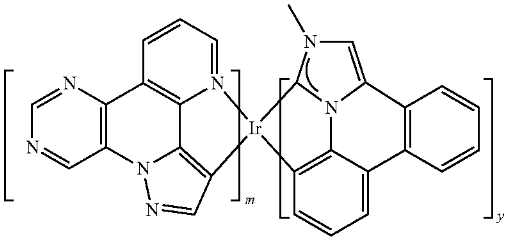
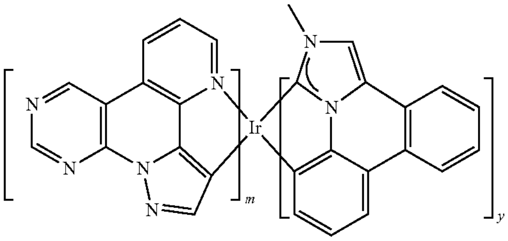
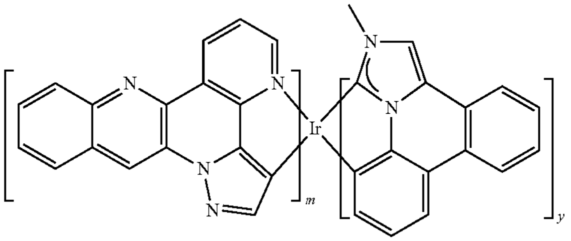
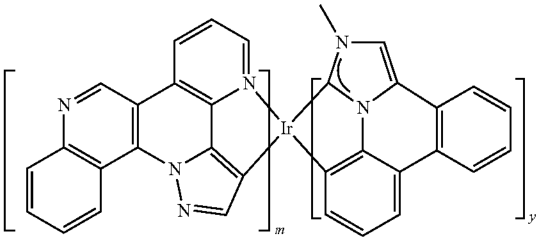

-continued
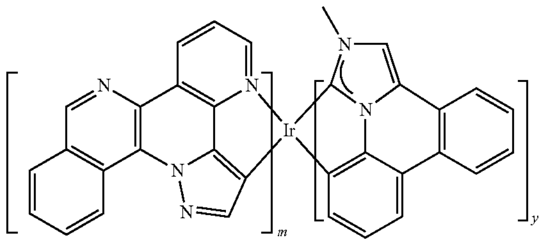
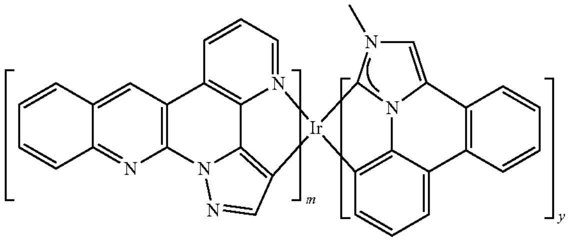
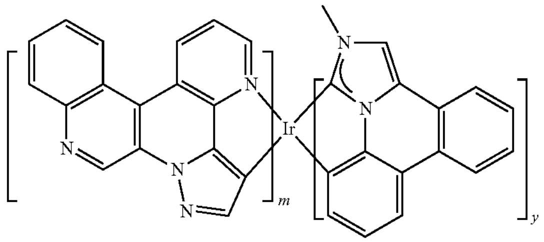
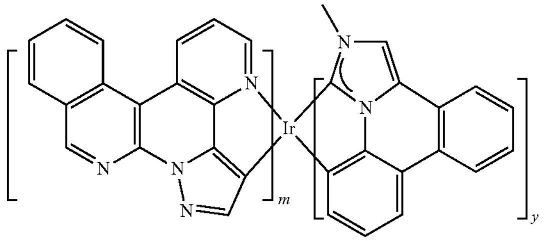
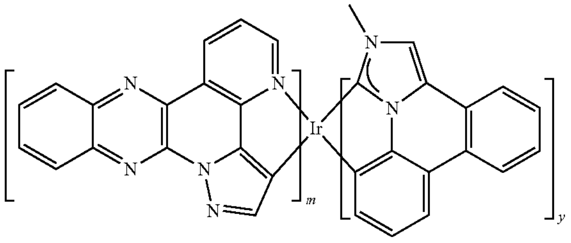
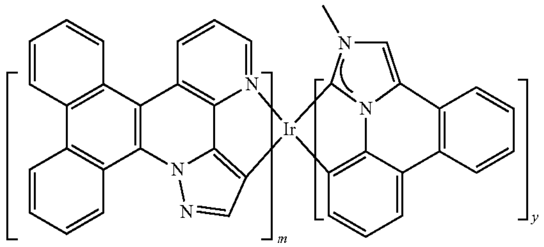
-continued
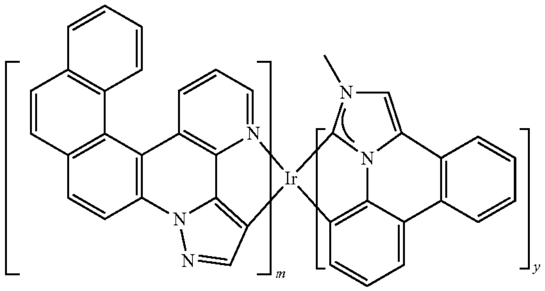
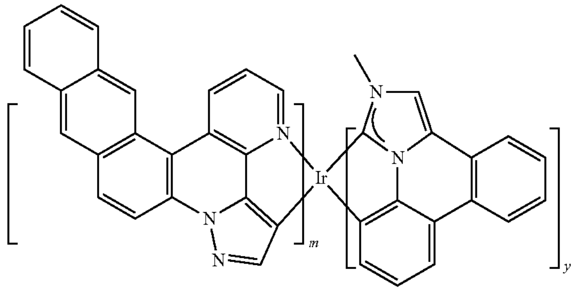
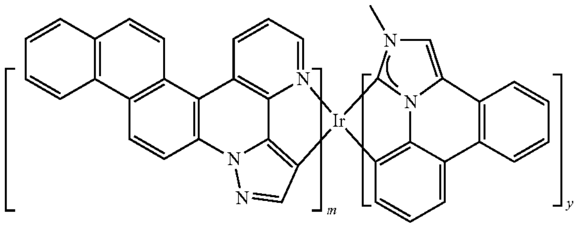
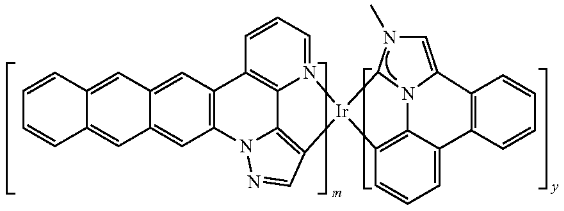
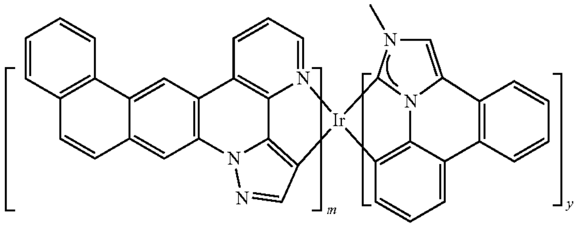
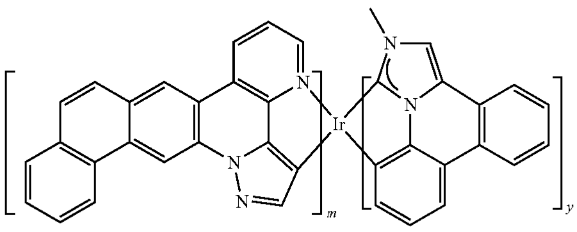
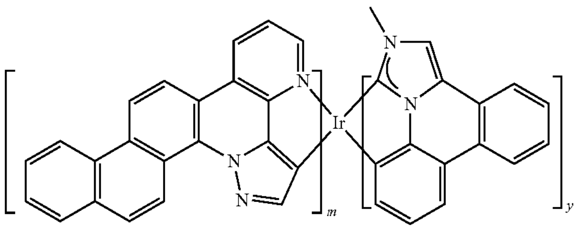

-continued

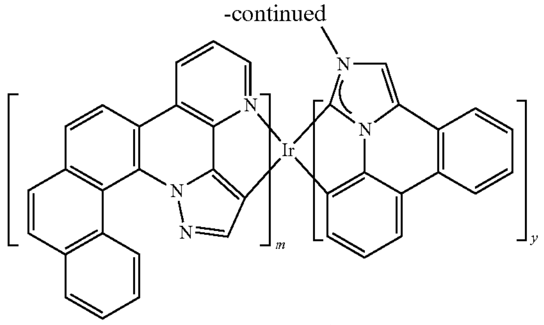

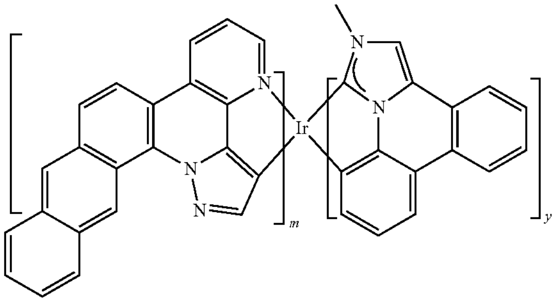

As referred to herein, a linking atom or group connects two atoms such as, for example, an N atom and a C atom. A linking atom or group is in one aspect disclosed as $L^1$, $L^2$, $L^3$, etc. herein. The linking atom can optionally, if valency permits, have other chemical moieties attached. For example, in one aspect, an oxygen would not have any other chemical groups attached as the valency is satisfied once it is bonded to two groups (e.g., N and/or C groups). In another aspect, when carbon is the linking atom, two additional chemical moieties can be attached to the carbon. Suitable chemical moieties include amine, amide, thiol, amyl, heteroaryl, cycloalkyl, and heterocyclyl moieties. The term "cyclic structure" or the like terms used herein refer to any cyclic chemical structure which includes, but is not limited to, aryl, heteroaryl, cycloalkyl, cycloalkenyl, heterocyclyl, carbene, and N-heterocyclic carbene.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$", "$A^2$", "$A^3$", "$A^4$" and "$A^5$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent (s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy." a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The terms "alkoxy" and "alkoxyl" as used herein to refer to an alkyl or cycloalkyl group bonded through an ether linkage; that is, an "alkoxy" group can be defined as $—OA^1$ where $A^1$ is alkyl or cycloalkyl as defined above. "Alkoxy" also includes polymers of alkoxy groups as just described;

that is, an alkoxy can be a polyether such as —$OA^1$-$OA^2$ or —$OA^1$-$(OA^2)_a OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C{=}C(A^3A^4)$ are intended to include both the E and Z isomers. This can be presumed in structural formulae herein wherein an asymmetric alkene is present, or it can be explicitly indicated by the bond symbol C═C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C═C. Examples of cycloalkenyl groups include, but are not limited to cyclopropenyl, cyclobutenyl, cyclopentenyl, cyclopentadienyl, cyclohexenyl, cyclohexadienyl, norbornyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "amyl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C═O.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —$N(\text{-alkyl})_2$ where alkyl is a described herein. Representative examples include, but are not limited to, dimethylamino group, diethylamino group, dipropylamino group, diisopropylamino group, dibutyl amino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —$OC(O)A^1$ or —$C(O)OA^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula -$(A^1O(O)C\text{-}A^2\text{-}C(O)O)_a$— or -$(A^1O(O)C\text{-}A^2\text{-}OC(O))_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an alkyl, cycloalkyl, alkenyl, cycloalkenyl, alkynyl, cycloalkynyl, aryl or heteroaryl group described herein. The term "polyether" as used herein is represented by the formula -$(A^1O\text{-}A^2O)_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" or "halo" as used herein refers to the halogens fluorine, chlorine, bromine, and iodine.

The term "heterocyclyl," as used herein refers to single and multi-cyclic non-aromatic ring systems and "heteroaryl as used herein refers to single and multi-cyclic aromatic ring systems: in which at least one of the ring members is other than carbon. The terms includes azetidine, dioxane, furan, imidazole, isothiazole, isoxazole, morpholine, oxazole, oxazole, including, 1,2,3-oxadiazole, 1,2,5-oxadiazole and 1,3,4-oxadiazole, piperazine, piperidine, pyrazine, pyrazole, pyridazine, pyridine, pyrimidine, pyrrole, pyrrolidine, tetrahydrofuran, tetrahydropyran, tetrazine, including 1,2,4,5-tetrazine, tetrazole, including 1,2,3,4-tetrazole and 1,2,4,5-tetrazole, thiadiazole, including, 1,2,3-thiadiazole, 1,2,5-thiadiazole, and 1,3,4-thiadiazole, thiazole, thiophene, triazine, including 1,3,5-triazine and 1,2,4-triazine, triazole, including, 1,2,3-triazole, 1,3,4-triazole, and the like.

The term "hydroxyl" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" as used herein is represented by the formula $—N_3$.

The term "nitro" as used herein is represented by the formula $—NO_2$.

The term "cyanide" as used herein is represented by the formula —CN.

The term "silyl" as used herein is represented by the formula $—SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas $—S(O)A^1$, $—S(O)_2A^1$, $—OS(O)_2A^1$, or $—OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S═O. The term "sulfonyl" is used herein to refer to the sulfo-oxo group represented by the formula $—S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"R," "$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Compounds described herein may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. In is also contemplated that, in certain aspects, unless expressly indicated to the contrary, individual substituents can be further optionally substituted (i.e., further substituted or unsubstituted).

In some aspects, a structure of a compound can be represented by a formula:

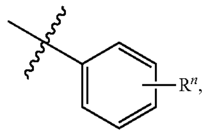

which is understood to be equivalent to a formula:

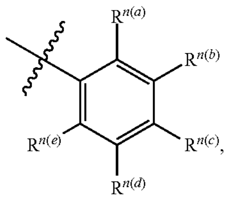

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance. In a case where there is a single $R^n$ (e.g., only $R^{n(a)}$), $R^n$ is referred to as a "single substituent." In a case where there are two or more $R^n$ (e.g., at least $R^{n(a)}$ and $R^{n(b)}$) $R^n$ is referred to as a "multiple substituents."

Several references to R, $R^1$, $R^2$, $R^3$, $R^4$, $R^5$, $R^6$, etc. are made in chemical structures and moieties disclosed and described herein. Any description of R, $R^1$, $R^2$, $R^3$, $R^4$, $R^5$, $R^6$, etc. in the specification is applicable to any structure or moiety reciting R, $R^1$, $R^2$, $R^3$, $R^4$, $R^5$, $R^6$, etc. respectively.

The compounds disclosed herein are suited for use in a wide variety of devices, including, for example, organic light emitting diodes (OLEDs) for full color displays and lighting applications.

Also disclosed herein are compositions including one or more compounds disclosed herein. The present disclosure provides light emitting device that include one or more compositions described herein. The present disclosure also provides a photovoltaic device comprising one or more complexes or compositions described herein. Further, the present disclosure also provides a luminescent display device comprising one or more compounds described herein.

Compounds described herein can be used in a light emitting device such as an OLED. FIG. 1 depicts a cross-sectional view of an OLED 100. OLED 100 includes substrate 102, anode 104, hole-transporting material(s) (HTL) 106, light processing material 108, electron-transporting material(s) (ETL) 110, and a metal cathode layer 112. Anode 104 is typically a transparent material, such as indium tin oxide. Light processing material 108 may be an emissive material (EML) including an emitter and a host.

In various aspects, any of the one or more layers depicted in FIG. 1 may include indium tin oxide (ITO), poly(3,4-ethylenedioxythiophene) (PEDOT), polystyrene sulfonate (PSS), N,N'-di-1-naphthyl-N,N-diphenyl-1,1'-biphenyl-4,4'diamine (NPD), 1,1-bis((di-4-tolylamino)phenyl)cyclohexane (TAPC), 2,6-Bis(N-carbazolyl)pyridine (mCpy), 2,8-bis(diphenylphosphoryl)dibenzothiophene (PO15), LiF, Al, or a combination thereof.

Light processing material 108 may include one or more compounds of the present disclosure optionally together with a host material. The host material can be any suitable host material known in the art. The emission color of an OLED is determined by the emission energy (optical energy gap) of the light processing material 108, which can be tuned by tuning the electronic structure of the emitting compounds, the host material, or both. Both the hole-transporting material in the HTL layer 106 and the electron-transporting material(s) in the ETL layer 110 may include any suitable hole-transporter known in the art.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to be limiting in scope. Some of these synthetic examples have been performed. Others are based on an understanding of related synthetic procedures and are predictive in nature. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Various methods for the preparation method of the compounds described herein are recited in the examples. These methods are provided to illustrate various methods of preparation, but are not intended to limit any of the methods recited herein. Accordingly, one of skill in the art in possession of this disclosure could readily modify a recited method or utilize a different method to prepare one or more of the compounds described herein. The following aspects are only exemplary and are not intended to be limiting in scope. Temperatures, catalysts, concentrations, reactant compositions, and other process conditions can vary, and one of skill in the art, in possession of this disclosure, could readily select appropriate reactants and conditions for a desired complex.

Examples of General Formulas I-XIII

Example 1

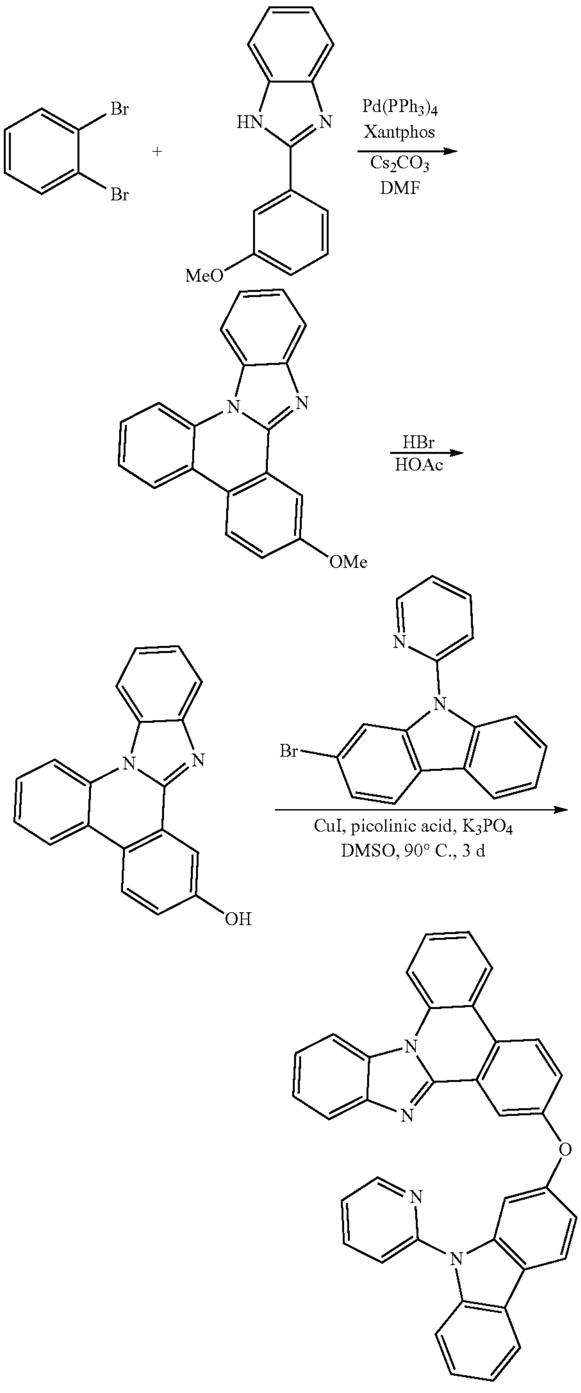

L1

Benzo[4,5]imidazo[1,2-f]phenanthridin-7-ol (284.3 mg, 1 mmol, 1.0 eq), 2-bromo-9-(pyridin-2-yl)-9H-carbazole (388 mg, 1.2 mmol, 1.2 eq), CuI (38 mg, 0.2 mmol, 0.2 eq), picolinic acid (49 mg, 0.4 mmol, 0.4 eq) and $K_3PO_4$ (4.25 mg, 2 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 90° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L1 in 30%~70% yield.

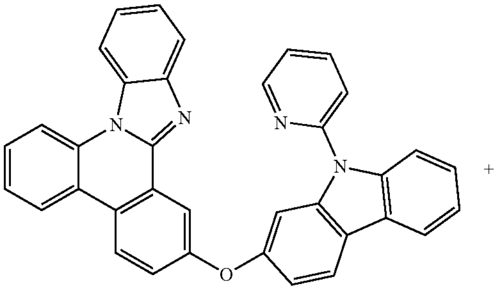

L1

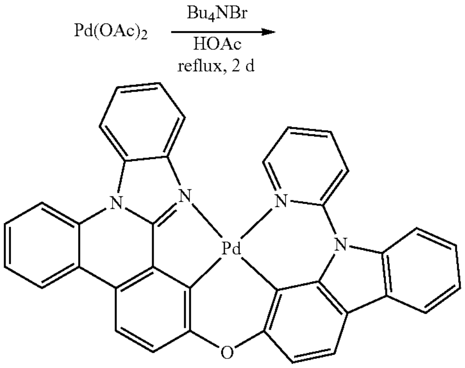

MC1

L1 (0.20 mmol, 1.0 eq), $Pd(OAc)_2$ (54 mg, 0.24 mmol, 1.2 eq) and n-$Bu_4NBr$ (6.5 mg, 0.02 mmol, 0.1 eq) were added to a dry pressure tube, which was taken into a glove box and acetic acid (10 mL) added. The mixture was bubbled with nitrogen for 30 minutes and then the tube was sealed. Then the mixture was heated to reflux in an oil bath and stirred for 2 days, cooled to ambient temperature and the solvent removed. Then the solid was purified through column chromatography on silica gel using dichloromethane as eluent to obtain to obtain the desired product MC1 in 10%~50% yield.

Example 2

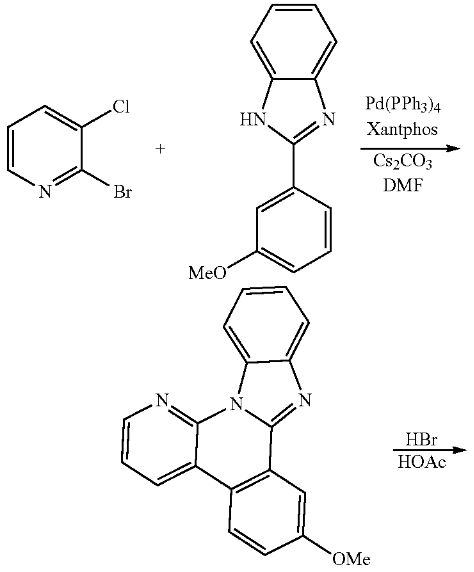

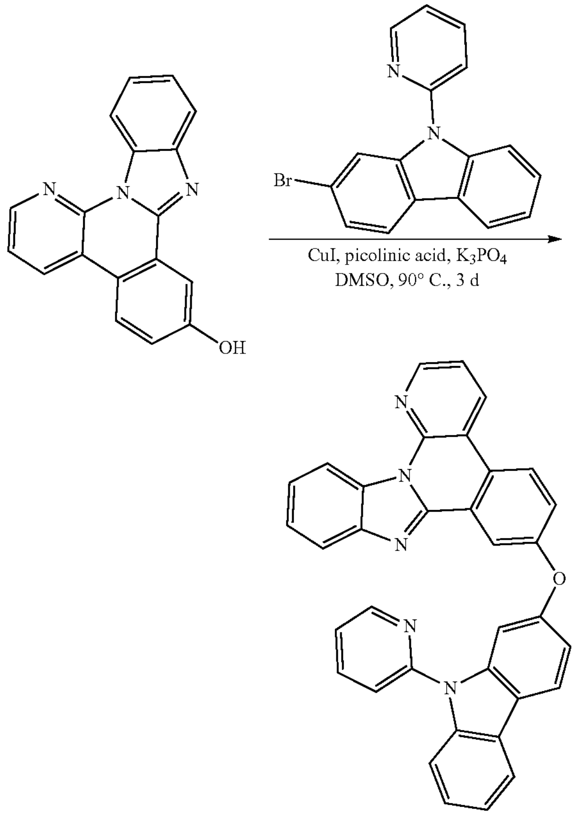

L2

Benzo[c]benzo[4,5]imidazo[1,2-a][1,8]naphthyridin-7-ol (285 rag, 1 mmol, 1.0 eq), 2-bromo-9-(pyridin-2-yl)-9H-carbazole (388 mg, 1.2 mmol, 1.2 eq), CuI (38 mg, 0.2 mmol, 0.2 eq), picolinic acid (49 mg, 0.4 mmol, 0.4 eq) and $K_3PO4$ (425 mg, 2 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 90° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L2 in 30%~70% yield.

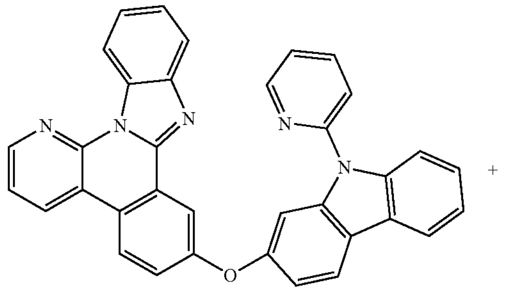

L2

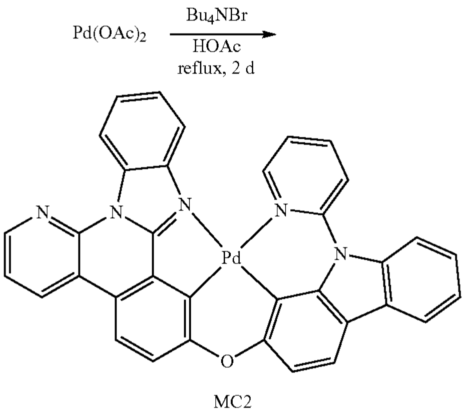

MC2

L2 (0.20 mmol, 1.0 eq), Pd(OAc)$_2$ (54 mg, 0.24 mmol, 1.2 eq) and n-Bu$_4$NBr (6.5 mg, 0.02 mmol, 0.1 eq) were added to a dry pressure tube, which was taken into a glove box and acetic acid (10 mL) was added. The mixture was bubbled with nitrogen for 30 minutes and then the tube was sealed. Then the mixture was heated to reflux in an oil bath and stirred for 2 days, cooled to ambient temperature and the solvent removed. Then the solid was purified through column chromatography on silica gel using dichloromethane as eluent to obtain to obtain the desired product MC2 in 10%~50% yield.

Example 3

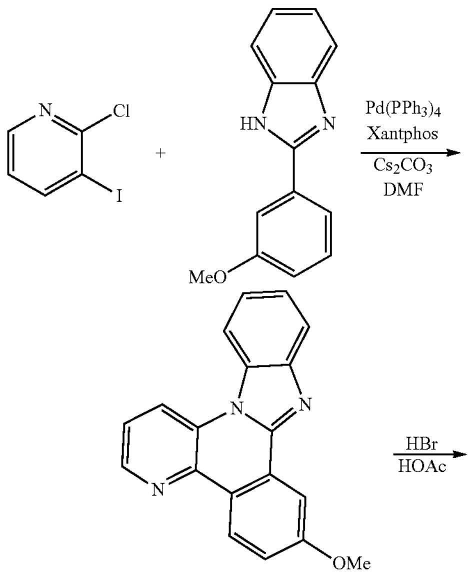

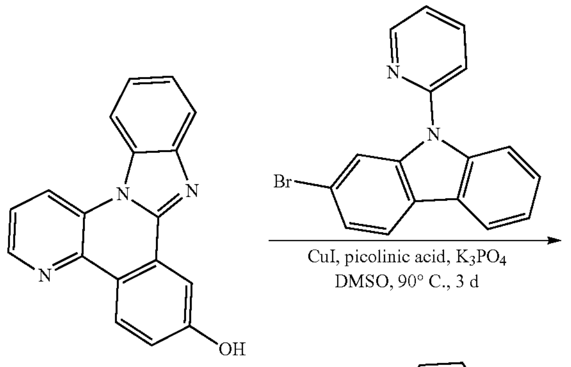

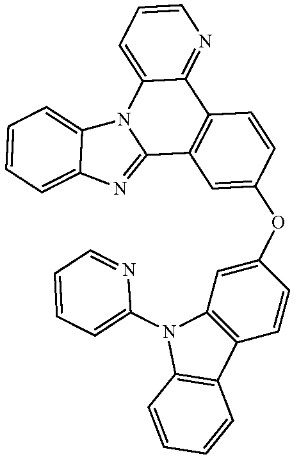

L3

Benzo[c]benzo[4,5]imidazo[1,2-a][1,5]naphthyridin-7-ol (100 mg, 0.35 mmol, 1.0 eq), 2-bromo-9-(pyridin-2-yl)-9H-carbazole (136 mg, 0.42 mmol, 1.2 eq), CuI (13 mg, 0.07 mmol, 0.2 eq), picolinic acid (9 mg, 0.07 mmol, 0.2 eq) and $K_3PO_4$ (149 mg, 0.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (5 mL) was added under the protection of nitrogen. The mixture was stirred in an oil bath at a temperature of 90° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L3 as an orange yellow solid 105 mg in 57% yield.

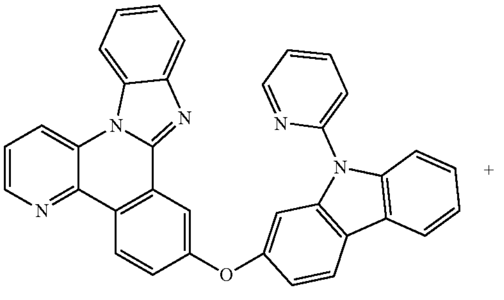

L3

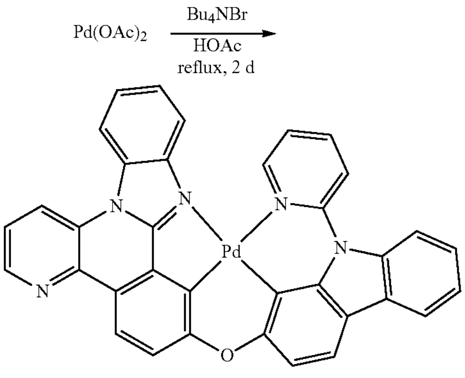

MC3

Figure 2:
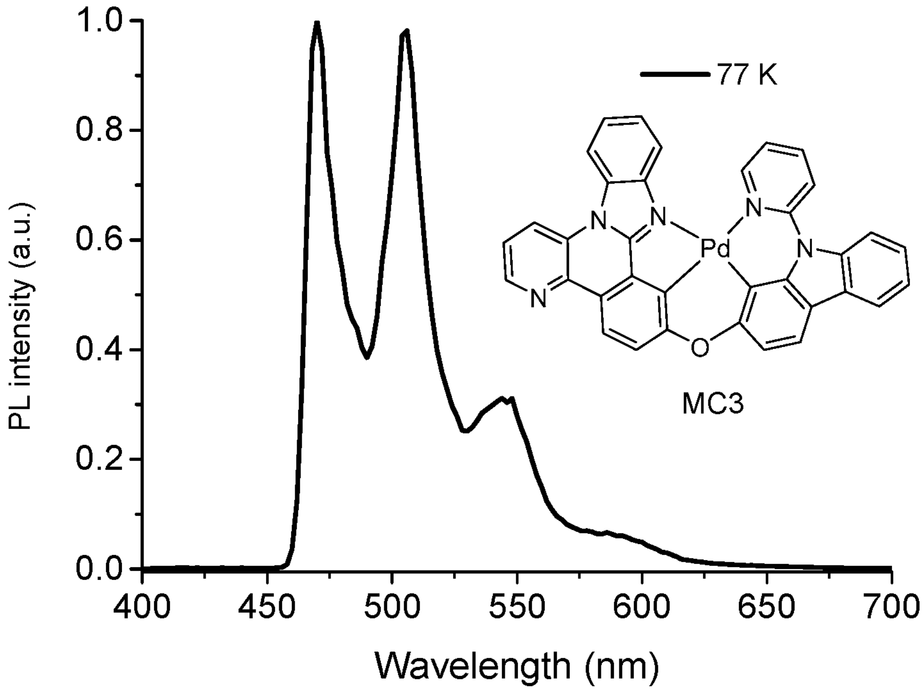
FIG. 2 is an emission spectrum of the metal-assisted delayed fluorescent emitter of Example 3 in tetrahydro-2-methylfuran at 77K.

L3 (95 mg, 0.18 mmol, 1.0 eq), Pd(OAc)$_2$ (43 mg, 0.19 mmol, 1.1 eq) and n-Bu$_4$NBr (6 mg, 0.018 mmol, 0.1 eq) were added to a dry pressure tube, which was taken into a glove box and acetic acid (11 mL) was added. The mixture was bubbled with nitrogen for 30 minutes and then the tube was sealed. Then the mixture was heated to reflux in an oil bath and stirred for 2 days, cooled to ambient temperature and the solvent removed. Then the solid was purified through column chromatography on silica gel using dichloromethane eluent to obtain the desired product MC3 as a white solid 100 mg in 86% yield. FIG. 2 shows an emission spectrum of MC3 in tetrahydro-2-methylfuran at 77K.

Example 4

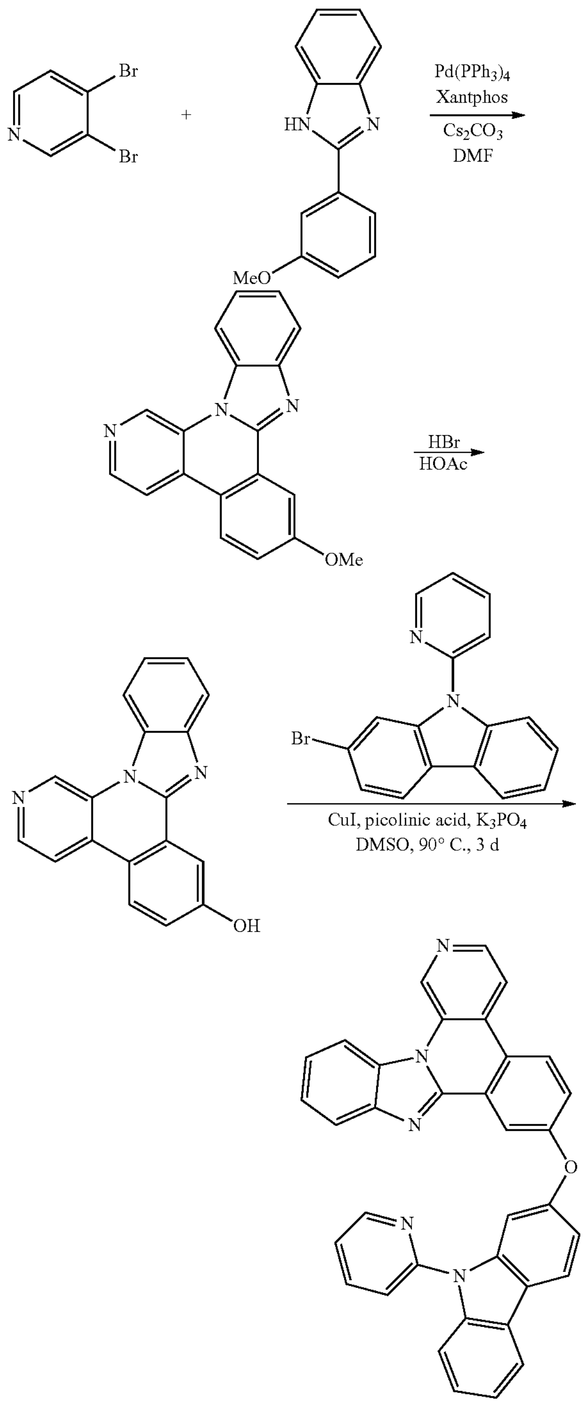

L4

Benzo[c]benzo[4,5]imidazo[1,2-a][1,7]naphthyridin-7-ol (100 mg, 0.35 mmol, 1.0 eq), 2-bromo-9-(pyridin-2-yl)-9H-carbazole (136 mg, 0.42 mmol, 1.2 eq), CuI (13 mg, 0.07 mmol, 0.2 eq), picolinic acid (9 mg, 0.07 mmol, 0.2 eq) and $K_3PO_4$ (149 Mg, 0.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (5 mL) was added under the protection of nitrogen. The mixture was stirred in an oil bath at a temperature of 90° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product L4 in 40%~70% yield.

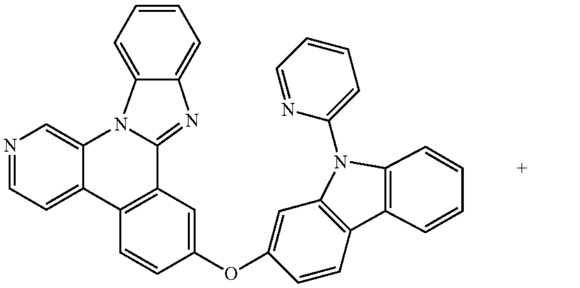

L4

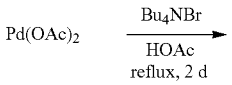

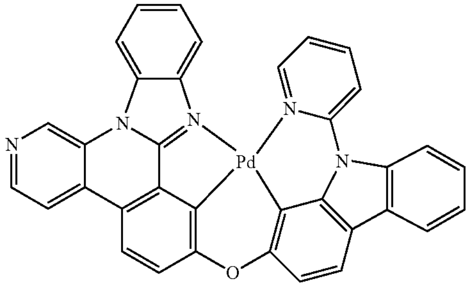

MC4

L4 (95 mg, 0.18 mmol, 1.0 eq), $Pd(OAc)_2$ (43 mg, 0.19 mmol, 1.1 eq) and $n\text{-}Bu_4NBr$ (6 mg, 0.018 mmol, 0.1 eq) were added to a dry pressure tube, which was taken into a glove box and acetic acid (11 mL) was added. The mixture was bubbled with nitrogen for 30 minutes and then the tube was sealed. Then the mixture was heated to reflux in an oil bath and stirred for 2 days, cooled to ambient temperature and the solvent removed. Then the solid was purified through column chromatography on silica gel using dichloromethane as eluent to obtain the desired product MC4 in 10%~50% yield.

Example 5

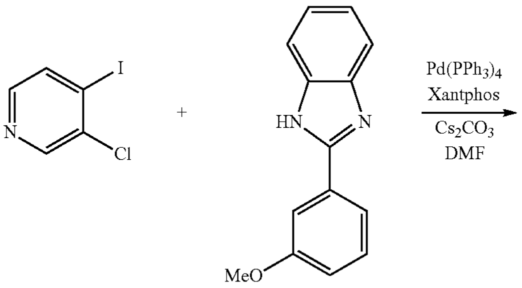

-continued

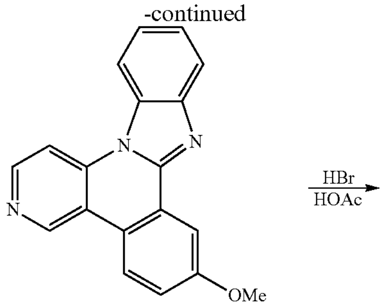

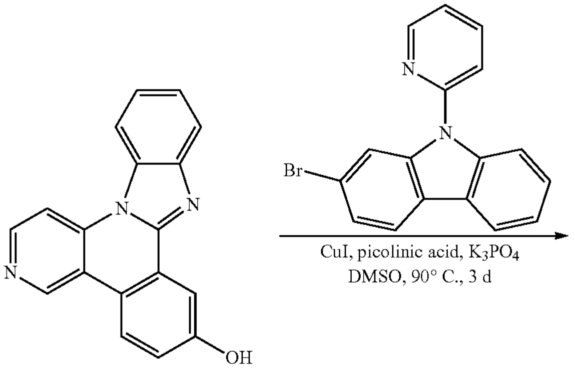

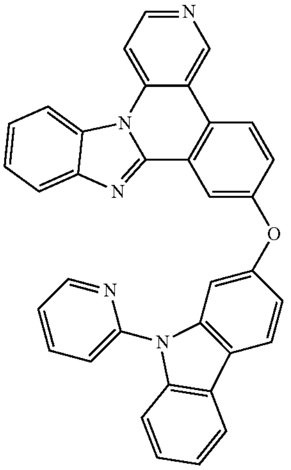

L5

Benzo[c]benzo[4,5]imidazo[1,2-a][1,6]naphthyridin-7-ol (100 mg, 0.35 mmol, 1.0 eq), 2-bromo-9-(pyridin-2-yl)-9H-carbazole (136 mg, 0.42 mmol, 1.2 eq), CuI (13 mg, 0.07 mmol, 0.2 eq), nicotinic acid (9 mg, 0.07 mmol, 0.2 eq) and $K_3PO_4$ (149 mg, 0.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (5 mL) was added under the protection of nitrogen. The mixture was stirred in an oil bath at a temperature of 90° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L5 in 40%~70% yield.

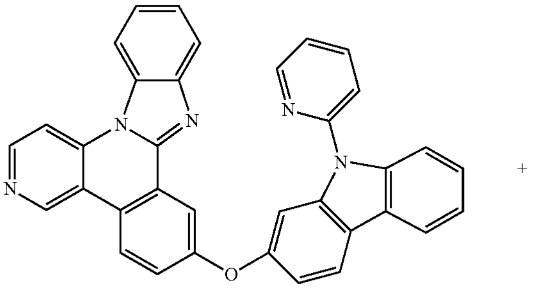

L5

Pd(OAc)$_2$ Bu$_4$NBr HOAc reflux, 2 d

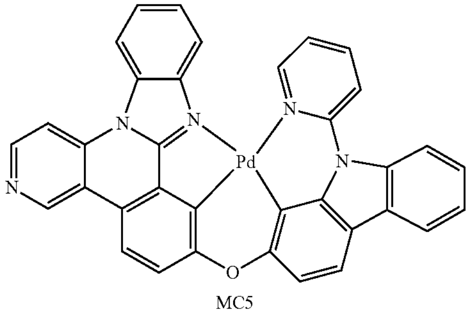

MC5

L5 (95 mg, 0.18 mmol, 1.0 eq), Pd(OAc)$_2$ (43 mg, 0.19 mmol, 1.1 eq) and n-Bu$_4$NBr (6 mg, 0.018 mmol, 0.1 eq) were added to a dry pressure tube, which was taken into a glove box and acetic acid (11 mL) was added. The mixture was bubbled with nitrogen for 30 minutes and then the tube was sealed. Then the mixture was heated to reflux in an oil bath and stirred for 2 days, cooled to ambient temperature and the solvent removed. Then the solid was purified through column chromatography on silica gel using dichloromethane as eluent to obtain the desired product MC5 in 10%~50% yield.

Example 6

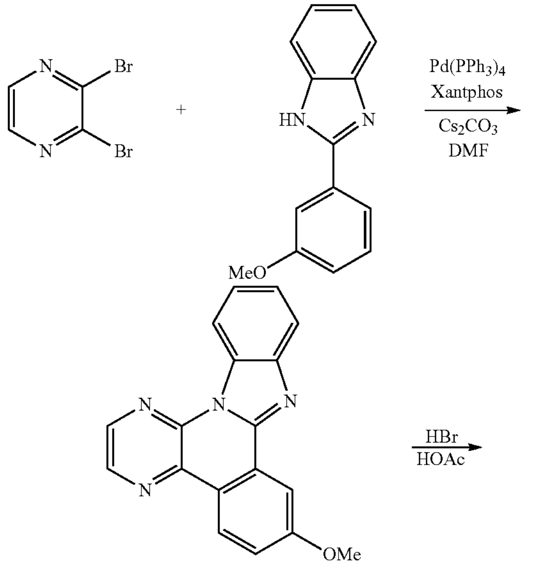

-continued

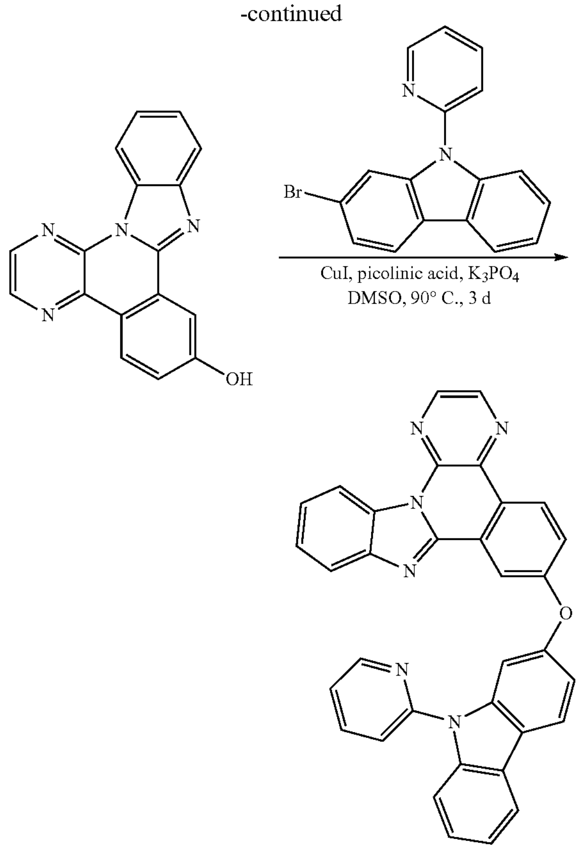

L6

Benzo[4,5]imidazo[2,1-a]pyrazino[2,3-c]isoquinolin-7-ol (286 mg, 1 mmol, 1.0 eq), 2-bromo-9-(pyridin-2-yl)-9H-carbazole (388 mg, 1.2 mmol, 1.2 eq), CuI (38 mg, 0.2 mmol, 0.2 eq), picolinic acid (49 mg, 0.4 mmol, 0.4 eq) and K$_3$PO$_4$ (425 mg, 2 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 90° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L6 in 30%~70% yield.

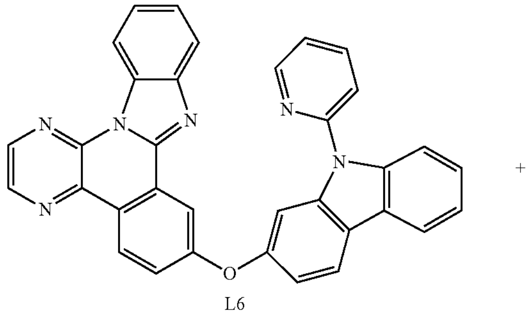

L6

-continued

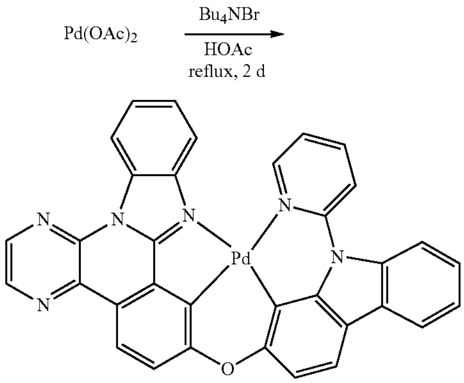

MC6

L6 (0.20 mmol, 1.0 eq), $Pd(OAc)_2$ (54 mg, 0.24 mmol, 1.2 eq) and n-$Bu_4NBr$ (6.5 mg, 0.02 mmol, 0.1 eq) were added to a dry pressure tube, which was taken into a glove box and acetic acid (10 mL) was added. The mixture was bubbled with nitrogen for 30 minutes and then the tube was sealed. Then the mixture was heated to reflux in an oil bath and stirred for 2 days, cooled to ambient temperature and the solvent removed. Then the solid was purified through column chromatography on silica gel using dichloromethane as eluent to obtain to obtain the desired product MC6 in 10%~50% yield.

Example 7

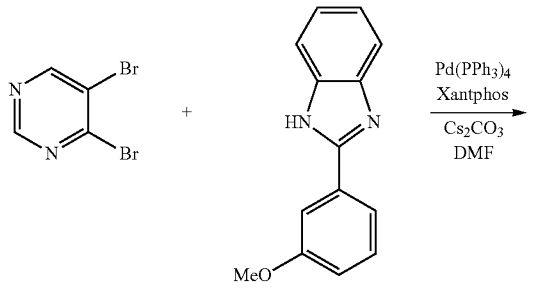

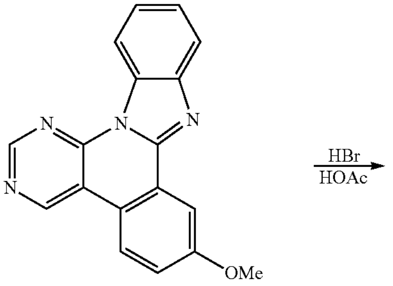

-continued

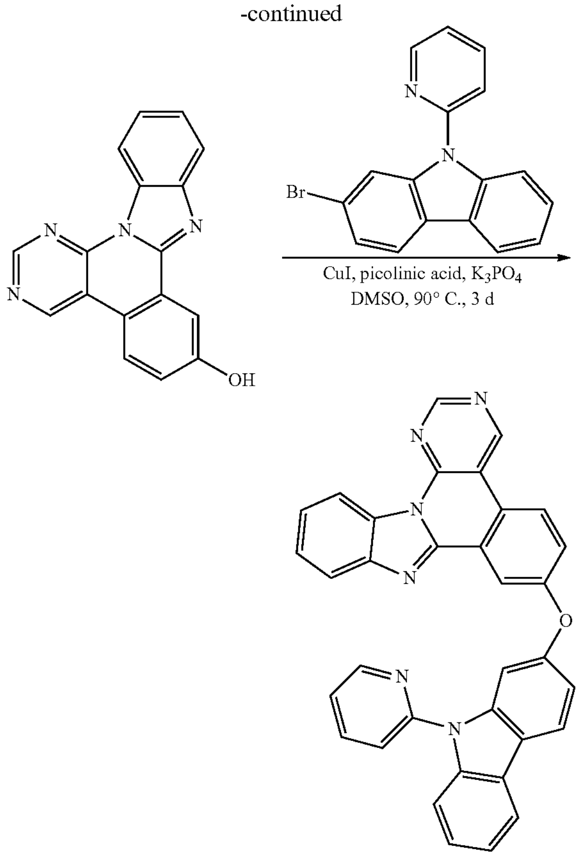

L7

Benzo[4,5]imidazo[2,1-a]pyrimido[4,5-c]isoquinolin-7-ol (286 mg, 1 mmol, 1.0 eq), 2-bromo-9-(pyridin-2-yl)-9H-carbazole (388 mg, 1.2 mmol, 1.2 eq), CuI (38 mg, 0.2 mmol, 0.2 eq), picolinic acid (49 mg, 0.4 mmol, 0.4 eq) and $K_3PO_4$ (425 mg, 2 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 90° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L7 in 30%~70% yield.

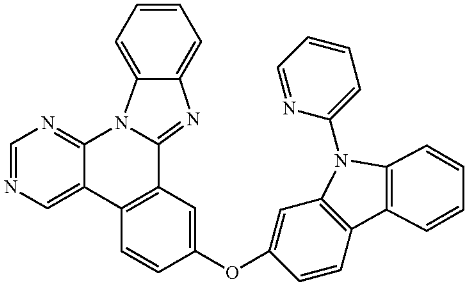

L7

+

-continued

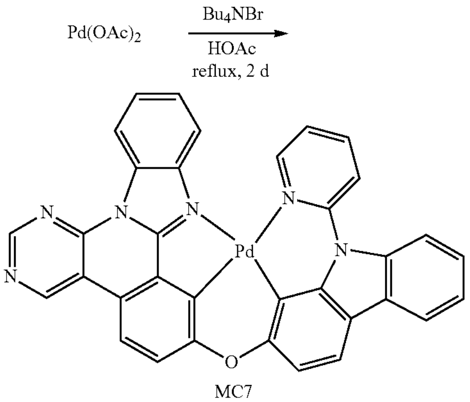

MC7

L7 (0.20 mmol, 1.0 eq), Pd(OAc)$_2$ (54 mg, 0.24 mmol, 1.2 eq) and n-Bu$_4$NBr (6.5 mg, 0.02 mmol, 0.1 eq) were added to a dry pressure tube, which was taken into a glove box and acetic acid (10 mL) was added. The mixture was bubbled with nitrogen for 30 minutes and then the tube was sealed. Then the mixture was heated to reflux in an oil bath and stirred for 2 days, cooled to ambient temperature and the solvent removed. Then the solid was purified through column chromatography on silica gel using dichloromethane as eluent to obtain to obtain the desired product MC7 in 10%~50% yield.

Example 8

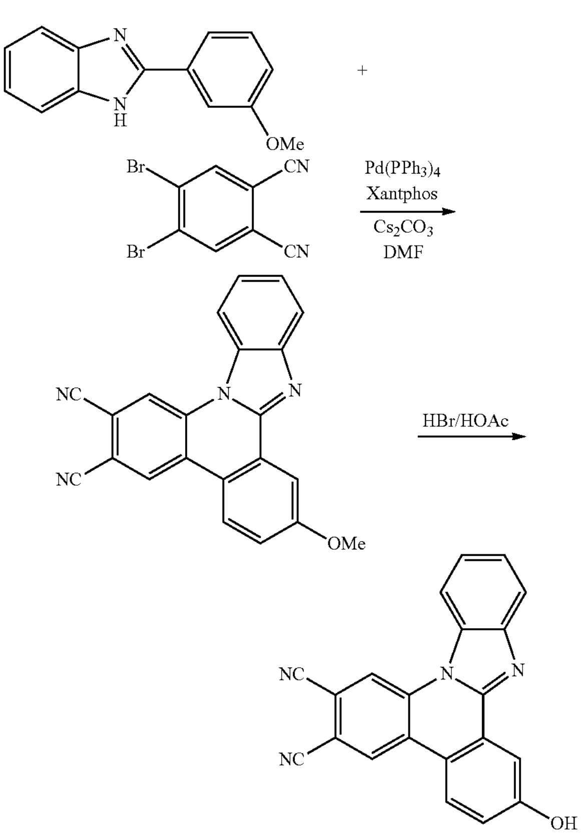

-continued

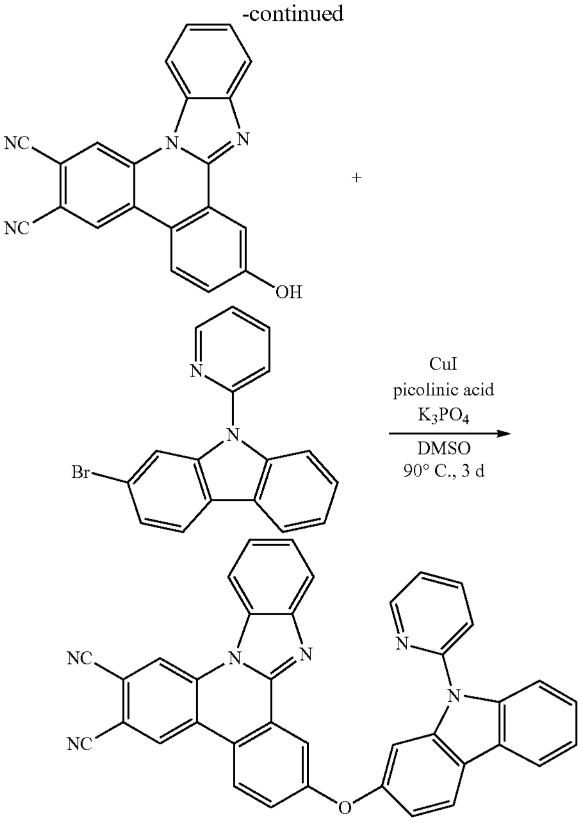

L8

7-hydroxybenzo[4,5]imidazo[1,2-f]phenanthridine-2,3-dicarbonitrile (334 mg, 1 mmol, 1.0 eq), 2-bromo-9-(pyridin-2-yl)-9H-carbazole (388 mg, 1.2 mmol, 1.2 eq), CuI (38 mg, 0.2 mmol, 0.2 eq), picolinic acid (49 mg, 0.4 mmol, 0.4 eq) and K$_3$PO$_4$ (425 mg, 2 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 90° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L8 in 30%~70% yield.

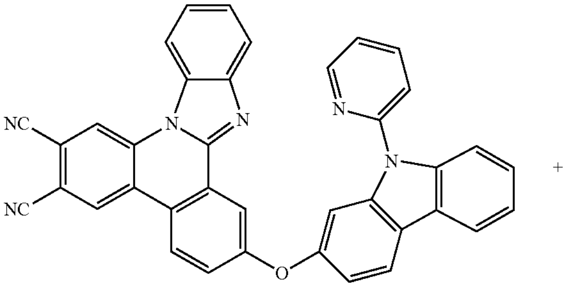

L8

-continued

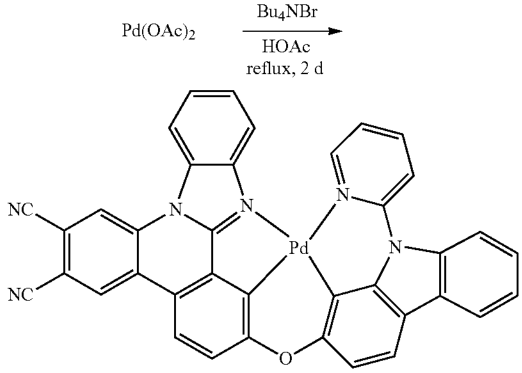

MC8

L8 (0.20 mmol, 1.0 eq), $Pd(OAc)_2$ (54 mg, 0.24 mmol, 1.2 eq) and n-$Bu_4NBr$ (6.5 mg, 0.02 mmol, 0.1 eq) were added to a dry pressure tube, which was taken into glove box and acetic acid (10 mL) was added. The mixture was bubbled with nitrogen for 30 minutes and then the tube was sealed. Then the mixture was heated to reflux in an oil bath and stirred for 2 days, cooled to ambient temperature and the solvent removed. Then the solid was purified through column chromatography on silica gel using dichloromethane as eluent to obtain to obtain the desired product MC8 in 10%~50% yield.

Example 9

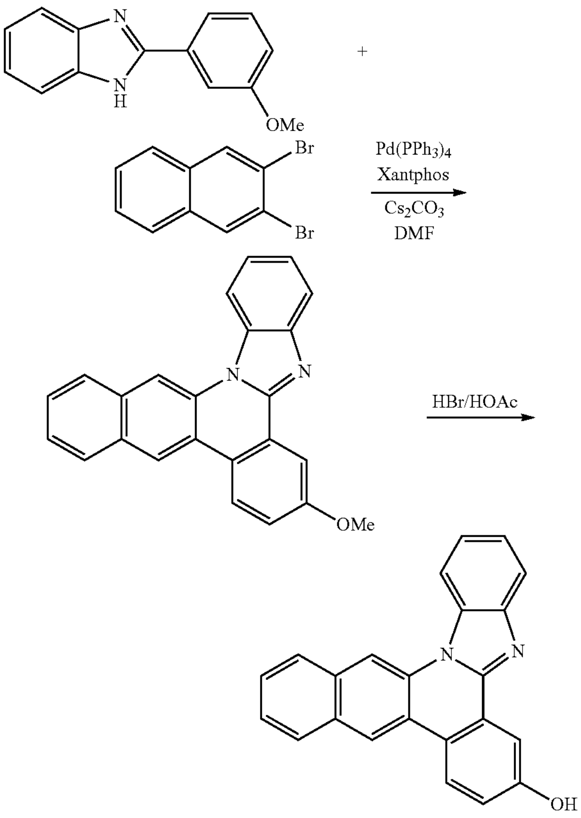

-continued

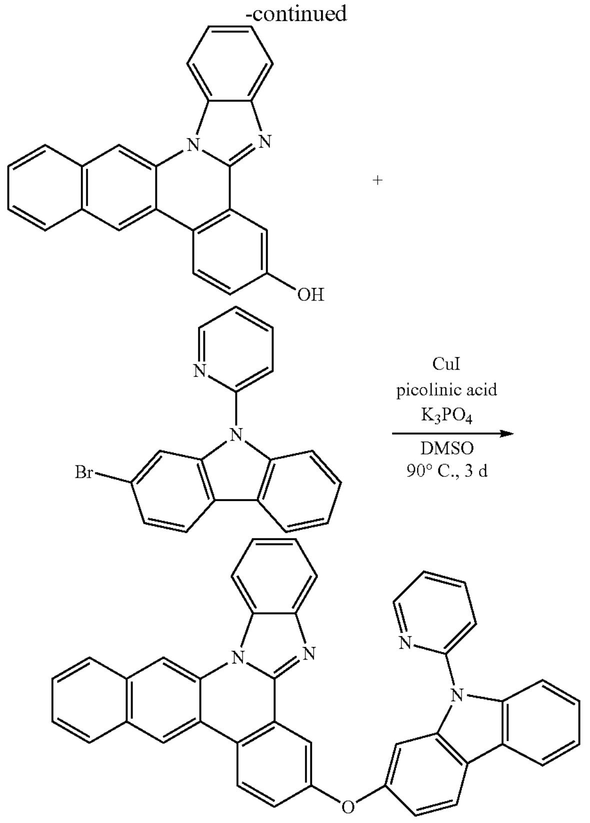

L9

Benzo[b]benzo[4,5]imidazo[1,2-f]phenanthridin-7-ol (217 mg, 0.65 mmol, 1.0 eq), 2-bromo-9-(pyridin-2-yl)-9H-carbazole (252 mg, 0.78 mmol, 1.2 eq), CuI (25 mg, 0.13 mmol, 0.2 eq), picolinic acid (16 mg, 0.13 mmol, 0.2 eq) and $K_3PO_4$ (275 mg, 1.3 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (5 mL) was added under the protection of nitrogen. The mixture was stirred in an oil bath at a temperature of 90° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L9 as a white solid 100 mg in 27% yield.

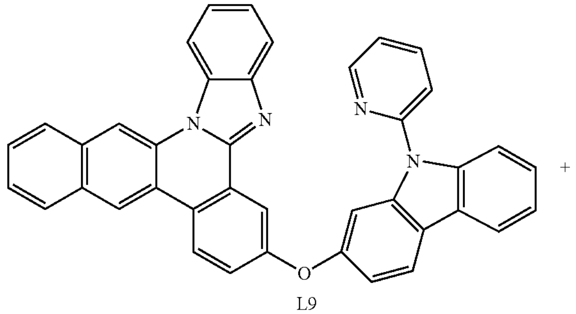

L9

-continued

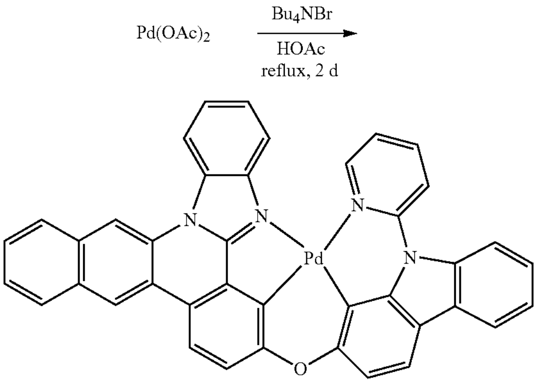

MC9

7-((9-(pyridin-2-yl)-9H-carbazol-2-yl)oxy)benzo[b]benzo[4,5]imidazo[1,2-f]phenanthridine (80 mg, 0.14 mmol, 1.0 eq), $Pd(OAc)_2$ (37 mg, 0.17 mmol, 1.2 eq) and n-$Bu_4NBr$ (5 mg, 0.014 mmol, 0.1 eq) were added to a dry pressure tube, which was taken into a glove box and acetic acid (9 mL) was added. The mixture was bubbled with nitrogen for 30 minutes and then the tube was sealed. Then the mixture was heated to reflux in an oil bath and stirred for 2 days, cooled to ambient temperature and the solvent removed. Then the solid was purified through column chromatography on silica gel using dichloromethane as eluent to obtain the desired product MC9 as a white solid 60 mg in 63% yield.

Example 10

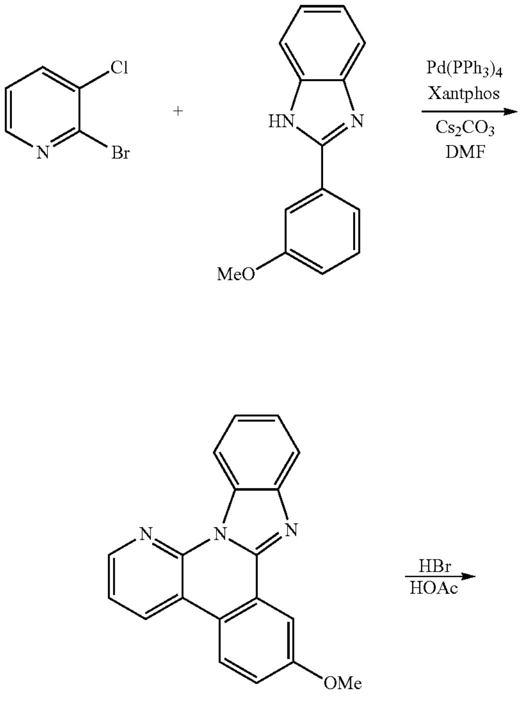

-continued

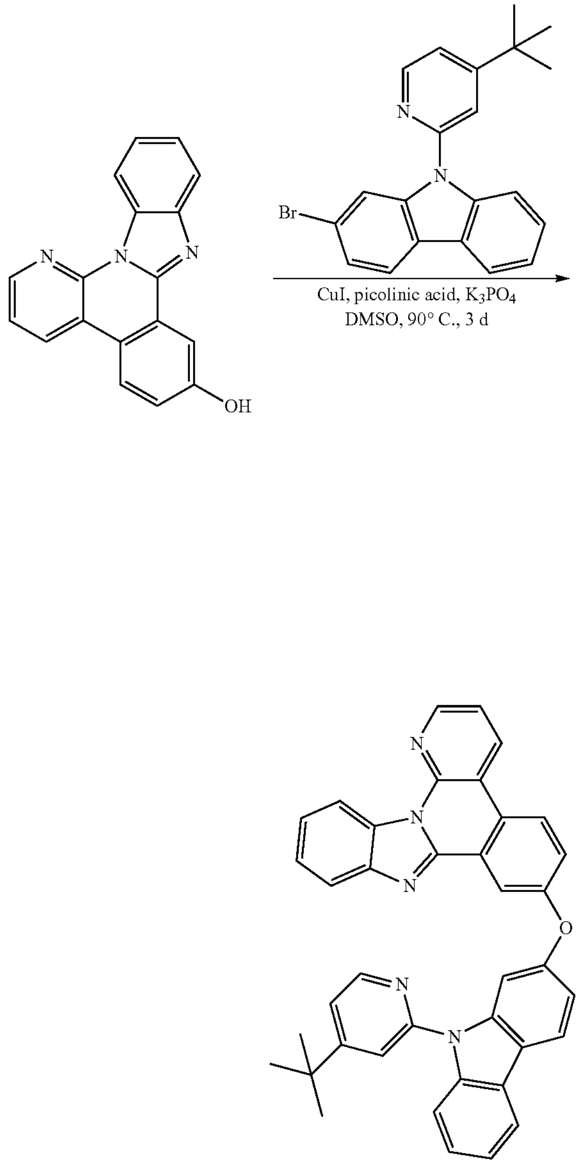

L10

Benzo[c]benzo[4,5]imidazo[1,2-a][1,8]naphthyridin-7-ol (145 mg, 0.51 mmol, 1.0 eq), 2-bromo-9-(4-(tert-butyl)pyridin-2-yl)-9H-carbazole (231 mg, 0.61 mmol, 1.2 eq), CuI (20 mg, 0.10 mmol, 0.2 eq), picolinic acid (13 mg, 0.10 mmol, 0.2 eq) and $K_3PO_4$ (217 mg, 1.02 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (5 mL) was added under the protection of nitrogen. The mixture was stirred in an oil bath at a temperature of 90° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L10 as an orange yellow solid 185 mg in 63% yield.

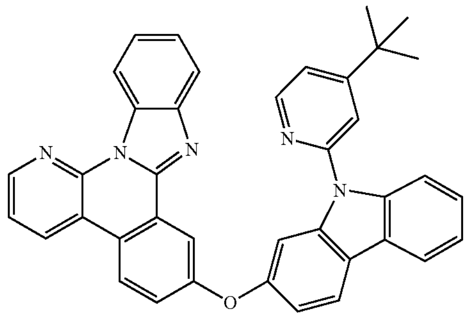

L10

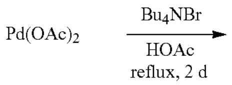

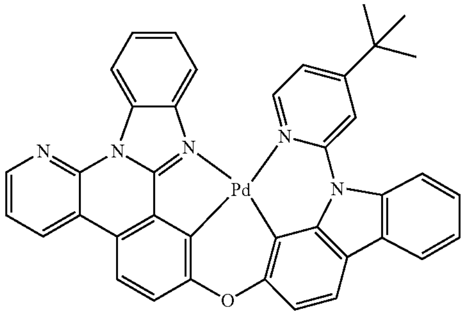

MC10

L10 (175 mg, 0.3 mmol, 1.0 eq), Pd(OAc)$_2$ (74 mg, 0.33 mmol, 1.1 eq) and n-$Bu_4NBr$ (10 mg, 0.03 mmol, 0.1 eq) were added to a dry pressure tube, which was taken into a glove box and acetic acid (19 mL) was added. The mixture was bubbled with nitrogen for 30 minutes and then the tube was sealed. Then the mixture was heated to reflux in an oil bath and stirred for 2 days, cooled to ambient temperature and the solvent removed. Then the solid was purified through column chromatography on silica gel using dichloromethane as eluent to obtain the desired product MC10 ire 10%~50% yield.

Example 11

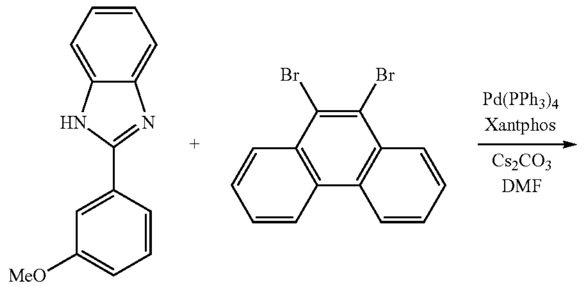

-continued

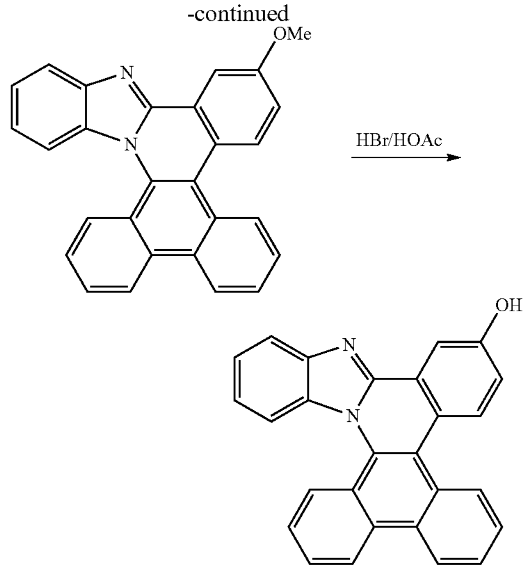

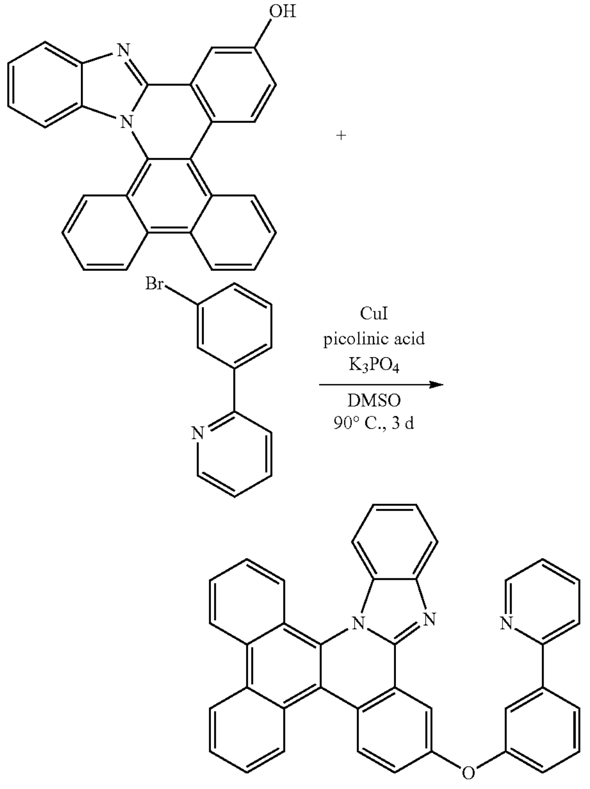

L11

Dibenzo[a,c]benzo[4,5]imidazo[1,2-f]phenanthridin-7-ol (384.4 mg, 1 mmol, 1.0 eq), 2-(3-bromophenyl)pyridine (281 mg, 1.2 mmol, 1.2 eq), CuI (38 mg, 0.2 mmol 0.2 eq), picolinic acid (49 mg, 0.4 mmol, 0.4 eq) and $K_3PO_4$ (425 mg, 2 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 90° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate (2:1) as eluent to obtain the desired product ligand L11 as a white solid 350 mg in 65% yield.

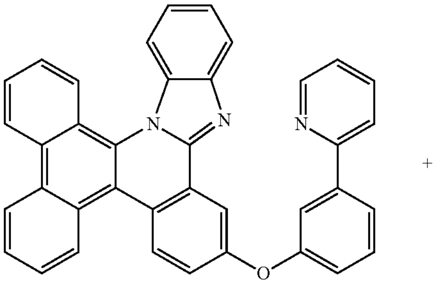

L11

Pd(OAc)$_2$ Bu$_4$NBr HOAc reflux, 2 d

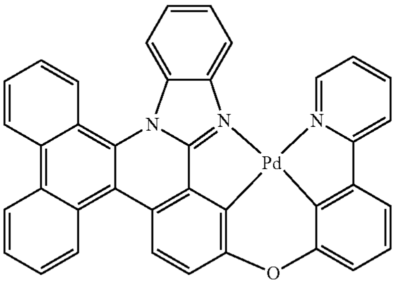

MC11

L11 (107.6 mg, 0.2.0 mmol, 1.0 eq), Pd(OAc)$_2$ (54 mg, 0.24 mmol, 1.2 eq) and n-Bu$_4$NBr (6.5 mg, 0.02 mmol, 0.1 eq) were added to a dry pressure tube was then taken into a glove box and acetic acid (10 mL) was added. The mixture was bubbled with nitrogen for 30 minutes and then the tube was sealed. Then the mixture was heated to reflux in an oil bath and stirred for 2 days, cooled to ambient temperature and removed the solvent. Then the solid was purified through column chromatography on silica gel using dichloromethane as eluent to obtain to obtain the desired product MC11 as a white solid 58 mg in 45% yield.

Example 12

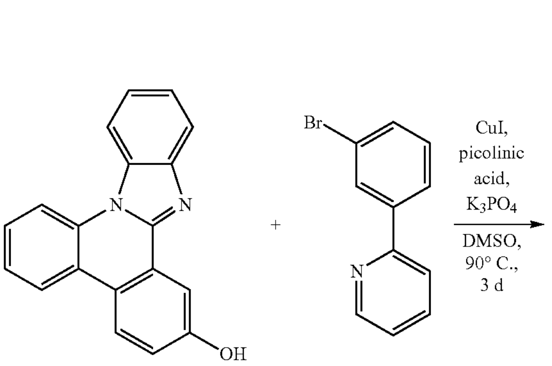

-continued

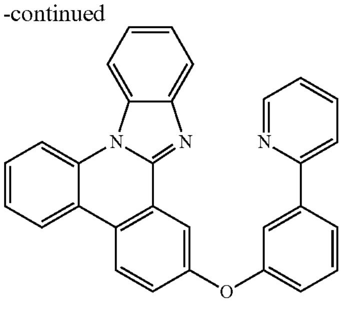

L12

Benzo[4,5]imidazo[1,2-f]phenanthridin-7-ol (284.3 mg, 1 mmol, 1.0 eq), 2-(3-bromophenyl)pyridine (281 mg, 1.2 mmol, 1.2 eq), CuI (38 mg, 0.2 mmol, 0.2 eq), picolinic acid (49 mg, 0.4 mmol, 0.4 eq) and K$_3$PO$_4$ (425 mg, 2 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 90° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate (2:1) as eluent to obtain the desired product ligand L12 as a white solid 306 mg in 70% yield.

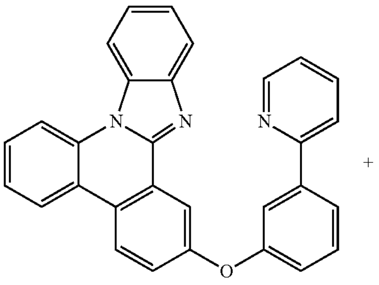

L12

Pd(OAc)$_2$ Bu$_4$NBr HOAc reflux, 2 d

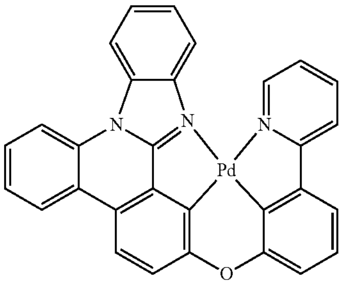

MC12

Figure 3:
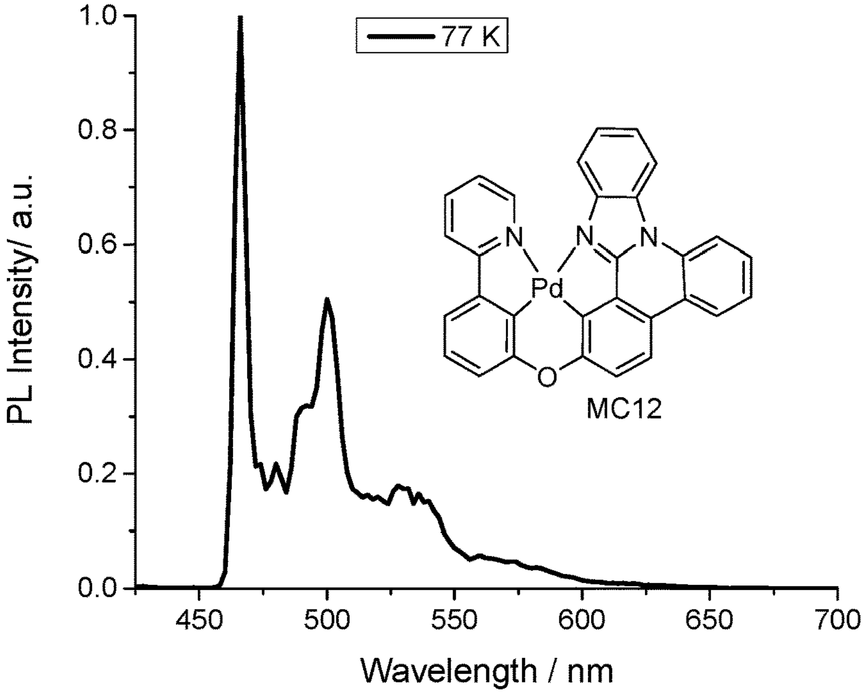
FIG. 3 is an emission spectrum of the metal-assisted delayed fluorescent emitter of Example 12 in tetrahydro-2-methylfuran at 77K.

LC12 (87.4 mg, 0.20 mmol, 1.0 eq), Pd(OAc)$_2$ (54 mg, 0.24 mmol, 1.2 eq) and n-Bu$_4$NBr (6.5 mg, 0.02 mmol, 0.1 eq) were added to a dry pressure tube, which was taken into a glove box and acetic acid (10 mL) was added. The mixture was bubbled with nitrogen for 30 minutes and then the tube was sealed. Then the mixture was heated to reflux in an oil bath and stirred for 2 days, cooled to ambient temperature and the solvent removed. Then the solid was purified through column chromatography on silica, gel using dichloromethane as eluent to obtain to obtain the desired product MC12 as a white solid 43 mg in 40% yield. FIG. 3 shows an emission spectrum of MC12 in tetrahydro-2-methylfuran at 77K.

Example 13

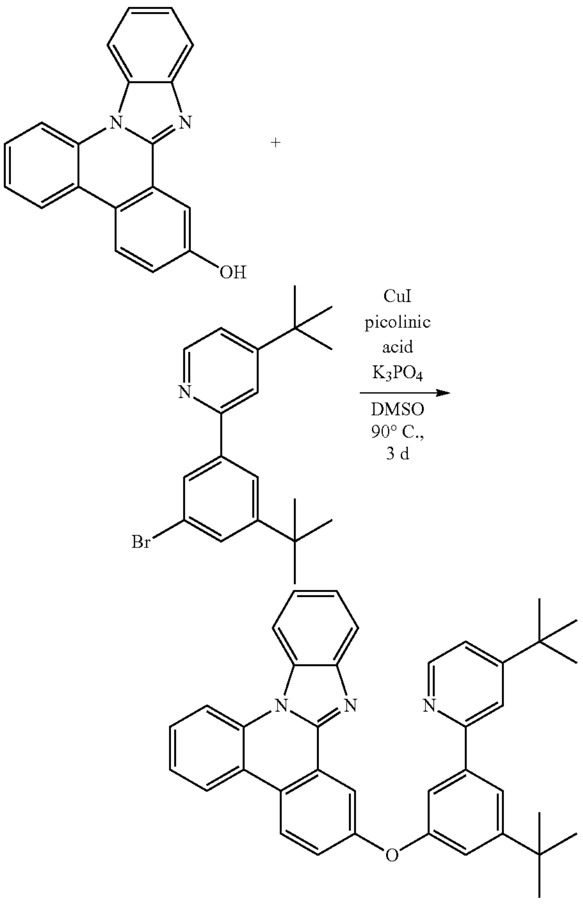

L13

Benzo[4,5]imidazo[1,2-f]phenanthridin-7-ol (355 mg, 1.03 mmol, 1.0 eq), 2-(3-bromo-5-(tert-butyl)phenyl)-4-(tert-butyl)pyridine (350 mg, 1.23 mmol, 1.2 eq), CuI (40 mg, 0.21 mmol, 0.2 eq), picolinic acid (25 mg, 0.21 mmol, 0.2 eq) and $K_3PO_4$ (437 mg, 2.06 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 90° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L13 as an orange yellow solid 310 mg in 55% yield.

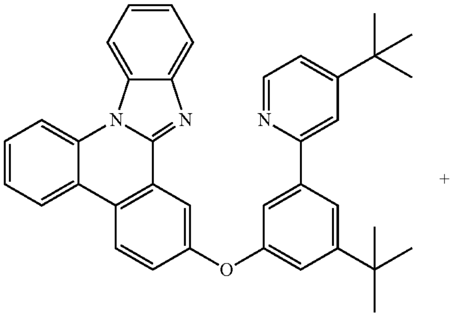

L13

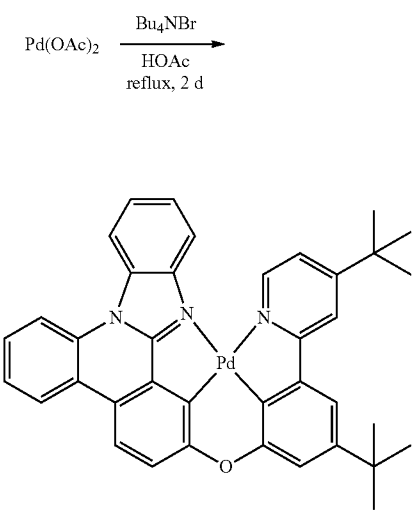

MC13

L13 (66 mg, 0.12 mmol, 1.0 eq), $Pd(OAc)_2$ (32 mg, 0.14 mmol, 1.2 eq) and n-$Bu_4NBr$ (4 mg, 0.012 mmol, 0.1 eq) were added to a dry pressure tube, which was taken into a glove box and acetic acid (8 mL) was added. The mixture was bubbled with nitrogen for 30 minutes and then the tube was sealed. Then the mixture was heated to reflux in an oil bath and stirred for 2 days, cooled to ambient temperature and the solvent removed. Then the solid was purified through column chromatography on silica gel using dichloromethane as eluent to obtain the desired product MC13 in 10%~50% yield.

Example 14

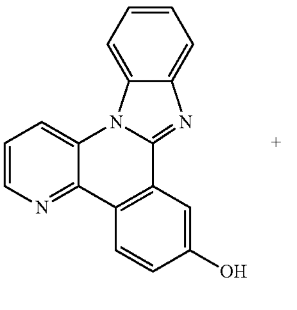

-continued

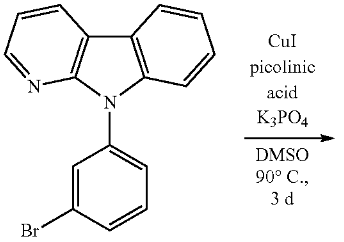

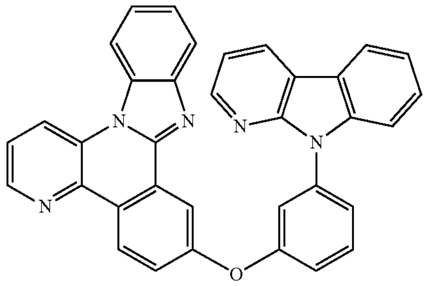

L14

Benzo[c]benzo[4,5]imidazo[1,2-a][1,5]naphthyridin-7-ol (100 mg, 0.35 mmol, 1.0 eq), 9-(3-bromophenyl)-9H-pyrido[2,3-b]indole (136 mg, 0.42 mmol, 1.2 eq), CuI (13 mg, 0.07 mmol, 0.2 eq), picolinic acid (9 mg, 0.07 mmol, 0.2 eq) and $K_3PO_4$ (149 mg, 0.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (5 mL) was added under the protection of nitrogen. The mixture was stirred in an oil bath at a temperature of 90° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L14 in 30%~70% yield.

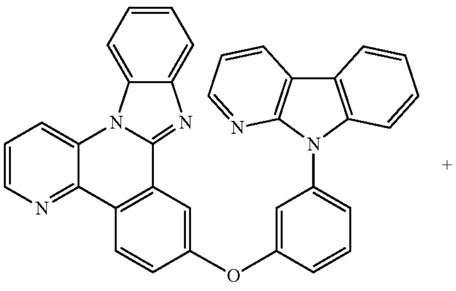

L14

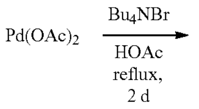

-continued

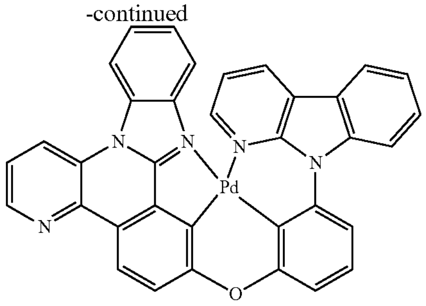

MC14

L14 (95 mg, 0.18 mmol, 1.0 eq), $Pd(OAc)_2$ (43 mg, 0.19 mmol, 1.1 eq) and n-$Bu_4NBr$ (6 mg, 0.018 mmol, 0.1 eq) were added to a dry pressure tube, which was taken into a glove box and acetic acid (11 mL) was added. The mixture was bubbled with nitrogen for 30 minutes and then the tube was sealed. Then the mixture was heated to reflux in an oil bath and stirred for 2 days, cooled to ambient temperature and the solvent removed. Then the solid was purified through column chromatography on silica gel using dichloromethane as eluent to obtain the desired product MC14 in 10%-50% yield.

Example 15

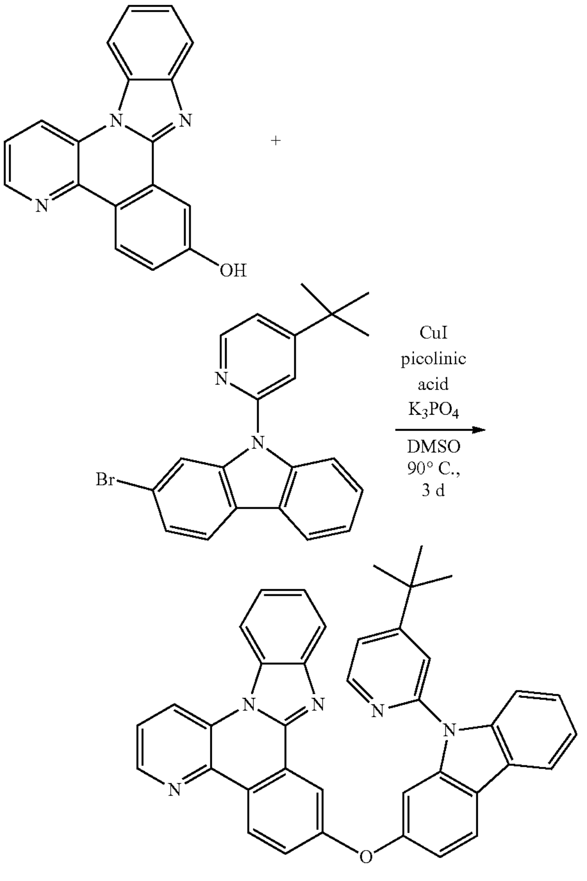

L15

Benzo[c]benzo[4,5]imidazo[1,2-a][1,5]naphthyridin-7-ol (100 mg, 0.35 mmol, 1.0 eq), 2-bromo-9-(4-(tert-butyl) pyridin-2-yl)-9H-carbazole (159 mg, 0.42 mmol, 1.2 eq), CuI (13 mg, 0.07 mmol, 0.2 eq), picolinic acid (9 mg, 0.07 mmol, 0.2 eq) and $K_3PO_4$ (149 mg, 0.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (5 mL) was added wider the protection of nitrogen. The mixture was stirred in an oil bath at a temperature of 90° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L15 in 30%~70% yield.

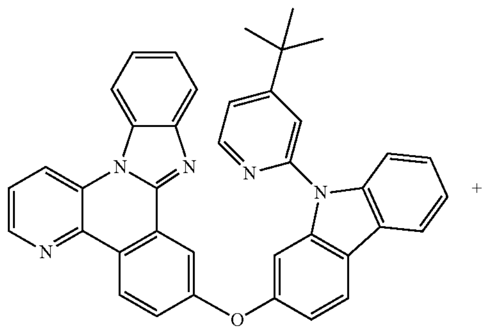

L15

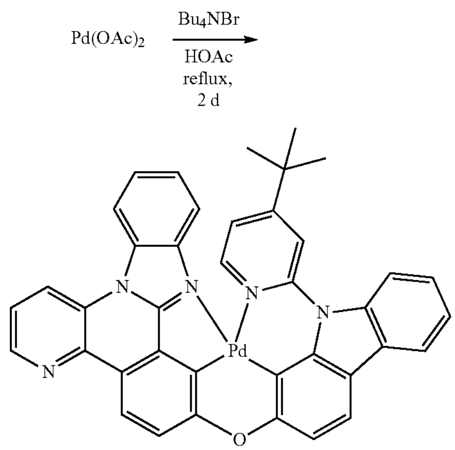

MC15

L15 (0.18 mmol, 1.0 eq), $Pd(OAc)_2$ (43 mg, 0.19 mmol, 1.1 eq) and $n\text{-}Bu_4NBr$ (6 mg, 0.018 mmol, 0.1 eq) were added to a dry pressure tube, which was taken into a glove box and acetic acid (11 mL) was added. The mixture was bubbled with nitrogen for 30 minutes and then the tube was sealed. Then the mixture was heated to reflux in an oil bath and stirred for 2 days, cooled to ambient temperature and the solvent removed. Then the solid was purified through column chromatography on silica gel using dichloromethane as eluent to obtain the desired product MC15 in 10%-50% yield.

Example 16

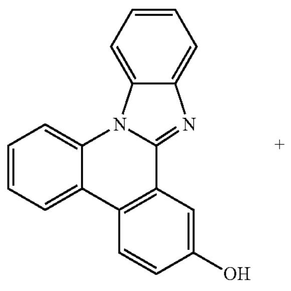

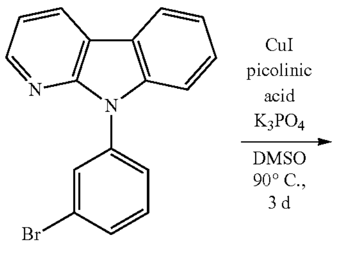

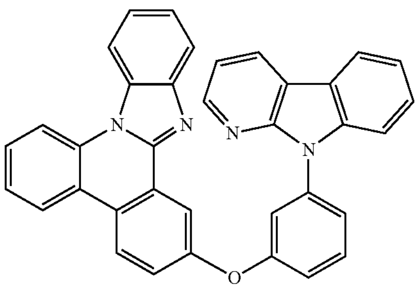

L16

Benzo[4,5]imidazo[1,2-f]phenanthridin-7-ol (284.3 mg, 1 mmol, 1.0 eq), 2-bromo-9-(pyridin-2-yl)-9H-carbazole (388 mg, 1.2 mmol, 1.2 eq), CuI (38 mg, 0.2 mmol, 0.2 eq), picolinic acid (49 mg, 0.4 mmol, 0.4 eq) and $K_3PO_4$ (425 mg, 2 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 90° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate (2:1) as and eluent to obtain the desired product ligand L16 as a white solid 316 mg in 60% yield.

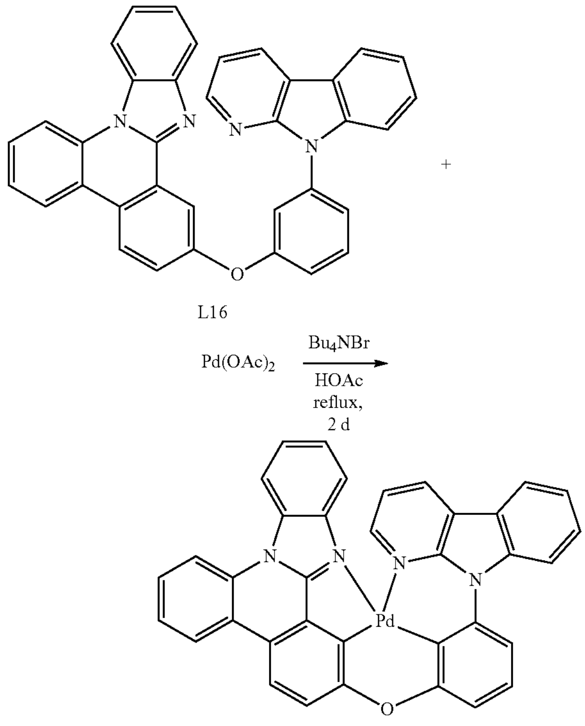

L16

MC16

L16 (105.4 mg, 0.20 mmol, 1.0 eq), Pd(OAc)$_2$ (54 mg, 0.24 mmol 1.2 eq) and n-Bu$_4$NBr (6.5 mg, 0.02 mmol, 0.1 eq) were added to a dry pressure tube was then taken into a glove box and acetic acid (10 mL) was added. The mixture was bubbled with nitrogen for 30 minutes and then the tube was sealed. Then the mixture was heated to reflux in an oil bath and stirred for 2 days, cooled to ambient temperature and removed the solvent. Then the solid was purified through column chromatography on silica gel using dichloromethane as eluent to obtain to obtain the desired product MC16 as a white solid 52 mg in 40% yield.

Example 17

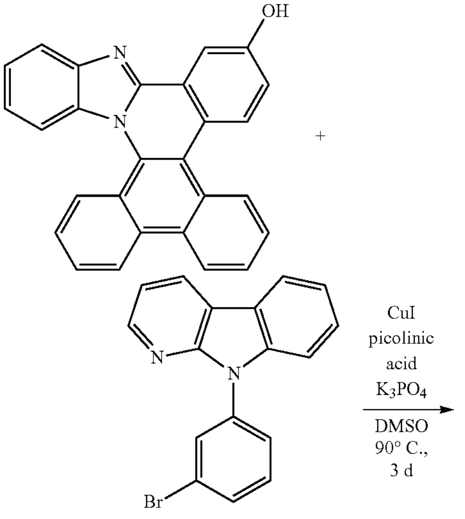

-continued

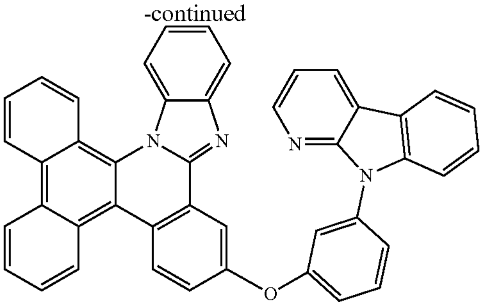

L17

Dibenzo[a,c]benzo[4,5]imidazo[1,2-f]phenanthridin-7-ol (384.3 mg, 1 mmol, 1.0 eq), 9-(3-bromophenyl)-9H-pyrido[2,3-b]indole (388 mg, 1.2 mmol, 1.2 eq.), CuI (38 mg, 0.2 mmol, 0.2 eq), picolinic acid (49 mg, 0.4 mmol, 0.4 eq) and K$_3$PO$_4$ (425 mg, 2 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 90° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate (2:1) as eluent to obtain the desired product ligand L17 as a white solid 352 mg in 56% yield.

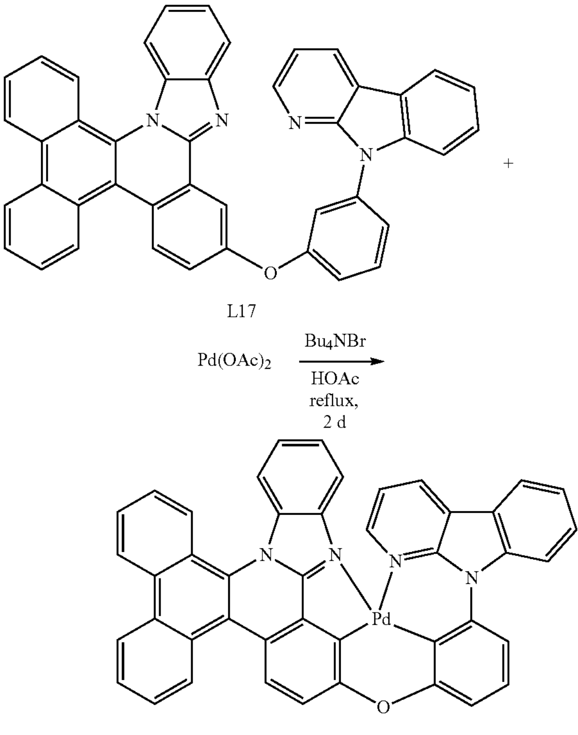

L17

M17

L17 (125.4 mg, 0.20 mmol, 1.0 eq), Pd(OAc)$_2$ (54 mg, 0.24 mmol, 1.2 eq) and n-Bu$_4$NBr (6.5 mg, 0.02 mmol, 0.1 eq) were added to a dry pressure tube was then taken into a glove box and acetic acid (10 mL) was added. The mixture was bubbled with nitrogen for 30 minutes and then the tube was sealed. Then the mixture was heated to reflux in an oil bath and stirred for 2 days, cooled to ambient temperature and removed the solvent. Then the solid was purified through column chromatography on silica gel using dichloromethane as eluent to obtain to obtain the desired product MC17 as a white solid 66 mg in 45% yield.

Example 18

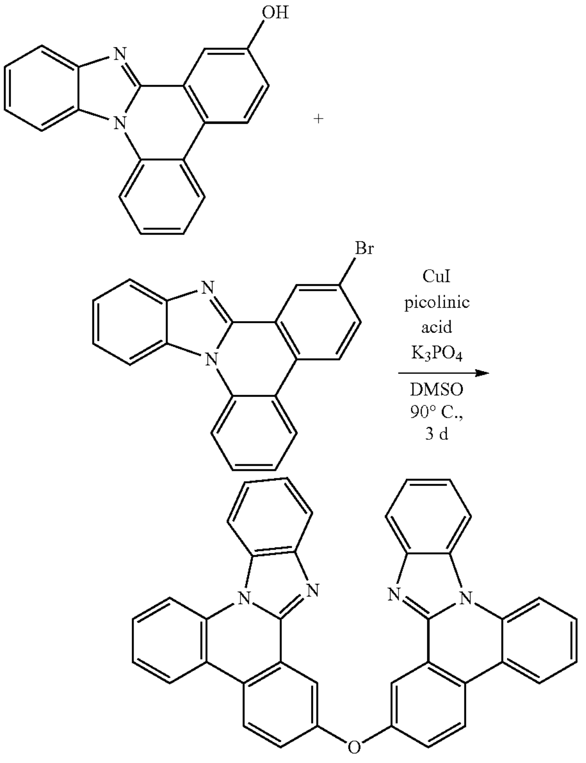

L18

Benzo[4,5]imidazo[1,2-f]phenanthridin-7-ol (1 mmol, 1.0 eq), 7-bromobenzo[4,5]imidazo[1,2-f]phenanthridine (1.2 mmol, 1.2 eq) CuI (38 mg, 0.2 mmol, 0.2 eq), picolinic acid (49 mg, 0.4 mmol, 0.4 eq) and $K_3PO_4$ (425 mg, 2 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 90° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate (2:1) as eluent to obtain the desired product ligand L18 as a white solid in 40%~70% yield.

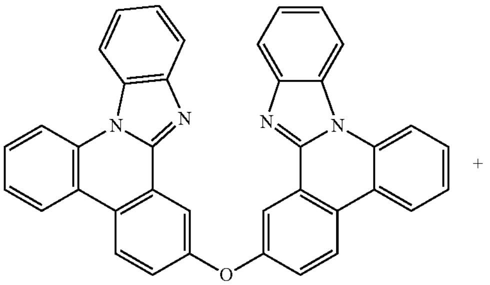

L18

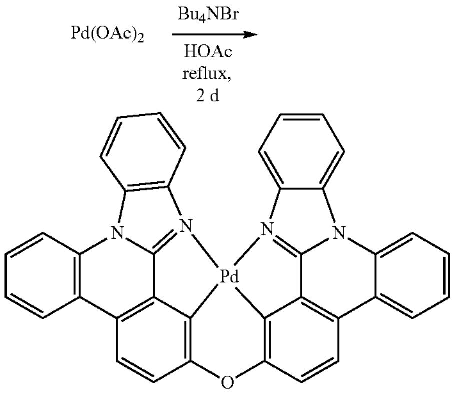

MC18

L18 (0.20 mmol, 1.0 eq), $Pd(OAc)_2$ (0.24 mmol, 1.2 eq) and n-$Bu_4NBr$ (6.5 mg, 0.02 mmol, 0.1 eq) were added to a dry pressure tube was then taken into a glove box and acetic acid (1.0 mL) was added. The mixture was bubbled with nitrogen for 30 minutes and then the tube was sealed. Then the mixture was heated to reflux in an oil bath and stirred for 2 days, cooled to ambient temperature and removed the solvent. Then the solid was purified through column chromatography on silica gel using dichloromethane as eluent obtain to obtain the desired product MC18 as a white solid in 10%~50% yield.

Example 19

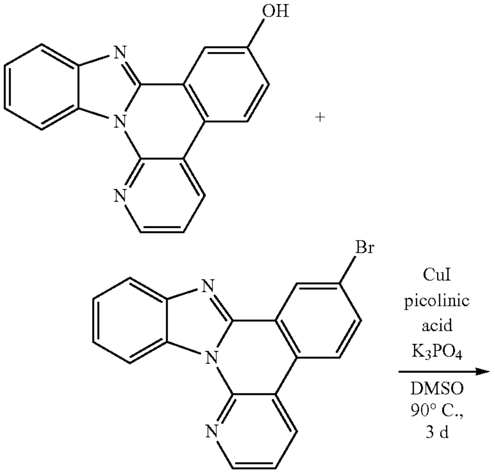

-continued

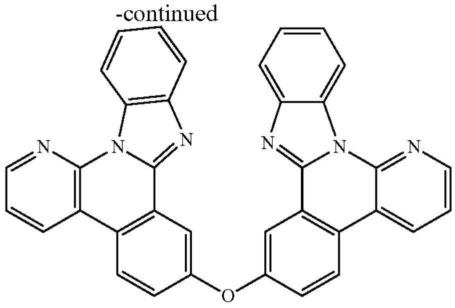

L19

Benzo[c]benzo[4,5]imidazo[1,2-a][1,8]naphthyridin-7-ol (1 mmol, 1.0 eq), 7-bromobenzo[c]benzo[4,5]imidazo[1,2-a][1,8]naphthyridine (1.2 mmol, 1.2 eq), CuI (38 mg, 0.2 mmol, 0.2 eq), picolinic acid (49 mg, 0.4 mmol, 0.4 eq) and $K_3PO_4$ (425 mg, 2 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 90° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate (2:1) as eluent to obtain the desired product ligand L19 as a white solid in 40%~70% yield.

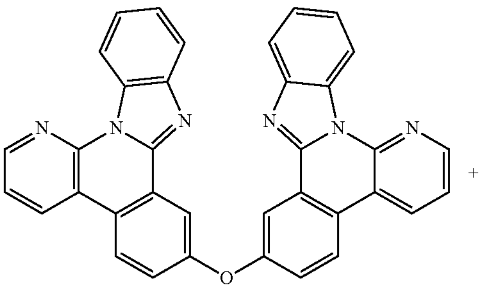

L19

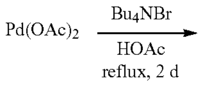

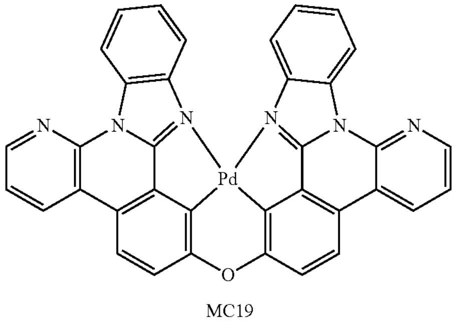

MC19

L19 (0.20 mmol, 1.0 eq), $Pd(OAc)_2$ (0.24 mmol, 1.2 eq) and n-$Bu_4NBr$ (6.5 mg, 0.02 mmol, 0.1 eq) were added to a dry pressure tube was then taken into a glove box and acetic acid (1.0 mL) was added. The mixture was bubbled with nitrogen for 30 minutes and then the tube was sealed. Then the mixture was heated to reflux in an oil bath and stirred for 2 days, cooled to ambient temperature and removed the solvent. Then the solid was purified through column chromatography on silica gel using dichloromethane as eluent to obtain to obtain the desired product MC19 as a white solid in 10%~50% yield.

Example 20

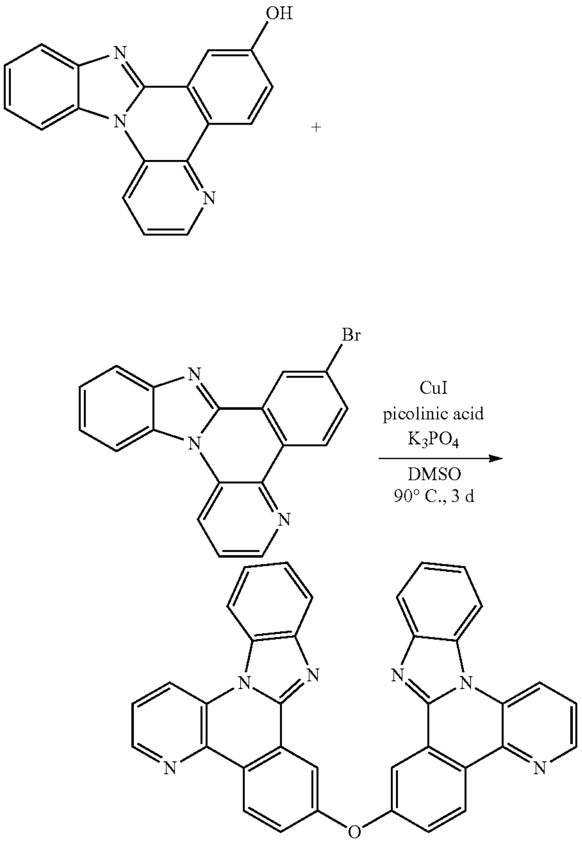

L20

Benzo[c]benzo[4,5]imidazo[1,2-a][1,5]naphthyridin-7-ol (1 mmol, 1.0 eq), 7-bromobenzo[c]benzo[4,5]imidazo[1,2-a][1,5]naphthyridine (1.2 mmol, 1.2 eq), CuI (38 mg, 0.2 mmol, 0.2 eq), picolinic acid (49 mg, 0.4 mmol 0.4 eq) and $K_3PO_4$ (425 mg, 2 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 90° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate (2:1) as eluent to obtain the desired product ligand L20 as a white solid in 40%~70% yield.

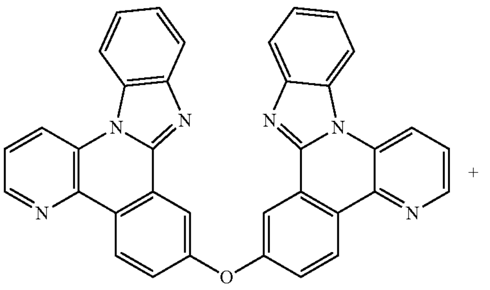

L20

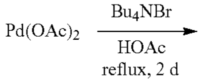

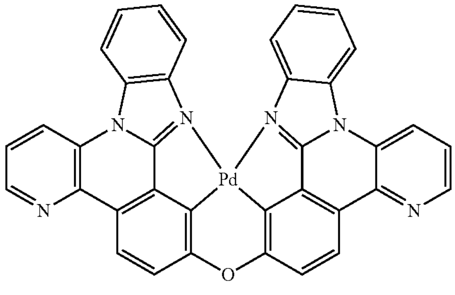

MC20

L20 (0.20 mmol, 1.0 eq), $Pd(OAc)_2$ (0.24 mmol, 1.2 eq) and n-$Bu_4NBr$ (6.5 mg, 0.02 mmol, 0.1 eq) were added to a dry pressure tube was then taken into a glove box and acetic acid (10 mL) was added. The mixture was bubbled with nitrogen for 30 minutes and then the tube was sealed. Then the mixture was heated to reflux in an oil bath and stirred for 2 days, cooled to ambient temperature and removed the solvent. Then the solid was purified through column chromatography on silica, gel using dichloromethane as eluent to obtain to obtain the desired product MC20 as a white solid in 10%~50% yield.

Example 21

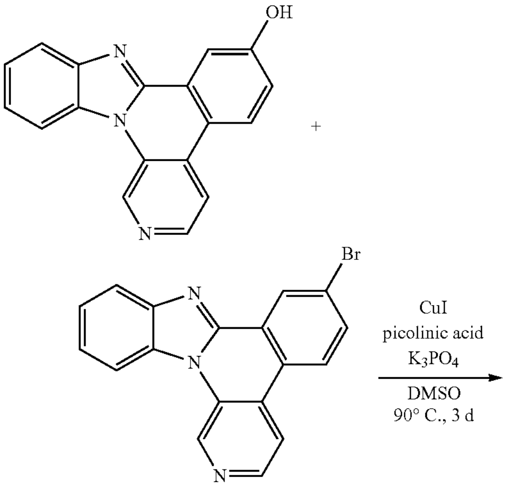

-continued

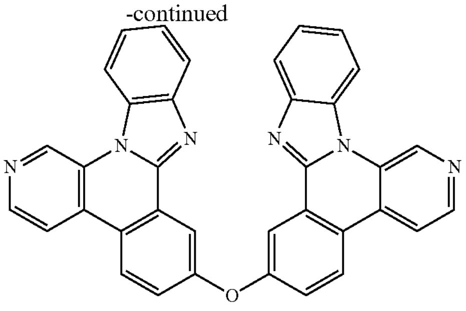

L21

Benzo[c]benzo[4,5]imidazo[1,2-a][1,7]naphthyridin-7-ol (1 mmol, 1.0 eq), 7-bromobenzo[c]benzo[4,5]imidazo[1,2-a][1,7]naphthyridine (1.2 mmol, 1.2 eq), CuI (38 mg, 0.2 mmol, 0.2 eq), picolinic acid (49 mg, 0.4 mmol, 0.4 eq) and $K_3PO_4$ (425 mg, 2 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 90° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate (2:1) as eluent to obtain the desired product ligand L21 as a white solid in 40%~70% yield.

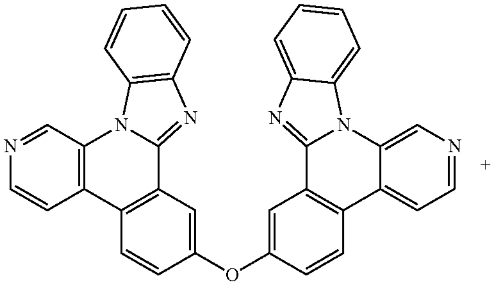

L21

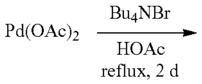

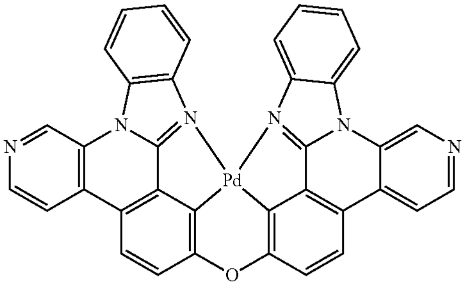

MC21

L21 (0.20 mmol, 1.0 eq), $Pd(OAc)_2$ (0.24 mmol, 1.2 eq) and n-$Bu_4NBr$ (6.5 mg, 0.02 mmol, 0.1 eq) were added to a dry pressure tube was then taken into a glove box and acetic acid (10 mL) was added. The mixture was bubbled with nitrogen for 30 minutes and then the tube was sealed. Then the mixture was heated to reflux in an oil bath and stirred for 2 days, cooled to ambient temperature and removed the solvent. Then the solid was purified through column chromatography on silica gel using dichloromethane as eluent to obtain to obtain the desired product MC21 as a white solid in 10%~50% yield.

Example 22

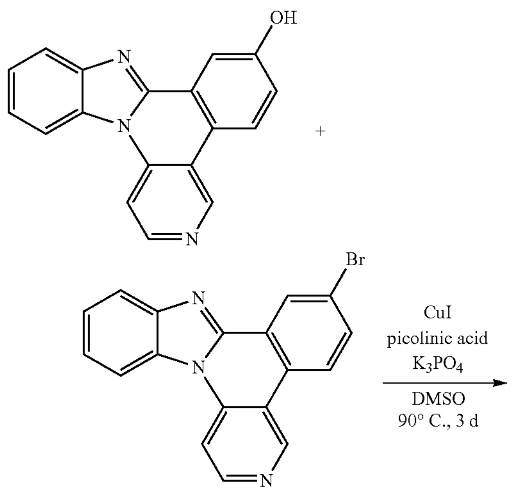

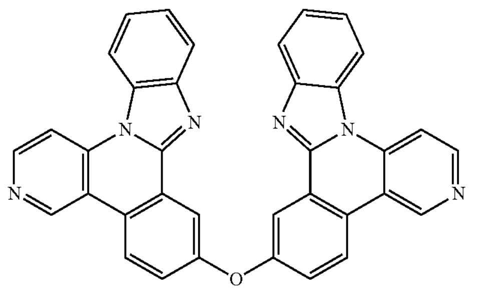

L22

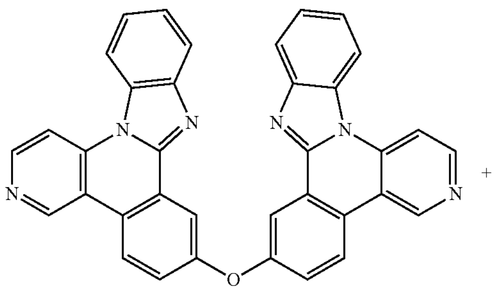

L22

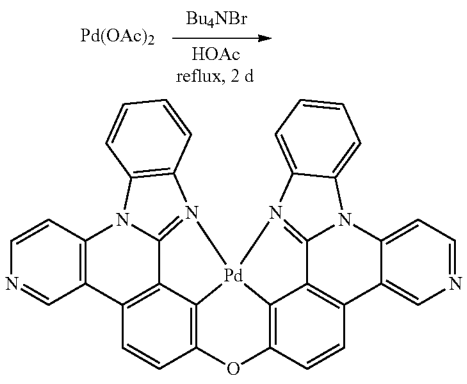

MC22

Benzo[c]benzo[4,5]imidazo[1,2-a][1,6]naphthyridin-7-ol (1 mmol, 1.0 eq), 7-bromobenzo[e]benzo[4,5]imidazo[1,2-a][1,6]naphthyridine (1.2 mmol, 1.2 eq), CuI (38 mg, 0.2 mmol, 0.2 eq), picolinic acid (49 mg, 0.4 mmol, 0.4 eq) and $K_3PO_4$ (425 mg, 2 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 90° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate (2:1) as eluent to obtain the desired product ligand L22 as a white solid in 40%~70% yield.

L22 (0.20 mmol, 1.0 eq), $Pd(OAc)_2$ (0.24 mmol, 1.2 eq) and n-$Bu_4NBr$ (6.5 mg, 0.02 mmol, 0.1 eq) were added to a dry pressure tube was then taken into a glove box and acetic acid (10 mL) was added. The mixture was bubbled with nitrogen for 30 minutes and then the tube was sealed. Then the mixture was heated to reflux in an oil bath and stirred for 2 days, cooled to ambient temperature and removed the solvent. Then the solid was purified through column chromatography on silica gel using dichloromethane as eluent to obtain to obtain the desired product MC22 as a white solid in 10%~50% yield.

Example 23

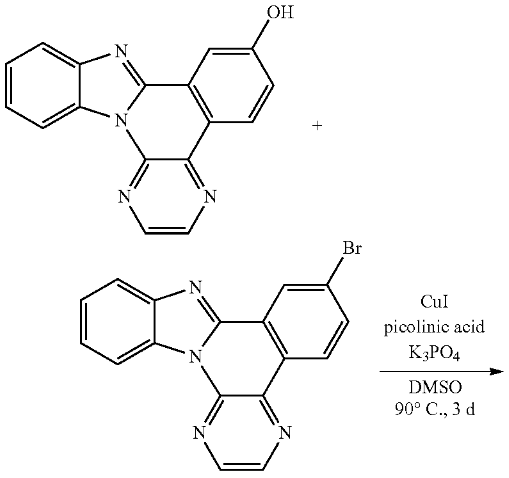

-continued

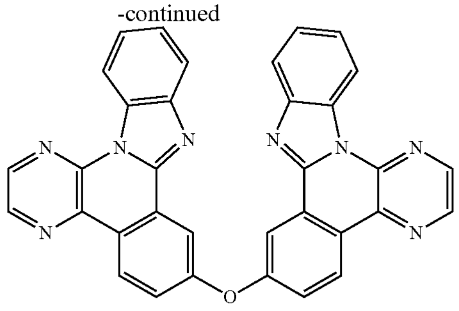

L23

Benzo[4,5]imidazo[2,1-a]pyrazino[2,3-c]isoquinolin-7-ol (1 mmol, 1.0 eq), 7-bromobenzo[4,5]imidazo[2,1-a]pyrazino[2,3-c]isoquinoline (1.2 mmol, 1.2 eq), CuI (38 mg, 0.2 mmol, 0.2 eq), picolinic acid (49 mg, 0.4 mmol, 0.4 eq) and $K_3PO_4$ (425 mg, 2 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 90° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate (2:1) as eluent to obtain the desired product ligand L23 as a white solid in 40%~70% yield.

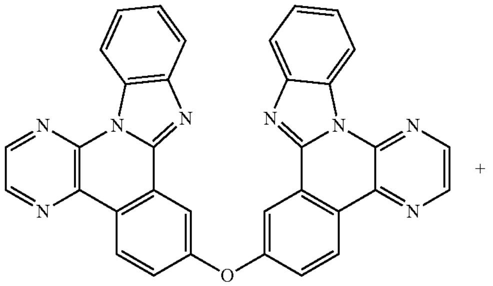

L23

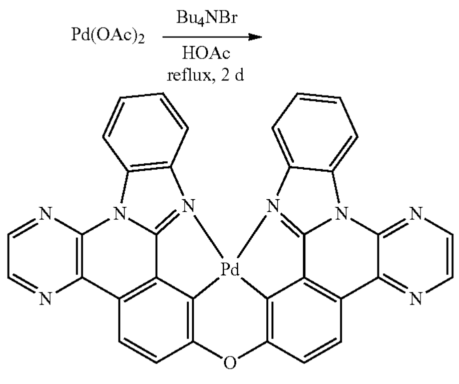

MC23

L23 (0.20 mmol, 1.0 eq), $Pd(OAc)_2$ (0.24 mmol, 1.2 eq) and $n\text{-}Bu_4NBr$ (6.5 mg, 0.02 mmol, 0.1 eq) were added to a dry pressure tube was then taken into a glove box and acetic acid (10 mL) was added. The mixture was bubbled with nitrogen for 30 minutes and then the tube was sealed. Then the mixture was heated to reflux in an oil bath and stirred for 2 days, cooled to ambient temperature and removed the solvent. Then the solid was purified through column chromatography on silica gel using dichloromethane as eluent to obtain to obtain the desired product MC23 as a white solid in 10%~50% yield.

Example 24

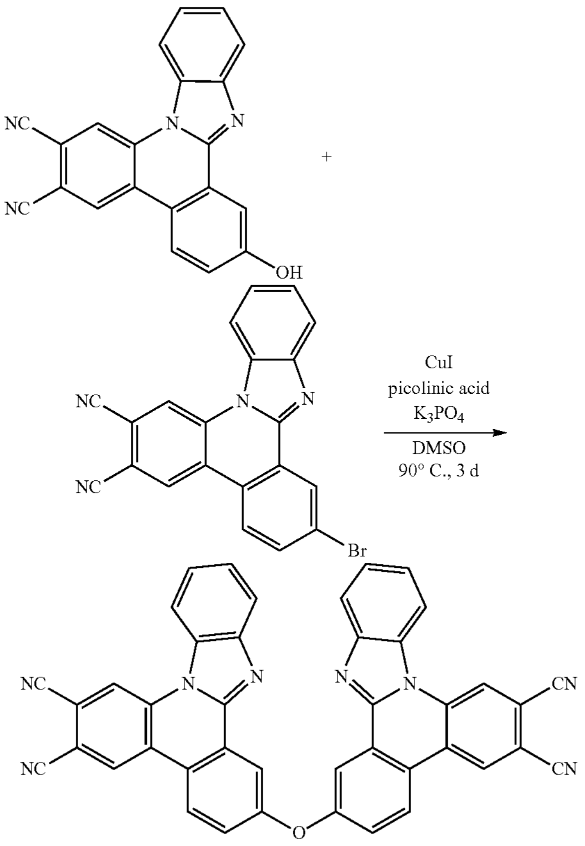

L24

7-hydroxybenzo[4,5]imidazo[1,2-f]phenanthridine-2,3-dicarbonitrile (1 mmol, 1.0 eq), 7-bromobenzo[4,5]imidazo[1,2-f]phenanthridine-2,3-dicarbonitrile (1.2 mmol, 1.2 eq), CuI (38 mg, 0.2 mmol, 0.2 eq), picolinic acid (49 mg, 0.4 mmol, 0.4 eq) and $K_3PO_4$ (425 mg, 2 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 90° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate (2:1) as eluent to obtain the desired product ligand L24 as a white solid in 40%~70% yield.

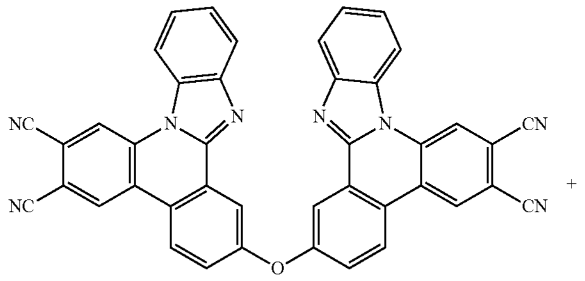

L24

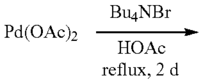

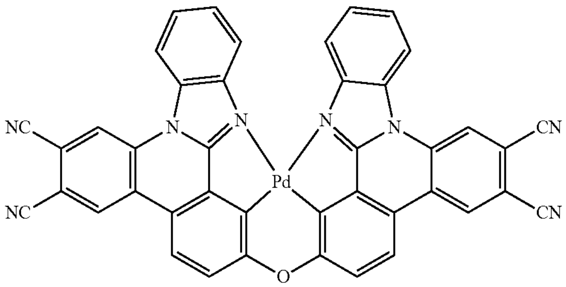

MC24

L24 (0.20 mmol, 1.0 eq), Pd(OAc)$_2$ (0.24 mmol, 1.2 eq) and n-Bu$_4$NBr (6.5 mg, 0.02 mmol, 0.1 eq) were added to a dry pressure tube was then taken into a glove box and acetic acid (1.0 mL) was added. The mixture was bubbled with nitrogen for 30 minutes and then the tube was sealed. Then the mixture was heated to reflux in an oil bath and stirred for 2 days, cooled to ambient temperature and removed the solvent. Then the solid was purified through column chromatography on silica gel using dichloromethane as eluent to obtain to obtain the desired product MC24 as a white solid in 10%~50% yield.

Example 25

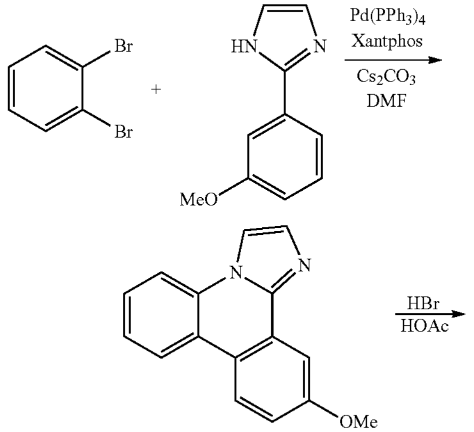

-continued

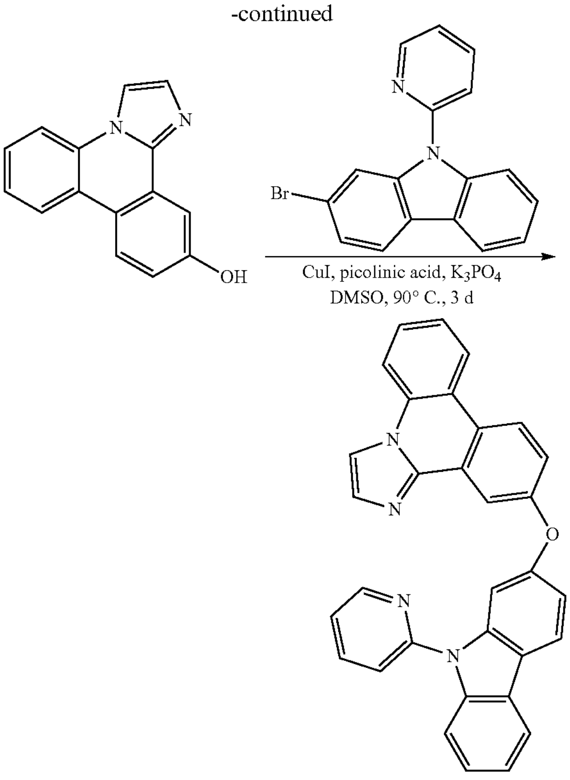

L25

Imidazo[1,2-f]phenanthridin-11-ol (200 mg, 0.85 mmol, 1.0 eq), 2-bromo-9-(pyridin-2-yl)-9H-carbazole (359 mg, 1.10 mmol, 1.3 eq), CuI (32 mg, 0.17 mmol, 0.2 eq), picolinic acid (21 mg, 0.17 mmol, 0.2 eq) and K$_3$PO$_4$ (356 mg, 1.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 100° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L25 as a light orange solid 350 mg in 86% yield.

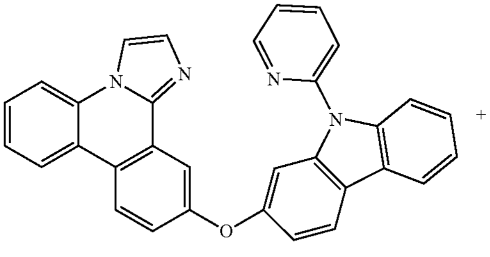

L25

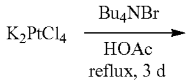

-continued

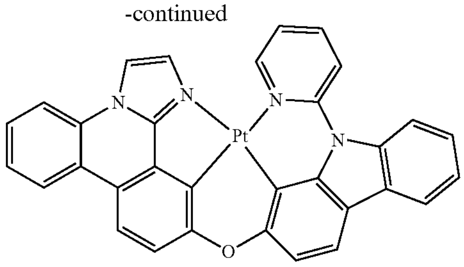

MC25

L25 (50 mg, 0.11 ol, 1.0 eq), $K_2PtCl_4$ (48 mg, 0.12 mmol, 1.1 eq) and n-$Bu_4NBr$ (3 mg, 0.011 mmol, 0.1 eq) were added to a dry pressure tube, which was taken into a glove box and acetic acid (7 mL) was added. The mixture was bubbled with nitrogen for 30 minutes and then the tube was sealed. Then the mixture was heated to reflux in an oil bath and stirred for 3 days, cooled to ambient temperature and the solvent removed. Then the solid was purified through column chromatography on silica gel using dichloromethane as eluent to obtain the desired product MC25 as a white solid 15 mg in 21% yield.

Example 26

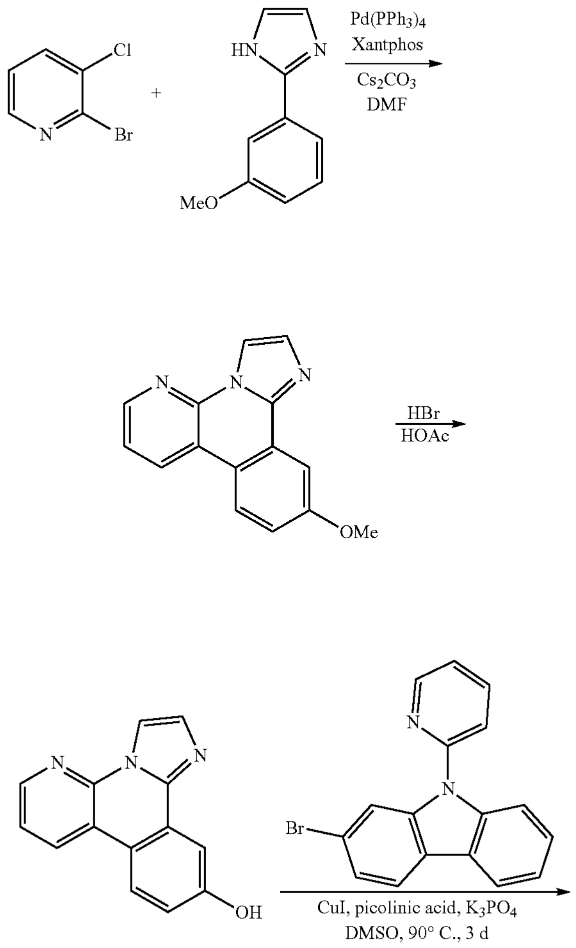

-continued

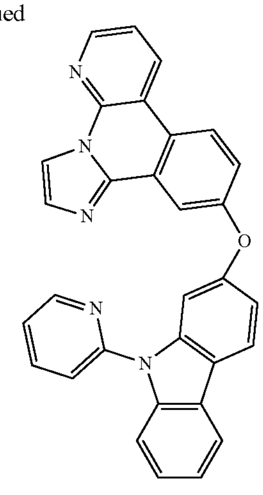

L26

11-bromobenzo[c]imidazolo[1,2-a][1,8]naphthyridine (250 mg, 0.84 mmol, 1.0 eq), 9-(pyridin-2-yl)-9H-carbazol-2-ol (262 mg, 1.01 mmol, 1.2 eq), CuI (32 mg, 0.17 mmol, 0.2 eq), picolinic acid (21 mg, 0.17 mmol, 0.2 eq) and $K_3PO_4$ (356 mg, 1.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 100° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L26 as a light orange solid 200 mg in 50% yield.

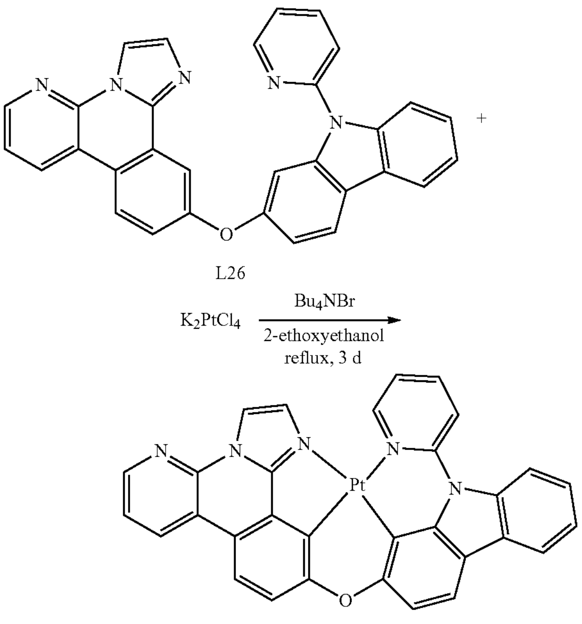

MC26

L26 (140 mg, 0.29 mmol, 1.0 eq), $K_2PtCl_4$ (134 mg, 0.32 mmol, 1.1 eq) and n-$Bu_4NBr$ (9 mg, 0.030 mmol, 0.1 eq) were added to a dry pressure tube, which was taken into a glove box and acetic acid (20 mL) was added. The mixture was bubbled with nitrogen for 30 minutes and then the tube was sealed. Then the mixture was heated to reflux in an oil bath and stirred for 3 days, cooled to ambient temperature and the solvent removed. Then the solid was purified through column chromatography on silica gel using dichloromethane as eluent to obtain the desired product MC26 as a white solid 65 mg in 33% yield.

Example 27

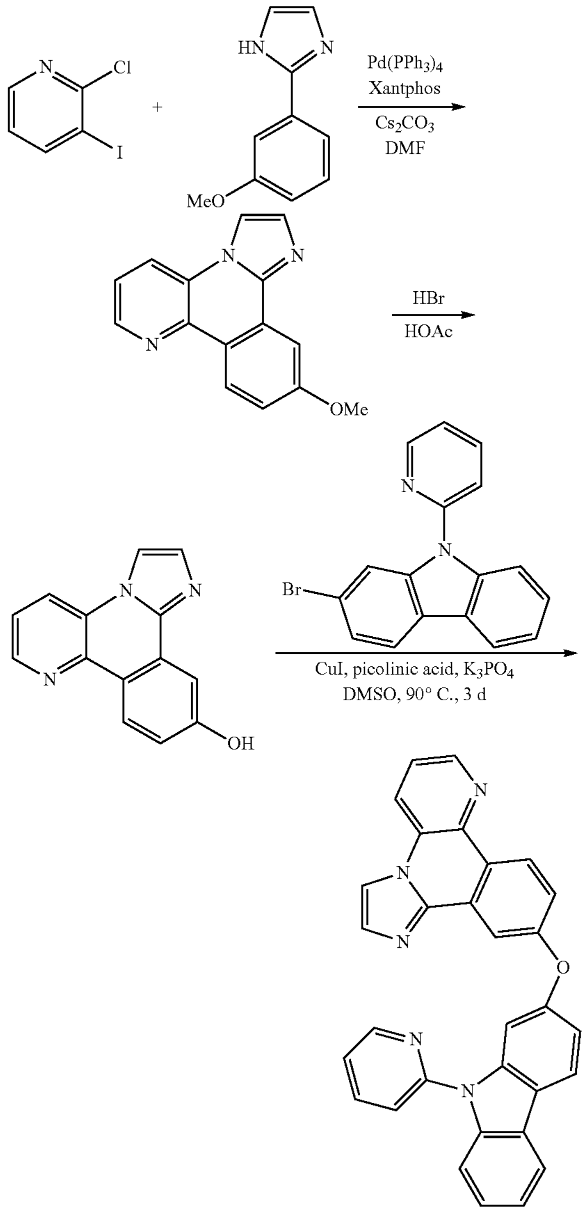

L27

Benzo[c]imidazo[1,2-a][1,5]naphthyridin-11-ol (305 mg, 1.30 mmol, 1.0 eq), 2-bromo-9-(pyridin-2-yl)-9H-carbazole (494 mg, 1.56 mmol, 1.2 eq), CuI (50 mg, 0.26 mmol, 0.2 eq), picolinic acid (32 mg, 0.26 mmol, 0.2 eq) and $K_3PO_4$ (552 mg, 2.6 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 100° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L27 as a white solid 485 mg in 78% yield.

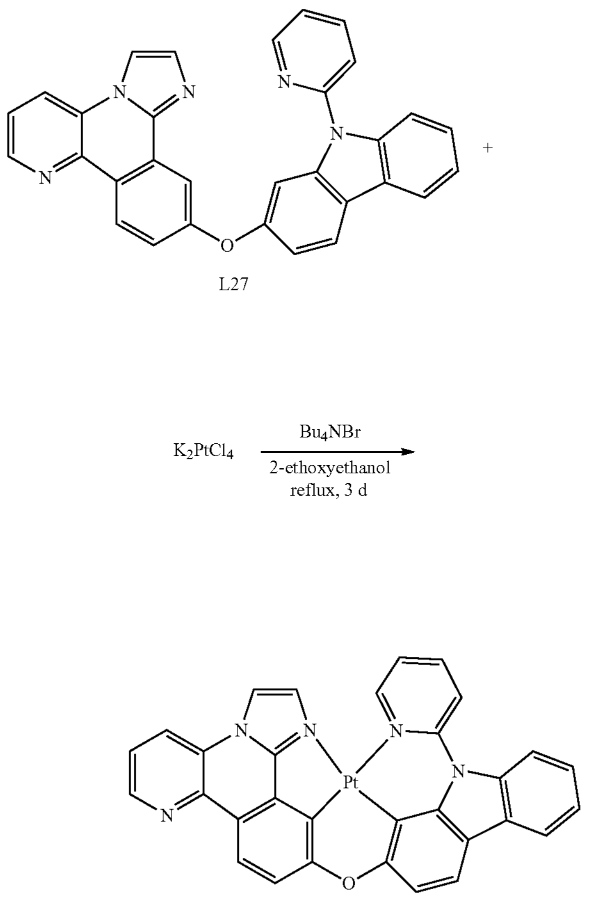

MC27

Figure 4:
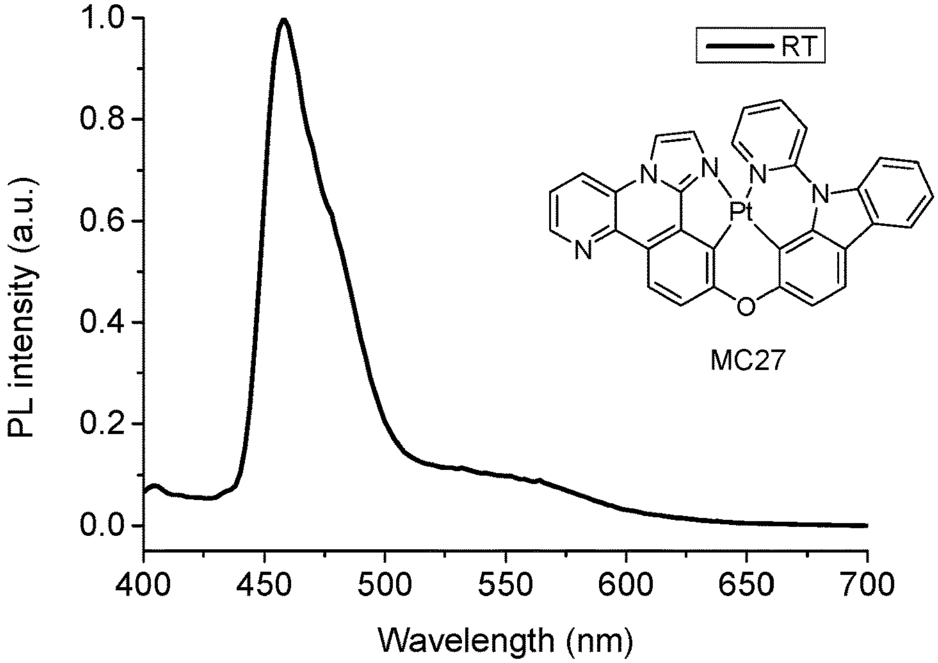
FIG. 4 is an emission spectrum of the metal-assisted delayed fluorescent emitter of Example 27 in methylene chloride at room temperature.

L27 (485 mg, 1.02 mmol, 1.0 eq), $K_2PtCl_4$ (443 mg, 1.07 mmol, 1.05 eq) and n-$Bu_4NBr$ (33 mg, 0.102 mmol, 0.1 eq) were added to a dry pressure tube, which was taken into a glove box and acetic acid (60 mL) was added. The mixture was bubbled with nitrogen for 30 minutes and then the tube was sealed. Then the mixture was heated to reflux in an oil bath and stirred for 3 days, cooled to ambient temperature and the solvent removed. Then the solid was purified through column chromatography on silica gel using dichloromethane as eluent to obtain the desired product MC27 as a white solid 268 mg in 40% yield. FIG. 4 shows an emission spectrum of MC27 in methylene chloride at room temperature.

Example 28

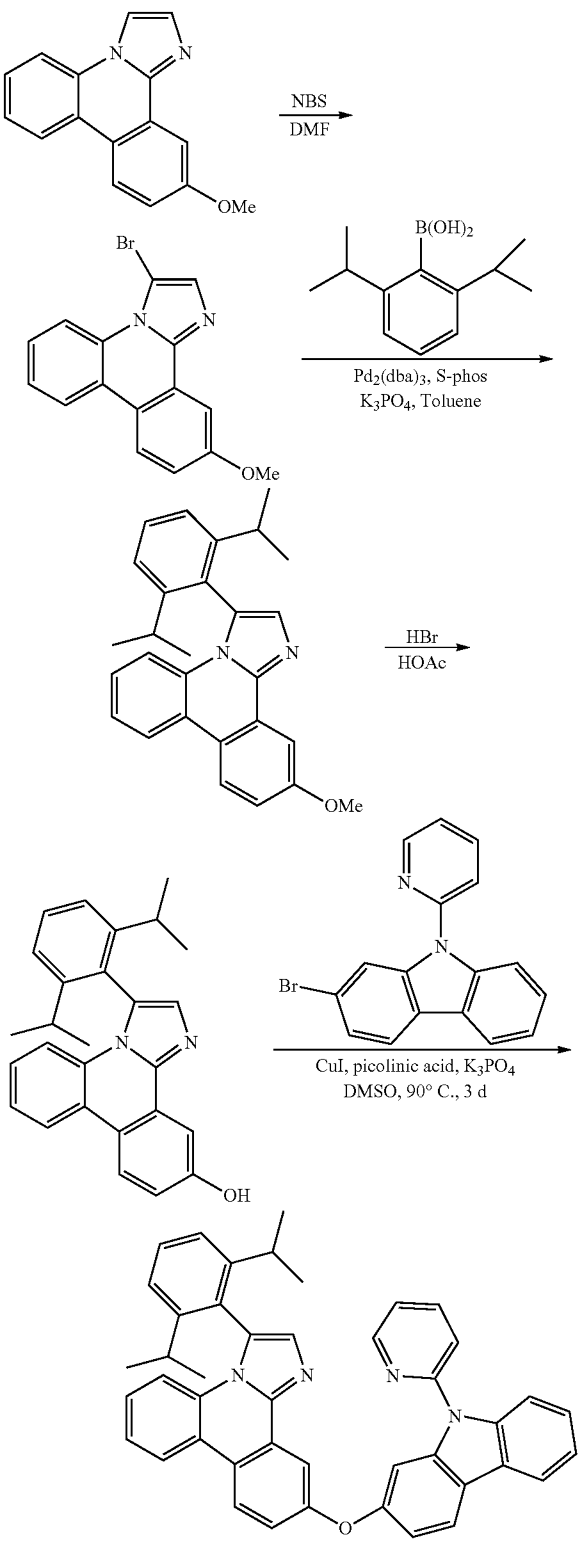

L28

3-(2,6-diisopropylphenyl)imidazo[1,2-f]phenanthridin-11-ol (0.85 mmol, 1.0 eq), 2-bromo-9-(pyridin-2-yl)-9H-carbazole (359 mg, 1.10 mmol, 1.3 eq), CuI (32 mg, 0.17 mmol, 0.2 eq), picolinic acid (21 mg, 0.17 mmol, 0.2 eq) and $K_3PO_4$ (356 mg, 1.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 100° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L28 in 50%~80% yield.

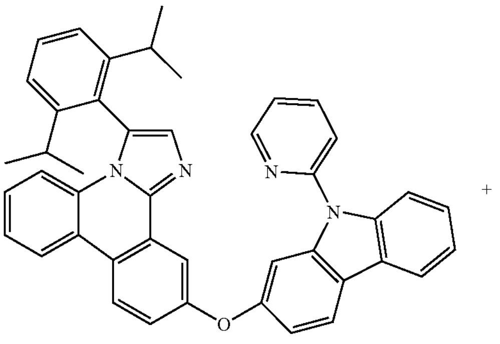

L28

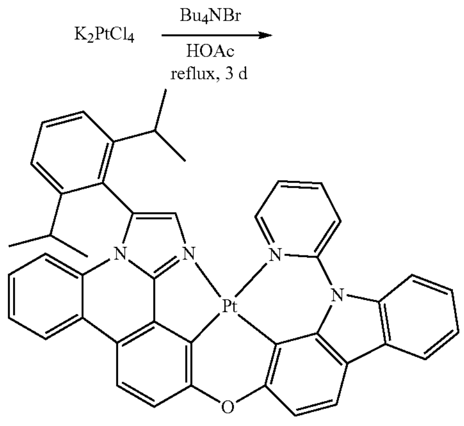

MC28

L28 (1.02 mmol, 1.0 eq), $K_2PtCl_4$ (443 mg, 1.07 mmol, 1.05 eq) and n-$Bu_4NBr$ (33 mg, 0.102 mmol, 0.1 eq) were added to a dry pressure tube, which was taken into a glove box and acetic acid (60 mL) added. The mixture was bubbled with nitrogen for 30 minutes and then the tube was sealed. Then the mixture was heated to reflux in an oil bath and stirred for 3 days, cooled to ambient temperature and the solvent removed. Then the solid was purified through column chromatography on silica gel using dichloromethane as eluent to obtain the desired product MC28 in 10%-50% yield.

Example 29

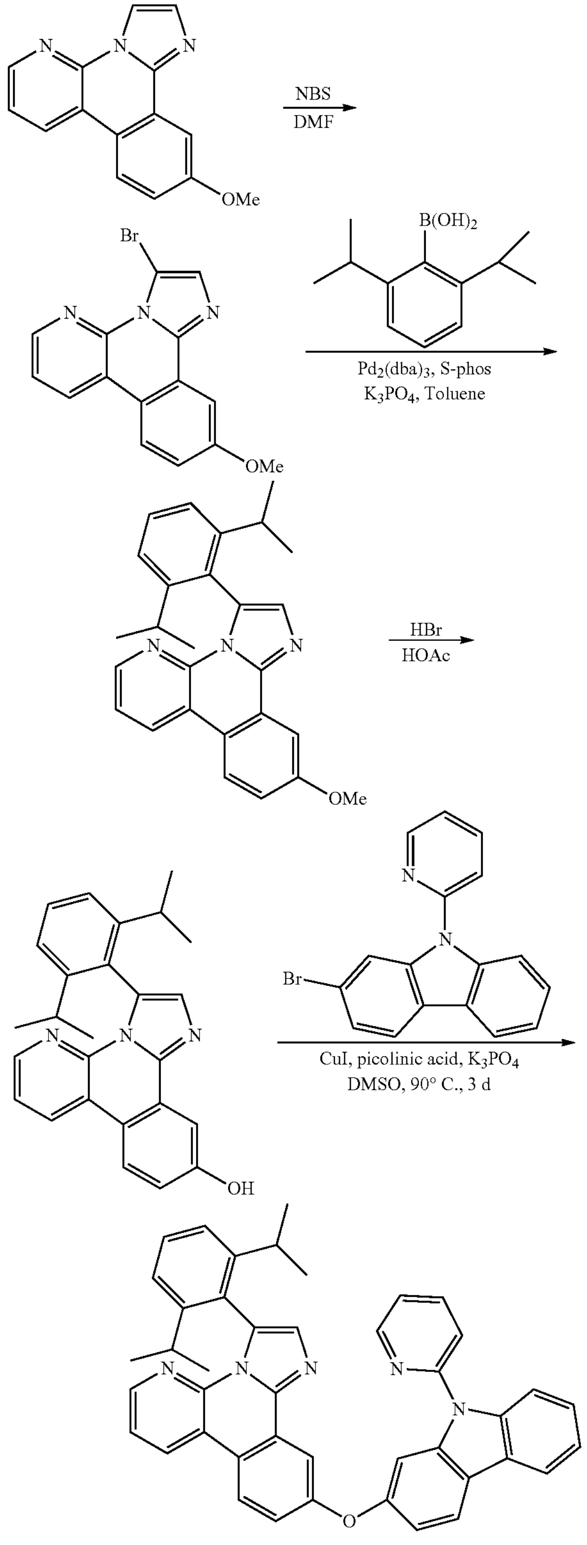

L29

3-(2,6-diisopropylphenyl)benzo[c]imidazo[1,2-a][1,8]naphthyridin-11-ol (0.85 mmol, 1.0 eq), 2-bromo-9-(pyridin-2-yl)-9H-carbazole (359 mg, 1.10 mmol, 1.3 eq), CuI (32 mg, 0.17 mmol, 0.2 eq), picolinic acid (21 mg, 0.17 mmol, 0.2 eq) and $K_3PO_4$ (356 mg, 1.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 100° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L29 in 50%~80% yield.

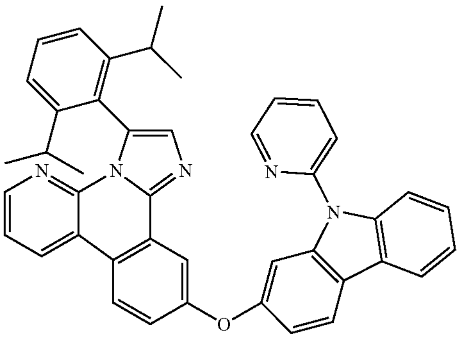

L29

+

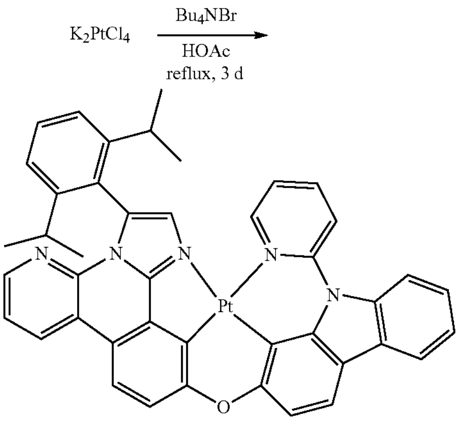

MC29

L29 (1.02 mmol, 1.0 eq), $K_2PtCl_4$ (443 mg, 1.07 mmol, 1.05 eq) and n-$Bu_4NBr$ (33 mg, 0.1025 mmol, 0.1 eq) were added to a dry pressure tube, which was taken into a glove box and acetic acid (60 mL) was added. The mixture was bubbled with nitrogen for 30 minutes and then the tube was sealed. Then the mixture was heated to reflux in an oil bath and stirred for 3 days, cooled to ambient temperature and the solvent removed. Then the solid was purified through column chromatography on silica gel using dichloromethane as eluent to obtain the desired product MC29 in 10%-50% yield.

Example 30

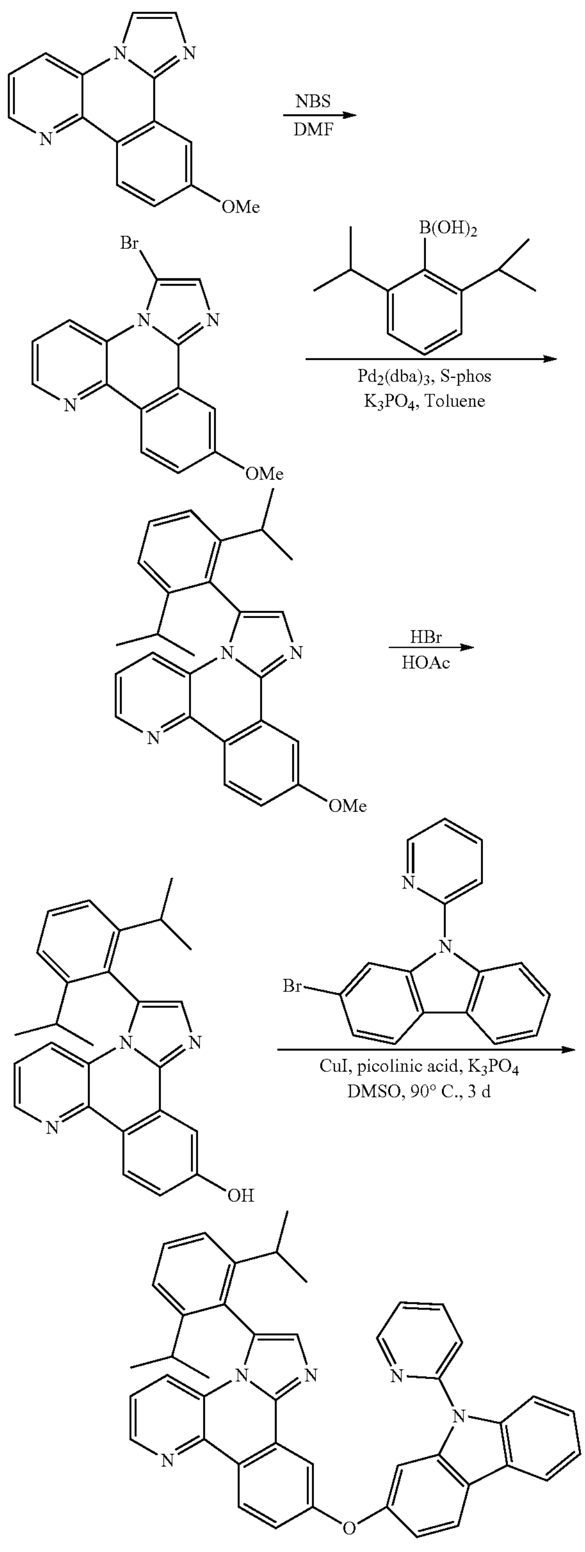

L30

3-(2,6-diisopropylphenyl)benzo[c]imidazo[1,2-a][1,5]naphthyridin-11-ol (0.85 mmol, 1.0 eq), 2-bromo-9-(pyridin-2-yl)-9H-carbazole (359 mg, 1.10 mmol, 1.3 eq), CuI (32 mg, 0.17 mmol, 0.2 eq), picolinic acid (21 mg, 0.17 mmol, 0.2 eq) and $K_3PO_4$ (356 mg, 1.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 100° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L30 in 50%~80% yield.

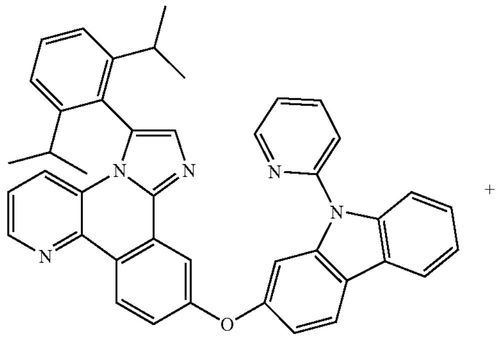

L30

$K_2PtCl_4$ $Bu_4NBr$

HOAc reflux, 3 d

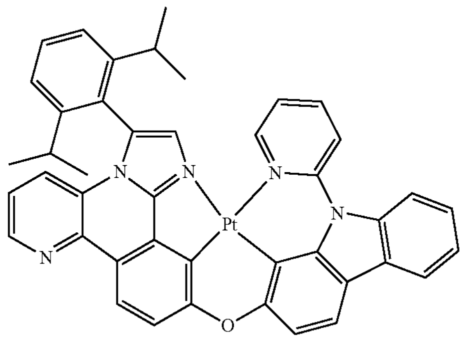

MC30

L30 (1.02 mmol, 1.0 eq), $K_2PtCl_4$ (443 mg, 1.07 mmol, 1.05 eq) and n-$Bu_4NBr$ (33 mg, 0.102 mmol, 0.1 eq) were added to a dry pressure tube, which was taken into a glove box and acetic acid (60 mL) was added. The mixture was bubbled with nitrogen for 30 minutes and then the tube was sealed. Then the mixture was heated to reflux in an oil bath and stirred for 3 days, cooled to ambient temperature and the solvent removed. Then the solid was purified through column chromatography on silica gel using dichloromethane as eluent to obtain the desired product MC30 in 10%-50% yield.

Example 31

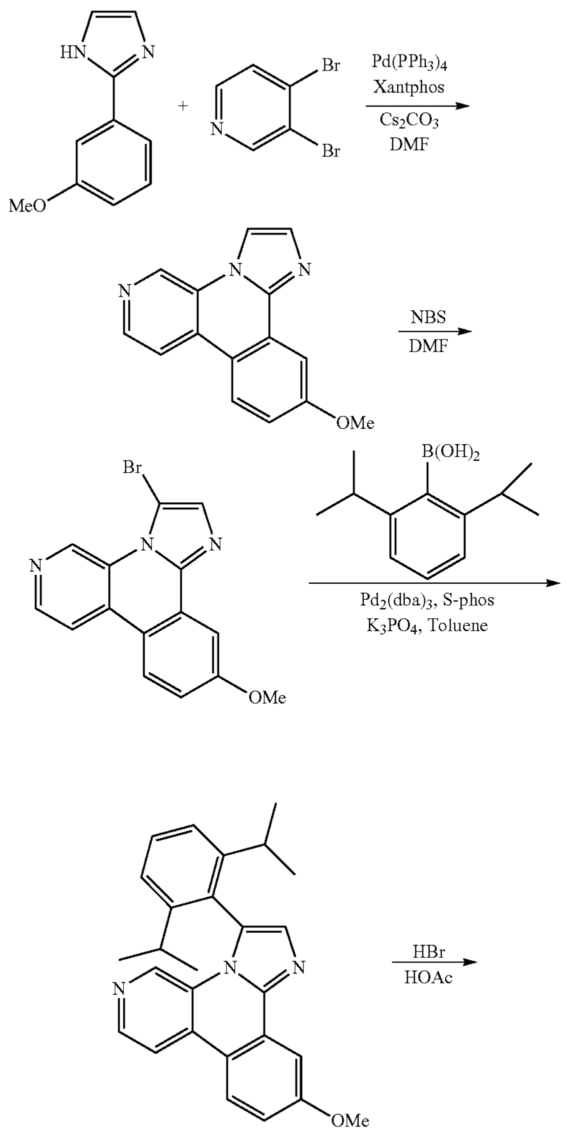

-continued

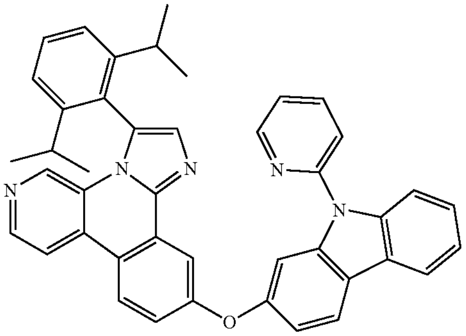

L31

3-(2,6-diisopropylphenyl)benzo[c]imidazo[1,2-a][1,7]naphthyridin-11-ol (0.85 mmol, 1.0 eq), 2-bromo-9-(pyridin-2-yl)-9H-carbazole (359 mg, 1.10 mmol, 1.3 eq), CuI (32 mg, 0.17 mmol, 0.2 eq), picolinic acid (21 mg, 0.17 mmol, 0.2 eq) and $K_3PO_4$ (356 mg, 1.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 100° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L31 in 50%~80% yield.

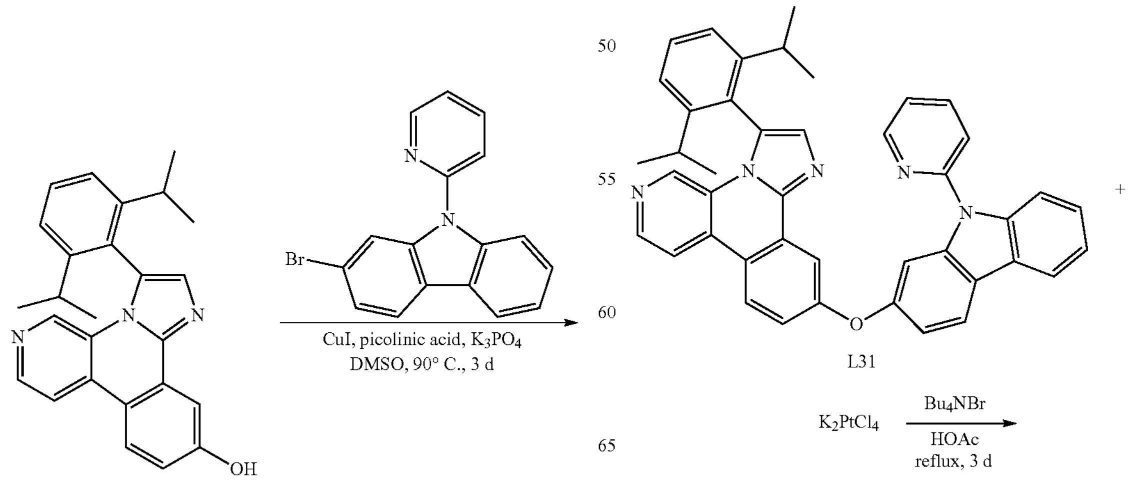

-continued

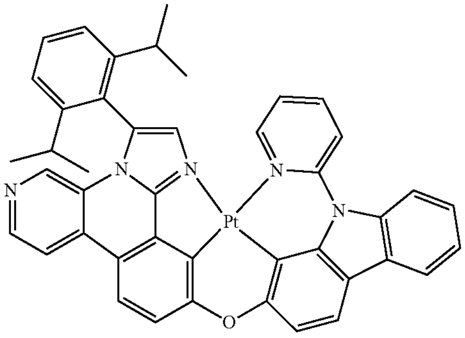

MC31

L31 (1.02 mmol, 1.0 eq), $K_2PtCl_4$ (443 mg, 1.07 mmol, 1.05 eq) and n-$Bu_4NBr$ (33 mg, 0.102 mmol, 0.1 eq) were added to a dry pressure tube, which was taken into a glove box and acetic acid (60 mL) was added. The mixture was bubbled with nitrogen for 30 minutes and then the tube was sealed. Then the mixture was heated to reflux in an oil bath and stirred for 3 days, cooled to ambient temperature and the solvent removed. Then the solid was purified through column chromatography on silica gel using dichloromethane as eluent to obtain the desired product MC31 in 10%-50% yield.

Example 32

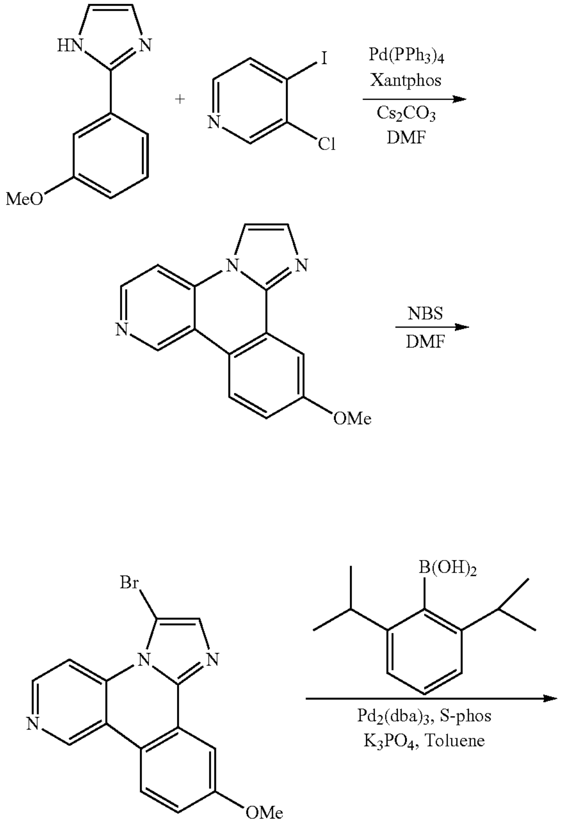

-continued

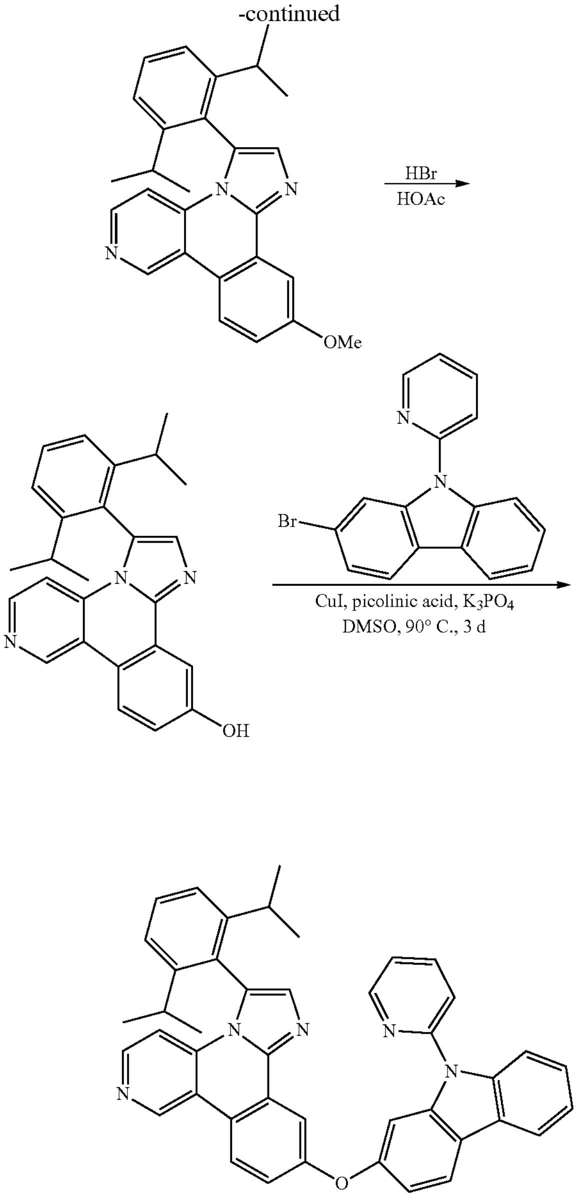

L32

3-(2,6-diisopropylphenyl)benzo[c]imidazo[1,2-a][1,6]naphthyridin-11-ol (0.85 mmol, 1.0 eq), 2-bronco-9-(pyridin-2-yl)-9H-carbazole (359 mg, 1.10 mmol, 1.3 eq.), CuI (32 mg, 0.17 mmol, 0.2 eq), picolinic acid (21 mg, 0.17 mmol, 0.2 eq) and $K_3PO_4$ (356 mg, 1.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 100° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L32 in 50%~80% yield.

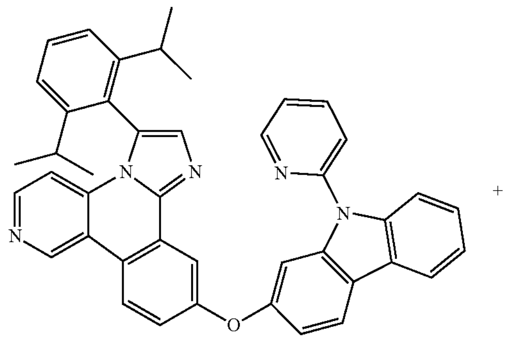

L32

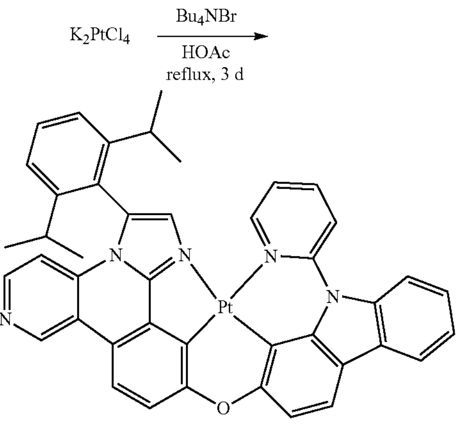

MC32

L32 (1.02 mmol, 1.0 eq), $K_2PtCl_4$ (443 mg, 1.07 mmol, 1.05 eq) and n-$Bu_4NBr$ (33 mg, 0.102 mmol, 0.1 eq) were added to a dry pressure tube, which was taken into a glove box and acetic acid (60 mL) was added. The mixture was bubbled with nitrogen for 30 minutes and then the tube was sealed. Then the mixture was heated to reflux in an oil bath and stirred for 3 days, cooled to ambient temperature and the solvent removed. Then the solid was purified through column chromatography on silica gel using dichloromethane as eluent to obtain the desired product MC32 in 10%-50% yield.

Example 33

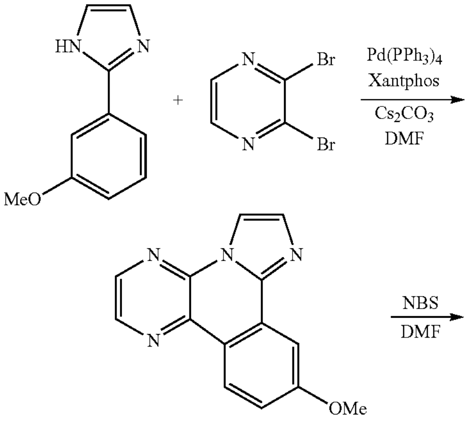

-continued

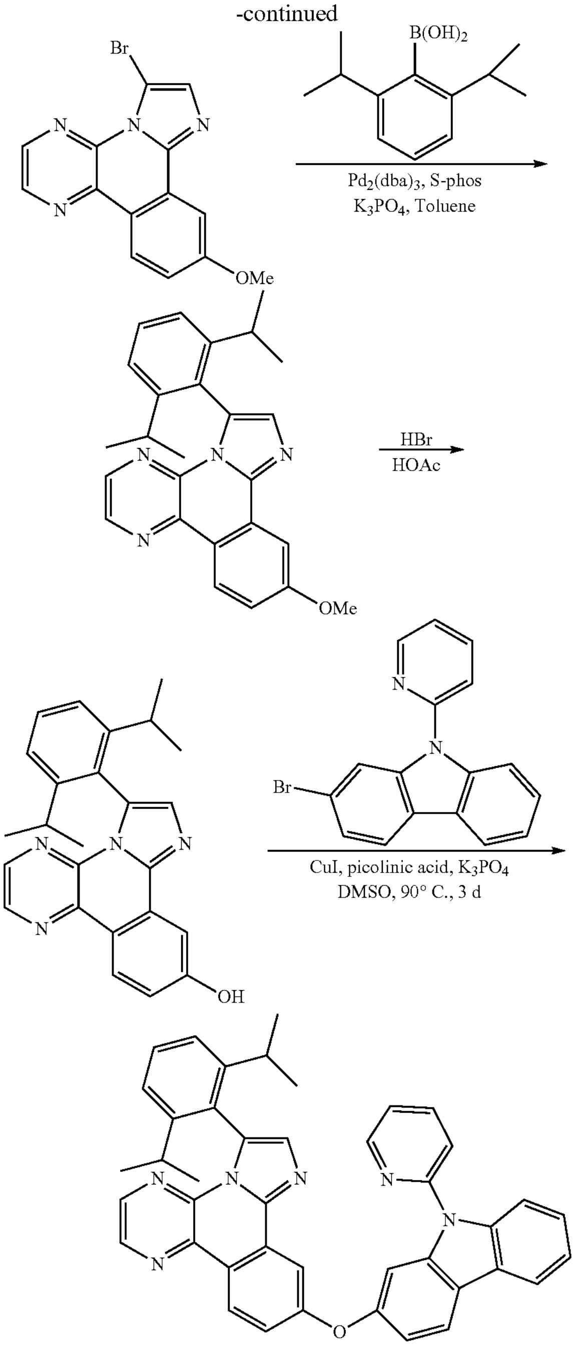

L33

3-(2,6-diisopropylphenyl)imidazo[2,1-a]pyrazino[2,3-c]isoquinolin-11-ol (0.85 mmol, 1.0 eq), 2-bromo-9-(pyridin-2-yl)-9H-carbazole (359 mg, 1.10 mmol, 1.3 eq), CuI (32 mg, 0.17 mmol, 0.2 eq), picolinic acid (21 mg, 0.17 mmol, 0.2 eq) and $K_3PO_4$ (356 mg, 1.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 100° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L33 in 50%~80% yield.

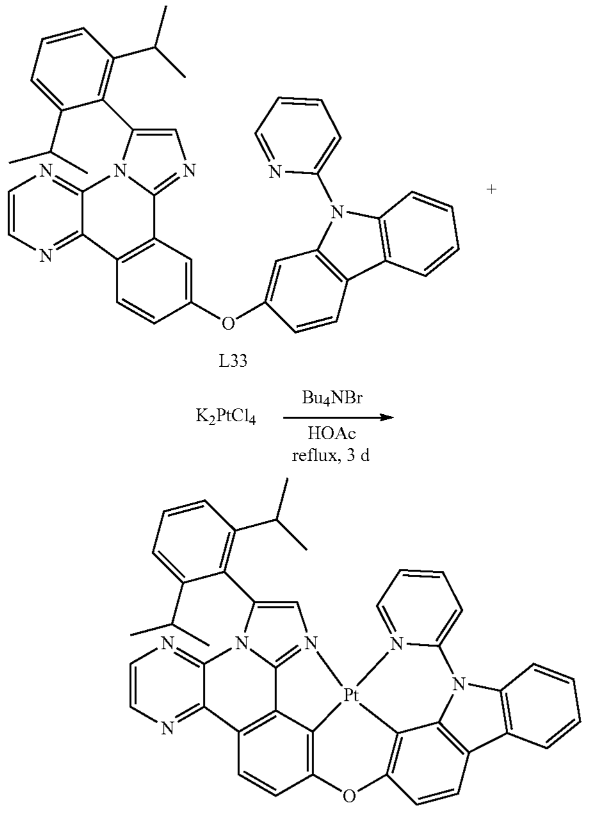

L33

MC33

L33 (1.02 mmol, 1.0 eq), $K_2PtCl_4$ (443 mg, 1.07 mmol, 1.05 eq) and n-$Bu_4NBr$ (33 mg, 0.102 mmol, 0.1 eq) were added to a dry pressure tube, which was taken into a glove box and acetic acid (60 mL) was added. The mixture was bubbled with nitrogen for 30 minutes and then the tube was sealed. Then the mixture was heated to reflux in an oil bath and stirred for 3 days, cooled to ambient temperature and the solvent removed. Then the solid was purified through column chromatography on silica gel using dichloromethane as eluent to obtain the desired product MC33 in 10%-50% yield.

Example 34

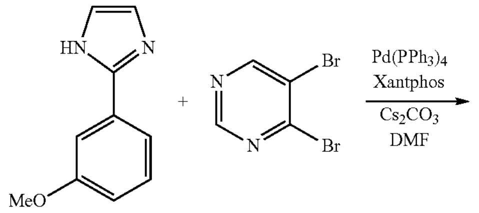

-continued

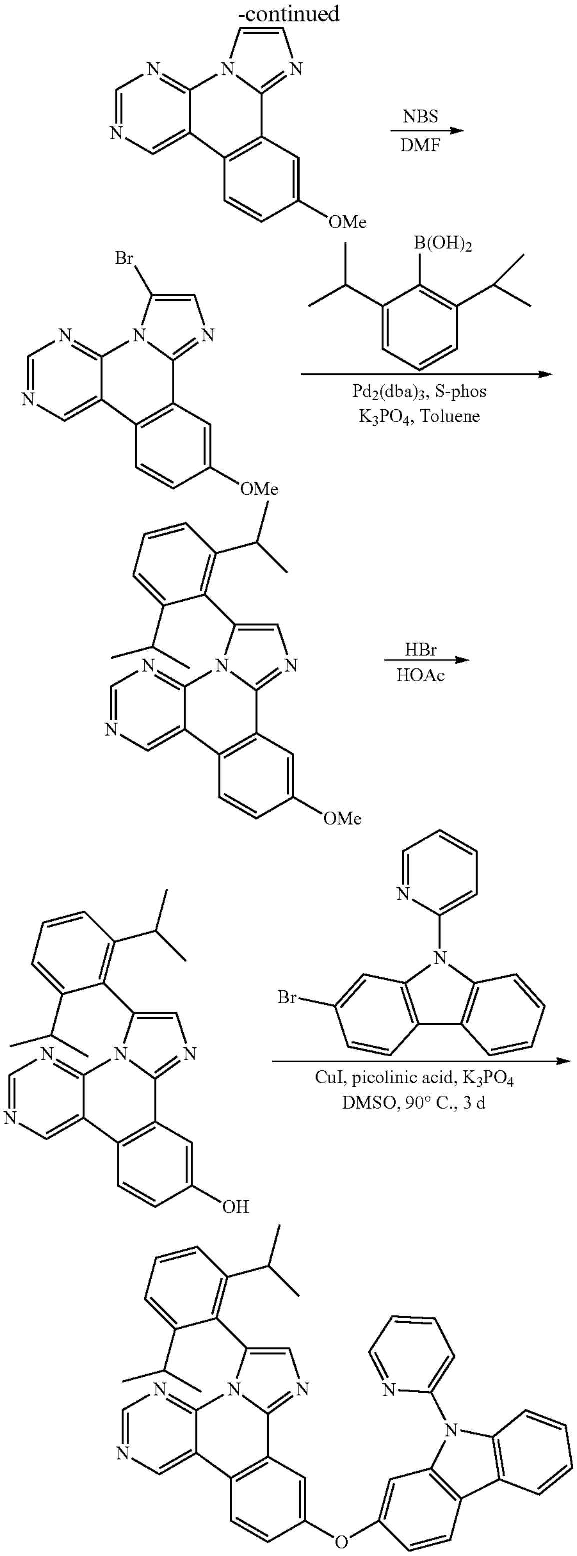

L34

11-(2,6-diisopropylphenyl)imidazo[2,1-a]pyrimido[4,5-c]isoquinolin-7-ol (0.85 mmol, 1.0 eq), 2-bronco-9-(pyridin-2-yl)-9H-carbazole (359 mg, 1.10 mmol, 1.3 eq), CuI (32 mg, 0.17 mmol, 0.2 eq), picolinic acid (21 mg, 0.17 mmol, 0.2 eq) and $K_3PO_4$ (356 mg, 1.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 100° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L34 in 50%~80% yield.

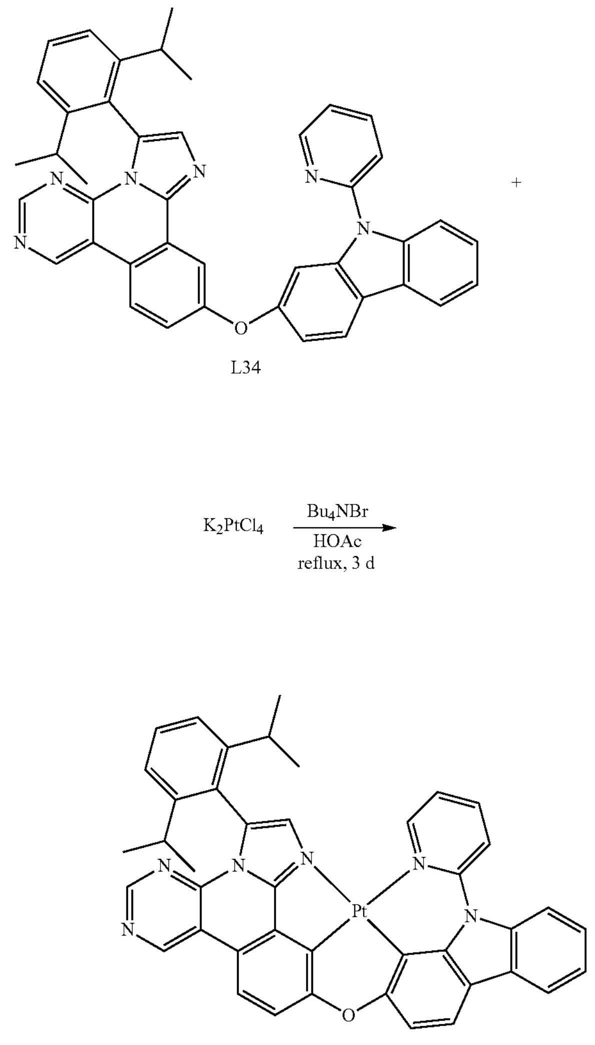

MC34

L34 (1.02 mmol, 1.0 eq), $K_2PtCl_4$ (443 mg, 1.07 mmol, 1.05 eq) and n-$Bu_4NBr$ (33 mg, 0.102 mmol, 0.1 eq) were added to a dry pressure tube, which was taken into a glove box and acetic acid (60 mL) was added. The mixture was bubbled with nitrogen for 30 minutes and then the tube was sealed. Then the mixture was heated to reflux in an oil bath and stirred for 3 days, cooled to ambient temperature and the solvent removed. Then the solid was purified through column chromatography on silica gel using dichloromethane as eluent to obtain the desired product MC34 in 10%-50% yield.

Example 35

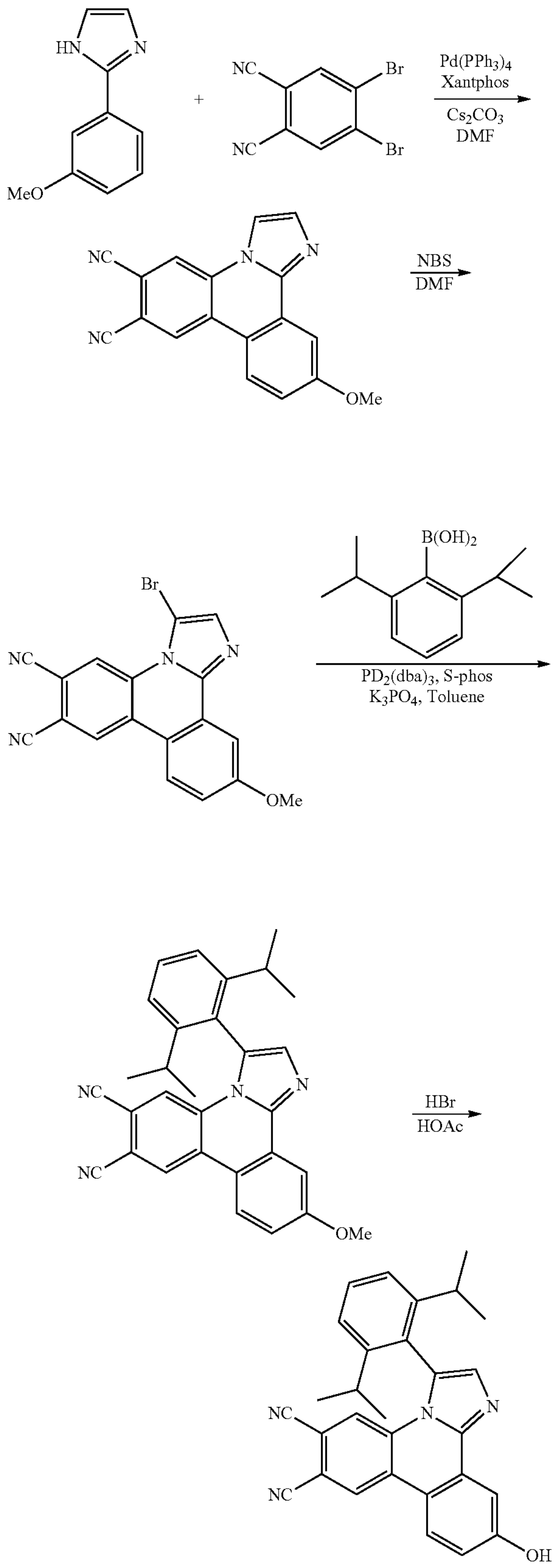

-continued

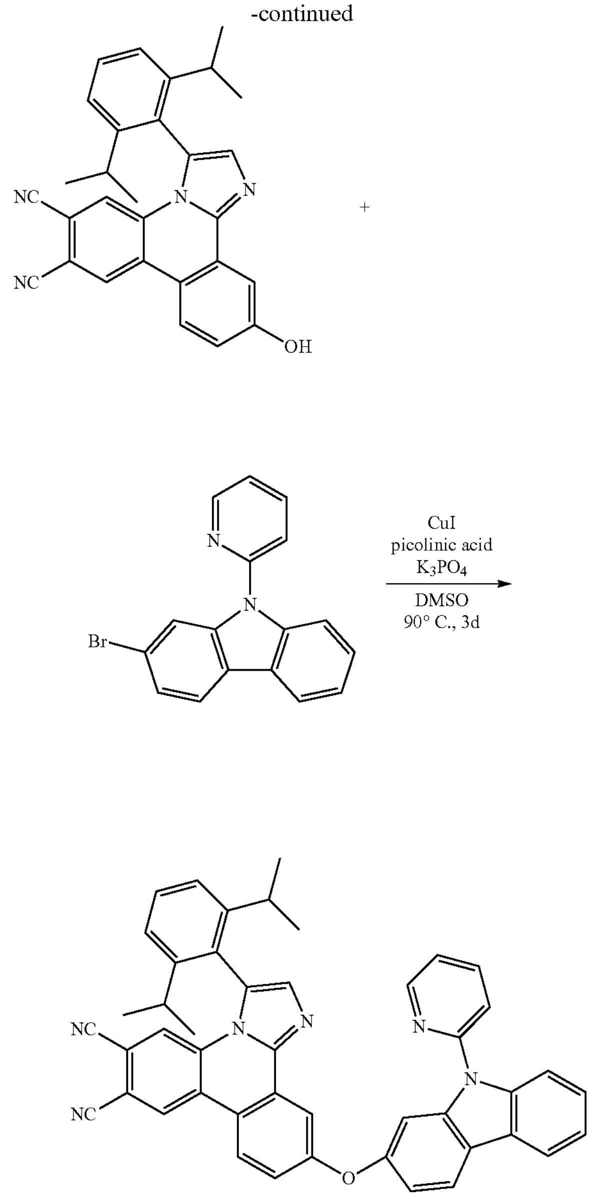

L35

3-(2,6-diisopropylphenyl)-11-hydroxyimidazo[1,2-f]phenanthridine-6,7-dicarbonitrile (0.85 mmol, 1.0 eq), 2-bromo-9-(pyridin-2-yl)-9H-carbazole (359 mg, 1.10 mmol, 1.3 eq), CuI (32 mg, 0.17 mmol, 0.2 eq), picolinic acid (21 mg, 0.17 mmol, 0.2 eq) and $K_3PO_4$ (356 mg, 1.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 100° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L35 in 50%~80% yield.

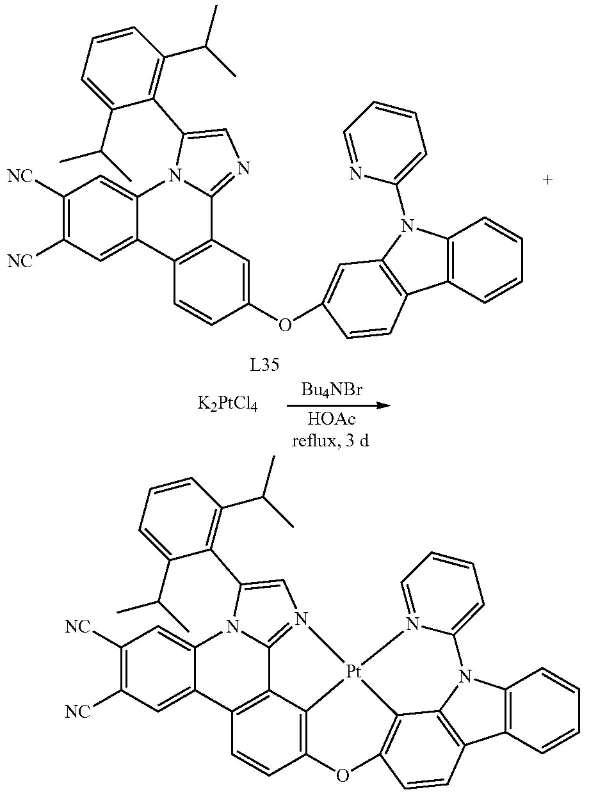

MC35

L35 (1.02 mmol, 1.0 eq), $K_2PtCl_4$ (443 mg, 1.07 mmol, 1.05 eq) and n-$Bu_4NBr$ (33 mg, 0.102 mmol, 0.1 eq) were added to a dry pressure tube, which was taken into a glove box and acetic acid (60 mL) was added. The mixture was bubbled with nitrogen for 30 minutes and then the tube was sealed. Then the mixture was heated to reflux in an oil bath and stirred for 3 days, cooled to ambient temperature and the solvent removed. Then the solid was purified through column chromatography on silica gel using dichloromethane as eluent to obtain the desired product MC35 in 10%-50% yield.

Example 36

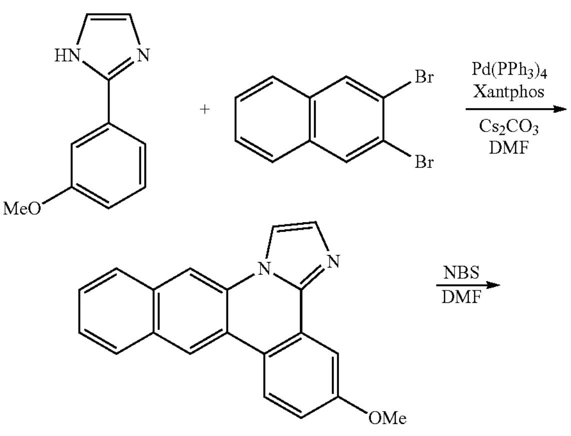

-continued

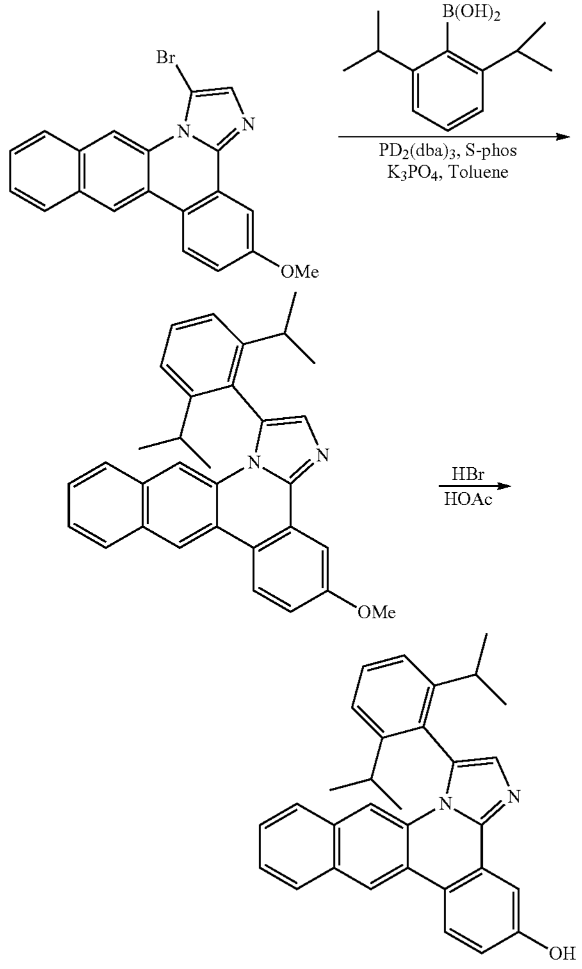

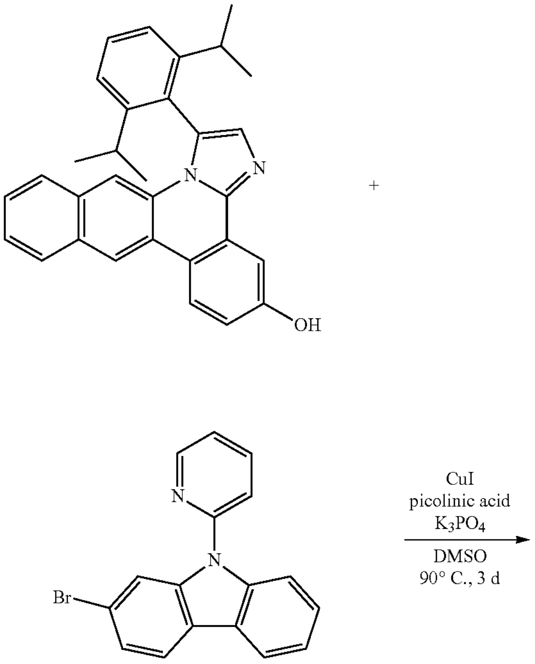

-continued

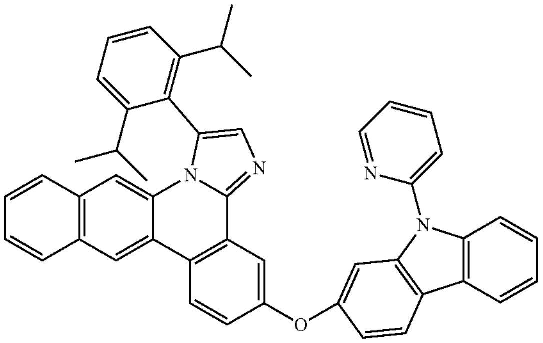

L36

1-(2,6-diisopropylphenyl)benzo[b]imidazo[1,2-f]phenanthridin-5-ol (0.85 mmol, 1.0 eq), 2-bromo-9-(pyridin-2-yl)-9H-carbazole (359 mg, 1.10 mmol, 1.3 eq), CuI (32 mg, 0.17 mmol, 0.2 eq), picolinic acid (21 mg, 0.17 mmol, 0.2 eq) and $K_3PO_4$ (356 mg, 1.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 100° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L36 in 50%~80% yield.

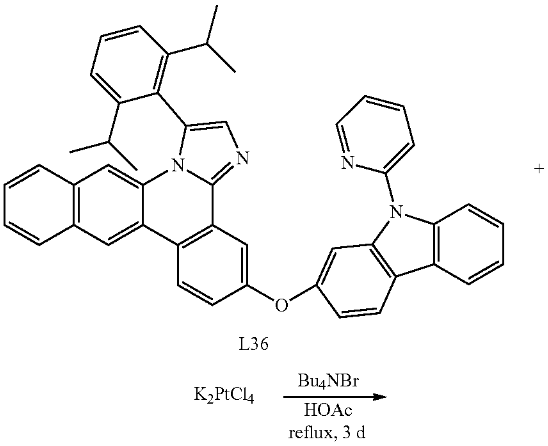

L36

-continued

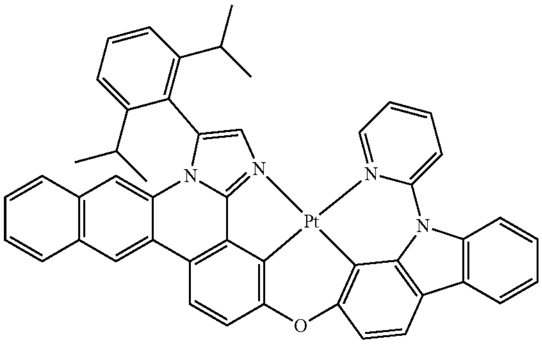

MC36

L36 (1.02 mmol, 1.0 eq), $K_2PtCl_4$ (443 mg, 1.07 mmol, 1.05 eq) and n-$Bu_4NBr$ (33 mg, 0.102 mmol, 0.1 eq) were added to a dry pressure tube, which was taken into a glove box and acetic acid (60 mL) was added. The mixture was bubbled with nitrogen for 30 minutes and then the tube was sealed. Then the mixture was heated to reflux in an oil bath and stirred for 3 days, cooled to ambient temperature and the solvent removed. Then the solid was purified through column chromatography on silica gel using dichloromethane as eluent to obtain the desired product MC36 in 10%-50% yield.

Example 37

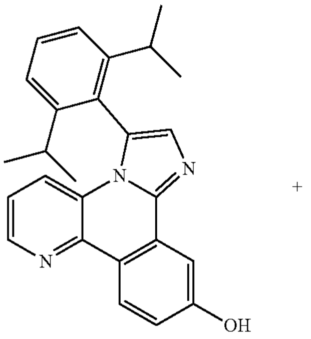

-continued

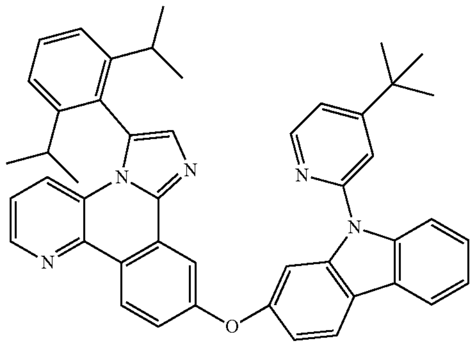

L37

3-(2,6-diisopropylphenyl)benzo[c]imidazo[1,2-a][1,5]naphthyridin-11-ol (0.85 mmol, 1.0 eq), 2-bromo-9-(4-(tert-butyl)pyridin-2-yl)-9H-carbazole (417 mg, 1.10 mmol, 1.3 eq), CuI (32 mg, 0.17 mmol, 0.2 eq), picolinic acid (21 mg, 0.17 mmol, 0.2 eq) and $K_3PO_4$ (356 mg, 1.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 100° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L37 in 50%~80% yield.

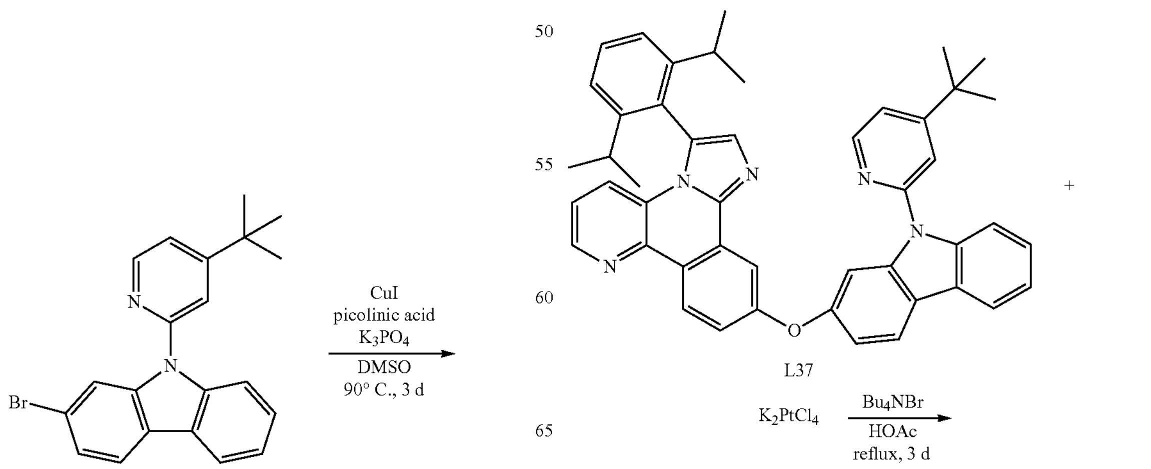

-continued

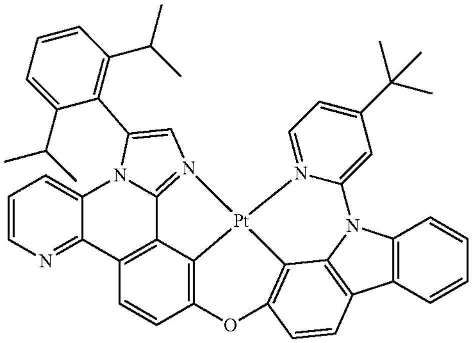

MC37

L37 (1.02 mmol, 1.0 eq), $K_2PtCl_4$ (443 mg, 1.07 mmol, 1.05 eq) and n-$Bu_4NBr$ (33 mg, 0.102 mmol, 0.1 eq) were added to a dry pressure tube, which was taken into a glove box and acetic acid (60 mL) was added. The mixture was bubbled with nitrogen for 30 minutes and then the tube was sealed. Then the mixture was heated to reflux in an oil bath and stirred for 3 days, cooled to ambient temperature and the solvent removed. Then the solid was purified through column chromatography on silica gel using dichloromethane as eluent to obtain the desired product MC37 in 10%-50% yield.

Example 38

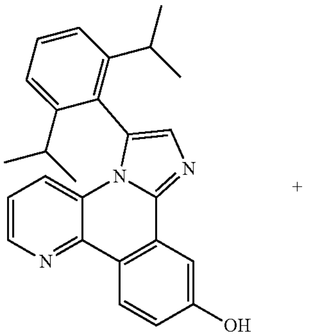

+

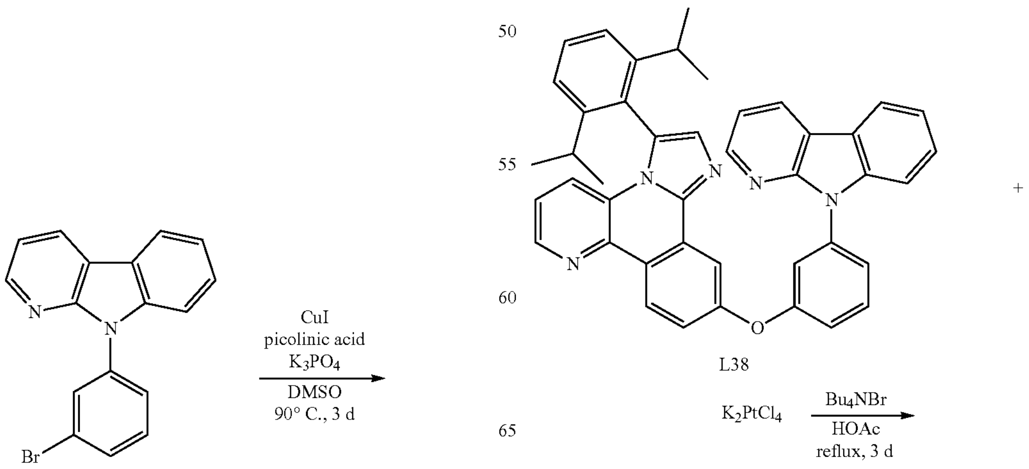

L38

-continued

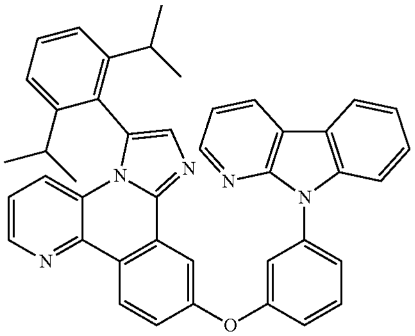

L38

3-(2,6-diisopropylphenyl)benzo[c]imidazo[1,2-a][1,5]naphthyridin-11-ol (0.85 mmol, 1.0 eq), 9-(3-bromophenyl)-9H-pyrido[2,3-b]indole (359 mg, 1.10 mmol, 1.3 eq), CuI (32 mg, 0.17 mmol, 0.2 eq), picolinic acid (21 mg, 0.17 mmol, 0.2 eq) and $K_3PO_4$ (356 mg, 1.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 100° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L38 in 50%~80% yield.

-continued

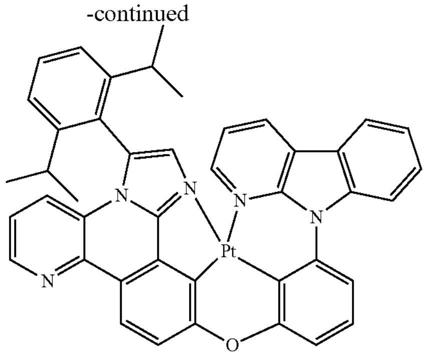

MC38

L38 (1.02 mmol, 1.0 eq), $K_2PtCl_4$ (443 mg, 1.07 mmol, 1.05 eq) and n-$Bu_4NBr$ (33 mg, 0.102 mmol, 0.1 eq) were added to a dry pressure tube, which was taken into a glove box and acetic acid (60 mL) was added. The mixture was bubbled with nitrogen for 30 minutes and then the tube was sealed. Then the mixture was heated to reflux in an oil bath and stirred for 3 days, cooled to ambient temperature and the solvent removed. Then the solid was purified through column chromatography on silica gel using dichloromethane as eluent to obtain the desired product MC38 in 10%-50% yield.

Example 39

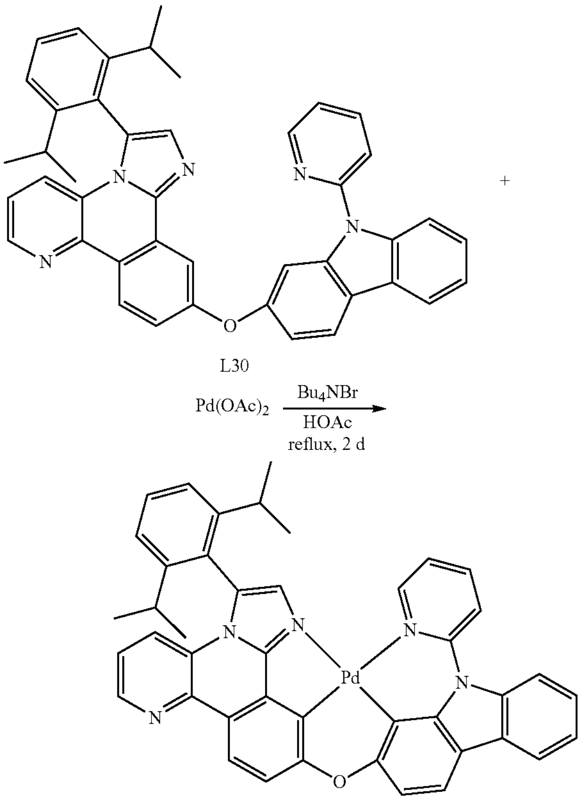

MC39

L30 (1.02 mmol, 1.0 eq), $Pd(OAc)_2$ (239 mg, 1.07 mmol, 1.05 eq) and n-$Bu_4NBr$ (33 mg, 0.102 mmol, 0.1 eq) were added to a dry pressure tube, which was taken into a glove box and acetic acid (60 mL) was added. The mixture was bubbled with nitrogen for 30 minutes and then the tube was sealed. Then the mixture was heated to reflux in an oil bath and stirred for 2 days, cooled to ambient temperature and the solvent removed. Then the solid was purified through column chromatography on silica gel using dichloromethane as eluent to obtain the desired product MC39 in 10%-50% yield.

Example 40

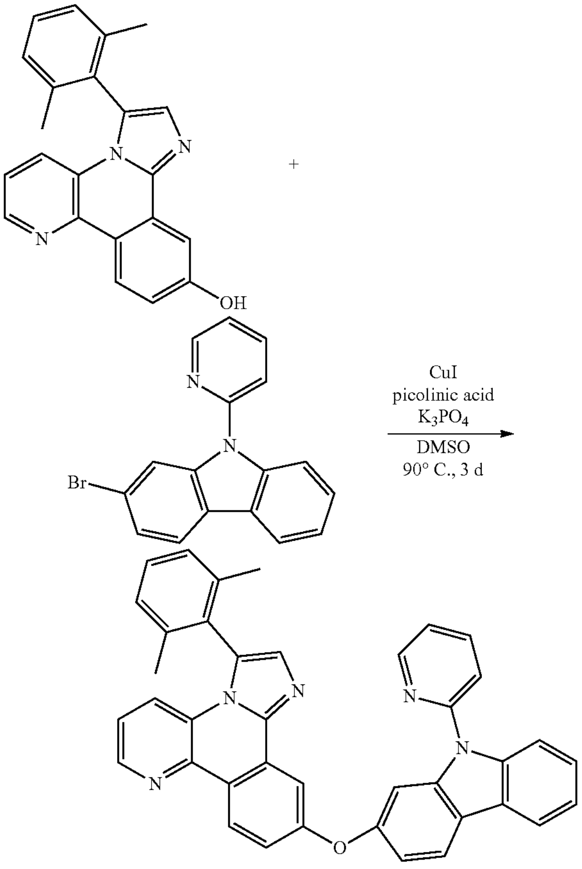

L40

3-(2,6-dimethylphenyl)benzo[c]imidazo[1,2-a][1,5]naphthyridin-11-ol (0.85 mmol, 1.0 eq), 2-bromo-9-(pyridin-2-yl)-9H-carbazole (359 mg, 1.10 mmol, 1.3 eq), CuI (32 mg, 0.17 mmol, 0.2 eq), picolinic acid (21 mg, 0.17 mmol, 0.2 eq) and $K_3PO_4$ (356 mg, 1.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 100° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L40 in 50%~80% yield.

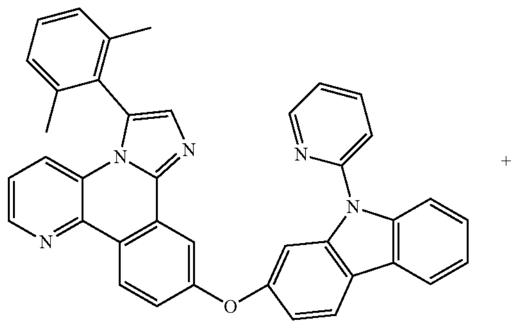

L40

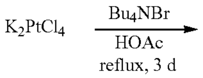

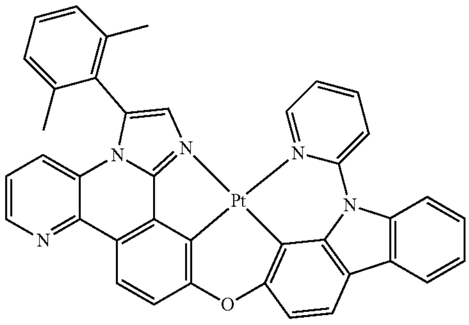

MC40

L40 (1.02 mmol, 1.0 eq), $K_2PtCl_4$ (443 mg, 1.07 mmol, 1.05 eq) and n-$Bu_4NBr$ (33 mg, 0.102 mmol, 0.1 eq) were added to a dry pressure tube, which was taken into a glove box and acetic acid (60 mL) was added. The mixture was bubbled with nitrogen for 30 minutes and then the tube was sealed. Then the mixture was heated to reflux in an oil bath and stirred for 3 days, cooled to ambient temperature and the solvent removed. Then the solid was purified through column chromatography on silica gel using dichloromethane as eluent to obtain the desired product MC40 in 10%-50% yield.

Example 41

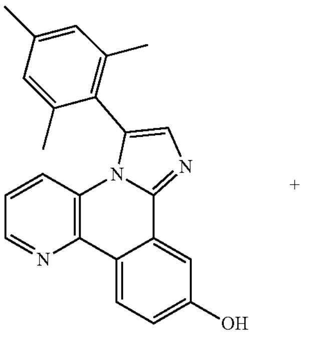

-continued

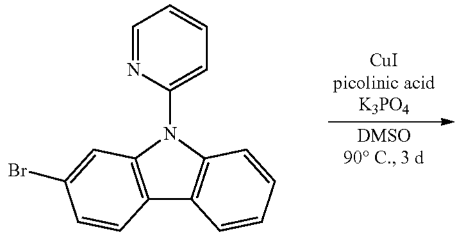

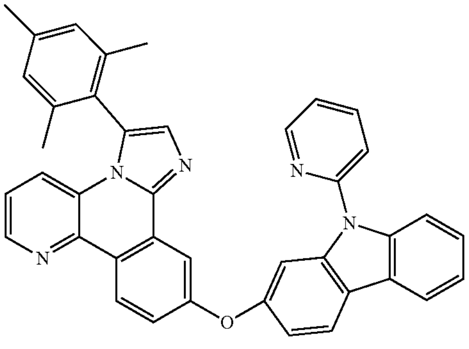

L41

3-mesitylbenzo[c]imidazo[1,2-a][1,5]naphthyridin-11-ol (300 mg, 0.85 mmol, 1.0 eq), 2-bromo-9-(pyridin-2-yl)-9H-carbazole (359 mg, 1.10 mmol, 1.3 eq), CuI (32 mg, 0.17 mmol, 0.2 eq), picolinic acid (21 mg, 0.17 mmol, 0.2 eq) and $K_3PO_4$ (356 mg, 1.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 100° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L41 in 75% yield.

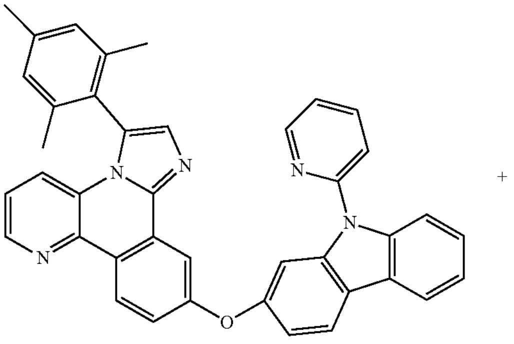

L41

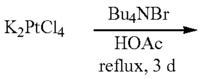

-continued

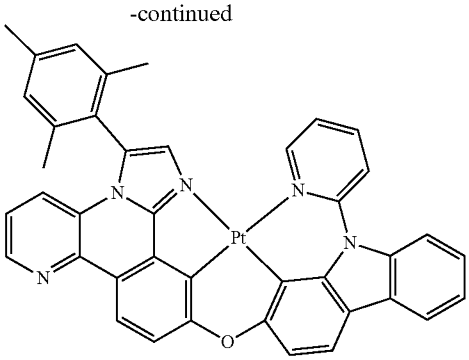

MC41

L41 (238 g, 0.4 mmol, 1.0 eq), $K_2PtCl_4$ (174 mg, 0.42 mmol, 1.05 eq) and n-$Bu_4NBr$ (13 mg, 0.04 mmol, 0.1 eq) were added to a dry pressure tube, which was taken into a glove box and acetic acid (60 mL) was added. The mixture was bubbled with nitrogen for 30 minutes and then the tube was sealed. Then the mixture was heated to reflux in an oil bath and stirred for 3 days, cooled to ambient temperature and the solvent removed. Then the solid was purified through column chromatography on silica gel using dichloromethane as eluent to obtain the desired product MC41 in 72% yield.

Example 42

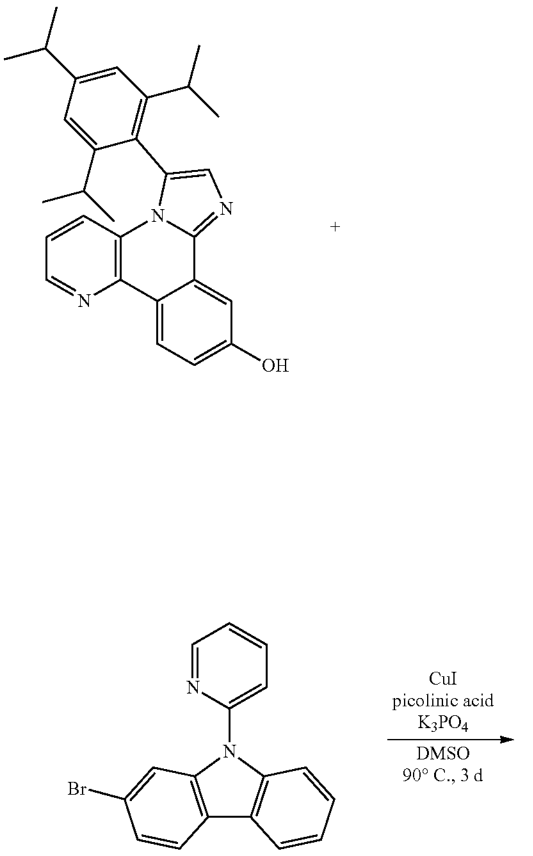

-continued

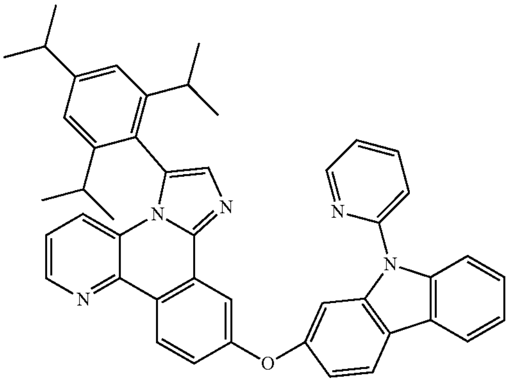

L42

3-(2,4,6-triisopropylphenyl)benzo[c]imidazo[1,2-a][1,5]naphthyridin-11-ol (0.85 mmol, 1.0 eq), 2-bromo-9-(pyridin-2-yl)-9H-carbazole (359 mg, 1.10 mmol, 1.3 eq), CuI (32 mg, 0.17 mmol, 0.2 eq), picolinic acid (21 mg, 0.17 mmol, 0.2 eq) and $K_3PO_4$ (356 mg, 1.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 100° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L42 in 50%~80% yield.

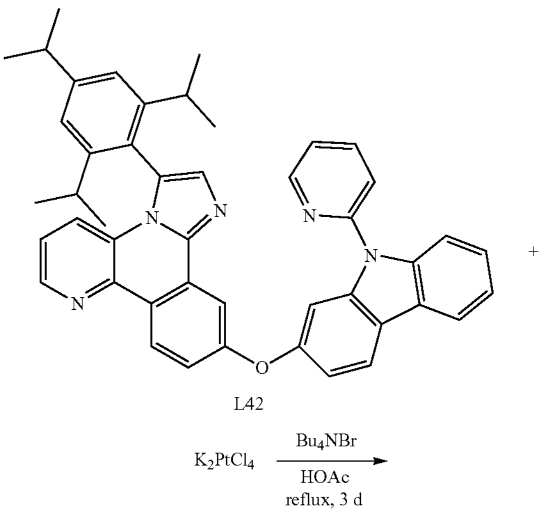

-continued

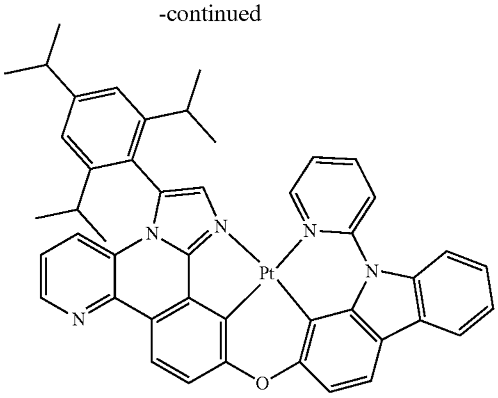

MC42

L42 (1.02 mmol, 1.0 eq), $K_1PtCl_4$ (443 mg, 1.07 mmol, 1.05 eq) and n-$Bu_4NBr$ (33 mg, 0.102 mmol, 0.1 eq) were added to a dry pressure tube, which was taken into a glove box and acetic acid (60 mL) was added. The mixture was bubbled with nitrogen for 30 minutes and then the tube was sealed. Then the mixture was heated to reflux in an oil bath and stirred for 3 days, cooled to ambient temperature and the solvent removed. Then the solid was purified through column chromatography on silica gel using dichloromethane as eluent to obtain the desired product MC42 in 10%-50% yield.

Example 43

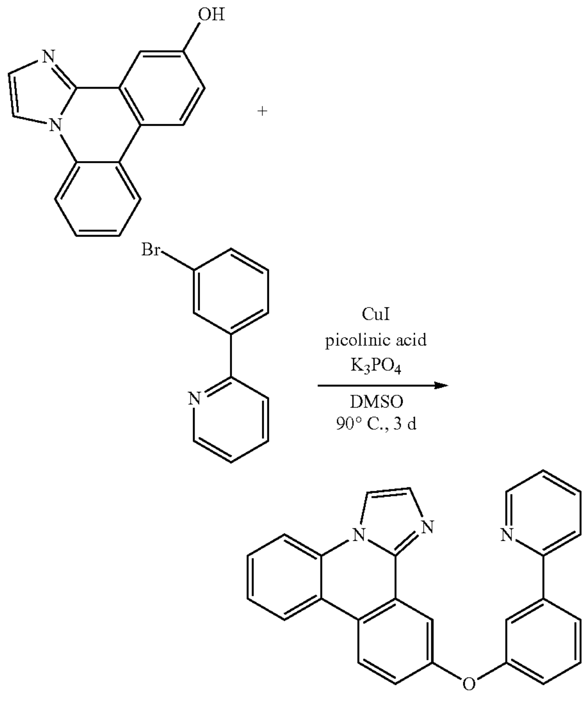

L43

Imidazo[1,2-f]phenanthridin-11-ol (1 mmol, 1.0 eq), 2-(3-bromophenyl)pyridine (281 mg, 1.2 mmol, 1.2 eq), CuI (38 mg, 0.2 mmol, 0.2 eq), picolinic acid (49 mg, 0.4 mmol, 0.4 eq) and $K_3PO_4$ (425 mg, 2 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 90° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate (2:1) as eluent to obtain the desired product ligand L43 as a white solid in 72% yield.

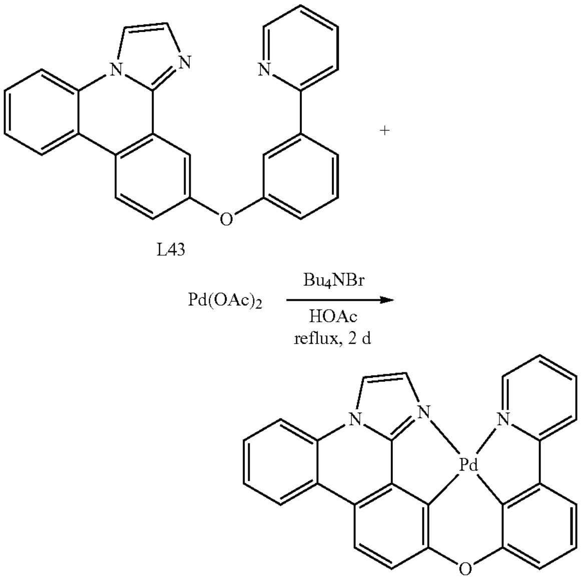

MC43

L43 (0.20 mmol, 1.0 eq), $Pd(OAc)_2$ (54 mg, 0.24 mmol, 1.2 eq) and n-$Bu_4NBr$ (6.5 mg, 0.02 mmol, 0.1 eq) were added to a dry pressure tube was then taken into a glove box and acetic acid (10 mL) was added. The mixture was bubbled with nitrogen for 30 minutes and then the tube was sealed. Then the mixture was heated to reflux in an oil bath and stirred for 2 days, cooled to ambient temperature and removed the solvent. Then the solid was purified through column chromatography on silica gel using dichloromethane as eluent to obtain to obtain the desired product MC43 as a white solid in 53% yield.

Example 44

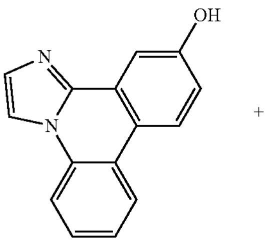

-continued

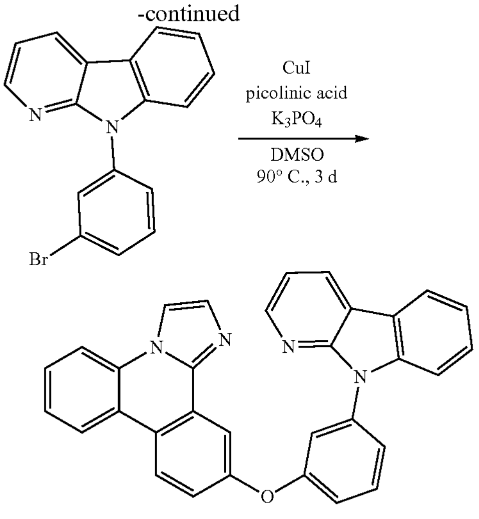

L44

Imidazo[1,2-f]phenanthridin-11-ol (1 mmol, 1.0 eq), 9-(3-bromophenyl)-9H-pyrido[2,3-b]indole (388 mg, 1.2 mmol, 1.2 eq), CuI (38 mg, 0.2 mmol, 0.2 eq), picolinic acid (49 mg, 0.4 mmol, 0.4 eq) and $K_3PO_4$ (425 mg, 2 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 90° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate (2:1) as eluent to obtain the desired product ligand L44 as a white solid in 66% yield.

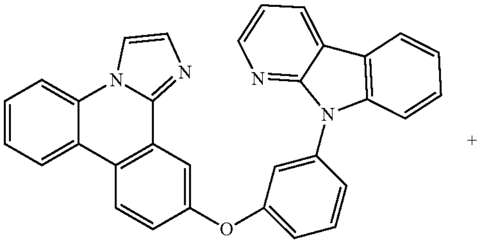

L44

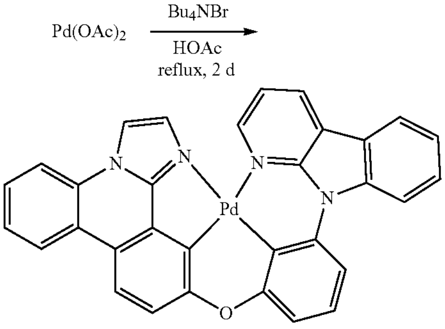

MC44

L44 (0.20 mmol, 1.0 eq), $Pd(OAc)_2$ (54 mg, 0.24 mmol, 1.2 eq) and n-$Bu_4NBr$ (6.5 mg, 0.02 mmol, 0.1 eq) were added to a dry pressure tube was then taken into a glove box and acetic acid (10 mL) was added. The mixture was bubbled with nitrogen for 30 minutes and then the tube was sealed. Then the mixture was heated to reflux in an oil bath and stirred for 2 days, cooled to ambient temperature and removed the solvent. Then the solid was purified through column chromatography on silica gel using dichloromethane as eluent to obtain to obtain the desired product MC44 as a white solid in 45% yield.

Example 45

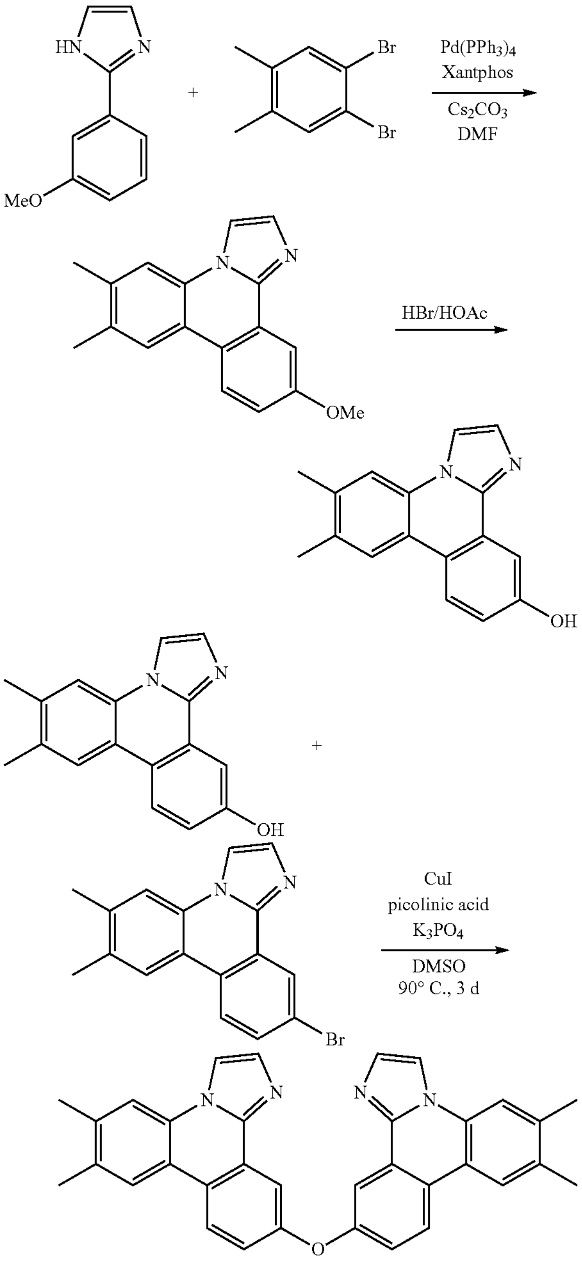

L45

6,7-dimethylimidazo[1,2-f]phenanthridin-11-ol (0.85 mmol, 1.0 eq), 11-bromo-6,7-dimethylimidazo[1,2-f]phenanthridine (1.10 mmol, 1.3 eq), CuI (32 mg, 0.17 mmol, 0.2 eq), picolinic acid (21 mg, 0.17 mmol, 0.2 eq) and $K_3PO_4$ (356 mg, 1.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 90° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L45 in 30%~70% yield.

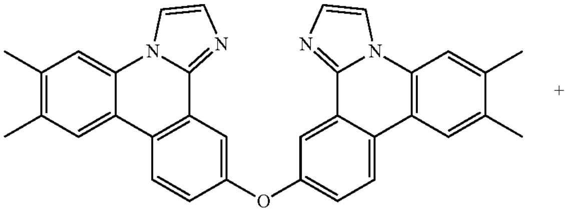

L45

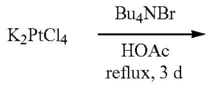

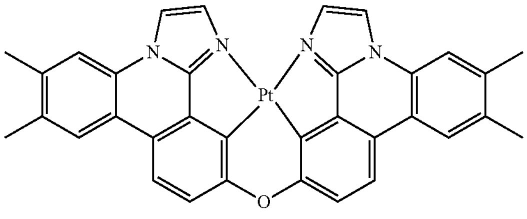

MC45

L45 (0.11 mmol, 1.0 eq), $K_2PtCl_4$ (48 mg, 0.12 mmol, 1.1 eq) and n-$Bu_4NBr$ (3 mg, 0.011 mmol, 0.1 eq) were added to a dry pressure tube, which was taken into a glove box and acetic acid (7 mL) was added. The mixture was bubbled with nitrogen for 30 minutes and then the tube was sealed. Then the mixture was heated to reflux in an oil bath and stirred for 3 days, cooled to ambient temperature and the solvent removed. Then the solid was purified through column chromatography on silica gel using dichloromethane as eluent to obtain the desired product MC45 in 10%~50% yield.

Example 46

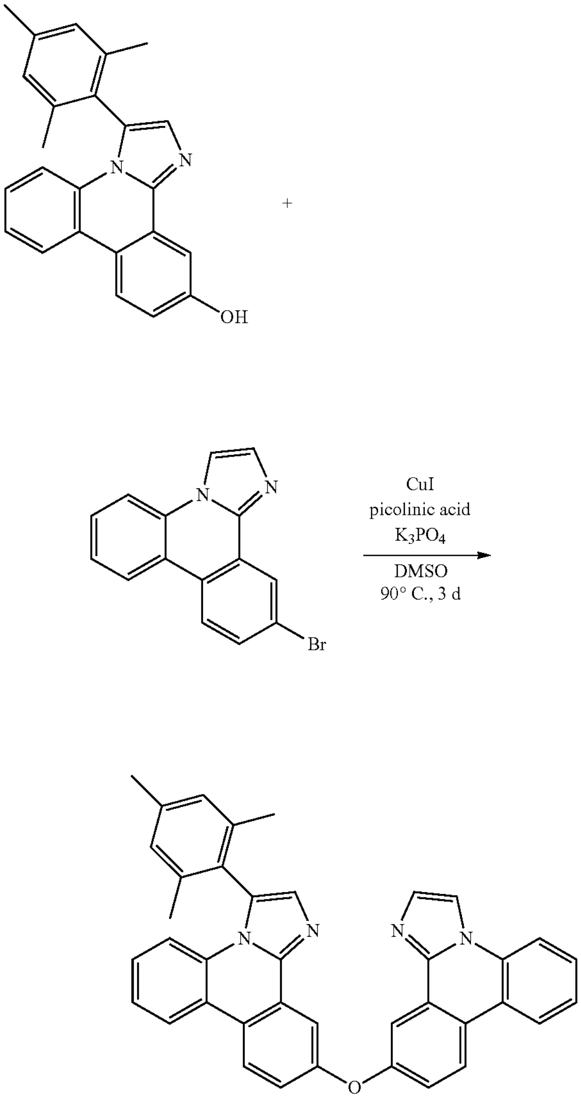

L46

3-mesitylimidazo[1,2-f]phenanthridin-11-ol (270 mg, 0.76 mmol, 1.0 eq), 11-bromoimidazo[1,2-f]phenanthridine (250 mg, 1.10 mmol, 1.3 eq), CuI (29 mg, 0.15 mmol, 0.2 eq), picolinic acid (19 mg, 0.15 mmol, 0.2 eq) and $K_3PO_4$ (323 mg, 1.5 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 90° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L46 as a white solid of 300 mg in 70% yield.

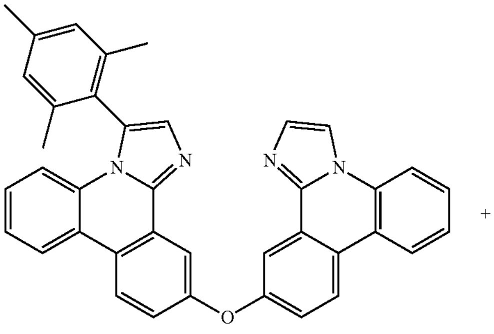

L46

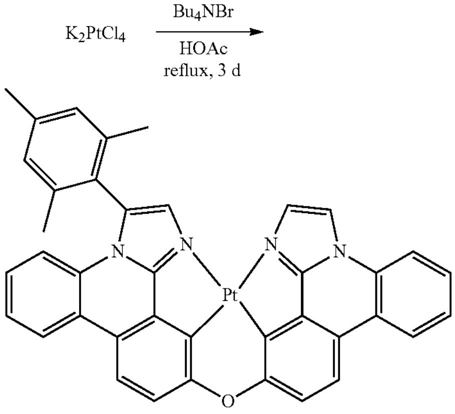

MC46

L46 (220 mg, 0.39 mmol, 1.0 eq), $K_2PtCl_4$ (190 mg, 0.46 mmol, 1.2 eq) and n-$Bu_4NBr$ (13 mg, 0.039 mmol, 0.1 eq) were added to a dry pressure tube, which was taken into a glove box and acetic acid (25 mL) was added. The mixture was bubbled with nitrogen for 30 minutes and then the tube was sealed. Then the mixture was heated to reflux in an oil bath and stirred for 3 days, cooled to ambient temperature and the solvent removed. Then the solid was purified through column chromatography on silica gel using dichloromethane as eluent to obtain the desired product MC46 of 100 mg in 33% yield.

Figure 5A:
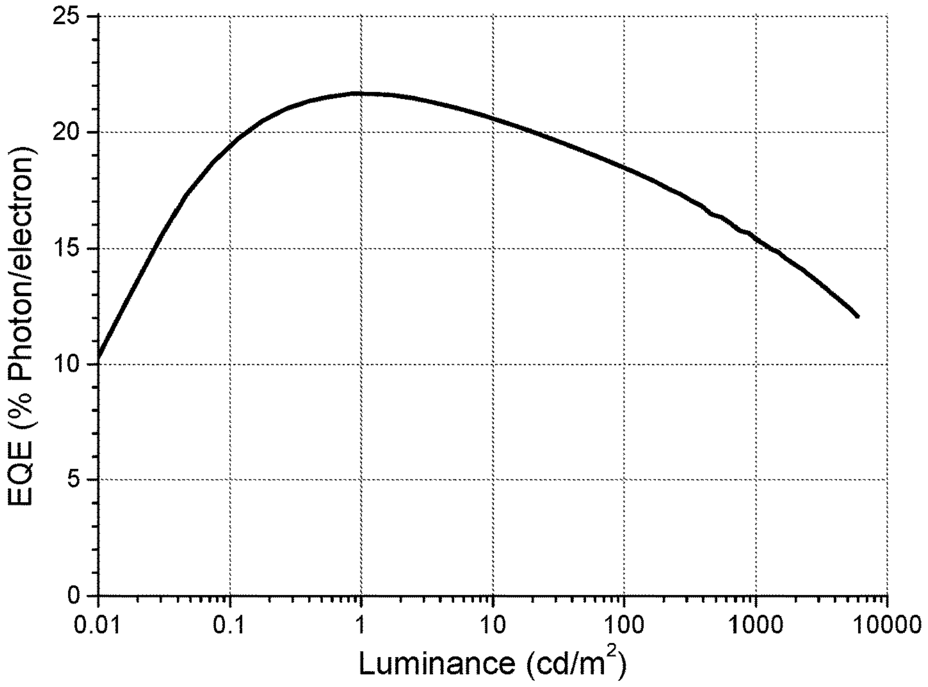
FIGS. 5A-5C show external quantum efficiency (EQE) versus luminance, EQE versus current density, and an electroluminescent spectrum, respectively, for a light-emitting device including the emitter of Example 46.
Figure 5B:
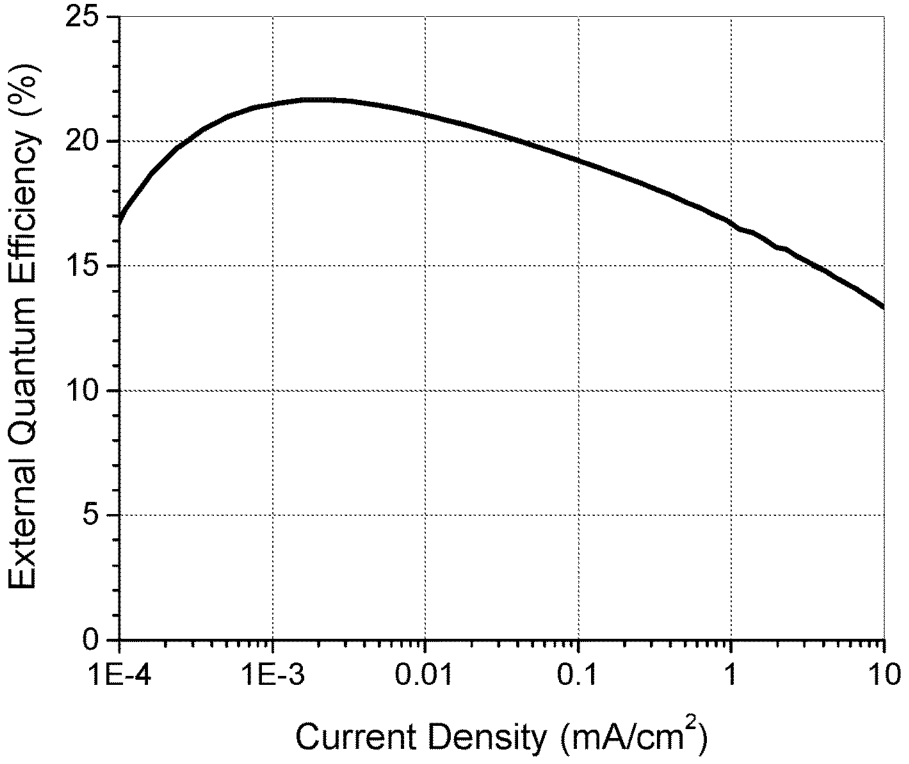
Figure 5C:
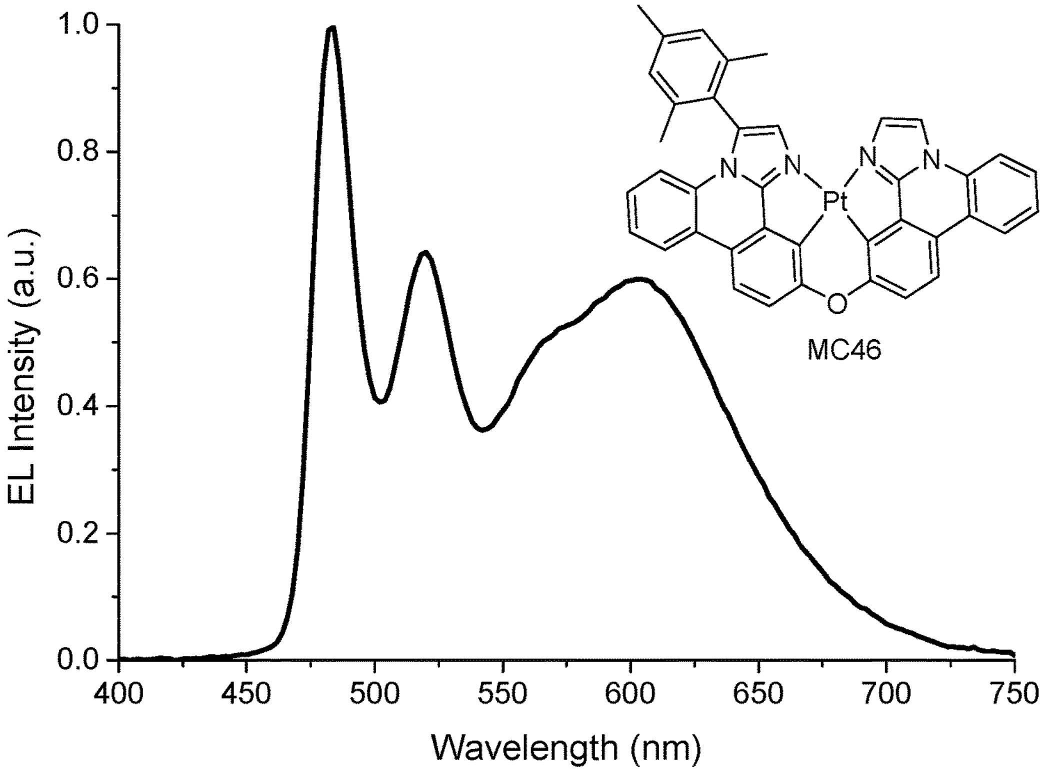
Figure 6A:
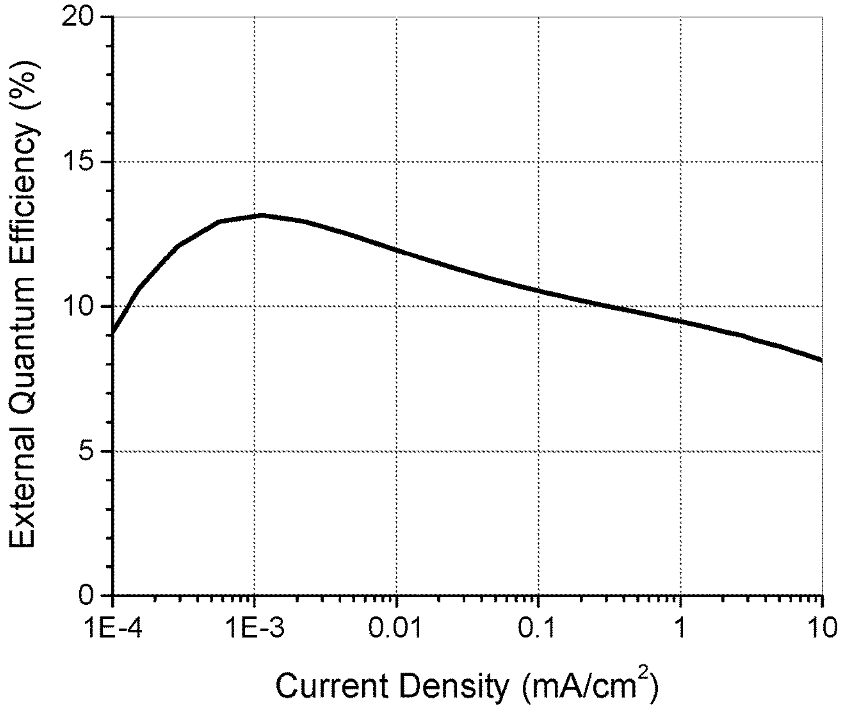
FIGS. 6A-6C show external quantum efficiency (EQE) versus luminance, EQE versus current density, and an electroluminescent spectrum, respectively, for a light-emitting device including the emitter of Example 46.
Figure 6B:
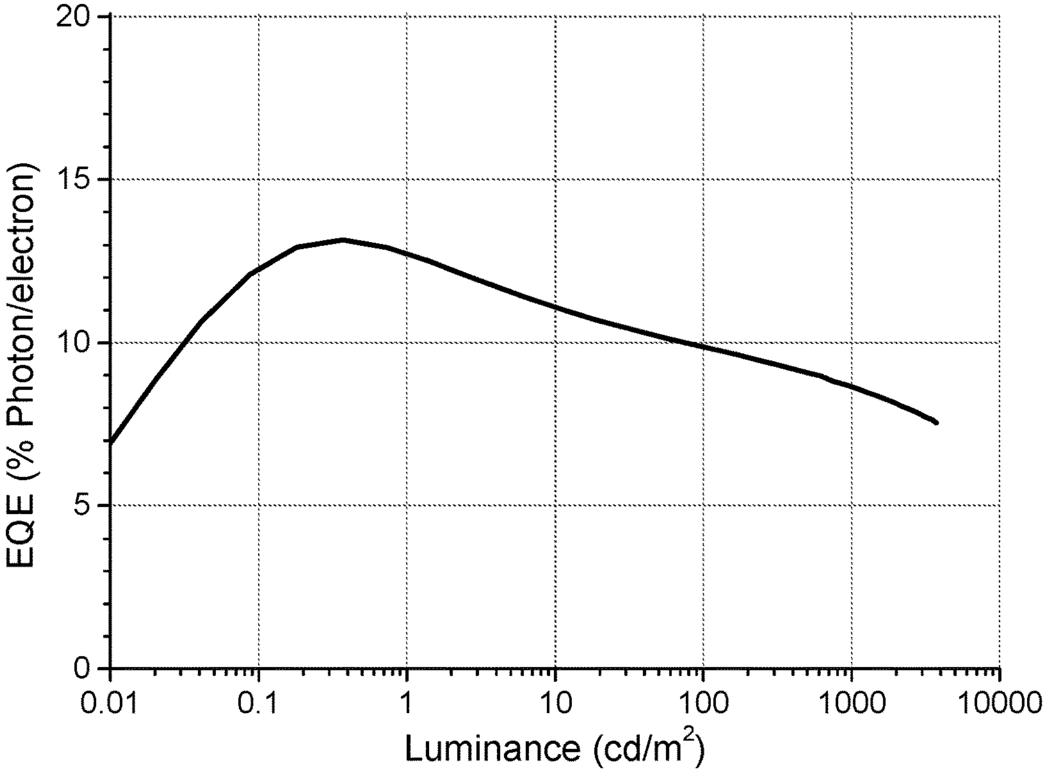
Figure 6C:
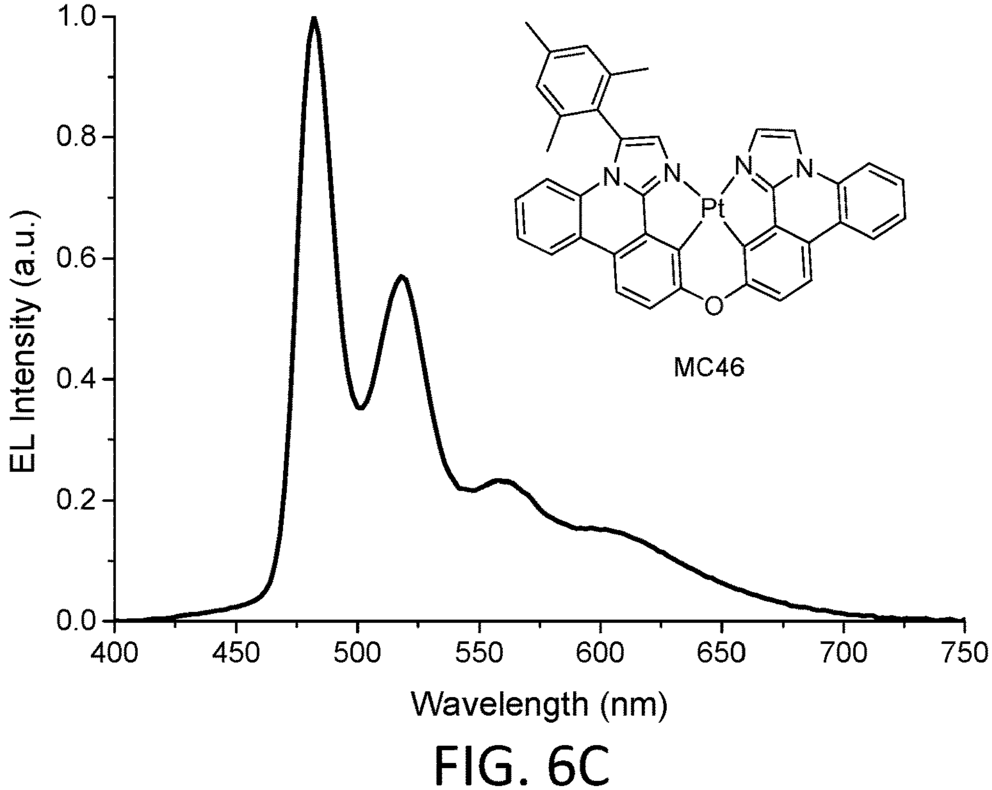

FIGS. 5A-5C show external quantum efficiency (EQE) versus luminance, EQE versus current density, and electroluminescent spectrum, respectively, for Device type 1 with MC46. Device type 1: ITO (100 nm)/HATCN (10 nm)/NPD (40 nm)/BCN34 (10 nm)/20% Pt2O2-P2M:mCBP (10 nm)/10% Pt2O2-P2M:mCBP (20 nm)/Balq (10 nm)/BPyTP (40 nm)/Liq (2 nm)/Al (100 nm). FIGS. 6A-6C show external quantum efficiency (EQE) versus luminance, EQE versus current density, and electroluminescent spectrum, respectively, for Device type 1 with MC46. Device type 2: ITO (100 nm)/HATCN (10 nm)/NPD (40 nm)/BCN34 (10 nm)/10% % Pt2O2-P2M:mCBP (20 nm)/Balq (10 nm)/BPyTP (40 nm)/Liq (2 nm)/AL (100 nm). In Device types 1 and 2: ITO: Indium tin oxide; HATCN: 1,4,5,8,9,11-hexaazatriphenylenehexacarbonitrile; HatCN: NPD: N,N'-diphenyl-N,N'-bis(1-naphthyl)-1,1'-biphenyl-4,4"-diamine; BCN34: 5,12-diphenyl-5,12-dihydroindolo[3,2-a]carbazole; Pt2O2-P2M: MC46; mCBP: 3,3-Di(9H-carbazol-9-yl)biphenyl; Balq: bis(2-methyl-8-quinolinolato)(biphenyl-4-olato)aluminum; BPyTP: (2,7-di(2,2'-bipyridin-5-yl)triphenylene); Liq: 8-Quinolinolato lithium; Al: aluminum.

Example 47

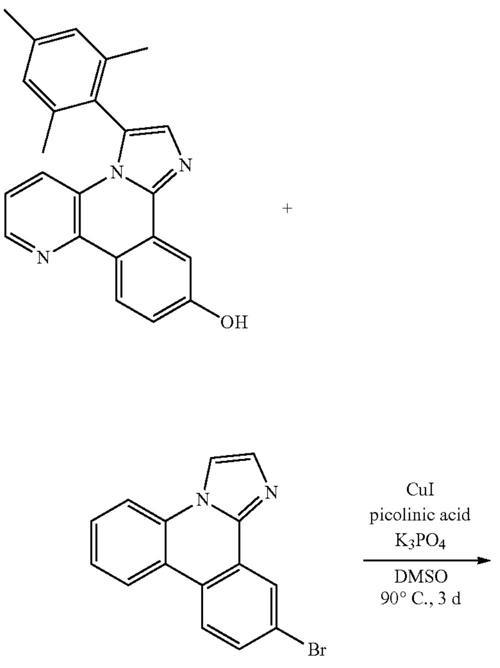

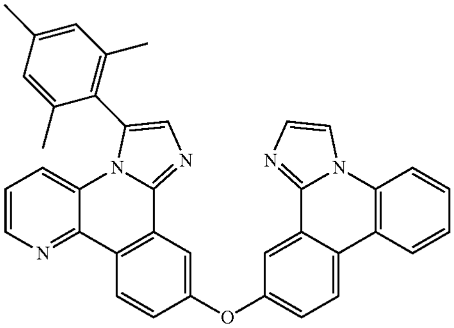

L47

3-mesitylbenzo[c]imidazo[1,2-a][1,5]naphthyridin-11-ol (0.85 mmol, 1.0 eq), 11-bromoimidazo[1,2-f]phenanthridine (1.10 mmol, 1.3 eq), CuI (32 mg, 0.17 mmol, 0.2 eq), picolinic acid (21 mg, 0.17 mmol, 0.2 eq) and $K_3PO_4$ (356 mg, 1.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 90° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L47 in 30%~70% yield.

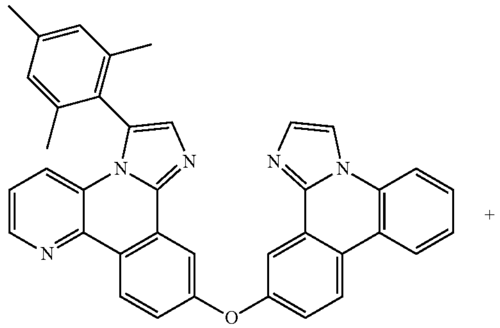

L47

$K_2PtCl_4$ $Bu_4NBr$

HOAc reflux, 3 d

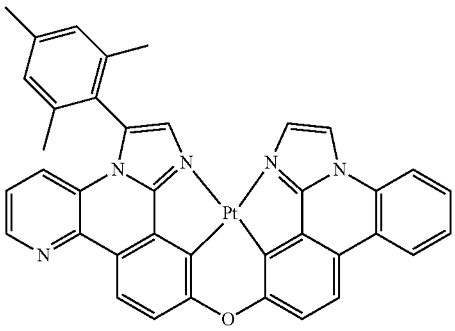

MC47

L47 (0.11 mmol, 1.0 eq), $K_2PtCl_4$ (48 mg, 0.12 mmol, 1.1 eq) and n-$Bu_4NBr$ (3 mg, 0.011 mmol, 0.1 eq) were added to a dry pressure tube, which was taken into a glove box and acetic acid (7 mL) as added. The mixture was bubbled with nitrogen for 30 minutes and then the tube was sealed. Then the mixture was heated to reflux in an oil bath and stirred for 3 days, cooled to ambient temperature and the solvent removed. Then the solid was purified through column chromatography on silica gel using dichloro ethane as eluent to obtain the desired product MC47 in 10%~50% yield.

Example 48

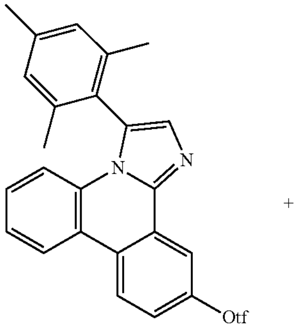

Otf-48

-continued

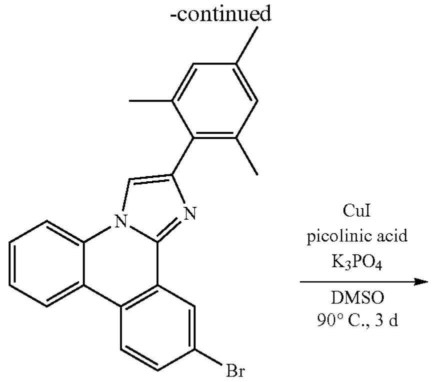

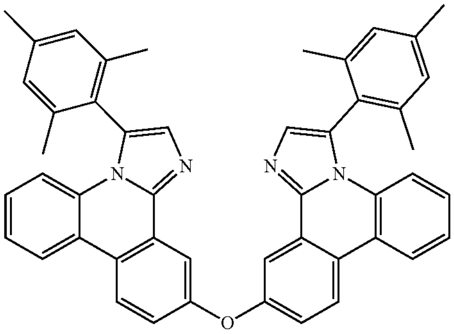

L48

Otf-48 (0.85 mmol, 1.0 eq), 11-bromo-2-mesitylimidazo [1,2-f]phenanthridine (1.10 mmol, 1.3 eq), CuI (32 mg, 0.17 mmol, 0.2 eq), picolinic acid (21 mg, 0.17 mmol, 0.2 eq) and $K_3PO_4$ (356 mg, 1.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 90° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L48 in 30%~70% yield.

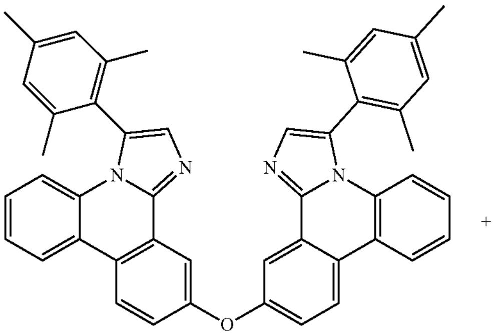

L48

$K_2PtCl_4$ $Bu_4NBr$

HOAc reflux, 3 d

-continued

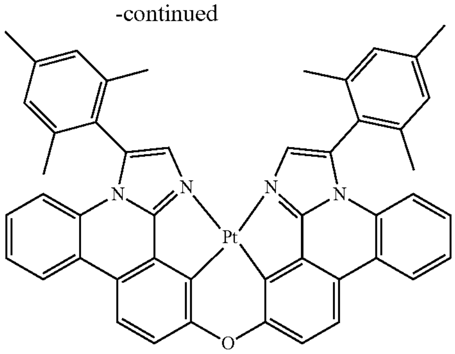

MC48

L48 (0.11 mmol, 1.0 eq), $K_2PtCl_4$ (48 mg, 0.12 mmol, 1.1 eq) and n-$Bu_4NBr$ (3 mg, 0.011 mmol, 0.1 eq) were added to a dry pressure tube, which was taken into a glove box and acetic acid (7 mL) was added. The mixture was bubbled with nitrogen for 30 minutes and then the tube was sealed. Then the mixture was heated to reflux in an oil bath and stirred for 3 days, cooled to ambient temperature and the solvent removed. Then the solid was purified through column chromatography on silica gel using dichloromethane as eluent to obtain the desired product MC48 in 10%~50% yield.

Example 49

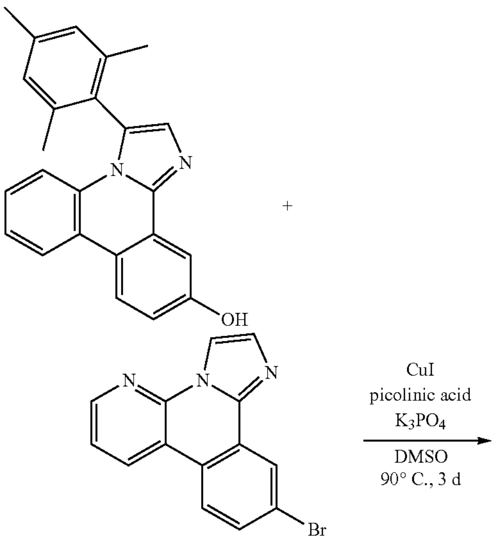

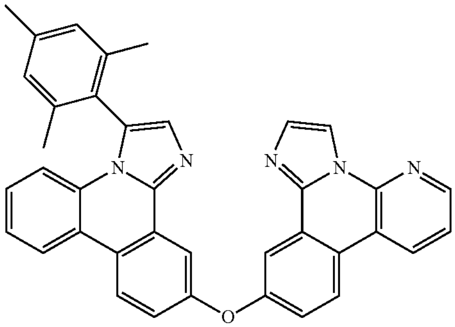

L49

3-mesitylimidazo[1,2-f]phenanthridin-11-ol (0.85 mmol, 1.0 eq), 11-bromobenzo[c]imidazo[1,2-f][1,8]naphthyridine (1.10 mmol, 1.3 eq), CuI (32 mg, 0.17 mmol, 0.2 eq), picolinic acid (21 mg, 0.17 mmol, 0.2 eq) and $K_3PO_4$ (356 mg, 1.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 90° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L49 in 30%~70% yield.

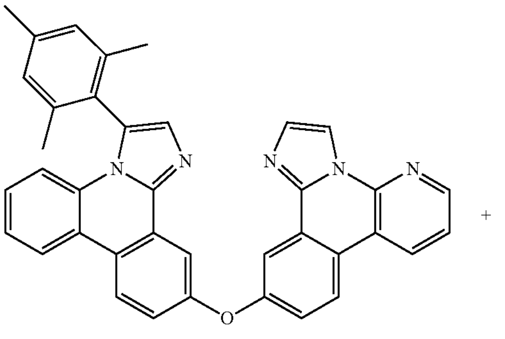

L49

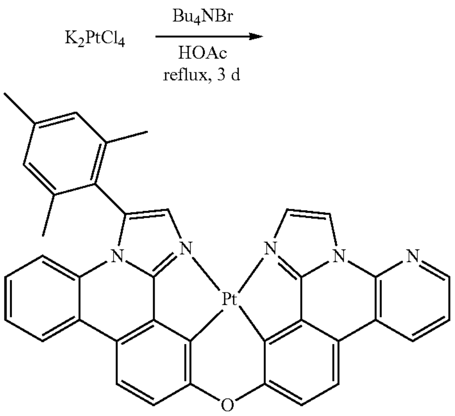

MC49

L49 (0.11 mmol, 1.0 eq), $K_2PtCl_4$ (48 mg, 0.12 mmol, 1.1 eq) and n-$Bu_4NBr$ (3 mg, 0.011 mmol, 0.1 eq) were added to a dry pressure tube, which was taken into a glove box and acetic acid (7 mL) was added. The mixture was bubbled with nitrogen for 30 minutes and then the tube was sealed. Then the mixture was heated to reflux in an oil bath and stirred for 3 days, cooled to ambient temperature and the solvent removed. Then the solid was purified through column chromatography on silica gel using dichloromethane as eluent to obtain the desired product MC49 in 10%~50% yield.

Example 50

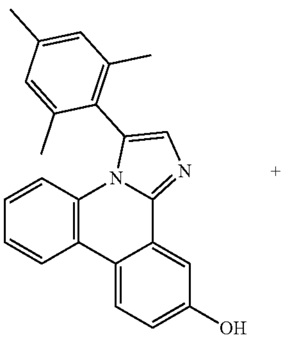

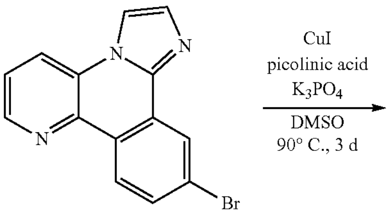

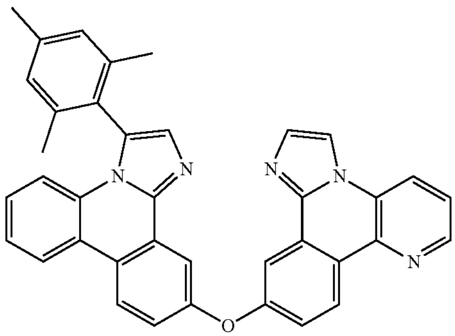

L50

3-mesitylimidazo[1,2-f]phenanthridin-11-ol (0.85 mmol, 1.0 eq), 11-bromobenzo[c]imidazo[1,2-a][1,5]naphthyridine (1.10 mmol, 1.3 eq), CuI (32 mg, 0.17 mmol, 0.2 eq), picolinic acid (21 mg, 0.17 mmol, 0.2 eq) and $K_3PO_4$ (356 mg, 1.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 90° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L50 in 30%~70% yield.

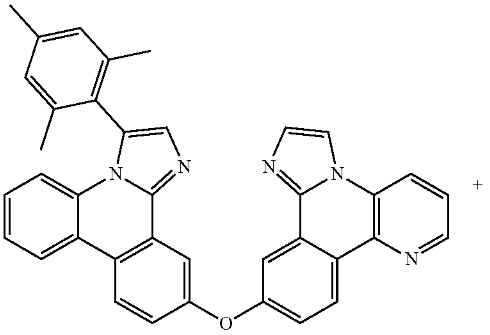

L50

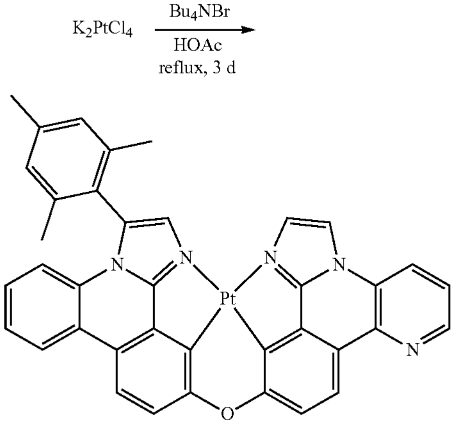

MC50

L50 mmol, 1.0 eq), $K_2PtCl_4$ (48 mg, 0.12 mmol, 1.1 eq) and n-$Bu_4NBr$ (3 mg, 0.011 mmol 0.1 eq) were added to a dry pressure tube, which was taken into a glove box and acetic acid (7 mL) was added. The mixture was bubbled with nitrogen for 30 minutes and then the tube was sealed. Then the mixture was heated to reflux in an oil bath and stirred for 3 days, cooled to ambient temperature and the sol roved. Then the solid was purified through column chromatography on silica gel using dichloromethane as eluent to obtain the desired product MC50 in 10%~50% yield.

Example 51

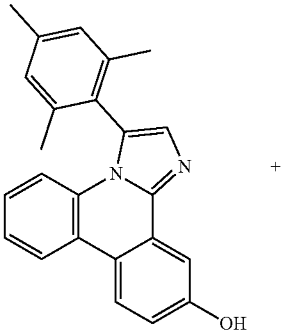

-continued

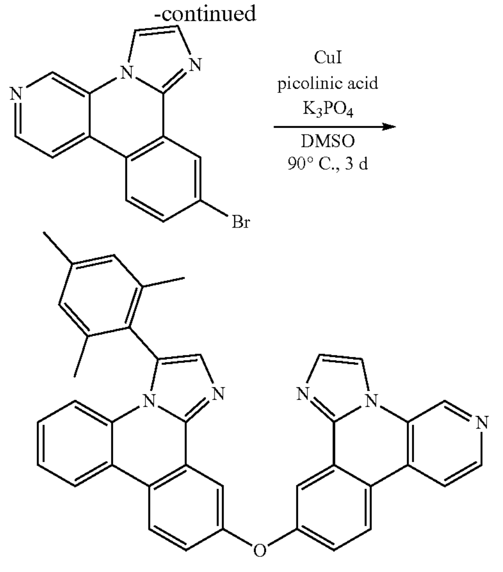

L51

3-mesitylimidazo[1,2-f]phenanthridin-11-ol (0.85 mmol, 1.0 eq), 11-bromobenzo[c]imidazo[1,2-a][1,7]naphthyridine (110 mmol, 1.3 eq), CuI (32 mg, 0.17 mmol, 0.2 eq), picolinic acid (21 mg, 0.17 mmol, 0.2 eq) and $K_3PO_4$ (356 mg, 1.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 90° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L51 in 30%~70% yield.

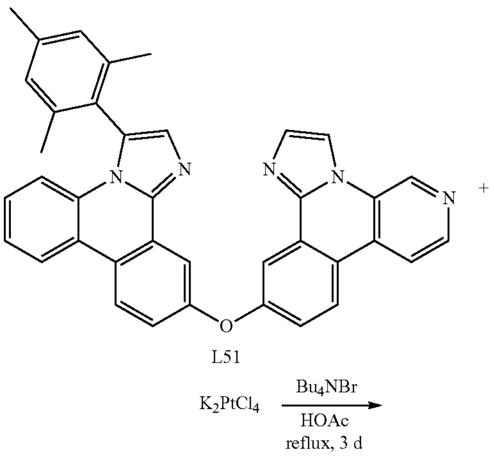

-continued

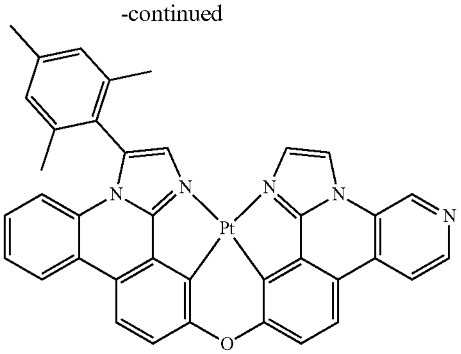

MC51

L51 (0.11 mmol, 1.0 eq), $K_2PtCl_4$ (48 mg, 0.12 mmol, 1.1 eq) and n-$Bu_4NBr$ (3 mg, 0.011 mmol 0.1 eq) added to a dry pressure tube, which was taken into a glove box and acetic acid (7 mL) was added. The mixture was bubbled with nitrogen for 30 minutes and then the tube was sealed. Then the mixture was heated to reflux in an oil bath and stirred for 3 days, cooled to ambient temperature and the sol roved. Then the solid was purified through column chromatography on silica gel using dichloromethane as eluent obtain the desired product MC51 in 10%~50% yield.

Example 52

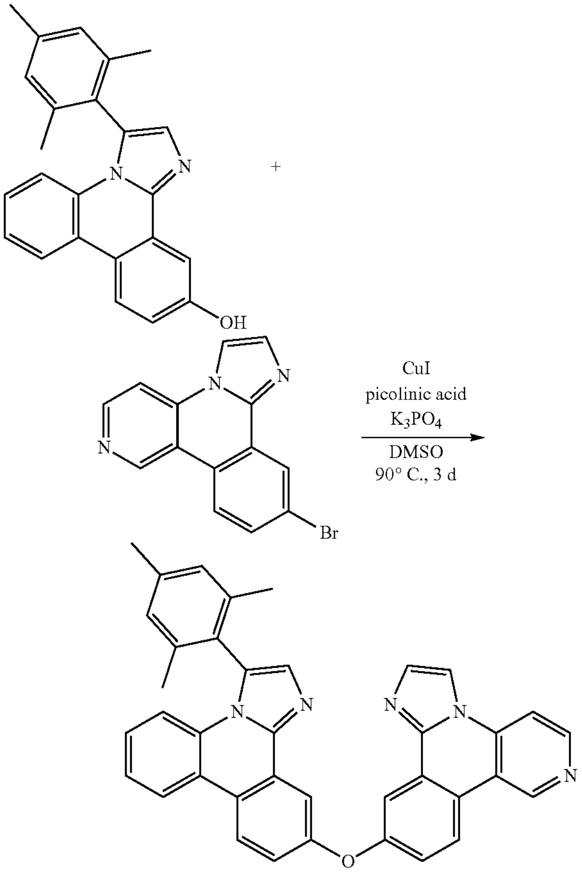

L52

3-mesitylimidazo[1,2-f]phenanthridin-11-ol (0.85 mmol, 1.0 eq), 11-bromobenzo[c]imidazo[1,2-a][1,6]naphthyridine (1.10 mmol, 1.3 eq), CuI (32 mg, 0.17 mmol, 0.2 eq), picolinic acid (21 mg, 0.17 mmol, 0.2 eq) and $K_3PO_4$ (356 mg, 1.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 90° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L52 in 30%~70% yield.

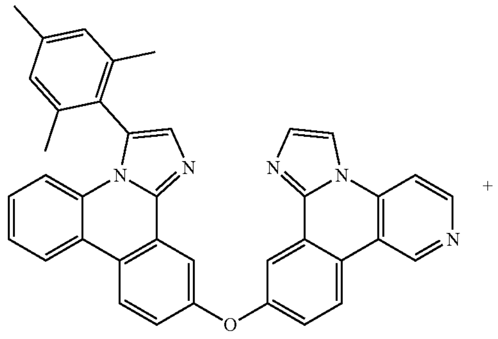

L52

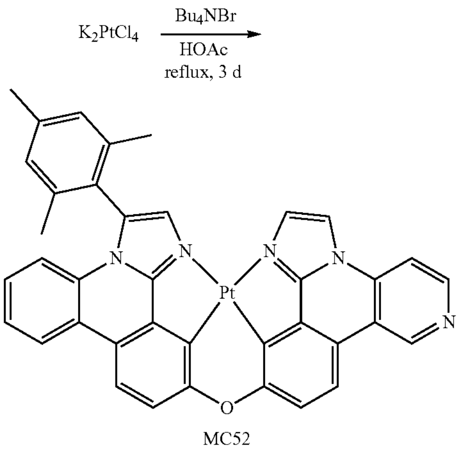

MC52

L52 (0.11 mmol, 1.0 eq), $K_2PtCl_4$ (48 mg, 0.12 mmol, 1.1 eq) and n-$Bu_4NBr$ (3 mg, 0.011 mmol, 0.1 eq) were added to a dry pressure tube, which was taken into a glove box and acetic acid (7 mL) was added. The mixture was bubbled with nitrogen for 30 minutes and then the tube was sealed. Then the mixture was heated to reflux in an oil bath and stirred for 3 days, cooled to ambient temperature and the solvent removed. Then the solid was purified through column chromatography on silica gel using dichloromethane as eluent to obtain the desired product MC52 in 10%~50% yield.

Example 53

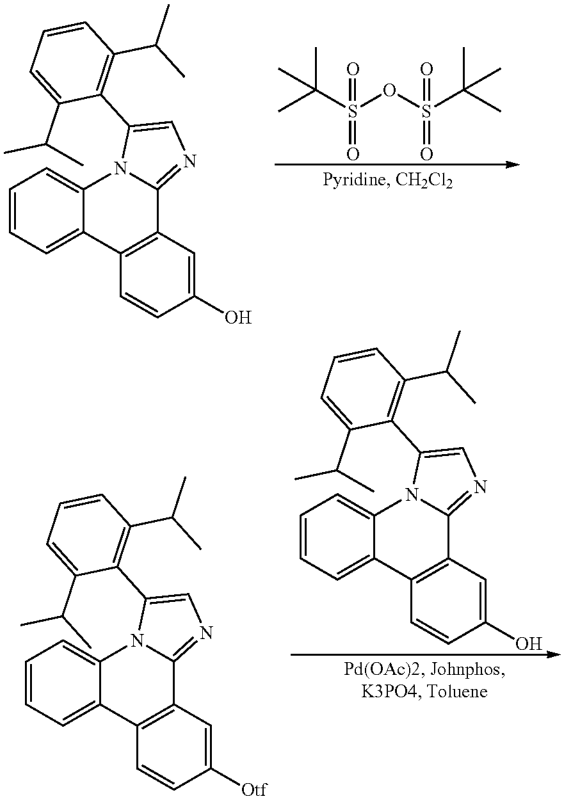

Otf-53

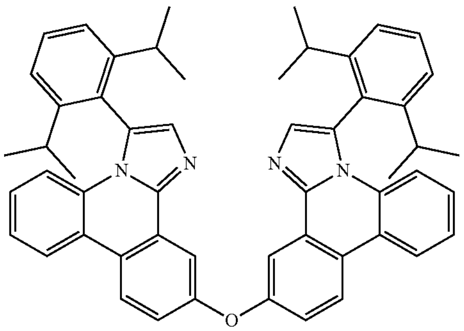

L53

Otf-53 (0.85 mmol, 1.0 eq), 3-(2,6-diisopropylphenyl) imidazo[1,2-f]phenanthridin-11-ol (1.10 mmol, 1.3 eq), CuI (32 mg, 0.17 mmol, 0.2 eq), picolinic acid (21 mg, 0.17 mmol, 0.2 eq) and $K_3PO_4$ (356 mg, 1.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 90° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L53 in 30%~70% yield.

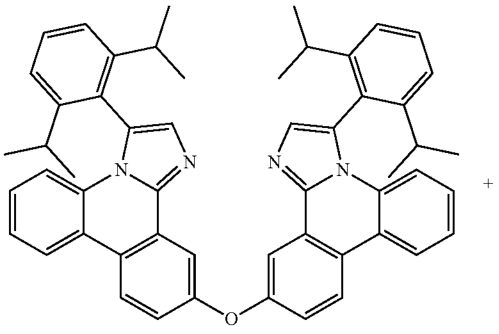

L53

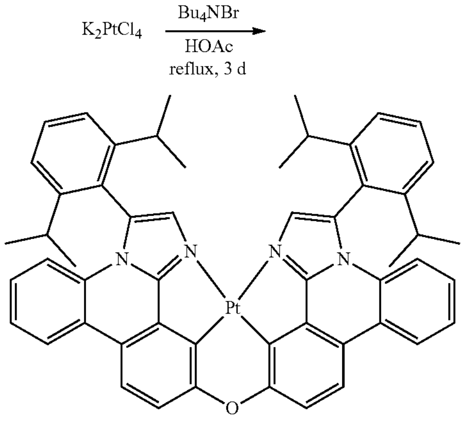

MC53

L53 (0.11 mmol, 1.0 eq), $K_2PtCl_1$ (48 mg, 0.12 mmol, 1.1 eq) and n-$Bu_4NBr$ (3 mg, 0.011 mmol, 0.1 eq) were added to a dry pressure tube, which was taken into a glove box and acetic acid (7 mL) was added. The mixture was bubbled with nitrogen for 30 minutes and then the tube was sealed. Then the mixture was heated to reflux in an oil bath and stirred for 3 days, cooled to ambient temperature and the solvent removed. Then the solid was purified through column chromatography on silica gel using dichloromethane as eluent to obtain the desired product MC53 in 10%~50% yield.

Example 54

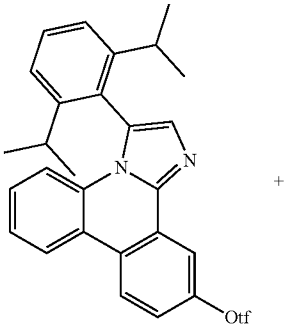

Otf-53

-continued

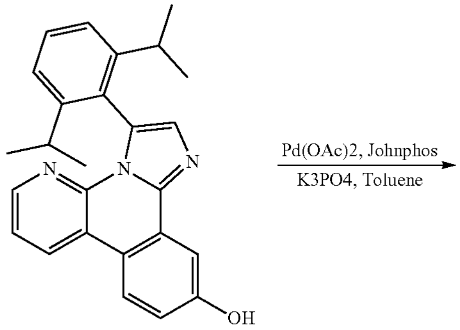

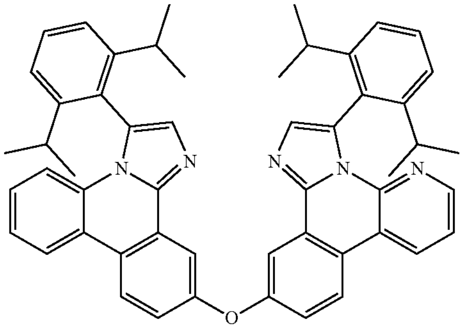

L54

Otf-53 (0.85 mmol, 1.0 eq), 3-(2,6-diisopropylphenyl) benzo[c]imidazo[1,2-a][1,8]naphthyridin-11-ol (1.10 mmol, 1.3 eq), CuI (32 mg, 0.17 mmol, 0.2 eq), picolinic acid (21 mg, 0.17 mmol, 0.2 eq) and $K_3PO_4$ (356 mg, 1.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 90° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L54 in 30%~70% yield.

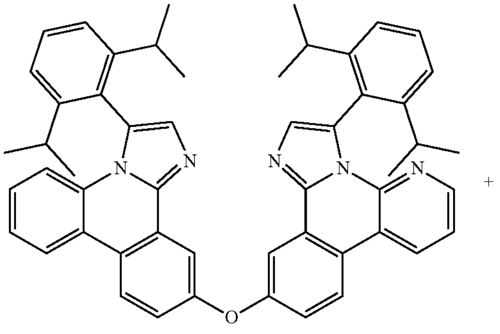

L54

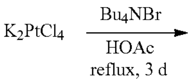

-continued

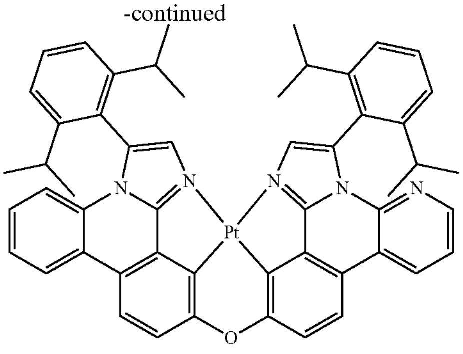

MC54

L54 (0.11 mmol, 1.0 eq), $K_2PtCl_4$ (48 mg, 0.12 mmol, 1.1 eq) and n-$Bu_4NBr$ (3 mg, 0.011 mmol, 0.1 eq) were added to a dry pressure tube, which was taken into a glove box and acetic acid (7 mL) was added. The mixture was bubbled with nitrogen for 30 minutes and then the tube was sealed. Then the mixture was heated to reflux in an oil bath and stirred for 3 days, cooled to ambient temperature and the solvent removed. Then the solid was purified through column chromatography on silica gel using dichloromethane as eluent to obtain the desired product MC54 in 10%~50% yield.

Example 55

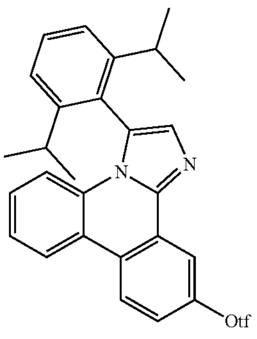

Otf-53

+

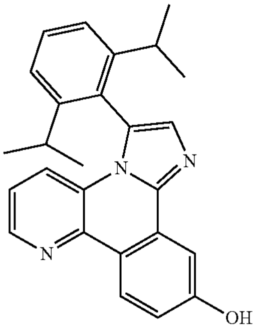

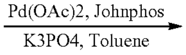

-continued

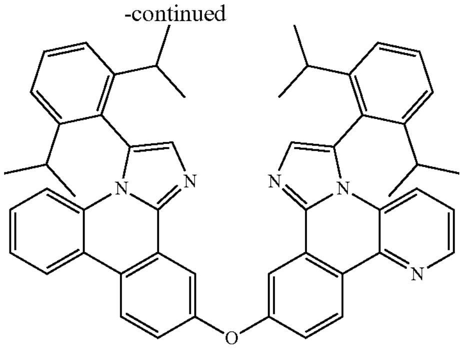

L55

Otf-53 (0.85 mmol, 1.0 eq), 3-(2,6-diisopropylphenyl) benzo[c]imidazo[1,2-a][1,5]naphthyridin-11-ol (1.10 mmol, 1.3 eq), CuI (32 mg, 0.17 mmol, 0.2 eq), picolinic acid (21 mg, 0.17 mmol, 0.2 eq) and $K_3PO_4$ (356 mg, 1.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 90° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L55 in 30%~70% yield.

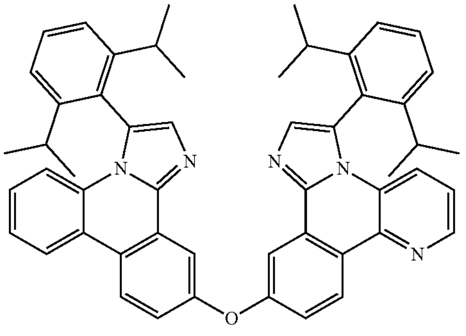

L55

+

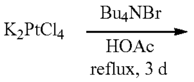

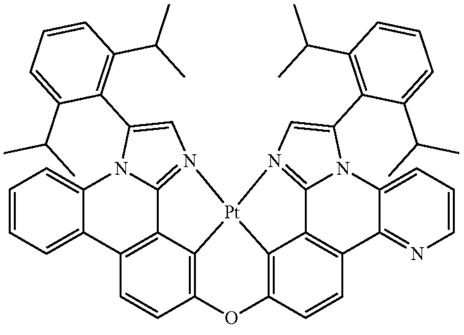

MC55

L55 (0.11 mmol, 1.0 eq), $K_2PtCl_4$ (48 mg, 0.12 mmol, 1.1 eq) and n-$Bu_4NBr$ (3 mg, 0.011 mmol, 0.1 eq) were added to a dry pressure tube, which was taken into a glove box and acetic acid (7 mL) was added. The mixture was bubbled with nitrogen for 30 minutes and then the tube was sealed. Then the mixture was heated to reflux in an oil bath and stirred for 3 days, cooled to ambient temperature and the solvent removed. Then the solid was purified through column chromatography on silica gel using dichloromethane as eluent to obtain the desired product MC55 in 10%~50% yield.

Example 56

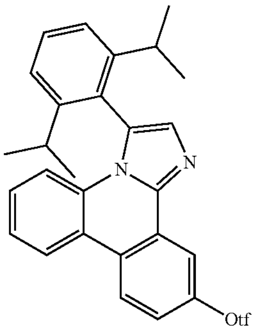

Otf-53

+

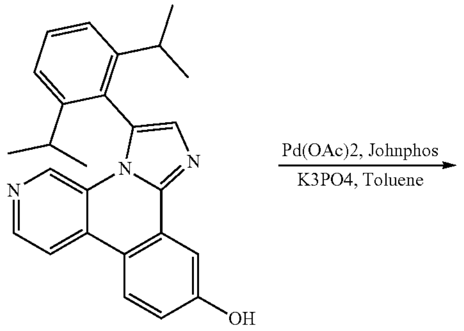

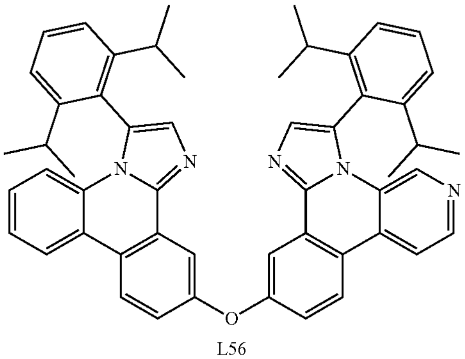

L56

Otf-53 (0.85 mmol, 1.0 eq), 3-(2,6-diisopropylphenyl)benzo[c]imidazo[1,2-a][1,7]naphthyridin-11-ol (1.10 mmol, 1.3 eq), CuI (32 mg, 0.17 mmol, 0.2 eq), picolinic acid (21 mg, 0.17 mmol, and $K_3PO_4$ (356 mg, 1.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 90° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L56 in 30%~70% yield.

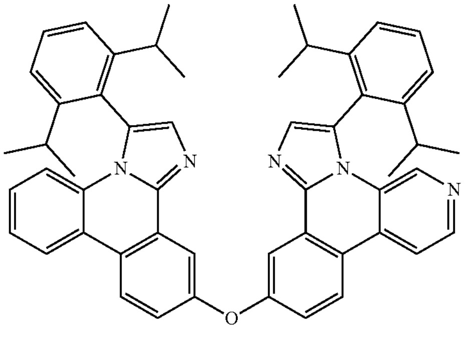

L56

+

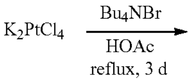

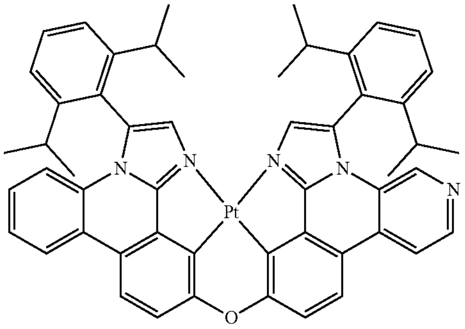

MC56

L56 (0.11 mmol, 1.0 eq), $K_2PtCl_4$ (48 mg, 0.12 mmol, 1.1 eq) and n-$Bu_4NBr$ (3 mg, 0.011 mmol, 0.1 eq) were added to a dry pressure tube, which was taken into a glove box and acetic acid (7 mL) was added. The mixture was bubbled with nitrogen for 30 minutes and then the tube was sealed. Then the mixture was heated to reflux in an oil bath and stirred for 3 days, cooled to ambient temperature and the solvent removed. Then the solid was purified through column chromatography on silica gel using dichloromethane as eluent to obtain the desired product MC56 in 10%~50% yield.

Example 57

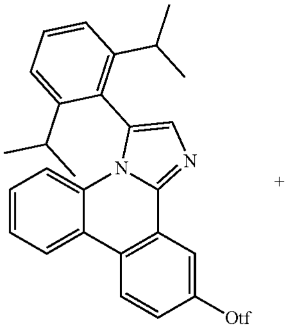

Otf-53

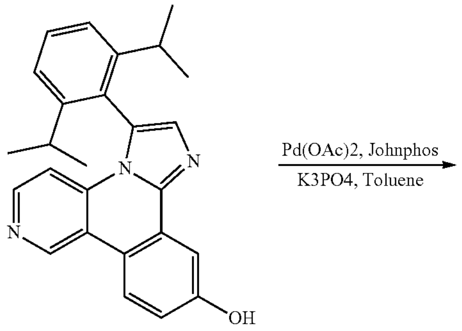

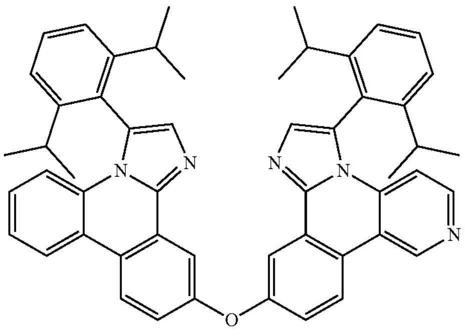

L57

Otf-53 (0.85 mmol, 1.0 eq), 3-(2,6-diisopropylphenyl) benzo[c]imidazo[1,2-a][1,6]naphthyridin-11-ol (1.10 mmol, 1.3 eq), CuI (32 mg, 0.17 mmol, 0.2 eq), picolinic acid (21 mg, 0.17 mmol, 0.2 eq) and $K_3PO_4$ (356 mg, 1.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 90° C. for 3 days and then cooled down to ambient temperature, diluted with ethyl acetate. The mixture was washed with water three times and then dried over sodium sulfate and filtered. The solvent was removed wider reduced pressure, and the residue was purified through column chromatography on silica gel using hexane/ethyl acetate as eluent to obtain the desired product ligand L57 in 30%~70% yield.

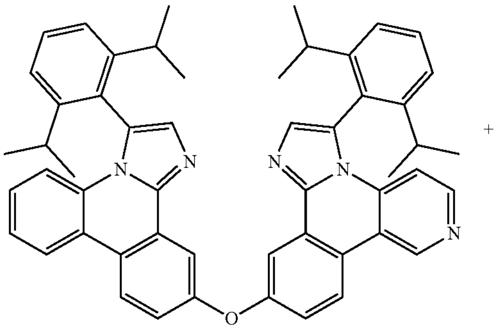

L57

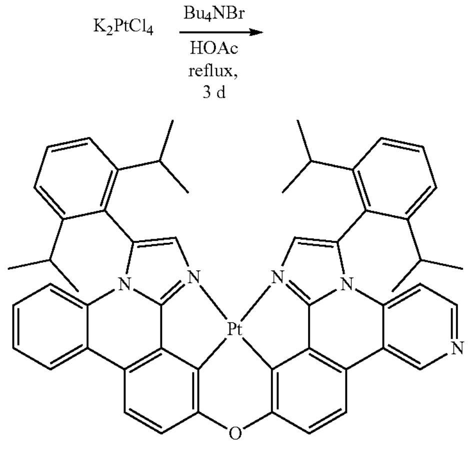

MC57

L57 (0.11 mmol, 1.0 eq), $K_2PtCl_4$ (48 mg, 0.12 mmol, 1.1 eq) and n-$Bu_4NBr$ (3 mg, 0.011 mmol, 0.1 eq) were added to a dry pressure tube, which was taken into a glove box and acetic acid (7 mL) was added. The mixture was bubbled with nitrogen for 30 minutes and then the tube was sealed. Then the mixture was heated to reflux in an oil bath and stirred for 3 days, cooled to ambient temperature and the solvent removed. Then the solid was purified through column chromatography on silica gel using dichloromethane as eluent to obtain the desired product MC57 in 10%~50% yield.

Example 58

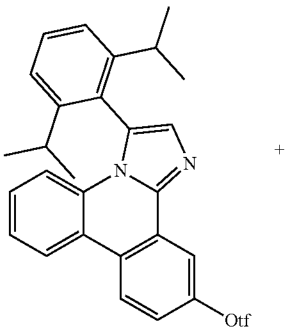

Otf-53

-continued

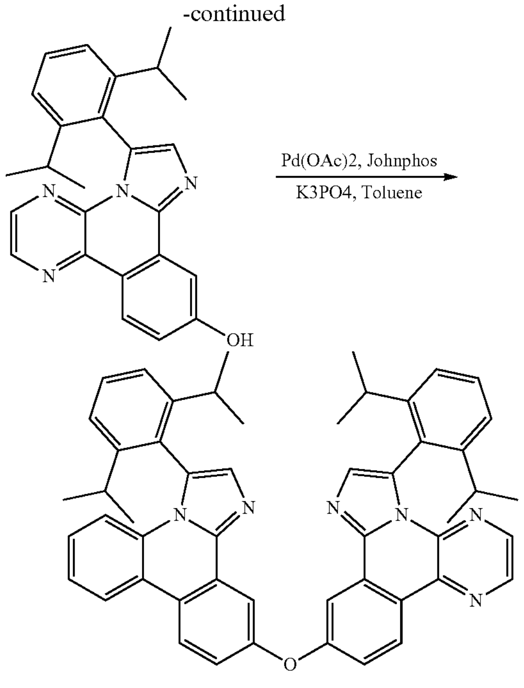

L58

Otf-53 (0.85 mmol, 1.0 eq), 3-(2,6-diisopropylphenyl) imidazo[2,1-a]pyrazino[2,3-c]isoquinolin-11-ol (1.10 mmol, 1.3 eq), CuI (32 mg, 0.17 mmol, 0.2 eq), picolinic acid (21 mg, 0.17 mmol, 0.2 eq) and $K_3PO_4$ (356 mg, 1.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 90° C. for 3 days and then cooled down to ambient temperature, diluted with ethyl acetate. The mixture was washed with water three times and then dried over sodium sulfate and filtered. The solvent was removed wider reduced pressure, and the residue was purified through column chromatography on silica gel using hexane/ethyl acetate as eluent to obtain the desired product ligand L58 in 30%~70% yield.

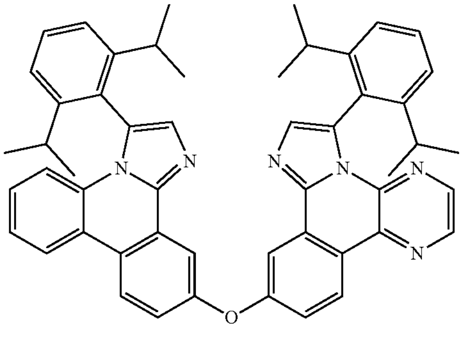

+

L58

$K_2PtCl_4$ $Bu_4NBr$
HOAc
reflux,
3 d

-continued

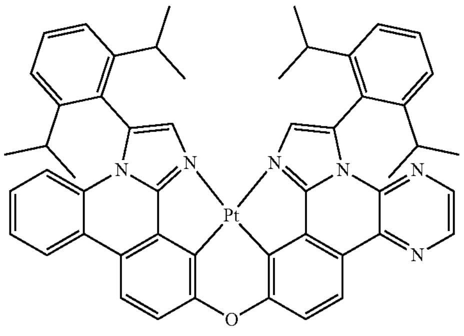

MC58

L58 (0.11 mmol, 1.0 eq), $K_2PtCl_4$ (48 mg, 0.12 mmol, 1.1 eq) and n-$Bu_4NBr$ (3 mg, 0.011 mmol, 0.1 eq) were added to a dry pressure tube, which was taken into a glove box and acetic acid (7 mL) was added. The mixture was bubbled with nitrogen for 30 minutes and then the tube was sealed. Then the mixture was heated to reflux in an oil bath and stirred for 3 days, cooled to ambient temperature and the solvent removed. Then the solid was purified through column chromatography on silica gel using dichloromethane as eluent to obtain the desired product MC58 in 10%~50% yield.

Example 59

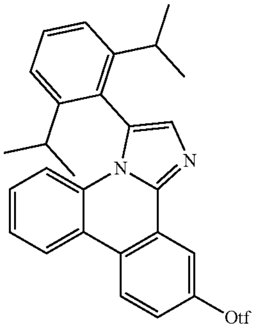

Otf-53

+

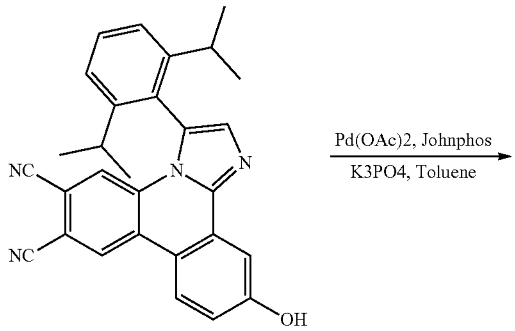

-continued

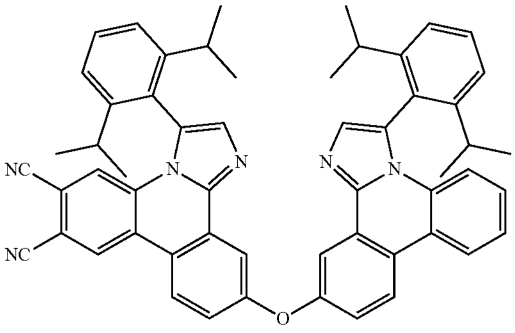

L59

-continued

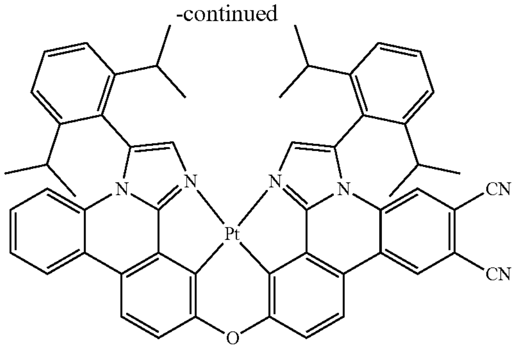

MC59

Otf-53 (0.85 mmol, 1.0 eq), 3-(2,6-diisopropylphenyl)-11-hydroxyimidazo[1,2-f]phenanthridine-6,7-dicarbonitrile (1.10 mmol, 1.3 eq), CuI (32 mg, 0.17 mmol, 0.2 eq), picolinic acid (21 mg, 0.17 mmol, 0.2 eq) and $K_3PO_4$ (356 mg, 1.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 90° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand. L59 in 30%~70% yield.

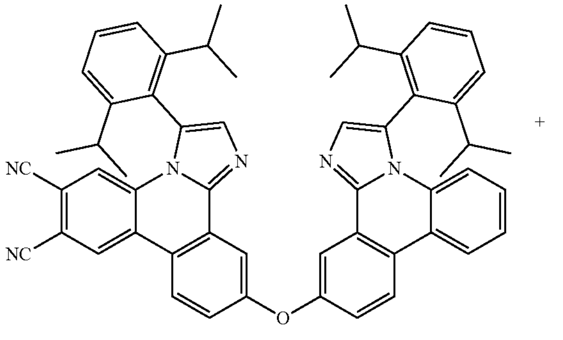

L59

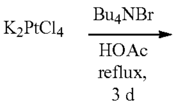

L59 (0.11 mmol, 1.0 eq), $K_2PtCl_4$ (48 mg, 0.12 mmol, 1.1 eq) and n-$Bu_4NBr$ (3 mg, 0.011 mmol, 0.1 eq) were added to a dry pressure tube, which was taken into a glove box and acetic acid (7 mL) was added. The mixture was bubbled with nitrogen for 30 minutes and then the tube was sealed. Then the mixture was heated to reflux in an oil bath and stirred for 3 days, cooled to ambient temperature and the solvent removed. Then the solid was purified through column chromatography on silica gel using dichloromethane as eluent to obtain the desired product MC59 in 10%~50% yield.

Example 60

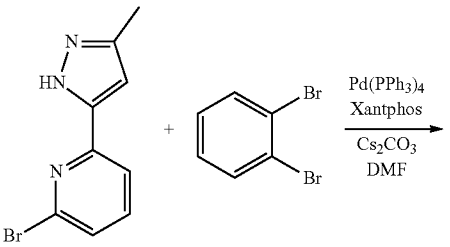

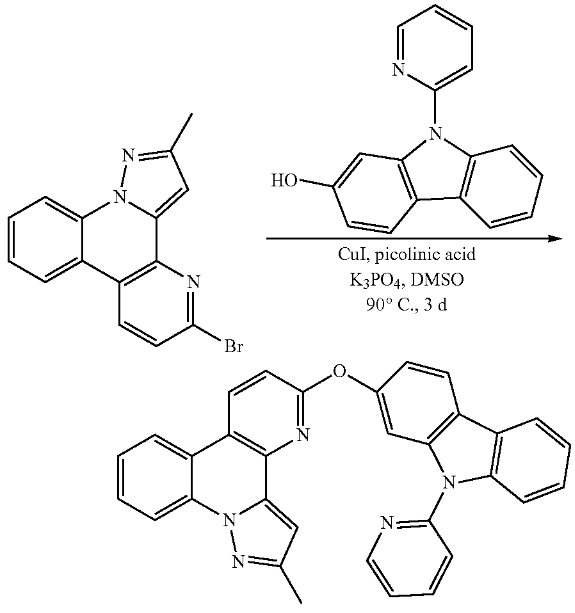

L60

5-bromo-2-methylbenzo[f]pyrazolo[1,5-h][1,7]naphthyridine (0.85 mmol, 1.0 eq), 9-(pyridin-2-yl)-9H-carbazol-2-ol (359 mg, 1.10 mmol, 1.3 eq), CuI (32 mg, 0.17 mmol, 0.2 eq), picolinic acid (21 mg, 0.17 mmol, 0.2 eq) and $K_3PO_4$ (356 mg, 1.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 100° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L60 in 20%-70% yield.

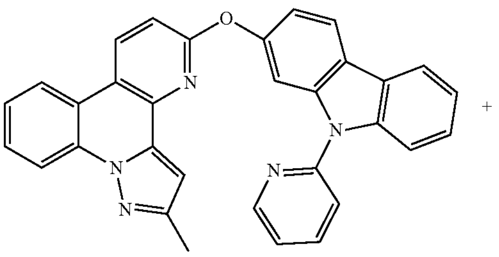

L60

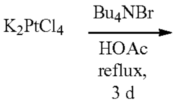

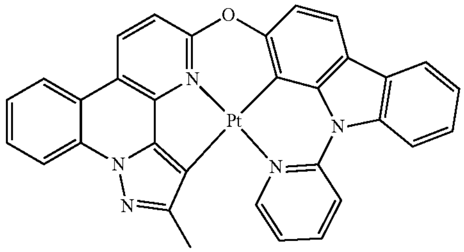

MC60

L60 (0.11 mmol 1.0 eq), $K_2PtCl_4$ (48 mg, 0.12 mmol, 1.1 eq) and n-$Bu_4NBr$ (3 mg, 0.011 mmol, 0.1 eq) were added to a dry pressure tube, which was taken into a glove box and acetic acid (7 mL) as added. The mixture was bubbled with nitrogen for 30 minutes and then the tube was sealed. Then the mixture was heated to reflux in an oil bath and stirred for 3 days, cooled to ambient temperature and the solvent removed. Then the solid was purified through column chromatography on silica gel using dichloromethane as eluent to obtain the desired product MC60 in 10%~50% yield.

Example 61

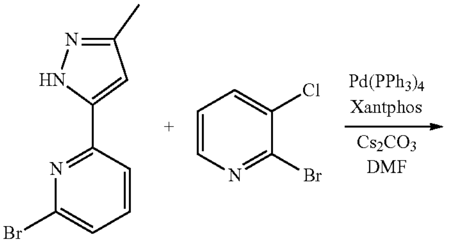

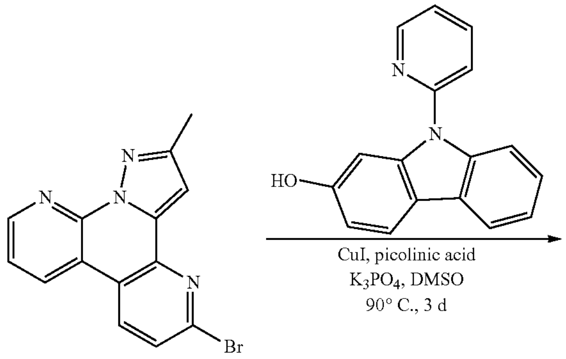

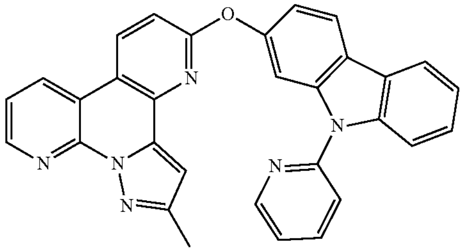

L61

5-bromo-2-methylpyrazolo[1,5-h]pyrido[3,2-f][1,7]naphthyridine (0.85 mmol, 1.0 eq), 9-(pyridin-2-yl)-9H-carbazol-2-ol (359 mg, 1.10 mmol, 1.3 eq), CuI (32 mg, 0.17 mmol, 0.2 eq), picolinic acid (21 mg, 0.17 mmol, 0.2 eq) and $K_3PO_4$ (356 mg, 1.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 100° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L61 in 20%-70% yield.

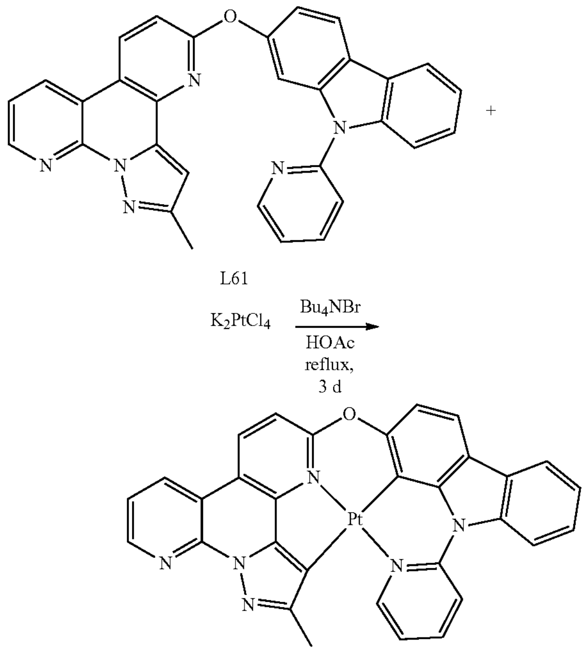

L61

MC61

L61 (0.11 mmol, 1.0 eq), $K_2PtCl_4$ (48 mg, 0.12 mmol, 1.1 eq) and n-$Bu_4NBr$ (3 mg, 0.011 mmol, 0.1 eq) were added to a dry pressure tube, which was taken into a glove box and acetic acid (7 mL) was added. The mixture was bubbled with nitrogen for 30 minutes and then the tube was sealed. Then the mixture was heated to reflux in an oil bath and stirred for 3 days, cooled to ambient temperature and the solvent removed. Then the solid was purified through column chromatography on silica gel using dichloromethane as eluent to obtain the desired product MC61 in 10%~50% yield.

Example 62

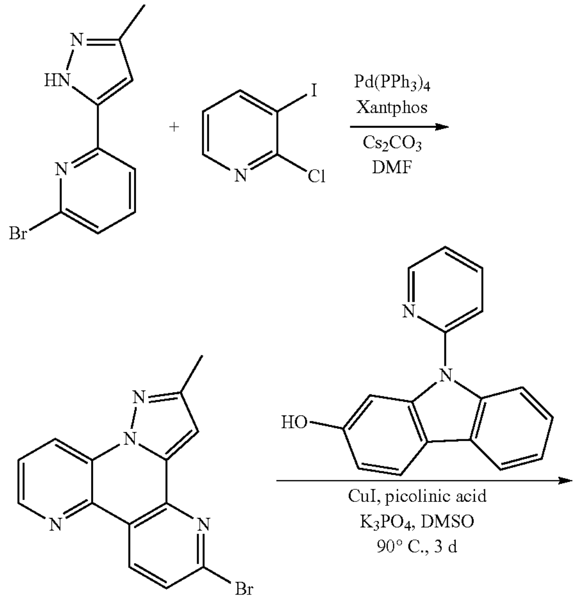

-continued

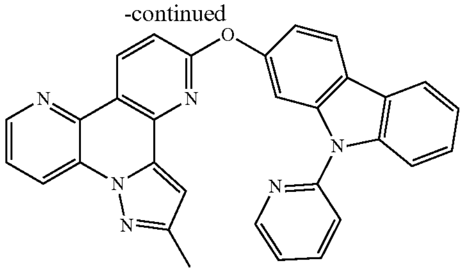

L62

5-bromo-2-methylpyrazolo[1,5-a]pyrido[2,3-c][1,5]naphthyridine (0.85 mmol, 1.0 eq), 9-(pyridin-2-yl)-9H-carbazol-2-ol (359 mg, 1.10 mmol, 1.3 eq), CuI (32 mg, 0.17 mmol, 0.2 eq), picolinic acid (21 mg, 0.17 mmol, 0.2 eq) and $K_3PO_4$ (356 mg, 1.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 100° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L62 in 20%-70% yield.

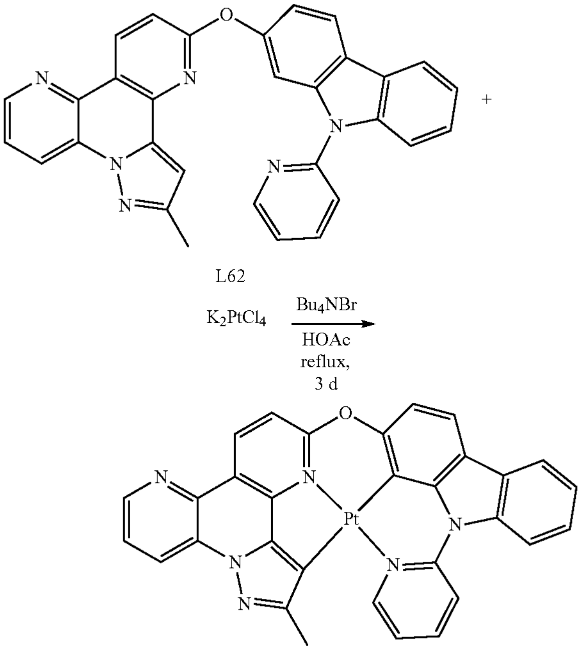

L62

MC62

L62 (0.11 mmol, 1.0 eq), $K_2PtCl_4$ (48 mg, 0.12 mmol, 1.1 eq) and n-$Bu_4NBr$ (3 mg, 0.011 mmol, 0.1 eq) were added to a dry pressure tube, which was taken into a glove box and acetic acid (7 mL) was added. The mixture was bubbled with nitrogen for 30 minutes and then the tube was sealed. Then the mixture was heated to reflux in an oil bath and stirred for 3 days, cooled to ambient temperature and the solvent removed. Then the solid was purified through column chromatography on silica gel using dichloromethane as eluent to obtain the desired product MC62 in 10%~50% yield.

Example 63

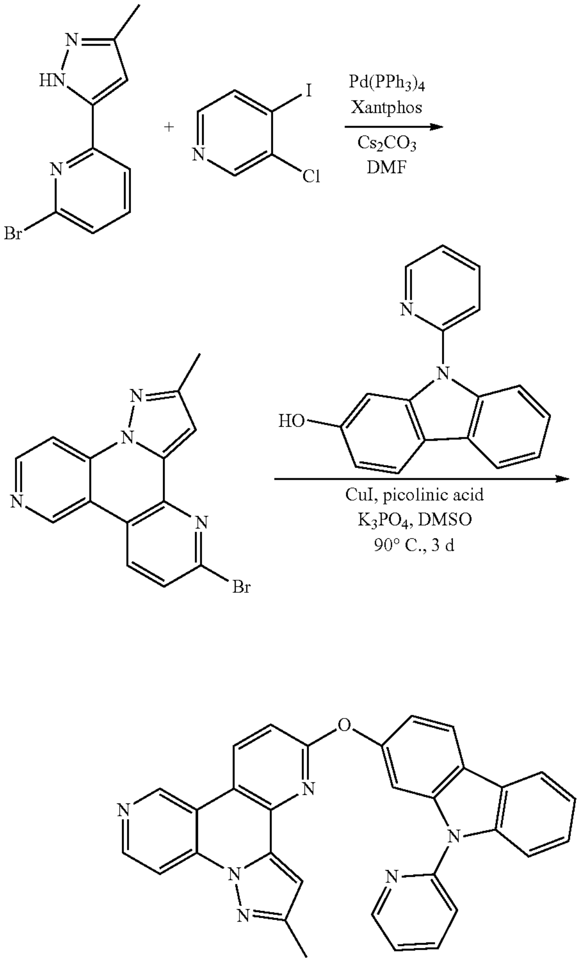

L63

5-bromo-2-methylpyrazolo[1,5-a]pyrido[2,3-c][1,6] naphthyridine (0.85 mmol, 1.0 eq), 9-(pyridin-2-yl)-9H-carbazol-2-ol (359 mg, 1.10 mmol, 1.3 eq), CuI (32 mg, 0.17 mmol, 0.2 eq), picolinic acid (21 mg, 0.17 mmol, 0.2 eq) and $K_3PO_4$ (356 mg, 1.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 100° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L63 in 20%-70% yield.

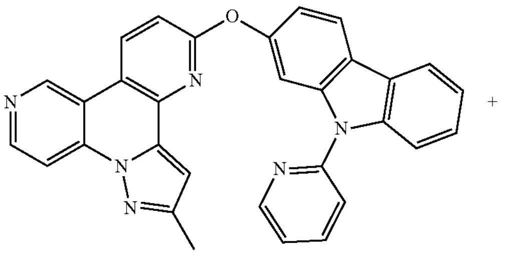

L63

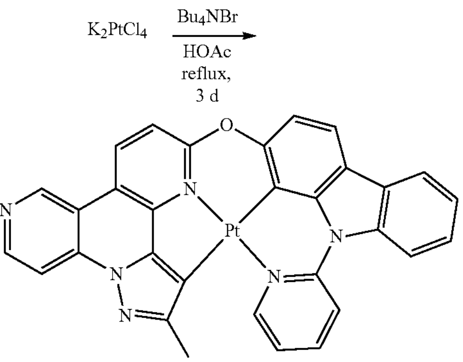

MC63

L63 (0.11 mmol, 1.0 eq), $K_2PtCl_4$ (48 mg, 0.12 mmol, 1.1 eq) and n-$Bu_4NBr$ (3 mg, 0.011 mmol, 0.1 eq) were added to a dry pressure tube, which was taken into a glove box and acetic acid (7 mL) was added. The mixture was bubbled with nitrogen for 30 minutes and then the tube was sealed. Then the mixture was heated to reflux in an oil bath and stirred for 3 days, cooled to ambient temperature and the solvent removed. Then the solid was purified through column chromatography on silica gel using dichloromethane as eluent to obtain the desired product MC63 in 10%~50% yield.

Example 64

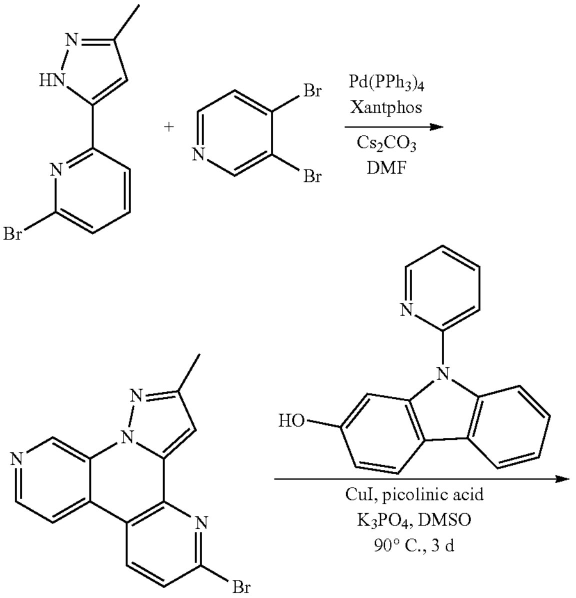

-continued

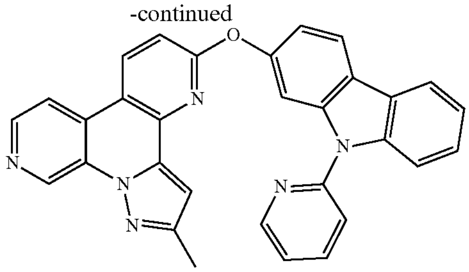

L64

5-bromo-2-methylpyrazolo[1,5-a]pyrido[2,3-c][1,7] naphthyridine (0.85 mmol, 1.0 eq), 9-(pyridin-2-yl)-9H-carbazol-2-ol (359 mg, 1.10 mmol, 1.3 eq), CuI (32 mg, 0.17 mmol, 0.2 eq), picolinic acid (21 mg, 0.17 mmol, 0.2 eq) and $K_3PO_4$ (356 mg, 1.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 100° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L64 in 20%-70% yield.

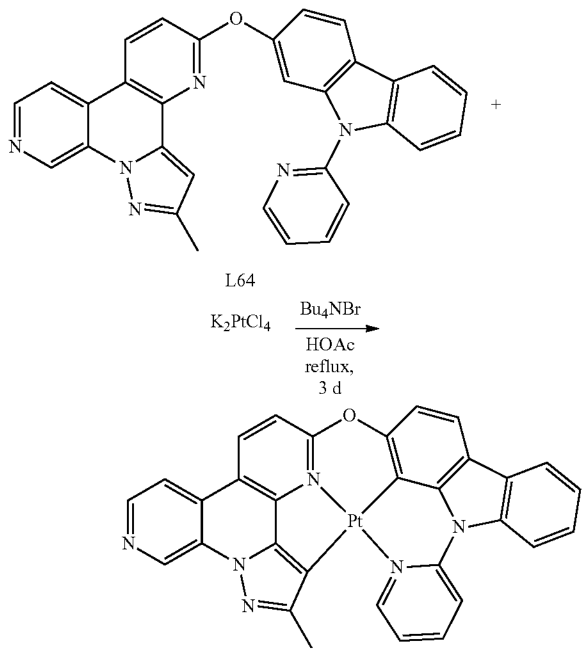

MC64

L64 (0.11 mmol, 1.0 eq), $K_2PtCl_4$ (48 mg, 0.12 mmol, 1.1 eq) and n-$Bu_4NBr$ (3 mg, 0.011 mmol, 0.1 eq) were added to a dry pressure tube, which was taken into a glove box and acetic acid (7 mL) was added. The mixture was bubbled with nitrogen for 30 minutes and then the tube was sealed. Then the mixture was heated to reflux in an oil bath and stirred for 3 days, cooled to ambient temperature and the solvent removed. Then the solid was purified through column chromatography on silica gel using dichloromethane as eluent to obtain the desired product MC64 in 10%~50% yield.

Example 65

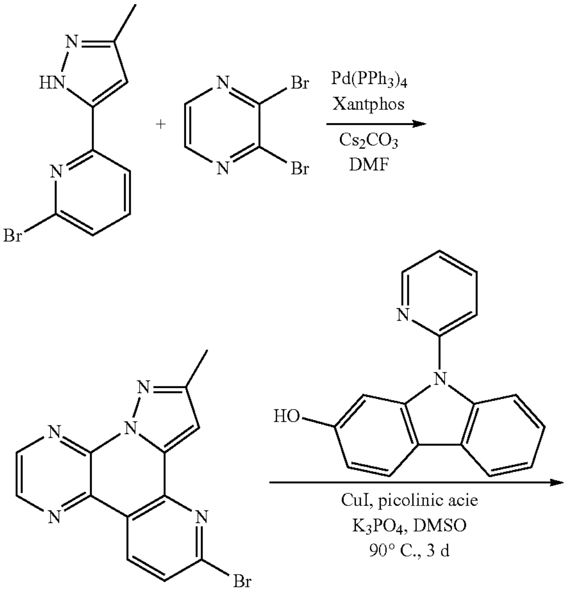

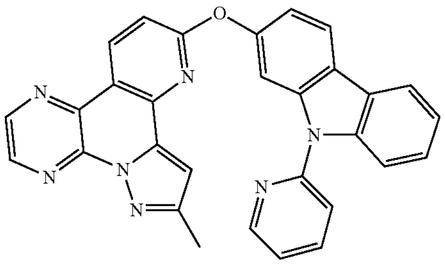

L65

10-bromo-7-methylpyrazino[2,3-f]pyrazolo[1,5-h][1,7] naphthyridine (0.85 mmol, 1.0 eq), 9-(pyridin-2-yl)-9H-carbazol-2-ol (359 mg, 1.10 mmol, 1.3 eq), CuI (32 mg, 0.17 mmol, 0.2 eq), picolinic acid (21 mg, 0.17 mmol, 0.2 eq) and $K_3PO_4$ (356 mg, 1.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 100° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L65 in 20%-70% yield.

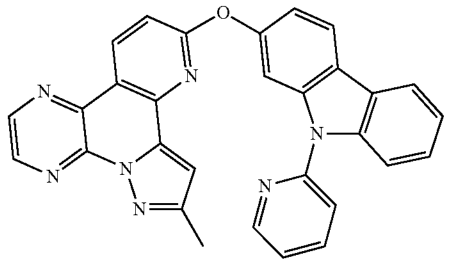

L65

Bu$_4$NBr
$K_2PtCl_4$
HOAc
reflux, 3 d

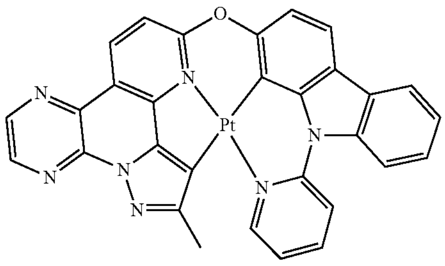

MC65

L65 (0.11 mmol, 1.0 eq), $K_2PtCl_4$ (48 mg, 0.12 mmol, 1.1 eq) and n-Bu$_4$NBr (3 mg, 0.011 mmol, 0.1 eq) were added to a dry pressure tube, which was taken into a glove box and acetic acid (7 mL) was added. The mixture was bubbled with nitrogen for 30 minutes and then the tube was sealed. Then the mixture was heated to reflux in an oil bath and stirred for 3 days, cooled to ambient temperature and the solvent removed. Then the solid was purified through column chromatography on silica gel using dichloromethane as eluent to obtain the desired product MC65 in 10%~50% yield.

Example 66

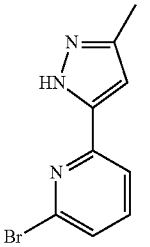

+

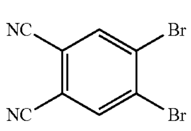

Pd(PPh$_3$)$_4$
Xantphos
$Cs_2CO_3$
DMF

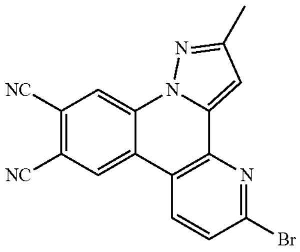

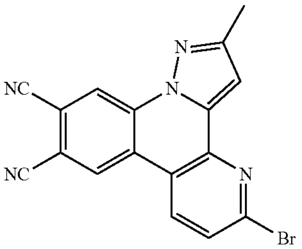

+

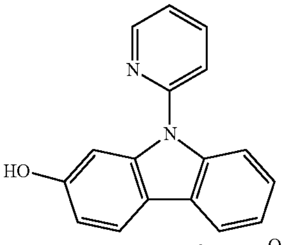

CuI
picolinic acid
$K_3PO_4$
DMSO
90° C., 3 d

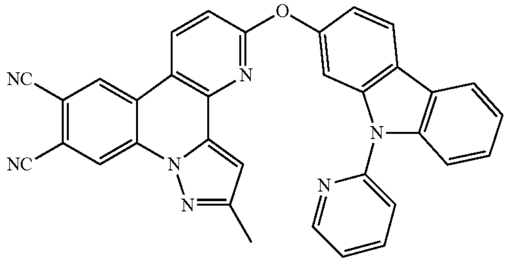

L66

5-bromo-2-methylbenzo[f]pyrazolo[1,5-h][1,7]naphthyridine-9,10-dicarbonitrile (0.85 mmol, 1.0 eq), 9-(pyridin-2-yl)-9H-carbazol-2-ol (359 mg, 1.10 mmol, 1.3 eq), CuI (32 mg, 0.17 mmol, 0.2 eq), picolinic acid (21 mg, 0.17 mmol, 0.2 eq) and $K_3PO_4$ (356 mg, 1.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 100° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L66 in 20%-70% yield.

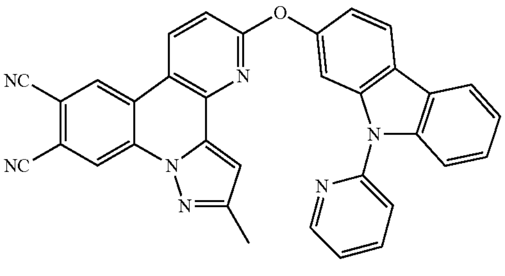

+

L66

Bu$_4$NBr
$K_2PtCl_4$
HOAc
reflux, 3 d

-continued

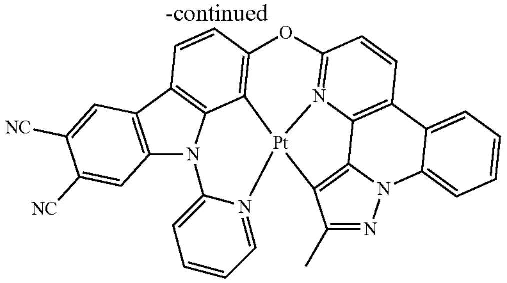

MC66

-continued

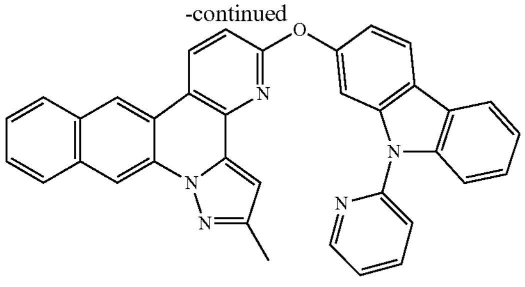

L67

L66 (0.11 mmol, 1.0 eq), $K_2PtCl_4$ (48 mg, 0.12 mmol, 1.1 eq) and n-$Bu_4NBr$ (3 mg, 0.011 mmol, 0.1 eq) were added to a dry pressure tube, which was taken into a glove box and acetic acid (7 mL) was added. The mixture was bubbled with nitrogen for 30 minutes and then the tube was sealed. Then the mixture was heated to reflux in an oil bath and stirred for 3 days, cooled to ambient temperature and the solvent removed. Then the solid was purified through column chromatography on silica gel using dichloromethane as eluent to obtain the desired product MC66 in 10%~50% yield.

Example 67

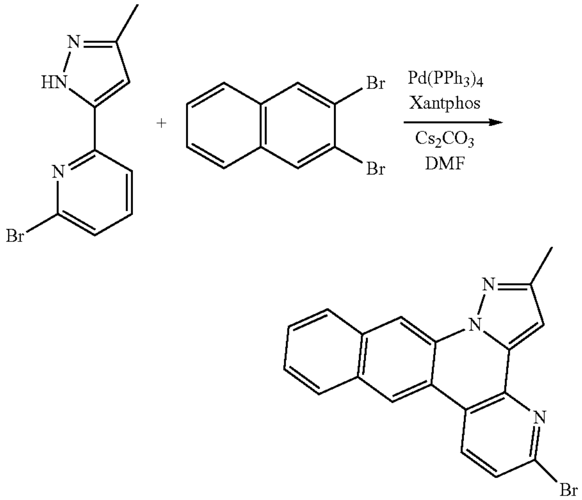

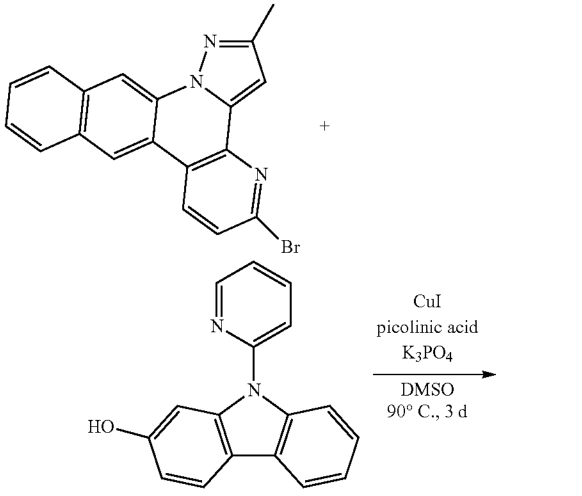

5-bromo-2-methylnaphtho[2,3-f]pyrazolo[1,5-h][1,7]naphthyridine (0.85 mmol, 1.0 eq), 9-(pyridin-2-yl)-9H-carbazol-2-ol (359 mg, 1.10 mmol, 1.3 eq), CuI (32 mg, 0.17 mmol, 0.2 eq), picolinic acid (21 mg, 0.17 mmol, 0.2 eq) and $K_3PO_4$ (356 mg, 1.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 100° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L67 in 20%-70% yield.

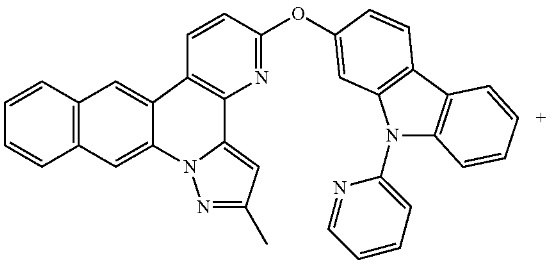

L67

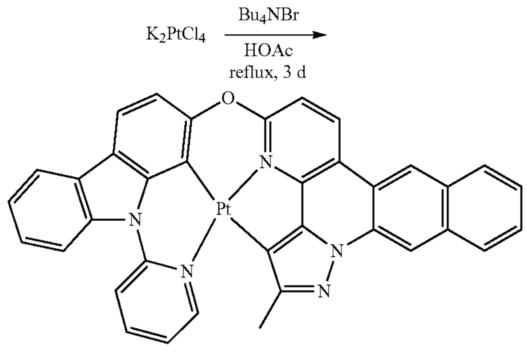

MC67

L67 (0.11 mmol, 1.0 eq), $K_2PtCl_4$ (48 mg, 0.12 mmol, 1.1 eq) and n-$Bu_4NBr$ (3 mg, 0.011 mmol, 0.1 eq) were added to a dry pressure tube, which was taken into a glove box and acetic acid (7 mL) was added. The mixture was bubbled with nitrogen for 30 minutes and then the tube was sealed. Then the mixture was heated to reflux in an oil bath and stirred for 3 days, cooled to ambient temperature and the solvent removed. Then the solid was purified through column chromatography on silica gel using dichloromethane as eluent to obtain the desired product MC67 in 10%~50% yield.

Example 68

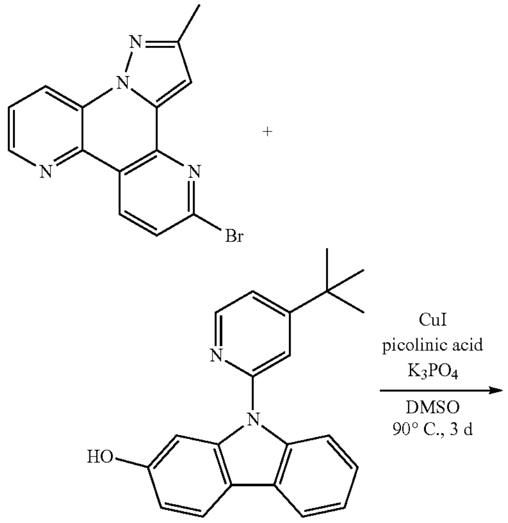

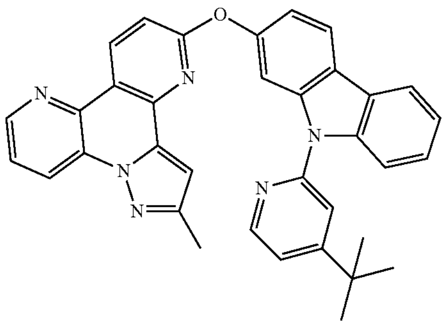

L68

5-bromo-2-methylpyrazolo[1,5-a]pyrido[2,3-c][1,5]naphthyridine (0.35 mmol, 1.0 eq), 2-bromo-9-(4-(tert-butyl)pyridin-2-yl)-9H-carbazole (159 mg, 0.42 mmol, 1.2 eq), CuI (13 mg, 0.07 mmol, 0.2 eq), picolinic acid (9 mg, 0.07 mmol, 0.2 eq) and $K_3PO_4$ (149 mg, 0.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (5 mL) was added under the protection of nitrogen. The mixture was stirred in an oil bath at a temperature of 90° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L68 in 30%~70% yield.

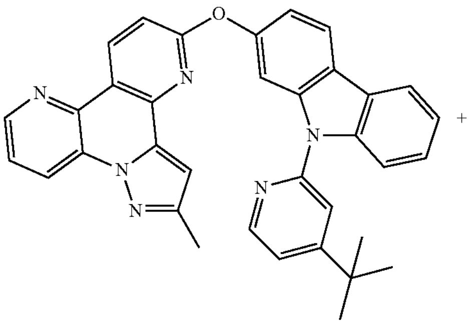

L68

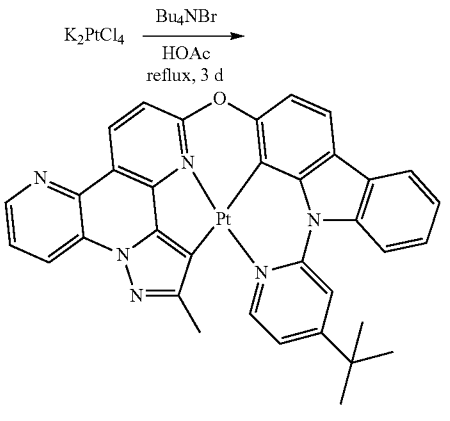

MC68

L68 (0.11 mmol, 1.0 eq), $K_2PtCl_4$ (48 mg, 0.12 mmol, 1.1 eq) and n-$Bu_4NBr$ (3 mg, 0.011 mmol, 0.1 eq) were added to a dry pressure tube, which was taken into a glove box and acetic acid (7 mL) was added. The mixture was bubbled with nitrogen for 30 minutes and then the tube was sealed. Then the mixture was heated to reflux in an oil bath and stirred for 3 days, cooled to ambient temperature and the solvent removed. Then the solid was purified through column chromatography on silica gel using dichloromethane as eluent to obtain the desired product MC68 in 10%~50% yield.

Example 69

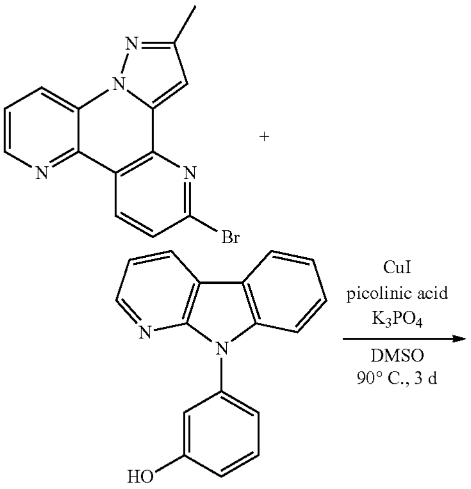

-continued

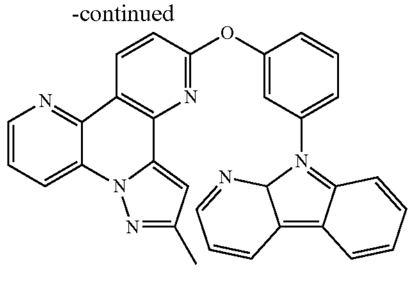

L69

5-bromo-2-methylpyrazolo[1,5-a]pyrido[2,3-c][1,5]naphthyridine (0.85 mmol, 1.0 eq), 3-(9H-pyrido[2,3-b]indol-9-yl)phenol (359 mg, 1.10 mmol, 1.3 eq), CuI (32 mg, 0.17 mmol, 0.2 eq), picolinic acid (21 mg, 0.17 mmol, 0.2 eq) and $K_3PO_4$ (356 mg, 1.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 100° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L69 in 20%-70% yield.

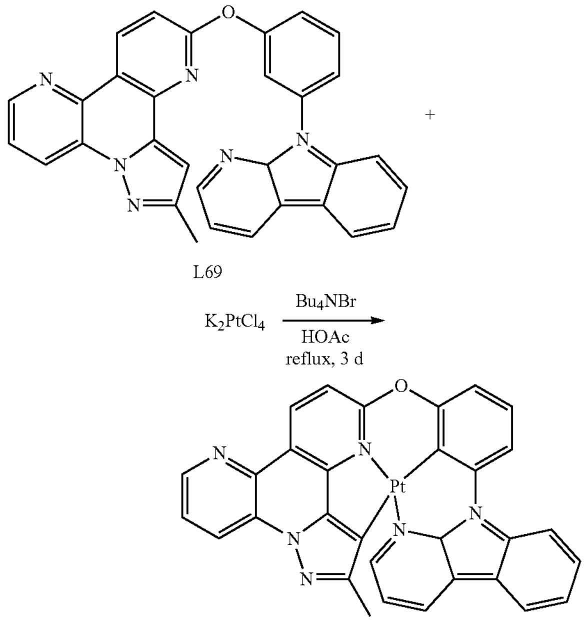

MC69

L69 (0.11 mmol, 1.0 eq), $K_2PtCl_4$ (48 mg, 0.12 mmol, 1.1 eq) and n-$Bu_4NBr$ (3 mg, 0.011 mmol, 0.1 eq) were added to a dry pressure tube, which was taken into a glove box and acetic acid (7 mL) was added. The mixture was bubbled with nitrogen for 30 minutes and then the tube was sealed. Then the mixture was heated to reflux in an oil bath and stirred for 3 days, cooled to ambient temperature and the solvent removed. Then the solid was purified through column chromatography on silica gel using dichloromethane as eluent to obtain the desired product MC69 in 10%~50% yield.

Example 70

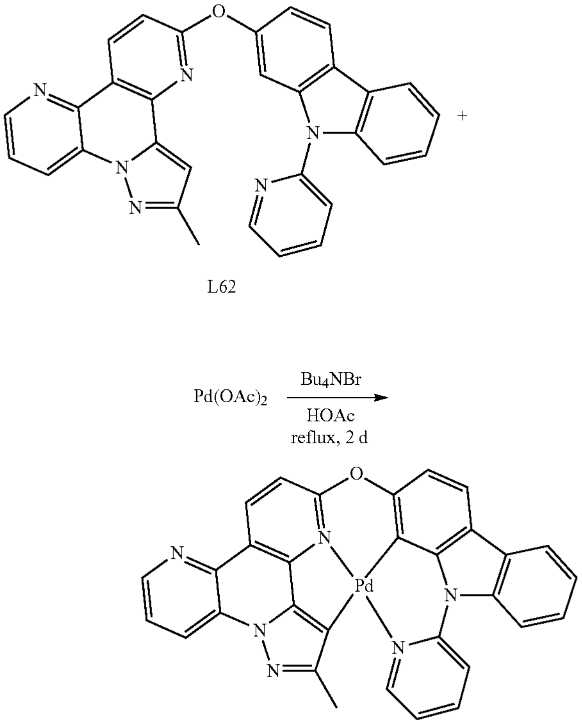

L70

L62 (0.11 mmol, 1.0 eq), $Pd(OAc)_2$ (27 mg, 0.12 mmol, 1.1 eq) and n-$Bu_4NBr$ (3 mg, 0.011 mmol, 0.1 eq) were added to a dry pressure tube, which was taken into a glove box and acetic acid (7 mL) was added. The mixture was bubbled with nitrogen for 30 minutes and then the tube was sealed. Then the mixture was heated to reflux in an oil bath and stirred for 2 days, cooled to ambient temperature and the solvent removed. Then the solid was purified through column chromatography on silica gel using dichloromethane as eluent to obtain the desired product MC70 in 10%~50% yield.

Example 71

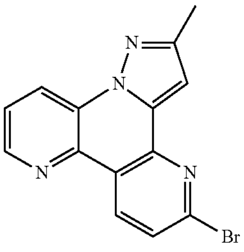

+

-continued

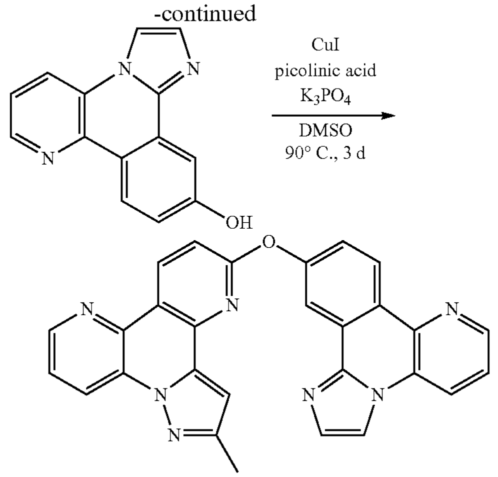

L71

5-bromo-2-methylpyrazolo[1,5-a]pyrido[2,3-c][1,5]naphthyridine (0.85 mmol, 1.0 eq), benzo[c]imidazo[1,2-a][1,5]naphthyridin-11-ol (1.10 mmol, 1.3 eq), CuI (32 mg, 0.17 mmol, 0.2 eq), picolinic acid (21 mg, 0.17 mmol 0.2 eq) and $K_3PO_4$ (356 mg, 1.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 100° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L71 in 20%-70% yield.

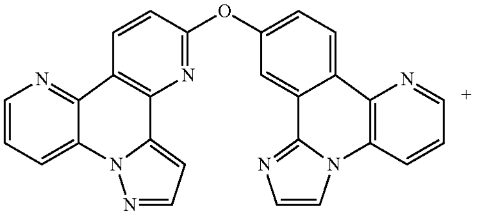

L71

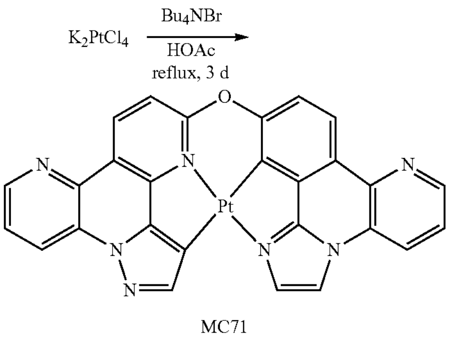

MC71

L71 (0.11 mmol, 1.0 eq), $K_2PtCl_4$ (48 mg, 0.12 mmol, 1.1 eq) and n-$Bu_4NBr$ (3 mg, 0.011 mmol, 0.1 eq) were added to a dry pressure tube, which was taken into a glove box and acetic acid (7 mL) was added. The mixture was bubbled with nitrogen for 30 minutes and then the tube was sealed. Then the mixture was heated to reflux in an oil bath and stirred for 3 days, cooled to ambient temperature and the solvent removed. Then the solid was purified through column chromatography on silica gel using dichloromethane as eluent to obtain the desired product MC71 in 10%~50% yield.

Example 72

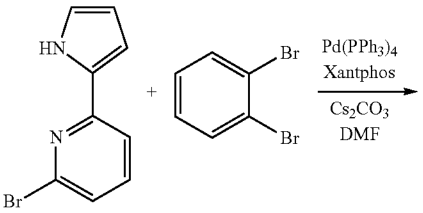

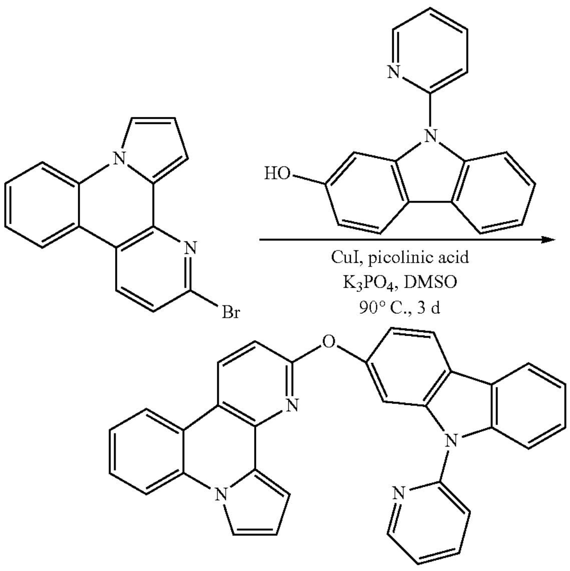

L72

2-bromobenzo[f]pyrrolo[1,2-h][1,7]naphthyridine (0.85 mmol 1.0 eq), 9-(pyridin-2-yl)-9H-carbazol-2-ol (359 mg, 1.10 mmol, 1.3 eq), CuI (32 mg, 0.17 mmol, 0.2 eq), picolinic acid (21 mg, 0.17 mmol, 0.2 eq) and $K_3PO_4$ (356 mg, 1.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 100° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L72 in 20%-70% yield.

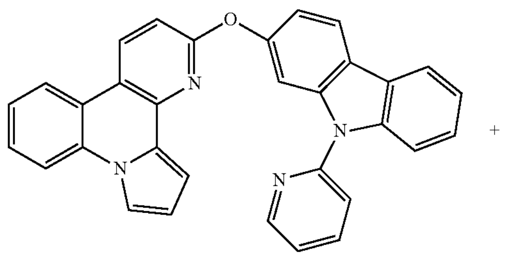

L72

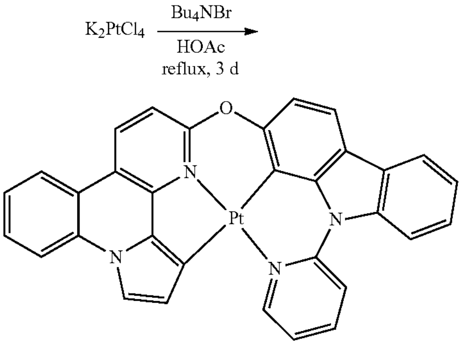

MC72

L72 (0.11 mmol, 1.0 eq), $K_2PtCl_4$ (48 mg, 0.12 mmol, 1.1 eq) and n-$Bu_4NBr$ (3 mg, 0.011 mmol, 0.1 eq) were added to a dry pressure tube, which was taken into a glove box and acetic acid (7 mL) was added. The mixture was bubbled with nitrogen for 30 minutes and then the tube was sealed. Then the mixture was heated to reflux in an oil bath and stirred for 3 days, cooled to ambient temperature and the solvent removed. Then the solid was purified through column chromatography on silica eel using dichloromethane as eluent to obtain the desired product MC72 in 10%~50% yield.

Example 73

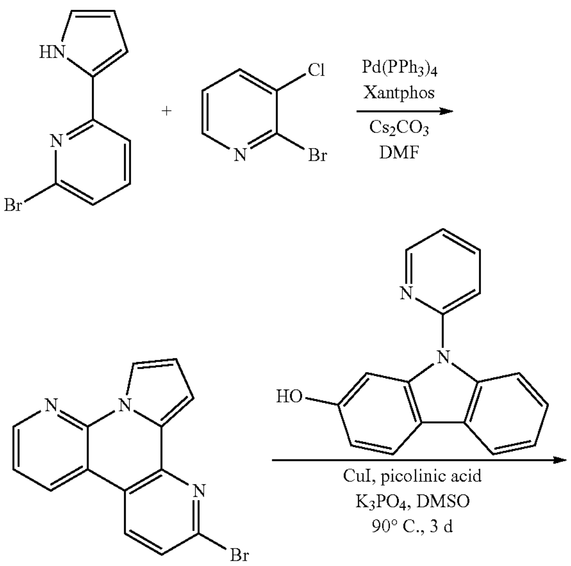

-continued

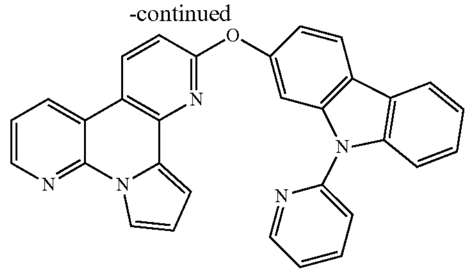

L73

2-bromopyrido[3,2-f]pyrrolo[1,2-h][1,7]naphthyridine (0.85 mmol, 1.0 eq), 9-(pyridin-2-yl)-9H-carbazol-2-ol (359 mg, 1.10 mmol, 1.3 eq), CuI (32 mg, 0.17 mmol, 0.2 eq), picolinic acid (21 mg, 0.17 mmol, 0.2 eq) and $K_3PO_4$ (356 mg, 1.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 100° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica, gel using hexane/ethyl acetate as eluent to obtain the desired product ligand L73 in 20%-70% yield.

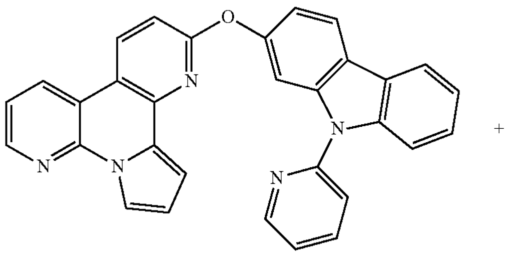

L73

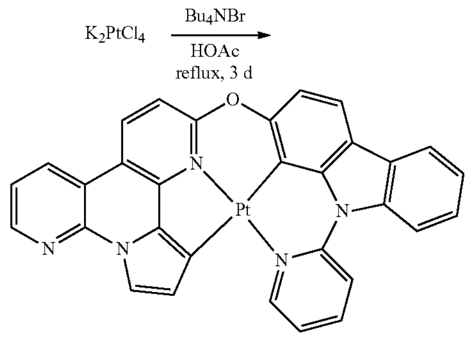

MC73

L73 (0.11 mmol, 1.0 eq), $K_2PtCl_4$ (48 mg, 0.12 mmol, 1.1 eq) and n-$Bu_4NBr$ (3 mg, 0.011 mmol, 0.1 eq) were added to a dry pressure tube, which was taken into a glove box and acetic acid (7 mL) was added. The mixture was bubbled with nitrogen for 30 minutes and then the tube was sealed. Then the mixture was heated to reflux in an oil bath and stirred for 3 days, cooled to ambient temperature and the solvent removed. Then the solid was purified through column chromatography on silica gel using dichloromethane as eluent to obtain the desired product MC73 in 10%~50% yield.

Example 74

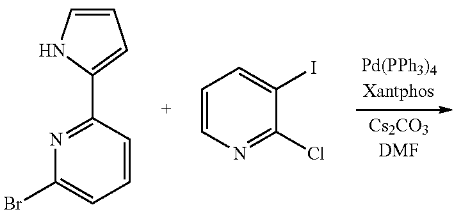

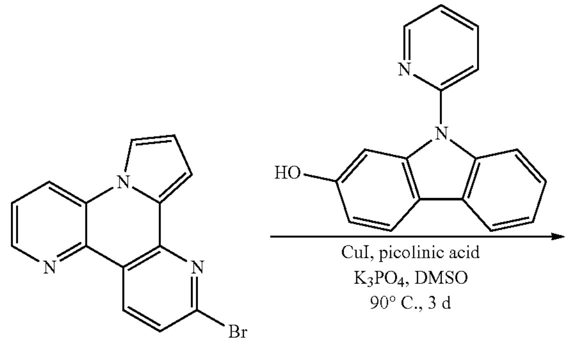

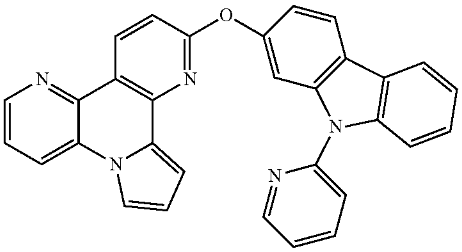

L74

2-bromopyrido[2,3-c]pyrrolo[1,2-a]naphthyridine (0.85 mmol, 1.0 eq), 9-(pyridin-2-yl)-9H-carbazol-2-ol (359 mg, 1.10 mmol, 1.3 eq), CuI (32 mg, 0.17 mmol, 0.2 eq), picolinic acid (21 mg, 0.17 mmol, 0.2 eq) $K_3PO_4$ (356 mg, 1.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 100° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L74 in 20%-70% yield.

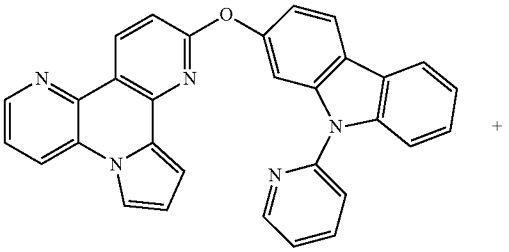

L74

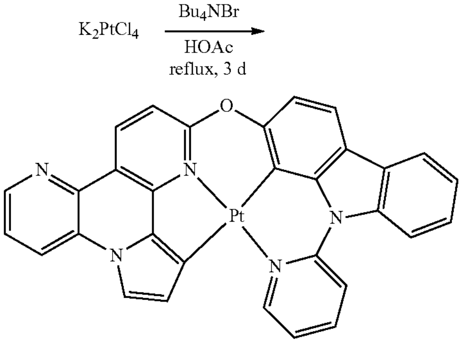

MC74

L74 (0.11 mmol, 1.0 eq), $K_2PtCl_4$ (48 mg, 0.12 mmol, 1.1 eq) and n-$Bu_4NBr$ (3 mg, 0.011 mmol, 0.1 eq) were added to a dry pressure tube, which was taken into a dove box and acetic acid (7 mL) was added. The mixture was bubbled with nitrogen for 30 minutes and then the tube was sealed. Then the mixture was heated to reflux in an oil bath and stirred for 3 days, cooled to ambient temperature and the solvent removed. Then the solid was purified through column chromatography on silica gel using dichloromethane as eluent to obtain the desired product MC74 in 10%~50% yield.

Example 75

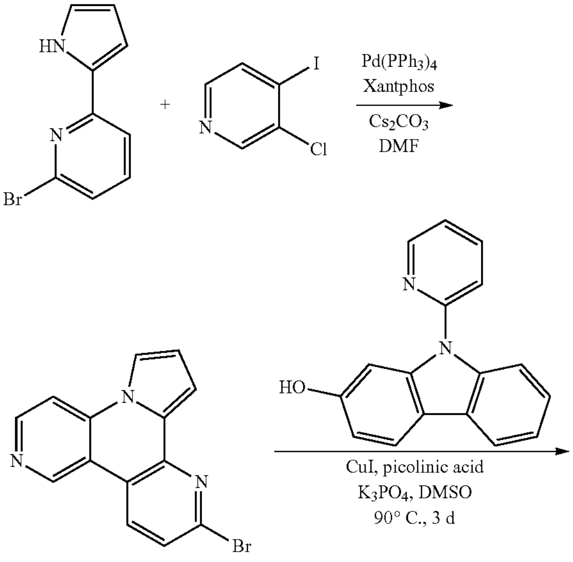

-continued

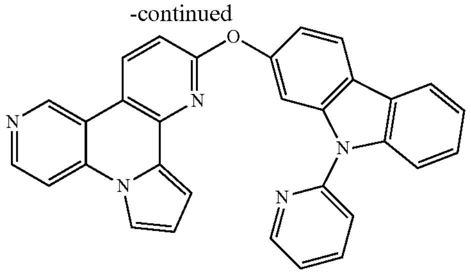

L75

2-bromopyrido[2,3-c]pyrrolo[1,2-a][1,6]naphthyridine (0.85 mmol, 1.0 eq), 9-(pyridin-2-yl)-9H-carbazol-2-ol (359 mg, 1.10 mmol, 1.3 eq), CuI (32 mg, 0.17 mmol, 0.2 eq), picolinic acid (21 mg, 0.17 mmol, 0.2 eq) and $K_3PO_4$ (356 mg, 1.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 100° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L75 in 20%-70% yield.

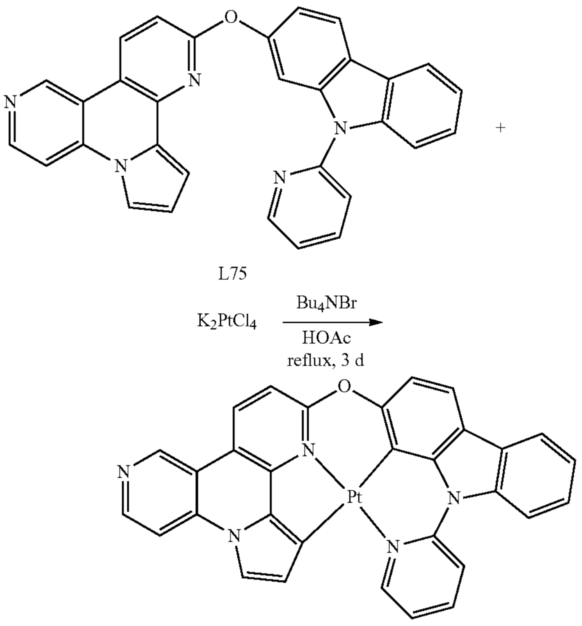

MC75

L75 (0.11 mmol, 1.0 eq), $K_2PtCl_4$ (48 mg, 0.12 mmol, 1.1 eq) and n-$Bu_4NBr$ (3 mg, 0.011 mmol, 0.1 eq) were added to a dry pressure tube, which was taken into a glove box and acetic acid (7 mL) was added. The mixture was bubbled with nitrogen for 30 minutes and then the tube was sealed. Then the mixture was heated to reflux in an oil bath and stirred for 3 days, cooled to ambient temperature and the solvent removed. Then the solid was purified through column chromatography on silica gel using dichloromethane as eluent to obtain the desired product MC75 in 10%~50% yield.

Example 76

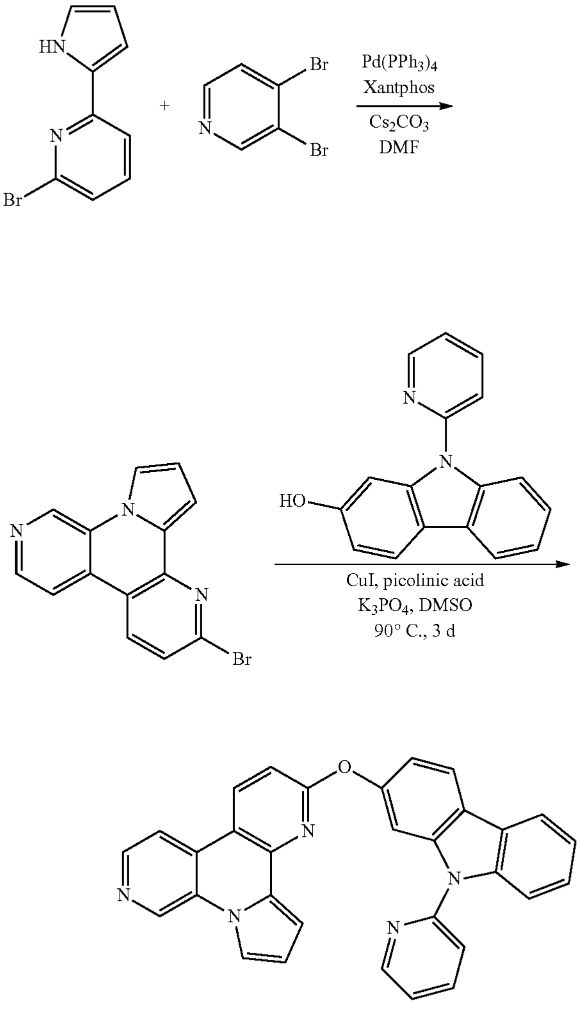

L76

2-bromopyrido[2,3-c]pyrrolo[1,2-a][1,7]naphthyridin (0.85 mmol, 1.0 eq), 9-(pyridin-2-yl)-9H-carbazol-2-ol (359 mg, 1.10 mmol, 1.3 eq), CuI (32 mg, 0.17 mmol, 0.2 eq), picolinic acid (21 mg, 0.17 mmol, 0.2 eq) and $K_3PO_4$ (356 mg, 1.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 100° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L76 in 20%-70% yield.

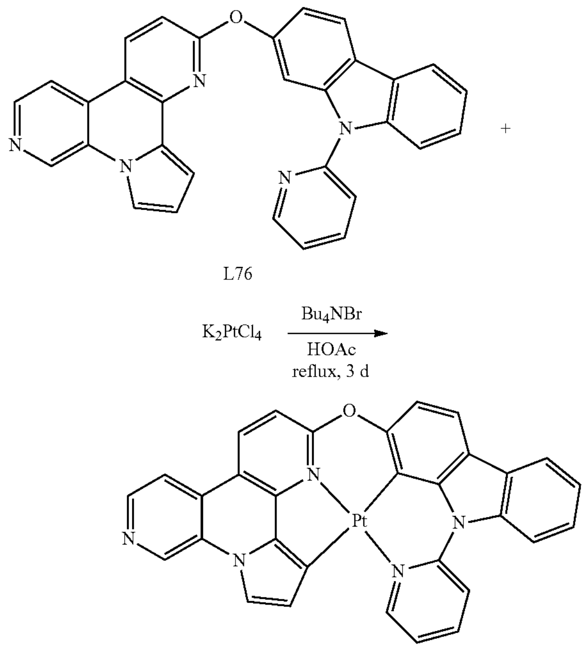

L76

MC76

L76 (0.11 mmol, 1.0 eq), $K_2PtCl_4$ (48 mg, 0.12 mmol, 1.1 eq) and n-$Bu_4NBr$ (3 mg, 0.011 mmol, 0.1 eq) were added to a dry pressure tube, which was taken into a glove box and acetic acid (7 mL) was added. The mixture was bubbled with nitrogen for 30 minutes and then the tube was sealed. Then the mixture was heated to reflux in an oil bath and stirred for 3 days, cooled to ambient temperature and the solvent removed. Then the solid was purified through column chromatography on silica gel using dichloromethane as eluent to obtain the desired product MC76 in 10%~50% yield.

Example 77

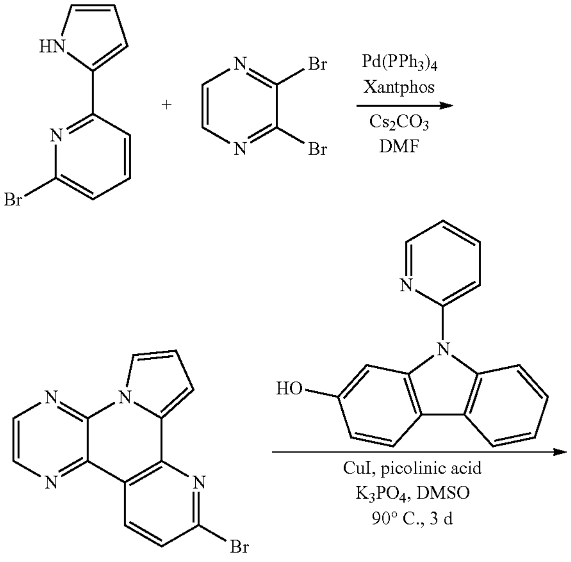

-continued

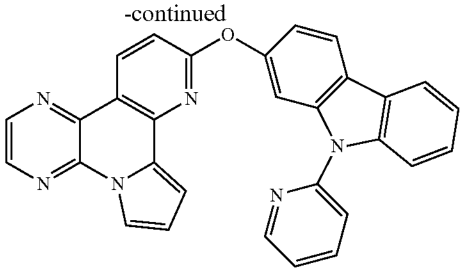

L77

10-bromopyrazino[2,3-f]pyrrolo[1,2-h][1,7]naphthyridine (0.85 mmol, 1.0 eq), 9-(pyridin-2-yl)-9H-carbazol-2-ol (359 mg, 1.10 mmol, 1.3 eq), CuI (32 mg, 0.17 mmol, 0.2 eq), picolinic acid (21 mg, 0.17 mmol, 0.2 eq) and $K_3PO_4$ (1356 mg, 1.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 100° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L77 in 20%-70% yield.

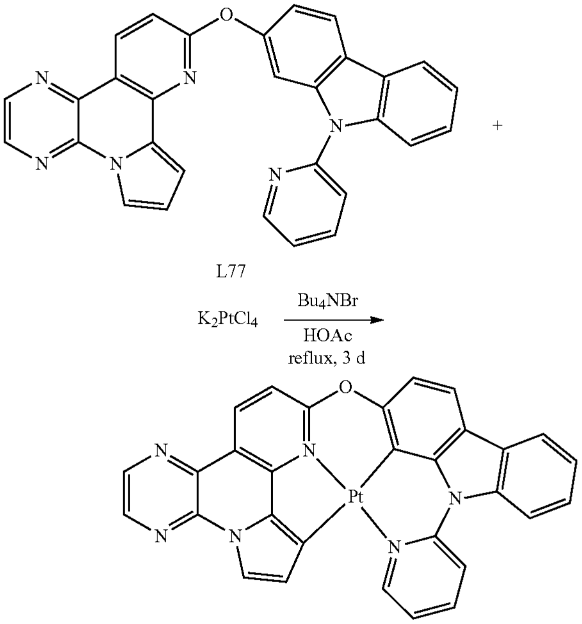

L77

MC77

L77 (0.11 mmol, 1.0 eq), $K_2PtCl_4$ (48 mg, 0.12 mmol, 1.1 eq) and n-$Bu_4NBr$ (3 mg, 0.011 mmol, 0.1 eq) were added to a dry pressure tube, which was taken into a glove box and acetic acid (7 mL) was added. The mixture was bubbled with nitrogen for 30 minutes and then the tube was sealed. Then the mixture was heated to reflux in an oil bath and stirred for 3 days, cooled to ambient temperature and the solvent removed. Then the solid was purified through column chromatography on silica gel using dichloromethane as eluent to obtain the desired product MC77 in 10%~50% yield.

Example 78

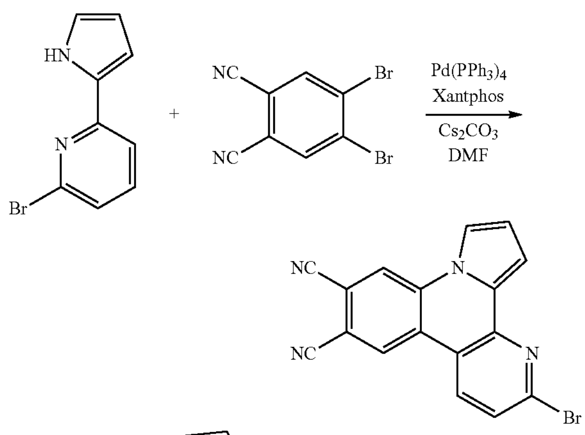

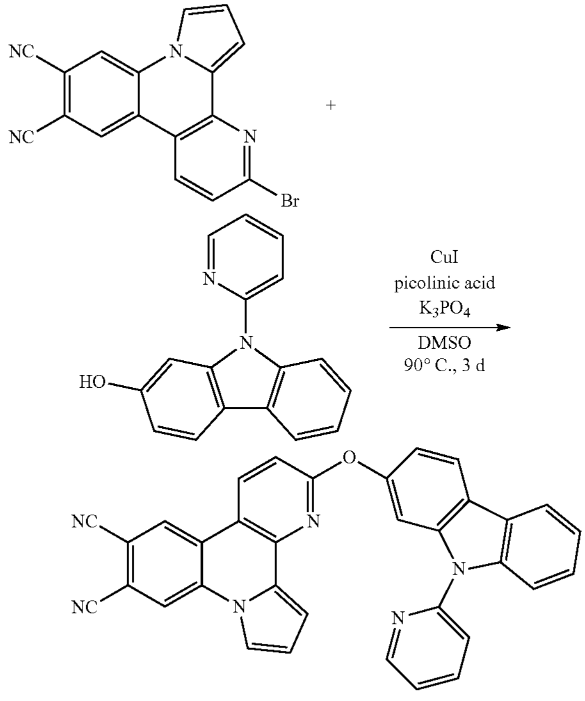

L78

2-bromobenzo[f]pyrrolo[1,2-h][1,7]naphthyridine-6,7-dicarbonitrile (0.85 mmol, 1.0 eq), 9-(pyridin-2-yl)-9H-carbazol-2-ol (359 mg, 1.10 mmol, 1.3 eq), CuI (32 mg, 0.17 mmol, 0.2 eq), picolinic acid (21 mg, 0.17 mmol, 0.2 eq) and $K_3PO_4$ (356 mg, 1.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 100° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L78 in 20%-70% yield.

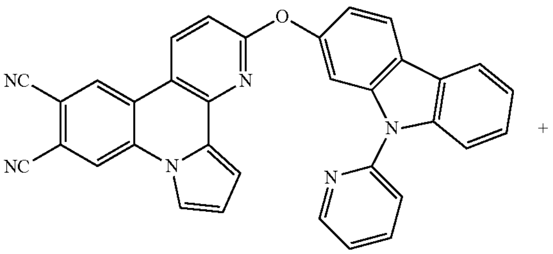

L78

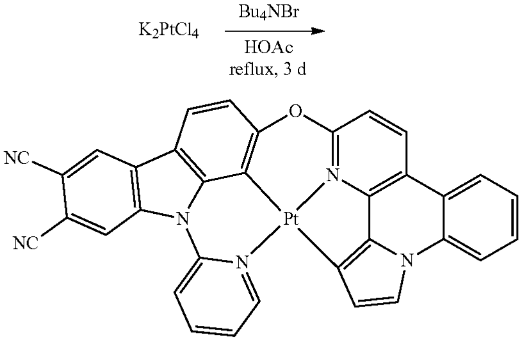

MC78

L78 (0.11 mmol, 1.0 eq), $K_2PtCl_4$ (48 mg, 0.12 mmol, 1.1 eq) and n-$Bu_4NBr$ (3 mg, 0.011 mmol, 0.1 eq) were added to a dry pressure tube, which was taken into a glove box and acetic acid (7 mL) was added. The mixture was bubbled with nitrogen for 30 minutes and then the tube was sealed. Then the mixture was heated to reflux in an oil bath and stirred for 3 days, cooled to ambient temperature and the solvent removed. Then the solid was purified through column chromatography on silica gel using dichloromethane as eluent to obtain the desired product MC78 in 10%~50% yield.

Example 79

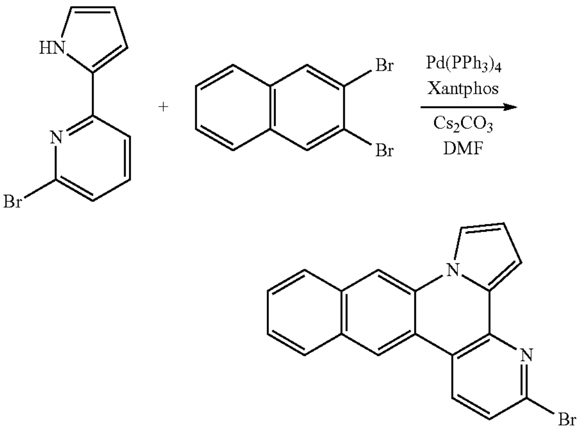

-continued

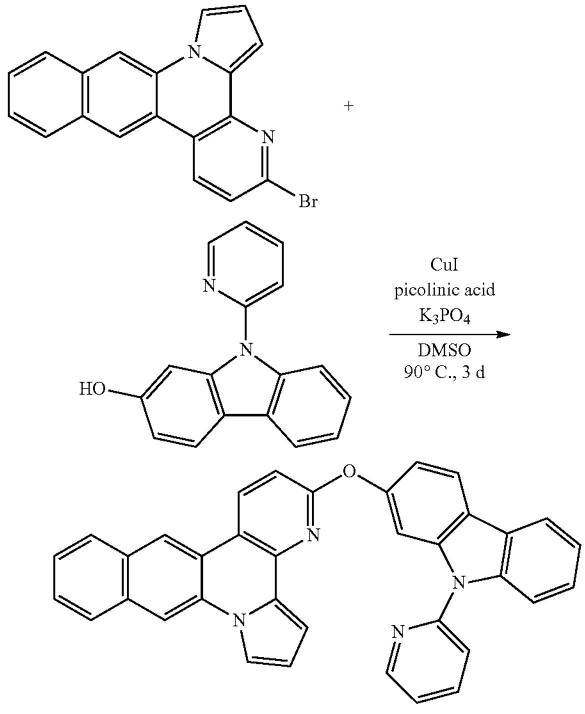

L79

3-bromonaphtho[2,3-f]pyrrolo[1,2-h][1,7]naphthyridine (0.85 mmol, 1.0 eq), 9-(pyridin-2-yl)-9H-carbazol-2-ol (359 mg, 1.10 mmol, 1.3 eq), CuI (32 mg, 0.17 mmol, 0.2 eq), picolinic acid (21 mg, 0.17 mmol, 0.2 eq) and $K_3PO_4$ (356 mg, 1.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 100° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L79 in 20%-70% yield.

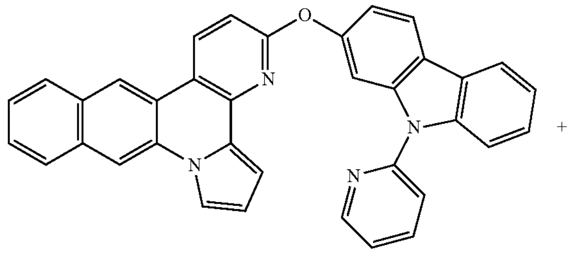

L79

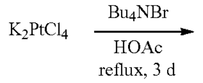

-continued

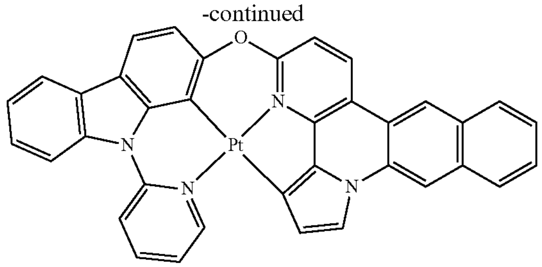

MC79

L79 (0.11 mmol, 1.0 eq), $K_2PtCl_4$ (48 mg, 0.12 mmol, 1.1 eq) and n-$Bu_4NBr$ (3 mg, 0.011 mmol, 0.1 eq) were added to a dry pressure tube, which was taken into a glove box and acetic acid (7 mL) was added. The mixture was bubbled with nitrogen for 30 minutes and then the tube was sealed. Then the mixture was heated to reflux in an oil bath and stirred for 3 days, cooled to ambient temperature and the solvent removed. Then the solid was purified through column chromatography on silica gel using dichloromethane as eluent to obtain the desired product MC79 in 10%~50% yield.

Example 80

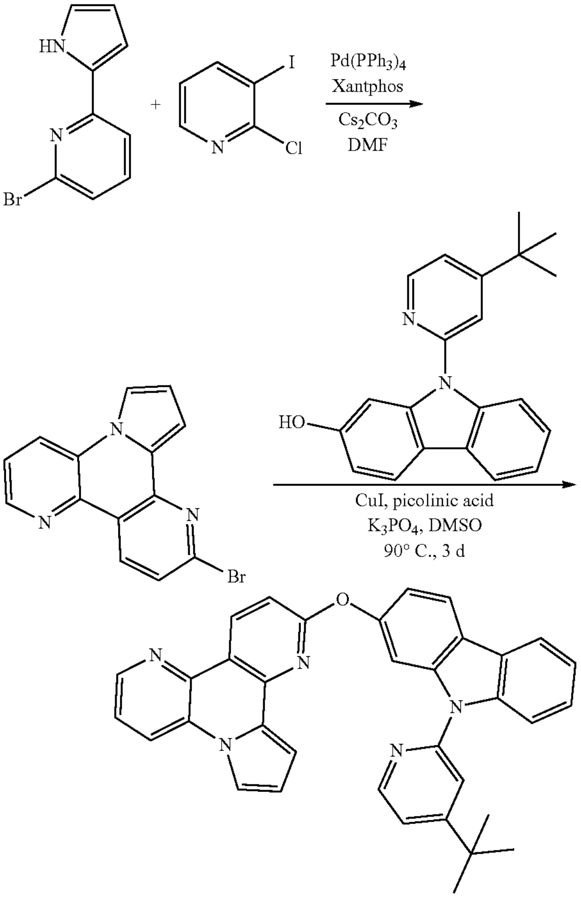

L80

2-bromopyrido[2,3-c]pyrrolo[1,2-a][1,5]naphthyridine (0.85 mmol, 1.0 eq), 9-(4-(tert-butyl)pyridin-2-yl)-9H-carbazol-2-ol (359 mg, 1.10 mmol, 1.3 eq), CuI (32 mg, 0.17 mmol, 0.2 eq), picolinic acid (21 mg, 0.17 mmol, 0.2 eq) and $K_3PO_4$ (356 mg, 1.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 100° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L80 in 20%-70% yield.

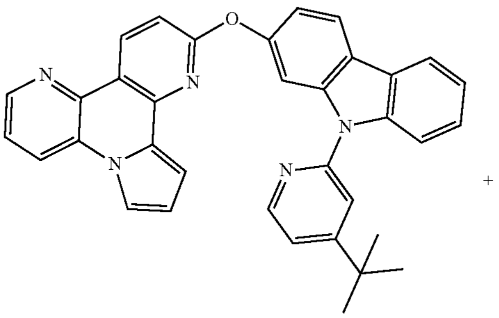

L80

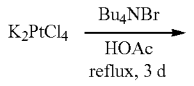

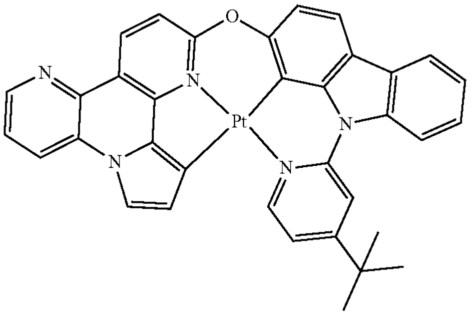

MC80

L80 (0.11 mmol, 1.0 eq), $K_2PtCl_4$ (48 mg, 0.12 mmol, 1.1 eq) and n-$Bu_4NBr$ (3 mg, 0.011 mmol, 0.1 eq) were added to a dry pressure tube, which was taken into a glove box and acetic acid (7 mL) was added. The mixture was bubbled with nitrogen for 30 minutes and then the tube was sealed. Then the mixture was heated to reflux in an oil bath and stirred for 3 days, cooled to ambient temperature and the solvent removed. Then the solid was purified through column chromatography on silica gel using dichloromethane as eluent to obtain the desired product MC80 in 10%~50% yield.

Example 81

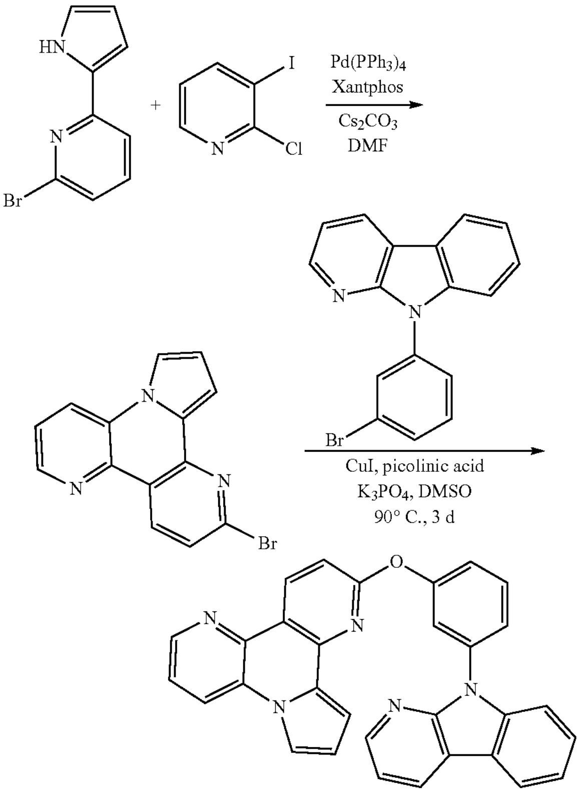

L81

2-bromopyrido[2,3-c]pyrrolo[1,2-a][1,5]naphthyridine (0.85 mmol, 1.0 eq), 9-(3-bromophenyl)-9H-pyrido[2,3-b]indole (359 mg, 1.10 mmol, 1.3 eq), CuI (32 mg, 0.17 mmol, 0.2 eq), picolinic acid (21 mg, 0.17 mmol, 0.2 eq) and $K_3PO_4$ (356 mg, 1.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 100° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L81 in 20%-70% yield.

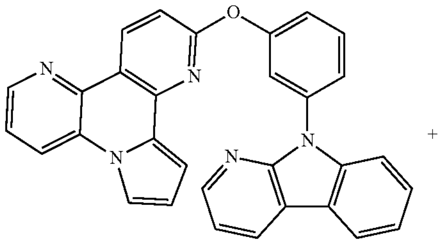

L81

-continued

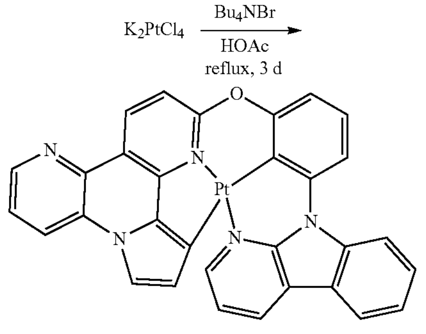

MC81

L81 (0.11 mmol, 1.0 eq), $K_2PtCl_4$ (48 mg, 0.12 mmol, 1.1 eq) and n-$Bu_4NBr$ (3 mg, 0.011 mmol, 0.1 eq) were added to a dry pressure tube, which was taken into a glove box and acetic acid (7 mL) was added. The mixture was bubbled with nitrogen for 30 minutes and then the tube was sealed. Then the mixture was heated to reflux in an oil bath and stirred for 3 days, cooled to ambient temperature and the solvent removed. Then the solid was purified through column chromatography on silica gel using dichloromethane as eluent to obtain the desired product MC81 in 10%~50% yield.

Example 82

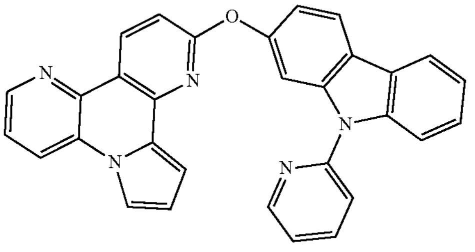

+

L74

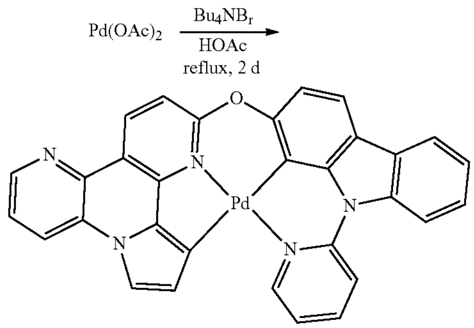

MC82

L74 (0.11 mmol, 1.0 eq), $Pd(OAc)_2$ (0.12 mmol, 1.1 eq) and n-$Bu_4NBr$ (3 mg, 0.011 mmol, 0.1 eq) were added to a dry pressure tube, which was taken into a glove box and acetic acid (7 mL) was added. The mixture was bubbled with nitrogen for 30 minutes and then the tube was sealed. Then the mixture was heated to reflux in an oil bath and stirred for 2 days, cooled to ambient temperature and the solvent removed. Then the solid was purified through column chromatography on silica gel using dichloromethane as eluent to obtain the desired product MC82 in 10%~50% yield.

Example 83

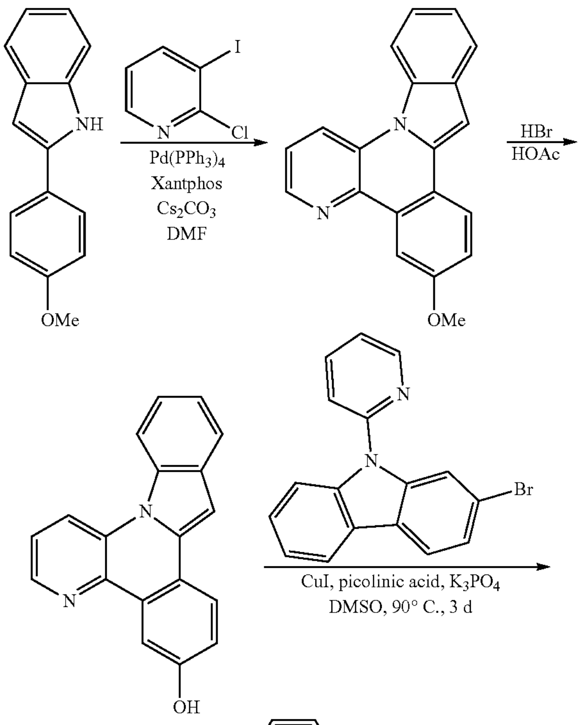

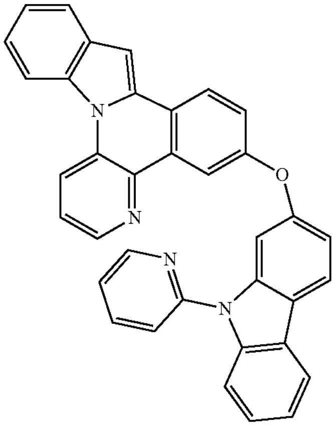

L83

Benzo[c]indolo[1,2-a][1,5]naphthyridin-6-ol (1 mmol, 1.0 eq), 2-bromo-9-(pyridin-2-yl)-9H-carbazole (388 mg, 1.2 mmol, 1.2 eq), CuI (38 mg, 0.2 mmol, 0.2 eq), picolinic acid (49 mg, 0.4 mmol, 0.4 eq) and $K_3PO_4$ (425 mg, 2 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 90° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate (2:1) as eluent to obtain the desired product ligand L83 as a white solid in 65% yield.

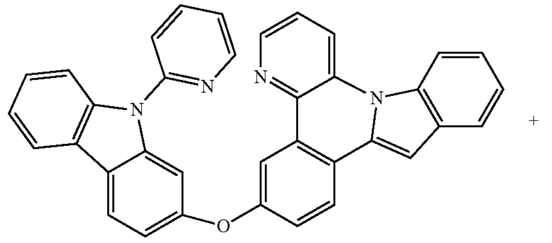

L83

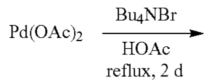

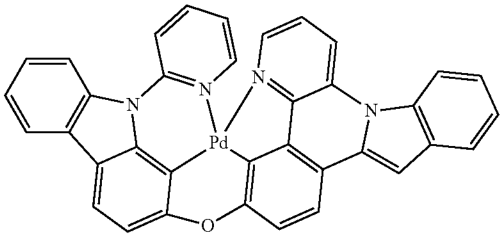

MC83

L83 (0.20 mmol, 1.0 eq), $Pd(OAc)_2$ (54 mg, 0.24 mmol, 1.2 eq) and $n\text{-}Bu_4NBr$ (6.5 mg, 0.02 mmol, 0.1 eq) were added to a dry pressure tube was then taken into a glove box and acetic acid (10 mL) was added. The mixture was bubbled with nitrogen for 30 minutes and then the tube was sealed. Then the mixture was heated to reflux in an oil bath and stirred for 2 days, cooled to ambient temperature and removed the solvent. Then the solid was purified through column chromatography on silica gel using dichloromethane as eluent to obtain to obtain the desired product MC83 as a white solid in 35% yield.

Example 84

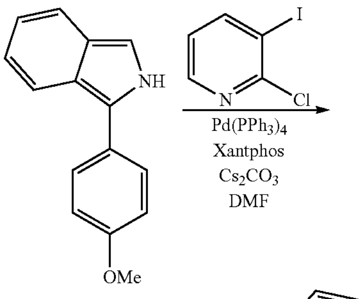

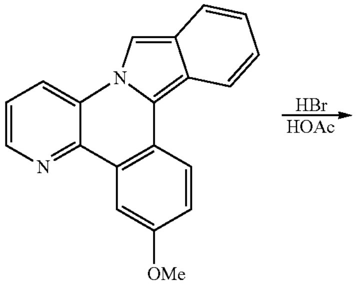

-continued

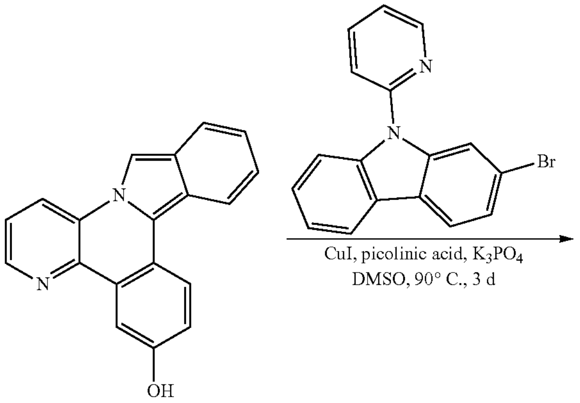

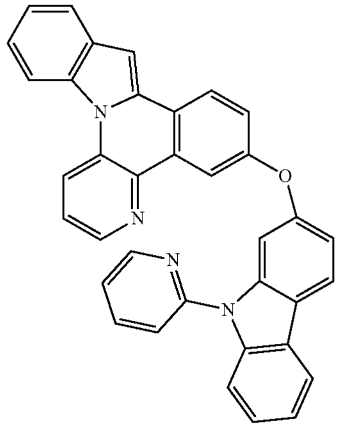

L84

Benzo[c]isoindolo[2,1-a][1,5]naphthyridin-6-ol (1 mmol, 1.0 eq), 2-bromo-9-(pyridin-2-yl)-9H-carbazole (388 mg, 1.2 mmol, 1.2 eq), CuI (38 mg, 0.2 mmol, 0.2 eq), picolinic acid (49 mg, 0.4 mmol, 0.4 eq) and $K_3PO_4$ (425 mg, 2 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 90° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate (2:1) as eluent to obtain the desired product ligand L84 as a white solid in 65% yield.

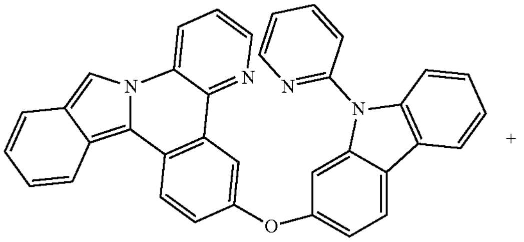

L84

-continued

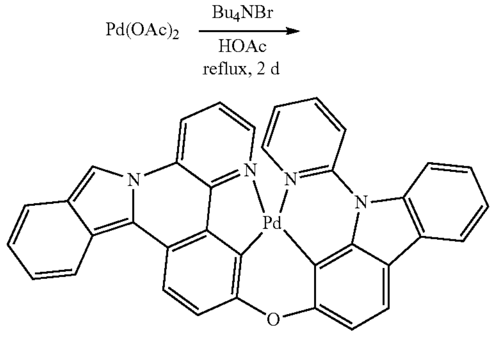

MC84

L84 (0.20 mmol, 1.0 eq), $Pd(OAc)_2$ (54 mg, 0.24 mmol, 1.2 eq) and n-$Bu_4NBr$ (6.5 mg, 0.02 mmol, 0.1 eq) were added to a dry pressure tube was then taken into a glove box and acetic acid (10 mL) was added. The mixture was bubbled with nitrogen for 30 minutes and then the tube was sealed. Then the mixture was heated to reflux in an oil bath and stirred for 2 days, cooled to ambient temperature and removed the solvent. Then the solid was purified through column chromatography on silica gel using dichloromethane as eluent to obtain to obtain the desired product MC84 as a white solid in 35% yield.

Example 85

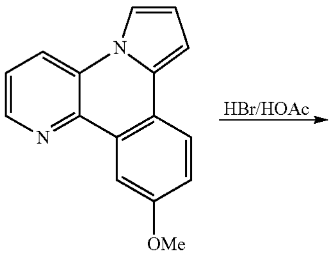

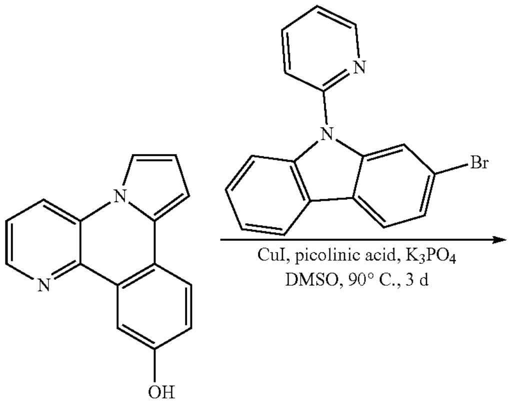

-continued

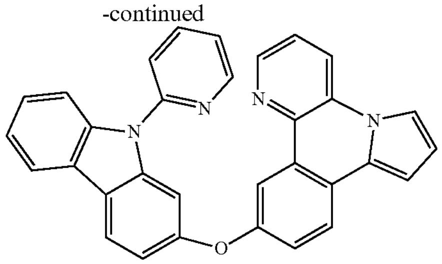

L85

Benzo[c]pyrrolo[1,2-a][1,5]naphthyridin-11-ol (1 mmol, 1.0 eq), 2-bromo-9-(pyridin-2-yl)-9H-carbazole (388 mg, 1.2 mmol, 1.2 eq), CuI (38 mg, 0.2 mmol, 0.2 eq), picolinic acid (49 mg, 0.4 mmol, 0.4 eq) and $K_3PO_4$ (425 mg, 2 mmol, 2.0 eq) were added to a thy Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 90° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate (2:1) as eluent to obtain the desired product ligand L85 as a white solid in 65% yield.

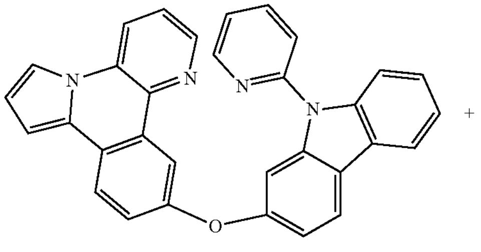

L85

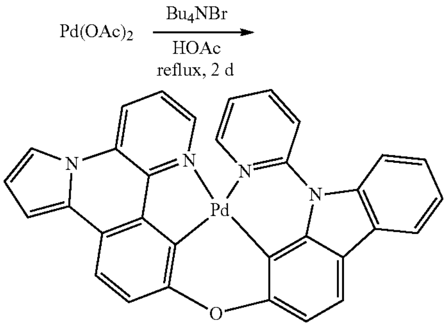

MC85

L85 (0.20 mmol, 1.0 eq), $Pd(OAc)_2$ (54 mg, 0.24 mmol, 1.2 eq) and n-$Bu_4NBr$ (6.5 mg, 0.02 mmol, 0.1 eq) were added to a dry pressure tube was then taken into a glove box and acetic acid (10 mL) was added. The mixture was bubbled with nitrogen for 30 minutes and then the tube was sealed. Then the mixture was heated to reflux in an oil bath and stirred for 2 days, cooled to ambient temperature and removed the solvent. Then the solid was purified through column chromatography on silica gel using dichloromethane as eluent to obtain to obtain the desired product MC85 as a white solid in 35% yield.

Example 86

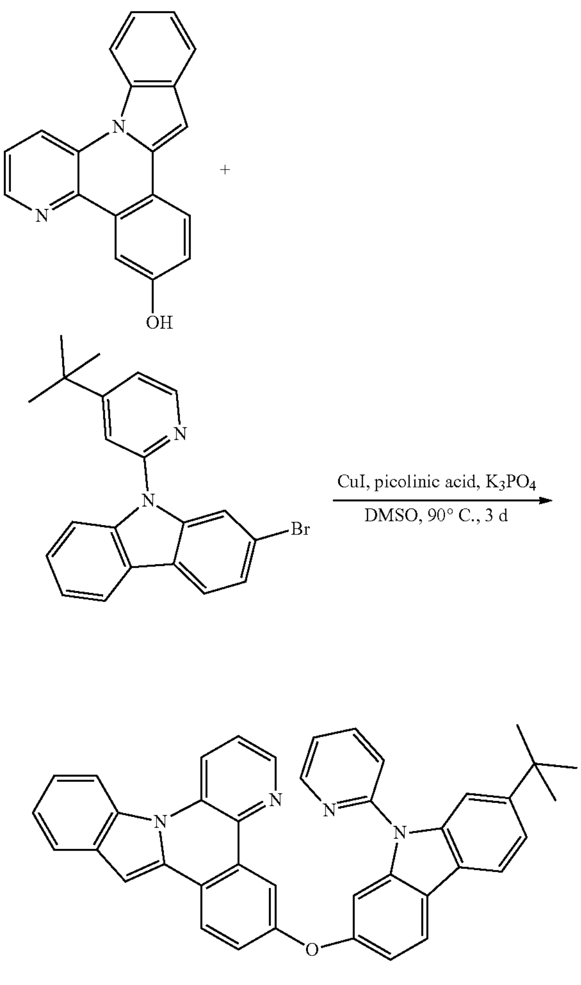

L86

Benzo[c]indolo[1,2-a][1,5]naphthyridin-6-ol (1 mmol, 1.0 eq), 2-bromo-9-(4-(tert-butyl)pyridin-2-yl)-9H-carbazole (1.2 mmol, 1.2 eq), CuI (38 mg, 0.2 mmol 0.2 eq), picolinic acid (49 mg, 0.4 mmol, 0.4 eq) and $K_3PO_4$ (425 mg, 2 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 90° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate (2:1) as eluent to obtain the desired product ligand L86 as a white solid in 65% yield.

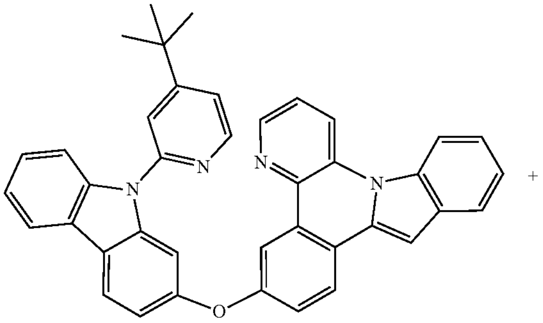

L86

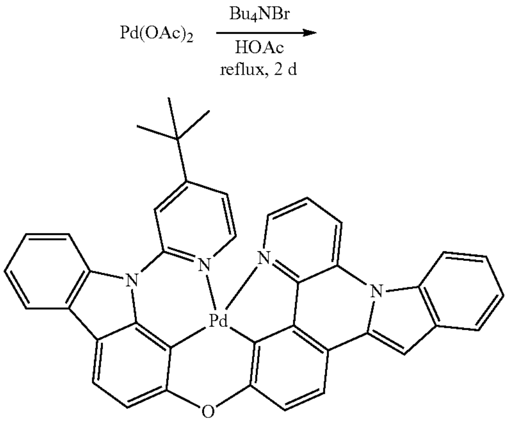

MC86

L86 (0.20 mmol, 1.0 eq), $Pd(OAc)_2$ (54 mg, 0.24 mmol, 1.2 eq) and n-$Bu_4NBr$ (6.5 mg, 0.02 mmol, eq) were added to a dry pressure tube was then taken into a glove box and acetic acid (10 mL) was added. The mixture was bubbled with nitrogen for 30 minutes and then the tube was sealed. Then the mixture was heated to reflux in an oil bath and stirred for 2 days, cooled to ambient temperature and removed the solvent. Then the solid was purified through column chromatography on silica gel using dichloromethane as eluent to obtain to obtain the desired product MC86 as a white solid in 35% yield.

Example 87

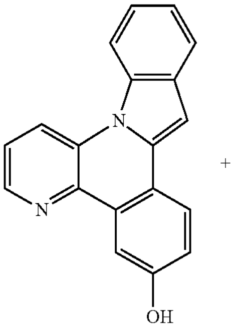

-continued

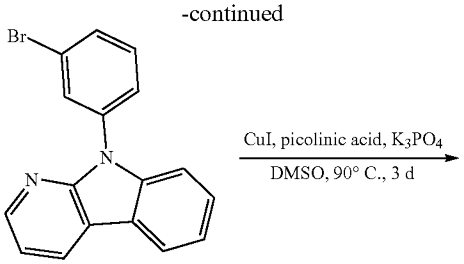

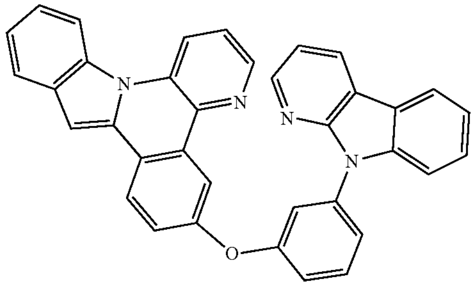

L87

Benzo[c]indolo[1,2-a][1,5]naphthyridin-6-ol (1 mmol, 1.0 eq), 9-(3-bromophenyl)-9H-pyrido[2,3-b]indole (388 mg, 1.2 mmol, 1.2 eq), CuI (38 mg, 0.2 mmol, 0.2 eq), picolinic acid (49 mg, 0.4 mmol 0.4 eq) and $K_4PO_4$ (425 mg, 2 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 90° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate (2:1) as eluent to obtain the desired product ligand L87 as a white solid in 65% yield.

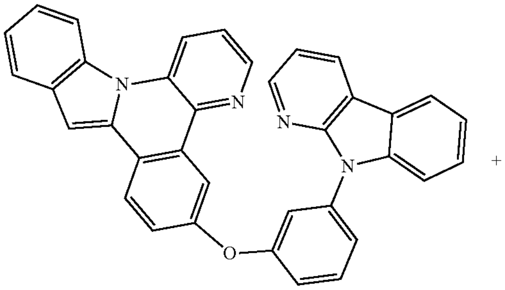

L87

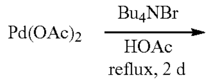

-continued

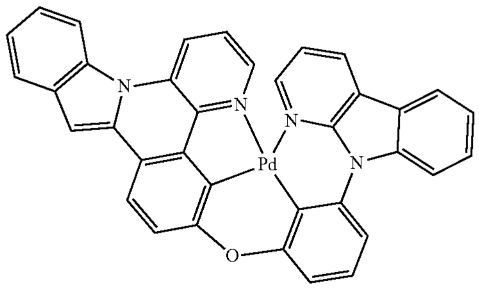

MC87

L87 (0.20 mmol, 1.0 eq), $Pd(OAc)_2$ (54 mg, 0.24 mmol, 1.2 eq) and n-$Bu_4NBr$ (6.5 mg, 0.02 mmol, 0.1 eq) were added to a dry pressure tube was then taken into a glove box and acetic acid (10 mL) was added. The mixture was bubbled with nitrogen for 30 minutes and then the tube was sealed. Then the mixture was heated to reflux in an oil bath and stirred for 2 days, cooled to ambient temperature and removed the solvent. Then the solid was purified through column chromatography on silica gel using dichloromethane as eluent to obtain to obtain the desired product MC87 as a white solid in 350 yield.

Example 88

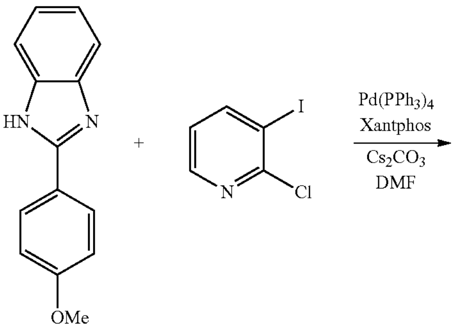

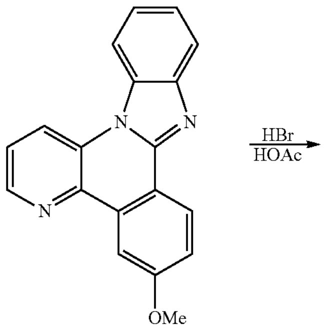

-continued

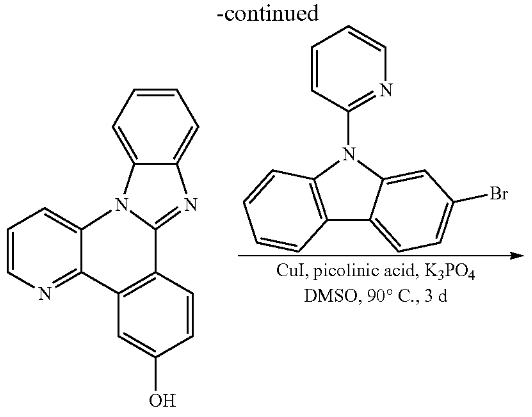

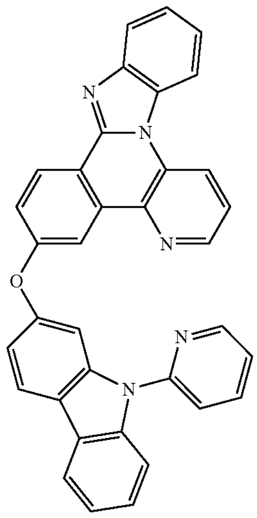

L88

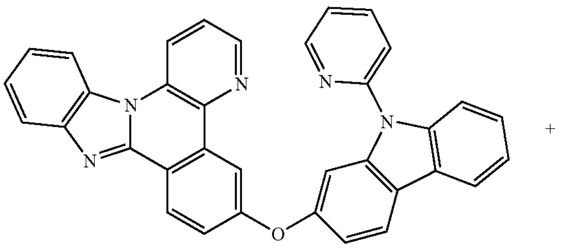

L88

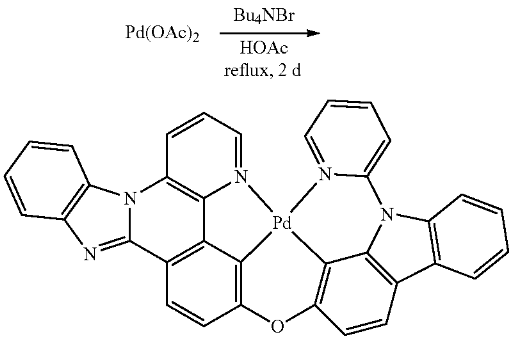

MC88

Benzo[c]benzo[4,5]imidazo[1,2-a][1,5]naphthyridin-6-ol (114 mg, 0.4 mmol, 1.0 eq), 2-bromo-9-(pyridin-2-yl)-9H-carbazole (156 mg, 0.48 mmol, 1.2 eq), CuI (15 mg, 0.08 mmol, 0.2 eq), picolinic acid (10 mg, 0.08 mmol, 0.2 eq) and $K_3PO_4$ (170 mg, 0.8 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (5 mL) was added under the protection of nitrogen. The mixture was stirred in an oil bath at a temperature of 90° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L88 as an orange yellow solid 92 mg in 44% yield.

L88 (52 mg, 0.09 mmol, 1.0 eq), $Pd(OAc)_2$ (23 mg, 0.10 mmol, 1.1 eq) and n-$Bu_4NBr$ (3 mg, 0.01 mmol, 0.1 eq) were added to a dry pressure tube, which was taken into a glove box and acetic acid (10 mL) was added. The mixture was bubbled with nitrogen for 30 minutes and then the tube was sealed. Then the mixture was heated to reflux in an oil bath and stirred for 2 days, cooled to ambient temperature and the solvent removed. Then the solid was purified through column chromatography on silica gel using dichloromethane as eluent to obtain the desired product MC88 in 10%~-50% yield.

Example 89

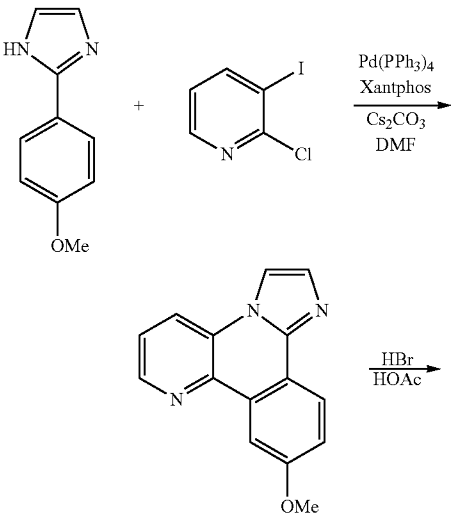

-continued

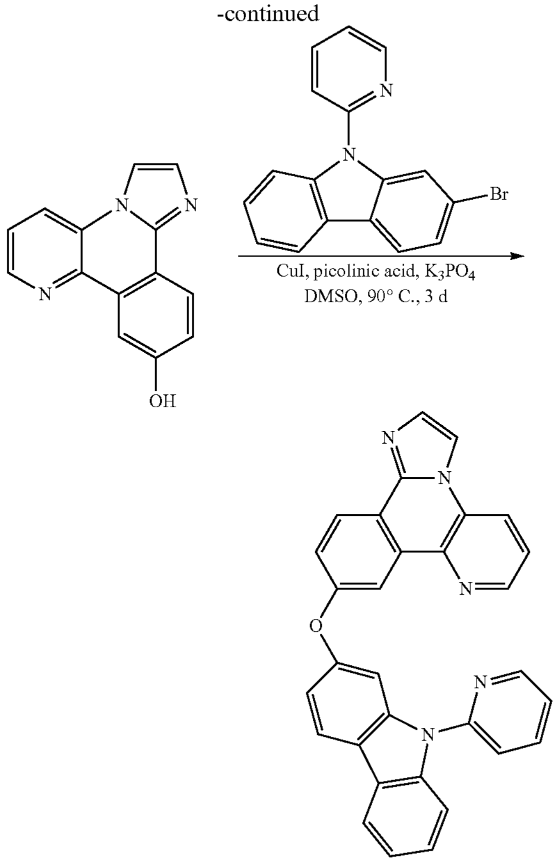

L89

Benzo[c]imidazo[1,2-a][1,5]naphthyridin-10-ol (0.4 mmol, 1.0 eq), 2-bromo-9-(pyridin-2-yl)-9H-carbazole (156 mg, 0.48 mmol, 1.2 eq), CuI (15 mg, 0.08 mmol, 0.2 eq), picolinic acid (10 mg, 0.08 mmol, 0.2 eq) and $K_3PO_4$ (170 mg 0.8 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (5 mL) was added under the protection of nitrogen. The mixture was stirred in an oil bath at a temperature of 90° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L89 in 30%~70% yield.

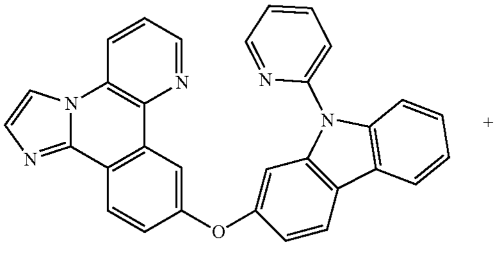

L89

-continued

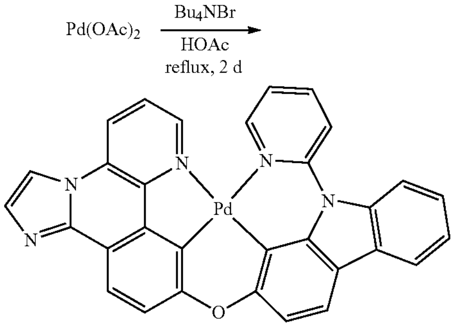

MC89

L89 (0.09 mmol, 1.0 eq), $Pd(OAc)_2$ (23 mg, 0.10 mmol, 1.1 eq) and n-$Bu_4NBr$ (3 mg, 0.01 mmol, 0.1 eq) were added to a dry pressure tube, which was taken into a glove box and acetic acid (10 mL) was added. The mixture was bubbled with nitrogen for 30 minutes and then the tube was sealed. Then the mixture was heated to reflux in an oil bath and stirred for 2 days, cooled to ambient temperature and the solvent removed. Then the solid was purified through column chromatography on silica gel using dichloromethane as eluent to obtain the desired product MC89 in 10%~50% yield.

Example 90

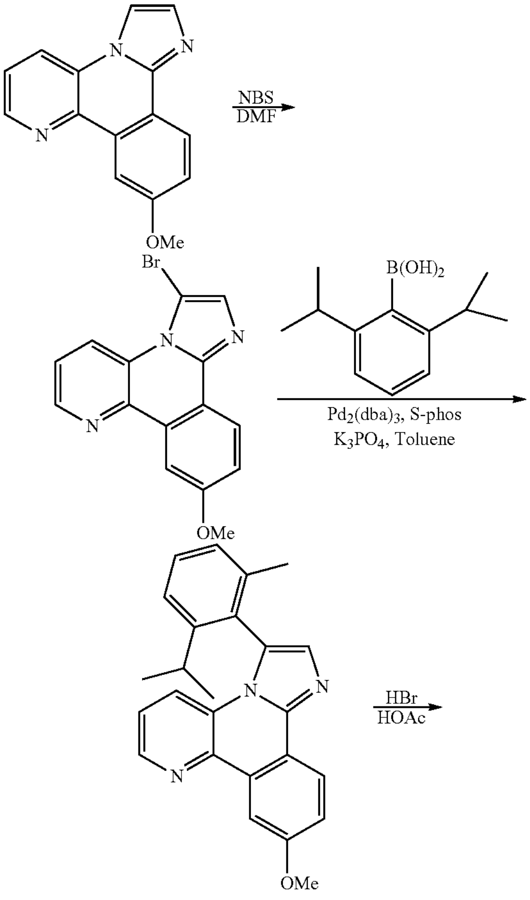

-continued

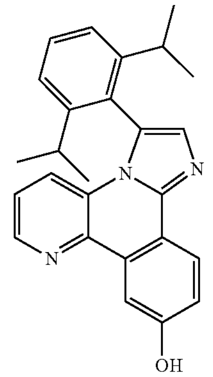

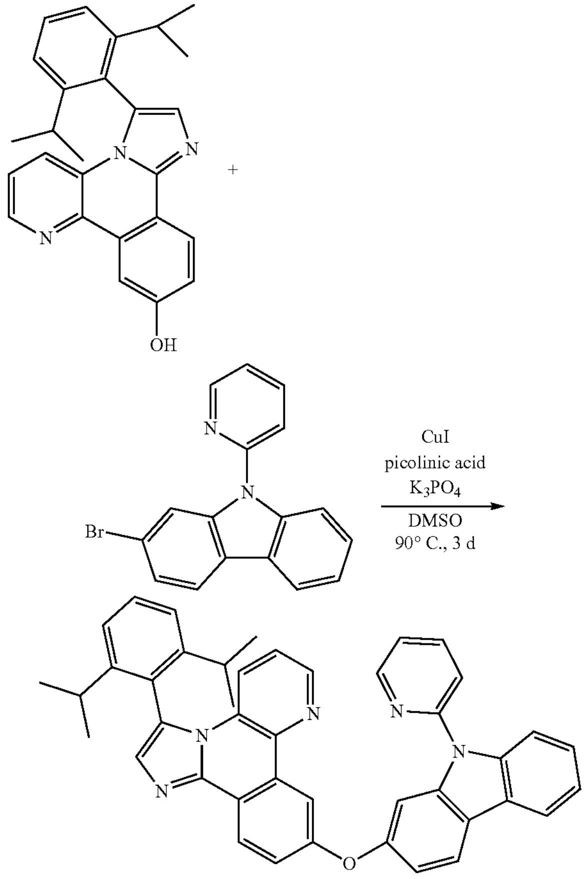

L90

3-(2,6-diisopropylphenyl)benzo[c]imidazo[1,2-a][1,5]naphthyridin-10-ol (0.4 mmol, 1.0 eq), 2-bromo-9-(pyridin-2-yl)-9H-carbazole (156 mg, 0.48 mmol, 1.2 eq), CuI (15 mg, 0.08 mmol, 0.2 eq), picolinic acid (10 mg, 0.08 mmol, 0.2 eq) and $K_3PO_4$ (170 mg, 0.8 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (5 mL) was added wider the protection of nitrogen. The mixture was stirred in an oil bath at a temperature of 90° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L90 in 30%~70% yield.

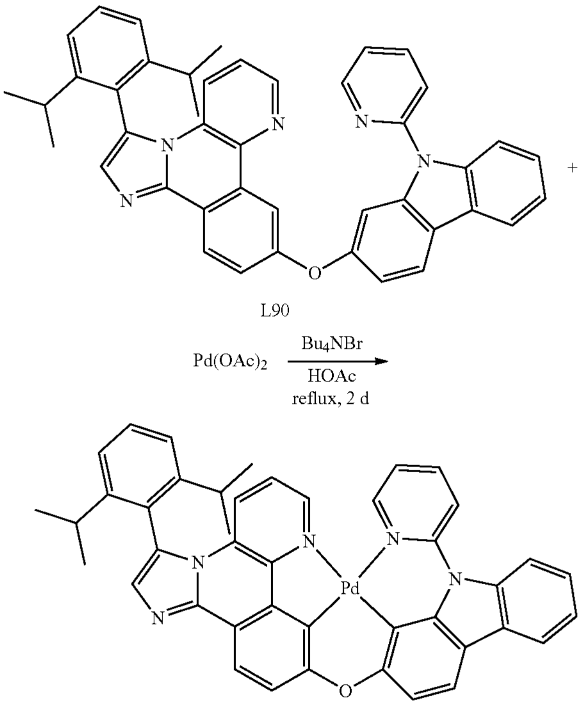

MC90

L90 (0.09 mmol, 1.0 eq), $Pd(OAc)_2$ (23 mg, 0.10 mmol, 1.1 eq) and n-$Bu_4NBr$ (3 mg, 0.01 mmol, 0.1 eq) were added to a dry pressure tube, which was taken into a glove box and acetic acid (10 mL) was added. The mixture was bubbled with nitrogen for 30 minutes and then the tube was sealed. Then the mixture was heated to reflux in an oil bath and stirred for 2 days, cooled to ambient temperature and the solvent removed. Then the solid was purified through column chromatography on silica gel using dichloromethane as eluent to obtain the desired product MC90 in 10%~50% yield.

Example 91

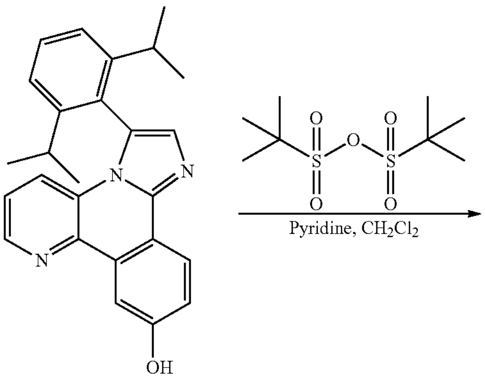

-continued

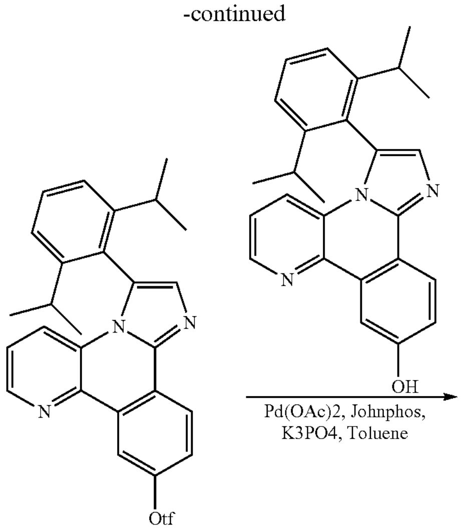

Otf-91

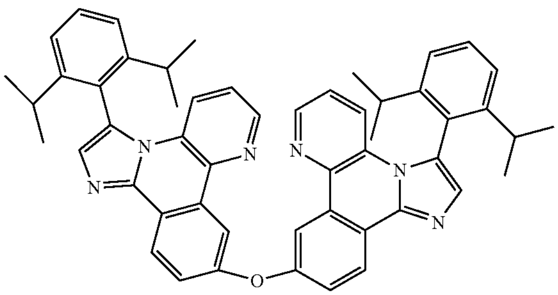

L91

Otf-91 (0.85 mmol, 1.0 eq), 3-(2,6-diisopropylphenyl) benzo[c]imidazo[1,2-a][1,5]naphthyridin-10-ol (1.10 mmol, 1.3 eq), CuI (32 mg, 0.17 mmol, 0.2 eq), picolinic acid (21 mg, 0.17 mmol, 0.2 eq) and $K_3PO_4$ (356 mg, 1.7 mmol, 2.0 eq) were added to a dry Shlenck tube equipped with a magnetic stir bar. The tube was evacuated and backfilled with nitrogen. The evacuation and backfill procedure was repeated for a total of three times. Then solvent DMSO (10 mL) was added under the protection of nitrogen. The mixture was stirred in an oil bath at a temperature of 90° C. for 3 days and then cooled down to ambient temperature, diluted with ethyl acetate. The mixture was washed with water three times and then dried over sodium sulfate and filtered. The solvent was removed under reduced pressure, and the residue was purified through column chromatography on silica gel using hexane/ethyl acetate as eluent to obtain the desired product ligand L91 in 30%~70% yield.

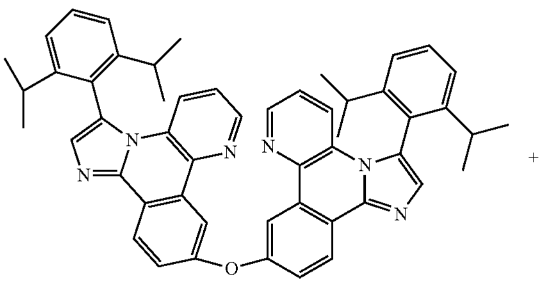

L91

-continued

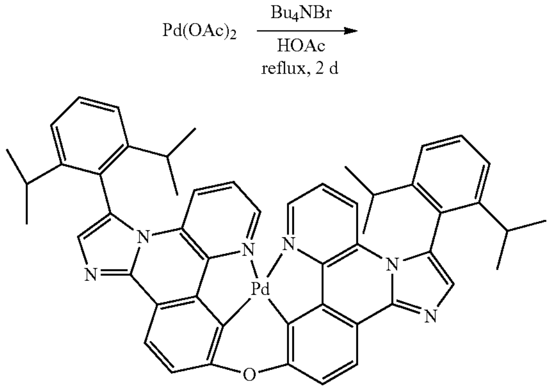

MC91

L91 (0.11 mmol, 1.0 eq), $K_2PtCl_4$ (48 mg, 0.12 mmol, 1.1 eq) and n-$Bu_4NBr$ (3 mg, 0.011 mmol, 0.1 eq) were added to a dry pressure tube, which was taken into a glove box and acetic acid (7 mL) was added. The mixture was bubbled with nitrogen for 30 minutes and then the tube was sealed. Then the mixture was heated to reflux in an oil bath and stirred for 3 days, cooled to ambient temperature and the solvent removed. Then the solid was purified through column chromatography on silica gel using dichloromethane as eluent to obtain the desired product MC91 in 10%~50% yield.

Examples of General Formulas XIV-XVII

Example 92

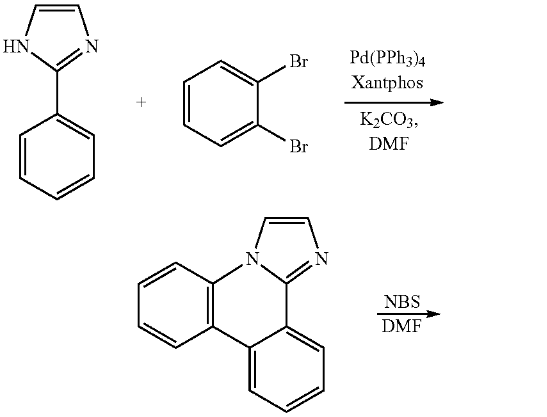

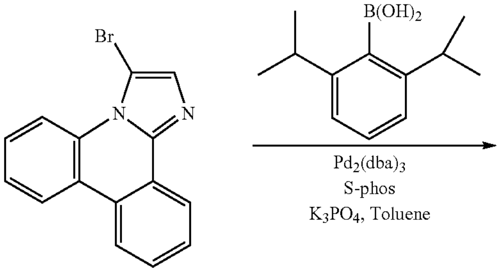

-continued

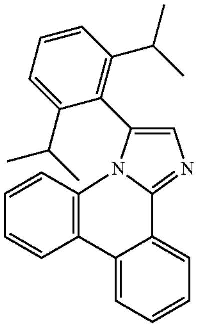

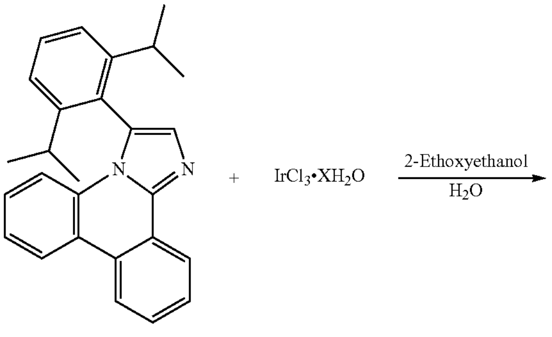

IrL1

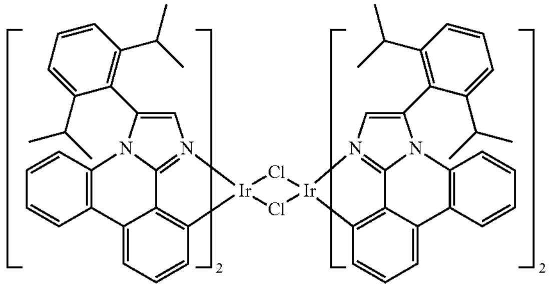

D1

IrL1 (2.2 mmol, 2.2 eq) and $IrCl_3.XH_2O$ (1.0 mmol, 1.0 eq) were added to a dry Shlenck tube equipped with a magnetic stir bar. The tube was evacuated and backfilled with nitrogen. The evacuation and backfill procedure was repeated for a total of three times. Then 2-ethoxyethanol (30 mL) and $H_2O$ (10 mL) were added under the protection of nitrogen. The mixture was stirred in an oil bath at a temperature of 110° C. overnight and then cooled down to ambient temperature. The precipitate was filtered and washed with methanol several times to obtain the desired product chlorodimer D1 in 40%~80% yield.

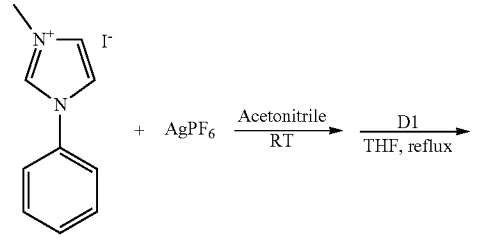

A1

-continued

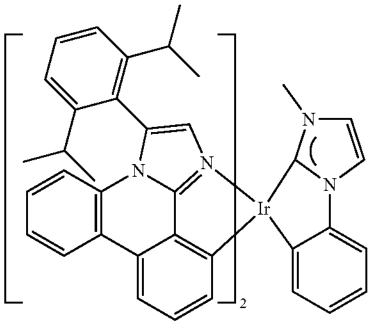

IrCl

A mixture of ancillary ligand A1 (1.5 mmol, 1.5 eq) and $AgPF_6$ (0.75 mmol, 0.75 eq) was stirred in a solution of 100 mL of acetonitrile at room temperature for 24 h. The solvent was evaporated to dryness under reduced pressure. Then chlorodimer D1 (1.0 mmol, 1.0 eq) and 150 mL of THF were added. The reaction mixture was heated to reflux for 24 h. Then the mixture was cooled to room temperature, and the precipitate was filtered off. The filtrate was evaporated to dryness under reduced pressure, and then purified by column chromatography to obtain the emitter IrCl in 20%~60% yield.

Example 93

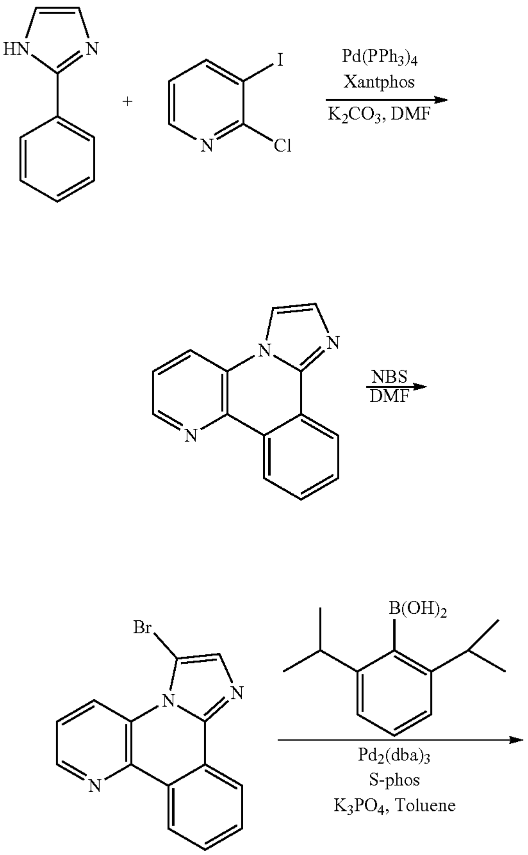

-continued

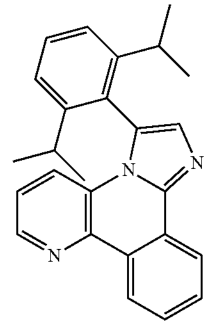

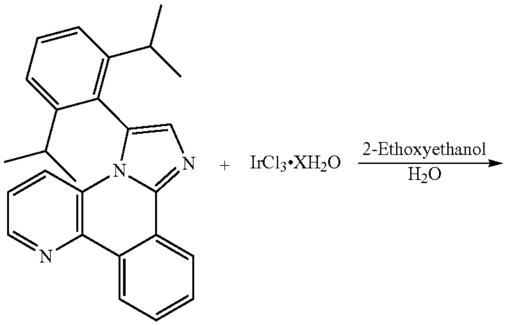

IrL2

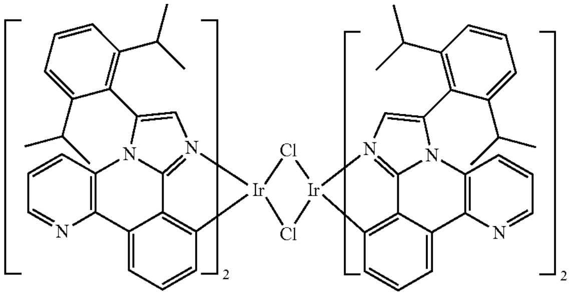

D2

IrL2 (2.2 mmol, 2.2 eq) and $IrCl_3.XH_2O$ (1.0 mmol, 1.0 eq) were added to a dry Shlenck tube equipped with a magnetic stir bar. The tube was evacuated and backfilled with nitrogen. The evacuation and backfill procedure was repeated for a total of three times. Then 2-ethoxyethanol (30 mL) and $H_2O$ (10 mL) were added under the protection of nitrogen. The mixture was stirred in an oil bath at a temperature of 110° C. overnight and then cooled down to ambient temperature. The precipitate was filtered and washed with methanol several times to obtain the desired product chlorodimer D2 in 40%~80% yield.

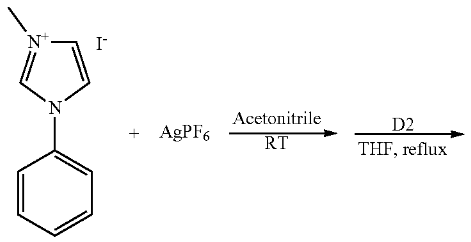

A1

-continued

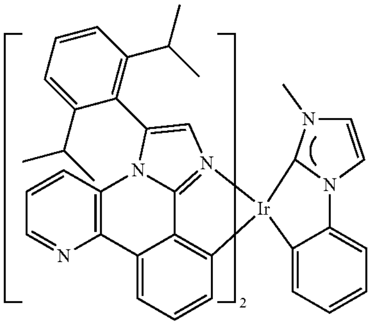

IrC2

A mixture of ancillary ligand A1 (1.5 mmol, 1.5 eq) and $AgPF_6$ (0.75 mmol, 0.75 eq) was stirred in a solution of 100 mL of acetonitrile at room temperature for 24 h. The solvent was evaporated to dryness under reduced pressure. Then chlorodimer D2 (1.0 mmol, 1.0 eq) and 150 mL of THF were added. The reaction mixture was heated to reflux for 24 h. Then the mixture was cooled to room temperature, and the precipitate was filtered off. The filtrate was evaporated to dryness wider reduced pressure, and then purified by column chromatography to obtain the emitter IrC2 in 20%~60% yield.

Example 94

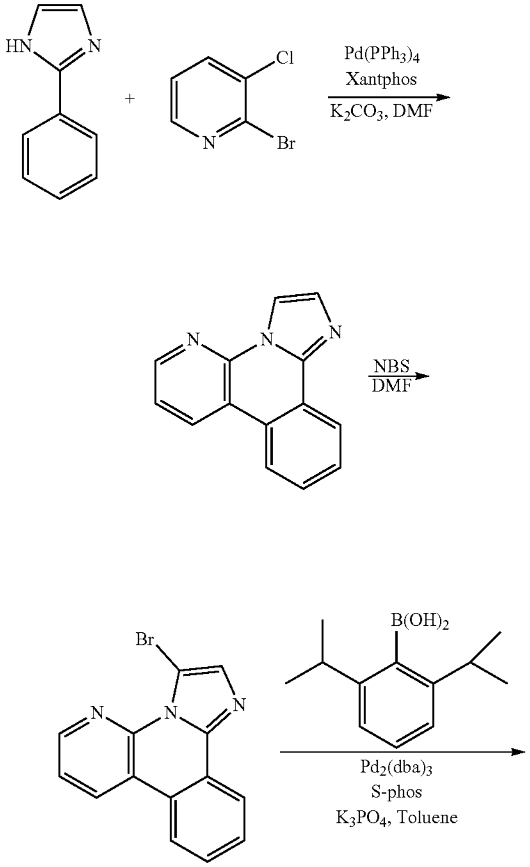

-continued

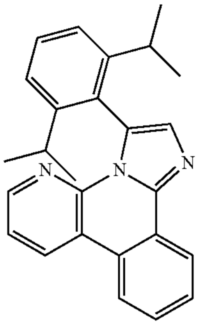

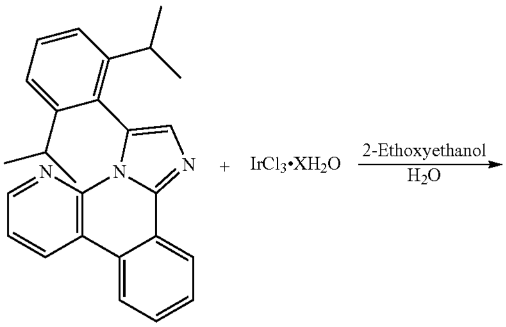

IrL3

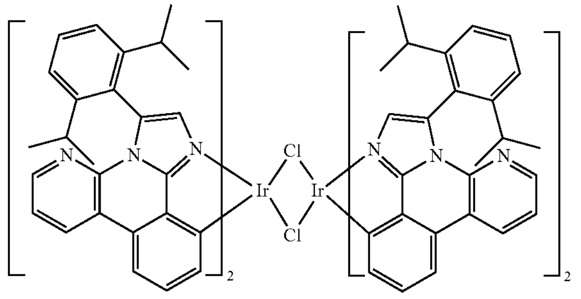

D3

IrL3 (2.2 mmol, 2.2 eq) and $IrCl_3.XH_2O$ (1.0 mmol, 1.0 eq) were added to a dry Shlenck tube equipped with a magnetic stir bar. The tube was evacuated and backfilled with nitrogen. The evacuation and backfill procedure was repeated for a total of three times. Then 2-ethoxyethanol (30 mL) and $H_2O$ (10 mL) were added under the protection of nitrogen. The mixture was stirred in an oil bath at a temperature of 110° C. overnight and then cooled down to ambient temperature. The precipitate was filtered and washed with methanol several times to obtain the desired product chlorodimer D3 in 40%~80% yield.

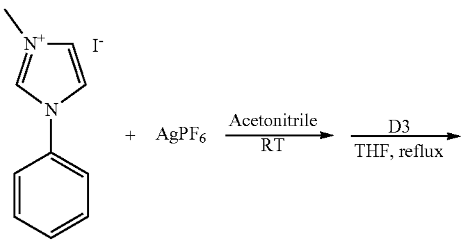

A1

-continued

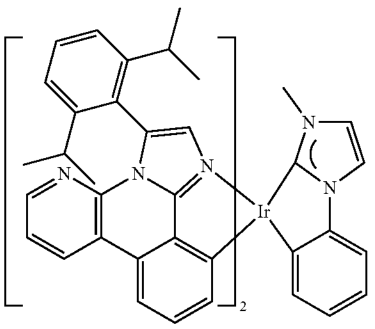

IrC3

A mixture of ancillary ligand A1 (1.5 mmol, 1.5 eq) and $AgPF_6$ (0.75 mmol 0.75 eq) was stirred in a solution of 100 mL of acetonitrile at room temperature for 24 h. The solvent was evaporated to dryness under reduced pressure. Then chlorodimer D3 (1.0 mmol, 1.0 eq) and 150 mL of THF were added. The reaction mixture was heated to reflux for 24 h. Then the mixture was cooled to room temperature, and the precipitate was filtered off. The filtrate was evaporated to dryness under reduced pressure, and then purified by column chromatography to obtain the emitter IrC3 in 20%~60% yield.

Example 95

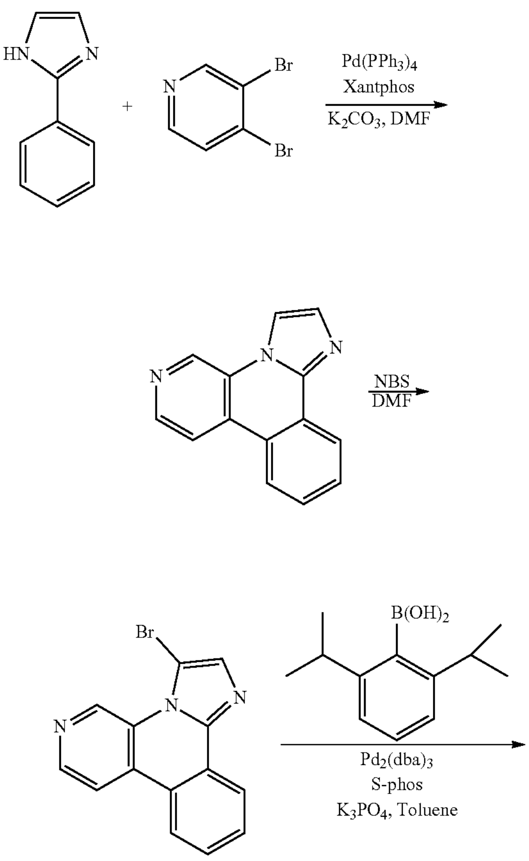

-continued

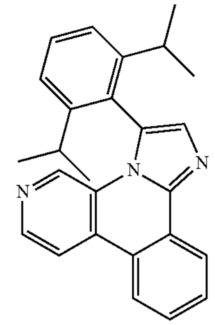

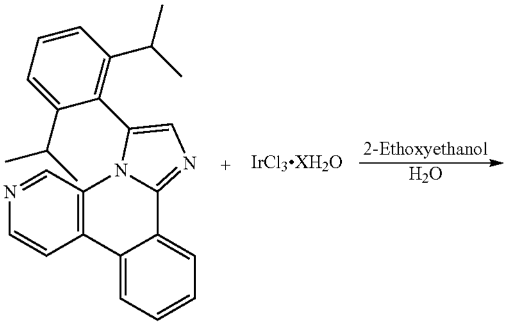

IrL4

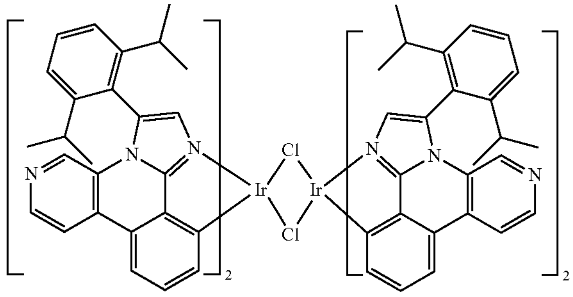

D4

IrL4 (2.2 mmol, 2.2 eq) and $IrCl_3.XH_2O$ (1.0 mmol, 1.0 eq) were added to a dry Shlenck tube equipped with a magnetic stir bar. The tube was evacuated and backfilled with nitrogen. The evacuation and backfill procedure was repeated for a total of three times. Then 2-ethoxyethanol (30 mL) and $H_2O$ (10 mL) were added under the protection of nitrogen. The mixture was stirred in an oil bath at a temperature of 110° C. overnight and then cooled down to ambient temperature. The precipitate was filtered and washed with methanol several times to obtain the desired product chlorodimer D4 in 40%~80% yield.

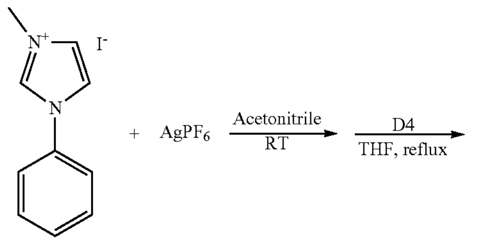

A1

-continued

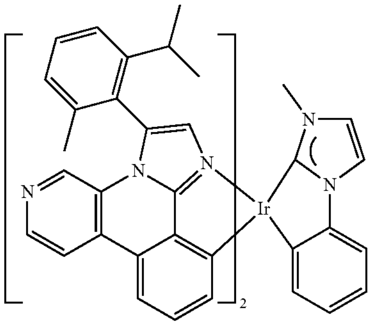

IrC4

A mixture of ancillary ligand A1 (1.5 mmol, 1.5 eq) and $AgPF_6$ (0.75 mmol, 0.75 eq) was stirred in a solution of 100 mL of acetonitrile at room temperature for 24 h. The solvent was evaporated to dryness under reduced pressure. Then chlorodimer D4 (1.0 mmol, 1.0 eq) and 150 ml, of THF were added. The reaction mixture was heated to reflux for 24 h. Then the mixture was cooled to room temperature, and the precipitate was filtered off. The filtrate was evaporated to dryness under reduced pressure, and then purified by column chromatography to obtain the emitter IrC4 in 20%~60% yield.

Example 96

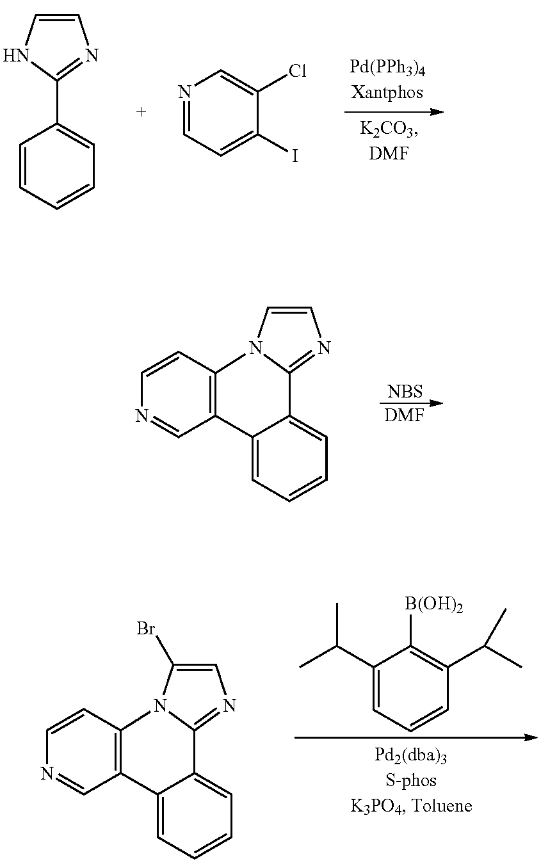

-continued

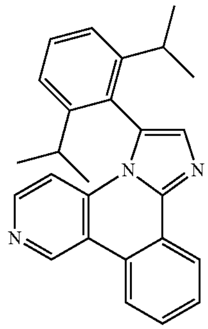

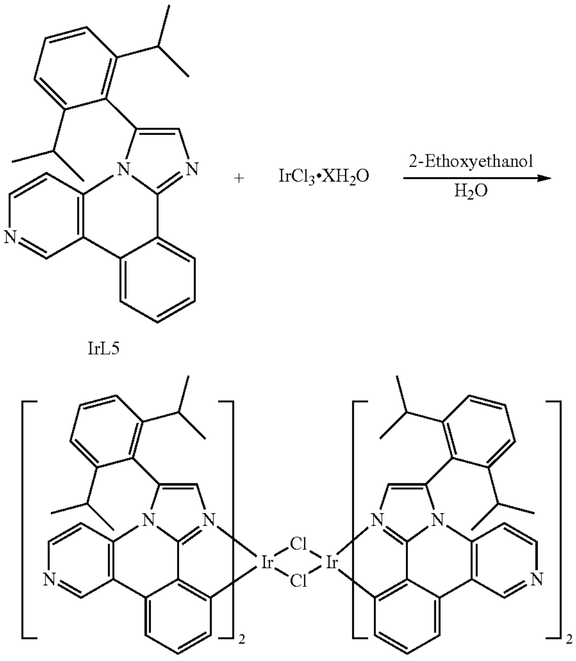

IrL5

D5

IrL5 (2.2 mmol, 2.2 eq) and $IrCl_3.XH_2O$ (1.0 mmol, 1.0 eq) were added to a dry Shlenck tube equipped with a magnetic stir bar. The tube was evacuated and backfilled with nitrogen. The evacuation and backfill procedure was repeated for a total of three times. Then 2-ethoxyethanol (30 mL) and $H_2O$ (10 mL) were added under the protection of nitrogen. The mixture was stirred in an oil bath at a temperature of 110° C. overnight and then cooled down to ambient temperature. The precipitate was filtered and washed with methanol several times to obtain the desired product chlorodimer D5 in 40%~80% yield.

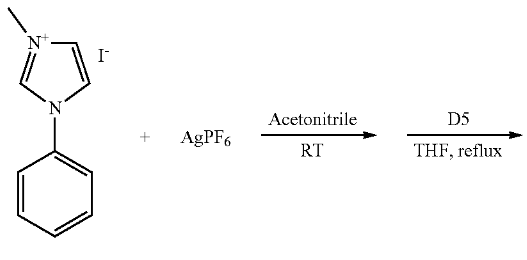

A1

-continued

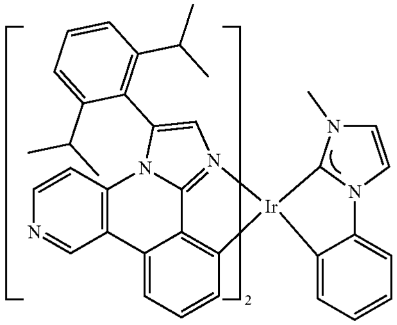

IrC5

A mixture of ancillary ligand A1 (1.5 mmol, 1.5 eq) and $AgPF_6$ (0.75 mmol, 0.75 eq) was stirred in a solution of 100 mL of acetonitrile at room temperature for 24 h. The solvent was evaporated to dryness under reduced pressure. Then chlorodimer D5 (1.0 mmol, 1.0 eq) and 150 mL of THF were added. The reaction mixture was heated to reflux for 24 h. Then the mixture was cooled to room temperature, and the precipitate was filtered off. The filtrate was evaporated to dryness under reduced pressure, and then purified by column chromatography to obtain the emitter IrC5 in 20%~60% yield.

Example 97

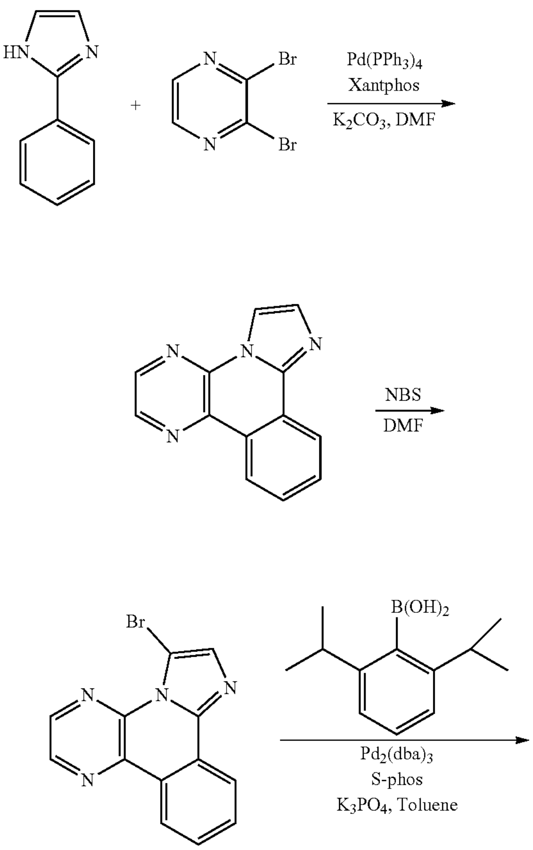

-continued

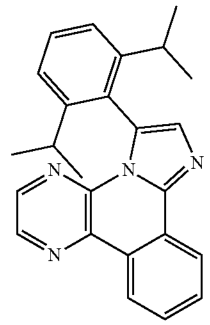

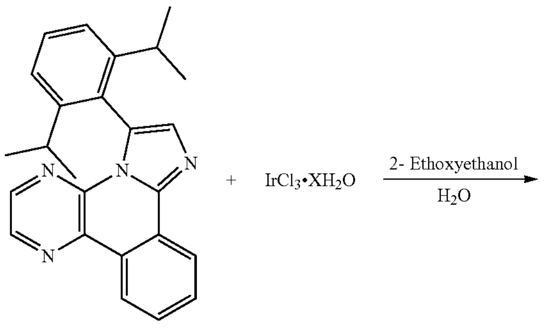

IrL6

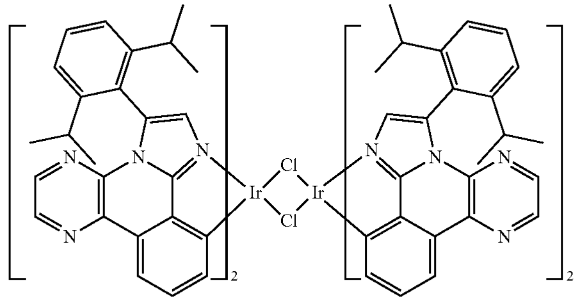

D6

IrL6 (2.2 mmol, 2.2 eq) and $IrCl_3.XH_2O$ (1.0 mmol, 1.0 eq) were added to a dry Shlenck tube equipped with a magnetic stir bar. The tube was evacuated and backfilled with nitrogen. The evacuation and backfill procedure was repeated for a total of three times. Then 2-ethoxyethanol (30 mL) and $H_2O$ (10 mL) were added under the protection of nitrogen. The mixture was stirred in an oil bath at a temperature of 110° C. overnight and then cooled down to ambient temperature. The precipitate was filtered and washed with methanol several times to obtain the desired product chlorodimer D6 in 40%~80% yield.

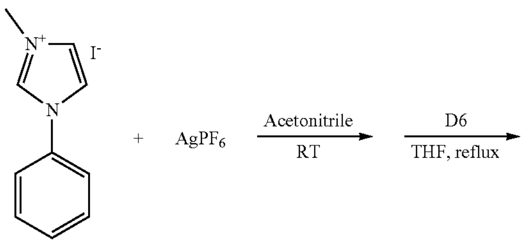

A1

-continued

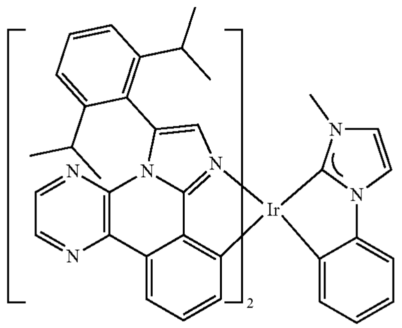

IrC6

A mixture of ancillary ligand A1 (1.5 mmol, 1.5 eq) and $AgPF_6$ (0.75 mmol, 0.75 eq) was stirred in a solution of 100 mL of acetonitrile at room temperature for 24 h. The solvent was evaporated to dryness under reduced pressure. Then chlorodimer D6 (1.0 mmol, 1.0 eq) and 150 mL of THF were added. The reaction mixture was heated to reflux for 24 h. Then the mixture was cooled to room temperature, and the precipitate was filtered off. The filtrate was evaporated to dryness wider reduced pressure, and then purified by column chromatography to obtain the emitter IrC6 in 20%~60% yield.

Example 98

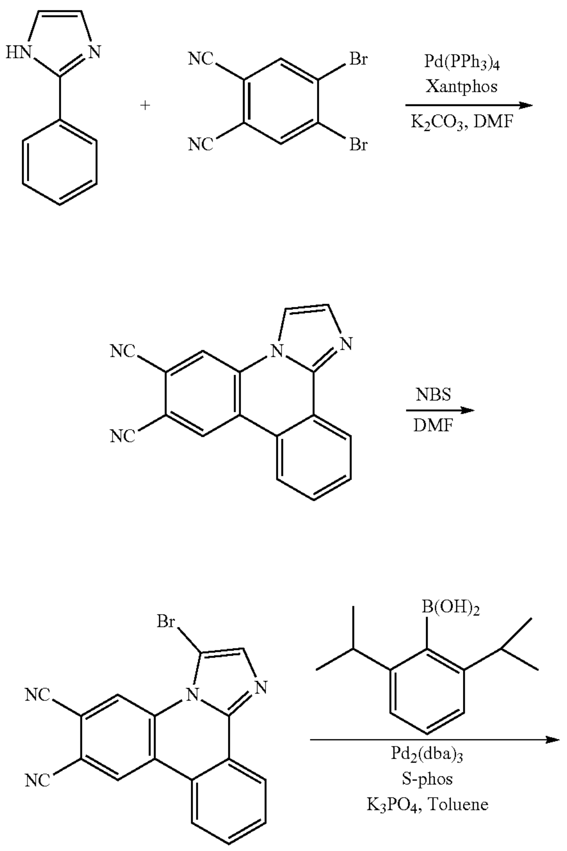

-continued

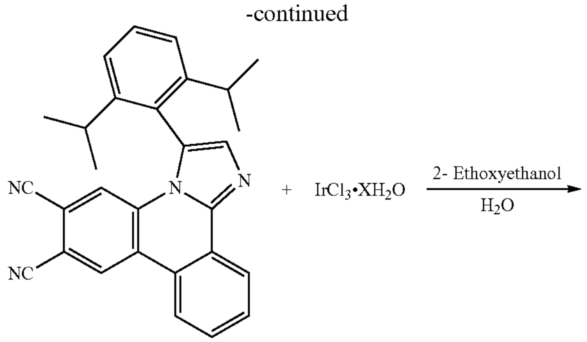

IrL7

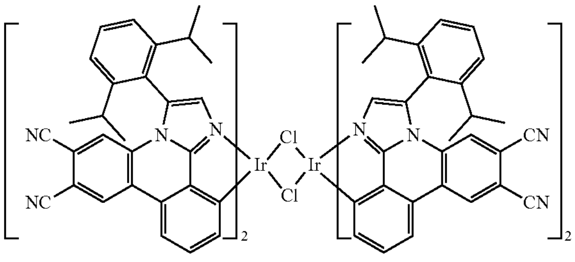

D7

IrL7 (2.2 mmol, 2.2 eq) and $IrCl_3$.$XH_2O$ (1.0 mmol, 1.0 eq) were added to a dry Shlenck tube equipped with a magnetic stir bar. The tube was evacuated and backfilled with nitrogen. The evacuation and backfill procedure was repeated for a total of three times. Then 2-ethoxyethanol (30 mL) and $H_2O$ (10 mL) were added under the protection of nitrogen. The mixture was stirred in an oil bath at a temperature of 110° C. overnight and then cooled down to ambient temperature. The precipitate was filtered and washed with methanol several times to obtain the desired product chlorodimer D7 in 40%~80% yield.

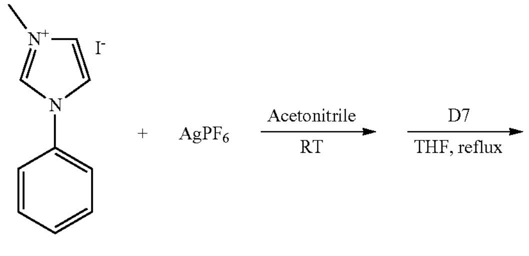

A1

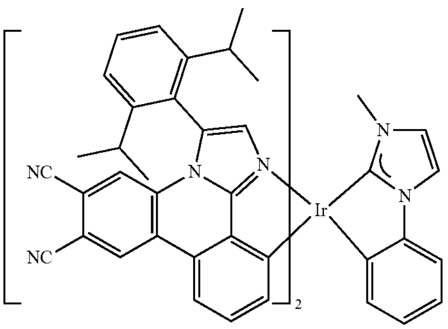

IrC7

A mixture of ancillary ligand A1 (1.5 mmol, 1.5 eq) and $AgPF_6$ (0.75 mmol, 0.75 eq) was stirred in a solution of 100 mL of acetonitrile at room temperature for 24 h. The solvent was evaporated to dryness under reduced pressure. Then chlorodimer D7 (1.0 mmol, 1.0 eq) and 150 mL of THF were added. The reaction mixture was heated to reflux for 24 h. Then the mixture was cooled to room temperature, and the precipitate was filtered off. The filtrate was evaporated to dryness under reduced pressure, and then purified by column chromatography to obtain the emitter IrC7 in 20%~60% yield.

Example 99

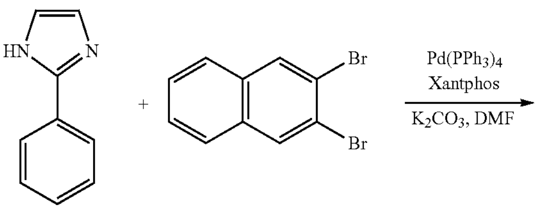

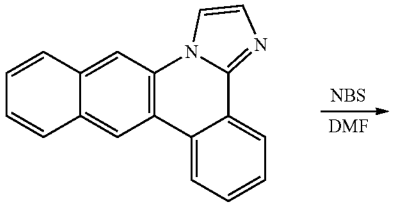

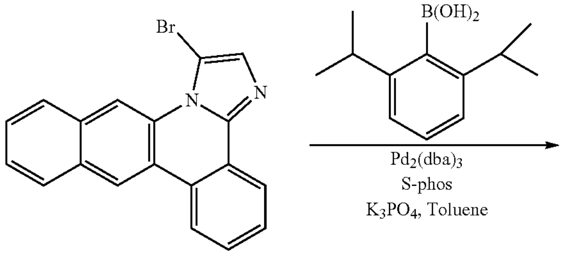

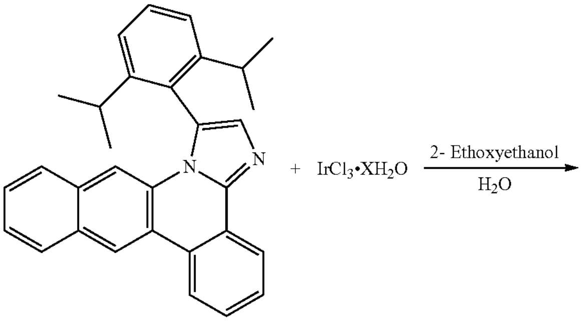

IrL8

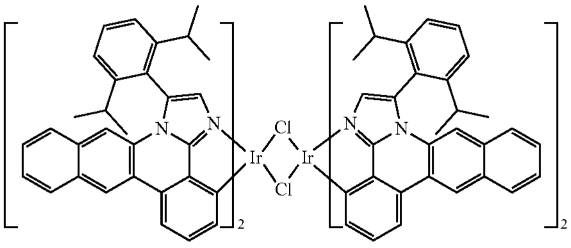

D8

IrL8 (2.2 mmol, 2.2 eq) and $IrCl_3.XH_2O$ (1.0 mmol, 1.0 eq) were added to a dry Shlenck tube equipped with a magnetic stir bar. The tube was evacuated and backfilled with nitrogen. The evacuation and backfill procedure was repeated for a total of three times. Then 2-ethoxyethanol (30 mL) and $H_2O$ (10 mL) were added under the protection of nitrogen. The mixture was stirred in an oil bath at a temperature of 110° C. overnight and then cooled down to ambient temperature. The precipitate was filtered and washed with methanol several times to obtain the desired product chlorodimer D8 in 40%~80% yield.

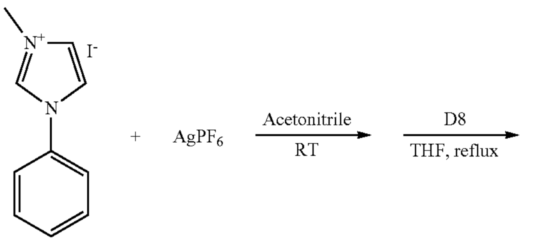

A1

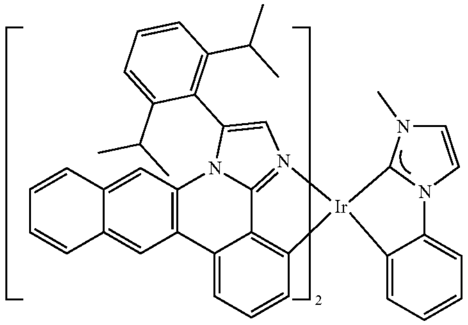

IrC8

A mixture of ancillary ligand A1 (1.5 mmol, 1.5 eq) and $AgPF_6$ (0.75 mmol, 0.75 eq) was stirred in a solution of 100 mL of acetonitrile at room temperature for 24 h. The solvent was evaporated to dryness under reduced pressure. Then chlorodimer D8 (1.0 mmol, 1.0 eq) and 150 mL of THF were added. The reaction mixture was heated to reflux for 24 h. Then the mixture was cooled to room temperature, and the precipitate was filtered off. The filtrate was evaporated to dryness under reduced pressure, and then purified by column chromatography to obtain the emitter IrC8 in 20%~60% yield.

Example 100

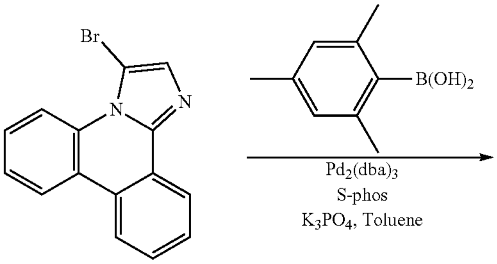

-continued

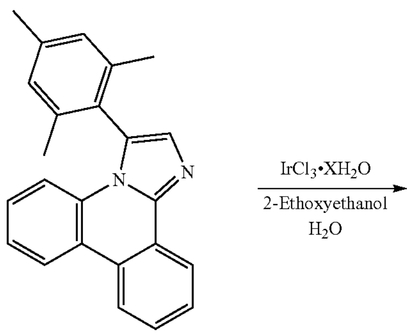

IrL9

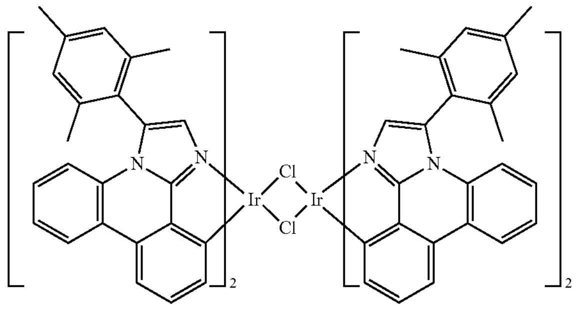

D9

IrL9 (2.2 mmol, 2.2 eq) and $IrCl_3.XH_2O$ (1.0 mmol, 1.0 eq) were added to a dry Shlenck tube equipped with a magnetic stir bar. The tube was evacuated and backfilled with nitrogen. The evacuation and backfill procedure was repeated for a total of three times. Then 2-ethoxyethanol (30 mL) and $H_2O$ (10 mL) were added under the protection of nitrogen. The mixture was stirred in an oil bath at a temperature of 110° C. overnight and then cooled down to ambient temperature. The precipitate was filtered and washed with methanol several times to obtain the desired product chlorodimer D9 in 40%~80% yield.

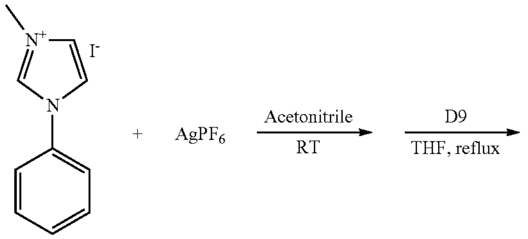

A1

-continued

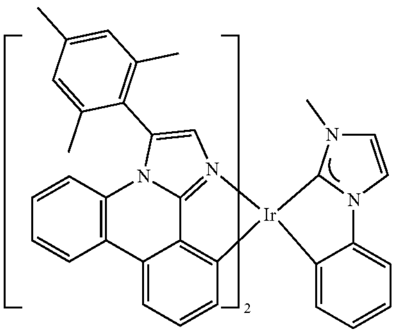

IrC9

A mixture of ancillary ligand A1 (1.5 mmol, 1.5 eq) and $AgPF_6$ (0.75 mmol, 0.75 eq) was stirred in a solution of 100 mL of acetonitrile at room temperature for 24 h. The solvent was evaporated to dryness under reduced pressure. Then chlorodimer D9 (1.0 mmol, 1.0 eq) and 150 mL of THF were added. The reaction mixture was heated to reflux for 24 h. Then the mixture was cooled to room temperature, and the precipitate was filtered off. The filtrate was evaporated to dryness under reduced pressure, and then purified by column chromatography to obtain the emitter IrC9 in 20%~60% yield.

Example 101

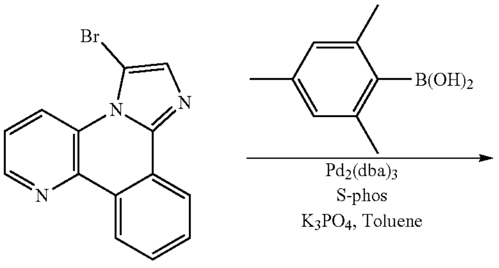

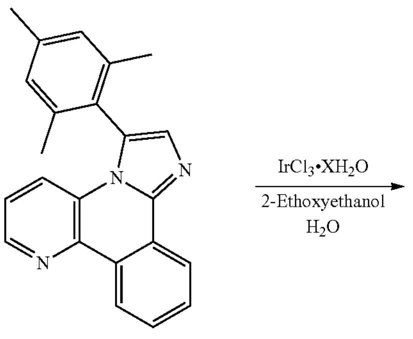

IrL10

-continued

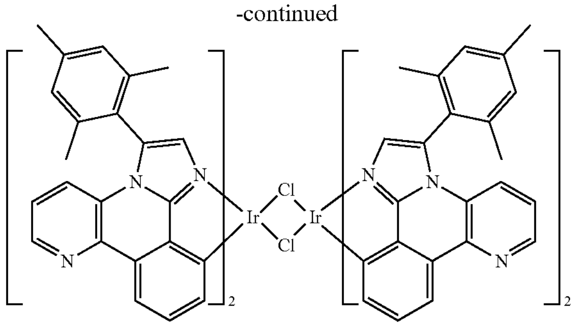

D10

IrL10 (2.2 mmol, 2.2 eq) and $IrCl_3.XH_2O$ (1.0 mmol, 1.0 eq) were added to a dry Shlenck tube equipped with a magnetic stir bar. The tube was evacuated and backfilled with nitrogen. The evacuation and backfill procedure was repeated for a total of three times. Then 2-ethoxyethanol (30 mL) and $H_2O$ (10 mL) were added under the protection of nitrogen. The mixture was stirred in an oil bath at a temperature of 110° C. overnight and then cooled down to ambient temperature. The precipitate was filtered and washed with methanol several times to obtain the desired product chlorodimer D10 in 40%~80% yield.

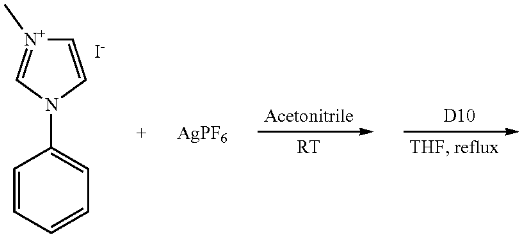

A1

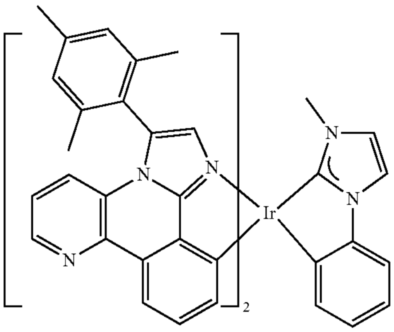

IrC10

A mixture of ancillary ligand A1 (1.5 mmol, 1.5 eq) and $AgPF_6$ (0.75 mmol, 0.75 eq) was stirred in a solution of 100 mL of acetonitrile at room temperature for 24 h. The solvent was evaporated to dryness under reduced pressure. Then chlorodimer D10 (1.0 mmol, 1.0 eq) and 1.50 ml, of THF were added. The reaction mixture was heated to reflux for 24 h. Then the mixture was cooled to room temperature, and the precipitate was filtered off. The filtrate was evaporated to dryness under reduced pressure, and then purified by column chromatography to obtain the emitter IrC10 in 20%~60% yield.

Example 102

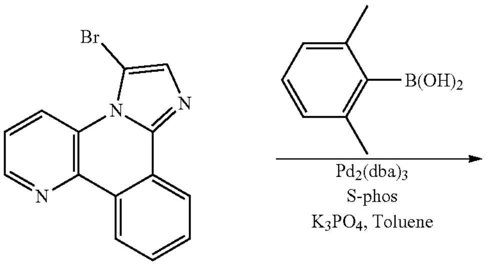

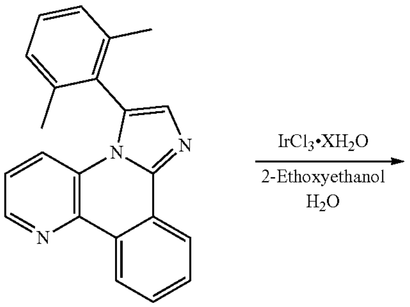

IrL11

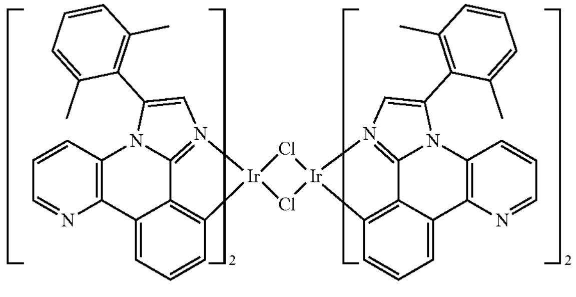

D11

IrL11 (2.2 mmol, 2.2 eq) and $IrCl_3.XH_2O$ (1.0 mmol, 1.0 eq) were added to a dry Shlenck tube equipped with a magnetic stir bar. The tube was evacuated and backfilled with nitrogen. The evacuation and backfill procedure was repeated for a total of three times. Then 2-ethoxyethanol (30 mL) and $H_2O$ (10 ml) were added under the protection of nitrogen. The mixture was stirred in an oil bath at a temperature of 110° C. overnight and then cooled down to ambient temperature. The precipitate was filtered and washed with methanol several times to obtain the desired product chlorodimer D11 in 40%~80% yield.

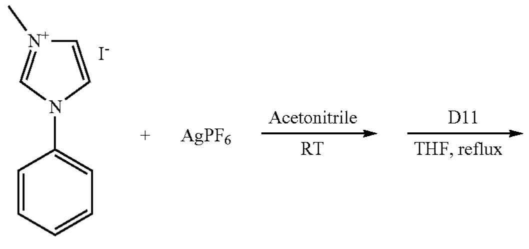

A1

-continued

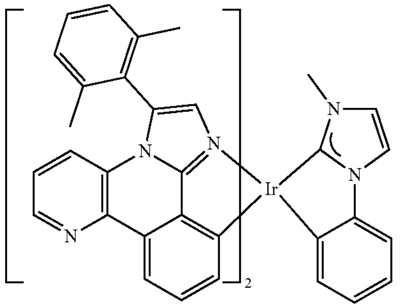

IrC11

A mixture of ancillary ligand A1 (1.5 mmol, 1.5 eq) and $AgPF_6$ (0.75 mmol, 0.75 eq) was stirred in a solution of 100 mL of acetonitrile at room temperature for 24 h. The solvent was evaporated to dryness under reduced pressure. Then chlorodimer D11 (1.0 mmol, 1.0 eq) and 150 mL of THF were added. The reaction mixture was heated to reflux for 24 h. Then the mixture was cooled to room temperature, and the precipitate was filtered off. The filtrate was evaporated to dryness under reduced pressure, and then purified by column chromatography to obtain the emitter IrC11 in 2%~60% yield.

Example 103

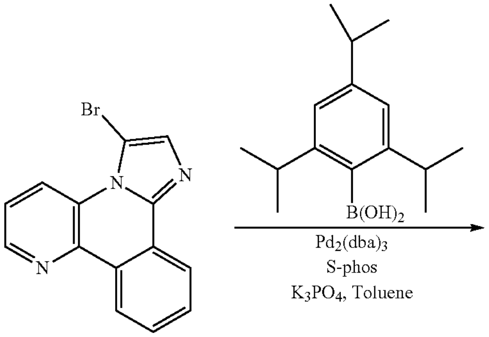

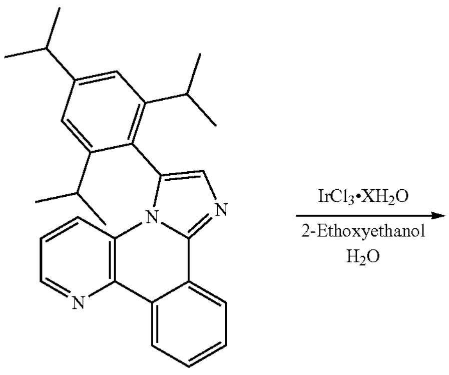

IrL12

-continued

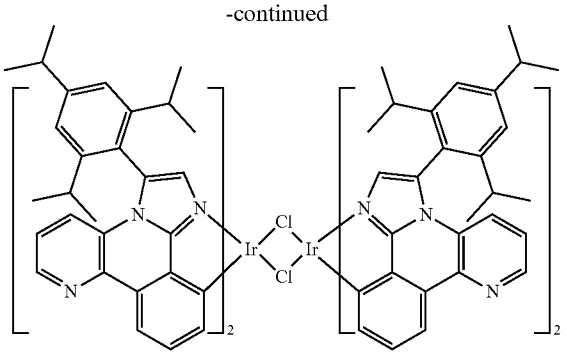

D12

IrL12 (2.2 mmol, 2.2 eq) and $IrCl_3.XH_2O$ (1.0 mmol, 1.0 eq) were added to a dry Shlenck tube equipped with a magnetic stir bar. The tube was evacuated and backfilled with nitrogen. The evacuation and backfill procedure was repeated for a total of three times. Then 2-ethoxyethanol (30 mL) and $H_2O$ (10 mL) were added under the protection of nitrogen. The mixture was stirred in an oil bath at a temperature of 110° C. overnight and then cooled down to ambient temperature. The precipitate was filtered and washed with methanol several times to obtain the desired product chlorodimer D12 in 40%~80% yield.

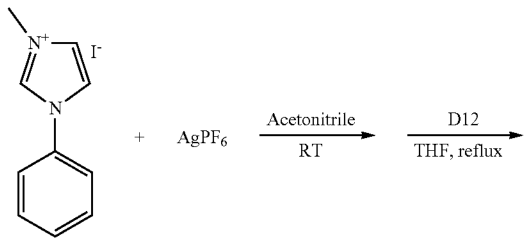

A1

-continued

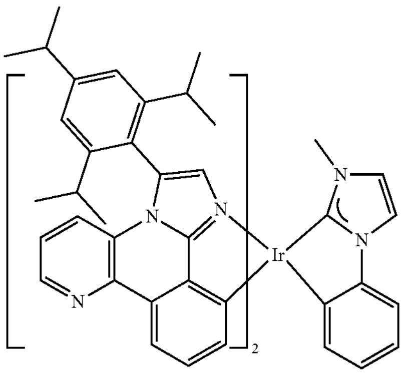

IrC12

A mixture of ancillary ligand A1 (1.5 mmol, 1.5 eq) and $AgPF_6$ (0.75 mmol, 0.75 eq) was stirred in a solution of 100 mL of acetonitrile at room temperature for 24 h. The solvent was evaporated to dryness under reduced pressure. Then chlorodimer D12 (1.0 mmol, 1.0 eq) and 150 ml, of THF were added. The reaction mixture was heated to reflux for 24 h. Then the mixture was cooled to room temperature, and the precipitate was filtered off. The filtrate was evaporated to dryness under reduced pressure, and then purified by column chromatography to obtain the emitter IrC12 in 20%~60% yield.

Example 104

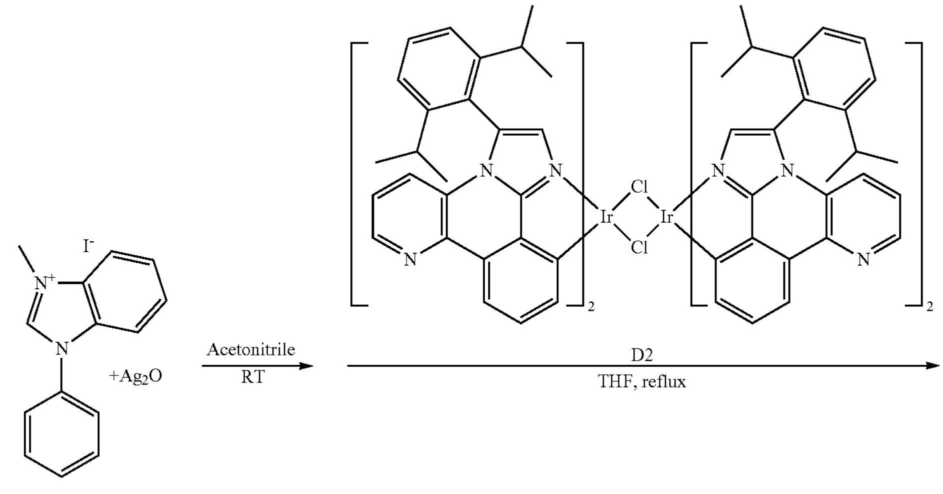

A2

-continued

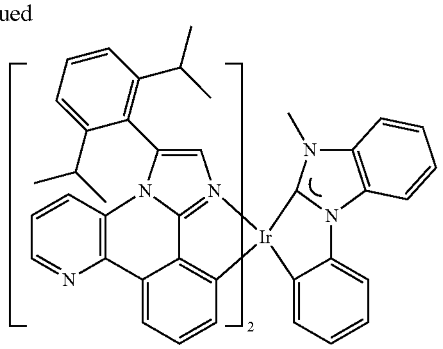

IrC13

A mixture of ancillary ligand A2 (1.5 mmol, 1.5 eq) and $AgPF_6$ (0.75 mmol, 0.75 eq) was stirred in a solution of 100 mL of acetonitrile at room temperature for 24 h. The solvent was evaporated to dryness under reduced pressure. Then chlorodimer D2 (1.0 mmol, 1.0 eq) and 150 mL of THF were added. The reaction mixture was heated to reflux for 24 h. Then the mixture was cooled to room temperature, and the precipitate was filtered off. The filtrate was evaporated to dryness under reduced pressure, and then purified by column chromatography to obtain the emitter IrC13 in 20%—60% yield.

Example 105

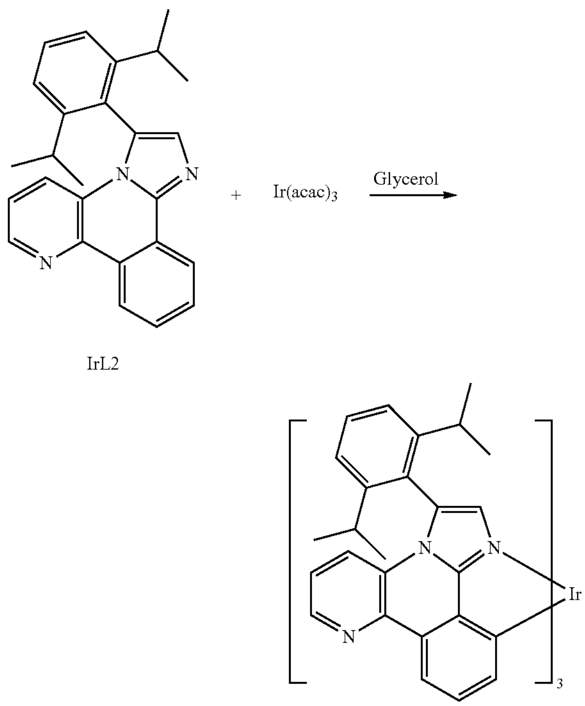

IrL2

IrC14

IrL2 (2.5 mmol, 5.0 eq) and $Ir(acac)_3$ (0.5 mmol, 1.0 eq) were added to a dry Shlenck tube equipped with a magnetic stir bar. The tube was evacuated and backfilled with nitrogen. The evacuation and backfill procedure was repeated for a total of three times. Then 45 mL of glycerol was added under the protection of nitrogen. The mixture was stirred in an oil bath at a temperature of 240° C. for 3 days. After the mixture was cooled down to ambient temperature, 150 mL of 1M HCl solution was added, and the product was thrice extracted with $CH_2Cl_2$. Then the organic extracts were combined, and dried with $MgSO_4$. The mixture was evaporated to dryness under reduced pressure, and then purified by column chromatography to obtain the emitter IrC14 in 5%~50% yield.

Example 106

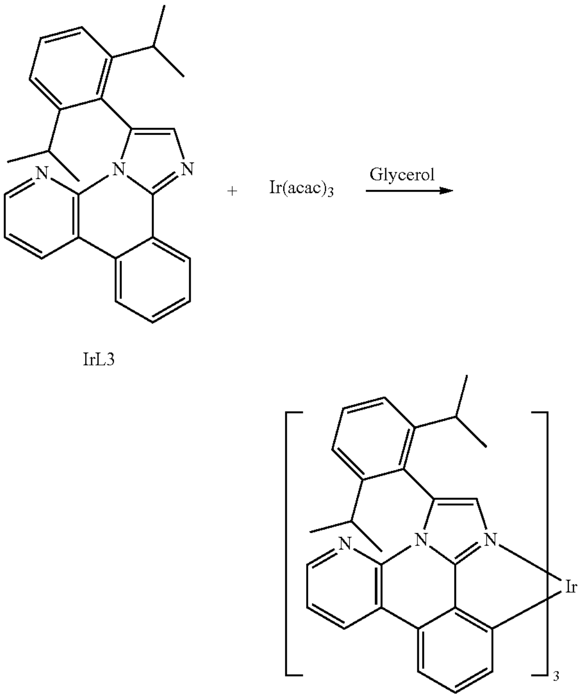

IrL3

IrC15

IrL3 (2.5 mmol, 5.0 eq) and $Ir(acac)_3$ (0.5 mmol, 1.0 eq) were added to a dry Shlenck tube equipped with a magnetic stir bar. The tube was evacuated and backfilled with nitrogen. The evacuation and backfill procedure was repeated for a total of three times. Then 45 mL of glycerol was added under the protection of nitrogen. The mixture was stirred in an oil bath at a temperature of 240° C. for 3 days. After the mixture was cooled down to ambient temperature, 150 mL of 1M HCl solution was added, and the product was thrice extracted with $CH_2Cl_2$. Then the organic extracts were combined, and dried with $MgSO_4$. The mixture was evaporated to dryness under reduced pressure, and then purified by column chromatography to obtain the emitter IrC15 in 5%~50% yield.

Example 107

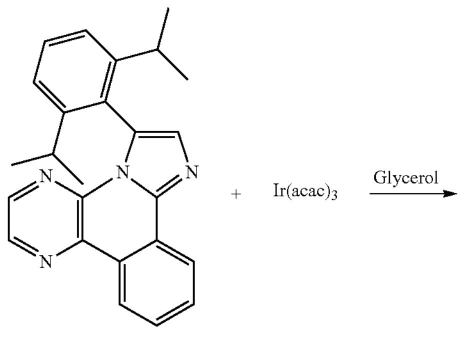

IrL6

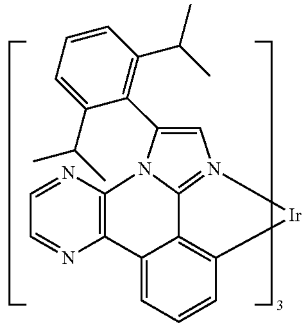

IrC16

IrL6 (2.5 mmol, 5.0 eq) and $Ir(acac)_3$ (0.5 mmol, 1.0 eq) were added to a dr Shlenck tube equipped with a magnetic stir bar. The tube was evacuated and backfilled with nitrogen. The evacuation and backfill procedure was repeated for a total of three times. Then 45 mL of glycerol was added under the protection of nitrogen. The mixture was stirred in an oil bath at a temperature of 240° C. for 3 days. After the mixture was cooled down to ambient temperature, 150 mL of 1 M HCl solution was added, and the product was thrice extracted with $CH_2Cl_2$. Then the organic extracts were combined, and dried with $MgSO_4$. The mixture was evaporated to dryness under reduced pressure, and then purified by column chromatography to obtain the emitter IrC16 in 5%~50% yield.

Example 108

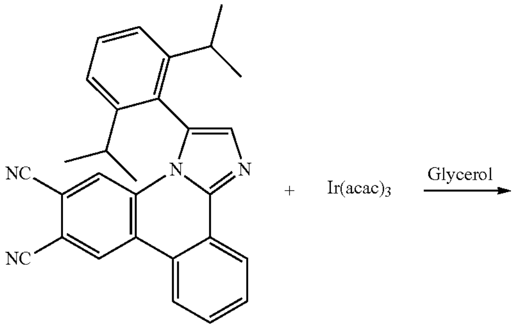

IrL7

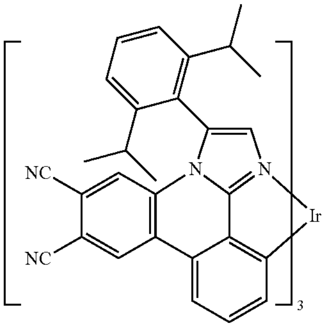

IrC17

IrL6 (2.5 mmol, 5.0 eq) and $Ir(acac)_3$ (0.5 mmol, 1.0 eq) were added to a dry Shlenck tube equipped with a magnetic stir bar. The tube was evacuated and backfilled with nitrogen. The evacuation and backfill procedure was repeated for a total of three times. Then 45 mL of glycerol was added under the protection of nitrogen. The mixture was stirred in an oil bath at a temperature of 240° C. for 3 days. After the mixture was cooled down to ambient temperature, 150 mL of 1M HCl solution was added, and the product was thrice extracted with $CH_2Cl_2$. Then the organic extracts were combined, and dried with $MgSO_4$. The mixture was evaporated to dryness under reduced pressure, and then purified by column chromatography to obtain the emitter IrC17 in 5%~50% yield.

Example 109

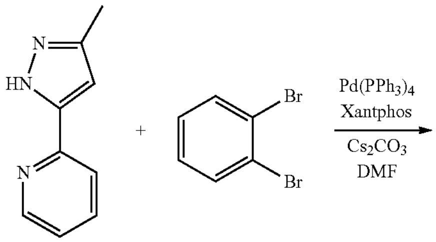

-continued

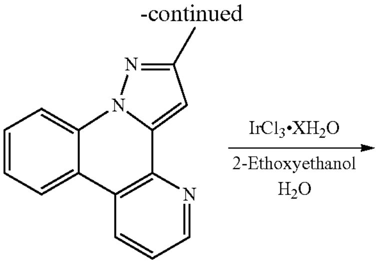

IrL18

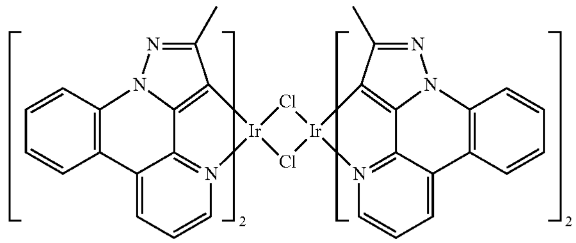

D18

IrL18 (2.2 nmol, 2.2 eq) and $IrCl_3.XH_2O$ (1.0 mmol, 1.0 eq) were added to a dry Shlenck tube equipped with a magnetic stir bar. The tube was evacuated and backfilled with nitrogen. The evacuation and backfill procedure was repeated for a total of three times. Then 2-ethoxyethanol (30 mL) and $H_2O$ (10 mL) were added under the protection of nitrogen. The mixture was stirred in an oil bath at a temperature of 110° C. overnight and then cooled down to ambient temperature. The precipitate was filtered and washed with methanol several times to obtain the desired product chlorodimer D18 in 40%~80% yield.

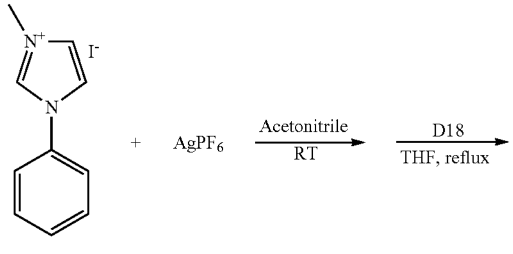

A1

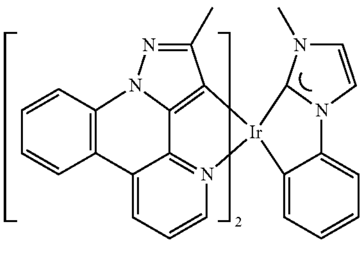

IrC18

A mixture of ancillary ligand A1 (1.5 mmol, 1.5 eq) and $AgPF_6$ (0.75 mmol, 0.75 eq) was stirred in a solution of 100 mL of acetonitrile at room temperature for 24 h. The solvent was evaporated to dryness under reduced pressure. Then chlorodimer D18 (1.0 mmol, 1.0 eq) and 150 mL of THF were added. The reaction mixture was heated to reflux for 24 h. Then the mixture was cooled to room temperature, and the precipitate was filtered off. The filtrate was evaporated to dryness under reduced pressure, and then purified by column chromatography to obtain the emitter IrC18 in 20%~60% yield.

Example 110

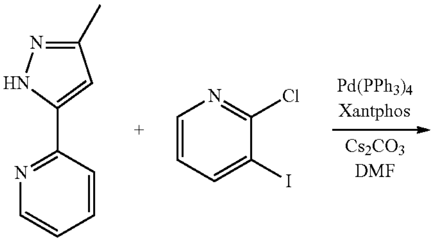

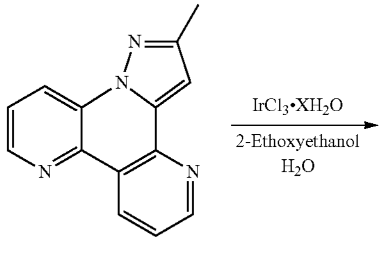

IrL19

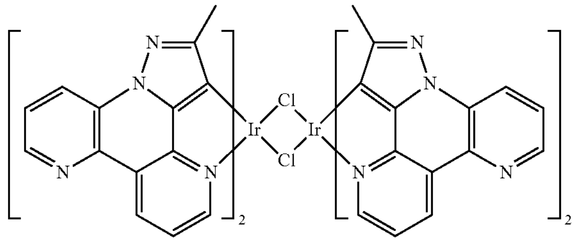

D19

IrL19 (2.2 mmol, 2.2 eq) and $IrCl_3.XH_2O$ (1.0 mmol, 1.0 eq) were added to a dry Shlenck tube equipped with a magnetic stir bar. The tube was evacuated and backfilled with nitrogen. The evacuation and backfill procedure was repeated for a total of three times. Then 2-ethoxyethanol (30 mL) and $H_2O$ (10 mL) were added under the protection of nitrogen. The mixture was stirred in an oil bath at a temperature of 110° C. overnight and then cooled down to ambient temperature. The precipitate was filtered and washed with methanol several times to obtain the desired product chlorodimer D19 in 40%~80% yield.

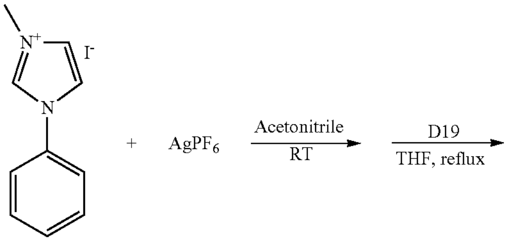

A1

-continued

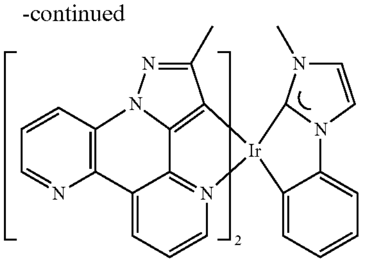

IrC19

A mixture of ancillary ligand A1 (1.5 mmol, 1.5 eq) and $AgPF_6$ (0.75 mmol, 0.75 eq) was stirred in a solution of 100 mL of acetonitrile at room temperature for 24 h. The solvent was evaporated to dryness under reduced pressure. Then chlorodimer D19 (1.0 mmol, 1.0 eq) and 150 mL of THF were added. The reaction mixture was heated to reflux for 24 h. Then the mixture was cooled to room temperature, and the precipitate was filtered off. The filtrate was evaporated to dryness under reduced pressure, and then purified by column chromatography to obtain the emitter IrC19 in 20%~60% yield.

Example 111

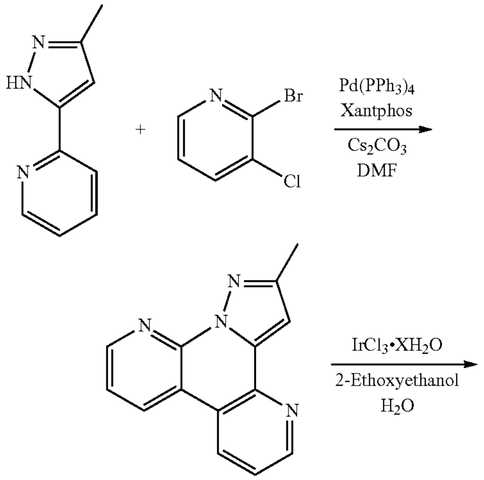

IrL20

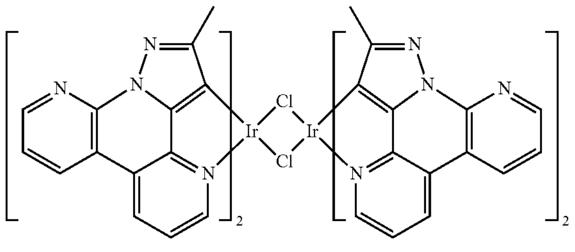

D20

IrL20 (2.2 mmol, 2.2 eq) and $IrCl_3.XH_2O$ (1.0 mmol, 1.0 eq) were added to a dry Shlenck tube equipped with a magnetic stir bar. The tube was evacuated and backfilled with nitrogen. The evacuation and backfill procedure was repeated for a total of three times. Then 2-ethoxyethanol (30 mL) and $H_2O$ (10 mL) were added under the protection of nitrogen. The mixture was stirred in an oil bath at a temperature of 110° C. overnight and then cooled down to ambient temperature. The precipitate was filtered and washed with methanol several times to obtain the desired product chlorodimer D20 in 40%~80% yield.

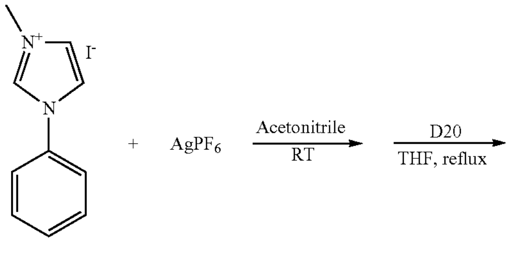

A1

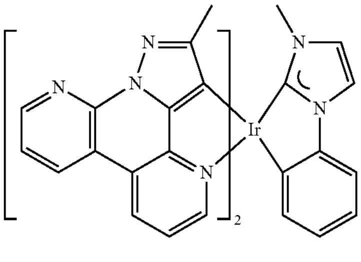

IrC20

A mixture of ancillary ligand A1 (1.5 mmol, 1.5 eq) and $AgPF_6$ (0.75 mmol, 0.75 eq) was stirred in a solution of 100 mL of acetonitrile at room temperature for 24 h. The solvent was evaporated to dryness under reduced pressure. Then chlorodimer D20 (1.0 mmol, 1.0 eq) and 150 mL of THF were added. The reaction mixture was heated to reflux for 24 h. Then the mixture was cooled to room temperature, and the precipitate was filtered off. The filtrate was evaporated to dryness under reduced pressure, and then purified by column chromatography to obtain the emitter IrC20 in 20%~60% yield.

Example 112

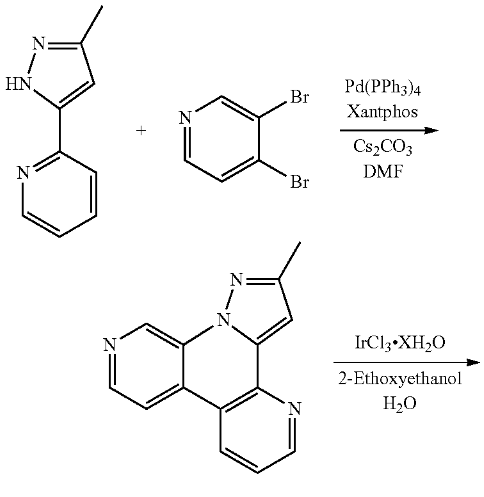

IrL21

-continued

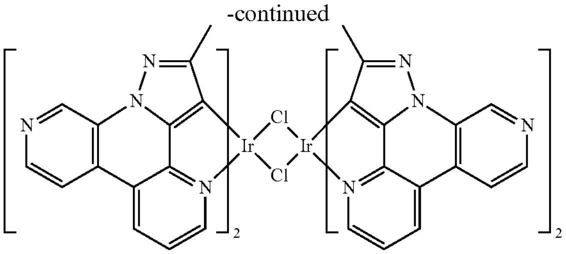

D21

IrL21 (2.2 nmol, 2.2 eq) and $IrCl_3.XH_2O$ (1.0 mmol, 1.0 eq) were added to a dry Shlenck tube equipped with a magnetic stir bar. The tube was evacuated and backfilled with nitrogen. The evacuation and backfill procedure was repeated for a total of three times. Then 2-ethoxyethanol (30 mL) and $H_2O$ (10 mL) were added under the protection of nitrogen. The mixture was stirred in an oil bath at a temperature of 110° C. overnight and then cooled down to ambient temperature. The precipitate was filtered and washed with methanol several times to obtain the desired product chlorodimer D21 in 40%~80% yield.

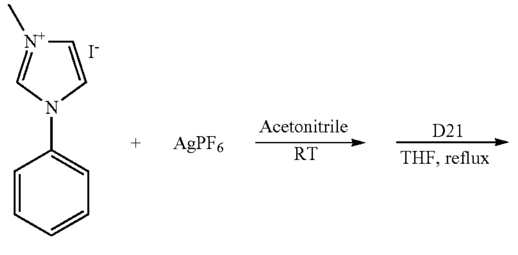

A1

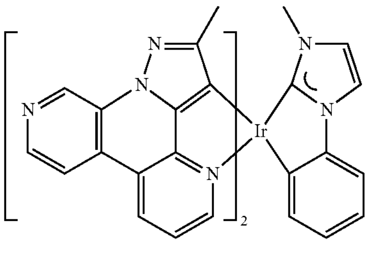

IrC21

A mixture of ancillary ligand A1 (1.5 mmol, 1.5 eq) and $AgPF_6$ (0.75 mmol, 0.75 eq) was stirred in a solution of 100 mL of acetonitrile at room temperature for 24 h. The solvent was evaporated to dryness under reduced pressure. Then chlorodimer D21 (1.0 mmol, 1.0 eq) and 150 mL of THF were added. The reaction mixture was heated to reflux for 24 h. Then the mixture was cooled to room temperature, and the precipitate was filtered off. The filtrate was evaporated to dryness under reduced pressure, and then purified by column chromatography to obtain the emitter IrC21 in 20%~60% yield.

Example 113

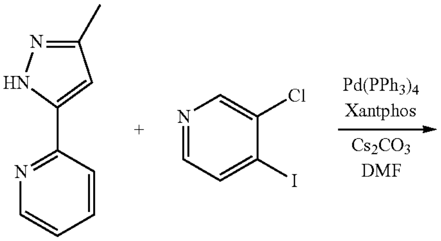

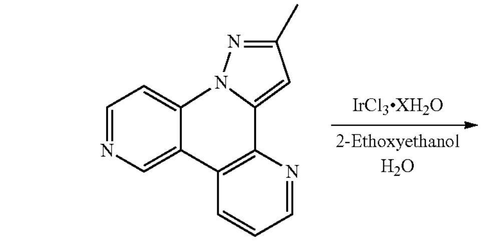

IrL22

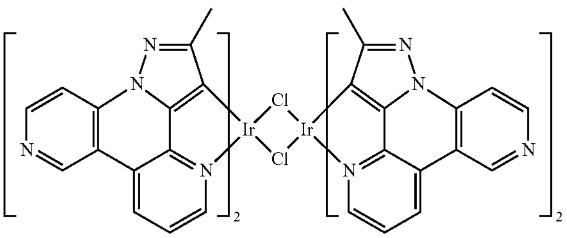

D22

IrL22 (2.2 mmol, 2.2 eq) and $IrCl_3.XH_2O$ (1.0 mmol, 1.0 eq) were added to a dry Shlenck tube equipped with a magnetic stir bar. The tube was evacuated and backfilled with nitrogen. The evacuation and backfill procedure was repeated for a total of three times. Then 2-ethoxyethanol (30 mL) and $H_2O$ (10 mL) were added under the protection of nitrogen. The mixture was stirred in an oil bath at a temperature of 110° C. overnight and then cooled down to ambient temperature. The precipitate was filtered and washed with methanol several times to obtain the desired product chlorodimer D22 in 40%~80% yield.

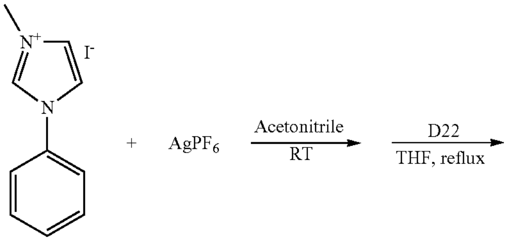

A1

-continued

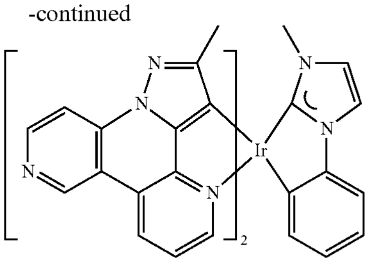

IrC22

A mixture of ancillary ligand A1 (1.5 mmol, 1.5 eq) and $AgPF_6$ (0.75 mmol, 0.75 eq) was stirred in a solution of 100 mL of acetonitrile at room temperature for 24 h. The solvent was evaporated to dryness under reduced pressure. Then chlorodimer D22 (1.0 mmol, 1.0 eq) and 150 mL of THF were added. The reaction mixture was heated to reflux for 24 h. Then the mixture was cooled to room temperature, and the precipitate was filtered off. The filtrate was evaporated to dryness under reduced pressure, and then purified by column chromatography to obtain the emitter IrC22 in 20%~60% yield.

Example 114

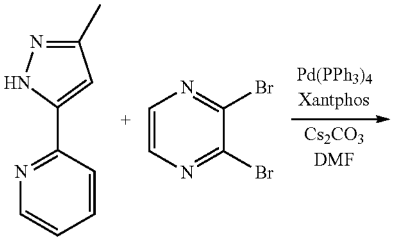

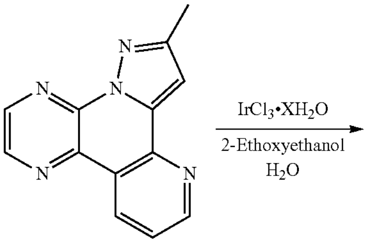

IrL23

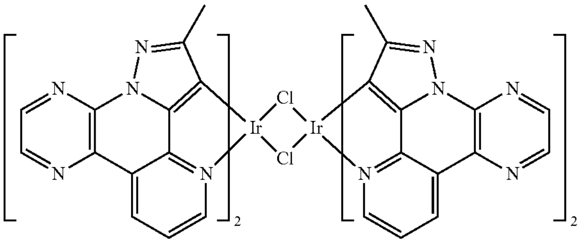

D23

IrL23 (2.2 mmol, 2.2 eq) and $IrCl_3.XH_2O$ (1.0 mmol, 1.0 eq) were added to a dry Shlenck tube equipped with a magnetic stir bar. The tube was evacuated and backfilled with nitrogen. The evacuation and backfill procedure was repeated for a total of three times. Then 2-ethoxyethanol (30 mL) and $H_2O$ (10 mL) were added under the protection of nitrogen. The mixture was stirred in an oil bath at a temperature of 110° C. overnight and then cooled down to ambient temperature. The precipitate was filtered and washed with methanol several times to obtain the desired product chlorodimer D23 in 40%~80% yield.

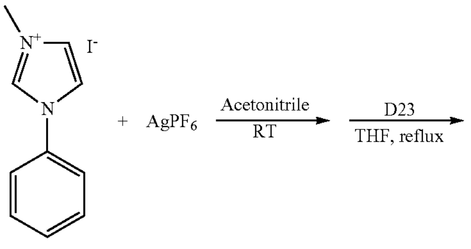

A1

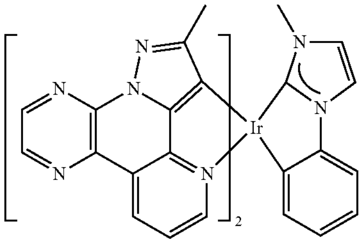

IrC23

A mixture of ancillary ligand A1 (1.5 mmol, 1.5 eq) and $AgPF_6$ (0.75 mmol, 0.75 eq) was stirred in a solution of 100 mL of acetonitrile at room temperature for 24 h. The solvent was evaporated to dryness under reduced pressure. Then chlorodimer D23 (1.0 mmol, 1.0 eq) and 150 mL of THF were added. The reaction mixture was heated to reflux for 24 h. Then the mixture was cooled to room temperature, and the precipitate was filtered off. The filtrate was evaporated to dryness under reduced pressure, and then purified by column chromatography to obtain the emitter IrC23 in 20%~60% yield.

Example 115

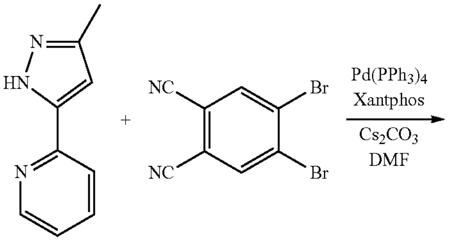

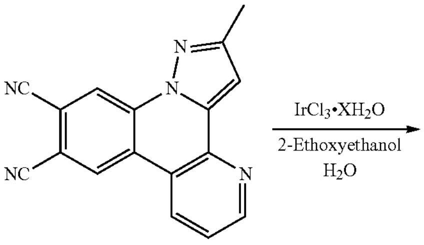

IrL24

-continued

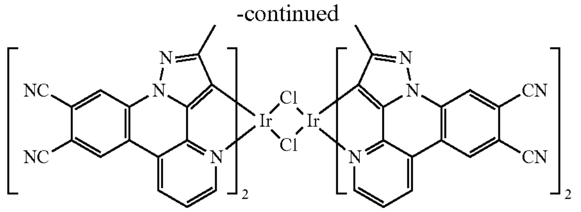

D24

IrL24 (2.2 mmol, 2.2 eq) and $IrCl_3.XH_2O$ (1.0 mmol, 1.0 eq) were added to a dry Shlenck tube equipped with a magnetic stir bar. The tube was evacuated and backfilled with nitrogen. The evacuation and backfill procedure was repeated for a total of three times. Then 2-ethoxyethanol (30 mL) and $H_2O$ (10 mL) were added under the protection of nitrogen. The mixture was stirred in an oil bath at a temperature of 110° C. overnight and then cooled down to ambient temperature. The precipitate was filtered and washed with methanol several times to obtain the desired product chlorodimer D24 in 40%~80% yield.

-continued

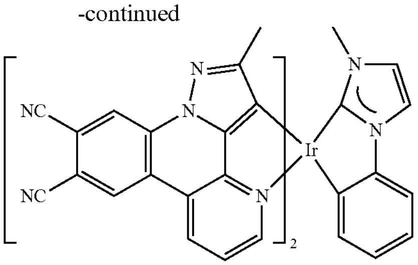

IrC24

A mixture of ancillary ligand A1 (1.5 mmol, 1.5 eq) and $AgPF_6$ (0.75 mmol, 0.75 eq) was stirred in a solution of 100 mL of acetonitrile at room temperature for 24 h. The solvent was evaporated to dryness under reduced pressure. Then chlorodimer D24 (1.0 mmol, 1.0 eq) and 150 mL of THF were added. The reaction mixture was heated to reflux for 24 h. Then the mixture was cooled to room temperature, and the precipitate was filtered off. The filtrate was evaporated to dryness under reduced pressure, and then purified by column chromatography to obtain the emitter IrC24 in 20%~60% yield.

Example 116

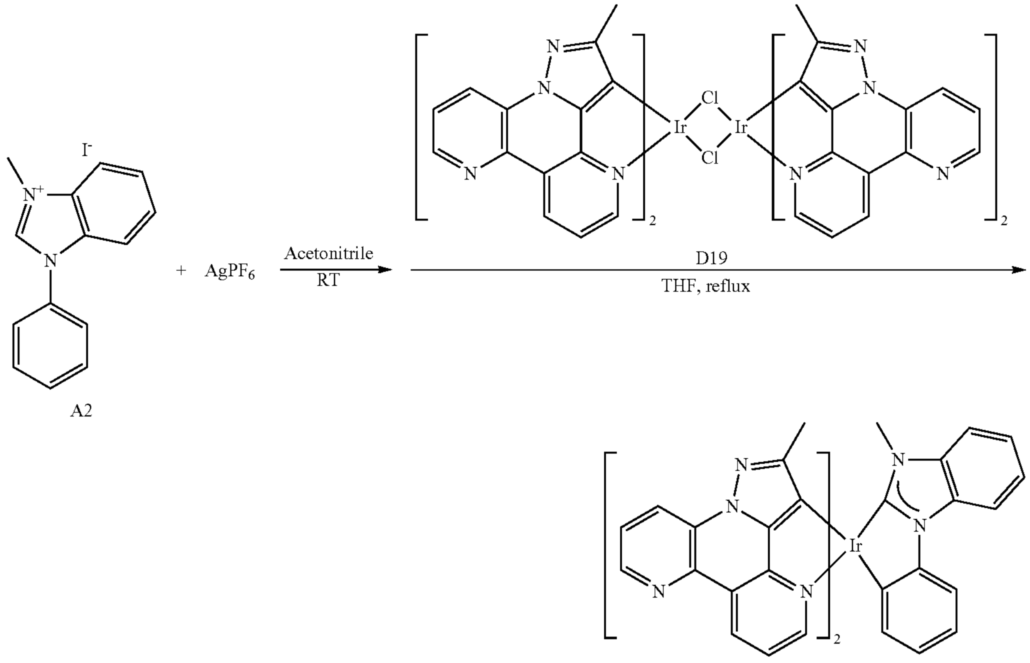

A2

IrC25

A mixture of ancillary ligand A2 (1.5 mmol, 1.5 eq) and $AgPF_6$ (0.75 mmol, 0.75 eq) was stirred in a solution of 100 mL of acetonitrile at room temperature for 24 h. The solvent was evaporated to dryness under reduced pressure. Then chlorodimer D19 (1.0 mmol, 1.0 eq) and 150 mL of THF were added. The reaction mixture was heated to reflux for 24 h. Then the mixture was cooled to room temperature, and the precipitate was filtered off. The filtrate was evaporated to dryness under reduced pressure, and then purified by column chromatography to obtain the emitter IrC25 in 20%~60% yield.

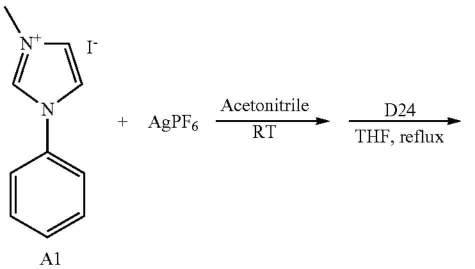

A1

Example 117

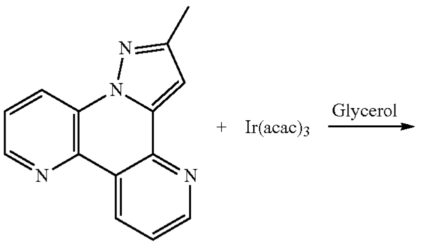

IrL19

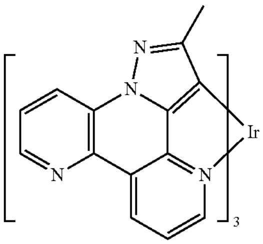

IrC26

IrL19 (2.5 mmol, 5.0 eq) and Ir(acac)$_3$ (0.5 mmol, 1.0 eq) were added to a dry Shlenck tube equipped with a magnetic stir bar. The tube was evacuated and backfilled with nitrogen. The evacuation and backfill procedure was repeated for a total of three times. Then 45 mL of glycerol was added under the protection of nitrogen. The mixture was stirred in an oil bath at a temperature of 240° C. for 3 days. After the mixture was cooled down to ambient temperature, 150 mL of 1M HCl solution was added, and the product was thrice extracted with $CH_2Cl_2$. Then the organic extracts were combined, and dried with $MgSO_4$. The mixture was evaporated to dryness under reduced pressure, and then purified by column chromatography to obtain the emitter IrC26 in 5%~50% yield.

Example 118

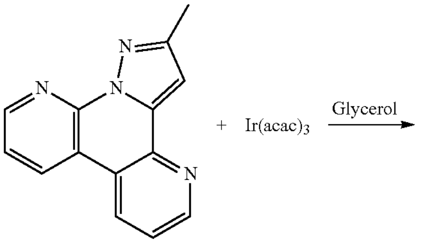

IrL20

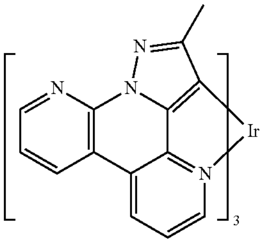

IrC27

IrL20 (2.5 mmol, 5.0 eq) and Ir(acac)$_3$ (0.5 mmol, 1.0 eq) were added to a dry Shlenck tube equipped with a magnetic stir bar. The tube was evacuated and backfilled with nitrogen. The evacuation and backfill procedure was repeated for a total of three times. Then 45 mL of glycerol was added under the protection of nitrogen. The mixture was stirred in an oil bath at a temperature of 240° C. for 3 days. After the mixture was cooled down to ambient temperature, 150 mL of 1M HCl solution was added, and the product was thrice extracted with $CH_2Cl_2$. Then the organic extracts were combined, and dried with $MgSO_4$. The mixture was evaporated to dryness under reduced pressure, and then purified by column chromatography to obtain the emitter IrC27 in 5%~50% yield.

Example 119

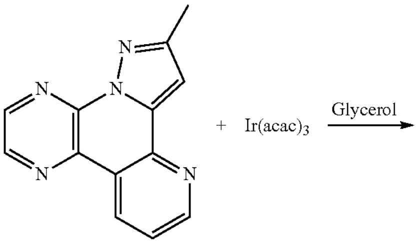

IrL23

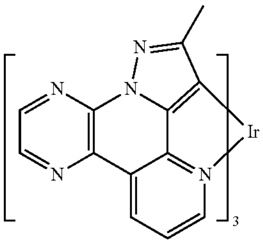

IrC28

IrL23 (2.5 mmol, 5.0 eq) and Ir(acac)$_3$ (0.5 mmol, 1.0 eq) were added to a dry Shlenck tube equipped with a magnetic stir bar. The tube was evacuated and backfilled with nitrogen. The evacuation and backfill procedure was repeated for a total of three times. Then 45 mL of glycerol was added under the protection of nitrogen. The mixture was stirred in an oil bath at a temperature of 240° C. for 3 days. After the mixture was cooled down to ambient temperature, 150 mL of 1M HCl solution was added, and the product was thrice extracted with $CH_2Cl_2$. Then the organic extracts were combined, and dried with $MgSO_4$. The mixture was evaporated to dryness under reduced pressure, and then purified by column chromatography to obtain the emitter IrC28 in 5%~50% yield.

Example 120

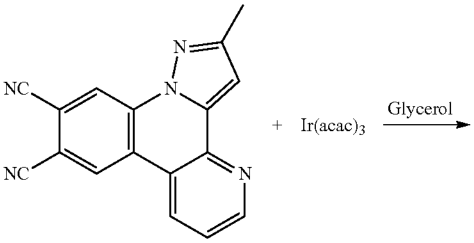

IrL24

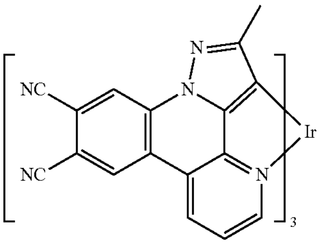

IrC29

IrL24 (2.5 mmol, 5.0 eq) and Ir(acac)$_3$ (0.5 mmol, 1.0 eq) were added to a dry Shlenck tube equipped with a magnetic stir bar. The tube was evacuated and backfilled with nitrogen. The evacuation and backfill procedure was repeated for a total of three times. Then 45 mL of glycerol was added under the protection of nitrogen. The mixture was stirred in an oil bath at a temperature of 240° C. for 3 days. After the mixture was cooled down to ambient temperature, 150 mL of 1M HCl solution was added, and the product was thrice extracted with $CH_2Cl_2$. Then the organic extracts were combined, and dried with $MgSO_4$. The mixture was evaporated to dryness under reduced pressure, and then purified by column chromatography to obtain the emitter IrC29 in 5%~50% yield.

Example 121

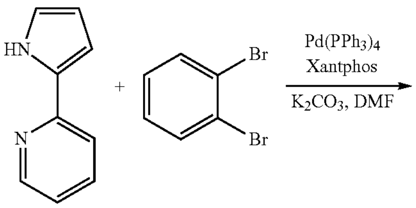

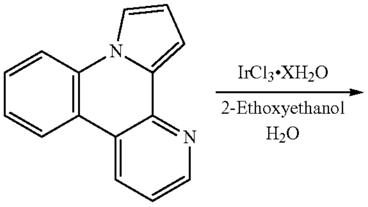

IrL30

-continued

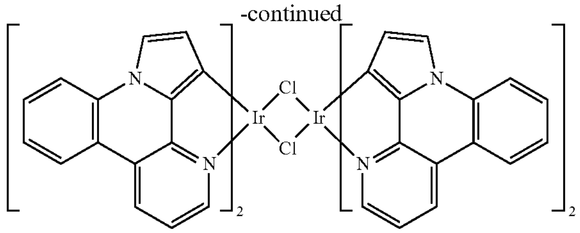

D30

IrL30 (2.2 mmol, 2.2 eq) and $IrCl_3.XH_2O$ (1.0 mmol, 1.0 eq) were added to a dry Shlenck tube equipped with a magnetic stir bar. The tube was evacuated and backfilled with nitrogen. The evacuation and backfill procedure was repeated for a total of three times. Then 2-ethoxyethanol (30 mL) and $H_2O$ (10 mL) were added under the protection of nitrogen. The mixture was stirred in an oil bath at a temperature of 110° C. overnight and then cooled down to ambient temperature. The precipitate was filtered and washed with methanol several times to obtain the desired product chlorodimer D30 in 40%~80% yield.

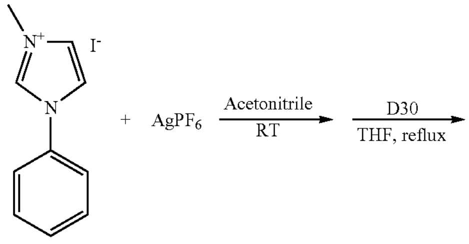

A1

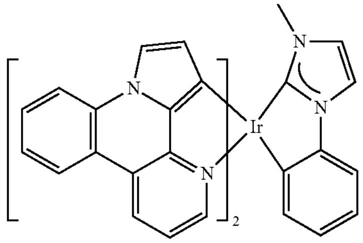

IrC30

A mixture of ancillary ligand A1 (1.5 mmol, 1.5 eq) and $AgPF_6$ (0.75 mmol, 0.75 eq) was stirred in a solution of 100 mL of acetonitrile at room temperature for 24 h. The solvent was evaporated to dryness under reduced pressure. Then chlorodimer D30 (1.0 mmol, 1.0 eq) and 150 mL of THF were added. The reaction mixture was heated to reflux for 24 h. Then the mixture was cooled to room temperature, and the precipitate was filtered off. The filtrate was evaporated to dryness under reduced pressure, and then purified by column chromatography to obtain the emitter IrC30 in 20%~60% yield.

Example 122

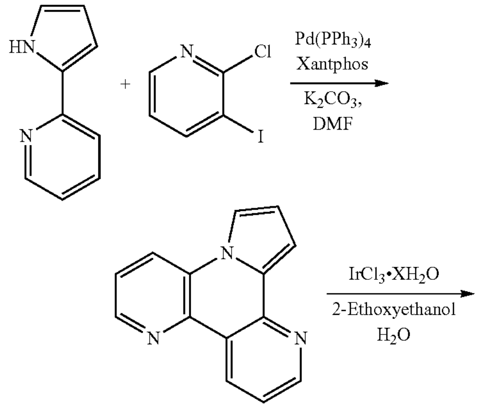

IrL31

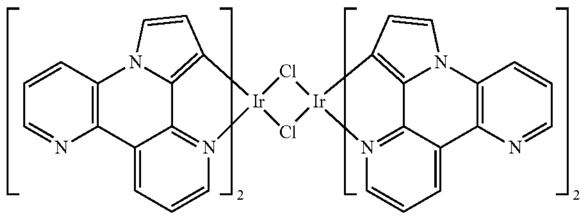

D31

IrL31 (2.2 mmol, 2.2 eq) and $IrCl_3.X_2O$ (1.0 mmol, 1.0 eq) were added to a dry Shlenck tube equipped with a magnetic stir bar. The tube was evacuated and backfilled with nitrogen. The evacuation and backfill procedure was repeated for a total of three times. Then 2-ethoxyethanol (30 mL) and $H_2O$ (10 mL) were added under the protection of nitrogen. The mixture was stirred in an oil bath at a temperature of 110° C. overnight and then cooled down to ambient temperature. The precipitate was filtered and washed with methanol several times to obtain the desired product chlorodimer D31 in 40%~80% yield.

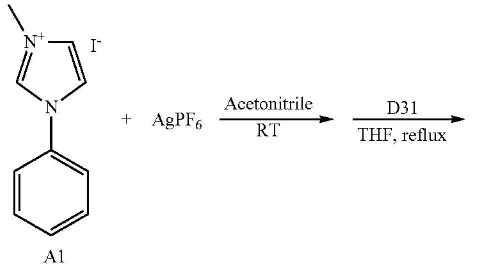

A1

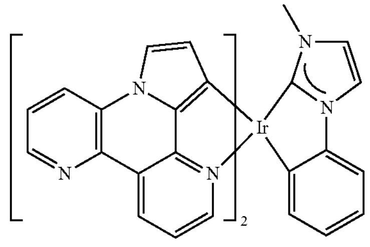

IrC31

A mixture of ancillary ligand A1 (1.5 mmol, 1.5 eq) and $AgPF_6$ (0.75 mmol, 0.75 eq) was stirred in a solution of 100 mL of acetonitrile at room temperature for 24 h. The solvent was evaporated to dryness under reduced pressure. Then chlorodimer D31 (1.0 mmol, 1.0 eq) and 150 mL of THF were added. The reaction mixture was heated to reflux for 24 h. Then the mixture was cooled to room temperature, and the precipitate was filtered off. The filtrate was evaporated to dryness under reduced pressure, and then purified by column chromatography to obtain the emitter IrC31 in 20%~60% yield.

Example 123

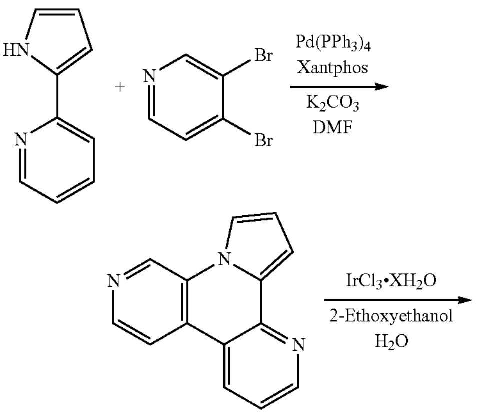

IrL32

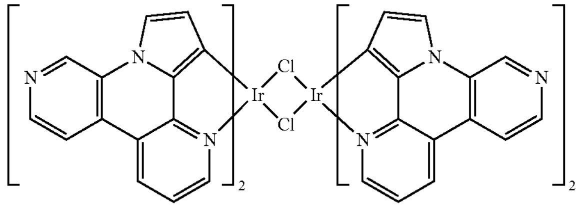

D32

IrL32 (2.2 mmol, 2.2 eq) and $IrCl_3.XH_2O$ (1.0 mmol, 1.0 eq) were added to a dry Shlenck tube equipped with a magnetic stir bar. The tube was evacuated and backfilled with nitrogen. The evacuation and backfill procedure was repeated for a total of three times. Then 2-ethoxyethanol (30 mL) and $H_2O$ (10 mL) were added under the protection of nitrogen. The mixture was stirred in an oil bath at a temperature of 110° C. overnight and then cooled down to ambient temperature. The precipitate was filtered and washed with methanol several times to obtain the desired product chlorodimer D32 in 40%~80% yield.

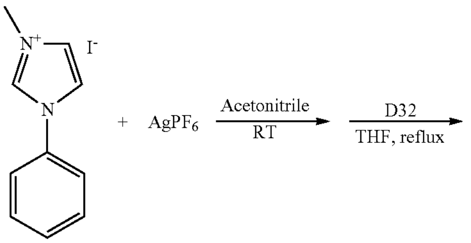

A1

-continued

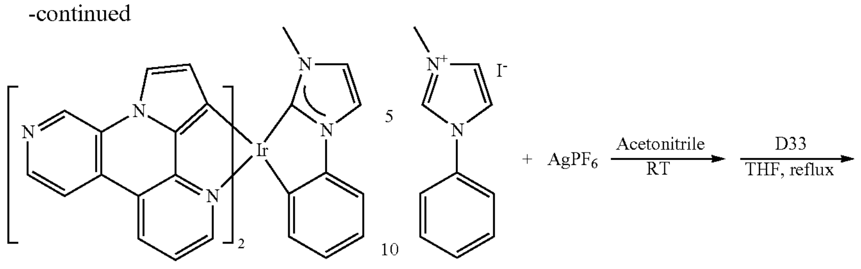

IrC32

A1

A mixture of ancillary ligand A1 (1.5 mmol, 1.5 eq) and $AgPF_6$ (0.75 mmol, 0.75 eq) was stirred in a solution of 100 mL of acetonitrile at room temperature for 24 h. The solvent was evaporated to dryness under reduced pressure. Then chlorodimer D32 (1.0 mmol, 1.0 eq) and 150 mL of THF were added. The reaction mixture was heated to reflux for 24 h. Then the mixture was cooled to room temperature, and the precipitate was filtered off. The filtrate was evaporated to dryness under reduced pressure, and then purified by column chromatography to obtain the emitter IrC32 in 20%~60% yield.

Example 124

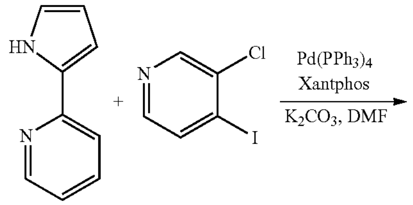

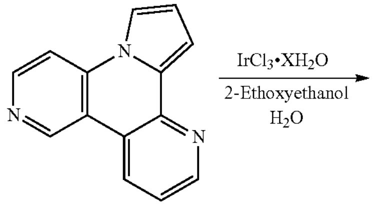

IrL33

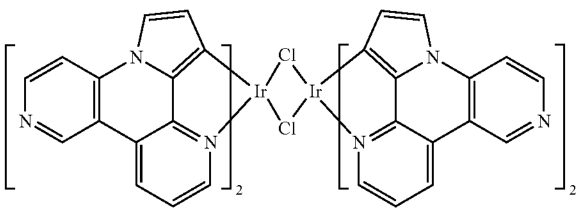

D33

IrL33 (2.2 mmol, 2.2 eq) and $IrCl_3.XH_2O$ (1.0 mmol, 1.0 eq) were added to a dry Shlenck tube equipped with a magnetic stir bar. The tube was evacuated and backfilled with nitrogen. The evacuation and backfill procedure was repeated for a total of three times. Then 2-ethoxyethanol (30 mL) and $H_2O$ (10 mL) were added under the protection of nitrogen. The mixture was stirred in an oil bath at a temperature of 110° C. overnight and then cooled down to ambient temperature. The precipitate was filtered and washed with methanol several times to obtain the desired product chlorodimer D33 in 40%~80% yield.

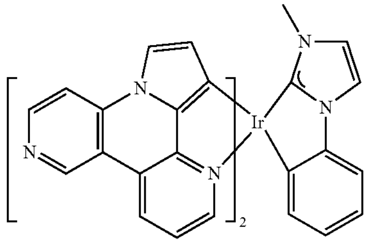

IrC33

A mixture of ancillary ligand A1 (1.5 mmol, 1.5 eq) and $AgPF_6$ (0.75 mmol, 0.75 eq) was stirred in a solution of 100 mL of acetonitrile at room temperature for 24 h. The solvent was evaporated to dryness under reduced pressure. Then chlorodimer D33 (1.0 mmol, 1.0 eq) and 150 mL of THF were added. The reaction mixture was heated to reflux for 24 h. Then the mixture was cooled to room temperature, and the precipitate was filtered off. The filtrate was evaporated to dryness under reduced pressure, and then purified by column chromatography to obtain the emitter IrC33 in 20%~60% yield.

Example 125

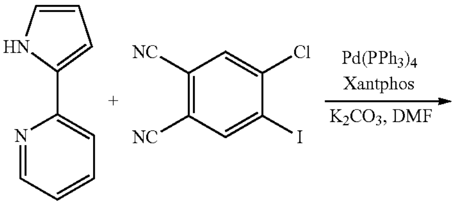

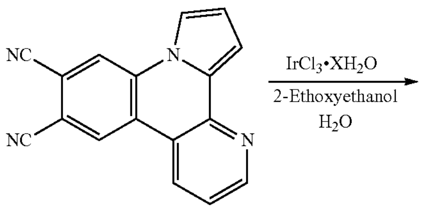

IrL34

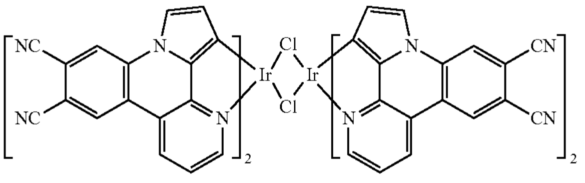

D34

IrL34 (2.2 mmol, 2.2 eq) and $IrCl_3.XH_2O$ (1.0 mmol, 1.0 eq) were added to a dry Shlenck tube equipped with a magnetic stir bar. The tube was evacuated and backfilled with nitrogen. The evacuation and backfill procedure was repeated for a total of three times. Then 2-ethoxyethanol (30 mL) and $H_2O$ (10 mL) were added under the protection of nitrogen. The mixture was stirred in an oil bath at a temperature of 110° C. overnight and then cooled down to ambient temperature. The precipitate was filtered and washed with methanol several times to obtain the desired product chlorodimer D34 in 40%~80% yield.

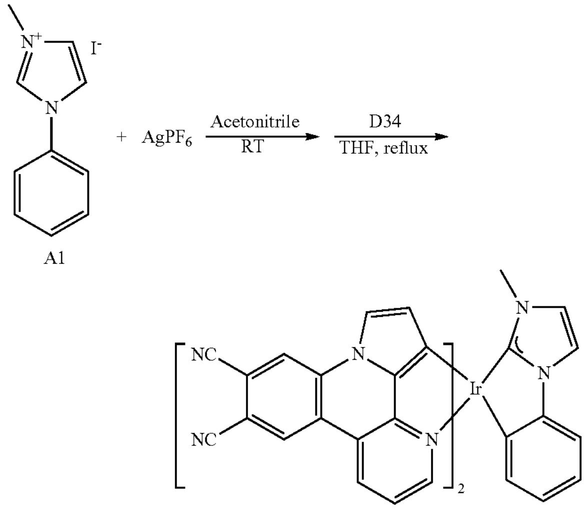

A1

IrC34

A mixture of ancillary ligand A1 (1.5 mmol, 1.5 eq) and $AgPF_6$ (0.75 mmol, 0.75 eq) was stirred in a solution of 100 mL of acetonitrile at room temperature for 24 h. The solvent was evaporated to dryness under reduced pressure. Then chlorodimer D34 (1.0 mmol, 1.0 eq) and 150 mL of THF were added. The reaction mixture was heated to reflux for 24 h. Then the mixture was cooled to room temperature, and the precipitate was filtered off. The filtrate was evaporated to dryness under reduced pressure, and then purified by column chromatography to obtain the emitter IrC34 in 20%~60% yield.

Example 126

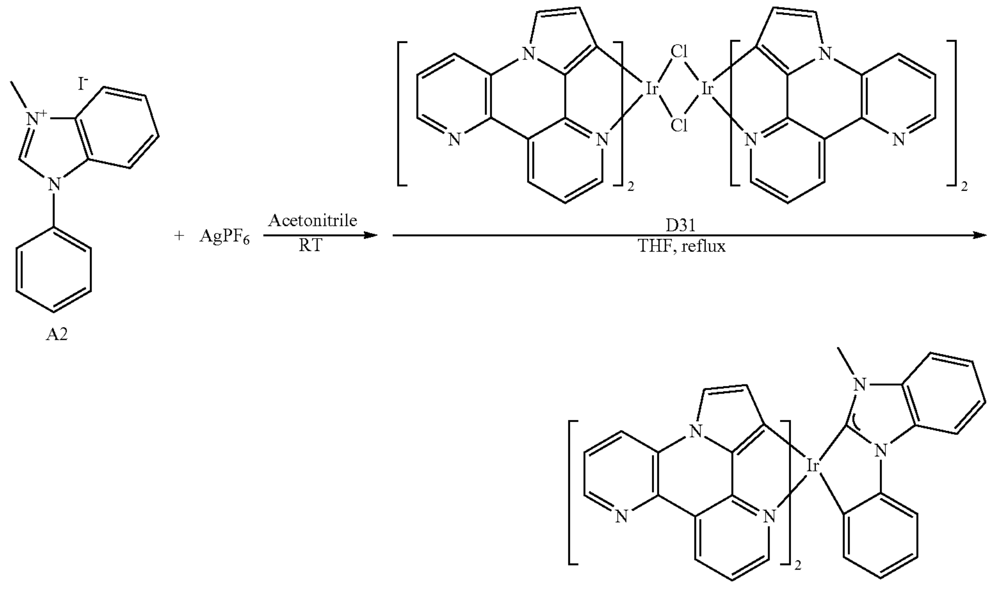

A2

IrC35

A mixture of ancillary ligand A2 (1.5 mmol 1.5 eq) and $AgPF_6$ (0.75 mmol, 0.75 eq) was stirred in a solution of 100 mL of acetonitrile at room temperature for 24 h. The solvent was evaporated to dryness under reduced pressure. Then chlorodimer D31 (1.0 mmol, 1.0 eq) and 150 mL of THF were added. The reaction mixture was heated to reflux for 24 h. Then the mixture was cooled to room temperature, and the precipitate was filtered off. The filtrate was evaporated to dryness under reduced pressure, and then purified by column chromatography to obtain the emitter IrC35 in 20%~60% yield.

Example 127

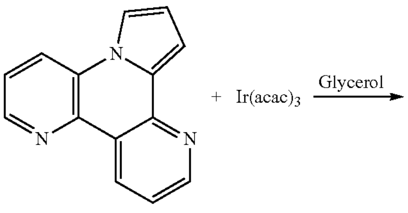

IrL31

-continued

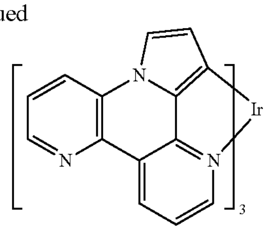

IrC36

IrL31 (2.5 mmol, 5.0 eq) and Ir(acac)$_3$ (0.5 mmol, 1.0 eq) were added to a dry Shlenck tube equipped with a magnetic stir bar. The tube was evacuated and backfilled with nitrogen. The evacuation and backfill procedure was repeated for a total of three times. Then 45 mL of glycerol was added under the protection of nitrogen. The mixture was stirred in an oil bath at a temperature of 240° C. for 3 days. After the mixture was cooled down to ambient temperature, 150 mL of 1M HCl solution was added, and the product was thrice extracted with $CH_2Cl_2$. Then the organic extracts were combined, and dried with $MgSO_4$. The mixture was evaporated to dryness under reduced pressure, and then purified by column chromatography to obtain the emitter IrC36 in 5%~50% yield.

Example 128

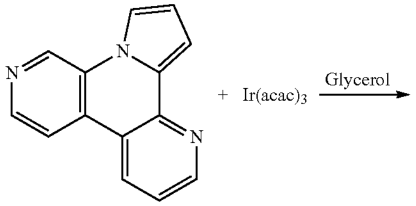

IrL32

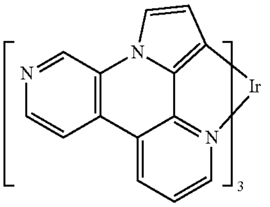

IrC37

IrL32 (2.5 mmol, 5.0 eq) and Ir(acac)$_3$ (0.5 mmol, 1.0 eq) were added to a dry Shlenck tube equipped with a magnetic stir bar. The tube was evacuated and backfilled with nitrogen. The evacuation and backfill procedure was repeated for a total of three times. Then 45 of glycerol was added under the protection of nitrogen. The mixture was stirred in an oil bath at a temperature of 240° C. for 3 days. After the mixture was cooled down to ambient temperature, 150 mL of 1M HCl solution was added, and the product was thrice extracted with $CH_2Cl_2$. Then the organic extracts were combined, and dried with $MgSO_4$. The mixture was evaporated to dryness under reduced pressure, and then purified by column chromatography to obtain the emitter IrC37 in 5%~50% yield.

Example 129

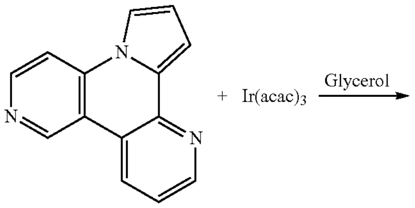

IrL33

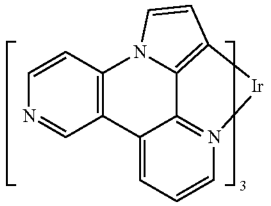

IrC38

IrL33 (2.5 mmol, 5.0 eq) and Ir(acac)$_3$ (0.5 mmol, 1.0 eq) were added to a dry Shlenck tube equipped with a magnetic stir bar. The tube was evacuated and backfilled with nitrogen. The evacuation and backfill procedure was repeated for a total of three times. Then 45 mL of glycerol was added under the protection of nitrogen. The mixture was stirred in an oil bath at a temperature of 240° C. for 3 days. After the mixture was cooled down to ambient temperature, 150 mL of 1M HCl solution was added, and the product was thrice extracted with $CH_2Cl_2$. Then the organic extracts were combined, and dried with $MgSO_4$. The mixture was evaporated to dryness under reduced pressure, and then purified by column chromatography to obtain the emitter IrC38 in 5%~50% yield.

Example 130

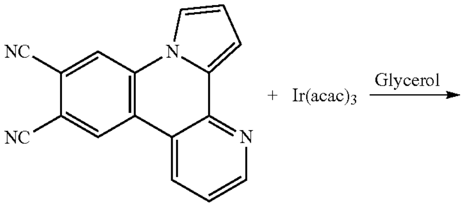

IrL34

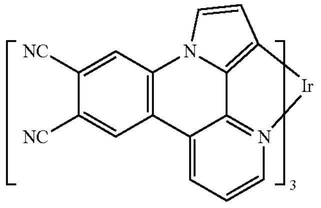

IrC39

IrL34 (2.5 mmol, 5.0 eq) and Ir(acac)$_3$ (0.5 mmol, 1.0 eq) were added to a dry Shlenck tube equipped with a magnetic stir bar. The tube was evacuated and backfilled with nitrogen. The evacuation and backfill procedure was repeated for a total of three times. Then 45 mL of glycerol was added under the protection of nitrogen. The mixture was stirred in an oil bath at a temperature of 240° C. for 3 days. After the mixture was cooled down to ambient temperature, 150 mL of 1M HCl solution was added, and the product was thrice extracted with $CH_2Cl_2$. Then the organic extracts were combined, and dried with $MgSO_4$. The mixture was evaporated to dryness under reduced pressure, and then purified by column chromatography to obtain the emitter IrC39 in 5%~50% yield.

Example 131

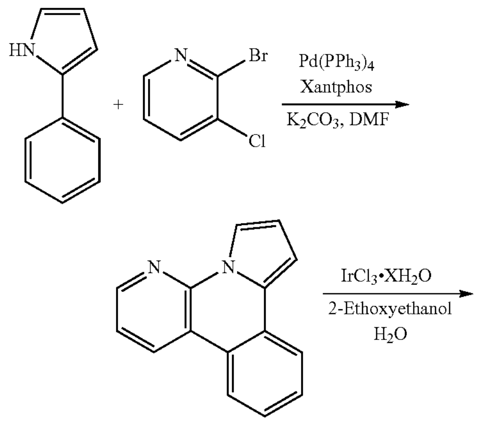

IrL40

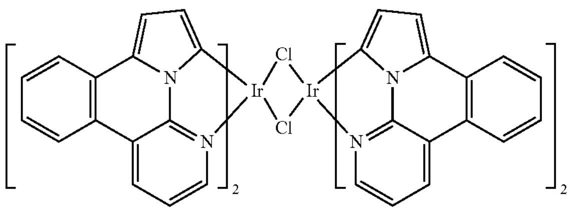

D40

IrL40 (2.2 mmol, 2.2 eq) and $IrCl_3.XH_2O$ (1.0 mmol, 1.0 eq) were added to a dry Shlenck tube equipped with a magnetic stir bar. The tube was evacuated and backfilled with nitrogen. The evacuation and backfill procedure was repeated for a total of three times. Then 2-ethoxyethanol (30 mL) and $H_2O$ (10 mL) were added under the protection of nitrogen. The mixture was stirred in an oil bath at a temperature of 110° C. overnight and then cooled down to ambient temperature. The precipitate was filtered and washed with methanol several times to obtain the desired product chlorodimer D40 in 40%~80% yield.

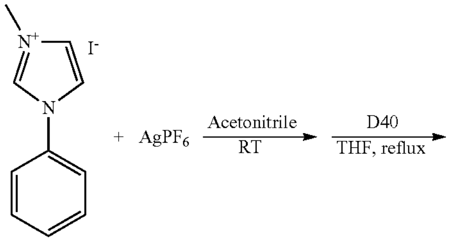

A1

-continued

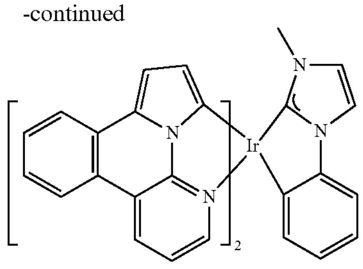

IrC40

A mixture of ancillary ligand A1 (1.5 mmol, 1.5 eq) and $AgPF_6$ (0.75 mmol, 0.75 eq) was stirred in a solution of 100 mL of acetonitrile at room temperature for 24 h. The solvent was evaporated to dryness under reduced pressure. Then chlorodimer D40 (1.0 mmol, 1.0 eq) and 150 mL of THF were added. The reaction mixture was heated to reflux for 24 h. Then the mixture was cooled to room temperature, and the precipitate was filtered off. The filtrate was evaporated to dryness under reduced pressure, and then purified by column chromatography to obtain the emitter IrC40 in 20%~60% yield.

Example 132

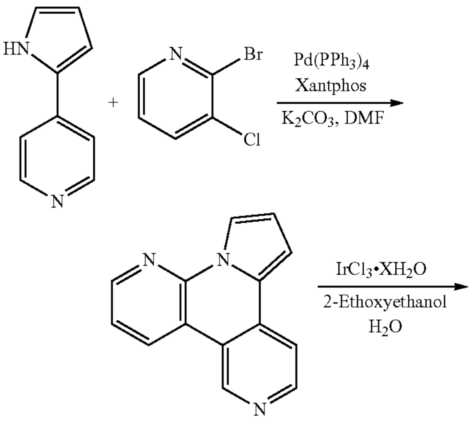

IrL41

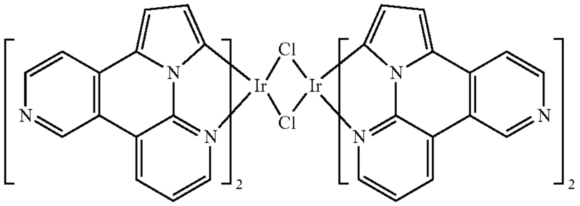

D41

IrL41 (2.2 mmol, 2.2 eq) and $IrCl_3.XH_2O$ (1.0 mmol, 1.0 eq) were added to a dry Shlenck tube equipped with a magnetic stir bar. The tube was evacuated and backfilled with nitrogen. The evacuation and backfill procedure was repeated for a total of three times. Then 2-ethoxyethanol (30 mL) and $H_2O$ (10 mL) were added under the protection of nitrogen. The mixture was stirred in an oil bath at a temperature of 110° C. overnight and then cooled down to ambient temperature. The precipitate was filtered and washed with methanol several times to obtain the desired product chlorodimer D41 in 40%~80% yield.

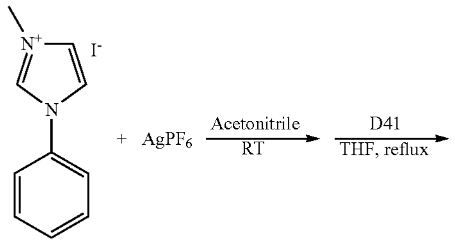

A1

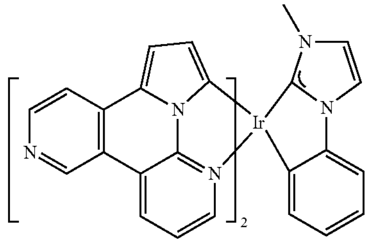

IrC41

A mixture of ancillary ligand A1 (1.5 mmol, 1.5 eq) and $AgPF_6$ (0.75 mmol, 0.75 eq) was stirred in a solution of 100 mL of acetonitrile at room temperature for 24 h. The solvent was evaporated to dryness under reduced pressure. Then chlorodimer D41 (1.0 mmol, 1.0 eq) and 150 mL of THF were added. The reaction mixture was heated to reflux for 24 h. Then the mixture was cooled to room temperature, and the precipitate was filtered off. The filtrate was evaporated to dryness under reduced pressure, and then purified by column chromatography to obtain the emitter IrC41 in 20%~60% yield.

Example 133

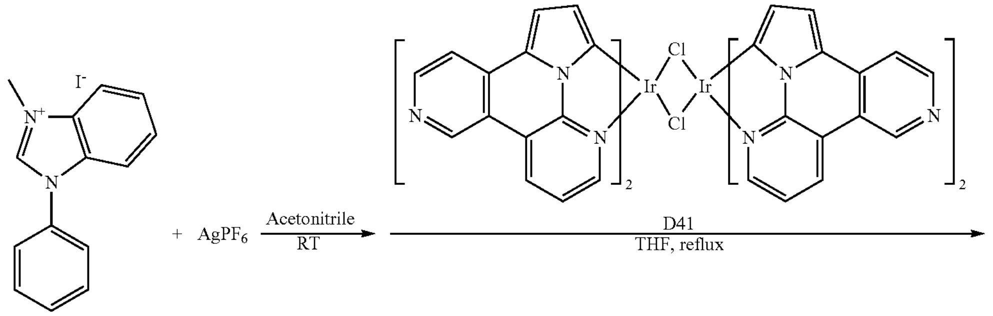

A2

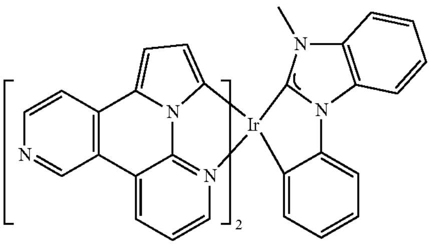

IrC42

A mixture of ancillary ligand A2 (1.5 mmol, 1.5 eq) and $AgPF_6$ (0.75 mmol, 0.75 eq) was stirred in a solution of 100 mL of acetonitrile at room temperature for 24 h. The solvent was evaporated to dryness under reduced pressure. Then chlorodimer D41 (1.0 mmol, 1.0 eq) and 150 mL of THF were added. The reaction mixture was heated to reflux for 24 h. Then the mixture was cooled to room temperature, and the precipitate was filtered off. The filtrate was evaporated to dryness under reduced pressure, and then purified by column chromatography to obtain the emitter IrC42 in 20%~60% yield.

Example 134

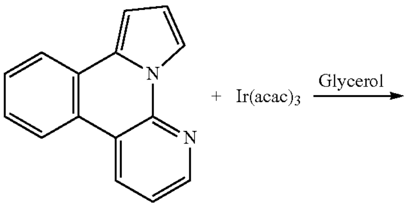

IrL40

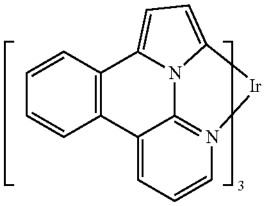

IrC43

IrL40 (2.5 mmol, 5.0 eq) and $Ir(acac)_3$ (0.5 mmol, 1.0 eq) were added to a dry Shlenck tube equipped with a magnetic stir bar. The tube was evacuated and backfilled with nitrogen. The evacuation and backfill procedure was repeated for a total of three times. Then 45 mL of glycerol was added under the protection of nitrogen. The mixture was stirred in an oil bath at a temperature of 240° C. for 3 days. After the mixture was cooled down to ambient temperature, 150 mL of 1M HCl solution was added, and the product was thrice extracted with $CH_2Cl_2$.

Then the organic extracts were combined, and dried with $MgSO_4$. The mixture was evaporated to dryness under reduced pressure, and then purified by column chromatography to obtain the emitter IrC43 in 5%~50% yield.

Example 135

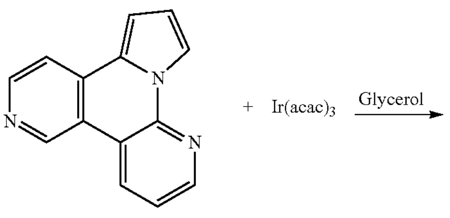

IrL41

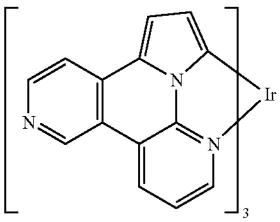

IrC44

IrL41 (2.5 mmol, 5.0 eq) and $Ir(acac)_3$ (0.5 mmol, 1.0 eq) were added to a dry Shlenck tube equipped with a magnetic stir bar. The tube was evacuated and backfilled with nitrogen. The evacuation and backfill procedure was repeated for a total of three times. Then 45 mL of glycerol was added under the protection of nitrogen. The mixture was stirred in an oil bath at a temperature of 240° C. for 3 days. After the mixture was cooled down to ambient temperature, 150 mL of 1M HCl solution was added, and the product was thrice extracted with $CH_2Cl_2$. Then the organic extracts were combined, and dried with $MgSO_4$. The mixture was evaporated to dryness under reduced pressure, and then purified by column chromatography to obtain the emitter IrC44 in 5%~50% yield.

Example 136

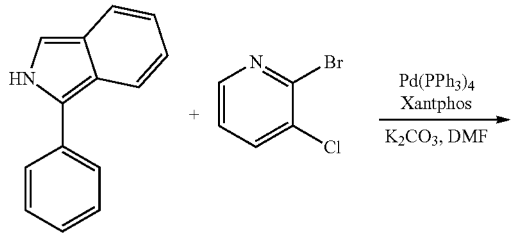

-continued

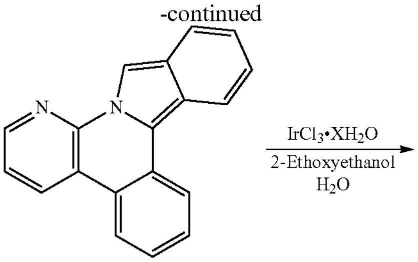

IrL45

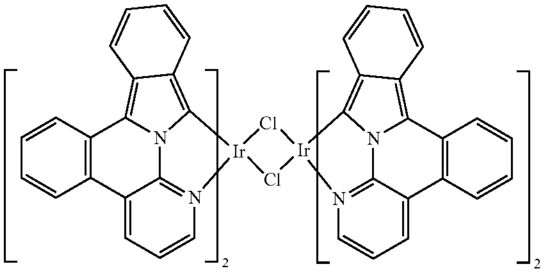

D45

IrL45 (2.2 mmol, 2.2 eq) and $IrCl_3.XH_2O$ (1.0 mmol, 1.0 eq) were added to a dry Shlenck tube equipped with a magnetic stir bar. The tube was evacuated and backfilled with nitrogen. The evacuation and backfill procedure was repeated for a total of three times. Then 2-ethoxyethanol (30 mL) and $H_2O$ (10 mL) were added under the protection of nitrogen. The mixture was stirred in an oil bath at a temperature of 110° C. overnight and then cooled down to ambient temperature. The precipitate was filtered and washed with methanol several times to obtain the desired product chlorodimer D45 in 40%~80% yield.

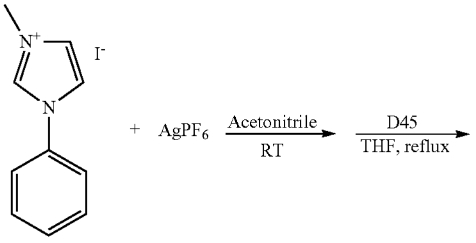

A1

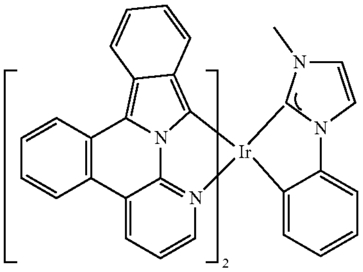

IrC45

A mixture of ancillary ligand A1 (1.5 mmol, 1.5 eq) and $AgPF_6$ (0.75 mmol, 0.75 eq) was stirred in a solution of 100 mL of acetonitrile at room temperature for 24 h. The solvent was evaporated to dryness under reduced pressure. Then chlorodimer D45 (1.0 mmol, 1.0 eq) and 150 mL of THF were added. The reaction mixture was heated to reflux for 24 h. Then the mixture was cooled to room temperature, and the precipitate was filtered off. The filtrate was evaporated to dryness under reduced pressure, and then purified by column chromatography to obtain the emitter IrC45 in 20%~60% yield.

Example 137

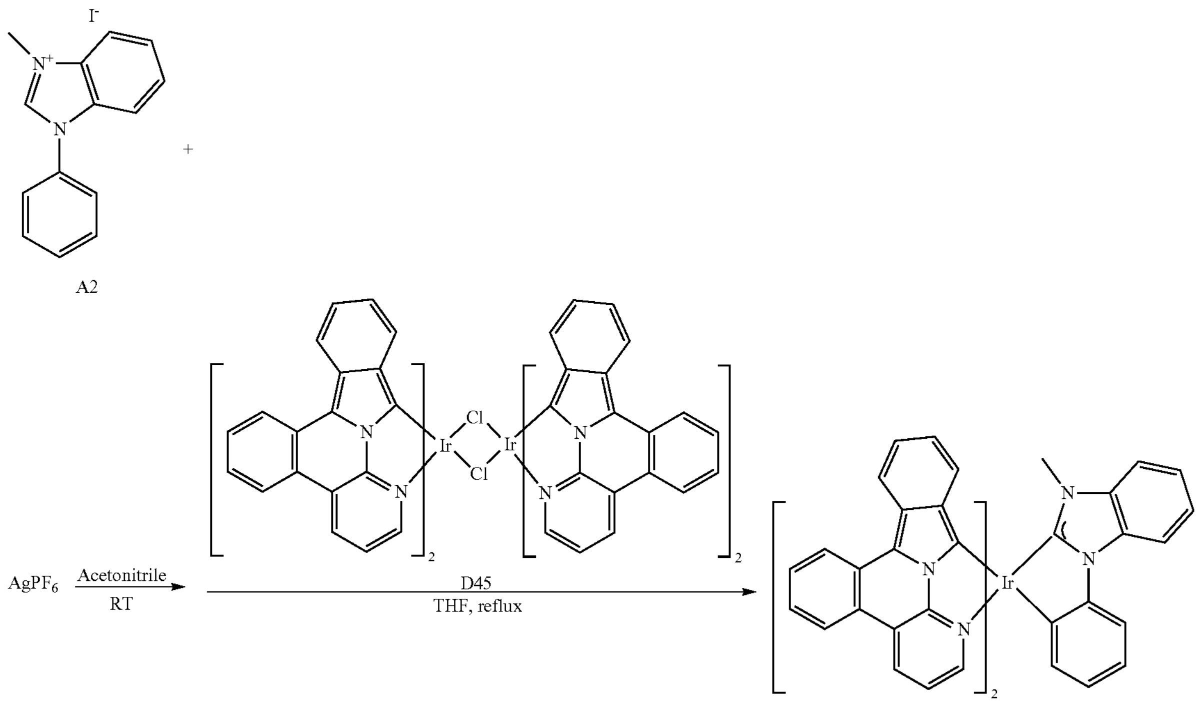

A2

D45

IrC46

A mixture of ancillary ligand A2 (1.5 mmol, 1.5 eq) and $AgPF_6$ (0.75 mmol, 0.75 eq) was stirred in a solution of 100 mL of acetonitrile at room temperature for 24 h. The solvent was evaporated to dryness under reduced pressure. Then chlorodimer D45 (1.0 mmol, 1.0 eq) and 150 mL of THF were added. The reaction mixture was heated to reflux for 24 h. Then the mixture was cooled to room temperature, and the precipitate was filtered off. The filtrate was evaporated to dryness wider reduced pressure, and then purified by column chromatography to obtain the emitter IrC46 in 20%~60% yield.

Example 138

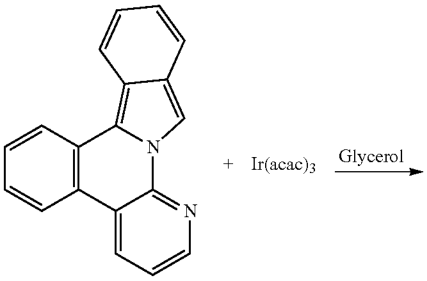

IrL45

-continued

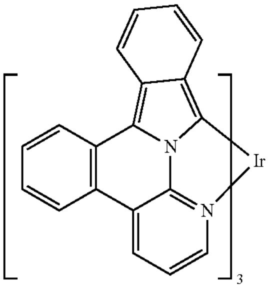

IrC47

IrL45 (2.5 mmol, 5.0 eq) and $Ir(acac)_3$ (0.5 mmol, 1.0 eq) were added to a dry Shlenck tube equipped with a magnetic stir bar. The tube was evacuated and backfilled with nitrogen. The evacuation and backfill procedure was repeated for a total of three times. Then 45 mL of glycerol was added under the protection of nitrogen. The mixture was stirred in an oil bath at a temperature of 240° C. for 3 days. After the mixture was cooled down to ambient temperature, 150 mL of 1M HCl solution was added, and the product was thrice extracted with $CH_2Cl_2$. Then the organic extracts were combined, and dried with $MgSO_4$. The mixture was evaporated to dryness under reduced pressure, and then purified by column chromatography to obtain the emitter IrC47 in 5%~50% yield.

Example 139

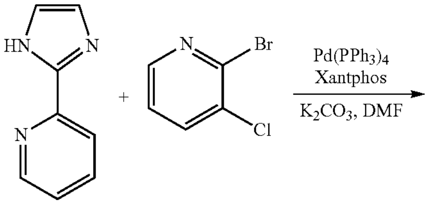

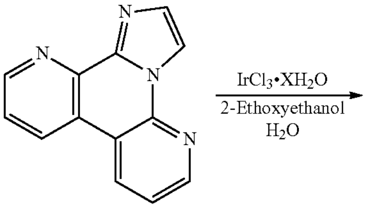

IrL48

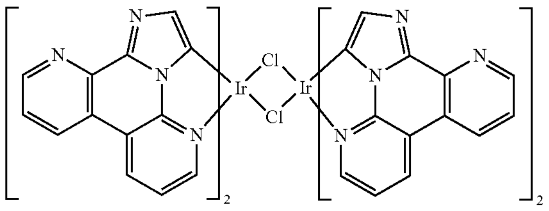

D48

IrL48 (2.2 mmol, 2.2 eq) and $IrCl_3XH_2O$ (1.0 mmol, 1.0 eq) were added to a dry Shlenck tube equipped with a magnetic stir bar. The tube was evacuated and backfilled with nitrogen. The evacuation and backfill procedure was repeated for a total of three times. Then 2-ethoxyethanol (30 mL) and $H_2O$ (10 mL) were added under the protection of nitrogen. The mixture was stirred in an oil bath at a temperature of 110° C. overnight and then cooled down to ambient temperature. The precipitate was filtered and washed with methanol several times to obtain the desired product chlorodimer D48 in 40%~80% yield.

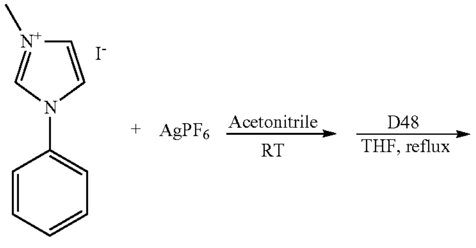

A1

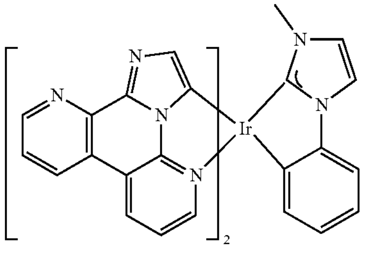

IrC48

A mixture of ancillary ligand A1 (1.5 mmol, 1.5 eq) and $AgPF_6$ (0.75 mmol, 0.75 eq) was stirred in a solution of 100 mL of acetonitrile at room temperature for 24 h. The solvent was evaporated to dryness under reduced pressure. Then chlorodimer D48 (1.0 mmol, 1.0 eq) and 150 mL of THF were added. The reaction mixture was heated to reflux for 24 h. Then the mixture was cooled to room temperature, and the precipitate was filtered off. The filtrate was evaporated to dryness under reduced pressure, and then purified by column chromatography to obtain the emitter IrC48 in 20%~60% yield.

Example 140

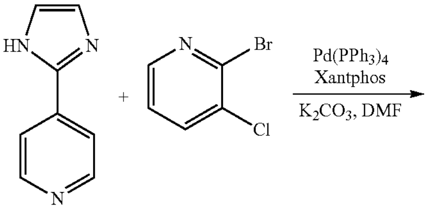

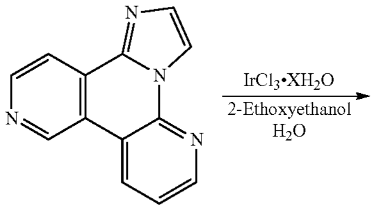

IrL49

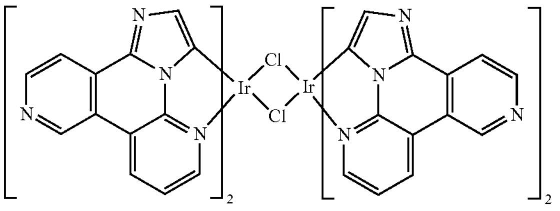

D49

IrL49 (2.2 mmol, 2.2 eq) and $IrCl_3.XH_2O$ (1.0 mmol, 1.0 eq) were added to a dry Shlenck tube equipped with a magnetic stir bar. The tube was evacuated and backfilled with nitrogen. The evacuation and backfill procedure was repeated for a total of three times. Then 2-ethoxyethanol (30 mL) and $H_2O$ (10 mL) were added under the protection of nitrogen. The mixture was stirred in an oil bath at a temperature of 110° C. overnight and then cooled down to ambient temperature. The precipitate was filtered and washed with methanol several times to obtain the desired product chlorodimer D49 in 40%~80% yield.

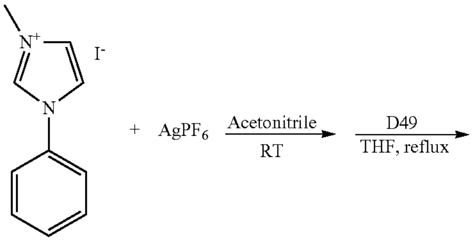

A1

-continued

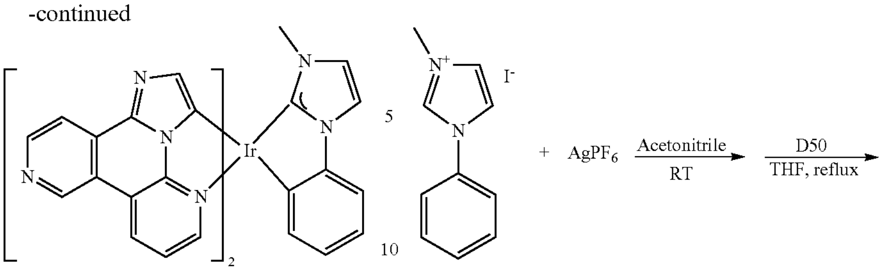

IrC49 A1

A mixture of ancillary ligand A1 (1.5 mmol, 1.5 eq) and $AgPF_6$ (0.75 mmol, 0.75 eq) was stirred in a solution of 100 mL of acetonitrile at room temperature for 24 h. The solvent was evaporated to dryness under reduced pressure. Then chlorodimer D49 (1.0 mmol, 1.0 eq) and 150 mL of THF were added. The reaction mixture was heated to reflux for 24 h. Then the mixture was cooled to room temperature, and the precipitate was filtered off. The filtrate was evaporated to dryness under reduced pressure, and then purified by column chromatography to obtain the emitter IrC49 in 20%~60% yield.

Example 141

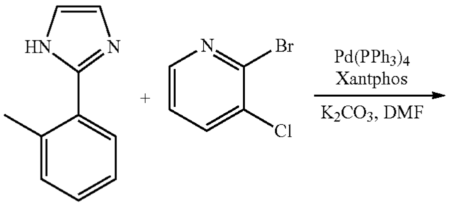

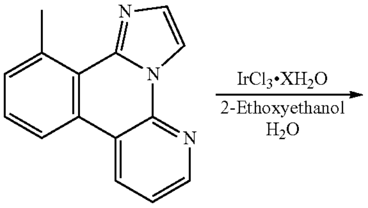

IrL50

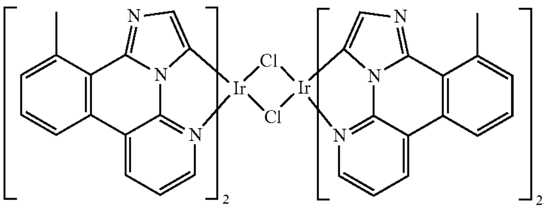

D50

IrL50 (2.2 mmol, 2.2 eq) and $IrCl_3.XH_2O$ (1.0 mmol, 1.0 eq) were added to a dry Shlenck tube equipped with a magnetic stir bar. The tube was evacuated and backfilled with nitrogen. The evacuation and backfill procedure was repeated for a total of three times. Then 2-ethoxyethanol (30 mL) and $H_2O$ (10 mL) were added under the protection of nitrogen. The mixture was stirred in an oil bath at a temperature of 110° C. overnight and then cooled down to ambient temperature. The precipitate was filtered and washed with methanol several times to obtain the desired product chlorodimer D50 in 40%~80% yield.

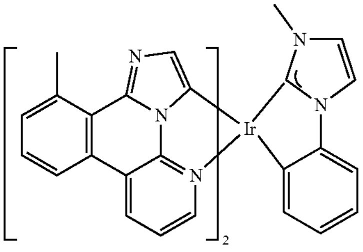

IrC50

A mixture of ancillary ligand A1 (1.5 mmol, 1.5 eq) and $AgPF_6$ (0.75 mmol, 0.75 eq) was stirred in a solution of 100 m of acetonitrile at room temperature for 24 h. The solvent was evaporated to dryness under reduced pressure. Then chlorodimer D50 (1.0 mmol, 1.0 eq) and 150 mL of THF were added. The reaction mixture was heated to reflux for 24 h. Then the mixture was cooled to room temperature, and the precipitate was filtered off. The filtrate was evaporated to dryness under reduced pressure, and then purified by column chromatography to obtain the emitter IrC50 in 20%~60% yield.

Example 142

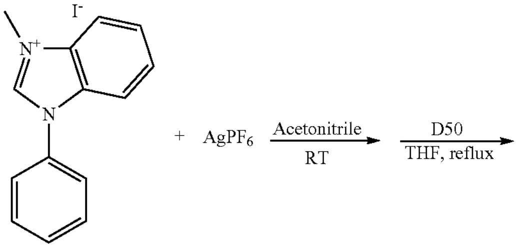

A2

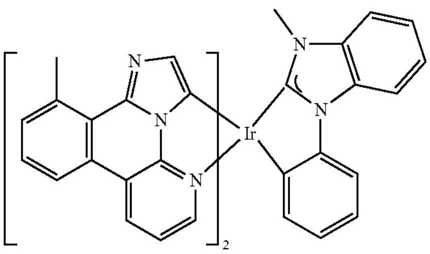

IrC51

A mixture of ancillary ligand A2 (1.5 mmol 1.5 eq) and $AgPF_6$ (0.75 mmol, 0.75 eq) was stirred in a solution of 100 mL of acetonitrile at room temperature for 24 h. The solvent was evaporated to dryness under reduced pressure. Then chlorodimer D50 (1.0 mmol, 1.0 eq) and 150 mL of THF were added. The reaction mixture was heated to reflux for 24 h. Then the mixture was cooled to room temperature, and the precipitate was filtered off. The filtrate was evaporated to dryness under reduced pressure, and then purified by column chromatography to obtain the emitter IrC51 in 20%~60% yield.

Example 143

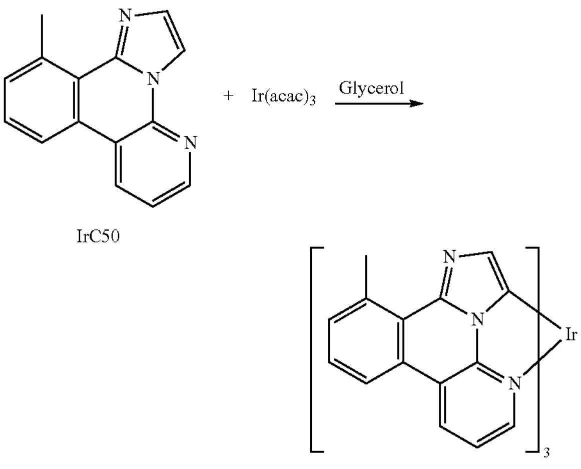

IrC50

IrC52

IrL50 (2.5 mmol, 5.0 eq) and $Ir(acac)_3$ (0.5 mmol, 1.0 eq) were added to a dry Shlenck tube equipped with a magnetic stir bar. The tube was evacuated and backfilled with nitrogen. The evacuation and backfill procedure was repeated for a total of three times. Then 45 mL of glycerol was added under the protection of nitrogen. The mixture was stirred in an oil bath at a temperature of 240° C. for 3 days. After the mixture was cooled down to ambient temperature, 150 mL of 1M HCl solution was added, and the product was thrice extracted with $CH_2Cl_2$. Then the organic extracts were combined, and dried with $MgSO_4$. The mixture was evaporated to dryness under reduced pressure, and then purified by column chromatography to obtain the emitter IrC52 in 5%~50% yield.

Only a few implementations are described and illustrated. Variations, enhancements and improvements of the described implementations and other implementations can be made based on what is described and illustrated in this document.

What is claimed is:

1. A complex represented by General Formula VII:

General Formula VII

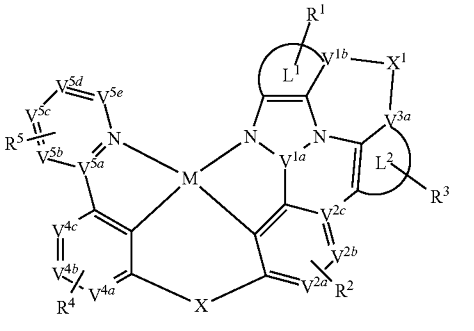

wherein:

M is Pt (II) or Pd (II),

N is nitrogen, each of $V^{1a}$-$V^{1b}$ are carbon, each of $V^{2a}$-$V^{2c}$, $V^{3a}$, $V^{4a}$-$V^{4c}$, and $V^{5a}$-$V^{5e}$ is independently N, or C, represents a single bond, $CR^7R^8$, C═O, $SiR^7R^8$, $GeR^7R^8$, $NR^7$, $PR^7$, $PR^7R^8$, $R^7P$═O, $AsR^7$, $R^7As$═O, O, S, S═O, $SO_2$, Se, Se═O, $SeO_2$, $BR^7$, $BR^7R^8$, $AlR^7$, $AlR^7R^8$, $R^7Bi$═O, or $BiR^7$, $X^1$ is absent, each of $L^1$ and $L^2$ independently represents a substituted or unsubstituted aryl, heteroaryl, or N-heterocyclic carbene, each of R, $R^1$, $R^2$, $R^3$, $R^4$, $R^5$, $R^7$, and $R^8$ is independently absent or present as a single substituent or multiple substituents, valency permitting, and each R, $R^1$, $R^2$, $R^3$, $R^4$, $R^5$, $R^7$, and $R^8$ present independently represents deuterium, halogen, hydroxyl, thiol, nitro, cyanide, isocyanide, sulfinyl, mercapto, sulfo, carboxyl, hydrazino; substituted or unsubstituted: aryl, cycloalkyl, cycloalkenyl, heterocyclyl, heteroaryl, alkyl, alkenyl, alkynyl, amino, monoalkylamino, dialkylamino, monoarylamino, diarylamino, alkoxy, aryloxy, haloalkyl, aralkyl, ester, alkoxycarbonyl, acylamino, alkoxycarbonylamino, aryloxycarbonylamino, sulfonylamino, sulfamoyl, carbamoyl, alkylthio, ureido, phosphoramide, silyl, polymeric; or any conjugate or combination thereof.

2. A light emitting diode comprising the complex of claim 1.

3. A light emitting device comprising the light emitting diode of claim 2.

4. A complex selected from the group consisting of:

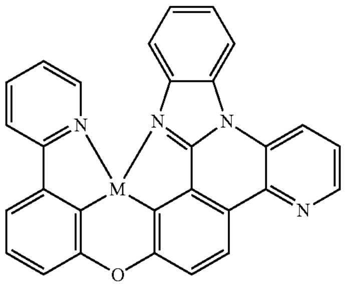

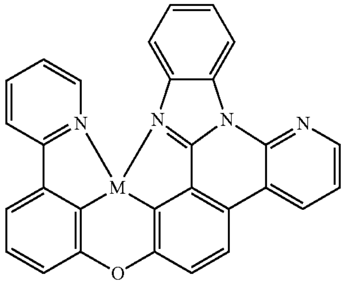

-continued
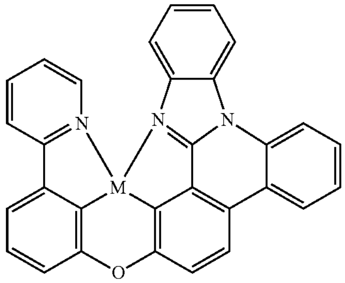
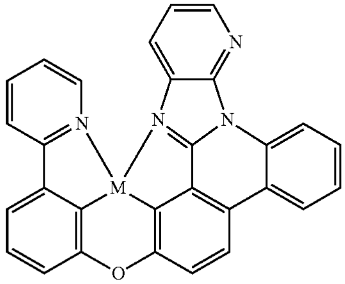
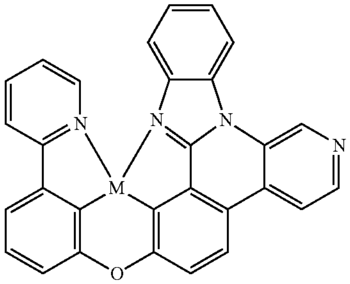
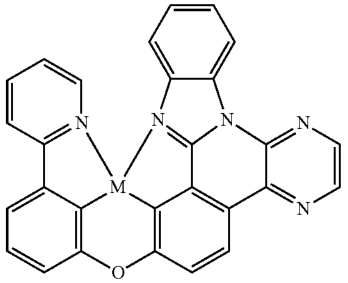
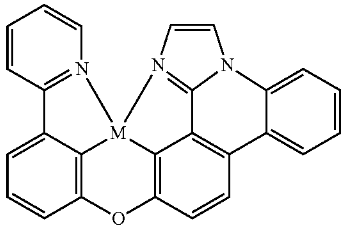
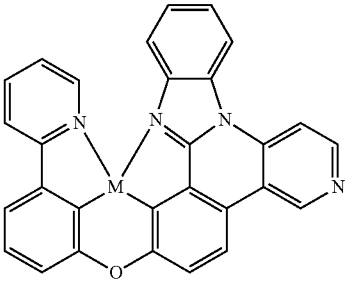
-continued
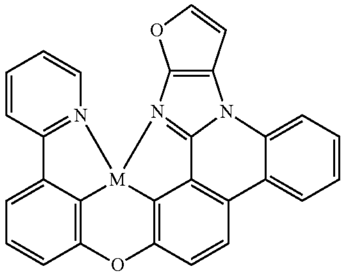
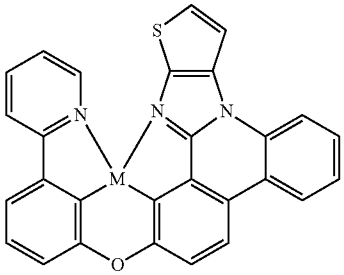
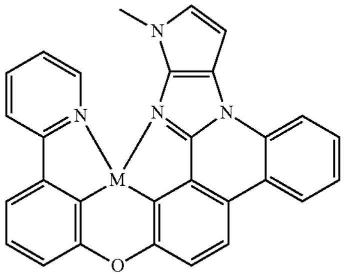
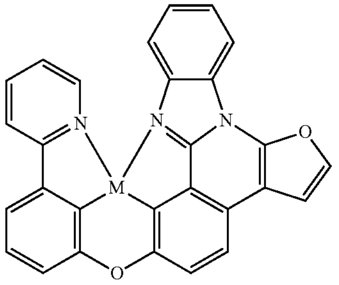
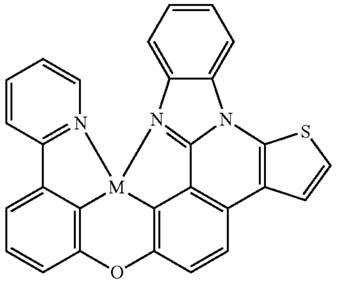
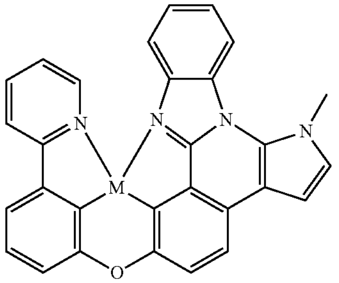

-continued
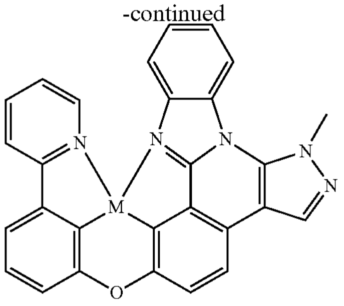
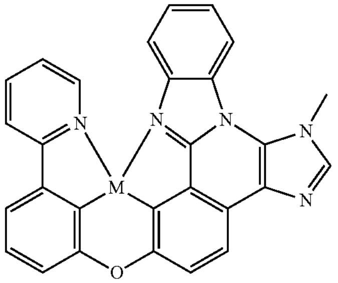
and
-continued
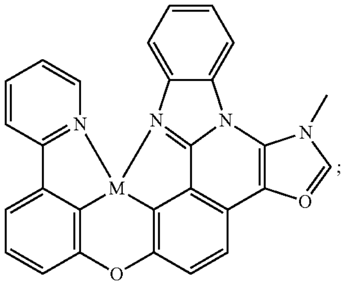
;
wherein M is Pt (II) or Pd (II).
5. A light emitting diode comprising the complex of claim 4.
6. A light emitting device comprising the light emitting diode of claim 5.
* * * * *